US010196681B2

(12) United States Patent
Deciu et al.

(10) Patent No.: US 10,196,681 B2

(45) Date of Patent: Feb. 5, 2019

(54) METHODS AND PROCESSES FOR NON-INVASIVE ASSESSMENT OF GENETIC VARIATIONS

(71) Applicant: SEQUENOM, INC., San Diego, CA (US)

(72) Inventors: Cosmin Deciu, San Diego, CA (US); Zeljko Dzakula, San Diego, CA (US); John Allen Tynan, San Diego, CA (US); Grant Hogg, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 13/829,164

(22) Filed: Mar. 14, 2013

(65) Prior Publication Data

US 2013/0288244 A1 Oct. 31, 2013

Related U.S. Application Data

(63) Continuation-in-part of application No. 13/669,136, filed on Nov. 5, 2012, now Pat. No. 9,367,663, which is a continuation of application No. PCT/US2012/059123, filed on Oct. 5, 2012.

(60) Provisional application No. 61/709,899, filed on Oct. 4, 2012, provisional application No. 61/709,909, filed on Oct. 4, 2012, provisional application No. 61/663,477, filed on Jun. 22, 2012, provisional application No. 61/544,251, filed on Oct. 6, 2011.

(51) Int. Cl.

| | |
|---|---|
| ***C12Q 1/683*** | (2018.01) |
| ***G06F 19/18*** | (2011.01) |
| ***C12Q 1/6827*** | (2018.01) |
| ***G06F 19/00*** | (2018.01) |
| ***C12Q 1/68*** | (2018.01) |

(52) U.S. Cl.

CPC ........... *C12Q 1/683* (2013.01); *C12Q 1/6827* (2013.01); *G06F 19/18* (2013.01); *C12Q 2600/156* (2013.01)

(58) Field of Classification Search

CPC .......... G06F 19/18; G06F 19/22; G06F 19/24; G06F 19/20; C12Q 2537/16; C12Q 1/6827; C12Q 2537/165; C12Q 1/6869; C12Q 2535/122

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,075,212 | A | 12/1991 | Rotbart |
| 5,091,652 | A | 2/1992 | Mathies et al. |
| 5,432,054 | A | 7/1995 | Saunders et al. |
| 5,445,934 | A | 8/1995 | Fodor |
| 5,670,325 | A | 9/1997 | Lapidus et al. |
| 5,720,928 | A | 2/1998 | Schwartz et al. |
| 5,786,146 | A | 7/1998 | Herman et al. |
| 5,928,870 | A | 7/1999 | Lapidus et al. |
| 5,939,598 | A | 8/1999 | Kucherlapati et al. |
| 6,015,714 | A | 6/2000 | Baldarelli et al. |
| 6,090,550 | A | 7/2000 | Collinge et al. |
| 6,100,029 | A | 8/2000 | Lapidus et al. |
| 6,214,558 | B1 | 4/2001 | Shuber et al. |
| 6,214,560 | B1 | 4/2001 | Yguerabide et al. |
| 6,235,475 | B1 | 5/2001 | Brenner et al. |
| 6,258,540 | B1 | 7/2001 | Lo et al. |
| 6,263,286 | B1 | 7/2001 | Gilmanshin et al. |
| 6,403,311 | B1 | 6/2002 | Chan |
| 6,566,101 | B1 | 5/2003 | Shuber et al. |
| 6,617,133 | B1 | 9/2003 | Deamer |
| 6,772,070 | B2 | 8/2004 | Gilmanshin et al. |
| 6,818,395 | B1 | 11/2004 | Quake et al. |
| 6,927,028 | B2 | 8/2005 | Dennis et al. |
| 6,936,422 | B2 | 8/2005 | Akeson et al. |
| 7,005,264 | B2 | 2/2006 | Su et al. |
| 7,169,560 | B2 | 1/2007 | Lapidus et al. |
| 7,279,337 | B2 | 10/2007 | Zhu |
| 7,282,337 | B1 | 10/2007 | Harris |
| 7,947,454 | B2 | 5/2011 | Akeson et al. |
| 7,960,105 | B2 | 6/2011 | Schwartz et al. |
| 7,972,858 | B2 | 7/2011 | Meller et al. |
| 8,688,388 | B2 | 4/2014 | Dzakula et al. |

(Continued)

FOREIGN PATENT DOCUMENTS

| | | |
|---|---|---|
| WO | WO 00/006770 | 2/2000 |
| WO | WO 01/032887 | 5/2001 |

(Continued)

OTHER PUBLICATIONS

Margulies et al. An initial strategy for the systematic identification of functional elements in the human genome by low-rdundancy comparative sequencing. Proceedings of the National Academy of Sciences USA vol. 102, pp. 4795-4800 (2005).*

(Continued)

*Primary Examiner* — John S Brusca

(74) *Attorney, Agent, or Firm* — Fish & Richardson P.C.

(57) ABSTRACT

Provided herein are methods, processes and apparatuses for determining the fraction of fetal nucleic acid in a test sample derived from a pregnant female with improved accuracy and/or precision. Also, provided herein are methods, processes and apparatuses for determining the presence or absence of a genetic variation in a fetus with improved accuracy and/or precision. Certain methods include using fetal fraction measurements for the determination of a fetal genetic variation.

19 Claims, 184 Drawing Sheets

Specification includes a Sequence Listing.

(56) References Cited

U.S. PATENT DOCUMENTS

| | | | |
|---|---|---|---|
| 2001/0014850 A1 | 8/2001 | Gilmanshin et al. | |
| 2001/0049102 A1 | 12/2001 | Huang et al. | |
| 2002/0006621 A1 | 1/2002 | Bianchi | |
| 2002/0045176 A1 | 4/2002 | Lo et al. | |
| 2002/0110818 A1 | 8/2002 | Chan | |
| 2002/0119469 A1 | 8/2002 | Shuber et al. | |
| 2002/0164629 A1 | 11/2002 | Quake et al. | |
| 2003/0013101 A1 | 1/2003 | Balasubramanian | |
| 2003/0082600 A1 | 5/2003 | Olek et al. | |
| 2003/0180779 A1 | 9/2003 | Lofton-Day et al. | |
| 2003/0207326 A1 | 11/2003 | Su et al. | |
| 2003/0232346 A1 | 12/2003 | Su | |
| 2004/0081993 A1 | 4/2004 | Cantor et al. | |
| 2004/0110208 A1 | 6/2004 | Chan et al. | |
| 2004/0137470 A1 | 7/2004 | Dhallan et al. | |
| 2005/0019784 A1 | 1/2005 | Su et al. | |
| 2005/0095599 A1 | 5/2005 | Pittaro et al. | |
| 2005/0112590 A1 | 5/2005 | Boom et al. | |
| 2005/0147980 A1 | 7/2005 | Berlin et al. | |
| 2005/0164241 A1 | 7/2005 | Hahn et al. | |
| 2005/0227278 A1 | 10/2005 | Wall | |
| 2005/0287592 A1 | 12/2005 | Kless | |
| 2006/0046258 A1 | 3/2006 | Lapidus et al. | |
| 2006/0063171 A1 | 3/2006 | Akeson et al. | |
| 2006/0252071 A1 | 11/2006 | Lo et al. | |
| 2007/0065823 A1 | 3/2007 | Dressman et al. | |
| 2007/0202525 A1 | 8/2007 | Quake et al. | |
| 2008/0020390 A1 | 1/2008 | Mitchell et al. | |
| 2008/0070792 A1* | 3/2008 | Stoughton et al. | 506/9 |
| 2008/0081330 A1 | 4/2008 | Kahvejian et al. | |
| 2008/0138809 A1 | 6/2008 | Kapur et al. | |
| 2008/0187915 A1 | 8/2008 | Polonsky et al. | |
| 2008/0233575 A1 | 9/2008 | Harris | |
| 2009/0026082 A1 | 1/2009 | Rothberg et al. | |
| 2009/0029377 A1 | 1/2009 | Lo et al. | |
| 2009/0075252 A1 | 3/2009 | Harris | |
| 2009/0129647 A1 | 5/2009 | Dimitrova et al. | |
| 2009/0191565 A1 | 7/2009 | Lapidus et al. | |
| 2009/0197257 A1 | 8/2009 | Harris | |
| 2009/0317817 A1 | 12/2009 | Oeth et al. | |
| 2009/0317818 A1 | 12/2009 | Ehrich et al. | |
| 2010/0105049 A1 | 4/2010 | Ehrich et al. | |
| 2010/0112575 A1 | 5/2010 | Fan et al. | |
| 2010/0112590 A1 | 6/2010 | Lo et al. | |
| 2010/0138165 A1 | 6/2010 | Fan et al. | |
| 2010/0151471 A1 | 6/2010 | Faham et al. | |
| 2010/0216151 A1 | 8/2010 | Lapidus et al. | |
| 2010/0216153 A1 | 8/2010 | Lapidus et al. | |
| 2010/0109197 A1 | 9/2010 | Stoddart et al. | |
| 2010/0261285 A1 | 10/2010 | Goldstein et al. | |
| 2010/0310421 A1 | 12/2010 | Oliver et al. | |
| 2010/0330557 A1 | 12/2010 | Yakhini et al. | |
| 2011/0086769 A1 | 4/2011 | Oliphant et al. | |
| 2011/0151442 A1 | 6/2011 | Fan et al. | |
| 2011/0159601 A1 | 6/2011 | Golovchenko et al. | |
| 2011/0171634 A1 | 7/2011 | Xiao et al. | |
| 2011/0174625 A1 | 7/2011 | Akeson et al. | |
| 2011/0177498 A1 | 7/2011 | Clarke et al. | |
| 2011/0177517 A1 | 7/2011 | Rava et al. | |
| 2011/0201507 A1 | 8/2011 | Rava et al. | |
| 2011/0224087 A1 | 9/2011 | Quake et al. | |
| 2011/0230358 A1 | 9/2011 | Rava | |
| 2011/0288780 A1 | 11/2011 | Rabinowitz et al. | |
| 2011/0294699 A1 | 12/2011 | Lee et al. | |
| 2011/0312503 A1 | 12/2011 | Chuu et al. | |
| 2011/0319272 A1 | 12/2011 | Fan et al. | |
| 2012/0046877 A1 | 2/2012 | Hyland et al. | |
| 2012/0122701 A1 | 5/2012 | Ryan et al. | |
| 2012/0165203 A1 | 6/2012 | Quake et al. | |
| 2012/0184449 A1 | 7/2012 | Hixson et al. | |
| 2012/0214678 A1 | 8/2012 | Rava et al. | |
| 2012/0264115 A1 | 10/2012 | Rava | |
| 2012/0270212 A1 | 10/2012 | Rabinowitz et al. | |
| 2012/0270739 A1 | 10/2012 | Rava et al. | |
| 2013/0012399 A1 | 1/2013 | Meyers | |
| 2013/0022977 A1 | 1/2013 | Lapidus et al. | |
| 2013/0034546 A1 | 2/2013 | Rava et al. | |
| 2013/0085681 A1 | 4/2013 | Deciu et al. | |
| 2013/0096011 A1 | 4/2013 | Rava et al. | |
| 2013/0130921 A1 | 5/2013 | Gao et al. | |
| 2013/0130923 A1 | 5/2013 | Ehrich et al. | |
| 2013/0150253 A1 | 6/2013 | Deciu et al. | |
| 2013/0196317 A1 | 8/2013 | Lapidus et al. | |
| 2013/0237431 A1 | 9/2013 | Lo et al. | |
| 2013/0245961 A1 | 9/2013 | Lo et al. | |
| 2013/0261983 A1 | 10/2013 | Dzakula et al. | |
| 2013/0304392 A1 | 11/2013 | Deciu et al. | |
| 2013/0309666 A1 | 11/2013 | Deciu et al. | |
| 2013/0310260 A1 | 11/2013 | Kim et al. | |
| 2013/0325360 A1 | 12/2013 | Deciu et al. | |
| 2013/0338933 A1 | 12/2013 | Deciu et al. | |
| 2014/0100792 A1 | 4/2014 | Deciu et al. | |
| 2014/0180594 A1 | 6/2014 | Kim et al. | |
| 2014/0235474 A1 | 8/2014 | Tang et al. | |
| 2014/0242588 A1 | 8/2014 | Van Den Boom et al. | |
| 2014/0322709 A1 | 10/2014 | Lapidus et al. | |
| 2015/0005176 A1 | 1/2015 | Kim et al. | |
| 2015/0100244 A1 | 4/2015 | Hannum | |
| 2015/0347676 A1 | 12/2015 | Zhao et al. | |
| 2016/0034640 A1 | 2/2016 | Zhao et al. | |
| 2016/0110497 A1 | 4/2016 | Dzakula et al. | |
| 2016/0224724 A1 | 8/2016 | Zhao et al. | |
| 2016/0319335 A1 | 11/2016 | Deciu et al. | |

FOREIGN PATENT DOCUMENTS

| | | |
|---|---|---|
| WO | WO 2002/042496 | 5/2002 |
| WO | WO 03/000920 | 1/2003 |
| WO | WO 03/106620 | 12/2003 |
| WO | WO 05/023091 | 3/2005 |
| WO | WO 06/056480 | 6/2006 |
| WO | WO 07/140417 | 12/2007 |
| WO | WO 07/147063 | 12/2007 |
| WO | WO 08/121828 | 10/2008 |
| WO | WO 09/007743 | 1/2009 |
| WO | WO 09/032779 | 3/2009 |
| WO | WO 09/032781 | 3/2009 |
| WO | WO 09/046445 | 4/2009 |
| WO | WO 10/004265 | 1/2010 |
| WO | WO 10/033578 | 3/2010 |
| WO | WO 10/033639 | 3/2010 |
| WO | WO 10/056728 | 5/2010 |
| WO | WO 10/059731 | 5/2010 |
| WO | WO 10/065470 | 6/2010 |
| WO | WO 10/115016 | 10/2010 |
| WO | WO 11/034631 | 3/2011 |
| WO | WO 11/038327 | 3/2011 |
| WO | WO 11/050147 | 4/2011 |
| WO | WO 2011/057094 | 5/2011 |
| WO | WO 11/087760 | 7/2011 |
| WO | WO 11/090556 | 7/2011 |
| WO | WO 11/090558 | 7/2011 |
| WO | WO 11/090559 | 7/2011 |
| WO | WO 11/091063 | 7/2011 |
| WO | WO 11/102998 | 8/2011 |
| WO | WO 11/143659 | 11/2011 |
| WO | WO 11/146632 | 11/2011 |
| WO | WO 2012/012703 | 1/2012 |
| WO | WO 12/088348 | 6/2012 |
| WO | WO 12/088456 | 6/2012 |
| WO | WO 12/108920 | 8/2012 |
| WO | WO 2012/103031 | 8/2012 |
| WO | WO 2012/118745 | 9/2012 |
| WO | WO 12/177792 | 12/2012 |
| WO | WO 2013/000100 | 1/2013 |
| WO | WO 13/052907 | 4/2013 |
| WO | WO 13/052913 | 4/2013 |
| WO | WO 2013/055817 | 4/2013 |
| WO | WO 13/109981 | 7/2013 |
| WO | WO 2013/177086 | 11/2013 |
| WO | WO 13/192562 | 12/2013 |
| WO | WO 2014/039556 | 3/2014 |
| WO | WO 14/055774 | 4/2014 |
| WO | WO 14/055790 | 4/2014 |

(56) References Cited

FOREIGN PATENT DOCUMENTS

| | | |
|---|---|---|
| WO | WO 14/116598 | 7/2014 |
| WO | WO 2014/165596 | 10/2014 |
| WO | WO 2014/190286 | 11/2014 |
| WO | WO 2015/040591 | 3/2015 |
| WO | WO 2015/051163 | 4/2015 |
| WO | WO 2015/054080 | 4/2015 |
| WO | WO 2015/183872 | 12/2015 |
| WO | WO 16/019042 | 2/2016 |

OTHER PUBLICATIONS

Mujezinovic et al. Procedure-Related Complications fo Amniocentesis and Chorionic Villous Sampling Obstetrics & Gynecology vol. 110, pp. 687-694 (2007).*

Mansfield et al. Termination Rates After Prenatal Diagnosis of Down Syndrome, Spina Bifida, Anencephaly, and Turner and Klinefelter Syndromes: A Systematic Literature Review Prenatal Diagnosis vol. 19, pp. 808-812 (1999).*

Agarwal et al. Commercial Landscape of noninvasive prenatal testing in the United States Prenatal Diagnosis vol. 33, pp. 521-531 (Year: 2013).*

Office Action dated Dec. 26, 2013 in U.S. Appl. No. 13/797,508, filed Mar. 12, 2013 and published as US 2013-0261983 on Oct. 3, 2013.

International Preliminary Report on Patentability and Written Opinion dated Jan. 9, 2014 in International Application No. PCT/US2012/043388, filed on Jun. 20, 2012 and published as WO 2012/177792 on Dec. 27, 2012.

Adinolfi et al., "Rapid detection of aneuploidies by microsatellite and the quantitative fluorescent polymerase chain reaction." Prenat Diagn. Dec. 1997;17(13):1299-311.

Akeson et al., "Microsecond Time-Scale Discrimination Among Polycytidylic Acid, Polyadenylic Acid, and Polyuridylic Acid as Homopolymers or as Segments Within Single RNA Molecules," Biophysical Journal vol. 77 Dec. 1999 3227-3233.

Alkan, C., et al., Personalized copy number and segmental duplication maps using nextgeneration sequencing. Nat Genet, 2009. 41(10): p. 1061-7.

Amicucci et al., "Prenatal Diagnosis of Myotonic Dystrophy Using Fetal DNA Obtained from Maternal Plasma," Clin. Chem. 46:301-302, 2000.

Anantha et al., "Porphyrin binding to quadrupled T4G4." Biochemistry. Mar. 3, 1998;37(9):2709-14.

Armour et al., "Measurement of locus copy number by hybridisation with amplifiable probes." Nucleic Acids Res. Jan. 15, 2000;28(2):605-9.

Armour et al., "The detection of large deletions or duplications in genomic DNA." Hum Mutat. Nov. 2002;20(5):325-37.

Ashkenasy et al., "Recognizing a Single Base in an Individual DNA Strand: A Step Toward Nanopore DNA Sequencing," Angew Chem Int Ed Engl. Feb. 18, 2005; 44(9): 1401-1404.

Ashoor, et al., (2012): Chromosome-selective sequencing of maternal plasma cell-free DNA for first trimester detection of trisomy 21 and trisomy 18, American Journal of Obstetrics and Gynecology, doi: 10.1016/j.ajog.2012.01.029.

Avent et al., "Non-invasive diagnosis of fetal sex; utilization of free fetal DNA in maternal plasma and ultrasound," Prenatal Diagnosis, 2006, 26: 598-603.

Beaucage and Caruthers, Tetrahedron Letts., 22:1859-1862, (1981).

Brizot et al., "Maternal serum hCG and fetal nuchal translucency thickness for the prediction of fetal trisomies in the first trimester of pregnancy." Br J Obstet Gynaecol. Feb. 1995;102(2):127-32.

Brizot et al., "Maternal serum pregnancy-associated plasma protein A and fetal nuchal translucency thickness for the prediction of fetal trisomies in early pregnancy." Obstet Gynecol. Dec. 1994;84(6):918-22.

Brown, L., et al., Validation of QF-PCR for prenatal aneuploidy screening in the United States. Prenat Diagn, 2006. 26(11): p. 1068-74.

Brünger, "Free R value: a novel statistical quantity for assessing the accuracy of crystal structures," Nature 355, 472-475 (Jan. 30, 1992); doi:10.1038/355472a0.

Bullard et al., "Evaluation of statistical methods for normalization and differential expression in mRNA-Seq experiments," Bioinformatics 2010, 11:94, pp. 1-13.

Campbell et al., "Identification of somatically acquired rearrangements in cancer using genome-wide massively parallel paired-end sequencing." Nat Genet. Jun. 2008;40(6):722-9. doi: 10.1038/ng.128. Epub Apr. 27, 2008.

Canick et al., "DNA sequencing of maternal plasma to identify Down syndrome and other trisomies in multiple gestations," Prenat Diagn. May 14, 2012:1-5.

Canick, et al., "A New Prenatal Blood Test for Down Syndrome (RNA)," Jul. 2012 found on the internet at: clinicaltrials.gov/show/A15NCT00877292.

Chen et al., "Noninvasive Prenatal Diagnosis of Fetal Trisomy 18 and Trisomy 13 by Maternal Plasma DNA Sequencing," PLoS ONE, Jul. 2011, vol. 6, Issue 7, e21791, pp. 1-7.

Chim et al. (2008). "Systematic search for placental DNA-methylation markers on chromosome 21: toward a maternal plasma-based epigenetic test for fetal trisomy 21." Clin Chem 54(3): 500-11.

Chiu et al. "Maternal plasma DNA analysis with massively parallel sequencing by ligation for noninvasive prenatal diagnosis of trisomy 21." Clin Chem 56(3): 459-63, (2010).

Chiu et al. (2008). "Noninvasive prenatal diagnosis of fetal chromosomal aneuploidy by massively parallel genomic sequencing of DNA in maternal plasma." Proc Natl Acad Sci U S A 105(51): 20458-20463.

Chiu et al., "Non-invasive prenatal assessment of trisomy 21 by multiplexed maternal plasma DNA sequencing: large scale validity study," BMJ 2011;342:c7401, 1-9.

Chiu et al., "Prenatal exclusion of thalassaemia major by examination of maternal plasma," Lancet 360:998-1000, 2002.

Chu et al. (2009). "Statistical model for whole genome sequencing and its application to minimally invasive diagnosis of fetal genetic disease." Bioinformatics 25(10): 1244-50.

Costa et al., "New Strategy for Prenatal Diagnosis of X-Linked Disorders" N. Engl. J. Med. 346:1502, 2002.

Current Protocols in Molecular Biology, John Wiley&Sons, N.Y. 6.3.1-6.3.6(1989).

D'Alton ME., "Prenatal diagnostic procedures." Semin Perinatol. Jun. 1994;18(3):140-62.

Data Sheet: Illumina Sequencing: TruSeq RNA and DNA Sample Preparation Kits v2, Publication No. 970-2009-039 Apr. 27, 2011.

Deamer et al., "Nanopores and Nucleic Acids: Prospects for ultrarapid sequencing." Focus Tibtech Apr. 2000, (vol. 18) pp. 147-151.

Derrien et al. (2012) Fast Computation and Applications of Genome Mappability. PLoS ONE 7(1): e30377, doi:10.1371/journal.pone.0030377.

Ding et al., "A high-throughput gene expression analysis technique using competitive PCR and matrix-assisted laser desorption ionization time-of-flight MS." Proc Natl Acad Sci USA. Mar. 18, 2003;100(6):3059-64. Epub Mar. 6, 2003.

Dohm et al., "Substantial biases in ultra-short read data sets from high-throughput DNA sequencing," Nucleic Acids Res. Sep. 2008;36(16):e105. Epub Jul. 26, 2008.

Edelmann, L., et al., A common molecular basis for rearrangement disorders on chromosome 22q11. Hum Mol Genet, 1999. 8(7): p. 1157-67.

Egger et al., "Reverse transcription multiplex PCR for differentiation between polio- and enteroviruses from clinical and environmental samples." J Clin Microbiol. Jun. 1995;33(6):1442-7.

Ehrich et al., Noninvasive detection of fetal trisomy 21 by sequencing of DNA in maternal blood: a study in a clinical setting, American Journal of Obstetrics and Gynecology—Amer J Obstet Gynecol, vol. 204, No. 3, pp. 205.e1-205.e11, 2011 DOI: 10.1016/j.

Eiben et al., "First-trimester screening: an overview." J Histochem Cytochem. Mar. 2005;53(3):281-3.

Ensenauer, R.E., et al., Microduplication 22q11.2, an emerging syndrome: clinical, cytogenetic, and molecular analysis of thirteen patients. Am J Hum Genet, 2003. 73(5): p. 1027-40.

(56) References Cited

OTHER PUBLICATIONS

Fan et al., (2008). "Noninvasive diagnosis of fetal aneuploidy by shotgun sequencing DNA from maternal blood." Proc Natl Acad Sci U S A 105(42): 16266-71.
Fan et al., (2010). "Sensitivity of noninvasive prenatal detection of fetal aneuploidy from maternal plasma using shotgun sequencing is limited only by counting statistics." PLoS One 5(5): e10439.
Gebhard et al., "Genome-wide profiling of CpG methylation identifies novel targets of aberrant hypermethylation in myeloid leukemia." Cancer Res. Jun. 15, 2006;66(12):6118-28.
Goya, R., et al. (2010) SNVMix: predicting single nucleotide variants from nextgeneration sequencing of tumors, *Bioinformatics*, 26, 730-736.
Hahn et al., "Cell-free nucleic acids as potential markers for preeclampsia." Placenta. Feb. 2011;32 Suppl:S17-20. doi: 10.1016/j.placenta.2010.06.018.
Harris et al., "Single-molecule DNA sequencing of a viral genome." Science. Apr. 4, 2008;320(5872)106-9. doi: 10.1126/science.1150427.
Hill, Craig, "Gen-Probe Transcription-Mediated Amplification: System Principles," Jan. 1996 httl://www.gen-probe.com/pdfs/tma_whiteppr.pdf.
Hulten et al., "Rapid and simple prenatal diagnosis of common chromosome disorders: advantages and disadvantages of the molecular methods FISH and QF-PCR." Reproduction. Sep. 2003;126(3):279-97.
Human Genome Mutations, D. N. Cooper and M. Krawczak, BIOS Publishers, 1993.
Innis et al., PCR Protocols: A Guide to Methods and Applications, Innis et al., eds, 1990.
International Human Genome Sequencing Consortium Initial sequencing and analysis of the human genome Nature vol. 409, pp. 860-921 (2001).
James/James "Mathematics Dictionary," Fifth Edition, Chapman & Hall, International Thomson Publishing, 1992, pp. 266-267_270.
Jensen et al. "High-Throughput Massively Parallel Sequencing for Fetal Aneuploidy Detection from Maternal Plasma" Mar. 6, 2013. PLoS ONE 8(3): e57381.
Jensen et al., "Detection of microdeletion 22q11.2 in a fetus by next-generation sequencing of maternal plasma," Clin Chem. Jul. 2012;58(7):1148-1151.
Jiang et al., "*FetalQuant*: Deducing Fractional Fetal DNA Concentration from Massively Parallel Sequencing of DNA in Maternal Plasma," Bioinformatics, Nov. 15, 2012;28(22):2883-2890.
Kalinina et al., "Nanoliter scale PCR with TaqMan detection." Nucleic Acids Res. May 15, 1997;25(10):1999-2004.
Kitzman et al., (2012): Noninvasive whole-genome sequencing of a human fetus. Science Translational Medicine, 4 (137):137ra76.
Kulkarni et al., "Global DNA methylation patterns in placenta and its association with maternal hypertension in pre-eclampsia." DNA Cell Biol. Feb. 2011;30(2):79-84. doi: 10.1089/dna.2010.1084. Epub Nov. 2, 2010.
Langmead et al., "Ultrafast and memory-efficient alignment of short DNA sequences to the human genome." Genome Biol. 2009;10(3):R25. doi: 10.1186/gb-2009-10-3-r25. Epub Mar. 4, 2009.
Li et al., "Mapping short DNA sequencing reads and calling variants using mapping quality scores." Genome Res. Nov. 2008;18(11):1851-8. doi: 10.1101/gr.078212.108. Epub Aug. 19, 2008.
Liao et al., (2012): Noninvasive Prenatal Diagnosis of Fetal Trisomy 21 by Allelic Ratio Analysis Using Targeted Massively Parallel Sequencing of Maternal Plasma DNA. PLoS ONE, 7(5):e38154, p. 1-7.
Liao, G.J., et al., Targeted massively parallel sequencing of maternal plasma DNA permits efficient and unbiased detection of fetal alleles. Clin Chem, 2010. 57(1): p. 92-101.
Lo "Recent advances in fetal nucleic acids in maternal plasma." J Histochem Cytochem. Mar. 2005;53(3):293-296.
Lo et al. (1997). "Presence of fetal DNA in maternal plasma and serum." Lancet 350(9076): 485-487.
Lo et al. (2007). "Digital PCR for the molecular detection of fetal chromosomal aneuploidy." Proc Natl Acad Sci U S A 104(32): 13116-21.
Lo et al. (2007). "Plasma placental RNA allelic ratio permits noninvasive prenatal chromosomal aneuploidy detection." Nat Med 13(2): 218-23.
Lo et al., "Prenatal Diagnosis of Fetal RhD Status by Molecular Analysis of Maternal Plasma," N. Engl. J. Med. 339:1734-1738, 1998.
Lo et al., "Quantative Abnormalities of Fetal NDA in Maternal Serum in Preeclampsia," Clin. Chem. 45:184-188, 1999.
Lo et al.,"Increased Fetal DNA Concentrations in the Plasma of Pregnant Women Carrying Fetuses with Trisomy 21," Clin. Chem. 45:1747-1751, 1999.
Lo, Y.M., et al., Maternal plasma DNA sequencing reveals the genome-wide genetic and mutational profile of the fetus. Sci Transl Med, 2010. 2(61): p. 61 ra91.
Lun et al. (2008). "Microfluidics digital PCR reveals a higher than expected fraction of fetal DNA in maternal plasma." Clin Chem 54(10): 1664-72.
Mann et al., "Development and implementation of a new rapid aneuploidy diagnostic service within the UK National Health Service and implications for the future of prenatal diagnosis." Lancet. Sep. 29, 2001;358(9287):1057-61.
Margulies et al., "Genome sequencing in microfabricated high-density picolitre reactors." Nature. Sep. 15, 2005;437(7057):376-80. Epub Jul. 31, 2005.
Mazloom, Amin, "Gender Prediction with Bowtie Alignments using Male Specific Regions," May 10, 2012.
Metzker ML., "Sequencing technologies—the next generation." Nat Rev Genet. Jan. 2010;11(1):31-46. doi: 10.1038/nrg2626. Epub Dec. 8, 2009.
Miller et al., Consensus statement: chromosomal microarray is a first-tier clinical diagnostic test for individuals with developmental disabilities or congenital anomalies. Am J Hum Genet, 2010. 86(5): p. 749-64.
Moudrianakis et al., "Base Sequence Determination in Nucleic Acids with the Electron Microscope, III. Chemistry and Microscopy of Guanine-Labeled DNA." Proc Natl Acad Sci U S A. Mar. 1965;53:564-571.
Nakano et al., "Single-molecule PCR using water-in-oil emulsion." J Biotechnol. Apr. 24, 2003;102(2):117-1+A11024.
Needham-VanDevanter et al., "Characterization of an adduct between CC-1065 and a defined oligodeoxynucleotide duplex." Nucleic Acids Res. Aug. 10, 1984;12(15):6159-68.
Ng et al. (2003). "mRNA of placental origin is readily detectable in maternal plasma." Proc Natl Acad Sci U S A 100(8): 4748-53.
Nicolaides et al., "One-stop clinic for assessment of risk of chromosomal defects at 12 weeks of gestation." J Matern Fetal Neonatal Med. Jul. 2002;12(1):9-18.
Nolte FS., "Branched DNA signal amplification for direct quantitation of nucleic acid sequences in clinical specimens." Adv Clin Chem. 1998;33:201-35.
Nygren, A. O., J. Dean, et al. (2010) "Quantification of fetal DNA by use of methylation-based DNA discrimination." Clin Chem 56(10): 1627-35.
Ohno, S. (1967). Sex chromosomes and Sex-linked Genes. Berlin, Springer. p. 111.
Old et al. (2007). "Candidate epigenetic biomarkers for non-invasive prenatal diagnosis of Down syndrome." Reprod Biomed Online 15(2): 227-35.
Oudejans et al. (2003). "Detection of chromosome 21-encoded mRNA of placental origin in maternal plasma." Clin Chem 49(9): 1445-9.
Palomaki et al., DNA sequencing of maternal plasma to detect Down syndrome: an international clinical validation study. Genet Med., Nov. 2011;13(11):913-920.
Palomaki, et al. "DNA sequencing of maternal plasma reliably identifies trisomy 18 and trisomy 13 as well as Down syndrome: an international collaborative study" Genet Med 2012;14:296-305.
Pandya et al., "Screening for fetal trisomies by maternal age and fetal nuchal translucency thickness at 10 to 14 weeks of gestation." Br J Obstet Gynaecol. Dec. 1995;102(12):957-62.

(56) References Cited

OTHER PUBLICATIONS

Pearson and Regnier, "High-Performance Anion-Exchange Chromatogrtaphy of Oligonucleotides," J. Chrom., 255:137-149, 1983.
Pekalska et al., "Classifiers for dissimilarity-based pattern recognition," 15th International Conference on Pattern Recognition (ICPR'00), vol. 2, Barcelona, Spain, Sep. 3-8, 2000.
Pertl et al., "Rapid molecular method for prenatal detection of Down's syndrome." Lancet. May 14, 1994;343(8907):1197-8.
Peters et al. "Noninvasive Prenatal Diagnosis of a Fetal Microdeletion Syndrome," Correspondence to the Editor, New England Journal of Medicine, 365:19 Nov. 10, 2011, pp. 1847-1848.
Poon et al., "Differential DNA methylation between fetus and mother as a strategy for detecting fetal DNA in maternal plasma." Clin Chem. Jan. 2002;48(1):35-41.
Product Sheet for: Nextera™ DNA Sample Prep Kit (Illumina®-Compatible) Cat. Nos. GA09115, GA091120, GA0911-50, GA0911-96, and GA6C0950, from: Epicentre, an Illumina Company, Literature # 307, Jun. 2011.
Qu et al., "Analysis of drug-DNA binding data." Methods Enzymol. 2000;321:353-69.
Robin, N.H. and R.J. Shprintzen, Defining the clinical spectrum of deletion 22q11.2. J Pediatr, 2005. 147(1): p. 90-6.
Romero and Rotbart in Diagnostic Molecular Biology: Principles and Applications pp. 401-406; Persing et al., eds., Mayo Foundation, Rochester, Minn., 1993.
Ross et al., "The DNA sequence of the human X chromosome." Nature. Mar. 17, 2005;434(7031):325-337.
Roth, A., et al. (2012) JointSNVMix: a probabilistic model for accurate detection of somatic mutations in normal/tumour paired next-generation sequencing data, *Bioinformatics*, 28, 907-913.
Saito et al., "Prenatal DNA diagnosis of a singlegene disorder from maternal plasma," Lancet 356:1170, 2000.
Schouten et al., "Relative quantification of 40 nucleic acid sequences by multiplex ligation-dependent probe amplification." Nucleic Acids Res. Jun. 15, 2002;30(12):e57.
Sehnert et al., "Optimal Detection of Fetal Chromosomal Abnormalities by Massively Parallel DNA Sequencing of Cell-Free Fetal DNA from Maternal Blood," Clinical Chemistry, 57:7, pp. 1042-1049 (2011).
Sekizawa et al., "Cell-free Fetal DNA is increased in Plasma of Women wit Hyperemisis Gravidarum," Clin. Chem. 47:2164-2165, 2001.
Shah, S.P., et al. (2009) Mutational evolution in a lobular breast tumour profiled at single nucleotide resolution, *Nature*, 461, 809-813.
Shen et al., "A hidden Markov model for copy number variant prediction from whole genome resequencing data". BMC Bioinformatics, 2011. 12(Suppl 6):54, p. 1-7.
Sherman, S. L., E. G. Allen, et al. (2007). "Epidemiology of Down syndrome." Ment Retard Dev Disabil Res Rev 13(3): 221-7.
Shin, M., L. M. Besser, et al. (2009). "Prevalence of Down syndrome among children and adolescents in 10 regions of the United States." Pediatrics 124(6): 1565-71.
Skaletsy et al., "The male-specific region of the human Y chromosome is a mosaic of discrete sequence classes." Nature. Jun. 19, 2003;423(6942):825-37.
Slater et al., "Rapid, high throughput prenatal detection of aneuploidy using a novel quantitative method (MLPA)." J Med Genet. Dec. 2003;40(12):907-12.
Snijders et al., "Assembly of microarrays for genome-wide measurement of DNA copy number." Nat Genet. Nov. 2001;29(3):263-4.
Snijders et al., "First-trimester ultrasound screening for chromosomal defects." Ultrasound Obstet Gynecol. Mar. 1996;7(3):216-26.
Snijders et al., "UK multicentre project on assessment of risk of trisomy 21 by maternal age and fetal nuchal-translucency thickness at 10-14 weeks of gestation. Fetal Medicine Foundation First Trimester Screening Group." Lancet. Aug. 1, 1998;352(9125):343-6.
Soni et al., "Progress toward ultrafast DNA sequencing using solid-state nanopores." Clin Chem. Nov. 2007;53(11):1996-2001. Epub Sep. 21, 2007.
Sparks et al., (2012): "Selective analysis of cell-free DNA in maternal blood for evaluation of fetal trisomy," Prenatal Diagnosis, 32, 3-9.
Sparks et al., (2012): Non-invasive Prenatal Detection and Selective Analysis of Cell-free DNA Obtained from Maternal Blood: Evaluation for Trisomy 21 and Trisomy 18, American Journal of Obstetrics and Gynecology, pp. 319.e1-319.e9, doi: 10.1016/j.ajog.2012.01.030.
Stagi et al., "Bone density and metabolism in subjects with microdeletion of chromosome 22q11 (del22q11)." Eur J Endocrinol, 2010. 163(2): p. 329-37.
Stanghellini, I., R. Bertorelli, et al. (2006). "Quantitation of fetal DNA in maternal serum during the first trimester of pregnancy by the use of a DAZ repetitive probe." Mol Hum Reprod 12(9): 587-91.
Strachan, The Human Genome, T. BIOS Scientific Publishers, 1992.
Tabor et al. (1986). "Randomised controlled trial of genetic amniocentesis in 4606 low-risk women." Lancet 1(8493): 1287-93.
Timp et al., "Nanopore Sequencing: Electrical Measurements of the Code of Life," IEEE Trans Nanotechnol. May 1, 2010; 9(3): 281-294.
Van den Berghe H, Parloir C, David G et al. A new characteristic karyotypic anomaly in lymphoproliferative disorders. Cancer 1979; 44: 188-95.
Veltman et al., "High-throughput analysis of subtelomeric chromosome rearrangements by use of array-based comparative genomic hybridization." Am J Hum Genet. May 2002;70(5):1269-76. Epub Apr. 9, 2002.
Verma et al., "Rapid and simple prenatal DNA diagnosis of Down's syndrome." Lancet Jul. 4, 1998;352(9121):9-12.
Vincent et al., "Helicase-dependent isothermal DNA amplification." EMBO Rep. Aug. 2004;5(8):795-800. Epub Jul. 9, 2004.
Voelkerding et al., "Next-generation sequencing: from basic research to diagnostics." Clin Chem. Apr. 2009;55(4):641-58. doi: 10.1373/clinchem.2008.112789. Epub Feb. 26, 2009.
Vogelstein et al., "Digital PCR." Proc Natl Acad Sci U S A. Aug. 3, 1999;96(16):9236-41.
Wapner et al., "First-trimester screening for trisomies 21 and 18." N Engl J Med. Oct. 9, 2003;349(15):1405-13.
Wright et al., "The use of cell-free fetal nucleic acids in maternal blood for non-invasive diagnosis," Human Reproduction Update 2009, vol. 15, No. 1, pp. 139-151.
Wu et al., "Genetic and environmental influences on blood pressure and body mass index in Han Chinese: a twin study," (Feb. 2011) Hypertens Res. Hypertens Res 34: 173-179; advance online publication, Nov. 4, 2010.
Zhao et al., "Quantification and application of the placental epigenetic signature of the RASSF1A gene in maternal plasma." Prenat Diagn. Aug. 2010;30(8):778-82.
Zhong et al., "Elevation of both maternal and fetal extracellular circulating deoxyribonucleic acid concentrations in the plasma of pregnant women with preeclampsia," Am. J. Obstet. Gynecol. 184:414-419, 2001.
Zhou et al., "Recent Patents of Nanopore DNA Sequencing Technology: Progress and Challenges," Recent Patents on DNA & Gene Sequences 2010, 4, 192-201.
Zimmermann et al. (2007). "Real-time quantitative polymerase chain reaction measurement of male fetal DNA in maternal plasma." Methods Mol Med 132:43-49.
International Search Report and Written Opinion dated: Sep. 26, 2012 in International Application No. PCT/US2011/066639 filed: Dec. 21, 2011 and published as: WO 12/088348 Jun. 28, 2012.
International Search Report and Written Opinion dated Apr. 5, 2013 in International Application No. PCT/US2012/043388 filed: Jun. 20, 2012 and published as: WO 12/177792 Dec. 27, 2012.
International Search Report and Written Opinion dated Mar. 6, 2013 in International Application No. PCT/US2012/059592 filed: Oct. 10, 2012.
Invitation to Pay Additional Fees and Partial Search Report dated Jan. 18, 2013 in International Application No. PCT/US2012/059592 filed: Oct. 10, 2012.

(56) References Cited

OTHER PUBLICATIONS

Office Action dated Feb. 15, 2012 in U.S. Appl. No. 13/669,136, filed Nov. 5, 2012 and published as: US 2013-0085681 on Apr. 4, 2013.
Office Action dated Feb. 20, 2013 in U.S. Appl. No. 13/656,328, filed Oct. 19, 2012, not yet published.
Zhong et al., "Cell-free fetal DNA in the maternal circulation does not stem from the transplacental passage of fetal erythroblasts" Molecular Human Reproduction (2002) 8(9):864-870.
Office Action dated Oct. 16, 2013 in U.S. Appl. No. 13/933,935, filed Jul. 2, 2013 and published as US 2013-0304392 on Nov. 14, 2013.
Office Action dated Oct. 17, 2013 in U.S. Appl. No. 13/669,136, filed Nov. 5, 2012 and published as US 2013-0085681 on Apr. 4, 2013.
Office Action dated Oct. 18, 2013 in U.S. Appl. No. 13/656,328, filed Oct. 19, 2012 and published as US 2013-0103320 on Apr. 25, 2013.
International Search Report and Written Opinion dated Sep. 9, 2013 in International Application No. PCT/US2012/059123, filed on Oct. 5, 2012 and published as WO/2013/052913 on Apr. 11, 2013.
International Search Report and Written Opinion dated Sep. 9, 2013 in International Application No. PCT/US2012/059114, filed on Oct. 5, 2012 and published as WO/2013/052907 on Apr. 11, 2013.
Office Action dated Sep. 12, 2013 in U.S. Appl. No. 13/669,136, filed Nov. 5, 2012 and published as: US 2013-0085681 on Apr. 4, 2013.
Office Action dated Sep. 12, 2013 in U.S. Appl. No. 13/656,328, filed Oct. 19, 2012 and published as US 2013-0103320 on Apr. 25, 2013.
Invitation to Pay Additional Fees and Partial Search Report dated Jul. 3, 2013 in International Application No. PCT/US2012/059123 filed: Oct. 5, 2012 and published as: WO/2013/052913 on Apr. 11, 2013.
International Search Report and Written Opinion dated: Jul. 4, 2013 in International Application No. PCT/US2013/022290 filed: Jan. 18, 2013, and published as: WO/2013/109981 on Jul. 25, 2013.
Office Action dated: May 3, 2013 in U.S. Appl. No. 13/333,842, filed Dec. 21, 2011 and published as:-2012/0184449 on: Jul. 19, 2012.
Office Action dated: May 7, 2013 in U.S. Appl. No. 13/754,817, filed Jan. 30, 2013.
Office Action dated: Aug. 22, 2013 in U.S. Appl. No. 13/797,508, filed Mar. 12, 2013.
Aston et al. "Optical mapping: an approach for fine mapping," (1999) Methods Enzymol. 303:55-73.
Aston et al. "Optical mapping and its potential for large-scale sequencing project," (1999) Trends Biotechnol. 17(7):297-302.
Berger et al., "Universal bases for hybridization, replication and chain termination," (2000) Nucleic Acids Res. 28(15): 2911-2914.
Bergstrom et al. "Synthesis, Structure, and Deoxyribonucleic Acid Sequencing with a Universal Nucleoside: 1-(2'-Deoxy-.beta.-D-ribofuranosyl)-3-nitropyrrole," (1995) J. Am. Chem. Soc. 117, 1201-1209.
Brown and Lin "Synthesis and duplex stability of oligonucleotides containing adenine-guanine analogues," (1991) Carbohydrate Research 216, 129-139.
Burlingame et al. Anal. Chem. 70:647R-716R (1998).
Carlson et al., "Molecular Definition of 22q11 Deletions in 151 Velo-Cardio-Facial Syndrome Patients," The American Journal of Human Genetics, vol. 61, Issue 3, 620-629, Sep. 1, 1997.
Chan et al. "Size Distribution of Maternal and Fetal DNA in Maternal Plasma," (2004) Clin. Chem. 50:88-92.
Chiang et al., High-resolution mapping of copy-number alterations with massively parallel sequencing, Nat Methods. Jan. 2009 ; 6(1): 99-103.
Cohen et al. (2005): GC Composition of the Human Genome: In Search of Isochores. Mole Biol. Evol. 22(5):1260-1272.
Dan et al., "Prenatal detection of aneuploidy and imbalanced chromosomal arrangements by massively parallel sequencing," PLoS ONE 7(2): e27835, (2012).
Buckheit et al. (1995), "WaveLab and Reproducible Research," Stanford University, Stanford CA 94305, USA, pp. 1-27.
Hsu, S. Self, D. Grove, T. Randolph, K. Wang, J. Delrow, L. Loo, and P. Porter, "Denoising array-based comparative genomic hybridization data using wavelets", Biostatistics (Oxford, England), vol. 6, No. 2, pp. 211-226, 2005.
Hudson et al. "An STA-Based Map of the Human Genome," Science, vol. 270, pp. 1945-1954 (1995).
Hupe,P. et al. (2004) "Analysis of array CGH data: from signal ratio to gain and loss of DNA regions", Bioinformatics, 20, 3413-3422.
Jing et al. (1998) Proc Natl Acad Sci USA. 95(14):8046-51.
Jorgez et al.. "Improving Enrichment of Circulating Fetal DNA for genetic Testing: Size Fractionatiion Followed by Whole Gene Amplification." Fetal Diagnosis and Therapy, Karger Basel, CH, vol. 25, No. 3 Jan. 1, 2009, pp. 314-319.
Jurinke et al. (2004) Mol. Biotechnol. 26, 147-164.
Lai et al. (1999) Nat Genet. 23(3):309-313.
Lai et al., (2005). Comparative analysis of algorithms for identifying amplifications and deletions in array CGH data. Bioinformatics, 21, 19:3763-3770.
Lin and Brown, "Synthesis and duplex stability of oligonucleotides containing cytosine-thymine analogues.," (1989) Nucleic Acids Res. 17, 10373-10383.
Lin and Brown "Synthesis of oligodeoxyribonucleotides containing degenerate bases and their use as primers in the polymerase chain reaction," (1992) Nucleic Acids Res. 20, 5149-5152.
Lo YM, et al.(1998) Am J Hum Genet 62:768-775.
Loakes and Brown "5-Nitroindole as an universal base analogue," (1994) Nucleic Acids Res. 22, 4039-4043.
WaveThresh (WaveThresh : Wavelets statistics and transforms [online],[retrieved on Apr. 24, 2013], retrieved from the internet <URL:*>http://cran.r-project.org/web/packages/wavethresh/index.html<>) and a detailed description of WaveThresh ( Package 'wavethresh' [online, PDF], Apr. 2, 2013, [retrieved on Apr, 24, 2013], retrieved from the internet <URL:*>http://cran.r-project.org/web/packages/wavethresh/wavethresh.pdf<>).
Nason, G.P. (2008) "Wavelet methods in Statistics", table of contents. R. Springer, New York ISBN: 978-0-387-75960-9 (Print) 978-0-387-75961-6 (Online).
Nichols et al. "A universal nucleoside for use at ambiguous sites in DNA primers," (1994) Nature 369, 492-493.
Olshen et al., "Circular binary segmentation for the analysis of array-based DNA copy number data," Biostatistics. Oct. 2004;5(4):557-572.
Sambrook and Russell, Molecular Cloning: A Laboratory Manual 3d ed., 2001, pp. i-xx.
Schwinger et al., "Clinical utility gene card for: DiGeorge syndrome, velocardiofacial syndrome, Shprintzen syndrome, chromosome 22q11.2 deletion syndrome (22q11.2, TBX1)," European Journal of Human Genetics (2010) 18, published online Feb. 3, 2010.
Srinivasan et al., Noninvasive Detection of Fetal Subchromosome Abnormalities via Deep Sequencing of Maternal Plasma, The American Journal of Human Genetics (2013) Feb. 7, 2013;92(2):167-76.
DNAcopy [online],[retrieved on Apr. 24, 2013], retrieved from the internet <URL:* >http://bioconductor.org/packages/2.12/bioc/html/DNAcopy.html.
Venkatraman, ES, Olshen, AB (2007) "A faster circular binary segmentation algorithm for the analysis of array CGH data", Bioinformatics, 23, 6:657-63.
Verbeck et al. in the Journal of Biomolecular Techniques (vol. 13, Issue 2, 56-61), (2002).
Wang and S. Wang, "A novel stationary wavelet denoising algorithm for array-based DNA copy number data", International Journal of Bioinformatics Research and Applications, vol. 3, No. 2, pp. 206-222, 2007.
Willenbrock H, Fridlyand J. A comparison study: applying segmentation to array CGH data for downstream analyses. Bioinformatics Nov. 15, 2005;21(22):4084-91.

(56) References Cited

OTHER PUBLICATIONS

Zhang et al., "A single cell level based method for copy number variation analysis by low coverage massively parallel sequencing," PLoS ONE 8(1): e54236. doi:10.1371/journal.pone.0054236, 2013.
International Search Report and Written Opinion dated Sep. 18, 2013 in International Application No. PCT/US2013/047131, filed on Jun. 21, 2013 and published as WO 2013/192562 on Dec. 27, 2013.
International Search Report and Written Opinion dated Dec. 13, 2013 in International Application No. PCT/US2013/063287, filed Oct. 3, 2013.
Davanos et al., "Relative quantitation of cell-free fetal DNA in maternal plasma using autosomal DNA markers" Clinica Chimica Acta (2011) 412:1539-1543.
Office Action dated Jan. 17, 2014 in U.S. Appl. No. 13/333,842, filed Dec. 21, 2011 and published as US 2012/0184449 on Jul. 19, 2012.
Zhou et al., "Detection of DNA copy number abnormality by microarray expression analysis" Hum. Genet. (2004) 114:464-467.
Office Action dated Jan. 30, 2014 in U.S. Appl. No. 13/933,935, filed Jul. 2, 2013 and published as US 2013-0304392 on Nov. 14, 2013.
Office Action dated Apr. 7, 2014 in U.S. Appl. No. 13/754,817, filed Jan. 30, 2013 and published as US 2013-0150253 on Jun. 13, 2013.
Haar, Alfred (1910) "Zur Theorie der orthogonalen Funktionensysteme", Mathematische Annalen 69 (3): 331-371, English translation "On the Theory of Orthogonal Function Systems" 1-37.
Nguyen, Nha, "Denoising of Array-Based DNA Copy number Data Using the Dual-tree Complex Wavelet Transform," Bioinformatics and Bioengineering, 2007. BIBE 2007. Proceedings of the 7th IEEE International Conference, Boston MA, on Oct. 14-17, 2007, pp. 137-144.
International Preliminary Report on Patentability and Written Opinion dated Apr. 24, 2014 in International Application No. PCT/US2012/059592, filed on Oct. 10, 2012 and published as WO 2013/055817 on Apr. 18, 2013.
International Search Report and Written Opinion dated Apr. 2, 2014 in International Application No. PCT/US2013/063314, filed on Oct. 3, 2013 and published as WO 2014/055790 on Apr. 10, 2014.
International Search Report and Written Opinion dated May 9, 2014 in International Application No. PCT/US2014/012369, filed Jan. 21, 2014.
International Preliminary Report on Patentability dated Jun. 9, 2014 in International Application No. PCT/US2012/059114, filed on Oct. 5, 2012 and published as WO 2013/052907 on Apr. 11, 2013.
International Search Report and Written Opinion dated Sep. 24, 2014 in International Application No. PCT/US2014/043497, filed on Jun. 20, 2014.
Liu et al., "CUSHAW: a CUDA compatible short read aligner to large genomes based on the Burrows-Wheeler transform" Bioinformatics (2012) 28(14):1830-1837.
Office Action dated Oct. 6, 2014 in U.S. Appl. No. 13/754,817, filed Jan. 30, 2013 and published as US 2013-0150253 on Jun. 13, 2013.
International Search Report and Written Opinion dated Feb. 18, 2015 in International Application No. PCT/US2014/058885, filed on Oct. 2, 2014.
Office Action dated Mar. 19, 2015 in U.S. Appl. No. 13/797,508, filed Mar. 12, 2013 and published as US 2013-0261983 on Oct. 3, 2013.
Shendure et al., "Next-generation DNA sequencing" in Nature Biotechnology (2008) 26:1135-1145.
Chen et al., "A method for noninvasive detection of fetal large deletions/duplications by low coverage massively parallel sequencing" Prenatal Diagnosis (2013) 33(6):584-590, and supplementary material pp. 1-6.
Hsu et al., "A model-based circular binary segmentation algorithm for the analysis of array CGH data" BMC Research Notes (2011) 4:394.
Kim et al., "Identification of significant regional genetic variations using continuous CNV values in aCGH data" Genomics (2009) 94(5):317-323.
Oh et al., "CAM: a web tool for combining array CGH and microarray gene expression data from multiple samples" Computers in Biology and Medicine (2009) 40(9):781-785.
International Search Report and Written Opinion dated Dec. 17, 2014 in International Application No. PCT/US2014/039389, filed on May 23, 2014 and published as WO 2014/190286 on Nov. 27, 2014.
International Preliminary Report on Patentability dated Dec. 31, 2014 in International Application No. PCT/US2013/047131, filed on Jun. 21, 2013 and published as WO 2013/192562 on Dec. 27, 2013.
International Search Report and Written Opinion dated Jul. 14, 2014 in International Application No. PCT/US2014/032687, filed on Apr. 2, 2014.
Office Action dated Jul. 28, 2014 in U.S. Appl. No. 13/797,508, filed Mar. 12, 2013 and published as US 2013-0261983 on Oct. 3, 2013.
International Preliminary Report on Patentability dated Jul. 31, 2014 in International Application No. PCT/US2013/022290, filed on Jan. 18, 2013 and published as WO 2013/109981 on Jul. 25, 2013.
Office Action dated Aug. 13, 2014 in U.S. Appl. No. 13/669,136, filed Nov. 5, 2012 and published as US 2013-0085681 on Apr. 4, 2013.
Office Action dated Aug. 14, 2014 in U.S. Appl. No. 13/933,935, filed Jul. 2, 2013 and published as US 2013-0304392 on Nov. 14, 2013.
Office Action dated Apr. 16, 2015 in U.S. Appl. No. 13/669,136, filed Nov. 5, 2012 and published as US 2013-0085681 on Apr. 4, 2013.
Office Action dated Apr. 16, 2015 in U.S. Appl. No. 13/933,935, filed Jul. 2, 2013 and published as US 2013-0304392 on Nov. 14, 2013.
International Preliminary Report on Patentability dated Apr. 16, 2015 in International Application No. PCT/US2013/063314, filed on Oct. 3, 2013 and published as WO 2014/055790 on Apr. 10, 2014
International Preliminary Report on Patentability dated Apr. 16, 2015 in International Application No. PCT/US2013/063287, filed Oct. 3, 2013.
Office Action dated Apr. 21, 2015 in U.S. Appl. No. 13/754,817, filed Jan. 30, 2013 and published as US 2013-0150253 on Jun. 13, 2013.
Office Action dated May 12, 2015 in U.S. Appl. No. 13/669,136, filed Nov. 5, 2012 and published as US 2013-0085681 on Apr. 4, 2013.
Office Action dated May 13, 2015 in U.S. Appl. No. 13/333,842, filed Dec. 21, 2011 and published as US 2012/0184449 on Jul. 19, 2012.
Hinds et al., "Whole-genome patterns of common DNA variation in three human populations" Science (2005) 307:1072-1079.
Pushkarev et al., "Single-molecule sequencing of an individual human genome" Nature Biotechnology (2009) 27(9):847-852.
Hudecova et al., "Maternal plasma fetal DNA fractions in pregnancies with low and high risks for fetal chromosomal aneuploidies" PLoS One (2014) 9(2):e88484.
Palomaki et al., "DNA sequencing of maternal plasma to detect Down syndrome: an international clinical validation study" Genet Med. (2011) 13:913-920, and Expanded Methods Appendix A, pp. 1-65.
Office Action dated Feb. 12, 2016 in U.S. Appl. No. 13/797,930, filed Mar. 12, 2013 and published as US 2013-0325360 on Dec. 5, 2013.
Forabosco et al., "Incidence of non-age-dependent chromosomal abnormalities: a population-based study on 88965 amniocenteses" European Journal of Human Genetics (2009) 17:897-903.
Grati, "Chromosomal Mosaicism in Human Feto-Placental Development: Implications for Prenatal Diagnosis" J. Clin. Med. (2014) 3:809-837.
Bianchi et al., "Isolation of fetal DNA from nucleated erythrocytes in maternal blood," PNAS, 1990,87(9): 3279-3283.

(56) References Cited

OTHER PUBLICATIONS

Borsenberger et al, "Chemically Labeled Nucleotides and Oligonucleotides Encode DNA for Sensing with Nanopores," J. Am. Chem. Soc., 131, 7530-7531, 2009.
Branton et al, "The potential and challenges of nanopore sequencing", Nature Biotechnology, 26:1146-1153, 2008.
Braslaysky et al., "Sequence information can be obtained from single DNA molecules," PNAS, 2003, 100(7): 3960-3964.
Brown et al. A step-by-step guide to non-linear regression analysis of experimental data using a Microsoft Excel spreadsheet Computer Methods and Programs in Biomedicine vol. 65, pp. 191-200 (2001).
Bruch et al., Trophoblast-like cells sorted from peripheral maternal blood using flow cytometry: a multiparametric study involving transmission electron microscopy and fetal DNA amplification,: Prenatal Diagnosis 11:787-798, 1991.
Cann et al., "A heterodimeric DNA polymerase: evidence that members of Euryarchaeota possess a distinct DNA polymerase." 1998, Proc. Natl. Acad. Sci. USA 95:14250.
Cariello et al., "Fidelity of Thermococcus litoralis DNA polymerase (Vent) in PCR determined by denaturing gradient gel electrophoresis," Nucleic Acids Res. Aug. 11, 1991;19(15):4193-8.
Chien et al., "Deoxyribonucleic acid polymerase from the extreme thermophile Thermus aquaticus," 1976, J. Bacteoriol, 127: 1550-1557.
Costa et al., "Fetal RHD genotyping in maternal serum during the first trimester of pregnancy" British Journal of Haematology (2002) 119:255-260.
Cunningham et al., in Williams Obstetrics, McGraw-Hill, New York, p. 942, 2002.
Dhallan et al., "Methods to increase the percentage of free fetal DNA recovered from the maternal circulation," J. Am. Med. Soc. 291(9): 1114-1119, Mar. 2004).
Diaz and Sabino, "Accuracy of replication in the polymerase chain reaction. Comparison between Thermotoga maritima DNA polymerase and Thermus aquaticus DNA polymerase." Diaz RS, Sabino EC. 1998 Braz J. Med. Res, 31: 1239.
DNA Replication 2nd edition, Kornberg and Baker, W. H. Freeman, New York, N.Y. (1991).
Drmanac et al., "Sequencing by hybridization: towards an automated sequencing of one million M13 clones arrayed on membranes," Electrophoresis, 13(8): p. 566-573, 1992.
Herzenberg et al., "Fetal cells in the blood of pregnant women: detection and enrichment by fluorescence-activated cell sorting," PNAS 76:1453-1455, 1979.
Hinnisdaels et al., "Direct cloning of PCR products amplified with Pwo DNA polymerase," 1996, Biotechniques, 20: 186-188.
Huber et al. "High-resolution liquid chromatography of DNA fragments on non-porous poly(styrene-divinylbenzene) particles," Nucleic Acids Res. 21(5):1061-1066, 1993.
Huse et al., "Accuracy and quality of massively parallel DNA pyrosequencing" Genome Biology (2007) 8(7):R143.
Johnston et al., "Autoradiography using storage phosphor technology," Electrophoresis. May 1990;11(5):355-360.
Joos et al., "Covalent attachment of hybridizable oligonucleotides to glass supports," Analytical Biochemistry 247:96-101, 1997.
Juncosa-Ginesta et al., "Improved efficiency in site-directed mutagenesis by PCR using a *Pyrococcus* sp. GB-D polymerase," 1994, Biotechniques, 16(5): pp. 820-823.
Kato et al., "A new packing for separation of DNA restriction fragments by high performance liquid chromatography," J. Biochem, 95(1):83-86, 1984.
Khandjian, "UV crosslinking of RNA to nylon membrane enhances hybridization signals," Mol. Bio. Rep. 11: 107-115, 1986.
Kornberg and Baker, W. H. Freeman, New York, N.Y. (1991).
Lecomte and Doubleday, "Selective inactivation of the 3' to 5' exonuclease activity of *Escherichia coli* DNA polymerase I by heat," 1983, Polynucleotides Res. 11:7505-7515.
Levin, "It's prime time for reverse transcriptase," Cell 88:5-8 (1997).
Li et al., "Detection of paternally inherited fetal point mutations for beta-thalassemia using size-fractionated cell-free DNA in maternal plasma.," J. Amer. Med. Assoc. 293:843-849, 2005.
Lo et al., "Fetal DNA in maternal plasma: application to non-invasive blood group genotyping of the fetus" Transfus. Clin. Biol. (2001) 8:306-310.
Lundberg et al., "High-fidelity amplification using a thermostable DNA polymerase isolated from Pyrococcus furiosus," 1991 Gene, 108:1-6.
Mitchell & Howorka, "Chemical tags facilitate the sensing of individual DNA strands with nanopores," Angew. Chem. Int. Ed. 47:5565-5568, 2008.
Myers and Gelfand, "Reverse transcription and DNA amplification by a Thermus thermophilus DNA polymerase," Biochemistry 1991, 30:7661-7666.
Nevin, N.C., "Future direction of medical genetics", The Ulster Medical Journal, vol. 70, No. 1, (2001), pp. 1-2.
Ng et al. "The Concentration of Circulating Corticotropin-releasing Hormone mRNA in Maternal Plasma Is Increased in Preeclampsia," Clinical Chemistry 49:727-731, 2003.
Nordstrom et al., "Characterization of bacteriophage T7 DNA polymerase purified to homogeneity by antithioredoxin immunoadsorbent chromatography," 1981, J. Biol. Chem. 256:3112-3117.
Oroskar et al., "Detection of immobilized amplicons by ELISA-like techniques." Clin. Chem. 42:1547-1555, 1996.
PCT International Search Report and Written Opinion of the international Searching Authority for International Application No. PCT/US11/24132, dated Aug. 8, 2011. 15 pages.
Purnell and Schmidt, "Discrimination of single base substitutions in a DNA strand immobilized in a biological nanopore," ACS Nano, 3:2533, 2009.
Sambrook, Chapter 10 of Molecular Cloning, a Laboratory Manual, 3.sup.ed Edition, J. Sambrook, and D. W. Russell, Cold Spring Harbor Press (2001).
Smid et al., "Evaluation of Different Approaches for Fetal DNA Analysis from Maternal Plasma and Nucleated Blood Cells," Clinical Chemistry, 1999, 45(9): 1570-1572.
Smith et al., " Direct mechanical measurements of the elasticity of single DNA molecules by using magnetic beads," Science 258:5085, pp. 1122-1126, Nov. 13, 1992.
Stenesh and McGowan, "DNA polymerase from mesophilic and thermophilic bacteria. III. Lack of fidelity in the replication of synthetic polydeoxyribonucleotides by DNA polymerase from Bacillus licheniformis and Bacillus stearothermophilus," 1977, Biochim Biophys Acta 475:32-41.
Stoddart et al, "Single-nucleotide discrimination in immobilized DNA oligonucleotides with a biological nanopore," Proc. Nat. Acad. Sci. 2009, 106(19): pp. 7702-7707.
Takagi et al., "Characterization of DNA polymerase from *Pyrococcus* sp. strain KOD1 and its application to PCR," 1997, Appl. Environ. Microbiol. 63(11): pp. 4504-4510.
Taylor et al., "Characterization of chemisorbed monolayers by surface potential measurements," J. Phys. D. Appl. Phys. 24(8):1443-1450, 1991.
Verma, "The reverse transcriptase," Biochim Biophys Acta 473(1):1-38 (Mar. 21, 1977).
Wei, Chungwen et al., "Detection and Quantification by Homogenous PCR of Cell-free Fetal DNA in Maternal Plasma", Clinical Chemistry, vol. 47, No. 2, (2001), pp. 336-338.
Wu et al., "Reverse Transcriptas," CRC Crit. Rev Biochem. 3(3): pp. 289-347 (Jan. 1975).
Yershov et al., "DNA analysis and diagnostics on oligonucleotide microchips," Proc. Natl. Acad. Sci. 93(10): pp. 4913-4918 (May 14, 1996).
Yoon et al., "Sensitive and accurate detection of copy number variants using read depth of coverage" Genome Research (2009) 19:1586-1592.
Office Action dated Aug. 22, 2013 in U.S. Appl. No. 13/619,039, filed Sep. 14, 2012 and published as: US 2013/0022977 on: Jan. 24, 2013.

(56) References Cited

OTHER PUBLICATIONS

Office Action dated Jan. 10, 2013 in U.S. Appl. No. 13/619,039, filed Sep. 14, 2012 and published as: US 2013/0022977 on: Jan. 24, 2013.
Office Action dated Jul. 14, 2014 in U.S. Appl. No. 12/727,824, filed Sep. 13, 2012 and published as: US 2010/0216153 on: Aug. 26, 2010.
Office Action dated Oct. 18, 2011 in U.S. Appl. No. 12/727,824, filed Sep. 13, 2012 and published as: US 2010/0216153 on: Aug. 26, 2010.
Office Action dated May 16, 2011 in U.S. Appl. No. 12/727,824, filed Sep. 13, 2012 and published as: US 2010/0216153 on: Aug. 26, 2010.
Office Action dated Feb. 25, 2015 in U.S. Appl. No. 12/727,824, filed Sep. 13, 2012 and published as: US 2010/0216153 on: Aug. 26, 2010.
Office Action dated May 29, 2015 in U.S. Appl. No. 14/187,876, filed Feb. 24, 2014 and published as US 2014-0322709 on Oct. 30, 2014.
Kim et al., "Determination of fetal DNA fraction from the plasma of pregnant women using sequence read counts" Prenat. Diagn. (2015) 35(8):810-815.
Extended European Search Report dated Dec. 2, 2015 in European Application No. EP11745050.2, filed on Feb. 9, 2011 and published as EP 2 536 852 on Dec. 26, 2012.
Omont et al., "Gene-based bin analysis of genome-wide association studies" BMC Proceedings (2008) 2 (Suppl 4):S6.
Trapnell and Salzberg, "How to map billions of short reads onto genomes" Nat. Biotechnol. (2009) 27(5):455-457.
International Search Report and Written Opinion dated Jan. 5, 2016 in International Application No. PCT/US2015/042701, filed on Jul. 29, 2015.
Office Action dated Feb. 1, 2016 in U.S. Appl. No. 13/669,136, filed Nov. 5, 2012 and published as US 2013-0085681 on Apr. 4, 2013.
Canick et al., "The impact of maternal plasma DNA fetal fraction on next generation sequencing tests for common fetal aneuploidies" Prenat. Diagn. (2013) 33(7):667-674.
Office Action dated Oct. 22, 2015 in U.S. Appl. No. 13/781,530, filed Feb. 28, 2013 and published as US 2014-0100792 on Apr. 10, 2014.
Office Action dated Oct. 27, 2015 in U.S. Appl. No. 13/333,842, filed Dec. 21, 2011 and published as US 2012/0184449 on Jul. 19, 2012.
Invitation to Pay Additional Fees and Partial International Search Report dated Oct. 14, 2015 in International Application No. PCT/US2015/042701, filed on Jul. 29, 2015.
Yu et al., "Size-based molecular diagnostics using plasma DNA for noninvasive prenatal testing" PNAS USA (2014) 111(23):8583-8588.
International Search Report and Written Opinion dated Oct. 2, 2015 in International Application No. PCT/US2015/032550, filed on May 27, 2015 and published as WO 2015/183872 on Dec. 3, 2015.
Yu et al., "Noninvasive prenatal molecular karyotyping from maternal plasma" PLoS One (2013) 8(4):e60968.
Bollen, "Bioconductor: Microarray versus next-generation sequencing tool sets" retrieved from the internet: http://dspace.library.uu.nl/bitstream/handle/1874/290489/Sander_Bollen_writing_assignment.pdf, retrieved on Sep. 23, 2015.
International Preliminary Report on Patentability dated Dec. 3, 2015 in International Application No. PCT/US2014/039389, filed on May 23, 2014 and published as WO 2014/190286 on Nov. 27, 2014.
Office Action dated Jul. 27, 2015 in U.S. Appl. No. 13/782,857, filed Mar. 1, 2013 and published as US 2013-0310260 on Nov. 21, 2013.
International Preliminary Report on Patentability dated Aug. 6, 2015 in International Application No. PCT/US2014/012369, filed Jan. 21, 2014 and published as WO 2014/116598 on Jul. 31, 2014.
Supplementary Partial European Search Report dated Aug. 10, 2015 in European Application No. EP11745050.2, filed on Feb. 9, 2011 and published as EP 2 536 852 on Dec. 26, 2012.
Office Action dated Aug. 27, 2015 in U.S. Appl. No. 13/933,935, filed Jul. 2, 2013 and published as US 2013-0304392 on Nov. 14, 2013.
Office Action dated Sep. 8, 2015 in U.S. Appl. No. 13/669,136, filed Nov. 5, 2012 and published as US 2013-0085681 on Apr. 4, 2013.
Office Action dated Sep. 8, 2015 in U.S. Appl. No. 13/797,508, filed Mar. 12, 2013 and published as US 2013-0261983 on Oct. 3, 2013.
Office Action dated Sep. 18, 2015 in U.S. Appl. No. 12/727,824, filed Mar. 19, 2010 and published as US 2010-0216153 on Aug. 26, 2010.
Office Action dated Sep. 22, 2015 in U.S. Appl. No. 13/779,638, filed Feb. 27, 2013 and published as US 2013-0309666 on Nov. 21, 2013.
Office Action dated Sep. 28, 2015 in U.S. Appl. No. 14/187,876, filed Feb. 24, 2014 and published as US 2014-0322709 on Oct. 30, 2014.
Office Action dated Oct. 2, 2015 in U.S. Appl. No. 13/754,817, filed Jan. 30, 2013 and published as US 2013-0150253 on Jun. 13, 2013.
Office Action dated Oct. 2, 2015 in U.S. Appl. No. 13/782,883, filed Mar. 1, 2013 and published as US 2014-0180594 on Jun. 26, 2014.
International Preliminary Report on Patentability dated Oct. 15, 2015 in International Application No. PCT/US2014/032687, filed on Apr. 2, 2014 and published as WO 2014/165596 on Oct. 9, 2014.
Romiguier et al., "Contrasting GC-content dynamics across 33 mammalian genomes: relationship with life-history traits and chromosome sizes" Genome Research (2010) 20:1001-1009.
National Human Genome Research Institute, Chromosomes fact sheet , (http://www.genome.gov/26524120, downloaded Sep. 9, 2015).
Leek et al., "Tackling the widespread and critical impact of batch effects in high-throughput data" Nature Reviews Genetics (2010) 11:733-739.
The International SNP Map Working Group "A map of human genome sequence variation containing 1.42 million single nucleotide polymorphisms" Nature (2001) 409:928-933.
Fan et al., "Analysis of the size distributions of fetal and maternal cell-free DNA by paired-end sequencing" Clinical Chemistry (2010) 56(8):1279-1286.
Alkan et al., "Personalized copy number and segmental duplication maps using next-generation sequencing", Nature Genetics, vol. 41, No. 10, Oct. 30, 2009 (Oct. 30, 2009), pp. 1061-1067, and Supplementary Information 1-68.
Office Action dated Oct. 6, 2016 in U.S. Appl. No. 13/797,930, filed Mar. 12, 2013 and published as US 2013-0325360 on Dec. 5, 2013.
Office Action dated Feb. 23, 2016 in U.S. Appl. No. 14/812,432, filed Jul. 29, 2015 and published as US 2016-0034640 on Feb. 4, 2016.
Office Action dated Mar. 3, 2016 in U.S. Appl. No. 13/829,373, filed Mar. 14, 2013 and published as US 2013-0338933 on Dec. 19, 2013.
Office Action dated Mar. 11, 2016 in U.S. Appl. No. 13/782,857, filed Mar. 1, 2013 and published as US 2013-0310260 on Nov. 21, 2013.
Office Action dated Mar. 22, 2016 in U.S. Appl. No. 12/727,824, filed Mar. 19, 2010 and published as US 2010-0216153 on Aug. 26, 2010.
Zhao et al., "Detection of fetal subchromosomal abnormalities by sequencing circulating cell-free DNA from maternal plasma" Clinical Chemistry (2015) 61(4):608-616.
Lefkowitz et al., "Clinical validation of a noninvasive prenatal test for genomewide detection of fetal copy number variants" American Journal of Obstetrics & Gynecology (Dec. 2, 2015) S0002-9378(16)00318-5. doi: 10.1016/j.ajog.2016.02.030. [Epub ahead of print].
Avent, "Refining noninvasive prenatal diagnosis with single-molecule next-generation sequencing" Clin. Chem. (2012) 58(4):657-658.
Boeva et al., "Control-free calling of copy number alterations in deep-sequencing data using GC-content normalization" Bioinformatics (2011) 27(2):268-269.
Chung et al., "Discovering transcription factor binding sites in highly repetitive regions of genomes with multi-read analysis of ChIP-Seq data" PLoS Computational Biology (2011) 7(7):e1002111.

(56) References Cited

OTHER PUBLICATIONS

Chandrananda et al., "Investigating and correcting plasma DNA sequencing coverage bias to enhance aneuploidy discovery" PloS One (2014) 9:e86993.
Benjamini et al., "Summarizing and correcting the GC content bias in high-throughput sequencing" Nucleic Acids Research (2012) 40(10):e72.
International Preliminary Report on Patentability dated Apr. 14, 2016 in International Application No. PCT/US2014/058885, filed on Oct. 2, 2014 and published as WO 2015/051163 on Apr. 9, 2015.
International Preliminary Report on Patentability dated Apr. 21, 2016 in International Application No. PCT/US2014/059156, filed on Oct. 3, 2014 and published as WO 2015/054080 on Apr. 16, 2015.
Yuk et al., "Genomic Analysis of Fetal Nucleic Acids in Maternal Blood" Annual Review of Genomics and Human Genetics (2012) 13:285-306.
Office Action dated Apr. 26, 2016 in U.S. Appl. No. 13/797,508, filed Mar. 12, 2013 and published as US 2013-0261983 on Oct. 3, 2013.
Office Action dated Apr. 27, 2016 in U.S. Appl. No. 13/933,935, filed Jul. 2, 2013 and published as US 2013-0304392 on Nov. 14, 2013.
Office Action dated May 25, 2016 in U.S. Appl. No. 14/187,876, filed Feb. 24, 2014 and published as US 2014-0322709 on Oct. 30, 2014.
Miller et al., "ReadDepth: a parallel R package for detecting copy number alterations from short sequencing reads" PLoS One (2011) 6(1):e16327.
Xie et al., "CNV-seq, a new method to detect copy number variation using high-throughput sequencing" BMC Bioinformatics (2009) 10:80.
Shaffer et al., "Variation in the decision to terminate pregnancy in the setting of fetal aneuploidy" Prenatal Diagnosis (2006) 26:667-671.
Agarwal et al., "Commercial landscape of noninvasive prenatal testing in the United States" Prenatal Diagnosis (2013) 33(6):521-531.
Dan et al., "Clinical application of massively parallel sequencing-based prenatal noninvasive fetal trisomy test for trisomies 21 and 18 in 11,105 pregnancies with mixed risk factors" Prenatal Diagnosis (2012) 32:1225-1232.
Jauch et al., "Reconstruction of genomic rearrangements in great apes and gibbons by chromosome painting" PNAS USA (1992) 89:8611-8615.
Ingersoll et al., "Comparison of gene expression profiles between human and mouse monocyte subsets" Blood (2010) 115:e10-e19.
Office Action dated Jun. 12, 2017 in U.S. Appl. No. 12/727,824, filed Mar. 19, 2010 and published as US 2010-0216153 on Aug. 26, 2010.
Office Action dated Dec. 7, 2016 in U.S. Appl. No. 12/727,824, filed Mar. 19, 2010 and published as US 2010-0216153 on Aug. 26, 2010.
Zhong et al., "Cell-free DNA in urine: a marker for kidney graft rejection, but not for prenatal diagnosis?" Annals New York Academy of Sciences (2001) 945:250-257.
Lichtensen et al., "Circulating Nucleic Acids and Apoptosis" Annals New York Academy of Sciences (2001) 945:239-249.
Saito-Hisaminato et al., "Genome-wide profiling of gene expression in 29 normal human tissues with a cDNA microarray" DNA Research (2002) 9:35-45.
Office Action dated Feb. 27, 2017 in U.S. Appl. No. 13/797,508, filed Mar. 12, 2013 and published as US 2013-0261983 on Oct. 3, 2013.
Larsson et al., "Reference values for clinical chemistry tests during normal pregnancy" BJOG (2008) 115:874-881.
Office Action dated Jul. 14, 2017 in U.S. Appl. No. 13/797,930, filed Mar. 12, 2013 and published as US 2013-0325360 on Dec. 5, 2013.
Office Action dated Aug. 1, 2017 in U.S. Appl. No. 13/797,508, filed Mar. 12, 2013 and published as US 2013-0261983 on Oct. 3, 2013.

* cited by examiner

Fetal fraction estimates based on
Chr 21 vs. measured fetal fractions.

Design of the recombinant MBD-Fc protein

MBD Protein

Fractionating DNA
Based on Methylation

EpiTYPER Results

Quantitation of Methylation Ratios

1. Selection of differentially methylated targets for specific DNA sequence capture 2. Distribution of CCF DNA after capture 3. Distribution of CCF DNA after digestion 4. Quantification of non-digested DNA molecules $$\longrightarrow \frac{\text{Meth(Ratio(D/C))}}{\text{Total(Ratio(D/C))}} \times \frac{\text{\# Comps (Meth)}}{\text{\# Comps (Total)}} = \text{Ratio (Meth/Total)}$$

Meth = 2x fetal genomes G(f)

Total = 2x fetal G(f) and 2x maternal genomes G(m)

G(f) is a fraction of G(m) = kG(m)

$$\frac{2\,G(f)}{2G(f)+2G(m)} = \frac{k}{k+1} = R \longrightarrow k = R(k+1) \longrightarrow k = \frac{R}{1-R}$$

FIG. 163

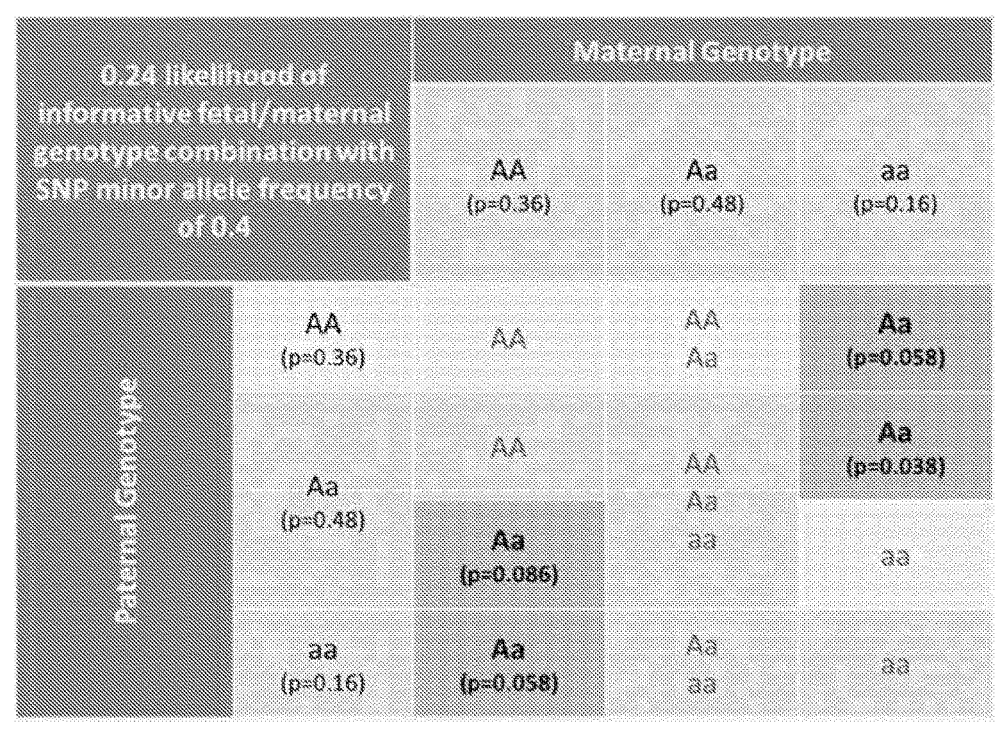

| 0.24 likelihood of informative fetal/maternal genotype combination with SNP minor allele frequency of 0.4 | | Maternal Genotype | | |
|---|---|---|---|---|
| | | AA<br>(p=0.36) | Aa<br>(p=0.48) | aa<br>(p=0.16) |
| Paternal Genotype | AA<br>(p=0.36) | AA | AA<br>Aa | **Aa**<br>**(p=0.058)** |
| | Aa<br>(p=0.48) | AA<br>**Aa**<br>**(p=0.086)** | AA<br>Aa<br>aa | **Aa**<br>**(p=0.038)**<br>aa |
| | aa<br>(p=0.16) | **Aa**<br>**(p=0.058)** | Aa<br>aa | aa |

Detected SNPs have high minor allele population frequency

Maternal genotype
GG

Paternal genotype
GA

Fetal genotype
GA

CCF DNA from plasma of pregnant mother

Maternal CCF copies of GG = 900
Fetal CCF copies of GA = 100
Total CCF DNA copies = 1000

Perform multiplex PCR of 67 SNPs (one amplicon shown)

Amplicon sequencing and alignment

$$\text{Fetal fraction} = \frac{\text{\# of reads allele A}}{(\text{\# of reads allele A} + \text{\# of reads allele G})} \times 2 = 10\%$$

Graph probabilities assume 0.4 MAF SNPs

METHODS AND PROCESSES FOR NON-INVASIVE ASSESSMENT OF GENETIC VARIATIONS

RELATED PATENT APPLICATIONS

This patent application claims the benefit of U.S. Provisional Patent Application No. 61/709,909 filed on Oct. 4, 2012, entitled METHODS AND PROCESSES FOR NON-INVASIVE ASSESSMENT OF GENETIC VARIATIONS, naming Cosmin Deciu, Mathias Ehrich, Zeljko Dzakula and Amin Mazloom as inventors, and is a continuation-in-part of U.S. patent application Ser. No. 13/669,136 filed Nov. 5, 2012, entitled METHODS AND PROCESSES FOR NON-INVASIVE ASSESSMENT OF GENETIC VARIATIONS, naming Cosmin Deciu, Zeljko Dzakula, Mathias Ehrich and Sung Kim as inventors, which is a continuation of International PCT Application No. PCT/US2012/059123 filed Oct. 5, 2012, entitled METHODS AND PROCESSES FOR NON-INVASIVE ASSESSMENT OF GENETIC VARIATIONS, naming Cosmin Deciu, Zeljko Dzakula, Mathias Ehrich and Sung Kim as inventors, which (i) claims the benefit of U.S. Provisional Patent Application No. 61/709,899 filed on Oct. 4, 2012, entitled METHODS AND PROCESSES FOR NON-INVASIVE ASSESSMENT OF GENETIC VARIATIONS, naming Cosmin Deciu, Zeljko Dzakula, Mathias Ehrich and Sung Kim as inventors, (ii) claims the benefit of U.S. Provisional Patent Application No. 61/663,477 filed on Jun. 22, 2012, entitled METHODS AND PROCESSES FOR NON-INVASIVE ASSESSMENT OF GENETIC VARIATIONS, naming Zeljko Dzakula and Mathias Ehrich as inventors, and (iii) claims the benefit of U.S. Provisional Patent Application No. 61/544,251 filed on Oct. 6, 2011, entitled METHODS AND PROCESSES FOR NON-INVASIVE ASSESSMENT OF GENETIC VARIATIONS, naming Zeljko Dzakula and Mathias Ehrich as inventors. The entire content of the foregoing application is incorporated herein by reference, including all text, tables and drawings.

SEQUENCE LISTING

The instant application contains a Sequence Listing which has been submitted in ASCII format via EFS-Web and is hereby incorporated by reference in its entirety. Said ASCII copy, created on Jul. 11, 2013, is named SEQ-6034-CP2T_SL.txt and is 434,112 bytes in size.

FIELD

Technology provided herein relates in part to methods, processes and apparatuses for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure. In certain embodiments, identification of one or more genetic variations or variances involves the analysis of cell-free DNA. Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, maternal bloodstream and used for various noninvasive prenatal diagnostics.

Non-invasive prenatal testing is becoming a field of rapidly growing interest. Early detection of pregnancy-related conditions, including complications during pregnancy and genetic defects of the fetus is of crucial importance, as it allows early medical intervention necessary for the safety of both the mother and the fetus. Prenatal diagnosis has been conducted using cells isolated from the fetus through procedures such as chorionic villus sampling (CVS) or amniocentesis. However, these conventional methods are invasive and present an appreciable risk to both the mother and the fetus. The National Health Service currently cites a miscarriage rate of between 1 and 2 percent following the invasive amniocentesis and chorionic villus sampling (CVS) tests.

An alternative to these invasive approaches has been developed for prenatal screening, e.g., to detecting fetal abnormalities, following the discovery that circulating cell-free fetal nucleic acid can be detected in maternal plasma and serum (Lo et al., Lancet 350:485-487, 1997; and U.S. Pat. No. 6,258,540). Circulating cell free fetal nucleic acid (cffNA) has several advantages making it more applicable for non-invasive prenatal testing. For example, cell free nucleic acid is present at higher levels than fetal cells and at concentrations sufficient for genetic analysis. Also, cffNA is cleared from the maternal bloodstream within hours after delivery, preventing contamination from previous pregnancies. The presence of fetal nucleic acid in maternal plasma allows for non-invasive prenatal diagnosis through the analysis of a maternal blood sample. Hence, fetal nucleic acid analysis in maternal plasma can be a useful mechanism for the monitoring of fetomaternal well-being.

Examples of prenatal tests performed by detecting fetal DNA in maternal plasma or serum include fetal rhesus D (RhD) genotyping (Lo et al., N. Engl. J. Med. 339:1734-1738, 1998), fetal sex determination (Costa et al., N. Engl. J. Med. 346:1502, 2002), and diagnosis of several fetal disorders (Amicucci et al., Clin. Chem. 46:301-302, 2000; Saito et al., Lancet 356:1170, 2000; and Chiu et al., Lancet 360:998-1000, 2002). In addition, quantitative abnormalities of fetal DNA in maternal plasma/serum have been reported in preeclampsia (Lo et al., Clin. Chem. 45:184-188, 1999 and Zhong et al., Am. J. Obstet. Gynecol. 184:414-419, 2001), fetal trisomy 21 (Lo et al., Clin. Chem. 45:1747-1751, 1999 and Zhong et al., Prenat. Diagn. 20:795-798, 2000) and hyperemesis gravidarum (Sekizawa et al., Clin. Chem. 47:2164-2165, 2001).

SUMMARY

Provided herein, in some embodiments is a method for determining fetal ploidy according to nucleic acid sequence reads, comprising (a) determining a fraction of fetal nucleic acid in a sample, which sample comprises circulating cell-free nucleic acid from the blood of a pregnant female bearing a fetus, (b) obtaining counts of sequence reads mapped to portions of a reference genome, which sequence reads are from the nucleic acid in the sample, (c) calculating a genomic section level for each of the portions of the reference genome, thereby providing calculated genomic section levels, and (d) determining fetal ploidy according to (i) the calculated genomic section levels for a subset of portions of the reference genome and (ii) the fraction of fetal nucleic acid determined in (a). In some embodiments the fetal fraction is determined from a first part of the test sample and the genomic section levels are determined from a second part of the test sample. In some embodiments calculating the genomic section level for each of the portions of the reference genome comprises normalizing counts of reads mapped to the reference genome according to guanine and cytosine (GC) content for each of the portions. In certain embodiments, the method comprises (1) determining a guanine and cytosine (GC) bias for each of the portions of the reference genome for multiple samples from a fitted relation for each sample between (i) the counts of the sequence reads mapped to each of the portions of the reference genome, and (ii) GC content for each of the portions, and (2) calculating the genomic section level for each of the portions of the reference genome from a fitted relation between (i) the GC bias and (ii) the counts of the sequence reads mapped to each of the portions of the reference genome, thereby providing calculated genomic section levels, whereby bias in the counts of the sequence reads mapped to each of the portions of the reference genome is reduced in the calculated genomic section levels. In some embodiments of the method, the subset of portions of the reference genome in (d)(i) is portions of a chromosome or a segment thereof. In some embodiments the chromosome is chosen from chromosome 13, chromosome 18 and chromosome 21. In some embodiments the method comprises determining a reference count and an uncertainty value according to the reference count. In some embodiments the reference count is determined according to calculated genomic section levels for a subset of portions of the reference genome for one or more pregnant females bearing a fetus. In some embodiments the reference count is determined where the subset of portions of the reference genome for one or more pregnant females are known to be euploid for the fetus and/or the mother, and where the reference count is not determined from the sample. In some embodiments the reference count is determined from the same subset of portions of the reference genome as in (d). In some embodiments the reference count is normalized by bin-wise normalization, normalization by GC content, linear and nonlinear least squares regression, LOESS, GC LOESS, LOWESS, PERUN, RM, GCRM and combinations thereof. In some embodiments a maternal ploidy is determined. In certain embodiments the fetal ploidy is determined in (d) according to (i) the calculated genomic section levels for a subset of portions of the reference genome, (ii) the fraction of fetal nucleic acid determined in (a), (iii) a maternal ploidy, (iv) the reference count and (v) an uncertainty value σ for the reference count. In some embodiments the fraction of fetal nucleic acid determined in (a) is fixed at its determined value and fetal ploidy X is determined according to Equation 8 below, or a derivation thereof:

$$y_i=(1-F)M_if_i+FXf_i \tag{8}$$

where $y_i$ represents the calculated genomic section level for portion i of a reference genome, F represents the fraction of fetal nucleic acid determined in (a), $f_i$ represents a reference count for i, X represents the fetal ploidy, and $M_i$ represents the maternal ploidy of portion i. In some embodiments determining the fetal fraction comprises determining the sum of squared residuals according to equation (8) and for multiple bins i for a subset of portions of the reference genome. In some embodiments the fetal fraction is fixed at a value determined in (a) and the fetal ploidy is varied to optimize the sum of squared residuals according to equation (8) or a variation thereof. In some embodiments a linear regression is determined according to the sum of square residuals. In some embodiments the fetal ploidy is determined according to Equation 20 below:

$$X=\frac{\sum_{i=1}^{N}\frac{f_iy_i}{\sigma_i^2}-(1-F)\sum_{i=1}^{N}\frac{M_if_i^2}{\sigma_i^2}}{F\sum_{i=1}^{N}\frac{f_i^2}{\sigma_i^2}}. \tag{20}$$

wherein $y_i$ represents the calculated genomic section level for portion i of a reference genome, F represents the fraction of fetal nucleic acid determined in (a), $f_i$ represents a reference count for i, σ represents the uncertainty value for $f_i$, X represents the fetal ploidy, and $M_i$ represents the maternal ploidy of portion i. In some embodiments the fetal ploidy is determined according to Equation 21 below:

$$X=\frac{\Xi_{fy}-(1-F)\Xi_{ff}}{F\Xi_{ff}}=\frac{\Xi_{fy}}{F\Xi_{ff}}-\frac{1-F}{F}=1+\frac{1}{F}\left(\frac{\Xi_{fy}}{\Xi_{ff}}-1\right) \tag{21}$$

wherein $$\Xi_{ff}=\sum_{i=1}^{N}\frac{f_i^2}{\sigma_i^2},\ \Xi_{fy}=\sum_{i=1}^{N}\frac{y_if_i}{\sigma_i^2},$$

$y_i$ represents the calculated genomic section level for portion i of a reference genome, F represents the fraction of fetal nucleic acid determined in (a), $f_i$ represents a reference count for i, σ represents the uncertainty value for $f_i$, and X represents the fetal ploidy. In some embodiments the presence or absence of a fetal chromosome aneuploidy is determined according to the fetal ploidy determined in (d). In some embodiments the fetal ploidy determined in (d) is about 1.4 or greater and the presence of a fetal chromosome aneuploidy is determined. In some embodiments the fetal ploidy determined in (d) is about 1.2 or less and the absence of a fetal chromosome aneuploidy is determined. In some embodiments the fetal chromosome aneuploidy is a trisomy. In some embodiments the trisomy is selected from a trisomy of chromosome 13, 18 and 21. In some embodiments determining the fraction of fetal nucleic acid comprises analyzing the calculated genomic sections levels for a subset of portions of the reference genome, which subset is a first subset, the subset in (d) is a second subset, and the first subset of portions of the reference genome is portions of a Y chromosome or a segment thereof. In some embodiments determining the fraction of fetal nucleic acid comprises (1) obtaining counts of nucleic acid sequence reads mapped to genomic sections of a reference genome, which sequence reads are reads of circulating cell-free nucleic acid from the blood of a pregnant female bearing a male fetus, (2) from the counts in (1), generating an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof, (3) determining the fraction of the fetal nucleic acid in the blood of the pregnant female according to the experimental Y chromosome representation generated in (2) and a fitted relationship, wherein the fitted relationship is between (i) an experimental Y chromosome representation determined from a set of pregnant females bearing a male fetus and (ii) an X chromosome representation determined from a set of pregnant females, and the fitted relationship is fitted to a median chromosome X representation and a median chromosome Y representation for a set of pregnant females bearing a female fetus. In some embodiments determining the fraction of fetal nucleic acid comprises analyzing one or more loci in sample nucleic acid, wherein at least one of the one or more loci vary between fetal nucleic acid and maternal nucleic acid. In some embodiments the one or more loci comprise one or more polymorphic sites, comprising (1) enriching nucleic acid in a first part of the test sample for a plurality of polymorphic sites, (2) obtaining nucleotide sequences for some or all of the polymorphic sites by a sequencing process, (3) analyzing the nucleotide sequences of (2), and (4) determining the fraction of fetal nucleic acid based on the analysis of (3), wherein the polymorphic sites and number thereof result in at least five polymorphic sites being informative for determining the fetal fraction for at least 90% of samples. In some embodiments the one or more loci comprise one or more methylation regions, comprising, (1) contacting the test sample with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid, and (2) determining the fraction of fetal nucleic acid in the sample based on the differentially modified nucleic acid. In some embodiments the one or more agents are methylation sensitive restriction enzymes.

Also provided herein is a system comprising one or more processors and memory, which memory comprises instructions executable by the one or more processors and which memory comprises counts of nucleic acid sequence reads mapped to portions of a reference genome, which sequence reads are reads of circulating cell-free nucleic acid from a test sample obtained from a pregnant female bearing a fetus, and which instructions executable by the one or more processors are configured to (a) determine a fraction of fetal nucleic acid in the test sample, (b) calculate a genomic section level for each of the portions of the reference genome, thereby providing calculated genomic section levels, and (c) determine fetal ploidy according to (i) the calculated genomic section levels for a subset of portions of the reference genome and (ii) the fraction of fetal nucleic acid determined in (a).

As used herein, the term "genomic sections" of a reference genome is the same as "portions of a reference genome".

Certain aspects of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

In FIG. 6, the two bottom traces show a patient with a large deletion in chromosome 18. See Example 1 for experimental details and results.

Example 3 addresses FIGS. 52 to 61F.

Figure 52:
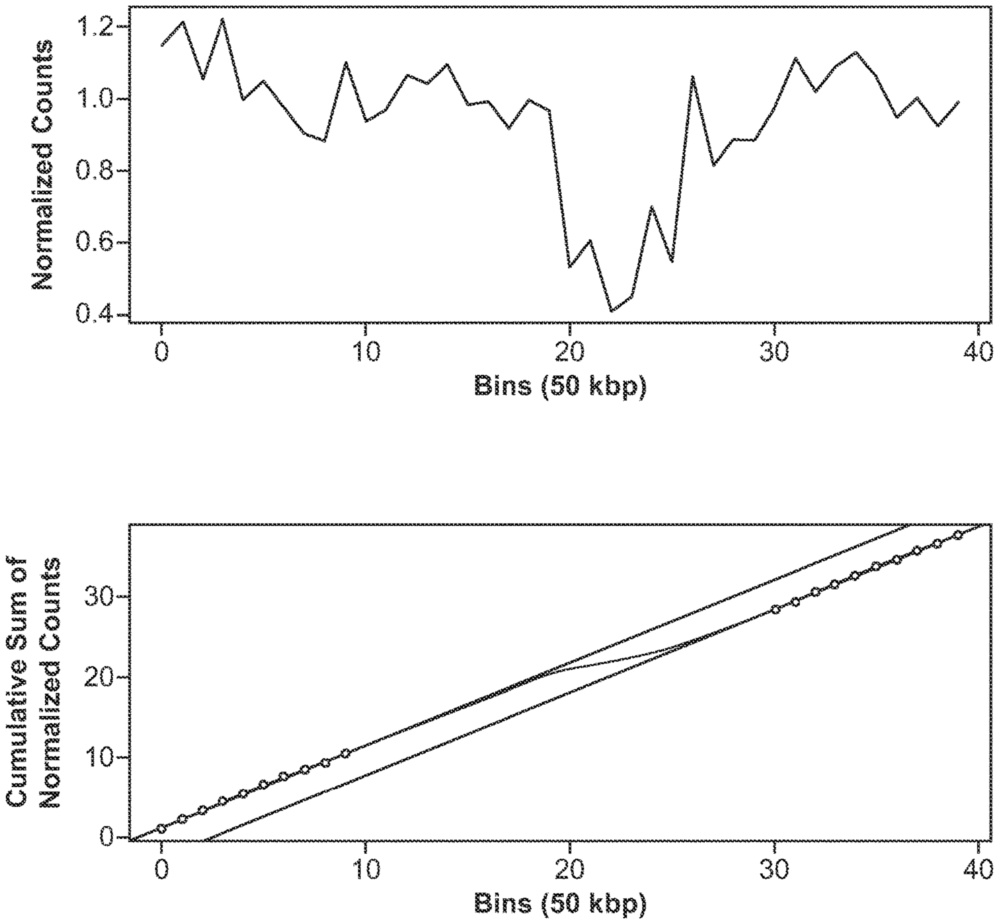

FIG. 52 graphically illustrates an example of application of the cumulative sum algorithm to a heterozygous maternal microdeletion in chromosome 12, bin 1457. The difference between the intercepts associated with the left and the right linear models is 2.92, indicating that the heterozygous deletion is 6 bins wide.

Figure 53:
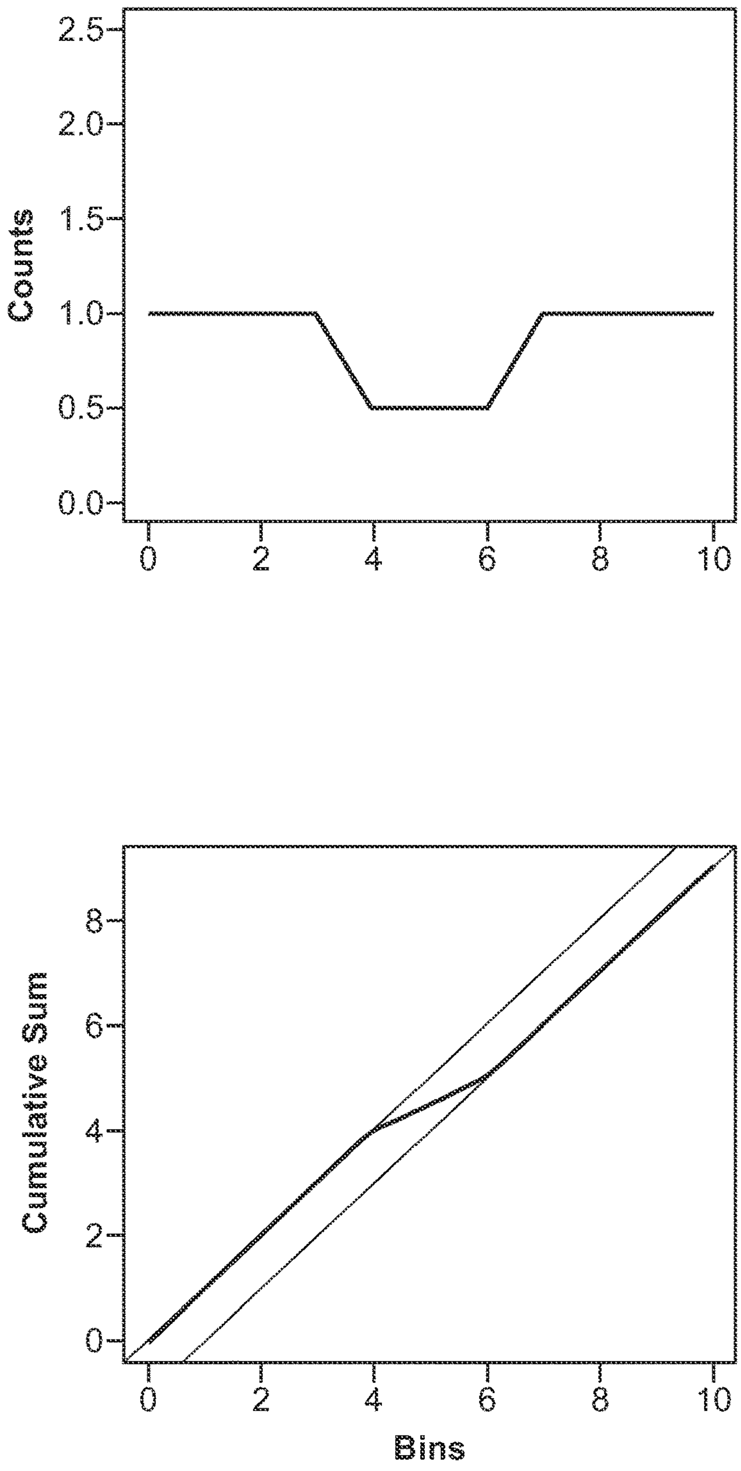

FIG. 53 graphically illustrates a hypothetical heterozygous deletion, approximately 2 genomic sections wide, and its associated cumulative sum profile. The difference between the left and the right intercepts is −1.

Figure 54:
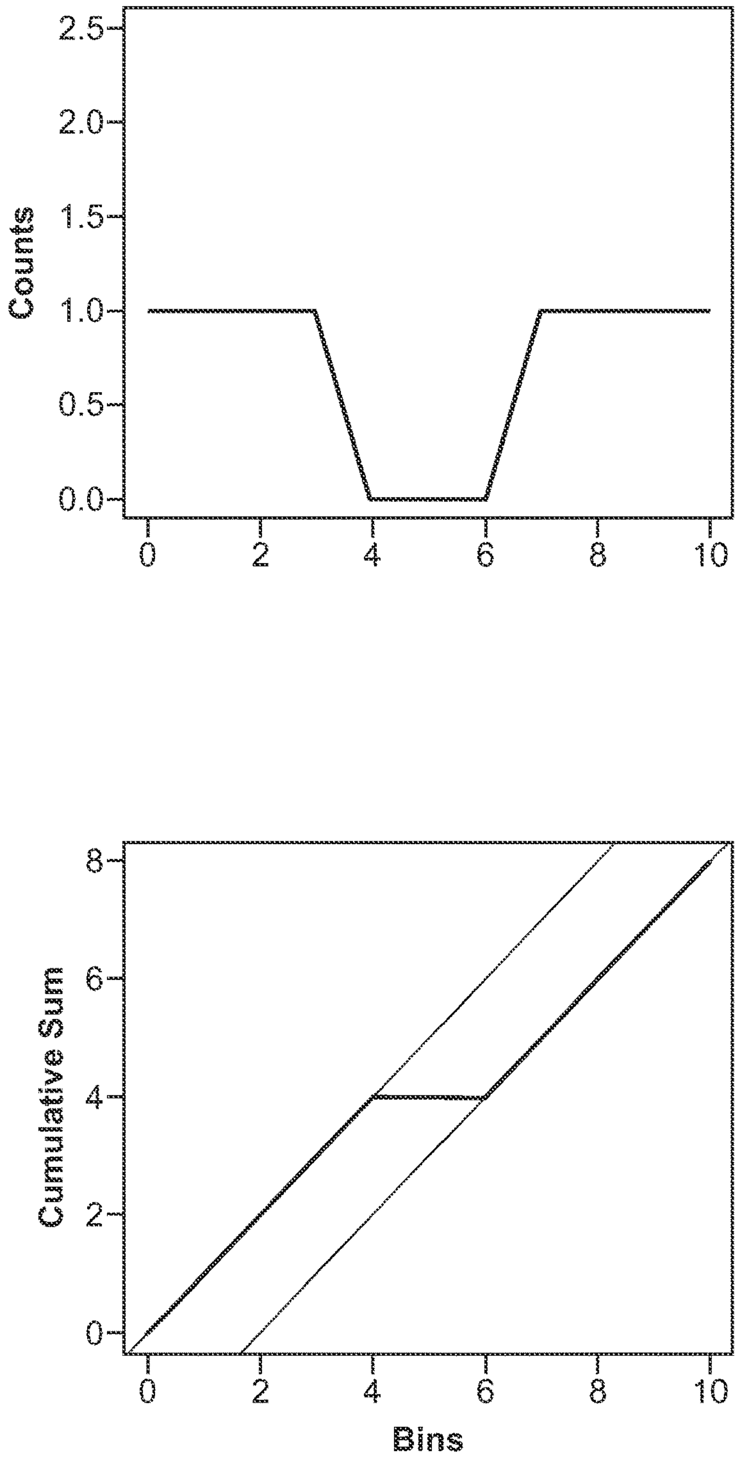

FIG. 54 graphically illustrates a hypothetical homozygous deletion, approximately 2 genomic sections wide, and its associated cumulative sum profile. The difference between the left and the right intercepts is −2.

Figure 55:
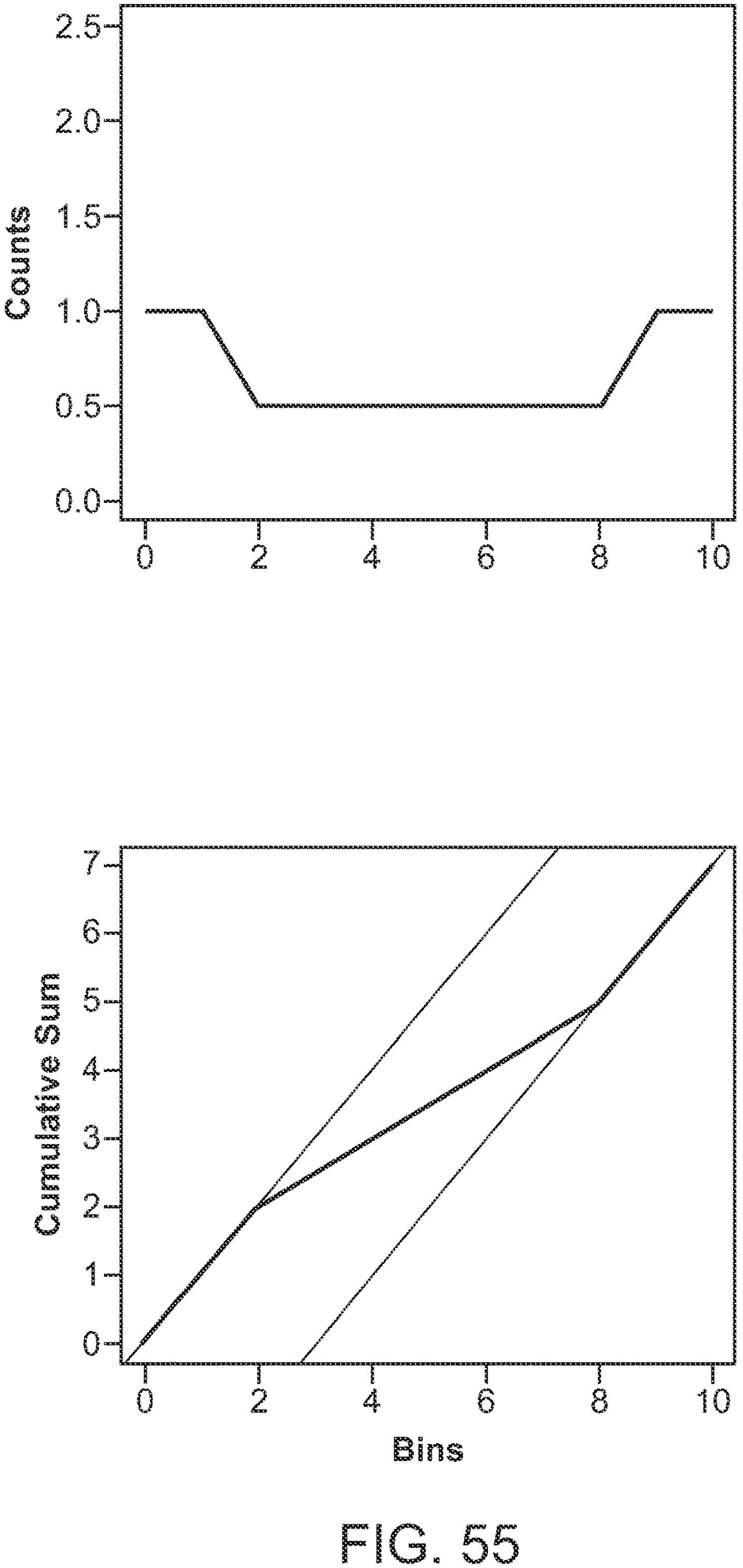

FIG. 55 graphically illustrates a hypothetical heterozygous deletion, approximately 6 genomic sections wide, and its associated cumulative sum profile. The difference between the left and the right intercepts is −3.

Figure 56:
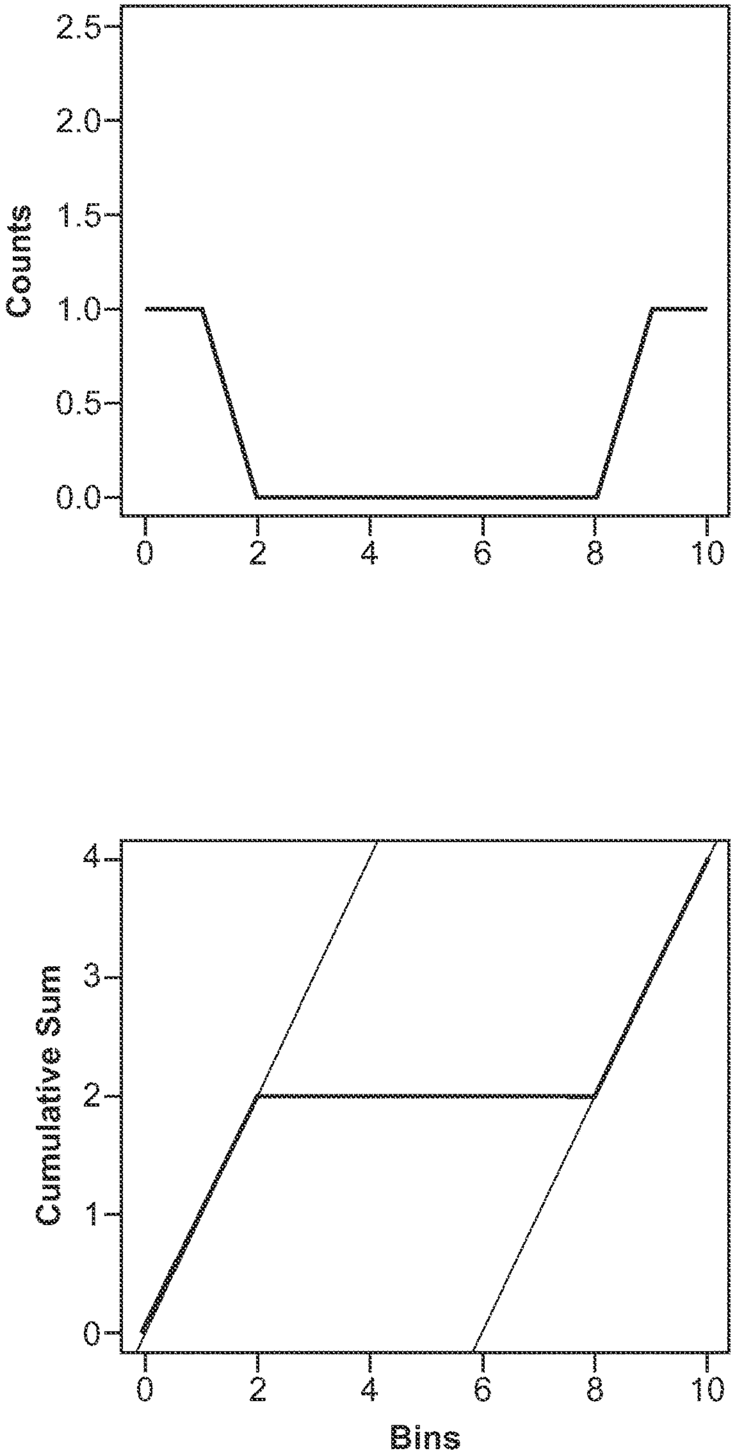

FIG. 56 graphically illustrates a hypothetical homozygous deletion, approximately 6 genomic sections wide, and its associated cumulative sum profile. The difference between the left and the right intercepts is −6.

Figure 57:
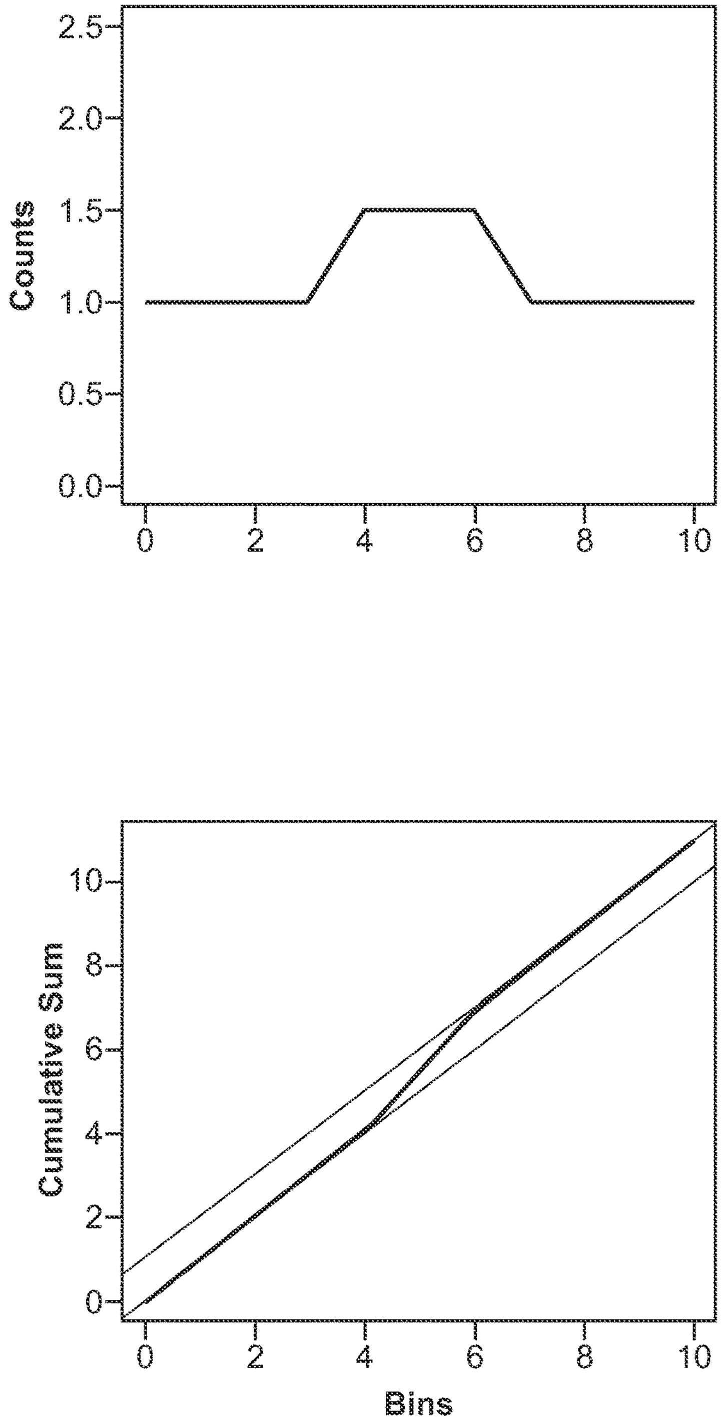

FIG. 57 graphically illustrates a hypothetical heterozygous duplication, approximately 2 genomic sections wide, and its associated cumulative sum profile. The difference between the left and the right intercepts is 1.

Figure 58:
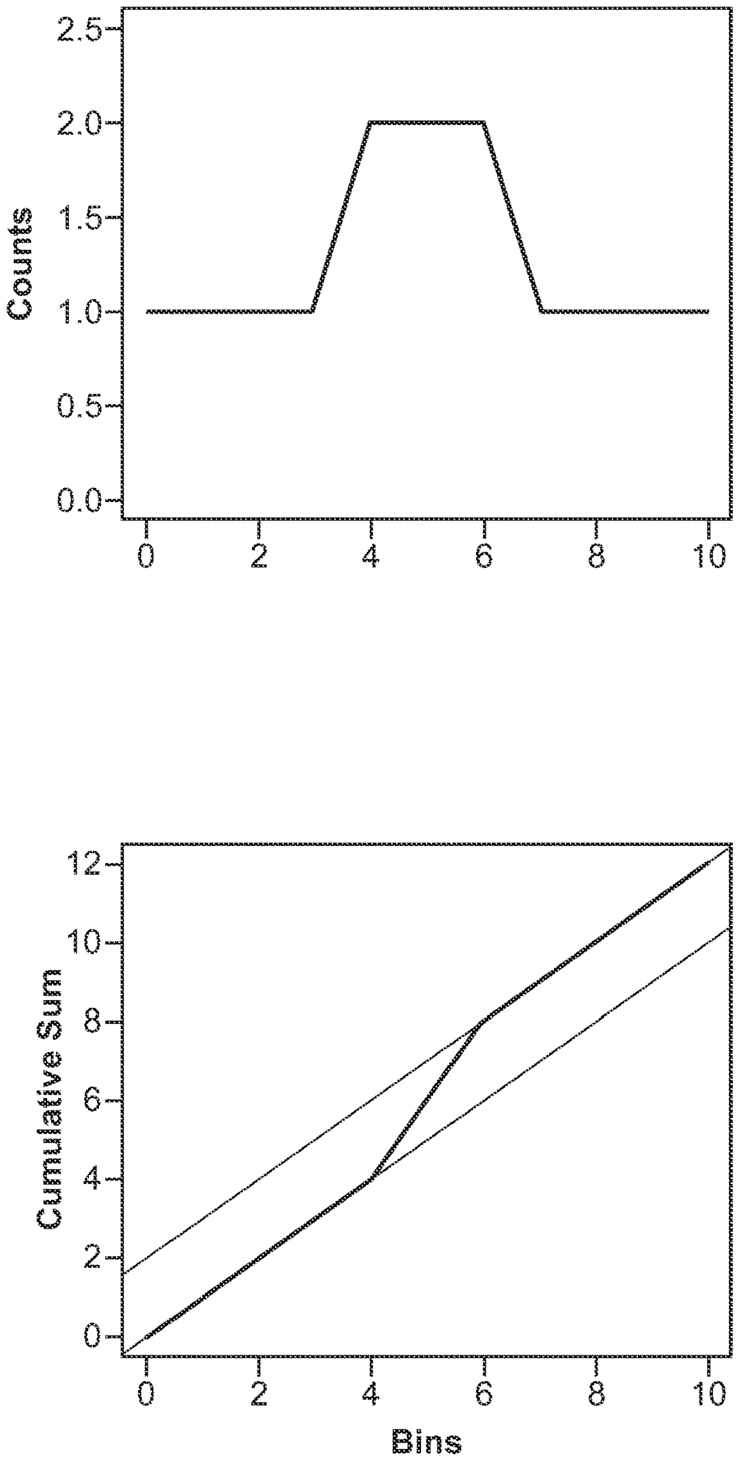

FIG. 58 graphically illustrates a hypothetical homozygous duplication, approximately 2 genomic sections wide, and its associated cumulative sum profile. The difference between the left and the right intercepts is 2.

Figure 59:
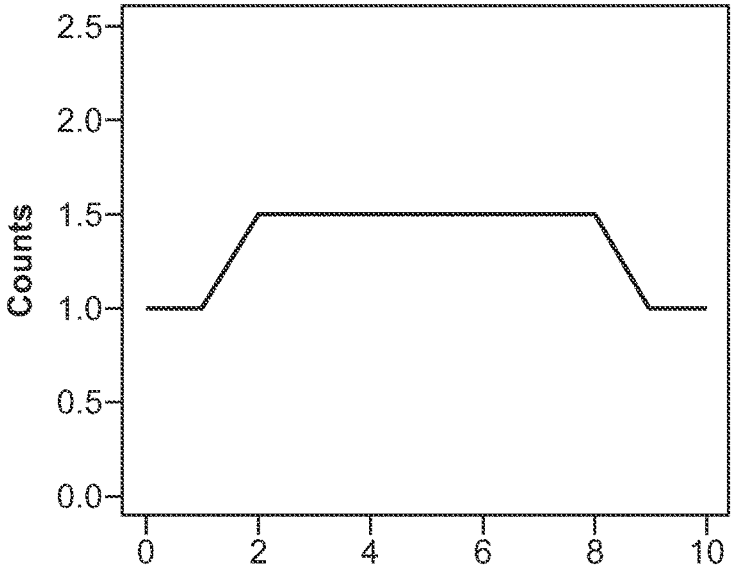
Figure 59:
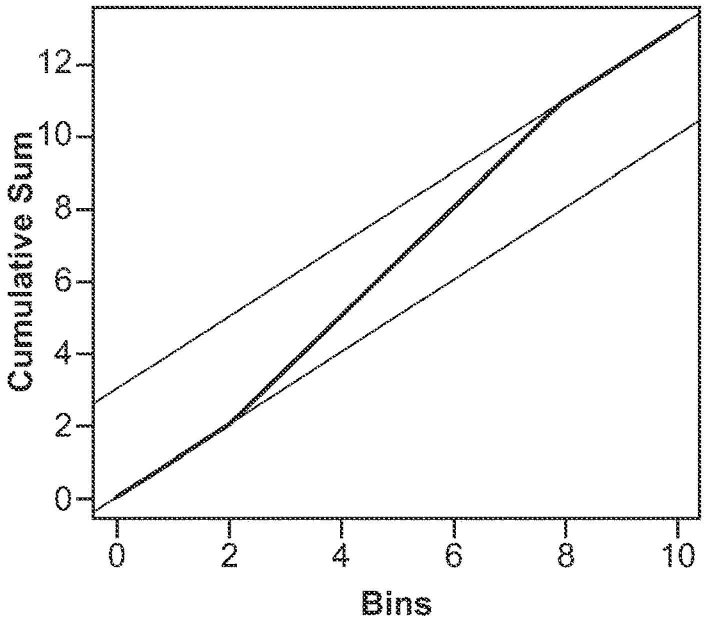

FIG. 59 graphically illustrates a hypothetical heterozygous duplication, approximately 6 genomic sections wide, and its associated cumulative sum profile. The difference between the left and the right intercepts is 3.

Figure 60:
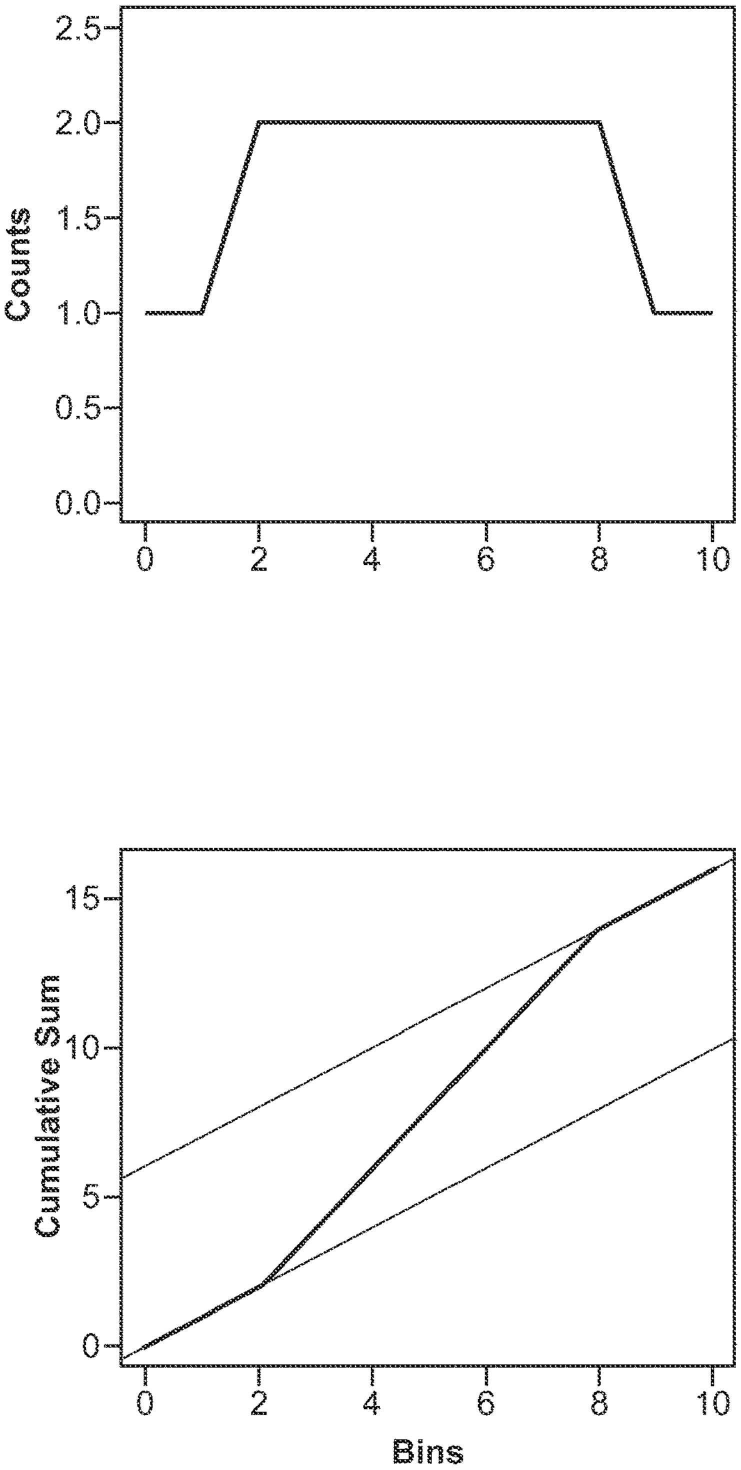
Figure 61A:
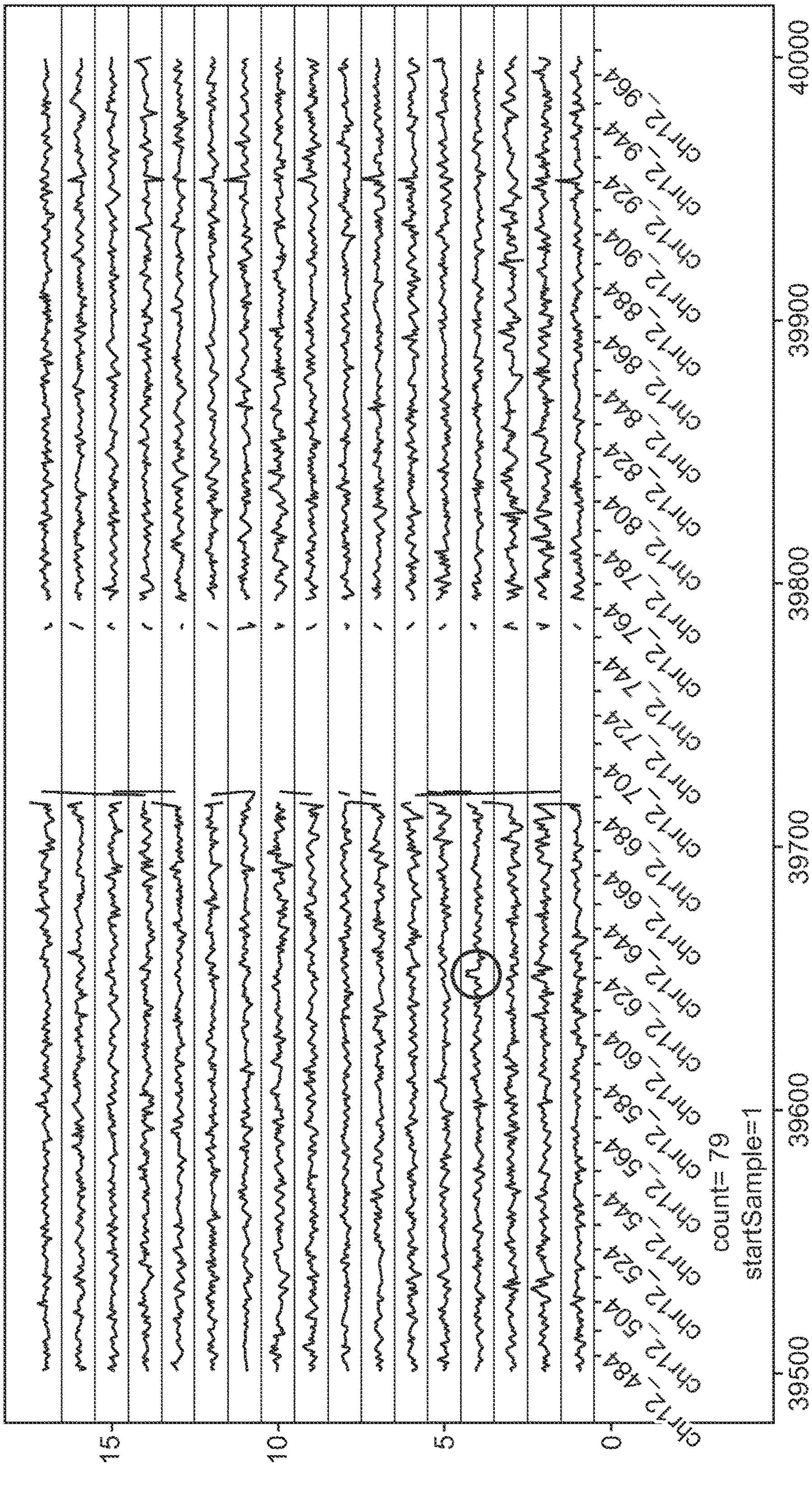
Figure 61B:
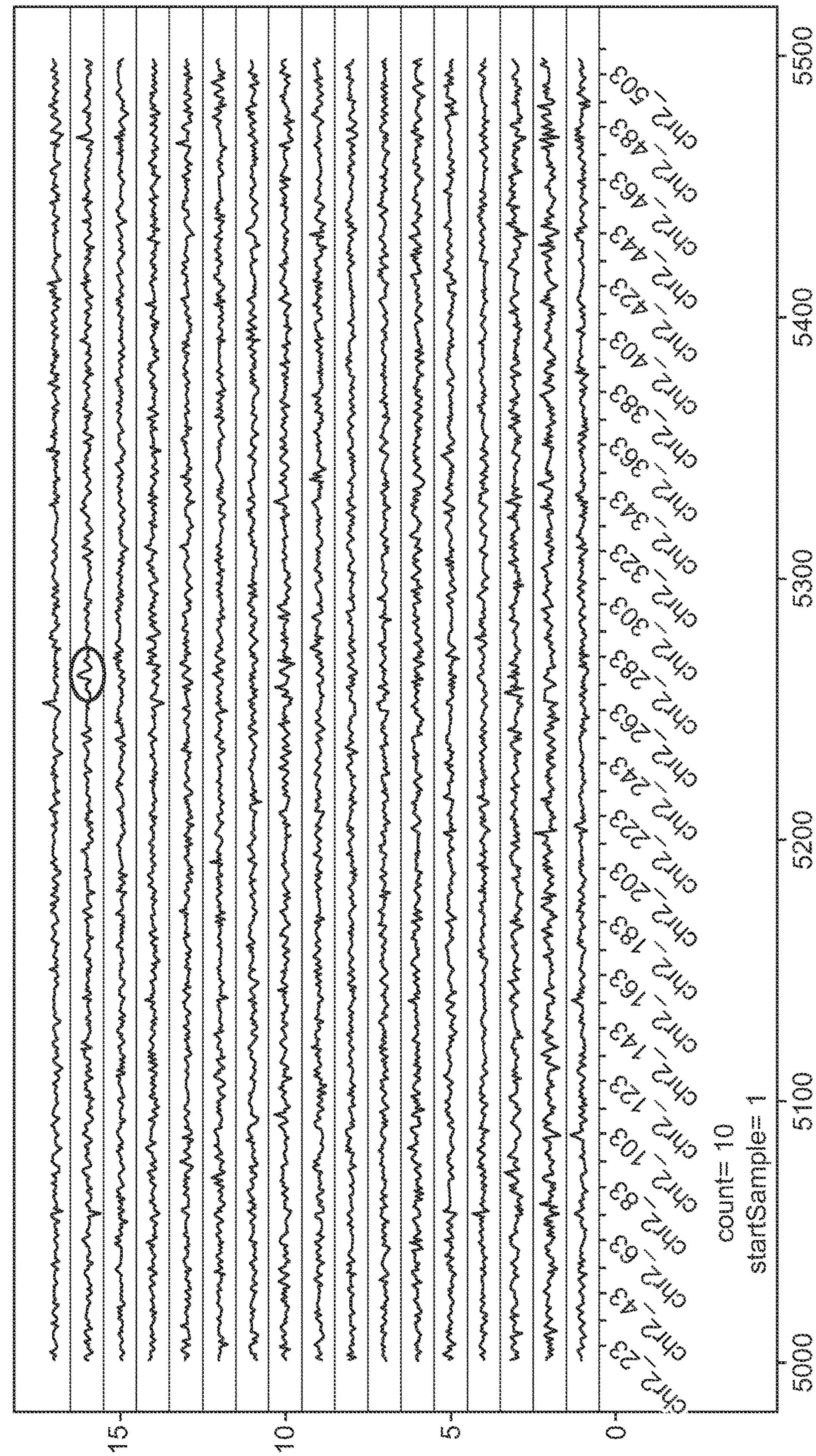
Figure 61C:
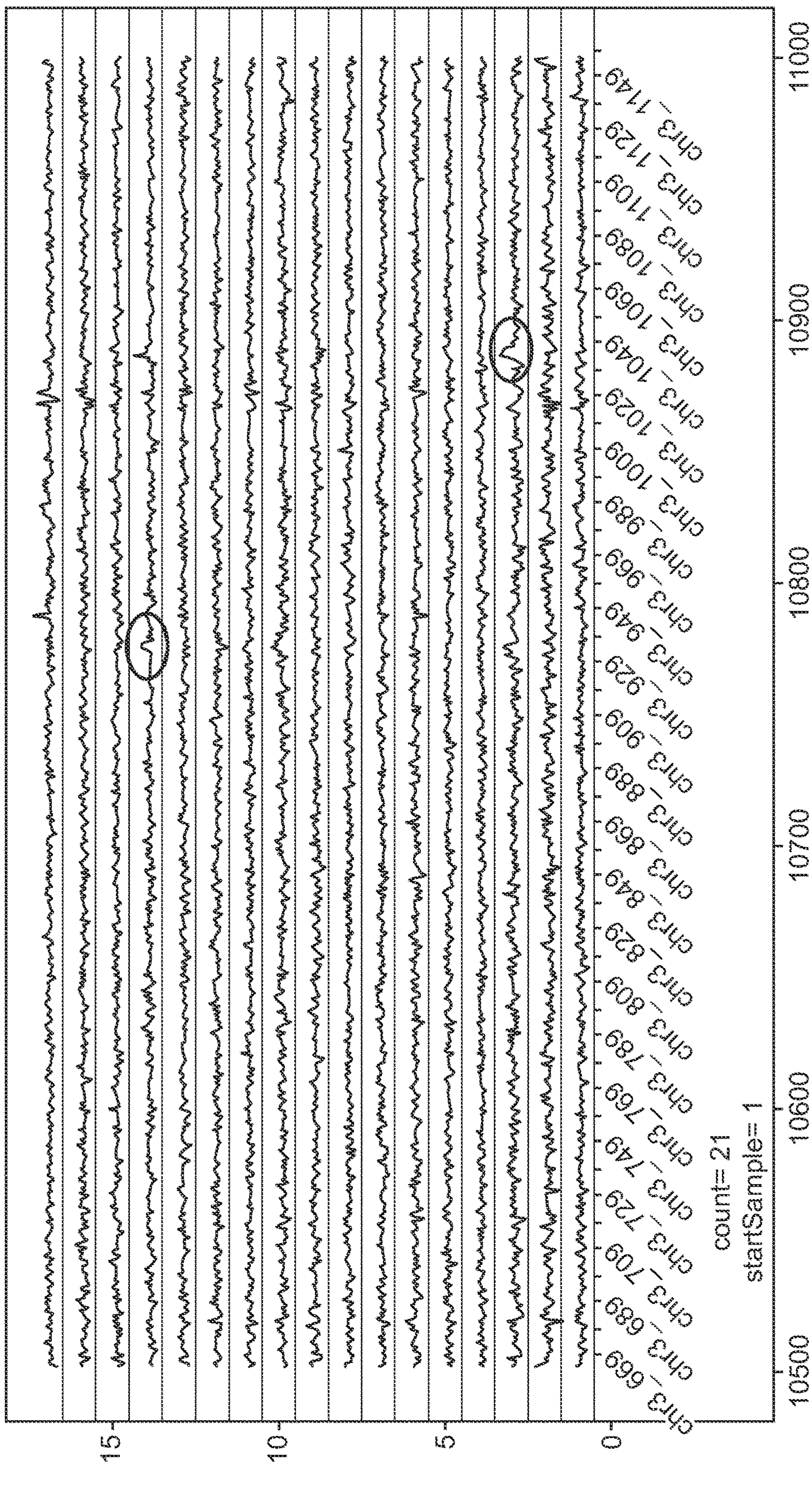
Figure 61D:
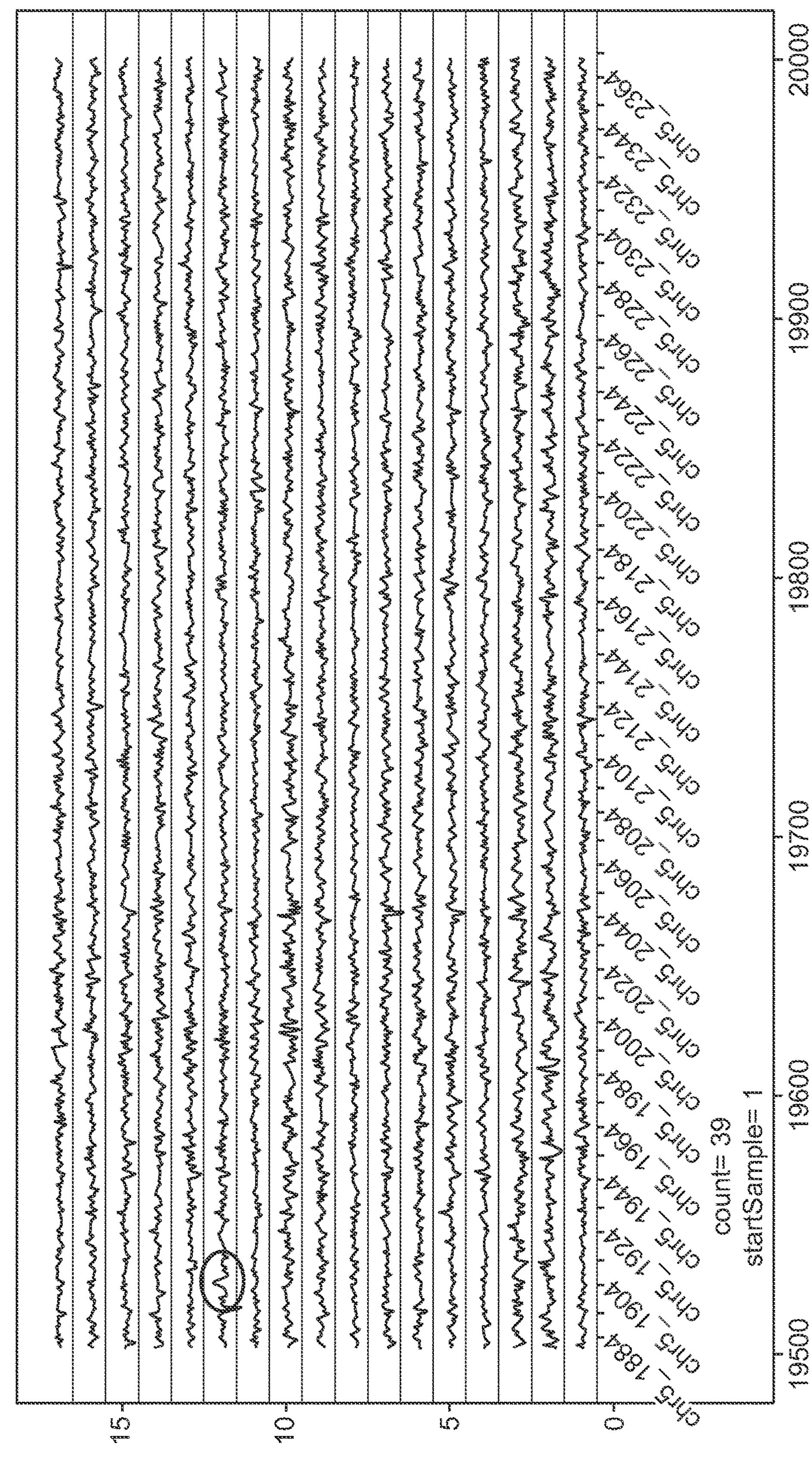
Figure 61E:
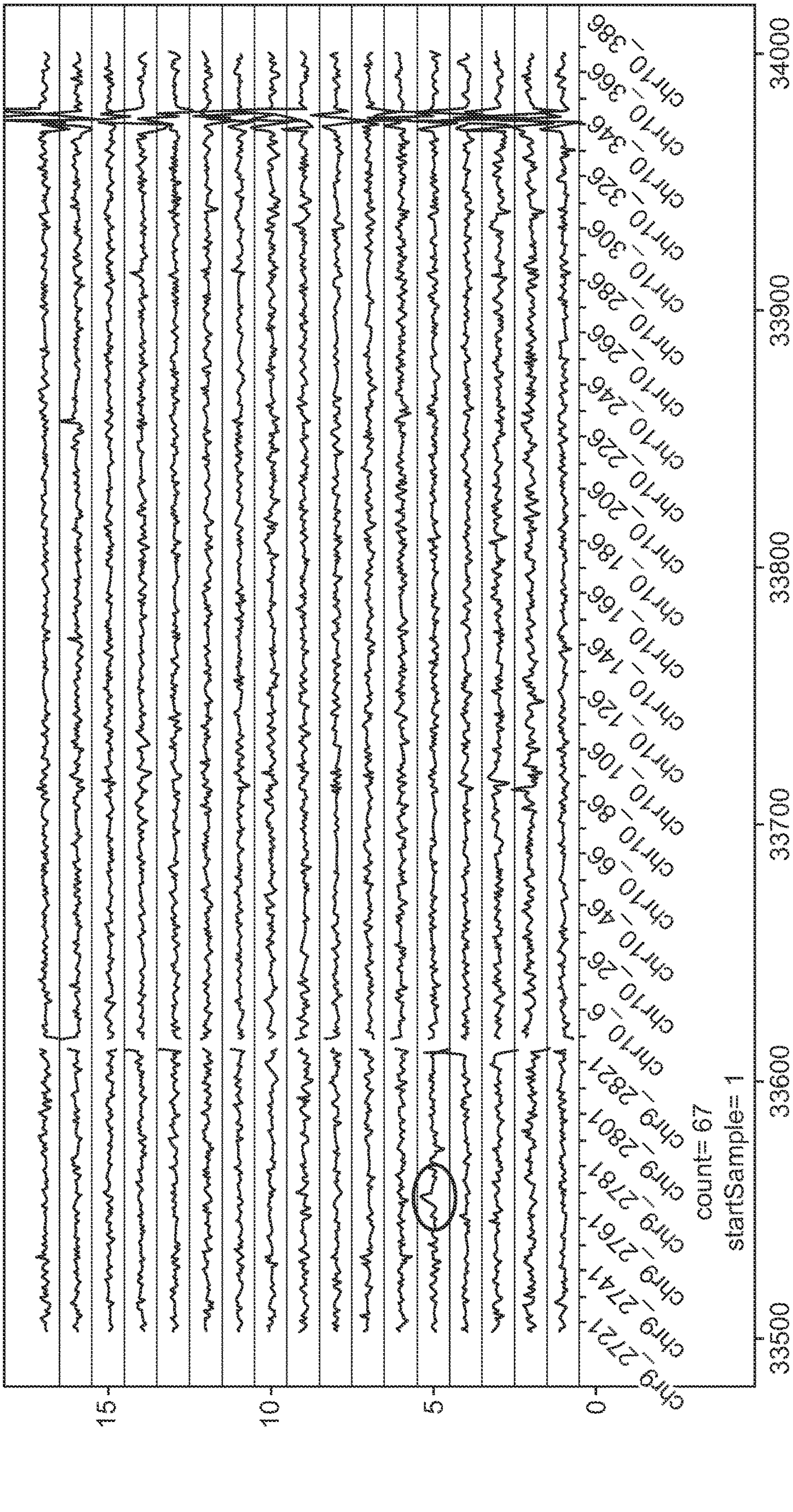
Figure 61F:
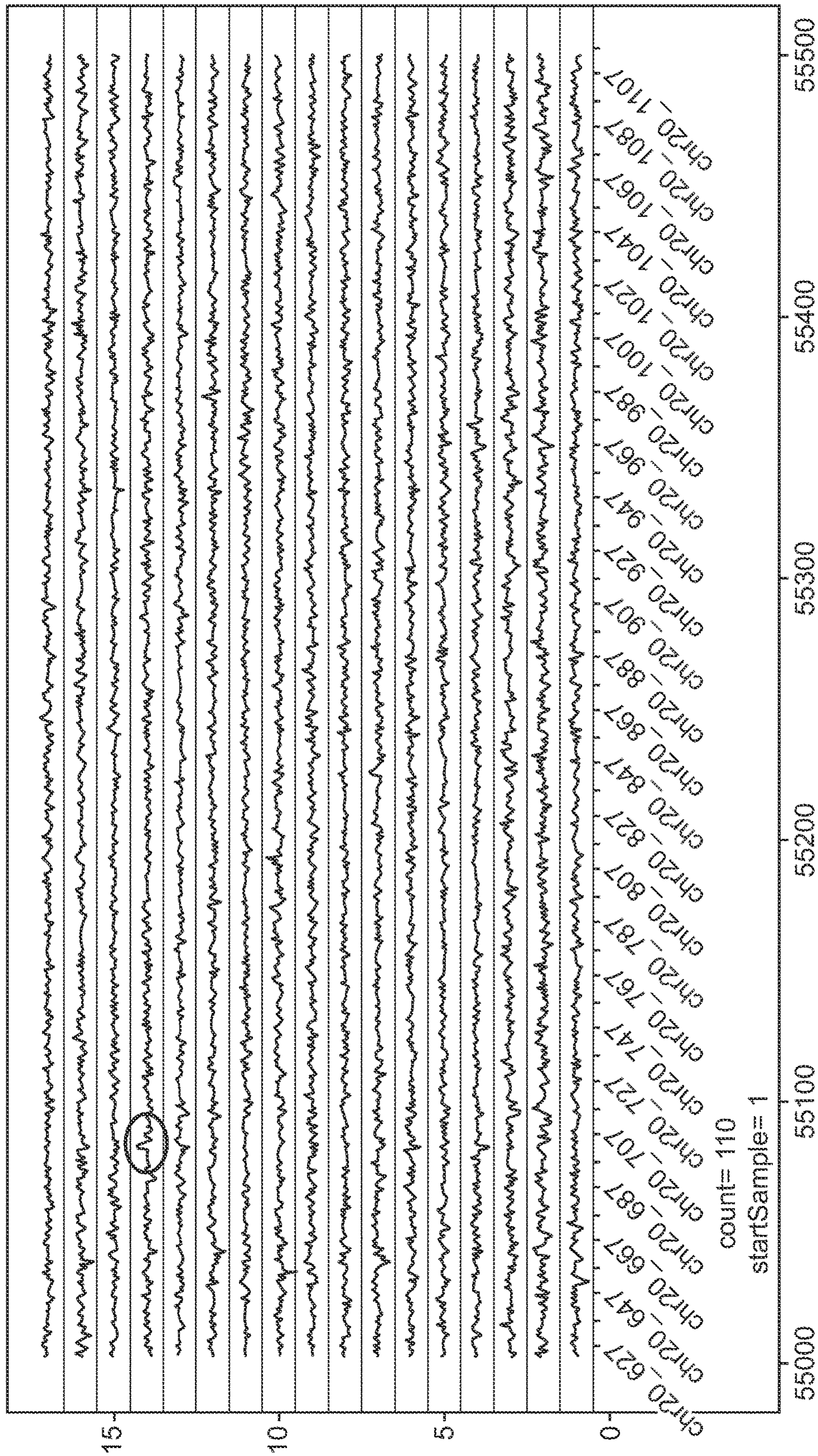

FIG. 60 graphically illustrates a hypothetical homozygous duplication, approximately 6 genomic sections wide, and its associated cumulative sum profile. The difference between the left and the right intercepts is 6.

FIG. 61A-F graphically illustrate candidates for fetal heterozygous duplications in data obtained from women and infant clinical studies with high fetal fraction values (40-50%). To rule out the possibility that the aberrations originate from the mother and not the fetus, independent maternal profiles were used. The profile elevation in the affected regions is approximately 1.25, in accordance with the fetal fraction estimates.

FIG. 62 to FIG. 111 are described in Example 4 herein.

Figure 112A:
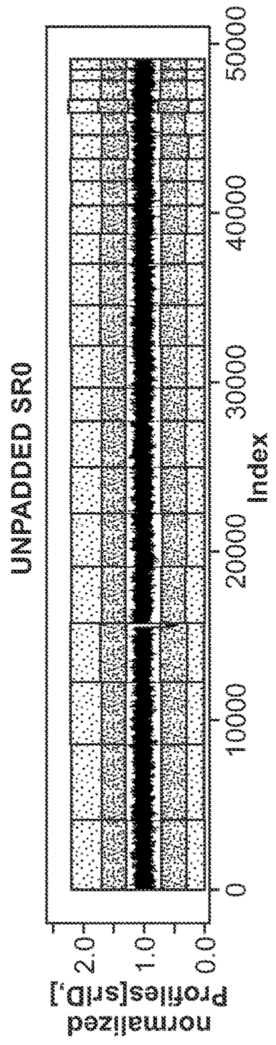
Figure 112B:
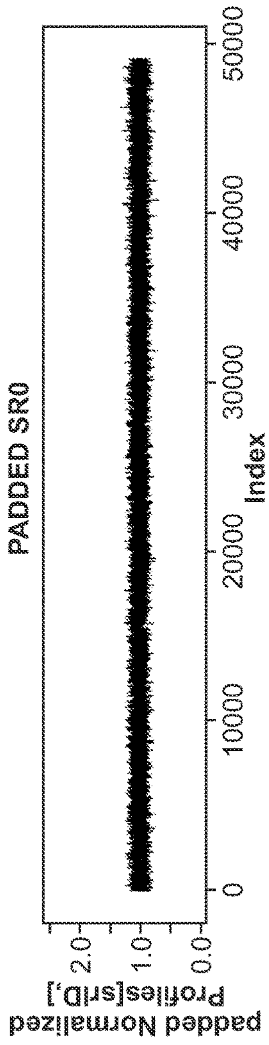
Figure 112C:
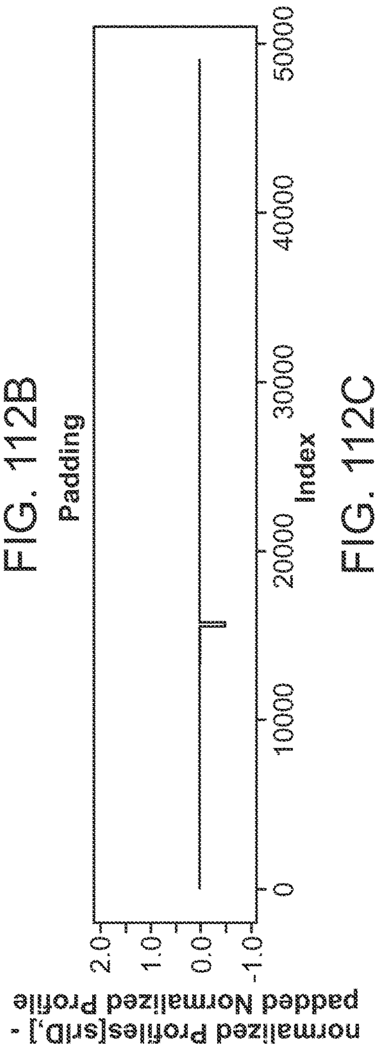

FIG. 112A-C illustrates padding of a normalized autosomal profile for a euploid WI sample. FIG. 112A is an example of an unpadded profile. FIG. 112B is an example of a padded profile. FIG. 112C is an example of a padding correction (e.g., an adjusted profile, an adjusted elevation).

Figures 113A, 113B, 113C:
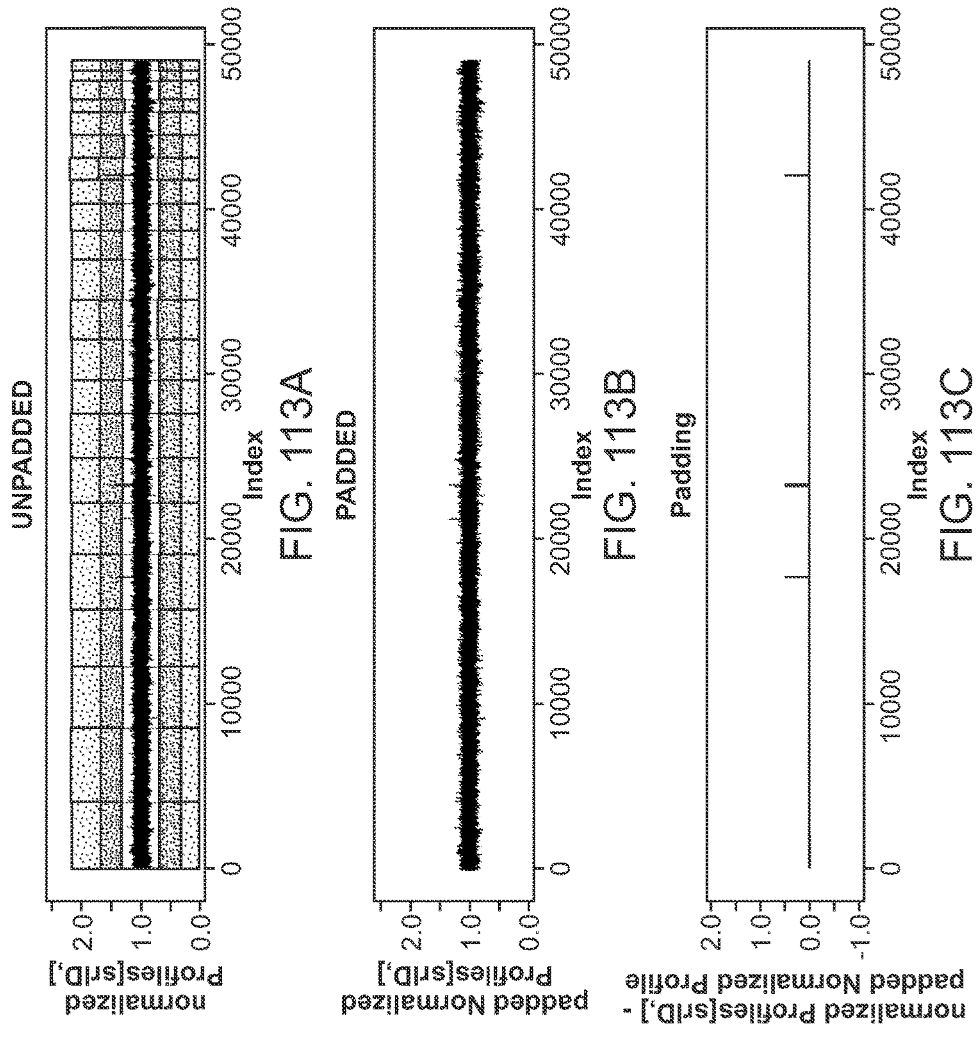

FIG. 113A-C illustrates padding of a normalized autosomal profile for a euploid WI sample. FIG. 113A is an example of an unpadded profile. FIG. 113B is an example of a padded profile. FIG. 113C is an example of a padding correction (e.g., an adjusted profile, an adjusted elevation).

Figure 114A:
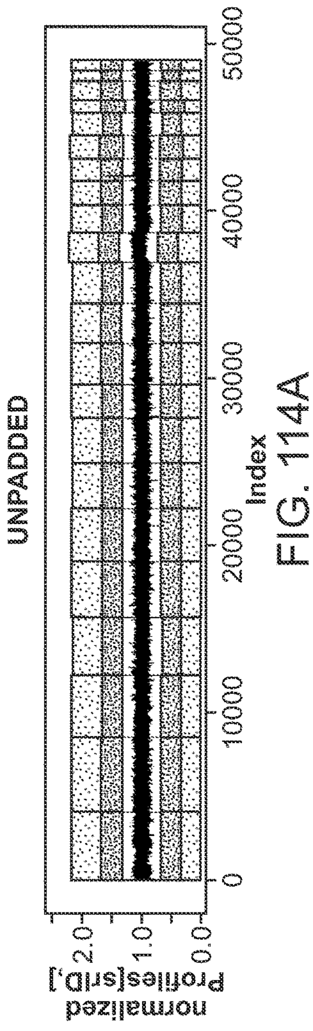
Figure 114B:
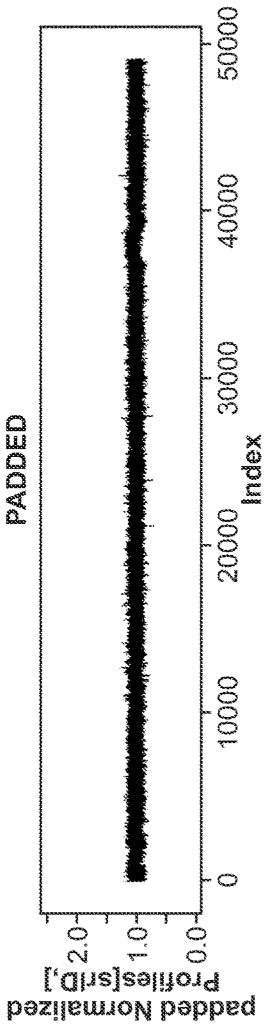
Figure 114C:
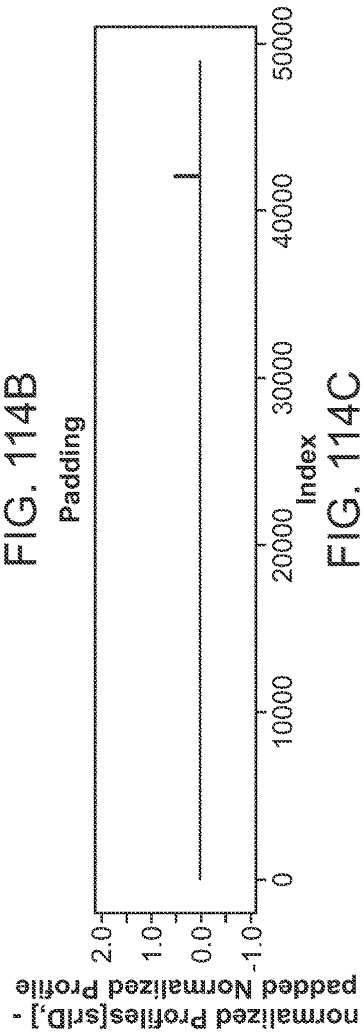

FIG. 114A-C illustrates padding of a normalized autosomal profile for a trisomy 13 WI sample. FIG. 114A is an example of an unpadded profile. FIG. 114B is an example of a padded profile. FIG. 114C is an example of a padding correction (e.g., an adjusted profile, an adjusted elevation).

Figure 115A:
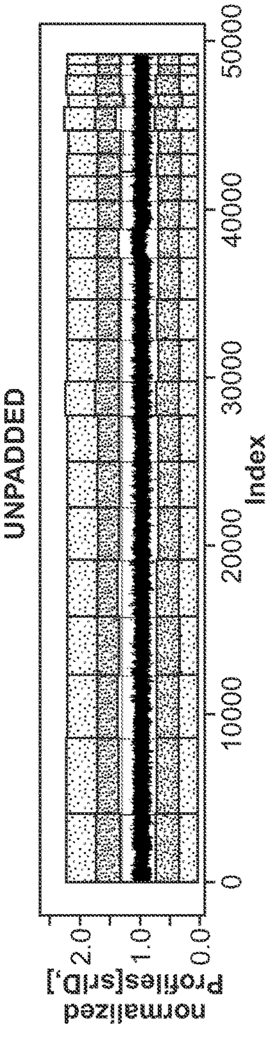
Figure 115B:
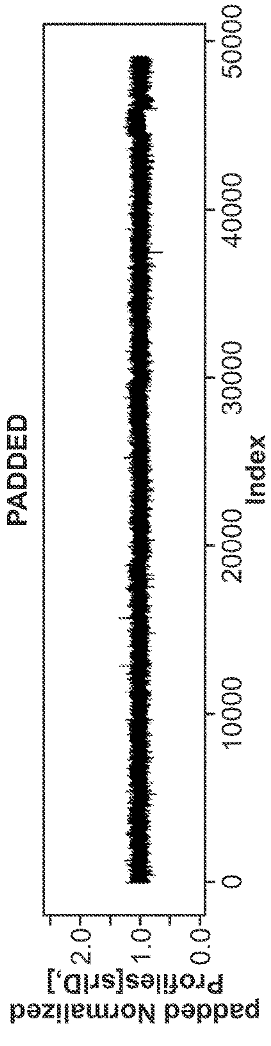
Figure 115C:
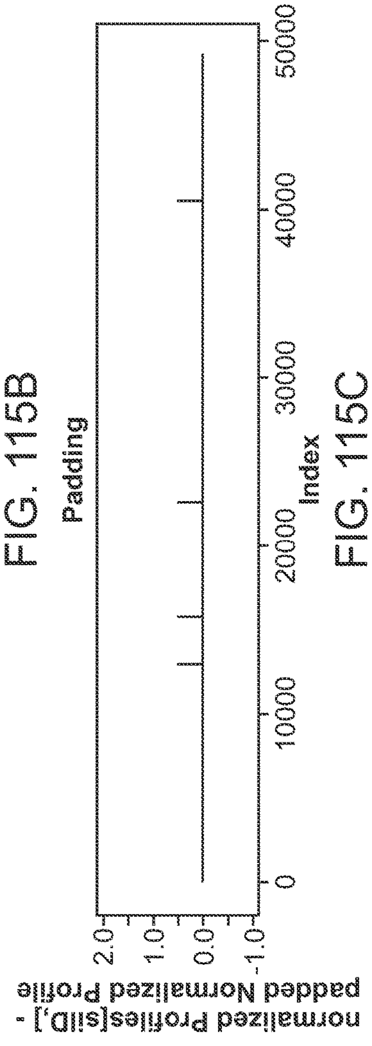
Figure 116:
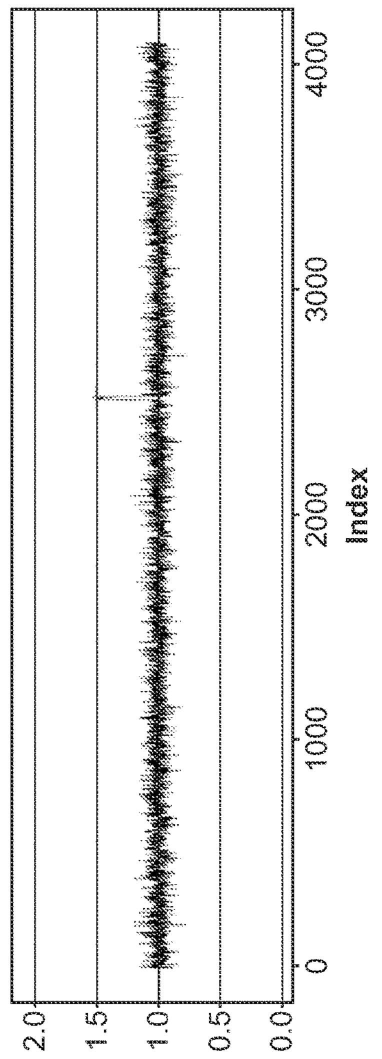
Figure 117:
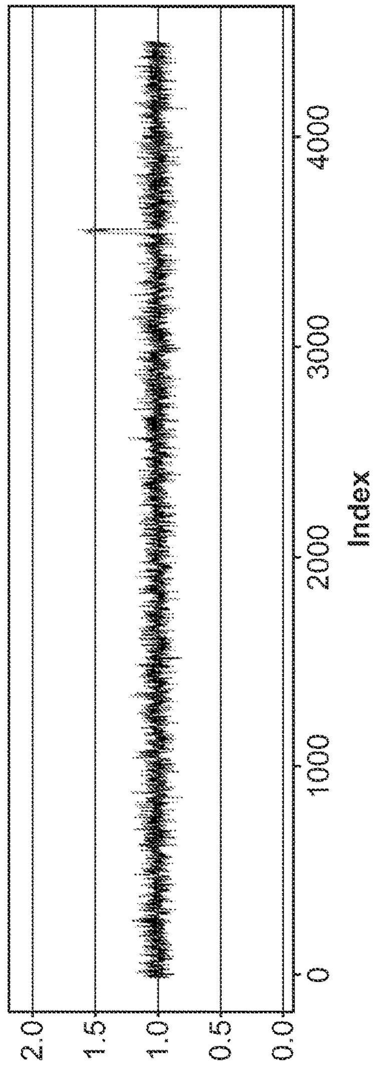
Figure 118:
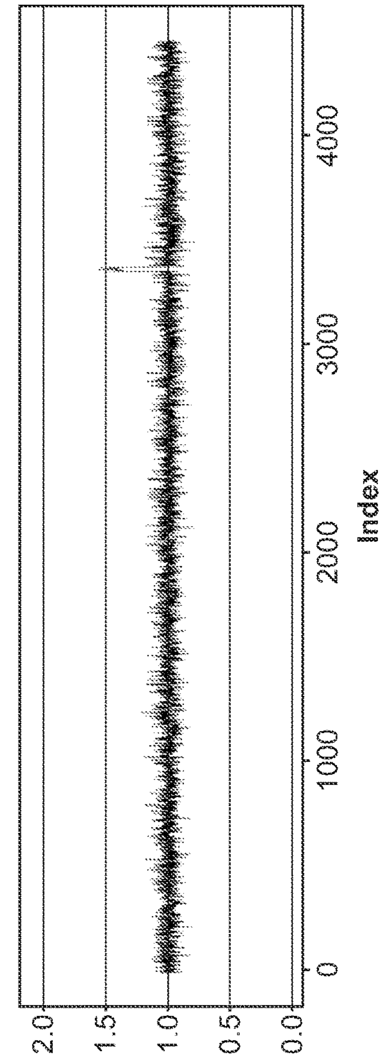
Figure 119:
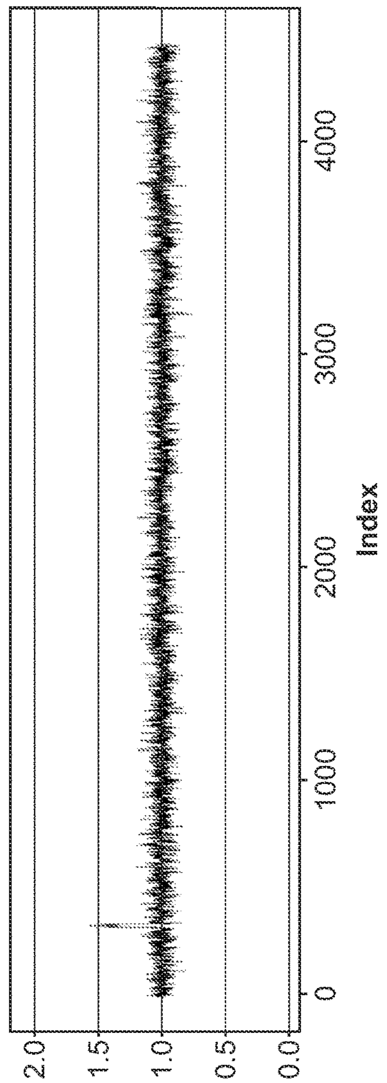
Figure 120:
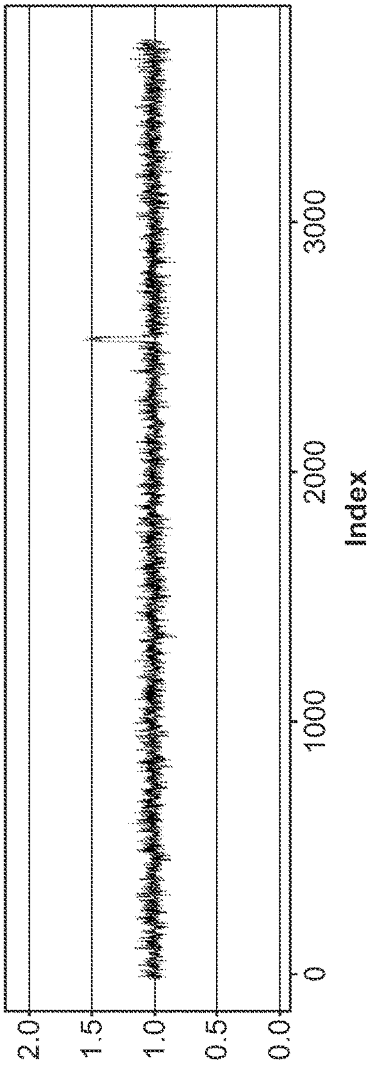
Figure 121:
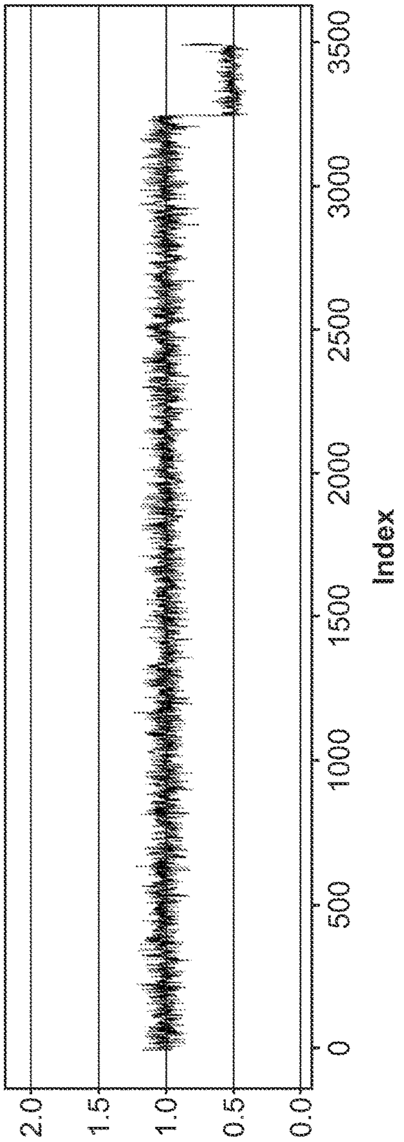
Figure 122:
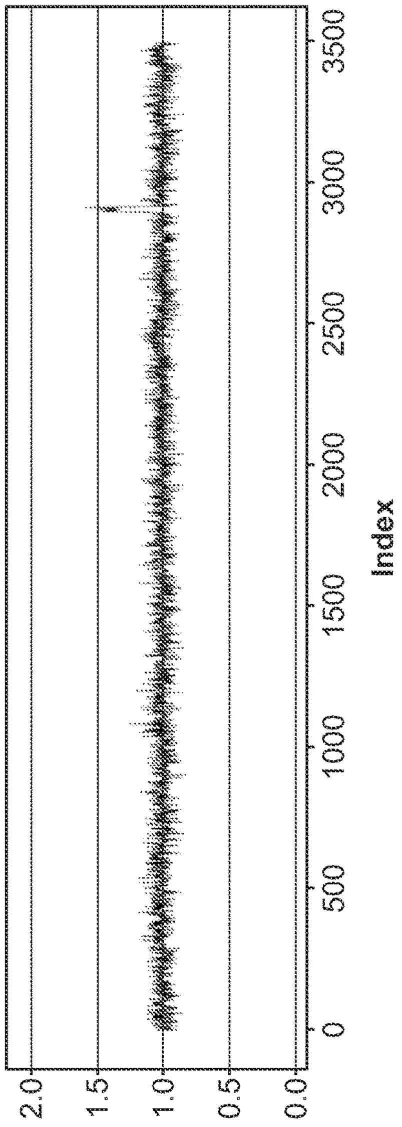
Figure 123:
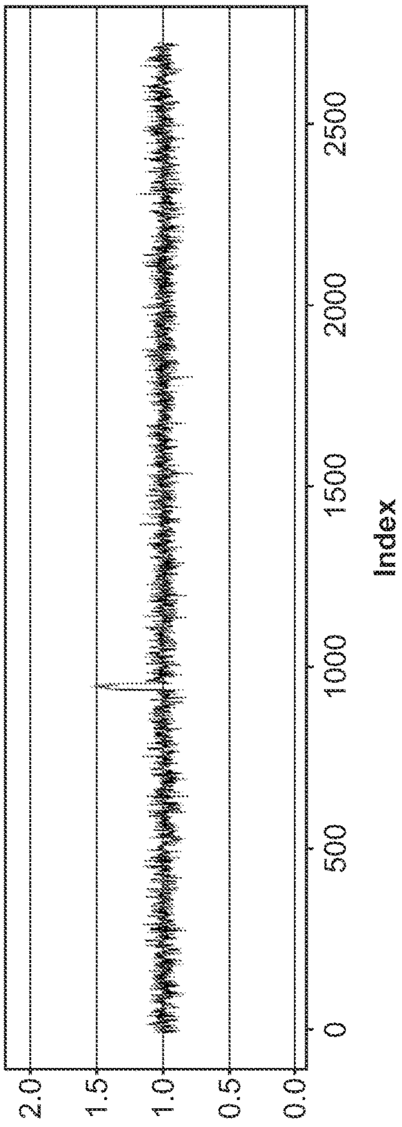
Figure 124:
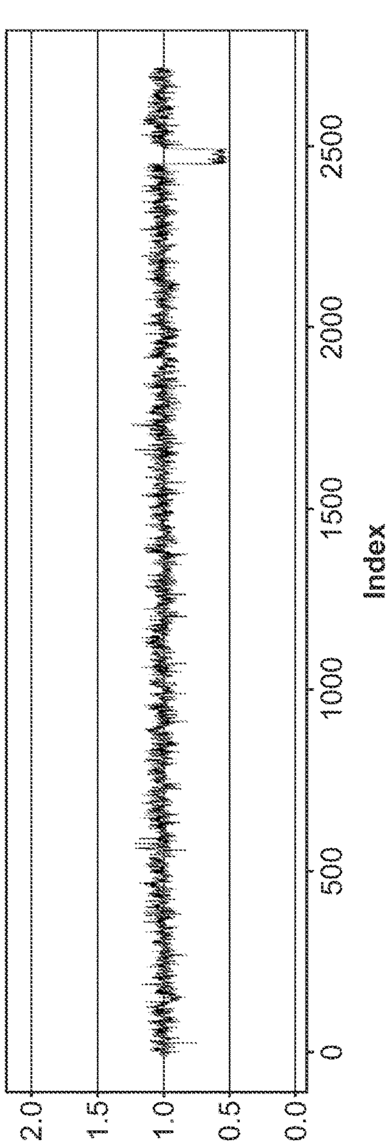
Figure 125:
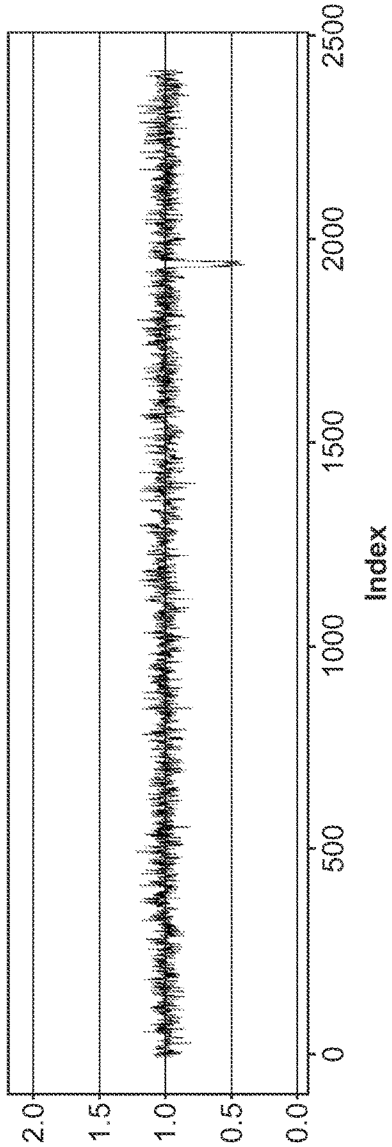
Figure 126:
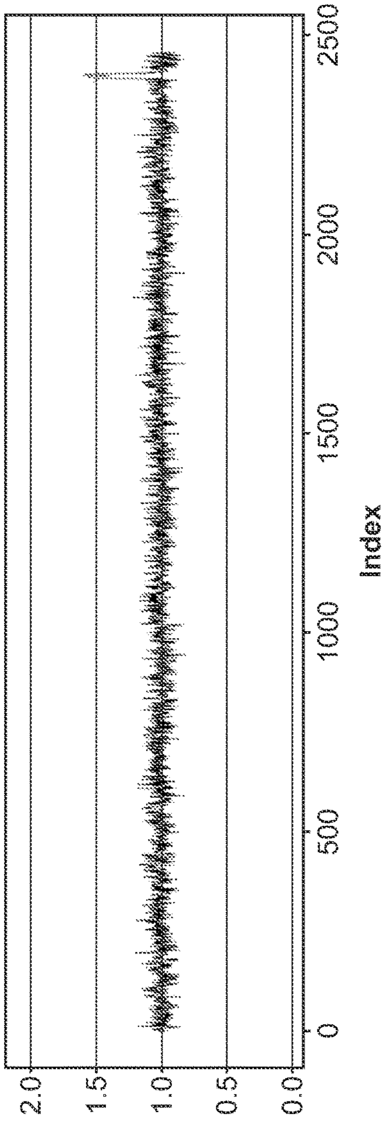
Figure 127:
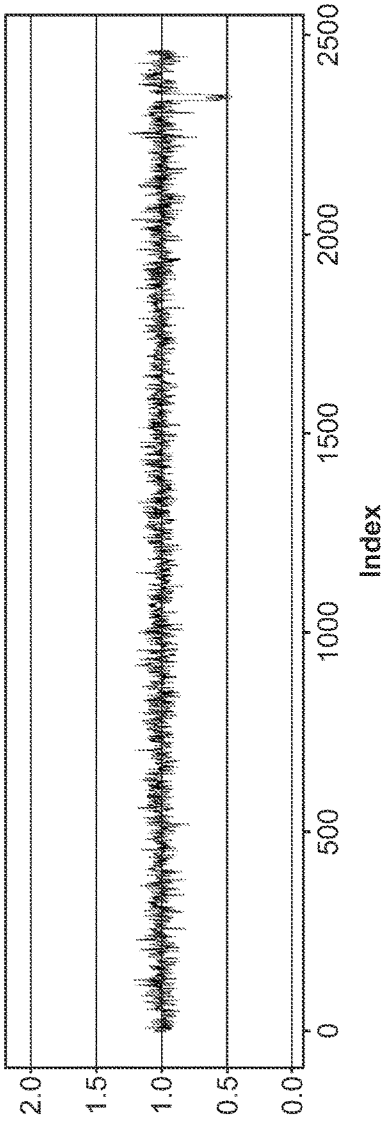
Figure 128:
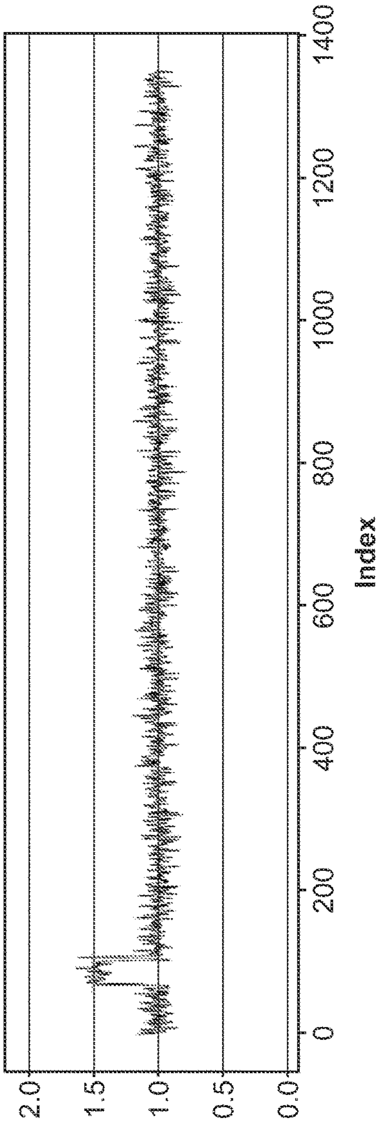
Figure 129:
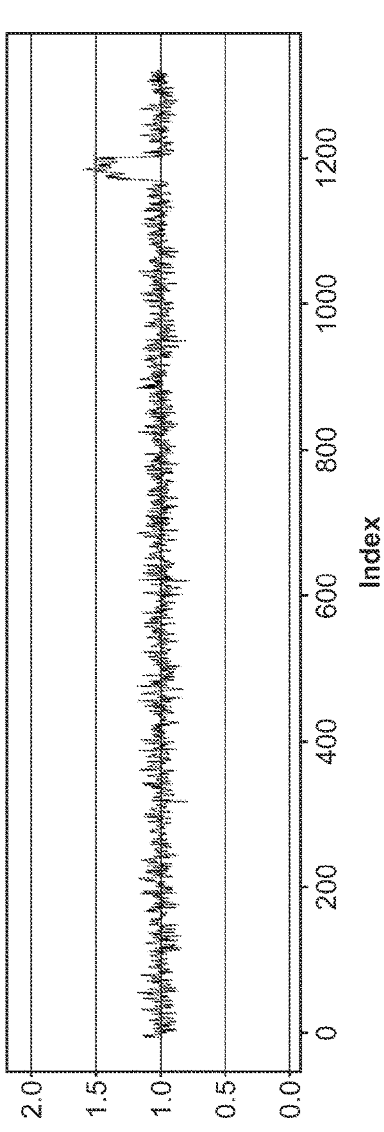
Figure 130:
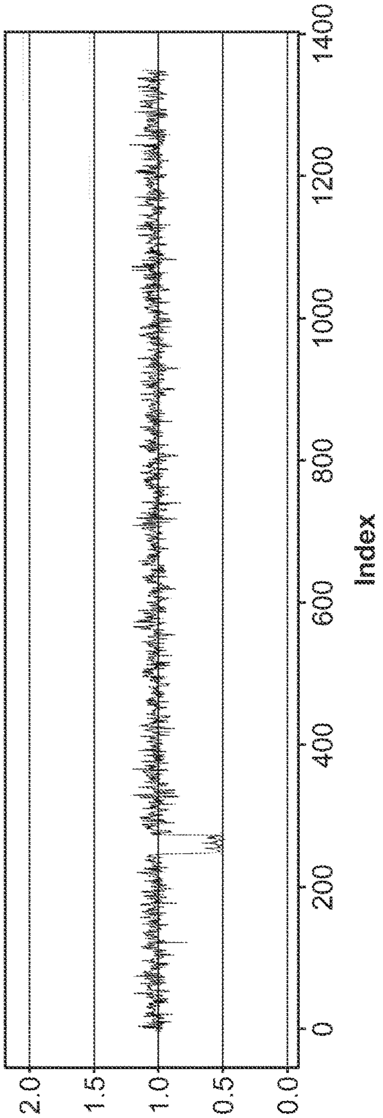
Figure 131:
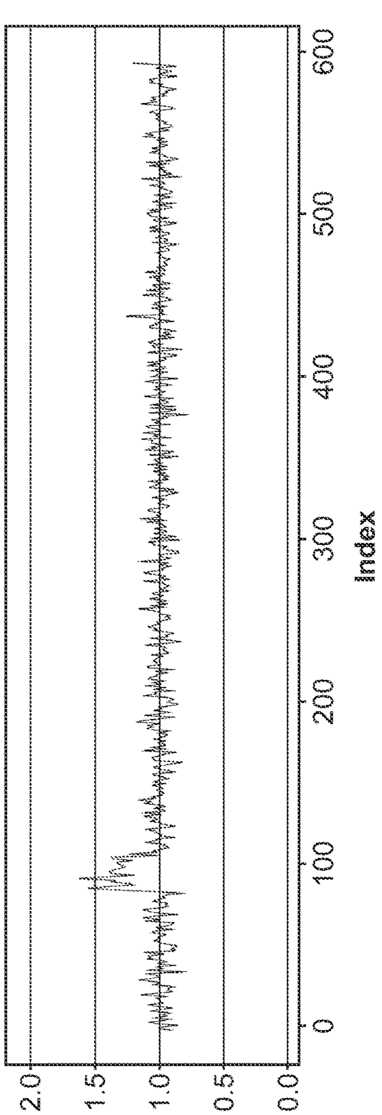

FIG. 115A-C illustrates padding of a normalized autosomal profile for a trisomy 18 WI sample. FIG. 115A is an example of an unpadded profile. FIG. 115B is an example of a padded profile. FIG. 115C is an example of a padding correction (e.g., an adjusted profile, an adjusted elevation).

FIGS. 116-120, 122, 123, 126, 128, 129 and 131 show a maternal duplication within a profile.

FIGS. 121, 124, 125, 127 and 130 show a maternal deletion within a profile.

Figure 132:
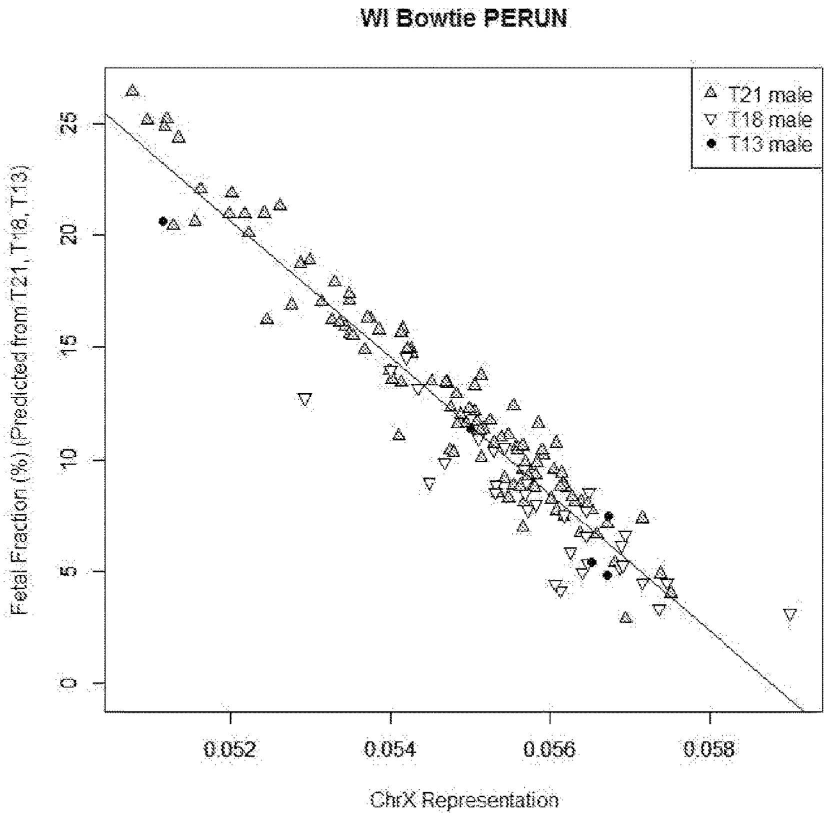

FIG. 132 shows a linear relationship between (i) fetal fraction (%) determined from a pregnant female bearing a male fetus comprising a trisomy 21, trisomy 18 or trisomy 13 chromosome according to equation AB (Y axis) and (ii) an experimental X chromosome representation (e.g., an MCR for ChrX) determined from a pregnant female bearing a male fetus comprising a trisomy 21, trisomy 18 or trisomy 13 chromosome (X axis). The relationship is described according to equation AD.

Figure 133:
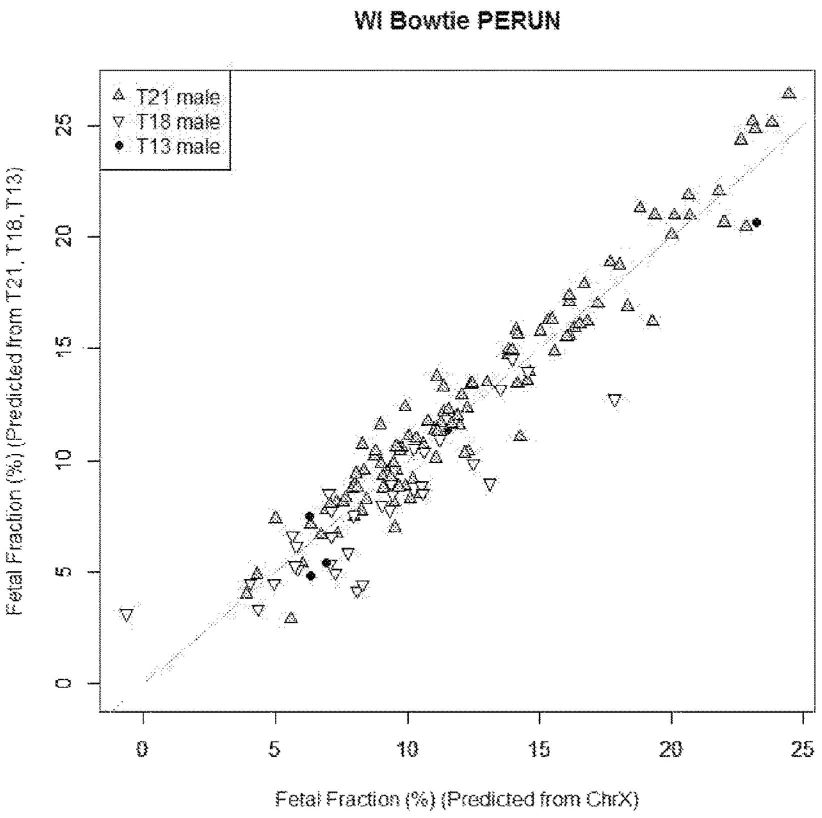

FIG. 133 shows a linear relationship between (i) fetal fraction (%) determined from a pregnant female bearing a male fetus comprising a trisomy 21, trisomy 18 or trisomy 13 chromosome according to equation AB (Y axis) and (ii) a fetal fraction determined from an MCR for ChrX as per equation AC(X axis).

Figure 134:
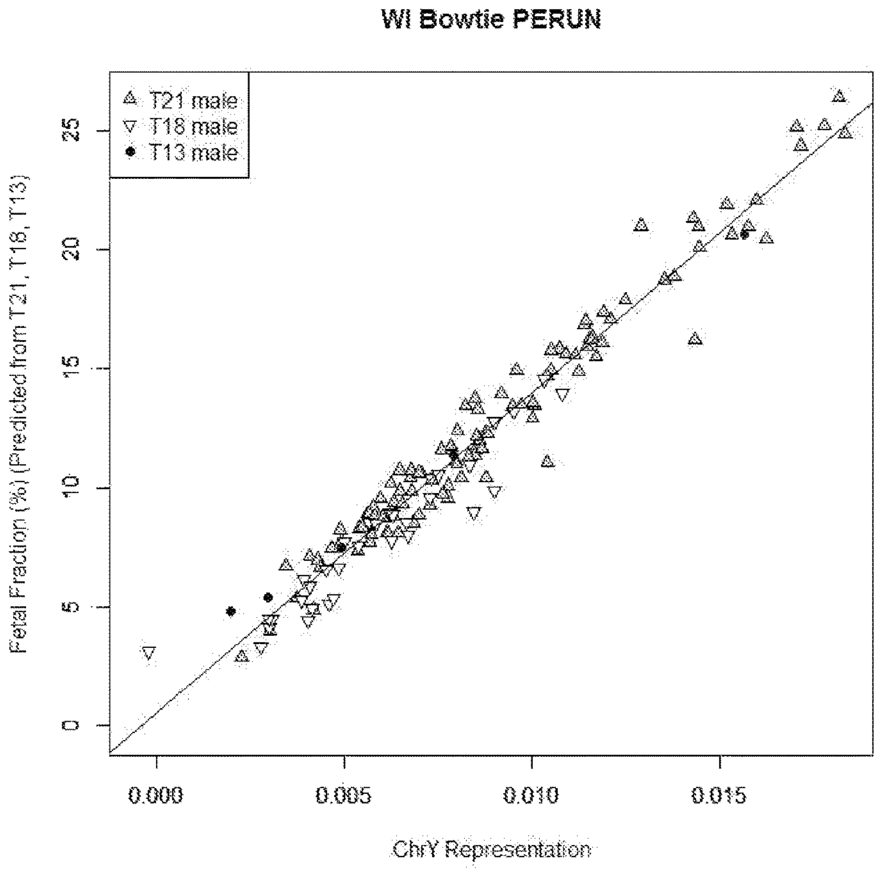

FIG. 134 shows a linear relationship between (i) fetal fraction (%) determined from a pregnant female bearing a male fetus comprising a trisomy 21, trisomy 18 or trisomy 13 chromosome according to equation AB (Y axis) and (ii) an experimental Y chromosome representation (e.g., an MCR for ChrY) determined from a pregnant female bearing a male fetus comprising a trisomy 21, trisomy 18 or trisomy 13 chromosome (X axis). The relationship is described according to equation AE.

Figure 135:
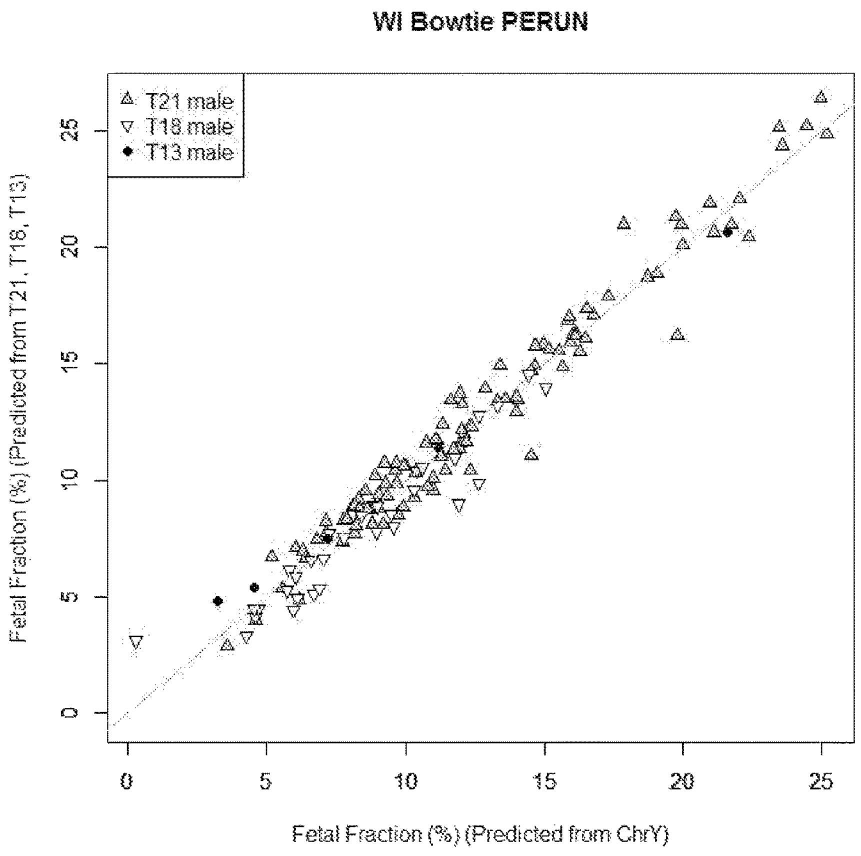

FIG. 135 shows a linear relationship between (i) fetal fraction (%) determined from a pregnant female bearing a male fetus comprising a trisomy 21, trisomy 18 or trisomy 13 chromosome according to equation AB (Y axis) and (ii) a fetal fraction determined from an MCR for ChrY (X axis).

Figure 136:
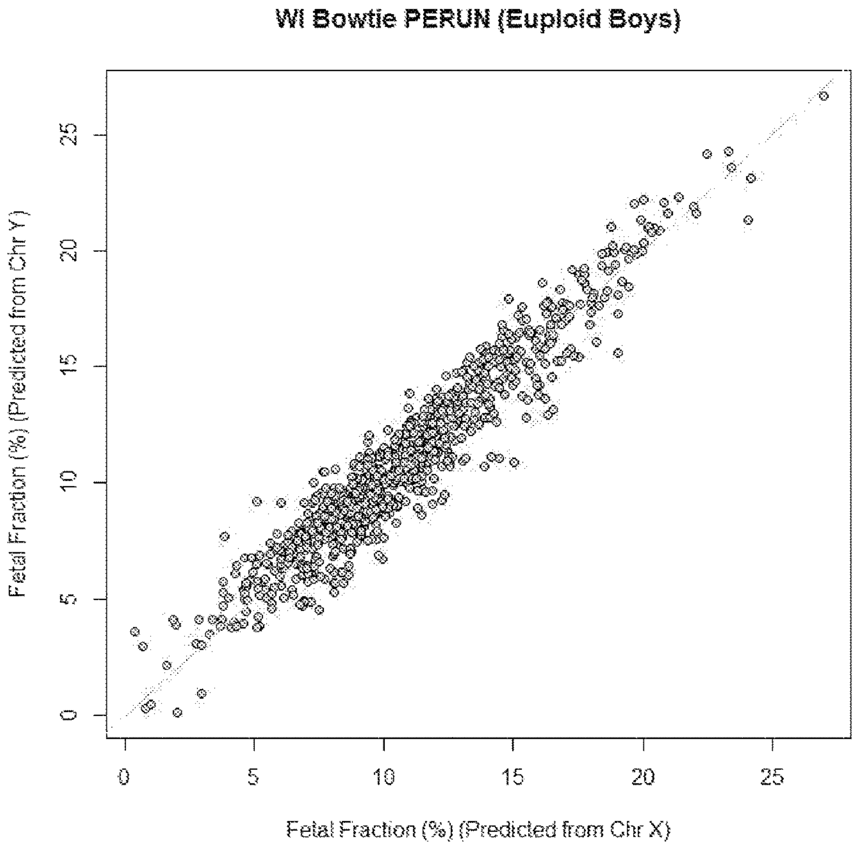

FIG. 136 shows a linear relationship between (i) fetal fraction (%) determined from a pregnant female bearing a male fetus predicted from chromosome Y (Y axis) and (ii) fetal fraction (%) determined from a pregnant female bearing a male fetus predicted from chromosome X (X axis). The figure shows results obtained on euploid male pregnancies.

Figure 137:
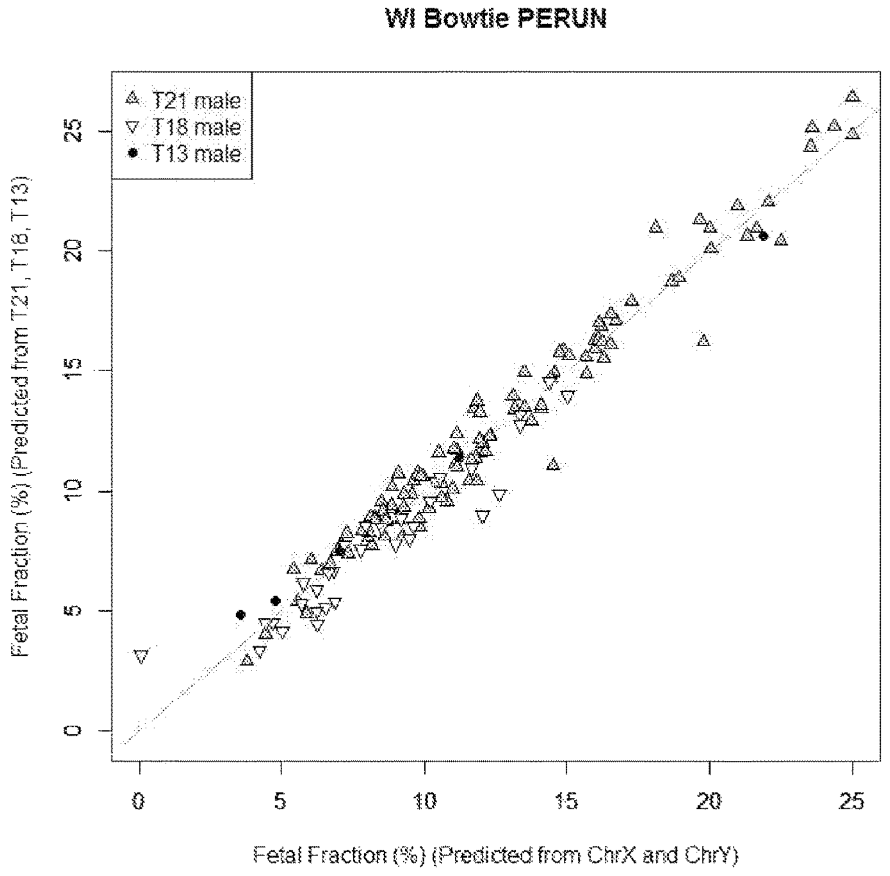

FIG. 137 shows a linear relationship between (i) fetal fraction (%) determined from a pregnant female bearing a male fetus comprising a trisomy 21, trisomy 18 or trisomy 13 chromosome according to equation AB (Y axis) and (ii) fetal fraction (%) determined for a pregnant female bearing a male fetus according to equation AF (x axis) using both ChrX and ChrY measured representations.

Figure 138:
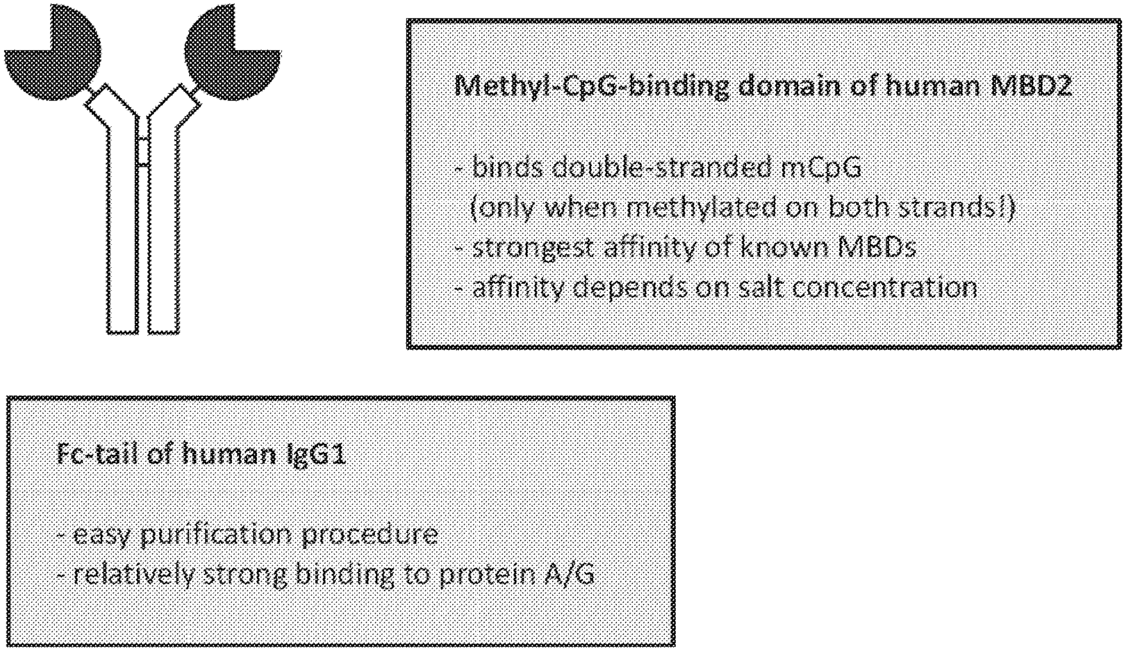

FIG. 138 shows the design of the recombinant MBD-Fc protein used to separate differentially methylated DNA.

Figure 139:
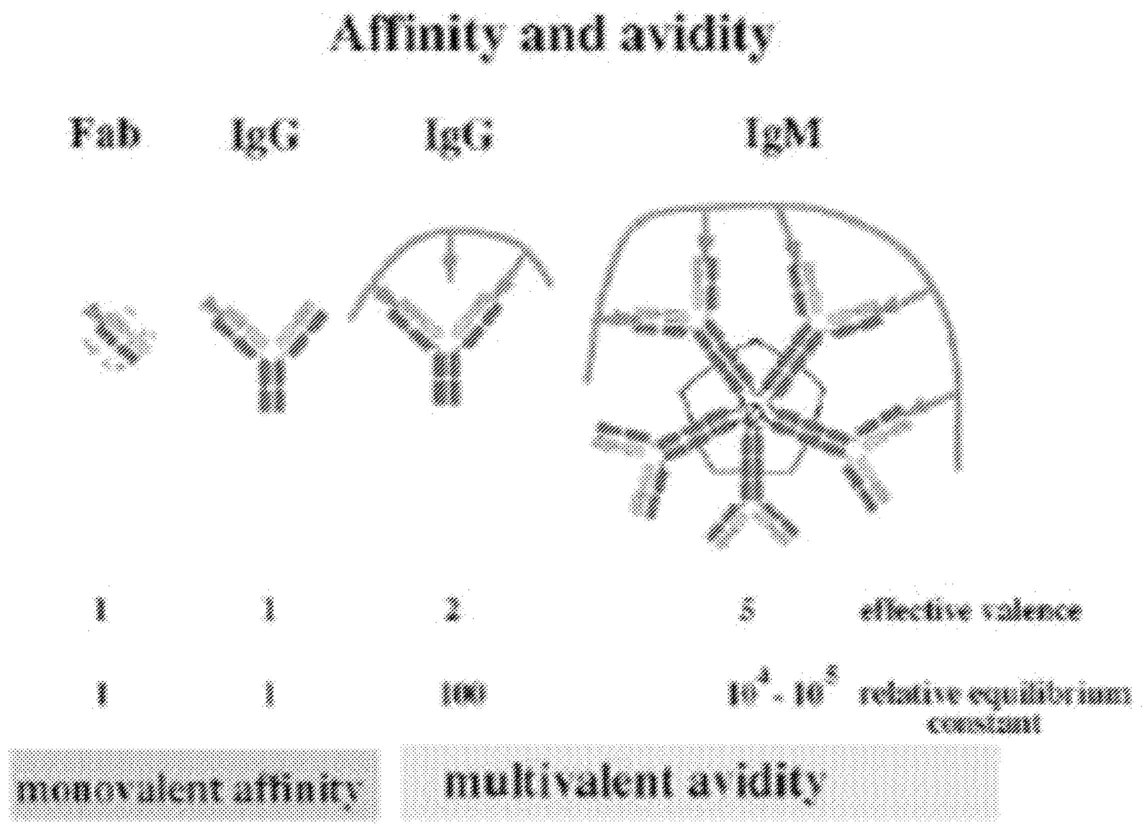

FIG. 139 shows the methyl-CpG-binding, antibody-like protein has a high affinity and high avidity to its "antigen", which is preferably DNA that is methylated at CpG dinucleotides.

Figure 140:
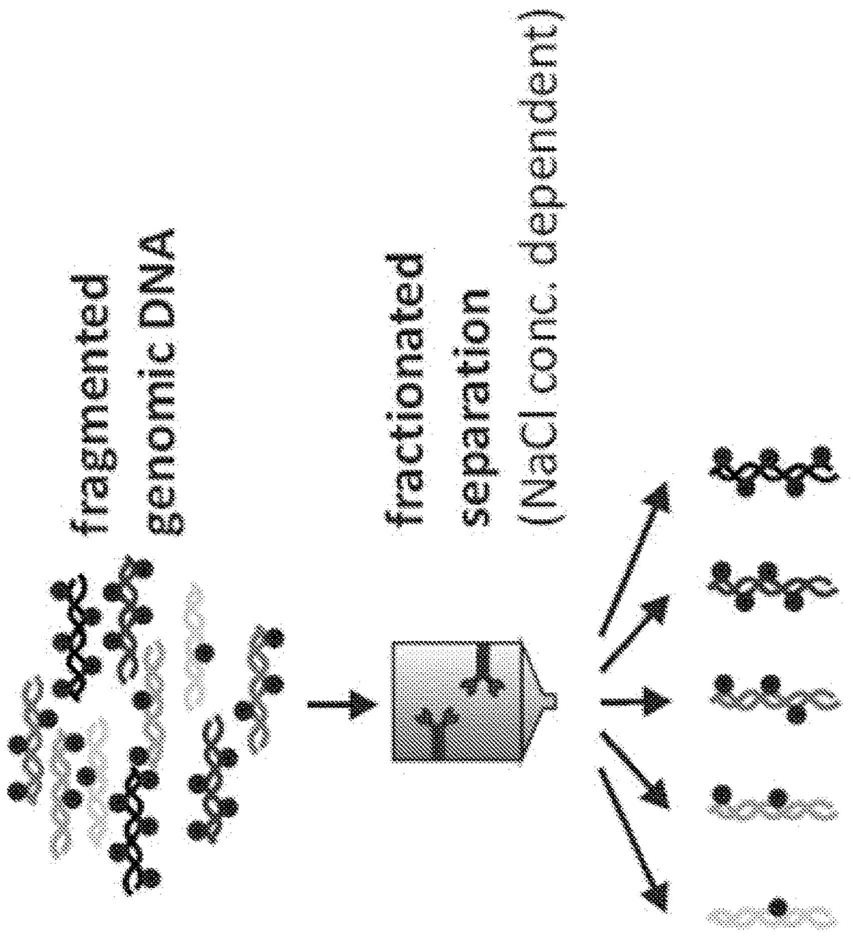

FIG. 140 shows the methyl binding domain of MBD-FC binds all DNA molecules regardless of their methylation status. The strength of this protein/DNA interaction is defined by the level of DNA methylation. After binding genomic DNA, eluate solutions of increasing salt concentrations can be used to fractionate non-methylated and methylated DNA allowing for a controlled separation.

Figure 141:
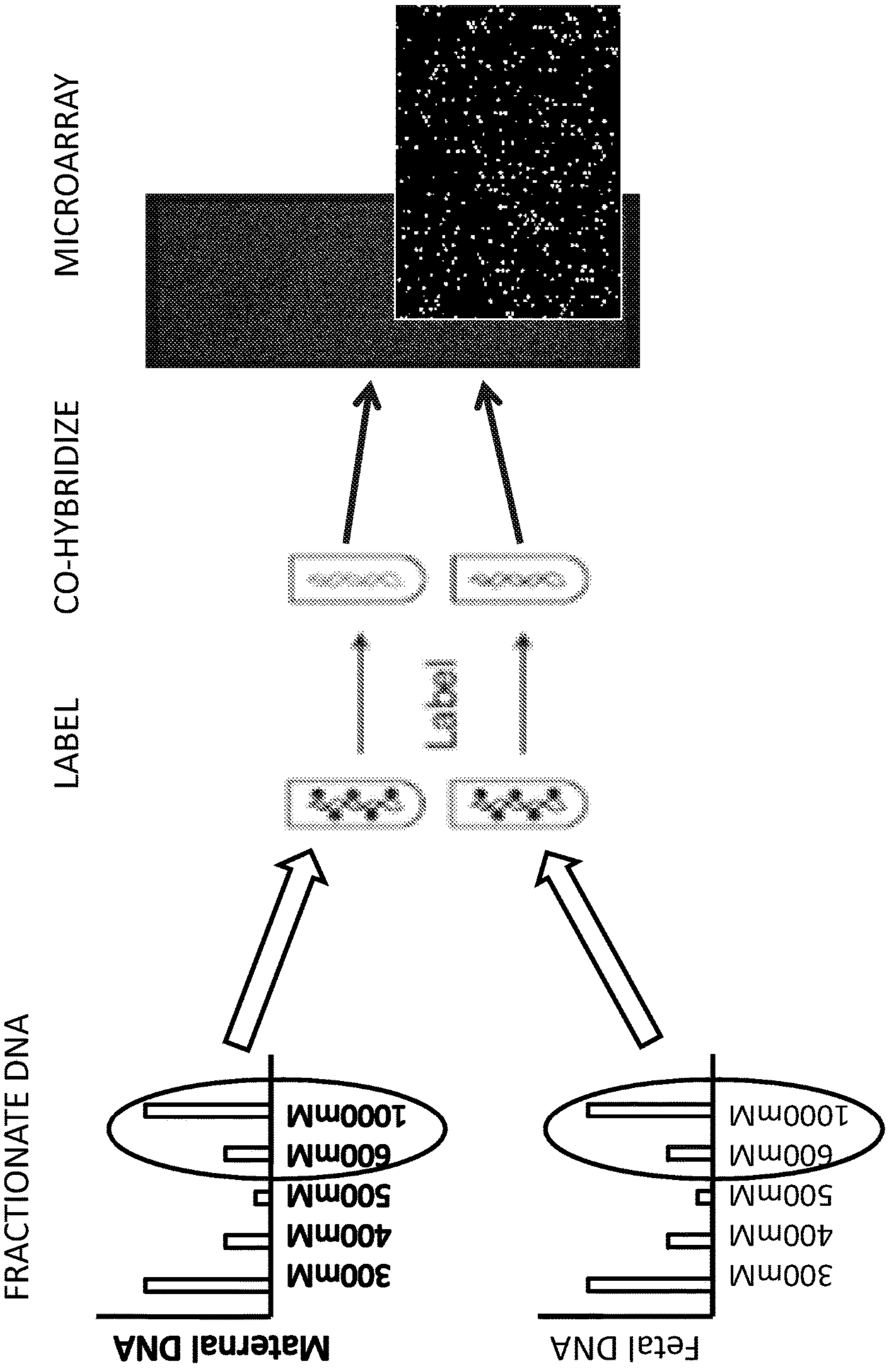

FIG. 141 shows the experiment used to identify differentially methylated DNA from a fetus and mother using the recombinant MBD-Fc protein and a microarray.

Figure 142:
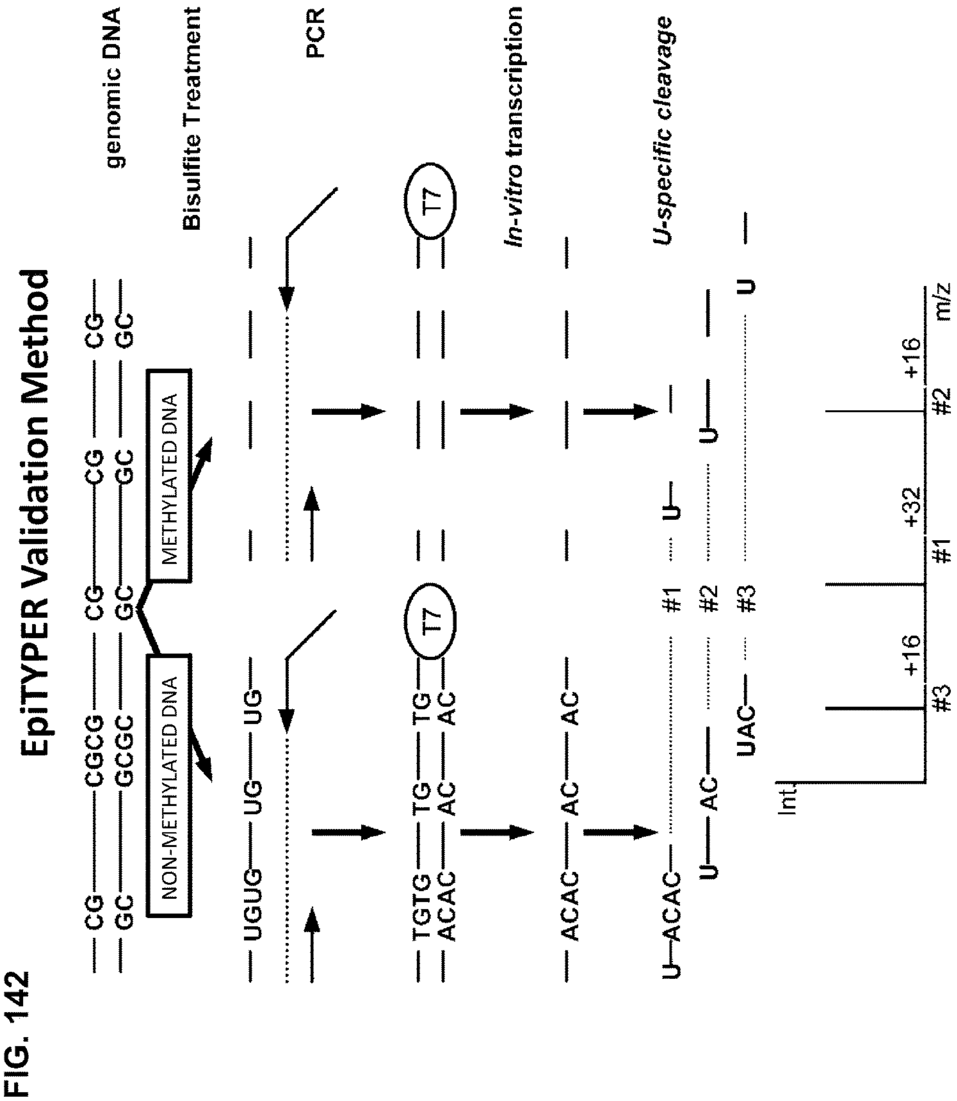

FIG. 142 shows typical results generated by Sequenom® EpiTYPER™ method, which was used to validate the results generated from the experiment illustrated in FIG. 141.

Figure 143:
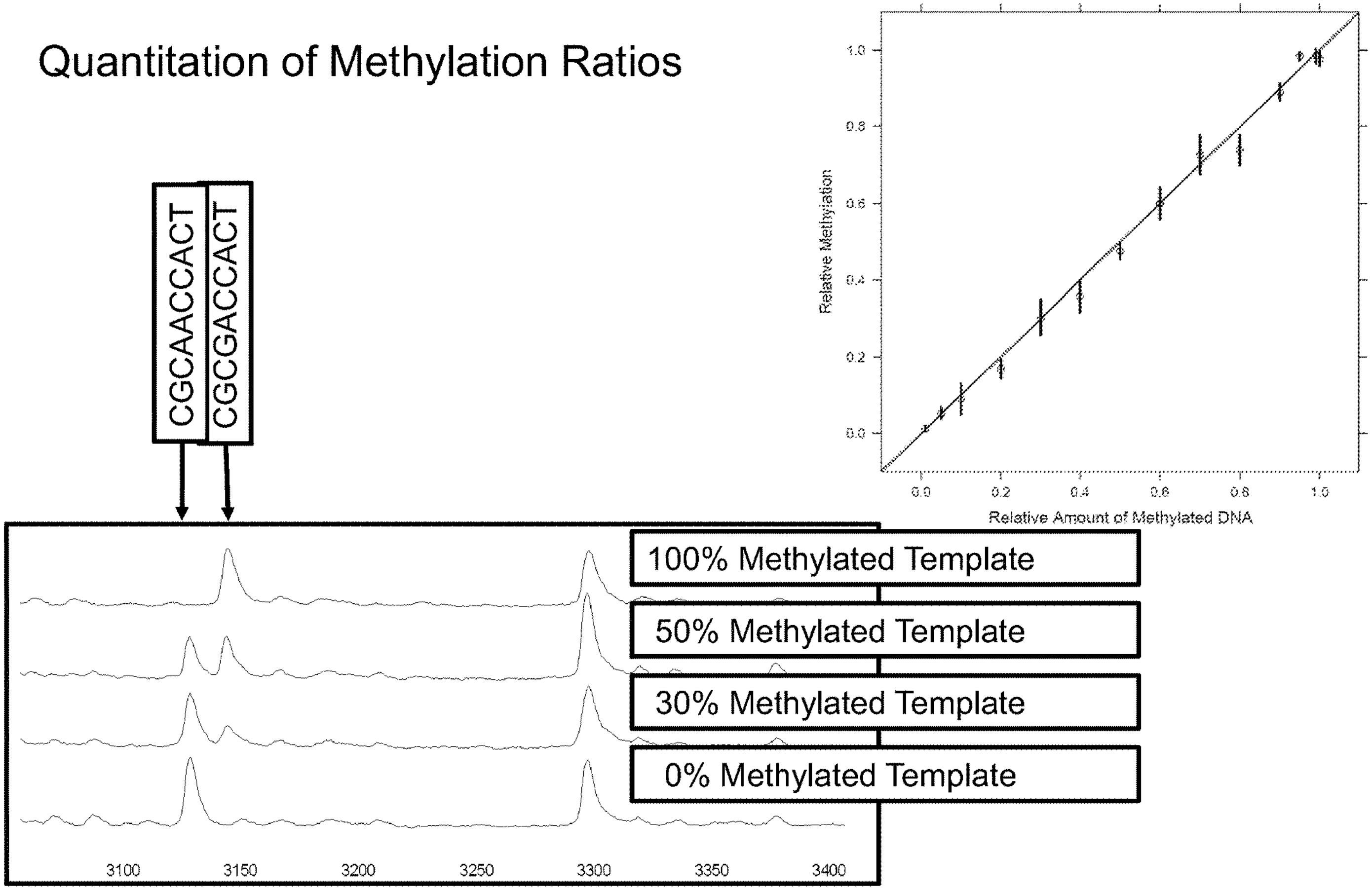

FIG. 143 shows the correlation between the log ratios derived from microarray analysis (x axis) and methylation differences obtained by EpiTYPER™ analysis (y axis). Each data point represents the average for one region across all measured samples. The microarray analysis is comparative in nature because the highly methylated fraction of the maternal DNA is hybridized together with the highly methylated fraction of placenta DNA. Positive values indicate higher methylation of the placenta samples. In mass spectrometry each samples is measured individually. The difference in methylation was calculated by subtracting the maternal methylation values from the placenta methylation value. To compare the results with the microarray data the average of the differences for all maternal/placenta DNA pairs was calculated. FIG. 143 discloses SEQ ID NOS 374-375, respectively, in order of appearance.

Figure 144:
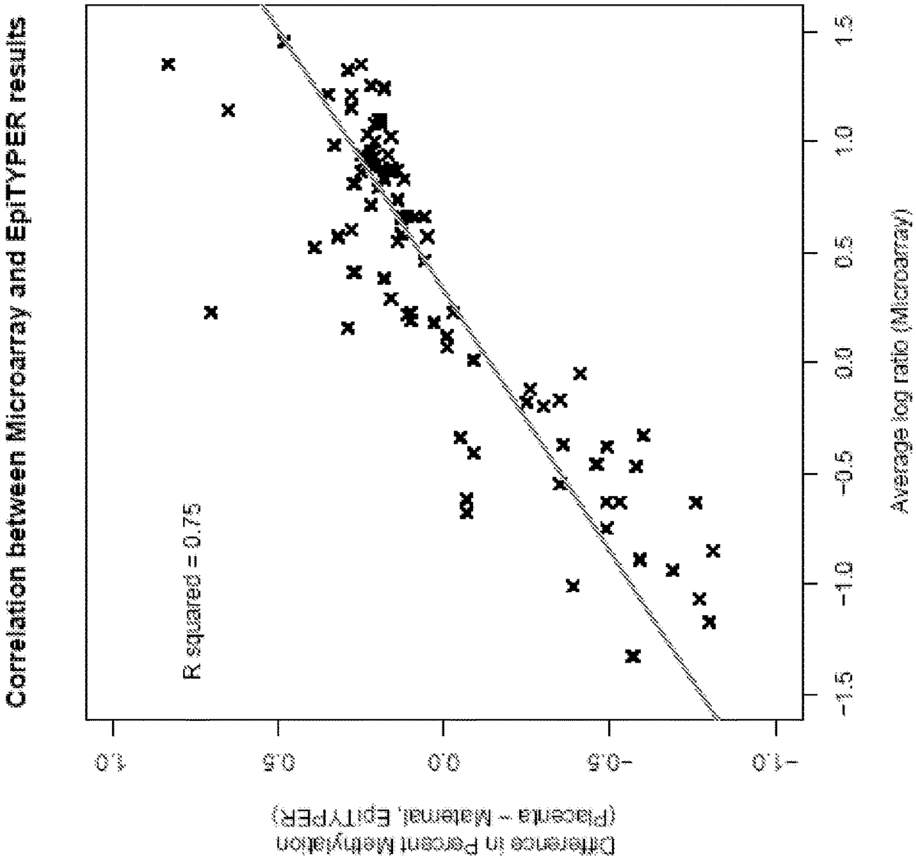

FIG. 144 shows a correlation between microarray and EpiTYPER™ results.

Figure 145:
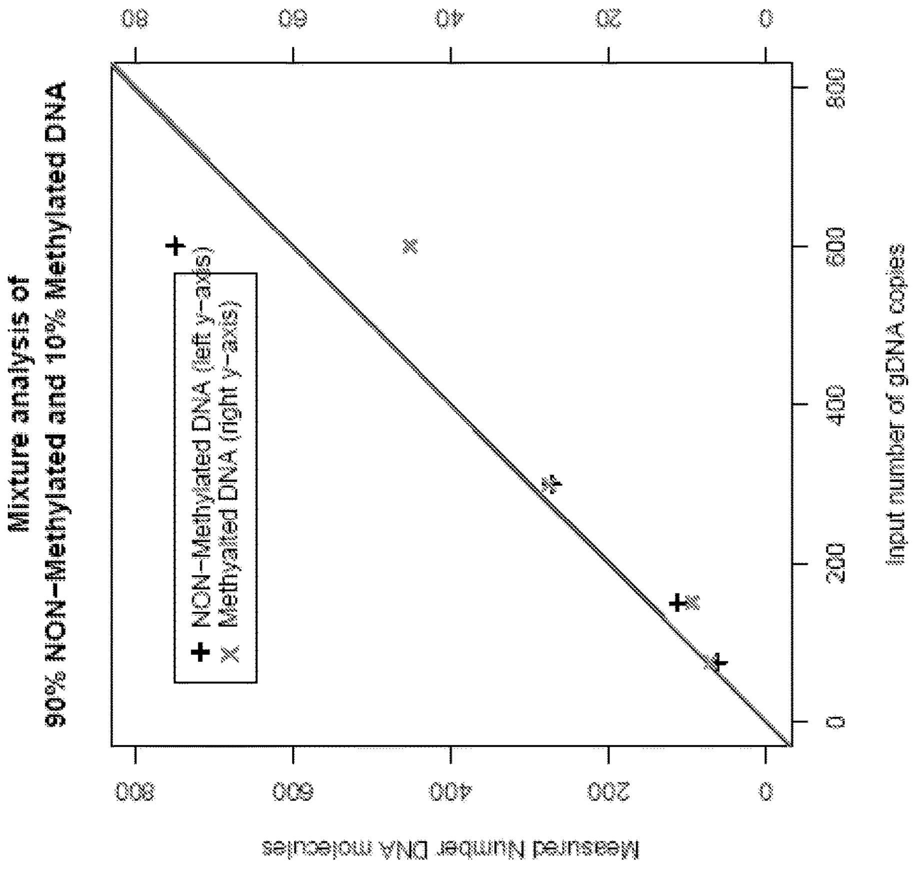
Figure 146A:
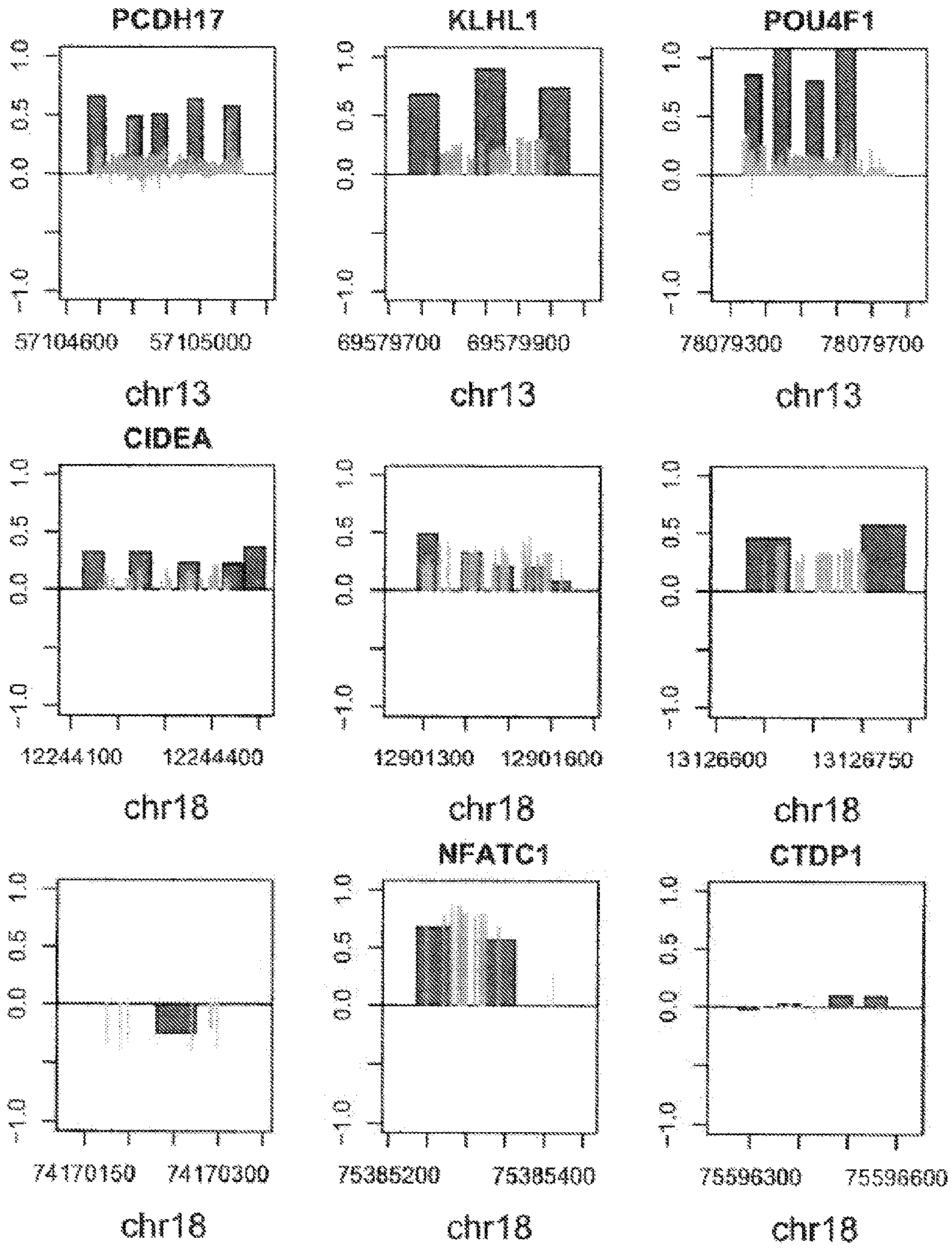
Figure 146B:
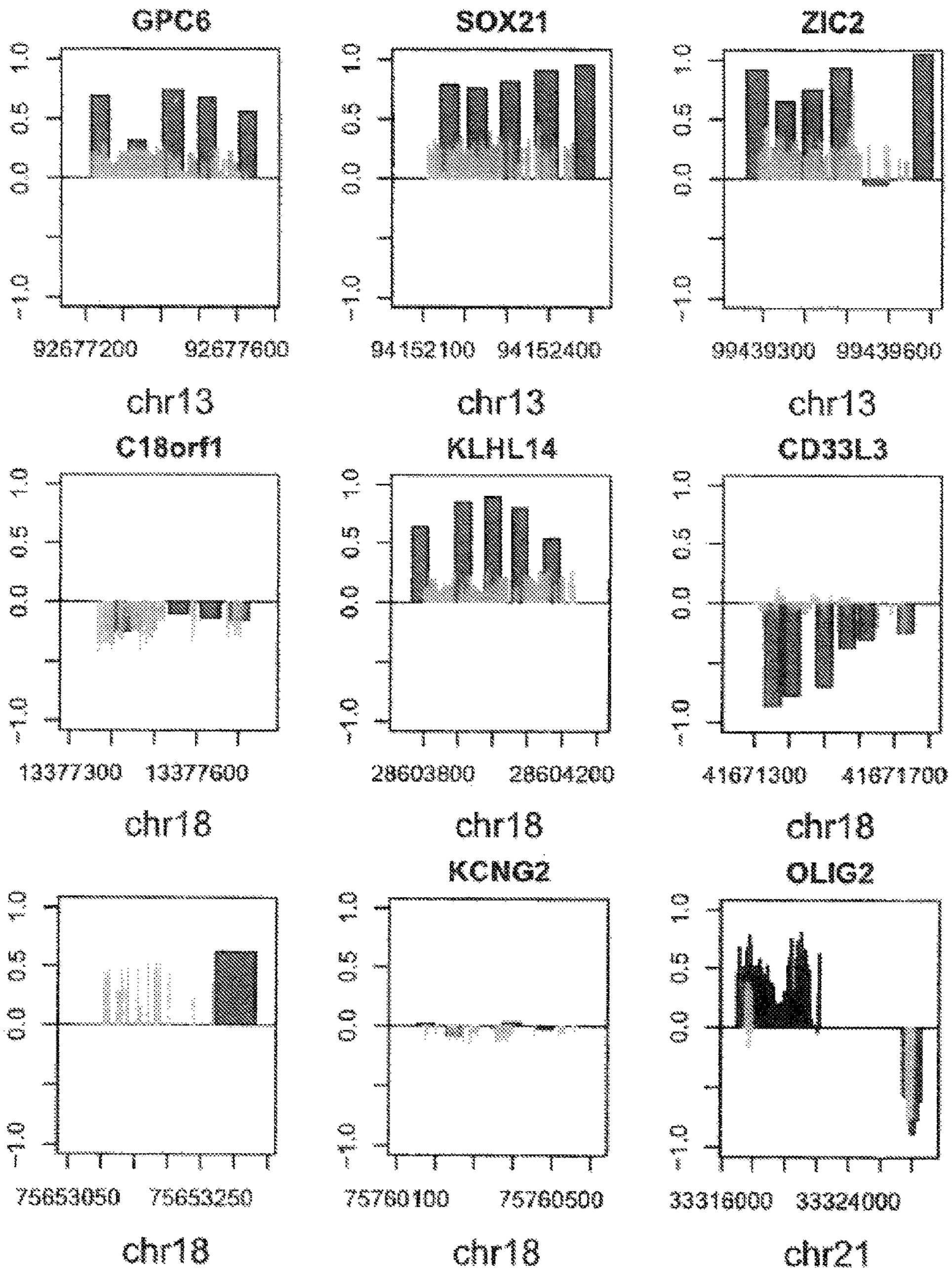
Figure 146C:
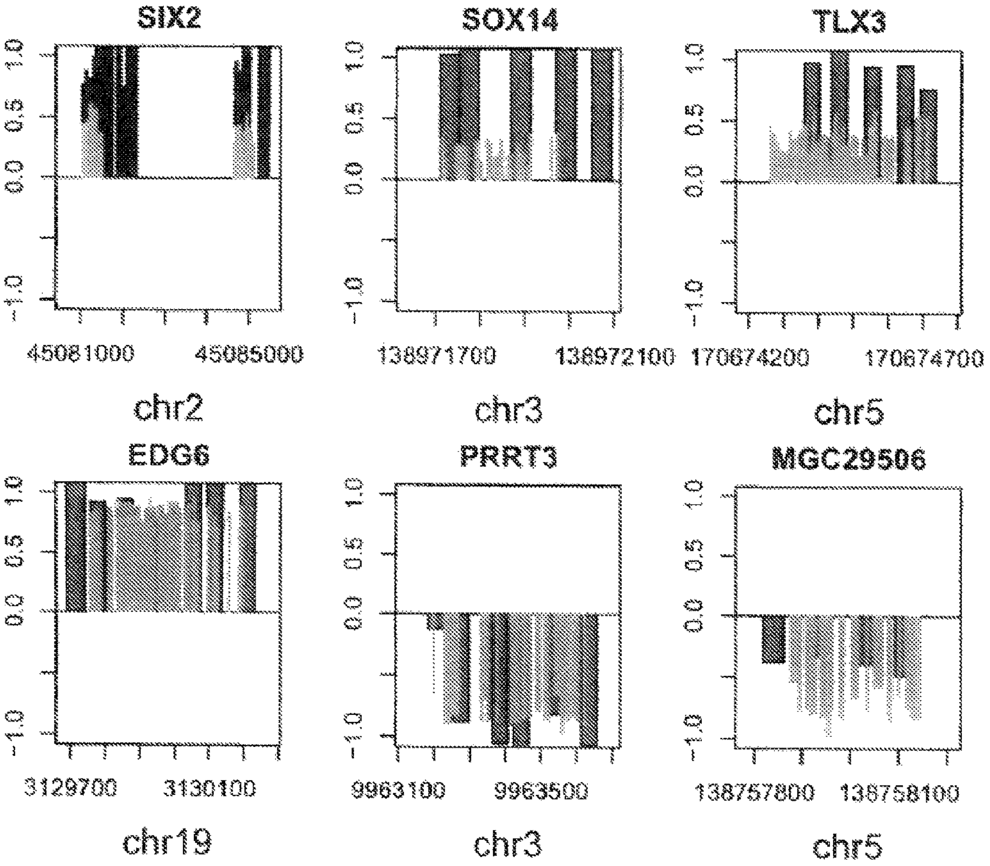
Figure 146D:
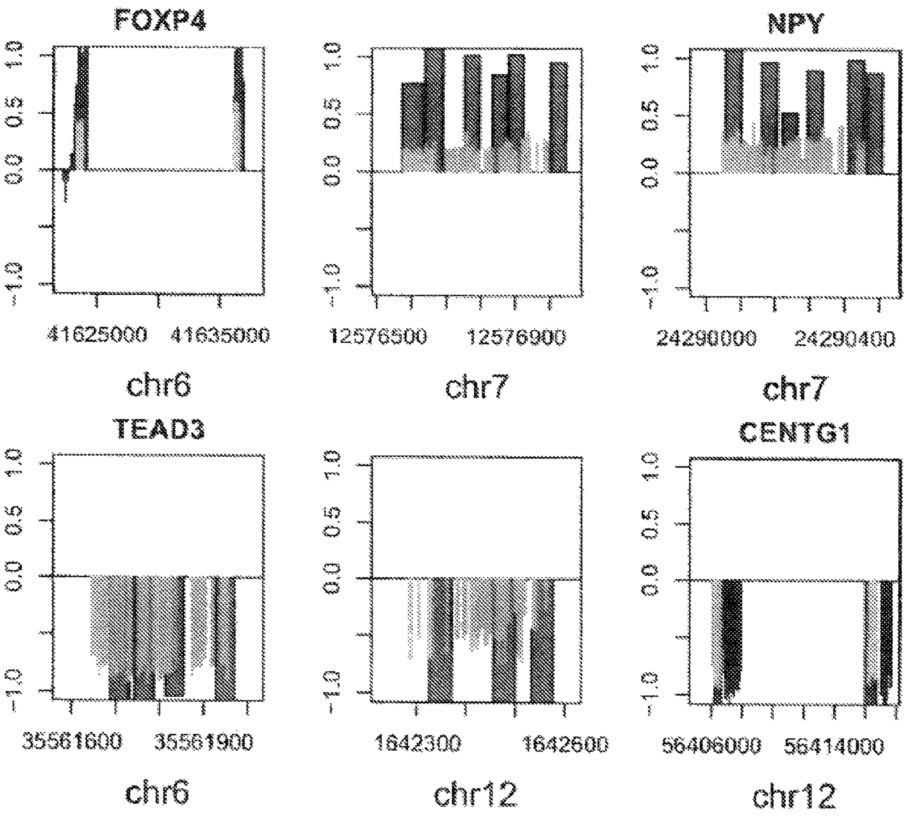
Figure 146E:
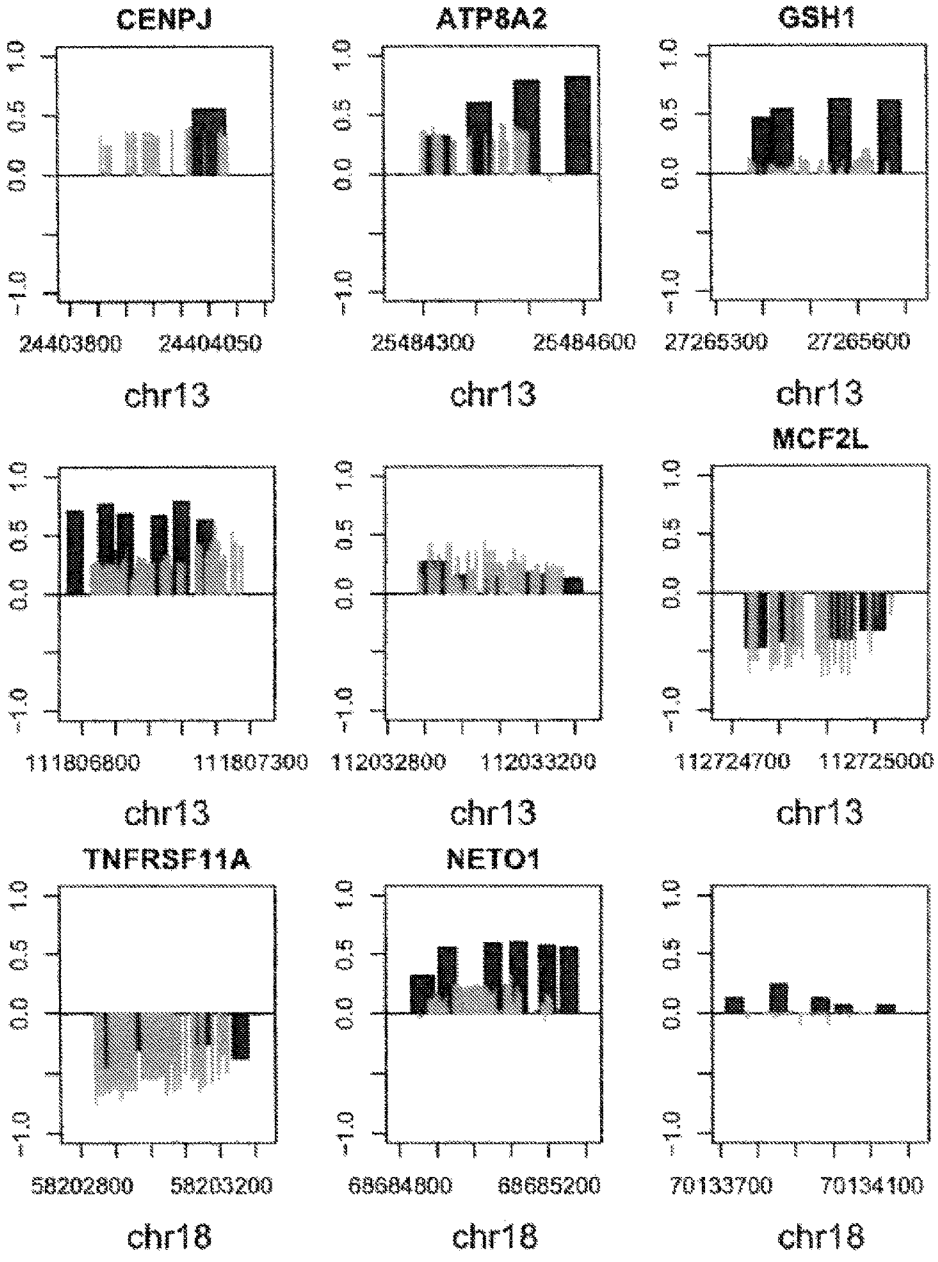
Figure 146F:
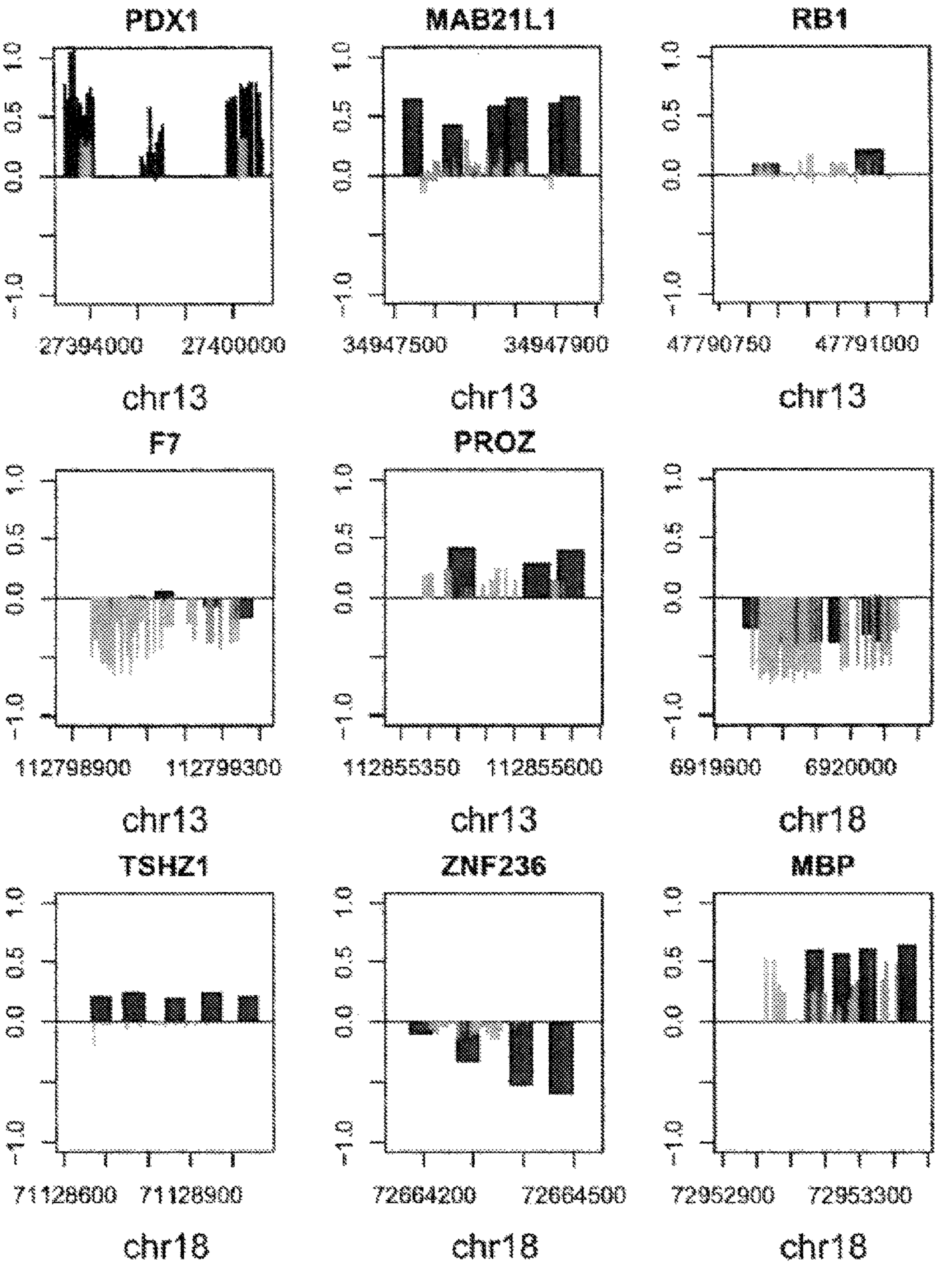
Figure 146G:
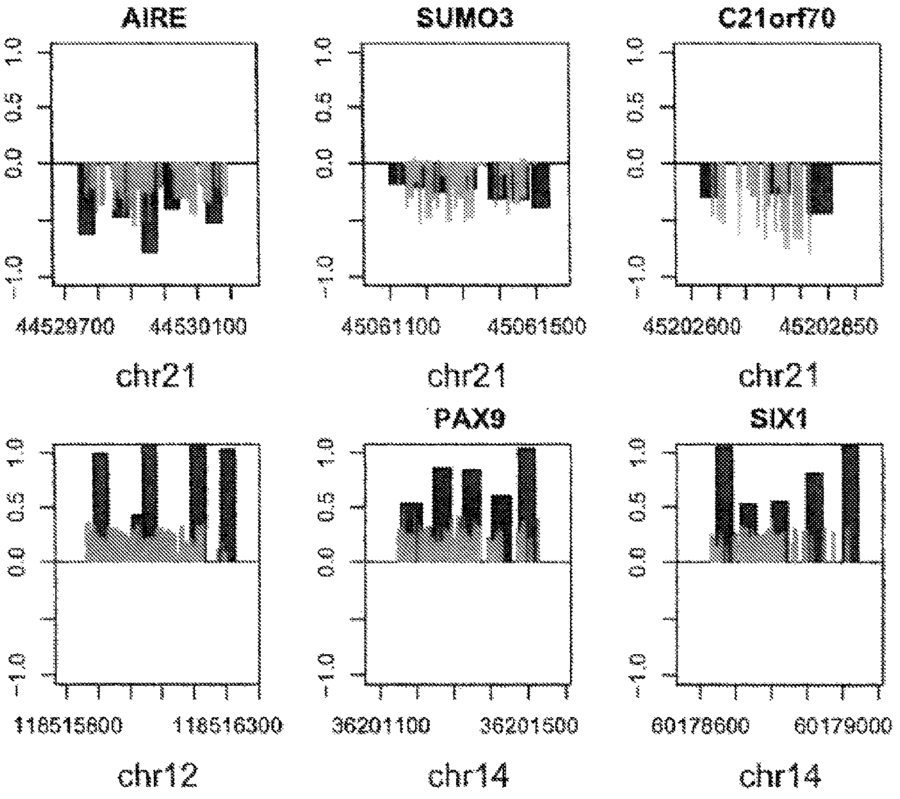
Figure 146H:
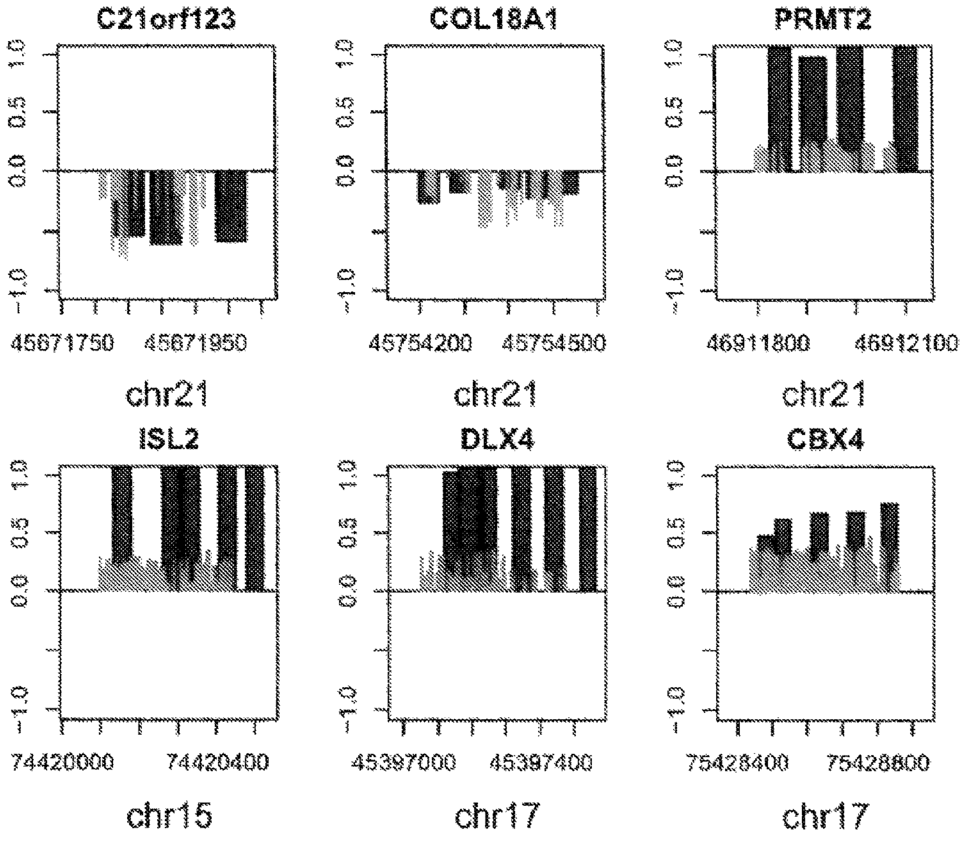
Figure 146I:
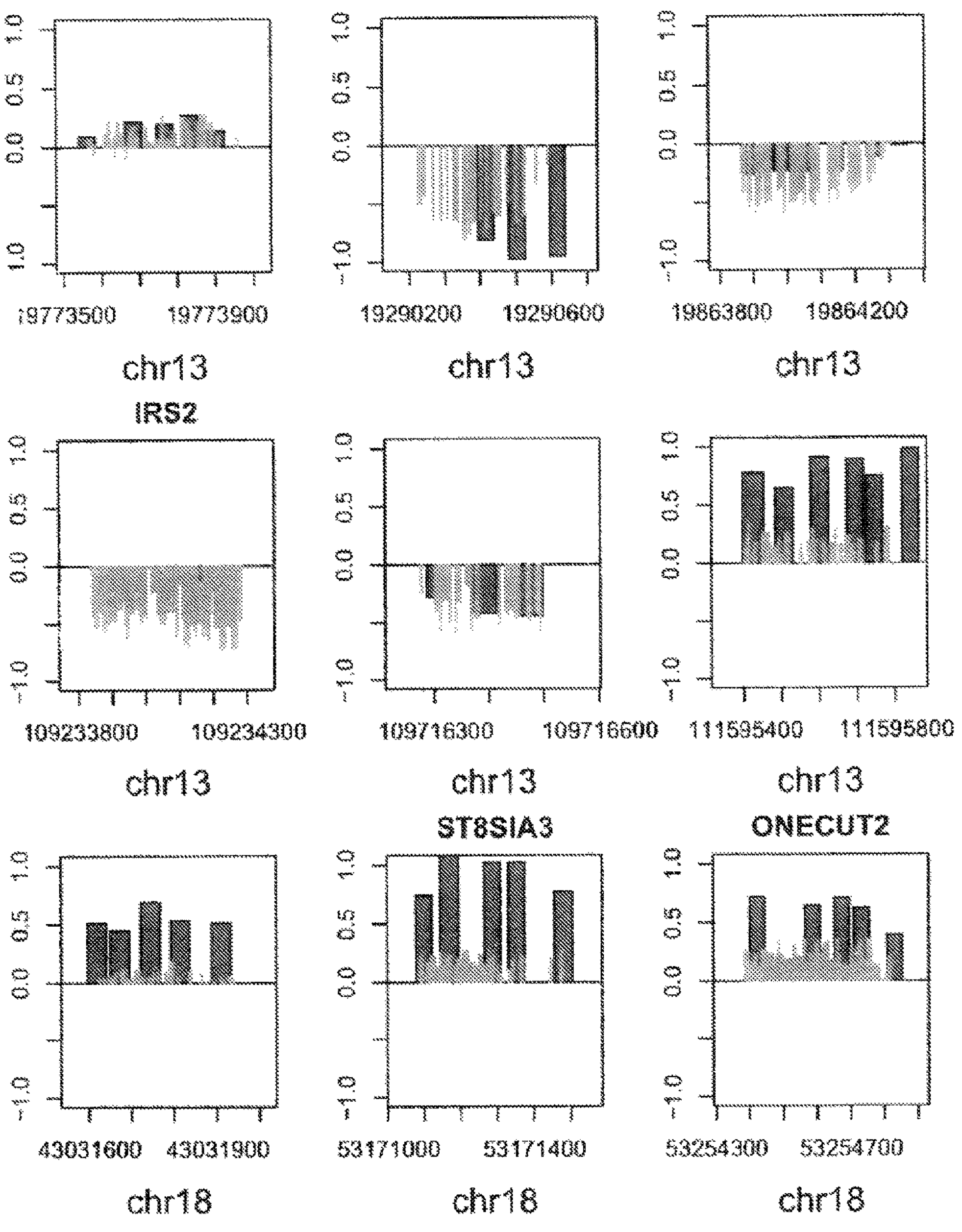
Figure 146J:
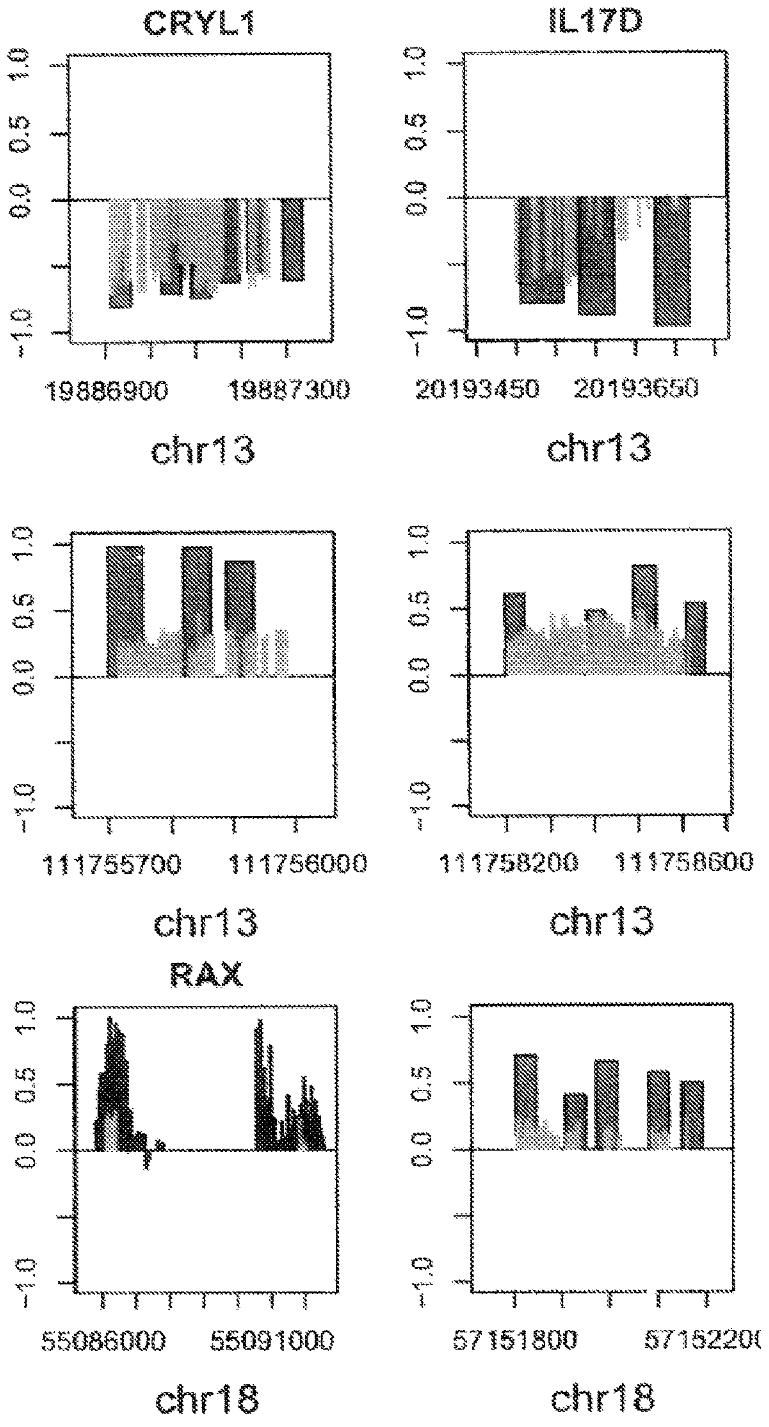
Figure 146K:
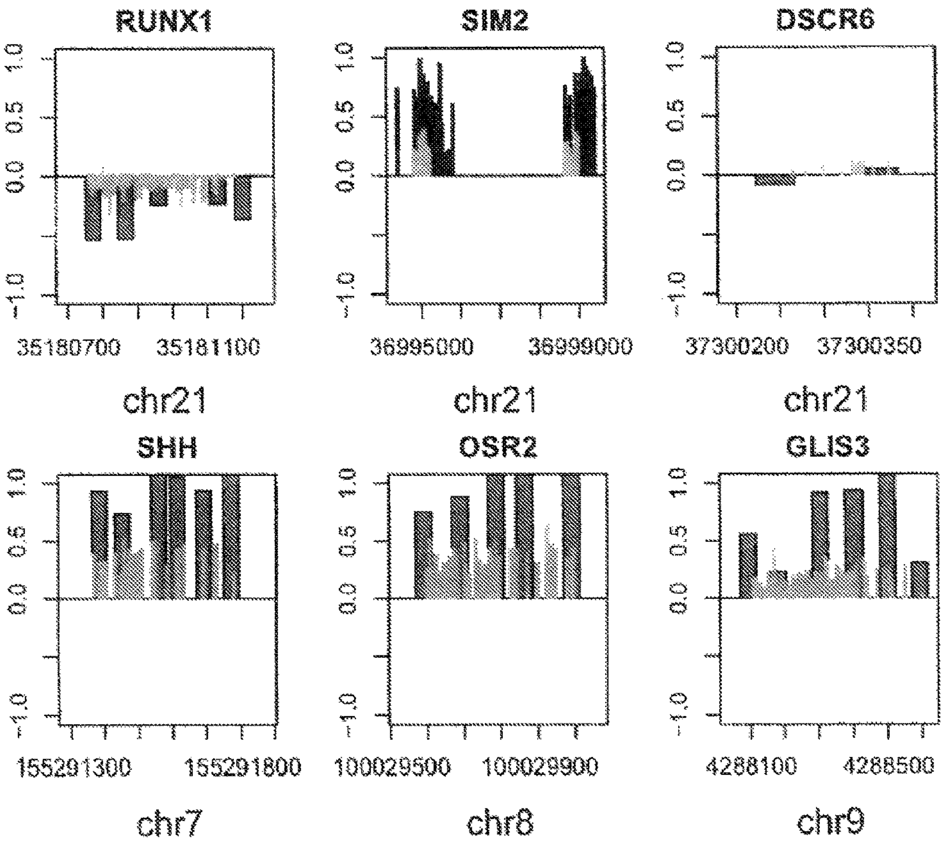
Figure 146L:
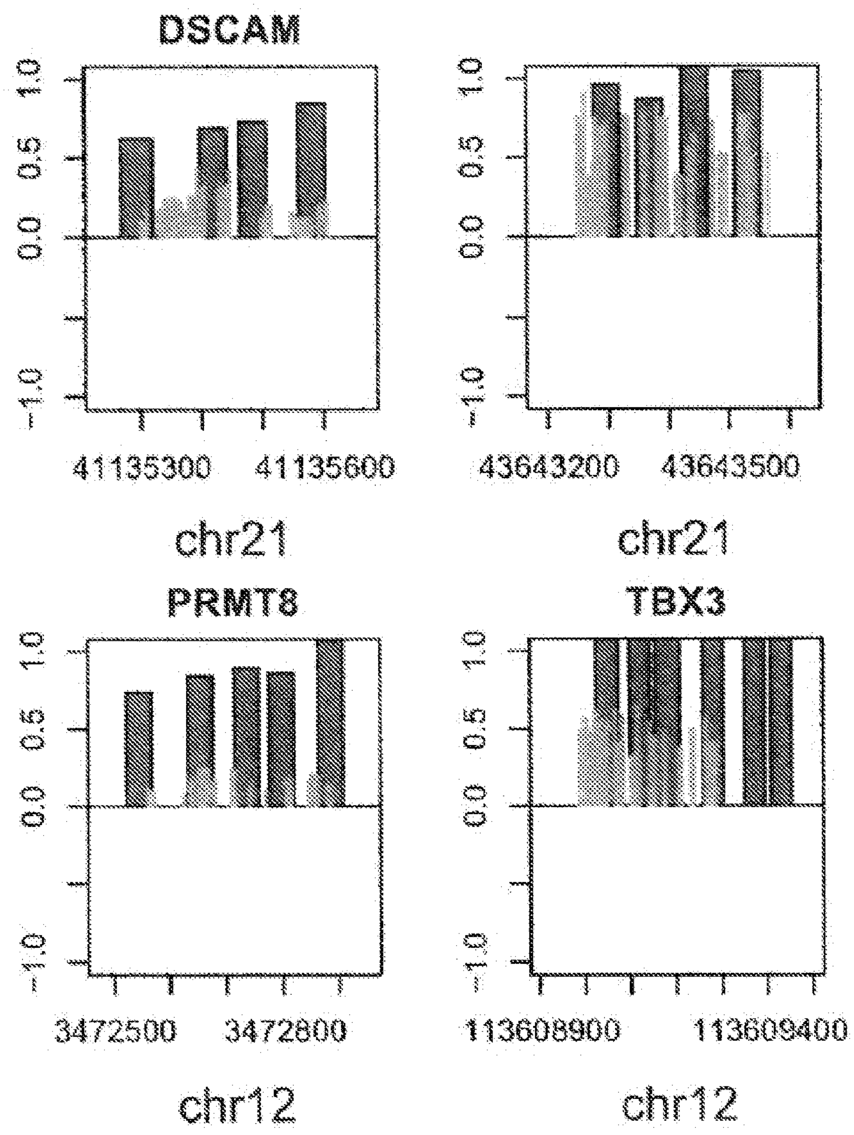

FIG. 145 shows the correlation between the number of gDNA molecules that were expected and the number of molecules measured by competitive PCR in combination with mass spectrometry analysis. In this experiment, DNA derived from whole blood (black plus signs) and commercially available fully methylated DNA (grey crosses) were used in a 90 to 10 ratio. The MBD-FC fusion protein was used to separate the non-methylated and the methylated fraction of DNA. Each fraction was subject to competitive PCR analysis with mass spectrometry readout. The method has been described earlier for the analysis of copy number variations and is commercially available for gene expression analysis. The approach allows absolute quantification of DNA molecules with the help of a synthetic oligonucleotides of know concentration. In this experiment the MGMT locus was targeted, which was not methylated in the whole blood sample used here. Using an input of 300 total gDNA copies, 270 copies of non-methylated DNA and 30 copies of methylated DNA was expected. The measured copy numbers are largely in agreement with the expected values. The data point at 600 copies of input DNA indicates a bias in the reaction. This initial data indicates the feasibility of the approach for capturing and quantifying a few copies of methylated DNA in the presence of an excess of unmethylated DNA species.

FIG. 146A-146L show bar graph plots of the methylation differences obtained from the microarray analysis (dark bars) and the mass spectrometry analysis (light grey bars) with respect to their genomic location. For each of the 85 regions that were identified to be differentially methylated by microarray an individual plot is provided. The x axis for each plot shows the chromosomal position of the region. The y axis depicts the log ration (in case of the microarrays) and the methylation differences (in case of the mass spectrometry results). For the microarrays each hybridization probe in the area is shown as a single black (or dark grey) bar. For the mass spectrometry results each CpG site, is shown as a light grey bar. Bars showing values greater than zero indicate higher DNA methylation in the placenta samples compared to the maternal DNA. For some genes the differences are small (i.e. RB1 or DSCR6) but still statistically significant. Those regions would be less suitable for a fetal DNA enrichment strategy.

Figure 147:
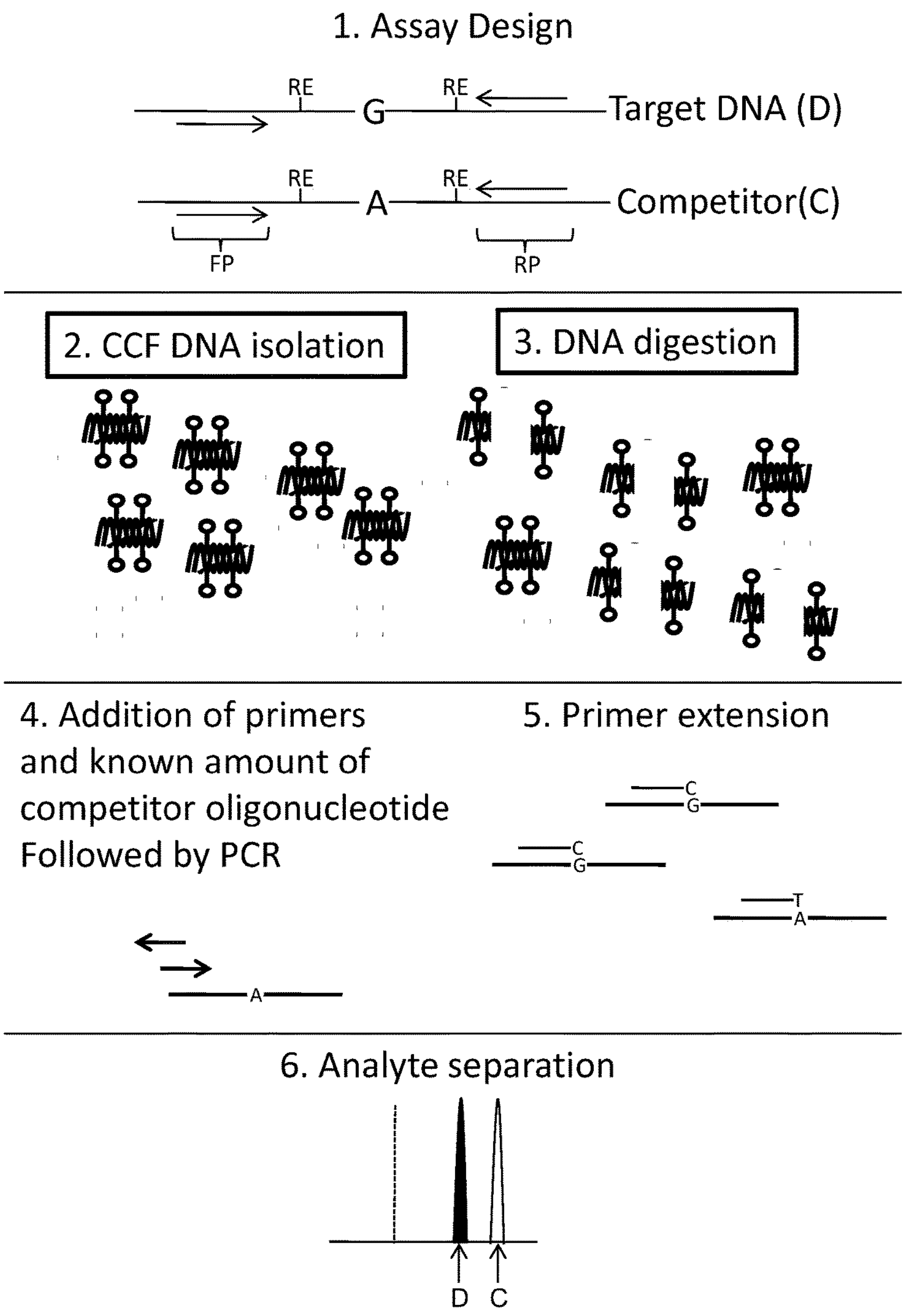

FIG. 147 shows one embodiment of the Fetal Quantifier Method. Maternal nucleic acid is selectively digested and the remaining fetal nucleic acid is quantified using a competitor of known concentration. In this schema, the analyte is separated and quantified by a mass spectrometer.

Figure 148:
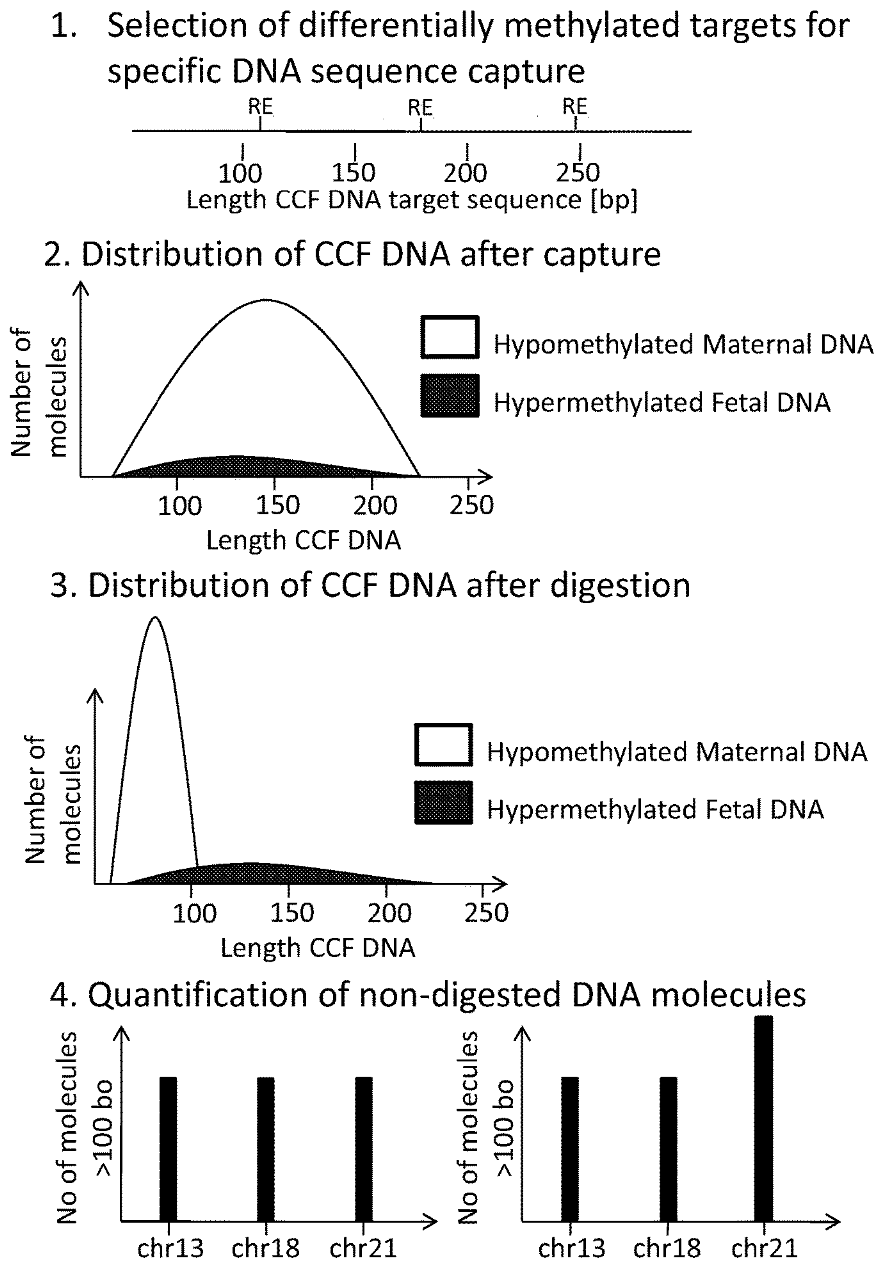

FIG. 148 shows one embodiment of the Methylation-Based Fetal Diagnostic Method. Maternal nucleic acid is selectively digested and the remaining fetal nucleic acid is quantified for three different chromosomes (13, 18 and 21). Parts 2 and 3 of the Figure illustrate the size distribution of the nucleic acid in the sample before and after digestion. The amplification reactions can be size-specific (e.g., greater than 100 base pair amplicons) such that they favor the longer, non-digested fetal nucleic acid over the digested maternal nucleic acid, thereby further enriching the fetal nucleic acid. The spectra at the bottom of the Figure show an increased amount of chromosome 21 fetal nucleic acid indicative of trisomy 21.

Figure 149:
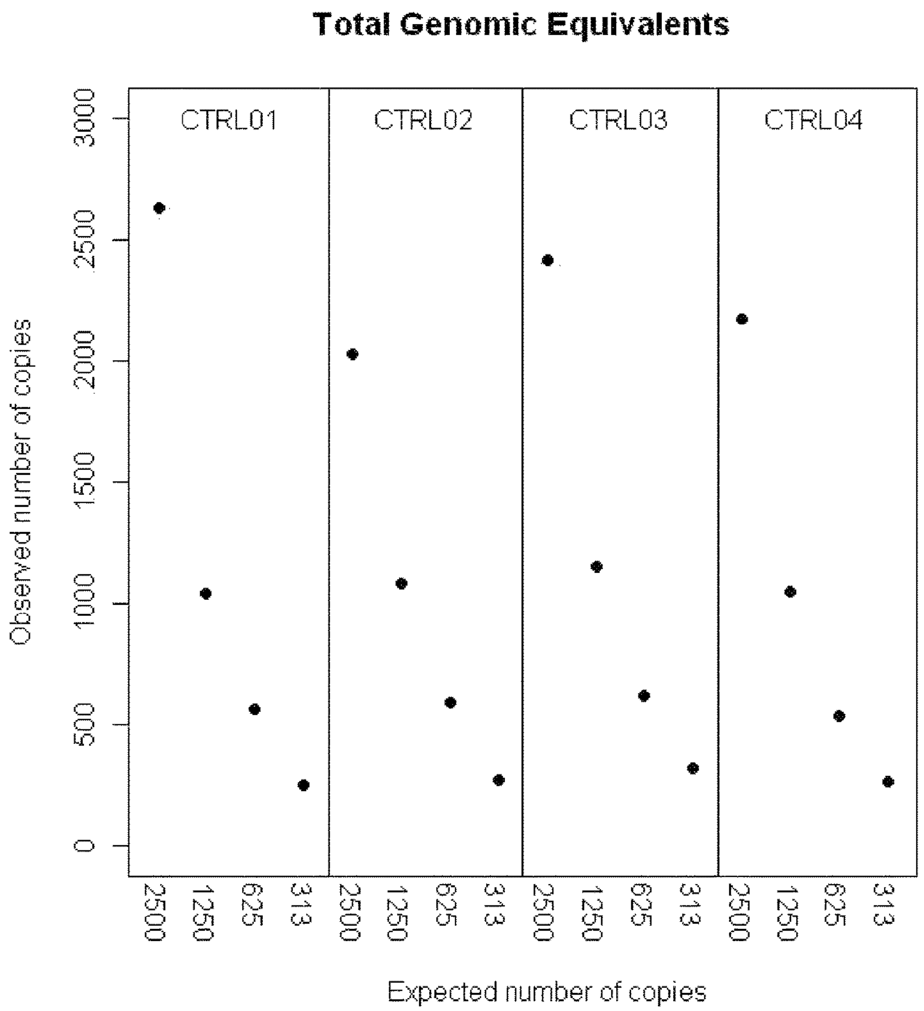

FIG. 149 shows the total number of amplifiable genomic copies from four different DNA samples isolated from the blood of non-pregnant women. Each sample was diluted to contain approximately 2500, 1250, 625 or 313 copies per reaction. Each measurement was obtained by taking the mean DNA/competitor ratio obtained from two total copy number assays (ALB and RNAseP in Table X). As shown, the total copy number is accurate and stable across the different samples, thus validating the usefulness of the competitor-based approach.

Figure 150A:
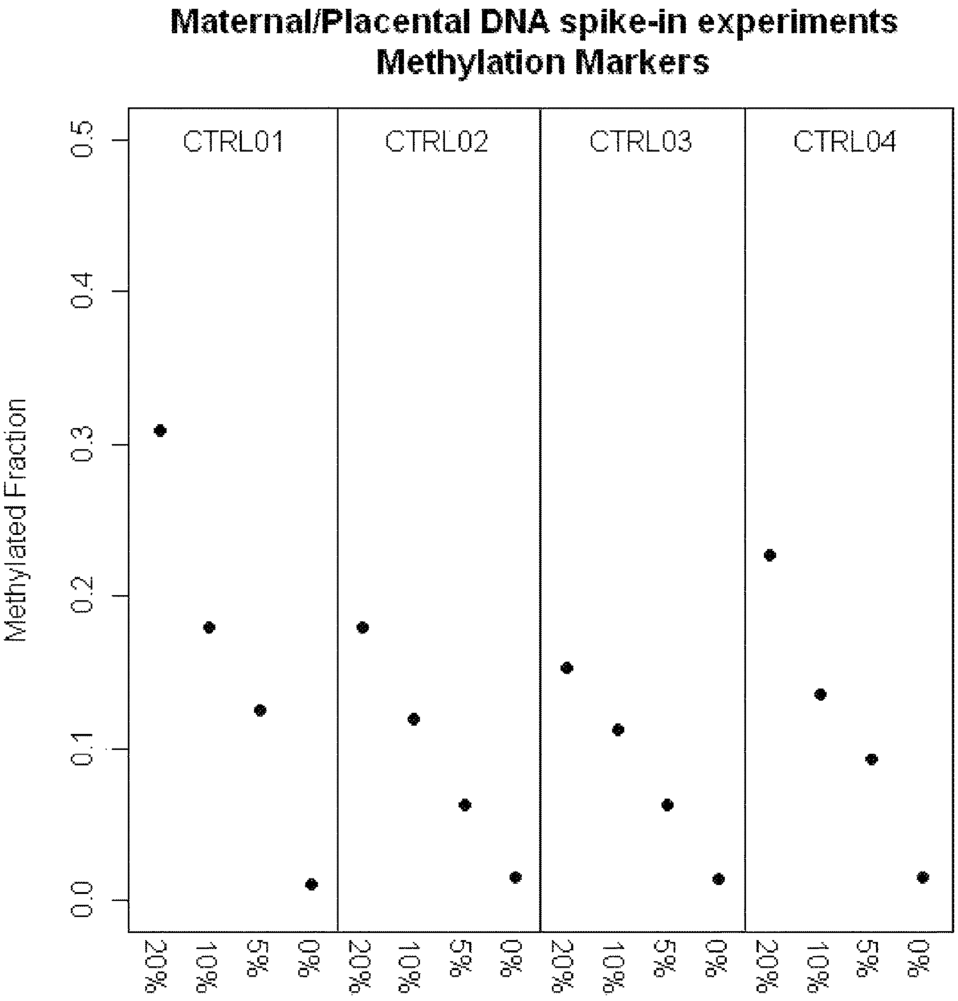
Figure 150B:
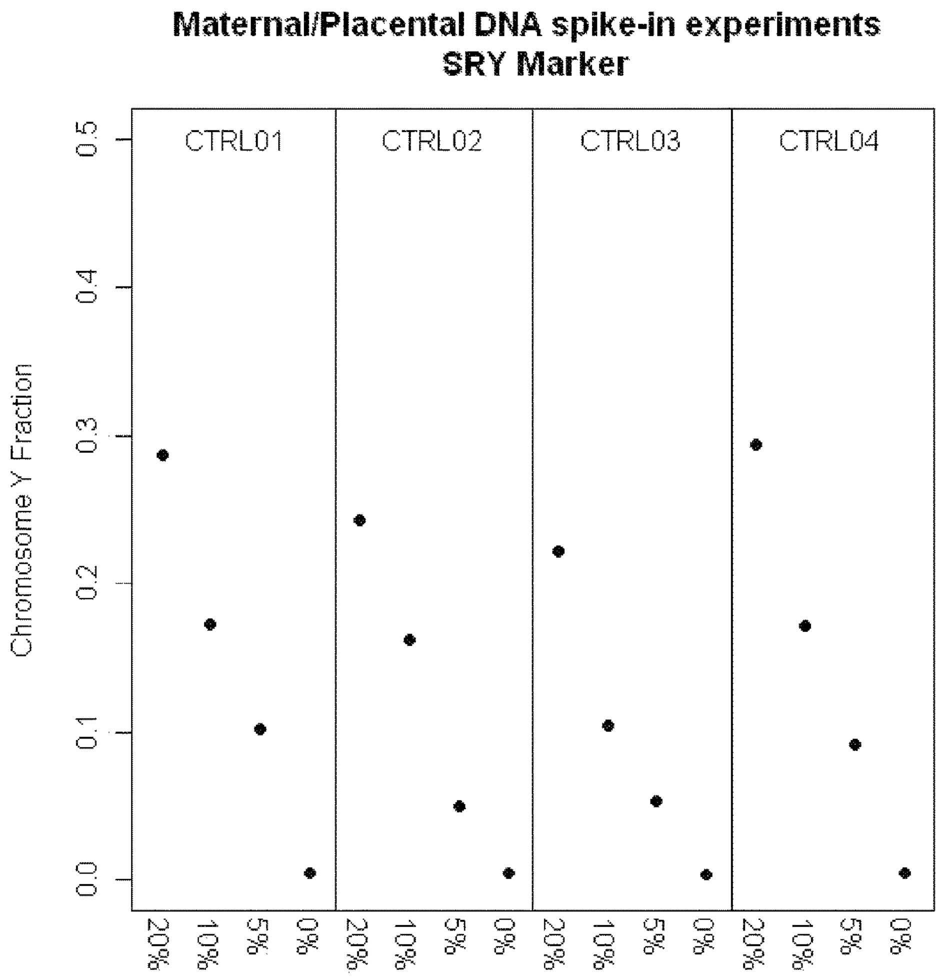

FIGS. 150A-150B show a model system that was created that contained a constant number of maternal non-methylated DNA with varying amounts of male placental methylated DNA spiked-in. The samples were spiked with male placental amounts ranging from approximately 0 to 25% relative to the maternal non-methylated DNA. The fraction of placental DNA was calculated using the ratios obtained from the methylation assays (FIG. 150A) and the Y-chromosome marker (FIG. 150B) as compared to the total copy number assay. The methylation and Y-chromosome markers are provided in Table X.

Figure 151A:
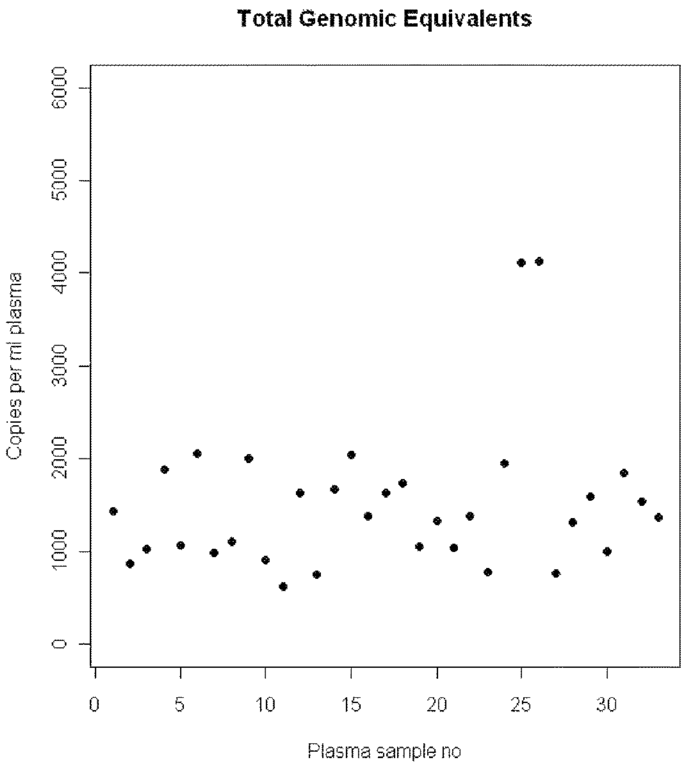
Figure 151B:
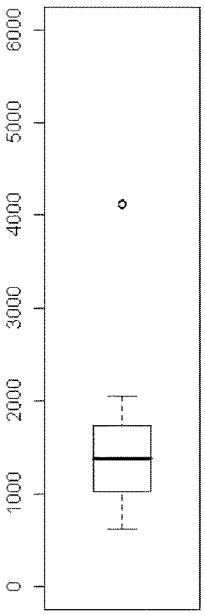

FIGS. 151A and 151B show the results of the total copy number assay from plasma samples. In FIG. 151A, the copy number for each sample is shown. Two samples (no 25 and 26) have a significantly higher total copy number than all the other samples. A mean of approximately 1300 amplifiable copies/ml plasma was obtained (range 766-2055). FIG. 151B shows a box-and-whisker plot of the given values, summarizing the results.

Figures 152A, 152B:
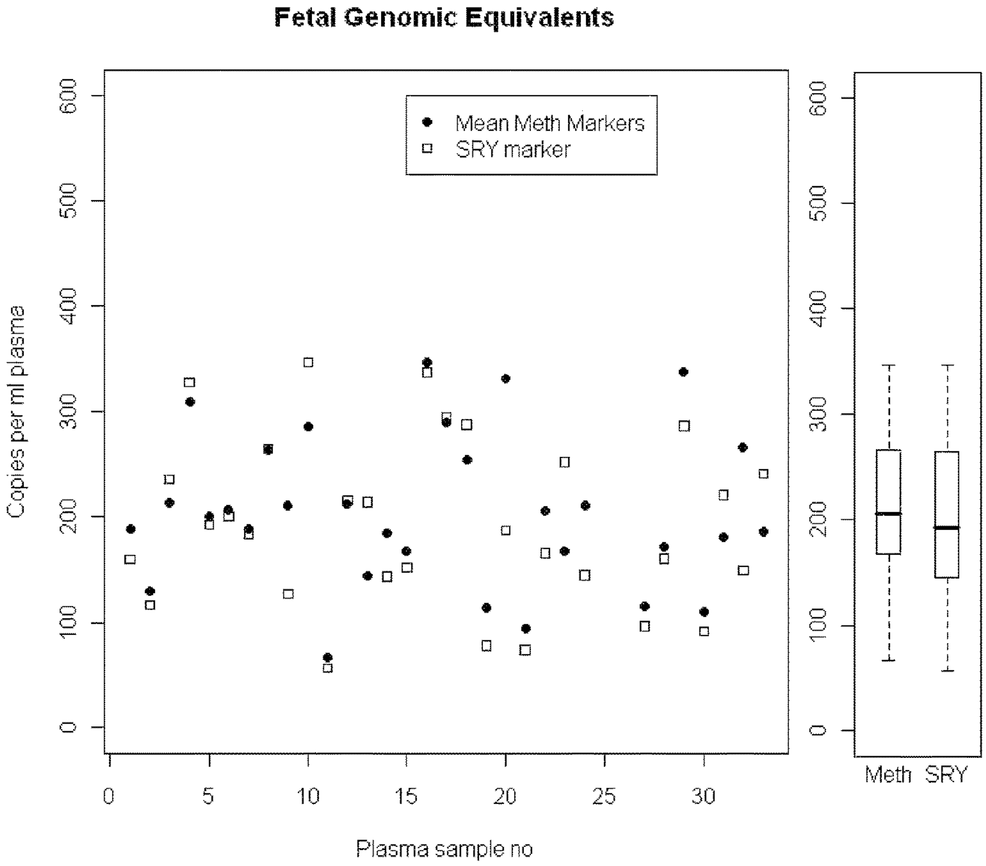

FIGS. 152A and 152B show the amount (or copy numbers) of fetal nucleic acid from 33 different plasma samples taken from pregnant women with male fetuses plotted. The copy numbers obtained were calculated using the methylation markers and the Y-chromosome-specific markers using the assays provided in Table X. As can be seen in FIG. 152B, the box-and-whisker plot of the given values indicated minimal difference between the two different measurements, thus validating the accuracy and stability of the method.

Figure 153:
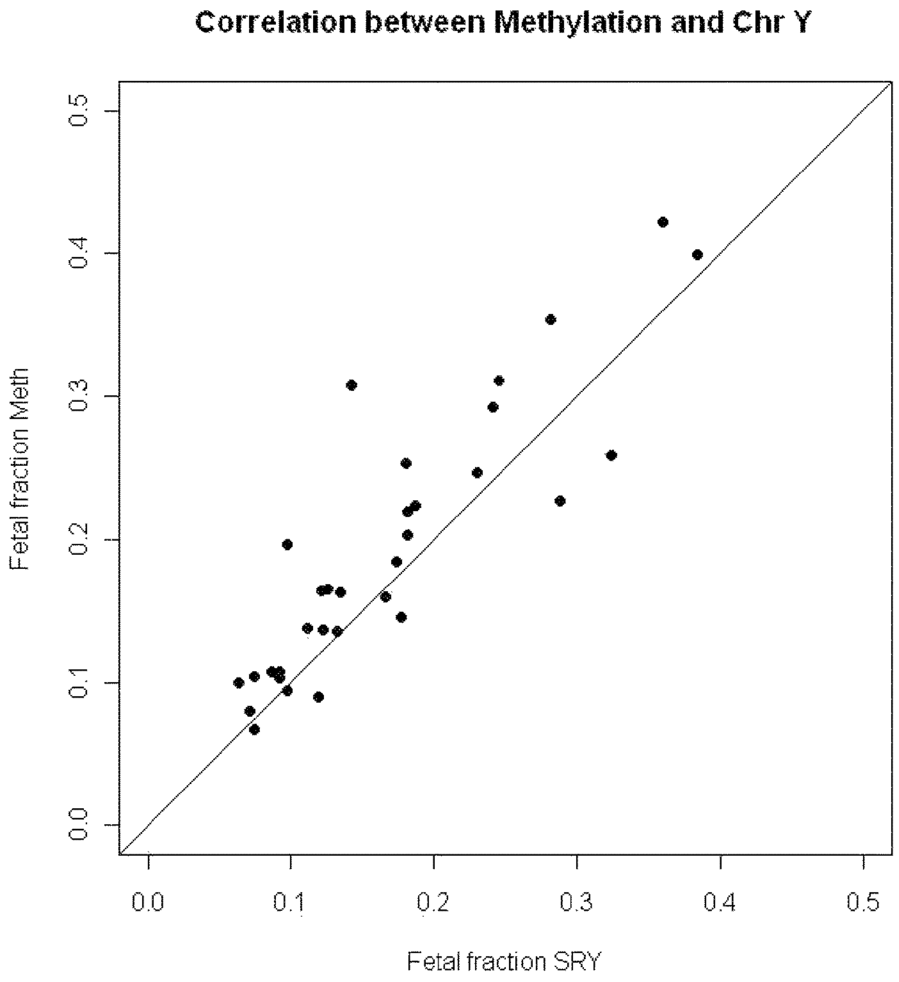

FIG. 153 shows a paired correlation between the results obtained using the methylation markers versus the Y-chromosome marker from FIG. 152A.

Figure 154:
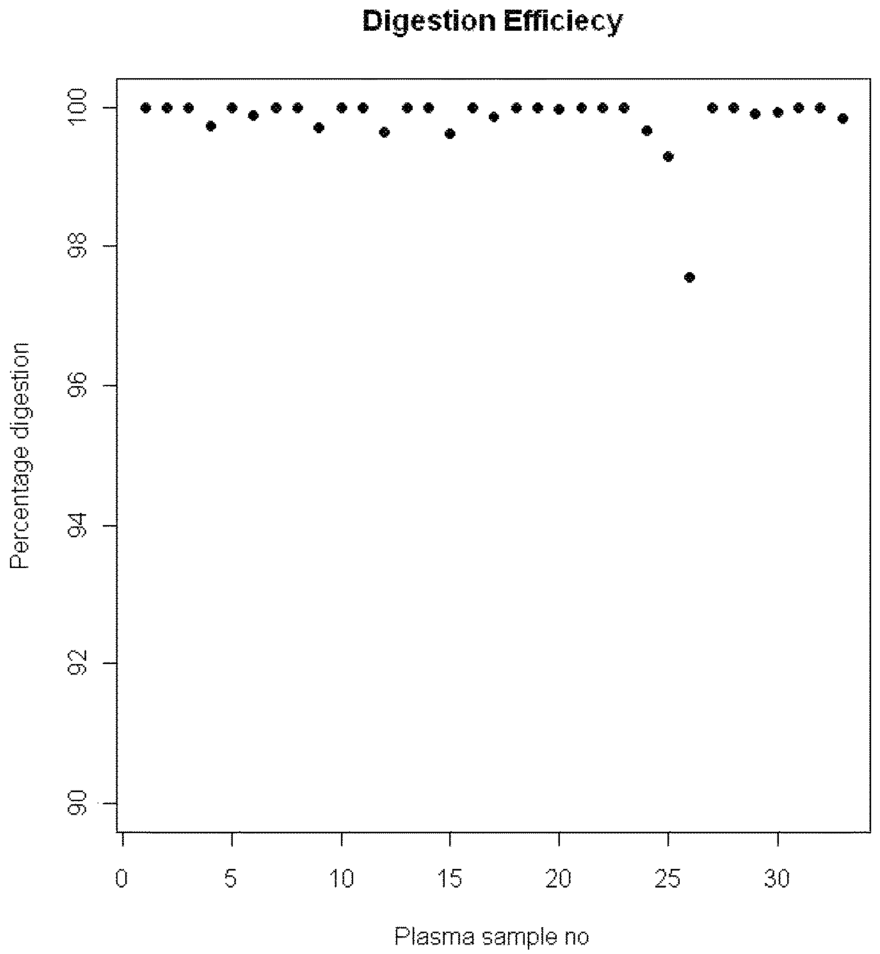

FIG. 154 shows the digestion efficiency of the restriction enzymes using the ratio of digestion for the control versus the competitor and comparing this value to the mean total copy number assays. Apart from sample 26 all reactions indicate the efficiency to be above about 99%.

Figure 155:
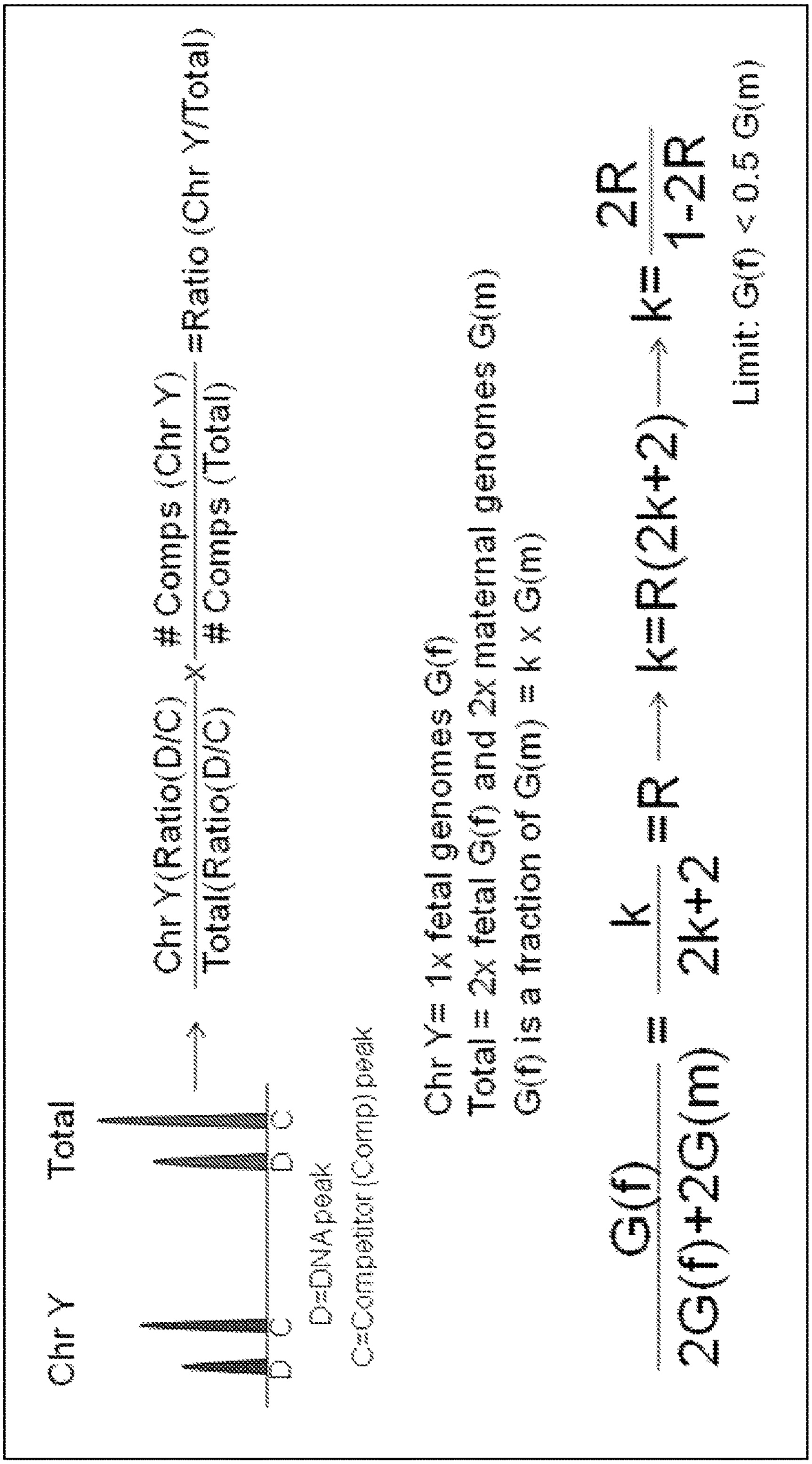

FIG. 155 provides a specific method for calculating fetal DNA fraction (or concentration) in a sample using the Y-chromosome-specific markers for male pregnancies and the mean of the methylated fraction for all pregnancies (regardless of fetal sex).

Figure 156:
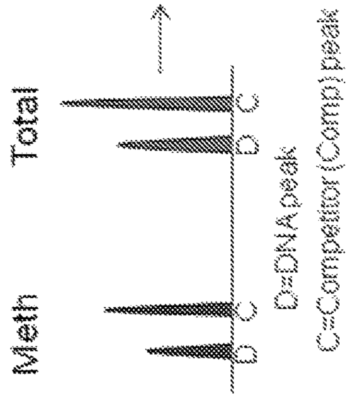

FIG. 156 provides a specific method for calculating fetal DNA fraction (or concentration) in a sample without the Y-chromosome-specific markers. Instead, only the Assays for Methylation Quantification were used to determine the concentration of fetal DNA.

Figure 157:
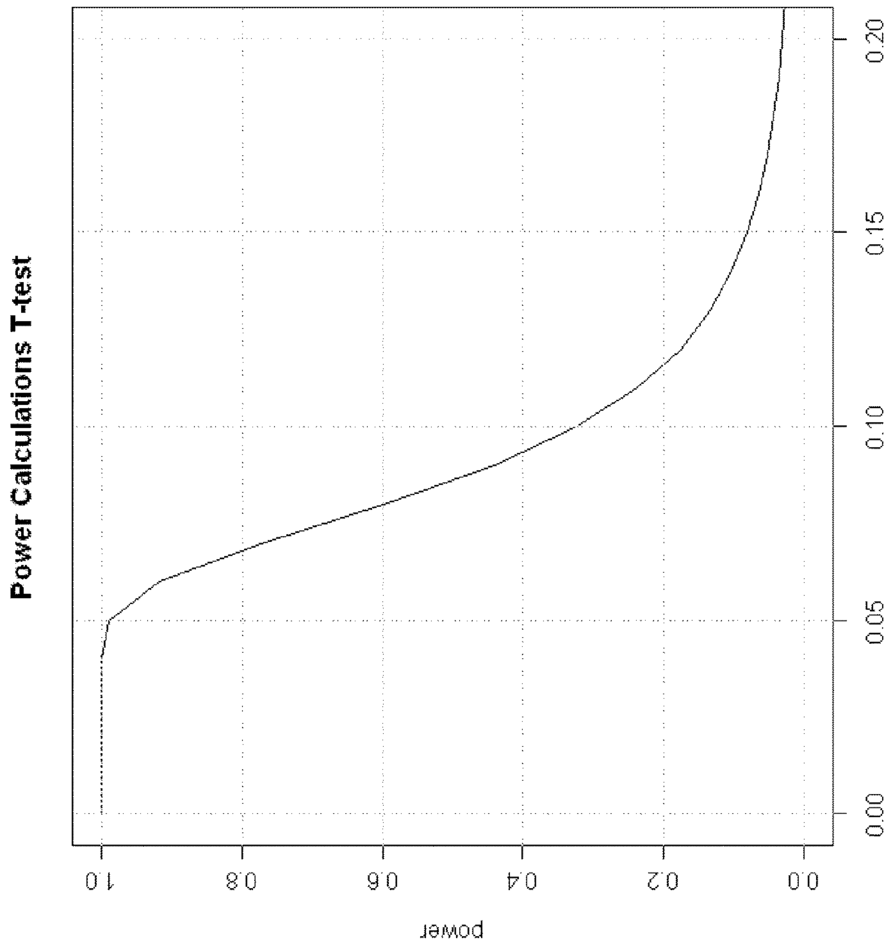

FIG. 157 shows a power calculation t-test for a simulated trisomy 21 diagnosis using the methods of the technology herein. The Figure shows the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less.

Figure 158:
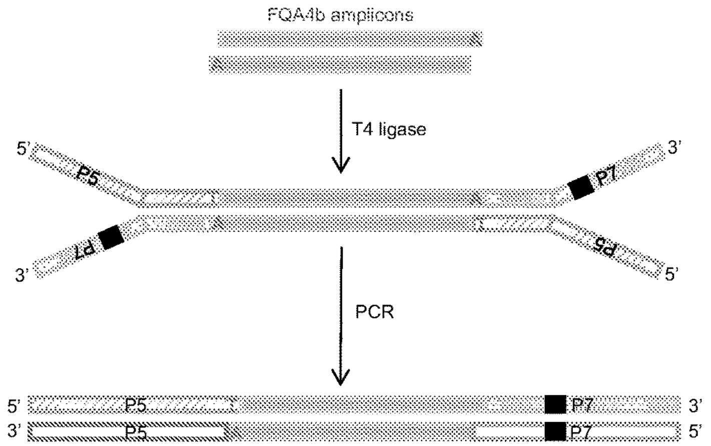

FIG. 158 shows a scheme for ligating a PCR amplicon with Illumina sequencing adaptors.

Figure 159:
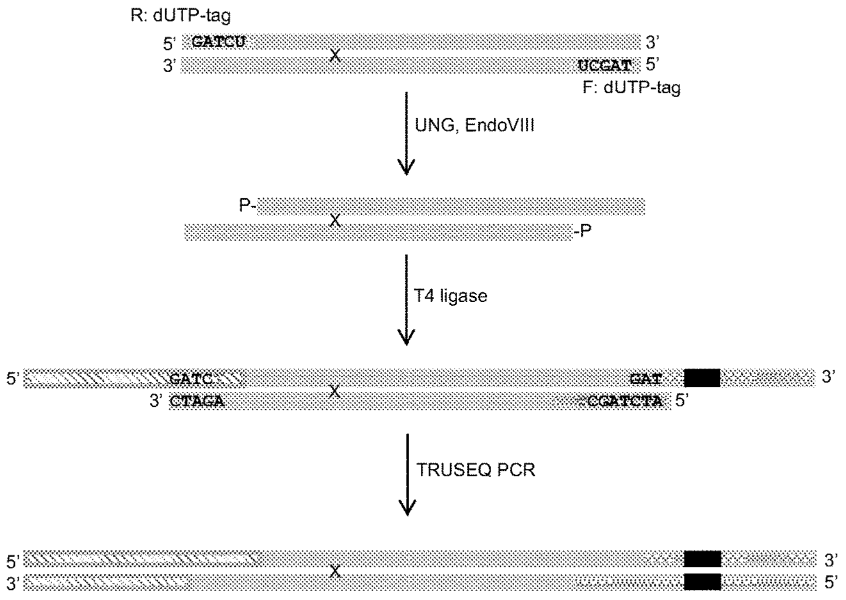

FIG. 159 shows a modified ligation scheme.

Figure 160:
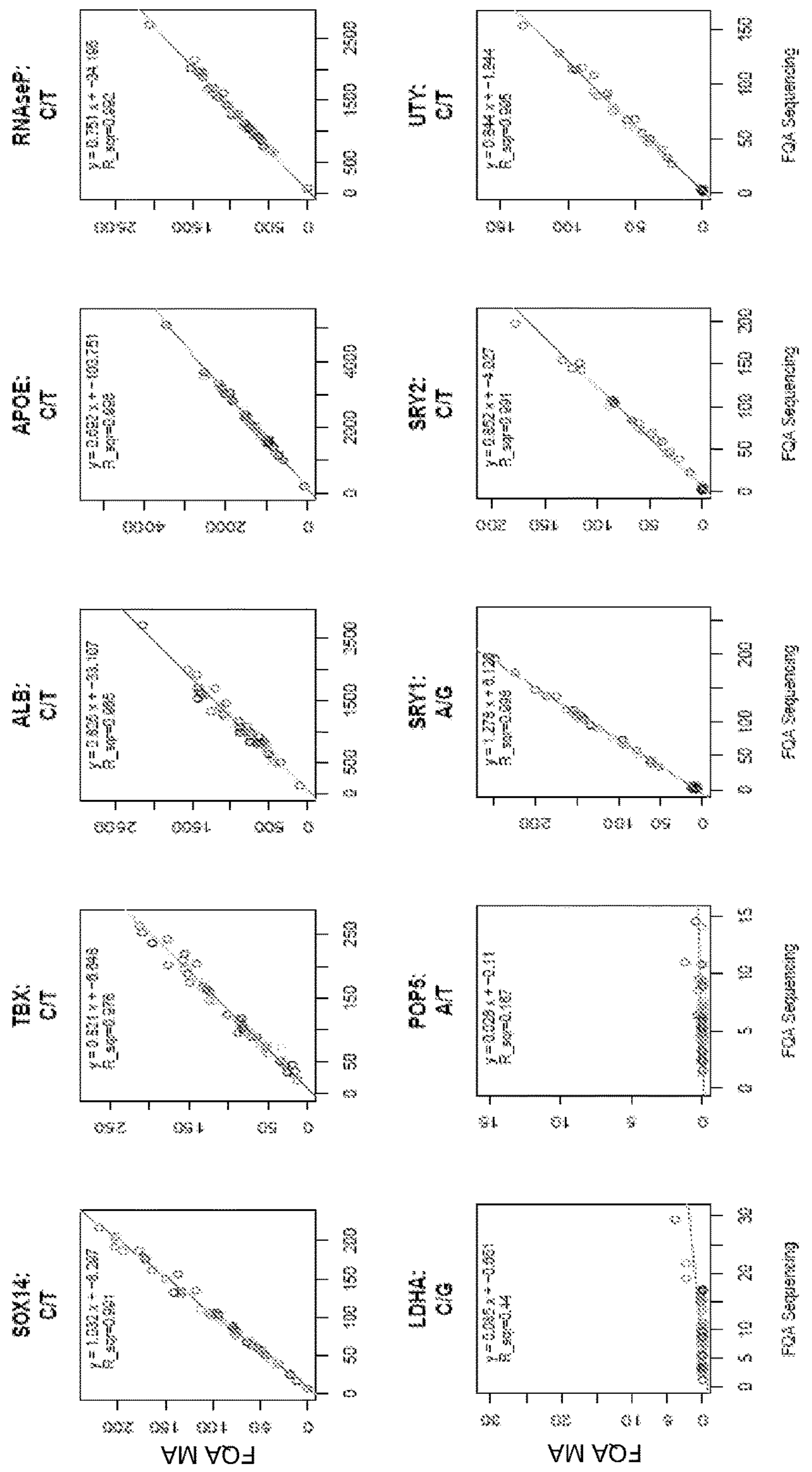

FIG. 160 shows a comparison of copy numbers of individual markers determined by a fetal quantification assay using MPSS (FQA Sequencing; x-axis) with those obtained by a fetal quantification assay using MASSARRAY (FQA MA; y-axis). The results from both methods were highly correlated ($R^2$>0.97). In some cases, platform-specific allele bias resulted in slight copy number differences and slopes of the linear fit which deviated from 1.

Figure 161:
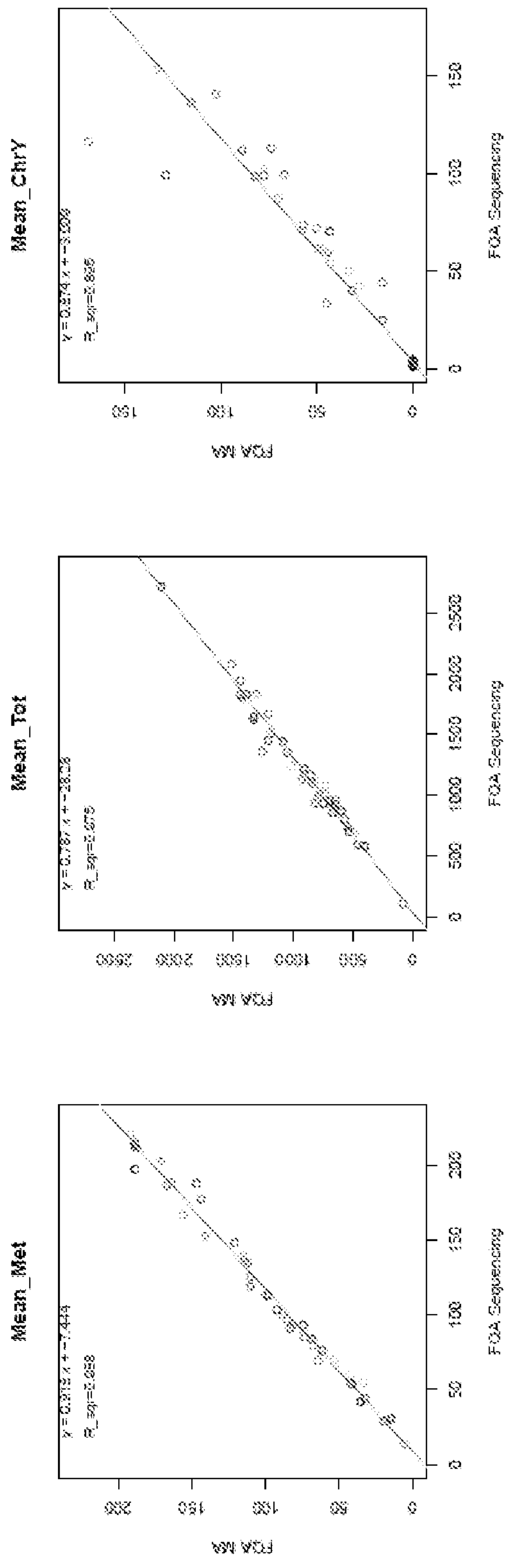

FIG. 161 shows a comparison of mean copy numbers for each of the marker groups determined by a fetal quantification assay using MPSS (FQA Sequencing; x-axis) with those obtained by a fetal quantification assay using MASSARRAY (FQA MA; y-axis).

Figure 162:
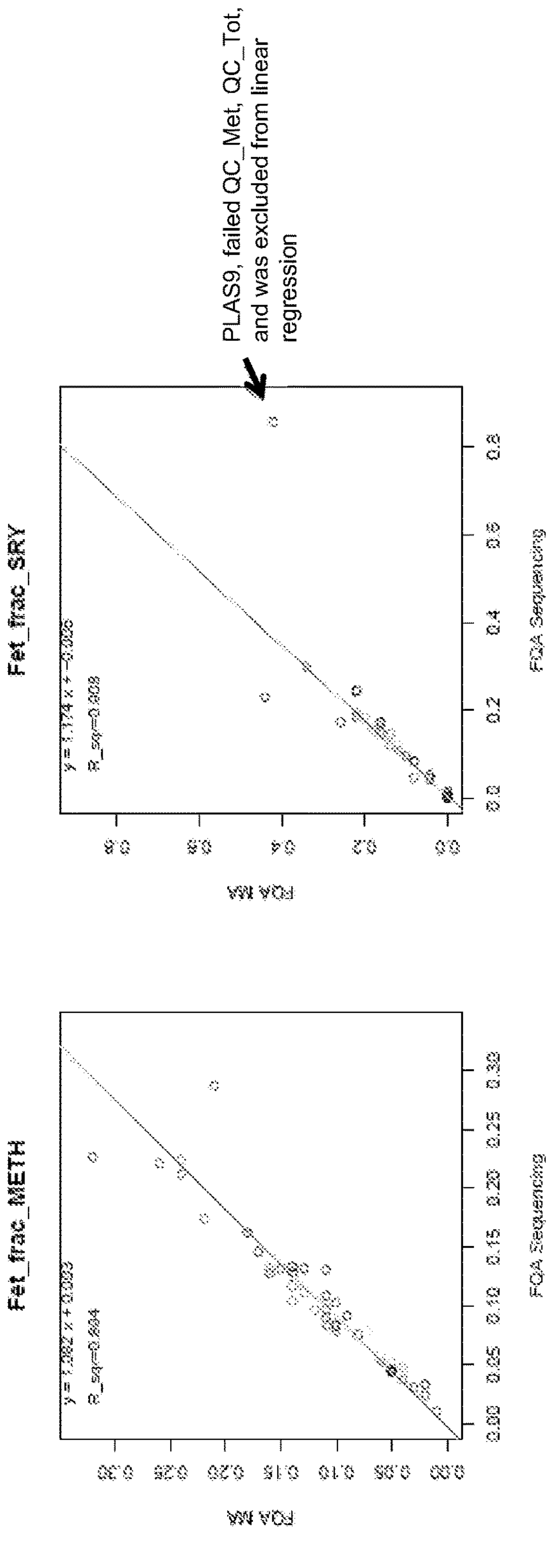

FIG. 162 shows a comparison of fetal fractions derived from either methylation (left) or Y-chromosome markers determined by a fetal quantification assay using MPSS (FQA Sequencing; x-axis) with those obtained by a fetal quantification assay using MASSARRAY (FQA MA; y-axis).

FIG. 163 shows an example of a likelihood chart for an informative fetal/maternal genotype combination.

Figure 164:
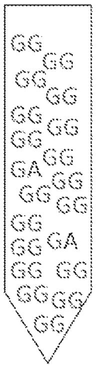

FIG. 164 shows an embodiment of a possible distribution of maternal and paternal alleles. In such an embodiment a fetus with a homozygous mother (GG) and heterozygous father (GA) has a 50% probability of having genotype GA. In some embodiments the paternal allele A is only observed in the fetal component of ccf DNA from plasma of a pregnant mother.

Figure 165:
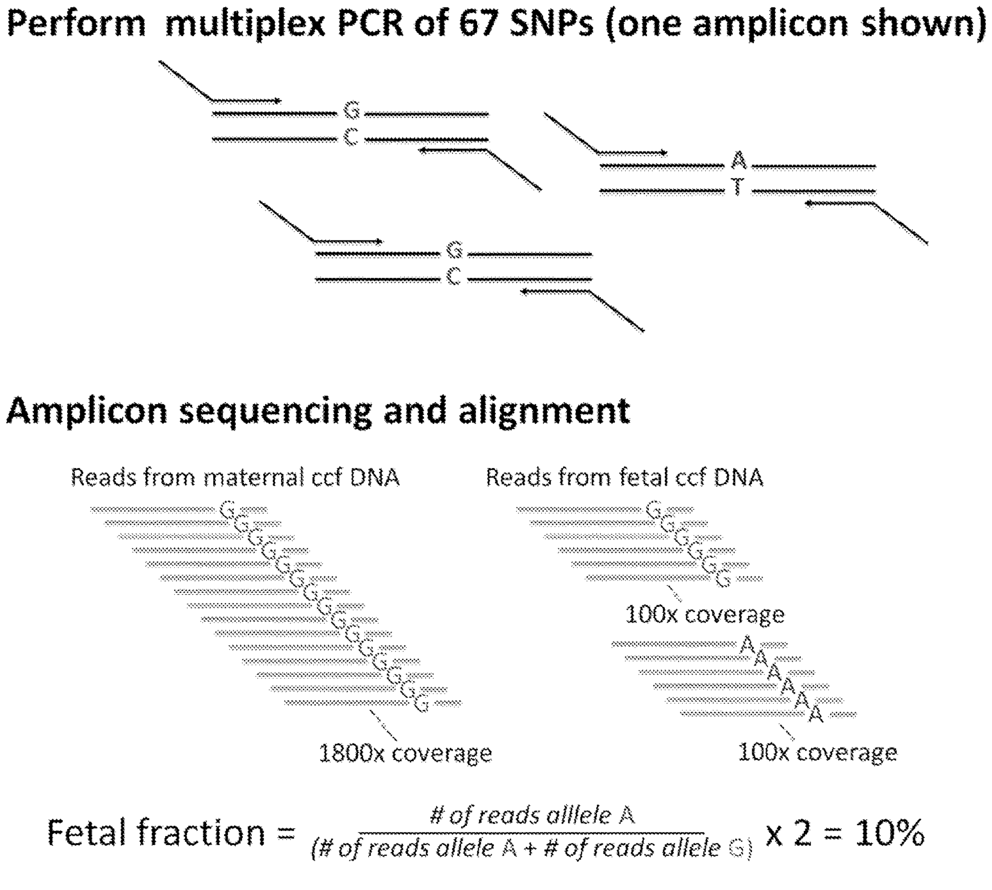

FIG. 165 shows one embodiment for calculating fetal fraction by MPSS. In this example ccf DNA from plasma of a pregnant mother with a 10% fetal fraction is targeted for 67 SNPs and sequenced at a coverage of 2000×. For the SNP shown, the mother has a genotype of GG and the fetus has a genotype of GA. In some embodiments the maternal allele G would be expected to be sequenced at a coverage of 1800×. In some embodiments the fetal alleles, G (derived from the mother) and A (derived from the father), would be expected to be sequenced at a coverage of 100×. In some embodiments the fetal fraction is calculated by calculating the fraction of paternal coverage to total coverage and multiplying by 2.

Figure 166:
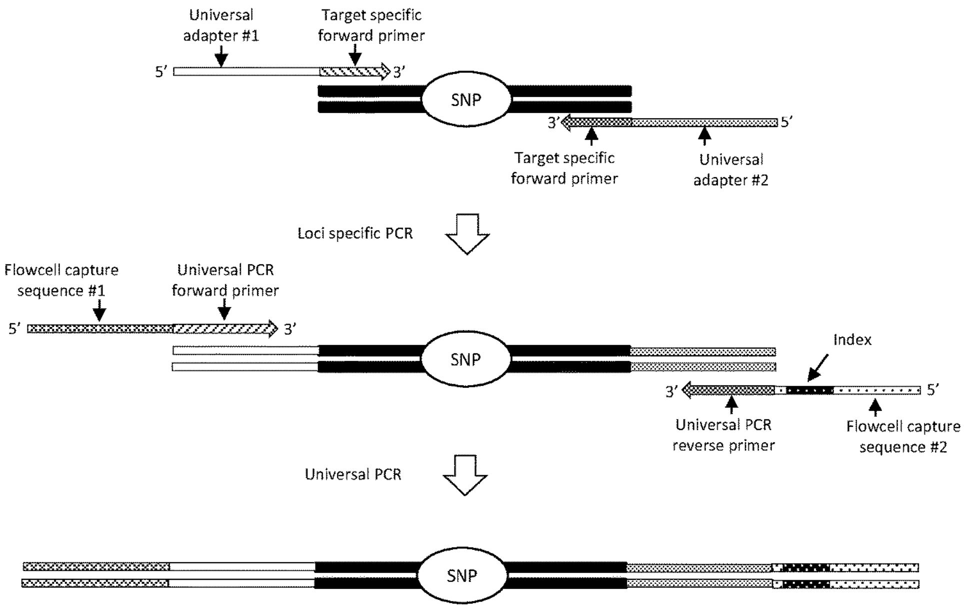

FIG. 166 illustrates a scheme for multiplexed amplicon library generation and sequencing. Loci-specific PCR amplifies targeted sequences each containing a single SNP. The Loci-specific PCR simultaneously incorporates a tag that can be used as a template for primers in a subsequent universal PCR. The universal PCR incorporates full length flowcell capture sequences and an index sequence to each amplicon.

Figure 167:
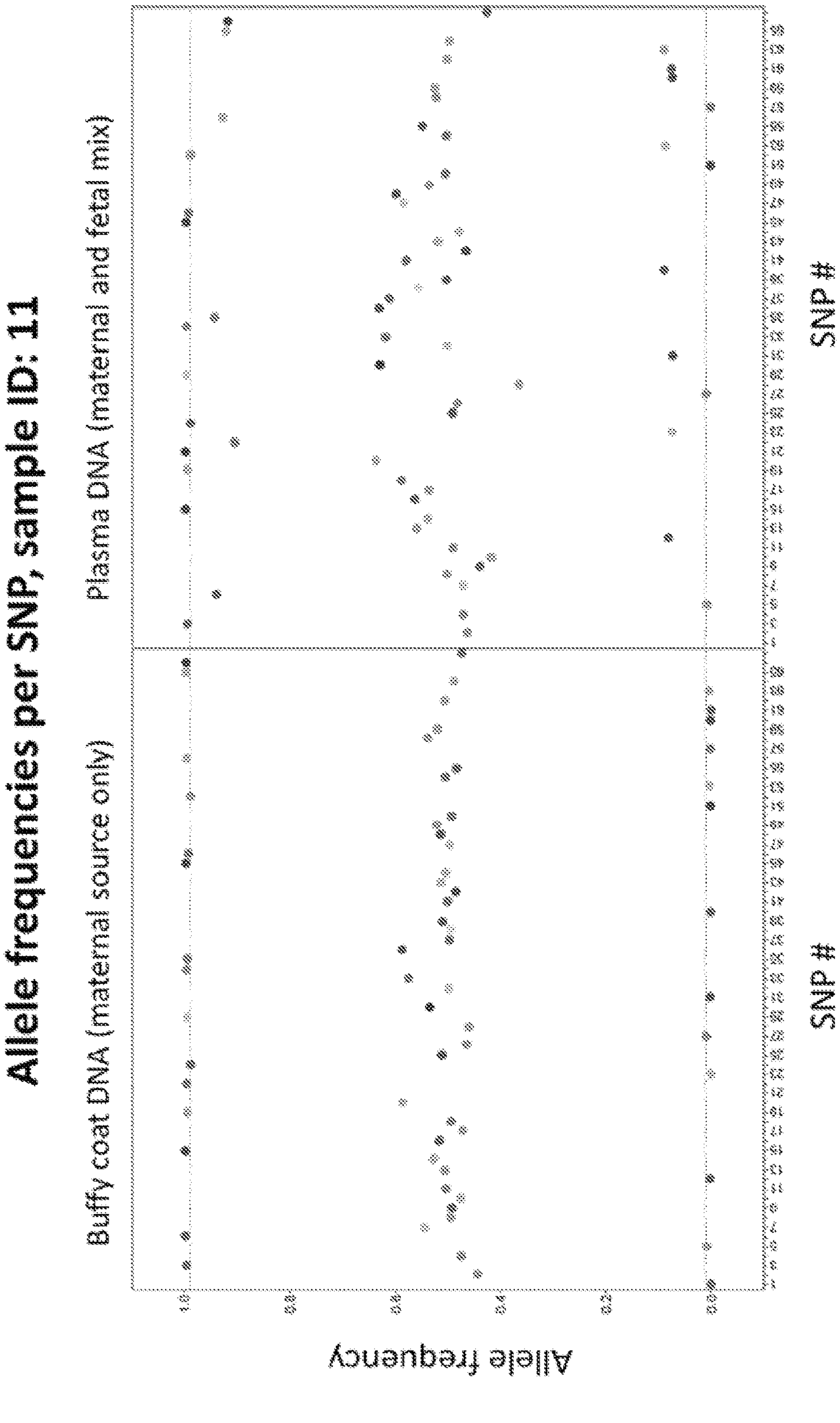

FIG. 167 shows allele frequencies per SNP for multiple samples. Each data-point on the X-axis corresponds to a targeted SNP while the Y-axis shows the measured allele frequency for each SNP. The plot is grouped into allele frequencies measured for buffy coat (maternal genotypes only) and the paired pregnant plasma DNA (maternal and fetal genotypes). Dotted lines show allele frequencies of 0.01 and 0.99 which distinguish homozygote allele frequencies from putative Type 1 allele frequencies. Type 1 informative genotypes are expected to have allele frequencies between 0.01-0.25 or between 0.75-0.99. For example, SNP #12 is <0.01 in buffy coat sample but >0.01 in plasma DNA indicating that SNP #12 is an informative genotype.

Figure 168:
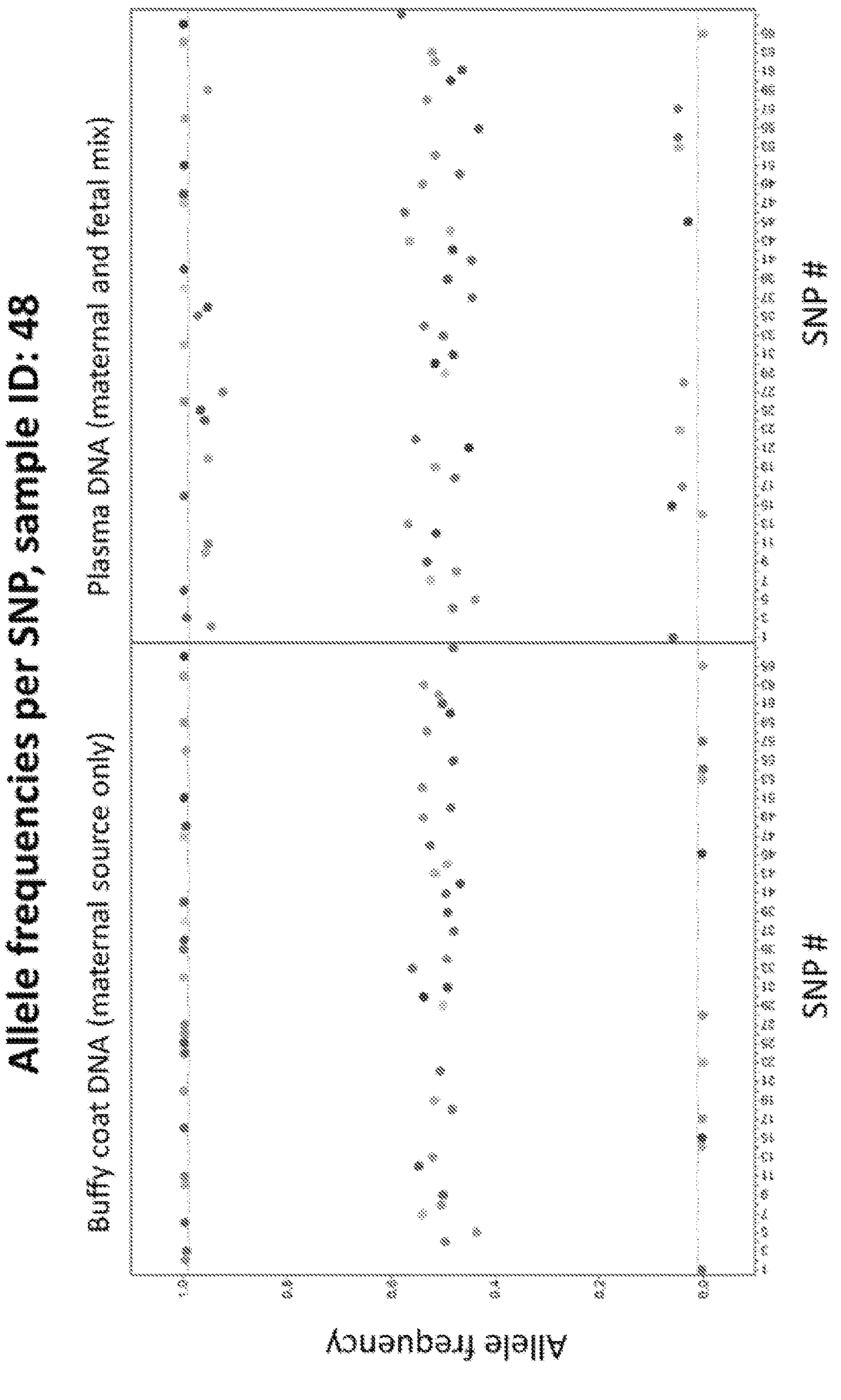

FIG. 168 shows allele frequencies per SNP for multiple samples. Each data-point on the X-axis corresponds to a targeted SNP while the Y-axis shows the measured allele frequency for each SNP. The plot is grouped into allele frequencies measured for buffy coat (maternal genotypes only) and the paired pregnant plasma DNA (maternal and fetal genotypes). Dotted lines show allele frequencies of 0.01 and 0.99 which distinguish homozygote allele frequencies from putative Type 1 allele frequencies. Type 1 informative genotypes are expected to have allele frequencies between 0.01-0.25 or between 0.75-0.99. For example, SNP #1 is >0.99 in buffy coat sample but <0.99 in plasma DNA suggesting that SNP #1 is an informative genotype.

Figure 169:
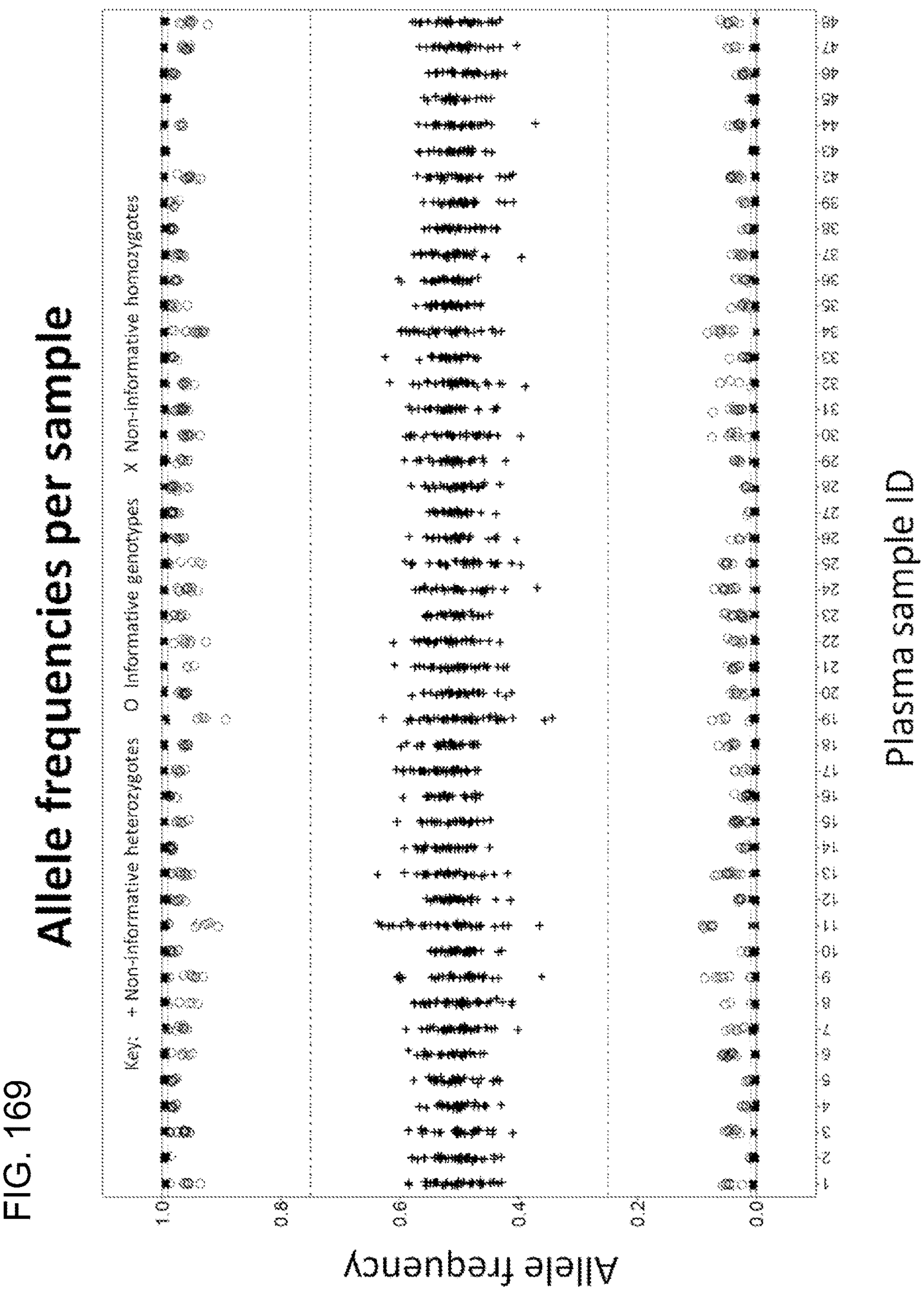

FIG. 169 shows allele frequencies per sample for a collection of 46 samples. Each data-point on the X-axis corresponds to a pregnant plasma DNA sample while the Y-axis shows the measured allele frequencies for 67 targeted SNPs. Dotted lines show allele frequencies of 0.01, 0.25, 0.75 and 0.99. Type 1 informative genotypes (marker: ○) were defined to have allele frequencies between 0.01-0.25 or between 0.75-0.99. Non-informative homozygotes (marker: X) have allele frequencies <0.01 or >0.99. Non-informative heterozygotes (marker: +) have allele frequencies between 0.25-0.75.

Figure 170:
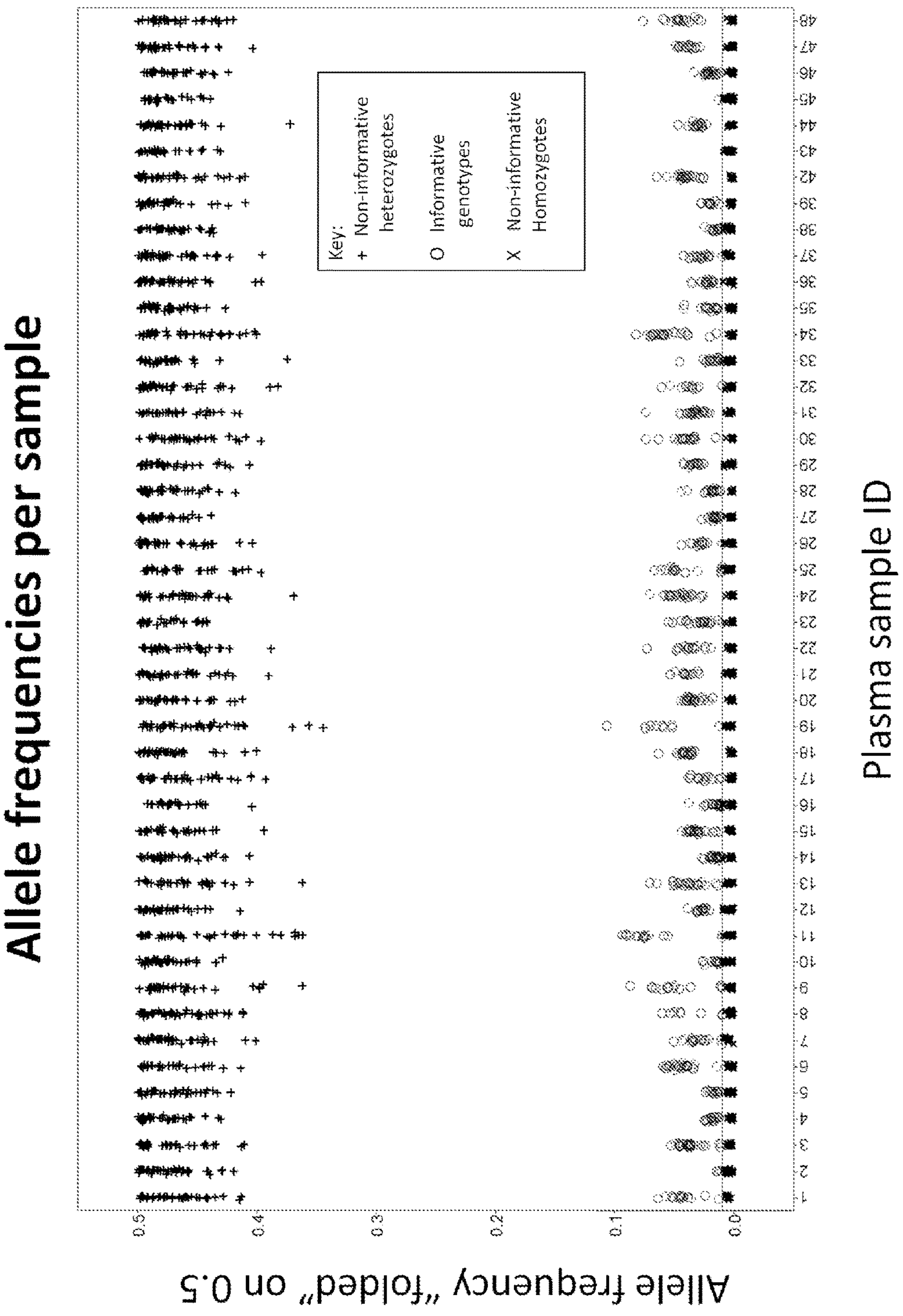

FIG. 170 shows allele frequencies per sample (folded on 0.5, i.e., if the allele frequency is greater than 0.5, subtract the allele frequency value from 1) for a collection of 46 samples. Each data-point on the X-axis corresponds to a pregnant plasma DNA sample while the Y-axis shows the measured allele frequencies for 67 targeted SNPs folded on 0.5. Dotted line shows allele frequency of 0.01. Type 1 informative genotypes (marker: 0) have allele frequencies between 0.01-0.25. Non-informative homozygotes (marker: X) have allele frequencies <0.01. Non-informative heterozygotes (marker: +) have allele frequencies between 0.25-0.5.

Figure 171:
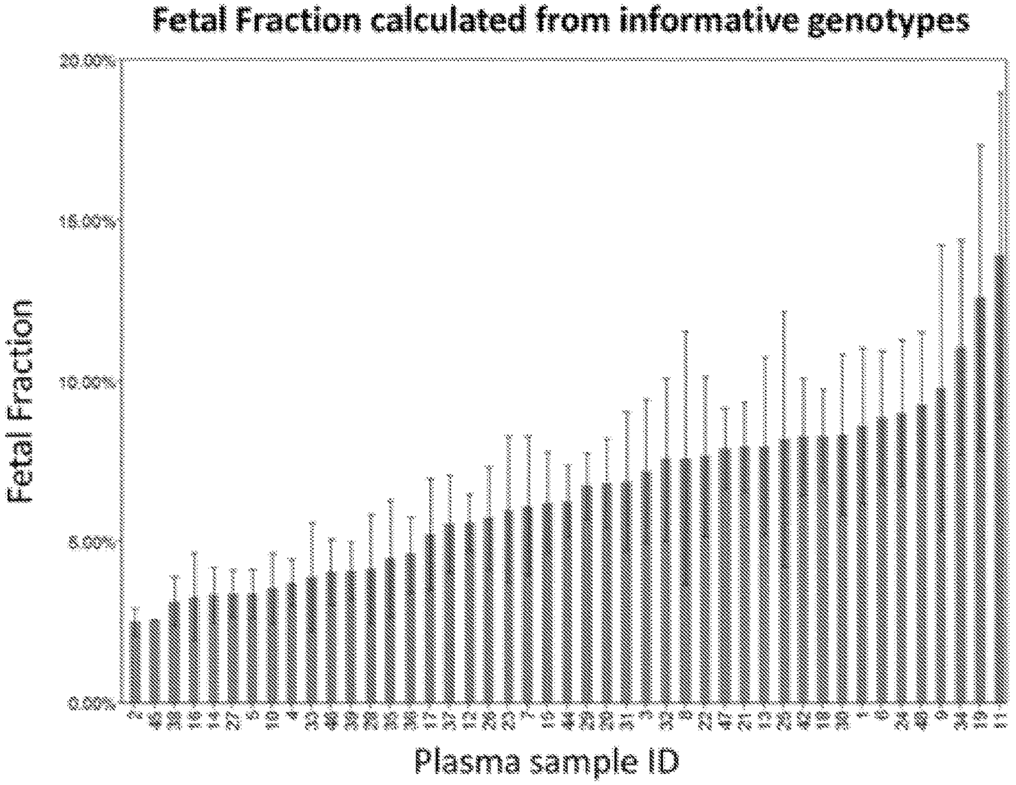

FIG. 171 shows fetal fraction values calculated from informative genotypes for 46 samples. Each data-point on the X-axis corresponds to a pregnant plasma DNA sample while the Y-axis shows the measured fetal fraction. The error bars correspond to the standard deviation of the fetal fraction calculated by individual informative SNPs. The fetal fractions are ordered from low fetal fraction to high.

Figure 172:
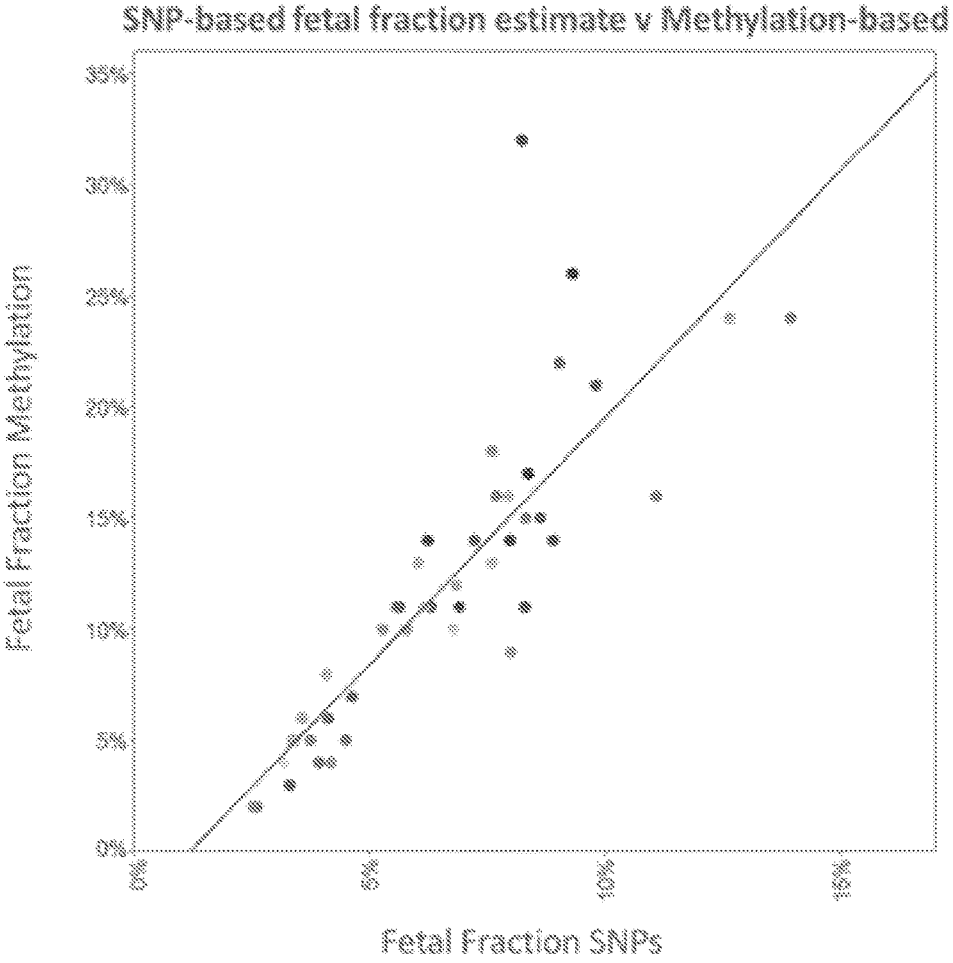

FIG. 172 shows a correlation plot for SNP-based fetal fraction estimates versus methylation-based fetal fraction estimates. Each data-point on the X-axis corresponds to the fetal fraction measured from 67 targeted SNPs. Each data-point on the Y-axis corresponds to the fetal fraction from a methylation-based estimate. There are 46 data-points. The line shows the linear fit of the correlation between the SNP-based estimate of the fetal fraction and the methylation-based estimate ($R^2$=0.72).

Figure 173:
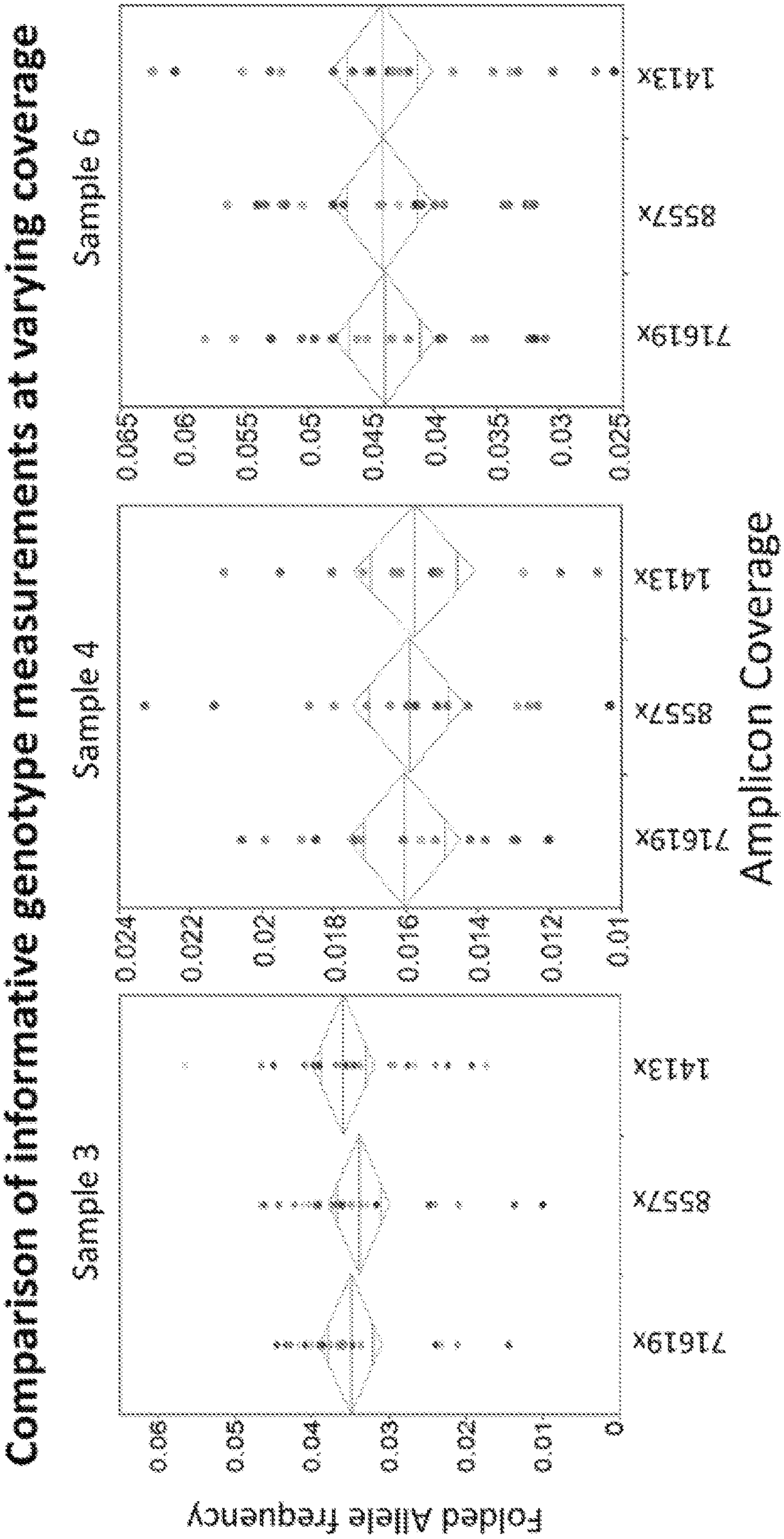

FIG. 173 shows a comparison of informative genotype measurements at varying sequencing coverage. Each group on the X-axis corresponds to a sequenced sample with mean amplicon coverage of 71619×, 8557× and 1413×, respectively. Each data-point on the Y-axis corresponds to the allele frequency (folded on 0.5) of informative genotypes assigned from 67 targeted SNPs. Diamond plots show mean folded allele frequencies of informative genotypes ±1 standard deviation. Each plot shows the result from 1 of 3 samples.

Figure 174:
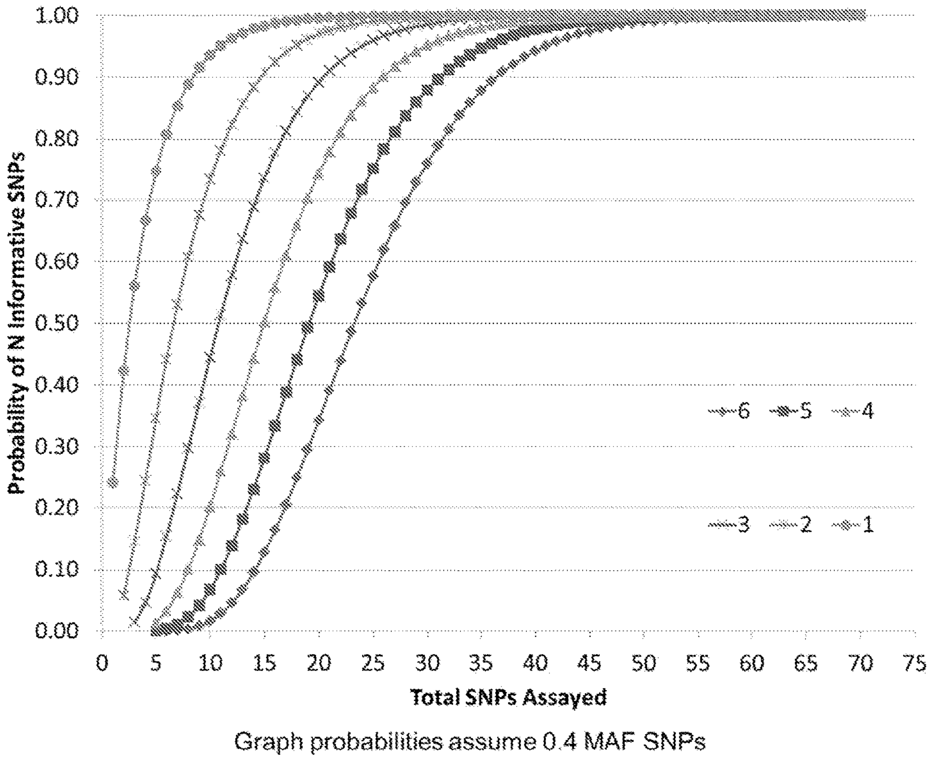

FIG. 174 shows probabilities of the number of informative SNPs for each of the selected thresholds (1-6 informative SNPs) at increasing numbers of total SNPs assayed. Each data-point on the X-axis corresponds to the total number of SNPs assayed. Each data-point on the y-axis corresponds to the probability of detecting N number of informative SNPs. The six curves from left to right show the probability of detecting 1-6 informative genotypes, respectively. Probabilities assume a minor allele frequency of 0.4 for each SNP in the population sampled.

Figure 175:
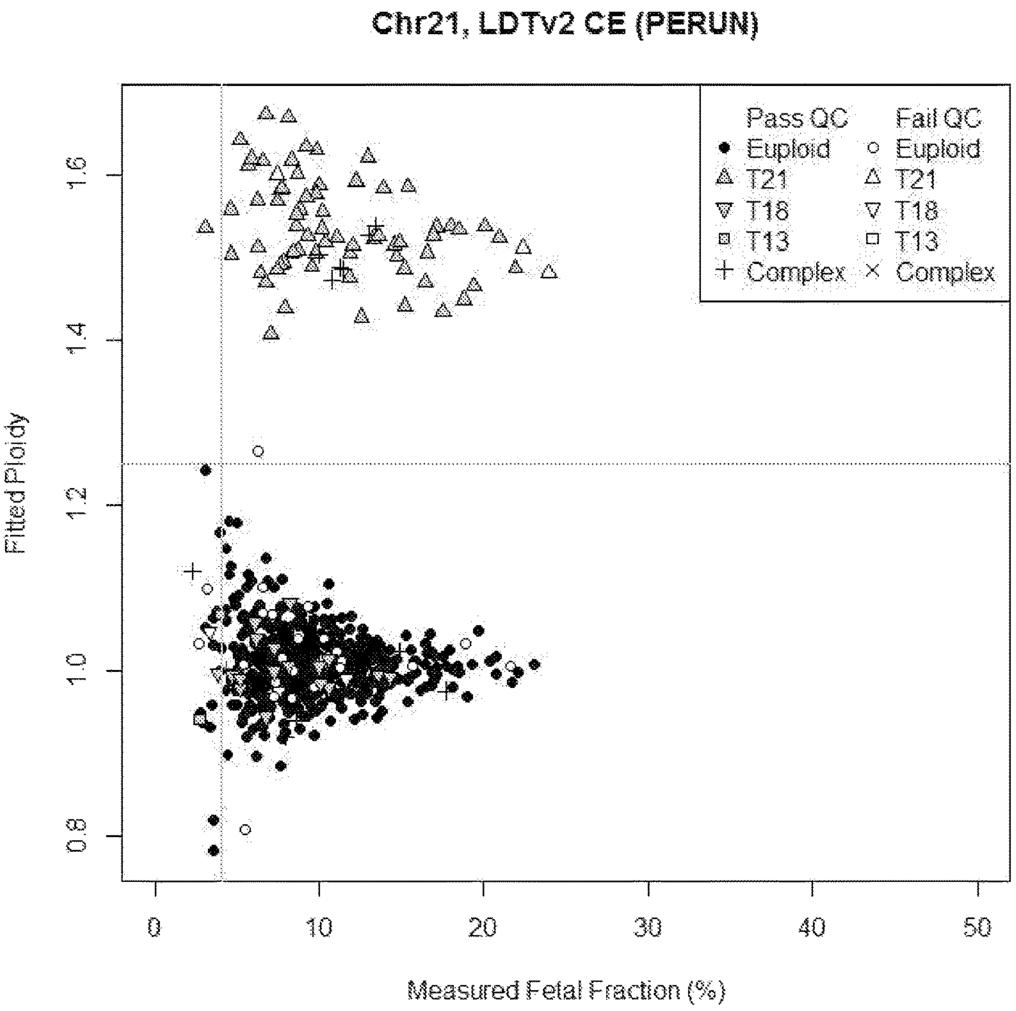

FIG. 175 shows fitted ploidy (y axis) for chromosome 21 derived from PERUN profiles of chr21 in male LDTv2CE pregnancies. The input fetal fraction (x axis) was derived from PERUN chromosome Y profiles. Green data points: euploids, red: T21, blue: T18, solid black: T13. Solid triangles: QC failures. Hollow black circles: excluded samples.

Figure 176:
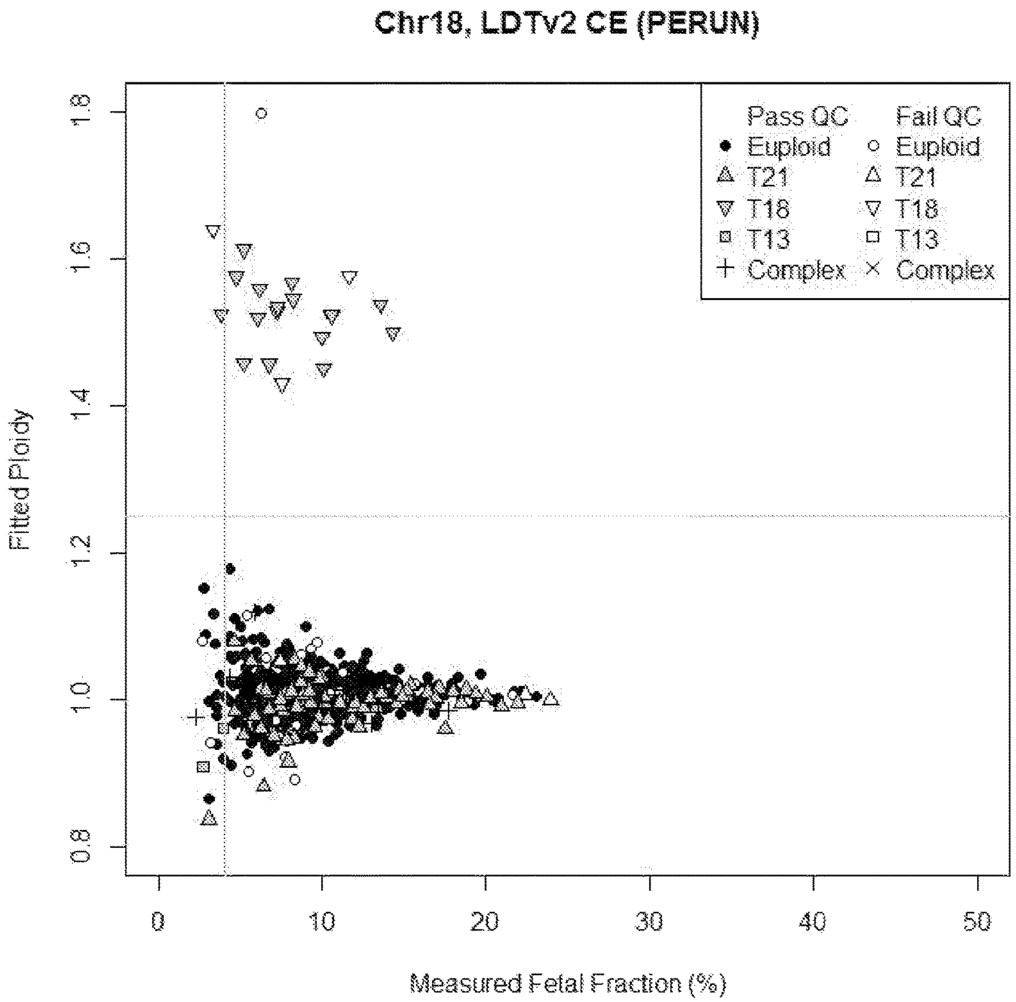

FIG. 176 shows fitted ploidy (y axis) for chromosome 18 derived from PERUN profiles of chr18 in male LDTv2CE pregnancies. The input fetal fraction (x axis) was derived from PERUN chromosome Y profiles. Green data points: euploids, red: T21, blue: T18, solid black: T13. Solid triangles: QC failures. Hollow black circles: excluded samples.

Figure 177:
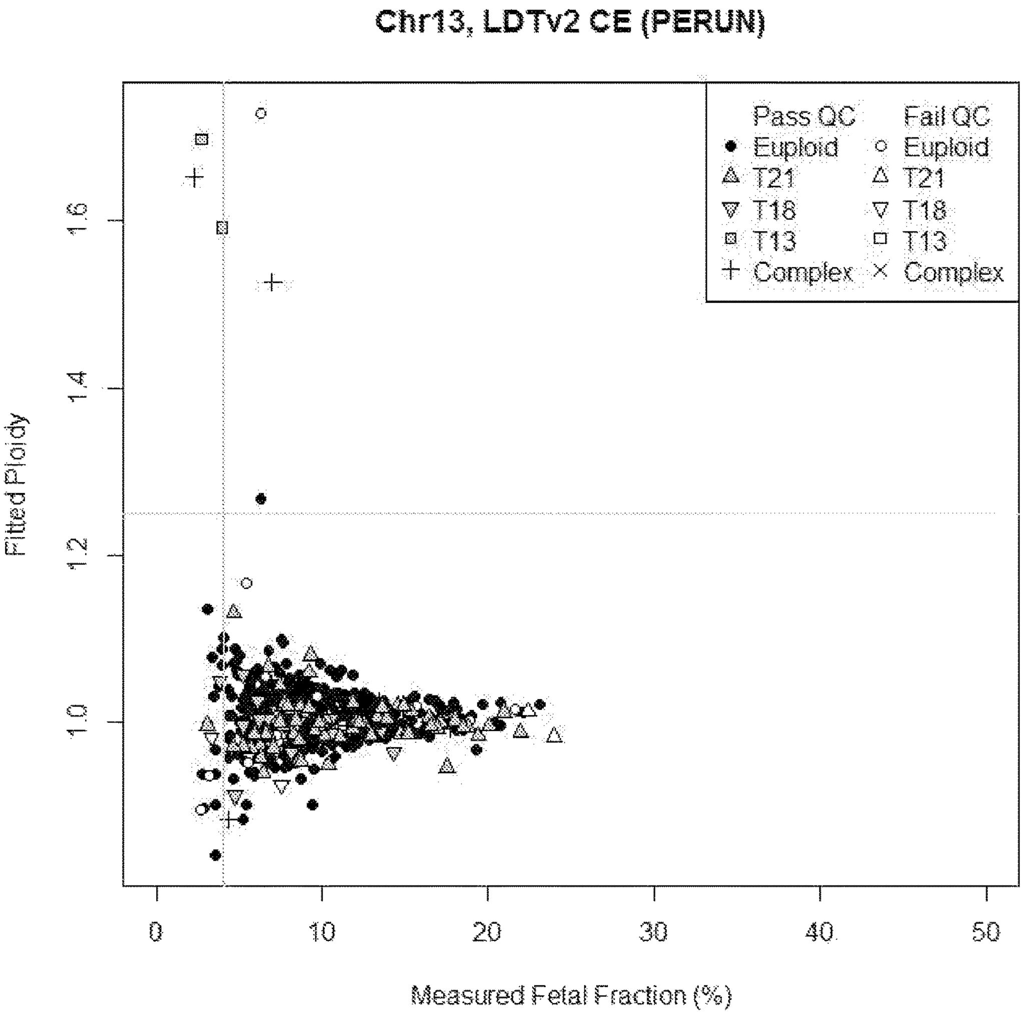

FIG. 177 show fitted ploidy (y axis) for chromosome 13 derived from PERUN profiles of chr21 in male LDTv2CE pregnancies. The input fetal fraction (x axis) was derived from PERUN chromosome Y profiles. Green data points: euploids, red: T21, blue: T18, solid black: T13. Solid triangles: QC failures. Hollow black circles: excluded samples.

Figure 178:
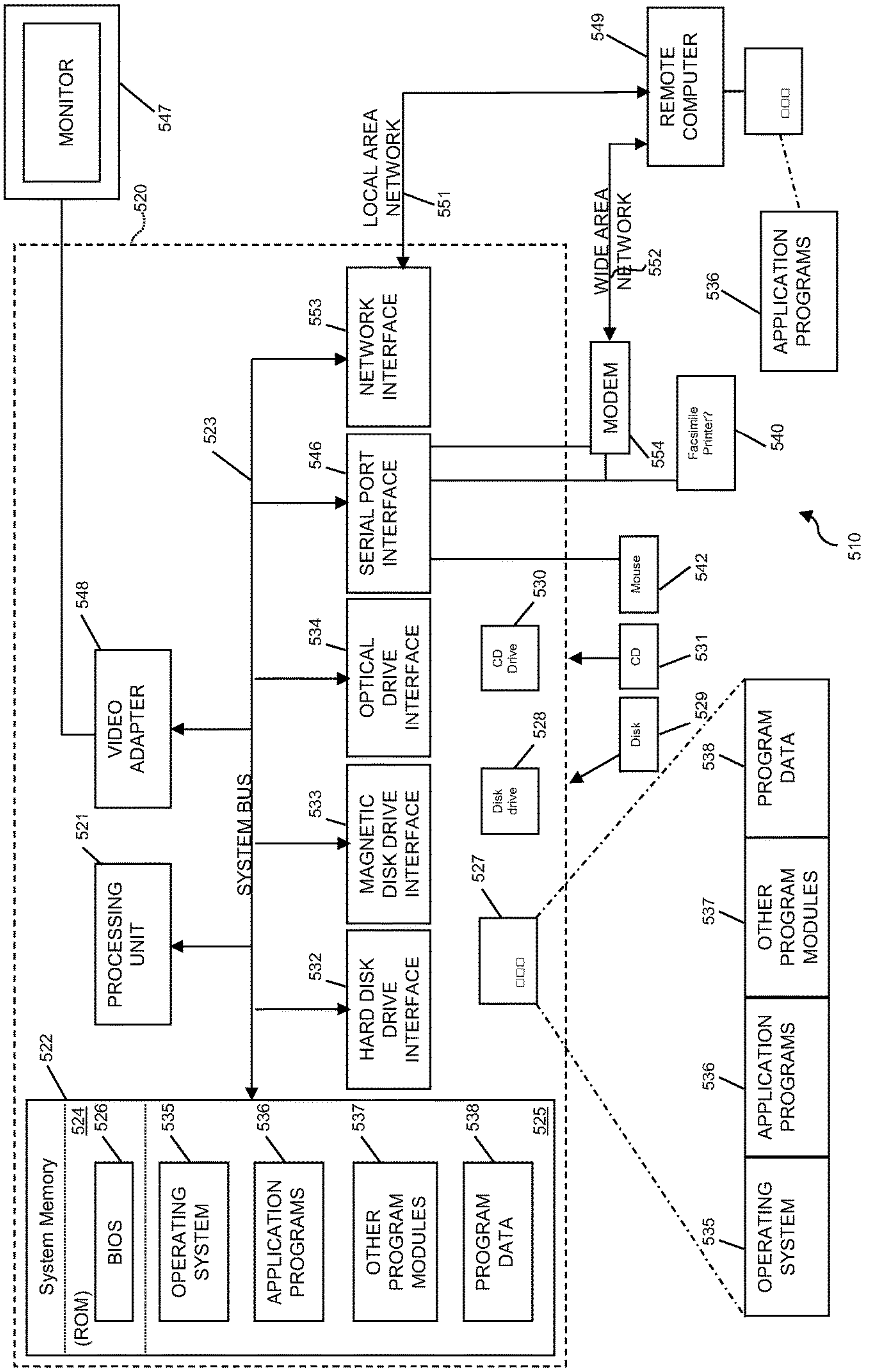

FIG. 178 shows an illustrative embodiment of a system in which certain embodiments of the technology may be implemented.

DEFINITIONS

The term "pregnancy-associated disorder," as used in this application, refers to any condition or disease that may affect a pregnant woman, the fetus, or both the woman and the fetus. Such a condition or disease may manifest its symptoms during a limited time period, e.g., during pregnancy or delivery, or may last the entire life span of the fetus following its birth. Some examples of a pregnancy-associated disorder include ectopic pregnancy, preeclampsia, preterm labor, RhD incompatibility, fetal chromosomal abnormalities such as trisomy 21, and genetically inherited fetal disorders such as cystic fibrosis, beta-thalassemia or other monogenic disorders. The compositions and processes described herein are particularly useful for diagnosis, prognosis and monitoring of pregnancy-associated disorders associated with quantitative abnormalities of fetal DNA in maternal plasma/serum, including but not limited to, preeclampsia (Lo et al., Clin. Chem. 45:184-188, 1999 and Zhong et al., Am. J. Obstet. Gynecol. 184:414-419, 2001), fetal trisomy (Lo et al., Clin. Chem. 45:1747-1751, 1999 and Zhong et al., Prenat. Diagn. 20:795-798, 2000) and hyperemesis gravidarum (Sekizawa et al., Clin. Chem. 47:2164-2165, 2001). For example, an elevated level of fetal nucleic acid in maternal blood (as compared to a normal pregnancy or pregnancies) may be indicative of a preeclamptic pregnancy. Further, the ability to enrich fetal nucleic from a maternal sample may prove particularly useful for the noninvasive prenatal diagnosis of autosomal recessive diseases such as the case when a mother and father share an identical disease causing mutation, an occurrence previously perceived as a challenge for maternal plasma-based non-trisomy prenatal diagnosis.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. For example, the nucleic acids provided in SEQ ID NOs: 1-261 (see Tables 4A-4C) can be in any form useful for conducting processes herein (e.g., linear, circular, supercoiled, single-stranded, double-stranded and the like) or may include variations (e.g., insertions, deletions or substitutions) that do not alter their utility as part of the present technology. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

A "nucleic acid comprising one or more CpG sites" or a "CpG-containing genomic sequence" as used herein refers to a segment of DNA sequence at a defined location in the genome of an individual such as a human fetus or a pregnant woman. Typically, a "CpG-containing genomic sequence" is at least 15 nucleotides in length and contains at least one cytosine. Preferably, it can be at least 30, 50, 80, 100, 150, 200, 250, or 300 nucleotides in length and contains at least 2, 5, 10, 15, 20, 25, or 30 cytosines. For anyone "CpG-containing genomic sequence" at a given location, e.g., within a region centering around a given genetic locus (see Tables 1A-1C), nucleotide sequence variations may exist from individual to individual and from allele to allele even for the same individual. Typically, such a region centering around a defined genetic locus (e.g., a CpG island) contains the locus as well as upstream and/or downstream sequences. Each of the upstream or downstream sequence (counting from the 5' or 3' boundary of the genetic locus, respectively) can be as long as 10 kb, in other cases may be as long as 5 kb, 2 kb, 1 kb, 500 bp, 200 bp, or 100 bp. Furthermore, a "CpG-containing genomic sequence" may encompass a nucleotide sequence transcribed or not transcribed for protein production, and the nucleotide sequence can be an inter-gene sequence, intra-gene sequence, protein-coding sequence, a non protein-coding sequence (such as a transcription promoter), or a combination thereof.

As used herein, a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring, however, for purposes herein, thymine is not considered a methylated nucleotide when present in DNA since thymine is a typical nucleotide base of DNA. Typical nucleoside bases for DNA are thymine, adenine, cytosine and guanine. Typical bases for RNA are uracil, adenine, cytosine and guanine. Correspondingly a "methylation site" is the location in the target gene nucleic acid region where methylation has, or has the possibility of occurring. For example a location containing CpG is a methylation site where the cytosine may or may not be methylated.

As used herein, a "CpG site" or "methylation site" is a nucleotide within a nucleic acid that is susceptible to methylation either by natural occurring events in vivo or by an event instituted to chemically methylate the nucleotide in vitro.

As used herein, a "methylated nucleic acid molecule" refers to a nucleic acid molecule that contains one or more methylated nucleotides that is/are methylated.

A "CpG island" as used herein describes a segment of DNA sequence that comprises a functionally or structurally deviated CpG density. For example, Yamada et al. (Genome Research 14:247-266, 2004) have described a set of standards for determining a CpG island: it must be at least 400 nucleotides in length, has a greater than 50% GC content, and an OCF/ECF ratio greater than 0.6. Others (Takai et al., Proc. Natl. Acad. Sci. U.S.A. 99:3740-3745, 2002) have defined a CpG island less stringently as a sequence at least 200 nucleotides in length, having a greater than 50% GC content, and an OCF/ECF ratio greater than 0.6.

The term "epigenetic state" or "epigenetic status" as used herein refers to any structural feature at a molecular level of a nucleic acid (e.g., DNA or RNA) other than the primary nucleotide sequence. For instance, the epigenetic state of a genomic DNA may include its secondary or tertiary structure determined or influenced by, e.g., its methylation pattern or its association with cellular proteins.

The term "methylation profile" "methylation state" or "methylation status," as used herein to describe the state of methylation of a genomic sequence, refers to the characteristics of a DNA segment at a particular genomic locus relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation due to, e.g., difference in the origin of the alleles. The term "methylation" profile" or "methylation status" also refers to the relative or absolute concentration of methylated C or unmethylated C at any particular stretch of residues in a biological sample. For example, if the cytosine (C) residue(s) within a DNA sequence are methylated it may be referred to as "hypermethylated"; whereas if the cytosine (C) residue(s) within a DNA sequence are not methylated it may be referred to as "hypomethylated". Likewise, if the cytosine (C) residue(s) within a DNA sequence (e.g., fetal nucleic acid) are methylated as compared to another sequence from a different region or from a different individual (e.g., relative to maternal nucleic acid), that sequence is considered hypermethylated compared to the other sequence. Alternatively, if the cytosine (C) residue(s) within a DNA sequence are not methylated as compared to another sequence from a different region or from a different individual (e.g., the mother), that sequence is considered hypomethylated compared to the other sequence. These sequences are said to be "differentially methylated", and more specifically, when the methylation status differs between mother and fetus, the sequences are considered "differentially methylated maternal and fetal nucleic acid".

The term "agent that binds to methylated nucleotides" as used herein refers to a substance that is capable of binding to methylated nucleic acid. The agent may be naturally-occurring or synthetic, and may be modified or unmodified. In one embodiment, the agent allows for the separation of different nucleic acid species according to their respective methylation states. An example of an agent that binds to methylated nucleotides is described in PCT Patent Application No. PCT/EP2005/012707, which published as WO06056480A2 and is hereby incorporated by reference. The described agent is a bifunctional polypeptide comprising the DNA-binding domain of a protein belonging to the family of Methyl-CpG binding proteins (MBDs) and an Fc portion of an antibody (see FIG. 138). The recombinant methyl-CpG-binding, antibody-like protein can preferably bind CpG methylated DNA in an antibody-like manner. That means, the methyl-CpG-binding, antibody-like protein has a high affinity and high avidity to its "antigen", which is preferably DNA that is methylated at CpG dinucleotides. The agent may also be a multivalent MBD (see FIG. 139).

The term "polymorphism" or "polymorphic nucleic acid target" as used herein refers to a sequence variation within different alleles of the same genomic sequence. A sequence that contains a polymorphism is considered a "polymorphic sequence". Detection of one or more polymorphisms allows differentiation of different alleles of a single genomic sequence or between two or more individuals. As used herein, the term "polymorphic marker" or "polymorphic sequence" refers to segments of genomic DNA that exhibit heritable variation in a DNA sequence between individuals. Such markers include, but are not limited to, single nucleotide polymorphisms (SNPs), restriction fragment length polymorphisms (RFLPs), short tandem repeats, such as di-, tri- or tetra-nucleotide repeats (STRs), deletions, duplications, and the like. Polymorphic markers according to the present technology can be used to specifically differentiate between a maternal and paternal allele in the enriched fetal nucleic acid sample.

The terms "single nucleotide polymorphism" or "SNP" as used herein refer to the polynucleotide sequence variation present at a single nucleotide residue within different alleles of the same genomic sequence. This variation may occur within the coding region or non-coding region (i.e., in the promoter or intronic region) of a genomic sequence, if the genomic sequence is transcribed during protein production. Detection of one or more SNP allows differentiation of different alleles of a single genomic sequence or between two or more individuals.

The term "allele" as used herein is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archeabacteria.

The terms "ratio of the alleles" or "allelic ratio" as used herein refer to the ratio of the population of one allele and the population of the other allele in a sample. In some trisomic cases, it is possible that a fetus may be tri-allelic for a particular locus. In such cases, the term "ratio of the alleles" refers to the ratio of the population of any one allele against one of the other alleles, or any one allele against the other two alleles.

The term "non-polymorphism-based quantitative method" as used herein refers to a method for determining the amount of an analyte (e.g., total nucleic acid, Y-chromosome nucleic acid, or fetal nucleic acid) that does not require the use of a polymorphic marker or sequence. Although a polymorphism may be present in the sequence, said polymorphism is not required to quantify the sequence. Examples of non-polymorphism-based quantitative methods include, but are not limited to, RT-PCR, digital PCR, array-based methods, sequencing methods, nanopore-based methods, nucleic acid-bound bead-based counting methods and competitor-based methods where one or more competitors are introduced at a known concentration(s) to determine the amount of one or more analytes. In some embodiments, some of the above exemplary methods (for example, sequencing) may need to be actively modified or designed such that one or more polymorphisms are not interrogated.

As used herein, a "competitor oligonucleotide" or "competitive oligonucleotide" or "competitor" is a nucleic acid polymer that competes with a target nucleotide sequence for hybridization of amplification primers. Often, a competitor has a similar nucleotide sequence as a corresponding target nucleotide sequence. In some cases, a competitor sequence and a corresponding target nucleotide sequence differ by one or more nucleotides. In some cases, a competitor sequence and a corresponding target nucleotide sequence are the same length. In some cases, the competitor optionally has an additional length of nucleotide sequence that is different from the target nucleotide sequence. In some embodiments, a known amount, or copy number, of competitor is used. In some embodiments, two or more competitors are used. In some cases, the two or more competitors possess similar characteristics (e.g. sequence, length, detectable label). In some cases, the two or more competitors possess different characteristics (e.g. sequence, length, detectable label). In some embodiments, one or more competitors are used for a particular region. In some cases, the competitor possesses a characteristic that is unique for each set of competitors for a given region. Often, competitors for different regions possess different characteristics.

A competitor oligonucleotide may be composed of naturally occurring and/or non-naturally occurring nucleotides (e.g., labeled nucleotides), or a mixture thereof. Competitor oligonucleotides suitable for use with embodiments described herein, may be synthesized and labeled using known techniques. Competitor oligonucleotides may be chemically synthesized according to any suitable method known, for example, the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of competitor oligonucleotides can be effected by any suitable method known, for example, native acrylamide gel electrophoresis or by anion-exchange high-performance liquid chromatography (HPLC), for example, as described in Pearson and Regnier, J. Chrom., 255:137-149, 1983.

The terms "absolute amount" or "copy number" as used herein refers to the amount or quantity of an analyte (e.g., total nucleic acid or fetal nucleic acid). The present technology provides compositions and processes for determining the absolute amount of fetal nucleic acid in a mixed maternal sample. Absolute amount or copy number represents the number of molecules available for detection, and may be expressed as the genomic equivalents per unit. The term "concentration" refers to the amount or proportion of a substance in a mixture or solution (e.g., the amount of fetal nucleic acid in a maternal sample that comprises a mixture of maternal and fetal nucleic acid). The concentration may be expressed as a percentage, which is used to express how large/small one quantity is, relative to another quantity as a fraction of 100. Platforms for determining the quantity or amount of an analyte (e.g., target nucleic acid) include, but are not limited to, mass spectrometery, digital PCR, sequencing by synthesis platforms (e.g., pyrosequencing), fluorescence spectroscopy and flow cytometry.

The term "sample" as used herein refers to a specimen containing nucleic acid. Examples of samples include, but are not limited to, tissue, bodily fluid (for example, blood, serum, plasma, saliva, urine, tears, peritoneal fluid, ascitic fluid, vaginal secretion, breast fluid, breast milk, lymph fluid, cerebrospinal fluid or mucosa secretion), umbilical cord blood, chorionic villi, amniotic fluid, an embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, embryonic tissues, lymph fluid, cerebrospinal fluid, mucosa secretion, or other body exudate, fecal matter, an individual cell or extract of the such sources that contain the nucleic acid of the same, and subcellular structures such as mitochondria, using protocols well established within the art.

Fetal DNA can be obtained from sources including but not limited to maternal blood, maternal serum, maternal plasma, fetal cells, umbilical cord blood, chorionic villi, amniotic fluid, urine, saliva, lung lavage, cells or tissues.

The term "blood" as used herein refers to a blood sample or preparation from a pregnant woman or a woman being tested for possible pregnancy. The term encompasses whole blood or any fractions of blood, such as serum and plasma as conventionally defined.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent or agent that "differentially modifies" methylated or non-methylated DNA encompasses any reagent that modifies methylated and/or unmethylated DNA in a process through which distinguishable products result from methylated and non-methylated DNA, thereby allowing the identification of the DNA methylation status. Such processes may include, but are not limited to, chemical reactions (such as a C.fwdarw.U conversion by bisulfite) and enzymatic treatment (such as cleavage by a methylation-dependent endonuclease). Thus, an enzyme that preferentially cleaves or digests methylated DNA is one capable of cleaving or digesting a DNA molecule at a much higher efficiency when the DNA is methylated, whereas an enzyme that preferentially cleaves or digests unmethylated DNA exhibits a significantly higher efficiency when the DNA is not methylated.

The terms "non-bisulfite-based method" and "non-bisulfite-based quantitative method" as used herein refer to any method for quantifying methylated or non-methylated nucleic acid that does not require the use of bisulfite. The terms also refer to methods for preparing a nucleic acid to be quantified that do not require bisulfite treatment. Examples of non-bisulfite-based methods include, but are not limited to, methods for digesting nucleic acid using one or more methylation sensitive enzymes and methods for separating nucleic acid using agents that bind nucleic acid based on methylation status.

The terms "methyl-sensitive enzymes" and "methylation sensitive restriction enzymes" are DNA restriction endonucleases that are dependent on the methylation state of their DNA recognition site for activity. For example, there are methyl-sensitive enzymes that cleave or digest at their DNA recognition sequence only if it is not methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated. As used herein, the terms "cleave", "cut" and "digest" are used interchangeably.

The term "target nucleic acid" as used herein refers to a nucleic acid examined using the methods disclosed herein to determine if the nucleic acid is part of a pregnancy-related disorder or chromosomal abnormality. For example, a target nucleic acid from chromosome 21 could be examined using the methods of the technology herein to detect Down's Syndrome.

The term "control nucleic acid" as used herein refers to a nucleic acid used as a reference nucleic acid according to the methods disclosed herein to determine if the nucleic acid is part of a chromosomal abnormality. For example, a control nucleic acid from a chromosome other than chromosome 21 (herein referred to as a "reference chromosome") could be as a reference sequence to detect Down's Syndrome. In some embodiments, the control sequence has a known or predetermined quantity.

The term "sequence-specific" or "locus-specific method" as used herein refers to a method that interrogates (for example, quantifies) nucleic acid at a specific location (or locus) in the genome based on the sequence composition. Sequence-specific or locus-specific methods allow for the quantification of specific regions or chromosomes.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), where the amino acid residues are linked by covalent peptide bonds.

The term “amino acid” refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

“Primers” as used herein refer to oligonucleotides that can be used in an amplification method, such as a polymerase chain reaction (PCR), to amplify a nucleotide sequence based on the polynucleotide sequence corresponding to a particular genomic sequence, e.g., one located within the CpG island CGI137, PDE9A, or CGI009 on chromosome 21, in various methylation status. At least one of the PCR primers for amplification of a polynucleotide sequence is sequence-specific for the sequence.

The term “template” refers to any nucleic acid molecule that can be used for amplification in the technology herein. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The term “amplification reaction” as used herein refers to a process for copying nucleic acid one or more times. In embodiments, the method of amplification includes but is not limited to polymerase chain reaction, self-sustained sequence reaction, ligase chain reaction, rapid amplification of cDNA ends, polymerase chain reaction and ligase chain reaction, Q-beta phage amplification, strand displacement amplification, or splice overlap extension polymerase chain reaction. In some embodiments, a single molecule of nucleic acid is amplified, for example, by digital PCR.

The term “sensitivity” as used herein refers to the number of true positives divided by the number of true positives plus the number of false negatives, where sensitivity (sens) may be within the range of $0 \leq sens \leq 1$. Ideally, method embodiments herein have the number of false negatives equaling zero or close to equaling zero, so that no subject is wrongly identified as not having at least one chromosome abnormality or other genetic disorder when they indeed have at least one chromosome abnormality or other genetic disorder. Conversely, an assessment often is made of the ability of a prediction algorithm to classify negatives correctly, a complementary measurement to sensitivity. The term “specificity” as used herein refers to the number of true negatives divided by the number of true negatives plus the number of false positives, where sensitivity (spec) may be within the range of $0 \leq spec \leq 1$. Ideally, methods embodiments herein have the number of false positives equaling zero or close to equaling zero, so that no subject wrongly identified as having at least one chromosome abnormality other genetic disorder when they do not have the chromosome abnormality other genetic disorder being assessed. Hence, a method that has sensitivity and specificity equaling one, or 100%, sometimes is selected.

One or more prediction algorithms may be used to determine significance or give meaning to the detection data collected under variable conditions that may be weighed independently of or dependently on each other. The term “variable” as used herein refers to a factor, quantity, or function of an algorithm that has a value or set of values. For example, a variable may be the design of a set of amplified nucleic acid species, the number of sets of amplified nucleic acid species, percent fetal genetic contribution tested, percent maternal genetic contribution tested, type of chromosome abnormality assayed, type of genetic disorder assayed, type of sex-linked abnormalities assayed, the age of the mother and the like. The term “independent” as used herein refers to not being influenced or not being controlled by another. The term “dependent” as used herein refers to being influenced or controlled by another. For example, a particular chromosome and a trisomy event occurring for that particular chromosome that results in a viable being are variables that are dependent upon each other.

One of skill in the art may use any type of method or prediction algorithm to give significance to the data of the present technology within an acceptable sensitivity and/or specificity. For example, prediction algorithms such as Chi-squared test, z-test, t-test, ANOVA (analysis of variance), regression analysis, neural nets, fuzzy logic, Hidden Markov Models, multiple model state estimation, and the like may be used. One or more methods or prediction algorithms may be determined to give significance to the data having different independent and/or dependent variables of the present technology. And one or more methods or prediction algorithms may be determined not to give significance to the data having different independent and/or dependent variables of the present technology. One may design or change parameters of the different variables of methods described herein based on results of one or more prediction algorithms (e.g., number of sets analyzed, types of nucleotide species in each set). For example, applying the Chi-squared test to detection data may suggest that specific ranges of maternal age are correlated to a higher likelihood of having an offspring with a specific chromosome abnormality, hence the variable of maternal age may be weighed differently verses being weighed the same as other variables.

In certain embodiments, several algorithms may be chosen to be tested. These algorithms can be trained with raw data. For each new raw data sample, the trained algorithms will assign a classification to that sample (i.e. trisomy or normal). Based on the classifications of the new raw data samples, the trained algorithms' performance may be assessed based on sensitivity and specificity. Finally, an algorithm with the highest sensitivity and/or specificity or combination thereof may be identified.

DETAILED DESCRIPTION

Provided are methods for determining the fraction of fetal nucleic acid in a test sample derived from a pregnant female with improved accuracy and/or precision. In some embodiments, provided herein are methods of using fetal fraction measurements to determine the presence or absence of a genetic variation in a fetus with improved accuracy and/or precision. In some embodiments the determination of fetal fraction and the determination of the presence or absence of a fetal genetic variation are obtained from the same sample, sequencing run, sequencing reads and/or the same data obtained from the same flow cell. Also provided herein are improved data manipulation methods as well as systems, apparatuses, modules and procedures that, in some embodiments, carry out the methods described herein. In some embodiments identifying a genetic variation sometimes comprises detecting a copy number variation and/or sometimes comprises adjusting an elevation comprising a copy number variation. In some embodiments, an elevation is adjusted providing an identification of one or more genetic variations or variances with a reduced likelihood of a false positive or false negative diagnosis. In some embodiments, identifying a genetic variation by a method described herein can lead to a diagnosis of, or determining a predisposition to, a particular medical condition. Identifying a genetic variance can result in facilitating a medical decision and/or employing a helpful medical procedure.

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods and apparatuses described herein often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman).

Nucleic acid may be isolated from any type of suitable biological specimen or sample (e.g., a test sample). A sample or test sample can be any specimen that is isolated or obtained from a subject (e.g., a human subject, a pregnant female). Non-limiting examples of specimens include fluid or tissue from a subject, including, without limitation, umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo), celocentesis sample, fetal nucleated cells or fetal cellular remnants, washings of female reproductive tract, urine, feces, sputum, saliva, nasal mucous, prostate fluid, lavage, semen, lymphatic fluid, bile, tears, sweat, breast milk, breast fluid, embryonic cells and fetal cells (e.g. placental cells). In some embodiments, a biological sample is a cervical swab from a subject. In some embodiments, a biological sample may be blood and sometimes plasma or serum. As used herein, the term "blood" encompasses whole blood or any fractions of blood, such as serum and plasma as conventionally defined, for example. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain embodiments buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments fetal cells or cancer cells may be included in the sample.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In certain embodiments a fluid or tissue sample is collected from a pregnant female during or just after (e.g., 0 to 72 hours after) giving birth (e.g., vaginal or non-vaginal birth (e.g., surgical delivery)).

Acquisition of Blood Samples and Extraction of DNA

The present technology relates to separating, enriching and analyzing fetal DNA found in maternal blood as a non-invasive means to detect the presence and/or to monitor the progress of a pregnancy-associated condition or disorder. Thus, the first steps of practicing the technology herein are to obtain a blood sample from a pregnant woman and extract DNA from the sample.

Acquisition of Blood Samples

A blood sample is obtained from a pregnant woman at a gestational age suitable for testing using a method of the present technology. The suitable gestational age may vary depending on the disorder tested, as discussed below. Collection of blood from a woman is performed in accordance with the standard protocol hospitals or clinics generally follow. An appropriate amount of peripheral blood, e.g., typically between 5-50 ml, is collected and may be stored according to standard procedure prior to further preparation. Blood samples may be collected, stored or transported in a manner known to the person of ordinary skill in the art to minimize degradation or the quality of nucleic acid present in the sample.

Preparation of Blood Samples

The analysis of fetal DNA found in maternal blood according to the present technology may be performed using, e.g., the whole blood, serum, or plasma. The methods for preparing serum or plasma from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

In some embodiments, the sample may first be enriched or relatively enriched for fetal nucleic acid by one or more methods. For example, the discrimination of fetal and maternal DNA can be performed using the compositions and processes of the present technology alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

Nucleic Acid Isolation and Processing

Nucleic acid may be derived from one or more sources (e.g., cells, serum, plasma, buffy coat, lymphatic fluid, skin, soil, and the like) by methods known in the art. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

The terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome or fragment thereof (e.g., a nucleic acid sample may be from one chromosome of a sample obtained from a diploid organism). In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term “extracellular nucleic acid” as used herein can refer to nucleic acid isolated from a source having substantially no cells and also is referred to as “cell-free” nucleic acid and/or “cell-free circulating” nucleic acid. Extracellular nucleic acid can be present in and obtained from blood (e.g., from the blood of a pregnant female). Extracellular nucleic acid often includes no detectable cells and may contain cellular elements or cellular remnants. Non-limiting examples of acellular sources for extracellular nucleic acid are blood, blood plasma, blood serum and urine. As used herein, the term “obtain cell-free circulating sample nucleic acid” includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a “ladder”).

Extracellular nucleic acid can include different nucleic acid species, and therefore is referred to herein as “heterogeneous” in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less). In some embodiments, the majority of fetal nucleic acid in nucleic acid is of a length of about 50 base pairs or less (e.g., about 80, 85, 90, 91, 92, 93, 94, 95, 96, 97, 98, 99 or 100% of fetal nucleic acid is of a length of about 50 base pairs or less). In some embodiments, the majority of fetal nucleic acid in nucleic acid is of a length of about 25 base pairs or less (e.g., about 80, 85, 90, 91, 92, 93, 94, 95, 96, 97, 98, 99 or 100% of fetal nucleic acid is of a length of about 25 base pairs or less).

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term “isolated” as used herein refers to nucleic acid removed from its original environment (e.g., the natural environment if it is naturally occurring, or a host cell if expressed exogenously), and thus is altered by human intervention (e.g., “by the hand of man”) from its original environment. The term “isolated nucleic acid” as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term “purified” as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term “purified” as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, nucleosomes comprising small fragments of fetal nucleic acid can be purified from a mixture of larger nucleosome complexes comprising larger fragments of maternal nucleic acid.

The term “amplified” as used herein refers to subjecting a target nucleic acid in a sample to a process that linearly or exponentially generates amplicon nucleic acids having the same or substantially the same nucleotide sequence as the target nucleic acid, or segment thereof. The term “amplified” as used herein can refer to subjecting a target nucleic acid (e.g., in a sample comprising other nucleic acids) to a process that selectively and linearly or exponentially generates amplicon nucleic acids having the same or substantially the same nucleotide sequence as the target nucleic acid, or segment thereof. The term “amplified” as used herein can refer to subjecting a population of nucleic acids to a process that non-selectively and linearly or exponentially generates amplicon nucleic acids having the same or substantially the same nucleotide sequence as nucleic acids, or portions thereof, that were present in the sample prior to amplification. In certain embodiments the term “amplified” refers to a method that comprises a polymerase chain reaction (PCR).

Nucleic acid also may be processed by subjecting nucleic acid to a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by a suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of nucleotide sequence information.

Nucleic acid fragments may contain overlapping nucleotide sequences, and such overlapping sequences can facilitate construction of a nucleotide sequence of the non-fragmented counterpart nucleic acid, or a segment thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

Nucleic acid can be fragmented by various methods known in the art, which include without limitation, physical, chemical and enzymatic processes. Non-limiting examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected to generate non-specifically cleaved fragments or specifically cleaved fragments. Non-limiting examples of processes that can generate non-specifically cleaved fragment nucleic acid include, without limitation, contacting nucleic acid with apparatus that expose nucleic acid to shearing force (e.g., passing nucleic acid through a syringe needle; use of a French press); exposing nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the segment of an amplified product thereof containing the corresponding nucleotide sequence of a nucleic acid template gene molecule. For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from portions of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel).

Nucleic acid may be specifically cleaved or non-specifically cleaved by contacting the nucleic acid with one or more enzymatic cleavage agents (e.g., nucleases, restriction enzymes). The term "specific cleavage agent" as used herein refers to an agent, sometimes a chemical or an enzyme that can cleave a nucleic acid at one or more specific sites. Specific cleavage agents often cleave specifically according to a particular nucleotide sequence at a particular site. Non-specific cleavage agents often cleave nucleic acids at non-specific sites or degrade nucleic acids. Non-specific cleavage agents often degrade nucleic acids by removal of nucleotides from the end (either the 5' end, 3' end or both) of a nucleic acid strand.

Any suitable non-specific or specific enzymatic cleavage agent can be used to cleave or fragment nucleic acids. A suitable restriction enzyme can be used to cleave nucleic acids, in some embodiments. Examples of enzymatic cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind III, Hind III, Hpa I, Hpa II, Kpn I, Ksp I, Mlu I, MIuN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I; glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Nucleic acid may be treated with a chemical agent, and the modified nucleic acid may be cleaved. In non-limiting examples, nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any form useful for conducting a sequence analysis or manufacture process described herein, such as solid or liquid form, for example. In certain embodiments, nucleic acid may be provided in a liquid form optionally comprising one or more other components, including without limitation one or more buffers or salts.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of *E. Coli* RecA protein and/or by alteration of salt concentration, for example, using methods known in the art.

Genomic DNA Target Sequences

In some embodiments of the methods provided herein, one or more nucleic acid species, and sometimes one or more nucleotide sequence species, are targeted for amplification and quantification. In some embodiments, the targeted nucleic acids are genomic DNA sequences. Certain genomic DNA target sequences are used, for example, because they can allow for the determination of a particular feature for a given assay. Genomic DNA target sequences can be referred to herein as markers for a given assay. In some cases, genomic target sequences are polymorphic, as described herein. In some embodiments, more than one genomic DNA target sequence or marker can allow for the determination of a particular feature for a given assay. Such genomic DNA target sequences are considered to be of a particular "region". As used herein, a "region" is not intended to be limited to a description of a genomic location, such as a particular chromosome, stretch of chromosomal DNA or genetic locus. Rather, the term "region" is used herein to identify a collection of one or more genomic DNA target sequences or markers that can be indicative of a particular assay. Such assays can include, but are not limited to, assays for the detection and quantification of fetal nucleic acid, assays for the detection and quantification of maternal nucleic acid, assays for the detection and quantification of total DNA, assays for the detection and quantification of methylated DNA, assays for the detection and quantification of fetal specific nucleic acid (e.g. chromosome Y DNA), and assays for the detection and quantification of digested and/or undigested DNA, as an indicator of digestion efficiency. In some embodiments, the genomic DNA target sequence is described as being within a particular genomic locus. As used herein, a genomic locus can include any or a combination of open reading frame DNA, non-transcribed DNA, intronic sequences, extronic sequences, promoter sequences, enhancer sequences, flanking sequences, or any sequences considered by one of skill in the art to be associated with a given genomic locus.

Assays for the Determination of Methylated DNA

In some embodiments of the methods provided herein, one or more genomic DNA target sequences are used that can allow for the determination of methylated DNA. Generally, genomic DNA target sequences used for the determination of methylated DNA are differentially methylated in fetal and maternal nucleic acid, and thus, differentially digested according to the methods provided herein for methylation-sensitive restriction enzymes. In some cases, a genomic DNA target sequence is a single copy gene. In some cases, a genomic DNA target sequence is located on chromosome 13, chromosome 18, chromosome 21, chromosome X, or chromosome Y. In some cases, a genomic DNA target sequence is not located on chromosome 13. In some cases, a genomic DNA target sequence is not located on chromosome 18. In some cases, a genomic DNA target sequence is not located on chromosome 21. In some cases, a genomic DNA target sequence is not located on chromosome X. In some cases, a genomic DNA target sequence is not located on chromosome Y. In some cases, a genomic DNA target sequence is typically methylated in one DNA species such as, for example, placental DNA (i.e. at least about 50% or greater methylation). In some cases, the genomic DNA target sequence is minimally methylated in another DNA species such as, for example, maternal DNA (i.e. less than about 1% methylation). In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some cases, the genomic DNA target sequence contains at least two restriction sites within the amplified region. In some embodiments, the genomic DNA target sequence length is about 50 base pairs to about 200 base pairs. In some cases, the genomic DNA target sequence length is 70 base pairs. In some cases, the genomic DNA target sequence does not possess any negative AG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of methylated DNA is within the TBX3 locus. In some embodiments, the genomic DNA target sequence used for the determination of methylated DNA is within the SOX14 locus. Additional genomic targets that can be used for the determination of methylated DNA in conjunction with the methods provided herein are presented in Example 3.

Assays for the Determination of Total DNA

In some embodiments of the methods provided herein, one or more genomic DNA target sequences are used that can allow for the determination of total DNA. Generally, genomic DNA target sequences used for the determination of total DNA are present in every genome copy (e.g. is present in fetal DNA and maternal DNA, cancer DNA and normal DNA, pathogen DNA and host DNA). In some cases, a genomic DNA target sequence is a single copy gene. In some cases, a genomic DNA target sequence is located on chromosome 13, chromosome 18, chromosome 21, chromosome X, or chromosome Y. In some cases, a genomic DNA target sequence is not located on chromosome 13. In some cases, a genomic DNA target sequence is not located on chromosome 18. In some cases, a genomic DNA target sequence is not located on chromosome 21. In some cases, a genomic DNA target sequence is not located on chromosome X. In some cases, a genomic DNA target sequence is not located on chromosome Y. In some cases, a genomic DNA target sequence does not contain any known single nucleotide polymorphisms (SNPs) within the PCR primer hybridization sequences. In some cases, a genomic DNA target sequence does not contain any known mutations within the PCR primer hybridization sequences. In some cases, a genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. Nucleic Acids Res. 31 (13), 3406-15, (2003)). In some embodiments, the genomic DNA target sequence used for the determination of total DNA is within the ALB locus. In some embodiments, the genomic DNA target sequence used for the determination of total DNA is within the APOE or RNAseP locus.

Assays for the Determination of Fetal DNA

In some embodiments of the methods provided herein, one or more genomic DNA target sequences are used that can allow for the determination of fetal DNA. In some embodiments, genomic DNA target sequences used for the determination of fetal DNA are specific to the Y chromosome. In some cases, the genomic DNA target sequence is a single copy gene. In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some cases, the genomic DNA target sequence does not contain the restriction site GCGC within the amplified region. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of fetal DNA is within the UTY locus. In some embodiments, the genomic DNA target sequence used for the determination of fetal DNA is within the SRY1 or SRY2 locus.

Assays for the Determination of Fetal Gender

In some embodiments, the prediction of a fetal gender or gender related disorder (e.g., sex chromosome aneuploidy) can be determined by a method or apparatus described herein. Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production. Individuals with XX are female and XY are male and non-limiting variations, often referred to as sex chromosome aneuploidies, include X0, XYY, XXX and XXY. In certain embodiments, males have two X chromosomes and one Y chromosome (XXY; Klinefelter's Syndrome), or one X chromosome and two Y chromosomes (XYY syndrome; Jacobs Syndrome), and some females have three X chromosomes (XXX; Triple X Syndrome) or a single X chromosome instead of two (X0; Turner Syndrome). In certain embodiments, only a portion of cells in an individual are affected by a sex chromosome aneuploidy which may be referred to as a mosaicism (e.g., Turner mosaicism). Other cases include those where SRY is damaged (leading to an XY female), or copied to the X (leading to an XX male).

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder. Sex-linked disorders include, without limitation, X-linked and Y-linked disorders. X-linked disorders include X-linked recessive and X-linked dominant disorders. Examples of X-linked recessive disorders include, without limitation, immune disorders (e.g., chronic granulomatous disease (CYBB), Wiskott-Aldrich syndrome, X-linked severe combined immunodeficiency, X-linked agammaglobulinemia, hyper-IgM syndrome type 1, IPEX, X-linked lymphoproliferative disease, Properdin deficiency), hematologic disorders (e.g., Hemophilia A, Hemophilia B, X-linked sideroblastic anemia), endocrine disorders (e.g., androgen insensitivity syndrome/Kennedy disease, KAL1 Kallmann syndrome, X-linked adrenal hypoplasia congenital), metabolic disorders (e.g., ornithine transcarbamylase deficiency, oculocerebrorenal syndrome, adrenoleukodystrophy, glucose-6-phosphate dehydrogenase deficiency, pyruvate dehydrogenase deficiency, Danon disease/glycogen storage disease Type IIb, Fabry's disease, Hunter syndrome, Lesch-Nyhan syndrome, Menkes disease/occipital horn syndrome), nervous system disorders (e.g., Coffin-Lowry syndrome, MASA syndrome, X-linked alpha thalassemia mental retardation syndrome, Siderius X-linked mental retardation syndrome, color blindness, ocular albinism, Norrie disease, choroideremia, Charcot-Marie-Tooth disease (CMTX2-3), Pelizaeus-Merzbacher disease, SMAX2), skin and related tissue disorders (e.g., dyskeratosis congenital, hypohidrotic ectodermal dysplasia (EDA), X-linked ichthyosis, X-linked endothelial corneal dystrophy), neuromuscular disorders (e.g., Becker's muscular dystrophy/Duchenne, centronuclear myopathy (MTM1), Conradi-Hünermann syndrome, Emery-Dreifuss muscular dystrophy 1), urologic disorders (e.g., Alport syndrome, Dent's disease, X-linked nephrogenic diabetes insipidus), bone/tooth disorders (e.g., AMELX Amelogenesis imperfecta), and other disorders (e.g., Barth syndrome, McLeod syndrome, Smith-Fineman-Myers syndrome, Simpson-Golabi-Behmel syndrome, Mohr-Tranebjrg syndrome, Nasodigitoacoustic syndrome). Examples of X-linked dominant disorders include, without limitation, X-linked hypophosphatemia, Focal dermal hypoplasia, Fragile X syndrome, Aicardi syndrome, Incontinentia pigmenti, Rett syndrome, CHILD syndrome, Lujan-Fryns syndrome, and Orofaciodigital syndrome 1. Examples of Y-linked disorders include, without limitation, male infertility, retinits pigmentosa, and azoospermia.

Fetal gender can be determined by a suitable method, non-limiting examples of which include chorionic villus sampling, amniocentesis, obstetric ultrasonography, the like and methods described in International Patent Application No. PCT/US12/59592 and U.S. patent application Ser. No. 13/656,328 both of which are incorporated herein by reference.

Assays for the Determination of Digested and/or Undigested DNA

In some embodiments of the methods provided herein, one or more genomic DNA target sequences are used that can allow for the determination of the amount of digested or undigested nucleic acid, as an indicator of digestion efficiency. Such genomic DNA target sequences are present in every genome in the sample (e.g. maternal and fetal species genomes). Generally, genomic DNA target sequences used for the determination of digested or undigested DNA contain at least one restriction site present in a genomic DNA target sequence used in another assay. Thus, the genomic DNA target sequences used for the determination of digested or undigested DNA serve as controls for assays that include differential digestion. Generally, the genomic DNA target sequence is unmethylated in all nucleic acid species tested (e.g. unmethylated in both maternal and fetal species genomes). In some cases, the genomic DNA target sequence is a single copy gene. In some cases, the genomic DNA target sequence is not located on chromosome 13. In some cases, the genomic DNA target sequence is not located on chromosome 18. In some cases, the genomic DNA target sequence is not located on chromosome 21. In some cases, the genomic DNA target sequence is not located on chromosome X. In some cases, the genomic DNA target sequence is not located on chromosome Y. In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some embodiments, the genomic DNA target sequence length is about 50 base pairs to about 200 base pairs. In some cases, the genomic DNA target sequence length is 70 base pairs. In some cases, the genomic DNA target sequence does not possess any negative AG values for secondary structure of the complete amplicon prediction using mfold (M. Zuker, Mfold web server for nucleic acid folding and hybridization prediction. Nucleic Acids Res. 31 (13), 3406-15, (2003)). In some embodiments, the genomic DNA target sequence used for the determination of digested or undigested DNA is within the POPS locus. In some embodiments, the genomic DNA target sequence used for the determination of digested or undigested DNA is within the LDHA locus.

Methylation Specific Separation of Nucleic Acid

The methods provided herein offer an alternative approach for the enrichment of fetal DNA based on the methylation-specific separation of differentially methylated DNA. It has recently been discovered that many genes involved in developmental regulation are controlled through epigenetics in embryonic stem cells. Consequently, multiple genes can be expected to show differential DNA methylation between nucleic acid of fetal origin and maternal origin. Once these regions are identified, a technique to capture methylated DNA can be used to specifically enrich fetal DNA. For identification of differentially methylated regions, a novel approach was used to capture methylated DNA. This approach uses a protein, in which the methyl binding domain of MBD2 is fused to the Fc fragment of an antibody (MBD-FC) (Gebhard C, Schwarzfischer L, Pham T H, Schilling E, Klug M, Andreesen R, Rehli M (2006) Genome wide profiling of CpG methylation identifies novel targets of aberrant hypermethylation in myeloid leukemia. Cancer Res 66:6118-6128). This fusion protein has several advantages over conventional methylation specific antibodies. The MBD-FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC on the other hand binds all DNA molecules regardless of their methylation status. The strength of this protein-DNA interaction is defined by the level of DNA methylation. After binding genomic DNA, eluate solutions of increasing salt concentrations can be used to fractionate non-methylated and methylated DNA allowing for a more controlled separation (Gebhard C, Schwarzfischer L, Pham T H, Andreesen R, Mackensen A, Rehli M (2006) Rapid and sensitive detection of CpG-methylation using methyl-binding (MB)-PCR. Nucleic Acids Res 34:e82). Consequently this method, called Methyl-CpG immunoprecipitation (MCIP), cannot only enrich, but also fractionate genomic DNA according to methylation level, which is particularly helpful when the unmethylated DNA fraction should be investigated as well.

Methylation Sensitive Restriction Enzyme Digestion

The technology herein also provides compositions and processes for determining the amount of fetal nucleic acid from a maternal sample. The technology herein allows for the enrichment of fetal nucleic acid regions in a maternal sample by selectively digesting nucleic acid from said maternal sample with an enzyme that selectively and completely or substantially digests the maternal nucleic acid to enrich the sample for at least one fetal nucleic acid region. Preferably, the digestion efficiency is greater than about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Following enrichment, the amount of fetal nucleic acid can be determined by quantitative methods that do not require polymorphic sequences or bisulfite treatment, thereby, offering a solution that works equally well for female fetuses and across different ethnicities and preserves the low copy number fetal nucleic acid present in the sample.

For example, there are methyl-sensitive enzymes that preferentially or substantially cleave or digest at their DNA recognition sequence if it is non-methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated.

Methyl-sensitive enzymes that digest unmethylated DNA suitable for use in methods of the technology herein include, but are not limited to, HpaII, HhaI, MaeII, BstUI and AciI. An enzyme that can be used is HpaII that cuts only the unmethylated sequence CCGG. Another enzyme that can be used is HhaI that cuts only the unmethylated sequence GCGC. Both enzymes are available from New England BioLabs®, Inc. Combinations of two or more methyl-sensitive enzymes that digest only unmethylated DNA can also be used. Suitable enzymes that digest only methylated DNA include, but are not limited to, DpnI, which cuts at a recognition sequence GATC, and McrBC, which belongs to the family of AAA.sup.+ proteins and cuts DNA containing modified cytosines and cuts at recognition site 5' . . . Pu.sup.mC(N.sub.40-3000) Pu.sup.mC . . . 3' (New England BioLabs, Inc., Beverly, Mass.).

Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al., Molecular Biology: A laboratory Approach, Cold Spring Harbor, N.Y. 1989) provide a general description of methods for using restriction enzymes and other enzymes. Enzymes often are used under conditions that will enable cleavage of the maternal DNA with about 95%-100% efficiency, preferably with about 98%-100% efficiency.

Other Methods for Methylation Analysis

Various methylation analysis procedures are known in the art, and can be used in conjunction with the present technology. These assays allow for determination of the methylation state of one or a plurality of CpG islands within a DNA sequence. In addition, the methods maybe used to quantify methylated nucleic acid. Such assays involve, among other techniques, DNA sequencing of bisulfite-treated DNA, PCR (for sequence-specific amplification), Southern blot analysis, and use of methylation-sensitive restriction enzymes.

Genomic sequencing is a technique that has been simplified for analysis of DNA methylation patterns and 5-methylcytosine distribution by using bisulfite treatment (Frommer et al., Proc. Natl. Acad. Sci. USA 89:1827-1831, 1992). Additionally, restriction enzyme digestion of PCR products amplified from bisulfite-converted DNA may be used, e.g., the method described by Sadri & Hornsby (Nucl. Acids Res. 24:5058-5059, 1996), or COBRA (Combined Bisulfite Restriction Analysis) (Xiong & Laird, Nucleic Acids Res. 25:2532-2534, 1997).

COBRA analysis is a quantitative methylation assay useful for determining DNA methylation levels at specific gene loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

The MethyLight™ assay is a high-throughput quantitative methylation assay that utilizes fluorescence-based real-time PCR (TaqMan®) technology that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an “unbiased” (with primers that do not overlap known CpG methylation sites) PCR reaction, or in a “biased” (with PCR primers that overlap known CpG dinucleotides) reaction. Sequence discrimination can occur either at the level of the amplification process or at the level of the fluorescence detection process, or both.

The MethyLight assay may be used as a quantitative test for methylation patterns in the genomic DNA sample, where sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not “cover” known methylation sites (a fluorescence-based version of the “MSP” technique), or with oligonucleotides covering potential methylation sites.

The MethyLight process can by used with a “TaqMan” probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent “reporter” and “quencher” molecules, and is designed to be specific for a relatively high GC content region so that it melts out at about 10.degree. C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific gene (or methylation-altered DNA sequence or CpG island); TaqMan® probes; optimized PCR buffers and deoxynucleotides; and Taq polymerase.

The Ms-SNuPE technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

MSP (methylation-specific PCR) allows for assessing the methylation status of virtually any group of CpG sites within a CpG island, independent of the use of methylation-sensitive restriction enzymes (Herman et al. Proc. Nat. Acad. Sci. USA 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

The MCA technique is a method that can be used to screen for altered methylation patterns in genomic DNA, and to isolate specific sequences associated with these changes (Toyota et al., Cancer Res. 59:2307-12, 1999). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Another method for analyzing methylation sites is a primer extension assay, including an optimized PCR amplification reaction that produces amplified targets for subsequent primer extension genotyping analysis using mass spectrometry. The assay can also be done in multiplex. This method (particularly as it relates to genotyping single nucleotide polymorphisms) is described in detail in PCT publication WO05012578A1 and US publication US20050079521A1. For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Four additional methods for DNA methylation analysis include restriction landmark genomic scanning (RLGS, Costello et al., 2000), methylation-sensitive-representational difference analysis (MS-RDA), methylation-specific AP-PCR (MS-AP-PCR) and methyl-CpG binding domain column/segregation of partly melted molecules (MBD/SPM).

Additional methylation analysis methods that may be used in conjunction with the present technology are described in the following papers: Laird, P. W. Nature Reviews Cancer 3, 253-266 (2003); Biotechniques; Uhlmann, K. et al. Electrophoresis 23:4072-4079 (2002)—PyroMeth; Colella et al. Biotechniques. 2003 July; 35(1): 146-50; Dupont J M, Tost J, Jammes H, and Gut I G. Anal Biochem, October 2004; 333(1): 119-27; and Tooke N and Pettersson M. IVDT. November 2004; 41.

Nucleic Acid Quantification

In some embodiments, the amount of fetal nucleic acid in a sample is determined. In some cases, the amount of fetal nucleic acid is determined based on a quantification of sequence read counts described herein. Quantification may be achieved by direct counting of sequence reads covering particular methylation sites and/or target sites, or by competitive PCR (i.e., co-amplification of competitor oligonucleotides of known quantity, as described herein). The term "amount" as used herein with respect to nucleic acids refers to any suitable measurement, including, but not limited to, absolute amount (e.g. copy number), relative amount (e.g. fraction or ratio), weight (e.g., grams), and concentration (e.g., grams per unit volume (e.g., milliliter); molar units).

Fraction Determination

In some embodiments, a fraction or ratio can be determined for the amount of one nucleic acid relative to the amount of another nucleic acid. In some embodiments, the fraction of fetal nucleic acid in a sample relative to the total amount of nucleic acid in the sample is determined. To calculate the fraction of fetal nucleic acid in a sample relative to the total amount of the nucleic acid in the sample, the following equation can be applied:

The fraction of fetal nucleic acid=(amount of fetal nucleic acid)/[(amount of total nucleic acid)].

Copy Number Determination Using Competitors

In some embodiments, the absolute amount (e.g. copy number) of fetal nucleic acid is determined. Often, the copy number of fetal nucleic acid is determined based on the amount of a competitor oligonucleotide used. In some embodiments, the copy number of maternal nucleic acid is determined. To calculate the copy number of fetal nucleic acid in a sample, the following equation can be applied:

Copy number (fetal nucleic acid)=[(amount of the fetal nucleic acid)/(amount of the fetal competitor)]×$C$ where C is the number of competitor oligonucleotides added into the reaction. In some cases, the amounts of the fetal nucleic acid and fetal competitor are obtained in a readout generated by a sequencing reaction (e.g. sequence read counts).

Additional Methods for Determining Fetal Nucleic Acid Content

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction". In certain embodiments "fetal fraction" refers to the fraction of fetal nucleic acid in circulating cell-free nucleic acid in a sample (e.g., a blood sample, a serum sample, a plasma sample) obtained from a pregnant female. In some embodiments a fetal fraction is a percentage of fetal nucleic in a sample comprising fetal and maternal nucleic acid. In certain embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. In certain embodiments, the amount of fetal nucleic acid from a maternal sample can be determined relative to the total amount of nucleic acid present, thereby providing the percentage of fetal nucleic acid in the sample. In certain embodiments, the copy number of fetal nucleic acid can be determined in a maternal sample. In certain embodiments, the amount of fetal nucleic acid can be determined in a sequence-specific (or locus-specific) manner and sometimes with sufficient sensitivity to allow for accurate chromosomal dosage analysis (for example, to detect the presence or absence of a fetal aneuploidy).

A fetal quantifier assay (FQA) can be performed in conjunction with any of the methods described herein. Such an assay can be performed by any method known in the art and/or described in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching the fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In certain embodiments, the restriction efficiency can be determined and the efficiency rate is used to further determine the amount of fetal DNA.

Polymorphism-Based Fetal Quantifier Assay

Determination of fetal nucleic acid content (e.g., fetal fraction) sometimes is performed using a polymorphism-based fetal quantifier assay (FQA), as described herein. This type of assay allows for the detection and quantification of fetal nucleic acid in a maternal sample based on allelic ratios of polymorphic sequences (e.g., single nucleotide polymorphisms (SNPs)). In some cases, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. In some cases, fetal alleles are identified, for example, by their relative minor contribution to the mixture of fetal and maternal nucleic acids in the sample when compared to the major contribution to the mixture by the maternal nucleic acids. In some cases, fetal alleles are identified by a deviation of allele frequency from an expected allele frequency, as described below. In some cases, the relative abundance of fetal nucleic acid in a maternal sample can be determined as a parameter of the total number of unique sequence reads mapped to a target nucleic acid sequence on a reference genome for each of the two alleles of a polymorphic site. In some cases, the relative abundance of fetal nucleic acid in a maternal sample can be determined as a parameter of the relative number of sequence reads for each allele from an enriched sample.

In some embodiments, determining fetal fraction comprises enriching a sample nucleic acid for one or more polymorphic nucleic acid targets. In some cases, a plurality of polymorphic targets is enriched. A plurality of polymorphic nucleic acid targets is sometimes referred to as a collection or a panel (e.g., target panel, SNP panel, SNP collection). A plurality of polymorphic targets can comprise two or more targets. For example, a plurality of polymorphic targets can comprise 2, 3, 4, 5, 6, 7, 8, 9, 10, 20, 30, 40, 50, 60, 70, 80, 90, 100, 200, 300, 400, 500, 600, 700, 800, 900, 1000, or more targets. In some cases, 10 or more polymorphic nucleic acid targets are enriched. In some cases, 50 or more polymorphic nucleic acid targets are enriched. In some cases, 100 or more polymorphic nucleic acid targets are enriched. In some cases, 500 or more polymorphic nucleic acid targets are enriched. In some cases, about 10 to about 500 polymorphic nucleic acid targets are enriched. In some cases, about 20 to about 400 polymorphic nucleic acid targets are enriched. In some cases, about 30 to about 200 polymorphic nucleic acid targets are enriched. In some cases, about 40 to about 100 polymorphic nucleic acid targets are enriched. In some cases, about 60 to about 90 polymorphic nucleic acid targets are enriched. For example, in certain embodiments, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 polymorphic nucleic acid targets are enriched.

In some embodiments, at least one polymorphic nucleic acid target of the plurality of polymorphic nucleic acid targets is informative for determining fetal fraction in a given sample. A polymorphic nucleic acid target that is informative for determining fetal fraction, sometimes referred to as an informative target, informative polymorphism, or informative SNP, typically differs in some aspect between the fetus and the mother. For example, an informative target may have one allele for the fetus and a different allele for the mother (e.g., the mother has allele A at the polymorphic target and the fetus has allele B at the polymorphic target site). Typically, a fetal allele that differs from either of the maternal alleles is paternally inherited (i.e., is from the father). Thus, paternally inherited alleles that differ from maternal alleles can be useful for identifying and/or quantifying fetal nucleic acid (e.g., determining fetal fraction).

In some cases, polymorphic nucleic acid targets are informative in the context of certain maternal/fetal genotype combinations. For a biallelic polymorphic target (i.e., two possible alleles (e.g., A and B)), possible maternal/fetal genotype combinations include: 1) maternal AA, fetal AA; 2) maternal AA, fetal AB; 3) maternal AB, fetal AA; 4) maternal AB, fetal AB; 5) maternal AB; fetal BB; 6) maternal BB, fetal AB; and 7) maternal BB, fetal BB. Genotypes AA and BB are considered homozygous genotypes and genotype AB is considered a heterozygous genotype. In some cases, informative genotype combinations (i.e., genotype combinations for a polymorphic nucleic acid target that may be informative for determining fetal fraction) include combinations where the mother is homozygous and the fetus is heterozygous (e.g., maternal AA, fetal AB; or maternal BB, fetal AB). Such genotype combinations may be referred to as Type 1 informative genotypes or informative heterozygotes. In some cases, informative genotype combinations (i.e., genotype combinations for a polymorphic nucleic acid target that may be informative for determining fetal fraction) include combinations where the mother is heterozygous and the fetus is homozygous (e.g., maternal AB, fetal AA; or maternal AB, fetal BB). Such genotype combinations may be referred to as Type 2 informative genotypes or informative homozygotes. In some cases, non-informative genotype combinations (i.e., genotype combinations for a polymorphic nucleic acid target that may not be informative for determining fetal fraction) include combinations where the mother is heterozygous and the fetus is heterozygous (e.g., maternal AB, fetal AB). Such genotype combinations may be referred to as non-informative genotypes or non-informative heterozygotes. In some cases, non-informative genotype combinations (i.e., genotype combinations for a polymorphic nucleic acid target that may not be informative for determining fetal fraction) include combinations where the mother is homozygous and the fetus is homozygous (e.g., maternal AA, fetal AA; or maternal BB, fetal BB). Such genotype combinations may be referred to as non-informative genotypes or non-informative homozygotes.

Figure 37:
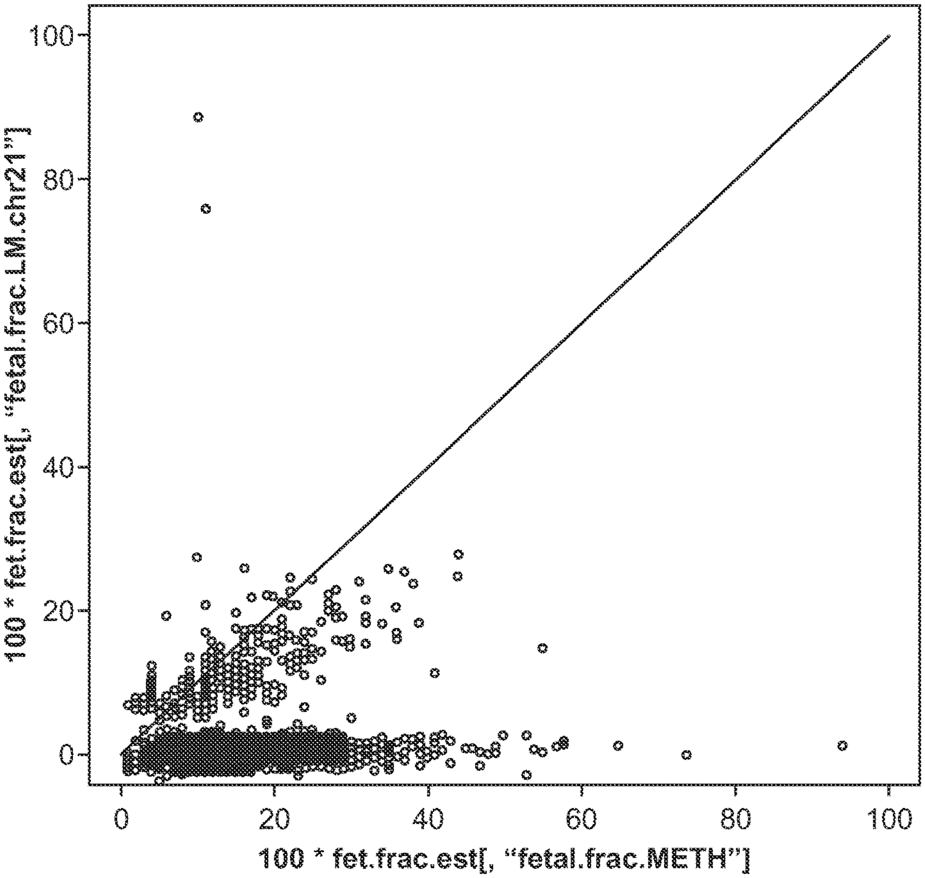
FIG. 37 graphically illustrates fetal fraction estimates based on chromosome 21 (Chr21) plotted against measured fetal fractions.

In some embodiments, individual polymorphic nucleic acid targets and/or panels of polymorphic nucleic acid targets are selected based on certain criteria, such as, for example, minor allele population frequency, variance, coefficient of variance, MAD value, and the like. In some cases, polymorphic nucleic acid targets are selected so that at least one polymorphic nucleic acid target within a panel of polymorphic targets has a high probability of being informative for a majority of samples tested. Additionally, in some cases, the number of polymorphic nucleic acid targets (i.e., number of targets in a panel) is selected so that least one polymorphic nucleic acid target has a high probability of being informative for a majority of samples tested. For example, selection of a larger number of polymorphic targets generally increases the probability that least one polymorphic nucleic acid target will be informative for a majority of samples tested (see, FIG. 37, for example). In some cases, the polymorphic nucleic acid targets and number thereof (e.g., number of polymorphic targets selected for enrichment) result in at least about 2 to about 50 or more polymorphic nucleic acid targets being informative for determining the fetal fraction for at least about 80% to about 100% of samples. For example, the polymorphic nucleic acid targets and number thereof result in at least about 5, 10, 15, 20, 25, 30, 35, 40, 45, 50 or more polymorphic nucleic acid targets being informative for determining the fetal fraction for at least about 81%, 82%, 83%, 84%, 85%, 86%, 87%, 88%, 89%, 90%, 91%, 92%, 93%, 94%, 95%, 96%, 97%, 98%, or 99% of samples. In some cases, the polymorphic nucleic acid targets and number thereof result in at least five polymorphic nucleic acid targets being informative for determining the fetal fraction for at least 90% of samples. In some cases, the polymorphic nucleic acid targets and number thereof result in at least five polymorphic nucleic acid targets being informative for determining the fetal fraction for at least 95% of samples. In some cases, the polymorphic nucleic acid targets and number thereof result in at least five polymorphic nucleic acid targets being informative for determining the fetal fraction for at least 99% of samples. In some cases, the polymorphic nucleic acid targets and number thereof result in at least ten polymorphic nucleic acid targets being informative for determining the fetal fraction for at least 90% of samples. In some cases, the polymorphic nucleic acid targets and number thereof result in at least ten polymorphic nucleic acid targets being informative for determining the fetal fraction for at least 95% of samples. In some cases, the polymorphic nucleic acid targets and number thereof result in at least ten polymorphic nucleic acid targets being informative for determining the fetal fraction for at least 99% of samples.

In some embodiments, individual polymorphic nucleic acid targets are selected based, in part, on minor allele population frequency. In some cases, polymorphic nucleic acid targets having minor allele population frequencies of about 10% to about 50% are selected. For example, polymorphic nucleic acid targets having minor allele population frequencies of about 15%, 20%, 25%, 30%, 35%, 36%, 37%, 38%, 39%, 40%, 41%, 42%, 43%, 44%, 45%, 46%, 47%, 48%, or 49% are selected. In some embodiments, polymorphic nucleic acid targets having a minor allele population frequency of about 40% or more are selected.

In some embodiments, individual polymorphic nucleic acid targets and/or panels of polymorphic nucleic acid targets are selected based, in part, on degree of variance for an individual polymorphic target or a panel of polymorphic targets. Variance, in come cases, can be specific for certain polymorphic targets or panels of polymorphic targets and can be from systematic, experimental, procedural, and or inherent errors or biases (e.g., sampling errors, sequencing errors, PCR bias, and the like). Variance of an individual polymorphic target or a panel of polymorphic targets can be determined by any method known in the art for assessing variance and may be expressed, for example, in terms of a calculated variance, an error, standard deviation, p-value, mean absolute deviation, median absolute deviation, median adjusted deviation (MAD score), coefficient of variance (CV), and the like. In some embodiments, measured allele frequency variance (i.e., background allele frequency) for certain SNPs (when homozygous, for example) can be from about 0.001 to about 0.01 (i.e., 0.1% to about 1.0%). For example, measured allele frequency variance can be about 0.002, 0.003, 0.004, 0.005, 0.006, 0.007, 0.008, or 0.009. In some cases, measured allele frequency variance is about 0.007.

In some cases, noisy polymorphic targets are excluded from a panel of polymorphic nucleic acid targets selected for determining fetal fraction. The term "noisy polymorphic targets" or "noisy SNPs" refers to (a) targets or SNPs that have significant variance between data points (e.g., measured fetal fraction, measured allele frequency) when analyzed or plotted, (b) targets or SNPs that have significant standard deviation (e.g., greater than 1, 2, or 3 standard deviations), (c) targets or SNPs that have a significant standard error of the mean, the like, and combinations of the foregoing. Noise for certain polymorphic targets or SNPs sometimes occurs due to the quantity and/or quality of starting material (e.g., nucleic acid sample), sometimes occurs as part of processes for preparing or replicating DNA used to generate sequence reads, and sometimes occurs as part of a sequencing process. In certain embodiments, noise for some polymorphic targets or SNPs results from certain sequences being over represented when prepared using PCR-based methods. In some cases, noise for some polymorphic targets or SNPs results from one or more inherent characteristics of the site such as, for example, certain nucleotide sequences and/or base compositions surrounding, or being adjacent to, a polymorphic target or SNP. A SNP having a measured allele frequency variance (when homozygous, for example) of about 0.005 or more may be considered noisy. For example, a SNP having a measured allele frequency variance of about 0.006, 0.007, 0.008, 0.009, 0.01 or more may be considered noisy.

In some embodiments, variance of an individual polymorphic target or a panel of polymorphic targets can be represented using coefficient of variance (CV). Coefficient of variance (i.e., standard deviation divided by the mean) can be determined, for example, by determining fetal fraction for several aliquots of a single maternal sample comprising maternal and fetal nucleic acid, and calculating the mean fetal fraction and standard deviation. In some cases, individual polymorphic nucleic acid targets and/or panels of polymorphic nucleic acid targets are selected so that fetal fraction is determined with a coefficient of variance (CV) of 0.30 or less. For example, fetal fraction may determined with a coefficient of variance (CV) of 0.25, 0.20, 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, 0.01 or less, in some embodiments. In some cases, fetal fraction is determined with a coefficient of variance (CV) of 0.20 or less. In some cases, fetal fraction is determined with a coefficient of variance (CV) of 0.10 or less. In some cases, fetal fraction is determined with a coefficient of variance (CV) of 0.05 or less.

In some embodiments, an allele frequency is determined for each of the polymorphic nucleic acid targets in a sample. This sometimes is referred to as measured allele frequency. Allele frequency can be determined, for example, by counting the number of sequence reads for an allele (e.g., allele B) and dividing by the total number of sequence reads for that locus (e.g., allele B+allele A). In some cases, an allele frequency average, mean or median is determined. Fetal fraction can be determined based on the allele frequency mean (e.g., allele frequency mean multiplied by two), in some cases.

In some embodiments, determining whether a polymorphic nucleic acid target is informative comprises comparing its measured allele frequency to a fixed cutoff frequency. In some cases, determining which polymorphic nucleic acid targets are informative comprises identifying informative genotypes by comparing each allele frequency to one or more fixed cutoff frequencies. Fixed cutoff frequencies may be predetermined threshold values based on one or more qualifying data sets, for example. In some cases, the fixed cutoff for identifying informative genotypes from non-informative genotypes is expressed as a percent (%) shift in allele frequency from an expected allele frequency. Generally, expected allele frequencies for a given allele (e.g., allele A) are 0 (for a BB genotype), 0.5 (for an AB genotype) and 1.0 (for an AA genotype), or equivalent values on any numerical scale. A deviation from an expected allele frequency that is beyond one or more fixed cutoff frequencies may be considered informative. The degree of deviation generally is proportional to fetal fraction (i.e., large deviations from expected allele frequency may be observed in samples having high fetal fraction).

In some cases, the fixed cutoff for identifying informative genotypes from non-informative homozygotes is about a 0.5% or greater shift in allele frequency. For example, a fixed cutoff may be about a 0.6%, 0.7%, 0.8%, 0.9%, 1%, 1.5%, 2%, 3%, 4%, 5%, 10% or greater shift in allele frequency. In some cases, the fixed cutoff for identifying informative genotypes from non-informative homozygotes is about a 1% or greater shift in allele frequency. In some cases, the fixed cutoff for identifying informative genotypes from non-informative homozygotes is about a 2% or greater shift in allele frequency. In some embodiments, the fixed cutoff for identifying informative genotypes from non-informative heterozygotes is about a 10% or greater shift in allele frequency. For example, a fixed cutoff may be about a 10%, 15%, 20%, 21%, 22%, 23%, 24%, 25%, 26%, 27%, 28%, 29%, 30%, 35%, 40%, 45%, 50%, 55%, 60%, 70%, 80% or greater shift in allele frequency. In some cases, the fixed cutoff for identifying informative genotypes from non-informative heterozygotes is about a 25% or greater shift in allele frequency. In some cases, the fixed cutoff for identifying informative genotypes from non-informative heterozygotes is about a 50% or greater shift in allele frequency.

In some embodiments, determining whether a polymorphic nucleic acid target is informative comprises comparing its measured allele frequency to a target-specific cutoff value. In some embodiments, target-specific cutoff frequencies are determined for each polymorphic nucleic acid target. Typically, target-specific cutoff frequency is determined based on the allele frequency variance for the corresponding polymorphic nucleic acid target. In some embodiments, variance of individual polymorphic targets can be represented by a median absolute deviation (MAD), for example. In some cases, determining a MAD value for each polymorphic nucleic acid target can generate unique (i.e., target-specific) cutoff values. To determine median absolute deviation, measured allele frequency can be determined, for example, for multiple replicates (e.g., 5, 6, 7, 8, 9, 10, 15, 20 or more replicates) of a maternal only nucleic acid sample (e.g., buffy coat sample). Each polymorphic target in each replicate will typically have a slightly different measured allele frequency due to PCR and/or sequencing errors, for example. A median allele frequency value can be identified for each polymorphic target. A deviation from the median for the remaining replicates can be calculated (i.e., the difference between the observed allele frequency and the median allele frequency). The absolute value of the deviations (i.e., negative values become positive) is taken and the median value of the absolute deviations is calculated to provide a median absolute deviation (MAD) for each polymorphic nucleic acid target. A target-specific cutoff can be assigned, for example, as a multiple of the MAD (e.g., 1×MAD, 2×MAD, 3×MAD, 4×MAD or 5×MAD). Typically, polymorphic targets having less variance have a lower MAD and therefore a lower cutoff value than more variable targets.

In some embodiments, enriching comprises amplifying the plurality of polymorphic nucleic acid targets. In some cases, the enriching comprises generating amplification products in an amplification reaction. Amplification of polymorphic targets may be achieved by any method described herein or known in the art for amplifying nucleic acid (e.g., PCR). In some cases, the amplification reaction is performed in a single vessel (e.g., tube, container, well on a plate) which sometimes is referred to herein as multiplexed amplification.

In some embodiments, certain parental genotypes are known prior to the enriching of polymorphic nucleic acid targets. In some cases, the maternal genotype for one or more polymorphic targets is known prior to enriching. In some cases, the paternal genotype for one or more polymorphic targets is known prior to enriching. In some cases, the maternal genotype and the paternal genotype for one or more polymorphic targets are known prior to enriching. In some embodiments, certain parental genotypes are not known prior to the enriching of polymorphic nucleic acid targets. In some cases, the maternal genotype for one or more polymorphic targets is not known prior to enriching. In some cases, the paternal genotype for one or more polymorphic targets is not known prior to enriching. In some cases, the maternal genotype and the paternal genotype for one or more polymorphic targets are not known prior to enriching. In some embodiments, parental genotypes are not known for any of the polymorphic nucleic acid targets prior to enriching. In some cases, the maternal genotype for each of the polymorphic targets is not known prior to enriching. In some cases, the paternal genotype for each of the polymorphic targets is not known prior to enriching. In some cases, the maternal genotype and the paternal genotype for each of the polymorphic targets are not known prior to enriching.

In some embodiments, the polymorphic nucleic acid targets each comprise at least one single nucleotide polymorphism (SNP). In some embodiments, the SNPs are selected from: rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, rs985462, rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

In some embodiments, the SNPs are selected from: rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, and rs985462.

In some embodiments, SNPs are selected from: rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

SNPs may be selected from any SNP provided herein or known in the art that meets any one or all of the criteria described herein for SNP selection. In some cases, SNPs can be located on any chromosome (e.g., chromosome 1, 2, 3, 4, 5, 6, 7, 8, 9, 10, 11, 12, 13, 14, 15, 16, 17, 18, 19, 20, 21, 22, X and/or Y). In some cases, SNPs can be located on autosomes (e.g., chromosome 1, 2, 3, 4, 5, 6, 7, 8, 9, 10, 11, 12, 13, 14, 15, 16, 17, 18, 19, 20, 21, 22), and not on chromosome X or chromosome Y. In some cases, SNPs can be located on certain autosomes (e.g., chromosome 1, 2, 3, 4, 5, 6, 7, 8, 9, 10, 11, 12, 14, 15, 16, 17, 19, 20, 22 and not chromosome 13, 18 or 22). In some cases, SNPs can be located on certain chromosomes suspected of having a genetic variation (e.g., aneuploidy), such as, for example, chromosome 13, 18, 21, X and/or Y (i.e., test chromosome(s)). In some cases, SNPs are located on a reference chromosome. In some cases, fetal fraction and the presence or absence of a genetic variation (e.g., aneuploidy) are determined simultaneously using a method provided herein.

In some embodiments, enriched (e.g., amplified) polymorphic nucleic acid targets are sequenced by a sequencing process. In some cases, the sequencing process is a sequencing by synthesis method, as described herein. Typically, sequencing by synthesis methods comprise a plurality of synthesis cycles, whereby a complementary nucleotide is added to a single stranded template and identified during each cycle. The number of cycles generally corresponds to read length. In some cases, polymorphic targets are selected such that a minimal read length (i.e., minimal number of cycles) is required to include amplification primer sequence and the polymorphic target site (e.g., SNP) in the read. In some cases, amplification primer sequence includes about 10 to about 30 nucleotides. For example, amplification primer sequence may include about 11, 12, 13, 14, 15, 16, 17, 18, 19, 20, 21, 22, 23, 24, 25, 26, 27, 28, or 29 nucleotides, in some embodiments. In some cases, amplification primer sequence includes about 20 nucleotides. In some embodiments, a SNP site is located within 1 nucleotide base position (i.e., adjacent to) to about 30 base positions from the 3' terminus of an amplification primer. For example, a SNP site may be within 2, 3, 4, 5, 6, 7, 8, 9, 10, 11, 12, 13, 14, 15, 16, 17, 18, 19, 20, 21, 22, 23, 24, 25, 26, 27, 28, or 29 nucleotides of an amplification primer terminus. Read lengths can be any length that is inclusive of an amplification primer sequence and a polymorphic sequence or position. In some embodiments, read lengths can be about 10 nucleotides in length to about 50 nucleotides in length. For example, read lengths can be about 15, 20, 21, 22, 23, 24, 25, 26, 27, 28, 29, 30, 31, 32, 33, 34, 35, 36, 37, 38, 39, 40, or 45 nucleotides in length. In some cases, read length is about 36 nucleotides. In some cases, read length is about 27 nucleotides. Thus, in some cases, the sequencing by synthesis method comprises about 36 cycles and sometimes comprises about 27 cycles.

In some embodiments, a plurality of samples is sequenced in a single compartment (e.g., flow cell), which sometimes is referred to herein as sample multiplexing. Thus, in some embodiments, fetal fraction is determined for a plurality of samples in a multiplexed assay. For example, fetal fraction may be determined for about 10, 20, 30, 40, 50, 60, 70, 80, 90, 100, 200, 300, 400, 500, 600, 700, 800, 900, 1000, 2000 or more samples. In some cases, fetal fraction is determined for about 10 or more samples. In some cases, fetal fraction is determined for about 100 or more samples. In some cases, fetal fraction is determined for about 1000 or more samples.

Determination of fetal nucleic acid content (e.g., fetal fraction) sometimes is performed using a methylation-based fetal quantifier assay (FQA) as described herein and, for example, in U.S. Patent Application Publication No. 2010/0105049, which is hereby incorporated by reference. In certain embodiments, a fetal quantifier assay (FQA) can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. In certain embodiments, the absolute copy number of fetal nucleic acid in a maternal sample can be determined, for example, using mass spectrometry and/or a system that uses a competitive PCR approach for absolute copy number measurements. See for example, Ding and Cantor (2003) Proc Natl Acad Sci USA 100:3059-3064, and U.S. Patent Application Publication No. 2004/0081993, both of which are hereby incorporated by reference.

In certain embodiments, fetal fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. In certain embodiments, fetal alleles are identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target nucleic acid sequence on a reference genome for each of the two alleles of a polymorphic site.

The amount of fetal nucleic acid in extracellular nucleic acid (e.g., fetal fraction) can be quantified and used in conjunction with other methods for assessing a genetic variation (e.g., fetal aneuploidy, fetal gender). Thus, in certain embodiments, methods for determining the presence or absence of a genetic variation, for example, comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call).

The determination of fetal nucleic acid content (e.g., fetal fraction) can be performed before, during, at any one point in a method for assessing a genetic variation (e.g., aneuploidy detection, fetal gender determination), or after such methods. For example, to achieve a fetal gender or aneuploidy determination method with a given sensitivity or specificity, a fetal nucleic acid quantification method may be implemented prior to, during or after fetal gender or aneuploidy determination to identify those samples with greater than about 2%, 2.5%, 3%, 3.5%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for fetal gender or aneuploidy determination, or the presence or absence of aneuploidy or genetic variation, for example. In certain embodiments, determinations of, for example, fetal gender or the presence or absence of aneuploidy are selected (e.g., selected and communicated to a patient) only for samples having a certain threshold amount of fetal nucleic acid (e.g., about 15% or more fetal nucleic acid; about 4% or more fetal nucleic acid).

Additional Methods for Enriching for a Subpopulation of Nucleic Acid

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, fetal nucleic acid. In certain embodiments, a method for determining fetal fraction described above also can be used to enrich for fetal nucleic acid. In certain embodiments, maternal nucleic acid is selectively removed (partially, substantially, almost completely or completely) from the sample. In certain embodiments, enriching for a particular low copy number species nucleic acid (e.g., fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, all of which are incorporated by reference herein.

In some embodiments, nucleic acid is enriched for certain target fragment species and/or reference fragment species. In certain embodiments, nucleic acid is enriched for a specific nucleic acid fragment length or range of fragment lengths using one or more length-based separation methods described below. In certain embodiments, nucleic acid is enriched for fragments from a select genomic region (e.g., chromosome) using one or more sequence-based separation methods described herein and/or known in the art. Certain methods for enriching for a nucleic acid subpopulation (e.g., fetal nucleic acid) in a sample are described in detail below.

Some methods for enriching for a nucleic acid subpopulation (e.g., fetal nucleic acid) that can be used with a method described herein include methods that exploit epigenetic differences between maternal and fetal nucleic acid. For example, fetal nucleic acid can be differentiated and separated from maternal nucleic acid based on methylation differences. Methylation-based fetal nucleic acid enrichment methods are described in U.S. Patent Application Publication No. 2010/0105049, which is incorporated by reference herein. Such methods sometimes involve binding a sample nucleic acid to a methylation-specific binding agent (methyl-CpG binding protein (MBD), methylation specific antibodies, and the like) and separating bound nucleic acid from unbound nucleic acid based on differential methylation status. Such methods also can include the use of methylation-sensitive restriction enzymes (as described above; e.g., HhaI and HpaII), which allow for the enrichment of fetal nucleic acid regions in a maternal sample by selectively digesting nucleic acid from the maternal sample with an enzyme that selectively and completely or substantially digests the maternal nucleic acid to enrich the sample for at least one fetal nucleic acid region.

Another method for enriching for a nucleic acid subpopulation (e.g., fetal nucleic acid) that can be used with a method described herein is a restriction endonuclease enhanced polymorphic sequence approach, such as a method described in U.S. Patent Application Publication No. 2009/0317818, which is incorporated by reference herein. Such methods include cleavage of nucleic acid comprising a non-target allele with a restriction endonuclease that recognizes the nucleic acid comprising the non-target allele but not the target allele; and amplification of uncleaved nucleic acid but not cleaved nucleic acid, where the uncleaved, amplified nucleic acid represents enriched target nucleic acid (e.g., fetal nucleic acid) relative to non-target nucleic acid (e.g., maternal nucleic acid). In certain embodiments, nucleic acid may be selected such that it comprises an allele having a polymorphic site that is susceptible to selective digestion by a cleavage agent, for example.

Some methods for enriching for a nucleic acid subpopulation (e.g., fetal nucleic acid) that can be used with a method described herein include selective enzymatic degradation approaches. Such methods involve protecting target sequences from exonuclease digestion thereby facilitating the elimination in a sample of undesired sequences (e.g., maternal DNA). For example, in one approach, sample nucleic acid is denatured to generate single stranded nucleic acid, single stranded nucleic acid is contacted with at least one target-specific primer pair under suitable annealing conditions, annealed primers are extended by nucleotide polymerization generating double stranded target sequences, and digesting single stranded nucleic acid using a nuclease that digests single stranded (i.e. non-target) nucleic acid. In certain embodiments, the method can be repeated for at least one additional cycle. In certain embodiments, the same target-specific primer pair is used to prime each of the first and second cycles of extension, and in some cases, different target-specific primer pairs are used for the first and second cycles.

Some methods for enriching for a nucleic acid subpopulation (e.g., fetal nucleic acid) that can be used with a method described herein include massively parallel signature sequencing (MPSS) approaches. MPSS typically is a solid phase method that uses adapter (i.e. tag) ligation, followed by adapter decoding, and reading of the nucleic acid sequence in small increments. Tagged PCR products are typically amplified such that each nucleic acid generates a PCR product with a unique tag. Tags are often used to attach the PCR products to microbeads. After several rounds of ligation-based sequence determination, for example, a sequence signature can be identified from each bead. Each signature sequence (MPSS tag) in a MPSS dataset is analyzed, compared with all other signatures, and all identical signatures are counted.

In certain embodiments, certain MPSS-based enrichment methods can include amplification (e.g., PCR)-based approaches. In certain embodiments, loci-specific amplification methods can be used (e.g., using loci-specific amplification primers). In certain embodiments, a multiplex SNP allele PCR approach can be used. In certain embodiments, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In certain embodiments, a multiplex SNP allele PCR approach can be used in combination with a three-primer system and indexed sequencing. For example, such an approach can involve the use of multiplex PCR (e.g., MASSARRAY system) with primers having a first capture probe incorporated into certain loci-specific forward PCR primers and adapter sequences incorporated into loci-specific reverse PCR primers, to thereby generate amplicons, followed by a secondary PCR to incorporate reverse capture sequences and molecular index barcodes for sequencing using, for example, the Illumina MPSS system. In certain embodiments, a multiplex SNP allele PCR approach can be used in combination with a four-primer system and indexed sequencing. For example, such an approach can involve the use of multiplex PCR (e.g., MASSARRAY system) with primers having adaptor sequences incorporated into both loci-specific forward and loci-specific reverse PCR primers, followed by a secondary PCR to incorporate both forward and reverse capture sequences and molecular index barcodes for sequencing using, for example, the Illumina MPSS system. In certain embodiments, a microfluidics approach can be used. In certain embodiments, an array-based microfluidics approach can be used. For example, such an approach can involve the use of a microfluidics array (e.g., Fluidigm) for amplification at low plex and incorporation of index and capture probes, followed by sequencing. In certain embodiments, an emulsion microfluidics approach can be used, such as, for example, digital droplet PCR.

In certain embodiments, universal amplification methods can be used (e.g., using universal or non-loci-specific amplification primers). In certain embodiments, universal amplification methods can be used in combination with pull-down approaches. In certain embodiments, a method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In certain embodiments, pull-down approaches can be used in combination with ligation-based methods. In certain embodiments, a method can include biotinylated ultramer pull down with sequence specific adapter ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In certain embodiments, pull-down approaches can be used in combination with extension and ligation-based methods. In certain embodiments, a method can include molecular inversion probe (MIP) extension and ligation. For example, such an approach can involve the use of molecular inversion probes in combination with sequence adapters followed by universal amplification and sequencing. In certain embodiments, complementary DNA can be synthesized and sequenced without amplification.

In certain embodiments, extension and ligation approaches can be performed without a pull-down component. In certain embodiments, a method can include loci-specific forward and reverse primer hybridization, extension and ligation. Such methods can further include universal amplification or complementary DNA synthesis without amplification, followed by sequencing. Such methods can reduce or exclude background sequences during analysis, in some cases.

In certain embodiments, pull-down approaches can be used with an optional amplification component or with no amplification component. In certain embodiments, a method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In certain embodiments, a method can include a biotinylated pull-down assay with extension and ligation of adaptor sequence in combination with circular single stranded ligation. For example, such an approach can involve the use of selector probes to capture regions of interest (i.e. target sequences), extension of the probes, adaptor ligation, single stranded circular ligation, optional amplification, and sequencing. In certain embodiments, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments typically are isolated away from the remaining fragments in the nucleic acid sample. In certain embodiments, the separated target fragments and the separated reference fragments also are isolated away from each other (e.g., isolated in separate assay compartments). In certain embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a segment or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome).

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain embodiments, length-based separation approaches can include fragment circularization, chemical treatment (e.g., formaldehyde, polyethylene glycol (PEG)), mass spectrometry and/or size-specific nucleic acid amplification, for example.

Certain length-based separation methods that can be used with methods described herein employ a selective sequence tagging approach, for example. The term "sequence tagging" refers to incorporating a recognizable and distinct sequence into a nucleic acid or population of nucleic acids. The term "sequence tagging" as used herein has a different meaning than the term "sequence tag" described later herein. In such sequence tagging methods, a fragment size species (e.g., short fragments) nucleic acids are subjected to selective sequence tagging in a sample that includes long and short nucleic acids. Such methods typically involve performing a nucleic acid amplification reaction using a set of nested primers which include inner primers and outer primers. In certain embodiments, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Nucleic Acid Amplification and Detection

Following separation of nucleic acid in a methylation-differential manner, nucleic acid may be amplified and/or subjected to a detection process (e.g., sequence-based analysis, mass spectrometry). Furthermore, once it is determined that one particular genomic sequence of fetal origin is hypermethylated or hypomethylated compared to the maternal counterpart, the amount of this fetal genomic sequence can be determined. Subsequently, this amount can be compared to a standard control value and serve as an indication for the potential of certain pregnancy-associated disorder.

Nucleotide sequences, or amplified nucleic acid sequences, or detectable products prepared from the foregoing, can be detected by a suitable detection process. Non-limiting examples of methods of detection, quantification, sequencing and the like include mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), direct DNA sequencing, Molecular Inversion Probe (MIP) technology from Affymetrix, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization using at least one probe, hybridization using at least one fluorescently labeled probe, cloning and sequencing, electrophoresis, the use of hybridization probes and quantitative real time polymerase chain reaction (QRT-PCR), digital PCR, nanopore sequencing, chips and combinations thereof. In some embodiments the amount of each amplified nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

Nucleic acid detection and/or quantification also may include, for example, solid support array based detection of fluorescently labeled nucleic acid with fluorescent labels incorporated during or after PCR, single molecule detection of fluorescently labeled molecules in solution or captured on a solid phase, or other sequencing technologies such as, for example, sequencing using ION TORRENT or MISEQ platforms or single molecule sequencing technologies using instrumentation such as, for example, PACBIO sequencers, HELICOS sequencer, or nanopore sequencing technologies.

In some cases, nucleotide sequences, or amplified nucleic acid sequences, or detectable products prepared from the foregoing, are detected using a sequencing process (e.g., such as a sequencing process described herein). Nucleic acid quantifications generated by a method comprising a sequencing detection process may be compared to nucleic acid quantifications generated by a method comprising a different detection process (e.g., mass spectrometry). Such comparisons may be expressed using an $R^2$ value, which is a measure of correlation between two outcomes (e.g., nucleic acid quantifications). In some cases, nucleic acid quantifications (e.g., fetal copy number quantifications) are highly correlated (i.e., have high $R^2$ values) for quantifications generated using different detection processes (e.g., sequencing and mass spectrometry). In some cases, $R^2$ values for nucleic acid quantifications generated using different detection processes may be between about 0.90 and about 1.0. For example, $R^2$ values may be about 0.91, 0.92, 0.93, 0.94, 0.95, 0.96, 0.97, 0.98, or 0.99.

Amplification of Nucleotide Sequences

In many instances, it is desirable to amplify a nucleic acid sequence of the technology herein using any of several nucleic acid amplification procedures which are well known in the art (listed above and described in greater detail below). Specifically, nucleic acid amplification is the enzymatic synthesis of nucleic acid amplicons (copies) which contain a sequence that is complementary to a nucleic acid sequence being amplified. Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a polynucleotide sequence is typically used in practicing the present technology, one of skill in the art will recognize that the amplification of a genomic sequence found in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of the technology herein, which represents a particular methylation pattern, or to quantitatively determine the amount of this particular genomic sequence in the maternal blood. For a review of branched-DNA signal amplification for direct quantitation of nucleic acid sequences in clinical samples, see Nolte, Adv. Clin. Chem. 33:201-235, 1998.

The compositions and processes of the technology herein are also particularly useful when practiced with digital PCR. Digital PCR was first developed by Kalinina and colleagues (Kalinina et al., "Nanoliter scale PCR with TaqMan detection." Nucleic Acids Research. 25; 1999-2004, (1997)) and further developed by Vogelstein and Kinzler (Digital PCR. Proc Natl Acad Sci USA. 96; 9236-41, (1999)). The application of digital PCR for use with fetal diagnostics was first described by Cantor et al. (PCT Patent Publication No. WO05023091A2) and subsequently described by Quake et al. (US Patent Publication No. US 20070202525), which are both hereby incorporated by reference. Digital PCR takes advantage of nucleic acid (DNA, cDNA or RNA) amplification on a single molecule level, and offers a highly sensitive method for quantifying low copy number nucleic acid. Fluidigm® Corporation offers systems for the digital analysis of nucleic acids.

The terms "amplify", "amplification", "amplification reaction", or "amplifying" refer to any in vitro process for multiplying the copies of a nucleic acid. Amplification sometimes refers to an "exponential" increase in nucleic acid. However, "amplifying" as used herein can also refer to linear increases in the numbers of a select nucleic acid, but is different than a one-time, single primer extension step. In some embodiments a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions, for example, and also may reduce amplification biases due to nucleotide sequence or abundance of the nucleic acid. In some embodiments a one-time primer extension may be performed as a prelude to linear or exponential amplification.

Any suitable amplification technique can be utilized. Amplification of polynucleotides include, but are not limited to, polymerase chain reaction (PCR); ligation amplification (or ligase chain reaction (LCR)); amplification methods based on the use of Q-beta replicase or template-dependent polymerase (see US Patent Publication Number US20050287592); helicase-dependent isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, digital PCR, combinations thereof, and the like. For example, amplification can be accomplished using digital PCR, in certain embodiments (see e.g. Kalinina et al., "Nanoliter scale PCR with TaqMan detection." Nucleic Acids Research. 25; 1999-2004, (1997); Vogelstein and Kinzler (Digital PCR. Proc Natl Acad Sci USA. 96; 9236-41, (1999); PCT Patent Publication No. WO05023091A2; US Patent Publication No. US 20070202525). Digital PCR takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation). Reagents and hardware for conducting PCR are commercially available.

A generalized description of an amplification process is presented herein. Primers and nucleic acid are contacted, and complementary sequences anneal to one another, for example. Primers can anneal to a nucleic acid, at or near (e.g., adjacent to, abutting, and the like) a sequence of interest. In some embodiments, the primers in a set hybridize within about 10 to 30 nucleotides from a nucleic acid sequence of interest and produce amplified products. In some embodiments, the primers hybridize within the nucleic acid sequence of interest.

A reaction mixture, containing components necessary for enzymatic functionality, is added to the primer-nucleic acid hybrid, and amplification can occur under suitable conditions. Components of an amplification reaction may include, but are not limited to, e.g., primers (e.g., individual primers, primer pairs, primer sets and the like) a polynucleotide template, polymerase, nucleotides, dNTPs and the like. In some embodiments, non-naturally occurring nucleotides or nucleotide analogs, such as analogs containing a detectable label (e.g., fluorescent or colorimetric label), may be used for example. Polymerases can be selected by a person of ordinary skill and include polymerases for thermocycle amplification (e.g., Taq DNA Polymerase; Q-Bio™ Taq DNA Polymerase (recombinant truncated form of Taq DNA Polymerase lacking 5'-3' exo activity); SurePrime™ Polymerase (chemically modified Taq DNA polymerase for "hot start" PCR); Arrow™ Taq DNA Polymerase (high sensitivity and long template amplification)) and polymerases for thermostable amplification (e.g., RNA polymerase for transcription-mediated amplification (TMA) described at World Wide Web URL "gen-probe.com/pdfs/tma_whiteppr.pdf"). Other enzyme components can be added, such as reverse transcriptase for transcription mediated amplification (TMA) reactions, for example.

PCR conditions can be dependent upon primer sequences, abundance of nucleic acid, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. Digital PCR is also known in the art; see, e.g., United States Patent Application Publication no. 20070202525, filed Feb. 2, 2007, which is hereby incorporated by reference). PCR is typically carried out as an automated process with a thermostable enzyme. In this process, the temperature of the reaction mixture is cycled through a denaturing step, a primer-annealing step, and an extension reaction step automatically. Some PCR protocols also include an activation step and a final extension step. Machines specifically adapted for this purpose are commercially available. A non-limiting example of a PCR protocol that may be suitable for embodiments described herein is, treating the sample at 95° C. for 5 minutes; repeating thirty-five cycles of 95° C. for 45 seconds and 68° C. for 30 seconds; and then treating the sample at 72° C. for 3 minutes. A completed PCR reaction can optionally be kept at 4° C. until further action is desired. Multiple cycles frequently are performed using a commercially available thermal cycler. Suitable isothermal amplification processes known and selected by the person of ordinary skill in the art also may be applied, in certain embodiments.

In some embodiments, an amplification product may include naturally occurring nucleotides, non-naturally occurring nucleotides, nucleotide analogs and the like and combinations of the foregoing. An amplification product often has a nucleotide sequence that is identical to or substantially identical to a nucleic acid sequence herein, or complement thereof. A "substantially identical" nucleotide sequence in an amplification product will generally have a high degree of sequence identity to the nucleotide sequence species being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of infidelity of the polymerase used for extension and/or amplification, or additional nucleotide sequence(s) added to the primers used for amplification.

Primers

Primers useful for detection, amplification, quantification, sequencing and analysis of nucleic acid are provided. The term "primer" as used herein refers to a nucleic acid that includes a nucleotide sequence capable of hybridizing or annealing to a target nucleic acid, at or near (e.g., adjacent to) a specific region of interest. Primers can allow for specific determination of a target nucleic acid nucleotide sequence or detection of the target nucleic acid (e.g., presence or absence of a sequence or copy number of a sequence), or feature thereof, for example. A primer may be naturally occurring or synthetic. The term "specific" or "specificity", as used herein, refers to the binding or hybridization of one molecule to another molecule, such as a primer for a target polynucleotide. That is, "specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "primer", "oligo", or "oligonucleotide" may be used interchangeably throughout the document, when referring to primers.

A primer nucleic acid can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein, may be synthesized and labeled using known techniques. Primers may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of primers can be effected by native acrylamide gel electrophoresis or by anion-exchange high-performance liquid chromatography (HPLC), for example, as described in Pearson and Regnier, J. Chrom., 255:137-149, 1983.

All or a portion of a primer nucleic acid sequence (naturally occurring or synthetic) may be substantially complementary to a target nucleic acid, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are target and primer sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complimentary to a target nucleic acid sequence are also substantially identical to the compliment of the target nucleic acid sequence. That is, primers are substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Primer sequences and length may affect hybridization to target nucleic acid sequences. Depending on the degree of mismatch between the primer and target nucleic acid, low, medium or high stringency conditions may be used to effect primer/target annealing. As used herein, the term "stringent conditions" refers to conditions for hybridization and washing. Methods for hybridization reaction temperature condition optimization are known to those of skill in the art, and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile. Features of primers can be applied to probes and oligonucleotides, such as, for example, the competitive and inhibitory oligonucleotides provided herein.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

In some embodiments primers can include a nucleotide subsequence that may be complementary to a solid phase nucleic acid primer hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). A primer may contain a nucleotide subsequence not complementary to or not substantially complementary to a solid phase nucleic acid primer hybridization sequence (e.g., at the 3' or 5' end of the nucleotide subsequence in the primer complementary to or substantially complementary to the solid phase primer hybridization sequence).

A primer, in certain embodiments, may contain a modification such as one or more inosines, abasic sites, locked nucleic acids, minor groove binders, duplex stabilizers (e.g., acridine, spermidine), Tm modifiers or any modifier that changes the binding properties of the primers or probes. A primer, in certain embodiments, may contain a detectable molecule or entity (e.g., a fluorophore, radioisotope, colorimetric agent, particle, enzyme and the like, as described above for labeled competitor oligonucleotides).

A primer also may refer to a polynucleotide sequence that hybridizes to a subsequence of a target nucleic acid or another primer and facilitates the detection of a primer, a target nucleic acid or both, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

In some embodiments, the primers are complementary to genomic DNA target sequences. In some cases, the forward and reverse primers hybridize to the 5' and 3' ends of the genomic DNA target sequences. In some embodiments, primers that hybridize to the genomic DNA target sequences also hybridize to competitor oligonucleotides that were designed to compete with corresponding genomic DNA target sequences for binding of the primers. In some cases, the primers hybridize or anneal to the genomic DNA target sequences and the corresponding competitor oligonucleotides with the same or similar hybridization efficiencies. In some cases the hybridization efficiencies are different. The ratio between genomic DNA target amplicons and competitor amplicons can be measured during the reaction. For example if the ratio is 1:1 at 28 cycles but 2:1 at 35, this could indicate that during the end of the amplification reaction the primers for one target (i.e. genomic DNA target or competitor) are either reannealing faster than the other, or the denaturation is less effective than the other.

In some embodiments primers are used in sets. As used herein, an amplification primer set is one or more pairs of forward and reverse primers for a given region. Thus, for example, primers that amplify genomic targets for region 1 (i.e. targets 1a and 1b) are considered a primer set. Primers that amplify genomic targets for region 2 (i.e. targets 2a and 2b) are considered a different primer set. In some embodiments, the primer sets that amplify targets within a particular region also amplify the corresponding competitor oligonucleotide(s). A plurality of primer pairs may constitute a primer set in certain embodiments (e.g., about 2, 3, 4, 5, 6, 7, 8, 9, 10, 15, 20, 25, 30, 35, 40, 45, 50, 55, 60, 65, 70, 75, 80, 85, 90, 95 or 100 pairs). In some embodiments a plurality of primer sets, each set comprising pair(s) of primers, may be used.

Determination of Polynucleotide Sequences

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present technology. Additional means suitable for detecting changes in a polynucleotide sequence for practicing the methods of the present technology include but are not limited to mass spectrometry, primer extension, polynucleotide hybridization, real-time PCR, and electrophoresis.

Use of a primer extension reaction also can be applied in methods of the technology herein. A primer extension reaction operates, for example, by discriminating the SNP alleles by the incorporation of deoxynucleotides and/or dideoxynucleotides to a primer extension primer which hybridizes to a region adjacent to the SNP site. The primer is extended with a polymerase. The primer extended SNP can be detected physically by mass spectrometry or by a tagging moiety such as biotin. As the SNP site is only extended by a complementary deoxynucleotide or dideoxynucleotide that is either tagged by a specific label or generates a primer extension product with a specific mass, the SNP alleles can be discriminated and quantified.

Reverse transcribed and amplified nucleic acids may be modified nucleic acids. Modified nucleic acids can include nucleotide analogs, and in certain embodiments include a detectable label and/or a capture agent. Examples of detectable labels include without limitation fluorophores, radioisotopes, colormetric agents, light emitting agents, chemiluminescent agents, light scattering agents, enzymes and the like. Examples of capture agents include without limitation an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments Mass spectrometry is a particularly effective method for the detection of a polynucleotide of the technology herein, for example a PCR amplicon, a primer extension product or a detector probe that is cleaved from a target nucleic acid. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. For a review of genotyping methods using Sequenom® standard iPLEX™ assay and MassARRAY® technology, see Jurinke, C., Oeth, P., van den Boom, D., "MALDI-TOF mass spectrometry: a versatile tool for high-performance DNA analysis." Mol. Biotechnol. 26, 147-164 (2004); and Oeth, P. et al., "iPLEX™ Assay: Increased Plexing Efficiency and Flexibility for MassARRAY® System through single base primer extension with mass-modified Terminators." SEQUENOM Application Note (2005), both of which are hereby incorporated by reference. For a review of detecting and quantifying target nucleic using cleavable detector probes that are cleaved during the amplification process and detected by mass spectrometry, see U.S. patent application Ser. No. 11/950,395, which was filed Dec. 4, 2007, and is hereby incorporated by reference.

Sequencing technologies are improving in terms of throughput and cost. Sequencing technologies, such as that achievable on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001), allow the sequencing of many nucleic acid molecules isolated from a specimen at high orders of multiplexing in a parallel fashion (Dear Brief Funct Genomic Proteomic 2003; 1: 397-416).

Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing. Nucleotide sequence species, amplification nucleic acid species and detectable products generated there from can be considered a "study nucleic acid" for purposes of analyzing a nucleotide sequence by such sequence analysis platforms.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled with more than one fluorescent label (e.g., 1 fluorescent label, 2, 3, or 4 fluorescent labels). An example of a system that can be used by a person of ordinary skill based on sequencing by ligation generally involves the following steps. Clonal bead populations can be prepared in emulsion microreactors containing study nucleic acid ("template"), amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein and performing emulsion amplification using the same or a different solid support originally used to generate the first amplification product. Such a system also may be used to analyze amplification products directly generated by a process described herein by bypassing an exponential amplification process and directly sorting the solid supports described herein on the glass slide.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphosulfate and luciferin. Nucleotide solutions are sequentially added and removed. Correct incorporation of a nucleotide releases a pyrophosphate, which interacts with ATP sulfurylase and produces ATP in the presence of adenosine 5' phosphosulfate, fueling the luciferin reaction, which produces a chemiluminescent signal allowing sequence determination.

An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., "Single-molecule PCR using water-in-oil emulsion;" Journal of Biotechnology 102: 117-124 (2003)). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslaysky et al., PNAS 100(7): 3960-3964 (2003)). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer-released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as nonspecific fluorescence. Following immobilization of the primer-released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis is facilitated by sequence analysis apparatus and components known to the person of ordinary skill in the art.

Methods provided herein allow for high-throughput detection of nucleic acid species in a plurality of nucleic acids (e.g., nucleotide sequence species, amplified nucleic acid species and detectable products generated from the foregoing). Multiplexing refers to the simultaneous detection of more than one nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of nucleic acid species (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction.

In certain embodiments, the number of nucleic acid species multiplexed include, without limitation, about 1 to about 500 (e.g., about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-

173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501).

Design methods for achieving resolved mass spectra with multiplexed assays can include primer and oligonucleotide design methods and reaction design methods. See, for example, the multiplex schemes provided in Tables X and Y. For primer and oligonucleotide design in multiplexed assays, the same general guidelines for primer design applies for uniplexed reactions, such as avoiding false priming and primer dimers, only more primers are involved for multiplex reactions. For mass spectrometry applications, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. In some embodiments multiplex analysis may be adapted to mass spectrometric detection of chromosome abnormalities, for example. In certain embodiments multiplex analysis may be adapted to various single nucleotide or nanopore based sequencing methods described herein. Commercially produced micro-reaction chambers or devices or arrays or chips may be used to facilitate multiplex analysis, and are commercially available.

Additional Methods for Obtaining Sequence Reads

In some embodiments, nucleic acids (e.g., nucleic acid fragments, sample nucleic acid, cell-free nucleic acid) may be sequenced. In certain embodiments, a full or substantially full sequence is obtained and sometimes a partial sequence is obtained. Sequencing, mapping and related analytical methods are known in the art (e.g., United States Patent Application Publication US200910029377, incorporated by reference). Certain aspects of such processes are described hereafter.

As used herein, "reads" (i.e., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

In some embodiments the nominal, average, mean or absolute length of single-end reads sometimes is about 20 contiguous nucleotides to about 50 contiguous nucleotides, sometimes about 30 contiguous nucleotides to about 40 contiguous nucleotides, and sometimes about 35 contiguous nucleotides or about 36 contiguous nucleotides. In certain embodiments the nominal, average, mean or absolute length of single-end reads is about 20 to about 30 bases in length. In certain embodiments the nominal, average, mean or absolute length of single-end reads is about 24 to about 28 bases in length. In certain embodiments the nominal, average, mean or absolute length of single-end reads is about 21, 22, 23, 24, 25, 26, 27, 28 or about 29 bases in length.

In certain embodiments, the nominal, average, mean or absolute length of the paired-end reads sometimes is about 10 contiguous nucleotides to about 25 contiguous nucleotides (e.g., about 11, 12, 13, 14, 15, 16, 17, 18, 19, 20, 21, 22, 23 or 24 nucleotides in length), sometimes is about 15 contiguous nucleotides to about 20 contiguous nucleotides, and sometimes is about 17 contiguous nucleotides or about 18 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

Sequence reads can be mapped and the number of reads or sequence tags mapping to a specified nucleic acid region (e.g., a chromosome, a bin, a genomic section) are referred to as counts. In some embodiments, counts can be manipulated or transformed (e.g., normalized, combined, added, filtered, selected, averaged, derived as a mean, the like, or a combination thereof). In some embodiments, counts can be transformed to produce normalized counts. Normalized counts for multiple genomic sections can be provided in a profile (e.g., a genomic profile, a chromosome profile, a profile of a segment or portion of a chromosome). One or more different elevations in a profile also can be manipulated or transformed (e.g., counts associated with elevations can be normalized) and elevations can be adjusted.

In some embodiments, one nucleic acid sample from one individual is sequenced. In certain embodiments, nucleic acid samples from two or more biological samples, where each biological sample is from one individual or two or more individuals, are pooled and the pool is sequenced. In the latter embodiments, a nucleic acid sample from each biological sample often is identified by one or more unique identification tags.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.1-fold to about 100-fold coverage, about 0.2-fold to 20-fold coverage, or about 0.2-fold to about 1-fold coverage (e.g., about 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In certain embodiments, a fraction of a nucleic acid pool that is sequenced in a run is further sub-selected prior to sequencing. In certain embodiments, hybridization-based techniques (e.g., using oligonucleotide arrays) can be used to first sub-select for nucleic acid sequences from certain chromosomes (e.g., a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected pool of nucleic acids is sequenced randomly. In some embodiments, the nucleic acid is amplified prior to sequencing. In some embodiments, a portion or subset of the nucleic acid is amplified prior to sequencing.

In certain embodiments, a sequencing library is prepared prior to or during a sequencing process. Methods for preparing a sequencing library are known in the art and commercially available platforms may be used for certain applications. Certain commercially available library platforms may be compatible with certain nucleotide sequencing processes described herein. For example, one or more commercially available library platforms may be compatible with a sequencing by synthesis process. In certain embodiments, a ligation-based library preparation method is used (e.g., ILLUMINA TRUSEQ, Illumina, San Diego Calif.). Ligation-based library preparation methods typically use a methylated adaptor design which can incorporate an index sequence at the initial ligation step and often can be used to prepare samples for single-read sequencing, paired-end sequencing and multiplexed sequencing. In certain embodiments, a transposon-based library preparation method is used (e.g., EPICENTRE NEXTERA, Epicentre, Madison Wis.). Transposon-based methods typically use in vitro transposition to simultaneously fragment and tag DNA in a single-tube reaction (often allowing incorporation of platform-specific tags and optional barcodes), and prepare sequencer-ready libraries.

Any sequencing method suitable for conducting methods described herein can be utilized. In some embodiments, a high-throughput sequencing method is used. High-throughput sequencing methods generally involve clonally amplified DNA templates or single DNA molecules that are sequenced in a massively parallel fashion within a flow cell (e.g. as described in Metzker M Nature Rev 11:31-46 (2010); Volkerding et al. Clin Chem 55:641-658 (2009)). Such sequencing methods also can provide digital quantitative information, where each sequence read is a countable "sequence tag" or "count" representing an individual clonal DNA template, a single DNA molecule, bin or chromosome. Next generation sequencing techniques capable of sequencing DNA in a massively parallel fashion are collectively referred to herein as "massively parallel sequencing" (MPS). High-throughput sequencing technologies include, for example, sequencing-by-synthesis with reversible dye terminators, sequencing by oligonucleotide probe ligation, pyrosequencing and real time sequencing. Non-limiting examples of MPS include Massively Parallel Signature Sequencing (MPSS), Polony sequencing, Pyrosequencing, Illumina (Solexa) sequencing, SOLiD sequencing, Ion semiconductor sequencing, DNA nanoball sequencing, Helioscope single molecule sequencing, single molecule real time (SMRT) sequencing, nanopore sequencing, ION Torrent and RNA polymerase (RNAP) sequencing.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

In some embodiments, first generation technology, such as, for example, Sanger sequencing including the automated Sanger sequencing, can be used in a method provided herein. Additional sequencing technologies that include the use of developing nucleic acid imaging technologies (e.g. transmission electron microscopy (TEM) and atomic force microscopy (AFM)), also are contemplated herein. Examples of various sequencing technologies are described below.

A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

In certain sequencing by synthesis procedures, for example, template DNA (e.g., circulating cell-free DNA (ccfDNA)) sometimes can be fragmented into lengths of several hundred base pairs in preparation for library generation. In some embodiments, library preparation can be performed without further fragmentation or size selection of the template DNA (e.g., ccfDNA). Sample isolation and library generation may be performed using automated methods and apparatus, in certain embodiments. Briefly, template DNA is end repaired by a fill-in reaction, exonuclease reaction or a combination of a fill-in reaction and exonuclease reaction. The resulting blunt-end repaired template DNA is extended by a single nucleotide, which is complementary to a single nucleotide overhang on the 3' end of an adapter primer, and often increases ligation efficiency. Any complementary nucleotides can be used for the extension/overhang nucleotides (e.g., A/T, C/G), however adenine frequently is used to extend the end-repaired DNA, and thymine often is used as the 3' end overhang nucleotide.

In certain sequencing by synthesis procedures, for example, adapter oligonucleotides are complementary to the flow-cell anchors, and sometimes are utilized to associate the modified template DNA (e.g., end-repaired and single nucleotide extended) with a solid support, such as the inside surface of a flow cell, for example. In some embodiments, the adapter also includes identifiers (i.e., indexing nucleotides, or "barcode" nucleotides (e.g., a unique sequence of nucleotides usable as an identifier to allow unambiguous identification of a sample and/or chromosome)), one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). Identifiers or nucleotides contained in an adapter often are six or more nucleotides in length, and frequently are positioned in the adaptor such that the identifier nucleotides are the first nucleotides sequenced during the sequencing reaction. In certain embodiments, identifier nucleotides are associated with a sample but are sequenced in a separate sequencing reaction to avoid compromising the quality of sequence reads. Subsequently, the reads from the identifier sequencing and the DNA template sequencing are linked together and the reads de-multiplexed. After linking and de-multiplexing the sequence reads and/or identifiers can be further adjusted or processed as described herein.

In certain sequencing by synthesis procedures, utilization of identifiers allows multiplexing of sequence reactions in a flow cell lane, thereby allowing analysis of multiple samples per flow cell lane. The number of samples that can be analyzed in a given flow cell lane often is dependent on the number of unique identifiers utilized during library preparation and/or probe design. Non limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively). A method described herein can be performed using any number of unique identifiers (e.g., 4, 8, 12, 24, 48, 96, or more). The greater the number of unique identifiers, the greater the number of samples and/or chromosomes, for example, that can be multiplexed in a single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell.

In certain sequencing by synthesis procedures, adapter-modified, single-stranded template DNA is added to the flow cell and immobilized by hybridization to the anchors under limiting-dilution conditions. In contrast to emulsion PCR, DNA templates are amplified in the flow cell by "bridge" amplification, which relies on captured DNA strands "arching" over and hybridizing to an adjacent anchor oligonucleotide. Multiple amplification cycles convert the single-molecule DNA template to a clonally amplified arching "cluster," with each cluster containing approximately 1000 clonal molecules. Approximately $50\times10^6$ separate clusters can be generated per flow cell. For sequencing, the clusters are denatured, and a subsequent chemical cleavage reaction and wash leave only forward strands for single-end sequencing. Sequencing of the forward strands is initiated by hybridizing a primer complementary to the adapter sequences, which is followed by addition of polymerase and a mixture of four differently colored fluorescent reversible dye terminators. The terminators are incorporated according to sequence complementarity in each strand in a clonal cluster. After incorporation, excess reagents are washed away, the clusters are optically interrogated, and the fluorescence is recorded. With successive chemical steps, the reversible dye terminators are unblocked, the fluorescent labels are cleaved and washed away, and the next sequencing cycle is performed. This iterative, sequencing-by-synthesis process sometimes requires approximately 2.5 days to generate read lengths of 36 bases. With $50\times10^6$ clusters per flow cell, the overall sequence output can be greater than 1 billion base pairs (Gb) per analytical run.

Another nucleic acid sequencing technology that may be used with a method described herein is 454 sequencing (Roche). 454 sequencing uses a large-scale parallel pyrosequencing system capable of sequencing about 400-600 megabases of DNA per run. The process typically involves two steps. In the first step, sample nucleic acid (e.g. DNA) is sometimes fractionated into smaller fragments (300-800 base pairs) and polished (made blunt at each end). Short adaptors are then ligated onto the ends of the fragments. These adaptors provide priming sequences for both amplification and sequencing of the sample-library fragments. One adaptor (Adaptor B) contains a 5'-biotin tag for immobilization of the DNA library onto streptavidin-coated beads. After nick repair, the non-biotinylated strand is released and used as a single-stranded template DNA (sstDNA) library. The sstDNA library is assessed for its quality and the optimal amount (DNA copies per bead) needed for emPCR is determined by titration. The sstDNA library is immobilized onto beads. The beads containing a library fragment carry a single sstDNA molecule. The bead-bound library is emulsified with the amplification reagents in a water-in-oil mixture. Each bead is captured within its own microreactor where PCR amplification occurs. This results in bead-immobilized, clonally amplified DNA fragments.

In the second step of 454 sequencing, single-stranded template DNA library beads are added to an incubation mix containing DNA polymerase and are layered with beads containing sulfurylase and luciferase onto a device containing pico-liter sized wells. Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing exploits the release of pyrophosphate (PPi) upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed (see, for example, Margulies, M. et al. Nature 437:376-380 (2005)).

Another nucleic acid sequencing technology that may be used in a method provided herein is Applied Biosystems' SOLiD™ technology. In SOLiD™ sequencing-by-ligation, a library of nucleic acid fragments is prepared from the sample and is used to prepare clonal bead populations. With this method, one species of nucleic acid fragment will be present on the surface of each bead (e.g. magnetic bead). Sample nucleic acid (e.g. genomic DNA) is sheared into fragments, and adaptors are subsequently attached to the 5' and 3' ends of the fragments to generate a fragment library. The adapters are typically universal adapter sequences so that the starting sequence of every fragment is both known and identical. Emulsion PCR takes place in microreactors containing all the necessary reagents for PCR. The resulting PCR products attached to the beads are then covalently bound to a glass slide. Primers then hybridize to the adapter sequence within the library template. A set of four fluorescently labeled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n−1 position for a second round of ligation cycles. Often, five rounds of primer reset are completed for each sequence tag. Through the primer reset process, each base is interrogated in two independent ligation reactions by two different primers. For example, the base at read position 5 is assayed by primer number 2 in ligation cycle 2 and by primer number 3 in ligation cycle 1.

Another nucleic acid sequencing technology that may be used in a method described herein is the Helicos True Single Molecule Sequencing (tSMS). In the tSMS technique, a polyA sequence is added to the 3' end of each nucleic acid (e.g. DNA) strand from the sample. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/$cm^2$. The flow cell is then loaded into a sequencing apparatus and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step (see, for example, Harris T. D. et al., Science 320:106-109 (2008)).

Another nucleic acid sequencing technology that may be used in a method provided herein is the single molecule, real-time (SMRT™) sequencing technology of Pacific Biosciences. With this method, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is then repeated.

Another nucleic acid sequencing technology that may be used in a method described herein is ION TORRENT (Life Technologies) single molecule sequencing which pairs semiconductor technology with a simple sequencing chemistry to directly translate chemically encoded information (A, C, G, T) into digital information (0, 1) on a semiconductor chip. ION TORRENT uses a high-density array of micro-machined wells to perform nucleic acid sequencing in a massively parallel way. Each well holds a different DNA molecule. Beneath the wells is an ion-sensitive layer and beneath that an ion sensor. Typically, when a nucleotide is incorporated into a strand of DNA by a polymerase, a hydrogen ion is released as a byproduct. If a nucleotide, for example a C, is added to a DNA template and is then incorporated into a strand of DNA, a hydrogen ion will be released. The charge from that ion will change the pH of the solution, which can be detected by an ion sensor. A sequencer can call the base, going directly from chemical information to digital information. The sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection (i.e. detection without scanning, cameras or light), each nucleotide incorporation is recorded in seconds.

Another nucleic acid sequencing technology that may be used in a method described herein is the chemical-sensitive field effect transistor (CHEMFET) array. In one example of this sequencing technique, DNA molecules are placed into reaction chambers, and the template molecules can be hybridized to a sequencing primer bound to a polymerase. Incorporation of one or more triphosphates into a new nucleic acid strand at the 3' end of the sequencing primer can be detected by a change in current by a CHEMFET sensor. An array can have multiple CHEMFET sensors. In another example, single nucleic acids are attached to beads, and the nucleic acids can be amplified on the bead, and the individual beads can be transferred to individual reaction chambers on a CHEMFET array, with each chamber having a CHEMFET sensor, and the nucleic acids can be sequenced (see, for example, U.S. Patent Application Publication No. 2009/0026082).

Another nucleic acid sequencing technology that may be used in a method described herein is electron microscopy. In one example of this sequencing technique, individual nucleic acid (e.g. DNA) molecules are labeled using metallic labels that are distinguishable using an electron microscope. These molecules are then stretched on a flat surface and imaged using an electron microscope to measure sequences (see, for example, Moudrianakis E. N. and Beer M. Proc Natl Acad Sci USA. 1965 March; 53:564-71). In certain embodiments, transmission electron microscopy (TEM) is used (e.g. Halcyon Molecular's TEM method). This method, termed Individual Molecule Placement Rapid Nano Transfer (IMPRNT), includes utilizing single atom resolution transmission electron microscope imaging of high-molecular weight (e.g. about 150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA (see, for example, International Patent Application No. WO 2009/046445).

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number. In sequencing by hybridization, the method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in a method described herein. Nanopore sequencing is a single-molecule sequencing technology whereby a single nucleic acid molecule (e.g. DNA) is sequenced directly as it passes through a nanopore. A nanopore is a small hole or channel, of the order of 1 nanometer in diameter. Certain transmembrane cellular proteins can act as nanopores (e.g. alpha-hemolysin). In certain embodiments, nanopores can be synthesized (e.g. using a silicon platform). Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree and generates characteristic changes to the current. The amount of current which can pass through the nanopore at any given moment therefore varies depending on whether the nanopore is blocked by an A, a C, a G, a T, or in some cases, methyl-C. The change in the current through the nanopore as the DNA molecule passes through the nanopore represents a direct reading of the DNA sequence. In certain embodiments a nanopore can be used to identify individual DNA bases as they pass through the nanopore in the correct order (see, for example, Soni G V and Meller A. Clin Chem 53: 1996-2001 (2007); International Patent Application No. WO2010/004265).

There are a number of ways that nanopores can be used to sequence nucleic acid molecules. In some embodiments, an exonuclease enzyme, such as a deoxyribonuclease, is used. In this case, the exonuclease enzyme is used to sequentially detach nucleotides from a nucleic acid (e.g. DNA) molecule. The nucleotides are then detected and discriminated by the nanopore in order of their release, thus reading the sequence of the original strand. For such an embodiment, the exonuclease enzyme can be attached to the nanopore such that a proportion of the nucleotides released from the DNA molecule is capable of entering and interacting with the channel of the nanopore. The exonuclease can be attached to the nanopore structure at a site in close proximity to the part of the nanopore that forms the opening of the channel. In certain embodiments, the exonuclease enzyme can be attached to the nanopore structure such that its nucleotide exit trajectory site is orientated towards the part of the nanopore that forms part of the opening.

In some embodiments, nanopore sequencing of nucleic acids involves the use of an enzyme that pushes or pulls the nucleic acid (e.g. DNA) molecule through the pore. In this case, the ionic current fluctuates as a nucleotide in the DNA molecule passes through the pore. The fluctuations in the current are indicative of the DNA sequence. For such an embodiment, the enzyme can be attached to the nanopore structure such that it is capable of pushing or pulling the target nucleic acid through the channel of a nanopore without interfering with the flow of ionic current through the pore. The enzyme can be attached to the nanopore structure at a site in close proximity to the part of the structure that forms part of the opening. The enzyme can be attached to the subunit, for example, such that its active site is orientated towards the part of the structure that forms part of the opening.

In some embodiments, nanopore sequencing of nucleic acids involves detection of polymerase bi-products in close proximity to a nanopore detector. In this case, nucleoside phosphates (nucleotides) are labeled so that a phosphate labeled species is released upon the addition of a polymerase to the nucleotide strand and the phosphate labeled species is detected by the pore. Typically, the phosphate species contains a specific label for each nucleotide. As nucleotides are sequentially added to the nucleic acid strand, the bi-products of the base addition are detected. The order that the phosphate labeled species are detected can be used to determine the sequence of the nucleic acid strand.

The length of the sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median or average length of about 15 bp to 900 bp long (e.g. about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp or more.

In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening ‘bridge’ oligo to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

In some embodiments, nucleic acids may include a fluorescent signal or sequence tag information. Quantification of the signal or tag may be used in a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

Mapping Reads

Mapping nucleotide sequence reads (i.e., sequence information from a fragment whose physical genomic position is unknown) can be performed in a number of ways, and often comprises alignment of the obtained sequence reads with a matching sequence in a reference genome (e.g., Li et al., "Mapping short DNA sequencing reads and calling variants using mapping quality score," Genome Res., 2008 Aug. 19.) In such alignments, sequence reads generally are aligned to a reference sequence and those that align are designated as being "mapped" or a "sequence tag." In certain embodiments, a mapped sequence read is referred to as a "hit" or a "count". In some embodiments, mapped sequence reads are grouped together according to various parameters and assigned to particular genomic sections, which are discussed in further detail below.

As used herein, the terms "aligned", "alignment", or "aligning" refer to two or more nucleic acid sequences that can be identified as a match (e.g., 100% identity) or partial match. Alignments can be done manually or by a computer algorithm, examples including the Efficient Local Alignment of Nucleotide Data (ELAND) computer program distributed as part of the Illumina Genomics Analysis pipeline. The alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In certain embodiments a nucleic acid sequence is aligned with the reverse complement of another nucleic acid sequence.

Various computational methods can be used to map each sequence read to a genomic section. Non-limiting examples of computer algorithms that can be used to align sequences include, without limitation, BLAST, BLITZ, FASTA, BOWTIE 1, BOWTIE 2, ELAND, MAQ, PROBEMATCH, SOAP or SEQMAP, or variations thereof or combinations thereof. In some embodiments, sequence reads can be aligned with sequences in a reference genome. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to sort the identified sequences into appropriate genomic sections (described hereafter), for example.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis. A "sequence tag" can be a nucleic acid (e.g. DNA) sequence (i.e. read) assigned specifically to a particular genomic section and/or chromosome (i.e. one of chromosomes 1-22, X or Y for a human subject). A sequence tag may be repetitive or non-repetitive within a single segment of the reference genome (e.g., a chromosome). In some embodiments, repetitive sequence tags are eliminated from further analysis (e.g. quantification). In some embodiments, a read may uniquely or non-uniquely map to portions in the reference genome. A read is considered to be "uniquely mapped" if it aligns with a single sequence in the reference genome. A read is considered to be "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments.

In some embodiments, no degree of mismatch is allowed for a read to be mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at www.ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. When a reference from the pregnant female is prepared ("maternal reference sequence") based on an external reference, reads from DNA of the pregnant female that contains substantially no fetal DNA often are mapped to the external reference sequence and assembled. In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

In certain embodiments, mappability is assessed for a genomic region (e.g., genomic section, genomic portion, bin). Mappability is the ability to unambiguously align a nucleotide sequence read to a portion of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

Genomic Sections

In some embodiments, mapped sequence reads (i.e. sequence tags) are grouped together according to various parameters and assigned to particular genomic sections. Often, the individual mapped sequence reads can be used to identify an amount of a genomic section present in a sample. In some embodiments, the amount of a genomic section can be indicative of the amount of a larger sequence (e.g. a chromosome) in the sample. The term "genomic section" can also be referred to herein as a "sequence window", "section", "bin", "locus", "region", "partition", "portion" (e.g., portion of a reference genome, portion of a chromosome) or "genomic portion." In some embodiments, a genomic section is an entire chromosome, portion of a chromosome, portion of a reference genome, multiple chromosome portions, multiple chromosomes, portions from multiple chromosomes, and/or combinations thereof. In some embodiments, a genomic section is predefined based on specific parameters. In some embodiments, a genomic section is arbitrarily defined based on partitioning of a genome (e.g., partitioned by size, portions, contiguous regions, contiguous regions of an arbitrarily defined size, and the like).

In some embodiments, a genomic section is delineated based on one or more parameters which include, for example, length or a particular feature or features of the sequence. Genomic sections can be selected, filtered and/or removed from consideration using any suitable criteria know in the art or described herein. In some embodiments, a genomic section is based on a particular length of genomic sequence. In some embodiments, a method can include analysis of multiple mapped sequence reads to a plurality of genomic sections. Genomic sections can be approximately the same length or the genomic sections can be different lengths. In some embodiments, genomic sections are of about equal length. In some embodiments genomic sections of different lengths are adjusted or weighted. In some embodiments, a genomic section is about 10 kilobases (kb) to about 100 kb, about 20 kb to about 80 kb, about 30 kb to about 70 kb, about 40 kb to about 60 kb, and sometimes about 50 kb. In some embodiments, a genomic section is about 10 kb to about 20 kb. A genomic section is not limited to contiguous runs of sequence. Thus, genomic sections can be made up of contiguous and/or non-contiguous sequences. A genomic section is not limited to a single chromosome. In some embodiments, a genomic section includes all or part of one chromosome or all or part of two or more chromosomes. In some embodiments, genomic sections may span one, two, or more entire chromosomes. In addition, the genomic sections may span joint or disjointed portions of multiple chromosomes.

In some embodiments, genomic sections can be particular chromosome portion in a chromosome of interest, such as, for example, chromosomes where a genetic variation is assessed (e.g. an aneuploidy of chromosomes 13, 18 and/or 21 or a sex chromosome). A genomic section can also be a pathogenic genome (e.g. bacterial, fungal or viral) or fragment thereof. Genomic sections can be genes, gene fragments, regulatory sequences, introns, exons, and the like.

In some embodiments, a genome (e.g. human genome) is partitioned into genomic sections based on the information content of the regions. The resulting genomic regions may contain sequences for multiple chromosomes and/or may contain sequences for portions of multiple chromosomes. In some embodiments, the partitioning may eliminate similar locations across the genome and only keep unique regions. The eliminated regions may be within a single chromosome or may span multiple chromosomes. The resulting genome is thus trimmed down and optimized for faster alignment, often allowing for focus on uniquely identifiable sequences.

In some embodiments, the partitioning may down weight similar regions. The process for down weighting a genomic section is discussed in further detail below. In some embodiments, the partitioning of the genome into regions transcending chromosomes may be based on information gain produced in the context of classification. For example, the information content may be quantified using the p-value profile measuring the significance of particular genomic locations for distinguishing between groups of confirmed normal and abnormal subjects (e.g. euploid and trisomy subjects, respectively). In some embodiments, the partitioning of the genome into regions transcending chromosomes may be based on any other criterion, such as, for example, speed/convenience while aligning tags, high or low GC content, uniformity of GC content, other measures of sequence content (e.g. fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual bins, and/or a targeted search for particular features.

A "segment" of a chromosome generally is part of a chromosome, and typically is a different part of a chromosome than a genomic section (e.g., bin). A segment of a chromosome sometimes is in a different region of a chromosome than a genomic section, sometimes does not share a polynucleotide with a genomic section, and sometimes includes a polynucleotide that is in a genomic section. A segment of a chromosome often contains a larger number of nucleotides than a genomic section (e.g., a segment sometimes includes a genomic section), and sometimes a segment of a chromosome contains a smaller number of nucleotides than a genomic section (e.g., a segment sometimes is within a genomic section).

Sequence Tag Density

"Sequence tag density" refers to the normalized value of sequence tags or reads for a defined genomic section where the sequence tag density is used for comparing different samples and for subsequent analysis. The value of the sequence tag density often is normalized within a sample. In some embodiments, normalization can be performed by counting the number of tags falling within each genomic section; obtaining a median value of the total sequence tag count for each chromosome; obtaining a median value of all of the autosomal values; and using this value as a normalization constant to account for the differences in total number of sequence tags obtained for different samples. A sequence tag density sometimes is about 1 for a disomic chromosome. Sequence tag densities can vary according to sequencing artifacts, most notably G/C bias, which can be corrected by use of an external standard or internal reference (e.g., derived from substantially all of the sequence tags (genomic sequences), which may be, for example, a single chromosome or a calculated value from all autosomes, in some embodiments). Thus, dosage imbalance of a chromosome or chromosomal regions can be inferred from the percentage representation of the locus among other mappable sequenced tags of the specimen. Dosage imbalance of a particular chromosome or chromosomal regions therefore can be quantitatively determined and be normalized. Methods for sequence tag density normalization and quantification are discussed in further detail below.

In some embodiments a proportion of all of the sequence reads are from a chromosome involved in an aneuploidy (e.g., chromosome 13, chromosome 18, chromosome 21), and other sequence reads are from other chromosomes. By taking into account the relative size of the chromosome involved in the aneuploidy (e.g., "target chromosome": chromosome 21) compared to other chromosomes, one could obtain a normalized frequency, within a reference range, of target chromosome-specific sequences, in some embodiments. If the fetus has an aneuploidy in a target chromosome, then the normalized frequency of the target chromosome-derived sequences is statistically greater than the normalized frequency of non-target chromosome-derived sequences, thus allowing the detection of the aneuploidy. The degree of change in the normalized frequency will be dependent on the fractional concentration of fetal nucleic acids in the analyzed sample, in some embodiments.

Counts

Sequence reads that are mapped or partitioned based on a selected feature or variable can be quantified to determine the number of reads that are mapped to a genomic section (e.g., bin, partition, genomic portion, portion of a reference genome, portion of a chromosome and the like), in some embodiments. In certain embodiments the quantity of sequence reads that are mapped to a genomic section are termed counts (e.g., a count). Often a count is associated with a genomic section. In certain embodiments counts for two or more genomic sections (e.g., a set of genomic sections) are mathematically manipulated (e.g., averaged, added, normalized, the like or a combination thereof). In some embodiments a count is determined from some or all of the sequence reads mapped to (i.e., associated with) a genomic section. In certain embodiments, a count is determined from a pre-defined subset of mapped sequence reads. Pre-defined subsets of mapped sequence reads can be defined or selected utilizing any suitable feature or variable. In some embodiments, pre-defined subsets of mapped sequence reads can include from 1 to n sequence reads, where n represents a number equal to the sum of all sequence reads generated from a test subject or reference subject sample.

In certain embodiments a count is derived from sequence reads that are processed or manipulated by a suitable method, operation or mathematical process known in the art. In certain embodiments a count is derived from sequence reads associated with a genomic section where some or all of the sequence reads are weighted, removed, filtered, normalized, adjusted, averaged, derived as a mean, added, or subtracted or processed by a combination thereof. In some embodiments, a count is derived from raw sequence reads and or filtered sequence reads. A count (e.g., counts) can be determined by a suitable method, operation or mathematical process. In certain embodiments a count value is determined by a mathematical process. In certain embodiments a count value is an average, mean or sum of sequence reads mapped to a genomic section. Often a count is a mean number of counts. In some embodiments, a count is associated with an uncertainty value. Counts can be processed (e.g., normalized) by a method known in the art and/or as described herein (e.g., bin-wise normalization, normalization by GC content, linear and nonlinear least squares regression, GC LOESS, LOWESS, PERUN, RM, GCRM, cQn and/or combinations thereof).

Counts (e.g., raw, filtered and/or normalized counts) can be processed and normalized to one or more elevations. Elevations and profiles are described in greater detail hereafter. In certain embodiments counts can be processed and/or normalized to a reference elevation. Reference elevations are addressed later herein. Counts processed according to an elevation (e.g., processed counts) can be associated with an uncertainty value (e.g., a calculated variance, an error, standard deviation, p-value, mean absolute deviation, etc.). An uncertainty value typically defines a range above and below an elevation. A value for deviation can be used in place of an uncertainty value, and non-limiting examples of measures of deviation include standard deviation, average absolute deviation, median absolute deviation, standard score (e.g., Z-score, Z-value, normal score, standardized variable) and the like.

Counts are often obtained from a nucleic acid sample from a pregnant female bearing a fetus. Counts of nucleic acid sequence reads mapped to a genomic section often are counts representative of both the fetus and the mother of the fetus (e.g., a pregnant female subject). In certain embodiments some of the counts mapped to a genomic section are from a fetal genome and some of the counts mapped to the same genomic section are from the maternal genome.

Data processing, Normalization & PER UN

Mapped sequence reads that have been counted are referred to herein as raw data, since the data represents unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative genomic sections or bins (e.g., bins with uninformative data, redundant mapped reads, genomic sections or bins with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing". Processing can render data more amenable to further analysis, and can generate an outcome in some embodiments.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being over represented when prepared using PCR-based methods. Methods described herein can reduce or eliminate the contribution of noisy data, and therefore reduce the effect of noisy data on the provided outcome.

The terms "uninformative data", "uninformative bins", and "uninformative genomic sections" as used herein refer to genomic sections, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation (e.g. a copy number variation, an aneuploidy, a chromosomal aberration, and the like). In certain embodiments a threshold is exceeded by results obtained by methods described herein and a subject is diagnosed with a genetic variation (e.g. trisomy 21). A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. An uncertainty value can be a standard deviation, standard error, calculated variance, p-value, or mean absolute deviation (MAD), in some embodiments. In some embodiments an uncertainty value can be calculated according to a formula in Example 6.

Any suitable procedure can be utilized for processing data sets described herein. Non-limiting examples of procedures suitable for use for processing data sets include filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments, one or more processing steps can comprise one or more filtering steps. The term "filtering" as used herein refers to removing genomic sections or bins from consideration. Bins can be selected for removal based on any suitable criteria, including but not limited to redundant data (e.g., redundant or overlapping mapped reads), non-informative data (e.g., bins with zero median counts), bins with over represented or under represented sequences, noisy data, the like, or combinations of the foregoing. A filtering process often involves removing one or more bins from consideration and subtracting the counts in the one or more bins selected for removal from the counted or summed counts for the bins, chromosome or chromosomes, or genome under consideration. In some embodiments, bins can be removed successively (e.g., one at a time to allow evaluation of the effect of removal of each individual bin), and in certain embodiments all bins marked for removal can be removed at the same time. In some embodiments, genomic sections characterized by a variance above or below a certain level are removed, which sometimes is referred to herein as filtering "noisy" genomic sections. In certain embodiments, a filtering process comprises obtaining data points from a data set that deviate from the mean profile elevation of a genomic section, a chromosome, or segment of a chromosome by a predetermined multiple of the profile variance, and in certain embodiments, a filtering process comprises removing data points from a data set that do not deviate from the mean profile elevation of a genomic section, a chromosome or segment of a chromosome by a predetermined multiple of the profile variance. In some embodiments, a filtering process is utilized to reduce the number of candidate genomic sections analyzed for the presence or absence of a genetic variation. Reducing the number of candidate genomic sections analyzed for the presence or absence of a genetic variation (e.g., micro-deletion, micro-duplication) often reduces the complexity and/or dimensionality of a data set, and sometimes increases the speed of searching for and/or identifying genetic variations and/or genetic aberrations by two or more orders of magnitude.

In some embodiments one or more processing steps can comprise one or more normalization steps. Normalization can be performed by a suitable method known in the art. In certain embodiments normalization comprises adjusting values measured on different scales to a notionally common scale. In certain embodiments normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Non-limiting examples of normalization methods include bin-wise normalization, normalization by GC content, linear and nonlinear least squares regression, LOESS, GC LOESS, LOWESS (locally weighted scatterplot smoothing), PERUN, repeat masking (RM), GC-normalization and repeat masking (GCRM), cQn and/or combinations thereof. In some embodiments, the determination of a presence or absence of a genetic variation (e.g., an aneuploidy) utilizes a normalization method (e.g., bin-wise normalization, normalization by GC content, linear and nonlinear least squares regression, LOESS, GC LOESS, LOWESS (locally weighted scatterplot smoothing), PERUN, repeat masking (RM), GC-normalization and repeat masking (GCRM), cQn, a normalization method known in the art and/or a combination thereof).

For example, LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relation between fragment count (e.g., sequence reads, counts) and GC composition for genomic sections. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated.

The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference genomic sections to the total number of counts mapped to the chromosome or the entire genome on which the selected genomic section or sections are mapped; normalizing raw count data for one or more selected genomic sections to a median reference count for one or more genomic sections or the chromosome on which a selected genomic section or segments is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing genomic sections, or bins, with respect to a normalizing value sometimes is referred to as "bin-wise normalization".

In certain embodiments, a processing step comprising normalization includes normalizing to a static window, and in some embodiments, a processing step comprising normalization includes normalizing to a moving or sliding window. The term "window" as used herein refers to one or more genomic sections chosen for analysis, and sometimes used as a reference for comparison (e.g., used for normalization and/or other mathematical or statistical manipulation). The term "normalizing to a static window" as used herein refers to a normalization process using one or more genomic sections selected for comparison between a test subject and reference subject data set. In some embodiments the selected genomic sections are utilized to generate a profile. A static window generally includes a predetermined set of genomic sections that do not change during manipulations and/or analysis. The terms "normalizing to a moving window" and "normalizing to a sliding window" as used herein refer to normalizations performed to genomic sections localized to the genomic region (e.g., immediate genetic surrounding, adjacent genomic section or sections, and the like) of a selected test genomic section, where one or more selected test genomic sections are normalized to genomic sections immediately surrounding the selected test genomic section. In certain embodiments, the selected genomic sections are utilized to generate a profile. A sliding or moving window normalization often includes repeatedly moving or sliding to an adjacent test genomic section, and normalizing the newly selected test genomic section to genomic sections immediately surrounding or adjacent to the newly selected test genomic section, where adjacent windows have one or more genomic sections in common. In certain embodiments, a plurality of selected test genomic sections and/or chromosomes can be analyzed by a sliding window process.

In some embodiments, normalizing to a sliding or moving window can generate one or more values, where each value represents normalization to a different set of reference genomic sections selected from different regions of a genome (e.g., chromosome). In certain embodiments, the one or more values generated are cumulative sums (e.g., a numerical estimate of the integral of the normalized count profile over the selected genomic section, domain (e.g., part of chromosome), or chromosome). The values generated by the sliding or moving window process can be used to generate a profile and facilitate arriving at an outcome. In some embodiments, cumulative sums of one or more genomic sections can be displayed as a function of genomic position. Moving or sliding window analysis sometimes is used to analyze a genome for the presence or absence of micro-deletions and/or micro-insertions. In certain embodiments, displaying cumulative sums of one or more genomic sections is used to identify the presence or absence of regions of genetic variation (e.g., micro-deletions, micro-duplications). In some embodiments, moving or sliding window analysis is used to identify genomic regions containing micro-deletions and in certain embodiments, moving or sliding window analysis is used to identify genomic regions containing micro-duplications.

A particularly useful normalization methodology for reducing error associated with nucleic acid indicators is referred to herein as Parameterized Error Removal and Unbiased Normalization (PERUN). PERUN methodology can be applied to a variety of nucleic acid indicators (e.g., nucleic acid sequence reads) for the purpose of reducing effects of error that confound predictions based on such indicators.

For example, PERUN methodology can be applied to nucleic acid sequence reads from a sample and reduce the effects of error that can impair nucleic acid elevation determinations (e.g., genomic section elevation determinations). Such an application is useful for using nucleic acid sequence reads to assess the presence or absence of a genetic variation in a subject manifested as a varying elevation of a nucleotide sequence (e.g., genomic section). Non-limiting examples of variations in genomic sections are chromosome aneuploidies (e.g., trisomy 21, trisomy 18, trisomy 13) and presence or absence of a sex chromosome (e.g., XX in females versus XY in males). A trisomy of an autosome (e.g., a chromosome other than a sex chromosome) can be referred to as an affected autosome. Other non-limiting examples of variations in genomic section elevations include microdeletions, microinsertions, duplications and mosaicism.

In certain applications, PERUN methodology can reduce experimental bias by normalizing nucleic acid indicators for particular genomic groups, the latter of which are referred to as bins. Bins include a suitable collection of nucleic acid indicators, a non-limiting example of which includes a length of contiguous nucleotides, which is referred to herein as a genomic section or portion of a reference genome. Bins can include other nucleic acid indicators as described herein. In such applications, PERUN methodology generally normalizes nucleic acid indicators at particular bins across a number of samples in three dimensions. A detailed description of particular PERUN applications is described in Example 4 and Example 5 herein.

In certain embodiments, PERUN methodology includes calculating a genomic section elevation for each bin from a fitted relation between (i) experimental bias for a bin of a reference genome to which sequence reads are mapped and (ii) counts of sequence reads mapped to the bin. Experimental bias for each of the bins can be determined across multiple samples according to a fitted relation for each sample between (i) the counts of sequence reads mapped to each of the bins, and (ii) a mapping feature fore each of the bins. This fitted relation for each sample can be assembled for multiple samples in three dimensions. The assembly can be ordered according to the experimental bias in certain embodiments (e.g., FIG. 82, Example 4), although PERUN methodology may be practiced without ordering the assembly according to the experimental bias.

A relation can be generated by a method known in the art. A relation in two dimensions can be generated for each sample in certain embodiments, and a variable probative of error, or possibly probative of error, can be selected for one or more of the dimensions. A relation can be generated, for example, using graphing software known in the art that plots a graph using values of two or more variables provided by a user. A relation can be fitted using a method known in the art (e.g., graphing software). Certain relations can be fitted by linear regression, and the linear regression can generate a slope value and intercept value. Certain relations sometimes are not linear and can be fitted by a non-linear function, such as a parabolic, hyperbolic or exponential function, for example.

In PERUN methodology, one or more of the fitted relations may be linear. For an analysis of cell-free circulating nucleic acid from pregnant females, where the experimental bias is GC bias and the mapping feature is GC content, the fitted relation for a sample between the (i) the counts of sequence reads mapped to each bin, and (ii) GC content for each of the bins, can be linear. For the latter fitted relation, the slope pertains to GC bias, and a GC bias coefficient can be determined for each bin when the fitted relations are assembled across multiple samples. In such embodiments, the fitted relation for multiple samples and a bin between (i) GC bias coefficient for the bin, and (ii) counts of sequence reads mapped to bin, also can be linear. An intercept and slope can be obtained from the latter fitted relation. In such applications, the slope addresses sample-specific bias based on GC-content and the intercept addresses a bin-specific attenuation pattern common to all samples. PERUN methodology can significantly reduce such sample-specific bias and bin-specific attenuation when calculating genomic section elevations for providing an outcome (e.g., presence or absence of genetic variation; determination of fetal sex).

Thus, application of PERUN methodology to sequence reads across multiple samples in parallel can significantly reduce error caused by (i) sample-specific experimental bias (e.g., GC bias) and (ii) bin-specific attenuation common to samples. Other methods in which each of these two sources of error are addressed separately or serially often are not able to reduce these as effectively as PERUN methodology. Without being limited by theory, it is expected that PERUN methodology reduces error more effectively in part because its generally additive processes do not magnify spread as much as generally multiplicative processes utilized in other normalization approaches (e.g., GC-LOESS).

Additional normalization and statistical techniques may be utilized in combination with PERUN methodology. An additional process can be applied before, after and/or during employment of PERUN methodology. Non-limiting examples of processes that can be used in combination with PERUN methodology are described hereafter.

In some embodiments, a secondary normalization or adjustment of a genomic section elevation for GC content can be utilized in conjunction with PERUN methodology. A suitable GC content adjustment or normalization procedure can be utilized (e.g., GC-LOESS, GCRM). In certain embodiments, a particular sample can be identified for application of an additional GC normalization process. For example, application of PERUN methodology can determine GC bias for each sample, and a sample associated with a GC bias above a certain threshold can be selected for an additional GC normalization process. In such embodiments, a predetermined threshold elevation can be used to select such samples for additional GC normalization.

In certain embodiments, a bin filtering or weighting process can be utilized in conjunction with PERUN methodology. A suitable bin filtering or weighting process can be utilized and non-limiting examples are described herein. Examples 4 and 5 describe utilization of R-factor measures of error for bin filtering.

In some embodiments, a normalization technique that reduces error associated with maternal insertions, duplications and/or deletions (e.g., maternal and/or fetal copy number variations), is utilized in conjunction with PERUN methodology.

Genomic section elevations calculated by PERUN methodology can be utilized directly for providing an outcome. In some embodiments, genomic section elevations can be utilized directly to provide an outcome for samples in which fetal fraction is about 2% to about 6% or greater (e.g., fetal fraction of about 4% or greater). Genomic section elevations calculated by PERUN methodology sometimes are further processed for the provision of an outcome. In some embodiments, calculated genomic section elevations are standardized. In certain embodiments, the sum, mean or median of calculated genomic section elevations for a test genomic section (e.g., chromosome 21) can be divided by the sum, mean or median of calculated genomic section elevations for genomic sections other than the test genomic section (e.g., autosomes other than chromosome 21), to generate an experimental genomic section elevation. An experimental genomic section elevation or a raw genomic section elevation can be used as part of a standardization analysis, such as calculation of a Z-score or Z-value. A Z-score can be generated for a sample by subtracting an expected genomic section elevation from an experimental genomic section elevation or raw genomic section elevation and the resulting value may be divided by a standard deviation for the samples. Resulting Z-scores can be distributed for different samples and analyzed, or can be related to other variables, such as fetal fraction and others, and analyzed, to provide an outcome, in certain embodiments.

As noted herein, PERUN methodology is not limited to normalization according to GC bias and GC content per se, and can be used to reduce error associated with other sources of error. A non-limiting example of a source of non-GC content bias is mappability. When normalization parameters other than GC bias and content are addressed, one or more of the fitted relations may be non-linear (e.g., hyperbolic, exponential). Where experimental bias is determined from a non-linear relation, for example, an experimental bias curvature estimation may be analyzed in some embodiments.

PERUN methodology can be applied to a variety of nucleic acid indicators. Non-limiting examples of nucleic acid indicators are nucleic acid sequence reads and nucleic acid elevations at a particular location on a microarray. Non-limiting examples of sequence reads include those obtained from cell-free circulating DNA, cell-free circulating RNA, cellular DNA and cellular RNA. PERUN methodology can be applied to sequence reads mapped to suitable reference sequences, such as genomic reference DNA, cellular reference RNA (e.g., transcriptome), and portions thereof (e.g., part(s) of a genomic complement of DNA or RNA transcriptome, part(s) of a chromosome).

Thus, in certain embodiments, cellular nucleic acid (e.g., DNA or RNA) can serve as a nucleic acid indicator. Cellular nucleic acid reads mapped to reference genome portions can be normalized using PERUN methodology.

Cellular nucleic acid, in some embodiments, is an association with one or more proteins, and an agent that captures protein-associated nucleic acid can be utilized to enrich for the latter, in some embodiments. An agent in certain cases is an antibody or antibody fragment that specifically binds to a protein in association with cellular nucleic acid (e.g., an antibody that specifically binds to a chromatin protein (e.g., histone protein)). Processes in which an antibody or antibody fragment is used to enrich for cellular nucleic acid bound to a particular protein sometimes are referred to chromatin immunoprecipitation (ChIP) processes. ChIP-enriched nucleic acid is a nucleic acid in association with cellular protein, such as DNA or RNA for example. Reads of ChIP-enriched nucleic acid can be obtained using technology known in the art. Reads of ChIP-enriched nucleic acid can be mapped to one or more portions of a reference genome, and results can be normalized using PERUN methodology for providing an outcome.

Thus, provided in certain embodiments are methods for calculating with reduced bias genomic section elevations for a test sample, comprising: (a) obtaining counts of sequence reads mapped to bins of a reference genome, which sequence reads are reads of cellular nucleic acid from a test sample obtained by isolation of a protein to which the nucleic acid was associated; (b) determining experimental bias for each of the bins across multiple samples from a fitted relation between (i) the counts of the sequence reads mapped to each of the bins, and (ii) a mapping feature for each of the bins; and (c) calculating a genomic section elevation for each of the bins from a fitted relation between the experimental bias and the counts of the sequence reads mapped to each of the bins, thereby providing calculated genomic section elevations, whereby bias in the counts of the sequence reads mapped to each of the bins is reduced in the calculated genomic section elevations.

In certain embodiments, cellular RNA can serve as nucleic acid indicators. Cellular RNA reads can be mapped to reference RNA portions and normalized using PERUN methodology for providing an outcome. Known sequences for cellular RNA, referred to as a transcriptome, or a segment thereof, can be used as a reference to which RNA reads from a sample can be mapped. Reads of sample RNA can be obtained using technology known in the art. Results of RNA reads mapped to a reference can be normalized using PERUN methodology for providing an outcome.

Thus, provided in some embodiments are methods for calculating with reduced bias genomic section elevations for a test sample, comprising: (a) obtaining counts of sequence reads mapped to bins of reference RNA (e.g., reference transcriptome or segment(s) thereof), which sequence reads are reads of cellular RNA from a test sample; (b) determining experimental bias for each of the bins across multiple samples from a fitted relation between (i) the counts of the sequence reads mapped to each of the bins, and (ii) a mapping feature for each of the bins; and (c) calculating a genomic section elevation for each of the bins from a fitted relation between the experimental bias and the counts of the sequence reads mapped to each of the bins, thereby providing calculated genomic section elevations, whereby bias in the counts of the sequence reads mapped to each of the bins is reduced in the calculated genomic section elevations.

In some embodiments, microarray nucleic acid levels can serve as nucleic acid indicators. Nucleic acid levels across samples for a particular address, or hybridizing nucleic acid, on an array can be analyzed using PERUN methodology, thereby normalizing nucleic acid indicators provided by microarray analysis. In this manner, a particular address or hybridizing nucleic acid on a microarray is analogous to a bin for mapped nucleic acid sequence reads, and PERUN methodology can be used to normalize microarray data to provide an improved outcome.

Thus, provided in certain embodiments are methods for reducing microarray nucleic acid level error for a test sample, comprising: (a) obtaining nucleic acid levels in a microarray to which test sample nucleic acid has been associated, which microarray includes an array of capture nucleic acids; (b) determining experimental bias for each of the capture nucleic acids across multiple samples from a fitted relation between (i) the test sample nucleic acid levels associated with each of the capture nucleic acids, and (ii) an association feature for each of the capture nucleic acids; and (c) calculating a test sample nucleic acid level for each of the capture nucleic acids from a fitted relation between the experimental bias and the levels of the test sample nucleic acid associated with each of the capture nucleic acids, thereby providing calculated levels, whereby bias in the levels of test sample nucleic acid associated with each of the capture nucleic acids is reduced in the calculated levels. The association feature mentioned above can be any feature correlated with hybridization of a test sample nucleic acid to a capture nucleic acid that gives rise to, or may give rise to, error in determining the level of test sample nucleic acid associated with a capture nucleic acid.

In some embodiments, a processing step comprises a weighting. The terms "weighted", "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more genomic sections or bins, based on the quality or usefulness of the data in the selected bin or bins). A weighting function can be used to increase the influence of data with a relatively small measurement variance, and/or to decrease the influence of data with a relatively large measurement variance, in some embodiments. For example, bins with under represented or low quality sequence data can be "down weighted" to minimize the influence on a data set, whereas selected bins can be "up weighted" to increase the influence on a data set. A non-limiting example of a weighting function is $[1/(\text{standard deviation})^2]$. A weighting step sometimes is performed in a manner substantially similar to a normalizing step. In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak elevations, determination of peak edge locations, calculation of peak area ratios, analysis of median chromosomal elevation, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median elevations, mean elevations, count distribution within a genomic region, relative representation of nucleic acid species, the like or combinations thereof.

In some embodiments, a processing step can include the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median elevations, mean elevations, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

After data sets have been counted, optionally filtered and normalized, the processed data sets can be further manipulated by one or more filtering and/or normalizing procedures, in some embodiments. A data set that has been further manipulated by one or more filtering and/or normalizing procedures can be used to generate a profile, in certain embodiments. The one or more filtering and/or normalizing procedures sometimes can reduce data set complexity and/or dimensionality, in some embodiments. An outcome can be provided based on a data set of reduced complexity and/or dimensionality.

Non-limiting examples of genomic section filtering is provided herein in Example 4 with respect to PERUN methods. Genomic sections may be filtered based on, or based on part on, a measure of error. A measure of error comprising absolute values of deviation, such as an R-factor, can be used for genomic section removal or weighting in certain embodiments. An R-factor, in some embodiments, is defined as the sum of the absolute deviations of the predicted count values from the actual measurements divided by the predicted count values from the actual measurements (e.g., Equation B herein). While a measure of error comprising absolute values of deviation may be used, a suitable measure of error may be alternatively employed. In certain embodiments, a measure of error not comprising absolute values of deviation, such as a dispersion based on squares, may be utilized. In some embodiments, genomic sections are filtered or weighted according to a measure of mappability (e.g., a mappability score; Example 5). A genomic section sometimes is filtered or weighted according to a relatively low number of sequence reads mapped to the genomic section (e.g., 0, 1, 2, 3, 4, 5 reads mapped to the genomic section). Genomic sections can be filtered or weighted according to the type of analysis being performed. For example, for chromosome 13, 18 and/or 21 aneuploidy analysis, sex chromosomes may be filtered, and only autosomes, or a subset of autosomes, may be analyzed.

In particular embodiments, the following filtering process may be employed. The same set of genomic sections (e.g., bins) within a given chromosome (e.g., chromosome 21) are selected and the number of reads in affected and unaffected samples are compared. The gap relates trisomy 21 and euploid samples and it involves a set of genomic sections covering most of chromosome 21. The set of genomic sections is the same between euploid and T21 samples. The distinction between a set of genomic sections and a single section is not crucial, as a genomic section can be defined. The same genomic region is compared in different patients. This process can be utilized for a trisomy analysis, such as for T13 or T18 in addition to, or instead of, T21.

After data sets have been counted, optionally filtered and normalized, the processed data sets can be manipulated by weighting, in some embodiments. One or more genomic sections can be selected for weighting to reduce the influence of data (e.g., noisy data, uninformative data) contained in the selected genomic sections, in certain embodiments, and in some embodiments, one or more genomic sections can be selected for weighting to enhance or augment the influence of data (e.g., data with small measured variance) contained in the selected genomic sections. In some embodiments, a data set is weighted utilizing a single weighting function that decreases the influence of data with large variances and increases the influence of data with small variances. A weighting function sometimes is used to reduce the influence of data with large variances and augment the influence of data with small variances (e.g., [1/(standard deviation)$^2$]). In some embodiments, a profile plot of processed data further manipulated by weighting is generated to facilitate classification and/or providing an outcome. An outcome can be provided based on a profile plot of weighted data Filtering or weighting of genomic sections can be performed at one or more suitable points in an analysis. For example, genomic sections may be filtered or weighted before or after sequence reads are mapped to portions of a reference genome. Genomic sections may be filtered or weighted before or after an experimental bias for individual genome portions is determined in some embodiments. In certain embodiments, genomic sections may be filtered or weighted before or after genomic section elevations are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected genomic sections, chromosomes, or portions of chromosomes. In some embodiments, processed data sets can be further manipulated by calculating P-values. Formulas for calculating Z-scores and P-values are presented in Example 1. In certain embodiments, mathematical and/or statistical manipulations include one or more assumptions pertaining to ploidy and/or fetal fraction. In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fetal fraction.

In certain embodiments, multiple manipulations are performed on processed data sets to generate an N-dimensional space and/or N-dimensional point, after data sets have been counted, optionally filtered and normalized. An outcome can be provided based on a profile plot of data sets analyzed in N-dimensions.

In some embodiments, data sets are processed utilizing one or more peak elevation analysis, peak width analysis, peak edge location analysis, peak lateral tolerances, the like, derivations thereof, or combinations of the foregoing, as part of or after data sets have processed and/or manipulated. In some embodiments, a profile plot of data processed utilizing one or more peak elevation analysis, peak width analysis, peak edge location analysis, peak lateral tolerances, the like, derivations thereof, or combinations of the foregoing is generated to facilitate classification and/or providing an outcome. An outcome can be provided based on a profile plot of data that has been processed utilizing one or more peak elevation analysis, peak width analysis, peak edge location analysis, peak lateral tolerances, the like, derivations thereof, or combinations of the foregoing.

In some embodiments, the use of one or more reference samples known to be free of a genetic variation in question can be used to generate a reference median count profile, which may result in a predetermined value representative of the absence of the genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for the selected genomic section or sections is expected to vary significantly from the predetermined value for non-affected genomic locations. In certain embodiments, the use of one or more reference samples known to carry the genetic variation in question can be used to generate a reference median count profile, which may result in a predetermined value representative of the presence of the genetic variation, and often deviates from a predetermined value in areas corresponding to the genomic location in which a test subject does not carry the genetic variation. In test subjects not at risk for, or suffering from a medical condition associated with a genetic variation, the numerical value for the selected genomic section or sections is expected to vary significantly from the predetermined value for affected genomic locations.

In some embodiments, analysis and processing of data can include the use of one or more assumptions. A suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

In those instances where the quality and/or depth of mapped sequence reads does not permit an outcome prediction of the presence or absence of a genetic variation at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

Profiles

In some embodiments, a processing step can comprise generating one or more profiles (e.g., profile plot) from various aspects of a data set or derivation thereof (e.g., product of one or more mathematical and/or statistical data processing steps known in the art and/or described herein). The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a portion or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a genomic section. In certain embodiments, a data point in a profile includes results of data manipulation for groups of genomic sections. In some embodiments, groups of genomic sections may be adjacent to one another, and in certain embodiments, groups of genomic sections may be from different parts of a chromosome or genome.

Data points in a profile derived from a data set can be representative of any suitable data categorization. Non-limiting examples of categories into which data can be grouped to generate profile data points include: genomic sections based on size, genomic sections based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile often is a collection of normalized or non-normalized counts for two or more genomic sections. A profile often includes at least one elevation, and often comprises two or more elevations (e.g., a profile often has multiple elevations). An elevation generally is for a set of genomic sections having about the same counts or normalized counts. Elevations are described in greater detail herein. In certain embodiments, a profile comprises one or more genomic sections, which genomic sections can be weighted, removed, filtered, normalized, adjusted, averaged, derived as a mean, added, subtracted, processed or transformed by any combination thereof. A profile often comprises normalized counts mapped to genomic sections defining two or more elevations, where the counts are further normalized according to one of the elevations by a suitable method. Often counts of a profile (e.g., a profile elevation) are associated with an uncertainty value.

A profile comprising one or more elevations can include a first elevation and a second elevation. In certain embodiments a first elevation is different (e.g., significantly different) than a second elevation. In some embodiments a first elevation comprises a first set of genomic sections, a second elevation comprises a second set of genomic sections and the first set of genomic sections is not a subset of the second set of genomic sections. In certain embodiments, a first set of genomic sections is different than a second set of genomic sections from which a first and second elevation are determined. In certain embodiments a profile can have multiple first elevations that are different (e.g., significantly different, e.g., have a significantly different value) than a second elevation within the profile. In certain embodiments a profile comprises one or more first elevations that are significantly different than a second elevation within the profile and one or more of the first elevations are adjusted. In certain embodiments a profile comprises one or more first elevations that are significantly different than a second elevation within the profile, each of the one or more first elevations comprise a maternal copy number variation, fetal copy number variation, or a maternal copy number variation and a fetal copy number variation and one or more of the first elevations are adjusted. In certain embodiments a first elevation within a profile is removed from the profile or adjusted (e.g., padded). A profile can comprise multiple elevations that include one or more first elevations significantly different than one or more second elevations and often the majority of elevations in a profile are second elevations, which second elevations are about equal to one another. In certain embodiments greater than 50%, greater than 60%, greater than 70%, greater than 80%, greater than 90% or greater than 95% of the elevations in a profile are second elevations.

A profile sometimes is displayed as a plot. For example, one or more elevations representing counts (e.g., normalized counts) of genomic sections can be plotted and visualized. Non-limiting examples of profile plots that can be generated include raw count (e.g., raw count profile or raw profile), normalized count, bin-weighted, z-score, p-value, area ratio versus fitted ploidy, median elevation versus ratio between fitted and measured fetal fraction, principle components, the like, or combinations thereof. Profile plots allow visualization of the manipulated data, in some embodiments. In certain embodiments, a profile plot can be utilized to provide an outcome (e.g., area ratio versus fitted ploidy, median elevation versus ratio between fitted and measured fetal fraction, principle components). The terms "raw count profile plot" or "raw profile plot" as used herein refer to a plot of counts in each genomic section in a region normalized to total counts in a region (e.g., genome, genomic section, chromosome, chromosome bins or a segment of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions (e.g., maternal contribution of nucleic acid (e.g., maternal fraction), fetal contribution of nucleic acid (e.g., fetal fraction), ploidy of reference sample, the like or combinations thereof). In certain embodiments, a test profile often centers around a predetermined value representative of the absence of a genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for a selected genomic section is expected to vary significantly from the predetermined value for non-affected genomic locations. Depending on starting assumptions (e.g., fixed ploidy or optimized ploidy, fixed fetal fraction or optimized fetal fraction or combinations thereof) the predetermined threshold or cutoff value or threshold range of values indicative of the presence or absence of a genetic variation can vary while still providing an outcome useful for determining the presence or absence of a genetic variation. In some embodiments, a profile is indicative of and/or representative of a phenotype.

By way of a non-limiting example, normalized sample and/or reference count profiles can be obtained from raw sequence read data by (a) calculating reference median counts for selected chromosomes, genomic sections or segments thereof from a set of references known not to carry a genetic variation, (b) removal of uninformative genomic sections from the reference sample raw counts (e.g., filtering); (c) normalizing the reference counts for all remaining bins to the total residual number of counts (e.g., sum of remaining counts after removal of uninformative bins) for the reference sample selected chromosome or selected genomic location, thereby generating a normalized reference subject profile; (d) removing the corresponding genomic sections from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered genomic sections in (b), can be included between (c) and (d). A data set profile can be generated by one or more manipulations of counted mapped sequence read data. Some embodiments include the following. Sequence reads are mapped and the number of sequence tags mapping to each genomic bin are determined (e.g., counted). A raw count profile is generated from the mapped sequence reads that are counted. An outcome is provided by comparing a raw count profile from a test subject to a reference median count profile for chromosomes, genomic sections or segments thereof from a set of reference subjects known not to possess a genetic variation, in certain embodiments.

In some embodiments, sequence read data is optionally filtered to remove noisy data or uninformative genomic sections. After filtering, the remaining counts typically are summed to generate a filtered data set. A filtered count profile is generated from a filtered data set, in certain embodiments.

After sequence read data have been counted and optionally filtered, data sets can be normalized to generate elevations or profiles. A data set can be normalized by normalizing one or more selected genomic sections to a suitable normalizing reference value. In some embodiments, a normalizing reference value is representative of the total counts for the chromosome or chromosomes from which genomic sections are selected. In certain embodiments, a normalizing reference value is representative of one or more corresponding genomic sections, portions of chromosomes or chromosomes from a reference data set prepared from a set of reference subjects known not to possess a genetic variation. In some embodiments, a normalizing reference value is representative of one or more corresponding genomic sections, portions of chromosomes or chromosomes from a test subject data set prepared from a test subject being analyzed for the presence or absence of a genetic variation. In certain embodiments, the normalizing process is performed utilizing a static window approach, and in some embodiments the normalizing process is performed utilizing a moving or sliding window approach. In certain embodiments, a profile comprising normalized counts is generated to facilitate classification and/or providing an outcome. An outcome can be provided based on a plot of a profile comprising normalized counts (e.g., using a plot of such a profile).

Elevations

In some embodiments, a value is ascribed to an elevation (e.g., a number). An elevation can be determined by a suitable method, operation or mathematical process (e.g., a processed elevation). The term "level" as used herein is synonymous with the term "elevation" as used herein. An elevation often is, or is derived from, counts (e.g., normalized counts) for a set of genomic sections. In certain embodiments an elevation of a genomic section is substantially equal to the total number of counts mapped to a genomic section (e.g., normalized counts). Often an elevation is determined from counts that are processed, transformed or manipulated by a suitable method, operation or mathematical process known in the art. In certain embodiments an elevation is derived from counts that are processed and non-limiting examples of processed counts include weighted, removed, filtered, normalized, adjusted, averaged, derived as a mean (e.g., mean elevation), added, subtracted, transformed counts or combination thereof. In certain embodiments an elevation comprises counts that are normalized (e.g., normalized counts of genomic sections). An elevation can be for counts normalized by a suitable process, non-limiting examples of which include bin-wise normalization, normalization by GC content, linear and nonlinear least squares regression, GC LOESS, LOWESS, PERUN, RM, GCRM, cQn, the like and/or combinations thereof. An elevation can comprise normalized counts or relative amounts of counts. In certain embodiments an elevation is for counts or normalized counts of two or more genomic sections that are averaged and the elevation is referred to as an average elevation. In certain embodiments an elevation is for a set of genomic sections having a mean count or mean of normalized counts which is referred to as a mean elevation. In certain embodiments an elevation is derived for genomic sections that comprise raw and/or filtered counts. In some embodiments, an elevation is based on counts that are raw. In certain embodiments an elevation is associated with an uncertainty value. An elevation for a genomic section, or a "genomic section elevation," is synonymous with a "genomic section level" herein.

Normalized or non-normalized counts for two or more elevations (e.g., two or more elevations in a profile) can sometimes be mathematically manipulated (e.g., added, multiplied, averaged, normalized, the like or combination thereof) according to elevations. For example, normalized or non-normalized counts for two or more elevations can be normalized according to one, some or all of the elevations in a profile. In certain embodiments normalized or non-normalized counts of all elevations in a profile are normalized according to one elevation in the profile. In certain embodiments normalized or non-normalized counts of a first elevation in a profile are normalized according to normalized or non-normalized counts of a second elevation in the profile.

Non-limiting examples of an elevation (e.g., a first elevation, a second elevation) are an elevation for a set of genomic sections comprising processed counts, an elevation for a set of genomic sections comprising a mean, median or average of counts, an elevation for a set of genomic sections comprising normalized counts, the like or any combination thereof. In some embodiments, a first elevation and a second elevation in a profile are derived from counts of genomic sections mapped to the same chromosome. In some embodiments, a first elevation and a second elevation in a profile are derived from counts of genomic sections mapped to different chromosomes.

In some embodiments an elevation is determined from normalized or non-normalized counts mapped to one or more genomic sections. In some embodiments, an elevation is determined from normalized or non-normalized counts mapped to two or more genomic sections, where the normalized counts for each genomic section often are about the same. There can be variation in counts (e.g., normalized counts) in a set of genomic sections for an elevation. In a set of genomic sections for an elevation there can be one or more genomic sections having counts that are significantly different than in other genomic sections of the set (e.g., peaks and/or dips). Any suitable number of normalized or non-normalized counts associated with any suitable number of genomic sections can define an elevation.

In certain embodiments one or more elevations can be determined from normalized or non-normalized counts of all or some of the genomic sections of a genome. Often an elevation can be determined from all or some of the normalized or non-normalized counts of a chromosome, or segment thereof. In certain embodiments, two or more counts derived from two or more genomic sections (e.g., a set of genomic sections) determine an elevation. In certain embodiments two or more counts (e.g., counts from two or more genomic sections) determine an elevation. In some embodiments, counts from 2 to about 100,000 genomic sections determine an elevation. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 genomic sections determine an elevation. In some embodiments counts from about 10 to about 50 genomic sections determine an elevation. In some embodiments counts from about 20 to about 40 or more genomic sections determine an elevation. In some embodiments, an elevation comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more genomic sections. In some embodiments, an elevation corresponds to a set of genomic sections (e.g., a set of genomic sections of a reference genome, a set of genomic sections of a chromosome or a set of genomic sections of a segment of a chromosome).

In some embodiments, an elevation is determined for normalized or non-normalized counts of genomic sections that are contiguous. In certain embodiments genomic sections (e.g., a set of genomic sections) that are contiguous represent neighboring segments of a genome or neighboring segments of a chromosome or gene. For example, two or more contiguous genomic sections, when aligned by merging the genomic sections end to end, can represent a sequence assembly of a DNA sequence longer than each genomic section. For example two or more contiguous genomic sections can represent of an intact genome, chromosome, gene, intron, exon or segment thereof. In certain embodiments an elevation is determined from a collection (e.g., a set) of contiguous genomic sections and/or non-contiguous genomic sections.

Significantly Different Elevations

In some embodiments, a profile of normalized counts comprises an elevation (e.g., a first elevation) significantly different than another elevation (e.g., a second elevation) within the profile. A first elevation may be higher or lower than a second elevation. In some embodiments, a first elevation is for a set of genomic sections comprising one or more reads comprising a copy number variation (e.g., a maternal copy number variation, fetal copy number variation, or a maternal copy number variation and a fetal copy number variation) and the second elevation is for a set of genomic sections comprising reads having substantially no copy number variation. In some embodiments, significantly different refers to an observable difference. In certain embodiments significantly different refers to statistically different or a statistically significant difference. A statistically significant difference is sometimes a statistical assessment of an observed difference. A statistically significant difference can be assessed by a suitable method in the art. Any suitable threshold or range can be used to determine that two elevations are significantly different. In certain embodiments two elevations (e.g., mean elevations) that differ by about 0.01 percent or more (e.g., 0.01 percent of one or either of the elevation values) are significantly different. In certain embodiments two elevations (e.g., mean elevations) that differ by about 0.1 percent or more are significantly different. In certain embodiments, two elevations (e.g., mean elevations) that differ by about 0.5 percent or more are significantly different. In certain embodiments two elevations (e.g., mean elevations) that differ by about 0.5, 0.75, 1, 1.5, 2, 2.5, 3, 3.5, 4, 4.5, 5, 5.5, 6, 6.5, 7, 7.5, 8, 8.5, 9, 9.5 or more than about 10% are significantly different. In certain embodiments two elevations (e.g., mean elevations) are significantly different and there is no overlap in either elevation and/or no overlap in a range defined by an uncertainty value calculated for one or both elevations. In certain embodiments the uncertainty value is a standard deviation expressed as sigma. In certain embodiments two elevations (e.g., mean elevations) are significantly different and they differ by about 1 or more times the uncertainty value (e.g., 1 sigma). In certain embodiments two elevations (e.g., mean elevations) are significantly different and they differ by about 2 or more times the uncertainty value (e.g., 2 sigma), about 3 or more, about 4 or more, about 5 or more, about 6 or more, about 7 or more, about 8 or more, about 9 or more, or about 10 or more times the uncertainty value. In certain embodiments two elevations (e.g., mean elevations) are significantly different when they differ by about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 times the uncertainty value or more. In some embodiments, the confidence level increases as the difference between two elevations increases. In certain embodiments, the confidence level decreases as the difference between two elevations decreases and/or as the uncertainty value increases. For example, sometimes the confidence level increases with the ratio of the difference between elevations and the standard deviation (e.g., MADs).

In some embodiments, a first set of genomic sections often includes genomic sections that are different than (e.g., non-overlapping with) a second set of genomic sections. For example, sometimes a first elevation of normalized counts is significantly different than a second elevation of normalized counts in a profile, and the first elevation is for a first set of genomic sections, the second elevation is for a second set of genomic sections and the genomic sections do not overlap in the first set and second set of genomic sections. In certain embodiments, a first set of genomic sections is not a subset of a second set of genomic sections from which a first elevation and second elevation are determined, respectively. In certain embodiments a first set of genomic sections is different and/or distinct from a second set of genomic sections from which a first elevation and second elevation are determined, respectively.

In certain embodiments a first set of genomic sections is a subset of a second set of genomic sections in a profile. For example, sometimes a second elevation of normalized counts for a second set of genomic sections in a profile comprises normalized counts of a first set of genomic sections for a first elevation in the profile and the first set of genomic sections is a subset of the second set of genomic sections in the profile. In certain embodiments an average, mean or median elevation is derived from a second elevation where the second elevation comprises a first elevation. In certain embodiments, a second elevation comprises a second set of genomic sections representing an entire chromosome and a first elevation comprises a first set of genomic sections where the first set is a subset of the second set of genomic sections and the first elevation represents a maternal copy number variation, fetal copy number variation, or a maternal copy number variation and a fetal copy number variation that is present in the chromosome.

In some embodiments, a value of a second elevation is closer to the mean, average or median value of a count profile for a chromosome, or segment thereof, than the first elevation. In some embodiments, a second elevation is a mean elevation of a chromosome, a portion of a chromosome or a segment thereof. In some embodiments, a first elevation is significantly different from a predominant elevation (e.g., a second elevation) representing a chromosome, or segment thereof. A profile may include multiple first elevations that significantly differ from a second elevation, and each first elevation independently can be higher or lower than the second elevation. In some embodiments, a first elevation and a second elevation are derived from the same chromosome and the first elevation is higher or lower than the second elevation, and the second elevation is the predominant elevation of the chromosome. In certain embodiments, a first elevation and a second elevation are derived from the same chromosome, a first elevation is indicative of a copy number variation (e.g., a maternal and/or fetal copy number variation, deletion, insertion, duplication) and a second elevation is a mean elevation or predominant elevation of genomic sections for a chromosome, or segment thereof.

In certain embodiments, a read in a second set of genomic sections for a second elevation substantially does not include a genetic variation (e.g., a copy number variation, a maternal and/or fetal copy number variation). Often, a second set of genomic sections for a second elevation includes some variability (e.g., variability in elevation, variability in counts for genomic sections). In certain embodiments, one or more genomic sections in a set of genomic sections for an elevation associated with substantially no copy number variation include one or more reads having a copy number variation present in a maternal and/or fetal genome. For example, sometimes a set of genomic sections include a copy number variation that is present in a small segment of a chromosome (e.g., less than 10 genomic sections) and the set of genomic sections is for an elevation associated with substantially no copy number variation. Thus a set of genomic sections that include substantially no copy number variation still can include a copy number variation that is present in less than about 10, 9, 8, 7, 6, 5, 4, 3, 2 or 1 genomic sections of an elevation.

In certain embodiments a first elevation is for a first set of genomic sections and a second elevation is for a second set of genomic sections and the first set of genomic sections and second set of genomic sections are contiguous (e.g., adjacent with respect to the nucleic acid sequence of a chromosome or segment thereof). In certain embodiments the first set of genomic sections and second set of genomic sections are not contiguous.

Relatively short sequence reads from a mixture of fetal and maternal nucleic acid can be utilized to provide counts which can be transformed into an elevation and/or a profile. Counts, elevations and profiles can be depicted in electronic or tangible form and can be visualized. Counts mapped to genomic sections (e.g., represented as elevations and/or profiles) can provide a visual representation of a fetal and/or a maternal genome, chromosome, or a portion or a segment of a chromosome that is present in a fetus and/or pregnant female.

Reference Elevation and Normalized Reference Value

In certain embodiments a profile comprises a reference elevation (e.g., an elevation used as a reference). Often a profile of normalized counts provides a reference elevation from which expected elevations and expected ranges are determined (see discussion below on expected elevations and ranges). A reference elevation often is for normalized counts of genomic sections comprising mapped reads from both a mother and a fetus. A reference elevation is often the sum of normalized counts of mapped reads from a fetus and a mother (e.g., a pregnant female). In certain embodiments a reference elevation is for genomic sections comprising mapped reads from a euploid mother and/or a euploid fetus. In certain embodiments a reference elevation is for genomic sections comprising mapped reads having a fetal genetic variation (e.g., an aneuploidy (e.g., a trisomy)), and/or reads having a maternal genetic variation (e.g., a copy number variation, insertion, deletion). In certain embodiments a reference elevation is for genomic sections that include substantially no maternal and/or fetal copy number variations. In certain embodiments a second elevation is used as a reference elevation. In certain embodiments a profile comprises a first elevation of normalized counts and a second elevation of normalized counts, the first elevation is significantly different from the second elevation and the second elevation is the reference elevation. In certain embodiments a profile comprises a first elevation of normalized counts for a first set of genomic sections, a second elevation of normalized counts for a second set of genomic sections, the first set of genomic sections includes mapped reads having a maternal and/or fetal copy number variation, the second set of genomic sections comprises mapped reads having substantially no maternal copy number variation and/or fetal copy number variation, and the second elevation is a reference elevation.

In some embodiments counts mapped to genomic sections for one or more elevations of a profile are normalized according to counts of a reference elevation. In some embodiments, normalizing counts of an elevation according to counts of a reference elevation comprise dividing counts of an elevation by counts of a reference elevation or a multiple or fraction thereof. Counts normalized according to counts of a reference elevation often have been normalized according to another process (e.g., PERUN) and counts of a reference elevation also often have been normalized (e.g., by PERUN). In certain embodiments the counts of an elevation are normalized according to counts of a reference elevation and the counts of the reference elevation are scalable to a suitable value either prior to or after normalizing. The process of scaling the counts of a reference elevation can comprise any suitable constant (i.e., number) and any suitable mathematical manipulation may be applied to the counts of a reference elevation.

A normalized reference value (NRV) is often determined according to the normalized counts of a reference elevation. Determining an NRV can comprise any suitable normalization process (e.g., mathematical manipulation) applied to the counts of a reference elevation where the same normalization process is used to normalize the counts of other elevations within the same profile. Determining an NRV often comprises dividing a reference elevation by itself. Determining an NRV often comprises dividing a reference elevation by a multiple of itself. Determining an NRV often comprises dividing a reference elevation by the sum or difference of the reference elevation and a constant (e.g., any number).

An NRV is sometimes referred to as a null value. An NRV can be any suitable value. In some embodiments, an NRV is any value other than zero. In certain embodiments an NRV is a whole number. In certain embodiments an NRV is a positive integer. In some embodiments, an NRV is 1, 10, 100 or 1000. Often, an NRV is equal to 1. In certain embodiments an NRV is equal to zero. The counts of a reference elevation can be normalized to any suitable NRV. In some embodiments, the counts of a reference elevation are normalized to an NRV of zero. Often the counts of a reference elevation are normalized to an NRV of 1.

Expected Elevations

An expected elevation is sometimes a pre-defined elevation (e.g., a theoretical elevation, predicted elevation). An "expected elevation" is sometimes referred to herein as a "predetermined elevation value". In some embodiments, an expected elevation is a predicted value for an elevation of normalized counts for a set of genomic sections that include a copy number variation. In certain embodiments, an expected elevation is determined for a set of genomic sections that include substantially no copy number variation. An expected elevation can be determined for a chromosome ploidy (e.g., 0, 1, 2 (i.e., diploid), 3 or 4 chromosomes) or a microploidy (homozygous or heterozygous deletion, duplication, insertion or absence thereof). Often an expected elevation is determined for a maternal microploidy (e.g., a maternal and/or fetal copy number variation).

An expected elevation for a genetic variation or a copy number variation can be determined by any suitable manner. Often an expected elevation is determined by a suitable mathematical manipulation of an elevation (e.g., counts mapped to a set of genomic sections for an elevation). In certain embodiments an expected elevation is determined by utilizing a constant sometimes referred to as an expected elevation constant. An expected elevation for a copy number variation is sometimes calculated by multiplying a reference elevation, normalized counts of a reference elevation or an NRV by an expected elevation constant, adding an expected elevation constant, subtracting an expected elevation constant, dividing by an expected elevation constant, or by a combination thereof. Often an expected elevation (e.g., an expected elevation of a maternal and/or fetal copy number variation) determined for the same subject, sample or test group is determined according to the same reference elevation or NRV.

Often an expected elevation is determined by multiplying a reference elevation, normalized counts of a reference elevation or an NRV by an expected elevation constant where the reference elevation, normalized counts of a reference elevation or NRV is not equal to zero. In certain embodiments an expected elevation is determined by adding an expected elevation constant to reference elevation, normalized counts of a reference elevation or an NRV that is equal to zero. In some embodiments, an expected elevation, normalized counts of a reference elevation, NRV and expected elevation constant are scalable. The process of scaling can comprise any suitable constant (i.e., number) and any suitable mathematical manipulation where the same scaling process is applied to all values under consideration.

Expected Elevation Constant

An expected elevation constant can be determined by a suitable method. In certain embodiments an expected elevation constant is arbitrarily determined. Often an expected elevation constant is determined empirically. In certain embodiments an expected elevation constant is determined according to a mathematical manipulation. In certain embodiments an expected elevation constant is determined according to a reference (e.g., a reference genome, a reference sample, reference test data). In some embodiments, an expected elevation constant is predetermined for an elevation representative of the presence or absence of a genetic variation or copy number variation (e.g., a duplication, insertion or deletion). In some embodiments, an expected elevation constant is predetermined for an elevation representative of the presence or absence of a maternal copy number variation, fetal copy number variation, or a maternal copy number variation and a fetal copy number variation. An expected elevation constant for a copy number variation can be any suitable constant or set of constants.

In some embodiments, the expected elevation constant for a homozygous duplication (e.g., a homozygous duplication) can be from about 1.6 to about 2.4, from about 1.7 to about 2.3, from about 1.8 to about 2.2, or from about 1.9 to about 2.1. In certain embodiments the expected elevation constant for a homozygous duplication is about 1.6, 1.7, 1.8, 1.9, 2.0, 2.1, 2.2, 2.3 or about 2.4. Often the expected elevation constant for a homozygous duplication is about 1.90, 1.92, 1.94, 1.96, 1.98, 2.0, 2.02, 2.04, 2.06, 2.08 or about 2.10. Often the expected elevation constant for a homozygous duplication is about 2.

In some embodiments, the expected elevation constant for a heterozygous duplication (e.g., a homozygous duplication) is from about 1.2 to about 1.8, from about 1.3 to about 1.7, or from about 1.4 to about 1.6. In certain embodiments the expected elevation constant for a heterozygous duplication is about 1.2, 1.3, 1.4, 1.5, 1.6, 1.7 or about 1.8. Often the expected elevation constant for a heterozygous duplication is about 1.40, 1.42, 1.44, 1.46, 1.48, 1.5, 1.52, 1.54, 1.56, 1.58 or about 1.60. In some embodiments, the expected elevation constant for a heterozygous duplication is about 1.5.

In some embodiments, the expected elevation constant for the absence of a copy number variation (e.g., the absence of a maternal copy number variation and/or fetal copy number variation) is from about 1.3 to about 0.7, from about 1.2 to about 0.8, or from about 1.1 to about 0.9. In certain embodiments the expected elevation constant for the absence of a copy number variation is about 1.3, 1.2, 1.1, 1.0, 0.9, 0.8 or about 0.7. Often the expected elevation constant for the absence of a copy number variation is about 1.09, 1.08, 1.06, 1.04, 1.02, 1.0, 0.98, 0.96, 0.94, or about 0.92. In some embodiments, the expected elevation constant for the absence of a copy number variation is about 1.

In some embodiments, the expected elevation constant for a heterozygous deletion (e.g., a maternal, fetal, or a maternal and a fetal heterozygous deletion) is from about 0.2 to about 0.8, from about 0.3 to about 0.7, or from about 0.4 to about 0.6. In certain embodiments the expected elevation constant for a heterozygous deletion is about 0.2, 0.3, 0.4, 0.5, 0.6, 0.7 or about 0.8. Often the expected elevation constant for a heterozygous deletion is about 0.40, 0.42, 0.44, 0.46, 0.48, 0.5, 0.52, 0.54, 0.56, 0.58 or about 0.60. In some embodiments, the expected elevation constant for a heterozygous deletion is about 0.5.

In some embodiments, the expected elevation constant for a homozygous deletion (e.g., a homozygous deletion) can be from about −0.4 to about 0.4, from about −0.3 to about 0.3, from about −0.2 to about 0.2, or from about −0.1 to about 0.1. In certain embodiments the expected elevation constant for a homozygous deletion is about −0.4, −0.3, −0.2, −0.1, 0.0, 0.1, 0.2, 0.3 or about 0.4. Often the expected elevation constant for a homozygous deletion is about −0.1, −0.08, −0.06, −0.04, −0.02, 0.0, 0.02, 0.04, 0.06, 0.08 or about 0.10. Often the expected elevation constant for a homozygous deletion is about 0.

Expected Elevation Range

In certain embodiments the presence or absence of a genetic variation or copy number variation (e.g., a maternal copy number variation, fetal copy number variation, or a maternal copy number variation and a fetal copy number variation) is determined by an elevation that falls within or outside of an expected elevation range. An expected elevation range is often determined according to an expected elevation. In certain embodiments an expected elevation range is determined for an elevation comprising substantially no genetic variation or substantially no copy number variation. A suitable method can be used to determine an expected elevation range.

In certain embodiments, an expected elevation range is defined according to a suitable uncertainty value calculated for an elevation. Non-limiting examples of an uncertainty value are a standard deviation, standard error, calculated variance, p-value, and mean absolute deviation (MAD). In certain embodiments, an expected elevation range for a genetic variation or a copy number variation is determined, in part, by calculating the uncertainty value for an elevation (e.g., a first elevation, a second elevation, a first elevation and a second elevation). In certain embodiments an expected elevation range is defined according to an uncertainty value calculated for a profile (e.g., a profile of normalized counts for a chromosome or segment thereof). In some embodiments, an uncertainty value is calculated for an elevation comprising substantially no genetic variation or substantially no copy number variation. In some embodiments, an uncertainty value is calculated for a first elevation, a second elevation or a first elevation and a second elevation. In some embodiments an uncertainty value is determined for a first elevation, a second elevation or a second elevation comprising a first elevation.

An expected elevation range is sometimes calculated, in part, by multiplying, adding, subtracting, or dividing an uncertainty value by a constant (e.g., a predetermined constant) n. A suitable mathematical procedure or combination of procedures can be used. The constant n (e.g., predetermined constant n) is sometimes referred to as a confidence interval. A selected confidence interval is determined according to the constant n that is selected. The constant n (e.g., the predetermined constant n, the confidence interval) can be determined by a suitable manner. The constant n can be a number or fraction of a number greater than zero. The constant n can be a whole number. Often the constant n is a number less than 10. In certain embodiments the constant n is a number less than about 10, less than about 9, less than about 8, less than about 7, less than about 6, less than about 5, less than about 4, less than about 3, or less than about 2. In certain embodiments the constant n is about 10, 9.5, 9, 8.5, 8, 7.5, 7, 6.5, 6, 5.5, 5, 4.5, 4, 3.5, 3, 2.5, 2 or 1. The constant n can be determined empirically from data derived from subjects (a pregnant female and/or a fetus) with a known genetic disposition.

Often an uncertainty value and constant n defines a range (e.g., an uncertainty cutoff). For example, sometimes an uncertainty value is a standard deviation (e.g., +/−5) and is multiplied by a constant n (e.g., a confidence interval) thereby defining a range or uncertainty cutoff (e.g., 5n to −5n).

In some embodiments, an expected elevation range for a genetic variation (e.g., a maternal copy number variation, fetal copy number variation, or a maternal copy number variation and fetal copy number variation) is the sum of an expected elevation plus a constant n times the uncertainty (e.g., n×sigma (e.g., 6 sigma)). In certain embodiments the expected elevation range for a genetic variation or copy number variation designated by k can be defined by the formula:

$$(\text{Expected Elevation Range})_k=(\text{Expected Elevation})_k+n\sigma \quad \text{Formula R:}$$

where σ is an uncertainty value, n is a constant (e.g., a predetermined constant) and the expected elevation range and expected elevation are for the genetic variation k (e.g., k=a heterozygous deletion, e.g., k=the absence of a genetic variation). For example, for an expected elevation equal to 1 (e.g., the absence of a copy number variation), an uncertainty value (i.e. a) equal to +/−0.05, and n=3, the expected elevation range is defined as 1.15 to 0.85. In some embodiments, the expected elevation range for a heterozygous duplication is determined as 1.65 to 1.35 when the expected elevation for a heterozygous duplication is 1.5, n=3, and the uncertainty value σ is +/−0.05. In some embodiments the expected elevation range for a heterozygous deletion is determined as 0.65 to 0.35 when the expected elevation for a heterozygous duplication is 0.5, n=3, and the uncertainty value σ is +/−0.05. In some embodiments the expected elevation range for a homozygous duplication is determined as 2.15 to 1.85 when the expected elevation for a heterozygous duplication is 2.0, n=3 and the uncertainty value σ is +/−0.05. In some embodiments the expected elevation range for a homozygous deletion is determined as 0.15 to −0.15 when the expected elevation for a heterozygous duplication is 0.0, n=3 and the uncertainty value σ is +/−0.05.

In certain embodiments an expected elevation range for a homozygous copy number variation (e.g., a maternal, fetal or maternal and fetal homozygous copy number variation) is determined, in part, according to an expected elevation range for a corresponding heterozygous copy number variation. For example, sometimes an expected elevation range for a homozygous duplication comprises all values greater than an upper limit of an expected elevation range for a heterozygous duplication. In certain embodiments an expected elevation range for a homozygous duplication comprises all values greater than or equal to an upper limit of an expected elevation range for a heterozygous duplication. In certain embodiments an expected elevation range for a homozygous duplication comprises all values greater than an upper limit of an expected elevation range for a heterozygous duplication and less than the upper limit defined by the formula R where σ is an uncertainty value and is a positive value, n is a constant and k is a homozygous duplication. In certain embodiments an expected elevation range for a homozygous duplication comprises all values greater than or equal to an upper limit of an expected elevation range for a heterozygous duplication and less than or equal to the upper limit defined by the formula R where σ is an uncertainty value, σ is a positive value, n is a constant and k is a homozygous duplication.

In some embodiments, an expected elevation range for a homozygous deletion comprises all values less than a lower limit of an expected elevation range for a heterozygous deletion. In certain embodiments an expected elevation range for a homozygous deletion comprises all values less than or equal to a lower limit of an expected elevation range for a heterozygous deletion. In certain embodiments an expected elevation range for a homozygous deletion comprises all values less than a lower limit of an expected elevation range for a heterozygous deletion and greater than the lower limit defined by the formula R where σ is an uncertainty value, σ is a negative value, n is a constant and k is a homozygous deletion. In certain embodiments an expected elevation range for a homozygous deletion comprises all values less than or equal to a lower limit of an expected elevation range for a heterozygous deletion and greater than or equal to the lower limit defined by the formula R where σ is an uncertainty value, σ is a negative value, n is a constant and k is a homozygous deletion.

An uncertainty value can be utilized to determine a threshold value. In some embodiments, a range (e.g., a threshold range) is obtained by calculating the uncertainty value determined from a raw, filtered and/or normalized counts. A range can be determined by multiplying the uncertainty value for an elevation (e.g. normalized counts of an elevation) by a predetermined constant (e.g., 1, 2, 3, 4, 5, 6, etc.) representing the multiple of uncertainty (e.g., number of standard deviations) chosen as a cutoff threshold (e.g., multiply by 3 for 3 standard deviations), whereby a range is generated, in some embodiments. A range can be determined by adding and/or subtracting a value (e.g., a predetermined value, an uncertainty value, an uncertainty value multiplied by a predetermined constant) to and/or from an elevation whereby a range is generated, in some embodiments. For example, for an elevation equal to 1, a standard deviation of +/−0.2, where a predetermined constant is 3, the range can be calculated as (1+3(0.2)) to (1+3(−0.2)), or 1.6 to 0.4. A range sometimes can define an expected range or expected elevation range for a copy number variation. In certain embodiments, some or all of the genomic sections exceeding a threshold value, falling outside a range or falling inside a range of values, are removed as part of, prior to, or after a normalization process. In some embodiments, some or all of the genomic sections exceeding a calculated threshold value, falling outside a range or falling inside a range are weighted or adjusted as part of, or prior to the normalization or classification process. Examples of weighting are described herein. The terms "redundant data", and "redundant mapped reads" as used herein refer to sample derived sequence reads that are identified as having already been assigned to a genomic location (e.g., base position) and/or counted for a genomic section.

In some embodiments an uncertainty value is determined according to the formula below:

$$Z = \frac{L_A - L_o}{\sqrt{\frac{\sigma_A^2}{N_A} + \frac{\sigma_o^2}{N_o}}}$$

Where Z represents the standardized deviation between two elevations, L is the mean (or median) elevation and sigma is the standard deviation (or MAD). The subscript 0 denotes a segment of a profile (e.g., a second elevation, a chromosome, an NRV, a "euploid level", a level absent a copy number variation), and A denotes another segment of a profile (e.g., a first elevation, an elevation representing a copy number variation, an elevation representing an aneuploidy (e.g., a trisomy). The variable $N_o$ represents the total number of genomic sections in the segment of the profile denoted by the subscript O. $N_A$ represents the total number of genomic sections in the segment of the profile denoted by subscript A.

Categorizing a Copy Number Variation

An elevation (e.g., a first elevation) that significantly differs from another elevation (e.g., a second elevation) can often be categorized as a copy number variation (e.g., a maternal and/or fetal copy number variation, a fetal copy number variation, a deletion, duplication, insertion) according to an expected elevation range. In some embodiments, the presence of a copy number variation is categorized when a first elevation is significantly different from a second elevation and the first elevation falls within the expected elevation range for a copy number variation. For example, a copy number variation (e.g., a maternal and/or fetal copy number variation, a fetal copy number variation) can be categorized when a first elevation is significantly different from a second elevation and the first elevation falls within the expected elevation range for a copy number variation. In certain embodiments a heterozygous duplication (e.g., a maternal, fetal, or maternal and fetal heterozygous duplication) or heterozygous deletion (e.g., a maternal, fetal, or maternal and fetal heterozygous deletion) is categorized when a first elevation is significantly different from a second elevation and the first elevation falls within the expected elevation range for a heterozygous duplication or heterozygous deletion, respectively. In certain embodiments a homozygous duplication or homozygous deletion is categorized when a first elevation is significantly different from a second elevation and the first elevation falls within the expected elevation range for a homozygous duplication or homozygous deletion, respectively.

Fetal Fraction Determination Based on Elevation

In some embodiments, a fetal fraction is determined according to an elevation categorized as representative of a maternal and/or fetal copy number variation. For example determining fetal fraction often comprises assessing an expected elevation for a maternal and/or fetal copy number variation utilized for the determination of fetal fraction. In certain embodiments a fetal fraction is determined for an elevation (e.g., a first elevation) categorized as representative of a copy number variation according to an expected elevation range determined for the same type of copy number variation. Often a fetal fraction is determined according to an observed elevation that falls within an expected elevation range and is thereby categorized as a maternal and/or fetal copy number variation. In certain embodiments a fetal fraction is determined when an observed elevation (e.g., a first elevation) categorized as a maternal and/or fetal copy number variation is different than the expected elevation determined for the same maternal and/or fetal copy number variation.

In some embodiments an elevation (e.g., a first elevation, an observed elevation), is significantly different than a second elevation, the first elevation is categorized as a maternal and/or fetal copy number variation, and a fetal fraction is determined according to the first elevation. In certain embodiments a first elevation is an observed and/or experimentally obtained elevation that is significantly different than a second elevation in a profile and a fetal fraction is determined according to the first elevation. In certain embodiments the first elevation is an average, mean or summed elevation and a fetal fraction is determined according to the first elevation. In certain embodiments a first elevation and a second elevation are observed and/or experimentally obtained elevations and a fetal fraction is determined according to the first elevation. In some instances a first elevation comprises normalized counts for a first set of genomic sections and a second elevation comprises normalized counts for a second set of genomic sections and a fetal fraction is determined according to the first elevation. In certain embodiments a first set of genomic sections of a first elevation includes a copy number variation (e.g., the first elevation is representative of a copy number variation) and a fetal fraction is determined according to the first elevation. In certain embodiments the first set of genomic sections of a first elevation includes a homozygous or heterozygous maternal copy number variation and a fetal fraction is determined according to the first elevation. In certain embodiments a profile comprises a first elevation for a first set of genomic sections and a second elevation for a second set of genomic sections, the second set of genomic sections includes substantially no copy number variation (e.g., a maternal copy number variation, fetal copy number variation, or a maternal copy number variation and a fetal copy number variation) and a fetal fraction is determined according to the first elevation.

In some embodiments an elevation (e.g., a first elevation, an observed elevation), is significantly different than a second elevation, the first elevation is categorized as for a maternal and/or fetal copy number variation, and a fetal fraction is determined according to the first elevation and/or an expected elevation of the copy number variation. In certain embodiments a first elevation is categorized as for a copy number variation according to an expected elevation for a copy number variation and a fetal fraction is determined according to a difference between the first elevation and the expected elevation. In certain embodiments an elevation (e.g., a first elevation, an observed elevation) is categorized as a maternal and/or fetal copy number variation, and a fetal fraction is determined as twice the difference between the first elevation and expected elevation of the copy number variation. In certain embodiments an elevation (e.g., a first elevation, an observed elevation) is categorized as a maternal and/or fetal copy number variation, the first elevation is subtracted from the expected elevation thereby providing a difference, and a fetal fraction is determined as twice the difference. In certain embodiments an elevation (e.g., a first elevation, an observed elevation) is categorized as a maternal and/or fetal copy number variation, an expected elevation is subtracted from a first elevation thereby providing a difference, and the fetal fraction is determined as twice the difference.

Often a fetal fraction is provided as a percent. For example, a fetal fraction can be multiplied by 100 thereby providing a percent value. For example, for a first elevation representative of a maternal homozygous duplication and having an elevation of 155 and an expected elevation for a maternal homozygous duplication having an elevation of 150, a fetal fraction can be determined as 0.01 (e.g., (fetal fraction=2×(0.155−0.150)) or 1%.

In some embodiments a fetal fraction is determined from two or more elevations within a profile that are categorized as copy number variations. For example, sometimes two or more elevations (e.g., two or more first elevations) in a profile are identified as significantly different than a reference elevation (e.g., a second elevation, an elevation that includes substantially no copy number variation), the two or more elevations are categorized as representative of a maternal and/or fetal copy number variation and a fetal fraction is determined from each of the two or more elevations. In certain embodiments a fetal fraction is determined from about 3 or more, about 4 or more, about 5 or more, about 6 or more, about 7 or more, about 8 or more, or about 9 or more fetal fraction determinations within a profile. In certain embodiments a fetal fraction is determined from about 10 or more, about 20 or more, about 30 or more, about 40 or more, about 50 or more, about 60 or more, about 70 or more, about 80 or more, or about 90 or more fetal fraction determinations within a profile. In certain embodiments a fetal fraction is determined from about 100 or more, about 200 or more, about 300 or more, about 400 or more, about 500 or more, about 600 or more, about 700 or more, about 800 or more, about 900 or more, or about 1000 or more fetal fraction determinations within a profile. In certain embodiments a fetal fraction is determined from about 10 to about 1000, about 20 to about 900, about 30 to about 700, about 40 to about 600, about 50 to about 500, about 50 to about 400, about 50 to about 300, about 50 to about 200, or about 50 to about 100 fetal fraction determinations within a profile.

In some embodiments a fetal fraction is determined as the average or mean of multiple fetal fraction determinations within a profile. In certain embodiments, a fetal fraction determined from multiple fetal fraction determinations is a mean (e.g., an average, a mean, a standard average, a median, or the like) of multiple fetal fraction determinations. Often a fetal fraction determined from multiple fetal fraction determinations is a mean value determined by a suitable method known in the art or described herein. In certain embodiments a mean value of a fetal fraction determination is a weighted mean. In certain embodiments a mean value of a fetal fraction determination is an unweighted mean. In some embodiments, a fetal fraction is determined from multiple first elevations significantly different than a second elevation where the elevation and/or independent fetal fraction determinations are weighted. In certain embodiments a fetal fraction determination is obtained from counts for multiple genomic sections where the counts for each genomic section or the counts for multiple sets of genomic sections are weighted. A mean, median or average fetal fraction determination (i.e., a mean, median or average fetal fraction determination value) generated from multiple fetal fraction determinations is sometimes associated with an uncertainty value (e.g., a variance, standard deviation, MAD, or the like). Before determining a mean, median or average fetal fraction value from multiple determinations, one or more deviant determinations are removed in some embodiments (described in greater detail herein).

Some fetal fraction determinations within a profile sometimes are not included in the overall determination of a fetal fraction (e.g., mean or average fetal fraction determination). In certain embodiments a fetal fraction determination is derived from a first elevation (e.g., a first elevation that is significantly different than a second elevation) in a profile and the first elevation is not indicative of a genetic variation. For example, some first elevations (e.g., spikes or dips) in a profile are generated from anomalies or unknown causes. Such values often generate fetal fraction determinations that differ significantly from other fetal fraction determinations obtained from true copy number variations. In certain embodiments fetal fraction determinations that differ significantly from other fetal fraction determinations in a profile are identified and removed from a fetal fraction determination. For example, some fetal fraction determinations obtained from anomalous spikes and dips are identified by comparing them to other fetal fraction determinations within a profile and are excluded from the overall determination of fetal fraction.

In certain embodiments, an independent fetal fraction determination that differs significantly from a mean, median or average fetal fraction determination is an identified, recognized and/or observable difference. In certain embodiments, the term "differs significantly" can mean statistically different and/or a statistically significant difference. An "independent" fetal fraction determination can be a fetal fraction determined (e.g., in some cases a single determination) from a specific elevation categorized as a copy number variation. Any suitable threshold or range can be used to determine that a fetal fraction determination differs significantly from a mean, median or average fetal fraction determination. In certain embodiments a fetal fraction determination differs significantly from a mean, median or average fetal fraction determination and the determination can be expressed as a percent deviation from the average or mean value. In certain embodiments a fetal fraction determination that differs significantly from a mean, median or average fetal fraction determination differs by about 10 percent or more. In certain embodiments a fetal fraction determination that differs significantly from a mean, median or average fetal fraction determination differs by about 15 percent or more. In certain embodiments a fetal fraction determination that differs significantly from a mean, median or average fetal fraction determination differs by about 15% to about 100% or more.

In certain embodiments a fetal fraction determination differs significantly from a mean, median or average fetal fraction determination according to a multiple of an uncertainty value associated with the mean or average fetal fraction determination. Often an uncertainty value and constant n (e.g., a confidence interval) defines a range (e.g., an uncertainty cutoff). For example, sometimes an uncertainty value is a standard deviation for fetal fraction determinations (e.g., +/−5) and is multiplied by a constant n (e.g., a confidence interval) thereby defining a range or uncertainty cutoff (e.g., 5n to −5n, sometimes referred to as 5 sigma). In certain embodiments an independent fetal fraction determination falls outside a range defined by the uncertainty cutoff and is considered significantly different from a mean, median or average fetal fraction determination. For example, for a mean value of 10 and an uncertainty cutoff of 3, an independent fetal fraction greater than 13 or less than 7 is significantly different. In certain embodiments a fetal fraction determination that differs significantly from a mean, median or average fetal fraction determination differs by more than n times the uncertainty value (e.g., n×sigma) where n is about equal to or greater than 1, 2, 3, 4, 5, 6, 7, 8, 9 or 10. In certain embodiments a fetal fraction determination that differs significantly from a mean, median or average fetal fraction determination differs by more than n times the uncertainty value (e.g., n×sigma) where n is about equal to or greater than 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0.

In some embodiments, an elevation is representative of a fetal and/or maternal microploidy. In certain embodiments an elevation (e.g., a first elevation, an observed elevation), is significantly different than a second elevation, the first elevation is categorized as a maternal and/or fetal copy number variation, and the first elevation and/or second elevation is representative of a fetal microploidy and/or a maternal microploidy. In certain embodiments a first elevation is representative of a fetal microploidy, In certain embodiments a first elevation is representative of a maternal microploidy. Often a first elevation is representative of a fetal microploidy and a maternal microploidy. In certain embodiments an elevation (e.g., a first elevation, an observed elevation), is significantly different than a second elevation, the first elevation is categorized as a maternal and/or fetal copy number variation, the first elevation is representative of a fetal and/or maternal microploidy and a fetal fraction is determined according to the fetal and/or maternal microploidy. In some instances a first elevation is categorized as a maternal and/or fetal copy number variation, the first elevation is representative of a fetal microploidy and a fetal fraction is determined according to the fetal microploidy. In certain embodiments a first elevation is categorized as a maternal and/or fetal copy number variation, the first elevation is representative of a maternal microploidy and a fetal fraction is determined according to the maternal microploidy. In certain embodiments a first elevation is categorized as a maternal and/or fetal copy number variation, the first elevation is representative of a maternal and a fetal microploidy and a fetal fraction is determined according to the maternal and fetal microploidy.

In some embodiments, a determination of a fetal fraction comprises determining a fetal and/or maternal microploidy. In certain embodiments an elevation (e.g., a first elevation, an observed elevation), is significantly different than a second elevation, the first elevation is categorized as a maternal and/or fetal copy number variation, a fetal and/or maternal microploidy is determined according to the first elevation and/or second elevation and a fetal fraction is determined. In certain embodiments a first elevation is categorized as a maternal and/or fetal copy number variation, a fetal microploidy is determined according to the first elevation and/or second elevation and a fetal fraction is determined according to the fetal microploidy. In certain embodiments a first elevation is categorized as a maternal and/or fetal copy number variation, a maternal microploidy is determined according to the first elevation and/or second elevation and a fetal fraction is determined according to the maternal microploidy. In certain embodiments a first elevation is categorized as a maternal and/or fetal copy number variation, a maternal and fetal microploidy is determined according to the first elevation and/or second elevation and a fetal fraction is determined according to the maternal and fetal microploidy.

A fetal fraction often is determined when the microploidy of the mother is different from (e.g., not the same as) the microploidy of the fetus for a given elevation or for an elevation categorized as a copy number variation. In certain embodiments a fetal fraction is determined when the mother is homozygous for a duplication (e.g., a microploidy of 2) and the fetus is heterozygous for the same duplication (e.g., a microploidy of 1.5). In certain embodiments a fetal fraction is determined when the mother is heterozygous for a duplication (e.g., a microploidy of 1.5) and the fetus is homozygous for the same duplication (e.g., a microploidy of 2) or the duplication is absent in the fetus (e.g., a microploidy of 1). In certain embodiments a fetal fraction is determined when the mother is homozygous for a deletion (e.g., a microploidy of 0) and the fetus is heterozygous for the same deletion (e.g., a microploidy of 0.5). In certain embodiments a fetal fraction is determined when the mother is heterozygous for a deletion (e.g., a microploidy of 0.5) and the fetus is homozygous for the same deletion (e.g., a microploidy of 0) or the deletion is absent in the fetus (e.g., a microploidy of 1).

In certain embodiments, a fetal fraction cannot be determined when the microploidy of the mother is the same (e.g., identified as the same) as the microploidy of the fetus for a given elevation identified as a copy number variation. For example, for a given elevation where both the mother and fetus carry the same number of copies of a copy number variation, a fetal fraction is not determined, in some embodiments. For example, a fetal fraction cannot be determined for an elevation categorized as a copy number variation when both the mother and fetus are homozygous for the same deletion or homozygous for the same duplication. In certain embodiments, a fetal fraction cannot be determined for an elevation categorized as a copy number variation when both the mother and fetus are heterozygous for the same deletion or heterozygous for the same duplication. In embodiments where multiple fetal fraction determinations are made for a sample, determinations that significantly deviate from a mean, median or average value can result from a copy number variation for which maternal ploidy is equal to fetal ploidy, and such determinations can be removed from consideration.

In some embodiments the microploidy of a maternal copy number variation and fetal copy number variation is unknown. In certain embodiments, in cases when there is no determination of fetal and/or maternal microploidy for a copy number variation, a fetal fraction is generated and compared to a mean, median or average fetal fraction determination. A fetal fraction determination for a copy number variation that differs significantly from a mean, median or average fetal fraction determination is sometimes because the microploidy of the mother and fetus are the same for the copy number variation. A fetal fraction determination that differs significantly from a mean, median or average fetal fraction determination is often excluded from an overall fetal fraction determination regardless of the source or cause of the difference. In some embodiments, the microploidy of the mother and/or fetus is determined and/or verified by a method known in the art (e.g., by targeted sequencing methods).

Elevation Adjustments

In some embodiments, one or more elevations are adjusted. A process for adjusting an elevation often is referred to as padding. In some embodiments, multiple elevations in a profile (e.g., a profile of a genome, a chromosome profile, a profile of a portion or segment of a chromosome) are adjusted. In certain embodiments, about 1 to about 10,000 or more elevations in a profile are adjusted. In certain embodiments about 1 to about a 1000, 1 to about 900, 1 to about 800, 1 to about 700, 1 to about 600, 1 to about 500, 1 to about 400, 1 to about 300, 1 to about 200, 1 to about 100, 1 to about 50, 1 to about 25, 1 to about 20, 1 to about 15, 1 to about 10, or 1 to about 5 elevations in a profile are adjusted. In certain embodiments one elevation is adjusted. In some embodiments, an elevation (e.g., a first elevation of a normalized count profile) that significantly differs from a second elevation is adjusted. In certain embodiments an elevation categorized as a copy number variation is adjusted. In certain embodiments an elevation (e.g., a first elevation of a normalized count profile) that significantly differs from a second elevation is categorized as a copy number variation (e.g., a copy number variation, e.g., a maternal copy number variation) and is adjusted. In some embodiments, an elevation (e.g., a first elevation) is within an expected elevation range for a maternal copy number variation, fetal copy number variation, or a maternal copy number variation and a fetal copy number variation and the elevation is adjusted. In certain embodiments, one or more elevations (e.g., elevations in a profile) are not adjusted. In some embodiments, an elevation (e.g., a first elevation) is outside an expected elevation range for a copy number variation and the elevation is not adjusted. Often, an elevation within an expected elevation range for the absence of a copy number variation is not adjusted. Any suitable number of adjustments can be made to one or more elevations in a profile. In some embodiments, one or more elevations are adjusted. In certain embodiments 2 or more, 3 or more, 5 or more, 6 or more, 7 or more, 8 or more, 9 or more and sometimes 10 or more elevations are adjusted.

In some embodiments, a value of a first elevation is adjusted according to a value of a second elevation. In certain embodiments a first elevation, identified as representative of a copy number variation, is adjusted to the value of a second elevation, where the second elevation is often associated with no copy number variation. In certain embodiments, a value of a first elevation, identified as representative of a copy number variation, is adjusted so the value of the first elevation is about equal to a value of a second elevation.

An adjustment can comprise a suitable mathematical operation. In certain embodiments an adjustment comprises one or more mathematical operations. In certain embodiments an elevation is adjusted by normalizing, filtering, averaging, multiplying, dividing, adding or subtracting or combination thereof. In certain embodiments an elevation is adjusted by a predetermined value or a constant. In certain embodiments an elevation is adjusted by modifying the value of the elevation to the value of another elevation. For example, a first elevation may be adjusted by modifying its value to the value of a second elevation. A value in such cases may be a processed value (e.g., mean, normalized value and the like).

In certain embodiments an elevation is categorized as a copy number variation (e.g., a maternal copy number variation) and is adjusted according to a predetermined value referred to herein as a predetermined adjustment value (PAV). Often a PAV is determined for a specific copy number variation. Often a PAV determined for a specific copy number variation (e.g., homozygous duplication, homozygous deletion, heterozygous duplication, heterozygous deletion) is used to adjust an elevation categorized as a specific copy number variation (e.g., homozygous duplication, homozygous deletion, heterozygous duplication, heterozygous deletion). In certain embodiments, an elevation is categorized as a copy number variation and is then adjusted according to a PAV specific to the type of copy number variation categorized. In certain embodiments an elevation (e.g., a first elevation) is categorized as a maternal copy number variation, fetal copy number variation, or a maternal copy number variation and a fetal copy number variation and is adjusted by adding or subtracting a PAV from the elevation. Often an elevation (e.g., a first elevation) is categorized as a maternal copy number variation and is adjusted by adding a PAV to the elevation. For example, an elevation categorized as a duplication (e.g., a maternal, fetal or maternal and fetal homozygous duplication) can be adjusted by adding a PAV determined for a specific duplication (e.g., a homozygous duplication) thereby providing an adjusted elevation. Often a PAV determined for a copy number duplication is a negative value. In some embodiments providing an adjustment to an elevation representative of a duplication by utilizing a PAV determined for a duplication results in a reduction in the value of the elevation. In some embodiments, an elevation (e.g., a first elevation) that significantly differs from a second elevation is categorized as a copy number deletion (e.g., a homozygous deletion, heterozygous deletion, homozygous duplication, homozygous duplication) and the first elevation is adjusted by adding a PAV determined for a copy number deletion. Often a PAV determined for a copy number deletion is a positive value. In some embodiments providing an adjustment to an elevation representative of a deletion by utilizing a PAV determined for a deletion results in an increase in the value of the elevation.

A PAV can be any suitable value. Often a PAV is determined according to and is specific for a copy number variation (e.g., a categorized copy number variation). In certain embodiments a PAV is determined according to an expected elevation for a copy number variation (e.g., a categorized copy number variation) and/or a PAV factor. A PAV sometimes is determined by multiplying an expected elevation by a PAV factor. For example, a PAV for a copy number variation can be determined by multiplying an expected elevation determined for a copy number variation (e.g., a heterozygous deletion) by a PAV factor determined for the same copy number variation (e.g., a heterozygous deletion). For example, PAV can be determined by the formula below:

$$PAV_k=(\text{Expected Elevation})_k\times(PAV\text{ factor})_k$$

for the copy number variation k (e.g., k=a heterozygous deletion)

A PAV factor can be any suitable value. In certain embodiments a PAV factor for a homozygous duplication is between about −0.6 and about −0.4. In certain embodiments a PAV factor for a homozygous duplication is about −0.60, −0.59, −0.58, −0.57, −0.56, −0.55, −0.54, −0.53, −0.52, −0.51, −0.50, −0.49, −0.48, −0.47, −0.46, −0.45, −0.44, −0.43, −0.42, −0.41 and −0.40. Often a PAV factor for a homozygous duplication is about −0.5.

For example, for an NRV of about 1 and an expected elevation of a homozygous duplication equal to about 2, the PAV for the homozygous duplication is determined as about −1 according to the formula above. In this case, a first elevation categorized as a homozygous duplication is adjusted by adding about −1 to the value of the first elevation, for example.

In certain embodiments a PAV factor for a heterozygous duplication is between about −0.4 and about −0.2. In certain embodiments a PAV factor for a heterozygous duplication is about −0.40, −0.39, −0.38, −0.37, −0.36, −0.35, −0.34, −0.33, −0.32, −0.31, −0.30, −0.29, −0.28, −0.27, −0.26, −0.25, −0.24, −0.23, −0.22, −0.21 and −0.20. Often a PAV factor for a heterozygous duplication is about −0.33.

For example, for an NRV of about 1 and an expected elevation of a heterozygous duplication equal to about 1.5, the PAV for the homozygous duplication is determined as about −0.495 according to the formula above. In this case, a first elevation categorized as a heterozygous duplication is adjusted by adding about −0.495 to the value of the first elevation, for example.

In certain embodiments a PAV factor for a heterozygous deletion is between about 0.4 and about 0.2. In certain embodiments a PAV factor for a heterozygous deletion is about 0.40, 0.39, 0.38, 0.37, 0.36, 0.35, 0.34, 0.33, 0.32, 0.31, 0.30, 0.29, 0.28, 0.27, 0.26, 0.25, 0.24, 0.23, 0.22, 0.21 and 0.20. Often a PAV factor for a heterozygous deletion is about 0.33.

For example, for an NRV of about 1 and an expected elevation of a heterozygous deletion equal to about 0.5, the PAV for the heterozygous deletion is determined as about 0.495 according to the formula above. In this case, a first elevation categorized as a heterozygous deletion is adjusted by adding about 0.495 to the value of the first elevation, for example.

In certain embodiments a PAV factor for a homozygous deletion is between about 0.6 and about 0.4. In certain embodiments a PAV factor for a homozygous deletion is about 0.60, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41 and 0.40. Often a PAV factor for a homozygous deletion is about 0.5.

For example, for an NRV of about 1 and an expected elevation of a homozygous deletion equal to about 0, the PAV for the homozygous deletion is determined as about 1 according to the formula above. In this case, a first elevation categorized as a homozygous deletion is adjusted by adding about 1 to the value of the first elevation, for example.

In certain embodiments, a PAV is about equal to or equal to an expected elevation for a copy number variation (e.g., the expected elevation of a copy number variation).

In some embodiments, counts of an elevation are normalized prior to making an adjustment. In certain embodiments, counts of some or all elevations in a profile are normalized prior to making an adjustment. For example, counts of an elevation can be normalized according to counts of a reference elevation or an NRV. In certain embodiments, counts of an elevation (e.g., a second elevation) are normalized according to counts of a reference elevation or an NRV and the counts of all other elevations (e.g., a first elevation) in a profile are normalized relative to the counts of the same reference elevation or NRV prior to making an adjustment.

In some embodiments, an elevation of a profile results from one or more adjustments. In certain embodiments, an elevation of a profile is determined after one or more elevations in the profile are adjusted. In some embodiments, an elevation of a profile is re-calculated after one or more adjustments are made.

In some embodiments, a copy number variation (e.g., a maternal copy number variation, fetal copy number variation, or a maternal copy number variation and a fetal copy number variation) is determined (e.g., determined directly or indirectly) from an adjustment. For example, an elevation in a profile that was adjusted (e.g., an adjusted first elevation) can be identified as a maternal copy number variation. In some embodiments, the magnitude of the adjustment indicates the type of copy number variation (e.g., heterozygous deletion, homozygous duplication, and the like). In certain embodiments, an adjusted elevation in a profile can be identified as representative of a copy number variation according to the value of a PAV for the copy number variation. For example, for a given profile, PAV is about −1 for a homozygous duplication, about −0.5 for a heterozygous duplication, about 0.5 for a heterozygous deletion and about 1 for a homozygous deletion. In the preceding example, an elevation adjusted by about −1 can be identified as a homozygous duplication, for example. In some embodiments, one or more copy number variations can be determined from a profile or an elevation comprising one or more adjustments.

In certain embodiments, adjusted elevations within a profile are compared. In certain embodiments anomalies and errors are identified by comparing adjusted elevations. For example, often one or more adjusted elevations in a profile are compared and a particular elevation may be identified as an anomaly or error. In certain embodiments an anomaly or error is identified within one or more genomic sections making up an elevation. An anomaly or error may be identified within the same elevation (e.g., in a profile) or in one or more elevations that represent genomic sections that are adjacent, contiguous, adjoining or abutting. In certain embodiments one or more adjusted elevations are elevations of genomic sections that are adjacent, contiguous, adjoining or abutting where the one or more adjusted elevations are compared and an anomaly or error is identified. An anomaly or error can be a peak or dip in a profile or elevation where a cause of the peak or dip is known or unknown. In certain embodiments adjusted elevations are compared and an anomaly or error is identified where the anomaly or error is due to a stochastic, systematic, random or user error. In certain embodiments adjusted elevations are compared and an anomaly or error is removed from a profile. In certain embodiments, adjusted elevations are compared and an anomaly or error is adjusted.

In certain embodiments an outcome is determined according to one or more elevations. In some embodiments, a determination of the presence or absence of a genetic variation (e.g., a chromosome aneuploidy) is determined according to one or more adjusted elevations. In certain embodiments, a determination of the presence or absence of a genetic variation (e.g., a chromosome aneuploidy) is determined according to a profile comprising 1 to about 10,000 adjusted elevations. Often a determination of the presence or absence of a genetic variation (e.g., a chromosome aneuploidy) is determined according to a profile comprising about 1 to about a 1000, 1 to about 900, 1 to about 800, 1 to about 700, 1 to about 600, 1 to about 500, 1 to about 400, 1 to about 300, 1 to about 200, 1 to about 100, 1 to about 50, 1 to about 25, 1 to about 20, 1 to about 15, 1 to about 10, or 1 to about 5 adjustments. In certain embodiments a determination of the presence or absence of a genetic variation (e.g., a chromosome aneuploidy) is determined according to a profile comprising about 1 adjustment (e.g., one adjusted elevation). In certain embodiments an outcome is determined according to one or more profiles (e.g., a profile of a chromosome or segment thereof) comprising one or more, 2 or more, 3 or more, 5 or more, 6 or more, 7 or more, 8 or more, 9 or more or sometimes 10 or more adjustments. In certain embodiments, a determination of the presence or absence of a genetic variation (e.g., a chromosome aneuploidy) is determined according to a profile where some elevations in a profile are not adjusted. In certain embodiments, a determination of the presence or absence of a genetic variation (e.g., a chromosome aneuploidy) is determined according to a profile where adjustments are not made.

In some embodiments, an adjustment of an elevation (e.g., a first elevation) in a profile reduces a false determination or false outcome. In some embodiments, an adjustment of an elevation (e.g., a first elevation) in a profile reduces the frequency and/or probability (e.g., statistical probability, likelihood) of a false determination or false outcome. A false determination or outcome can be a determination or outcome that is not accurate. A false determination or outcome can be a determination or outcome that is not reflective of the actual or true genetic make-up or the actual or true genetic disposition (e.g., the presence or absence of a genetic variation) of a subject (e.g., a pregnant female, a fetus and/or a combination thereof). In certain embodiments a false determination or outcome is a false negative determination. In some embodiments a negative determination or negative outcome is the absence of a genetic variation (e.g., aneuploidy, copy number variation). In certain embodiments a false determination or false outcome is a false positive determination or false positive outcome. In some embodiments a positive determination or positive outcome is the presence of a genetic variation (e.g., aneuploidy, copy number variation).

In some embodiments, a determination or outcome is utilized in a diagnosis. In some embodiments, a determination or outcome is for a fetus.

Determining a Chromosome Representation

A fetal fraction determination can be based in part on an expected chromosome representation and/or a measured chromosome representation.

Expected Chromosome Representation (ECR)

In some embodiments, fetal fraction is determined in part by generating an expected chromosome representation (ECR, e.g., an expected euploid chromosome representation) for a chromosome or segment thereof. An ECR is often for a euploid representation of a chromosome, or segment thereof. An ECR can be determined for an autosome, a sex chromosome or segment thereof. In certain embodiments an ECR is determined for an affected autosome (e.g., in the case of a trisomy, e.g., chromosome 13 is the affected autosome in the case of a trisomy 13, chromosome 18 is the affected autosome in the case of trisomy 18, or chromosome 21 is the affected autosome in the case of a trisomy 21). An ECR for chromosome n, or segment thereof, can be referred to as an "expected n chromosome representation". For example, an ECR for chromosome X can be referred to as an "expected X chromosome representation". In certain embodiments an ECR is determined according to the number of genomic sections in a normalized count profile. In certain embodiments the ECR for chromosome n is the ratio between the total number of genomic sections for chromosome n, or a segment thereof, and the total number of genomic sections in a profile (e.g., a profile of all autosomal chromosomes, a profile of most all autosomal chromosomes, a profile of a genome or segment of a genome). A profile can comprise one or more of any chromosome or segments thereof, a subset of chromosomes (e.g., including any chromosome or segment thereof), all autosomes, a subset of autosomes. A profile can comprise some or all chromosomes sequenced in a sample, from a single sequencing run and/or from a single flow cell. In certain embodiments an ECR is the ratio between the total area under an expected elevation representative of the genomic sections for chromosome n, or a segment thereof, and the total area under the expected elevation for all genomic sections of an entire profile (e.g., a profile of all autosomal chromosomes, a profile of most all autosomal chromosomes, a profile of a genome or segment of a genome). In certain embodiments, an ECR is determined according to an expected median or mean value of an expected elevation and/or profile. An ECR can be determined, in some cases, by equation Z described in Example 9. Often, an ECR is determined for chromosome n, or a segment thereof, where chromosome n is an aneuploid chromosome (e.g., a trisomy). In certain embodiments, an ECR is determined for chromosome X and/or chromosome Y for a pregnant female bearing a male fetus. In certain embodiments, an ECR is determined for chromosome X and/or chromosome Y for a pregnant female bearing a male fetus comprising a sex aneuploidy (e.g., Turner's Syndrome, Klinefelter syndrome, Double Y syndrome, Trisomy X syndrome, Four X syndrome). In some embodiments, an expected euploid chromosome representation for ChrX is the median or mean ChrX representation obtained from a female pregnancy or from a set of female pregnancies. In some embodiments, an expected chromosome representation for ChrX in a male pregnancy is the median or mean ChrX representation obtained from a female pregnancy or from a set of female pregnancies. In some embodiments, the MCR of ChrX in a male pregnancy differs from the ECR of ChrX in a female pregnancy and the deviation is proportional to fetal fraction. In certain embodiments fetal fraction is estimated from the MCR of ChrX in a male pregnancy.

Measured Chromosome Representation (MCR)

In some embodiments, a fetal fraction is determined, in part, by generating a measured (i.e., experimentally measured) chromosome representation (MCR). Often an MCR is an experimentally derived value. An MCR can be referred to as an experimental chromosome representation. An MCR for chromosome n can be referred to as an "experimental n chromosome representation". For example, an MCR for chromosome X can be referred to as an "experimental X chromosome representation". In certain embodiments an MCR is determined according to counts mapped to genomic sections of a chromosome or a segment thereof. In certain embodiments an MCR is determined from normalized counts. In certain embodiments an MCR is determined from raw counts. Often an MCR is determined from counts normalized by GC content, bin-wise normalization, GC LOESS, PERUN, GCRM, the like or a combination thereof. In certain embodiments an MCR is determined according to counts mapped to genomic sections of a sex chromosome (e.g., an X or Y chromosome) or a chromosome representing an aneuploidy (e.g., an affected autosome, a trisomy). In certain embodiments an MCR is determined according to a measured elevation of a chromosome or segment thereof. In certain embodiments, an MCR for a chromosome can be determined according to a median, average or mean value of one or more elevations in a profile. In certain embodiments, a fetal fraction is determined, in part, by generating an MCR for a chromosome, or segment thereof, representing an aneuploidy. In certain embodiments, a fetal fraction is determined, in part, by generating an MCR for an X and/or a Y chromosome, or segment thereof, for a pregnant female bearing a male fetus. In certain embodiments an MCR is determined according to counts mapped to genomic sections of a sex chromosome (e.g., an X or Y chromosome) for a pregnant female bearing a male fetus comprising a sex aneuploidy (e.g., Turner's Syndrome, Klinefelter syndrome, Double Y syndrome, Trisomy X syndrome, Four X syndrome). In some embodiments, an MCR for a sex chromosome is not determined for a pregnant female bearing a euploid female fetus. In certain embodiments an MCR for chromosome n is the ratio between the total number of counts (e.g., total normalized counts, mean, average or median of total counts) mapped to genomic sections of chromosome n, or a segment thereof, and the total number of counts (e.g., total normalized counts, mean, average or median of total counts) mapped to genomic sections of some or all chromosomes represented in a profile (e.g., a profile of a genome or segment thereof) where chromosome n can be any chromosome. In certain embodiments an MCR for chromosome n is the ratio between the total number of counts (e.g., total normalized counts, mean, average or median of total counts) mapped to genomic sections of chromosome n, or a segment thereof, and the total number of counts (e.g., total normalized counts, mean, average or median of total counts) mapped to genomic sections of some or all autosomes represented in a profile (e.g., a profile of a genome or segment thereof) where chromosome n can be any chromosome. In certain embodiments an MCR for chromosome n is the ratio between the total area under an elevation representative of chromosome n, or a segment thereof, and the total area under an elevation of an entire profile (e.g., a profile of all autosomal chromosomes, a profile of most all autosomal chromosomes, a profile of a genome or segment of a genome).

In certain embodiments a median chromosome representation is a median MCR for chromosome n, or a segment thereof, derived from two or more samples (e.g., two or more subjects). For example, a median chromosome representation can be a median of multiple MCRs for a chromosome or segment thereof.

Additional methods for Determining an MCR for a Sex Chromosome

In some embodiments the measured experimental Y chromosomal representation is determined for a test sample obtained from a pregnant female bearing a male fetus. In some embodiments the measured experimental Y chromosomal representation is determined for a test sample obtained from a pregnant female bearing a female fetus. The measured experimental Y chromosomal representation for a pregnant female bearing a female fetus is often zero or close to zero. In some embodiments the measured experimental Y chromosomal representation for a pregnant female bearing a female fetus is not zero due to noise. In certain embodiments a measured Y chromosome representation from a pregnant female bearing a female fetus represents noise and is used to normalize and/or correct (e.g., subtract out background) when determining fetal fraction and/or measured chromosome representations of other chromosomes. In some embodiments a measured Y chromosome representation from a pregnant female bearing a fetus is an average, mean or median measured Y chromosome representation. In some embodiments a measured Y chromosome representation from a pregnant female bearing a fetus is an average, mean or median measured Y chromosome representation where the average, mean or median is determined from multiple bins of a Y chromosome and/or from multiple samples (e.g., samples from multiple subjects). In certain embodiments an average, mean or median measured Y chromosome representation is used to determine a measure of noise and/or background.

In some embodiments the presence or absence of a Y chromosome, ploidy, counts or an MCR of a Y chromosome in a fetus is determined from sequence reads that map to substantially unique portions or segments of a Y chromosome. In certain embodiments the presence or absence of an X chromosome, ploidy, counts or an MCR of an X chromosome is determined according to sequence reads that map to substantially unique portions or segments of an X chromosome. The X and Y chromosomes comprise nucleic acid segments that are very similar and/or homologous (e.g., comprise high homology). The origin (e.g., from ChrX or ChrY) of sequence reads mapping to these high homology regions is sometimes difficult, if not impossible, to determine. In certain embodiments reads that map to both chromosome X and chromosome Y are not considered substantially unique to either the X or Y chromosome. In some embodiments bins comprising greater than about 40%, 30%, 25%, 20%, 15% or greater than about 10% of reads that map to both the X and Y chromosome are not substantially unique to either chromosome X or Y. In some embodiments bins that are not substantially unique to either chromosome X or Y are filtered and/or removed from any determination of fetal aneuploidy, fetal gender and/or fetal fraction. In some embodiments only sequence reads that map to portions or segments that are substantially unique to chromosome X and/or chromosome Y are utilized to determine fetal gender, fetal fraction and/or the presence of a fetal sex chromosome aneuploidy.

In some embodiments reads that map to the X chromosome and not to the Y chromosome are substantially unique to chromosome X. In some embodiments reads that map to the Y chromosome and not to the X chromosome are substantially unique to chromosome Y. In some embodiments sequence reads that map within the first 28 Mb from the 5' end of the Y chromosome are substantially unique to chromosome Y. In some embodiments a selected set of bins in the Y chromosome are used when determining the presence or absence of a Y chromosome, ploidy, counts, an ECR or an MCR of a Y chromosome. In certain embodiments a selected set of 20-30 bins of the Y chromosome are used. In some embodiments 20, 21, 22, 23, 24, 25, 26, 27, 28, 29 or 30 selected bins are used when determining the presence or absence of a Y chromosome, ploidy, counts, an ECR or an MCR of a Y chromosome. In some embodiments bins comprising greater than about 60%, 70%, 75%, 80%, 85%, 90%, 95%, or about 100% of mapped reads that are unique to the X or Y chromosome are bins that are substantially unique to the X or Y chromosome, respectively.

In some embodiments a measured chromosome representation for chromosome X and/or chromosome Y is determined according to counts that map to substantially unique segments or portions of chromosome X and/or chromosome Y. In some embodiments fetal gender, fetal fraction and/or a fetal aneuploidy is determined according, in part, to an MCR for a sex chromosome where the measured counts are determined from counts that map to substantially unique segments or portions of chromosome X and/or chromosome Y.

Determining Fetal Fraction from a Chromosomal Representation

In some embodiments, a difference in an elevation representing a chromosomes in a fetus comprising an aneuploidy (e.g., trisomy, a sex chromosome aneuploidy) and/or chromosome X and Y in the case of male fetuses can be used to determine fetal fraction. In certain embodiments raw counts are used to determine fetal fraction. In some embodiments normalized counts are used to determine fetal fraction. In some embodiments prior to determining fetal fraction by a method described herein, counts are normalized by a suitable method, non-limiting examples of which include bin-wise normalization, normalization by GC content, linear and nonlinear least squares regression, LOESS, GC LOESS, LOWESS, PERUN, RM, GCRM and/or combinations thereof. In some embodiments, a fetal fraction is determined from a chromosomal representation (e.g., a chromosome representation of an aneuploid chromosome, X chromosome or Y chromosome). In certain embodiments, a fetal fraction is determined when fetal ploidy differs from maternal ploidy. In certain embodiments, a fetal fraction is not determined when fetal ploidy is zero (e.g., the absence of a Y chromosome in a female fetus). In some embodiments, a fetal fraction is determined from a chromosome representation of an aneuploid chromosome when a pregnant female bears a fetus comprising a chromosome aneuploidy (e.g., a trisomy). In some embodiments, a fetal fraction is determined from a chromosome representation of an aneuploid chromosome when a pregnant female bears a male fetus comprising a chromosome aneuploidy (e.g., a trisomy). In certain embodiments, an MCR for an aneuploidy (e.g., a fetal trisomy) of chromosome n differs from an ECR for chromosome n according to the fraction of fetal nucleic acids present in a sample of cell-free nucleic acid obtained from a pregnant female. Thus, in some embodiments, a fetal fraction can be determined according to a ratio of an MCR for an aneuploidy and an ECR for the same affected chromosome. In certain embodiments, for a pregnant female bearing a fetus comprising an aneuploidy of an autosomal chromosome (e.g., a trisomy), a fetal fraction can be determined according to equation AA and/or according to equation AB in Example 9. In some embodiments, for a pregnant female bearing a fetus comprising a sex aneuploidy (e.g., TripleX syndrome), a fetal fraction can be determined according to equation AA and/or according to equation AB in Example 9 using an X chromosome representation. In equations AA and AB, the symbol $C_{in}$ represents an MCR and the symbol $C^0_n$ represents an ECR. For example, in the case of a trisomy, a fetal fraction can be determined by subtracting 1 from the ratio of an MCR and ECR and multiplying the result by 2. In certain embodiments the result of equation AB is multiplied by 100 to determine a percent fetal fraction (e.g., the percentage of fetal DNA in a mixture of maternal and fetal nucleic acid).

In some embodiments, a fetal fraction can be determined according to an ECR for chromosome X and an MCR for chromosome X for a pregnant female bearing a male fetus (XY), a fetus with Jacobs syndrome (i.e., XYY) or a fetus with Turner syndrome (i.e., X). In some embodiments, a fetal fraction can be determined according to the ratio of an ECR for chromosome X and an MCR for chromosome X. In some embodiments, for a pregnant female bearing a male fetus (XY), a fetus with Jacobs (i.e., XYY) or a fetus with Turner syndrome (i.e., X), a fetal fraction can be determined according to equation AC in Example 9. In equations AC the symbol $C_{in}$ represents an MCR and the symbol $C^{0}_{in}$ represents an ECR. In certain embodiments, $C_{in}$ represents the median chromosomal representation of ChrX in a female pregnancy. For example, in the case of a male fetus, a fetal fraction can be determined by subtracting the ratio of an MCR and ECR from 1 and multiplying the result by 2. In certain embodiments the result of equation AC is multiplied by 100 to determine a percent fetal fraction (e.g., the percentage of fetal DNA in a mixture of maternal and fetal nucleic acid).

In some embodiments, a fetal fraction can be determined according to an ECR for chromosome Y and an MCR for chromosome Y for a pregnant female bearing a male fetus (XY) or a fetus with Klinefelter's syndrome (i.e., XXY). In some embodiments, a fetal fraction can be determined according to the ratio of an ECR for chromosome Y and an MCR for chromosome Y. In some embodiments, for a pregnant female bearing a male fetus (XY) or a fetus with Klinefelter's syndrome (i.e., XXY), a fetal fraction can be determined according to equation AG in Example 9. The term ($C_y$) in equation AG represents a median chromosomal representation of chromosome Y (e.g., an ECR for ChrY) and $C_y$ represents an MCR for chromosome Y. In certain embodiments, $C_y$ represents the median chromosomal representation of ChrX in a female pregnancy. For example, in the case of a male fetus, a fetal fraction can be determined by subtracting the ratio of an MCR and ECR from 1 and multiplying the result by 2. In certain embodiments the result of equation AC is multiplied by 100 to determine a percent fetal fraction (e.g., the percentage of fetal DNA in a mixture of maternal and fetal nucleic acid). In certain embodiments a modified version of equation AG is used to determine fetal fraction from ChrY in Jacobs syndrome (XYY). In some embodiments the fetal fraction resulting from equation AG is divided by 2 to arrive at a fetal fraction for Jacobs syndrome. In some embodiments the $C_y$ value in equation AG is divided by 2 to arrive at a fetal fraction for Jacobs syndrome.

Determining Relationships

In some embodiments, a fetal fraction is, in part, generated according to a relationship. A relationship can be a mathematical relationship. In some embodiments, a relationship is a geometric and/or graphical relationship. In some embodiments, a relationship is plotted. In some embodiments a relationship is a linear relationship. In certain embodiments a linear relationship is an inverse relationship and sometimes a linear relationship is a direct relationship. In some embodiments, a relationship is a bivariate relationship. A relationship can be expressed by a mathematical equation. Often a relationship defines one or more constants.

In some embodiments a relationship is generated for a fetal fraction determination and an MCR (e.g., an MCR of a chromosome, an MCR of an X or a Y chromosome, an MCR of an affected autosome). In certain embodiments a fetal fraction determination from which a relationship is generated is a fetal fraction obtained from a chromosome representation of an aneuploid chromosome. For example, a fetal fraction obtained from a chromosome representation of an aneuploid chromosome can be determined from equation AA or AB or by a method described herein. In certain embodiments a fetal fraction determination from which a relationship is generated is a fetal fraction obtained from a chromosome representation of a trisomy 18, a trisomy 21 or a trisomy 13. Often a fetal fraction determination from which a relationship is generated is a fetal fraction obtained from a chromosome representation of a trisomy 18, a trisomy 21 or a trisomy 13 obtained from a pregnant female bearing a male fetus. Fetal fraction can be determined for such aneuploidy pregnancies by a convenient method known in the art or described herein. For example, a fetal fraction can be determined by an FQA. In certain embodiments, a fetal fraction can be determined according to an elevation and/or according to a copy number variation as described herein.

In some embodiments an MCR from which a relationship is generated is an MCR for an X or Y chromosome or segment thereof. In some embodiments an MCR from which a relationship is generated is an MCR for an X or Y chromosome or segment thereof obtained from equation AC or by a method described herein. In some embodiments an MCR from which a relationship is generated is an MCR for an X or Y chromosome obtained from a pregnant female bearing a male fetus. Often an MCR from which a relationship is generated is an MCR for an X or Y chromosome obtained from a pregnant female bearing a male fetus comprising a chromosome aneuploidy (e.g., a trisomy 13, 18, or 21). In certain embodiments an MCR from which a relationship is generated is an MCR for an X or Y chromosome obtained from a pregnant female bearing a male fetus comprising a sex chromosome aneuploidy (e.g., a sex chromosome aneuploidy as in Table 1A). In some embodiments a relationship is generated for (i) a fetal fraction determination obtained from an aneuploid chromosome and (ii) an MCR of an X or a Y chromosome where both the fetal fraction determination and MCR are obtained from a pregnant female bearing a male fetus comprising an aneuploid chromosome.

In some embodiments an MCR from which a relationship is generated is an MCR for an autosome or segment thereof (e.g., an affected autosome). In certain embodiments an MCR from which a relationship is generated is an MCR for an aneuploid chromosome (e.g., where the fetal representation of the chromosome is an aneuploid).

Often a relationship is generated from a fetal fraction determination and an MCR determination obtained from multiple subjects. In certain embodiments, a relationship is generated from greater than about 10, greater than about 100, greater than about 500 or greater than about 1000 subjects. In certain embodiments, a relationship is generated from about 500 to about 50,000, about 500 to about 25,000, about 500 to about 10,000, about 500 to about 5000, or about 500 to about 2500 subjects.

In some embodiments a relationship generated for a fetal fraction determination from a pregnant female bearing a male fetus comprising an aneuploidy (i.e., a male aneuploid pregnancy) and an MCR of an X chromosome from a pregnant female bearing a male fetus (i.e. a male pregnancy) is expressed mathematically. Often a relationship between a fetal fraction determination from a male aneuploid pregnancy and an MCR determination obtained from a male pregnancy is a linear relationship. Sometime an MCR determination obtained from a male pregnancy is obtained from a male aneuploid pregnancy. In certain embodiments a linear relationship generated for a fetal fraction determination from a male aneuploid pregnancy and an MCR of an X chromosome from a male pregnancy is represented by Equation AD2 below:

$$F_i=k-r(MCR_{ix}) \quad \text{(AD2)}$$

where k (e.g., y intercept) and r (e.g., slope) are constants defining the relationship for F, (the fetal fraction of sample i) and $MCR_{ix}$ (an MCR determined for chromosome X, or segment thereof, in sample i). In some embodiments, the relationship represented by Equation AD2 is generated for a fetal fraction determination obtained from an aneuploid chromosome and an MCR of an X chromosome where both the fetal fraction determination and MCR are obtained from a pregnant female bearing a male fetus comprising an aneuploid chromosome. In some embodiments, constants k and/or r are determined empirically from a fetal fraction determination and an MCR obtained from multiple subjects. Constants k or r can be a suitable number that defines the relationship between a fetal fraction determination and an MCR obtained from multiple subjects. Constants k or r can vary according to differences in experimental parameters and difference in methods of obtaining sequence reads (e.g., sequencing platform, sequencing recipe (e.g., how many bases are called), library/clustering, chemistry, normalization methods and/or normalization parameters, bin filtering, bin selection, the like or combinations thereof). In some embodiments k in equation AD2 equals about 150 to about 210, about 155 to about 205, about 160 to about 200, about 165 to about 195, about 170 to about 190, about 175 to about 185. In certain embodiments k is equal to about 175, 176, 177, 178, 179, 180, 181, 182, 183, 184, or about 185. In some embodiments k is equal to about 178.1, 178.2, 178.3, 178.4, 178.5, 178.6, 178.7, 178.8, 178.9, 179, 179.1, 179.2, 179.3, 179.4, 179.5, 179.6, 179.7, 179.8, or about 179.9. In certain embodiments k is equal to about 179.1. In some embodiments r in equation AD2 equals about 2500 to about 3500, about 2600 to about 3400, about 2700 to about 3300, about 2800 to about 3200, about 2900 to about 3100, or about 3000 to about 3100. In certain embodiments r in equation AD2 equals about 3005 to about 3085, about 3010 to about 3080, about 3015 to about 3075, about 3020 to about 3070, about 3025 to about 3065, about 3030 to about 3060, about 3035 to about 3055, or about 3040 to about 3050. In certain embodiments r in equation AD2 equals about 3040, 3041, 3042, 3043, 3044, 3045, 3046, 3047, 3048, 3049 or about 3050. In certain embodiments r in equation AD2 equals about 3045.1, 3045.2, 3045.3, 3045.4, 3045.5, 3045.6, 3045.7, 3045.8, 3045.9, 3046.0, 3046.1, 3046.2, 3046.3, 3046.4, or about 3046.5. In certain embodiments r in equation AD2 equals about 3045.74, 3045.75, 3045.76, 3045.77, 3045.78, 3045.79, 3045.80, 3045.81, 3045.82, 3045.83, 3045.84, 3045.85, 3045.86, 3045.87, 3045.88, 3045.89, or about 3045.90. In certain embodiments r in equation AD2 equals about 3045.82. In certain embodiments a relationship generated for a fetal fraction determination and an MCR of an X chromosome is represented by Equation AD.

In certain embodiments a fetal fraction is determined from a pregnant female bearing a male fetus from the relationship represented by equation AD2 or AD. In some embodiments, a fetal fraction is determined from a pregnant female bearing a male euploid fetus from the relationship represented by equation AD2 or AD. In certain embodiments an MCR for an X chromosome is provided for a pregnant female subject bearing a male fetus comprising a genetic variation (e.g., an aneuploidy) and a fetal fraction is determined according to Equation AD2 or AD. In certain embodiments an MCR for an X chromosome is provided for a pregnant female subject bearing a euploid male fetus and a fetal fraction is determined according to Equation AD2 or AD.

In some embodiments a relationship generated for a fetal fraction determination from a male aneuploid pregnancy and an MCR of a Y chromosome, or segment thereof, from a male pregnancy is expressed mathematically. In certain embodiments a linear relationship generated for a fetal fraction determination and an MCR of a Y chromosome is represented by Equation AE2:

$$F_i=k+r(MCR_{iy}) \quad \text{(AE2)}$$

where k (e.g., y intercept) and r (e.g., slope) are constants defining the relationship for F, (the fetal fraction of sample i) and $MCR_{iy}$ (an MCR determined for chromosome Y, or segment thereof, in sample i). In some embodiments, the relationship represented by Equation AE2 is generated for (i) a fetal fraction determination obtained from an aneuploid chromosome and (ii) an MCR of a Y chromosome where both the fetal fraction determination and MCR are obtained from a pregnant female bearing a male fetus comprising an aneuploid chromosome. In some embodiments, constants k and/or r are determined empirically from a fetal fraction determination and an MCR obtained from multiple subjects. Constants k or r can be a suitable number that defines the relationship between a fetal fraction determination and an MCR obtained from multiple subjects. Constants k or r can vary according to differences in experimental parameters and difference in methods of obtaining sequence reads (e.g., sequencing platform, sequencing recipe (e.g., how many bases are called), library/clustering, chemistry, normalization methods and/or normalization parameters, bin filtering, bin selection, the like or combinations thereof). In some embodiments k in equation AE2 equals about 0.43 to about 0.63, about 0.44 to about 0.62, about 0.45 to about 0.61, about 0.46 to about 0.60, about 0.47 to about 0.59, about 0.48 to about 0.58, about 0.49 to about 0.57, about 0.50 to about 0.56, about 0.51 to about 0.55 or about 0.52 to about 0.54. In certain embodiments k is equal to about 0.526 to about 0.546, about 0.527 to about 0.545, about 0.528 to about 0.544, about 0.529 to about 0.543, about 0.530 to about 0.542, about 0.531 to about 0.541, about 0.532 to about 0.540, about 0.533 to about 0.539, about 0.534 to about 0.538, about 0.535 to about 0.537. In some embodiments k is equal to about 0.5360, 0.5361, 0.5362, 0.5363, 0.5364, 0.5365, 0.5366, 0.5367, 0.5368, 0.5369, 0.5370, 0.5371, 0.5372, 0.5373, 0.5374, 0.5375, or about 0.5376. In certain embodiments k is equal to about 0.5368. In some embodiments r in equation AE2 equals about 1348 to about 1350, about 1347 to about 1349, about 1346 to about 1348, about 1345 to about 1347, about 1344 to about 1346 or about 1343 to about 1345. In certain embodiments r in equation AE2 equals about 1343.1 to about 1344.9, about 1343.2 to about 1344.8, about 1343.3 to about 1344.7, about 1343.4 to about 1344.6, about 1343.5 to about 1344.5, about 1343.6 to about 1344.4, about 1343.7 to about 1344.3, about 1343.8 to about 1344.2 or about 1343.9 to about 1344.1. In certain embodiments r in equation AE2 equals about 1343.96 to about 1344.06, about 1343.97 to about 1344.05, about 1343.98 to about 1344.04, about 1343.99 to about 1344.03, or about 1344.00 to about 1344.02. In certain embodiments r in equation AE2 equals about 1344.010, 1344.011, 1344.012, 1344.013, 1344.014, 1344.015, 1344.016, 1344.017, 1344.018, or about 1344.019. In certain embodiments r in equation AE2 equals about 1344.0158, 1344.0159, 1344.0160, 1344.0161, 1344.0162, 1344.0163, 1344.0164, 1344.0165, 1344.0166, or about 1344.0167. In certain embodiments r in equation AE2 equals about 1344.0162. In certain embodiments a relationship generated for a fetal fraction determination and an MCR of a Y chromosome is represented by Equation AE.

In certain embodiments a fetal fraction is determined from a pregnant female bearing a male fetus from the relationship represented by equation AE2 or AE. In some embodiments, a fetal fraction is determined from a pregnant female bearing a male euploid fetus from the relationship represented by equation AE2 or AE. In certain embodiments an MCR for a Y chromosome is provided for a pregnant female subject bearing a male fetus comprising a genetic variation (e.g., an aneuploidy) and a fetal fraction is determined according to Equation AE2 or AE. In certain embodiments an MCR for a Y chromosome is provided for a pregnant female subject bearing a euploid male fetus and a fetal fraction is determined according to Equation AE2 or AE.

In certain embodiments a relationship is generated for a fetal fraction determined by a first method and a fetal fraction determined by a second method. In certain embodiments a relationship is generated for a fetal fraction determined by a first method and a fetal fraction determined by a second method where the relationship is generated for multiple fetal fraction determinations. In certain embodiments a relationship is generated for greater than about 10, greater than about 100, greater than about 500 or greater than about 1000 fetal fraction determinations. In certain embodiments, a relationship is generated from about 500 to about 50,000, about 500 to about 25,000, about 500 to about 10,000, about 500 to about 5000, or about 500 to about 2500 fetal fraction determinations.

In some embodiments, a fetal fraction determined by a first method and/or a fetal fraction determined by a second method are determined by an FQA. In some embodiments, a fetal fraction determined by a first method and/or a fetal fraction determined by a second method are determined by a process that does not utilize sequence reads mapped to genomic sections of a reference genome. In some embodiments, a fetal fraction determined by a first method and/or a fetal fraction determined by a second method are determined by a process comprising mass spectrometry. In some embodiments, a fetal fraction determined by a first method and/or a fetal fraction determined by a second method are determined by a process utilizing MPS. In some embodiments, a fetal fraction of nucleic acids in the blood of a pregnant female is determined by a first method and a fetal fraction of nucleic acids in the blood of a different pregnant female is determined by a second method. In certain embodiments the first method and the second method are the same method. In certain embodiments the first method and the second method are different methods. In some embodiments, a fetal fraction determined by a first method is determined at a different time than a fetal fraction determined by a second method. For example, sometimes a fetal fraction determined by a first method is determined before or after a fetal fraction determined by a second method.

In certain embodiments a fetal fraction determined by a first method is determined from a first subject (e.g., from a sample obtained from a pregnant female subject) and a fetal fraction determined by a second method is determined from a second subject (e.g., from a sample obtained from a pregnant female subject) where the first subject and second subject are different subjects. In certain embodiments a fetal fraction determined by a first method is determined from a first set of multiple subjects (e.g., a pregnant female subjects) and a fetal fraction determined by a second method is determined from a second set of subjects (e.g., a pregnant female subjects) where the first set of subjects and second set of subjects are different subjects. In certain embodiments, a first set of multiple subjects (e.g., different than a second set of subjects) is greater than about 10, greater than about 100, greater than about 500 or greater than about 1000 subjects. In certain embodiments, a first set of multiple subjects (e.g., different than a second set of subjects) is from about 500 to about 50,000, about 500 to about 25,000, about 500 to about 10,000, about 500 to about 5000, or about 500 to about 2500 subjects. In some embodiments, a second set of subjects (e.g., different that a first set of multiple subjects) is 1 subject or greater than about 1, greater than about 10, greater than about 100, greater than about 500 or greater than about 1000 subjects. In certain embodiments, a second set of subjects (e.g., different that a first set of multiple subjects) is from about 1 to about 50,000, about 1 to about 25,000, about 1 to about 10,000, about 1 to about 5000, about 1 to about 2500, 1 to about 1000, or about 1 to about 500 subjects. In certain embodiments a second set of subjects (e.g., different that a first set of multiple subjects) is 1 subject.

In some embodiments, a fetal fraction determined by a first method is determined by a relationship for (i) a fetal fraction determination obtained from an aneuploid chromosome and (ii) an MCR of an X chromosome where both the fetal fraction determination and MCR are obtained from a pregnant female bearing a male fetus comprising an aneuploid chromosome. In certain embodiments a fetal fraction determined by a first method is a fetal fraction determined by Equation AD2 or AD. In some embodiments, a fetal fraction determined by a second method is determined by a relationship for (i) a fetal fraction determination obtained from an aneuploid chromosome and an (i) MCR of a Y chromosome where both the fetal fraction determination and MCR are obtained from a pregnant female bearing a male fetus comprising an aneuploid chromosome. In certain embodiments a fetal fraction determined by a second method is determined by Equation AE2 or AE.

In certain embodiments a relationship is generated for (i) a fetal fraction determined by a first method and (ii) a fetal fraction determined by a second method where the fetal fraction in (i) and (ii) is determined from an MCR for an X and a Y chromosome, respectively, obtained from a pregnant female bearing a male euploid fetus. In certain embodiments the fetal fraction in (i) and (ii) is determined from an MCR for an X and a Y chromosome where the MCR was determined for the same sample (e.g., same subject). In some embodiments a relationship In some embodiments a relationship generated for (i) a fetal fraction determined by a first method and (ii) a fetal fraction determined by a second method is expressed mathematically. In certain embodiments a relationship generated for (i) a fetal fraction determined by a first method and (ii) a fetal fraction determined by a second method is represented by Equation AF2:

$$F_i = k - r(MCR_{ix}) + t(MCR_{iy}) \quad \text{(AF2)}$$

where k, r and t are constants defining the relationship for $F_i$ (the fetal fraction of sample i), $MCR_{ix}$ (an MCR determined for chromosome X in sample i) and $MCR_{iy}$ (an MCR determined for chromosome Y in sample i). In some embodiments, the relationship in Equation AF2 is for sample obtained from a pregnant female bearing a male fetus. In some embodiments, constants k, r and/or t are determined empirically. Each constant k, r and/or t can be a suitable number that defines the relationship between (i) a fetal fraction determined by a first method and (ii) a fetal fraction determined by a second method. Constants k, r and/or t can vary according to differences in experimental parameters and difference in methods of obtaining sequence reads (e.g., sequencing platform, sequencing recipe (e.g., how many bases are called), library/clustering, chemistry, normalization methods and/or normalization parameters, bin filtering, bin selection, the like or combinations thereof). Constants k, r and t often are derived for a linear relationship. In some embodiments k in equation AF2 equals about 20 to about 29, about 21 to about 28, about 22 to about 27, about 23 to about 26 or about 24 to about 25. In some embodiments k in equation AF2 equals about 24.4 to about 25.3, about 24.5 to about 25.2, about 24.6 to about 25.1, about 24.7 to about 25.0, or about 24.8 to about 24.9. In some embodiments k in equation AF2 equals about 24.78, 24.79, 24.80, 24.81, 24.82, 24.83, 24.84, 24.85, 24.86, 24.87, 24.88, 24.89, 24.90, 24.91, 24.92, 24.93, 24.94, 24.95, 24.96 or about 24.97. In some embodiments k in equation AF2 equals about 24.88. In some embodiments r in equation AF2 equals about 411 to about 421, about 412 to about 420, about 413 to about 419, about 414 to about 418 or about 415 to about 417. In some embodiments r in equation AF2 equals about 416.0 to about 416.9, about 416.1 to about 416.8, about 416.2 to about 416.7, about 416.3 to about 416.6, about 416.4 to about 416.5. In some embodiments r in equation AF2 equals about 416.32, 416.33, 416.34, 416.35, 416.36, 416.37, 416.38, 416.39, 416.40, 416.41, 416.42, 416.43, 416.44, 416.45, 416.46, 416.47, 416.48, 416.49, 416.50, 416.51 or 416.52. In some embodiments r in equation AF2 equals about 416.42. In some embodiments t in equation AF2 equals about 1164 to about 1174, about 1165 to about 1173, about 1166 to about 1172, about 1167 to about 1171, about 1168 to about 1170. In some embodiments t in equation AF2 equals about 1169.0 to about 1169.9, about 1169.1 to about 1169.8, about 1169.2 to about 1169.7, about 1163.0 to about 1169.6 or about 1169.4 to about 1169.5. In some embodiments t in equation AF2 equals about 1169.36, about 1169.37, about 1169.38, about 1169.39, about 1169.40, about 1169.41, about 1169.42, about 1169.43, about 1169.44, about 1169.45, about 1169.46, about 1169.47, about 1169.48, about 1169.49, about 1169.50, about 1169.51, about 1169.52, about 1169.53, about 1169.54, about 1169.54 or about 1169.56. In some embodiments t in equation AF2 equals about 1169.46. In certain embodiments a relationship generated for (i) a fetal fraction determined by a first method and (ii) a fetal fraction determined by a second method is represented by Equation AF.

In certain embodiments the fraction of fetal nucleic acid in circulating cell-free nucleic acid obtained from the blood of a pregnant female is determined from the relationship represented by equation AF2 or AF. In certain embodiments a fetal fraction is determined for a pregnant female bearing a male fetus from the relationship represented by equation AF2 or AF. In certain embodiments the male fetus is euploid. In certain embodiments the male fetus comprises and aneuploidy (e.g., a trisomy 21, trisomy 13, trisomy 18). In certain embodiments an MCR for a Y chromosome and an MCR for an X chromosome is provided for a pregnant female subject bearing a male fetus and a fetal fraction is determined according to Equation AF2 or AF. In certain embodiments an MCR for a Y chromosome and an MCR for an X chromosome is provided for a pregnant female subject bearing a euploid male fetus and a fetal fraction is determined according to Equation AF2 or AF.

In certain embodiments a first relationship is generated for a fetal fraction determination according to (i) an MCR for chromosome Y for a pregnant female bearing a male fetus, (ii) an MCR for chromosome Y for a pregnant female bearing a female fetus and (iii) K a constant according to Equation AG. The constant K is determined by a second relationship relating (a) a fetal fraction determined from an aneuploid chromosome (e.g., a trisomy 13, 18 or 21) and (b) a fetal fraction determined from an MCR for chromosome Y determined from a pregnant female bearing a male fetus comprising an aneuploidy (e.g., a trisomy). In some embodiments, the constant K in Equation AG is the empirical slope of the second relationship. In certain embodiments K equals from about 0.001 to about 0.003. In certain embodiments K equals about 0.00017, 0.00018, 0.00019, 0.00020, 0.00021, 0.00022, 0.00023, 0.00024, 0.00025, or about 0.00026. In certain embodiments K equals about 0.0002179630. In certain embodiments the second relationship is a linear relationship. In some embodiments, a fetal fraction F for a male fetus is determined from an MCR of chromosome Y for a pregnant female bearing a male fetus using formula AG below:

$$F = \frac{C_y - \langle C_y \rangle}{K} \quad \text{(AG)}$$

where the term $\langle C_y \rangle$ represents a median chromosomal representation of chromosome Y for a female fetus, $C_y$ represents an MCR for chromosome Y for a pregnant female bearing a male fetus and K is the constant described above for Equation AG. In certain embodiments the term $\langle C_y \rangle$ is obtained from multiple measurements. In certain embodiments the term $\langle C_y \rangle$ represents noise. Often $\langle C_y \rangle$ is different from zero due to noise.

In some embodiments a fetal fraction is determined from the blood of a pregnant female according to a relationship described herein with an accuracy of equal to 90% or greater than 90% and/or a precision equal to 90% or greater than 90%. In some embodiments a fetal fraction is determined from the blood of a pregnant female according to a relationship described by equation AD, AD2, AE, AE2, ΔF, AF2 or AG with an accuracy of equal to 90% or greater than 90% and/or a precision equal to 90% or greater than 90%. In some embodiments a fetal fraction is provided by a fetal fraction module with an accuracy of equal to 90% or greater than 90% and/or a precision equal to 90% or greater than 90%. In some embodiments a fetal fraction is determined from the blood of a pregnant female according to a relationship described herein with an accuracy of about 90%, 91%, 92%, 93%, 94%, 95%, 96%, 97%, 98%, 99%, or about 100% and/or a precision of about 90%, 91%, 92%, 93%, 94%, 95%, 96%, 97%, 98%, 99%, or about 100%.

Determining Fetal Fraction from a Fixed Relationship

In some embodiments the fraction of the fetal nucleic acid in the blood of the pregnant female bearing a male fetus can be determined according to an experimental Y chromosome representation and a relationship (e.g., a linear relationship) that is fitted. An embodiment of this method is illustrated in Example 10. In certain embodiments the relationship is linear. In some embodiments the relationship is not linear. In some embodiments the relationship is fitted to a representation of chromosome X derived from one or more pregnant females bearing a female fetus. In some embodiments the fetal fraction f is determined according to equation (62) below or a variation thereof.

$$f = 2\frac{I + S\langle x \rangle - y}{S\langle x \rangle} \quad (62)$$

where f is the fraction of fetal nucleic acid in a test sample, y is the measured experimental Y chromosomal representation from a test sample obtained from a pregnant female bearing a male fetus, I is a slope, S is a slope and ⟨x⟩ is a median MCR of chromosome X obtained from multiple pregnant females bearing a female fetus. The parameters I (the intercept) and S (the slope) are derived from a fitted linear relationship (see Example 10). Parameters I and S are sometimes derived from a linear relationship for chromosome X (MCR of chromosome X) and chromosome Y (MCR of chromosome X) representations obtained from pregnant female bearing a male fetus after the linear relationship is fitted to a point (ie., forced to go through a point) representing a median chromosome X (median MCR of chromosome X, ⟨x⟩) and a median chromosome Y (median MCR of chromosome Y, ⟨y⟩) representation obtained from pregnant female bearing a female fetus. The resulting relationship (62) can determine the fraction of fetal nucleic acid in a test sample from a measured experimental Y chromosomal representation from a test sample where the test sample was obtained from a pregnant female bearing a male fetus. In some embodiments the fraction of the fetal nucleic acid is determined according to the slope and intercept of the fitted relationship, the measured experimental Y chromosomal representation from a test sample where the test sample was obtained from a pregnant female bearing a male fetus and a median X chromosome representation for a set of pregnant females bearing a female fetus.

In some embodiments ⟨x⟩, ⟨y⟩, S and/are derived from multiple MCRs for chromosome X and Y obtained from pregnant females bearing a male fetus and/or multiple pregnant females bearing a female fetus. In some embodiments a median of multiple MCRs for chromosome X and Y is determined from multiple MCRs obtained from pregnant females bearing a female fetus. In some embodiments, MCRs for chromosome X and Y are determined for multiple subjects. In some embodiments, S, I and ⟨x⟩ in equation (62) are constants or coefficients and are determined by methods described herein. In some embodiments, S, I and ⟨x⟩ in equation (62) are constants or coefficients and are determined from data obtained from multiple subjects. Multiple subjects is sometimes greater than about 10, greater than about 100, greater than about 500, greater than about 1000 or greater than about 10,000 subjects. In certain embodiments, multiple subjects is about 500 to about 50,000, about 500 to about 25,000, about 500 to about 10,000, about 500 to about 5000, or about 500 to about 2500 subjects.

In some embodiments, the mean chromosome X representation ⟨x⟩ is a ratio of (i) counts of sequence reads mapped to the genomic sections of the reference genome in the X chromosome, and (ii) counts of sequence reads mapped to genomic sections of the reference genome in the genome or segment thereof. In some embodiments, the sequence reads in (ii) are mapped to all chromosomes in a profile, all autosomes in a profile, a selected chromosome or a selected autosome in a profile. In some embodiments the sequence reads in (ii) are mapped to any subset of chromosomes, any chromosome or a segment thereof.

In some embodiments ⟨x⟩ is a constant with a value between about 0.027 and about 0.067, about 0.037 and about 0.057, or about 0.042 and about 0.053. In certain embodiments ⟨x⟩ is a constant with a value of about 0.042, 0.043, 0.044, 0.045, 0.046, 0.047, 0.048, 0.049, 0.050, 0.051, 0.052 or about 0.053. In some embodiments ⟨x⟩ is a constant with a value of about 0.04765159.

In some embodiments ⟨y⟩ is a constant with a value between about 0.00001 and about 0.0002, 0.00005 and about 0.00015, or between about 0.00005 and about 0.000125. In certain embodiments ⟨y⟩ is a constant with a value of about 0.00004, 0.00005, 0.00006, 0.00007, 0.00008, 0.00009, 0.00010, 0.00011, 0.00012, 0.00013, 0.00014 or about 0.00015. In some embodiments ⟨y⟩ is a constant with a value of about 0.0001054401.

In some embodiments S is a constant with a value between about 0.005 and about 0.03, about 0.0075 and about 0.025, or between about 0.010 and about 0.020. In certain embodiments S is a constant with a value of about 0.010, 0.011, 0.012, 0.013, 0.014, 0.015, 0.016, 0.017, 0.018, 0.019 or about 0.020. In some embodiments S is a constant with a value of about 0.01560178.

In some embodiments/is a constant with a value between about −0.1 and about −0.5, about −0.2 and about −0.4, or between about −0.275 and about −0.375. In certain embodiments/is a constant with a value of about −0.321, −0.322, −0.323, −0.324, −0.325, −0.326, −0.327, −0.328, −0.329, −0.330 or about −0.331. In some embodiments/is a constant with a value of about −0.3252008.

In some embodiments ⟨x⟩, ⟨y⟩, S and I are constants with values of about 0.04765159, 0.0001054401, 0.01560178 and −0.3252008, respectively.

Determining Fetal Ploidy from Fetal Fraction

A fetal ploidy can be determined, in part, from a measure of fetal fraction and the fetal ploidy determination is used to make a determination of the presence or absence of a genetic variation (e.g., a chromosome aneuploidy, a trisomy). For example, FIGS. 175-177 illustrate fetal ploidy determinations derived, in part, from fetal fractions measurements. A fetal ploidy can be determined, in part, from a measure of fetal fraction determined by any suitable method of fetal fraction determination including methods described herein. In some embodiments fetal ploidy is determined according to a fetal fraction determination and equation (8), (20), (21) or a variation or derivation thereof (see Example 2). In some embodiments, fetal ploidy is determined by a method described below. In some embodiments each method described below requires a calculated reference count $F_i$ (sometimes represented as $f_i$) determined for a portion (i.e. a bin, i) of a genome for multiple samples where the ploidy of the fetus for portion i of the genome is known to be euploid. In some embodiments an uncertainty value (e.g., a standard deviation, a) is determined for the reference count $f_i$. In some embodiments a reference count $f_i$, an uncertainty value, a test sample count and/or a measured fetal fraction (F) are used to determine fetal ploidy according to a method described below. In some embodiments a reference count (e.g., an average, mean or median reference count) is normalized by a method described herein (e.g., bin-wise normalization, normalization by GC content, linear and nonlinear least squares regression, LOESS, GC LOESS, LOWESS, PERUN, RM, GCRM and/or combinations thereof). In some embodiments a reference count of a segment of a genome known to be euploid is equal to 1 when the reference count is normalized by PERUN. In some embodiments both the reference count (e.g., for a fetus known to be euploid) and the counts of a test sample for a portion or segment of a genome are normalized by PERUN and the reference count is equal to 1. Likewise, in some embodiments, a reference count of a portion or segment of a genome known to be euploid is equal to 1 when the counts are normalized by (i.e., divided by) a median of the reference count. For example, in some embodiments both the reference count (e.g., for a fetus known to be euploid) and the counts of a test sample for a portion or segment of a genome are normalized by a median reference count, the normalized reference count is equal to 1 and the test sample count is normalized (e.g., divided by) the median reference count. In some embodiments both the reference count (e.g., for a fetus known to be euploid) and the counts of a test sample for a portion or segment of a genome are normalized by GCRM, GC, RM or a suitable method. In some embodiments a reference count is an average, mean or median reference count. A reference count is often a normalized count for a bin (e.g., a normalized genomic section level). In some embodiments a reference count and the counts for a test sample are raw counts. A reference count, in some embodiments, is determined from an average, mean or median count profile. In some embodiments, a reference count is a calculated genomic section level. In some embodiments a reference count of a reference sample and a count of a test sample (e.g., a patient sample, e.g., $y_i$) are normalized by the same method or process.

A Non-Limiting Example of a Fetal Ploidy Determination

In some embodiments a measurement of fetal fraction (F) is determined. This fetal fraction value is then used to determine fetal ploidy according to equation (8), a derivation or a variation thereof. In some embodiments, a negative value is returned if the fetus is euploid and a positive value is returned if the fetus is not euploid. In some embodiments a negative value indicates the fetus is euploid for the segment of the genome considered. In certain embodiments, a value that is not negative indicates the fetus comprises an aneuploidy (e.g., a duplication). In certain embodiments, a value that is not negative indicates the fetus comprises a trisomy. In certain embodiments, any positive value indicates the fetus comprises an aneuploidy (e.g., a trisomy, a duplication).

In some embodiments a sum of square residuals is determined. For example, an equation representing the sum of square residuals derived from equation (8) is illustrated in equation (18). In some embodiments a sum of square residuals is determined from equation (8) for a ploidy value X set to a value of 1 (see equation (9)) and for a ploidy value set to a value of 3/2 (see equation (13)). In some embodiments the sum of square residuals (equations (9) and (13)) are determined for a segment of a genome or chromosome (e.g., for all bins i in a segment of the genome). For example, the sum of square residuals (e.g., equations (9) and (13)) can be determined for chromosome 21, 13, 18 or a portion thereof. In some embodiments, to determine a ploidy status of a fetus, the result of equation (13) is subtracted from equation (9) to arrive at a value, phi (e.g., see equation (14)). In certain embodiments, the sign (i.e. positive or negative) of the value phi determines the presence or absence of a fetal aneuploidy. In certain embodiments, a phi value (e.g., from equation (14)) that is negative indicates the absence of an aneuploidy (e.g., the fetus is euploid for bins i) and a phi value that is not negative indicates the presence of an aneuploidy (e.g., a trisomy).

In some embodiments the reference count $f_i$, the uncertainty value for the reference count a and/or the measured fetal fraction (F) are used in equations (9) and (13) to determine the sum of square residuals for the sum of all bins i. In some embodiments the reference count $f_i$, the uncertainty value for the reference count a and/or the measured fetal fraction (F) are used in equations (9) and (13) to determine fetal ploidy. In some embodiments the counts (e.g., normalized counts, e.g., calculated genomic section level), represented by $y_i$ for bin i, for a test sample are used to determine the ploidy status of a fetus for bin i. For example, in certain embodiments, the ploidy status for a segment of a genome is determined according to a reference count $f_i$, an uncertainty value (e.g., from the reference count), a feta fraction (F) determined for a test sample and the counts $y_i$ determined for the test sample where the ploidy status is determined according to equation (14) or a derivation or variation thereof. In some embodiments the counts $y_i$ and/or reference counts are normalized by a method described herein (e.g., bin-wise normalization, normalization by GC content, linear and nonlinear least squares regression, LOESS, GC LOESS, LOWESS, PERUN, RM, GCRM and combinations thereof). In some embodiments a fetal ploidy status (e.g., euploid, aneuploid, trisomy) for a portion or segment of a genome or chromosome is determined by the non-limiting example described above and in Example 2.

Another Non-Limiting Example of a Fetal Ploidy Determination

In some embodiments a fetal fraction is determined from a test sample, counts y are determined for a test sample and both are used to determine a ploidy for a fetus from a test sample. In certain embodiments of the method described here, the value of fetal ploidy represented by X is not fixed or assumed. In certain embodiments of the method described here, fetal fraction F is fixed. In some embodiments, a ploidy (e.g., a ploidy value) is determined for a portion or segment of a genome according to equation (20) or (21) (see Example 2). In some embodiments of this method, a ploidy value is determined, where the value is close to 1, 3/2, or 5/4. In some embodiments a ploidy value of about 1 indicates a euploid fetus, a value of about 3/2 indicates a fetal trisomy and, in the case of twins, a value of about 5/4 indicates that one fetus comprises a trisomy and the other is euploid for the portion or segment of the genome considered. Additional information regarding determining the presence or absence of a fetal aneuploidy from a fetal ploidy determination is discussed in another section below.

In some embodiments, fetal fraction is determined, fixed at its determined value and fetal ploidy is determined from a regression. Any suitable regression can be utilized, non-limiting examples of which include a linear regression, a non-linear regression (e.g., a polynomial regression), and the like. In some embodiments, a linear regression is used according to equation (8), (20), (21) and/or a derivation or variation thereof. In some embodiments, the linear regression used is according to a sum of square residuals derived from equation (8), (20), (21) and/or a derivation or variation thereof. In some embodiments, fetal ploidy is determined according to equation (8), (20), (21) and/or a derivation or variation thereof and a regression is not used. In some embodiments, fetal ploidy is determined according to a sum of square residuals derived from equation (8), (20), (21) and/or a derivation or variation thereof for multiple bins i and a regression is not used. A derivation of an equation is any variation of the equation obtained from a mathematical proof of an equation.

In some embodiments a reference count $f_i$ (described previously herein), an uncertainty value a and/or a measured fetal fraction (F) are used in equations (20) and (21) to determine a fetal ploidy. In some embodiments a reference count $f_i$, an uncertainty value $\sigma$ and/or a measured fetal fraction (F) are used in equations (20) or (21) to determine a fetal ploidy X for bin i or for a sum of multiple bins i (e.g., for the sum of all bins i for a chromosome or segment thereof). In some embodiments the counts (e.g., normalized counts, calculated genomic section level), represented by $y_i$ for bin i, for a test sample are used to determine the ploidy of a fetus for a segment of a genome represented by multiple bins i. For example, in certain embodiments, the ploidy X for a segment of a genome is determined according to a reference count $f_i$, an uncertainty value, a feta fraction (F) determined for a test sample and the counts $y_i$ determined for the test sample where the ploidy is determined according to equation (20), (21) or a derivation or variation thereof. In some embodiments the counts $y_i$ and/or reference counts are normalized by a method described herein (e.g., bin-wise normalization, normalization by GC content, linear and nonlinear least squares regression, LOESS, GC LOESS, LOWESS, PERUN, RM, GCRM and combinations thereof). In some embodiments the counts $y_i$ and/or reference counts are normalized and/or processed by the same method (e.g., bin-wise normalization, normalization by GC content, linear and nonlinear least squares regression, LOESS, GC LOESS, LOWESS, PERUN, RM, GCRM, a method described herein or combinations thereof). In some embodiments counts $y_i$ and $f_i$ are counts mapped to the same portion or segment of a genome or chromosome.

The uncertainty value σ can be a suitable measure of error, non-limiting examples of which include standard deviation, standard error, calculated variance, p-value, and/or mean absolute deviation (MAD). The uncertainty value σ can be determined for any suitable measurement, non-limiting examples of which include Z-scores, Z-values, t-values, p-values, cross-validation error, genomic section level, calculated genomic section levels, elevations, counts, the like, or combinations thereof. In some embodiments σ is set to a value of 1. In some embodiments σ is not set to a value of 1. In some embodiments the value of σ is estimated and sometimes it is measured and/or calculated.

In some embodiments $M_i$ is the ploidy of the mother (i.e., maternal ploidy) for a portion of the genome i. In some embodiments $M_i$ is determined for the same patient (e.g., same test sample) from which $y_i$ is determined. In some embodiments the maternal ploidy $M_i$ is known or determined according to a method described herein. In some embodiments maternal ploidy is determined before or after padding (e.g., after making elevation adjustments). In certain embodiments $M_i$ is estimated or determined from visualizing a profile. In some embodiments the maternal ploidy $M_i$ is not known. In some embodiments the maternal ploidy $M_i$ is assumed. For example, in some embodiments it is assumed or known that the mother has no deletions and/or duplications in the segment of the genome being evaluated. In some embodiments it is assumed or known that maternal ploidy is 1. In some embodiments maternal ploidy is set to a value of 1 after padding (e.g., after making elevations adjustments). In some embodiments maternal ploidy is ignored and is set to a value of 1. In some embodiments equation (21) is derived from equation (20) with the assumption that the mother has no deletions and/or duplications in the segment of the genome being evaluated.

In some embodiments a method for determining fetal ploidy is according to nucleic acid sequence reads for a test sample obtained from a pregnant female. In some embodiments the sequence reads are reads of circulating cell-free nucleic acid from a sample (e.g., a test sample). In some embodiments, a method for determining fetal ploidy comprises obtaining counts of sequence reads mapped to portions of a reference genome. In some embodiments the sequence reads are mapped to a subset of portions of the reference genome. In some embodiments determining fetal ploidy comprises determining a fetal fraction. In some embodiments determining fetal ploidy comprises calculating or determining genomic section levels. In certain embodiments determining fetal ploidy comprises determining a fetal fraction and calculating or determining genomic section levels. In some embodiments the fetal fraction and the calculated genomic section levels are determined from the same test sample (e.g., same part of the test sample). In some embodiments the fetal fraction and the calculated genomic section levels are determined from the same reads obtained from the same test sample (e.g., same part of the test sample). In some embodiments the fetal fraction and the calculated genomic section levels are determined from the same reads obtained from the same sequencing run and/or from the same flow cell. In some embodiments the fetal fraction and the calculated genomic section levels are determined from the same equipment and/or machine (e.g., sequencing apparatus, flow cell, or the like).

In some embodiments a method for determining fetal ploidy is determined according to a fetal fraction determination and normalized counts (e.g., calculated genomic section levels) wherein the fetal fraction determination and the normalized counts (e.g., calculated genomic section levels) are determined from different parts of a test sample (e.g., different aliquots, or e.g., different test samples taken at about the same time from the same subject or patient). For example, sometimes a fetal fraction is determined from a first part of a test sample and normalized counts and/or genomic section levels are determined from a second part of the test sample. In some embodiments the fetal fraction and the calculated genomic section levels are determined from different test samples (e.g., different parts of a test sample) taken from the same subject (e.g., patient). In some embodiments the fetal fraction and the calculated genomic section levels are determined from reads obtained at different times. In some embodiments the fetal fraction determination and the normalized counts (e.g., calculated genomic section levels) are determined from different equipment and/or from different machines (e.g., sequencing apparatus, flow cell, or the like).

Some Embodiments of Determining a Chromosome Aneuploidy

In some embodiments the presence or absence of a fetal chromosomal aneuploidy (e.g., a trisomy) is determined from a fetal ploidy determination. In some embodiments a fetal ploidy is determined by a suitable method described herein. In some certain embodiments a fetal ploidy determination of about 1.20 or greater, 1.25 or greater, 1.30 or greater, about 1.35 or greater, about 1.4 or greater, or about 1.45 or greater indicates the presence of a fetal chromosome aneuploidy (e.g., the presence of a fetal trisomy). In some embodiments a fetal ploidy determination of about 1.20 to about 2.0, about 1.20 to about 1.9, about 1.20 to about 1.85, about 1.20 to about 1.8, about 1.25 to about 2.0, about 1.25 to about 1.9, about 1.25 to about 1.85, about 1.25 to about 1.8, about 1.3 to about 2.0, about 1.3 to about 1.9, about 1.3 to about 1.85, about 1.3 to about 1.8, about 1.35 to about 2.0, about 1.35 to about 1.9, about 1.35 to about 1.8, about 1.4 to about 2.0, about 1.4 to about 1.85 or about 1.4 to about 1.8 indicates the presence of a fetal chromosome aneuploidy (e.g., the presence of a fetal trisomy). In some embodiments the fetal aneuploidy is trisomy. In some embodiments the fetal aneuploidy is trisomy of chromosome 13, 18 and/or 21.

In some embodiments a fetal ploidy of less than about 1.35, less than about 1.30, less than about 1.25, less than about 1.20 or less than about 1.15 indicates the absence of a fetal aneuploidy (e.g., the absence of a fetal trisomy, e.g., euploid). In some embodiments a fetal ploidy determination of about 0.7 to about 1.35, about 0.7 to about 1.30, about 0.7 to about 1.25, about 0.7 to about 1.20, about 0.7 to about 1.15, about 0.75 to about 1.35, about 0.75 to about 1.30, about 0.75 to about 1.25, about 0.75 to about 1.20, about 0.75 to about 1.15, about 0.8 to about 1.35, about 0.8 to about 1.30, about 0.8 to about 1.25, about 0.8 to about 1.20, or about 0.8 to about 1.15 indicates the absence of a fetal chromosome aneuploidy (e.g., the absence of a fetal trisomy, e.g., euploid).

In some embodiments a fetal ploidy of less than about 0.8, less than about 0.75, less than about 0.70 or less than about 0.6 indicates the presence of a fetal aneuploidy (e.g., the presence of a chromosome deletion). In some embodiments a fetal ploidy determination of about 0 to about 0.8, about 0 to about 0.75, about 0 to about 0.70, about 0 to about 0.65, about 0 to about 0.60, about 0.1 to about 0.8, about 0.1 to about 0.75, about 0.1 to about 0.70, about 0.1 to about 0.65, about 0.1 to about 0.60, about 0.2 to about 0.8, about 0.2 to about 0.75, about 0.2 to about 0.70, about 0.2 to about 0.65, about 0.2 to about 0.60, about 0.25 to about 0.8, about 0.25 to about 0.75, about 0.25 to about 0.70, about 0.25 to about 0.65, about 0.25 to about 0.60, about 0.3 to about 0.8, about 0.3 to about 0.75, about 0.3 to about 0.70, about 0.3 to about 0.65, about 0.3 to about 0.60 indicates the presence of a fetal chromosome aneuploidy (e.g., the presence of a chromosome deletion). In some embodiments the fetal aneuploidy determined is a whole chromosome deletion.

In some embodiments a determination of the presence or absence of a fetal aneuploidy (e.g., according to one or more of the ranges of a ploidy determination above) is determined according to a call zone. In certain embodiments a call is made (e.g., a call determining the presence or absence of a genetic variation, e.g., an outcome) when a value (e.g. a ploidy value, a fetal fraction value, a level of uncertainty) or collection of values falls within a pre-defined range (e.g., a zone, a call zone). In some embodiments a call zone is defined according to a collection of values that are obtained from the same patient sample. In certain embodiments a call zone is defined according to a collection of values that are derived from the same chromosome or segment thereof. In some embodiments a call zone based on a ploidy determination is defined according a level of confidence (e.g., high level of confidence, e.g., low level of uncertainty) and/or a fetal fraction. In some embodiments a call zone is defined according to a ploidy determination and a fetal fraction of about 2.0% or greater, about 2.5% or greater, about 3% or greater, about 3.25% or greater, about 3.5% or greater, about 3.75% or greater, or about 4.0% or greater. For example, in some embodiments a call is made that a fetus comprises a trisomy 21 based on a ploidy determination of greater than 1.25 with a fetal fraction determination of 2% or greater or 4% or greater for a sample obtained from a pregnant female bearing a fetus. In certain embodiments, for example, a call is made that a fetus is euploid based on a ploidy determination of less than 1.25 with a fetal fraction determination of 2% or greater or 4% or greater for a sample obtained from a pregnant female bearing a fetus. In some embodiments a call zone is defined by a confidence level of about 99% or greater, about 99.1% or greater, about 99.2% or greater, about 99.3% or greater, about 99.4% or greater, about 99.5% or greater, about 99.6% or greater, about 99.7% or greater, about 99.8% or greater or about 99.9% or greater. In some embodiments a call is made without using a call zone. In some embodiments a call is made using a call zone and additional data or information. In some embodiments a call is made based on a ploidy value without the use of a call zone. In some embodiments a call is made without calculating a ploidy value. In some embodiments a call is made based on visual inspection of a profile (e.g., visual inspection of genomic section levels). A call can be made by any suitable method based in full, or in part, upon determinations, values and/or data obtained by methods described herein, non-limiting examples of which include a fetal ploidy determination, a fetal fraction determination, maternal ploidy, uncertainty and/or confidence determinations, genomic sections levels, profiles, z-scores, expected chromosome representations, measured chromosome representations, counts (e.g., normalized counts, raw counts), fetal or maternal copy number variations (e.g., categorized copy number variations), significantly different elevations, adjusted elevations (e.g., padding), the like or combinations thereof.

In some embodiments a no-call zone is where a call is not made. In some embodiments a no-call zone is defined by a value or collection of values that indicate low accuracy, high risk, high error, low level of confidence, high level of uncertainty, the like or a combination thereof. In some embodiments a no-call zone is defined, in part, by a fetal fraction of about 5% or less, about 4% or less, about 3% or less, about 2.5% or less, about 2.0% or less, about 1.5% or less or about 1.0% or less.

Outcome

Methods described herein can provide a determination of the presence or absence of a genetic variation (e.g., fetal aneuploidy) for a sample, thereby providing an outcome (e.g., thereby providing an outcome determinative of the presence or absence of a genetic variation (e.g., fetal aneuploidy)). A genetic variation often includes a gain, a loss and/or alteration (e.g., duplication, deletion, fusion, insertion, mutation, reorganization, substitution or aberrant methylation) of genetic information (e.g., chromosomes, segments of chromosomes, polymorphic regions, translocated regions, altered nucleotide sequence, the like or combinations of the foregoing) that results in a detectable change in the genome or genetic information of a test subject with respect to a reference. Presence or absence of a genetic variation can be determined by transforming, analyzing and/or manipulating sequence reads that have been mapped to genomic sections (e.g., genomic bins).

Methods described herein sometimes determine presence or absence of a fetal aneuploidy (e.g., full chromosome aneuploidy, partial chromosome aneuploidy or segmental chromosomal aberration (e.g., mosaicism, deletion and/or insertion)) for a test sample from a pregnant female bearing a fetus. In certain embodiments methods described herein detect euploidy or lack of euploidy (non-euploidy) for a sample from a pregnant female bearing a fetus. Methods described herein sometimes detect trisomy for one or more chromosomes (e.g., chromosome 13, chromosome 18, chromosome 21 or combination thereof) or segment thereof.

In some embodiments, presence or absence of a genetic variation (e.g., a fetal aneuploidy) is determined by a method described herein, by a method known in the art or by a combination thereof. Presence or absence of a genetic variation generally is determined from counts of sequence reads mapped to genomic sections of a reference genome. Counts of sequence reads utilized to determine presence or absence of a genetic variation sometimes are raw counts and/or filtered counts, and often are normalized counts. A suitable normalization process or processes can be used to generate normalized counts, non-limiting examples of which include bin-wise normalization, normalization by GC content, linear and nonlinear least squares regression, LOESS, GC LOESS, LOWESS, PERUN, RM, GCRM and combinations thereof. Normalized counts sometimes are expressed as one or more levels or elevations in a profile for a particular set or sets of genomic sections. Normalized counts sometimes are adjusted or padded prior to determining presence or absence of a genetic variation.

Presence or absence of a genetic variation (e.g., fetal aneuploidy) sometimes is determined without comparing counts for a set of genomic sections to a reference. Counts measured for a test sample and are in a test region (e.g., a set of genomic sections of interest) are referred to as "test counts" herein. Test counts sometimes are processed counts, averaged or summed counts, a representation, normalized counts, or one or more levels or elevations, as described herein. In certain embodiments test counts are averaged or summed (e.g., an average, mean, median, mode or sum is calculated) for a set of genomic sections, and the averaged or summed counts are compared to a threshold or range. Test counts sometimes are expressed as a representation, which can be expressed as a ratio or percentage of counts for a first set of genomic sections to counts for a second set of genomic sections. In certain embodiments the first set of genomic sections is for one or more test chromosomes (e.g., chromosome 13, chromosome 18, chromosome 21, or combination thereof) and sometimes the second set of genomic sections is for the genome or a part of the genome (e.g., autosomes or autosomes and sex chromosomes). In certain embodiments a representation is compared to a threshold or range. In certain embodiments test counts are expressed as one or more levels or elevations for normalized counts over a set of genomic sections, and the one or more levels or elevations are compared to a threshold or range. Test counts (e.g., averaged or summed counts, representation, normalized counts, one or more levels or elevations) above or below a particular threshold, in a particular range or outside a particular range sometimes are determinative of the presence of a genetic variation or lack of euploidy (e.g., not euploidy). Test counts (e.g., averaged or summed counts, representation, normalized counts, one or more levels or elevations) below or above a particular threshold, in a particular range or outside a particular range sometimes are determinative of the absence of a genetic variation or euploidy.

Presence or absence of a genetic variation (e.g., fetal aneuploidy) sometimes is determined by comparing test counts (e.g., raw counts, filtered counts, averaged or summed counts, representation, normalized counts, one or more levels or elevations, for a set of genomic sections) to a reference. A reference can be a suitable determination of counts. Counts for a reference sometimes are raw counts, filtered counts, averaged or summed counts, representation, normalized counts, one or more levels or elevations, for a set of genomic sections. Reference counts often are counts for a euploid test region.

In certain embodiments, test counts sometimes are for a first set of genomic sections and a reference includes counts for a second set of genomic sections different than the first set of genomic sections. Reference counts sometimes are for a nucleic acid sample from the same pregnant female from which the test sample is obtained. In certain embodiments reference counts are for a nucleic acid sample from one or more pregnant females different than the female from which the test sample was obtained. In some embodiments, a first set of genomic sections is in chromosome 13, chromosome 18, chromosome 21, segment thereof or combination of the foregoing, and the second set of genomic sections is in another chromosome or chromosomes or segment thereof. In a non-limiting example, where a first set of genomic sections is in chromosome 21 or segment thereof, a second set of genomic sections often is in another chromosome (e.g., chromosome 1, chromosome 13, chromosome 14, chromosome 18, chromosome 19, segment thereof or combination of the foregoing). A reference often is located in a chromosome or segment thereof that is typically euploid. For example, chromosome 1 and chromosome 19 often are euploid in fetuses owing to a high rate of early fetal mortality associated with chromosome 1 and chromosome 19 aneuploidies. A measure of deviation between the test counts and the reference counts can be generated.

In certain embodiments a reference comprises counts for the same set of genomic sections as for the test counts, where the counts for the reference are from one or more reference samples (e.g., often multiple reference samples from multiple reference subjects). A reference sample often is from one or more pregnant females different than the female from which a test sample is obtained. A measure of deviation between the test counts and the reference counts can be generated.

A suitable measure of deviation between test counts and reference counts can be selected, non-limiting examples of which include standard deviation, average absolute deviation, median absolute deviation, maximum absolute deviation, standard score (e.g., z-value, z-score, normal score, standardized variable) and the like. In some embodiments, reference samples are euploid for a test region and deviation between the test counts and the reference counts is assessed. A deviation of less than three between test counts and reference counts (e.g., 3-sigma for standard deviation) often is indicative of a euploid test region (e.g., absence of a genetic variation). A deviation of greater than three between test counts and reference counts often is indicative of a non-euploid test region (e.g., presence of a genetic variation). Test counts significantly below reference counts, which reference counts are indicative of euploidy, sometimes are determinative of a monosomy. Test counts significantly above reference counts, which reference counts are indicative of euploidy, sometimes are determinative of a trisomy. A measure of deviation between test counts for a test sample and reference counts for multiple reference subjects can be plotted and visualized (e.g., z-score plot).

Any other suitable reference can be factored with test counts for determining presence or absence of a genetic variation (or determination of euploid or non-euploid) for a test region of a test sample. For example, a fetal fraction determination can be factored with test counts to determine the presence or absence of a genetic variation. A suitable process for quantifying fetal fraction can be utilized, non-limiting examples of which include a mass spectrometric process, sequencing process or combination thereof.

Laboratory personnel (e.g., a laboratory manager) can analyze values (e.g., test counts, reference counts, level of deviation) underlying a determination of the presence or absence of a genetic variation (or determination of euploid or non-euploid for a test region). For calls pertaining to presence or absence of a genetic variation that are close or questionable, laboratory personnel can re-order the same test, and/or order a different test (e.g., karyotyping and/or amniocentesis in the case of fetal aneuploidy determinations), that makes use of the same or different sample nucleic acid from a test subject.

A genetic variation sometimes is associated with medical condition. An outcome determinative of a genetic variation is sometimes an outcome determinative of the presence or absence of a condition (e.g., a medical condition), disease, syndrome or abnormality, or includes, detection of a condition, disease, syndrome or abnormality (e.g., non-limiting examples listed in Table 1). In certain embodiments a diagnosis comprises assessment of an outcome. An outcome determinative of the presence or absence of a condition (e.g., a medical condition), disease, syndrome or abnormality by methods described herein can sometimes be independently verified by further testing (e.g., by karyotyping and/or amniocentesis).

Analysis and processing of data can provide one or more outcomes. The term "outcome" as used herein can refer to a result of data processing that facilitates determining the presence or absence of a genetic variation (e.g., an aneuploidy, a copy number variation). In certain embodiments the term "outcome" as used herein refers to a conclusion that predicts and/or determines the presence or absence of a genetic variation (e.g., an aneuploidy, a copy number variation). In certain embodiments the term "outcome" as used herein refers to a conclusion that predicts and/or determines a risk or probability of the presence or absence of a genetic variation (e.g., an aneuploidy, a copy number variation) in a subject (e.g., a fetus). A diagnosis sometimes comprises use of an outcome. For example, a health practitioner may analyze an outcome and provide a diagnosis bases on, or based in part on, the outcome. In some embodiments, determination, detection or diagnosis of a condition, syndrome or abnormality (e.g., listed in Table 1) comprises use of an outcome determinative of the presence or absence of a genetic variation. In some embodiments, an outcome based on counted mapped sequence reads or transformations thereof is determinative of the presence or absence of a genetic variation. In certain embodiments, an outcome generated utilizing one or more methods (e.g., data processing methods) described herein is determinative of the presence or absence of one or more conditions, syndromes or abnormalities listed in Table 1. In certain embodiments a diagnosis comprises a determination of a presence or absence of a condition, syndrome or abnormality. Often a diagnosis comprises a determination of a genetic variation as the nature and/or cause of a condition, syndrome or abnormality. In certain embodiments an outcome is not a diagnosis. An outcome often comprises one or more numerical values generated using a processing method described herein in the context of one or more considerations of probability. A consideration of risk or probability can include, but is not limited to: an uncertainty value, a measure of variability, confidence level, sensitivity, specificity, standard deviation, coefficient of variation (CV) and/or confidence level, Z-scores, Chi values, Phi values, ploidy values, fitted fetal fraction, area ratios, median elevation, the like or combinations thereof. A consideration of probability can facilitate determining whether a subject is at risk of having, or has, a genetic variation, and an outcome determinative of a presence or absence of a genetic disorder often includes such a consideration.

An outcome sometimes is a phenotype. An outcome sometimes is a phenotype with an associated level of confidence (e.g., an uncertainty value, e.g., a fetus is positive for trisomy 21 with a confidence level of 99%, a test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation or genomic section from a data set, with respect to a reference genome can lead to an identification of the presence or absence of a genetic variation, which genetic variation sometimes is associated with a medical condition (e.g., cancer, preeclampsia, trisomy, monosomy, and the like). In some embodiments, an outcome comprises an elevation, a profile and/or a plot (e.g., a profile plot). In those embodiments in which an outcome comprises a profile, a suitable profile or combination of profiles can be used for an outcome. Non-limiting examples of profiles that can be used for an outcome include z-score profiles, p-value profiles, chi value profiles, phi value profiles, the like, and combinations thereof.

An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in a suitable form, which form comprises without limitation, a probability (e.g., odds ratio, p-value), likelihood, value in or out of a cluster, value over or under a threshold value, value within a range (e.g., a threshold range), value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. In certain embodiments a predetermined threshold or cutoff value is an expected elevation or an expected elevation range. An outcome also can describe an assumption used in data processing. In certain embodiments, an outcome comprises a value that falls within or outside a predetermined range of values (e.g., a threshold range) and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative. The term "sensitivity" as used herein refers to the number of true positives divided by the number of true positives plus the number of false negatives, where sensitivity (sens) may be within the range of $0 \le sens \le 1$. Ideally, the number of false negatives equal zero or close to zero, so that no subject is wrongly identified as not having at least one genetic variation when they indeed have at least one genetic variation. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of $0 \le spec \le 1$. Ideally, the number of false positives equal zero or close to zero, so that no subject is wrongly identified as having at least one genetic variation when they do not have the genetic variation being assessed.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein. Specific examples of generating outcomes and associated confidence levels are described in the Example section.

A method that has sensitivity and specificity equaling one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

In some embodiments, presence or absence of a genetic variation (e.g., chromosome aneuploidy) is determined for a fetus. In such embodiments, presence or absence of a fetal genetic variation (e.g., fetal chromosome aneuploidy) is determined.

In certain embodiments, presence or absence of a genetic variation (e.g., chromosome aneuploidy) is determined for a sample. In such embodiments, presence or absence of a genetic variation in sample nucleic acid (e.g., chromosome aneuploidy) is determined. In some embodiments, a variation detected or not detected resides in sample nucleic acid from one source but not in sample nucleic acid from another source. Non-limiting examples of sources include placental nucleic acid, fetal nucleic acid, maternal nucleic acid, cancer cell nucleic acid, non-cancer cell nucleic acid, the like and combinations thereof. In non-limiting examples, a particular genetic variation detected or not detected (i) resides in placental nucleic acid but not in fetal nucleic acid and not in maternal nucleic acid; (ii) resides in fetal nucleic acid but not maternal nucleic acid; or (iii) resides in maternal nucleic acid but not fetal nucleic acid.

After one or more outcomes have been generated, an outcome often is used to provide a determination of the presence or absence of a genetic variation and/or associated medical condition. An outcome typically is provided to a health care professional (e.g., laboratory technician or manager; physician or assistant). Often an outcome is provided by an outcome module. In certain embodiments an outcome is provided by a plotting module. In certain embodiments an outcome is provided on a peripheral or component of an apparatus. For example, sometimes an outcome is provided by a printer or display. In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in a suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing. Various examples of outcome representations are shown in the drawings and are described in the Examples.

Generating an outcome can be viewed as a transformation of nucleic acid sequence read data, or the like, into a representation of a subject's cellular nucleic acid, in certain embodiments. For example, analyzing sequence reads of nucleic acid from a subject and generating a chromosome profile and/or outcome can be viewed as a transformation of relatively small sequence read fragments to a representation of relatively large chromosome structure. In some embodiments, an outcome results from a transformation of sequence reads from a subject (e.g., a pregnant female), into a representation of an existing structure (e.g., a genome, a chromosome or segment thereof) present in the subject (e.g., a maternal and/or fetal nucleic acid). In some embodiments, an outcome comprises a transformation of sequence reads from a first subject (e.g., a pregnant female), into a composite representation of structures (e.g., a genome, a chromosome or segment thereof), and a second transformation of the composite representation that yields a representation of a structure present in a first subject (e.g., a pregnant female) and/or a second subject (e.g., a fetus).

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by a communication means, a written and/or graphical representation comprising an outcome, which upon review allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by a other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file.

The term "providing an outcome" and grammatical equivalents thereof, as used herein also can refer to a method for obtaining such information, including, without limitation, obtaining the information from a laboratory (e.g., a laboratory file). A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

In some embodiments, an outcome can be provided to a health care professional, physician or qualified individual from a laboratory and the health care professional, physician or qualified individual can make a diagnosis based on the outcome. In some embodiments, an outcome can be provided to a health care professional, physician or qualified individual from a laboratory and the health care professional, physician or qualified individual can make a diagnosis based, in part, on the outcome along with additional data and/or information and other outcomes.

A healthcare professional or qualified individual, can provide a suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Genetic Variations and Medical Conditions

The presence or absence of a genetic variance can be determined using a method or apparatus described herein. In certain embodiments, the presence or absence of one or more genetic variations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy), partial chromosome abnormality or mosaicism, each of which is described in greater detail herein. Non-limiting examples of genetic variations include one or more deletions (e.g., micro-deletions), duplications (e.g., micro-duplications), insertions, mutations, polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 1,000 kilobases (kb) in length (e.g., about 10 bp, 50 bp, 100 bp, 500 bp, 1 kb, 5 kb, 10 kb, 50 kb, 100 kb, 500 kb, or 1000 kb in length).

A genetic variation is sometime a deletion. In certain embodiments a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a segment of a chromosome, an allele, a gene, an intron, an exon, any non-coding region, any coding region, a segment thereof or combination thereof. A deletion can comprise a microdeletion. A deletion can comprise the deletion of a single base.

A genetic variation is sometimes a genetic duplication. In certain embodiments a duplication is a mutation (e.g., a genetic aberration) in which a part of a chromosome or a sequence of DNA is copied and inserted back into the genome. In certain embodiments a genetic duplication (i.e. duplication) is any duplication of a region of DNA. In some embodiments a duplication is a nucleic acid sequence that is repeated, often in tandem, within a genome or chromosome. In some embodiments a duplication can comprise a copy of one or more entire chromosomes, a segment of a chromosome, an allele, a gene, an intron, an exon, any non-coding region, any coding region, segment thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation is sometimes an insertion. An insertion is sometimes the addition of one or more nucleotide base pairs into a nucleic acid sequence. An insertion is sometimes a microinsertion. In certain embodiments an insertion comprises the addition of a segment of a chromosome into a genome, chromosome, or segment thereof. In certain embodiments an insertion comprises the addition of an allele, a gene, an intron, an exon, any non-coding region, any coding region, segment thereof or combination thereof into a genome or segment thereof. In certain embodiments an insertion comprises the addition (i.e., insertion) of nucleic acid of unknown origin into a genome, chromosome, or segment thereof. In certain embodiments an insertion comprises the addition (i.e. insertion) of a single base.

As used herein a "copy number variation" generally is a class or type of genetic variation or chromosomal aberration. A copy number variation can be a deletion (e.g. micro-deletion), duplication (e.g., a micro-duplication) or insertion (e.g., a micro-insertion). Often, the prefix "micro" as used herein sometimes is a segment of nucleic acid less than 5 Mb in length. A copy number variation can include one or more deletions (e.g. micro-deletion), duplications and/or insertions (e.g., a micro-duplication, micro-insertion) of a segment of a chromosome. In certain embodiments a duplication comprises an insertion. In certain embodiments an insertion is a duplication. In certain embodiments an insertion is not a duplication. For example, often a duplication of a sequence in a genomic section increases the counts for a genomic section in which the duplication is found. Often a duplication of a sequence in a genomic section increases the elevation. In certain embodiments, a duplication present in genomic sections making up a first elevation increases the elevation relative to a second elevation where a duplication is absent. In certain embodiments an insertion increases the counts of a genomic section and a sequence representing the insertion is present (i.e., duplicated) at another location within the same genomic section. In certain embodiments an insertion does not significantly increase the counts of a genomic section or elevation and the sequence that is inserted is not a duplication of a sequence within the same genomic section. In certain embodiments an insertion is not detected or represented as a duplication and a duplicate sequence representing the insertion is not present in the same genomic section.

In some embodiments a copy number variation is a fetal copy number variation. Often, a fetal copy number variation is a copy number variation in the genome of a fetus. In some embodiments a copy number variation is a maternal and/or fetal copy number variation. In certain embodiments a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

"Ploidy" refers to the number of chromosomes present in a fetus or mother. In certain embodiments "Ploidy" is the same as "chromosome ploidy". In humans, for example, autosomal chromosomes are often present in pairs. For example, in the absence of a genetic variation, most humans have two of each autosomal chromosome (e.g., chromosomes 1-22). The presence of the normal complement of 2 autosomal chromosomes in a human is often referred to as euploid. "Microploidy" is similar in meaning to ploidy. "Microploidy" often refers to the ploidy of a segment of a chromosome. The term "microploidy" sometimes refers to the presence or absence of a copy number variation (e.g., a deletion, duplication and/or an insertion) within a chromosome (e.g., a homozygous or heterozygous deletion, duplication, or insertion, the like or absence thereof). "Ploidy" and "microploidy" sometimes are determined after normalization of counts of an elevation in a profile (e.g., after normalizing counts of an elevation to an NRV of 1). Thus, an elevation representing an autosomal chromosome pair (e.g., a euploid) is often normalized to an NRV of 1 and is referred to as a ploidy of 1. Similarly, an elevation within a segment of a chromosome representing the absence of a duplication, deletion or insertion is often normalized to an NRV of 1 and is referred to as a microploidy of 1. Ploidy and microploidy are often bin-specific (e.g., genomic section specific) and sample-specific. Ploidy is often defined as integral multiples of ½, with the values of 1, ½, 0, 3/2, and 2 representing euploid (e.g., 2 chromosomes), 1 chromosome present (e.g., a chromosome deletion), no chromosome present, 3 chromosomes (e.g., a trisomy) and 4 chromosomes, respectively. Likewise, microploidy is often defined as integral multiples of ½, with the values of 1, ½, 0, 3/2, and 2 representing euploid (e.g., no copy number variation), a heterozygous deletion, homozygous deletion, heterozygous duplication and homozygous duplication, respectively. Some examples of ploidy values for a fetus are provided in Table 2 for an NRV of 1.

In certain embodiments the microploidy of a fetus matches the microploidy of the mother of the fetus (i.e., the pregnant female subject). In certain embodiments the microploidy of a fetus matches the microploidy of the mother of the fetus and both the mother and fetus carry the same heterozygous copy number variation, homozygous copy number variation or both are euploid. In certain embodiments the microploidy of a fetus is different than the microploidy of the mother of the fetus. For example, sometimes the microploidy of a fetus is heterozygous for a copy number variation, the mother is homozygous for a copy number variation and the microploidy of the fetus does not match (e.g., does not equal) the microploidy of the mother for the specified copy number variation.

A microploidy is often associated with an expected elevation. For example, sometimes an elevation (e.g., an elevation in a profile, sometimes an elevation that includes substantially no copy number variation) is normalized to an NRV of 1 and the microploidy of a homozygous duplication is 2, a heterozygous duplication is 1.5, a heterozygous deletion is 0.5 and a homozygous deletion is zero.

A genetic variation for which the presence or absence is identified for a subject is associated with a medical condition in certain embodiments. Thus, technology described herein can be used to identify the presence or absence of one or more genetic variations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations, medical conditions and states are described hereafter.

Chromosome Abnormalities

In some embodiments, the presence or absence of a fetal chromosome abnormality can be determined by using a method or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, translocations, deletions and/or duplications of one or more nucleotide sequences (e.g., one or more genes), including deletions and duplications caused by unbalanced translocations. The term "chromosomal abnormality" or "aneuploidy" as used herein refers to a deviation between the structure of the subject chromosome and a normal homologous chromosome. The term "normal" refers to the predominate karyotype or banding pattern found in healthy individuals of a particular species, for example, a euploid genome (in humans, 46XX or 46XY). As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a segment of a chromosome. The term "euploid", in some embodiments, refers a normal complement of chromosomes.

The term "monosomy" as used herein refers to lack of one chromosome of the normal complement. Partial monosomy can occur in unbalanced translocations or deletions, in which only a segment of the chromosome is present in a single copy. Monosomy of sex chromosomes (45, X) causes Turner syndrome, for example. The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47, XYY in Jacobs Syndrome). In some embodiments, a trisomy is a duplication of most or all of an autosome. In certain embodiments a trisomy is a whole chromosome aneuploidy resulting in three chromosomes.

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing non-disjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the segment that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Tables 1A and 1B present a non-limiting list of chromosome conditions, syndromes and/or abnormalities that can be potentially identified by methods and apparatus described herein. Table 1B is from the DECIPHER database as of Oct. 6, 2011 (e.g., version 5.1, based on positions mapped to GRCh37; available at uniform resource locator (URL) dechipher.sanger.ac.uk).

TABLE 1A

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphproliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobsen Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion | Rubenstein-Taybi |
| 3 | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 1B

| Syndrome | Chromosome | Start | End | Interval (Mb) | Grade |
|---|---|---|---|---|---|
| 12q14 microdeletion syndrome | 12 | 65,071,919 | 68,645,525 | 3.57 | |
| 15q13.3 microdeletion syndrome | 15 | 30,769,995 | 32,701,482 | 1.93 | |
| 15q24 recurrent microdeletion syndrome | 15 | 74,377,174 | 76,162,277 | 1.79 | |
| 15q26 overgrowth syndrome | 15 | 99,357,970 | 102,521,392 | 3.16 | |
| 16p11.2 microduplication syndrome | 16 | 29,501,198 | 30,202,572 | 0.70 | |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |
| 22q11 deletion syndrome (Velocardiofacial/DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |
| 7q11.23 duplication syndrome | 7 | 72,332,743 | 74,616,901 | 2.28 | |

TABLE 1B-continued

| Syndrome | Chromosome | Start | End | Interval (Mb) | Grade |
|---|---|---|---|---|---|
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | 21 | 27,037,956 | 27,548,479 | 0.51 | |
| Familial Adenomatous Polyposis | 5 | 112,101,596 | 112,221,377 | 0.12 | |
| Hereditary Liability to Pressure Palsies (HNPP) | 17 | 13,968,607 | 15,434,038 | 1.47 | 1 |
| Leri-Weill dyschondrostosis (LWD) - SHOX deletion | X | 751,878 | 867,875 | 0.12 | |
| Leri-Weill dyschondrostosis (LWD) - SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |

TABLE 1B-continued

| Syndrome | Chromosome | Start | End | Interval (Mb) | Grade |
|---|---|---|---|---|---|
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population; functional data confirming single gene or multi-gene dosage effect; confirmed or strong candidate genes; clinical management implications defined; known cancer risk with implication for surveillance; multiple sources of information (OMIM, Genereviews, Orphanet, Unique, Wikipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, Genereviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

Preeclampsia

In some embodiments, the presence or absence of preeclampsia is determined by using a method or apparatus described herein. Preeclampsia is a condition in which hypertension arises in pregnancy (i.e. pregnancy-induced hypertension) and is associated with significant amounts of protein in the urine. In certain embodiments, preeclampsia also is associated with elevated levels of extracellular nucleic acid and/or alterations in methylation patterns. For example, a positive correlation between extracellular fetal-derived hypermethylated RASSF1A levels and the severity of pre-eclampsia has been observed. In certain examples, increased DNA methylation is observed for the H19 gene in preeclamptic placentas compared to normal controls.

Preeclampsia is one of the leading causes of maternal and fetal/neonatal mortality and morbidity worldwide. Circulating cell-free nucleic acids in plasma and serum are novel biomarkers with promising clinical applications in different medical fields, including prenatal diagnosis. Quantitative changes of cell-free fetal (cff)DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as measurement of total cell-free DNA or the use of gender-independent fetal epigenetic markers, such as DNA methylation, offer an alternative. Cell-free RNA of placental origin is another alternative biomarker that may be used for screening and diagnosing preeclampsia in clinical practice. Fetal RNA is associated with subcellular placental particles that protect it from degradation. Fetal RNA levels sometimes are ten-fold higher in pregnant females with preeclampsia compared to controls, and therefore is an alternative biomarker that may be used for screening and diagnosing preeclampsia in clinical practice.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g. strain).

Cancers

In some embodiments, the presence or absence of a cell proliferation disorder (e.g., a cancer) is determined by using a method or apparatus described herein. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Thus, it is further contemplated that a method provided herein can be used to identify a particular type of cancer.

Software can be used to perform one or more steps in the processes described herein, including but not limited to; counting, data processing, generating an outcome, and/or providing one or more recommendations based on generated outcomes, as described in greater detail hereafter.

Machines, Software and Interfaces

Certain processes and methods described herein (e.g., quantifying, mapping, normalizing, range setting, adjusting, categorizing, counting and/or determining sequence reads, counts, elevations (e.g., elevations) and/or profiles) often cannot be performed without a computer, processor, software, module or other apparatus. Methods described herein typically are computer-implemented methods, and one or more portions of a method sometimes are performed by one or more processors. Embodiments pertaining to methods described in this document generally are applicable to the same or related processes implemented by instructions in systems, apparatus and computer program products described herein. In some embodiments, processes and methods described herein (e.g., quantifying, counting and/or determining sequence reads, counts, elevations and/or profiles) are performed by automated methods. In some embodiments, an automated method is embodied in software, modules, processors, peripherals and/or an apparatus comprising the like, that determine sequence reads, counts, mapping, mapped sequence tags, elevations, profiles, normalizations, comparisons, range setting, categorization, adjustments, plotting, outcomes, transformations and identifications. As used herein, software refers to computer readable program instructions that, when executed by a processor, perform computer operations, as described herein.

Sequence reads, counts, elevations, and profiles derived from a test subject (e.g., a patient, a pregnant female) and/or from a reference subject can be further analyzed and processed to determine the presence or absence of a genetic variation. Sequence reads, counts, elevations and/or profiles sometimes are referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific, genomic section or bin specific], the like and combinations thereof). In certain embodiments, data or data sets can be organized into a matrix having two or more dimensions based on one or more features or variables. Data organized into matrices can be organized using any suitable features or variables. A non-limiting example of data in a matrix includes data that is organized by maternal age, maternal ploidy, and fetal contribution. In certain embodiments, data sets characterized by one or more features or variables sometimes are processed after counting.

Apparatuses, software and interfaces may be used to conduct methods described herein. Using apparatuses, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by a suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more apparatus. Each apparatus comprises one or more of memory, one or more processors, and instructions. Where a system includes two or more apparatus, some or all of the apparatus may be located at the same location, some or all of the apparatus may be located at different locations, all of the apparatus may be located at one location and/or all of the apparatus may be located at different locations. Where a system includes two or more apparatus, some or all of the apparatus may be located at the same location as a user, some or all of the apparatus may be located at a location different than a user, all of the apparatus may be located at the same location as the user, and/or all of the apparatus may be located at one or more locations different than the user.

A system sometimes comprises a computing apparatus and a sequencing apparatus, where the sequencing apparatus is configured to receive physical nucleic acid and generate sequence reads, and the computing apparatus is configured to process the reads from the sequencing apparatus. The computing apparatus sometimes is configured to determine the presence or absence of a genetic variation (e.g., copy number variation; fetal chromosome aneuploidy) from the sequence reads.

A user may, for example, place a query to software which then may acquire a data set via internet access, and in certain embodiments, a programmable processor may be prompted to acquire a suitable data set based on given parameters. A programmable processor also may prompt a user to select one or more data set options selected by the processor based on given parameters. A programmable processor may prompt a user to select one or more data set options selected by the processor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, apparatuses, or computer programs.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel.

Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus may serve as data that can be input via an input device. In certain embodiments, mapped sequence reads may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., sequencing module, logic processing module, data display organization module). The term "software" refers to computer readable program instructions that, when executed by a computer, perform computer operations. Instructions executable by the one or more processors sometimes are provided as executable code, that when executed, can cause one or more processors to implement a method described herein. A module described herein can exist as software, and instructions (e.g., processes, routines, subroutines) embodied in the software can be implemented or performed by a processor. For example, a module (e.g., a software module) can be a part of a program that performs a particular process or task. The term "module" refers to a self-contained functional unit that can be used in a larger apparatus or software system. A module can comprise a set of instructions for carrying out a function of the module. A module can transform data and/or information. Data and/or information can be in a suitable form. For example, data and/or information can be digital or analogue. In certain embodiments, data and/or information can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, elevations, ranges, thresholds, signals, displays, representations, or transformations thereof. A module can accept or receive data and/or information, transform the data and/or information into a second form, and provide or transfer the second form to an apparatus, peripheral, component or another module. A module can perform one or more of the following non-limiting functions: mapping sequence reads, providing counts, assembling genomic sections, providing or determining an elevation, providing a count profile, normalizing (e.g., normalizing reads, normalizing counts, and the like), providing a normalized count profile or elevations of normalized counts, comparing two or more elevations, providing uncertainty values, providing or determining expected elevations and expected ranges (e.g., expected elevation ranges, threshold ranges and threshold elevations), providing adjustments to elevations (e.g., adjusting a first elevation, adjusting a second elevation, adjusting a profile of a chromosome or a segment thereof, and/or padding), providing identification (e.g., identifying a copy number variation, genetic variation or aneuploidy), categorizing, plotting, and/or determining an outcome, for example. A processor can, in some cases, carry out the instructions in a module. In some embodiments, one or more processors are required to carry out instructions in a module or group of modules. A module can provide data and/or information to another module, apparatus or source and can receive data and/or information from another module, apparatus or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and processor capable of implementing instructions from a module can be located in an apparatus or in different apparatus. A module and/or processor capable of implementing an instruction for a module can be located in the same location as a user (e.g., local network) or in a different location from a user (e.g., remote network, cloud system). In embodiments in which a method is carried out in conjunction with two or more modules, the modules can be located in the same apparatus, one or more modules can be located in different apparatus in the same physical location, and one or more modules may be located in different apparatus in different physical locations.

An apparatus, in some embodiments, comprises at least one processor for carrying out the instructions in a module. Counts of sequence reads mapped to genomic sections of a reference genome sometimes are accessed by a processor that executes instructions configured to carry out a method described herein. Counts that are accessed by a processor can be within memory of a system, and the counts can be accessed and placed into the memory of the system after they are obtained. In some embodiments, an apparatus includes a processor (e.g., one or more processors) which processor can perform and/or implement one or more instructions (e.g., processes, routines and/or subroutines) from a module. In some embodiments, an apparatus includes multiple processors, such as processors coordinated and working in parallel. In some embodiments, an apparatus operates with one or more external processors (e.g., an internal or external network, server, storage device and/or storage network (e.g., a cloud)). In some embodiments, an apparatus comprises a module. In certain embodiments an apparatus comprises one or more modules. An apparatus comprising a module often can receive and transfer one or more of data and/or information to and from other modules. In certain embodiments, an apparatus comprises peripherals and/or components. In certain embodiments an apparatus can comprise one or more peripherals or components that can transfer data and/or information to and from other modules, peripherals and/or components. In certain embodiments an apparatus interacts with a peripheral and/or component that provides data and/or information. In certain embodiments peripherals and components assist an apparatus in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a processor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like,), the world wide web (www), the internet, a computer and/or another module.

One or more of a sequencing module, logic processing module and data display organization module can be utilized in a method described herein. In certain embodiments a logic processing module, sequencing module or data display organization module, or an apparatus comprising one or more such modules, gather, assemble, receive, provide and/or transfer data and/or information to or from another module, apparatus, component, peripheral or operator of an apparatus. For example, sometimes an operator of an apparatus provides a constant, a threshold value, a formula or a predetermined value to a logic processing module, sequencing module or data display organization module. A logic processing module, sequencing module or data display organization module can receive data and/or information from another module, non-limiting examples of which include a logic processing module, sequencing module, data display organization module, sequencing module, sequencing module, mapping module, counting module, normalization module, comparison module, range setting module, categorization module, adjustment module, plotting module, outcome module, data display organization module and/or logic processing module, the like or combination thereof. Data and/or information derived from or transformed by a logic processing module, sequencing module or data display organization module can be transferred from a logic processing module, sequencing module or data display organization module to a sequencing module, sequencing module, mapping module, counting module, normalization module, comparison module, range setting module, categorization module, adjustment module, plotting module, outcome module, data display organization module, logic processing module or other suitable apparatus and/or module. A sequencing module can receive data and/or information form a logic processing module and/or sequencing module and transfer data and/or information to a logic processing module and/or a mapping module, for example. In certain embodiments a logic processing module orchestrates, controls, limits, organizes, orders, distributes, partitions, transforms and/or regulates data and/or information or the transfer of data and/or information to and from one or more other modules, peripherals or devices. A data display organization module can receive data and/or information form a logic processing module and/or plotting module and transfer data and/or information to a logic processing module, plotting module, display, peripheral or device. An apparatus comprising a logic processing module, sequencing module or data display organization module can comprise at least one processor. In some embodiments, data and/or information are provided by an apparatus that includes a processor (e.g., one or more processors) which processor can perform and/or implement one or more instructions (e.g., processes, routines and/or subroutines) from the logic processing module, sequencing module and/or data display organization module. In some embodiments, a logic processing module, sequencing module or data display organization module operates with one or more external processors (e.g., an internal or external network, server, storage device and/or storage network (e.g., a cloud)).

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash drives, RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)). In some embodiments, provided are computer program products, such as, for example, a computer program product comprising a computer usable medium having a computer readable program code embodied therein, the computer readable program code adapted to be executed to implement a method comprising:

(a) obtaining sequence reads of sample nucleic acid from a test subject; (b) mapping the sequence reads obtained in (a) to a known genome, which known genome has been divided into genomic sections; (c) counting the mapped sequence reads within the genomic sections; (d) generating a sample normalized count profile by normalizing the counts for the genomic sections obtained in (c); and (e) determining the presence or absence of a genetic variation from the sample normalized count profile in (d).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more processors in certain embodiments. A processor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A processor may implement software in a system. In some embodiments, a processor may be programmed to automatically perform a task described herein that a user could perform. Accordingly, a processor, or algorithm conducted by such a processor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

One entity can generate counts of sequence reads, map the sequence reads to genomic sections, count the mapped reads, and utilize the counted mapped reads in a method, system, apparatus or computer program product described herein, in some embodiments. Counts of sequence reads mapped to genomic sections sometimes are transferred by one entity to a second entity for use by the second entity in a method, system, apparatus or computer program product described herein, in certain embodiments.

In some embodiments, one entity generates sequence reads and a second entity maps those sequence reads to genomic sections in a reference genome in some embodiments. The second entity sometimes counts the mapped reads and utilizes the counted mapped reads in a method, system, apparatus or computer program product described herein. In certain embodiments the second entity transfers the mapped reads to a third entity, and the third entity counts the mapped reads and utilizes the mapped reads in a method, system, apparatus or computer program product described herein. In certain embodiments the second entity counts the mapped reads and transfers the counted mapped reads to a third entity, and the third entity utilizes the counted mapped reads in a method, system, apparatus or computer program product described herein. In embodiments involving a third entity, the third entity sometimes is the same as the first entity. That is, the first entity sometimes transfers sequence reads to a second entity, which second entity can map sequence reads to genomic sections in a reference genome and/or count the mapped reads, and the second entity can transfer the mapped and/or counted reads to a third entity. A third entity sometimes can utilize the mapped and/or counted reads in a method, system, apparatus or computer program product described herein, wherein the third entity sometimes is the same as the first entity, and sometimes the third entity is different from the first or second entity.

In some embodiments, one entity obtains blood from a pregnant female, optionally isolates nucleic acid from the blood (e.g., from the plasma or serum), and transfers the blood or nucleic acid to a second entity that generates sequence reads from the nucleic acid.

FIG. 178 illustrates a non-limiting example of a computing environment 510 in which various systems, methods, algorithms, and data structures described herein may be implemented. The computing environment 510 is only one example of a suitable computing environment and is not intended to suggest any limitation as to the scope of use or functionality of the systems, methods, and data structures described herein. Neither should computing environment 510 be interpreted as having any dependency or requirement relating to any one or combination of components illustrated in computing environment 510. A subset of systems, methods, and data structures shown in FIG. 178 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 510 of FIG. 178 includes a general purpose computing device in the form of a computer 520, including a processing unit 521, a system memory 522, and a system bus 523 that operatively couples various system components including the system memory 522 to the processing unit 521. There may be only one or there may be more than one processing unit 521, such that the processor of computer 520 includes a single central-processing unit (CPU), or a plurality of processing units, commonly referred to as a parallel processing environment. The computer 520 may be a conventional computer, a distributed computer, or any other type of computer.

The system bus 523 may be any of several types of bus structures including a memory bus or memory controller, a peripheral bus, and a local bus using any of a variety of bus architectures. The system memory may also be referred to as simply the memory, and includes read only memory (ROM) 524 and random access memory (RAM). A basic input/output system (BIOS) 526, containing the basic routines that help to transfer information between elements within the computer 520, such as during start-up, is stored in ROM 524. The computer 520 may further include a hard disk drive interface 527 for reading from and writing to a hard disk, not shown, a magnetic disk drive 528 for reading from or writing to a removable magnetic disk 529, and an optical disk drive 530 for reading from or writing to a removable optical disk 531 such as a CD ROM or other optical media.

The hard disk drive 527, magnetic disk drive 528, and optical disk drive 530 are connected to the system bus 523 by a hard disk drive interface 532, a magnetic disk drive interface 533, and an optical disk drive interface 534, respectively. The drives and their associated computer-readable media provide nonvolatile storage of computer-readable instructions, data structures, program modules and other data for the computer 520. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 529, optical disk 531, ROM 524, or RAM, including an operating system 535, one or more application programs 536, other program modules 537, and program data 538. A user may enter commands and information into the personal computer 520 through input devices such as a keyboard 540 and pointing device 542. Other input devices (not shown) may include a microphone, joystick, game pad, satellite dish, scanner, or the like. These and other input devices are often connected to the processing unit 521 through a serial port interface 546 that is coupled to the system bus, but may be connected by other interfaces, such as a parallel port, game port, or a universal serial bus (USB). A monitor 547 or other type of display device is also connected to the system bus 523 via an interface, such as a video adapter 548. In addition to the monitor, computers typically include other peripheral output devices (not shown), such as speakers and printers.

The computer 520 may operate in a networked environment using logical connections to one or more remote computers, such as remote computer 549. These logical connections may be achieved by a communication device coupled to or a part of the computer 520, or in other manners. The remote computer 549 may be another computer, a server, a router, a network PC, a client, a peer device or other common network node, and typically includes many or all of the elements described above relative to the computer 520, although only a memory storage device 550 has been illustrated in FIG. 178. The logical connections depicted in FIG. 178 include a local-area network (LAN) 551 and a wide-area network (WAN) 552. Such networking environments are commonplace in office networks, enterprise-wide computer networks, intranets and the Internet, which all are types of networks.

When used in a LAN-networking environment, the computer 520 is connected to the local network 551 through a network interface or adapter 553, which is one type of communications device. When used in a WAN-networking environment, the computer 520 often includes a modem 554, a type of communications device, or any other type of communications device for establishing communications over the wide area network 552. The modem 554, which may be internal or external, is connected to the system bus 523 via the serial port interface 546. In a networked environment, program modules depicted relative to the personal computer 520, or portions thereof, may be stored in the remote memory storage device. It is appreciated that the network connections shown are non-limiting examples and other communications devices for establishing a communications link between computers may be used.

Modules

Sequencing Module

Sequencing and obtaining sequencing reads can be provided by a sequencing module or by an apparatus comprising a sequencing module. A "sequence receiving module" as used herein is the same as a "sequencing module". An apparatus comprising a sequencing module can be any apparatus that determines the sequence of a nucleic acid from a sequencing technology known in the art. In certain embodiments, an apparatus comprising a sequencing module performs a sequencing reaction known in the art. A sequencing module generally provides a nucleic acid sequence read according to data from a sequencing reaction (e.g., signals generated from a sequencing apparatus). In some embodiments, a sequencing module or an apparatus comprising a sequencing module is required to provide sequencing reads. In some embodiments a sequencing module can receive, obtain, access or recover sequence reads from another sequencing module, computer peripheral, operator, server, hard drive, apparatus or from a suitable source. In certain embodiments a sequencing module can manipulate sequence reads. For example, a sequencing module can align, assemble, fragment, complement, reverse complement, error check, or error correct sequence reads. An apparatus comprising a sequencing module can comprise at least one processor. In some embodiments, sequencing reads are provided by an apparatus that includes a processor (e.g., one or more processors) which processor can perform and/or implement one or more instructions (e.g., processes, routines and/or subroutines) from the sequencing module. In some embodiments, sequencing reads are provided by an apparatus that includes multiple processors, such as processors coordinated and working in parallel. In some embodiments, a sequencing module operates with one or more external processors (e.g., an internal or external network, server, storage device and/or storage network (e.g., a cloud)). In certain embodiments a sequencing module gathers, assembles and/or receives data and/or information from another module, apparatus, peripheral, component or specialized component (e.g., a sequencer). In some embodiments, sequencing reads are provided by an apparatus comprising one or more of the following: one or more flow cells, a camera, a photo detector, a photo cell, fluid handling components, a printer, a display (e.g., an LED, LCT or CRT) and the like. Often a sequencing module receives, gathers and/or assembles sequence reads. In certain embodiments a sequencing module accepts and gathers input data and/or information from an operator of an apparatus. For example, sometimes an operator of an apparatus provides instructions, a constant, a threshold value, a formula or a predetermined value to a module. In certain embodiments a sequencing module can transform data and/or information that it receives into a contiguous nucleic acid sequence. In some embodiments, a nucleic acid sequence provided by a sequencing module is printed or displayed. In some embodiments, sequence reads are provided by a sequencing module and transferred from a sequencing module to an apparatus or an apparatus comprising any suitable peripheral, component or specialized component. In some embodiments, data and/or information are provided from a sequencing module to an apparatus that includes multiple processors, such as processors coordinated and working in parallel. In certain embodiments, data and/or information related to sequence reads can be transferred from a sequencing module to any other suitable module. A sequencing module can transfer sequence reads to a mapping module or counting module, in some embodiments.

Mapping Module

Sequence reads can be mapped by a mapping module or by an apparatus comprising a mapping module, which mapping module generally maps reads to a reference genome or segment thereof. A mapping module can map sequencing reads by a suitable method known in the art. In some embodiments, a mapping module or an apparatus comprising a mapping module is required to provide mapped sequence reads. An apparatus comprising a mapping module can comprise at least one processor. In some embodiments, mapped sequencing reads are provided by an apparatus that includes a processor (e.g., one or more processors) which processor can perform and/or implement one or more instructions (e.g., processes, routines and/or subroutines) from the mapping module. In some embodiments, sequencing reads are mapped by an apparatus that includes multiple processors, such as processors coordinated and working in parallel. In some embodiments, a mapping module operates with one or more external processors (e.g., an internal or external network, server, storage device and/or storage network (e.g., a cloud)). An apparatus may comprise a mapping module and a sequencing module. In some embodiments, sequence reads are mapped by an apparatus comprising one or more of the following: one or more flow cells, a camera, fluid handling components, a printer, a display (e.g., an LED, LCT or CRT) and the like. A mapping module can receive sequence reads from a sequencing module, in some embodiments. Mapped sequencing reads can be transferred from a mapping module to a counting module or a normalization module, in some embodiments.

Counting Module

Counts can be provided by a counting module or by an apparatus comprising a counting module. A counting module can determine, assemble, and/or display counts according to a counting method known in the art. A counting module generally determines or assembles counts according to counting methodology known in the art. In some embodiments, a counting module or an apparatus comprising a counting module is required to provide counts. An apparatus comprising a counting module can comprise at least one processor. In some embodiments, counts are provided by an apparatus that includes a processor (e.g., one or more processors) which processor can perform and/or implement one or more instructions (e.g., processes, routines and/or subroutines) from the counting module. In some embodiments, reads are counted by an apparatus that includes multiple processors, such as processors coordinated and working in parallel. In some embodiments, a counting module operates with one or more external processors (e.g., an internal or external network, server, storage device and/or storage network (e.g., a cloud)). In some embodiments, reads are counted by an apparatus comprising one or more of the following: a sequencing module, a mapping module, one or more flow cells, a camera, fluid handling components, a printer, a display (e.g., an LED, LCT or CRT) and the like. A counting module can receive data and/or information from a sequencing module and/or a mapping module, transform the data and/or information and provide counts (e.g., counts mapped to genomic sections). A counting module can receive mapped sequence reads from a mapping module. A counting module can receive normalized mapped sequence reads from a mapping module or from a normalization module. A counting module can transfer data and/or information related to counts (e.g., counts, assembled counts and/or displays of counts) to any other suitable apparatus, peripheral, or module. In certain embodiments data and/or information related to counts are transferred from a counting module to a normalization module, a plotting module, a categorization module and/or an outcome module.

Filtering Module

Filtering genomic sections can be provided by a filtering module (e.g., by an apparatus comprising a filtering module). In some embodiments, a filtering module is required to provide filtered genomic section data (e.g., filtered genomic sections) and/or to remove genomic sections from consideration. In certain embodiments a filtering module removes counts mapped to a genomic section from consideration. In certain embodiments a filtering module removes counts mapped to a genomic section from a determination of an elevation or a profile. A filtering module can filter data (e.g., counts, counts mapped to genomic sections, genomic sections, genomic sections elevations, normalized counts, raw counts, and the like) by one or more filtering procedures known in the art or described herein. An apparatus comprising a filtering module can comprise at least one processor. In some embodiments, filtered data is provided by an apparatus that includes a processor (e.g., one or more processors) which processor can perform and/or implement one or more instructions (e.g., processes, routines and/or subroutines) from the filtering module. In some embodiments, filtered data is provided by an apparatus that includes multiple processors, such as processors coordinated and working in parallel. In some embodiments, a filtering module operates with one or more external processors (e.g., an internal or external network, server, storage device and/or storage network (e.g., a cloud)). In some embodiments, filtered data is provided by an apparatus comprising one or more of the following: one or more flow cells, a camera, fluid handling components, a printer, a display (e.g., an LED, LCT or CRT) and the like. A filtering module can receive data and/or information from a suitable apparatus or module. In certain embodiments a filtering module can receive data and/or information from a sequencing module, a normalization module, a weighting module, a mapping module or counting module. A filtering module can receive sequencing reads from a sequencing module, mapped sequencing reads from a mapping module and/or counts from a counting module, in some embodiments. Often a filtering module receives data and/or information from another apparatus or module, transforms the data and/or information and provides filtered data and/or information (e.g., filtered counts, filtered values, filtered genomic sections, and the like). Filtered data and/or information can be transferred from a filtering module to a comparison module, a normalization module, a weighting module, a range setting module, an adjustment module, a categorization module, and/or an outcome module, in certain embodiments.

Weighting Module

Weighting genomic sections can be provided by a weighting module (e.g., by an apparatus comprising a weighting module). In some embodiments, a weighting module is required to weight genomics sections and/or provide weighted genomic section values. A weighting module can weight genomic sections by one or more weighting procedures known in the art or described herein. An apparatus comprising a weighting module can comprise at least one processor. In some embodiments, weighted genomic sections are provided by an apparatus that includes a processor (e.g., one or more processors) which processor can perform and/or implement one or more instructions (e.g., processes, routines and/or subroutines) from the weighting module. In some embodiments, weighted genomic sections are provided by an apparatus that includes multiple processors, such as processors coordinated and working in parallel. In some embodiments, a weighting module operates with one or more external processors (e.g., an internal or external network, server, storage device and/or storage network (e.g., a cloud)). In some embodiments, weighted genomic sections are provided by an apparatus comprising one or more of the following: one or more flow cells, a camera, fluid handling components, a printer, a display (e.g., an LED, LCT or CRT) and the like. A weighting module can receive data and/or information from a suitable apparatus or module. In certain embodiments a weighting module can receive data and/or information from a sequencing module, a normalization module, a filtering module, a mapping module and/or a counting module. A weighting module can receive sequencing reads from a sequencing module, mapped sequencing reads from a mapping module and/or counts from a counting module, in some embodiments. In some embodiments a weighting module receives data and/or information from another apparatus or module, transforms the data and/or information and provides data and/or information (e.g., weighted genomic sections, weighted values, and the like). Weighted genomic section data and/or information can be transferred from a weighting module to a comparison module, a normalization module, a filtering module, a range setting module, an adjustment module, a categorization module, and/or an outcome module, in certain embodiments.

Normalization Module

Normalized data (e.g., normalized counts) can be provided by a normalization module (e.g., by an apparatus comprising a normalization module). In some embodiments, a normalization module is required to provide normalized data (e.g., normalized counts) obtained from sequencing reads. A normalization module can normalize data (e.g., counts, filtered counts, raw counts) by one or more normalization procedures known in the art. An apparatus comprising a normalization module can comprise at least one processor. In some embodiments, normalized data is provided by an apparatus that includes a processor (e.g., one or more processors) which processor can perform and/or implement one or more instructions (e.g., processes, routines and/or subroutines) from the normalization module. In some embodiments, normalized data is provided by an apparatus that includes multiple processors, such as processors coordinated and working in parallel. In some embodiments, a normalization module operates with one or more external processors (e.g., an internal or external network, server, storage device and/or storage network (e.g., a cloud)). In some embodiments, normalized data is provided by an apparatus comprising one or more of the following: one or more flow cells, a camera, fluid handling components, a printer, a display (e.g., an LED, LCT or CRT) and the like. A normalization module can receive data and/or information from a suitable apparatus or module. In certain embodiments a normalization module can receive data and/or information from a sequencing module, a normalization module, a mapping module or counting module. A normalization module can receive sequencing reads from a sequencing module, mapped sequencing reads from a mapping module and/or counts from a counting module, in some embodiments. Often a normalization module receives data and/or information from another apparatus or module, transforms the data and/or information and provides normalized data and/or information (e.g., normalized counts, normalized values, normalized reference values (NRVs), and the like). Normalized data and/or information can be transferred from a normalization module to a comparison module, a normalization module, a range setting module, an adjustment module, a categorization module, and/or an outcome module, in certain embodiments. In certain embodiments normalized counts (e.g., normalized mapped counts) are transferred to an expected representation module and/or to a representation module from a normalization module.

Comparison Module

A first elevation can be identified as significantly different from a second elevation by a comparison module or by an apparatus comprising a comparison module. In some embodiments, a comparison module or an apparatus comprising a comparison module is required to provide a comparison between two elevations. An apparatus comprising a comparison module can comprise at least one processor. In some embodiments, elevations are determined to be significantly different by an apparatus that includes a processor (e.g., one or more processors) which processor can perform and/or implement one or more instructions (e.g., processes, routines and/or subroutines) from the comparison module. In some embodiments, elevations are determined to be significantly different by an apparatus that includes multiple processors, such as processors coordinated and working in parallel. In some embodiments, a comparison module operates with one or more external processors (e.g., an internal or external network, server, storage device and/or storage network (e.g., a cloud)). In some embodiments, elevations are determined to be significantly different by an apparatus comprising one or more of the following: one or more flow cells, a camera, fluid handling components, a printer, a display (e.g., an LED, LCT or CRT) and the like. A comparison module can receive data and/or information from a suitable module. A comparison module can receive data and/or information from a sequencing module, a mapping module, a counting module, or a normalization module. A comparison module can receive normalized data and/or information from a normalization module. Data and/or information derived from, or transformed by, a comparison module can be transferred from a comparison module to a range setting module, a plotting module, an adjustment module, a categorization module or an outcome module. A comparison between two or more elevations and/or an identification of an elevation as significantly different from another elevation can be transferred from (e.g., provided to) a comparison module to a categorization module, range setting module or adjustment module.

Range Setting Module

Expected ranges (e.g., expected elevation ranges) for various copy number variations (e.g., duplications, insertions and/or deletions) or ranges for the absence of a copy number variation can be provided by a range setting module or by an apparatus comprising a range setting module. In certain embodiments, expected elevations are provided by a range setting module or by an apparatus comprising a range setting module. In some embodiments, a range setting module or an apparatus comprising a range setting module is required to provide expected elevations and/or ranges. In certain embodiments a range setting module gathers, assembles and/or receives data and/or information from another module or apparatus. In certain embodiments a range setting module or an apparatus comprising a range setting module provides and/or transfers data and/or information to another module or apparatus. In certain embodiments a range setting module accepts and gathers data and/or information from a component or peripheral. Often a range setting module gathers and assembles elevations, reference elevations, uncertainty values, and/or constants. In certain embodiments a range setting module accepts and gathers input data and/or information from an operator of an apparatus. For example, sometimes an operator of an apparatus provides a constant, a threshold value, a formula or a predetermined value to a module.

An apparatus comprising a range setting module can comprise at least one processor. In some embodiments, expected elevations and expected ranges are provided by an apparatus that includes a processor (e.g., one or more processors) which processor can perform and/or implement one or more instructions (e.g., processes, routines and/or subroutines) from the range setting module. In some embodiments, expected ranges and elevations are provided by an apparatus that includes multiple processors, such as processors coordinated and working in parallel. In some embodiments, a range setting module operates with one or more external processors (e.g., an internal or external network, server, storage device and/or storage network (e.g., a cloud)). In some embodiments, expected ranges are provided by an apparatus comprising a suitable peripheral or component. A range setting module can receive normalized data from a normalization module or comparison data from a comparison module. Data and/or information derived from or transformed by a range setting module (e.g., set ranges, range limits, expected elevation ranges, thresholds, and/or threshold ranges) can be transferred from a range setting module to an adjustment module, an outcome module, a categorization module, plotting module or other suitable apparatus and/or module.

Categorization Module

A copy number variation (e.g., a maternal and/or fetal copy number variation, a fetal copy number variation, a duplication, insertion, deletion) can be categorized by a categorization module or by an apparatus comprising a categorization module. In certain embodiments a copy number variation (e.g., a maternal and/or fetal copy number variation) is categorized by a categorization module. In certain embodiments an elevation (e.g., a first elevation) determined to be significantly different from another elevation (e.g., a second elevation) is identified as representative of a copy number variation by a categorization module. In certain embodiments the absence of a copy number variation is determined by a categorization module. In some embodiments, a determination of a copy number variation can be determined by an apparatus comprising a categorization module. A categorization module can be specialized for categorizing a maternal and/or fetal copy number variation, a fetal copy number variation, a duplication, deletion or insertion or lack thereof or combination of the foregoing. For example, a categorization module that identifies a maternal deletion can be different than and/or distinct from a categorization module that identifies a fetal duplication. In some embodiments, a categorization module or an apparatus comprising a categorization module is required to identify a copy number variation or an outcome determinative of a copy number variation. An apparatus comprising a categorization module can comprise at least one processor. In some embodiments, a copy number variation or an outcome determinative of a copy number variation is categorized by an apparatus that includes a processor (e.g., one or more processors) which processor can perform and/or implement one or more instructions (e.g., processes, routines and/or subroutines) from the categorization module. In some embodiments, a copy number variation or an outcome determinative of a copy number variation is categorized by an apparatus that may include multiple processors, such as processors coordinated and working in parallel. In some embodiments, a categorization module operates with one or more external processors (e.g., an internal or external network, server, storage device and/or storage network (e.g., a cloud)). In certain embodiments a categorization module transfers or receives and/or gathers data and/or information to or from a component or peripheral. Often a categorization module receives, gathers and/or assembles counts, elevations, profiles, normalized data and/or information, reference elevations, expected elevations, expected ranges, uncertainty values, adjustments, adjusted elevations, plots, comparisons and/or constants. In certain embodiments a categorization module accepts and gathers input data and/or information from an operator of an apparatus. For example, sometimes an operator of an apparatus provides a constant, a threshold value, a formula or a predetermined value to a module. In some embodiments, data and/or information are provided by an apparatus that includes multiple processors, such as processors coordinated and working in parallel. In some embodiments, identification or categorization of a copy number variation or an outcome determinative of a copy number variation is provided by an apparatus comprising a suitable peripheral or component. In certain embodiments a categorization module gathers, assembles and/or receives data and/or information from another module or apparatus. A categorization module can receive normalized data from a normalization module, expected elevations and/or ranges from a range setting module, comparison data from a comparison module, plots from a plotting module, and/or adjustment data from an adjustment module. A categorization module can transform data and/or information that it receives into a determination of the presence or absence of a copy number variation. A categorization module can transform data and/or information that it receives into a determination that an elevation represents a genomic section comprising a copy number variation or a specific type of copy number variation (e.g., a maternal homozygous deletion). Data and/or information related to a copy number variation or an outcome determinative of a copy number variation can be transferred from a categorization module to a suitable apparatus and/or module. A copy number variation or an outcome determinative of a copy number variation categorized by methods described herein can be independently verified by further testing (e.g., by targeted sequencing of maternal and/or fetal nucleic acid).

Adjustment Module

In some embodiments, adjustments (e.g., adjustments to elevations or profiles) are made by an adjustment module or by an apparatus comprising an adjustment module. In some embodiments, an adjustment module or an apparatus comprising an adjustment module is required to adjust an elevation. An apparatus comprising an adjustment module can comprise at least one processor. In some embodiments, an adjusted elevation is provided by an apparatus that includes a processor (e.g., one or more processors) which processor can perform and/or implement one or more instructions (e.g., processes, routines and/or subroutines) from the adjustment module. In some embodiments, an elevation is adjusted by an apparatus that may include multiple processors, such as processors coordinated and working in parallel. In some embodiments, an adjustment module operates with one or more external processors (e.g., an internal or external network, server, storage device and/or storage network (e.g., a cloud)). In certain embodiments an apparatus comprising an adjustment module gathers, assembles and/or receives data and/or information from another module or apparatus. In certain embodiments an apparatus comprising an adjustment module provides and/or transfers data and/or information to another module or apparatus.

In certain embodiments an adjustment module receives and gathers data and/or information from a component or peripheral. Often an adjustment module receives, gathers and/or assembles counts, elevations, profiles, reference elevations, expected elevations, expected elevation ranges, uncertainty values, adjustments and/or constants. Often an adjustment module receives gathers and/or assembles elevations (e.g., first elevations) that are categorized or determined to be copy number variations (e.g., a maternal copy number variation, fetal copy number variation, or a maternal copy number variation and a fetal copy number variation). In certain embodiments an adjustment module accepts and gathers input data and/or information from an operator of an apparatus. For example, sometimes an operator of an apparatus provides a constant, a threshold value, a formula or a predetermined value to a module. In some embodiments, data and/or information are provided by an apparatus that includes multiple processors, such as processors coordinated and working in parallel. In some embodiments, an elevation is adjusted by an apparatus comprising a suitable peripheral or component. An apparatus comprising an adjustment module can receive normalized data from a normalization module, ranges from a range setting module, comparison data from a comparison module, elevations identified (e.g., identified as a copy number variation) from a categorization module, and/or adjustment data from another adjustment module. An adjustment module can receive data and/or information, transform the received data and/or information and provide adjustments. Data and/or information derived from, or transformed by, an adjustment module can be transferred from an adjustment module to a categorization module or to a suitable apparatus and/or module. An elevation adjusted by methods described herein can be independently verified and/or adjusted by further testing (e.g., by targeted sequencing of maternal and or fetal nucleic acid).

Plotting Module

In some embodiments a count, an elevation, and/or a profile is plotted (e.g., graphed). In certain embodiments a plot (e.g., a graph) comprises an adjustment. In certain embodiments a plot comprises an adjustment of a count, an elevation, and/or a profile. In certain embodiments a count, an elevation, and/or a profile is plotted and a count, elevation, and/or a profile comprises an adjustment. Often a count, an elevation, and/or a profile is plotted and a count, elevation, and/or a profile are compared. In certain embodiments a copy number variation (e.g., an aneuploidy, copy number variation) is identified and/or categorized from a plot of a count, an elevation, and/or a profile. In certain embodiments an outcome is determined from a plot of a count, an elevation, and/or a profile. In some embodiments, a plot (e.g., a graph) is made (e.g., generated) by a plotting module or an apparatus comprising a plotting module. In some embodiments, a plotting module or an apparatus comprising a plotting module is required to plot a count, an elevation or a profile. A plotting module may display a plot or send a plot to a display (e.g., a display module). An apparatus comprising a plotting module can comprise at least one processor. In some embodiments, a plot is provided by an apparatus that includes a processor (e.g., one or more processors) which processor can perform and/or implement one or more instructions (e.g., processes, routines and/or subroutines) from the plotting module. In some embodiments, a plot is made by an apparatus that may include multiple processors, such as processors coordinated and working in parallel. In some embodiments, a plotting module operates with one or more external processors (e.g., an internal or external network, server, storage device and/or storage network (e.g., a cloud)). In certain embodiments an apparatus comprising a plotting module gathers, assembles and/or receives data and/or information from another module or apparatus. In certain embodiments a plotting module receives and gathers data and/or information from a component or peripheral. Often a plotting module receives, gathers, assembles and/or plots sequence reads, genomic sections, mapped reads, counts, elevations, profiles, reference elevations, expected elevations, expected elevation ranges, uncertainty values, comparisons, categorized elevations (e.g., elevations identified as copy number variations) and/or outcomes, adjustments and/or constants. In certain embodiments a plotting module accepts and gathers input data and/or information from an operator of an apparatus. For example, sometimes an operator of an apparatus provides a constant, a threshold value, a formula or a predetermined value to a plotting module. In some embodiments, data and/or information are provided by an apparatus that includes multiple processors, such as processors coordinated and working in parallel. In some embodiments, a count, an elevation and/or a profile is plotted by an apparatus comprising a suitable peripheral or component. An apparatus comprising a plotting module can receive normalized data from a normalization module, ranges from a range setting module, comparison data from a comparison module, categorization data from a categorization module, and/or adjustment data from an adjustment module. A plotting module can receive data and/or information, transform the data and/or information and provided plotted data. In certain embodiments an apparatus comprising a plotting module provides and/or transfers data and/or information to another module or apparatus. An apparatus comprising a plotting module can plot a count, an elevation and/or a profile and provide or transfer data and/or information related to the plotting to a suitable apparatus and/or module. Often a plotting module receives, gathers, assembles and/or plots elevations (e.g., profiles, first elevations) and transfers plotted data and/or information to and from an adjustment module and/or comparison module. Plotted data and/or information is sometimes transferred from a plotting module to a categorization module and/or a peripheral (e.g., a display or printer). In some embodiments, plots are categorized and/or determined to comprise a genetic variation (e.g., an aneuploidy) or a copy number variation (e.g., a maternal and/or fetal copy number variation). A count, an elevation and/or a profile plotted by methods described herein can be independently verified and/or adjusted by further testing (e.g., by targeted sequencing of maternal and or fetal nucleic acid).

Representation Module

In certain embodiments, a chromosome representation is determined by a representation module. In certain embodiments, an ECR is determined by an expected representation module. In certain embodiments, an MCR is determined by a representation module. A representation module can be a representation module or an expected representation module. In some embodiments, a representation module determines one or more ratios. As used herein the term "ratio" refers to a numerical value (e.g., a number arrived at) by dividing a first numerical value by a second numerical value. For example, a ratio between A and B can be expressed mathematically as A/B or B/A and a numerical value for the ratio can be obtained by dividing A by B or by dividing B by A. In certain embodiments, a representation module (e.g., a representation module) determines an MCR by generating a ratio of counts. In certain embodiments a representation module determines an MCR for an affected autosome (e.g., chromosome 13 in the case of a trisomy 13, chromosome 18 in the case of a trisomy 18 or chromosome 21 in the case of a trisomy 21). For example, sometimes a representation module (e.g., a representation module) determines an MCR by generating a ratio of counts mapped to genomic sections of chromosome n to the total number of counts mapped to genomic sections of all autosomal chromosomes represented in a profile. In certain embodiments a representation module (e.g., a representation module) determines an MCR by generating a ratio of counts mapped to genomic sections of a sex chromosome (e.g., chromosome X or Y) to the total number of counts mapped to genomic sections of all autosomal chromosomes represented in a profile. In certain embodiments, a representation module (e.g., an expected representation module) determines an ECR by generating a ratio of genomic sections. In certain embodiments an expected representation module determines an ECR for an affected autosome (e.g., chromosome 13 the case of a trisomy 13, chromosome 18 in the case of a trisomy 18 or chromosome 21 in the case of a trisomy 21). For example, sometimes a representation module (e.g., an expected representation module) determines an ECR by generating a ratio of genomic sections for chromosome n to all autosomal genomic sections in a profile. In some embodiments, a representation module can provide a ratio of an MCR to an ECR. In certain embodiments a representation module or an apparatus comprising a representation module gathers, assembles, receives, provides and/or transfers data and/or information to or from another module, apparatus, component, peripheral or operator of an apparatus. For example, sometimes an operator of an apparatus provides a constant, a threshold value, a formula or a predetermined value to a representation module. A representation module can receive data and/or information from a sequencing module, sequencing module, mapping module, counting module, normalization module, comparison module, range setting module, categorization module, adjustment module, plotting module, outcome module, data display organization module and/or logic processing module. In certain embodiments normalized mapped counts are transferred to a representation module from a normalization module. In certain embodiments normalized mapped counts are transferred to an expected representation module from a normalization module. Data and/or information derived from or transformed by a representation module can be transferred from a representation module to a normalization module, comparison module, range setting module, categorization module, adjustment module, plotting module, outcome module, data display organization module, logic processing module, fetal fraction module or other suitable apparatus and/or module. In certain embodiments an MCR for chromosome 21, 18, 15, an X and/or a Y chromosome is transferred to a fetal fraction module from a representation module (e.g., a representation module). In certain embodiments an ECR for chromosome 21, 18, 15, an X and/or a Y chromosome is transferred to a fetal fraction module from a representation module (e.g., an expected representation module). An apparatus comprising a representation module can comprise at least one processor. In some embodiments, a representation is provided by an apparatus that includes a processor (e.g., one or more processors) which processor can perform and/or implement one or more instructions (e.g., processes, routines and/or subroutines) from the representation module. In some embodiments, a representation module operates with one or more external processors (e.g., an internal or external network, server, storage device and/or storage network (e.g., a cloud)).

Relationship Module

In certain embodiments, a relationship is determined by a relationship module. In some embodiments a relationship is generated for a fetal fraction determination and an MCR of an X or a Y chromosome by a relationship module. In some embodiments a relationship is generated for (i) a fetal fraction determined by a first method and (ii) a fetal fraction determined by a second method by a relationship module. In certain embodiments a relationship module or an apparatus comprising a relationship module gathers, assembles, receives, provides and/or transfers data and/or information to or from another module, apparatus, component, peripheral or operator of an apparatus. For example, sometimes an operator of an apparatus provides a constant, a threshold value, a formula or a predetermined value to a relationship module. A relationship module can receive data and/or information from a sequencing module, sequencing module, mapping module, counting module, normalization module, comparison module, range setting module, categorization module, adjustment module, plotting module, outcome module, data display organization module, logic processing module and/or a representation module. Data and/or information derived from or transformed by a relationship module can be transferred from a relationship module to a normalization module, comparison module, range setting module, categorization module, adjustment module, plotting module, outcome module, data display organization module, logic processing module, representation module, fetal fraction module or other suitable apparatus and/or module. An apparatus comprising a relationship module can comprise at least one processor. In some embodiments, data and/or information are provided by an apparatus that includes a processor (e.g., one or more processors) which processor can perform and/or implement one or more instructions (e.g., processes, routines and/or subroutines) from the relationship module. In some embodiments, a relationship module operates with one or more external processors (e.g., an internal or external network, server, storage device and/or storage network (e.g., a cloud)).

Fetal Fraction Module

In certain embodiments, a fetal fraction is determined by a fetal fraction module. In certain embodiments a fetal fraction module or an apparatus comprising a fetal fraction module gathers, assembles, receives, provides and/or transfers data and/or information to or from another module, apparatus, component, peripheral or operator of an apparatus. For example, sometimes an operator of an apparatus provides a constant, a threshold value, a formula or a predetermined value to a fetal fraction module. A fetal fraction module can receive data and/or information from a sequencing module, sequencing module, mapping module, weighting module, filtering module, counting module, normalization module, comparison module, range setting module, categorization module, adjustment module, plotting module, outcome module, data display organization module, logic processing module, a representation module and/or a relationship module. Data and/or information derived from or transformed by a fetal fraction module can be transferred from a fetal fraction module to a normalization module, comparison module, range setting module, categorization module, adjustment module, plotting module, outcome module, data display organization module, logic processing module, representation module, relationship module, fetal fraction module or other suitable apparatus and/or module. An apparatus comprising a fetal fraction module can comprise at least one processor. In some embodiments, data and/or information are provided by an apparatus that includes a processor (e.g., one or more processors) which processor can perform and/or implement one or more instructions (e.g., processes, routines and/or subroutines) from the fetal fraction module. In some embodiments, a fetal fraction module operates with one or more external processors (e.g., an internal or external network, server, storage device and/or storage network (e.g., a cloud)).

In some embodiments an apparatus (e.g., a first apparatus) comprises a normalization module, a representation module, an expected representation module, a fetal fraction module and a relationship module. In some embodiments an apparatus (e.g., a second apparatus) comprises a mapping module and a counting module. In certain embodiments an apparatus (e.g., a third apparatus) comprises a sequencing module.

Outcome Module

The presence or absence of a genetic variation (an aneuploidy, a fetal aneuploidy, a copy number variation) can be identified by an outcome module or by an apparatus comprising an outcome module. In certain embodiments a genetic variation is identified by an outcome module. Often a determination of the presence or absence of an aneuploidy is identified by an outcome module. In some embodiments, an outcome determinative of a genetic variation (an aneuploidy, a copy number variation) can be identified by an outcome module or by an apparatus comprising an outcome module. An outcome module can be specialized for determining a specific genetic variation (e.g., a trisomy, a trisomy 21, a trisomy 18). For example, an outcome module that identifies a trisomy 21 can be different than and/or distinct from an outcome module that identifies a trisomy 18. In some embodiments, an outcome module or an apparatus comprising an outcome module is required to identify a genetic variation or an outcome determinative of a genetic variation (e.g., an aneuploidy, a copy number variation). An apparatus comprising an outcome module can comprise at least one processor. In some embodiments, a genetic variation or an outcome determinative of a genetic variation is provided by an apparatus that includes a processor (e.g., one or more processors) which processor can perform and/or implement one or more instructions (e.g., processes, routines and/or subroutines) from the outcome module. In some embodiments, a genetic variation or an outcome determinative of a genetic variation is identified by an apparatus that may include multiple processors, such as processors coordinated and working in parallel. In some embodiments, an outcome module operates with one or more external processors (e.g., an internal or external network, server, storage device and/or storage network (e.g., a cloud)). In certain embodiments an apparatus comprising an outcome module gathers, assembles and/or receives data and/or information from another module or apparatus. In certain embodiments an apparatus comprising an outcome module provides and/or transfers data and/or information to another module or apparatus. In certain embodiments an outcome module transfers, receives or gathers data and/or information to or from a component or peripheral. Often an outcome module receives, gathers and/or assembles counts, elevations, profiles, normalized data and/or information, reference elevations, expected elevations, expected ranges, uncertainty values, adjustments, adjusted elevations, plots, categorized elevations, comparisons and/or constants. In certain embodiments an outcome module accepts and gathers input data and/or information from an operator of an apparatus. For example, sometimes an operator of an apparatus provides a constant, a threshold value, a formula or a predetermined value to an outcome module. In some embodiments, data and/or information are provided by an apparatus that includes multiple processors, such as processors coordinated and working in parallel. In some embodiments, identification of a genetic variation or an outcome determinative of a genetic variation is provided by an apparatus comprising a suitable peripheral or component. An apparatus comprising an outcome module can receive normalized data from a normalization module, expected elevations and/or ranges from a range setting module, comparison data from a comparison module, categorized elevations from a categorization module, plots from a plotting module, and/or adjustment data from an adjustment module. An outcome module can receive data and/or information, transform the data and/or information and provide an outcome. An outcome module can provide or transfer data and/or information related to a genetic variation or an outcome determinative of a genetic variation to a suitable apparatus and/or module. A genetic variation or an outcome determinative of a genetic variation identified by methods described herein can be independently verified by further testing (e.g., by targeted sequencing of maternal and/or fetal nucleic acid).

Transformations

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These procedures can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

Fetal Fraction Determination Systems, Apparatus and Computer Program Products

Provided in certain aspects is a system comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to: (a) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof; and (b) determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X chromosome representation.

Also provided in certain aspects is an apparatus comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to: (a) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof; and (b) determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X chromosome representation.

Provided also in certain aspects is a computer program product tangibly embodied on a computer-readable medium, comprising instructions that when executed by one or more processors are configured to: (a) access counts of nucleic acid sequence reads mapped to genomic sections of a reference genome, which sequence reads are reads of circulating cell-free nucleic acid from the blood of a pregnant female bearing a male fetus; (b) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof; and (c) determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X chromosome representation.

Also provided in certain aspects is a system comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to: (a) generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental Y chromosome representation.

Provided also in certain aspects is an apparatus comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to: (a) generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental Y chromosome representation.

Also provided in certain aspects is a computer program product tangibly embodied on a computer-readable medium, comprising instructions that when executed by one or more processors are configured to: (a) access counts of nucleic acid sequence reads mapped to genomic sections of a reference genome, which sequence reads are reads of circulating cell-free nucleic acid from the blood of a pregnant female bearing a male fetus; (b) generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (c) determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental Y chromosome representation.

Provided also in certain aspects is a system comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to: (a) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof, and generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X and the experimental Y chromosome representation.

Also provided in certain aspects is an apparatus comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to: (a) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof, and generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X and the experimental Y chromosome representation.

Also provided in certain aspects is a computer program product tangibly embodied on a computer-readable medium, comprising instructions that when executed by one or more processors are configured to: (a) access counts of nucleic acid sequence reads mapped to genomic sections of a reference genome, which sequence reads are reads of circulating cell-free nucleic acid from the blood of a pregnant female bearing a male fetus; (b) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof, and generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (c) determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X and the experimental Y chromosome representation.

Provided also is a system comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a fetus bearing a trisomy of an autosome, which autosome is an affected autosome; and which instructions executable by the one or more processors are configured to: (a) generate an experimental affected autosome representation, which experimental affected autosome representation is a ratio of (i) counts of sequence reads mapped to the genomic sections of the reference genome in the affected autosome, and (ii) counts of sequence reads mapped to genomic sections of the reference genome in the genome or segment thereof; and (b) determine the fraction of the fetal nucleic acid in the blood of the pregnant female according to a relationship determined from (i) a fraction of fetal nucleic acid determined for nucleic acid from the blood of a pregnant female bearing a fetus having a chromosome aneuploidy, and (ii) the experimental affected autosome representation.

Also provided in certain aspects is an apparatus comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a fetus bearing a trisomy of an autosome, which autosome is an affected autosome; and which instructions executable by the one or more processors are configured to: (a) generate an experimental affected autosome representation, which experimental affected autosome representation is a ratio of (i) counts of sequence reads mapped to the genomic sections of the reference genome in the affected autosome, and (ii) counts of sequence reads mapped to genomic sections of the reference genome in the genome or segment thereof; and (b) determine the fraction of the fetal nucleic acid in the blood of the pregnant female according to a relationship determined from (i) a fraction of fetal nucleic acid determined for nucleic acid from the blood of a pregnant female bearing a fetus having a chromosome aneuploidy, and (ii) the experimental affected autosome representation.

Provided also in certain aspects is a computer program product tangibly embodied on a computer-readable medium, comprising instructions that when executed by one or more processors are configured to: (a) access counts of nucleic acid sequence reads mapped to genomic sections of a reference genome, which sequence reads are reads of circulating cell-free nucleic acid from the blood of a pregnant female bearing a fetus bearing a trisomy of an autosome, which autosome is an affected autosome; (b) generate an experimental affected autosome representation, which experimental affected autosome representation is a ratio of (i) counts of sequence reads mapped to the genomic sections of the reference genome in the affected autosome, and (ii) counts of sequence reads mapped to genomic sections of the reference genome in the genome or segment thereof; and (c) determine the fraction of the fetal nucleic acid in the blood of the pregnant female according to a relationship determined from (i) a fraction of fetal nucleic acid determined for nucleic acid from the blood of a pregnant female bearing a fetus having a chromosome aneuploidy, and (ii) the experimental affected autosome representation.

In certain embodiments, the system, apparatus and/or computer program product comprises a: (i) a sequencing module configured to obtain nucleic acid sequence reads; (ii) a mapping module configured to map nucleic acid sequence reads to portions of a reference genome; (iii) a weighting module configured to weight genomic sections, (iv) a filtering module configured to filter genomic sections or counts mapped to a genomic section; (v) a counting module configured to provide counts of nucleic acid sequence reads mapped to portions of a reference genome; (vi) a normalization module configured to provide normalized counts; (vii) a comparison module configured to provide an identification of a first elevation that is significantly different than a second elevation; (viii) a range setting module configured to provide one or more expected level ranges; (ix) a categorization module configured to identify an elevation representative of a copy number variation; (x) an adjustment module configured to adjust a level identified as a copy number variation; (xi) a plotting module configured to graph and display a level and/or a profile; (xii) an outcome module configured to determine an outcome (e.g., outcome determinative of the presence or absence of a fetal aneuploidy); (xiii) a data display organization module configured to indicate the presence or absence of a segmental chromosomal aberration or a fetal aneuploidy or both; (xiv) a logic processing module configured to perform one or more of map sequence reads, count mapped sequence reads, normalize counts and generate an outcome; (xv) a representation module configured to determine an experimental chromosome representation (e.g., X chromosome representation, Y chromosome representation, autosome representation); (xvi) a relationship module configured to determine a relationship between (a) a fraction of fetal nucleic acid determined for nucleic acid from the blood of a pregnant female bearing a fetus having a chromosome aneuploidy, and (b) an experimental affected autosome representation for a sample; (xvii) a fetal fraction module configured to determine fetal fraction from an experimental chromosome representation; or (xviii) combination of two or more of the foregoing. In certain embodiments, the copy number variation categorized from the first elevation is a maternal copy number variation. In some embodiments, the copy number variation categorized from the first elevation is a fetal copy number variation.

In some embodiments the sequencing module and mapping module are configured to transfer sequence reads from the sequencing module to the mapping module. The mapping module and counting module sometimes are configured to transfer mapped sequence reads from the mapping module to the counting module. The counting module and filtering module sometimes are configured to transfer counts from the counting module to the filtering module. The counting module and weighting module sometimes are configured to transfer counts from the counting module to the weighting module. The mapping module and filtering module sometimes are configured to transfer mapped sequence reads from the mapping module to the filtering module. The mapping module and weighting module sometimes are configured to transfer mapped sequence reads from the mapping module to the weighting module. In certain embodiments the weighting module, filtering module and counting module are configured to transfer filtered and/or weighted genomic sections from the weighting module and filtering module to the counting module. The weighting module and normalization module sometimes are configured to transfer weighted genomic sections from the weighting module to the normalization module. The filtering module and normalization module sometimes are configured to transfer filtered genomic sections from the filtering module to the normalization module. In some embodiments, the normalization module and/or comparison module are configured to transfer normalized counts to the comparison module and/or range setting module. The comparison module, range setting module and/or categorization module independently are configured to transfer (i) an identification of a first elevation that is significantly different than a second elevation and/or (ii) an expected level range from the comparison module and/or range setting module to the categorization module, in some embodiments. In certain embodiments, the categorization module and the adjustment module are configured to transfer an elevation categorized as a copy number variation from the categorization module to the adjustment module and/or fetal fraction module. In some embodiments, the adjustment module, plotting module and the outcome module are configured to transfer one or more adjusted levels from the adjustment module to the plotting module, outcome module or fetal fraction module. The normalization module sometimes is configured to transfer mapped normalized sequence read counts to one or more of the comparison module, range setting module, categorization module, adjustment module, outcome module, plotting module, fetal fraction module or representation module. In some embodiments, a relationship module is configured to receive information from the representation module, and is configured to transfer information to the fetal fraction module.

EXAMPLES

The following examples are provided by way of illustration only and not by way of limitation. Thus, the examples set forth below illustrate certain embodiments and do not limit the technology. Those of skill in the art will readily recognize a variety of non-critical parameters that could be changed or modified to yield essentially the same or similar results.

Example 1: General Methods for Detecting Conditions Associated with Genetic Variations The methods and underlying theory described herein can be utilized to detect various conditions associated with genetic variation and provide an outcome determinative of, or determine the presence or absence of a genetic variation. Non-limiting examples of genetic variations that can be detected with a method described herein include, segmental chromosomal aberrations (e.g., deletions, duplications), aneuploidy, gender, sample identification, disease conditions associated with genetic variation, the like or combinations of the foregoing.

Bin Filtering

Figure 1:
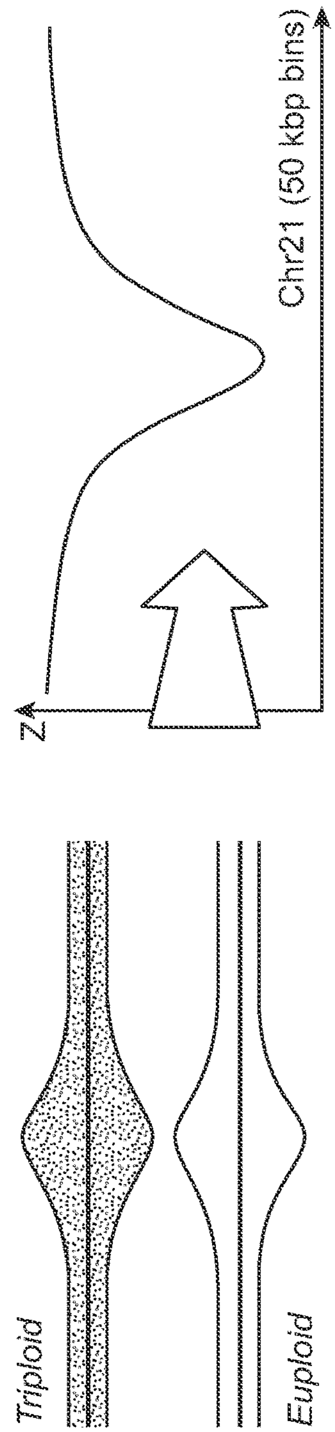
FIG. 1 graphically illustrates how increased uncertainty in bin counts within a genomic region sometimes reduces gaps between euploid and trisomy Z-values.
Figure 2:
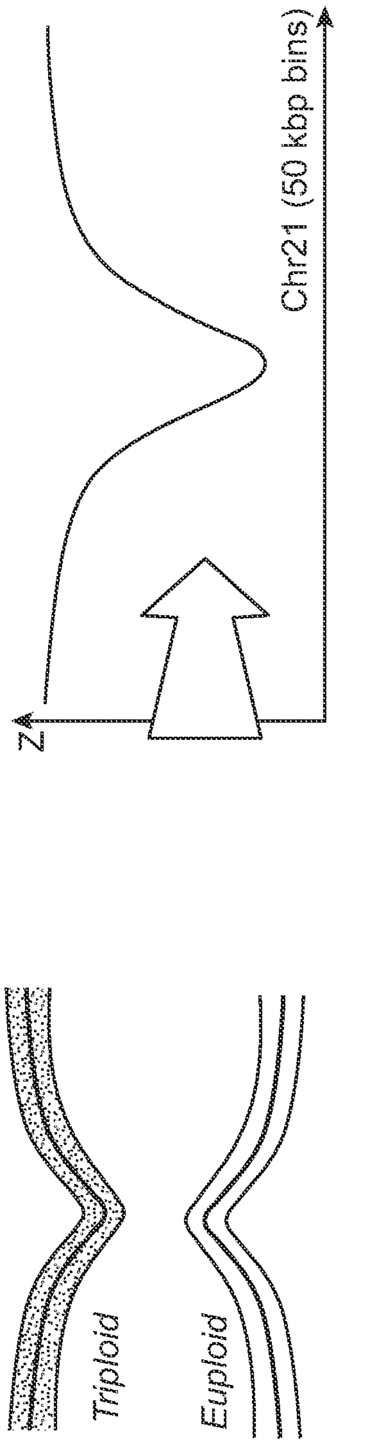
FIG. 2 graphically illustrates how decreased differences between triploid and euploid number of counts within a genomic region sometimes reduces predictive power of Z-scores. See Example 1 for experimental details and results.

The information content of a genomic region in a target chromosome can be visualized by plotting the result of the average separation between euploid and trisomy counts normalized by combined uncertainties, as a function of chromosome position. Increased uncertainty (see FIG. 1) or reduced gap between triploids and euploids (e.g. triploid pregnancies and euploid pregnancies) (see FIG. 2) both result in decreased Z-values for affected cases, sometimes reducing the predictive power of Z-scores.

Figure 3:
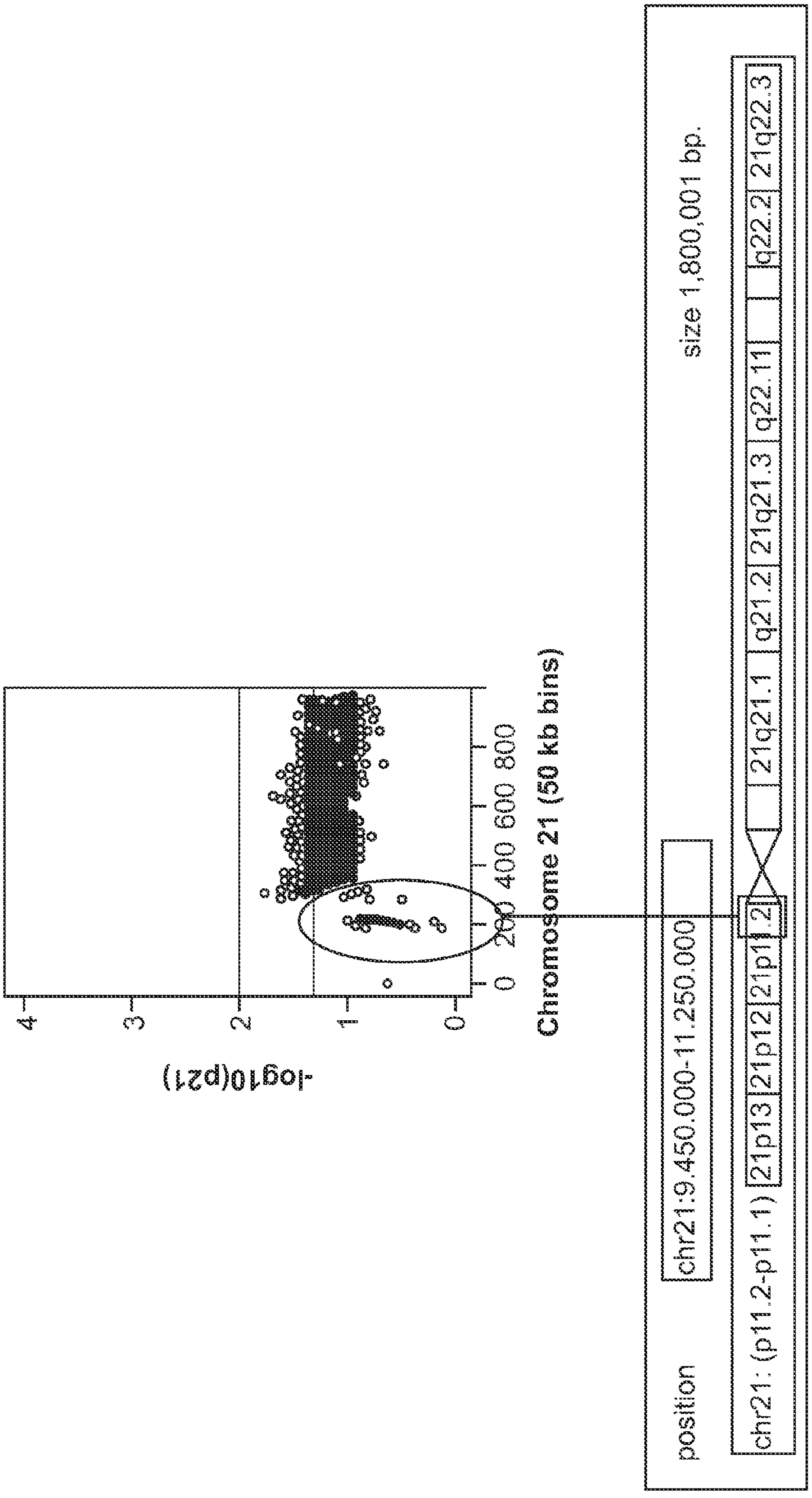
FIG. 3 graphically illustrates the dependence of p-values on the position of genomic bins within chromosome 21.

FIG. 3 graphically illustrates a p-value profile, based on t-distribution, plotted as a function of chromosome position along chromosome 21. Analysis of the data presented in FIG. 3 identifies 36 uninformative chromosome 21 bins, each about 50 kilo-base pairs (kbp) in length. The uninformative region is located in the p-arm, close to centromere (21p11.2-21p11.1). Removing all 36 bins from the calculation of Z-scores, as schematically outlined in FIG. 4, sometimes can significantly increase the Z-values for all trisomy cases, while introducing only random variations into euploid Z-values.

Figure 5:
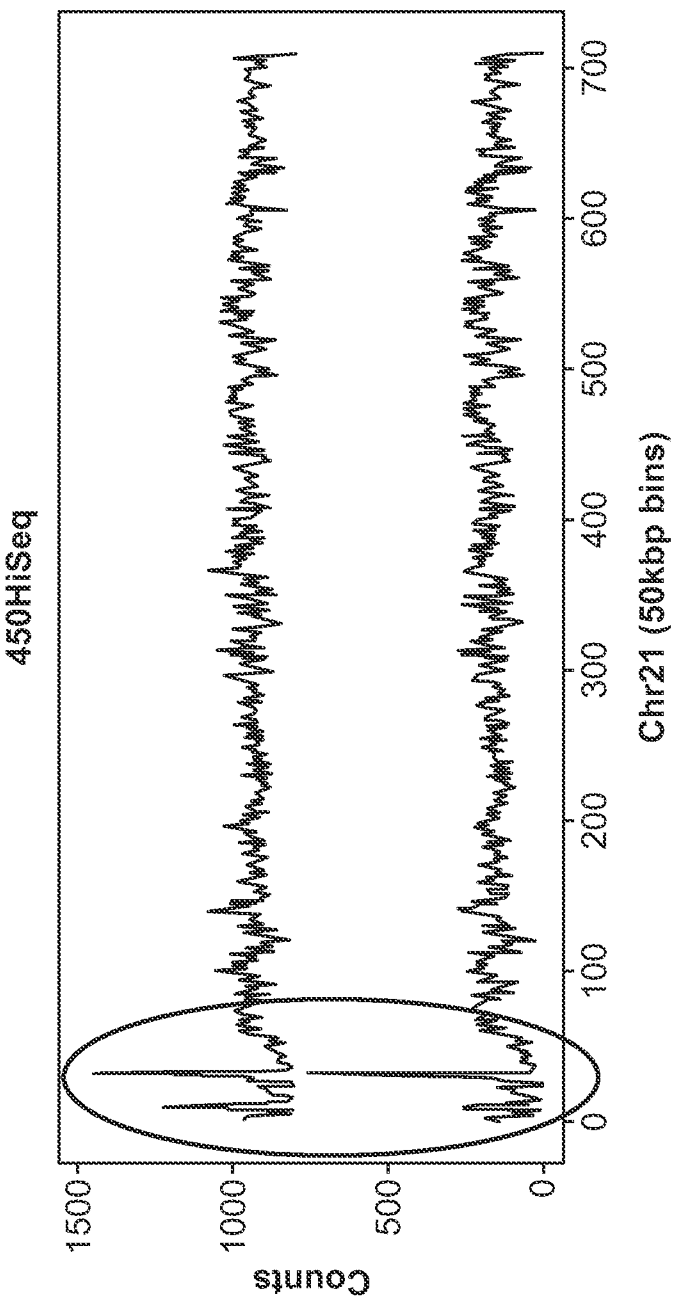
FIG. 5 graphically illustrates count profiles for chromosome 21 in two patients.

The improvement in predictive power afforded by removal of the 36 uninformative bins can be explained by examining the count profile for chromosome 21 (see FIG. 5). In FIG. 5, two arbitrarily chosen samples demonstrate the general tendency of count versus (vs) bin profiles to follow substantially similar trends, apart from short-range noise. The profiles shown in FIG. 5 are substantially parallel. The highlighted region of the profile plot presented in FIG. 5 (e.g., the region in the ellipse), while still exhibiting parallelism, also exhibit large fluctuations relative to the rest of chromosome. Removal of the fluctuating bins (e.g., the 36 uninformative bins) can improve precision and consistency of Z statistics, in some embodiments.

Bin Normalization

Filtering out uninformative bins, as described in Example 1, sometimes does not provide the desired improvement to the predictive power of Z-values. When chromosome 18 data is filtered to remove uninformative bins, as described in Example 1, the z-values did not substantially improve (see FIG. 6). As seen with the chromosome 21 count profiles presented in Example 1, the chromosome 18 count profiles also are substantially parallel, disregarding short range noise. However, two chromosome 18 samples used to evaluate binwise count uncertainties (see the bottom of FIG. 6) significantly deviate from the general parallelism of count profiles. The dips in the middle of the two traces, highlighted by the ellipse, represent large deletions. Other samples examined during the course of the experiment did not exhibit this deletion. The deletion coincides with the location of a dip in p-value profiles for chromosome 18, illustrated in by the ellipse shown in FIG. 7. That is, the dip observed in the p-value profiles for chromosome 18 are explained by the presence of the deletion in the chromosome 18 samples, which cause an increase in the variance of counts in the affected region. The variance in counts is not random, but represents a rare event (e.g., the deletion of a segment of chromosome 18), which, if included with other, random fluctuations from other samples, decreases the predictive power bin filtering procedure.

Two questions arise from this example; (1) how are p-value signals determined to be meaningful and/or useful, and (2) can the p-value approach described herein be generalized for use with any bin data (e.g., from within any chromosome, not only bins from within chromosomes 13, 18 or 21). A generalized procedure could be used to remove variability in the total counts for the entire genome, which can often be used as the normalization factor when evaluating Z-scores. The data presented in FIG. 8 can be used to investigate the answers to the questions above by reconstructing the general contour of the data by assigning the median reference count to each bin, and normalizing each bin count in the test sample with respect to the assigned median reference count.

The medians are extracted from a set of known euploid references. Prior to computing the reference median counts, uninformative bins throughout the genome are filtered out. The remaining bin counts are normalized with respect to the total residual number of counts. The test sample is also normalized with respect to the sum of counts observed for bins that are not filtered out. The resulting test profile often centers around a value of 1, except in areas of maternal deletions or duplication, and areas in which the fetus is triploid (see FIG. 9). The bin-wise normalized profile illustrated in FIG. 10 confirms the validity of the normalization procedure, and clearly reveals the heterozygous maternal deletion (e.g., central dip in the gray segment of the profile tracing) in chromosome 18 and the elevated chromosomal representation of chromosome 18 of the tested sample (see the gray area of profile tracing in FIG. 10). As can be seen from FIG. 10, the median value for the gray segment of the tracing centers around about 1.1, where the median value for the black segment of the tracing centers around 1.0.

Peak Elevation

Figure 11:
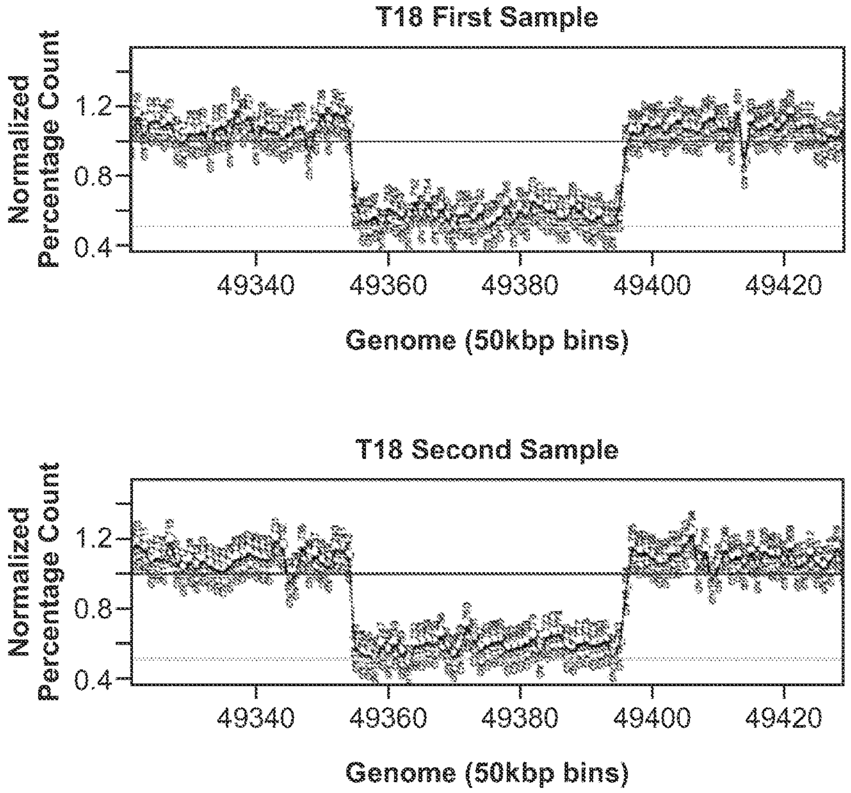
FIG. 11 graphically illustrates normalized binwise count profiles for two samples collected from the same patient with heterozygous maternal deletion in chromosome 18. The substantially identical tracings can be used to determine if two samples are from the same donor.

FIG. 11 graphically illustrates the results of analyzing multiple samples using bin-wise normalization, from a patient with a discernible feature or trait (e.g., maternal duplication, maternal deletion, the like or combinations thereof). The identities of the samples often can be determined by comparing their respective normalized count profiles. In the example illustrated in FIG. 11, the location of the dip in the normalized profile and its elevation, as well as its rarity, indicate that both samples originate from the same patient. Forensic panel data often can be used to substantiate these findings.

Figure 12:
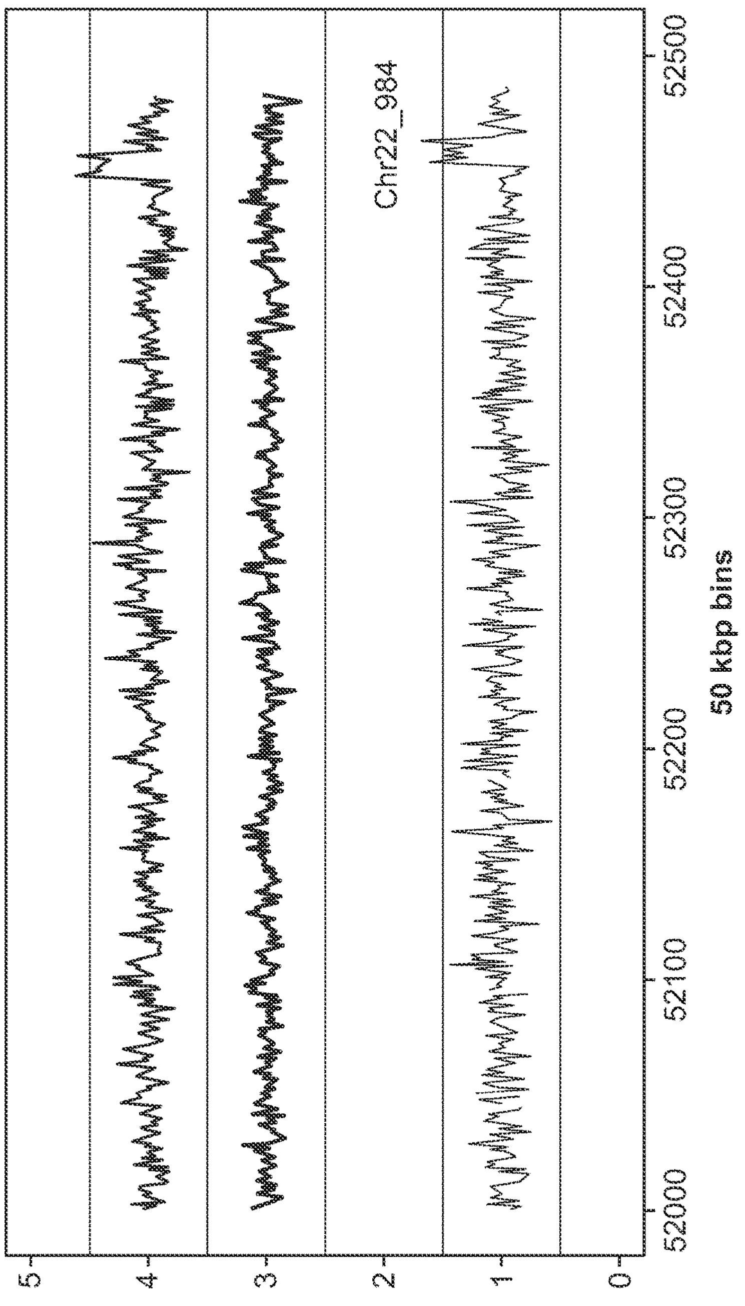
FIG. 12 graphically illustrates normalized binwise count profiles of a sample from one study, compared with two samples from a previous study. The duplication in chromosome 22 unambiguously points out the patient's identity.
Figure 13:
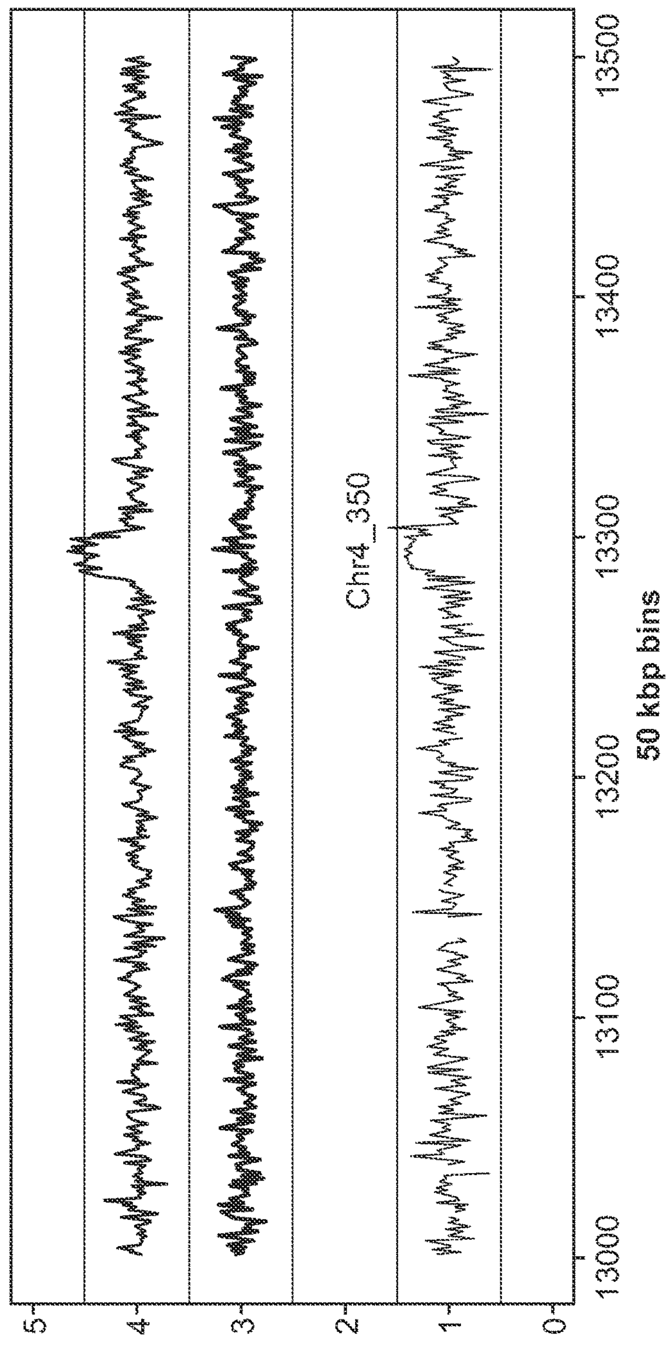
FIG. 13 graphically illustrates normalized binwise count profiles of chromosome 4 in the same three patients presented in FIG. 12. The duplication in chromosome 4 confirms the patient's identity established in FIG. 12. See Example 1 for experimental details and results.

FIGS. 12 and 13 graphically illustrate the results of the use of normalized bin profiles for identifying patient identity, or sample identity. The samples analyzed in FIGS. 12 and 13 carry wide maternal aberrations in chromosomes 4 and 22, which are absent in the other samples in the profile tracings, confirming the shared origin of the top and bottom traces. Results such as this can lead to the determination that a particular sample belongs to a specific patient, and also can be used to determine if a particular sample has already been analyzed.

Bin-wise normalization facilitates the detection of aberrations, however, comparison of peaks from different samples often is further facilitated by analyzing quantitative measures of peak elevations and locations (e.g., peak edges). The most prominent descriptor of a peak often is its elevation, followed by the locations of its edges. Features from different count profiles often can be compared using the following non-limiting analysis.

(a) Determine the confidence in a features detected peaks in a single test sample. If the feature is distinguishable from background noise or processing artifacts, the feature can be further analyzed against the general population.

(b) Determine the prevalence of the detected feature in the general population. If the feature is rare, it can be used as a marker for rare aberrations. Features that are found frequently in the general population are less useful for analysis. Ethnic origins can play a role in determining the relevance of a detected features peak elevation. Thus, some features provide useful information for samples from certain ethnic origins.

(c) Derive the confidence in the comparison between features observed in different samples.

Figure 14:
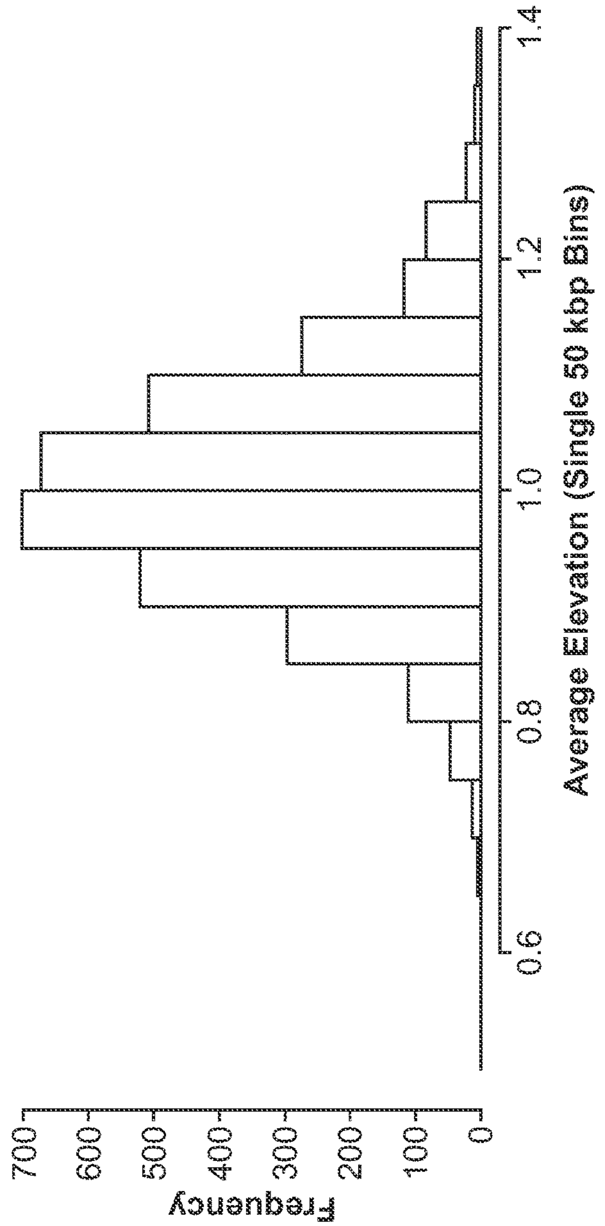
FIG. 14 graphically illustrates the distribution of normalized bin counts in chromosome 5 from a euploid sample.
Figure 15:
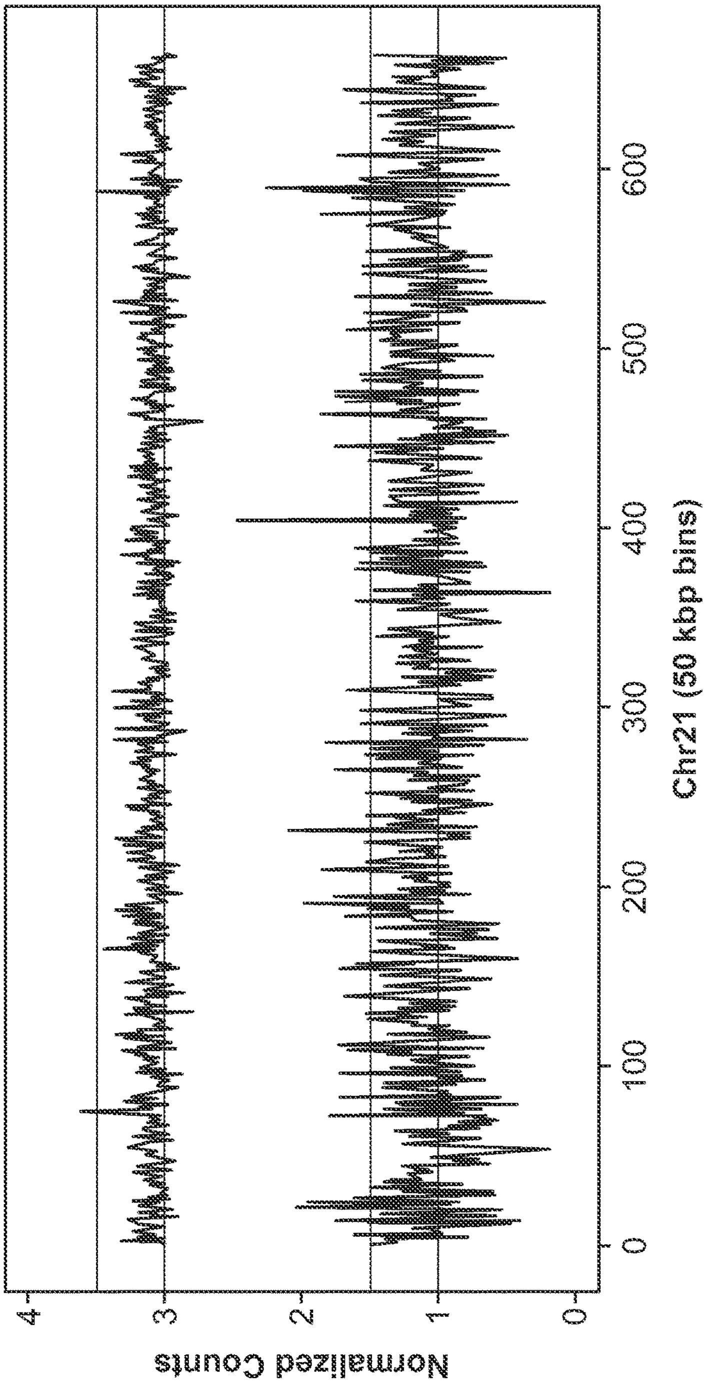
FIG. 15 graphically illustrates two samples with different levels of noise in their normalized count profiles.
Figure 16:
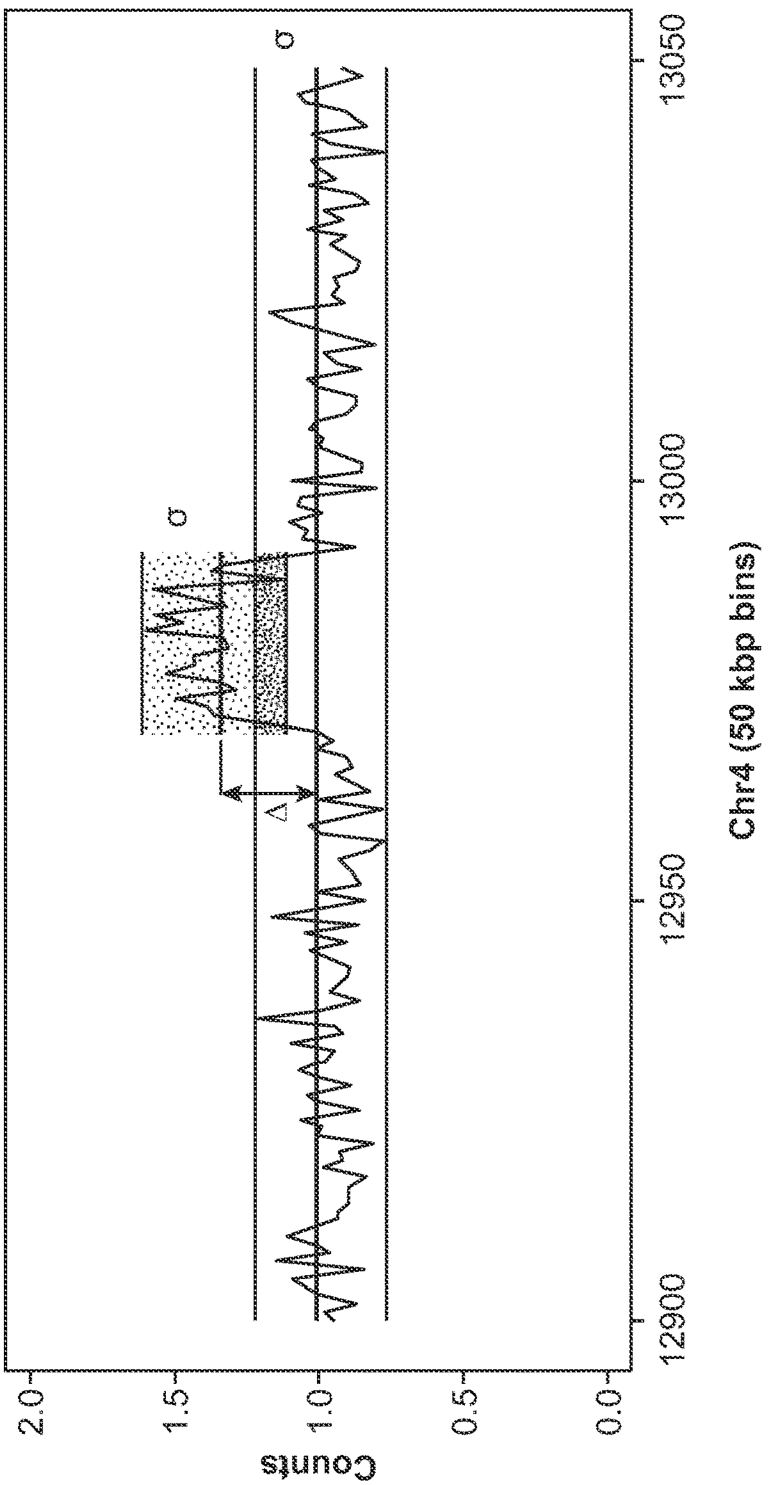
FIG. 16 schematically represents factors determining the confidence in peak elevation: noise standard deviation (e.g., $\sigma$) and average deviation from the reference baseline (e.g., $\Delta$). See Example 1 for experimental details and results.
Figure 17:
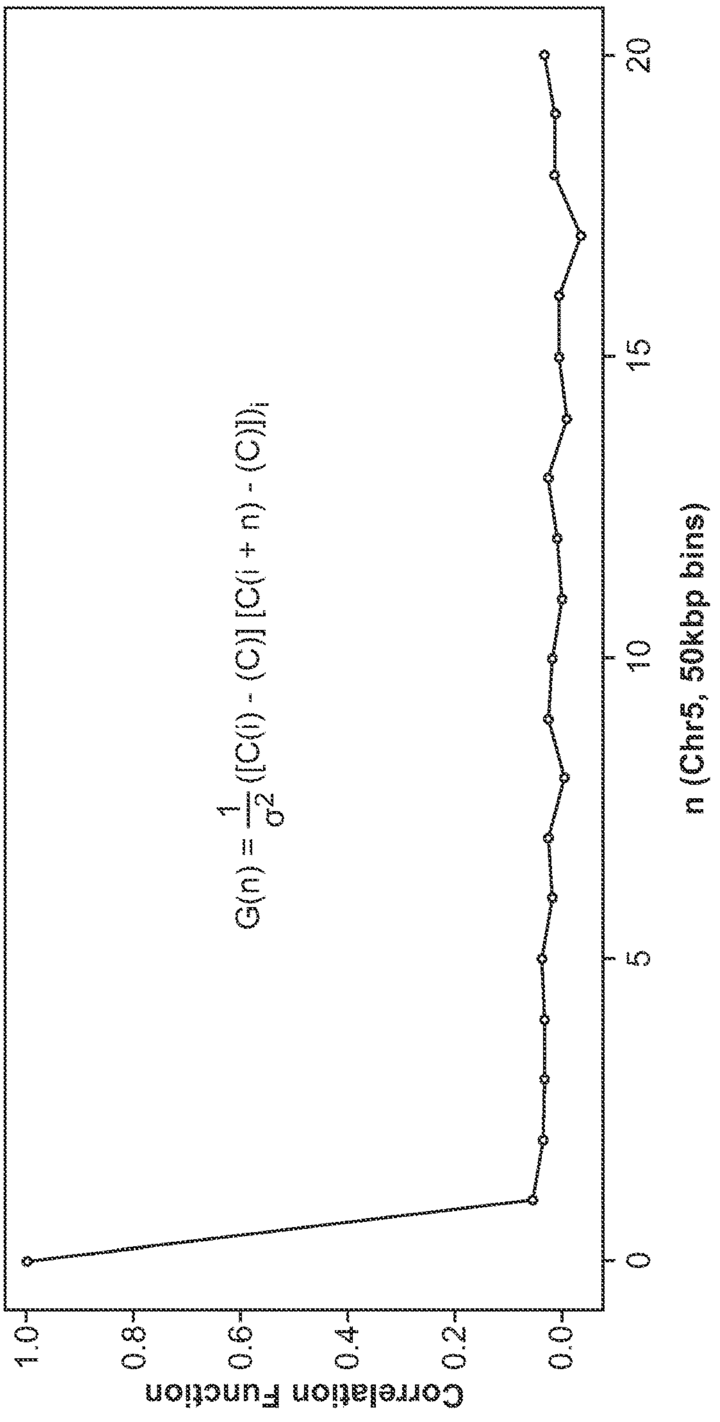
FIG. 17 graphically illustrates the results of applying a correlation function to normalized bin counts. The correlation function shown in FIG. 17 was used to normalize bin counts in chromosome 5 of an arbitrarily chosen euploid patient.
Figure 18:
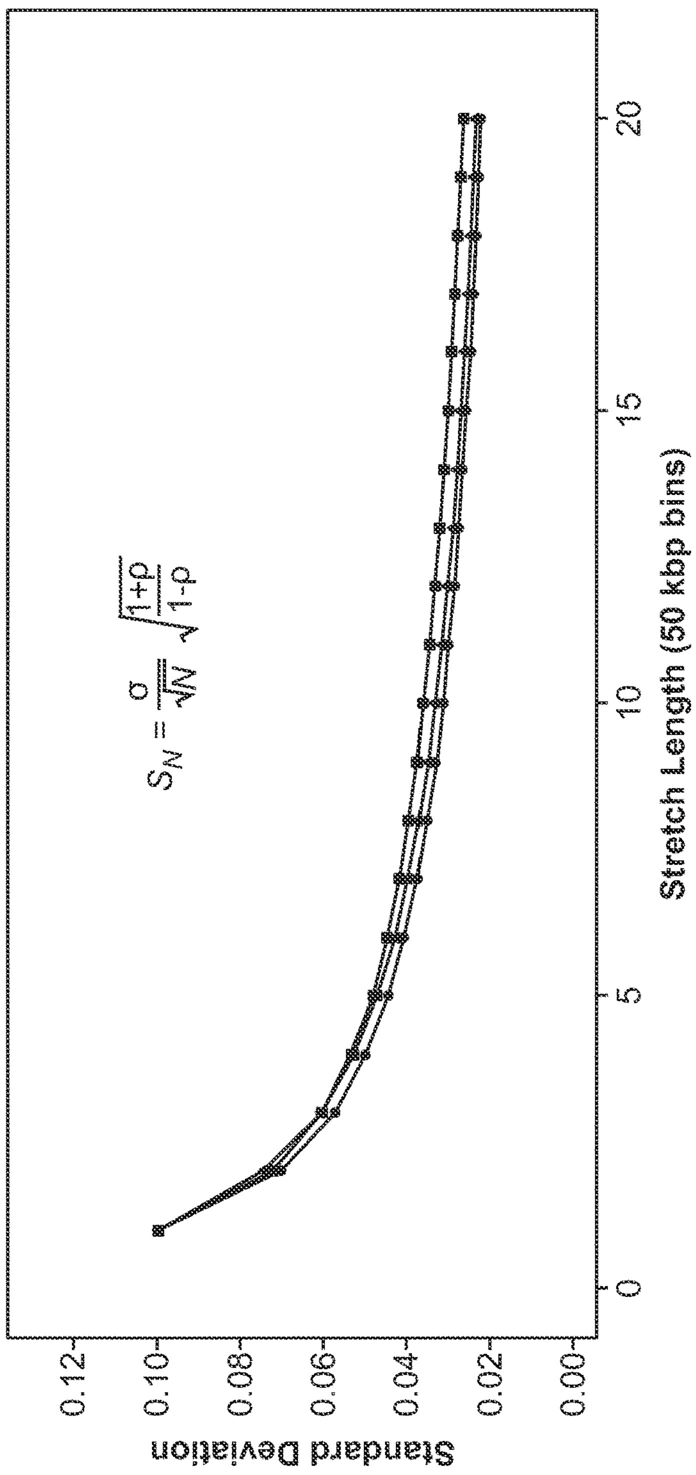
FIG. 18 graphically illustrates the standard deviation for the average stretch elevation in chromosome 5, evaluated as a sample estimate (square data points) and compared with the standard error of the mean (triangle data points) and with the estimate corrected for auto-correlation $\rho$=0.5 (circular data points). The aberration depicted in FIG. 18 is about 18 bins long. See Example 1 for experimental details and results.
Figure 19:
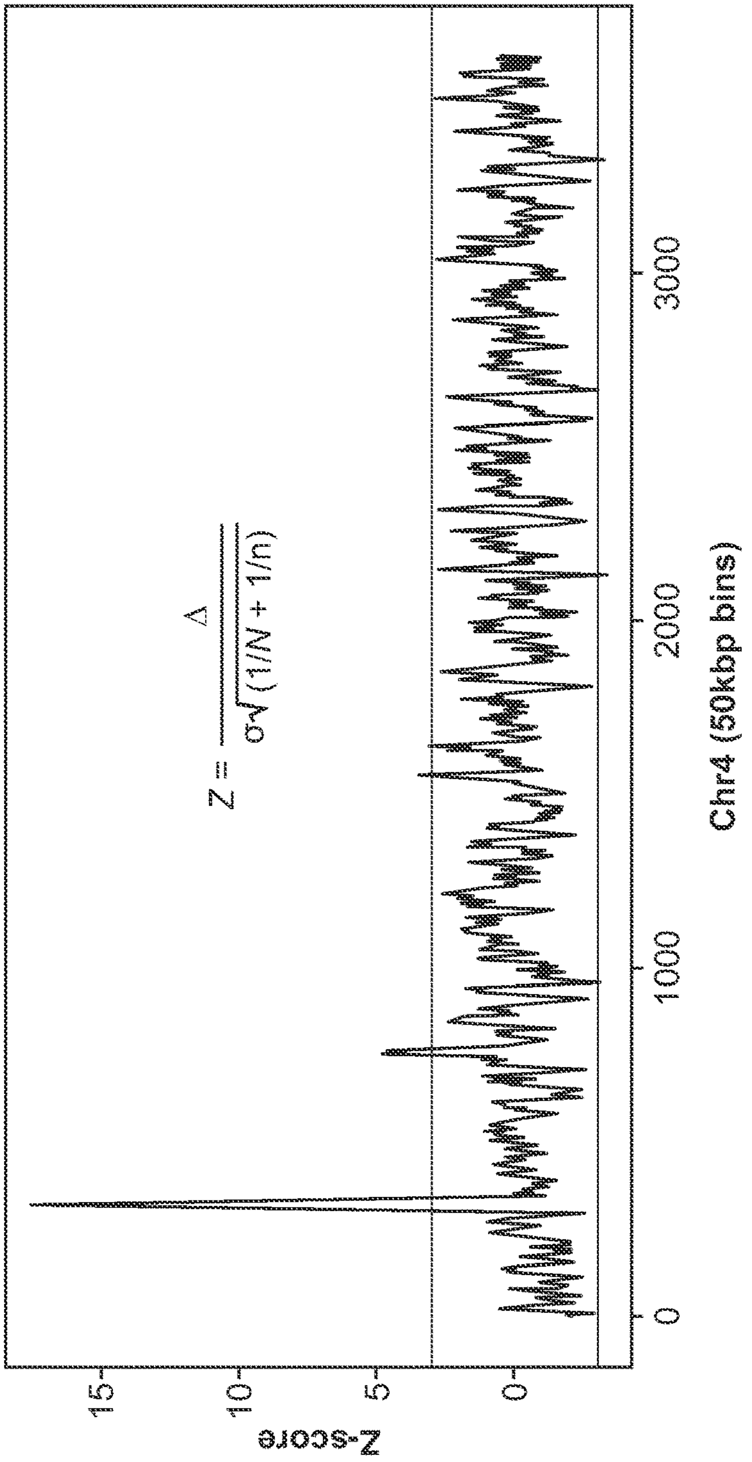
FIG. 19 graphically illustrates Z-values calculated for average peak elevation in chromosome 4. The patient has a heterozygous maternal duplication in chromosome 4 (see FIG. 13).
Figure 20:
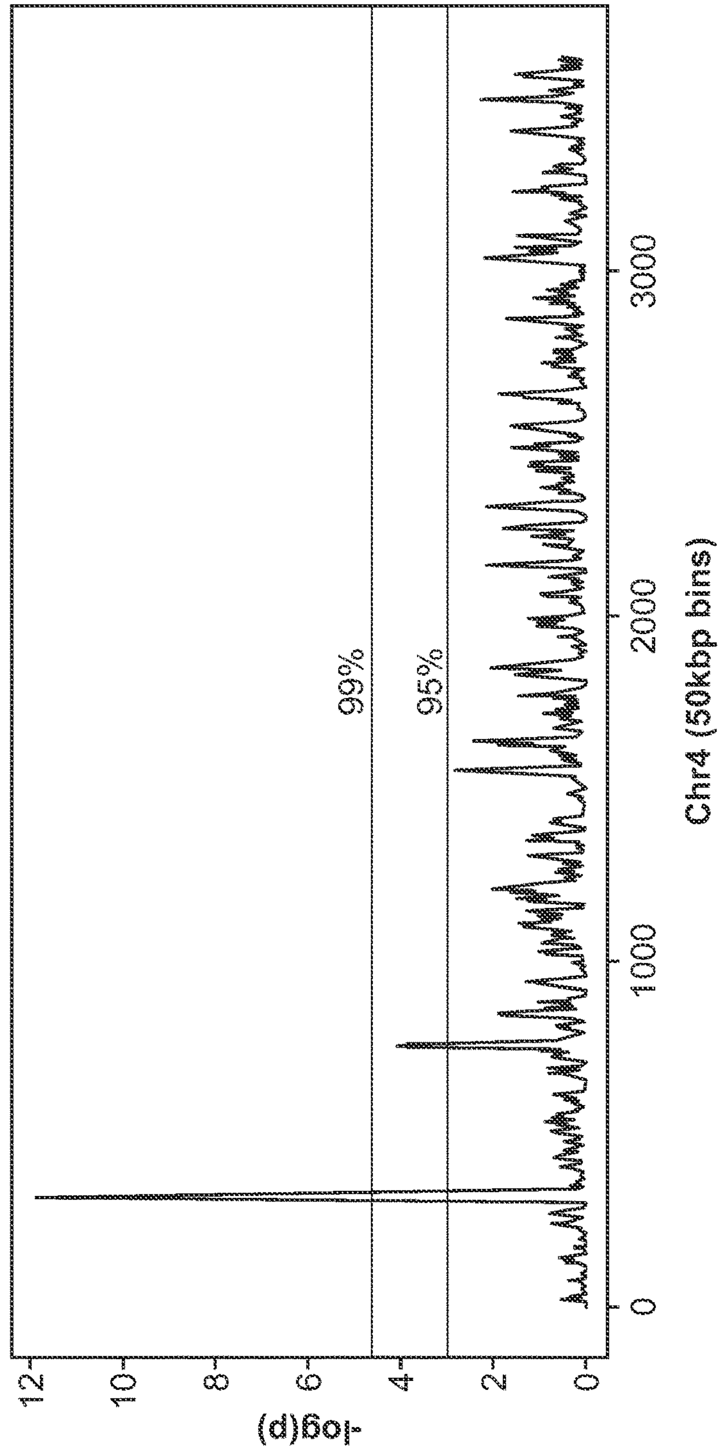
FIG. 20 graphically illustrates p-values for average peak elevation, based on a t-test and the Z-values from FIG. 19. The order of the t-distribution is determined by the length of the aberration. See Example 1 for experimental details and results.

Illustrated in FIG. 14 are the normalized bin counts in chromosome 5, from a euploid subject. The average elevation generally is the reference baseline from which the elevations of aberrations are measured, in some embodiments. Small and/or narrow deviations are less reliable predictors than wide, pronounced aberrations. Thus, the background noise or variance from low fetal contribution and/or processing artifacts is an important consideration when aberrations are not large or do not have a significant peak elevation above the background. An example of this is presented in FIG. 15, where a peak that would be significant in the upper trace, can be masked in the background noise observed in the bottom profile trace. The confidence in the peak elevation (see FIG. 16) can be determined by the average deviation from the reference (shown as the delta symbol), relative to the width of the euploid distribution (e.g., combined with the variance (shown as the sigma symbol) in the average deviation). The error in the average stretch elevation can be derived from the known formula for the error of the mean. If a stretch longer than one bin is treated as a random (non-contiguous) sample of all bins within a chromosome, the error in the average elevation decreases with the square root of the number of bins within the aberration. This reasoning neglects the correlation between neighboring bins, an assumption confirmed by the correlation function shown in FIG. 17 (e.g., the equation for G(n)). Non-normalized profiles sometimes exhibit strong medium-range correlations (e.g., the wavelike variation of the baseline), however, the normalized profiles smooth out the correlation, leaving only random noise. The close match between the standard error of the mean, the correction for autocorrelation, and the actual sample estimates of the standard deviation of the mean elevation in chromosome 5 (see FIG. 18) confirms the validity of the assumed lack of correlation. Z-scores (see FIG. 19) and p-values calculated from Z-scores associated with deviations from the expected elevation of 1 (see FIG. 20) can then be evaluated in light of the estimate for uncertainty in the average elevation. The p-values are based on a t-distribution whose order is determined by the number of bins in a peak. Depending on the desired level of confidence, a cutoff can suppress noise and allow unequivocal detection of the actual signal.

$$Z = \frac{\Delta_1 - \Delta_2}{\sqrt{\sigma_1^2\left(\frac{1}{N_1} + \frac{1}{n_1}\right) + \sigma_2^2\left(\frac{1}{N_2} + \frac{1}{n_2}\right)}} \quad (1)$$

Equation 1 can be used to directly compare peak elevation from two different samples, where N and n refer to the numbers of bins in the entire chromosome and within the aberration, respectively. The order of the t-test that will yield a p-value measuring the similarity between two samples is determined by the number of bins in the shorter of the two deviant stretches.

Peak Edge

Figure 21:
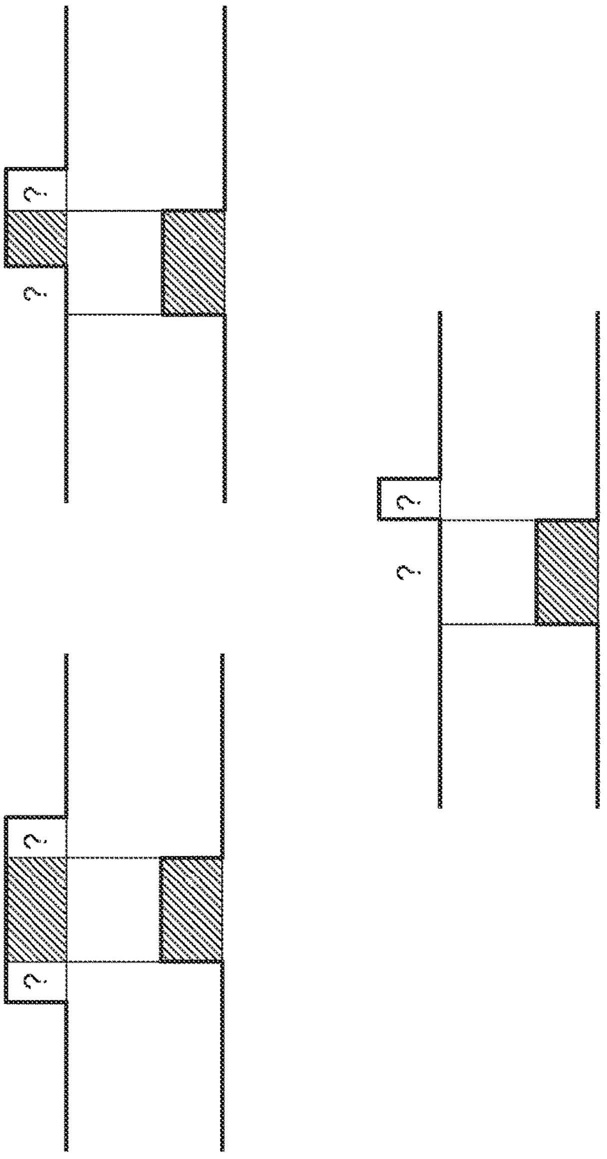
FIG. 21 schematically represents edge comparisons between matching aberrations from different samples. Illustrated in FIG. 21 are overlaps, containment, and neighboring deviations.
Figure 22:
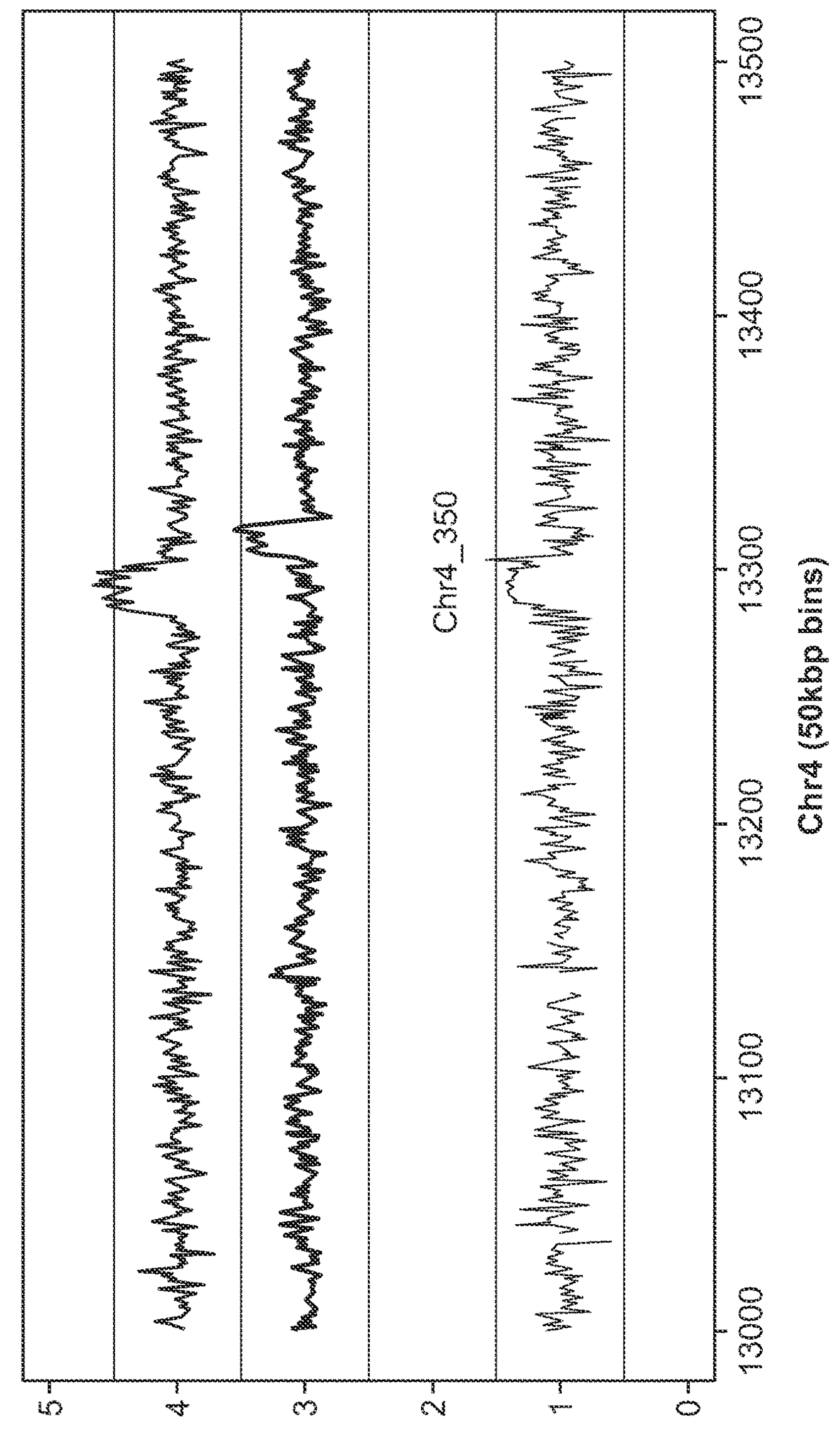
FIG. 22 graphically illustrates matching heterozygous duplications in chromosome 4 (dark gray top trace and black bottom trace), contrasted with a marginally touching aberration in an unrelated sample (light gray middle trace). See Example 1 for experimental details and results.

In addition to comparing average elevations of aberrations in a sample, the beginning and end of the compared stretches also can provide useful information for statistical analysis. The upper limit of resolution for comparisons of peak edges often is determined by the bin size (e.g., 50 kbps in the examples described herein). FIG. 21 illustrates 3 possible peak edge scenarios; (a) a peak from one sample can be completely contained within the matching peak from another sample, (b) the edges from one sample can partially overlap the edges of another sample, or (c) the leading edge from one sample can just marginally touch or overlap the trailing edge of another sample. FIG. 22 illustrates and example of the scenario described in (c) (e.g., see the middle, light gray trace, where the trailing edge of the middle trace marginally touches the leading edge of the upper trace).

Figure 23:
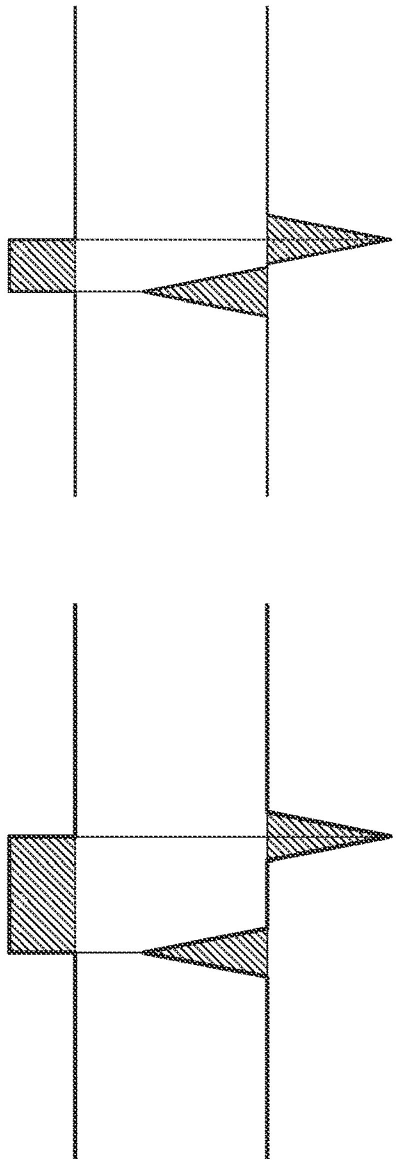
FIG. 23 schematically represents edge detection by means of numerically evaluated first derivatives of count profiles.

The lateral tolerance associated with an edge often can be used to distinguish random variations from true, aberration edges. The position and the width of an edge can be quantified by numerically evaluating the first derivative of the aberrant count profile, as shown in FIG. 23. If the aberration is represented as a composite of two Heaviside functions, its derivative will be the sum of two Dirac's delta functions. The starting edge corresponds to an upward absorption-shaped peak, while the ending edge is a downward, 180 degree-shifted absorption peak. If the aberration is narrow, the two spikes are close to one another, forming a dispersion-like contour. The locations of the edges can be approximated by the extrema of the first derivative spikes, while the edge tolerance is determined by their widths.

Figure 24:
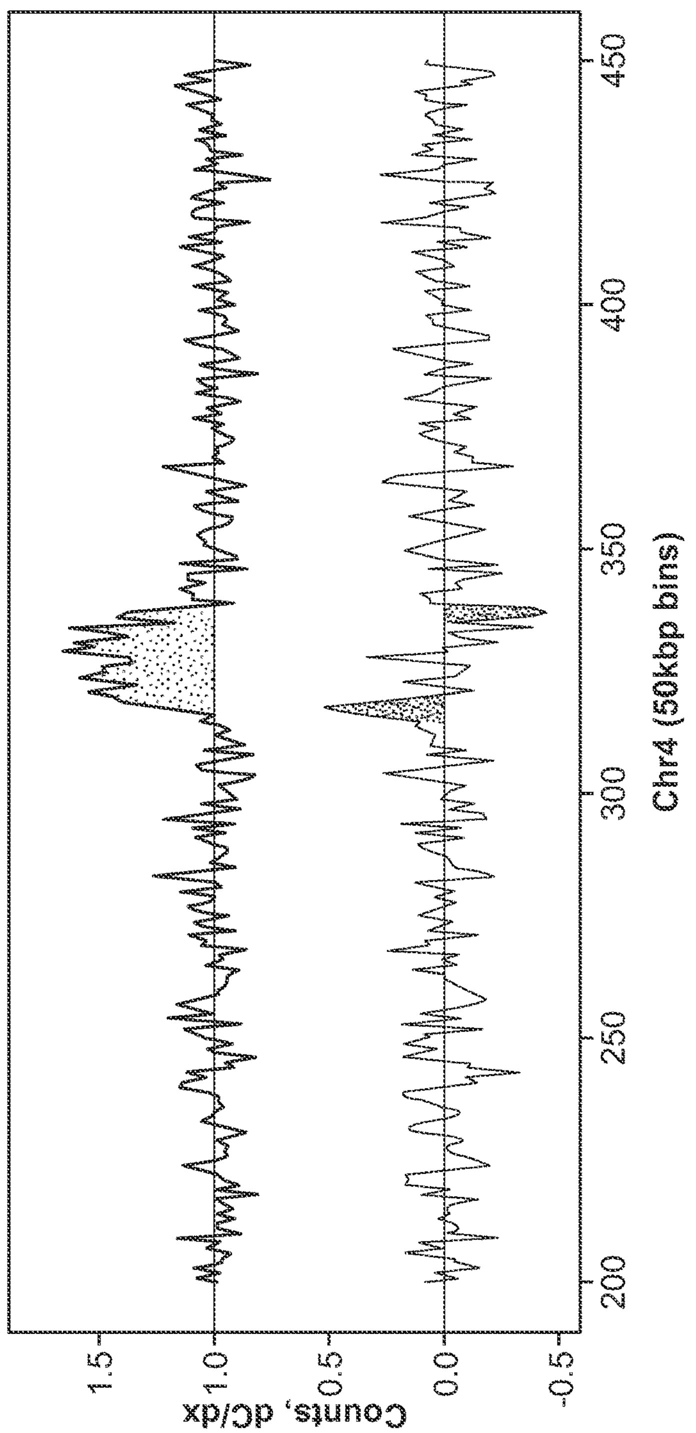
FIG. 24 graphically illustrates that first derivative of count profiles, obtained from real data, are difficult to distinguish from noise.
Figure 25:
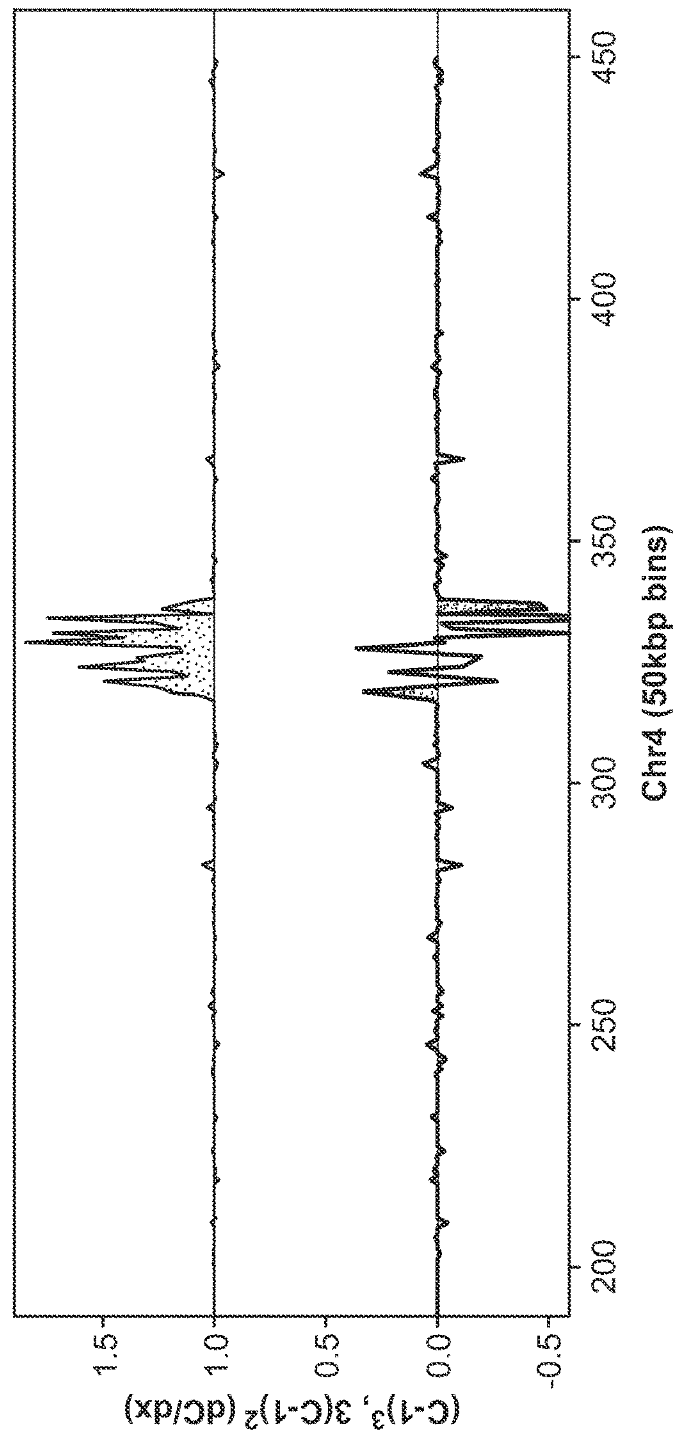
FIG. 25 graphically illustrates the third power of the count profile, shifted by 1 to suppress noise and enhance signal (see top trace). Also illustrated in FIG. 25 (see bottom trace) is a first derivative of the top trace. Edges are unmistakably detectable. See Example 1 for experimental details and results.

Comparison between different samples often can be reduced to determining the difference between two matching edge locations, divided by the combined edge uncertainties. However, the derivatives sometimes are lost in background noise, as illustrated in FIG. 24. While the aberration itself benefits from the collective information contributed from all its bins, the first derivative only can afford information from the few points at the edge of the aberration, which can be insufficient to overcome the noise. Sliding window averaging, used to create FIG. 24, is of limited value in this situation. Noise can be suppressed by combining the first derivative (e.g., akin to a point estimate) with the peak elevation (e.g., comparable to an integral estimate). In some embodiments the first derivative and the peak elevation can be combined by multiplying them together, which is equivalent to taking the first derivative of a power of the peak elevation, as shown in FIG. 25. The results presented in FIG. 25 successfully suppress noise outside of the aberration, however, noise within the aberration is enhanced by the manipulation. The first derivative peaks are still clearly discernible, allowing them to be used to extract edge locations and lateral tolerances, thereby allowing the aberration to be clearly identified in the lower profile tracing.

Median Chromosomal Elevation

Figure 9:
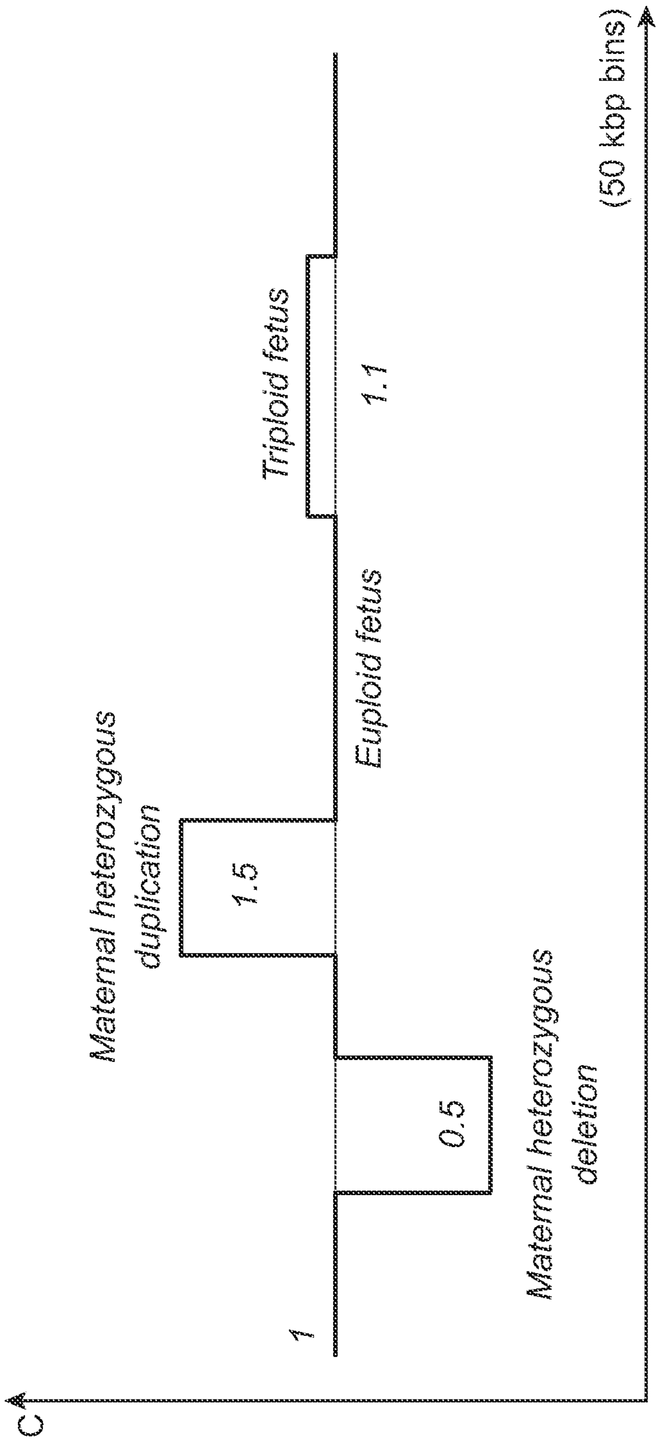
FIG. 9 graphically illustrates the expected behavior of normalized count profiles. The majority of normalized bin counts often will center on 1, with random noise superimposed. Maternal deletions and duplications sometimes shifts the elevation to an integer multiple of 0.5. Profile elevations corresponding to a triploid fetal chromosome often shifts upward in proportion to the fetal fraction. See Example 1 for experimental details and results.
Figure 10:
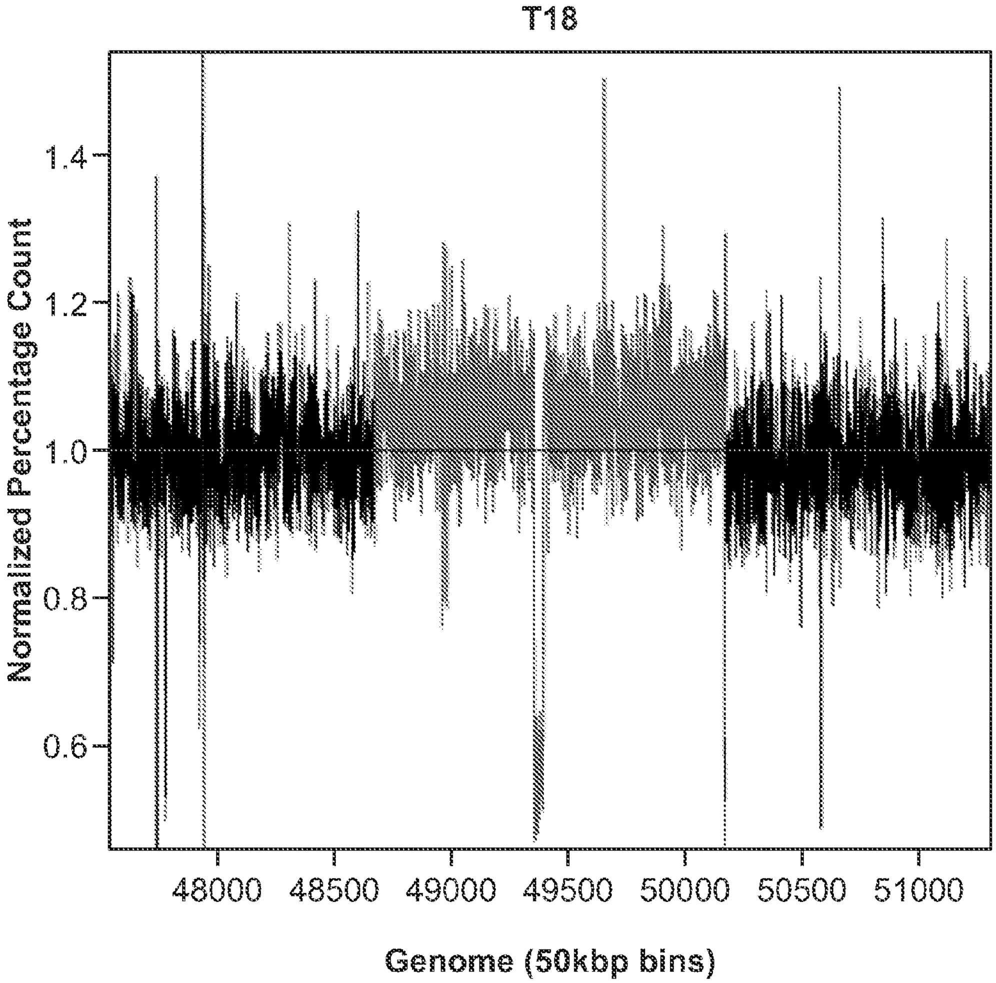
FIG. 10 graphically illustrates a normalized T18 count profile with a heterozygous maternal deletion in chromosome 18. The light gray segment of the graph tracing shows a higher average elevation than the black segment of the graph tracing. See Example 1 for experimental details and results.
Figure 26:
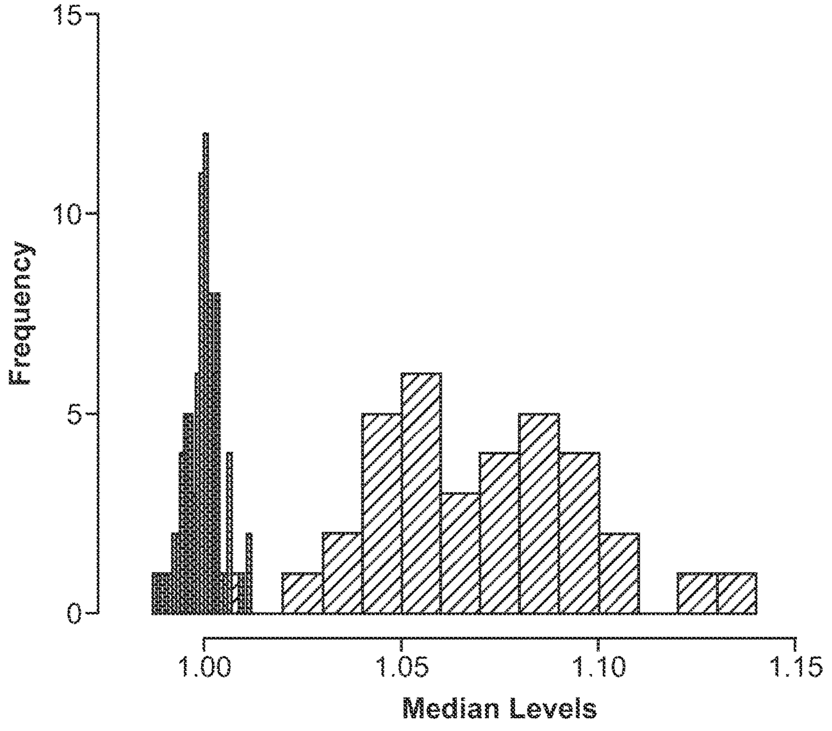
FIG. 26 graphically illustrates histograms of median chromosome 21 elevations for various patients. The black histogram illustrates median chromosome 21 elevations for 86 euploid patients. The gray histogram illustrates median chromosome 21 elevations for 35 trisomy 21 patients. The count profiles were normalized with respect to a euploid reference set prior to evaluating median elevations.

The median normalized elevation within the target chromosome in a euploid patient is expected to remain close to 1 regardless of the fetal fraction. However, as shown in FIGS. 9 and 10, median elevations in trisomy patients increase with the fetal fraction. The increase generally is substantially linear with a slope of 0.5. Experimental measurements confirm these expectations. FIG. 26 illustrates a histogram of median elevations for 86 euploid samples (shown in black in FIG. 26). The median values are tightly clustered around 1 (median=1.0000, median absolute deviation (MAD)=0.0042, mean=0.9996, standard deviation (SD)=0.0046). None of the euploid median elevations exceeds 1.012, as shown in the histogram presented in FIG. 26. In contrast, out of 35 trisomy samples shown (the gray samples) in FIG. 26, all but one have median elevations exceeding 1.02, significantly above the euploid range. The gap between the two groups of patients in this example is large enough to allow classification as euploid or aneuploid.

Fetal Fraction as the Limiting Factor in Classification Accuracy

The ratio between the fetal fraction and the width of the distribution of median normalized counts in euploids (e.g. euploid pregnancies) can be used to determine the reliability of classification using median normalized elevations, in some embodiments. Since median normalized counts, as well as other descriptors such as Z-values, linearly increase with the fetal fraction with the proportionality constant of 0.5, the fetal fraction must exceed four standard deviations of the distribution of median normalized counts to achieve 95% confidence in classification, or six standard deviations to achieve 99% confidence in classification. Increasing the number of aligned sequences tags can serve to decrease the error in measured profiles and sharpen the distribution of median normalized elevations, in certain embodiments. Thus, the effect of increasingly precise measurements is to improve the ratio between fetal fraction and the width of the distribution of euploid median normalized elevations.

Area Ratio

Figure 27:
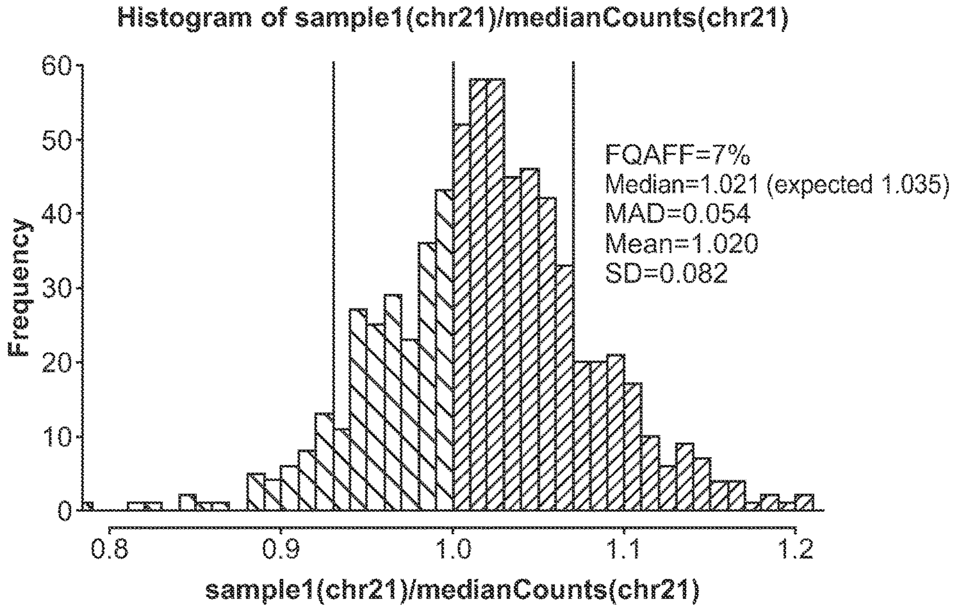
FIG. 27 graphically illustrates a distribution of normalized counts for chromosome 21 in a trisomy sample.

The median of the distribution of normalized counts generally is a point estimate and, as such, often is a less reliable estimate than integral estimates, such as areas under the distribution (e.g., area under the curve. Samples containing high fetal level fractions are not as affected by using a point estimate, however at low fetal fraction values, it becomes difficult to distinguish a truly elevated normalized profile from a euploid sample that has a slightly increased median count due to random errors. A histogram illustrating the median distribution of normalized counts from a trisomy case with a relatively low fetal fraction (e.g., F=about 7%; F(7%)) is shown in FIG. 27. The median of the distribution is 1.021, not far from 1+F/2=1.035. However, the width of the distribution (MAD=0.054, SD=0.082) far exceeds the deviation of the median from the euploid value of 1, precluding any claims that the sample is abnormal. Visual inspection of the distribution suggests an alternative analysis: although the shift of the peak to the right is relatively small, it significantly perturbs the balance between the areas to the left (dark gray) and to the right (light gray) from the euploid expectation of 1. Thus the ratio between the two areas, being an integral estimate, can be advantageous in cases where classification is difficult due to low fetal fraction values. Calculation of the integral estimate for the light gray and dark gray areas under the curve is explained in more detail below.

If a Gaussian distribution of normalized counts is assumed, then $$P(q) = \frac{1}{\sigma\sqrt{2\pi}}\exp\left[-\frac{(q-q_o)}{(2\sigma^2)}\right]. \quad (2)$$

In euploid cases, the expectation for the normalized counts is 1. For trisomy patients, the expectation is $$q_0 = 1 + F/2 \quad (3).$$

Since the reference point for calculating the area ratio is 1, the argument to the exponential function is $Z^2$, where $$z = -F/(2\pi\sqrt{2}) \quad (4).$$

The area to the left of the reference point is $$B = \int_{-\infty}^{1} P(q)dq = \tfrac{1}{2}[1 + ^{erf}(z)] \quad (5).$$

The error function erf(z) can be evaluated using its Taylor expansion:

$$\mathrm{erf}(z) = \frac{2}{\sqrt{\pi}}\sum_{n=o}^{\langle\cdot\rangle}\frac{(-1)^n z^{zn+1}}{n!(2n+1)}. \quad (6)$$

The area to the right from the reference point is 1−B. The ratio between two areas is therefore $$R = \frac{1-B}{B} = \frac{1-\text{erf}(z)}{1+\text{erf}(z)} = \frac{1-\text{erf}\left[-\frac{F}{(2\sigma\sqrt{2})}\right]}{1+\text{erf}\left[-\frac{F}{(2\sigma\sqrt{2})}\right]}. \quad (7)$$

Figure 28:
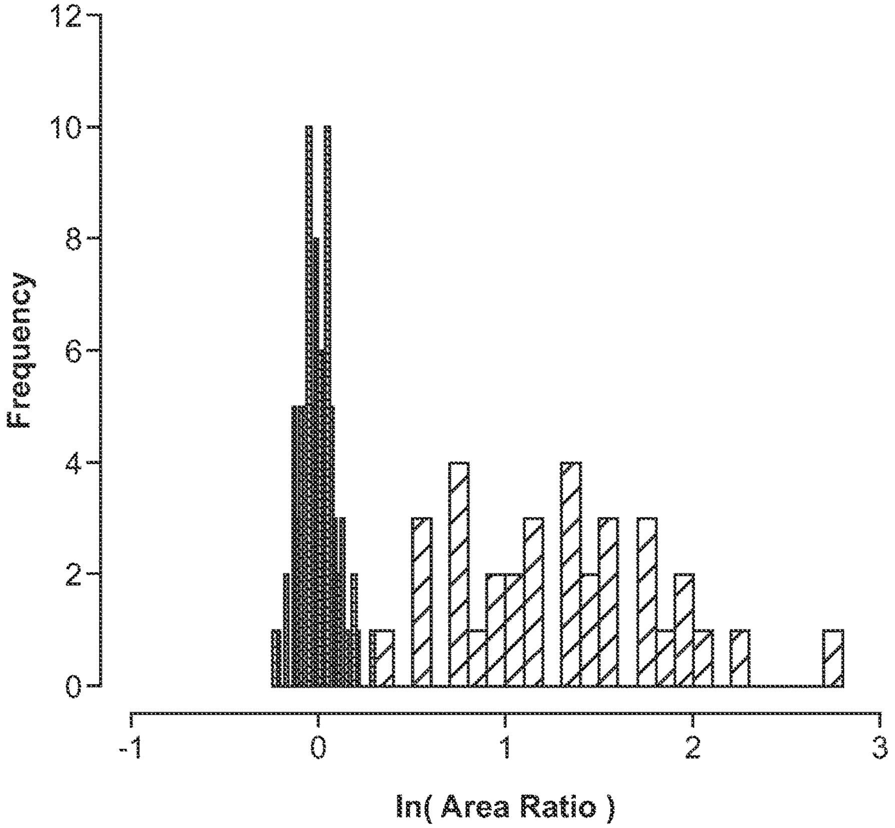
FIG. 28 graphically represents area ratios for various patients. The dark gray histogram illustrates chromosome 21 area ratios for 86 euploid patients. The light gray histogram illustrates chromosome 21 area ratios for 35 trisomy 21 patients. The count profiles were normalized with respect to a euploid reference set prior to evaluating area ratios. See Example 1 for experimental details and results.

Error propagation from measured fetal fractions into area ratios R can be estimated by simply replacing F in equation 7 with F−ΔF and F+ΔF. FIG. 28 shows the frequencies of euploid and trisomy area ratios in a set of 480 samples. The overlap between two groups involves trisomy samples with low fetal fractions.

Combined Classification Criteria

Figure 29:
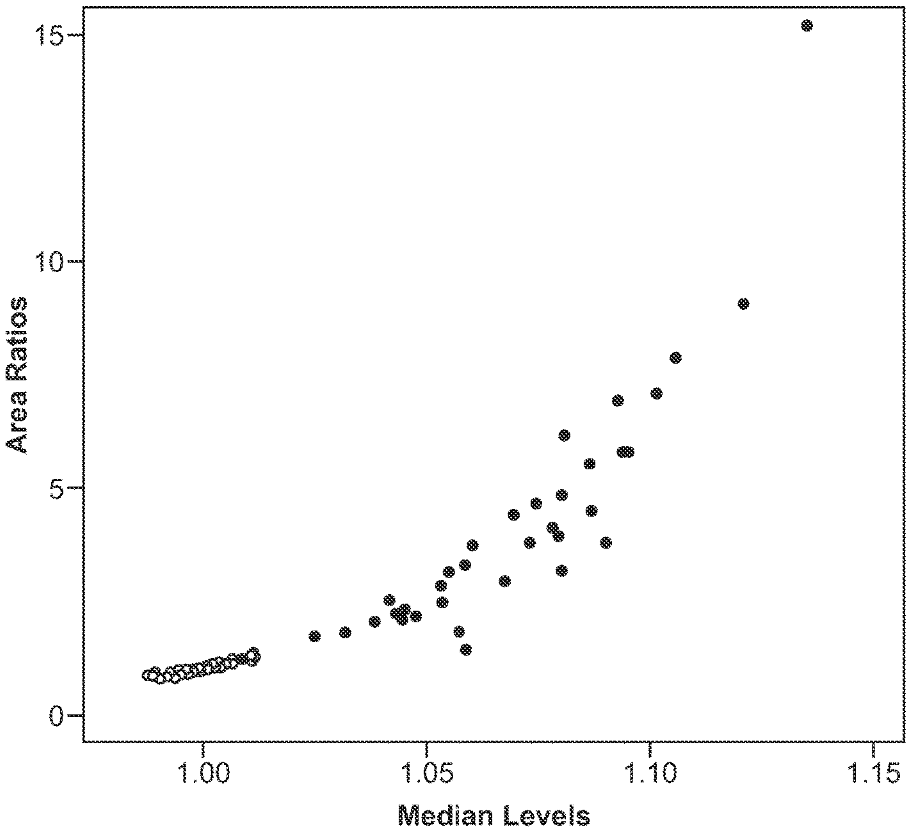
FIG. 29 graphically illustrates area ratio in chromosome 21 plotted against median normalized count elevations. The light gray data points represent about 86 euploid samples. The dark gray data points represent about 35 trisomy patients. See Example 1 for experimental details and results.
Figure 30:
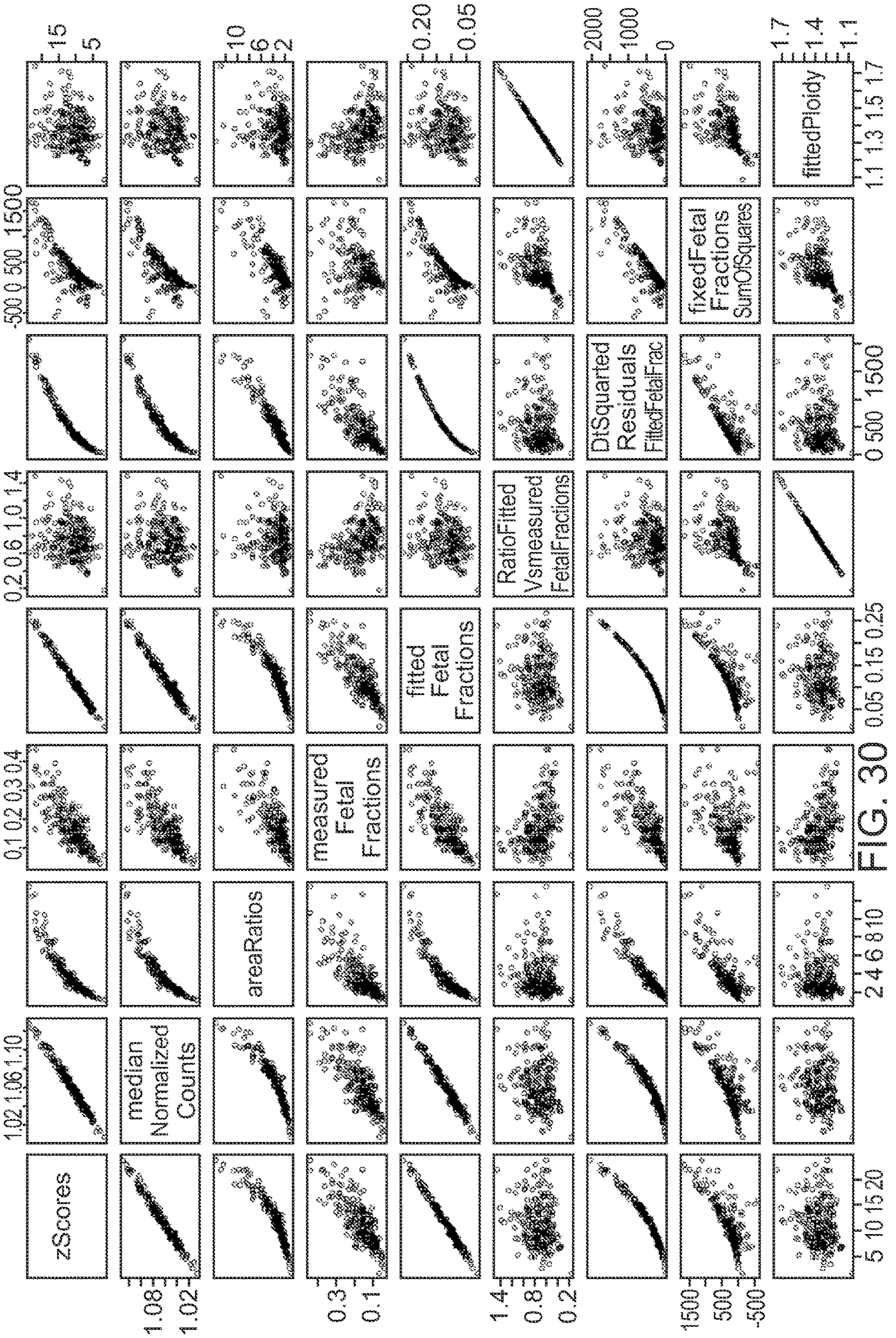
FIG. 30 graphically illustrates relationships among 9 different classification criteria, as evaluated for a set of trisomy patients. The criteria involve Z-scores, median normalized count elevations, area ratios, measured fetal fractions, fitted fetal fractions, the ratio between fitted and measured fetal fractions, sum of squared residuals for fitted fetal fractions, sum of squared residuals with fixed fetal fractions and fixed ploidy, and fitted ploidy values. See Example 1 for experimental details and results.

FIG. 29 illustrates the interrelation and interdependence of median elevations and area ratios, both of which described substantially similar phenomena. Similar relationships connect median elevations and area ratios with other classification criteria, such as Z-scores, fitted fetal fractions, various sums of squared residuals, and Bayesian p-values (see FIG. 30). Individual classification criteria can suffer from ambiguity stemming from partial overlap between euploid and trisomy distributions in gap regions, however, a combination of multiple criteria can reduce or eliminate any ambiguities. Spreading the signal along multiple dimensions can have the same effect as measuring NMR frequencies of different nuclei, in some embodiments, resolving overlapping peaks into well-defined, readily identifiable entities. Since no attempt is made to quantitatively predict any theoretical parameter using mutually correlated descriptors, the cross-correlations observed between different classification criteria do not interfere. Defining a region in multidimensional space that is exclusively populated by euploids, allows classification of any sample that is located outside of the limiting surface of that region. Thus the classification scheme is reduced to a consensus vote for euploid.

In some embodiments utilizing a combined classification criteria approach, classification criteria described herein can be combined with additional classification criteria known in the art. Certain embodiments can use a subset of the classification criteria listed here. Certain embodiments can mathematically combine (e.g., add, subtract, divide, multiply, and the like) one or more classification criteria among themselves and/or with fetal fraction to derive new classification criteria. Some embodiments can apply principal components analysis to reduce the dimensionality of the multidimensional classification space. Some embodiments can use one or more classification criteria to define the gap between affected and unaffected patients and to classify new data sets. Any combination of classification criteria can be used to define the gap between affected and unaffected patients and to classify new data sets. Non-limiting examples of classification criteria that can be used in combination with other classification criteria to define the gap between affected and unaffected patients and to classify new data sets include: linear discriminant analysis, quadratic discriminant analysis, flexible discriminant analysis, mixture discriminant analysis, k Nearest Neighbors, classification tree, bagging, boosting, neural networks, support vector machines, and/or random forest.

Example 2: Methods for Detection of Genetic Variations Associated with Fetal Aneuploidy Using Measured Fetal Fractions and Bin-Weighted Sums of Squared Residuals Z-value statistics and other statistical analysis of sequence read data frequently are suitable for determining the presence or absence of a genetic variation with respect to fetal aneuploidy, however, in some instances it can be useful to include additional analysis based on fetal fraction contribution and ploidy assumptions. When including fetal fraction contribution in a classification scheme, a reference median count profile from a set of known euploids (e.g. euploid pregnancies) generally is utilized for comparison. A reference median count profile can be generated by dividing the entire genome into N bins, where N is the number of bins. Each bin i is assigned two numbers: (i) a reference count $F_i$ and (ii) the uncertainty (e.g., standard deviation or a) for the bin reference counts.

The following relationship can be utilized to incorporate fetal fraction, maternal ploidy, and median reference counts into a classification scheme for determining the presence or absence of a genetic variation with respect to fetal aneuploidy, $$y_i=(1-F)M_if_i+FXf_i \quad (8)$$

where $Y_i$ represents the measured counts for a bin in the test sample corresponding to the bin in the median count profile, F represents the fetal fraction, X represents the fetal ploidy, and $M_i$ represents maternal ploidy assigned to each bin. Possible values used for X in equation (8) are: 1 if the fetus is euploid; 3/2, if the fetus is triploid; and, 5/4, if there are twin fetuses and one is affected and one is not. 5/4 is used in the case of twins where one fetus is affected and the other not, because the term F in equation (8) represents total fetal DNA, therefore all fetal DNA must be taken into account. In some embodiments, large deletions and/or duplications in the maternal genome can be accounted for by assigning maternal ploidy, $M_i$ to each bin or genomic section. Maternal ploidy often is assigned as a multiple of ½, and can be estimated using bin-wise normalization, in some embodiments. Because maternal ploidy often is a multiple of ½, maternal ploidy can be readily accounted for, and therefore will not be included in further equations to simplify derivations.

Fetal ploidy can be assessed using any suitable approach. In some embodiments, fetal ploidy can be assessed using equation (8), or derivations thereof. In certain embodiments, fetal ploidy can be classified using one of the following, equation (8) based, non-limiting approaches:

1) Measure fetal fraction F and use the value to form two sums of squared residuals. To calculate the sum of squared residuals, subtract the right hand side (RHS) of equation (8) from its left hand side (LHS), square the difference, and sum over selected genomic bins, or in those embodiments using all bins, sum over all bins. This process is performed to calculate each of the two sums of squared residuals. One sum of square residuals is evaluated with fetal ploidy set to 1 (e.g., X=1) and the other sum of squared residuals is evaluated with fetal ploidy set to 3/2 (e.g., X=3/2). If the fetal test subject is euploid, the difference between the two sums of squared residuals is negative, otherwise the difference is positive.
2) Fix fetal fraction at its measured value and optimize ploidy value. Fetal ploidy generally can take on only 1 of two discrete values, 1 or 3/2, however, the ploidy sometimes can be treated as a continuous function. Linear regression can be used to generate an estimate for ploidy. If the estimate resulting from linear regression analysis is close to 1, the fetal test sample can be classified as euploid. If the estimate is close to 3/2, the fetus can be classified as triploid.

3) Fix fetal ploidy and optimize fetal fraction using linear regression analysis. The fetal fraction can be measured and a restraint term can be included to keep the fitted fetal fraction close to the measured fetal fraction value, with a weighting function that is reciprocally proportional to the estimated error in the measure fetal fraction. Equation (8) is solved twice, once with ploidy set at 3/2, and once for fetal ploidy set to 1. When solving equation (8) with ploidy set to 1, the fetal fraction need not be fitted. A sum of square residuals is formed for each result and the sum of squared residuals subtracted. If the difference is negative, the fetal test subject is euploid. If the difference is positive, the fetal test subject is triploid.

The generalized approaches described in 1), 2) and 3) are described in further detail herein.

Fixed Ploidy, Fixed Fetal Fraction: Sums of Squared Residuals

In some embodiments, fetal aneuploidy can be determined using a model which analyzes two variables, fetal ploidy (e.g., X) and fetal nucleic acid fraction (e.g., fetal fraction; F). In certain embodiments, fetal ploidy can take on discrete values, and in some embodiments, fetal fraction can be a continuum of values. Fetal fraction can be measured, and the measured valued used to generate a result for equation (8), for each possible value for fetal ploidy. Fetal ploidy values that can be used to generate a result for equation (8) include 1 and 3/2 for a single fetus pregnancy, and in the case of a twin fetus pregnancy where one fetus is affected and the other fetus unaffected, 5/4 can be used. The sum of squared residuals obtained for each fetal ploidy value measures the success with which the method reproduces the measurements, in some embodiments. When evaluating equation (8) at X=1, (e.g., euploid assumption), the fetal fraction is canceled out and the following equation results for the sum of squared residuals:

$$\varphi_E = \sum_{i=1}^{N} \frac{1}{\sigma_i^2}(y_i - f_i)^2 = \sum_{i=1}^{N} \frac{y_i^2}{\sigma_i^2} - 2\sum_{i=1}^{N} \frac{y_i f_i}{\sigma_i^2} + \sum_{i=1}^{N} \frac{f_i^2}{\sigma_i^2} = \Xi_{yy} - 2\Xi_{fy} + \Xi_{ff} \tag{9}$$

To simplify equation (9) and subsequent calculations, the following notion is utilized:

$$\Xi_{yy} = \sum_{i=1}^{N} \frac{y_i^2}{\sigma_i^2} \tag{10}$$

$$\Xi_{ff} = \sum_{i=1}^{N} \frac{f_i^2}{\sigma_i^2} \tag{11}$$

$$\Xi_{fy} = \sum_{i=1}^{N} \frac{y_i f_i}{\sigma_i^2} \tag{12}$$

When evaluating equation (8) at X=3/2 (e.g., triploid assumption), the following equation results for the sum of the squared residuals:

$$\varphi_T = \Sigma_{i=1}^{N} \frac{1}{\sigma_i^2}\left(y_i - f_i - \frac{1}{2}Ff_i\right)^2 = \Xi_{yy} - 2\Xi_{fy} + \Xi_{ff} + F(\Xi_{ff} - \Xi_{fy}) + \frac{1}{4}F^2\Xi_{ff} \tag{13}$$

The difference between equations (9) and (13) forms the functional result (e.g., phi) that can be used to test the null hypothesis (e.g., euploid, X=1) against the alternative hypothesis (e.g., trisomy singleton, X=3/2):

$$\varphi = \varphi_E - \varphi_T = F(\Xi_{fy} - \Xi_{ff}) - \tfrac{1}{4}F^2\Xi_{ff} \tag{14}$$

The profile of phi with respect to F is a parabola defined to the right of the ordinate (since F is greater than or equal to 0). Phi converges to the origin as F approaches zero, regardless of experimental errors and uncertainties in the model parameters.

In some embodiments, the functional Phi is dependent on the measured fetal fraction F with a negative second-order quadratic coefficient (see equation (14)). Phi's dependence on the measured fetal fraction would seem to imply a convex shape for both euploid and triploid cases. If this analysis were correct, trisomy cases would reverse the sign at high F values, however equation (12) depends on F. Combining equations (8) and (14), disregarding maternal ploidy, setting X=3/2 and neglecting experimental errors, the equation for trisomy cases becomes:

$$\Xi_{fy} = \Sigma_{i=1}^{N} \frac{y_i f_i}{\sigma_i^2} = \Sigma_{i=1}^{N} \frac{f_i}{\sigma_i^2}[(1 - F)f_i + FXf_i] = \left(1 + \frac{1}{2}F\right)\Sigma_{i=1}^{N} \frac{f_i^2}{\sigma_i^2} = \left(1 + \frac{1}{2}F\right)\Xi_{ff} \tag{15}$$

The relationship between equations (11) and (12) for triploids holds under ideal circumstances, in the absence of any measurement errors. Combining equations (14) and (15) results in the following expression, which often yields a concave parabola in triploid cases:

$$\varphi = F(\Xi_{fy} - \Xi^{ff}) - \tfrac{1}{4}F^2\Xi_{ff} = F[(1 + \tfrac{1}{2}F)\Xi_{ff} - \Xi_{ff}] - \tfrac{1}{4}F^2\Xi_{ff} = \tfrac{1}{4}F^2\Xi_{ff} \tag{16}$$

For euploids, equations (11) and (12) should have the same value, with the exception of measurement errors, which sometimes yields a convex parabola:

$$\varphi = F(\Xi_{fy} - \Xi_{ff}) - \tfrac{1}{4}F^2\Xi_{ff} = -\tfrac{1}{4}F^2\Xi_{ff} \text{ (Euploids)} \tag{17}$$

Figure 31:
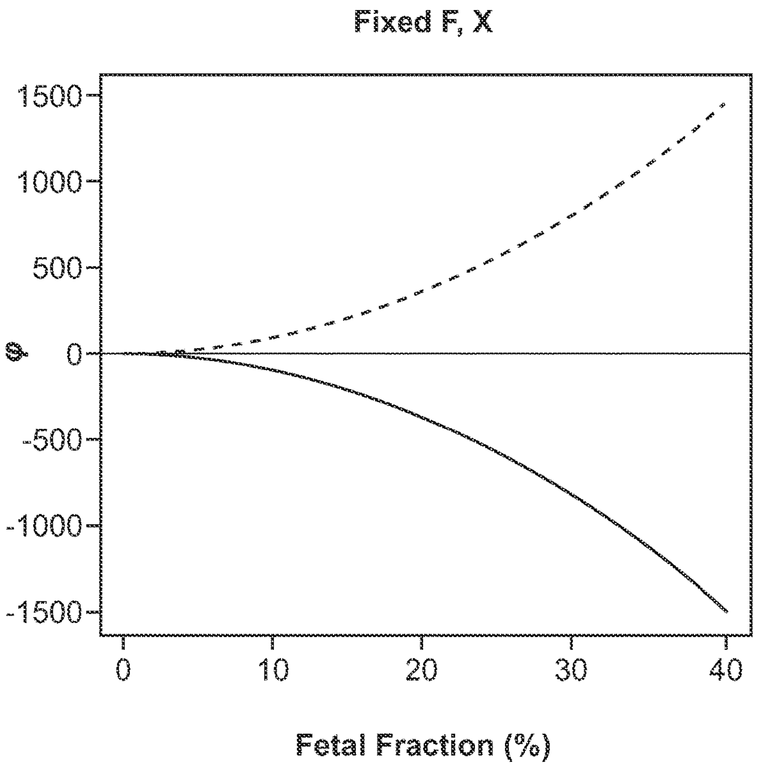
FIG. 31 graphically illustrates simulated functional Phi profiles for trisomy (light gray) and euploid cases (dark gray).
Figure 32:
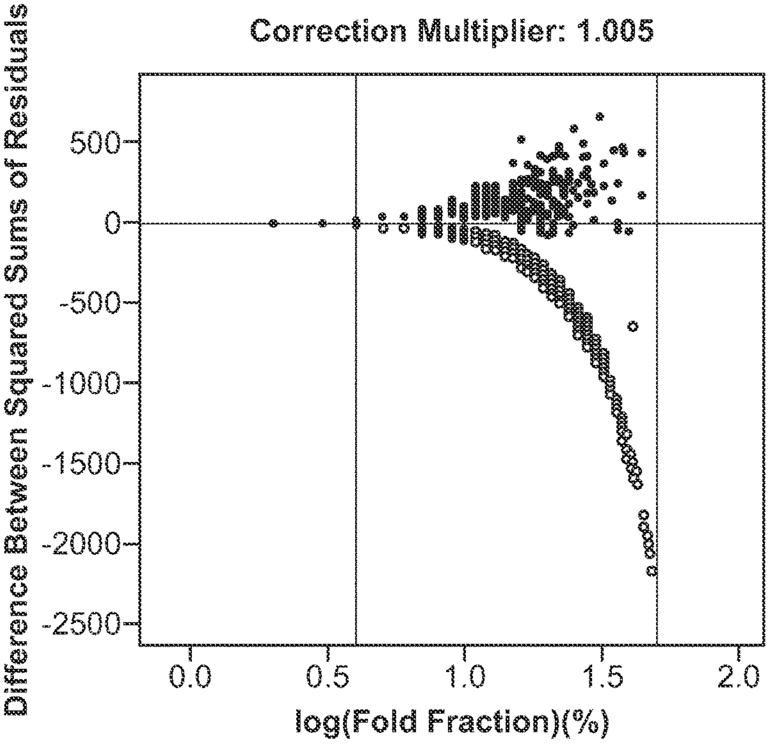
FIG. 32 graphically illustrates functional Phi values derived from measured trisomy (dark gray) and euploid data sets (light gray). See Example 2 for experimental details and results.

Simulated functional phi profiles for typical model parameter values are shown in FIG. 31, for trisomy (gray) and euploid (blue) cases. FIG. 32 shows an example using actual data. In FIGS. 31 and 32, data points below the abscissa generally represent cases classified as euploids. Data points above the abscissa generally represent cases classified as trisomy 21 (T21) cases. In FIG. 32, the solitary data point in the fourth quadrant (e.g., middle lower quadrant) is a twin pregnancy with one affected fetus. The data set utilized to generate FIG. 32 includes other affected twin samples as well, explaining the spread of T21 data points toward the abscissa.

Equations (9) and (10) often can be interpreted as follows: For triploids, the euploid model sometimes generates larger errors, implying that $phi_E$ (see equation (9)) is greater than $phi_T$ (see equation (13)). As a result, functional phi (see equation (7)) occupies the first quadrant (e.g., upper left quadrant). For euploids, the trisomy model sometimes generates larger errors, the rank of equations (2) and (6) reverses and functional phi (equation (7)) occupies in the fourth quadrant.

Thus, in principle, classification of a sample as euploid or triploid sometimes reduces to evaluating the sign of phi.

Figure 33:
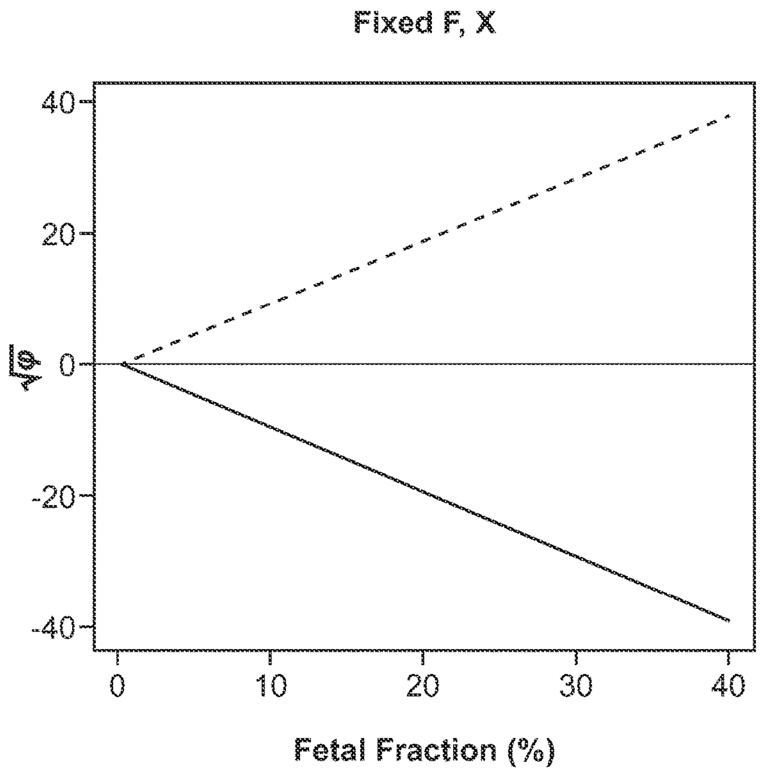
FIG. 33 graphically illustrates linearized sum of squared differences as a function of measured fetal fraction.

In some embodiments, the curvature of the data points shown in FIGS. 31 and 32 can be reduced or eliminated by replacing functional phi (equation (7)) with the square root of functional phi's absolute value, multiplied by its sign. The linear relationship generated with respect to F sometimes can improve separation between triploids and euploids at low fetal fraction values, as shown in FIG. 33. Linearizing the relationship with respect to F sometimes results in increase uncertainty intervals at low fetal fraction (e.g., F) values, therefore, the gains realized from this process are related to making visual inspection of the differences substantially easier; the gray area remains unchanged. Extension of the process to analysis of twin pregnancies is relatively straightforward. The reason used to generate equation (9) implies that in a twin pregnancy with one affected and one normal fetus, functional phi should reduce to zero, plus or minus experimental error, regardless of F. Twin pregnancies generally produce more fetal DNA than single pregnancies.

Optimized Ploidy, Fixed Fetal Fraction: Linear Regression

In certain embodiments, fetal aneuploidy can be determined using a model in which the fetal fraction is fixed at its measured value and ploidy is varied to optimize the sum of squared residuals. In some embodiments, the resulting fitted fetal fraction value can be used to classify a case as trisomy or euploid, depending on whether the value is close to 1, 3/2, or 5/4 in the case of twins. Starting from equation (8), the sum of squared residuals can be formed as follows:

$$\varphi = \Sigma_{i=1}^{N}\frac{1}{\sigma_i^2}[y_i-(1-F)M_if_i-FXf_i]^2 \quad (18)$$
$$= \Sigma_{i=1}^{N}\frac{1}{\sigma_i^2}[y_i^2-2(1-F)M_if_iy_i-2FXf_iy_i+(1-F)^2M_i^2f_i^2+2F(1-F)XM_if_i^2+F^2X^2f_i^2]$$

To minimize phi as a function of X, the first derivative of phi with respect to X is generated, set equal to zero, and the resulting equation solved for X. The resulting expression is presented in equation (19).

$$\frac{1}{2}\left(\frac{d\varphi}{dX}\right)=0=XF^2\Sigma_{i=1}^{N}\frac{f_i^2}{\sigma_i^2}-F\Sigma_{i=1}^{N}\frac{f_iy_i}{\sigma_i^2}+F(1-F)\Sigma_{i=1}^{N}\frac{M_if_i^2}{\sigma_i^2} \quad (19)$$

The optimal ploidy value sometimes is given by the following expression:

$$X=\frac{\Sigma_{i=1}^{N}\frac{f_iy_i}{\sigma_i^2}-(1-F)\Sigma_{i=1}^{N}\frac{M_if_i^2}{\sigma_i^2}}{F\Sigma_{i=1}^{N}\frac{f_i^2}{\sigma_i^2}} \quad (20)$$

As noted previously, the term for maternal ploidy, $M_i$ can be omitted from further mathematical derivations. The resulting expression for X corresponds to the relatively simple, and often most frequently occurring, special case of when the mother has no deletions or duplications in the chromosome or chromosomes being evaluated. The resulting expression is presented in FIG. 21.

$$X=\frac{\Xi_{fy}-(1-F)\Xi_{ff}}{F\Xi_{ff}}=\frac{\Xi_{fy}}{F\Xi_{ff}}-\frac{1-F}{F}=1+\frac{1}{F}\left(\frac{\Xi_{fy}}{\Xi_{ff}}-1\right) \quad (21)$$

$Xi_{ff}$ and $Xi_{fy}$ are given by equations (11) and (12), respectively. In embodiments where all experimental errors are negligible, solving equation (21) results in a value of 1 for euploids where $Xi_{ff}=Xi_{fy}$. In certain embodiments where all experimental errors are negligible, solving equation (21) results in a value of 3/2 for triploids (see equation (15) for triploid relationship between $Xi_{ff}$ and $Xi_{fy}$.

Optimized Ploidy, Fixed Fetal Fraction: Error Propagation

Optimized ploidy often is inexact due to various sources of error. Three, non-limiting examples of error sources include: reference bin counts $f_i$, measured bin counts $y_i$ and fetal fraction F. The contribution of the non-limiting examples of error will be examined separately.

Errors in Measured Fetal Fractions: Quality of Fitted Fetal Fraction

Figure 34:
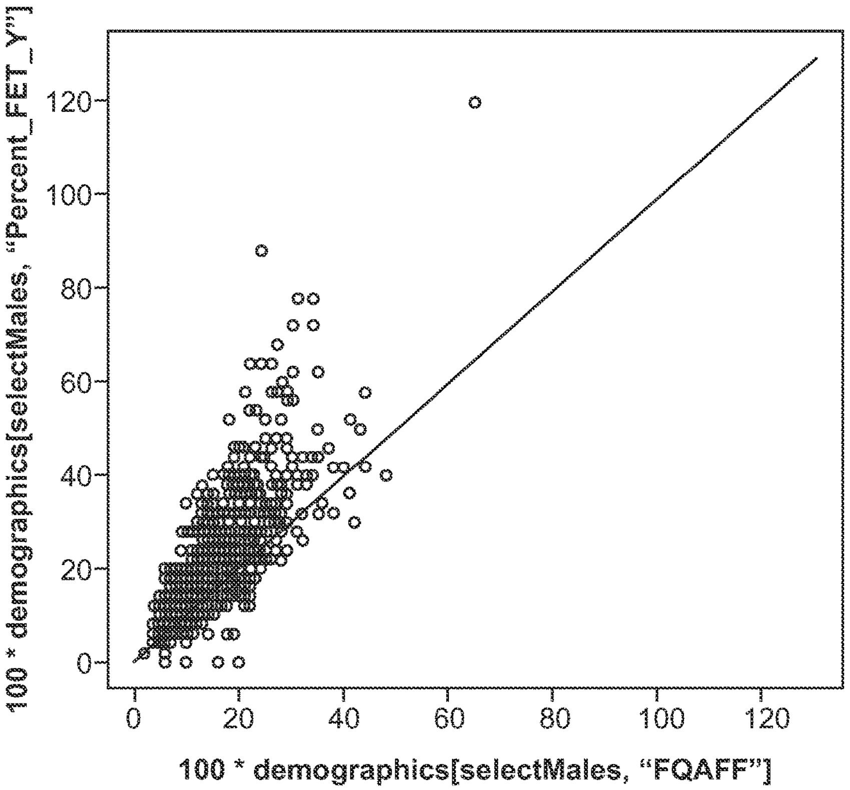
FIG. 34 graphically illustrates fetal fraction estimates based on Y-counts plotted against values obtained from a fetal quantifier assay (e.g., FQA) fetal fraction values.
Figure 35:
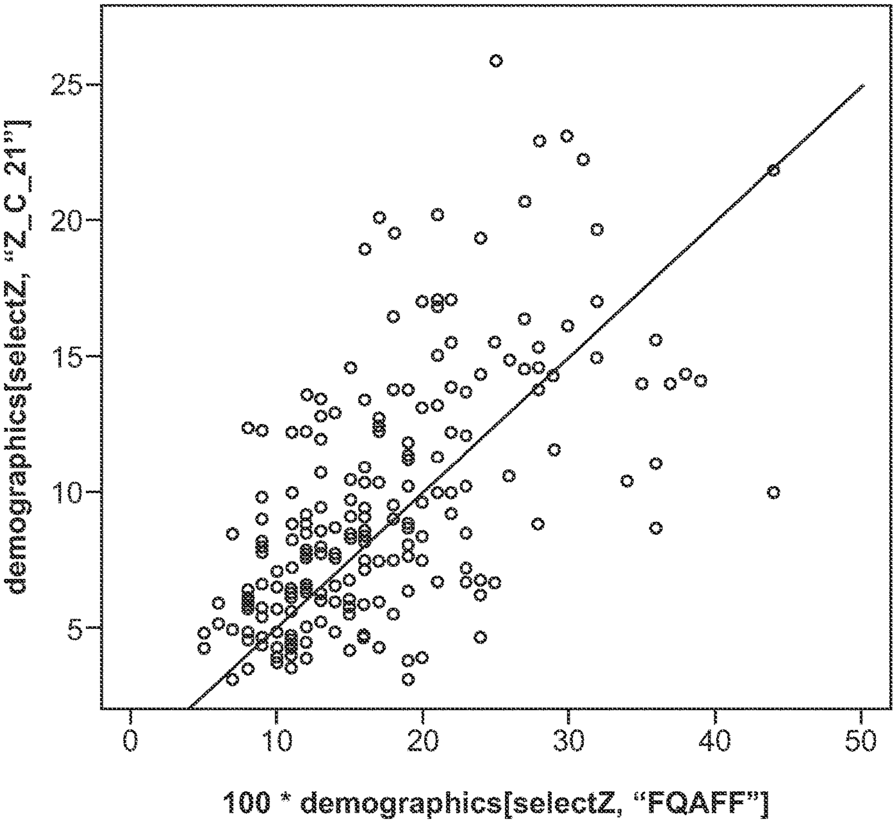
FIG. 35 graphically illustrates Z-values for T21 patients plotted against FQA fetal fraction measurements. For FIG. 33-35 see Example 2 for experimental details and results.
Figure 36:
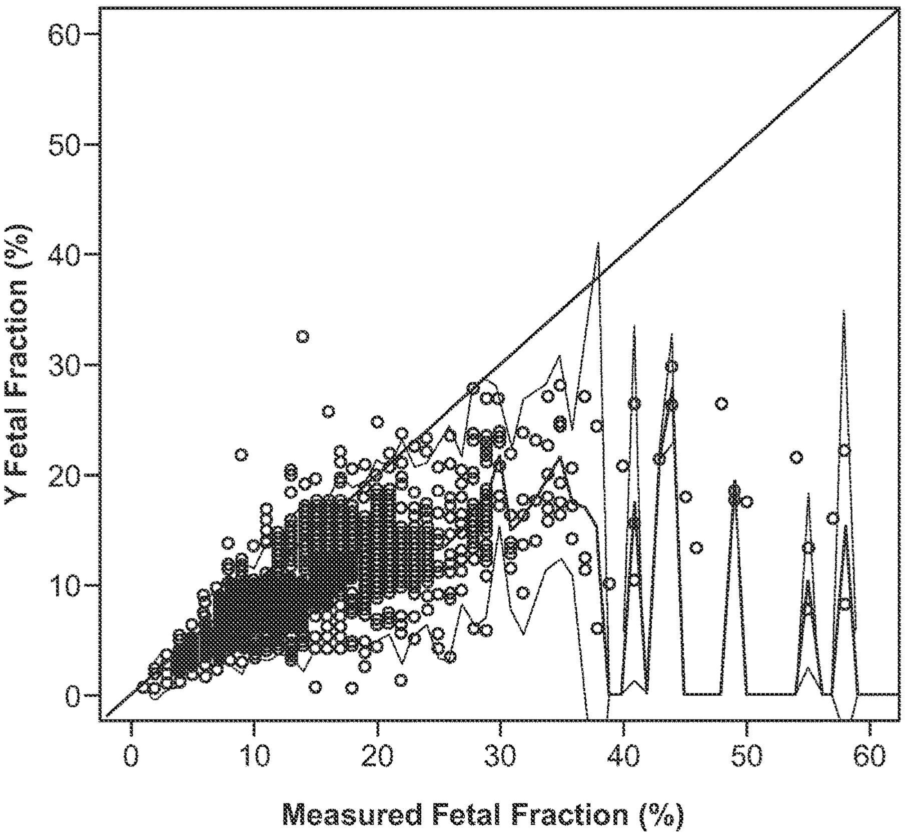
FIG. 36 graphically illustrates fetal fraction estimates based on chromosome Y plotted against measured fetal fractions.
Figure 38:
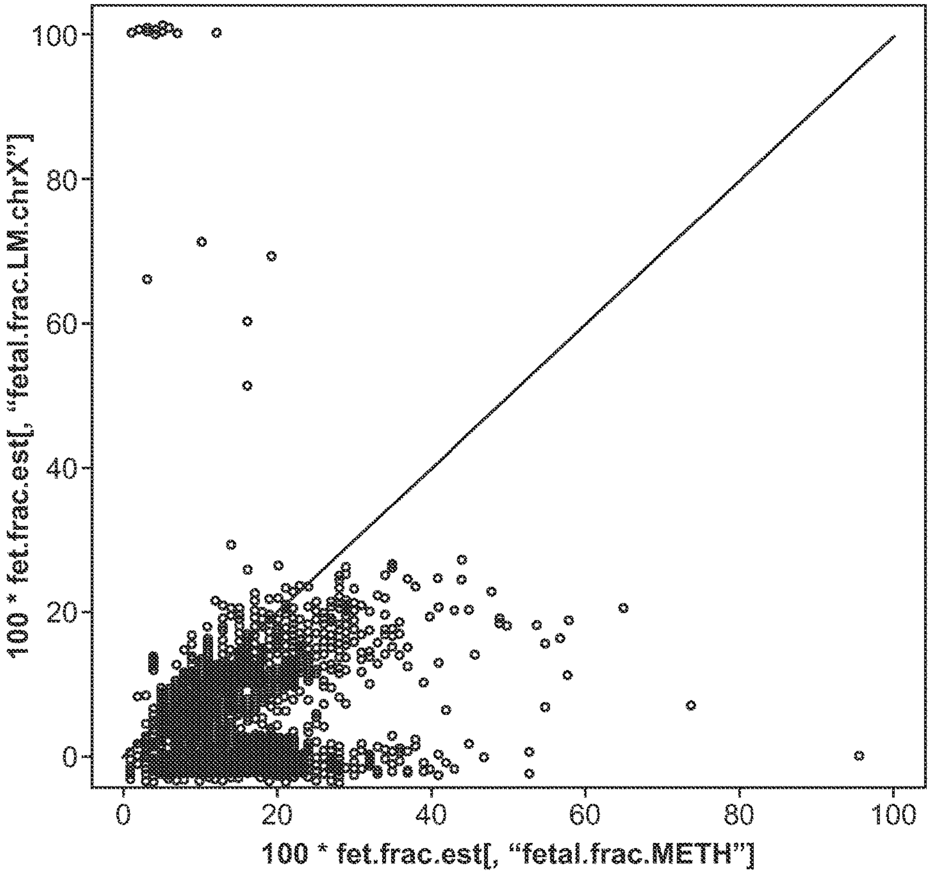
FIG. 38 graphically illustrates fetal fraction estimates derived from chromosome X counts plotted against measured fetal fractions.
Figure 39:
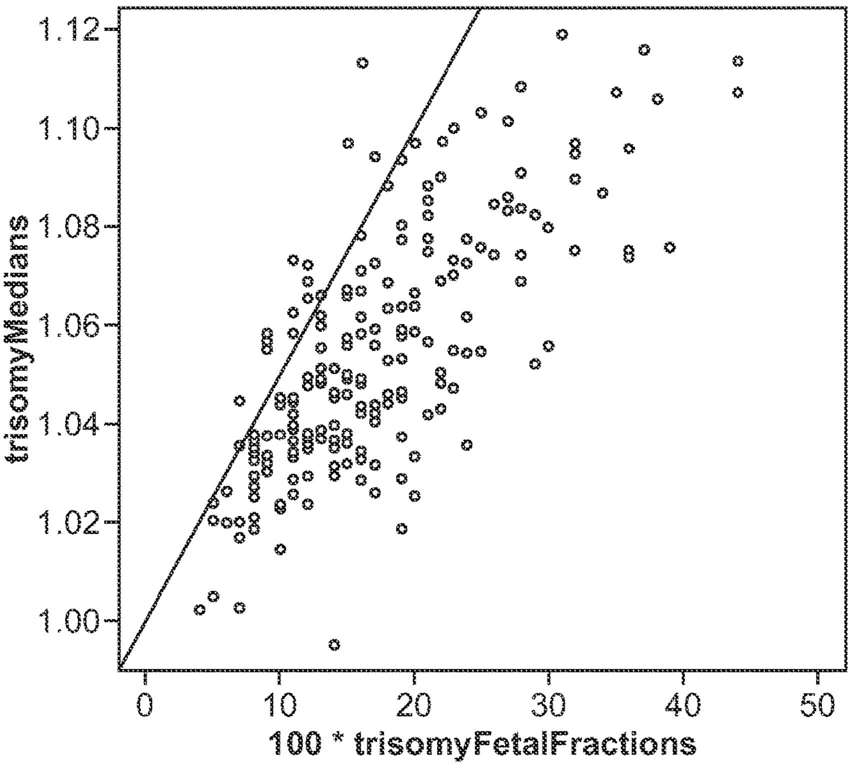
FIG. 39 graphically illustrates medians of normalized bin counts for T21 cases plotted against measured fetal fractions. For FIG. 36-39 see Example 2 for experimental details and results.

Fetal fraction estimates based on the number of sequence tags mapped to the Y chromosome (e.g., Y-counts) sometimes show relatively large deviations with respect to FQA fetal fraction values (see FIG. 34). Z-values for triploid often also exhibit a relatively wide spread around the diagonal shown in FIG. 35. The diagonal line in FIG. 35 represents a theoretically expected increase of the chromosomal representation for chromosome 21 with increasing fetal fraction in trisomy 21 cases. Fetal fraction can be estimated using a suitable method. A non-limiting example of a method that can be utilized to estimate fetal fraction is the fetal quantifier assay (e.g., FQA). Other methods for estimating fetal fraction are known in the art. Various methods utilized to estimate fetal fraction sometimes also show a substantially similar spread around the central diagonal, as shown in FIG. 36-39. In FIG. 36, the deviations are substantially similar (e.g., negative at high $F_0$) to those observed in fitted fetal fraction (see equation (33)). In some embodiments, the slope of the linear approximation to the average chromosome Y (e.g., chromosome Y) fetal fraction (see the dark gray line in FIG. 36) in the range between 0% and 20% is about ¾. In certain embodiments, the linear approximation for standard deviation (see FIG. 36, light gray line) is about ⅔+$F_0$/6. In some embodiments, fetal fraction estimates based on chromosome 21 (e.g., chromosome 21) are substantially similar to those obtained by fitting fetal fractions (see FIG. 37). Another qualitatively similar set of gender-based fetal fraction estimates is shown in FIG. 38. FIG. 39 illustrates the medians of normalized bin counts for T21 cases, which are expected to have a slope whose linear approximation is substantially similar to 1+$F_0$/2 (see gray line from origin to the midpoint of the top of the graph in FIG. 39).

FIG. 36-39 share the following common features:

a) slope not equal to 1 (either greater or less than 1, depending on the method, with the exception of Z-values), b) large spread fetal fraction estimation, and c) the extent of spread increases with fetal fraction.

To account for these observations, errors in measured fetal fraction will be modeled using the formula $\Delta F = ⅔ + F_0/6$, in some embodiments.

Errors in Measured Fetal Fractions: Error Propagation from Measured Fetal Fractions to Fitted Ploidy If the assumption is made that $f_i$ and $y_i$ are errorless, to simplify analysis, the measured fetal fraction F is composed of $F_v$ (e.g., the true fetal fraction) and ΔF (e.g., the error in measured fetal fraction):

$$F=F_V+\Delta F \quad (22).$$

In some instances, uncertainties in fitted X values originate from errors in measured fetal fraction, F. Optimized values for X are given by equation (21), however the true ploidy value is given by $X_V$, where $X_V=1$ or 3/2. $X_V$ varies discretely, whereas X varies continuously and only accumulates around $X_V$ under favorable conditions (e.g., relatively low error).

Assuming again that $f_i$ and $y_i$ are errorless, equation (8) becomes:

$$y_i=(1-F_V)M_i f_i+F_V X f_i \quad (23).$$

Combining equations (21) to (23) generates the following relationship between true ploidy $X_V$ and the ploidy estimate X that includes the error ΔF. The relationship also includes the assumption that maternal ploidy equals 1 (e.g., euploid), and the term for maternal ploidy, $M_i$, is replaced by 1.

$$X = 1 + \frac{1}{F_V + \Delta F}\left\{\frac{\sum_{i=1}^{N}\frac{f_i}{\sigma_i^2}[(1-F_V)f_i + F_V X_V f_i]}{\sum_{i=1}^{N}\frac{f_i^2}{\sigma_i^2}} - 1\right\} = 1 + \frac{F_V(X_V-1)}{F_V+\Delta F} \quad (24)$$

In some instances, the term $X_V-1$ is substantially identical to zero in euploids, and ΔF does not contribute to errors in X. In triploid cases, the error term does not reduce to zero (e.g., is not substantially identical to zero). Thus, in some embodiments, ploidy estimates can be viewed as a function of the error ΔF:

$$X=g(\Delta F) \quad (25)$$

Figure 40:
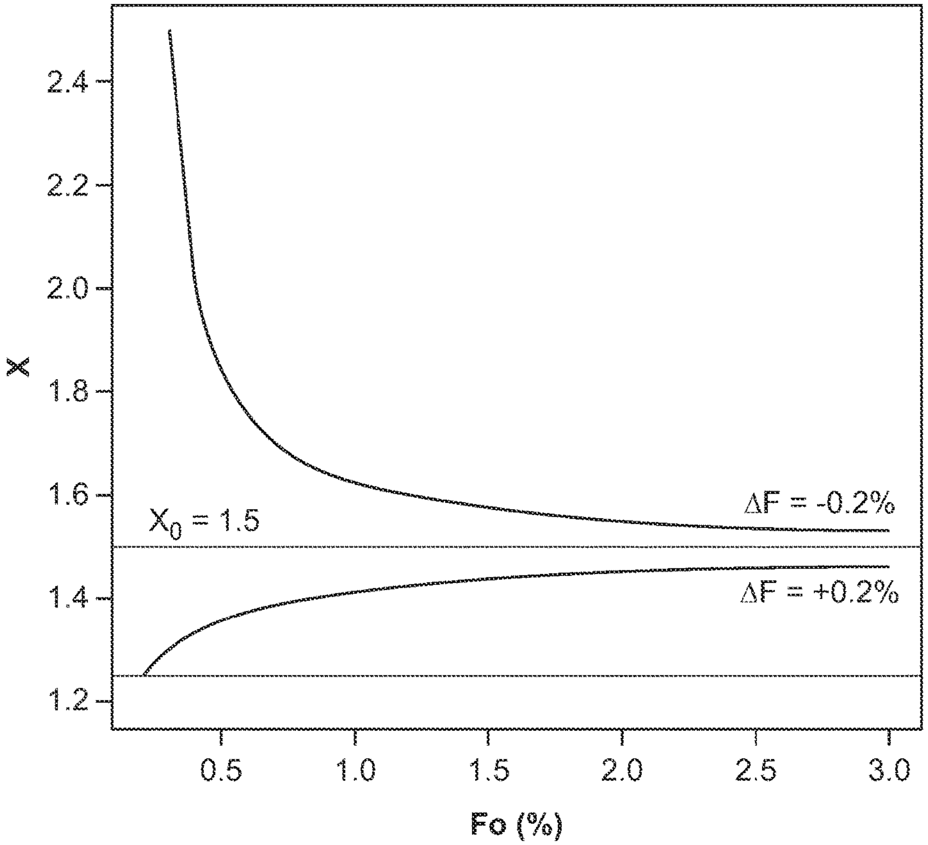
FIG. 40 graphically illustrates simulated profiles of fitted triploid ploidy (e.g., X) as a function of $F_0$ with fixed errors $\Delta F=+/-0.2\%$.
Figure 41:
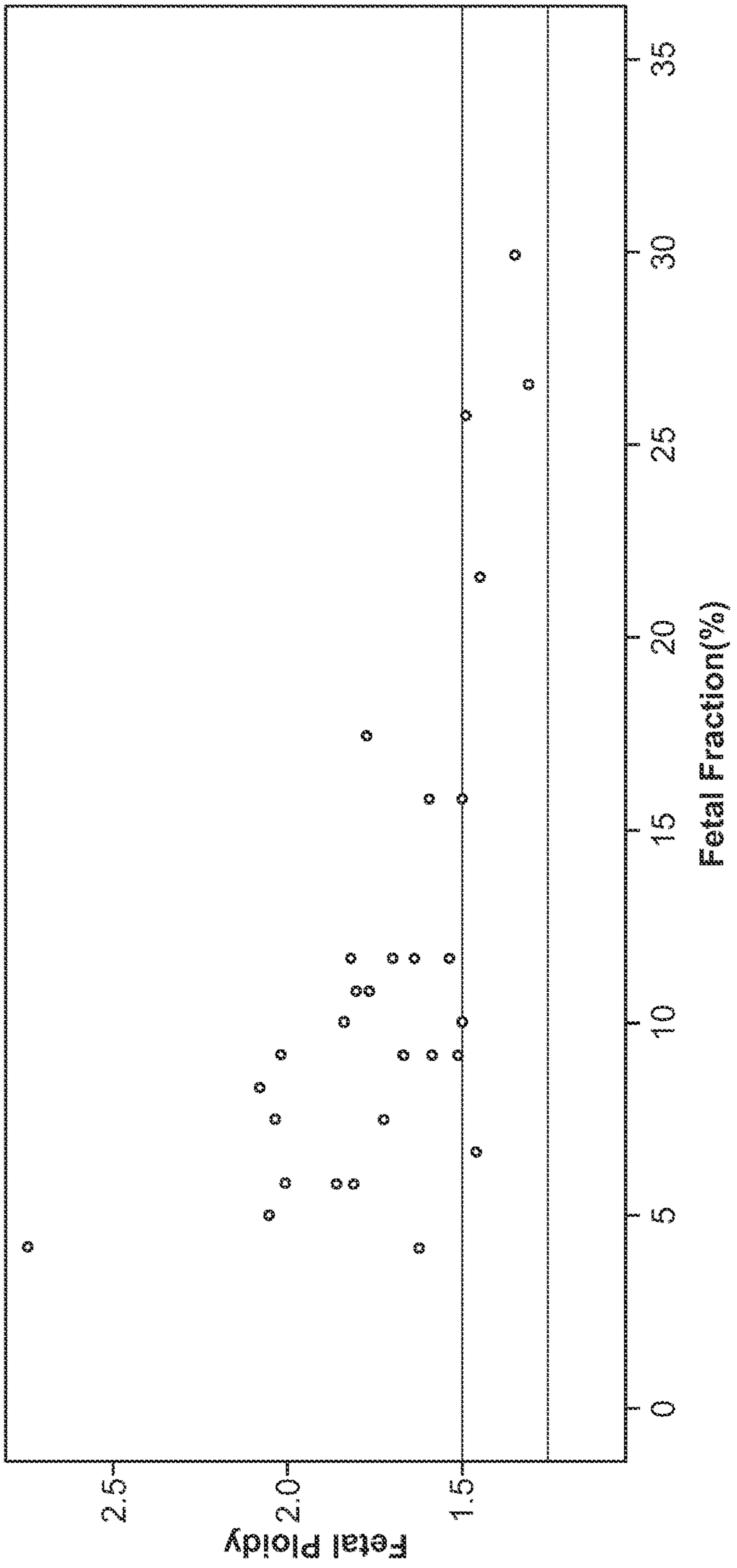
FIG. 41 graphically illustrates fitted triploid ploidy values as a function of measured fetal fractions. For FIGS. 40 and 41 see Example 2 for experimental details and results.

Simulated profiles of fitted triploid X as a function of $F_0$ with fixed errors ΔF=plus or minus 0.2% are shown in FIG. 40. Results obtained using actual data are shown in FIG. 41. The data points generally conform to the asymmetric trumpet-shaped contour predicted by equation (24). Smaller fetal fractions often are qualitatively associated with larger ploidy errors. Underestimated fetal fraction sometimes is compensated by ploidy overestimates; overestimated fetal fraction often is linked to underestimates in ploidy. The effect frequently is stronger when fetal fraction is underestimated. This is consistent with the asymmetry seen in the graphs presented in FIGS. 40 and 41, (e.g., as F decreases, the growth of the upper branch is substantially faster than the decay of the lower branch). Simulations with different levels of error in F follow the same pattern, with the extent of the deviations from $X_v$ increasing with ΔF.

A probability distribution for X can be used to quantify these observations. In some embodiments, the distribution of ΔF can be used to derive the density function for X using the following expression:

$$f_Y(y) = \left|\frac{1}{g'(g^{-1}(y))}\right| f_X(g^{-1}(y)) \quad (26)$$

where, $f_Y(y)$ is the unknown density function for y=g(x)

$f_X(x)$ is the given density function for x g'(x) is the first derivative of the given function y=g(x)

$g^{-1}(y)$ is the inverse of the given function $g:x=g^{-1}(y)$ $g'(g^{-1}(y))$ is the value of the derivative at the point $g^{-1}(y)$ In equation 26x is ΔF, y is X (e.g., ploidy estimate), and g(x) is given by equation (24). The derivative is evaluated according to the following expression:

$$\frac{dg}{d\Delta F} = -\frac{F_V(X_V-1)}{(F_V+\Delta F)^2} \quad (27)$$

The inverse $g^{-1}(y)$ can be obtained from equation (24), in some embodiments:

$$\Delta F = \frac{F_V(X_V-X)}{X-1} \quad (28)$$

If the error in F conforms to a Gaussian distribution, $f_x(x)$ in equation (26) can be replaced with the following expression:

$$P(\Delta F) = \frac{\exp[-(\Delta F)^2/(2\sigma^2)]}{\sigma\sqrt{2\pi}} \quad (29)$$

Figure 42:
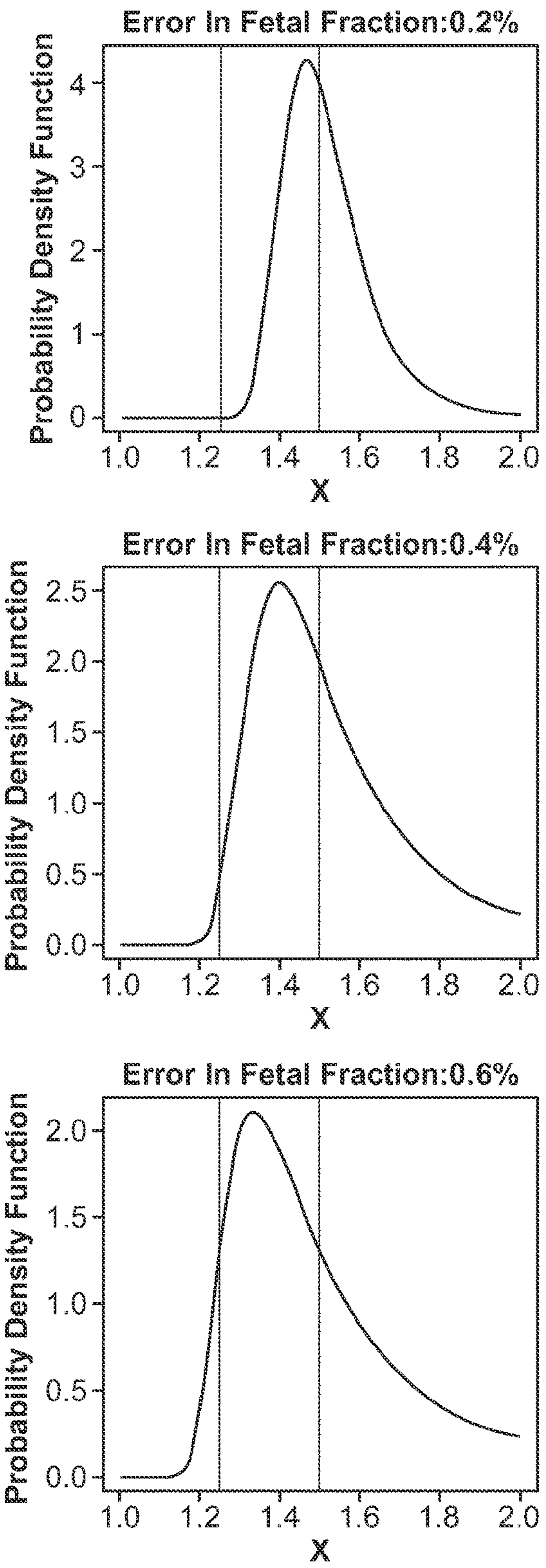
FIG. 42 graphically illustrates probability distributions for fitted ploidy at different levels of errors in measured fetal fractions. The top panel in FIG. 42 sets measured fetal fraction error to 0.2%. The middle panel in FIG. 42 sets measured fetal fraction error to 0.4%. The bottom panel in FIG. 42 sets measured fetal fraction error to 0.6%. See Example 2 for experimental details and results.

In certain embodiments, combining equations (26) to (29) results in a probability distribution for X at different levels of ΔF, as shown in FIG. 42.

Figure 43:
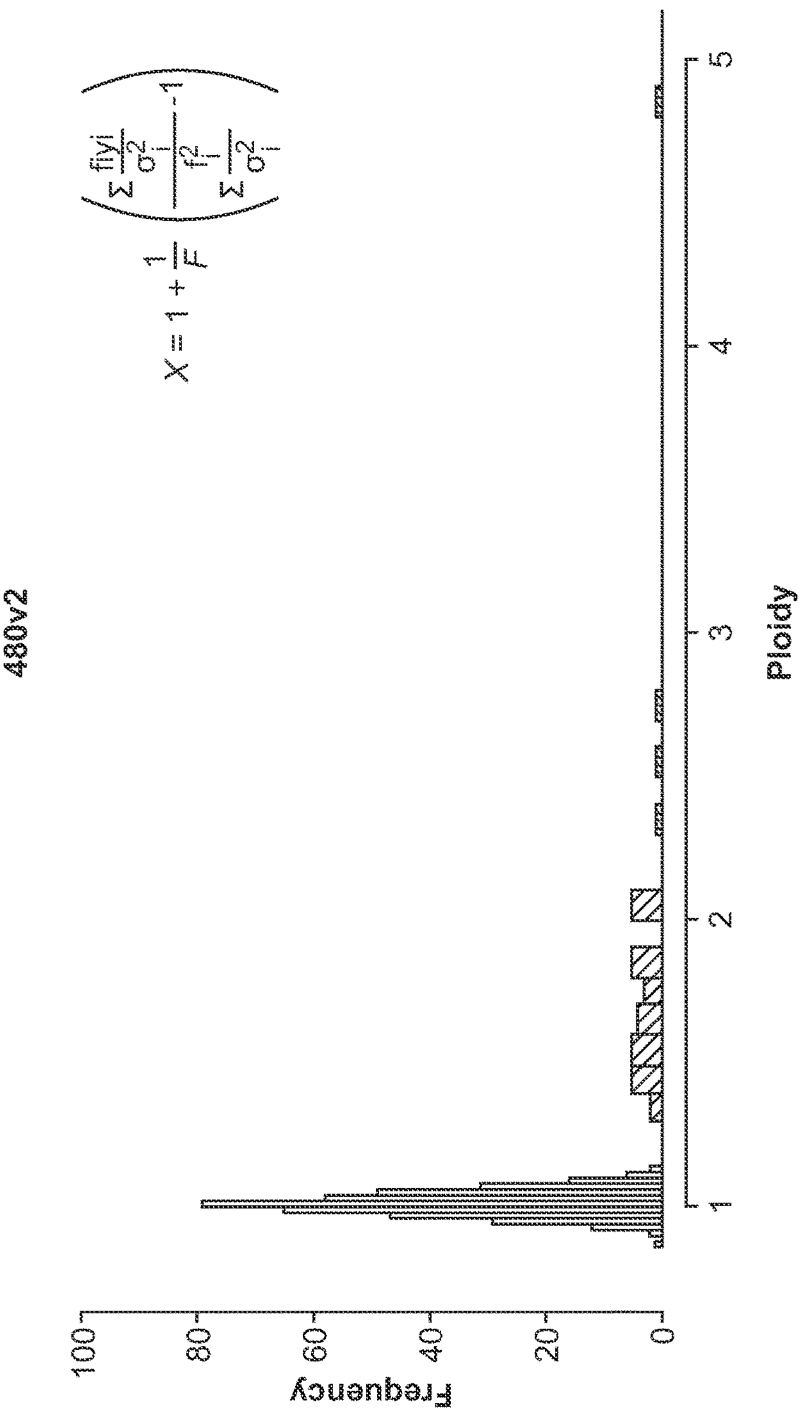
FIG. 43 graphically illustrates euploid and trisomy distributions of fitted ploidy values for a data set derived from patient samples.

In some instances, a bias towards higher ploidy values, which sometimes are prominent at high levels of errors in F, often is reflected in the asymmetric shape of the density function: a relatively long, slowly decaying tail to the right of the light gray line, vertically in line with X, along the X axis, as shown in FIG. 42, panels A-C. In some embodiments, for any value of ΔF, the area under the probability density function to the left of the light gray line ($X_V=3/2$) equals the area to the right of the light gray line. That is, one half of all fitted ploidy values often are overestimates, while the other half of all fitted ploidy values sometimes are underestimates. In some instances, the bias generally only concerns the extent of errors in X, not the prevalence of one or the other direction. The median of the distribution remains equal to $X_V$, in some embodiments. FIG. 43 illustrates euploid and trisomy distributions obtained for actual data. Uncertainties in measured fetal fraction values sometimes explain part of the variance seen in the fitted ploidy values for triploids, however errors in estimated X values for euploids often require examining error propagation from bin counts.

Fixed Ploidy, Optimized Fetal Fraction: Linear Regression

A continuously varying fetal fraction often can be optimized while keeping ploidy fixed at one of its possible values (e.g., 1 for euploids, 3/2 for singleton triploids, 5/4 for twin triploids), as opposed to fitting ploidy that often can take on a limited number of known discrete values. In embodiments in which the measured fetal fraction ($F_0$) is known, optimization of the fetal fraction can be restrained such that the fitted F remains close to $F_0$, within experimental error (e.g., ΔF). In some instances, the observed (e.g., measured) fetal fraction $F_0$, sometimes differs from fetal fraction, $F_V$, described in equations (22) to (28). A robust error propagation analysis should be able to distinguish between $F_0$ and $F_V$. To simplify the following derivations, difference between the observed fetal fraction and the true fetal fraction will be ignored.

Equation (8) is presented below in a rearranged format that also omits the maternal ploidy term (e.g., $M_i$).

$$y_i=F(X-1)f_i+f_i \tag{30}$$

A functional term that needs to be minimized is defined as follows, in some embodiments:

$$\begin{aligned}\varphi(F) &= \frac{(F-F_0)^2}{(\Delta F)^2}+\Sigma_{i=1}^{N}\frac{1}{\sigma_i^2}[y_i-F(X-1)f_i-f_i]^2 \\ &= \frac{(F-F_0)^2}{(\Delta F)^2}+\Sigma_{i=1}^{N}\frac{1}{\sigma_i^2}\left[y_i^2+F^2(X-1)^2f_i^2+f_i^2-2F(X-1)f_iy_i-2f_iy_i+2F(X-1)f_i^2\right] \\ &= \frac{(F-F_0)^2}{(\Delta F)^2}+F^2(X-1)^2\Sigma_{i=1}^{N}\frac{f_i^2}{\sigma_i^2}+2F(X-1)\Sigma_{i=1}^{N}\frac{f_i^2-f_iy_i}{\sigma_i^2}+\Sigma_{i=1}^{N}\frac{(y_i-f_i)^2}{\sigma_i^2}\end{aligned} \tag{31}$$

When equation (31) is evaluated for euploids (e.g., X=1), the term $$\frac{(F-F_0)^2}{(\Delta F)^2}$$

often depends on F, thus fitted F frequently equals $F_0$. In some instances, when equation (24) is evaluated for euploids, the equation sometimes reduces to $$\Sigma_{i=1}^{N}\frac{(y_i-f_i)^2}{\sigma_i^2}.$$

When equation (24) is evaluated for singleton trisomy cases (e.g., X=3/2), the coefficients that multiply F contain both fetal fraction measurements and bin counts, therefore the optimized value for F often depends on both parameters. The first derivative of equation (24) with respect to F reduces to zero in some instances:

$$\frac{1}{2}\left(\frac{d\varphi}{dF}\right)=0=\frac{(F-F_0)}{(\Delta F)^2}+F(X-1)^2\Sigma_{i=1}^{N}\frac{f_i^2}{\sigma_i^2}+(X-1)\Sigma_{i=1}^{N}\frac{f_i^2-f_iy_i}{\sigma_i^2} \tag{32}$$

In some embodiments, replacing X=3/2 and solving equation (32) for F yields an optimized value for F:

$$F=\frac{F_0+\frac{(\Delta F)^2}{2}\Sigma_{i=1}^{N}\frac{1}{\sigma_i^2}(f_iy_i-f_i^2)}{1+\frac{(\Delta F)^2}{4}\Sigma_{i=1}^{N}f_i^2/\sigma_i^2}. \tag{33}$$

To simplify further calculations and/or derivations, the following auxiliary variables will be utilized:

$$S_0=\frac{(\Delta F)^2}{4}\Sigma_{i=1}^{N}\frac{1}{\sigma_i^2} \tag{34}$$

$$S_f=\frac{(\Delta F)^2}{4}\Sigma_{i=1}^{N}\frac{f_i}{\sigma_i^2} \tag{35}$$

$$S_y=\frac{(\Delta F)^2}{4}\Sigma_{i=1}^{N}\frac{y_i}{\sigma_i^2} \tag{36}$$

$$S_{yy}=\frac{(\Delta F)^2}{4}\Sigma_{i=1}^{N}\frac{y_i^2}{\sigma_i^2} \tag{37}$$

-continued $$S_{ff}=\frac{(\Delta F)^2}{4}\Sigma_{i=1}^{N}\frac{f_i^2}{\sigma_i^2} \tag{38}$$

$$S_{fy}=\frac{(\Delta F)^2}{4}\Sigma_{i=1}^{N}\frac{y_if_i}{\sigma_i^2} \tag{39}$$

Utilizing the auxiliary variables, the optimized fetal fraction for X=3/2 for equation (33) then reduces to:

$$F=\frac{F_0+2S_{fy}-2S_{ff}}{1+S_{ff}} \tag{40}$$

Fitted F often is linearly proportional to the measured value $F_0$, but sometimes is not necessarily equal to $F_0$. The ratio between errors in fetal fraction measurements and uncertainties in bin counts determines the relative weight given to the measured $F_0$ versus individual bins, in some embodiments. In some instances, the larger the error ΔF, the stronger the influence that bin counts will exert on the fitted F. Alternatively, small AF generally implies that the fitted value F will be dominated by $F_0$. In some embodiments, if a data set comes from a trisomy sample, and all errors are negligible, equation (40) reduces to identity between F and $F_0$. By way of mathematic proof, using fetal ploidy set to X=3/2, and assuming that $F_0$ (observed) and $F_V$ (true) have the same value, equation (30) becomes:

$$y_i=\tfrac{1}{2}F_0f_i+f_i \tag{41}$$

The assumption that $F_0$ and $F_V$ generally is an acceptable assumption for the sake of the qualitative analysis presented herein. Combing equations (39) and (41) yields $$S_{fy}=\frac{(\Delta F)^2}{4}\Sigma_{i=1}^{N}\frac{y_if_i}{\sigma_i^2}=\frac{(\Delta F)^2}{4}\Sigma_{i=1}^{N}\frac{\left(\frac{1}{2}F_0f_i+f_i\right)}{\sigma_i^2}=\left(\frac{1.}{2}F_0+1\right)S_{ff}\tag{42}$$

Combining equations (40) and (42) results in identity between $F_0$ and $F_V$:

$$F=\frac{F_0+2S_{fy}-2S_{ff}}{1+S_{ff}}=\tag{43}$$

$$\frac{F_0+2\left(\frac{1}{2}F_0+1\right)S_{ff}-2S_{ff}}{1+S_{ff}}=\frac{F_0(1+S_{ff})}{1+S_{ff}}\equiv F_0\ QED$$

To further illustrate the theoretical model, if the true ploidy is 1 (e.g., euploid) but the ploidy value use in equation (40) is set to X=3/2 (e.g., triploid singleton), the resulting fitted F does not equal $F_0$, nor does it reduce to zero, and the following expression generally is true:

$$y_i=f_i\Rightarrow S_{fy}=\frac{(\Delta F)^2}{4}\Sigma_{i=1}^{N}\frac{y_if_i}{\sigma_i^2}=\tag{44}$$

-continued $$\frac{(\Delta F)^2}{4}\Sigma_{i=1}^{N}\frac{f_i^2}{\sigma_i^2}=S_{ff}\Rightarrow F=\frac{F_0+2S_{fy}-2S_{ff}}{1+S_{ff}}=\frac{F_0}{1+S_{ff}}.$$

Figure 44:
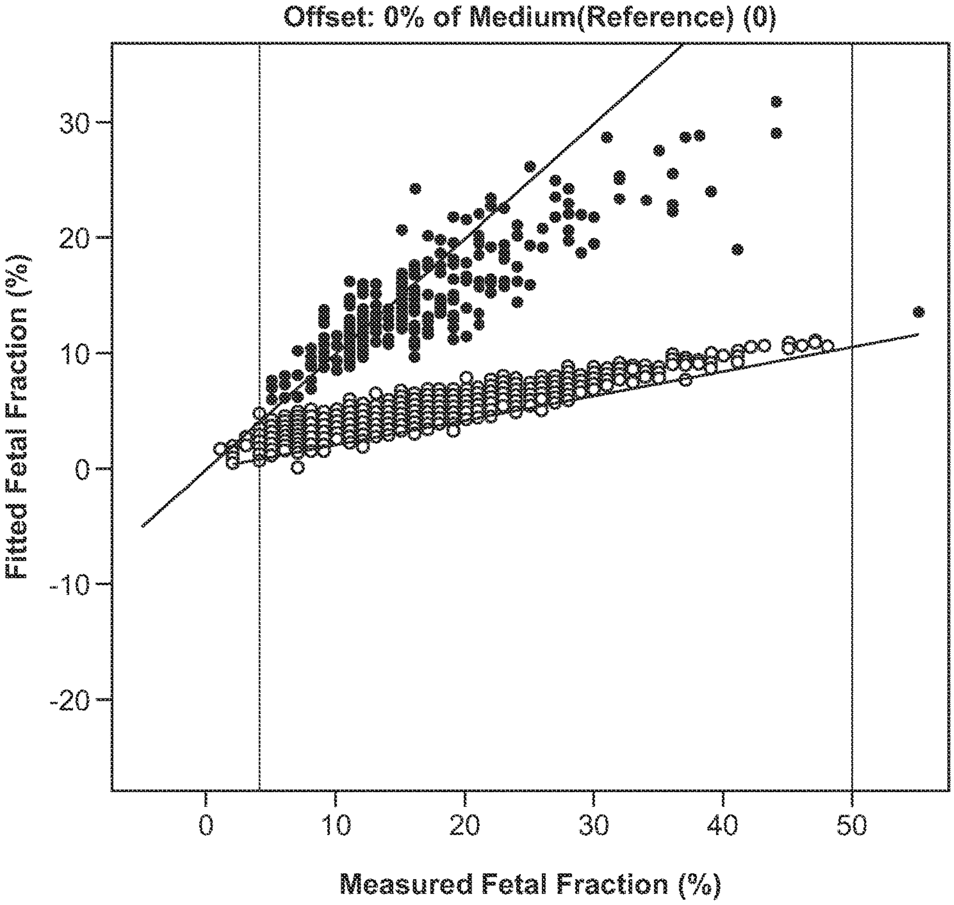
FIG. 44 graphically illustrates fitted fetal fractions plotted against measured fetal fractions. For FIGS. 43 and 44 see Example 2 for experimental details and results.

Thus, application of triploid equations when testing a euploid case generally results in a non-zero fitted F that is proportional to $F_0$ with a coefficient of proportionality between 0 and 1 (exclusive), depending on reference bin counts and associated uncertainties (cf. equation (38)), in certain embodiments. A similar analysis is shown in FIG. 44, using actual data from 86 know euploids as reference. The slope of the straight line from equation (44) is close to 20 degrees, as shown in FIG. 44.

The solitary data point between euploid and T21 cases (e.g., measured fetal fraction approximately 40%, fitted fraction approximately 20%) represents a T21 twin. When a constant AF is assumed the euploid branch of the graph shown in FIG. 44 generally is sloped, however when ΔF=⅔+$F_0$/6 is used the euploid branch of the graph often becomes substantially horizontal, as described herein in the section entitled "Fixed ploidy, optimized fetal fraction, error propagation: fitted fetal fractions".

Fixed Ploidy, Optimized Fetal Fraction: Sums of Squared Residuals

In some instances for euploid cases, were fitted F for equation (32) equals $F_0$ and X=1, the sum of square residuals for a euploid model follows from equation (31):

$$\varphi_E=\Sigma_{i=1}^{N}\frac{1}{\sigma_i^2}(y_i-f_i)^2=\Xi_{yy}-2\Xi_{fy}+\Xi_{ff}\tag{45}$$

which is substantially the same result as equation (9). In certain instances for euploid cases, equation (40) can be combined into equation (31). The resulting mathematical expression quadratically depends on $F_0$, in some embodiments. In certain embodiments, classification of a genetic variation is performed by subtracting the triploid sum of squared residuals from the euploid sum of squared residuals. The result of the classification obtained by subtracting the triploid sum of squared residuals from the euploid sum of squared residuals also frequently depends on $F_0$:

$$\varphi_E-\varphi_T=\frac{-1}{(\Delta F)^2}\left[\left(\frac{F_0+2S_{fy}-2S_{ff}}{1+S_{ff}}-F_0\right)^2+\left(\frac{F_0+2S_{fy}-2S_{ff}}{1+S_{ff}}\right)^2\frac{(\Delta F)^2}{4}\Sigma_{i=1}^{N}\frac{f_i^2}{\sigma_i^2}+\left(\frac{F_0+2S_{fy}-2S_{ff}}{1+S_{ff}}\right)(\Delta F)^2\Sigma_{i=1}^{N}\frac{f_i^2-f_iy_i}{\sigma_i^2}\right]\tag{46}$$

$$=\frac{-1}{(\Delta F)^2}\left[\left(\frac{F_0+2S_{fy}-S_{ff}}{1+S_{ff}}-F_0\right)^2+\left(\frac{F_02S_{fy}-2S_{ff}}{1+S_{ff}}\right)^2S_{ff}+4\left(\frac{F_0+2S_{fy}-2S_{ff}}{1+S_{ff}}\right)(S_{ff}-S_{fy})\right.$$

$$=\frac{-[(2S_{fy}-2S_{ff}-F_0S_{ff})^2+(F_0+2S_{fy}-2S_{ff})^2S_{ff}+4(F_0+2S_{fy}-2S_{ff})(1+S_{ff})(S_{ff}-S_{fy})]}{(\Delta F)^2(1+S_{ff})^2}$$

$$=\frac{-1}{(\Delta F)^2(1+S_{ff})^2}[(4S_{fy}^2+4S_{ff}^2+F_0^2S_{ff}^2-8S_{fy}S_{ff}-4F_0S_{fy}S_{ff}+4F_0S_{ff}^2)$$

$$+(F_0^2S_{ff}+4S_{fy}^2S_{ff}+4S_{ff}^3+4F_0S_{fy}S_{ff}-4F_0S_{ff}^2-8S_{fy}S_{ff}^2)$$

$$+(4F_0S_{ff}+8S_{fy}S_{ff}-8S_{ff}^2-4F_0S_{fy}-8F_0S_{fy}+8S_{fy}S_{ff}$$

$$+4F_0S_{ff}^2+8S_{fy}S_{ff}^2-8S_{ff}^2-4F_0S_{fy}S_{ff}-8S_{fy}^2S_{ff}+8S_{fy}S_{ff}^2)]$$

$$=\frac{-1}{(\Delta F)^2(1+S_{ff})}[F_0^2S_{ff}+4F_0(S_{ff}-S_{fy})-4(S_{ff}-S_{fy})^2]$$

The term $S_{fy}$ generally depends on fetal fraction, as also seen for equation (14). The dependence of $\varphi_E-\varphi_T$ on the measured fetal fraction can be analyzed by accounting for the fetal fraction, in some embodiments. The fetal fraction often can be accounted for by assuming that measured fetal fraction $F_0$ equals true fetal fraction $F_V$. In some embodiments, if the sample's karyotype is euploid, $S_{fy}$ and $S_{ff}$ have the same values (e.g., with the exception of experimental errors). As a result, the difference between the two sums of squared residuals often reduces to:

$$\varphi_E-\varphi_T=\frac{-F_0^2S_{ff}}{(\Delta F)^2(1+S_{ff})}\ \text{(Euploids)}\tag{47}$$

In certain embodiments, if the sample's karyotype is triploid, equations (41) and (42) can be combined with equation (46), yielding:

$$\varphi_E - \varphi_T = \frac{F_0^2 S_{ff}}{(\Delta F)^2} \text{ (Triploids)} \tag{48}$$

Thus, if the difference of $\varphi_E - \varphi_T$ is positive, the fetus is triploid, in some embodiments, and in certain embodiments, if the difference is negative, the fetus is unaffected. The graphical representation for the positive or negative result frequently is a parabola; concave for triploids and convex for euploids. Both branches tend towards zero as $F_0$ decreases, with experimental error having little effect on the shape of the graph. Neither branch has a substantially linear or free term, but the second order coefficients differ in size in addition to having different signs, in many instances. With AF approximately 2%, the value of the term $S_{ff}$ is close to 3.7, using the reference counts and uncertainties extracted from the 86 euploid set (see FIG. 45).

Figure 45:
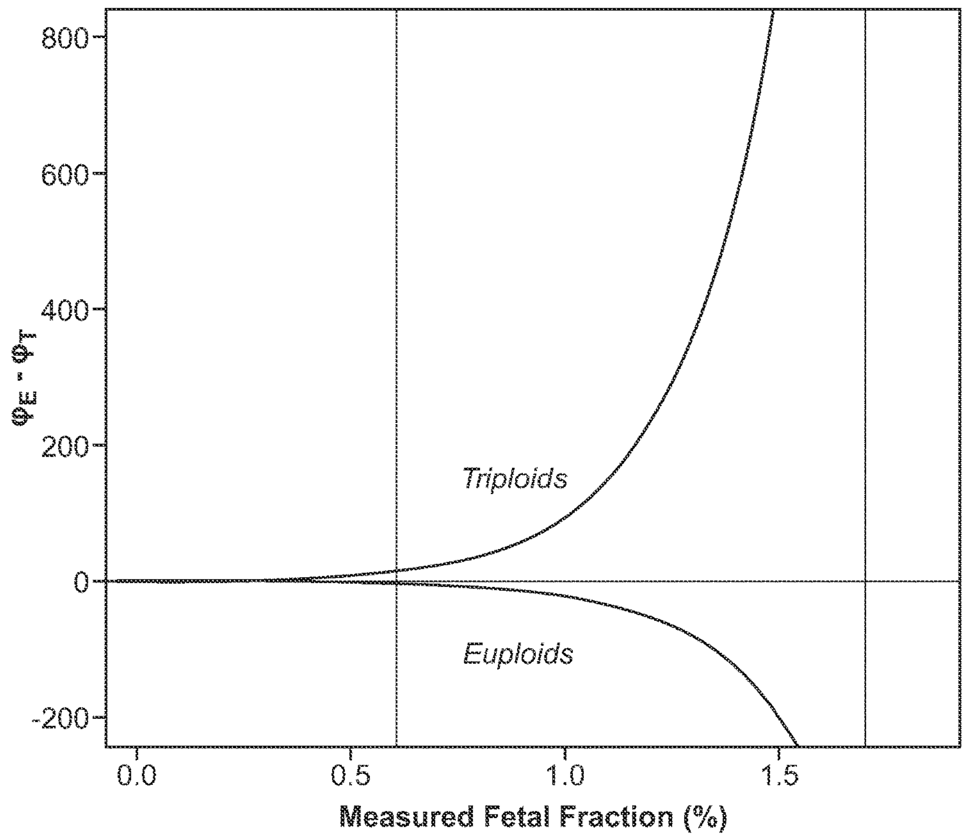
FIG. 45 schematically illustrates the predicted difference between euploid and trisomy sums of squared residuals for fitted fetal fraction as a function of the measured fetal fraction.
Figure 46:
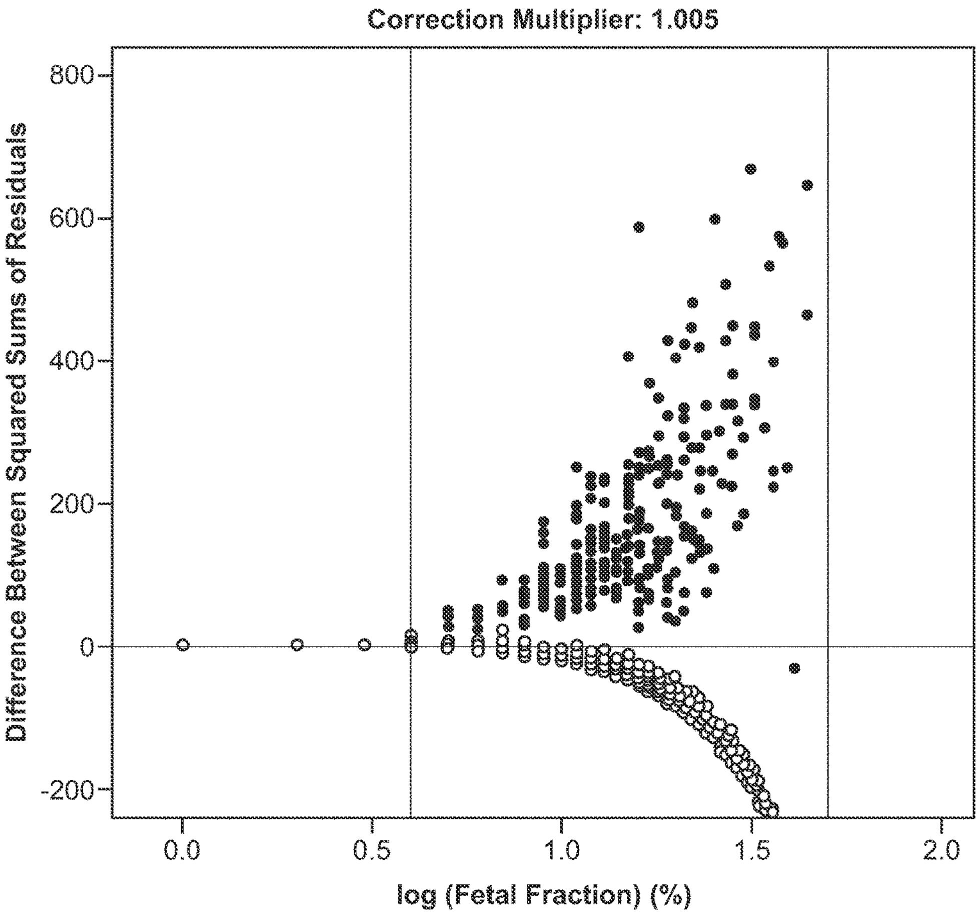
FIG. 46 graphically illustrates the difference between euploid and trisomy sums of squared residuals as a function of the measured fetal fraction using a data set derived from patient samples. The data points are obtained by fitting fetal fraction values assuming fixed uncertainties in fetal fraction measurements.

In the example shown in FIG. 45, the two branches often are asymmetric due to the different coefficients multiplying the square of the measured fetal fraction in equations (47) and (48). The triploid (e.g., positive) branch increases relatively quickly, becoming distinguishable from zero substantially earlier than the euploid branch. FIG. 46, obtained using a real data set, confirms the qualitative results shown in FIG. 45. In FIG. 46 the solitary dark gray point in the fourth quadrant (e.g., lower middle quadrant) is an affected twin. In the data set used to generate FIG. 46, both the euploid and T21 branches of the graph show curvature because both show quadratic dependence on $F_0$ from the trisomy version of equation (31)

Figure 47:
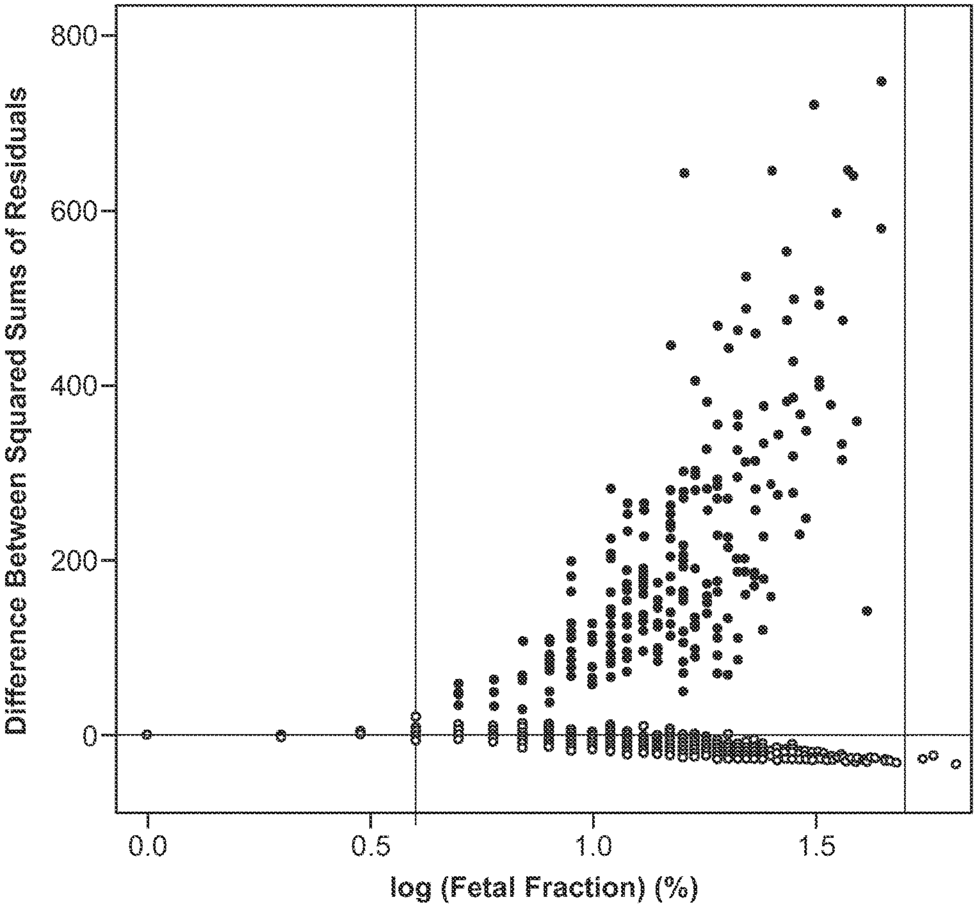
FIG. 47 graphically illustrates the difference between euploid and trisomy sums of squared residuals as a function of the measured fetal fraction. The data points are obtained by fitting fetal fraction values assuming that uncertainties in fetal fraction measurements are proportional to fetal fractions: $\Delta F=\frac{2}{3}+F_0/6$. For FIG. 45-47 see Example 2 for experimental details and results.

In some embodiments, both branches of the graph can be linearized to facilitate visual inspection. The value of the linearization often is conditioned on the error propagation analysis. The results presented in FIGS. 45 and 46 were based on the assumption that the error in measured fetal fractions is uniform the entire range of fetal fractions. However, the assumption is not always the case. In some instances, the more realistic assumption, based on a linear relationship between error $\Delta F$ and measured fetal fraction $F_0(\Delta F = 2/3 + F_0/6)$, produces the results presented in FIG. 47. In FIG. 47, the euploid branch is substantially flat, almost constant (e.g., the parabolic character is substantially lost), however, the trisomy branch remains parabolic. The three light gray points interspersed in the dark gray points of the trisomy branch represent data from twins. Twin data sometimes are elevated relative to the fixed error model.

Classification of whether or not a sample is affected by a genetic variation often is carried out using one of three processes: (1) classification based on parabolic differences of summed squares of residuals, (see FIGS. 45 and 46), (2) classification based on linear differences of summed squares of residuals, (see FIGS. 47 and 48), and (3) classification based on fitted fetal fraction (see equation (33)). In some embodiments, the chosen approach takes error propagation into account.

Fixed Ploidy, Optimized Fetal Fraction: Systematic Error-Reference Offset

Ideally, reference and measured bin counts should contain zero systematic error (e.g., offset), however, in practice, reference and measured bin counts sometimes are shifted with respect to one another. In some instances, the effect of the shift with respect to one another can be analyzed using equation (33), assuming the shift A is constant across the chromosome of interest. For euploid cases, if random errors are neglected, the following relationships hold, in some embodiments:

$$f_i = f_i^0 + \Delta \tag{49}$$

$$y_i = f_i^0 = f_i - \Delta \tag{50}$$

$f_i^0$ represents the true reference bin count i, and $f_i$ represents the reference bin counts used, including any systematic error $\Delta$. In certain embodiments, replacing equations (49) and (50) into equation (33) generates the following expression for the euploid branch of the fitted fetal fraction graph:

$$F_E = \frac{F_0 + \frac{(\Delta F)^2}{2}\Sigma_{i=1}^N \frac{1}{\sigma_i^2}(f_i y_i - f_i^2)}{1 + \frac{(\Delta F)^2}{4}\Sigma_{i=1}^N f_i^2/\sigma_i^2} = \frac{F_0 + \frac{(\Delta F)^2}{2}\Sigma_{i=1}^N \frac{1}{\sigma_i^2}\left[(f_i^0+\Delta)f_i^0 - (f_i^0+\Delta)^2\right]}{1 + \frac{(\Delta F)^2}{4}\Sigma_{i=1}^N (f_i^0+\Delta)^2/\sigma_i^2}$$
$$= \frac{F_0 - \frac{(\Delta F)^2}{2}\left(\Delta\Sigma_{i=1}^N \frac{f_i^0}{\sigma_i^2} + \Delta^2\Sigma_{i=1}^N \frac{1}{\sigma_i^2}\right)}{1 + \frac{(\Delta F)^2}{4}\left(\Sigma_{i=1}^N \frac{1}{\sigma_i^2}(f_i^0)^2 + 2\Delta\Sigma_{i=1}^N \frac{f_i^0}{\sigma_i^2} + \Delta^2\Sigma_{i=1}^N \frac{1}{\sigma_i^2}\right)} = \frac{F_0 - 2S_f^0\Delta - 2S_0^0\Delta^2}{1 + S_{ff}^0 + 2S_f^0\Delta + S_0^0\Delta^2} \tag{51}$$

The coefficients $S_0^0$, $S_f^0$ and $S_{ff}^0$, are generated from equations (33) to (39) by replacing $f_i$ with $f_i^0$, in some embodiments. In certain embodiments, the reciprocal slope of the linear functional relationship between fitted euploid value $F_E$ and measured $F_0$ equals $1+S_{ff}^0+2 S_f^0 \Delta+S_0^0 \Delta^2$, which often allows estimation of the systematic error $\Delta$ by solving a relatively simple quadratic equation. For triploids, assuming $F_0$ equals $F_V$, measured bin counts sometimes become:

$$y_i = f_i^0 + \tfrac{1}{2}F_0 f_i^0 \tag{52}$$

Combining equations (52), (49) and (33) generates the following expression for the triploid branch of the fitted fetal fraction graph:

$$F_T = \frac{F_0 + \frac{(\Delta F)^2}{2}\Sigma_{i=1}^N \frac{1}{\sigma_i^2}(f_i y_i - f_i^2)}{1 + \frac{(\Delta F)^2}{4}\Sigma_{i=1}^N f_i^2/\sigma_i^2} = \frac{F_0 + \frac{(\Delta F)^2}{2}\Sigma_{i=1}^N \frac{1}{\sigma_i^2}\left[(f_i^0+\Delta)\left(f_i^0 + \frac{1}{2}F_0 f_i^0\right) - (f_i^0+\Delta)^2\right]}{1 + \frac{(\Delta F)^2}{4}\Sigma_{i=1}^N (f_i^0+\Delta)^2/\sigma_i^2} \tag{53}$$

$$= \frac{F_0 + \frac{(\Delta F)^2}{2}\left(\frac{1}{2}F_0\Sigma_{i=1}^{N}\frac{1}{\sigma_i^2}(f_i^0)^2 + \frac{1}{2}F_0\Delta\Sigma_{i=1}^{N}\frac{f_i^0}{\sigma_i^2} - \Delta\Sigma_{i=1}^{N}\frac{f_i^0}{\sigma_i^2} - \Delta^2\Sigma_{i=1}^{N}\frac{1}{\sigma_i^2}\right)}{1 + \frac{(\Delta F)^2}{4}\left(\Sigma_{i=1}^{N}\frac{1}{\sigma_i^2}(f_i^0)^2 + 2\Delta\Sigma_{i=1}^{N}\frac{f_i^0}{\sigma_i^2} + \Delta^2\Sigma_{i=1}^{N}\frac{1}{\sigma_i^2}\right)} = \frac{F_0(1 + S_{ff}^0 + S_f^0\Delta) - S_f^0\Delta - S_0^0\Delta^2}{1 + S_{ff}^0 + 2S_f^0\Delta + S_0^0\Delta^2}$$

Figure 48:
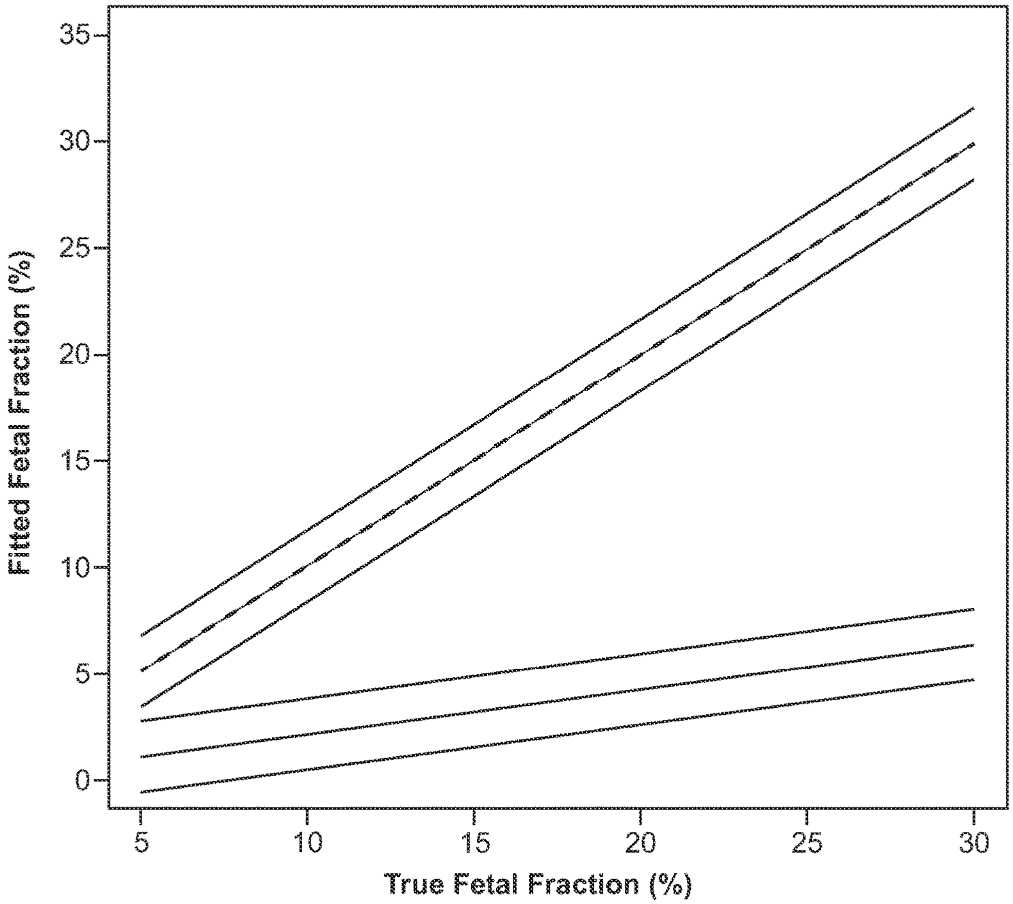
FIG. 48 schematically illustrates the predicted dependence of the fitted fetal fraction plotted against measured fetal fraction profiles on systematic offsets in reference counts. The lower and upper branches represent euploid and triploids cases, respectively.
Figure 49:
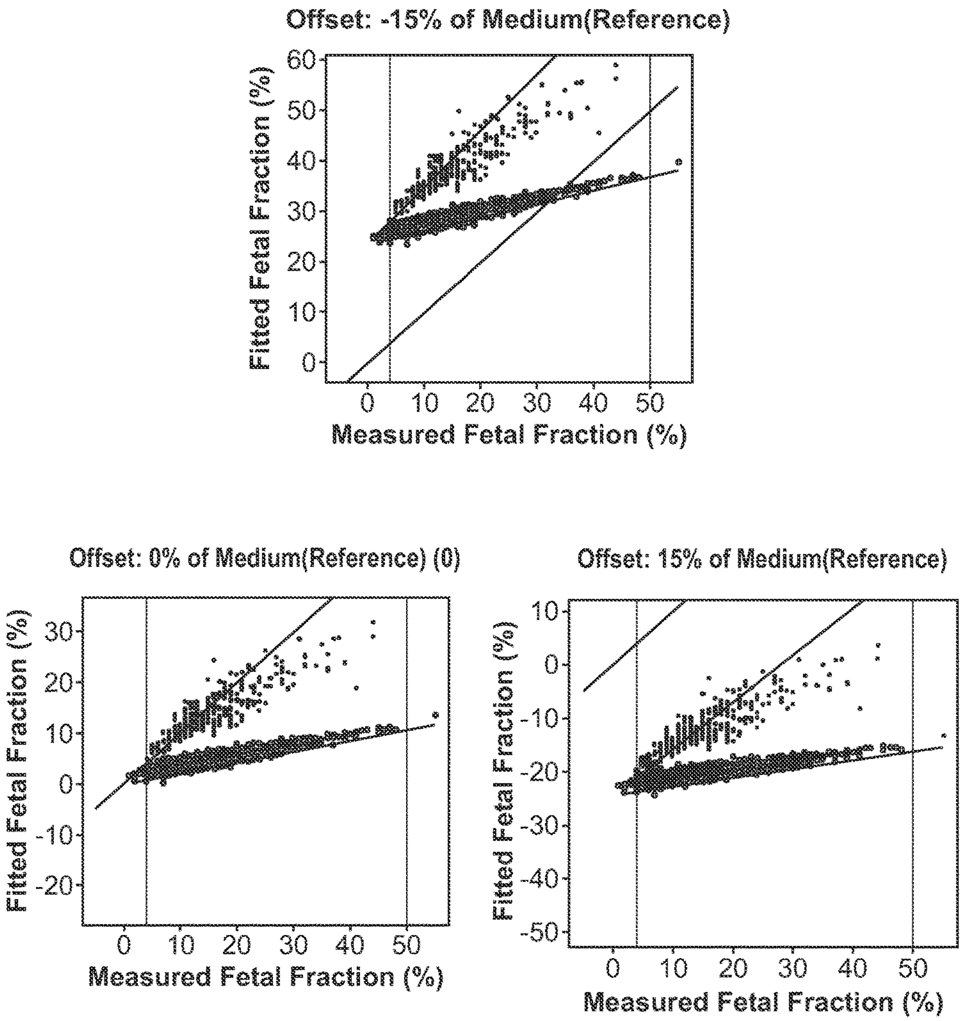
FIG. 49 graphically represents the effects of simulated systematic errors $\Delta$ artificially imposed on actual data. The main diagonal in the upper panel and the upper diagonal in the lower right panel represent ideal agreement. The dark gray line in all panels represents equations (51) and (53) for euploid and triploid cases, respectively. The data points represent actual measurements incorporating various levels of artificial systematic shifts. The systematic shifts are given as the offset above each panel. For FIGS. 48 and 49 see Example 2 for experimental details and results.

In some embodiments, equations (51) and (53) predict that fitted triploid and euploid fetal fractions will behave as shown in FIG. 48. In FIG. 48 black lines (e.g., upper lines in each set of 3 lines) correspond to negative offset $\Delta$, dark gray lines (e.g., bottom lines in each set of 3 lines) correspond to positive offset $\Delta$, and light gray lines (e.g., middle lines in each set of 3 lines), correspond to the absence of offset. FIG. 49 illustrates the effects of simulated systematic errors $\Delta$ artificially imposed on actual data.

Figure 50:
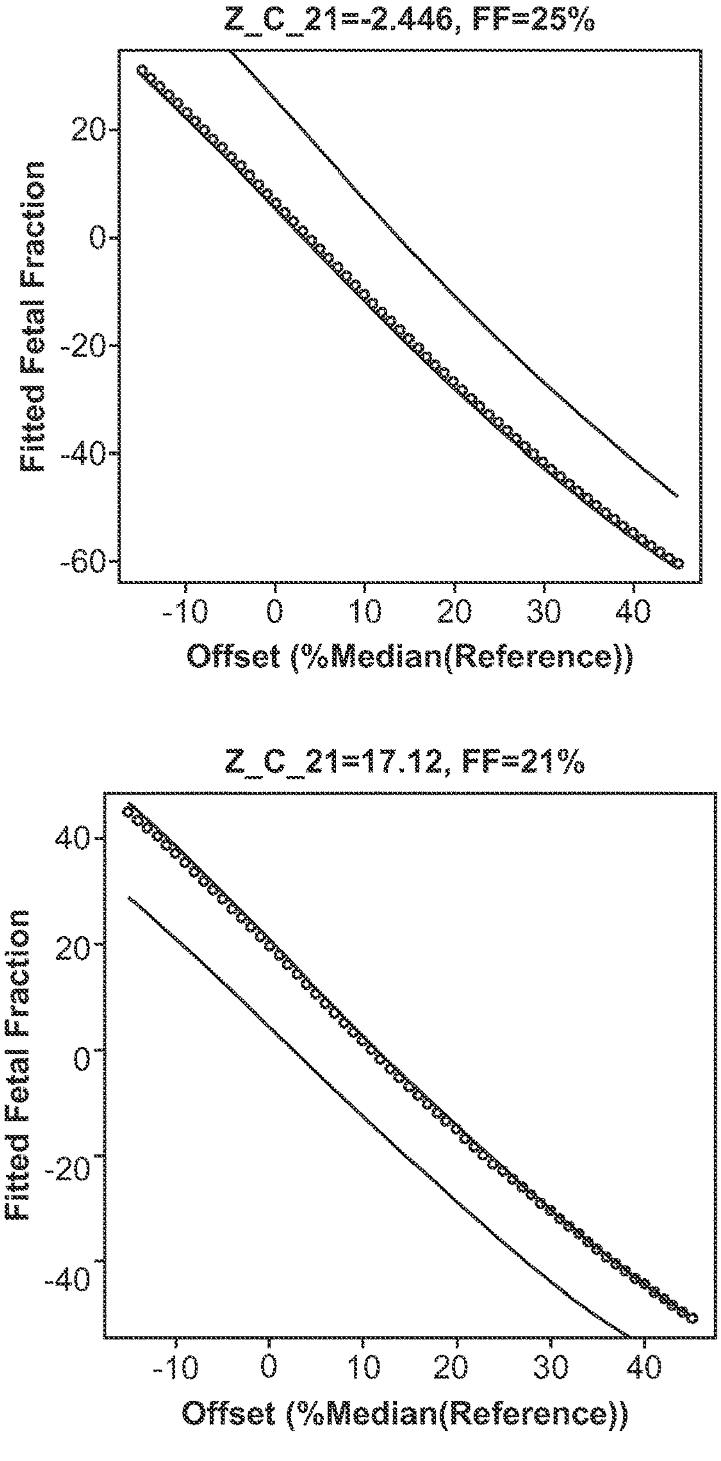
FIG. 50 graphically illustrates fitted fetal fraction as a function of the systematic offset, obtained for a euploid and for a triploid data set.

FIG. 50 illustrates the dependence of fitted fetal fraction on systematic error offset for euploid and triploid data sets. For both euploid and triploid cases, the theoretical expressions of equations (51) and (53) often capture the qualitative dependence of fitted fetal fraction on measured fetal fraction and on systematic error offset. Coefficients used for the graphs in FIGS. 49 and 50 were obtained from raw reference bin counts, without removing any potential systematic bias.

Fixed Ploidy, Optimized Fetal Fraction, Error Propagation: Fitted Fetal Fraction Contributions to errors in fitted fetal fractions often fall into one of two types of errors: 1) from measured fetal fractions, and 2) from measured and reference bin counts. The two types of errors will be analyzed separately, using different approaches, and later combined to generate final error ranges. Errors propagated from measure fetal fractions can be evaluated by replacing $F_0$ in equation (40) first with $F_0 - 2\Delta F$ (e.g., for the lower error boundary) and then with $F_0 + 2\Delta F$ (e.g., for the upper error boundary). This relatively simple approach produces correct qualitative behavior at 95% confidence intervals, in certain embodiments. For a different desired level of confidence, a more general pair of bounds, $F_0 - n\Delta F$ and $F_0 + n\Delta F$, can be utilized. The terms used to generate upper and lower error boundaries sometimes underestimates the total error because the contributions from errors in measure and reference bin counts often are neglected.

To better assess the contribution from measured and reference bin counts on error in fitted fetal fraction, equations (38) to (40) can be utilized, in some embodiments. In certain embodiments, equation (33) can be expanded for fitted fetal fraction into a Taylor series with respect to $f_i$ and $y_i$ truncated to the first order, square and average. In some instances, it can be assumed that uncertainties in $y_i$ often are the same as uncertainties in $f_i$. To simply analysis, cross-terms and higher-order terms are assumed to reduce to zero upon averaging. Taylor expansion coefficients often are obtained utilizing the chain rule. The mean squared variation in the fitted fetal fraction is then given by equation (54) shown below. The model represented by equation ignores contributions from estimates for $\Delta F$, in some embodiments. Partial derivatives can be evaluated using the expressions presented below equation (54).

$$(\delta F)^2 = \Sigma_{i=1}^{N}\left(\frac{\partial F}{\partial f_i}\right)^2 \sigma_i^2 + \Sigma_{i=1}^{N}\left(\frac{\partial F}{\partial y_i}\right)^2 \sigma_i^2 \qquad (54)$$

$$= \Sigma_{i=1}^{N}\left[\left(\frac{\partial F}{\partial S_{ff}}\right)\left(\frac{\partial S_{ff}}{\partial f_i}\right) + \left(\frac{\partial F}{\partial S_{fy}}\right)\left(\frac{\partial S_{fy}}{\partial f_i}\right)\right]^2 \sigma_i^2 + \Sigma_{i=1}^{N}\left[\left(\frac{\partial F}{\partial S_{fy}}\right)\left(\frac{\partial S_{fy}}{\partial y_i}\right)\right]^2 \sigma_i^2$$

$$\left(\frac{\partial F}{\partial S_{ff}}\right) = -\frac{F_0 + 2S_{fy} + 2}{(1+S_{ff})^2} \qquad (55)$$

$$\left(\frac{\partial F}{\partial S_{fy}}\right) = \frac{2}{1+S_{ff}} \qquad (56)$$

$$\left(\frac{\partial S_{ff}}{\partial f_i}\right) = \frac{(\Delta F)^2}{2}\left(\frac{f_i}{\sigma_i^2}\right) \qquad (57)$$

$$\left(\frac{\partial S_{fy}}{\partial f_i}\right) = \frac{(\Delta F)^2}{4}\left(\frac{y_i}{\sigma_i^2}\right) \qquad (58)$$

$$\left(\frac{\partial S_{fy}}{\partial y_i}\right) = \frac{(\Delta F)^2}{4}\left(\frac{f_i}{\sigma_i^2}\right) \qquad (59)$$

Combining equations (54) to (59) generates the following expression:

$$(\delta F)^2 = \left[\frac{(\Delta F)^2}{4}\right]^2 \left\{\sum_{i=1}^{N}\frac{1}{\sigma_i^2}\left[\frac{2y_i}{1+S_{ff}} - 2f_i\frac{F_0+2S_{fy}+2}{(1+S_{ff})^2}\right]^2 + \sum_{i=1}^{N}\frac{1}{\sigma_i^2}\left(\frac{2f_i}{1+S_{ff}}\right)^2\right\} \qquad (60)$$

$$= \left[\frac{(\Delta F)^2}{4}\right]^2 \sum_{i=1}^{N}\frac{1}{\sigma_i^2}\left[\left(\frac{2y_i}{1+S_{ff}}\right)^2 - 8f_iy_i\frac{F_0+2S_{fy}+2}{(1+S_{ff})^3} + 4f_i^2\frac{(F_0+2S_{fy}+2)^2}{(1+S_{ff})^4} + \left(\frac{2f_i}{1+S_{ff}}\right)^2\right]$$

-continued $$= \left[\frac{(\Delta F)}{4}\right]^2 \left\{ \begin{array}{c} \frac{4}{(1+S_{ff})^2} \sum_{i=1}^{N} \frac{y_i^2}{\sigma_i^2} - \\ 8\frac{F_0+2S_{fy}+2}{(1+S_{ff})^3} \sum_{i=1}^{N} \frac{f_i y_i}{\sigma_i^2} + \\ 4\left[ \begin{array}{c} \frac{(F_0+2S_{fy}+2)^3}{(1+S_{ff})^4} + \\ \frac{1}{(1+S_{ff})^2} \end{array} \right] \sum_{i=1}^{N} \frac{f_i^2}{\sigma_i^2} \end{array} \right\}$$

$$= (\Delta F)^2 \left\{ \begin{array}{c} \frac{S_{yy}}{(1+S_{ff})^2} - 2S_{fy}\frac{F_0+2S_{fy}+2}{(1+S_{ff})^2} + \\ S_{ff}\left[\frac{(F_0+2S_{fy}+2)^2}{(1+S_{ff})^4} + \frac{1}{(1+S_{ff})^2}\right] \end{array} \right\}$$

To evaluate equation (60) at a 95% confidence interval, the following upper and lower bounds can be used, in some embodiments:

$$\begin{bmatrix} F_{Lower} \\ F_{Upper} \end{bmatrix} = \frac{F_0+2S_{fy}-2S_{ff}}{1+S_{ff}} + \begin{bmatrix} -2 \\ 2 \end{bmatrix} \Delta F \left\{ \frac{1}{1+S_{ff}} + \sqrt{\frac{S_{yy}}{(1+S_{ff})^2} - 2S_{fy}\frac{F_0+2S_{fy}+2}{(1+S_{ff})^2} + S_{ff}\left[\frac{(F_0+2S_{fy}+2)^2}{(1+S_{ff})^4} + \frac{1}{(1+S_{ff})^2}\right]} \right\} \quad (61)$$

Figure 51:
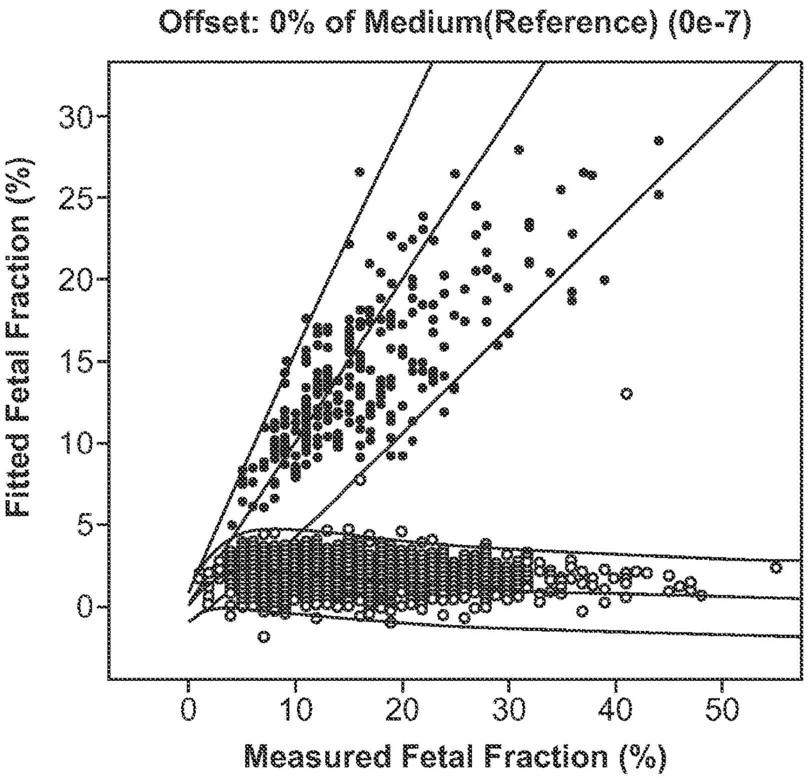
FIG. 51 graphically illustrates simulations based on equation (61), along with fitted fetal fractions for actual data. Black lines represent two standard deviations (obtained as square root of equation (61)) above and below equation (40). $\Delta F$ is set to $\frac{2}{3}+F_0/6$. For FIGS. 50 and 51 see Example 2 for experimental details and results.

In embodiments in which substantially all possible sources of error (e.g., $F_0$, $f_i$, $y_i$) are included in the Taylor expansion series, the same equation often is obtained. In some instances, dependence of F on $F_o$, can be accounted for through $S_{fy}$. In some embodiments, power series terms corresponding to $F_0$ often take the form;

$$\left[\left(\frac{\partial F}{\partial F_*}\right) + \left(\frac{\partial F}{\partial S_{fy}}\right)\left(\frac{\partial S_{fy}}{\partial F_*}\right)\right]^2 (\Delta F)^2,$$

but $$\left[\left(\frac{\partial F}{\partial F_*}\right) + \left(\frac{\partial F}{\partial S_{fy}}\right)\left(\frac{\partial S_{fy}}{\partial F_*}\right)\right]^2$$

equals 1 for triploids. Thus, relatively simple subtraction and addition of ΔF to $F_0$ often is justified, even though ΔF often increases with $F_0$ and becomes large at high $F_0$. The outcome is due to both F and $S_{fy}$ depending linearly on $F_0$, in some embodiments. Simulations based on equation (61) are shown in FIG. 51, along with fitted fetal fractions obtained from test subject derived data. In the simulations presented in FIG. 51, $\Delta F = 2/3 + F_0/6$, as described herein.

Example 3: Sliding Window Analysis and Cumulative Sums as a Function of Genomic Position Identification of recognizable features (e.g., regions of genetic variation, regions of copy number variation) in a normalized count profile sometimes is a relatively time consuming and/or relatively expensive process. The process of identifying recognizable features often is complicated by data sets containing noisy data and/or low fetal nucleic acid contribution. Identification of recognizable features that represent true genetic variations or copy number variations can help avoid searching large, featureless regions of a genome. Identification of recognizable features can be achieved by removing highly variable genomic sections from a data set being searched and obtaining, from the remaining genomic sections, data points that deviate from the mean profile elevation by a predetermined multiple of the profile variance.

In some embodiments, obtaining data points that deviate from the mean profile elevation by a predetermined multiple of the profile variance can be used to reduce the number of candidate genomic sections from greater than 50,000 or 100,000 genomic sections to in the range of about 100 to about 1000 candidate genomic sections that represent true signals or solitary noise spikes (e.g., about 100 genomic sections, about 200 genomic sections, about 300 genomic sections, about 400 genomic sections, about 500 genomic sections, about 600 genomic sections, about 700 genomic sections, about 800 genomic sections, about 900 genomic sections, or about 1000 genomic sections). The reduction in the number of candidate genomic sections can be achieved relatively quickly and easily and often speeds up the search for and/or identification of genetic aberrations by two or more orders of magnitude. Reduction in the number of genomic sections searched for the presence or absence of candidate regions of genomic variation often reduces the complexity and/or dimensionality of a data set.

After a reduced data set containing data points that deviate from the mean profile elevation by a predetermined multiple of the profile variance is generated, the reduced data set is filtered to eliminate solitary noise spikes, in some embodiments. Filtering a reduced data set to remove solitary noise spikes often generates a filtered, reduced data set. In some embodiments, a filtered, reduced data set retains contiguous clusters of data points, and in certain embodiments, a filtered, reduced data set retains clusters of data points that are largely contiguous with allowance for a predetermined number and/or size of gaps. Data points from the filtered, reduced data set that deviate from the average profile elevation in substantially the same direction are grouped together, in some embodiments.

Due to the background noise often present in nucleic acid samples (e.g., ratio of regions of interest compared to the total nucleic acid in a sample), distinguishing regions of genetic variation or genetic aberration from background noise often is challenging. Methods that improve the signal-to-noise ratio often are useful for facilitating the identification of candidate regions representative of regions of true genetic variation and/or genetic aberration. Any method that improves the signal-to-noise ratio of regions of true genetic variation with respect to the genomic background noise can be used. A non-limiting example of a method suitable for use in improving the signal-to-noise ratio of regions of true genetic variation with respect to the genomic background noise is the use of integrals over the suspected aberration and its immediate surroundings. In some embodiments, the use of integrals over the suspected aberration and its immediate surroundings is beneficial, because summation cancel out random noise. After noise has been reduced or eliminated, even relatively minor signals can become readily detectable using a cumulative sum of the candidate peak and its surroundings, in some embodiments. A cumulative sum sometimes is defined with respect to an arbitrarily chosen origin outside (e.g., on one side or the other) of the peak. A cumulative sum often is a numerical estimate of the integral of the normalized count profile over the selected genetic section or sections.

In the absence of aberrations, the cumulative sum as a function of the genomic position often behaves as a straight line with unit slope (e.g., slope equal to 1). If deletions or duplications are present, the cumulative sum profile often consists of two or more line segments. In some embodiments, areas outside of aberrations map to line segments with unit slopes. For areas within aberrations, the line segments are connected by other line segments whose slopes equal the count profile elevation or depression within the aberration, in certain embodiments.

In those samples having maternal aberrations, the slopes (e.g., equivalent to the count profile elevation) are relatively easily determined: 0 for homozygous maternal deletions, 0.5 for heterozygous maternal deletions, 1.5 for heterozygous maternal duplications, 2.0 for homozygous maternal duplications. In those samples having fetal aberrations, the actual slopes depend both on the type of the aberration (e.g., homozygous deletion, heterozygous deletion, homozygous duplication or heterozygous duplication) and on the fetal fraction. In some embodiments, inheritance of a maternal aberration by the fetus also is taken into account when evaluating fetal samples for genetic variations.

In some embodiments, line segments with unit slopes, corresponding to normal genomic areas to the left and to the right of an aberration, are vertically shifted with respect to one another. The difference (e.g., subtractive result) between their intercepts equals the product between the width of the aberration (number of affected genomic sections) and the aberration level (e.g., −1 for homozygous maternal deletion, −0.5 for heterozygous maternal deletion, +0.5 for heterozygous maternal duplication, +1 for homozygous maternal duplication, and the like). Refer to FIGS. 52-61F for examples of data sets processed using cumulative sums as a function of genomic position (e.g., sliding window analysis).

Example 4: Parameterized Error Removal and Unbiased Normalization (PERUN)

Variability of Measured Counts

Figure 62:
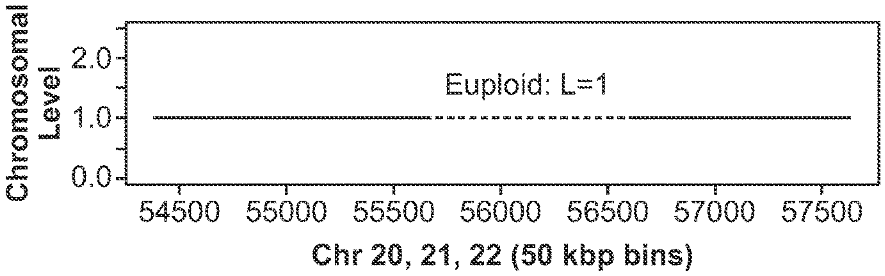

Ideally, the measured chromosomal elevation is a straight horizontal line with the elevation of 1 for euploids, as in FIG. 62. For trisomy pregnancies, the desired behavior of the measured chromosomal elevation is a step-function, with the deviation from 1 proportional to the fetal fraction, as simulated in FIG. 63 for fetal fraction equal to 15%. Exceptions arise out of maternal deletions/duplications, which are readily recognized and distinguished from fetal abnormalities based on their magnitudes, which are multiples of one-half.

Figure 64:
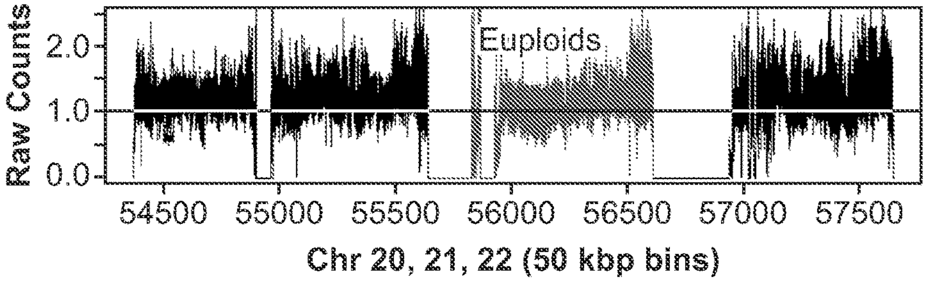
Figure 65:
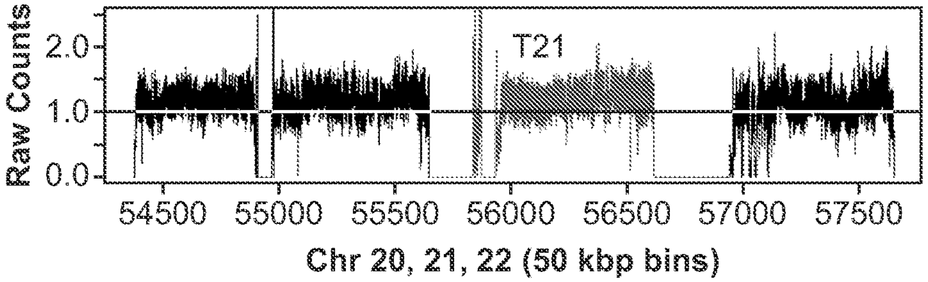

What was actually measured was not ideal. FIG. 64 shows overlaid raw counts for chromosomes 20, 21, and 22 collected from 1093 euploid pregnancies and FIG. 65 shows overlaid raw counts for chromosomes 20, 21, and 22 collected from 134 trisomy 21 pregnancies. Visual inspection of the two sets of profiles failed to confirm that chromosome 21 traces in trisomy cases were elevated. Stochastic noise and systematic bias both made the elevation of chromosome 21 difficult to visualize. Furthermore, the far right segment of chromosome 21 incorrectly suggested that euploid chromosome 21 traces were elevated, rather than the trisomy profiles. A large portion of the systematic bias originated from the GC content associated with a particular genomic region.

Figure 66:
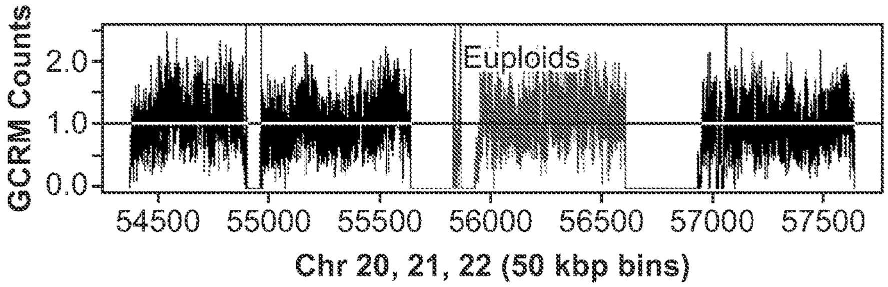
Figure 67:
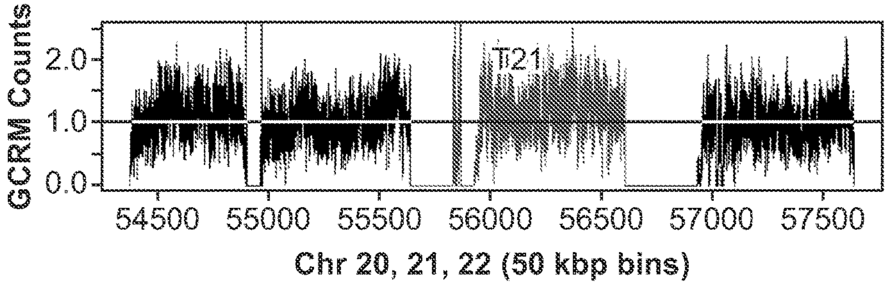

Attempts to remove the systematic bias due to GC content included multiplicative LOESS GC smoothing, Repeat Masking (RM), combination of LOESS and RM (GCRM), and others, such as cQN. FIG. 66 shows the results of a GCRM procedure as applied to 1093 euploid traces and FIG. 67 shows the GCRM profiles for 134 trisomy cases. GCRM successfully flattened the elevated, GC-rich, rightmost segment of chromosome 21 in euploids. However, the procedure evidently increased the overall stochastic noise. Moreover, it created a new systematic bias, absent from the raw measurements (leftmost region of chromosome 20 (Chr20)). The improvements that were due to GCRM were offset by increased noise and bias, rendering the usefulness of the procedure questionable. The tiny elevation from chromosome 21 as observed in FIG. 63 was lost in the high noise as shown in FIG. 66 and FIG. 67.

Figure 63:
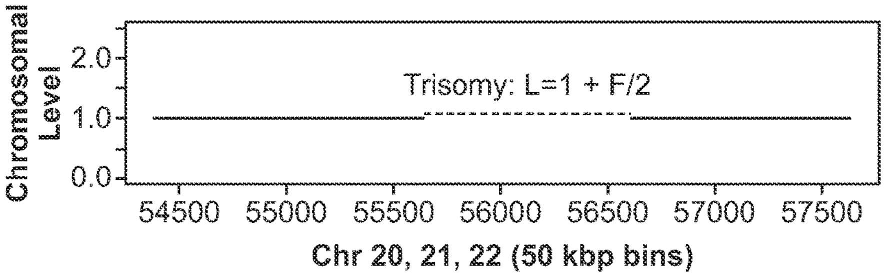
Figure 68:
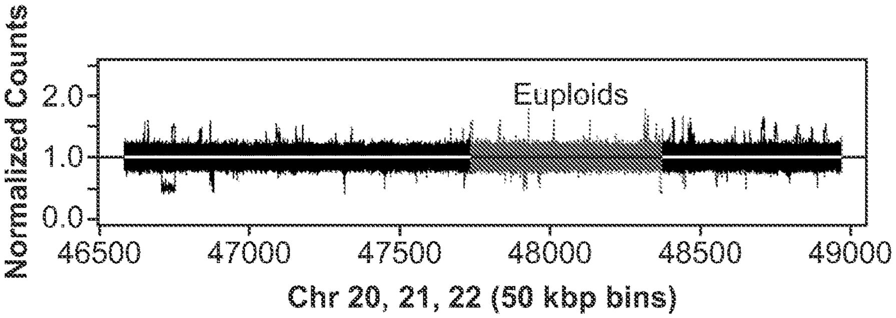
Figure 69:
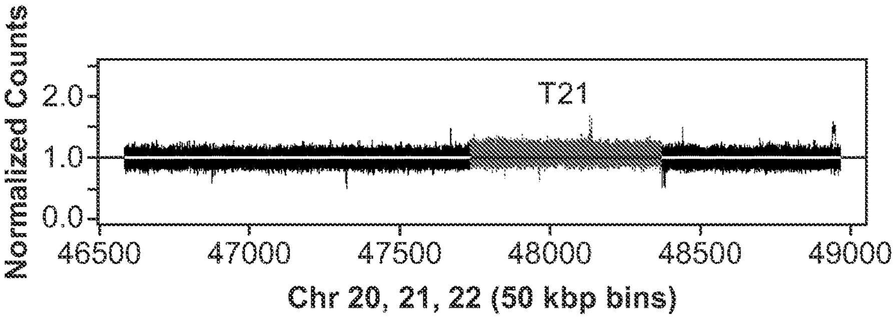

PERUN (Parameterized Error Removal and Unbiased Normalization) was developed as a viable alternative to previously described GC normalization methods. FIG. 68 and FIG. 69 contrast the PERUN method results against those presented in FIG. 64 through 67. PERUN results were obtained on the same two subpopulations of data that was analyzed in FIG. 64 through 67. Most of the systematic bias was absent from PERUN traces, only leaving stochastic noise and biological variation, such as the prominent deletion in chromosome 20 of one of the euploid samples (FIG. 68). The chromosome 20 deletion was also observable in raw count profiles (FIG. 64), but completely masked in the GCRM traces. The inability of GCRM to reveal this huge deviation clearly disqualifies it for the purposes of measuring the miniscule fetal T21 elevations. PERUN traces contain fewer bins than raw or GCRM profiles. As shown in FIG. 62-63, the PERUN results look at least as good as the measurement errors permit.

Normalization with Respect to Reference Median Count Profile

Figure 4:
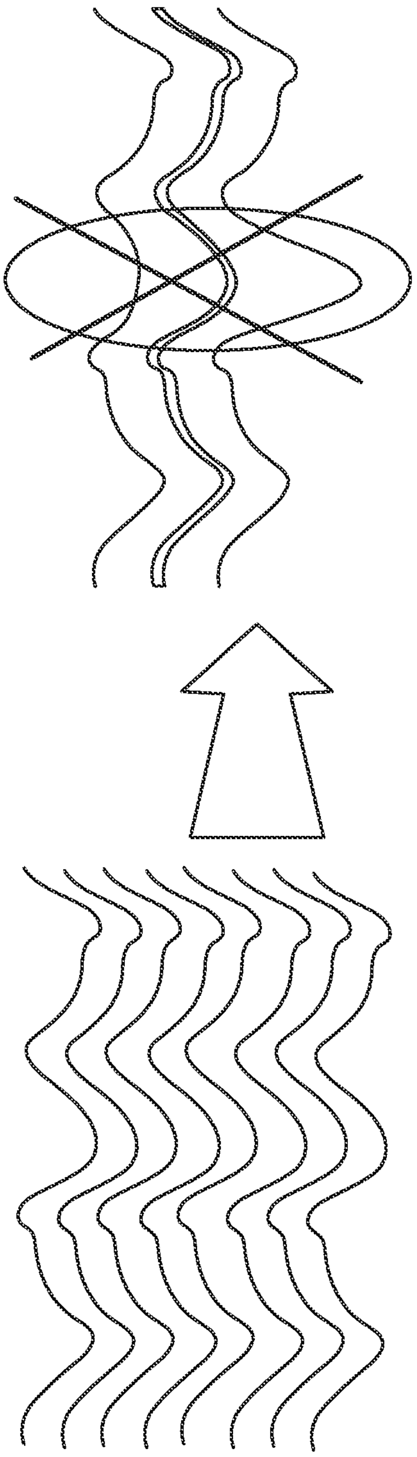
FIG. 4 schematically represents a bin filtering procedure. A large number of euploid samples are lined up, bin count uncertainties (SD or MAD values) are evaluated, and bins with largest uncertainties sometimes are filtered out.
Figure 6:
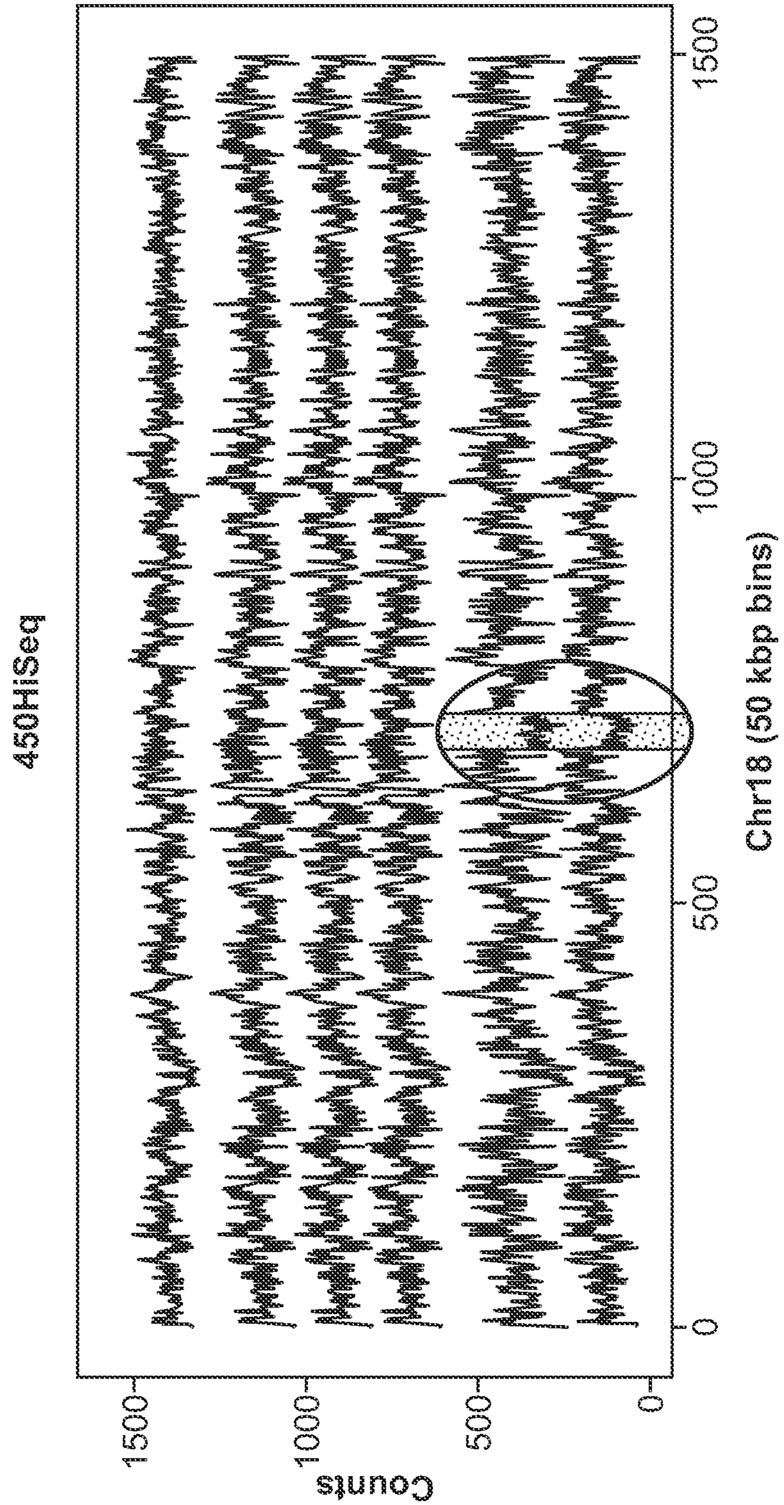
FIG. 6 graphically illustrates count profiles for patients used to filter out uninformative bins from chromosome 18.
Figure 7:
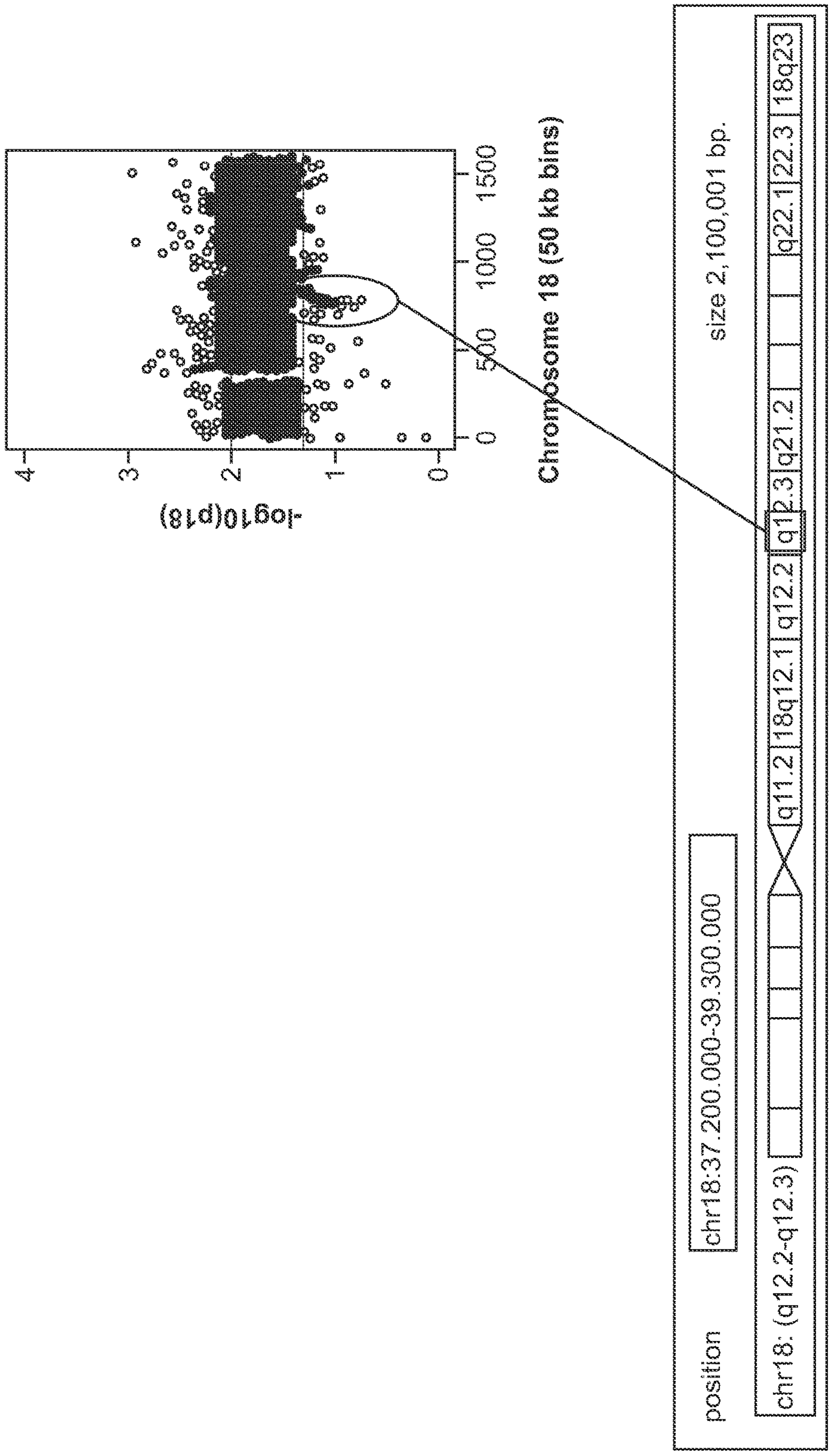
FIG. 7 graphically illustrates the dependence of p-values on the position of genomic bins within chromosome 18.
Figure 8:
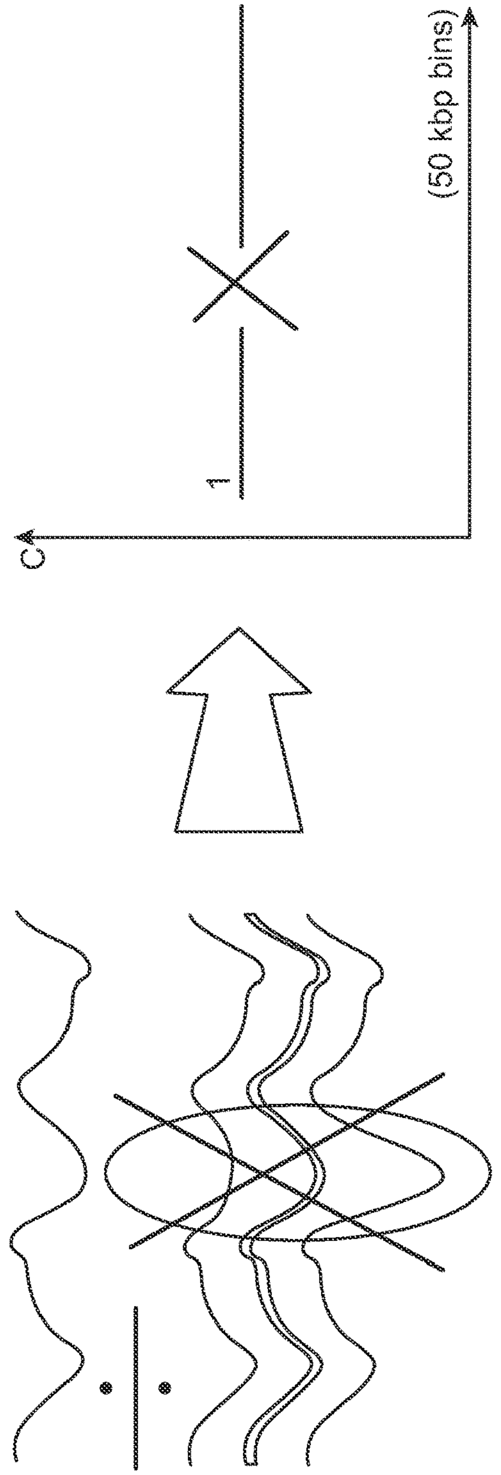
FIG. 8 schematically represents bin count normalization. The procedure first lines up known euploid count profiles, from a data set, and normalizes them with respect to total counts. For each bin, the median counts and deviations from the medians are evaluated. Bins with too much variability (exceeding 3 mean absolute deviations (e.g., MAD)), in certain embodiments, are eliminated. The remaining bins are normalized again with respect to residual total counts, and medians are re-evaluated following the renormalization, in some embodiments. Finally, the resulting reference profile (see bottom trace, left panel) is used to normalize bin counts in test samples (see top trace, left panel), smoothing the count contour (see trace on the right) and leaving gaps where uninformative bins have been excluded from consideration.

Conventional GC normalization procedures can perform suboptimally. A part of the reason has been that GC bias is not the only source of variation. A stack plot of many individual raw count profiles revealed parallelism between different samples. While some genomic regions were consistently over-represented, others were consistently under-represented, as illustrated by the traces from a 480v2 study (FIG. 6). While GC bias varied from one sample to another, the systematic, bin-specific bias observed in these profiles followed the same pattern for all samples. All the profiles in FIG. 6 zigzagged in a coordinated fashion. The only exceptions were the middle portions of the bottom two samples, which turned out to originate from maternal deletions. To correct for this bin-specific bias, a median reference profile was used. The median reference profile was constructed from a set of known euploids (e.g. euploid pregnancies) or from all the samples in a flow cell. The procedure generated the reference profile by evaluating median counts per bin for a set of reference samples. The MAD associated with a bin measured the reliability of a bin. Highly variable bins and bins that consistently have vanishing representations were removed from further analysis (FIG. 4). The measured counts in a test data set were then normalized with respect to the median reference profile, as illustrated in FIG. 8. The highly variable bins are removed from the normalized profile, leaving a trace that is approximately 1 in the diploid sections, 1.5 in the regions of maternal heterozygous duplication, 0.5 in the areas of maternal heterozygous deletion, and so on (FIG. 9). The resulting normalized profiles reasonably reduced the variability, enabling detection of maternal deletions and duplications and tracing of sample identities (FIG. 12, 22, 13, 11). Normalization based on median count profile can clarify outcomes, but GC bias still has a negative effect on such methods. PERUN methods described here can be used to address GC bias and provide outcomes with higher sensitivity and specificity.

Detrimental Effects of Multiplicative LOESS Correction

Figure 70:
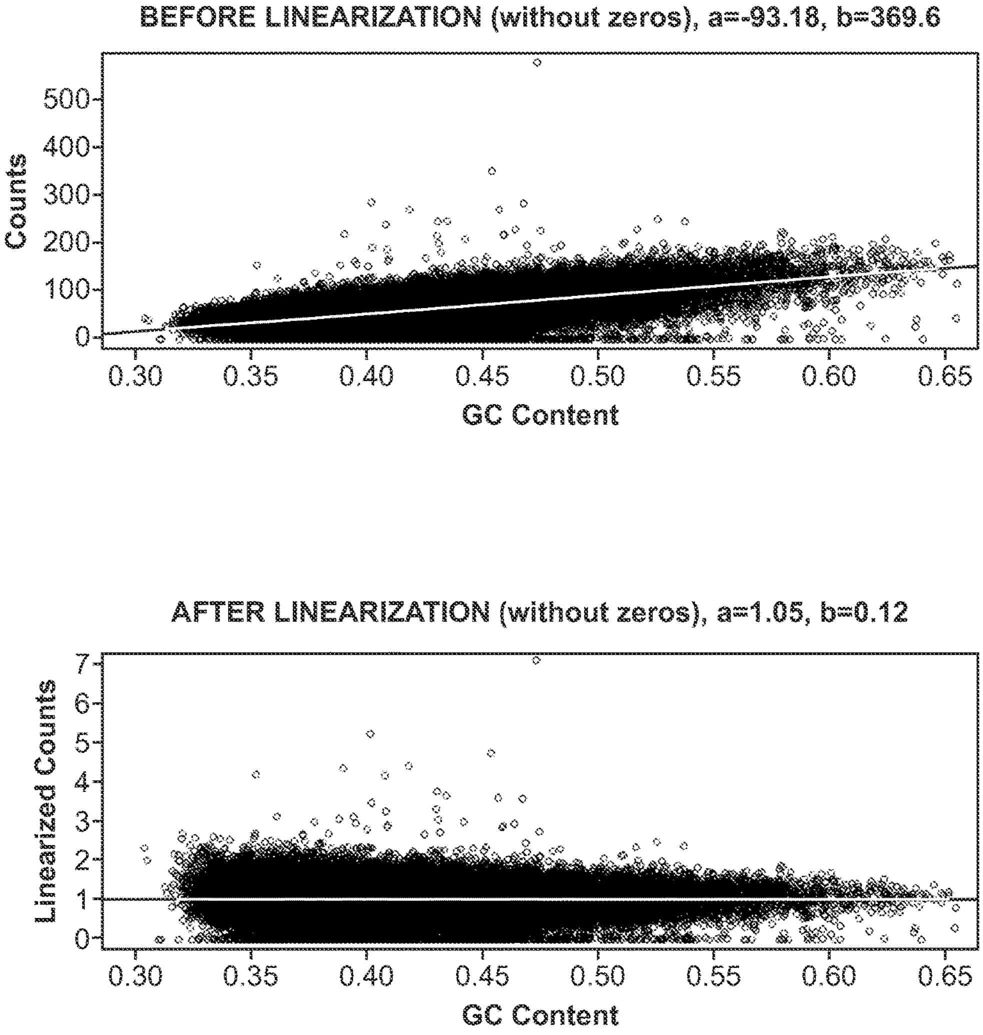

FIG. 11. illustrated why binwise counts fluctuate more after application of GC-LOESS or GCRM (FIG. 66-67) than before (FIG. 64-65). LOESS GC correction removed the trend from the raw counts (FIG. 70, upper panel) by dividing the raw counts with the regression line (straight line, FIG. 70, upper panel). The point defined by the median counts and the median genome GC content was kept immobile. On average, counts below the median count were divided by small numbers, while counts exceeding the median count were divided by large numbers. In either case, on average, counts were scaled up or down to match 1 (FIG. 70, lower panel). The scaling of small counts, in addition to inflating the counts, also inflated their variability. The end result (FIG. 70, lower panel) to the left from the median GC genome content displayed a larger spread than the corresponding raw counts (FIG. 70, upper panel), forming the typical triangular shape (FIG. 70, lower panel, triangle). To detrend the counts, GC LOESS/GCRM sacrificed precision as such corrective processes generally are multiplicative and not additive. Normalization provided by PERUN generally is additive in nature and enhances precision over multiplicative techniques.

Inadequacy of a Genome-Wide Pivot for GC-Bias Scaling

Figure 71:
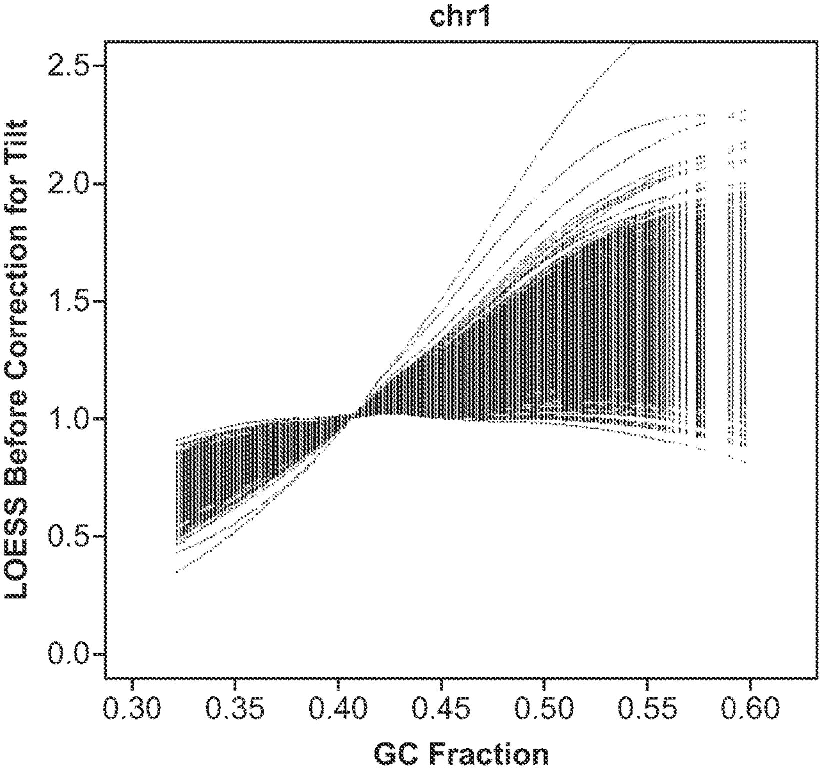

An alternative approach applied the LOESS correction separately to individual chromosomes instead of subjecting the entire genome to a collective GC-Bias scaling. The scaling of individual chromosomes was impractical for purposes of classifying samples as euploid or trisomy because it canceled out the signal from over-represented chromosomes. However, the conclusions from this study were eventually useful as catalyzers for developing the PERUN algorithm. FIG. 71 illustrates the fact that LOESS curves obtained for the same chromosome from multiple samples share a common intersection (pivot).

Figure 72:
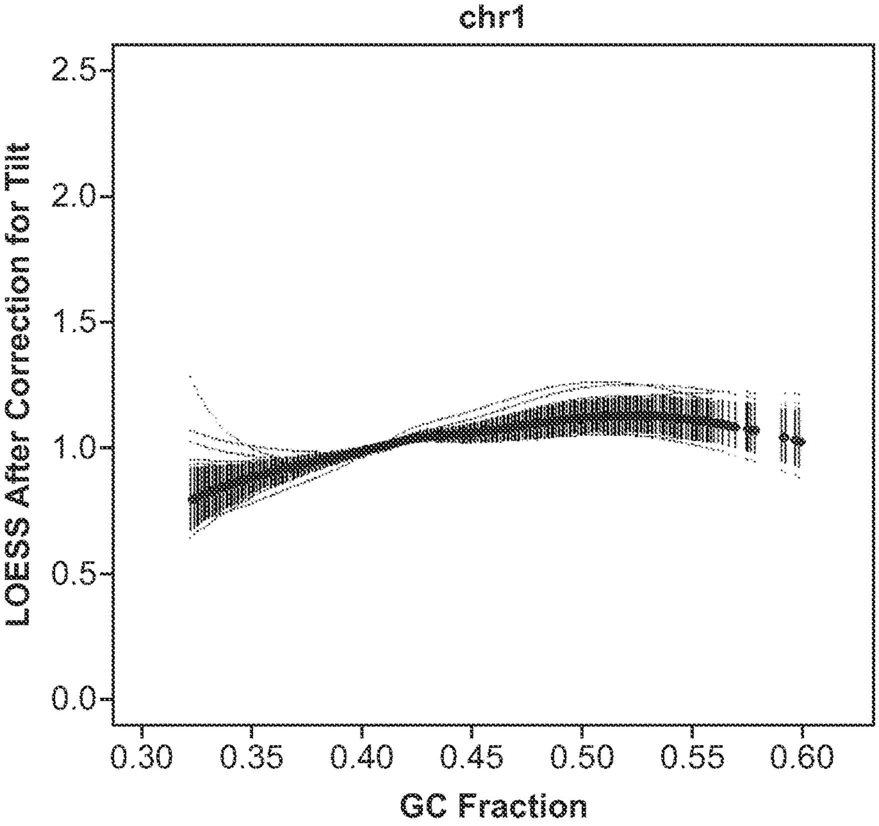
Figure 73:
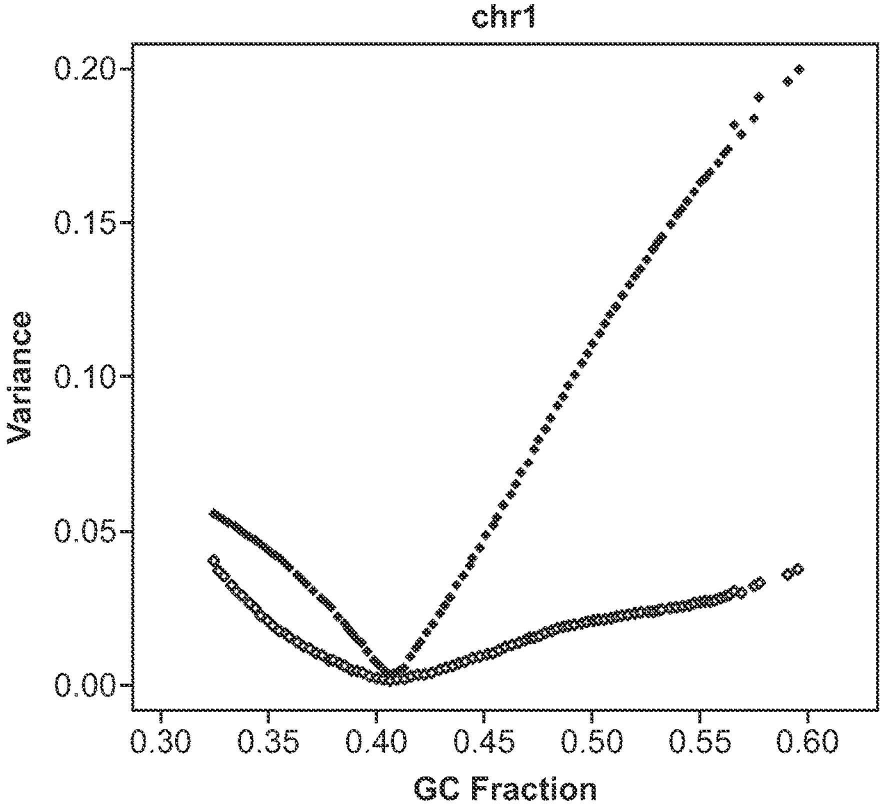
Figure 74:
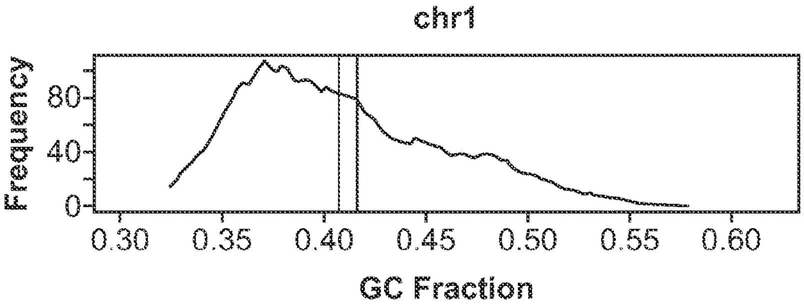
Figure 75A:
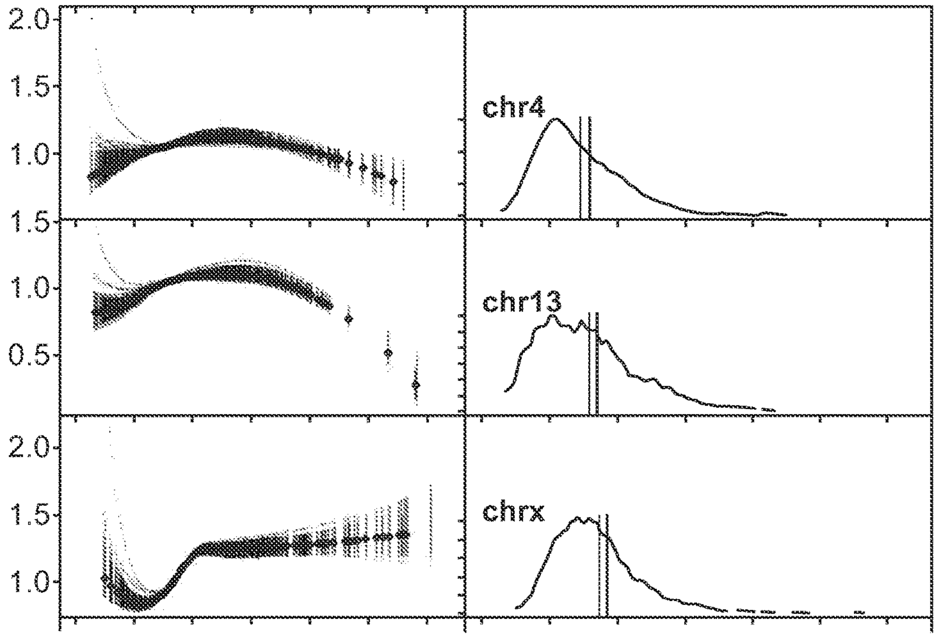
Figure 75B:
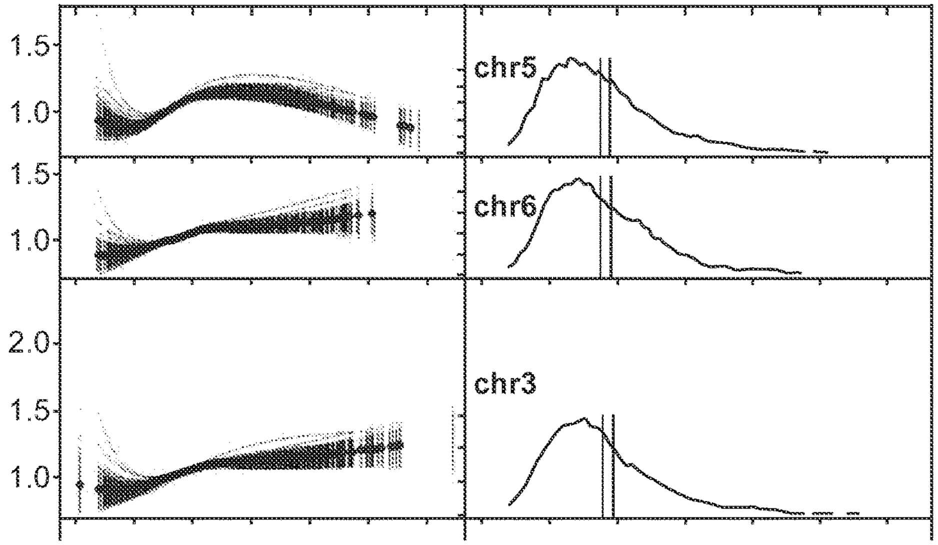
Figure 75C:
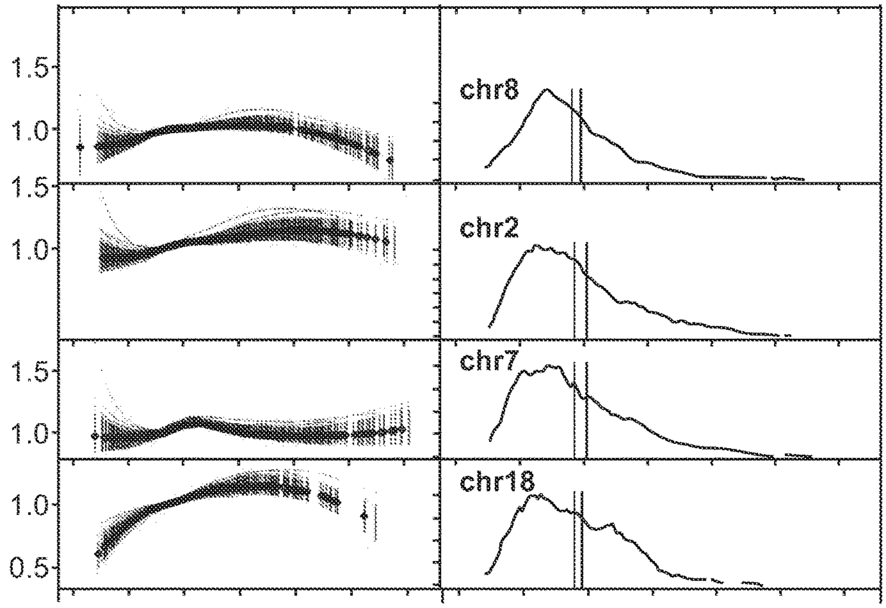
Figure 75D:
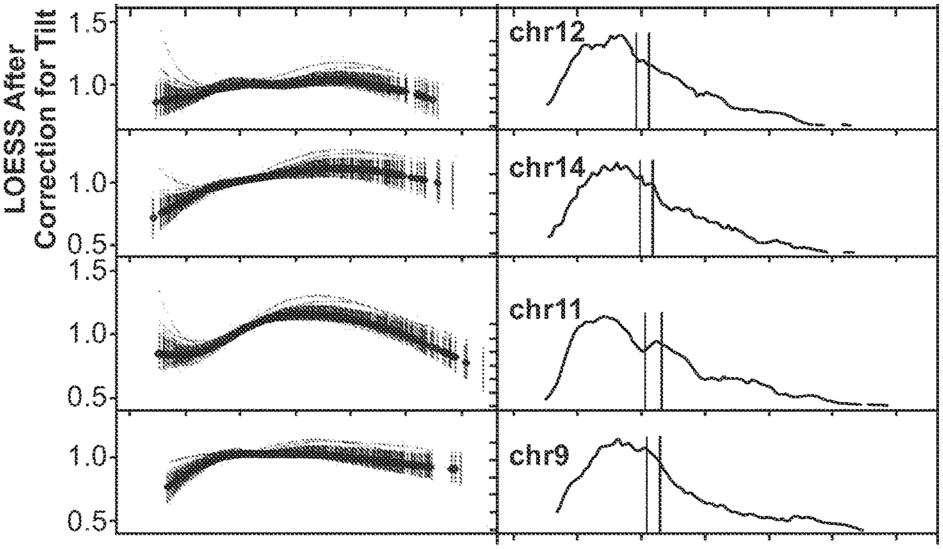
Figure 75E:
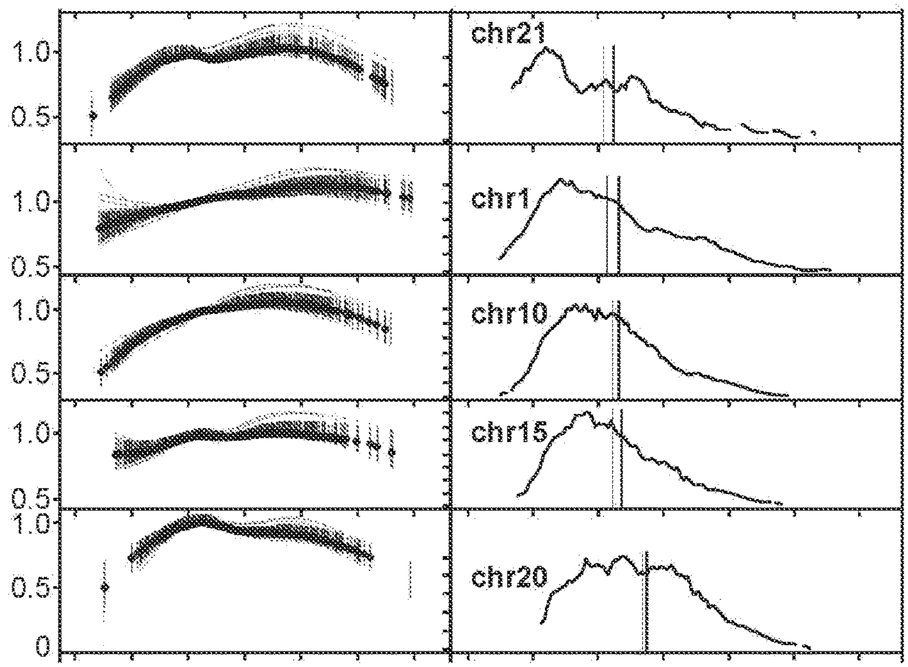
Figure 75F:
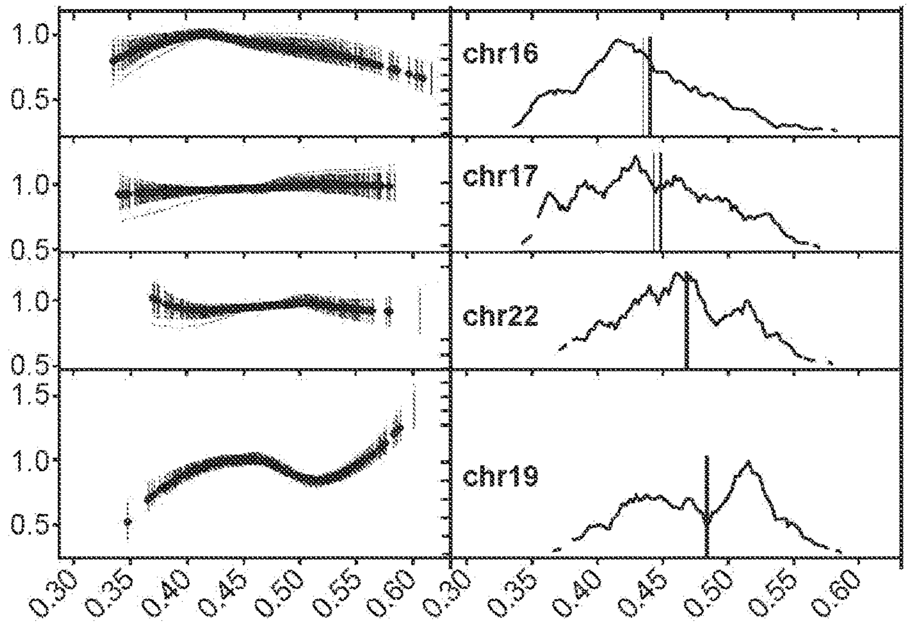

FIG. 72 demonstrated that tilting chromosome-specific LOESS curves around the pivot by an angle proportional to the GC bias coefficients measured in those samples caused all the curves to coalesce. The tilting of the chromosome-specific LOESS curves by the sample-specific GC bias coefficients significantly reduced the spread of the family of LOESS curves obtained for multiple samples, as shown in FIG. 73 (black v-shaped line (before tilting) and grey bottom line (after tilting)). The point where the black and grey curves touch coincided with the pivot. In addition, it became evident that the location on the GC content axis of the chromosome-specific pivot coincided with the median GC content of the given chromosome (FIG. 74, left vertical grey line: median, right vertical bold line: mean). Similar results were obtained for all chromosomes, as shown in FIG. 75A through FIG. 75F (left vertical grey line: median, right vertical bold line: mean). All autosomes and chromosome X were ordered according to their median GC content.

Figure 76:
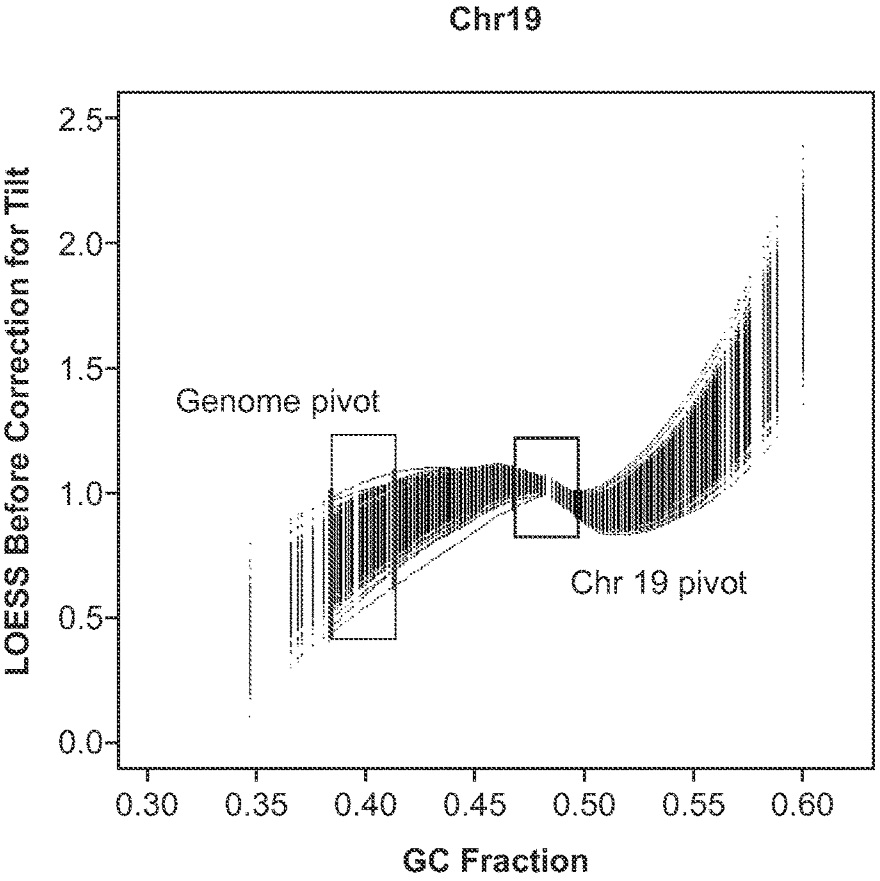
Figure 77:
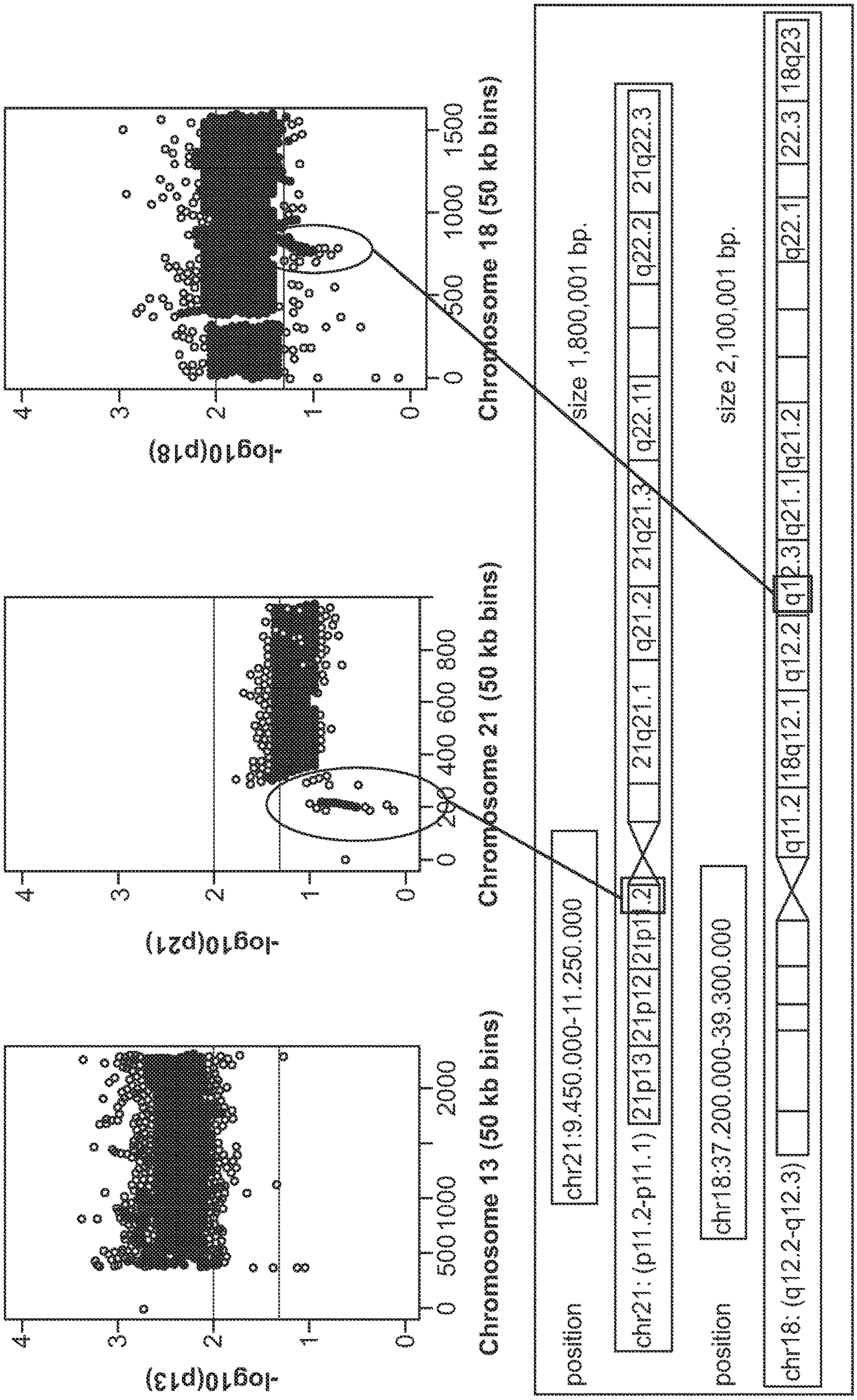
Figure 78:
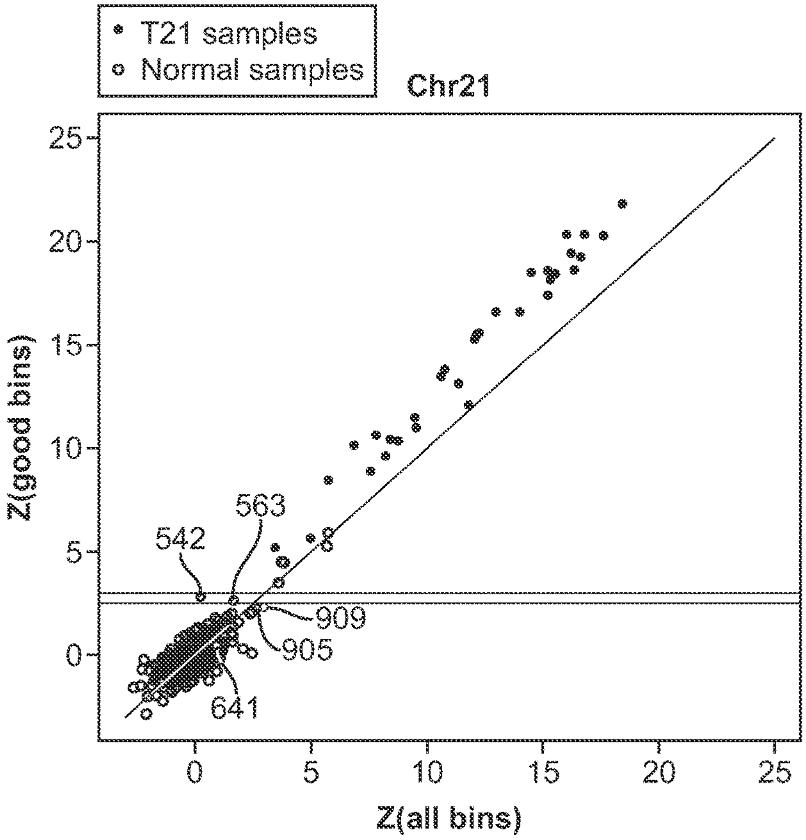

The genome-wide GC LOESS scaling pivoted the transformation on the median GC content of the entire genome, as shown in FIG. 76. That pivot was acceptable for chromosomes that have median GC content similar to the GC content of the entire genome, but became suboptimal for chromosomes with extreme GC contents, such as chromosomes 19, 20, 17, and 16 (extremely high GC content). The pivoting of those chromosomes centered on the median GC content of the entire genome maintained the spread observed within the left box in FIG. 76, missing the low-variability region enclosed by the right box in FIG. 76 (the chromosome-specific pivot).

Pivoting on the chromosome-specific median GC content, however, significantly reduced the variability (FIG. 75). The following observations were made:

1) GC correction should be done on small genomic sections or segments, rather than on the entire genome, to reduce the variability. The smaller the section or segment, the more focused GC correction becomes, minimizing the residual error.
2) In this particular instance, those small genomic sections or segments are identical to chromosomes. In principle, the concept is more general: the sections or segments could be any genomic regions, including 50 kbp bins.
3) The GC bias within individual genomic regions can be rectified using the sample-specific, genome-wide GC coefficient evaluated for the entire genome. This concept is important: while some descriptors of the genomic sections (such as the location of the pivot point, GC content distribution, median GC content, shape of the LOESS curve, and so on) are specific to each section and independent of the sample, the GC coefficient value used to rectify the bias is the same for all the sections and different for each sample.

These general conclusions guided the development of PERUN, as will become apparent from the detailed description of its processes.

Separability of Sources of Systematic Bias

Careful inspection of a multitude of raw count profiles measured using different library preparation chemistries, clustering environments, sequencing technologies, and sample cohorts consistently confirmed the existence of at least two independent sources of systematic variability:

1) sample-specific bias based on GC-content, affecting all bins within a given sample in the same manner, varying from sample to sample, and
2) bin-specific attenuation pattern common to all samples.

The two sources of variability are intermingled in the data. Thorough removal of both required their deconvolution. The deficiencies of the error-removal procedures predating PERUN stem from the fact that they only correct for one of the two sources of systematic bias, while neglecting the other.

For example, the GCRM (or GC LOESS) method treated identically all the bins with GC content values falling within a narrow GC content range. The bins belonging to that subset may be characterized by a wide range of different intrinsic elevations, as reflected by the reference median count profile. However, GCRM was blind to their inherent properties other than their GC content. GCRM therefore maintains (or even enlarges) the spread already present in the bin subset.

On the other hand, the binwise reference median count disregarded the modulation of the bin-specific attenuation pattern by the GC bias, maintaining the spread caused by the varying GC content.

The sequential application of methods dealing with the opposite extremes of the error spectrum unsuccessfully attempts to resolve the two biases globally (genome-wide), ignoring the need to dissociate the two biases on the bin elevation. Without being limited by theory, PERUN apparently owes its success to the fact that it separates the two sources of bias locally, on the bin elevation.

Removal of Uninformative Bins

Multiple attempts to remove uninformative bins have indicated that bin selection has the potential to improve classification. The first such approach evaluated the mean chromosome 21, chromosome 18, and chromosome 13 counts per bin for all 480v2 trisomy cases and compared it with the mean counts per bin for all 480v2 euploids. The gap between affected and unaffected cases was scaled with the combined binwise uncertainty derived from bin counts measured in both groups. The resulting t-statistic was used to evaluate binwise p-value profile, shown in FIG. 77. In the case of chromosome 21, the procedure identified 36 uninformative bins (center panel, labeled with ellipse on FIG. 77). Elimination of those bins from calculation of Z scores noticeably increased the Z-values for affected cases, while randomly perturbing the unaffected Z-scores (FIG. 78), thereby increasing the gap between euploids and trisomy 21 cases.

Figure 79:
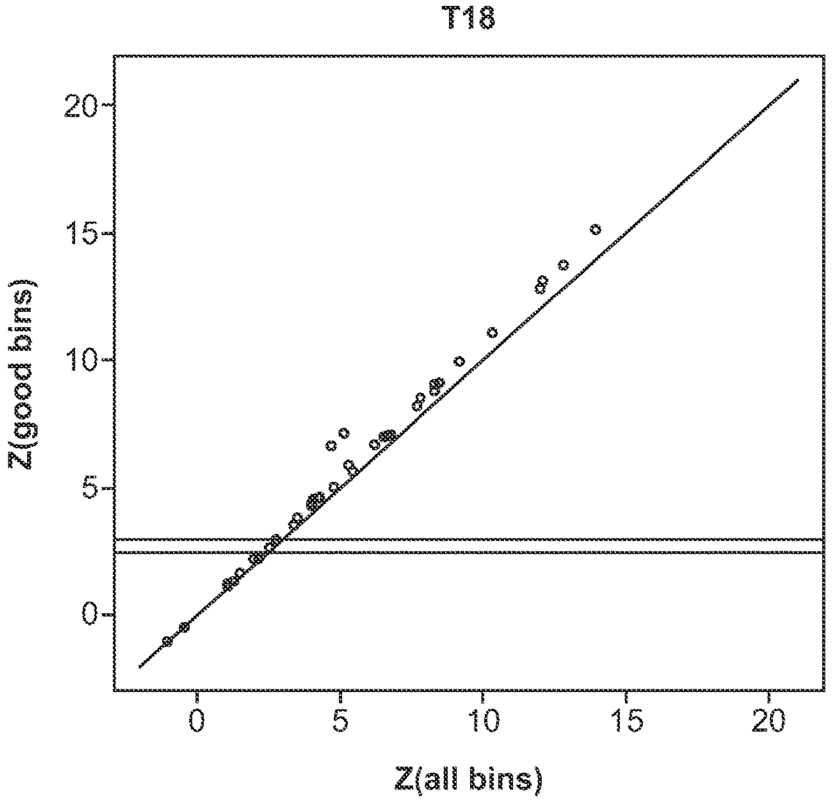
Figure 80:
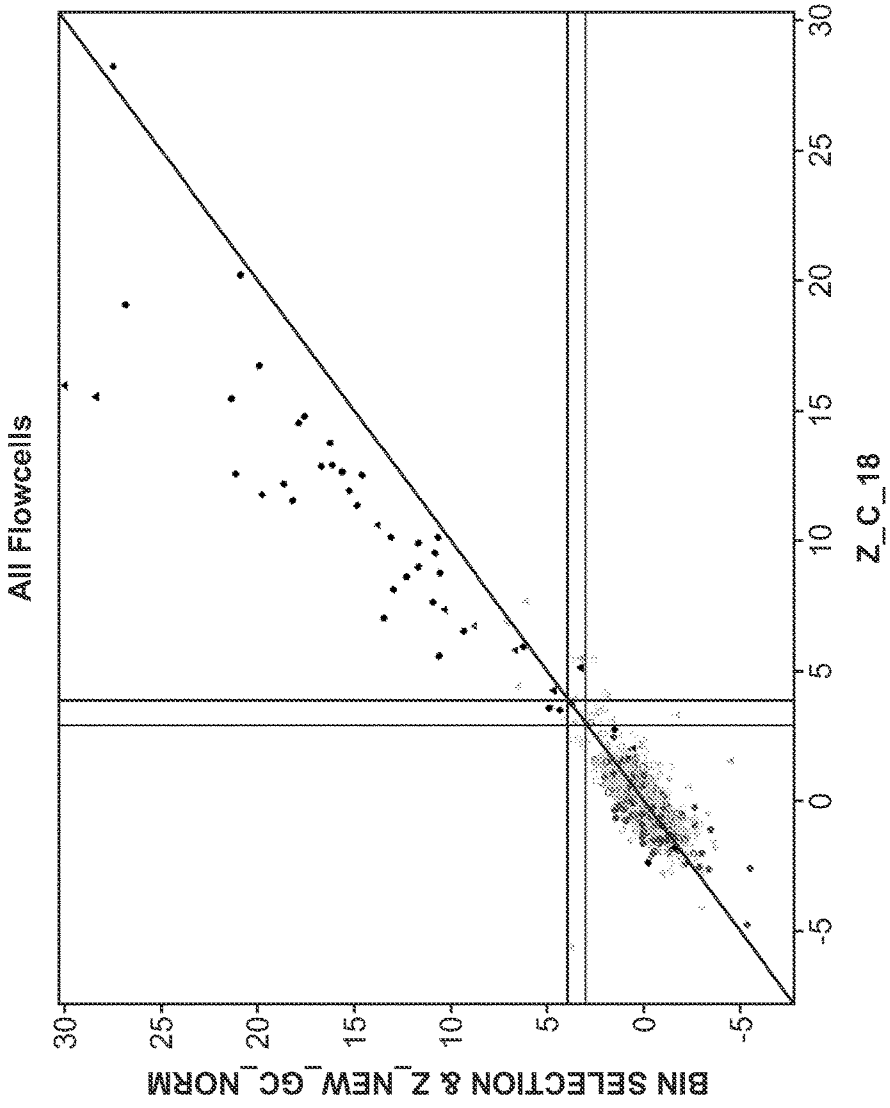

In chromosome 18, the procedure only improved Z scores for two affected cases (FIG. 79).

A post-hoc analysis showed that the improvement of the Z-scores in those two samples resulted from removal of the large maternal deletion in chromosome 18 (FIG. 11) and that the two samples actually come from the same patient. These improvements were sample-specific, with no generalizing power. In chromosome 13, the procedure did not lead to any improvements of Z-scores.

An alternative bin filtering scheme removes bins with extremely low or extremely high GC content.

This approach yielded mixed results, with noticeably reduced variance in chromosomes 9, 15, 16, 19, and 22 (depending on the cutoffs), but adverse effects on chromosomes 13 and 18.

Figure 81:
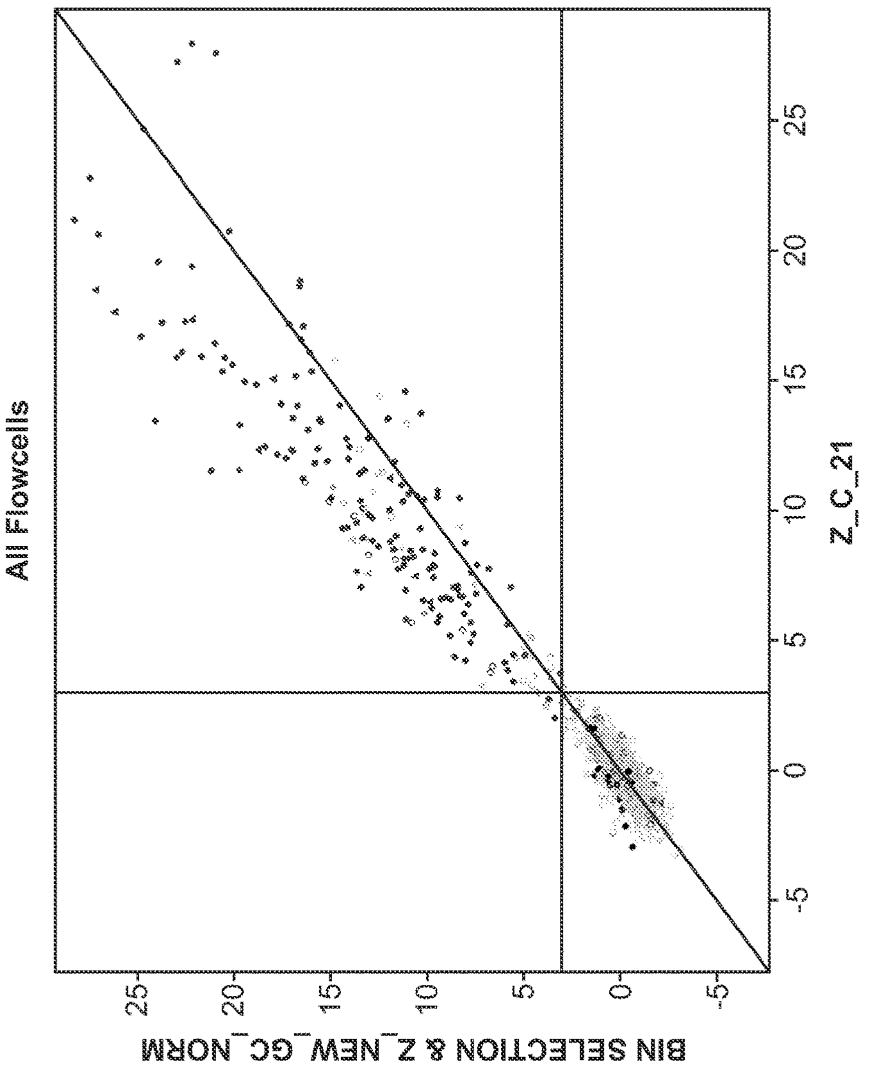

Yet another simple bin selection scheme eliminates bins with consistently low counts. The procedure corrected two LDTv2CE chromosome 18 false negatives (FIG. 80) and two chromosome 21 false negatives (FIG. 81). It also corrected at least three chromosome 18 false positives, but created at least one new chromosome 18 false positive (FIG. 80):

In conclusion, the different criteria used to filter out uninformative bins made it clear that data processing will benefit from bin selection based on how much useful information the bins contribute to the classification.

Separation of GC Bias from Systematic Bin Wise Bias

To resolve and eliminate the different systematic biases found in the measured counts, the data processing workflow needed to optimally combine the partial procedures described from the previous section entitled "Normalization with Respect to Reference Median Count Profile" to the section entitled "Removal of Uninformative Bias". The first step is to order different samples according to their GC bias coefficient values and then stack their plots of counts-vs.-GC content. The result is a three-dimensional surface that twists like a propeller, schematically shown on FIG. 82.

Figure 82:
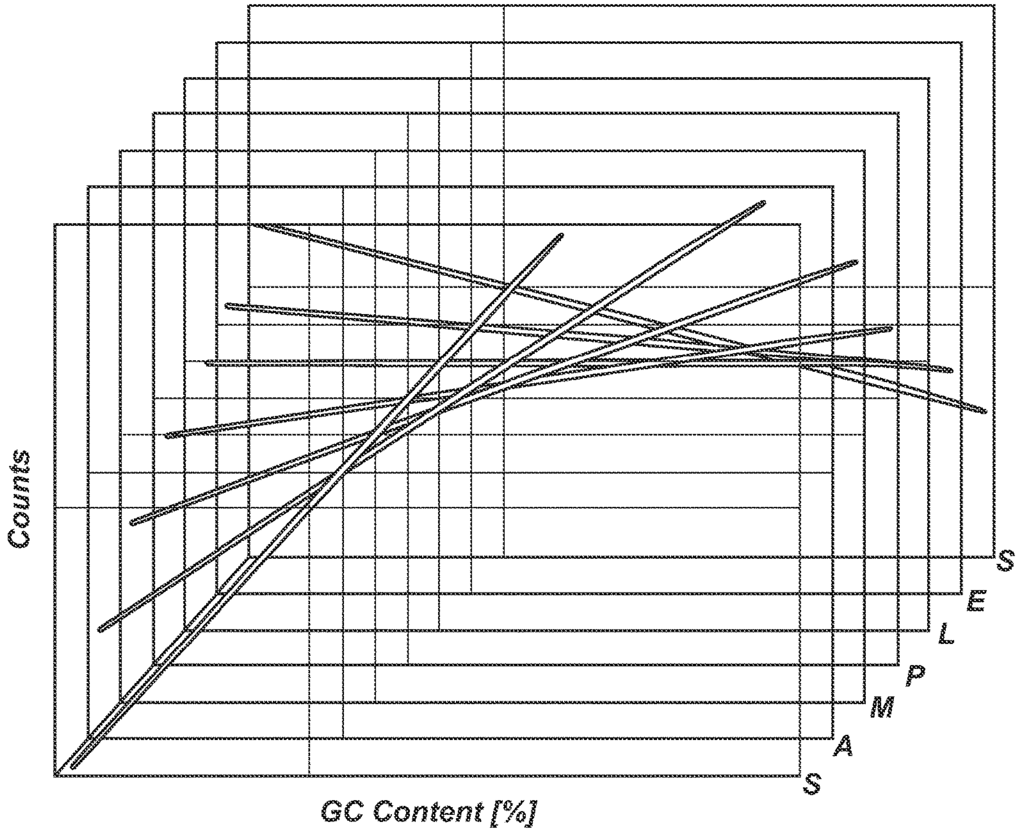

Thus arranged, the measurements suggest that a set of sample-specific GC bias coefficient can be applied to rectify errors within an individual genomic section or segment. In FIG. 82, the sections or segments are defined by their GC content. An alternative partition of the genome gives contiguous, non-overlapping bins. The successive starting locations of the bins uniformly cover the genome. For one such 50 kbp long bin, FIG. 83 explores the behavior of the count values measured within that bin for a set of samples. The counts are plotted against the GC bias coefficients observed in those samples. The counts within the bin evidently increase linearly with the sample-specific GC bias. The same pattern in observed in an overwhelming majority of bins. The observations can be modeled using the simple linear relationship:

$$M=LI+GS \quad \text{(A)}$$

The various terms in Eq. A have the following meanings:

M: measured counts, representing the primary information polluted by unwanted variation.

L: chromosomal elevation—this is the desired output from the data processing procedure. L indicates fetal and/or maternal aberrations from euploid. This is the quantity that is masked both by stochastic errors and by the systematic biases. The chromosomal elevation L is both sample specific and bin-specific.

G: GC bias coefficient measured using linear model, LOESS, or any equivalent approach. G represents secondary information, extracted from M and from a set of bin-specific GC content values, usually derived from the reference genome (but may be derived from actually observed GC contents as well). G is sample specific and does not vary along the genomic position. It encapsulates a portion of the unwanted variation.

I: Intercept of the linear model (green line in FIG. 83). This model parameter is fixed for a given experimental setup, independent on the sample, and bin-specific.

S: Slope of the linear model (green line in FIG. 83). This model parameter is fixed for a given experimental setup, independent on the sample, and bin specific.

The quantities M and G are measured. Initially, the bin-specific values I and S are unknown. To evaluate unknown I and S, we must assume that L=1 for all bins in euploid samples. The assumption is not always true, but one can reasonably expect that any samples with deletions/duplications will be overwhelmed by samples with normal chromosomal elevations. A linear model applied to the euploid samples extracts the I and S parameter values specific for the selected bin (assuming L=1). The same procedure is applied to all the bins in the human genome, yielding a set of intercepts I and slopes S for every genomic location. Cross-validation randomly selects a work set containing 90% of all LDTv2CE euploids and uses that subset to train the model. The random selection is repeated 100 times, yielding a set of 100 slopes and 100 intercepts for every bin. The previous section entitled "Cross-Validation of PERUN Parameters" describes the cross-validation procedure in more detail.

Figure 83:
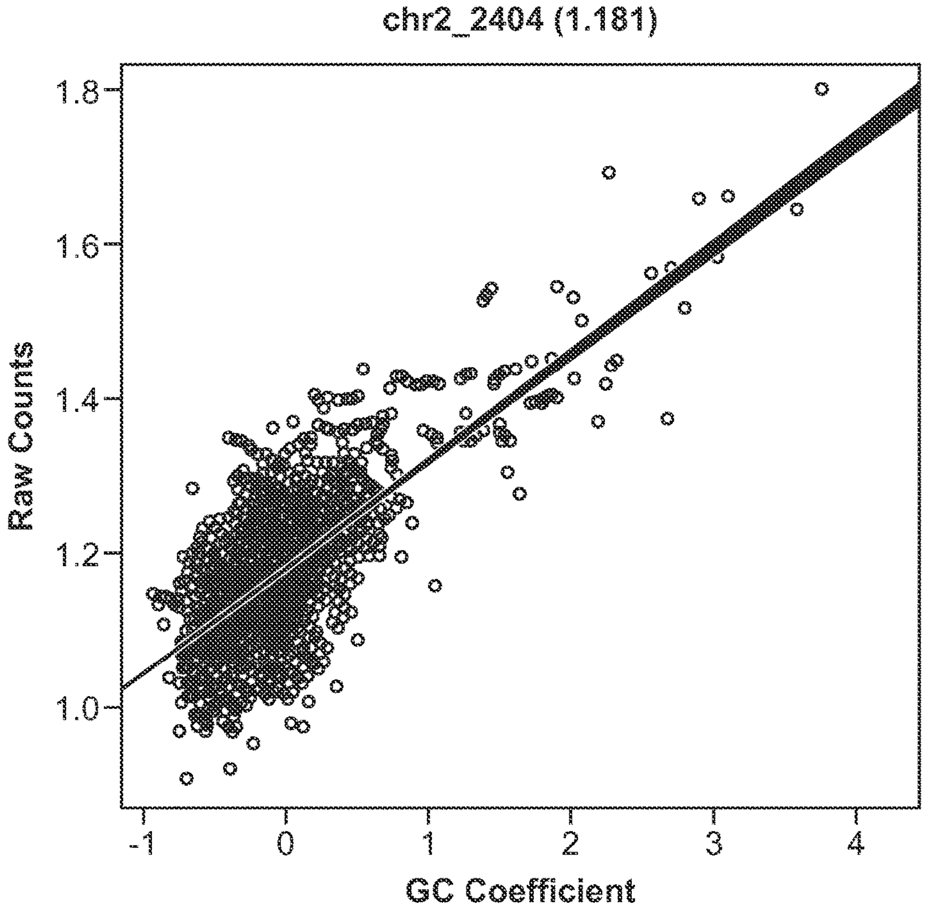
Figure 84:
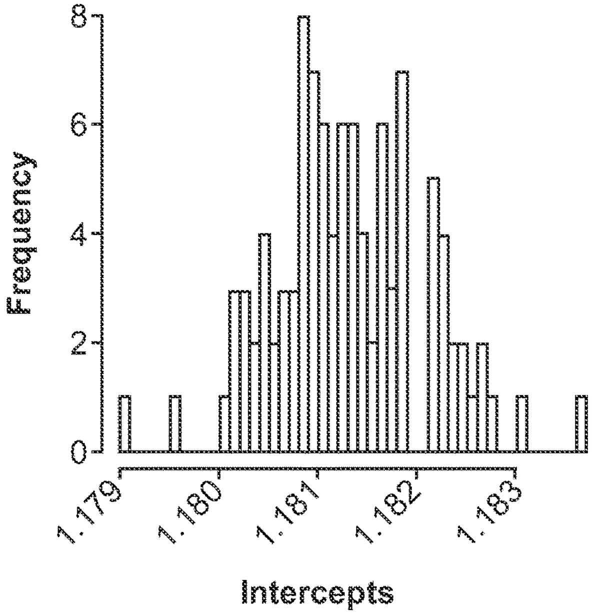
Figure 85:
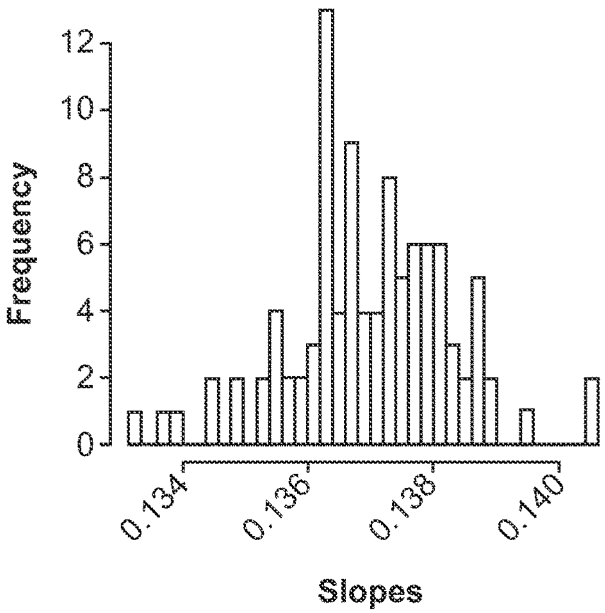

FIG. 84-85 show 100 intercept values and 100 slope values, respectively, evaluated for bin #2404 in chromosome 2. The two distributions correspond to 100 different 90% subsets of 1093 LDTv2CE euploids shown in FIG. 83. Both distributions are relatively narrow and irregularly shaped. Their spreads are similar to the errors in the coefficient as reported by the linear model. As a rule, the slope is less reliable than the intercept because fewer samples populate the extreme sections of the GC-bias range.

Interpretation of PERUN Parameters I and S

Figure 86:
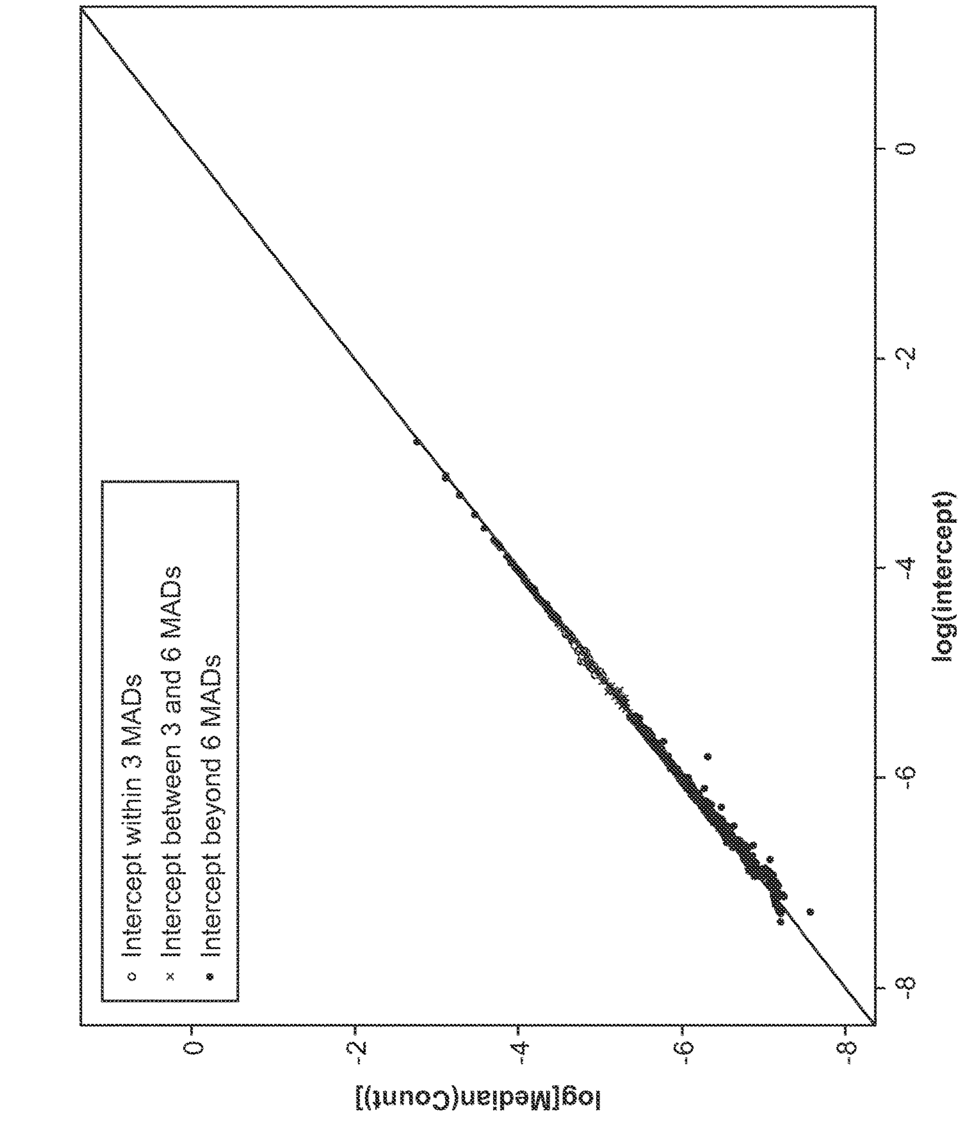

The meaning of the intercept I is illustrated by FIG. 86. The graph correlates the estimated bin intercepts with the data extracted from a set of technical replicates, obtained when one LDTv2CE flow cell was subjected to three separate sequencing runs. The y-axis contains median values of binwise counts from those three measurements. These median values are related conceptually to the median reference profile, previously used to normalize profiles as described in the section entitled "Normalization with Respect to Reference Median Count Profile". The binwise intercepts are plotted along the x-axis. The striking correlation between the two quantities reveals the true meaning of the intercepts as the expected counts per bin in the absence of GC bias. The problem with the median reference count profile is that it fails to account for the GC bias (see section entitled "Normalization with Respect to Reference Median Count Profile"). In PERUN, without being limited by theory, the task of an intercept/is to deal with the bin-specific attenuation, while the GC bias is relegated to the other model parameter, the slope S.

FIG. 86 excludes chromosome Y from the correlation because the set of technical replicates does not reflect the general population of male pregnancies.

The distribution of the slope S (FIG. 87) illustrates the meaning of that model parameter.

Figure 87:
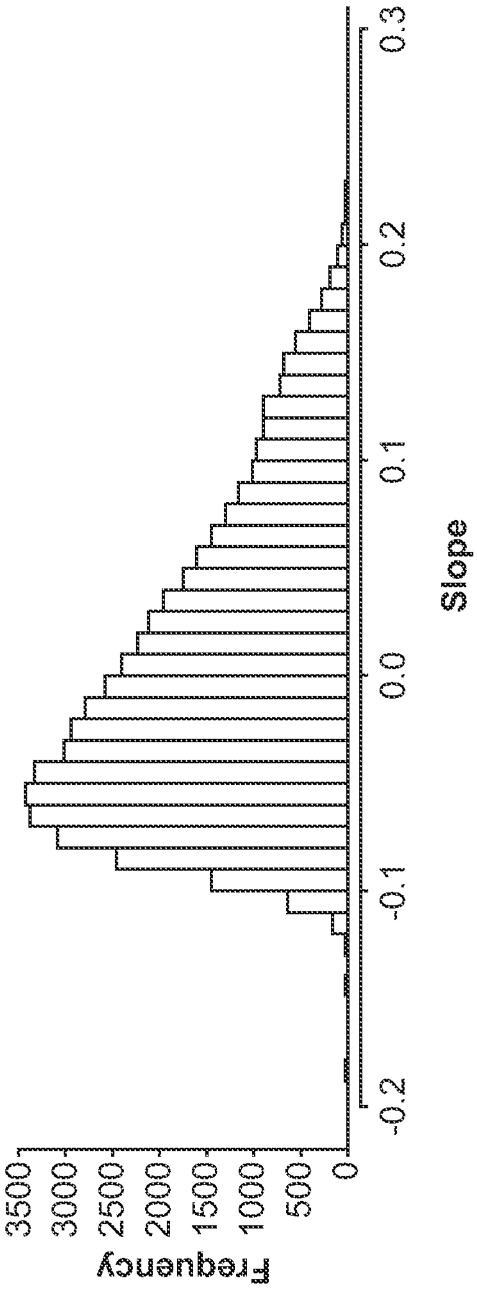
Figure 88:
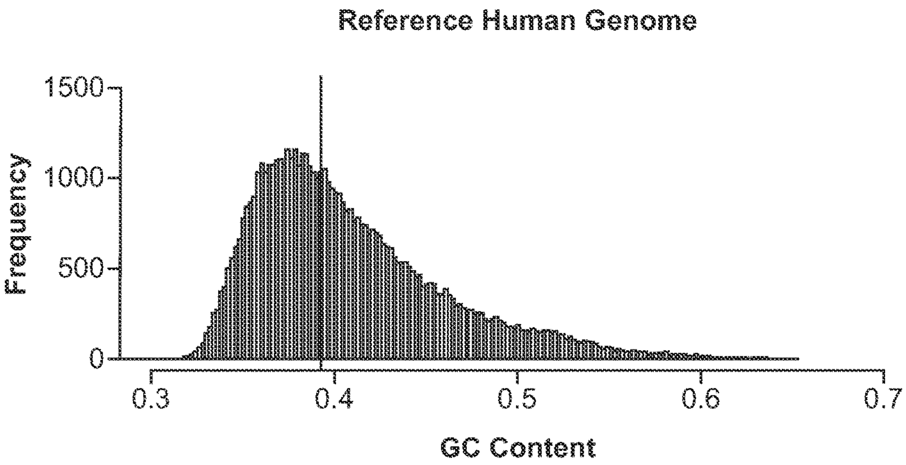

The marked semblance between the distribution from FIG. 87 and the distribution of the genome-wide GC content (FIG. 88) indicates that the slope S approximates the GC content of a bin, shifted by the median GC content of the containing chromosome. The thin vertical line in FIG. 88 marks the median GC content of the entire genome.

Figure 89:
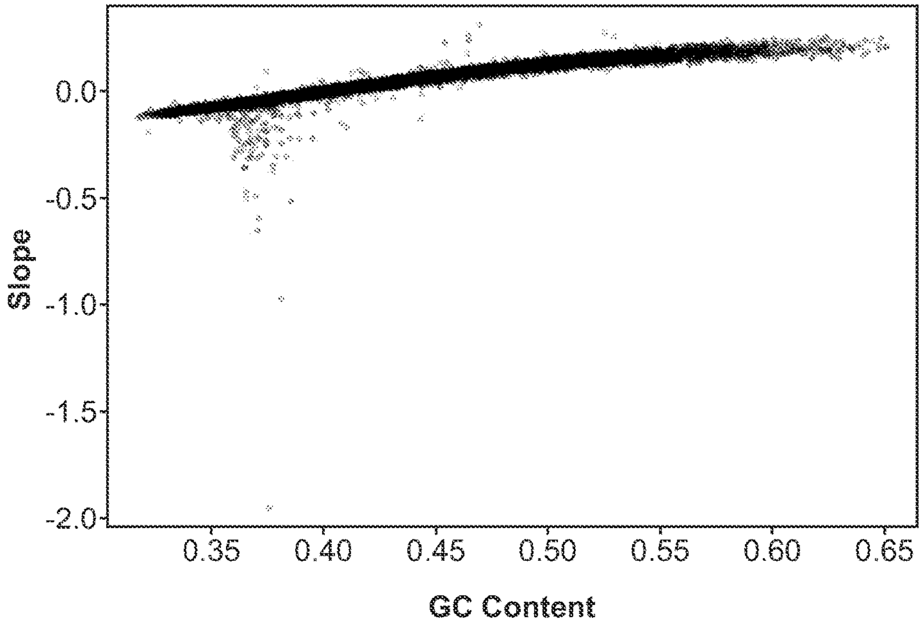

FIG. 89 reaffirms the close relationship between the slope S and the GC content per bin. While slightly bent, the observed trend is extremely tight and consistent, with only a handful of notable outlier bins.

Extraction of Chromosomal Elevation from Measured Counts

Assuming that the model parameter values I and S are available for every bin, measurements M collected on a new test sample are used to evaluate the chromosomal elevation according to the following expression:

$$L=(M-GS)/I \quad \text{(B)}$$

As in Eq. A, the GC bias coefficient G is evaluated as the slope of the regression between the binwise measured raw counts M and the GC content of the reference genome. The chromosomal elevation L is then used for further analyses (Z-values, maternal deletions/duplications, fetal microdeletions/microduplications, fetal gender, sex aneuploidies, and so on). The procedure encapsulated by Eq. B is named Parameterized Error Removal and Unbiased Normalization (PERUN).

Cross-Validation of PERUN Parameters

As inferred in the section entitled "Separation of GC Bias from Systematic Binwise Bias", the evaluation of I and S randomly selects 10% of known euploids (a set of 1093 LDTv2 in FIG. 83) and sets them aside for cross-validation. Linear model applied to the remaining 90% of euploids extracts the I and S parameter values specific for the selected bin (assuming L=1). Cross validation then uses the I and S estimates for a given bin to reproduce measured M values from measured G values both in the work set and in the remaining 10% euploids (again assuming L=1). The random selection of the cross-validation subset is repeated many times (100 times in FIG. 83, although 10 repetitions would suffice). 100 diagonal straight lines in FIG. 83 represent the linear models for 100 different 90% work subset selections. The same procedure is applied to all the bins in the human genome, yielding a set of intercepts/and slopes S for every genomic location.

To quantify the success of the model and avoid biasing the results, we use the R-factor, defined as follows:

$$R = \frac{\Sigma_{i=1}^{N} \mid M_i - P_i \mid}{\Sigma_{i=1}^{N} \mid M_i \mid^5} \quad \text{(C)}$$

The numerator in Eq. B sums up the absolute deviations of the predicted count values (P, Eq. B) from the actual measurements (M). The numerator simply sums up the measurements. The R factor may be interpreted as the residual error in the model, or the unexplained variation. The R factor is directly borrowed from the crystallographic model refinement practice, which is vulnerable to bias. In crystallography, the bias is detected and measured by the R-factor evaluated within the cross-validation subset of observables. The same concepts are applied in the context of genome-wide count bias removal.

Figure 90:
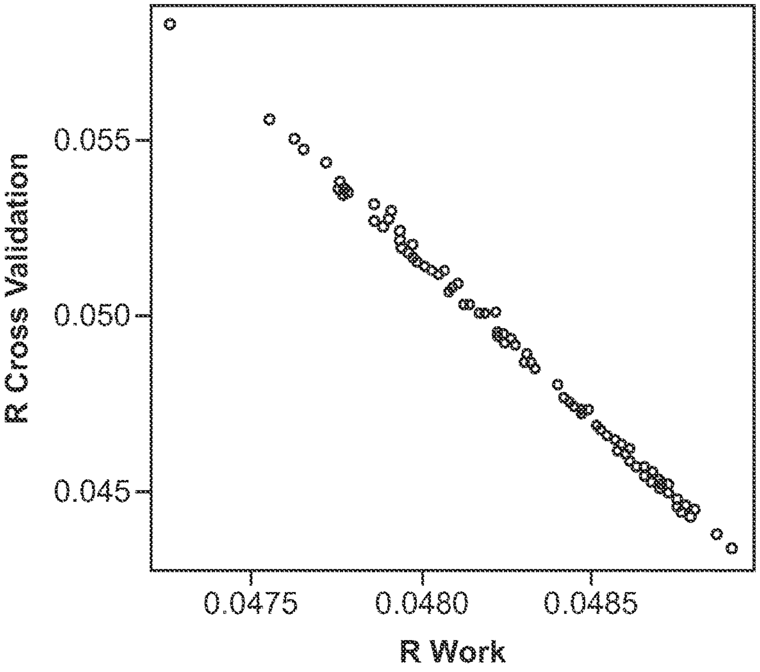

FIG. 90 shows the R-factors evaluated for the cross-validation subset (y-axis) plotted against R-factors evaluated for the work (training) set for bin #2404 from chromosome 2. There are 100 data points since the random selection of the cross-validation subset was repeated 100 times. Typical linear relationship is observed, with the increasing $R_{cv}$ values (measuring bias) accompanying the decreasing $R_{work}$.

FIG. 90 may be interpreted in terms of the percentage error (or relative error) of the model for this particular bin. $R_{cv}$ always exceeds $R_{work}$, usually by ~1%. Here, both $R_{cv}$ and $R_{work}$ remain below 6%, meaning that one can expect ~6% error in the predicted M values using the measured GC bias coefficient G and the model parameters I and S from the procedure described above.

Cross-Validation Error Values

Figure 91:
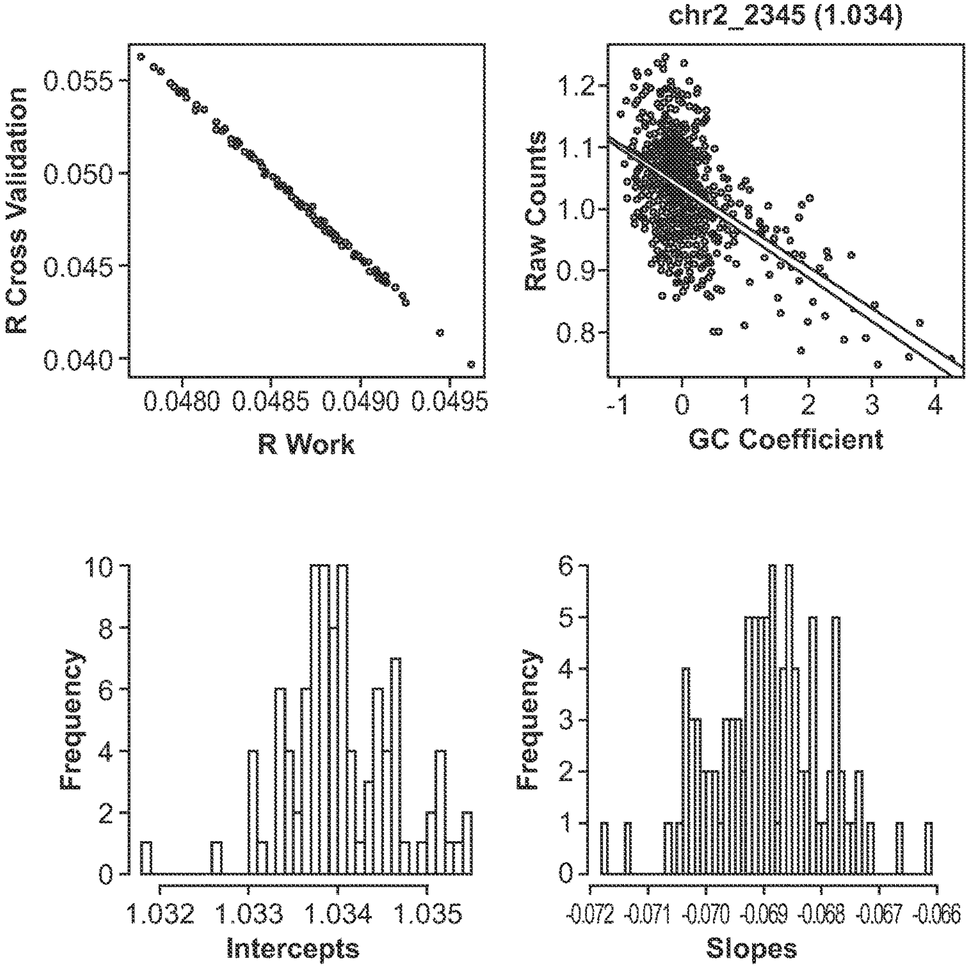
Figure 92:
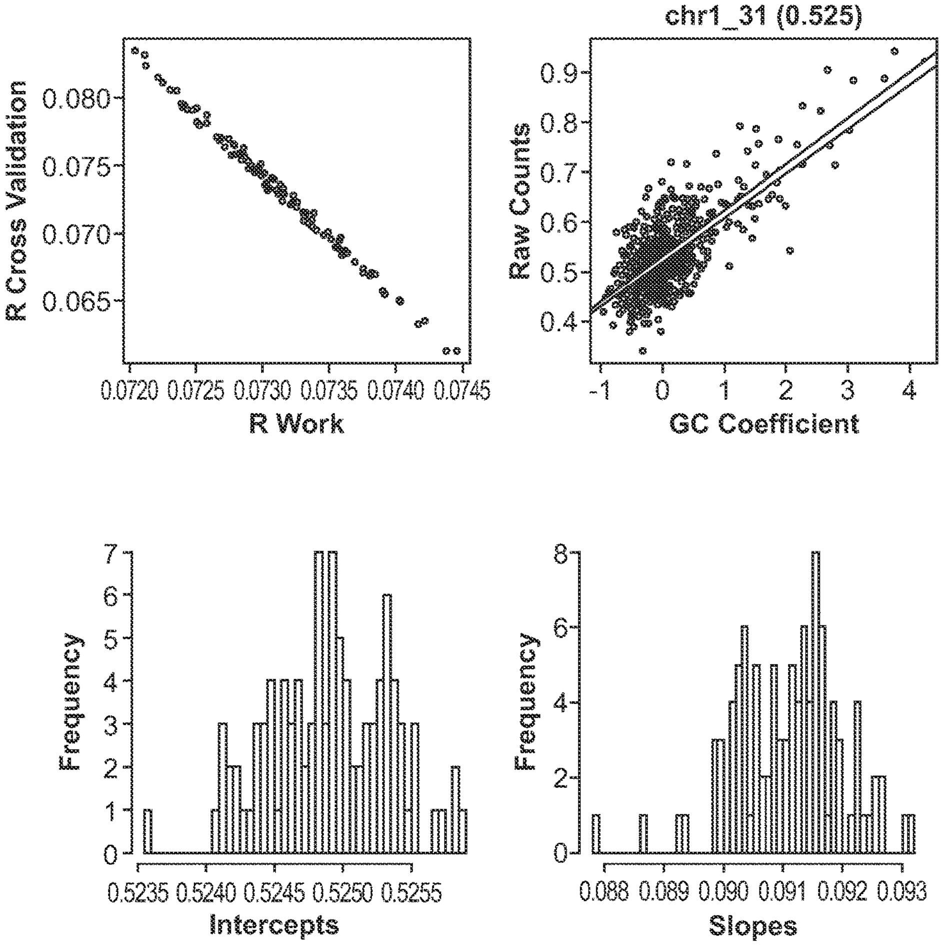
Figure 93:
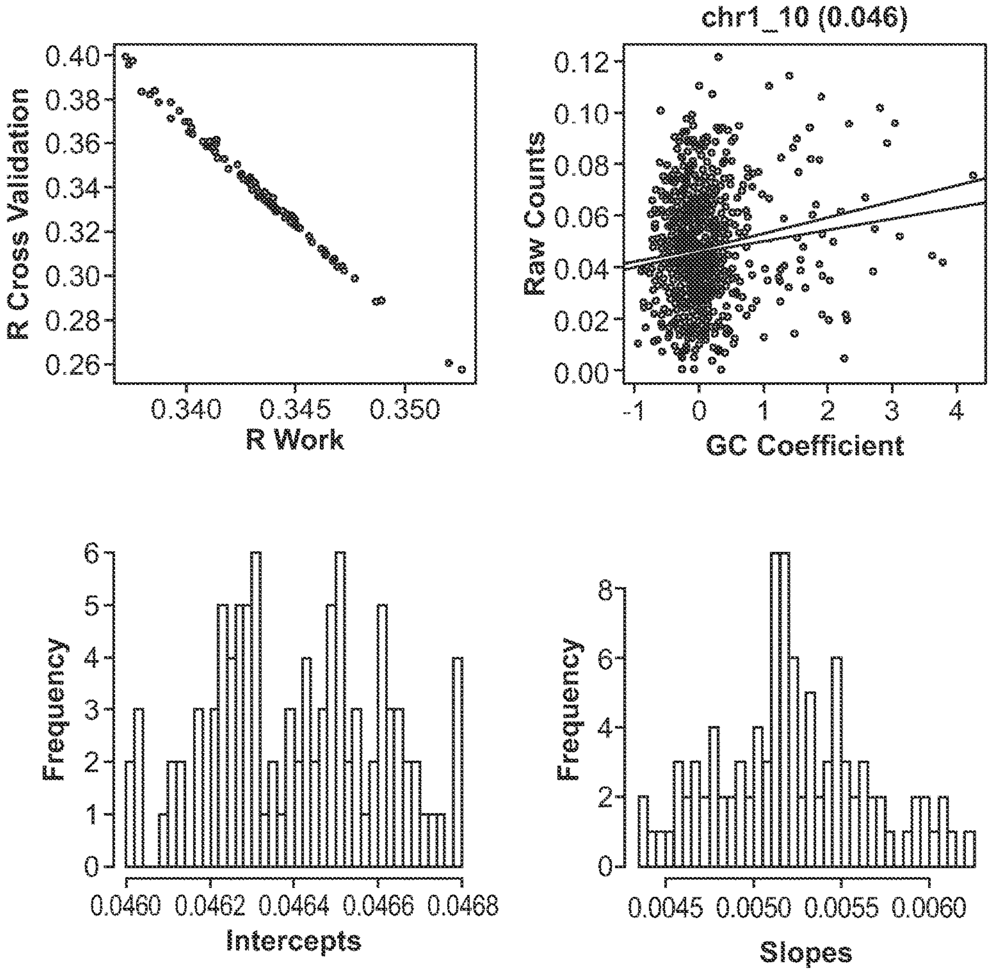
Figure 94:
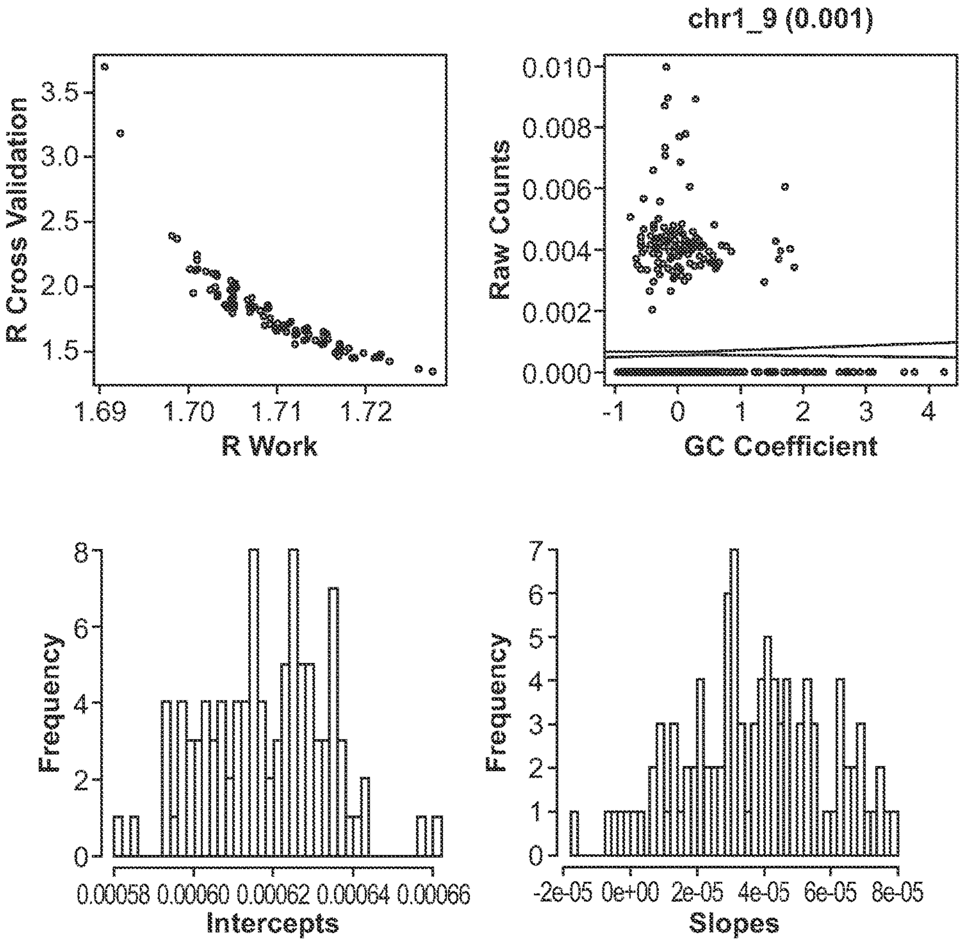
Figure 95:
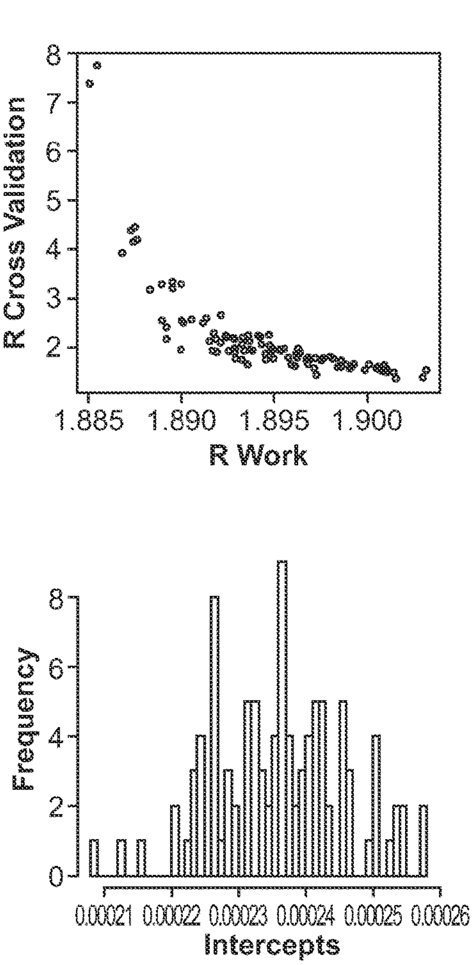

FIG. 90-91 show cross-validation errors for bins chr2_2404 and chr2_2345, respectively. For those and many other bins, the errors never exceed 6%. Some bins, such as chr1_31 (FIG. 92) have cross-validation errors approaching 8%. Still others (FIG. 93-95) have much larger cross-validation errors, at times exceeding 100% (40% for chr1_10 in FIG. 93, 350% for chr1_9 in FIG. 94, and 800% for chr1_8 in FIG. 95).

Figure 96:
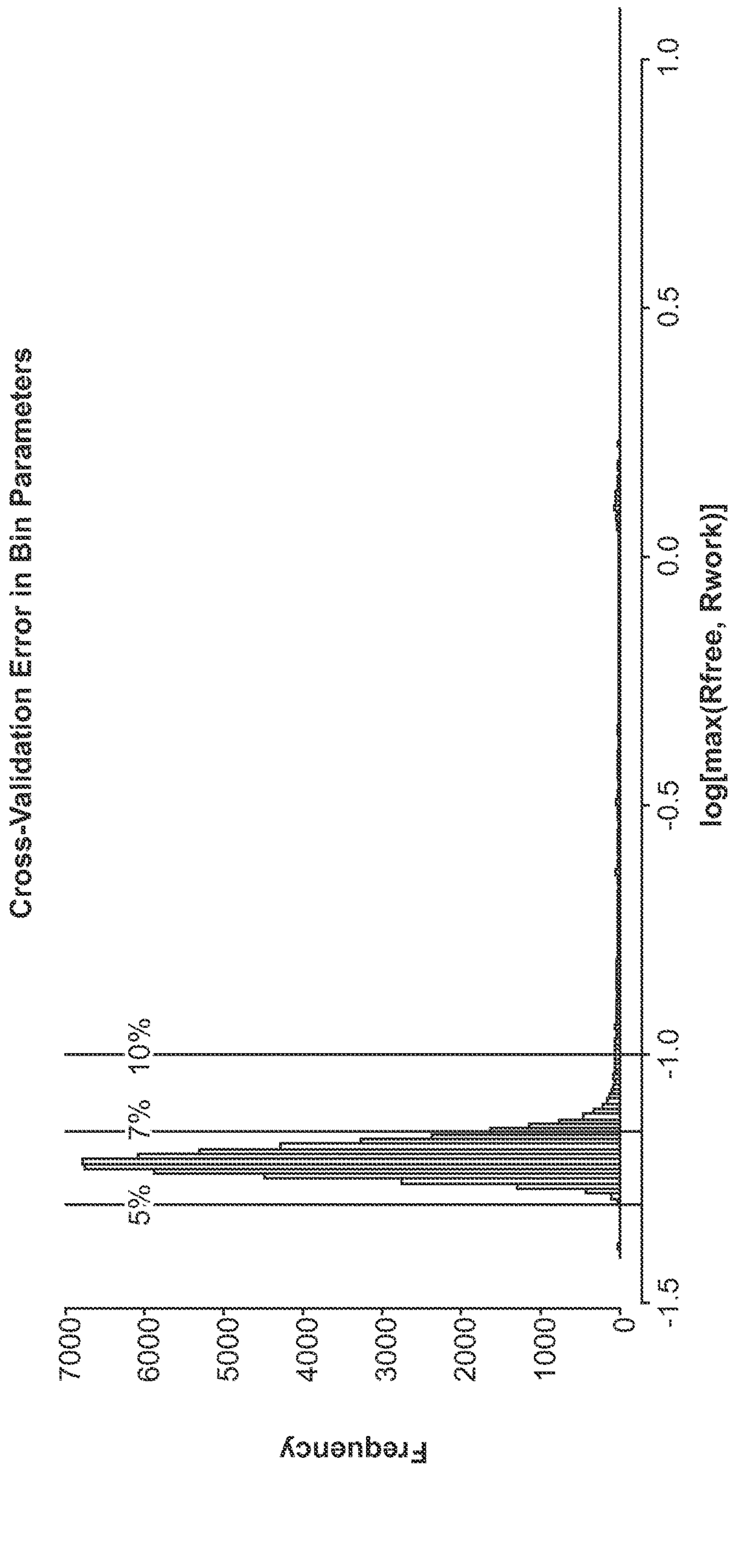

FIG. 96 shows the distribution of max($R_{cv}$, $R_{work}$) for all bins. Only a handful of bins have errors below 5%. Most bins have errors below 7% (48956 autosomes out of 61927 total including X and Y). A few bins have errors between 7% and 10%. The tail consists of bins with errors exceeding 10%.

Figure 97:
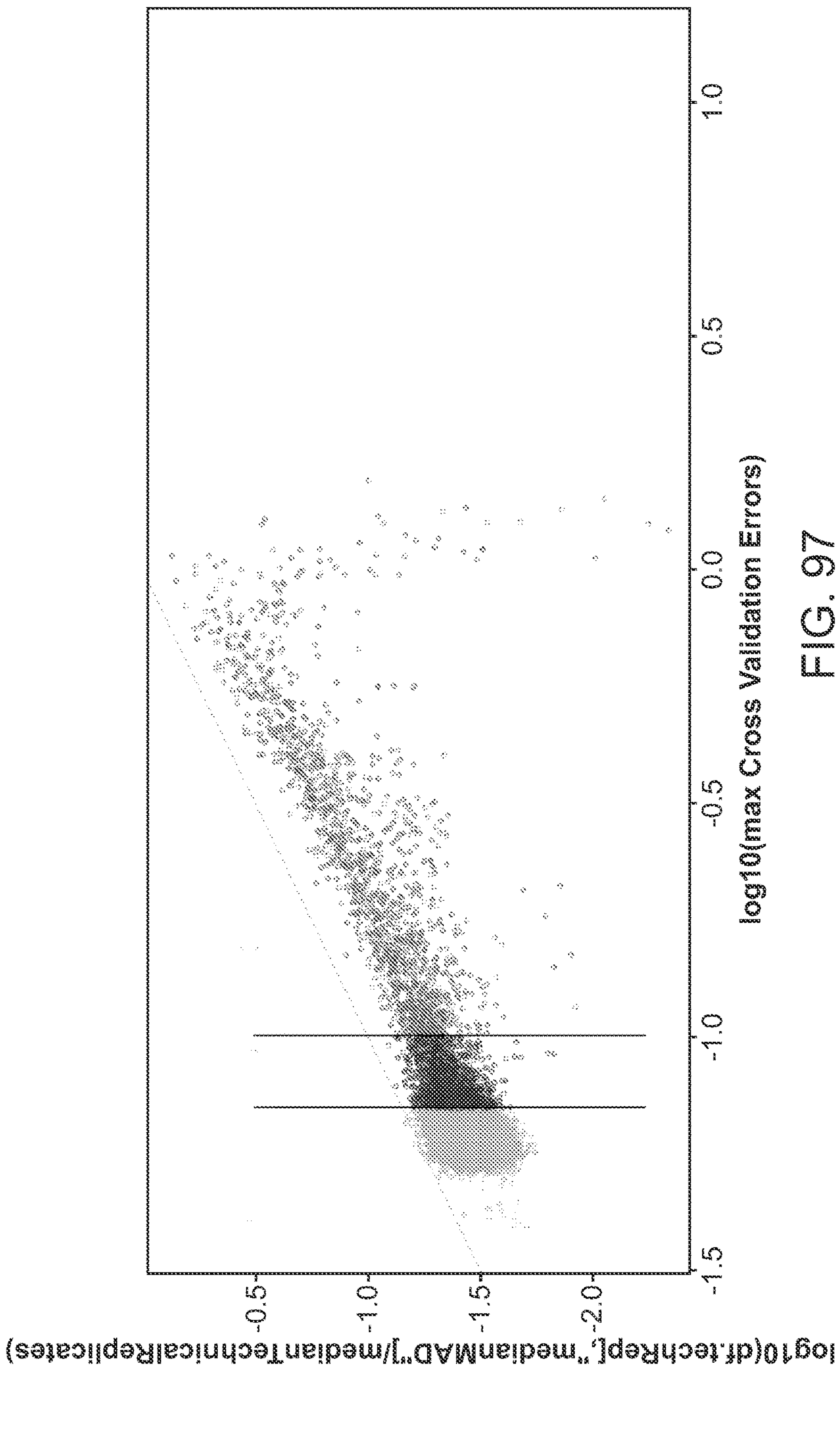

FIG. 97 correlates the cross-validation errors with the relative errors per bin estimated from the set of technical replicates. Data points in the blue region correspond to cross-validation errors between 7% and 10%. Data points in the red region denote bins with cross-validation error exceeding 10%. Data points in the grey region (error <7%) represent the bulk of bins.

In FIG. 91-95, the number in parentheses following the bin name above the top right inset indicates the ratio between the intercept found for that particular bin and the genome-wise median count per bin. The cross-validation errors evidently increase with the decreasing value of that ratio. For example, the bin chr1_8 never gets more than 3 counts and its relative error approaches 800%. The smaller the expected number of counts for a given bin, the less reliable that bin becomes.

Bin Selection Based on Cross-Validation

Figure 98:
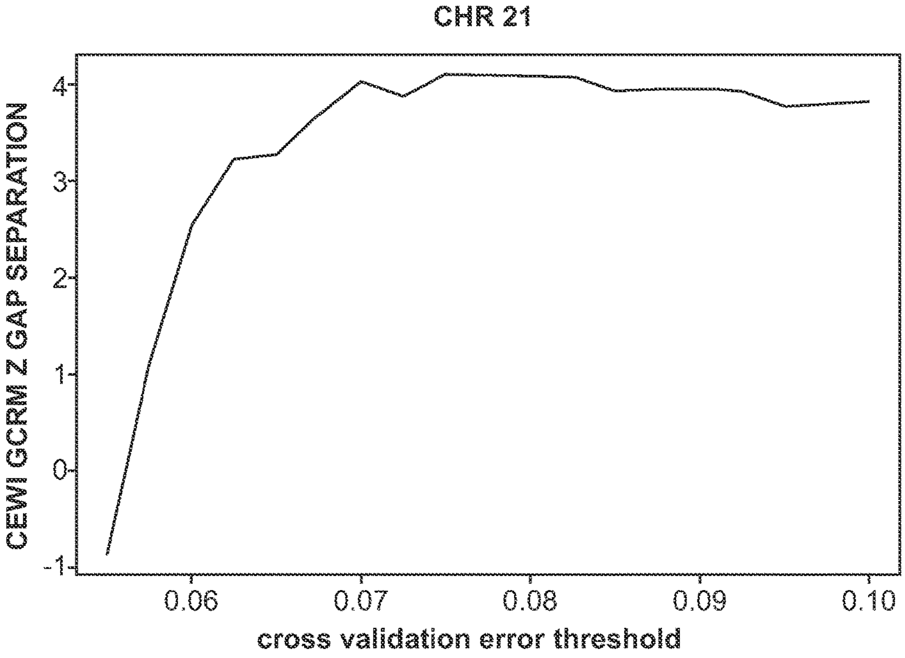

Based on the observations described in the previous section entitled "Removal of Uninformative Bins" (FIG. 78 and FIG. 80-81), cross-validation errors were used as a criterion for bin filtering. The selection procedure throws away all bins with cross-validation errors exceeding 7%. The filtering also eliminates all bins that consistently contain zero counts. The remaining subset contains 48956 autosomal bins. Those are the bins used to evaluate chromosomal representations and to classify samples as affected or euploid. The cutoff of 7% is justified by the fact that the gap separating euploid Z-scores from trisomy Z-scores plateaus at the 7% cross-validation error (FIG. 98).

Figure 99A:
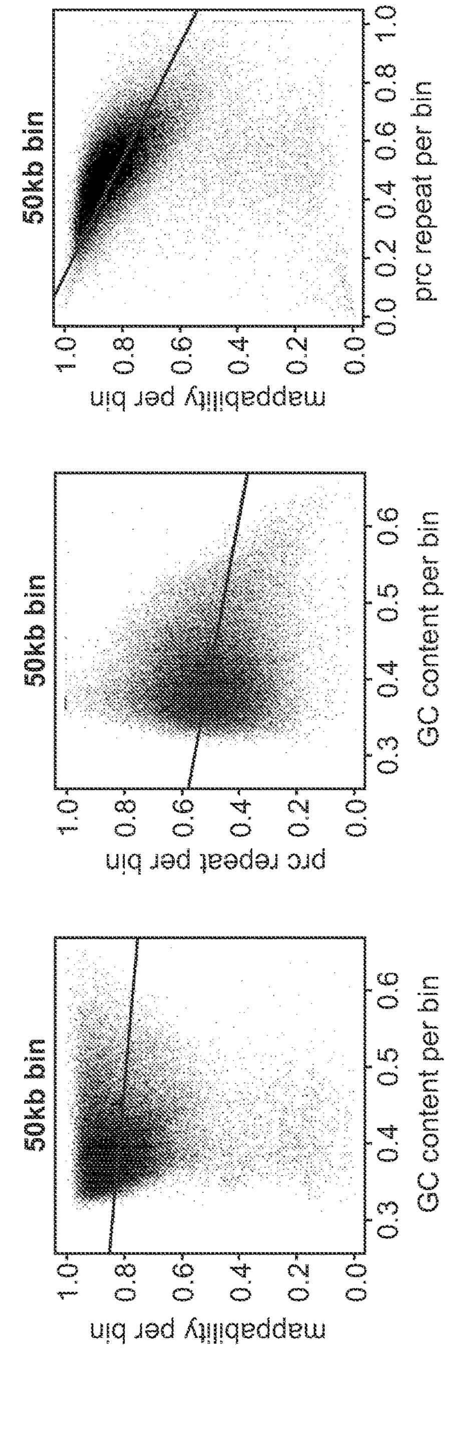
Figure 99B:
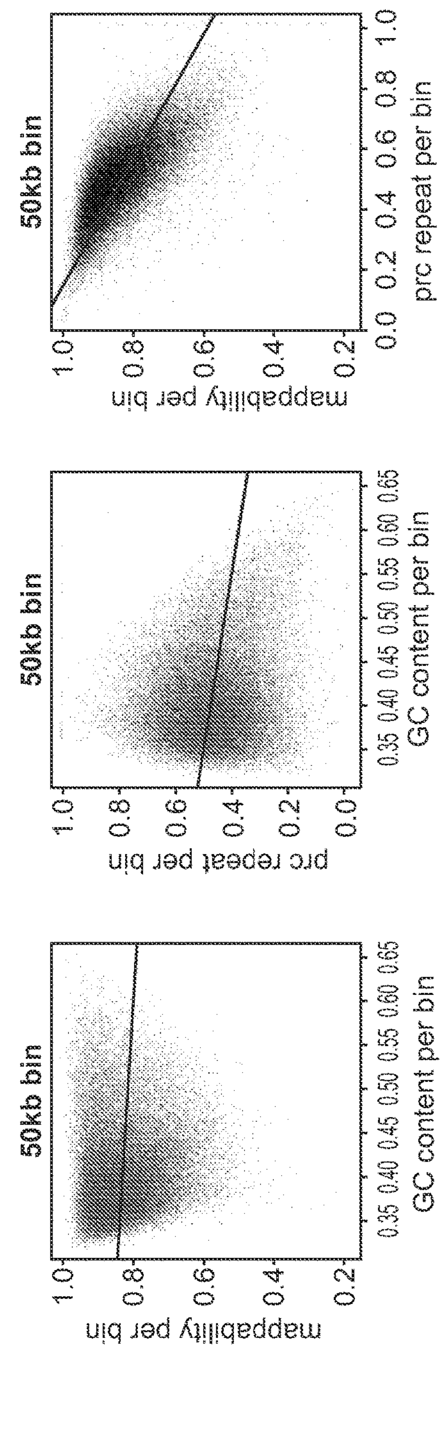

FIGS. 99A (all bins) and 99B (cross-validated bins) demonstrate that the bin selection described above mostly removes bins with low mappability.

As expected, most removed bins have intercepts far smaller than the genome-wide median bin count. Not surprisingly, the bin selection largely overlaps with the selection described in the previous section entitled "Removal of Uninformative Bins" (FIGS. 25 and 27-28).

Errors in Model Parameters

Figure 100:
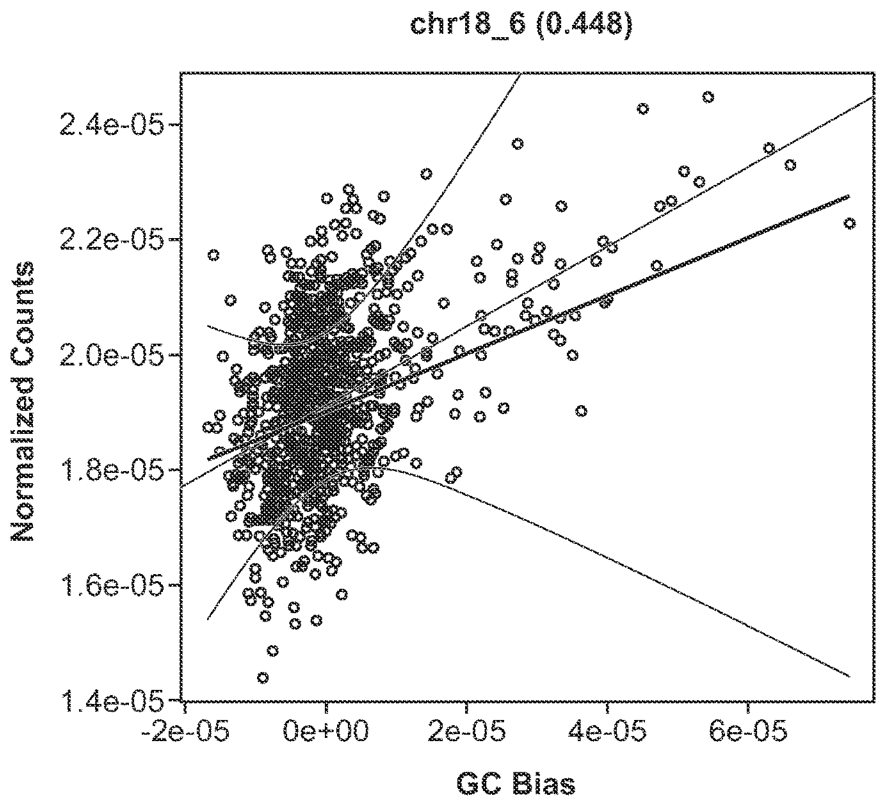
Figure 101:
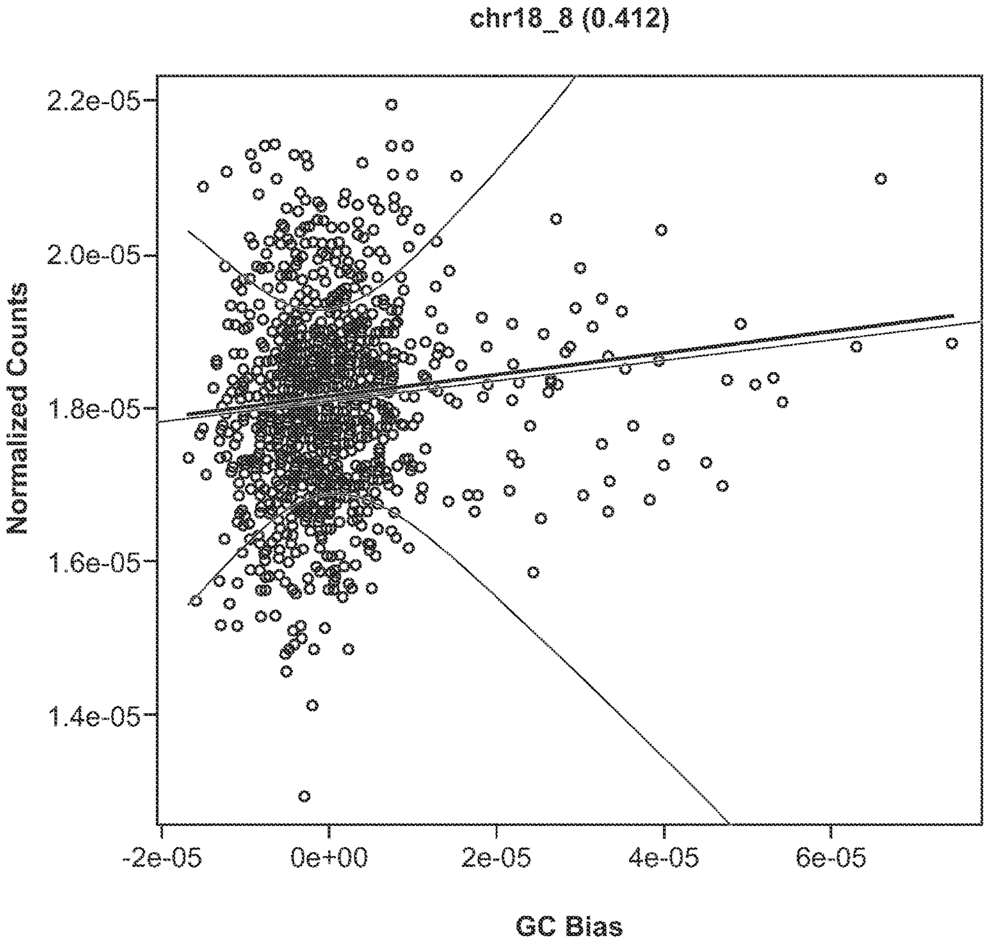

FIG. 100-101 show the 95% confidence intervals (curved lines) of the fitted linear model (thin straight line) for two bins (chr18_6 and chr18_8). The thick grey straight lines are obtained by replacing the S parameter with the difference between the GC contents of these two bins and the median GC content of chromosome 18. The error range is evaluated based on errors in the model parameters I and S for those two bins, as reported by the linear model. In addition, larger GC bias coefficients also contain larger errors. The large uncertainty corresponding to extremely large GC bias coefficients suggests that the range of applicability of the unmodified PERUN is limited to modest GC bias coefficients. Beyond that range, additional measures need to be taken to remove the residual GC bias. Fortunately, only very few samples are affected (roughly 10% of the LDTv2CE population).

Figure 102:
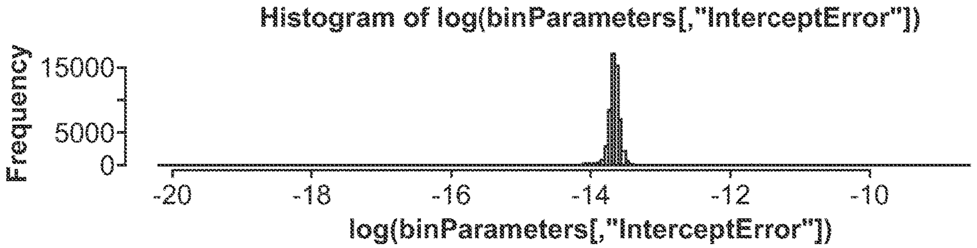
Figure 103:
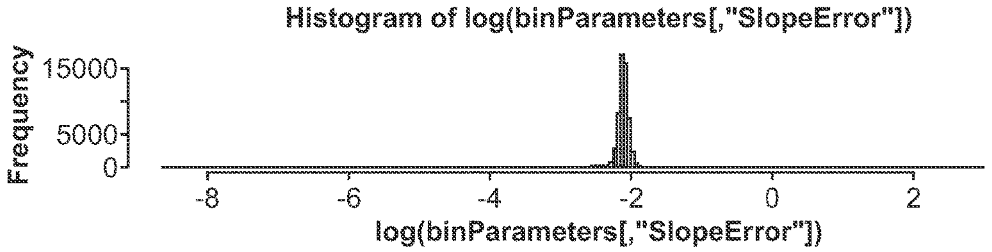
Figure 104:
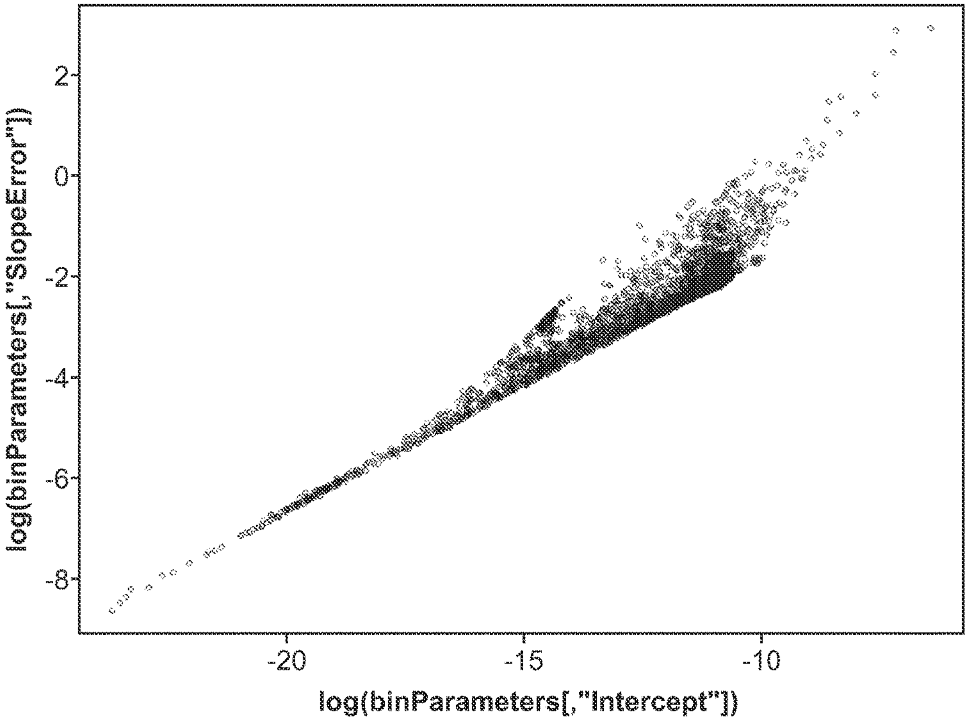

FIG. 102-104 show the errors in the model parameters I and S and the correlation between the error in S and the value of the intercept.

Secondary Normalization

High values of GC bias coefficients exceed the linear range assumed by the PERUN model and are remedied by an additional LOESS GC normalization step after PERUN normalization. The multiplicative nature of the LOESS procedure does not significantly inflate the variability since the normalized counts are already very close to 1. Alternatively, LOESS can be replaced with an additive procedure that subtracts residuals. The optional secondary normalization often is utilized only required for a minority of samples (roughly 10%).

Hole Padding (Padding)

Figure 105:
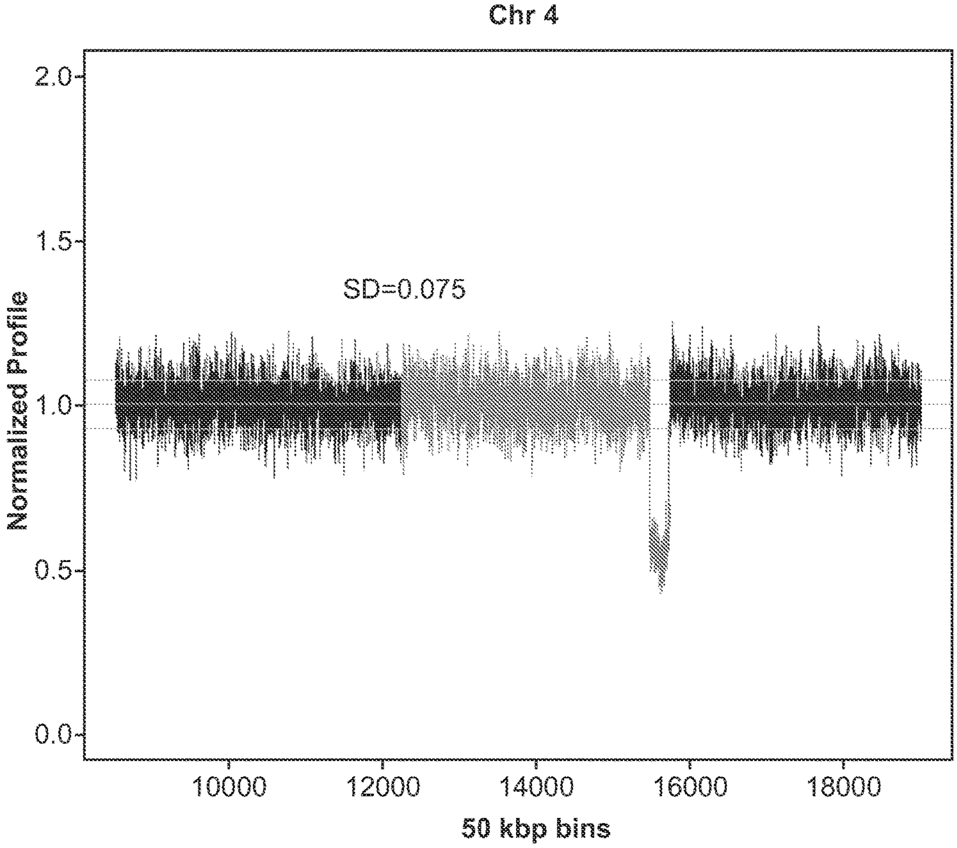

FIG. 68-69 confirm the presence of a large number of maternal deletions and duplications that have the potential to create false positives or false negatives, depending on their sizes and locations. An optional procedure called hole-padding has been devised to eliminate the interferences from these maternal aberrations. The procedure simply pads the normalized profile to remain close to 1 when it deviates above 1.3 or below 0.7. In LDTv2CE, hole padding (i.e., padding) did not significantly affect the classification. However, FIG. 105 shows a WI profile that contains a large deletion in chromosome 4. Hole padding converts that profile from chromosome 13 false positive to chromosome 13 true negative.

Results

This section discusses PERUN results for trisomy 13, trisomy 18 and trisomy 21 (T13, T18 and T21, respectively), gender determination, and sex aneuploidy.

Reduced Variability

Figure 106:
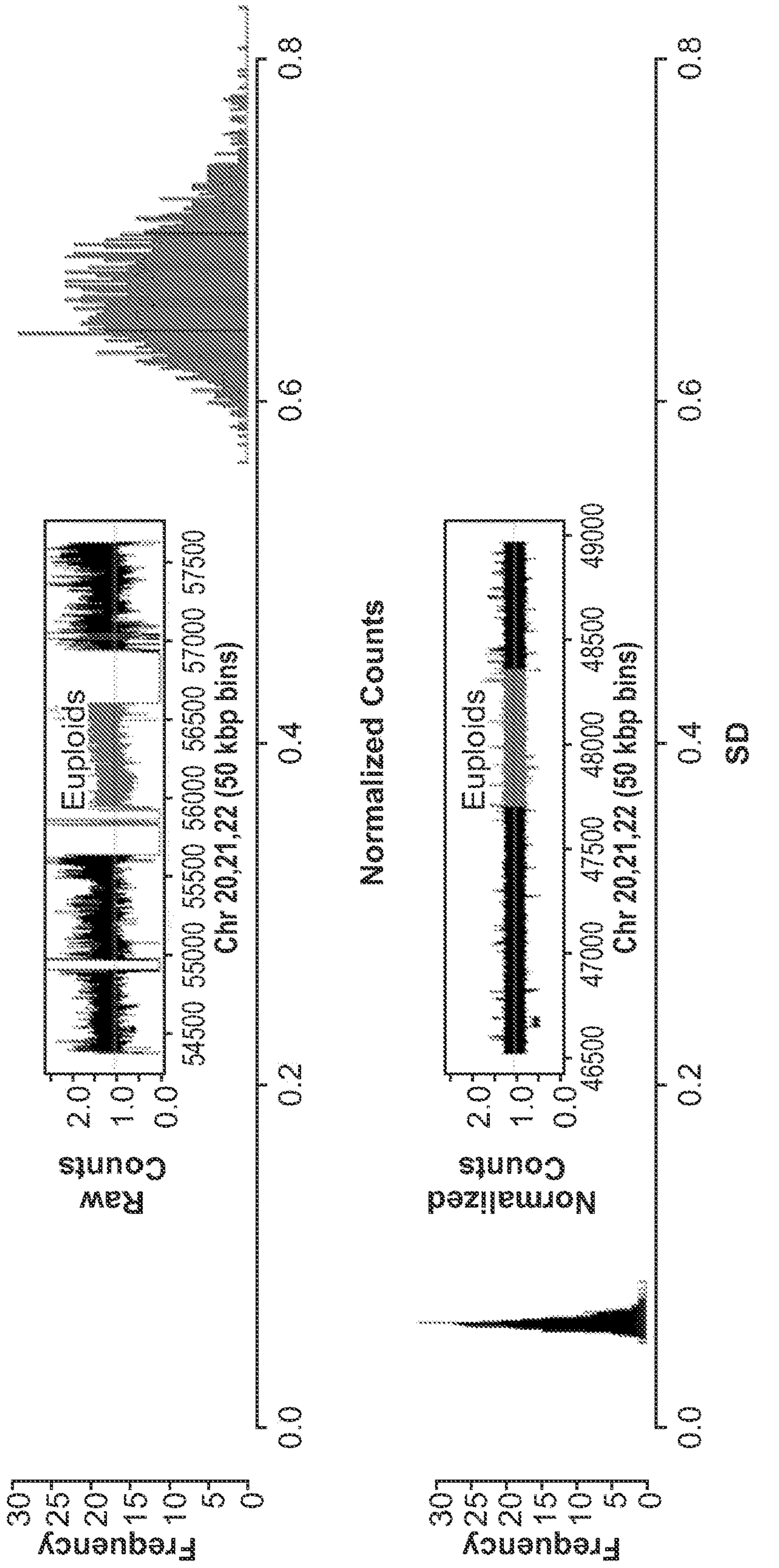
Figure 107:
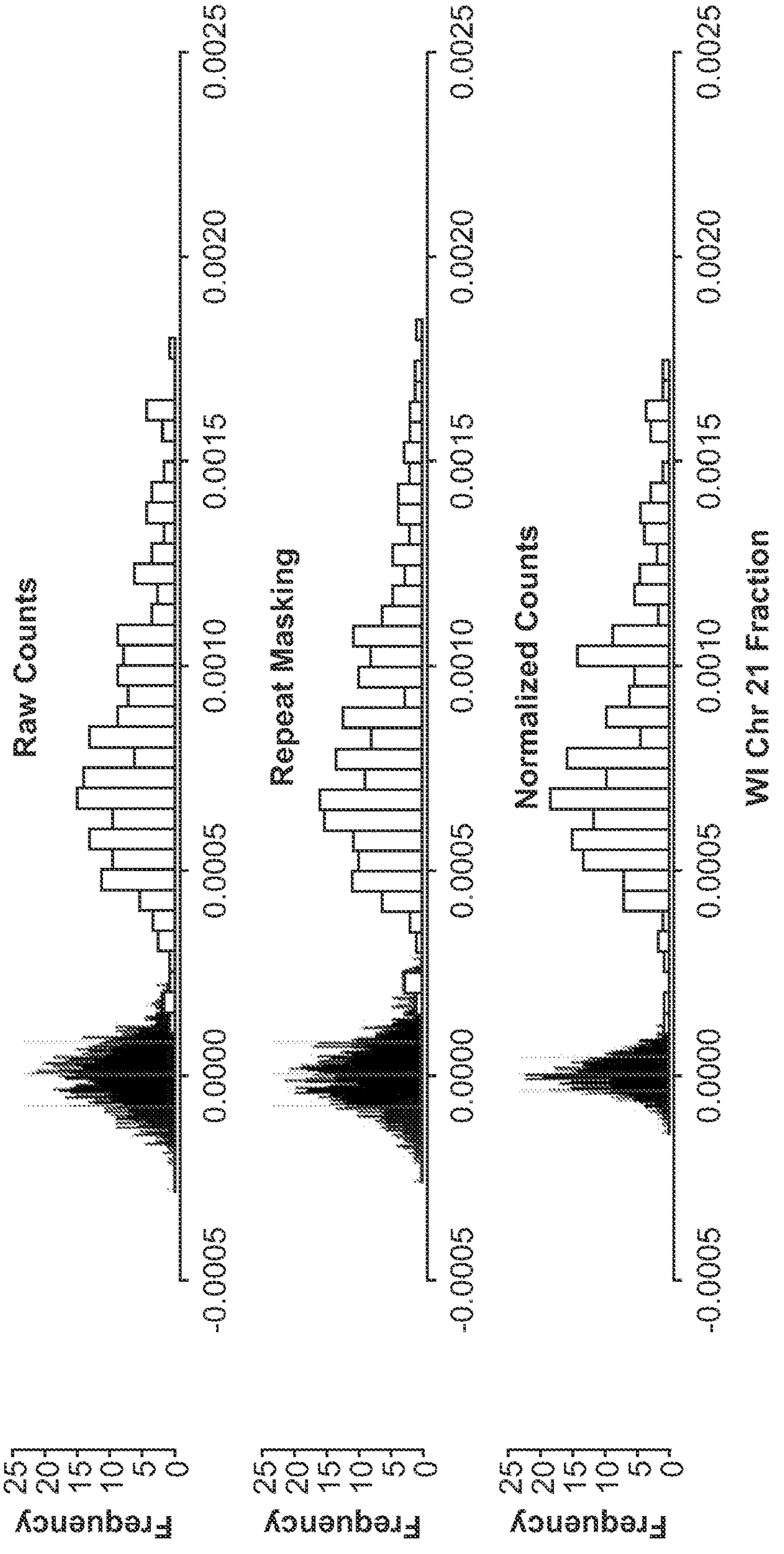
Figure 108:
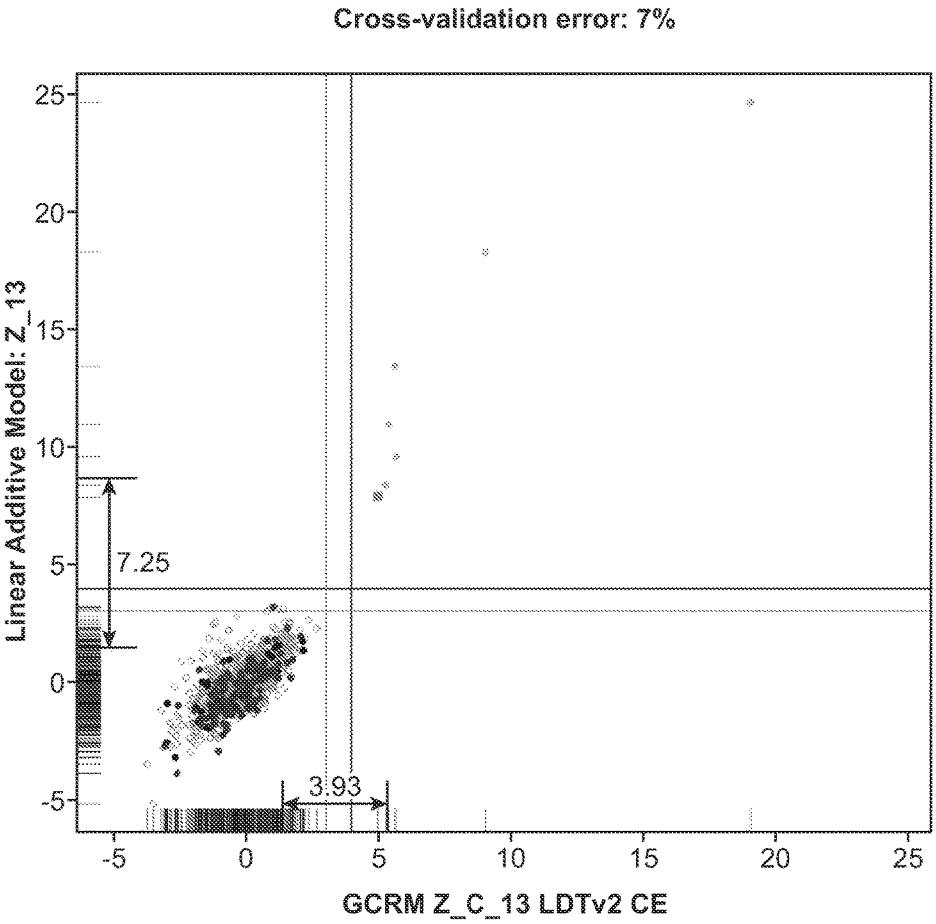
Figure 109:
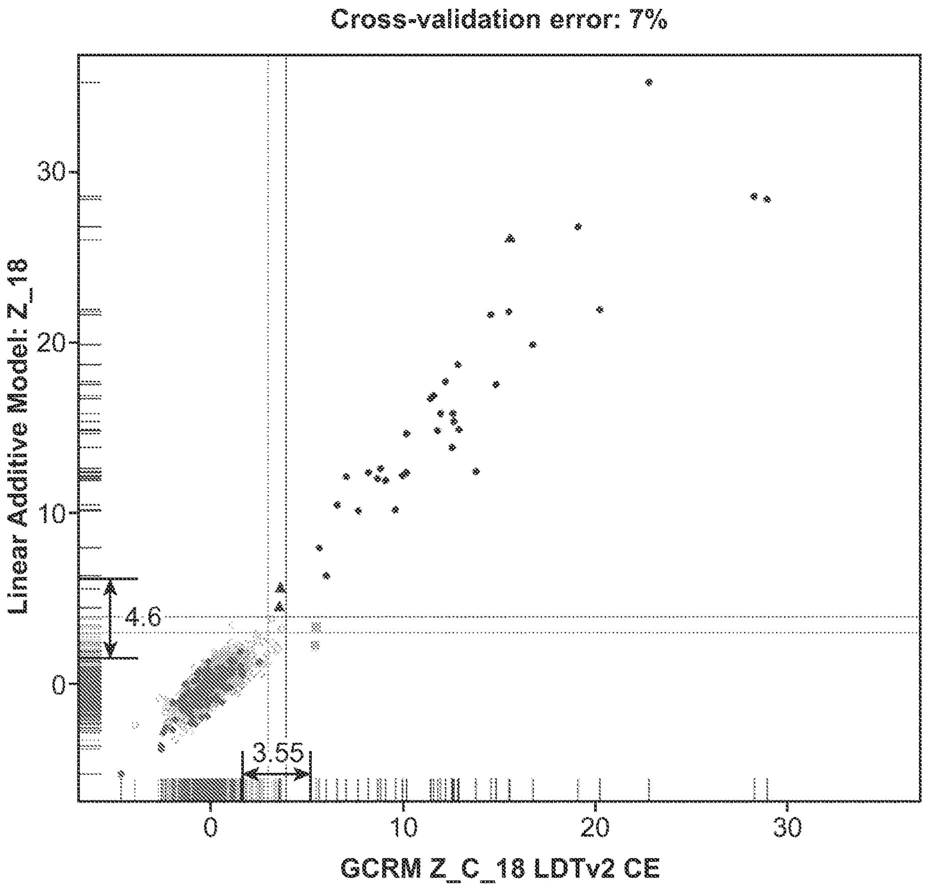
Figure 110:
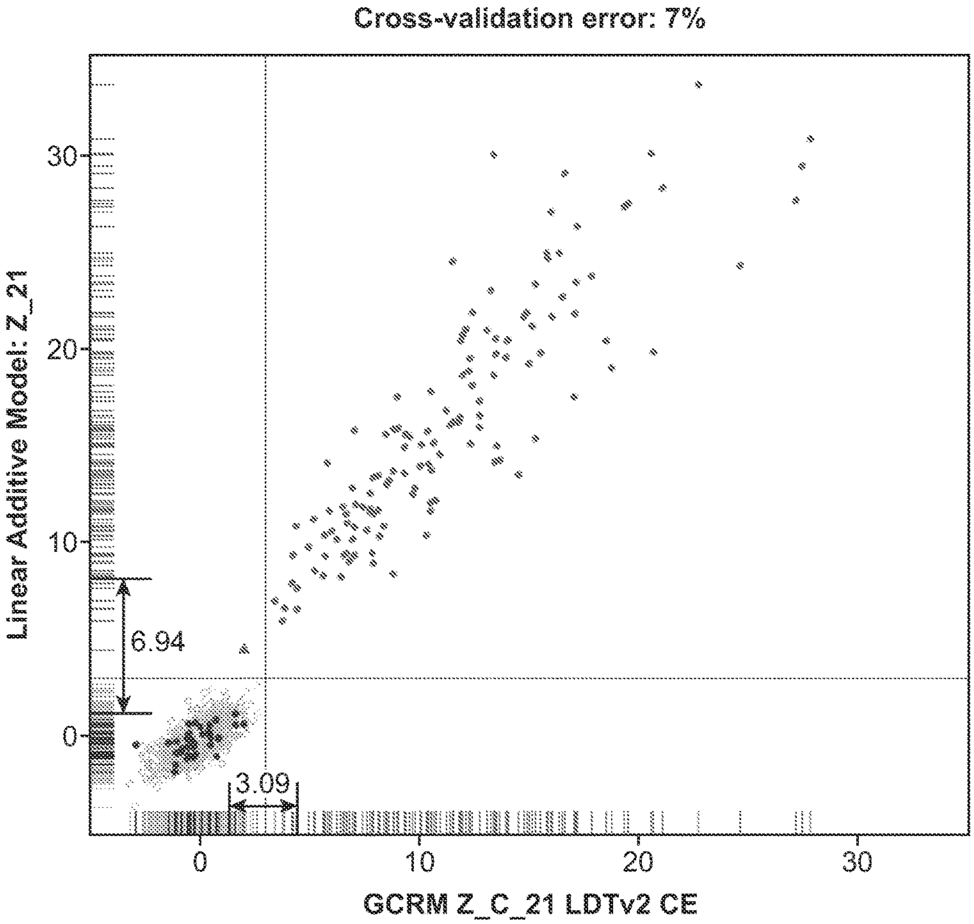
Figure 111:
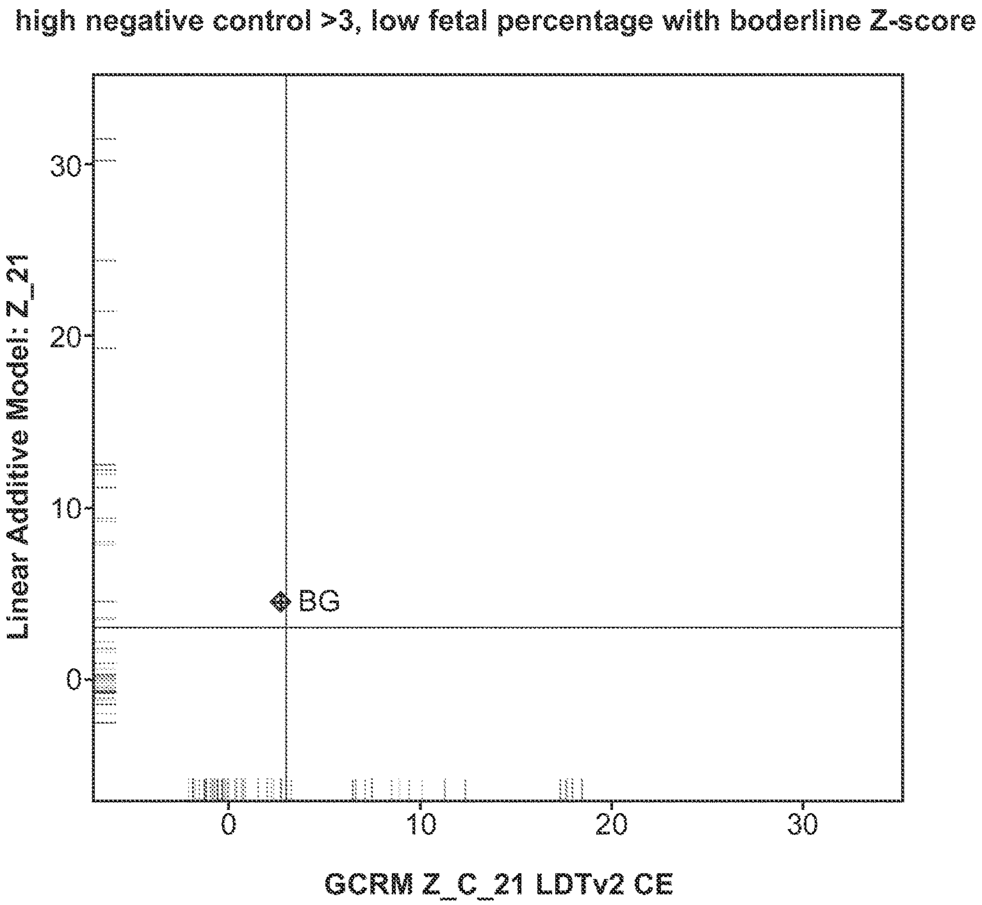

FIG. 106 compares the distribution of standard deviations of the binwise count profiles before and after PERUN normalization. The resulting distributions of chromosome representations for euploids and trisomy cases are shown in FIG. 107.

Improved T13, T18, and T21 Classification

FIG. 108-111 compare LDTv2CE PERUN classification results with those obtained using GCRM counts. In addition to removing two chromosome 18 false positives, two chromosome 18 false negatives, and two chromosome 21 false negatives, PERUN almost doubles the gap between the euploids and the affected cases, in spite of the fact that the higher plexing elevation decreased the number of counts per sample (ELAND data). Similar results are obtained when PERUN parameters trained on LDTv2CE Eland data are applied to WI measurements. Bowtie alignments require a different set of parameters and additional bin filtering, accounting for low mappability in some bins, but its results approach those seen with ELAND alignments.

Example 5: Additional Description of PERUN

Examples of parameterized Error Removal and Unbiased Normalization (PERUN) methods are described in Example 4, and an additional description of such methods is provided in this Example 5.

Massive parallel sequencing of cell-free circulating DNA (e.g. from maternal plasma) can, under ideal conditions, quantify chromosomal elevations by counting sequenced reads if unambiguously aligned to a reference human genome. Such methods that incorporate massive amounts of replicate data can, in some cases, show statistically significant deviations between the measured and expected chromosomal elevations that can imply aneuploidy [Chiu et al., Noninvasive prenatal diagnosis of fetal chromosomal aneuploidy by massively parallel genomic sequencing of DNA in maternal plasma. *Proc Natl Acad Sci USA.* 2008; 105: 20458-20463; Fan et al., Noninvasive diagnosis of fetal aneuploidy by shotgun sequencing DNA from maternal blood. *Proc Natl Acad Sci USA.* 2008; 105:16266-16271; Ehrich et al., Noninvasive detection of fetal trisomy 21 by sequencing of DNA in maternal blood: a study in a clinical setting, *American Journal of Obstetrics and Gynecology—AMER J OBSTET GYNECOL*, vol. 204, no. 3, pp. 205.e1-205.e11, 2011 DOI: 10.1016/j.ajog.2010.12.060]. Ideally, the distribution of aligned reads should cover euploid sections of the genome at a constant level (FIG. 62 and FIG. 63). In practice, uniformity can be difficult to attain because multiplexed Next Generation Sequencing (NGS) measurements typically yield low coverage (about 0.1) with sparsely scattered read start positions. In some embodiments, this problem is partially overcome by partitioning the genome into non-overlapping sections (bins) of equal lengths and assigning to each bin the number of the reads that align within it. In some embodiments, residual unevenness stemming from GC bias [Dohm J C, Lottaz C, Borodina T, Himmelbauer H. Substantial biases in ultra-short read data sets from high-throughput DNA sequencing. Nucleic Acids Res. 2008 September; 36(16):e105. Epub 2008 Jul. 26.] is largely suppressed using multiplicative detrending with respect to the binwise GC content (Fan H C, Quake S R (2010) Sensitivity of Noninvasive Prenatal Detection of Fetal Aneuploidy from Maternal Plasma Using Shotgun Sequencing Is Limited Only by Counting Statistics. PLoS ONE 5(5): e10439. doi:10.1371/journal.pone.0010439). In some embodiments, the resulting flattening of the count profile allows for successful classification of fetal trisomies in a clinical setting using quadruplex barcoding [Palomaki et al., DNA sequencing of maternal plasma to detect Down syndrome: an international clinical validation study. *Genet Med.,* 2011 November; 13(11):913-20.].

The transition from a quadruplex (i.e. 4 simultaneous sample reads) to higher sample plexing levels (e.g., dodecaplex (i.e. 12 simultaneous sample reads)) pushes the limits of NGS-based detection of genetic variations (e.g. aneuploidy, trisomy, and the like) in a test subject (e.g. a pregnant female), reducing both the number of reads per sample and the gap separating genetic variations (e.g. euploid from trisomy samples). The downsampling driven by increased multiplexing can impose new, more stringent requirements on data processing algorithms (FIG. 64, FIG. 65 and Example 4). In some embodiments, GC detrending, even when coupled with repeat masking, requires some improvement (FIG. 66, FIG. 67 and Example 4). In some embodiments, to maintain the sensitivity achieved with quadruplex barcoding (e.g., quadruplex indexing), methods and algorithms are presented that are capable of extracting a minute signal of interest from an overwhelming background noise as illustrated and described below and in FIG. 7, FIG. 8 and Example 4. In some embodiments, a novel method termed "PERUN" (Parameterized Error Removal and Unbiased Normalization) is described.

Conventional GC detrending can be multiplicative in nature (FIG. 17 and Example 4) and may not address additional sources of systematic bias, illustrated in FIG. 6. In certain embodiments, a reference median count profile constructed from a set of known euploid samples can eliminate additional bias and lead to qualitative improvements. In certain embodiments, a reference median count profile constructed from a set of known euploid samples can inherit a mixture of residual GC biases from the reference samples. In some embodiments, a normalization removes one or more orthogonal types of bias by separating them from one another at the bin elevation, rather than tackling them in bulk. In some embodiments GC bias is removed and binwise separation of the GC bias from the position-dependent attenuation is achieved (FIG. 68. FIG. 69 and Example 4). In some embodiments, substantially increased gaps between euploid and trisomy Z-scores are obtained relative to both quadruplex and dodecaplex GCRM results. In some embodiments, maternal and fetal microdeletions and duplications are detected. In some embodiments fetal fractions are accurately measured. In some embodiments gender is determined reliably. In some embodiments sex aneuploidy (e.g. fetal sex aneuploidy) is identified.

PERUN Method and Definitions

In some embodiments the entire reference genome is partitioned into an ordered set B of J bins:

$$B=\{b_j|j=1, \ldots, J\} \quad \text{(D)}$$

Bin lengths can be constrained to accommodate genomic stretches of relatively uniform GC content. In some embodiments adjacent bins can overlap. In some embodiments adjacent bins do not overlap. In some embodiments the bin edges can be equidistant or can vary to offset systematic biases, such as nucleotide composition or signal attenuation. In some embodiments a bin comprises genomic positions within a single chromosome. Each bin $b_j$ is characterized by the GC content $g_j^0$ of the corresponding segment of the reference genome. In some embodiments, the entire genome is assigned a reference GC content profile:

$$g^0=[g_1^0\ g_2^0 \ldots g_J^0] \quad \text{(E)}$$

The same $g^0$ profile can apply to all samples aligned to the chosen reference genome.

A proper or trivial subset of bins b, $$b \subseteq B \quad \text{(F)}$$

can be selected to satisfy certain criteria, such as to exclude bins with $g_j^0=0$, bins with extreme $g_j^0$ values, bins characterized by low complexity or low mappability (Derrien T, Estelle' J, Marco Sola S, Knowles D G, Raineri E, et al. (2012) Fast Computation and Applications of Genome Mappability. PLoS ONE 7(1): e30377, doi:10.1371/journal.pone.0030377), highly variable or otherwise uninformative bins, regions with consistently attenuated signal, observed maternal aberrations, or entire chromosomes (X, Y, triploid chromosomes, and/or chromosomes with extreme GC content). The symbol ||b|| denotes the size of b.

All sequenced reads from sample i unambiguously aligned within a bin $b_j$ form a set $a_{ij}$ whose cardinality $M_{ij}$ represents raw measured counts assigned to that bin. In some embodiments, the vector of measured bin counts for sample i constitutes the raw count profile for that sample. In some embodiments this is the primary observation for the purposes of PERUN:

$$M_i=[M_{i1}\ M_{i2} \ldots M_{iJ}] \quad \text{(G)}$$

To enable comparisons among different samples, the scaling constant $N_i$ is evaluated as the sum of raw bin counts over a subset of the bins:

$$N_i = \sum_{b \subseteq B} M_{ij} \quad \text{(H)}$$

In some embodiments b in Eq. H is restricted to autosomal bins. In some embodiments b in Eq. H is not restricted to autosomal bins. Division of $M_i$ by the total counts $N_i$ yields the scaled raw bin counts $m_{ij}$:

$$m_i=[m_{i1}\ m_{i2} \ldots m_{iJ}]=M_i/N_i \quad \text{(I)}$$

The nucleotide composition of the set $a_{ij}$ is described by the bin's observed GC content $g_{ij}$. The sample-specific observed GC content profile $g_i$ gathers individual bin-specific GC contents into a vector:

$$g_i=[g_{i1}\ g_{i2} \ldots g_{iJ}] \quad \text{(J)}$$

In some embodiments, $g_i \neq g^0$ and $g_{i_1} \neq g_{i_2 \neq i_1}$. The symbol g denotes the GC content profile regardless of its origin, i.e. whether it is derived from the reference genome or from the sample-specific read alignments. In some embodiments model equations use g. In some embodiments, actual implementations can substitute g with either $g^0$ or $g_i$.

For a single sample i, a linear relationship between $m_i$ and g is assumed, with $G_i$ and $r_i$ denoting the sample-specific slope of the regression line and the array of residuals, respectively:

$$m_i=G_i g+r_i \quad \text{(K)}$$

The regression can extend over the entire set B (Eq. D) or its proper subset b (Eq. F). The observed slope $G_i$ is also referred to as the scaled GC bias coefficient. $G_i$ expresses the bulk of the vulnerability of the sample i to the systematic GC bias. In some embodiments, to minimize the number of model parameters, higher-order terms, linked with curvature of the relationship $m_i(g)$ and encapsulated in the residuals $r_i$ are not explicitly addressed. In some embodiments, since sample-specific total counts $N_i$ confound the interactions among observables recorded on different samples, the unscaled equivalent of $G_i$, relating $M_i$ to g, is less useful and will not be considered.

The vector of true chromosomal elevations $l_{ij}$ corresponding to bins $b_j \in b$ in sample i form the sample-specific chromosomal elevation profile:

$$l_i=[l_{i1}\ l_{i2} \ldots l_{iJ}] \quad \text{(L)}$$

In some embodiments, the goal is to derive estimates for $l_i$ from $m_i$ by removing systematic biases present in $m_i$.

The values $l_{ij}$ are bin-specific and also sample-specific. They comprise both maternal and fetal contributions, proportional to their respective ploidy $P_{ij}^{M}$ and $P_{ij}^{F}$. The bin-specific and sample-specific ploidy $P_{ij}$ can be defined as an integral multiple of one-half, with the values of 1, ½, 0, 3/2, and 2 representing euploid, heterozygous deletion, homozygous deletion, heterozygous duplication, and homozygous duplication, respectively. In some instances, trisomy of a given chromosome implies ploidy values of 3/2 along the entire chromosome or its substantial portion.

When both the mother and the fetus are diploid ($P_{ij}^{M}=P_{ij}^{F}=1$), $l_{ij}$ equals some arbitrarily chosen euploid elevation E. In some embodiments, a convenient choice sets E to 1/||b||, thus ensuring that the profile $l_i$ is normalized. In the absence of bin selection, ||b||=||B||=J⇒ E=1/J. In some embodiments, E can be set to 1 for visualization. In some embodiments, the following relationship is satisfied:

$$l_{ij}=E[(1-f_i)P_{ij}^{M}+f_iP_{ij}^{F}] \quad \text{(M)}$$

The symbol $f_i$ stands for the fraction of the fetal DNA present in the cell-free circulating DNA from maternal plasma in sample i. Any deviations from euploid, either fetal ($P_{ij}^{F}\neq 1$) or maternal ($P_{ij}^{M}\neq 1$), cause differences between $l_{ij}$ and E that can be exploited to estimate $f_i$ and detect microdeletions/microduplications or trisomy.

To achieve the goal of extracting $l_i$ from $m_i$, a linear relationship is postulated between the bin-specific scaled raw counts $m_{ij}$ measured on a given sample and the sample-specific scaled GC bias coefficients:

$$m_i=l_iI+G_iS \quad \text{(N)}$$

The diagonal matrix I and the vector S gather bin-specific intercepts and slopes of the set of linear equations summarized by Eq. N:

$$I=\begin{bmatrix} I_1 & 0 & \cdots & 0 \\ 0 & I_2 & \cdots & 0 \\ \vdots & \vdots & \ddots & \vdots \\ 0 & 0 & \cdots & I_J \end{bmatrix} \quad \text{(O)}$$

$$S=[S_1\ S_2\ \cdots\ S_J] \quad \text{(P)}$$

Both I and S are sample-independent. The intercepts $I_j$ can be viewed as expected euploid values for scaled row counts in the absence of GC bias (i.e. when $G_i=0$). Their actual values reflect the convention adopted for E (vide supra). The intercepts $S_j$ are non-linearly related to the differences $g_j^0 - ⇒ g_k^0⟩$, where $⇒ g_k^0⟩$ represents the median GC content of the chromosome containing the bin j.

Once the values for the parameters I and S are known, the true chromosomal elevation profile $l_i$ is estimated from the scaled raw count profile in and the scaled GC bias coefficient G, by rearranging Eq. N:

$$l_i=(m_i-G_iS)I^{-1} \quad \text{(O)}$$

The diagonal character of the intercept matrix/provides for the matrix inversion in Eq. Q.

Parameter Estimation

Model parameters I and S are evaluated from a set of N scaled raw count profiles collected on samples karyotyped as euploid pregnancies. N is of the order of $10^3$. Scaled GC bias coefficients $G_i$ are determined for each sample (i=1, . . . , N). All samples are segregated into a small number of classes according to the sizes and signs of their $G_i$ values. The stratification balances the opposing needs to include sufficiently large numbers of representatives and a sufficiently small range of $G_i$ values within each shell. The compromise of four strata accommodates negative, near-zero, moderately positive, and extreme positive GC biases, with the near-zero shell being most densely populated. A fraction of samples (typically 10%) from each stratum can be randomly selected and set aside for cross-validation. The remaining samples make up the work set, used to train the model. Both the training and the subsequent cross-validation assume that all samples are free of maternal and fetal deletions or duplications along the entire genome:

$$P_{ij}^{M}=P_{ij}^{F}=1, \forall i=1, \ldots N, \forall j=1, \ldots, J \quad \text{(R)}$$

The large number of samples compensates for the occasional maternal deviations from the assumption R. For each bin j, $l_{ij}$ is set to E, allowing evaluation of the intercept $I_j$ and the slope $S_j$ as the coefficients of the linear regression applied to the training set according to Eq. N. The uncertainty estimates for $I_j$ and $S_j$ are recorded as well.

The random partitioning into the working and the cross-validation subsets is repeated multiple times (e.g. $10^2$), yielding distributions of values for the $I_j$ and $S_j$ parameters. In some embodiments the random partitioning is repeated between about 10 and about $10^5$ times. In some embodiments the random partitioning is repeated about 10, about $10^2$, about $10^3$, about $10^4$ or about $10^5$ times.

Cross-Validation

Once derived from the work set, the model parameters $I_j$ and $S_j$ are employed to back-calculate scaled raw counts from the scaled GC bias coefficients using Eq. N and assumption R. The symbol $p_{ij}$ denotes the predicted scaled raw counts for the bin $b_j$ in the sample i. The indices W and CV in further text designate the work and the cross-validation subsets, respectively. The back-calculation is applied to all samples, both from W and CV. R-factors, borrowed from the crystallographic structure refinement practice (Brünger, Free R value: a novel statistical quantity for assessing the accuracy of crystal structures, *Nature* 355, 472-475 (30 Jan. 1992); doi:10.1038/355472a0), are separately defined for the two subsets of samples:

$$R_j^W=\frac{\sum_{i\in W}|m_{ij}-p_{ij}|}{\sum_{i\in W}|m_{ij}|} \quad \text{(S)}$$

$$R_j^{CV}=\frac{\sum_{i\in CV}|m_{ij}-p_{ij}|}{\sum_{i\in CV}|m_{ij}|} \quad \text{(T)}$$

Both R-factors are bin-specific. As in crystallography, R-factors 16-17 can be interpreted as residual relative errors in the model. Having been excluded from the parameter estimation, the cross-validation R-factor $R_j^{CV}$ provides a true measure of the error for the given W/CV division, while the difference between $R_j^{CV}$ and $R_j^{W}$ reflects the model bias for the bin j. A separate pair of R-values is evaluated for each bin and for each random partitioning of the set of samples into W and CV. The maximum of all $R_j^{CV}$ and $R_j^{W}$ values obtained for the different random partitionings into W and CV is assigned to the bin j as its overall model error $\epsilon_j$.

Bin Selection

All the bins with zero GC content $g_j^0$ are eliminated from further consideration, as is the set $\{b_j : M_{ij}\equiv 0, \forall i=1, \ldots, N\}$ of bins that consistently receive zero counts across a large number of samples. In addition, a maximum tolerable cross-validation error value $\epsilon$ can be imposed on all bins. In some embodiments the bins with model errors $\epsilon_1$ exceeding the upper limit $\epsilon$ are rejected. In some embodiments, filtering uses bin mappability scores $\mu_j \in [0,1]$ and imposes a minimum acceptable mappability $\mu$, rejecting bins with $\mu_j < \mu$ (Derrien T, Estelle' J, Marco Sola S, Knowles D G, Raineri E, et al. (2012) Fast Computation and Applications of Genome Mappability. PLoS ONE 7(1): e30377, doi:10.1371/journal-.pone.0030377). For the purposes of determining fetal trisomy of chromosomes 21, 18, and 13, the sex chromosomes can be excluded as well. The subset $\beta$ of bins that survive all the phases of the bin selection can undergo further computations. In some embodiments, the same subset $\beta$ is used for all samples.

Normalization and Standardization

In some embodiments, for a given sample i, the chromosomal elevations $l_{ij}$ corresponding to the bin selection $\beta$ are estimated according to Eq. Q. In some embodiments, a secondary normalization is applied to remove any curvature from the $l_{ij}$-vs.-GC content correlation. In some embodiments $l_{ij}$ is already nearly unbiased, the secondary detrending is robust and is immune to error boosting. In some embodiments, standard textbook procedures suffice.

In some embodiments, the results of the normalization are summed up within each chromosome:

$$L_{in} = \sum_{bj \in \beta \cap Chr_n} l_{ij},\ n = 1, \ldots, 22 \quad \text{(U)}$$

The total autosomal material in sample i can be evaluated as the sum of all individual $L_{in}$ terms:

$$L_i = \sum_{n=1}^{22} L_{in} \quad \text{(V)}$$

The chromosomal representation of each chromosome of interest can be obtained by dividing $L_{in}$ with $L_1$:

$$\chi_{in} = L_{in}/L_i \quad \text{(W)}$$

The variability $\sigma_n$ of the representation of the chromosome n can be estimated as an uncensored MAD of $\chi_{in}$ values across a selection of samples spanning multiple flow cells. In some embodiments, the expectation $\langle \chi_n \rangle$ is evaluated as the median of $\chi_{in}$ values corresponding to a selection of samples from the same flow cell as the tested sample. Both sample selections can exclude high positive controls, low positive controls, high negative controls, blanks, samples that fail QC criteria, and samples with $SD(l_i)$ exceeding a predefined cutoff (typically 0.10). Together, the values $\sigma_n$ and $\langle \chi_n \rangle$ can provide the context for standardization and comparison of chromosomal representations among different samples using Z-scores:

$$Z_{in} = (\chi_{in} - \langle \chi_n \rangle)/\sigma_n \quad \text{(X)}$$

In some embodiments, aberrations such as trisomies 13, 18, and 21 are indicated by Z-values exceeding a predefined value, dictated by the desired confidence level.

Example 6: Examples of Formulas

Provided below are non-limiting examples of mathematical and/or statistical formulas that can be used in methods described herein.

$$Z = \frac{\Delta_1 - \Delta_2}{\sqrt{\sigma_1^2\left(\frac{1}{N_1} + \frac{1}{n_1}\right) + \sigma_2^2\left(\frac{1}{N_2} + \frac{1}{n_2}\right)}}$$

$$P(q) = \frac{1}{\sigma\sqrt{2\pi}} \exp[-(q - q_0)/(2\sigma^2)]$$

$$q_0 = 1 + F/2$$

$$z = -F/(2\sigma\sqrt{2})$$

$$B = \int_{-\infty}^{1} P dq = \frac{1}{2}[1 + erf(z)]$$

$$erf(z) = \frac{2}{\sqrt{\pi}} \Sigma_{n=0}^{\infty} \frac{(-1)^n z^{2n+1}}{n!(2n+1)}$$

$$R = \frac{1 - B}{B} = \frac{1 - erf(z)}{1 + erf(z)} = \frac{1 - erf[-F/(2\sigma\sqrt{2})]}{1 + erf[-F/(2\sigma\sqrt{2})]}$$

Example 7: Identifying and Adjusting (Padding) Elevations

Maternal deletions and duplications, often represented as first elevations in a profile, can be removed from count profiles normalized with PERUN to reduce variability when detecting T21, T18, or T13. The removal of deletions and duplication from a profile can reduce the variability (e.g., biological variability) found in measured chromosomal representations that originates from maternal aberrations.

All bins that significantly deviate from the expected chromosomal elevation of 1 are first identified. In this example some isolated bins are removed from the selection. This is optional. In this example only large enough groups of contiguous outlier bins are kept. This is also optional. Depending on the elevation assigned to an outlier bin or a group of contiguous outlier bins, a correction factor is added to the measured elevation to adjust it closer to the expected elevation of 1. The PAV values used in this example are +1 (for homozygous maternal deletions), +0.5 (for heterozygous maternal deletions), −0.5 (for heterozygous maternal duplications), −1 (for homozygous maternal duplications), or more (for large spikes). Large spikes are often not identified as maternal deletions and duplications.

This padding procedure corrected the classification (e.g., the classification as an aneuploidy, e.g., a trisomy) for samples that contains large maternal aberrations. Padding converted the WI sample from false positive T13 to true negative due to removal of a large maternal deletion in Chr4 (FIGS. 112-115).

Past simulations with experimental data have shown that depending on the chromosome, fetal fraction, and the type of aberration (homozygous or heterozygous, duplication or deletion), maternal aberrations in 20-40 bins long may push the Z-value over the classification edge (e.g., threshold) and result in a false positive or a false negative. Padding (e.g., adjusting) can circumvent this risk.

This padding procedure can remove uninteresting maternal aberrations (a confounding factor), reduce euploid variability, create tighter sigma-values used to standardize Z-scores and therefore enlarge the gap between euploids and trisomy cases.

Example 8: Determining Fetal Fractions from Maternal and/or Fetal Copy Number Variations A distinguishing feature of a method described herein is the use of maternal aberrations (e.g., maternal and/or fetal copy number variations) as a probe providing insight into the fetal fraction in the case of a pregnant female bearing a fetus (e.g., a euploid fetus). The detection and quantitation of maternal aberrations typically is aided by normalization of raw counts. In this example raw counts are normalized using PERUN. Alternatively, normalization with respect to a reference median count profile can be used in a similar manner and for the same purpose.

PERUN normalization of raw counts yields sample-specific binwise chromosomal levels (i counts samples, j counts bins). They comprise both maternal and fetal contributions, proportional to their respective ploidies $P_{ij}^M$ and $P_{ij}^F$. The bin-specific and sample-specific ploidy $P_{ij}$ is defined as an integral multiple of ½, with the values of 1, ½, 0, 3/2, and 2 representing euploid, heterozygous deletion, homozygous deletion, heterozygous duplication, and homozygous duplication, respectively. In particular, trisomy of a given chromosome implies ploidy values of 3/2 along the entire chromosome or its substantial portion.

When both the mother and the fetus are diploid ($P_{ij}^M=P_{ij}^F=1$), $l_{ij}$ equals some arbitrarily chosen euploid level E. A convenient choice sets E to $1/\|b\|$, where b denotes a proper or trivial subset of the set of all bins (8), thus ensuring that the profile $l_i$ is normalized. In the absence of bin selection, $\|b\|=\|B\|=J \Rightarrow E=1/J$. Alternatively and preferentially, E may be set to 1 for visualization. In general, the following relationship is satisfied:

$$l_{ij}E[(1-f_i)P_{ij}^M+f_iP_{ij}^F] \quad (Y)$$

The symbol $f_i$ stands for the fraction of the fetal DNA present in the cell-free circulating DNA from maternal plasma in sample i. Any deviations from euploid, either fetal ($P_{ij}^F \neq 1$) or maternal ($P_{ij}^M \neq 1$), cause differences between and E that can be exploited to estimate f and detect microdeletions/microduplications or trisomy.

Four different types of maternal aberrations are considered separately. All four account for possible fetal genotypes, as the fetus may (or in homozygous cases must) inherit the maternal aberration. In addition, the fetus may inherit a matching aberration from the father as well. In general, fetal fraction can only be measured when $P_{ij}^M \neq P_{ij}^F$.

A) Homozygous maternal deletion ($P_{ij}^M=0$). Two possible accompanying fetal ploidies include:
   a. $P_{ij}^F=0$, in which case $l_{ij}=0$ and the fetal fraction cannot be evaluated from the deletion.
   b. $P_{ij}^F=½$, in which case $l_{ij}=f_i/2$ and the fetal fraction is evaluated as twice the average elevation within the deletion.

B) Heterozygous maternal deletion ($P_{ij}^M=½$). Three possible accompanying fetal ploidies include:
   a. $P_{ij}^F=0$, in which case $l_{ij}=(1-f_i)/2$ and the fetal fraction is evaluated as twice the difference between ½ and the average elevation within the deletion.
   b. $P_{ij}^F=½$, in which case $l_{ij}=½$ and the fetal fraction cannot be evaluated from the deletion.
   c. $P_{ij}^F=1$, in which case $l_{ij}=(1+f_i)/2$ and the fetal fraction is evaluated as twice the difference between ½ and the average elevation within the deletion.

C) Heterozygous maternal duplication ($P_{ij}^M=3/2$). Three possible accompanying fetal ploidies include:
   a. $P_{ij}^F=1$, in which case $l_{ij}=(3-f_i)/2$ and the fetal fraction is evaluated as twice the difference between 3/2 and the average elevation within the duplication.
   b. $P_{ij}^F=3/2$, in which case $l_{ij}=3/2$ and the fetal fraction cannot be evaluated from the duplication.
   c. $P_{ij}^F=2$, in which case $l_{ij}=(3+f_i)/2$ and the fetal fraction is evaluated as twice the difference between 3/2 and the average elevation within the duplication.

D) Homozygous maternal duplication ($P_{ij}^M=2$). Two possible accompanying fetal ploidies include:
   a. $P_{ij}^F=2$, in which case $l_{ij}=2$ and the fetal fraction cannot be evaluated from the duplication.
   b. $P_{ij}^F=3/2$, in which case $l_{ij}=2-f_i/2$ and the fetal fraction is evaluated as twice the difference between 2 and the average elevation within the duplication.

The following LDTv2CE samples (FIG. 116-131) illustrate the application of determining fetal fraction from maternal and/or fetal copy number variations. The patients were not selected randomly and any agreement with FQA fetal fraction values should not be construed as the measure of merit of either technique.

Example 9: Determining Fetal Fractions from Chromosomal Representations of Chromosome X and Chromosome Y Measurements of fetal fraction (e.g., the measurement of the fraction of fetal DNA in the bodily fluids of a pregnant female) can be performed by an FQA, which is based on mass spectroscopy which does not make use of next generation sequencing (NGS) data obtained for detection of trisomies T21, T18, and T13 (e.g., PCT/US2010/027879 filed Mar. 18, 2010 entitled PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES, which is hereby incorporated by reference). Fetal fraction determinations can be made from untargeted NGS data collected on male euploids and/or aneuploidy pregnancies, including sex aneuploidies and trisomies T21, T18 and/or T13 as described here. Counts obtained from chromosome X (Chr X) and/or chromosome Y (ChrY) measurements (in the case of male pregnancies or sex aneuploidies) can be combined with chromosome 21, 18, and/or chromosome 13 measurements for trisomy pregnancies to determine fetal fraction.

In this example, the fraction of the fetal DNA in the circulating cell-free DNA from maternal plasma is determined using massively parallel sequencing data. Count profiles normalized with PERUN are used to measure fetal fractions from chromosomal representations of ChrX and ChrY in male pregnancies, pregnancies with sex aneuploidies, and/or chromosomal representations of chromosome 21 (Chr21), chromosome 18 (Chr18) and/or chromosome (Chr13) in trisomy pregnancies.

Detection and quantification of maternal aberrations is aided by normalization of raw counts. In this example, raw counts are normalized using PERUN. Alternatively, GCRM counts or normalization with respect to a reference median count profile can be used in a similar manner and for the same purpose. PERUN normalization of raw counts yields sample-specific binwise chromosomal levels $l_{ij}$ (i counts samples, j counts bins). Such levels are attributed to maternal and fetal contributions, proportional to their respective ploidies $P_{ij}^M$ and $P_{ij}^F$. The bin-specific and sample-specific ploidy $P_{ij}$ is defined as an integral multiple of ½, with the values of 1, ½, 0, 3/2, and 2 representing euploid, heterozygous deletion, homozygous deletion, heterozygous duplication, and homozygous duplication, respectively. In particular, trisomy of a given chromosome implies ploidy values of 3/2 along the entire chromosome or its substantial portion.

When both the mother and the fetus are diploid ($P_{ij}^{M}=P_{ij}^{F}=1$), $l_{ij}$ equals arbitrarily chosen euploid level E. A convenient choice sets E to $1/\|b\|$, where b denotes a proper or trivial subset of the set of all bins (8), thus ensuring that the profile $l_i$ is normalized. In the absence of bin selection, $\|b\|=\|B\|=J \Rightarrow E=1/J$. Alternatively and preferentially, E may be set to 1 for visualization. In general, the following relationship is satisfied:

$$l_{ij}=E\lfloor(1-f_i)P_{ij}^{M}+f_iP_{ij}^{F}\rfloor \quad (Y)$$

The symbol $f_i$ stands for the fraction of the fetal DNA present in the cell-free circulating DNA from maternal plasma in sample i. Any deviations from euploid, either fetal ($P_{ij}^{F}\neq 1$) or maternal ($P_{ij}^{M}\neq 1$), cause differences between $l_{ij}$ and E that can be exploited to estimate $f_i$ and detect microdeletions/microduplications or trisomy.

Table 2 summarizes fetal ploidy values for various types of pregnancies. Maternal contribution is fixed at $P_{ij}^{M}=1$ for every bin j belonging to chromosomes 21, 18, 13, and X. Maternal ploidy for ChrY is zero.

TABLE 2

| Pregnancy Status | Fetal Chr21 | Fetal Chr18 | Fetal Chr13 | Fetal ChrX | Fetal ChrY |
|---|---|---|---|---|---|
| Female T21 | $P_{ij}^{F} = 3/2$ | $P_{ij}^{F} = 1$ | $P_{ij}^{F} = 1$ | $P_{ij}^{F} = 1$ | $P_{ij}^{F} = 0$ |
| Female T18 | $P_{ij}^{F} = 1$ | $P_{ij}^{F} = 3/2$ | $P_{ij}^{F} = 1$ | $P_{ij}^{F} = 1$ | $P_{ij}^{F} = 0$ |
| Female T13 | $P_{ij}^{F} = 1$ | $P_{ij}^{F} = 1$ | $P_{ij}^{F} = 3/2$ | $P_{ij}^{F} = 1$ | $P_{ij}^{F} = 0$ |
| Male T21 | $P_{ij}^{F} = 3/2$ | $P_{ij}^{F} = 1$ | $P_{ij}^{F} = 1$ | $P_{ij}^{F} = 1/2$ | $P_{ij}^{F} = 1/2$ |
| Male T18 | $P_{ij}^{F} = 1$ | $P_{ij}^{F} = 3/2$ | $P_{ij}^{F} = 1$ | $P_{ij}^{F} = 1/2$ | $P_{ij}^{F} = 1/2$ |
| Male T13 | $P_{ij}^{F} = 1$ | $P_{ij}^{F} = 1$ | $P_{ij}^{F} = 3/2$ | $P_{ij}^{F} = 1/2$ | $P_{ij}^{F} = 1/2$ |
| Male Euploid | $P_{ij}^{F} = 1$ | $P_{ij}^{F} = 1$ | $P_{ij}^{F} = 1$ | $P_{ij}^{F} = 1/2$ | $P_{ij}^{F} = 1/2$ |
| Turner | $P_{ij}^{F} = 1$ | $P_{ij}^{F} = 1$ | $P_{ij}^{F} = 1$ | $P_{ij}^{F} = 1/2$ | $P_{ij}^{F} = 0$ |
| Jacobs | $P_{ij}^{F} = 1$ | $P_{ij}^{F} = 1$ | $P_{ij}^{F} = 1$ | $P_{ij}^{F} = 1/2$ | $P_{ij}^{F} = 1$ |
| Klinefelter | $P_{ij}^{F} = 1$ | $P_{ij}^{F} = 1$ | $P_{ij}^{F} = 1$ | $P_{ij}^{F} = 1$ | $P_{ij}^{F} = 1/2$ |
| TripleX | $P_{ij}^{F} = 1$ | $P_{ij}^{F} = 1$ | $P_{ij}^{F} = 1$ | $P_{ij}^{F} = 3/2$ | $P_{ij}^{F} = 0$ |

When fetal ploidy differs from maternal ploidy and from zero, the imbalance can be used to evaluate the fetal fraction for male fetuses. In this example, the imbalance is not used to evaluate fetal fraction in pregnant females bearing a euploid female fetus. The following illustrates the principles described above.

Let $N_n$ and N denote the number of bins in a given chromosome n and the total number of autosomal bins in the normalized profile, respectively. The expected euploid chromosomal representation is the ratio between the total area under the segment of the chromosome in question and the area under all autosomal bins:

$$c_n^{0}=N_n/N \quad (Z)$$

In practice, Equation Z may be substituted by the median (or mean) value of a large number of euploid chromosomal representations for a given chromosome. In a trisomy pregnancy, such as T21, T18, or T13, $P_{ij}^{F}=3/2$ and $P_{ij}^{M}=1$. The expected chromosomal representation is then modified by the fetal fraction as in Equation AA.

$$c_{in} = \frac{N_n}{N}\left(1+\frac{f_i}{2}\right) = c_n^0\left(1+\frac{f_i}{2}\right) \quad (AA)$$

The fetal fraction is therefore obtained from the measured chromosomal representation and the expected euploid value as per Equation AB.

$$f_i = 2\left(\frac{c_{in}}{c_n^0}-1\right) \quad (AB)$$

ChrX in male pregnancies follows a different relationship as shown in Equation AC.

$$f_i = 2\left(1-\frac{c_{in}}{c_n^0}\right) \quad (AC)$$

ChrY shows a strong linear correlation with fetal fraction. ChrY in male pregnancies can follow a relationship as shown in Equation AG. Due to large variability of ChrY normalized profiles, prediction of fetal fractions from measured ChrY values can be conveniently performed by calibrating the relationship ChrY-vs-fetal fraction in trisomy male pregnancies and then applying the calibration line to all male pregnancies. A similar procedure is also convenient for ChrX. Alternatively, both ChrX and ChrY in male trisomy pregnancies can be used together to generate a bivariate linear model, with the fetal fraction extracted from trisomy chromosomes as the response variable. Derivation of the appropriate relationships corresponding to Turner (X), Jacobs (XYY), Klinefelter (XXY), and TripleX (XXX) syndromes follows from the same line of reasoning. For example, for TripleX syndrome the relationship described in equation AB can be utilized and the X chromosome is treated as aneuploid. For Turner syndrome, equation AC is utilized to determine the fetal fraction using an X chromosome representation. For Klinefelter syndrome, equation AG is used to determine the fetal fraction from ChrY representation and equation AC is not used. For Jacobs syndrome, equation AC is utilized to determine the fetal fraction from ChrX representation and a variation of equation AG is used to determine the fetal fraction from ChrY representation. In some embodiments the fetal fraction resulting from equation AG is divided by 2 to arrive at a fetal fraction for Jacobs syndrome. In some embodiments the $C_y$ value in equation AG is divided by 2 to arrive at a fetal fraction for Jacobs syndrome.

WI samples normalized with PERUN are used to illustrate the application of a method described in this Example. Fetal fractions were obtained from Chr21 representations in 107 male T21 pregnancies, from Chr18 representations in 33 male T18 pregnancies, and from 5 male T13 pregnancies using Equation AB. The graph in FIG. 132 correlates ChrX chromosomal representations in those 145 trisomy male pregnancies. The linear model based on FIG. 132 yields the following linear relationship between the fetal fraction (multiplied by 100) and the chromosome X representation in male pregnancies as shown in Equation AD.

$$f_i=179.1-3045.82c_{iX} \quad (AD)$$

The agreement between fetal fractions obtained from ChrX using Equation AD and the fetal fractions obtained from Chr21, 18, and 13 in the male trisomy pregnancies is shown in FIG. 133.

FIG. 134 correlates chromosome Y representations in those same 145 trisomy male pregnancies. The resulting regression allows estimation of the fetal fraction from ChrY representation from Equation AE.

$$f_i=0.5368+13440162c_{iY} \quad (AE)$$

The agreement between fetal fractions obtained from ChrY using Equation AE and the fetal fractions obtained from Chr21, 18, and 13 in the male trisomy pregnancies is shown in FIG. 135. Equations AD and AE were used to evaluate fetal fractions in 858 euploid male pregnancies. FIG. 136 illustrates the agreement between fetal fractions derived from ChrX and from ChrY. Finally, when both ChrX and ChrY are trained on fetal fraction values derived from Chr21, 18, and 13 in trisomy male pregnancies, the following regression coefficients are obtained as per Equation AF below.

$$f_i=24.88-416.42c_{iX}+1169.46c_{iY} \quad \text{(AF)}$$

The model that combines ChrX and ChrY predicts fetal fractions shown in FIG. 137, along with the corresponding values obtained from Chr 21, 18, and 13 (male trisomy pregnancies). Extension to sex aneuploidies is straightforward as discussed previously.

Example 10: Determining Fetal Fraction from a Measured ChrY Representation

The fetal fraction f for a male pregnancy was determined from the measured chromosomal representation y of ChrY using the following formula:

$$f = 2\frac{i+S\langle x\rangle - y}{S\langle x\rangle} \quad (71)$$

The term $\langle x\rangle$ represents the median chromosomal representation of ChrX for female pregnancies. This was different from zero due to noise. I and S quantified the linear relationship between ChrX and ChrY representations in male pregnancies. The parameters I and S were evaluated using constrained linear regression between ChrX and ChrY representations in male pregnancies. The regression line was forced through the point representing median ChrX and ChrY representations for female fetuses ($\langle x\rangle$ and $\langle y\rangle$, respectively), leaving only one adjustable parameter—the slope S.

The value of the model parameter S was derived from the following assumption:

$$y-\langle y\rangle=S(x-\langle x\rangle) \quad (72)$$

To optimize the model parameter S, functional F was defined as the sum of squared residuals between the model (Eq. 72) and the actually measured ChrY representations:

$$\begin{aligned} F &= \Sigma_i[y_i - S(x_i-\langle x\rangle) - \langle y\rangle]^2 \\ &= \Sigma_i(y_i^2 + S^2x_i^2 + S^2\langle x\rangle^2 + \langle y\rangle^2 - 2Sx_iy_i + 2S\langle x\rangle y_i - 2\langle y\rangle y_i - 2S^2\langle x\rangle x_i + 2S\langle y\rangle x_i - 2S\langle x\rangle\langle y\rangle) \end{aligned} \quad (73)$$

Deviation between the observed and predicted ChrY representations was minimized as the first derivative of F with respect to S vanishes:

$$\begin{aligned} \frac{dF}{dS} = 0 &= \frac{d}{dS}\Sigma_i(y_i^2 + S^2x_i^2 + S^2\langle x\rangle^2 + \langle y\rangle^2 - 2Sx_iy_i + 2S\langle x\rangle y_i \\ &\quad - 2\langle y\rangle y_i - 2S^2\langle x\rangle x_i + 2S\langle y\rangle x_i - 2S\langle x\rangle\langle y\rangle) \\ &= 2\Sigma_i[S(x_i^2 - 2\langle x\rangle x_i + \langle x\rangle^2) + \langle x\rangle y_i + \langle y\rangle x_i - \langle x\rangle\langle y\rangle - x_iy_i] \\ &= 2S\Sigma_i(x_i-\langle x\rangle)^2 + 2\Sigma_i(x_i-\langle x\rangle)(y_i-\langle y\rangle) \end{aligned} \quad (74)$$

Solving Eq. 74 for S yielded the optimal slope:

$$S = \frac{\Sigma_i(x_i-\langle x\rangle)(y_i-\langle y\rangle)}{\Sigma_i(x_i-\langle x\rangle)^2} \quad (75)$$

The intercept I was introduced to simplify Eq. 72 and was defined as follows:

$$I=\langle y\rangle-S\langle x\rangle \quad (76)$$

Combining Eqs. 72 and 76 yielded the following expression:

$$y=I+Sx \quad (77)$$

The expression for fetal fraction based on ChrX has already been described in an earlier technology disclosure. It reads as follows:

$$f = -2\left(\frac{x}{\langle x\rangle} - 1\right) \quad (78)$$

The fetal fraction was evaluated from measured ChrY representation by introducing Eq. 77 into Eq. 78 and rearranging the resulting expression:

$$f = -2\left(\frac{y-I}{S\langle x\rangle} - 1\right) = 2\frac{I+S\langle x\rangle - y}{S\langle x\rangle} QED \quad (79)$$

This proved Eq. 71.

The R code used to evaluate model parameters I and S is shown below:

```
slope <- sum( ( chrRepresentations[ as.character( selectorBoys ),
          "Y" ] - girlsMedianY )*
          ( chrRepresentations[ as.character( selectorBoys ),
          "X" ] - girlsMedianX ), na.rm=T ) /
       sum( ( chrRepresentations[ as.character( selectorBoys ),
          "X" ] - girlsMedianX ) * ( chrRepresentations[ as.-
          character( selectorBoys ), "X" ] - girlsMedianX ), na.rm=T );
intercept <- girlsMedianY - slope * girlsMedianX;
slope
#[1] -0.3252008
intercept
#[1] 0.01560178
```

The model parameters $\langle x\rangle$, $\langle y\rangle$, I, and S have the following values:

$\langle x\rangle=0.04765159$ $\langle y\rangle=0.0001054401$

I=0.01560178

S=−0.3252008

The above values were derived from LDTv2CE PERUN data. The parameter values applied to v2 chemistry and the current PERUN parameterization (extended to cover chromosomes X and Y). The R code that evaluated fetal fractions from the measured chromosome representations of chromosomes 13, 18, 21, X, and Y is shown below:

```
evaluateFetalFractions <- function( chrRepresentations,
  median21=0.01265891,
  median18=0.02887715,
  median13=0.03599132,
  girlsMedianX=0.04765159,
  girlsMedianY=0.0001054401,
  #
  boysInterceptY=0.01560178,
  boysSlopeY= -0.3252008
  ) {
  fetalFractions <- c(
    200 * ( chrRepresentations[ "21" ] / median21 - 1 ),
    200 * ( chrRepresentations[ "18" ] / median18 - 1 ),
    200 * ( chrRepresentations[ "13" ] / median13 - 1 ),
    -200 * ( chrRepresentations[ "X" ] / girlsMedianX - 1 ),
    -200 * ( chrRepresentations[ "Y" ] - boysInterceptY -
      boysSlopeY * girlsMedianX ) / ( boysSlopeY * girlsMedianX )
    );
  names( fetalFractions ) <- c( "21", "18", "13", "X", "Y" );
  return( fetalFractions );
} # evaluateFetalFractions
```

Example 11

In this Example, a new fusion protein was used that captures methylated DNA in combination with CpG Island array to identify genomic regions that are differentially methylated between fetal placenta tissue and maternal blood. A stringent statistical approach was used to only select regions which show little variation between the samples, and hence suggest an underlying biological mechanism. Eighty-five differentially methylated genomic regions predominantly located on chromosomes 13, 18 and 21 were validated. For this validation, a quantitative mass spectrometry based approach was used that interrogated 261 PCR amplicons covering these 85 regions. The results are in very good concordance (95% confirmation), proving the feasibility of the approach.

Ten paired maternal and placental DNA samples were used to identify differentially methylated regions. These results were validated using a mass spectrometry-based quantitative methylation assay. First, genomic DNA from maternal buffy coat and corresponding placental tissue was first extracted. Next the MBD-FC was used to capture the methylated fraction of each DNA sample. See FIGS. 138-142. The two tissue fractions were labeled with different fluorescent dyes and hybridized to an Agilent® CpG Island microarray. See FIG. 141. This was done to identify differentially methylated regions that could be utilized for prenatal diagnoses. Therefore, two criteria were employed to select genomic regions as potential enrichment markers: the observed methylation difference had to be present in all tested sample pairs, and the region had to be more than 200 bp in length.

DNA Preparation and Fragmentation

Genomic DNA (gDNA) from maternal buffy coat and placental tissue was prepared using the QIAamp DNA Mini Kit™ and QIAamp DNA Blood Mini Kit™, respectively, from Qiagen® (Hilden, Germany). For MCIp, gDNA was quantified using the NanoDrop ND 1000™ spectrophotometer (Thermo Fisher®, Waltham, Mass., USA). Ultrasonication of 2.5 μg DNA in 500 μl TE buffer to a mean fragment size of 300-500 bp was carried out with the Branson Digital Sonifier 45™ (Danbury, Conn., USA) using the following settings: amplitude 20%, sonication time 110 seconds, pulse on/pulse off time 1.4/0.6 seconds. Fragment range was monitored using gel electrophoresis.

Methyl-CpG Immunoprecipitation

Per sample, 56 μg purified MBD-Fc protein and 150 μl of Protein A Sepharose 4 Fast Flow beads (Amersham Biosciences®, Piscataway, N.J., USA) were rotated in 15 ml TBS overnight at 4° C. Then, the MBD-Fc beads (150 μl/assay) were transferred and dispersed in to 2 ml Ultrafree-CL centrifugal filter devices (Millipore®, Billerica, Mass., USA) and spin-washed three times with Buffer A (20 mM Tris-HCl, pH8.0, 2 mM MgCl2, 0.5 mM EDTA 300 mM NaCl, 0.1% NP-40). Sonicated DNA (2 μg) was added to the washed MBD-Fc beads in 2 ml Buffer A and rotated for 3 hours at 4° C. Beads were centrifuged to recover unbound DNA fragments (300 mM fraction) and subsequently washed twice with 600 μl of buffers containing increasing NaCl concentrations (400, 500, 550, 600, and 1000 mM). The flow through of each wash step was collected in separate tubes and desalted using a MinElute PCR Purification Kit™ (Qiagen®). In parallel, 200 ng sonicated input DNA was processed as a control using the MinElute PCR Purification Kit™ (Qiagen®).

Microarray Handling and Analysis

To generate fluorescently labeled DNA for microarray hybridization, the 600 mM and 1M NaCl fractions (enriched methylated DNA) for each sample were combined and labeled with either Alexa Fluor 555-aha-dCTP (maternal) or Alexa Fluor 647-aha-dCTP (placental) using the BioPrime Total Genomic Labeling System™ (Invitrogen®, Carlsbad, Calif., USA). The labeling reaction was carried out according to the manufacturer's manual. The differently labeled genomic DNA fragments of matched maternal/placental pairs were combined to a final volume of 80 μl, supplemented with 50 μg Cot-1 DNA (Invitrogen®), 52 μl of Agilent 10× blocking reagent (Agilent Technologies®, Santa Clara, Calif., USA), 78 μl of deionized formamide, and 260 μl Agilent 2× hybridization buffer. The samples were heated to 95° C. for 3 min, mixed, and subsequently incubated at 37° C. for 30 min. Hybridization on Agilent CpG Island Microarray Kit™ was then carried out at 67° C. for 40 hours using an Agilent SureHyb™ chamber and an Agilent hybridization oven. Slides were washed in Wash I (6×SSPE, 0.005% N-lauroylsarcosine) at room temperature for 5 min and in Wash II (0.06×SSPE) at 37° C. for an additional 5 min. Next, the slides were submerged in acetonitrile and Agilent Ozone Protection Solution™, respectively, for 30 seconds. Images were scanned immediately and analyzed using an Agilent DNA Microarray Scanner™ Microarray images were processed using Feature Extraction Software v9.5 and the standard CGH protocol.

Bisulfite Treatment

Genomic DNA sodium bisulfite conversion was performed using EZ-96 DNA Methylation Kit™ (ZymoResearch, Orange County, CA). The manufacturer's protocol was followed using 1 ug of genomic DNA and the alternative conversion protocol (a two temperature DNA denaturation).

Quantitative Methylation Analysis

Sequenom's MassARRAY® System was used to perform quantitative methylation analysis. This system utilizes matrix-assisted laser desorption ionization time-of-flight (MALDI-TOF) mass spectrometry in combination with RNA base specific cleavage (Sequenom® MassCLEAVET™). A detectable pattern is then analyzed for methylation status. PCR primers were designed using Sequenom® EpiDESIGNER™ (www.epidesigner.com). A total of 261 amplicons, covering 85 target regions, were used for validation (median amplification length=367 bp, min=108, max=500; median number of CpG's per amplicon=23, min=4, max=65). For each reverse primer, an additional T7 promoter tag for in-vivo transcription was added, as well as a 10 mer tag on the forward primer to adjust for melting temperature differences. The MassCLEAVE™ biochemistry was performed as previously described (Ehrich M, et al. (2005) Quantitative high-throughput analysis of DNA methylation patterns by base specific cleavage and mass spectrometry. Proc Natl Acad Sci USA 102:15785-15790). Mass spectra were acquired using a MassARRAY™ Compact MALDI-TOF (Sequenom®, San Diego) and methylation ratios were generated by the EpiTYPER™ software v1.0 (Sequenom®, San Diego).

Statistical Analysis

All statistical calculations were performed using the R statistical software package (www.r-project.org). First, the array probes were grouped based on their genomic location. Subsequent probes that were less than 1000 bp apart were grouped together. To identify differentially methylated regions, a control sample was used as reference. In the control sample, the methylated fraction of a blood derived control DNA was hybridized against itself. Ideally this sample should show log ratios of the two color channels around 0. However because of the variability in hybridization behavior, the probes show a mean log ratio of 0.02 and a standard deviation of 0.18. Next the log ratios observed in the samples were compared to the control sample. A two way, paired t-test was used to test the NULL hypothesis that the groups are identical. Groups that contained less than 4 probes were excluded from the analysis. For groups including four or five probes, all probes were used in a paired t-test. For Groups with six or more probes, a sliding window test consisting of five probes at a time was used, whereby the window was moved by one probe increments. Each test sample was compared to the control sample and the p-values were recorded. Genomic regions were selected as being differentially methylated if eight out of ten samples showed a p value <0.01, or if six out of ten samples showed a p value <0.001. The genomic regions were classified as being not differentially methylated when the group showed less than eight samples with a p value <0.01 and less than six samples with a p value <0.001. Samples that didn't fall in either category were excluded from the analysis. For a subset of genomic regions that have been identified as differentially methylated, the results were confirmed using quantitative methylation analysis.

The Go analysis was performed using the online GOstat tool (http://gostat.wehi.edu.au/cgibin/-goStat.pl). P values were calculated using Fisher's exact test.

Microarray-Based Marker Discovery Results

To identify differentially methylated regions a standard sample was used, in which the methylated DNA fraction of monocytes was hybridized against itself. This standard provided a reference for the variability of fluorescent measurements in a genomic region. Differentially methylated regions were then identified by comparing the log ratios of each of the ten placental/maternal samples against this standard. Because the goal of this study was to identify markers that allow the reliable separation of maternal and fetal DNA, the target selection was limited to genes that showed a stable, consistent methylation difference over a contiguous stretch of genomic DNA. This focused the analysis on genomic regions where multiple probes indicated differential methylation. The selection was also limited to target regions where all samples showed differential methylation, excluding those with strong inter-individual differences. Two of the samples showed generally lower log ratios in the microarray analysis. Because a paired test was used for target selection, this did not negatively impact the results.

Based on these selection criteria, 3043 genomic regions were identified that were differentially methylated between maternal and fetal DNA. 21778 regions did not show a methylation difference. No inter-chromosomal bias in the distribution of differentially methylated regions was observed. The differentially methylated regions were located next to or within 2159 known genes. The majority of differentially methylated regions are located in the promoter area (18%) and inside the coding region (68%), while only few regions are located downstream of the gene (7%) or at the transition from promoter to coding region (7%). Regions that showed no differential methylation showed a similar distribution for promoter (13%) and downstream (5%) locations, but the fraction of regions located in the transition of promoter to coding region was higher (39%) and the fraction inside the coding region was lower (43%).

It has been shown in embryonic stem cells (ES) that genes targeted by the polycomb repressive complex2 (PRC2) are enriched for genes regulating development (Lee T I, et al. (2006) Control of developmental regulators by Polycomb in human embryonic stem cells. Cell 125:301-313). It has also been shown that differentially methylated genes are enriched for genes targeted by PRC2 in many cancer types (Ehrich M, et al. (2008) Cytosine methylation profiling of cancer cell lines. Proc Natl Acad Sci USA 105:4844-48). The set of genes identified as differentially methylated in this study is also enriched for genes targeted by PRC2 (p-value <0.001, odds ratio=3.6, 95% Cl for odds ratio=3.1-4.2). A GO analysis of the set of differentially methylated genes reveals that this set is significantly enriched for functions important during development. Six out of the ten most enriched functions include developmental or morphogenic processes [anatomical structure morphogenesis (GO:0009653, p value=0), developmental process (GO:0032502, p value=0), multicellular organismal development (GO:0007275, p value=0), developmental of an organ (GO:0048513, p value=0), system development (GO:0048731, p value=0) and development of an anatomical structure (GO:0048856, p value=0)].

Validation Using Sequenom® EpiTYPER™

To validate the microarray findings, 63 regions from chromosomes 13, 18 and 21 and an additional 26 regions from other autosomes were selected for confirmation by a different technology. Sequenom EpiTYPER™ technology was used to quantitatively measure DNA methylation in maternal and placental samples. For an explanation of the EpiTYPER™ methods, see Ehrich M, Nelson M R, Stanssens P, Zabeau M, Liloglou T, Xinarianos G, Cantor C R, Field J K, van den Boom D (2005) Quantitative high-throughput analysis of DNA methylation patterns by base specific cleavage and mass spectrometry. Proc Natl Acad Sci USA 102:15785-15790). For each individual CpG site in a target region the average methylation value across all maternal DNA samples and across all placenta samples was calculated. The difference between average maternal and placenta methylation was then compared to the microarray results. The results from the two technologies were in good concordance (see FIG. 144). For 85 target regions the quantitative results confirm the microarray results (95% confirmation rate). For 4 target regions, all located on chromosome 18, the results could not be confirmed. The reason for this discrepancy is currently unclear.

In contrast to microarrays, which focus on identification of methylation differences, the quantitative measurement of DNA methylation allowed analysis of absolute methylation values. In the validation set of 85 confirmed differentially methylated regions, a subset of 26 regions is more methylated in the maternal DNA sample and 59 regions are more methylated in the placental sample (see Table 3A). Interestingly, genes that are hypomethylated in the placental samples tend to show larger methylation differences than genes that are hypermethylated in the placental sample (median methylation difference for hypomethylated genes=39%, for hypermethylated genes=20%).

Example 12

Example 12 describes a non-invasive approach for detecting the amount of fetal nucleic acid present in a maternal sample (herein referred to as the "Fetal Quantifier Method"), which may be used to detect or confirm fetal traits (e.g., fetal sex of RhD compatibility), or diagnose chromosomal abnormalities such as Trisomy 21 (both of which are herein referred to as the "Methylation-Based Fetal Diagnostic Method"). FIG. 147 shows one embodiment of the Fetal Quantifier Method, and FIG. 148 shows one embodiment of the Methylation-Based Fetal Diagnostic Method. Both processes use fetal DNA obtained from a maternal sample. The sample comprises maternal and fetal nucleic acid that is differentially methylated. For example, the sample may be maternal plasma or serum. Fetal DNA comprises approximately 2-30% of the total DNA in maternal plasma. The actual amount of fetal contribution to the total nucleic acid present in a sample varies from pregnancy to pregnancy and can change based on a number of factors, including, but not limited to, gestational age, the mother's health and the fetus' health.

As described herein, the technical challenge posed by analysis of fetal DNA in maternal plasma lies in the need to be able to discriminate the fetal DNA from the co-existing background maternal DNA. The methods of the present technology exploit such differences, for example, the differential methylation that is observed between fetal and maternal DNA, as a means to enrich for the relatively small percentage of fetal DNA present in a sample from the mother. The non-invasive nature of the approach provides a major advantage over conventional methods of prenatal diagnosis such as, amniocentesis, chronic villus sampling and cordocentesis, which are associated with a small but finite risk of fetal loss. Also, because the method is not dependent on fetal cells being in any particular cell phase, the method provides a rapid detection means to determine the presence and also the nature of the chromosomal abnormality. Further, the approach is sex-independent (i.e., does not require the presence of a Y-chromosome) and polymorphic-independent (i.e., an allelic ratio is not determined). Thus, the compositions and methods of the technology herein represent improved universal, noninvasive approaches for accurately determining the amount of fetal nucleic acid present in a maternal sample.

Assay Design and Advantages

There is a need for accurate detection and quantification of fetal DNA isolated noninvasively from a maternal sample. The present technology takes advantage of the presence of circulating, cell free fetal nucleic acid (ccfDNA) in maternal plasma or serum. In order to be commercially and clinically practical, the methods of the technology herein should only consume a small portion of the limited available fetal DNA. For example, less than 50%, 40%, 30%, 25%, 20%, 15%, 10%, 5% or less of the sample. Further, the approach should preferably be developed in a multiplex assay format in which one or more (preferably all) of the following assays are included:

- Assays for the detection of total amount of genomic equivalents present in the sample, i.e., assays recognizing both maternal and fetal DNA species;
- Assays for the detection of fetal DNA isolated from a male pregnancy, i.e., sequences specific for chromosome Y;
- Assays specific for regions identified as differentially methylated between the fetus and mother; or
- Assays specific for regions known to be hypomethylated in all tissues to be investigated, which can serve as a control for restriction efficiency.

Other features of the assay may include one or more of the following:

- For each assay, a target-specific, competitor oligonucleotide that is identical, or substantially identical, to the target sequence apart from a distinguishable feature of the competitor, such as a difference in one or more nucleotides relative to the target sequence. This oligonucleotide when added into the PCR reaction will be co-amplified with the target and a ratio obtained between these two PCR amplicons will indicate the number of target specific DNA sequences (e.g., fetal DNA from a specific locus) present in the maternal sample.
- The amplicon lengths should preferably be of similar length in order not to skew the amplification towards the shorter fragments. However, as long as the amplification efficiency is about equal, different lengths may be used.
- Differentially methylated targets can be selected from Tables 3A-3C or from any other targets known to be differentially methylated between mother and fetus. These targets can be hypomethylated in DNA isolated from non-pregnant women and hypermethylated in samples obtained from fetal samples. These assays will serve as controls for the restriction efficiency.
- The results obtained from the different assays can be used to quantify one or more of the following:
  - Total number of amplifiable genomes present in the sample (total amount of genomic equivalents);
  - The fetal fraction of the amplifiable genomes (fetal concentration or percentage); or
  - Differences in copy number between fetally-derived DNA sequences (for example, between fetal chromosome 21 and a reference chromosome such as chromosome 3).

Examples of Assays Used in the Test

Below is an outline of the reaction steps used to perform a method of the technology herein, for example, as provided in FIG. 147. This outline is not intended to limit the scope of the technology herein. Rather it provides one embodiment of the technology herein using the Sequenom® MassARRAY® technology.

1) DNA isolation from plasma samples.
2) Digestion of the DNA targets using methylation sensitive restriction enzymes (for example, HhaI and HpaII).

For each reaction the available DNA was mixed with water to a final volume of 25 ul. 10 ul of a reaction mix consisting of 10 units HhaI, 10 units HpaII and a reaction buffer were added. The sample was incubated at an optimal temperature for the restriction enzymes. HhaI and HpaII digest non-methylated DNA (and will not digest hemi- or completely methylated DNA). Following digestion, the enzymes were denatured using a heating step.

3) Genomic Amplification—PCR was performed in a total volume of 50 ul by adding PCR reagents (Buffer, dNTPs, primers and polymerase). Exemplary PCR and extend primers are provided below. In addition, synthetic competitor oligonucleotide was added at known concentrations.

4) Replicates (optional)—Following PCR the 50 ul reaction was split into 5 ul parallel reactions (replicates) in order to minimize variation introduced during the post PCR steps of the test. Post PCR steps include SAP, primer extension (MassEXTEND® technology), resin treatment, dispensing of spectrochip and MassARRAY.

5) Quantification of the Amplifiable Genomes—Sequenom MassARRAY® technology was used to determine the amount of amplification product for each assay. Following PCR, a single base extension assay was used to interrogate the amplified regions (including the competitor oligonucleotides introduced in step 3). Specific extend primers designed to hybridize directly adjacent to the site of interest were introduced. See extend primers provided below. These DNA oligonucleotides are referred to as iPLEX® MassEXTEND® primers. In the extension reaction, the iPLEX primers were hybridized to the complementary DNA templates and extended with a DNA polymerase. Special termination mixtures that contain different combinations of deoxy- and dideoxynucleotide triphosphates along with enzyme and buffer, directed limited extension of the iPLEX primers. Primer extension occurs until a complementary dideoxynucleotide is incorporated.

The extension reaction generated primer products of varying length, each with a unique molecular weight. As a result, the primer extension products can be simultaneously separated and detected using Matrix Assisted Laser Desorption/Ionization, Time-Of-Flight (MALDI-TOF) mass spectrometry on the MassARRAY® Analyzer Compact. Following this separation and detection, SEQUENOM's proprietary software automatically analyzes the data.

6) Calculating the amount and concentration of fetal nucleic acid—Methods for calculating the total amount of genomic equivalents present in the sample, the amount (and concentration) of fetal nucleic acid isolated from a male pregnancy, and the amount (and concentration) of fetal nucleic based on differentially methylated targets are provided below and in FIGS. 155 and 156.

The above protocol can be used to perform one or more of the assays described below. In addition to the sequences provided immediately below, a multiplex scheme that interrogates multiple targets is provided in Table X below.

1) Assay for the Quantification of the Total Number of Amplifiable Genomic Equivalents in the Sample.

Targets were selected in housekeeping genes not located on the chromosomes 13, 18, 21, X or Y. The targets should be in a single copy gene and not contain any recognition sites for the methylation sensitive restriction enzymes.

Underlined sequences are PCR primer sites, italic is the site for the single base extend primer and bold letter (C) is the nucleotide extended on human DNA ApoE Chromosome 19:45409835-45409922 DNA target sequence with interrogated nucleotide C in bold. All of the chromosome positions provided in this section are from the February 2009 UCSC Genome Build.

```
GATTGACAGTTTCTCCTTCCCCAGACTGGCCAATCACAGGCAGGAA
GATGAAGGTTCTGTGGGCTGCGTTGCTGGTCACATTCCTGGC (SEQ ID NO: 262)

ApoE Forward Primer:
5'-ACGTTGGATG-TTGACAGTTTCTCCTTCCCC (SEQ ID NO: 263)
(Primer contains a 5'
10 bp MassTag separated by a dash)

ApoE Reverse Primer:
5'-ACGTTGGATG-GAATGTGACCAGCAACGCAG (SEQ ID NO: 264)
(Primer contains a
5' 10 bp MassTag separated by a dash)

ApoE Extension Primer:
5'-GCAGGAAGATGAAGGTT [C/T] (SEQ ID NO: 265)
Primer extends C on human DNA
targets and T on synthetic DNA targets

ApoE synthetic competitor oligonucleotide:
5'-GATTGACAGTTTCTCCTTCCCCAGACTGGCC
AATCACAGGCAGGAAGATGAAGGTTTTGT
GGGCTGCGTTGCTGGTCACATTCCTGGC (SEQ ID NO: 266)
(Bold T at position 57 is different from human
DNA)
```

2) Assay for the Quantification of the Total Number of Chromosome Y Sequences in the Sample.

Targets specific for the Y-chromosome were selected, with no similar or paralog sequences elsewhere in the genome. The targets should preferably be in a single copy gene and not contain any recognition sites for the methylation sensitive restriction enzyme(s).

Underlined sequences are PCR primer sites, and italic nucleotide(s) is the site for the single-base extend primer and bold letter (C) is the nucleotide extended on human DNA.

```
SRY on chrY: 2655628-2655717 (reverse complement)
GAGTTTTGGATAGTAAAATAAGTTTCGAACTCTGGCAC
CTTTCAATTTTGTCGCACTCTCCT
TGTTTTTGACAATGCAATCATATGCTTC (SEQ ID NO: 267)

SRY Forward Primer:
5'-ACG-TGGATAGTAAAATAAGTTTCGAACTCTG (SEQ ID NO: 268)
(Primer contains a 5' 3 bp MassTag
separated by a dash)

SRY Reverse Primer:
5'-GAAGCATATGATTGCATTGTCAAAAAC (SEQ ID NO: 269)

SRY Extension Primer:
5'-aTTTCAATTTTGTCGCACT [C/T] (SEQ ID NO: 270)
Primer extends C on human DNA targets
and T on synthetic DNA targets.
5' Lower case "a" is a non-complementary
nucleotide

SRY synthetic competitor oligonucleotide:
5'-GAGTTTTGGATAGTAAAATAAGTTTCGAACTCTGGCA
CCTTTCAATTTTGTCGCACTTTCCT
TGTTTTTGACAATGCAATCATATGCTTC (SEQ ID NO: 271)
```

3) Assay for the Quantification of Fetal Methylated DNA Sequences Present in the Sample.

Targets were selected in regions known to be differentially methylated between maternal and fetal DNA. Sequences were selected to contain several restriction sites for methylation sensitive enzymes. For this study the HhaI (GCGC) and HpaII (CCGG) enzymes were used.

Underlined sequences are PCR primer sites, italic is the site for the single base extend primer and bold letter (C) is the nucleotide extended on human DNA, lower case letter are recognition sites for the methylation sensitive restriction enzymes.

```
TBX3 on chr12: 115124905-115125001
GAACTCCTCTTTGTCTCTGCGTGCccggcgcgcC
CCCCTCccggTGGGTGATAAACCCACTCTG
gcgccggCCATgcgcTGGGTGATTAATTTGCGA (SEQ ID NO: 272)

TBX3 Forward Primer:
5'-ACGTTGGATG-TCTTTGTCTCTGCGTGCCC (SEQ ID NO: 273)
(Primer contains a 5'
10 bp MassTag separated by a dash)

TBX3 Reverse Primer:
5'-ACGTTGGATG-TTAATCACCCAGCGCATGGC (SEQ ID NO: 274)
(Primer contains a
5' 10 bp MassTag separated by a dash)

TBX3 Extension Primer:
5'-CCCCTCCCGGTGGGTGATAAA [C/T] (SEQ ID NO: 275)
Primer extends C on human DNA targets and T on
synthetic DNA targets. 5' Lower case "a" is a
non-complementary nucleotide

TBX3 synthetic competitor oligonucleotide:
5'-GAACTCCTCTTTGTCTCTGCGTGCCCGGC
GCGCCCCCCTCCCGGTGGGTGATAAATCCA
CTCTGGCGCCGGCCATGCGCTGGGTGATTAATTTGCGA (SEQ ID NO: 276)
```

4) Control Assay for the Enzyme Restriction Efficiency.

Targets were selected in regions known not to be methylated in any tissue to be investigated. Sequences were selected to contain no more than one site for each restriction enzyme to be used.

Underlined sequences are PCR primer sites, italic nucleotide(s) represent the site for the single-base extend primer and bold letter (G) is the reverse nucleotide extended on human DNA, lower case letter are recognition sites for the methylation sensitive restriction enzymes.

CACNA1G chr17: 48637892-48637977 (reverse complement)
CCATTGGCCGTCCGCCGTGGCAGTGCGGGCGGGAgcgcAGGGAGAGAAC
CACAGCTGGAATCCGATTCCCACCCCAAAACCCAGGA (SEQ ID NO: 277)

HhaI Forward Primer:
5'-ACGTTGGATG-CCATTGGCCGTCCGCCGTG (SEQ ID NO: 278)
(Primer contains a 5'
10 bp MassTag separated by a dash)

HhaI Reverse Primer:
5'-ACGTTGGATG-TCCTGGGTTTTGGGGTGGGAA (SEQ ID NO: 279)
(Primer contains a
5' 10 bp MassTag separated by a dash)

HhaI Extension Primer:
5'-TTCCAGCTGTGGTTCTCTC (SEQ ID NO: 280)

HhaI synthetic competitor oligonucleotide:
5'-CCATTGGCCGTCCGCCGTGGCAGTGCGGGCG
GGAGCGCAGAGAGAGAACCACAGCTGG
AATCCGATTCCCACCCCAAAACCCAGGA (SEQ ID NO: 281)

Validation Experiments

The sensitivity and accuracy of the present technology was measured using both a model system and clinical samples. In the different samples, a multiplex assay was run that contains 2 assays for total copy number quantification, 3 assays for methylation quantification, 1 assay specific for chromosome Y and 1 digestion control assay. See Table X. Another multiplex scheme with additional assays is provided in Table Y.

TABLE X

| Gene ID | * | PCR Primers and Extend Primers<br>First Primer (SEQ ID NOS 282 -288, respectively, in order of apperance) | Second Primer (SEQ ID NOS 289 -295, respectively, in order of apperance) | Extend Primer (SEQ ID NOS 296-302, respectively, in order of apperance) |
|---|---|---|---|---|
| SOX14 | M | ACGTTGGATGACATGGTCGGCCCCACGGAAT | ACGTTGGATGCTCCTTCCTAGTGTGAGAACCG | CAGGTTCCGGGGCTTGGG |
| HhaI_CTRL | D | ACGTTGGATGACCCATTGGCCGTCCGCCGT | ACGTTGGATGTTTTGGGGTGGGAATCGGATT | CGCAGGGAGAGAACCACAG |
| TBX3 | M | ACGTTGGATGGAACTCCTCTTTGTCTCTGCG | ACGTTGGATGTGGCATGGCCGGCGCCAGA | CCCCTCCCGGTGGGTGATAAA |
| SRY | Y | ACGTTGGATGCGCAGCAACGGGACCGCTACA | ACGTTGGCATCTAGGTAGGTCTTTGTAGCCAA | AAAGCTGTAGGACAATCGGGT |
| ALB | T | ACGTTGCGTAGCAACCTGTTACATATTAA | ACGTTGGATCTGAGCAAAGGCAATCAACACCC | CATTTTTCTACATCCTTTGTTT |
| EDG6 | M | ACGTTGGATGCATAGAGGCCCATGATGGTGG | ACGTTGGATGACCTTCTGCCCCTCTACTCCAA | agAAGATCACCAGGCAGA AGAGG |
| RNaseP | T | ACGTTGGATGGTGTGGTCAGCTCTTCCCTTCAT | ACGTTGGCCCACATGTAATGTGTTGAAAAAGCA | ACTTGGAGAACAAAGGAC ACCGTTA |

Competitor Oligonucleotide Sequence

| Gene ID | * | Competitor Oligonucleotide Sequence (SEQ ID NOS 303-309, respectively, in order of apperance) |
|---|---|---|
| SOX14 | M | GGTCGGCCCCACGGAATCCCGGCTCTGTGTGCGCCCAGGTTCCGGGGCTTGGGTGTTGCCGGTTCTCACACTAGGAAGGAG |
| HhaI_CTRL | D | CCATTGGCCGTCCGCCGTGGCAGTGCGGGCGGGAGCGCAGAGAGAGAACCACAGCTGGAATCCGATTCCCACCCCAAAA |
| TBX3 | M | GAACTCCTCTTTGTCTCTGCGTGCCCGGCGCGCCCCCCTCCCGGTGGGTGATAAATCCACTCTGGCGCCGGCCATGC |
| SRY | Y | GCAGCAACGGGACCGCTACAGCCACTGGACAAAGCCGTAGGACAATCGGGTAACATTGGCTACAAAGACCTACCTAGATGC |
| ALB | T | GCGTAGCAACCTGTTACATATTAAAGTTTTATTATACTACATTTTTCTACATCCTTTGTTTCAGAGTGTTGATTGCCTTTGCTCAGTATCT TCAG |
| EDG6 | M | CCTTCTGCCCCTCTACTCCAAGCGCTACACCCTCTTCTGCCTGGTGATCTTTGCCGGCGTCCTGGCCACCATCATGGGCCTCTATG |
| RNaseP | T | GTGTGGTCAGCTCTTCCCTTCATCACATACTTGGAGAACAAAGGACACCGTTATCCATGCTTTTTCAACACATTACATGTGGG |

TABLE Y

| Gene ID | * | PCR Primers and Extend Primers<br>First Primer (SEQ ID NOS 310-311, 263, 312, 268, 313, 273 and 314-316, respectively, in order of appearance) | Second Primer (SEQ ID NOS 317-318, 264, 289, 269, 319, 274 and 320-322, respectively, in order of appearance) | Extend Primer (SEQ ID NOS 323-331 and 300, respectively, in order of appearance) |
|---|---|---|---|---|
| EDG6 | M | ACGTTGGATGTTCTGCCCCTCTACTCCAAG | ACGTTGGATGCATAGAGGCCCATGATGGTG | TTCTGCCTGGTGATCTT |
| RNAseP | T | ACGTTGGATGTCAGCTCTTCCCTTCATCAC | ACGTTGGATGCCTACCTCCCACATGTAATGT | AACAAAGGACACCGTTA |
| ApoE | T | ACGTTGGATGTTGACAGTTTCTCCTTCCCC | ACGTTGGATGGAATGTGACCAGCAACGCAG | GCAGGAAGATGAAGGTT |
| SOX14 | M | ACGTTGGATGCGGTCGGCCCCACGGAAT | ACGTTGGATGCTCCTTCCTAGTGTGAGAACCG | aAGGTTCCGGGGCTTGGG |
| SRY no2 | Y | ACGTGGATAGTAAAATAAGTTTCGAACTCTG | GAAGCATATGATTGCATTGTCAAAAAC | aTTTCAATTTTGTCGCACT |
| SRY no1 | Y | ACGTTGGATGCACAGCTCACCGCAGCAACG | ACGTTGGATGCTAGGTAGGTCTTTGTAGCCAA | AGCTGTAGGACAATCGGGT |
| TBX3 | M | ACGTTGGATGTCTTTGTCTCTGCGTGCCC | ACGTTGGATGTTAATCACCCAGCGCATGGC | CCCTCCCGGTGGGTGATAAA |
| CACNA1G dig CTRL 1 | D | ACGTTGGATGGACTGAGCCCCAGAACTCG | ACGTTGGATGGTGGGTTTGTGCTTTCCACG | AGGGCCGGGGTCTGCGCGTG |
| DAPK1 dig CTRL 2 | D | ACGTTGGATGAAGCCAAGTTTCCCTCCGC | ACGTTGGATGCTTTTGCTTTCCCAGCCAGG | GAGGCACTGCCCGGACAAACC |
| ALB | T | ACGTTAGCGTAGCAACCTGTTACATATTAA | ACGTTGGATGCTGAGCAAAGGCAATCAACA | CATTTTTCTACATCCTTTGTTT |

| Gene ID | * | Competitor Oligonucleotide Sequence<br>Competitor (SEQ ID NOS 308, 332, 266, 333, 271, 334, 276 and, respectively, in order of appearance |
|---|---|---|
| EDG6 | M | CCTTCTGCCCCTCTACTCCAAGCGCTACACCCTCTTCTGCCTGGTGATCTTTGCCGGCGTCCTGGCCACCATCATGGGCCTCTATG |
| RNAseP | T | GTGTGGTCAGCTCTTCCCTTCATCACATACTTGGAGAACAAAGGACACCGTTATCCATGCTTTTTCAACACATTACATGTGGGAGGTAGG |
| ApoE | T | GATTGACAGTTTCTCCTTCCCCAGACTGGCCAATCACAGGCAGGAAGATGAAGGTTTTGTGGGCTGCGTTGCTGGTCACATTCCTGGC |
| SOX14 | M | AAAACCAGAGATTCGCGGTCGGCCCCACGGAATCCCGGCTCTGTGTGCGCCCAGGTTCCGGGGCTTGGGTGTTGCCGGTTCTCACACTA GGAAGGAGC |
| SRY no2 | Y | GAGTTTTGGATAGTAAAATAAGTTTCGAACTCTGGCACCTTTCAATTTTGTCGCACTTTCCTTGTTTTTGACAATGCAATCATATGCTTC |
| SRY no1 | Y | GCAGCCAGCTCACCGCAGCAACGGGACCGCTACAGCCACTGGACAAAGCTGTAGGACAATCGGGTGACATTGGCTACAAAGACCTACCTA GATGC |
| TBX3 | M | GAACTCCTCTTTGTCTCTGCGTGCCCGGCGCGCCCCCCTCCCGGTGGGTGATAAATCCACTCTGGCGCCGGCCATGCGCTGGGTGATT AATTTGCGA |
| CACNA1G dig CTRL 1 | D | GTGGGTTTGTGCTTTCCACGCGTGCACACACACGCGCAGACCCCGGCCCTTGCCCCGCCTACCTCCCCGAGTTCTGGGGCTCAGTC |
| DAPK1 dig CTRL 2 | D | GCGCCAGCTTTTGCTTTCCCAGCCAGGGCGCGGTGAGGTTTGTCCGGGCAGTGCCTCGAGCAACTGGGAAGGCCAAGGCGGAGGG AAAC |
| ALB | T | GCGTAGCAACCTGTTACATATTAAAGTTTTATTATACTACATTTTTCTACATCCTTTGTTTTAGGGTGTTGATTGCCTTTGCTCAGTAT CTTCAGC |

T = Assay for Total Amount
M = Assay for Methylation quantification
Y = Y-Chromosome Specific Assay
D = Digestion control Model System Using Genomic DNA In order to determine the sensitivity and accuracy of the method when determining the total number of amplifiable genomic copies in a sample, a subset of different DNA samples isolated from the blood of non-pregnant women was tested. Each sample was diluted to contain approximately 2500, 1250, 625 or 313 copies per reaction. The total number of amplifiable genomic copies was obtained by taking the mean DNA/competitor ratio obtained from the three total copy number assays. The results from the four different samples are shown in FIG. 149.

To optimize the reaction, a model system was developed to simulate DNA samples isolated from plasma. These samples contained a constant number of maternal non-methylated DNA and were spiked with different amounts of male placental methylated DNA. The samples were spiked with amounts ranging from approximately 0 to 25% relative to the maternal non-methylated DNA. The results are shown in FIGS. 150A and 150B. The fraction of placental DNA was calculated using the ratios obtained from the methylation assays (FIG. 150A), the SRY markers (FIG. 150B) and the total copy number assays. The primer sequences for the methylation assays (TBX), Y-chromosome assays (SRY) and total copy number (APOE) are provided above. The model system demonstrated that the methylation-based method performed equal to the Y-chromosome method (SRY markers), thus validating the methylation-based method as a sex-independent fetal quantifier.

Plasma Samples

To investigate the sensitivity and accuracy of the methods in clinical samples, 33 plasma samples obtained from women pregnant with a male fetus were investigated using the multiplex scheme from Table X. For each reaction, a quarter of the DNA obtained from a 4 ml extraction was used in order to meet the important requirement that only a portion of the total sample is used.

Total Copy Number Quantification

The results from the total copy number quantification can be seen in FIGS. 151A and 151B. In FIG. 151A, the copy number for each sample is shown. Two samples (nos. 25 and 26) have a significantly higher total copy number than all the other samples. In general, a mean of approximately 1300 amplifiable copies/ml plasma was obtained (range 766-2055). FIG. 151B shows a box-and-whisker plot of the given values, summarizing the results.

Correlation Between Results Obtained from the Methylation Markers and the Y-Chromosome Marker In FIGS. 152A and 152B, the numbers of fetal copies for each sample are plotted. As all samples were from male pregnancies. The copy numbers obtained can be calculated using either the methylation or the Y-chromosome-specific markers. As can be seen in FIG. 152B, the box-and-whisker plot of the given values indicated minimal difference between the two different measurements.

The results showing the correlation between results obtained from the methylation markers and the Y-chromosome marker (SRY) is shown in FIG. 153. Again, the methylation-based method performed equal to the Y-chromosome method (SRY markers), further validating the methylation-based method as a sex-independent and polymorphism-independent fetal quantifier. The multiplexed assays disclosed in Table X were used to determine the amount fetal nucleic.

Finally, the digestion efficiency was determined by using the ratio of digestion for the control versus the competitor and comparing this value to the mean total copy number assays. See FIG. 154. Apart from sample 26 all reactions indicate the efficiency to be above 99%.

Data Analysis

Mass spectra analysis was done using Typer 4 (a Sequenom software product). The peak height (signal over noise) for each individual DNA analyte and competitor assay was determined and exported for further analysis.

The total number of molecules present for each amplicon was calculated by dividing the DNA specific peak by the competitor specific peak to give a ratio. (The "DNA" Peak in FIGS. 155 and 156 can be thought of as the analyte peak for a given assay). Since the number of competitor molecules added into the reaction is known, the total number of DNA molecules can be determined by multiplying the ratio by the number of added competitor molecules.

The fetal DNA fraction (or concentration) in each sample was calculated using the Y-chromosome-specific markers for male pregnancies and the mean of the methylated fraction for all pregnancies. In brief, for chromosome Y, the ratio was obtained by dividing the analyte (DNA) peak by the competitor peak and multiplying this ratio by the number of competitor molecules added into the reaction. This value was divided by a similar ratio obtained from the total number of amplifiable genome equivalents determination (using the Assay(s) for Total Amount). See FIG. 155. Since the total amount of nucleic acid present in a sample is a sum of maternal and fetal nucleic acid, the fetal contribution can be considered to be a fraction of the larger, background maternal contribution. Therefore, translating this into the equation shown in FIG. 155, the fetal fraction (k) of the total nucleic acid present in the sample is equal to the equation: $k=2\times R/(1-2R)$, where R is the ratio between the Y-chromosome amount and the total amount. Since the Y-chromosome is haploid and Assays for the Total Amount are determined using diploid targets, this calculation is limited to a fetal fraction smaller than 50% of the maternal fraction.

In FIG. 156, a similar calculation for the fetal concentration is shown by using the methylation specific markers (see Assays for Methylation Quantification). In contrast to Y-chromosome specific markers, these markers are from diploid targets, therefore, the limitations stated for the Y-Chromosome Specific Assay can be omitted. Thus, the fetal fraction (k) can be determined using the equation: $k=R(1-R)$, where R is the ratio between the methylation assay and the total assay.

Simulation

A first simple power calculation was performed that assumes a measurement system that uses 20 markers from chromosome 21, and 20 markers from one or more other autosomes. Starting with 100 copies of fetal DNA, a measurement standard deviation of 25 copies and the probability for a type I error to be lower than 0.001, it was found that the methods of the technology herein will be able to differentiate a diploid from a triploid chromosome set in 99.5% of all cases. The practical implementation of such an approach could for example be achieved using mass spectrometry, a system that uses a competitive PCR approach for absolute copy number measurements. The method can run 20 assays in a single reaction and has been shown to have a standard deviation in repeated measurements of around 3 to 5%. This method was used in combination with known methods for differentiating methylated and non-methylated nucleic acid, for example, using methyl-binding agents to separate nucleic acid or using methylation-sensitive enzymes to digest maternal nucleic acid. FIG. 145 shows the effectiveness of MBD-FC protein (a methyl-binding agent) for capturing and thereby separating methylated DNA in the presence of an excess of unmethylated DNA (see FIG. 145).

A second statistical power analysis was performed to assess the predictive power of an embodiment of the Methylation-Based Fetal Diagnostic Method described herein. The simulation was designed to demonstrate the likelihood of differentiating a group of trisomic chromosome 21 specific markers from a group of reference markers (for example, autosomes excluding chromosome 21). Many parameters influence the ability to discriminate the two populations of markers reliably. For the present simulation, values were chosen for each parameter that have been shown to be the most likely to occur based on experimentation. The following parameters and respective values were used:

Copy Numbers

- Maternal copy numbers=2000
- Fetal copy numbers for chromosomes other than 21, X and Y=200
- Fetal copy numbers for chromosome 21 in case of euploid fetus=200
- Fetal copy numbers for chromosome 21 in case of aneuploid T21 fetus=300

Percent fetal DNA (before methylation-based enrichment) =10% (see above)

Methylation Frequency

- Average methylation percentage in a target region for maternal DNA=10%
- Average methylation percentage in a target region for fetal DNA=80%

Average percentage of non-methylated and non-digested maternal DNA (i.e., a function of restriction efficiency (among other things)=5%

Number of assays targeting chromosome 21=10

Number of assays targeting chromosomes other than 21, X and Y=10

The results are displayed in FIG. 157. Shown is the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less. Based on this simulation, the method represents a powerful noninvasive diagnostic method for the prenatal detection of fetal aneuploidy that is sex-independent and will work in all ethnicities (i.e., no allelic bias).

Example 13: Additional Differentially-Methylated Targets

Differentially-Methylated Targets not Located on Chromosome 21

Additional differentially-methylated targets were selected for further analysis based upon previous microarray analysis. See Example 11 for a description of the microarray analysis. During the microarray screen, differentially methylated regions (DMRs) were defined between placenta tissue and PBMC. Regions were selected for EpiTYPER confirmation based upon being hypermethylated in placenta relative to PBMC. After directionality of the change was selected for, regions were chosen based upon statistical significance with regions designed beginning with the most significant and working downward in terms of significance. These studies were performed in eight paired samples of PBMC and placenta. Additional non-chromosome 21 targets are provided in Table 3B, along with a representative genomic sequence from each target in Table 6B.

Differentially-Methylated Targets Located on Chromosome 21

The microarray screen uncovered only a subset of DMRs located on chromosome 21. The coverage of chromosome 21 by the microarray, however, was insufficient. Therefore a further analysis was completed to examine all 356 CpG islands on chromosome 21 using the standard settings of the UCSC genome browser. As shown in Table 3C below, some of these targets overlapped with those already examined in Table 5A. More specifically, CpG sites located on chromosome 21 including ~1000 bp upstream and downstream of each CpG was investigated using Sequenom's EpiTYPER® technology. See Example 11, "Validation using Sequenom® EpiTYPER™" for a description of Sequenom's EpiTYPER® technology. These studies were performed in eight paired samples of PBMC and placenta. In addition, since DMRs may also be located outside of defined CpG islands, data mining was performed on publicly available microarray data to identify potential candidate regions with the following characteristics: hypermethylated in placenta relative to maternal blood, not located in a defined CpG island, contained greater than 4 CpG dinucleotides, and contained a recognition sequence for methylation sensitive restriction enzymes. Regions that met these criteria were then examined using Sequenom's EpiTYPER® technology on eight paired PBMC and placenta samples. Additional chromosome 21 targets are provided in Table 3C, along with a representative genomic sequence from each target in Table 6C.

Tables 3B and 3C provide a description of the different targets, including their location and whether they were analyzed during the different phases of analysis, namely microarray analysis, EpiTYPER 8 analysis and EpiTYPER 73 analysis. A "YES" indicates it was analyzed and a "NO" indicates it was not analyzed. The definition of each column in Table 3B and 3C is listed below.

Region Name: Each region is named by the gene(s) residing within the area defined or nearby. Regions where no gene name is listed but rather only contain a locus have no refseq genes in near proximity.

Gene Region: For those regions contained either in close proximity to or within a gene, the gene region further explains the relationship of this region to the nearby gene.

Chrom: The chromosome on which the DMR is located using the hg18 build of the UCSC genome browser.

Start: The starting position of the DMR as designated by the hg18 build of the UCSC genome browser.

End: The ending position of the DMR as designated by the hg18 build of the UCSC genome browser.

Microarray Analysis: Describes whether this region was also/initially determined to be differentially methylated by microarray analysis. The methylated fraction of ten paired placenta and PBMC samples was isolated using the MBD-Fc protein. The two tissue fractions were then labeled with either Alexa Fluor 555-aha-dCTP (PBMC) or Alexa Fluor 647-aha-dCTP (placental) using the BioPrime Total Genomic Labeling System™ and hybridized to Agilent® CpG Island microarrays. Many regions examined in these studies were not contained on the initial microarray.

EpiTYPER 8 Samples: Describes whether this region was analyzed and determined to be differentially methylated in eight paired samples of placenta and peripheral blood mononuclear cells (PBMC) using EpiTYPER technology. Regions that were chosen for examination were based on multiple criteria. First, regions were selected based on data from the Microarray Analysis. Secondly, a comprehensive examination of all CpG islands located on chromosome 21 was undertaken. Finally, selected regions on chromosome 21 which had lower CpG frequency than those located in CpG islands were examined.

EpiTYPER 73 Samples: Describes whether this region was subsequently analyzed using EpiTYPER technology in a sample cohort consisting of 73 paired samples of placenta and PBMC. All regions selected for analysis in this second sample cohort were selected based on the results from the experimentation described in the EpiTYPER 8 column. More specifically, the regions in this additional cohort exhibited a methylation profile similar to that determined in the EpiTYPER 8 Samples analysis. For example, all of the regions listed in Tables 3B-3C exhibit different levels of DNA methylation in a significant portion of the examined CpG dinucleotides within the defined region. Differential DNA methylation of CpG sites was determined using a paired T Test with those sites considered differentially methylated if the p-value (when comparing placental tissue to PBMC) is $p<0.05$.

Previously Validated EpiTYPER: Describes whether this region or a portion of this region was validated using EpiTYPER during previous experimentation. (See Examples 1 and 2).

Relative Methylation Placenta to Maternal: Describes the direction of differential methylation. Regions labeled as “hypermethylation” are more methylated within the designated region in placenta samples relative to PBMC and “hypomethylation” are more methylated within the designated region in PBMC samples.

TABLE 3A

| GENE NAME | CHROM | START | END | CpG ISLAND | MEAN LOG RATIO MICRO-ARRAY | MEAN MATERNAL METHYLATION EPITYPER | MEAN PLACENTA METHYLATION EPITYPER | METHYLATION DIFFERENCE PLACENTA-MATERNAL | RELATIVE METHYLATION PLACENTA TO MATERNAL |
|---|---|---|---|---|---|---|---|---|---|
| chr13 group00016 | chr13 | 19773745 | 19774050 | chr13: 19773518-19774214 | 0.19 | 0.22 | 0.32 | 0.1 | HYPERMETHYLATION |
| chr13 group00005 | chr13 | 19290394 | 19290768 | :- | −0.89 | 0.94 | 0.35 | −0.59 | HYPOMETHYLATION |
| CRYL1 | chr13 | 19887090 | 19887836 | chr13: 19887007-19887336 | −0.63 | 0.74 | 0.21 | −0.53 | HYPOMETHYLATION |
| IL17D | chr13 | 20193675 | 20193897 | chr13: 20193611-20194438 | −1.01 | 0.53 | 0.13 | −0.39 | HYPOMETHYLATION |
| CENPJ | chr13 | 24404023 | 24404359 | :- | 0.57 | 0.17 | 0.49 | 0.32 | HYPERMETHYLATION |
| ATP8A2 | chr13 | 25484475 | 25484614 | chr13: 25484287-25484761 | 0.81 | 0.16 | 0.43 | 0.27 | HYPERMETHYLATION |
| GSH1 | chr13 | 27265542 | 27265834 | chr13: 27264549-27266505 | 0.57 | 0.13 | 0.19 | 0.05 | HYPERMETHYLATION |
| PDX1 | chr13 | 27393789 | 27393979 | chr13: 27392001-27394099 | 0.55 | 0.06 | 0.2 | 0.14 | HYPERMETHYLATION |
| PDX1 | chr13 | 27400459 | 27401165 | chr13: 27400362-27400744; chr13: 27401057-27401374 | 0.73 | 0.12 | 0.26 | 0.14 | HYPERMETHYLATION |
| MAB21L1 | chr13 | 34947737 | 34948062 | chr13: 34947570-34948159 | 0.66 | 0.11 | 0.17 | 0.06 | HYPERMETHYLATION |
| RB1 | chr13 | 47790983 | 47791646 | chr13: 47790636-47791858 | 0.18 | 0.45 | 0.48 | 0.03 | HYPERMETHYLATION |
| PCDH17 | chr13 | 57104856 | 57106841 | chr13: 57104527-57106931 | 0.46 | 0.15 | 0.21 | 0.06 | HYPERMETHYLATION |
| KLHL1 | chr13 | 69579933 | 69580146 | chr13: 69579733-69580220 | 0.79 | 0.09 | 0.28 | 0.2 | HYPERMETHYLATION |
| POU4F1 | chr13 | 78079515 | 78081073 | chr13: 78079328-78079615; chr13: 78080860-78081881 | 0.66 | 0.12 | 0.23 | 0.11 | HYPERMETHYLATION |
| GPC6 | chr13 | 92677402 | 92678666 | chr13: 92677246-92678878 | 0.66 | 0.06 | 0.19 | 0.13 | HYPERMETHYLATION |
| SOX21 | chr13 | 94152286 | 94153047 | chr13: 94152190-94153185 | 0.94 | 0.16 | 0.4 | 0.25 | HYPERMETHYLATION |
| ZIC2 | chr13 | 99439660 | 99440858 | chr13: 99439335-99440189; chr13: 99440775-99441095 | 0.89 | 0.13 | 0.35 | 0.22 | HYPERMETHYLATION |
| IRS2 | chr13 | 109232856 | 109235065 | chr13: 109232467-109238181 | −0.17 | 0.73 | 0.38 | −0.35 | HYPOMETHYLATION |
| chr13 group00350 | chr13 | 109716455 | 109716604 | chr13: 109716325-109716726 | −0.37 | 0.77 | 0.41 | −0.36 | HYPOMETHYLATION |
| chr13 group00385 | chr13 | 111595578 | 111595955 | chr13: 111595459-111596131 | 0.87 | 0.06 | 0.2 | 0.14 | HYPERMETHYLATION |
| chr13 group00390 | chr13 | 111756337 | 111756593 | chr13: 111755805-111756697 | 0.71 | 0.12 | 0.34 | 0.22 | HYPERMETHYLATION |
| chr13 group00391 | chr13 | 111759856 | 111760045 | chr13: 111757885-111760666 | 0.86 | 0.11 | 0.36 | 0.25 | HYPERMETHYLATION |
| chr13 group00395 | chr13 | 111808255 | 111808962 | chr13: 111806599-111808492; chr13: 111808866-111809114 | 0.96 | 0.13 | 0.35 | 0.22 | HYPERMETHYLATION |
| chr13 group00399 | chr13 | 112033503 | 112033685 | chr13: 112032967-112033734 | 0.38 | 0.26 | 0.43 | 0.18 | HYPERMETHYLATION |
| MCF2L | chr13 | 112724910 | 112725742 | chr13: 112724782-112725121; chr13: 112725628-112725837 | −0.47 | 0.91 | 0.33 | −0.58 | HYPOMETHYLATION |
| F7 | chr13 | 112799123 | 112799379 | chr13: 112798487-112799566 | −0.05 | 0.97 | 0.55 | −0.41 | HYPOMETHYLATION |
| PROZ | chr13 | 112855566 | 112855745 | chr13: 112855289-112855866 | 0.29 | 0.15 | 0.3 | 0.16 | HYPERMETHYLATION |
| chr18 group00039 | chr18 | 6919797 | 6919981 | chr18: 6919450-6920088 | −0.38 | 0.88 | 0.39 | −0.49 | HYPOMETHYLATION |
| CIDEA | chr18 | 12244327 | 12244696 | chr18: 12244147-12245089 | 0.23 | 0.14 | 0.23 | 0.1 | HYPERMETHYLATION |
| chr18 group00091 | chr18 | 12901467 | 12901643 | chr18: 12901024-12902704 | 0.16 | 0.15 | 0.43 | 0.29 | HYPERMETHYLATION |
| chr18 group00094 | chr18 | 13126819 | 13126986 | chr18: 13126596-13127564 | 0.41 | 0.07 | 0.34 | 0.27 | HYPERMETHYLATION |
| C18orf1 | chr18 | 13377536 | 13377654 | chr18: 13377385-13377686 | −0.12 | 0.95 | 0.69 | −0.26 | HYPOMETHYLATION |
| KLHL14 | chr18 | 28603978 | 28605183 | chr18: 28603688-28606300 | 0.83 | 0.07 | 0.19 | 0.12 | HYPERMETHYLATION |
| CD33L3 | chr18 | 41671477 | 41673011 | chr18: 41671386-41673101 | −0.34 | 0.49 | 0.44 | −0.05 | HYPOMETHYLATION |
| ST8SIA3 | chr18 | 53171265 | 53171309 | chr18: 53170705-53172603 | 1.02 | 0.09 | 0.25 | 0.16 | HYPERMETHYLATION |
| ONECUT2 | chr18 | 53254808 | 53259810 | chr18: 53254152-53259851 | 0.74 | 0.09 | 0.23 | 0.14 | HYPERMETHYLATION |
| RAX | chr18 | 55086286 | 55086436 | chr18: 55085813-55087807 | 0.88 | 0.11 | 0.26 | 0.16 | HYPERMETHYLATION |
| chr18 group00277 | chr18 | 57151972 | 57152311 | chr18: 57151663-57152672 | 0.58 | 0.08 | 0.21 | 0.13 | HYPERMETHYLATION |
| TNFRSF11A | chr18 | 58203013 | 58203282 | chr18: 58202849-58203367 | −0.33 | 0.88 | 0.28 | −0.6 | HYPOMETHYLATION |
| NETO1 | chr18 | 68685099 | 68687060 | chr18: 68684945-68687851 | 0.65 | 0.09 | 0.22 | 0.13 | HYPERMETHYLATION |
| chr18 group00304 | chr18 | 70133945 | 70134397 | chr18: 70133732-70134724 | 0.12 | 0.93 | 0.92 | −0.01 | NOT CONFIRMED |

TABLE 3A-continued

| GENE NAME | CHROM | START | END | CpG ISLAND | MEAN LOG RATIO MICRO-ARRAY | MEAN MATERNAL METHYLATION EPITYPER | MEAN PLACENTA METHYLATION EPITYPER | METHYLATION DIFFERENCE PLACENTA-MATERNAL | RELATIVE METHYLATION PLACENTA TO MATERNAL |
|---|---|---|---|---|---|---|---|---|---|
| TSHZ1 | chr18 | 71128742 | 71128974 | chr18: 71128638-71129076 | 0.23 | 0.95 | 0.92 | −0.03 | NOT CONFIRMED |
| ZNF236 | chr18 | 72664454 | 72664736 | chr18: 72662797-72664893 | −0.62 | 0.17 | 0.1 | −0.07 | HYPOMETHYLATION |
| MBP | chr18 | 72953150 | 72953464 | chr18: 72953137-72953402 | 0.6 | 0.44 | 0.72 | 0.28 | HYPERMETHYLATION |
| chr18 group00342 | chr18 | 74170347 | 74170489 | chr18: 74170210-74170687 | −0.2 | 0.78 | 0.48 | −0.3 | HYPOMETHYLATION |
| NFATC1 | chr18 | 75385424 | 75386008 | chr18: 75385279-75386532 | 0.23 | 0.14 | 0.84 | 0.7 | HYPERMETHYLATION |
| CTDP1 | chr18 | 75596358 | 75596579 | chr18: 75596009-75596899 | 0.07 | 0.97 | 0.96 | −0.01 | NOT CONFIRMED |
| chr18 group00430 | chr18 | 75653272 | 75653621 | :— | 0.52 | 0.24 | 0.62 | 0.39 | HYPERMETHYLATION |
| KCNG2 | chr18 | 75760343 | 75760820 | chr18: 75759900-75760988 | 0.01 | 0.84 | 0.75 | −0.09 | NOT CONFIRMED |
| OLIG2 | chr21 | 33317673 | 33321183 | chr21: 33316998-33322115 | 0.66 | 0.11 | 0.2 | 0.09 | HYPERMETHYLATION |
| OLIG2 | chr21 | 33327593 | 33328334 | chr21: 33327447-33328408 | −0.75 | 0.77 | 0.28 | −0.49 | HYPOMETHYLATION |
| RUNX1 | chr21 | 35180938 | 35185436 | chr21: 35180822-35181342; chr21: 35182320-35185557 | −0.68 | 0.14 | 0.07 | −0.07 | HYPOMETHYLATION |
| SIM2 | chr21 | 36994965 | 36995298 | chr21: 36990063-36995761 | 0.83 | 0.08 | 0.26 | 0.18 | HYPERMETHYLATION |
| SIM2 | chr21 | 36999025 | 36999410 | chr21: 36998632-36999555 | 0.87 | 0.06 | 0.24 | 0.18 | HYPERMETHYLATION |
| DSCR6 | chr21 | 37300407 | 37300512 | chr21: 37299807-37301307 | 0.22 | 0.04 | 0.14 | 0.11 | HYPERMETHYLATION |
| DSCAM | chr21 | 41135559 | 41135706 | chr21: 41135380-41135816 | 1.03 | 0.06 | 0.29 | 0.23 | HYPERMETHYLATION |
| chr21 group00165 | chr21 | 43643421 | 43643786 | chr21: 43643322-43643874 | 1.14 | 0.16 | 0.81 | 0.65 | HYPERMETHYLATION |
| AIRE | chr21 | 44529935 | 44530388 | chr21: 44529856-44530472 | −0.55 | 0.62 | 0.27 | −0.35 | HYPOMETHYLATION |
| SUMO3 | chr21 | 45061293 | 45061853 | chr21: 45061154-45063386 | −0.41 | 0.55 | 0.46 | −0.09 | HYPOMETHYLATION |
| C21orf70 | chr21 | 45202815 | 45202972 | chr21: 45202706-45203073 | −0.46 | 0.96 | 0.51 | −0.46 | HYPOMETHYLATION |
| C21orf123 | chr21 | 45671984 | 45672098 | chr21: 45671933-45672201 | −0.63 | 0.92 | 0.43 | −0.49 | HYPOMETHYLATION |
| COL18A1 | chr21 | 45754383 | 45754487 | chr21: 45753653-45754639 | −0.18 | 0.97 | 0.72 | −0.25 | HYPOMETHYLATION |
| PRMT2 | chr21 | 46911967 | 46912385 | chr21: 46911628-46912534 | 1.08 | 0.04 | 0.25 | 0.21 | HYPERMETHYLATION |
| SIX2 | chr2 | 45081223 | 45082129 | chr2: 45081148-45082287 | 1.15 | 0.08 | 0.36 | 0.28 | HYPERMETHYLATION |
| SIX2 | chr2 | 45084851 | 45085711 | chr2: 45084715-45084986; chr2: 45085285-45086054 | 1.21 | 0.07 | 0.35 | 0.28 | HYPERMETHYLATION |
| SOX14 | chr3 | 138971870 | 138972322 | chr3: 138971738-138972096; chr3: 138972281-138973691 | 1.35 | 0.08 | 0.33 | 0.25 | HYPERMETHYLATION |
| TLX3 | chr5 | 170674439 | 170676431 | chr5: 170674208-170675356; chr5: 170675783-170676712 | 0.91 | 0.11 | 0.35 | 0.24 | HYPERMETHYLATION |
| FOXP4 | chr6 | 41623666 | 41624114 | chr6: 41621630-41624167 | 1.1 | 0.07 | 0.27 | 0.2 | HYPERMETHYLATION |
| FOXP4 | chr6 | 41636384 | 41636779 | chr6: 41636244-41636878 | 1.32 | 0.04 | 0.33 | 0.29 | HYPERMETHYLATION |
| chr7 group00267 | chr7 | 12576755 | 12577246 | chr7: 12576690-12577359 | 0.94 | 0.08 | 0.26 | 0.17 | HYPERMETHYLATION |
| NPY | chr7 | 24290224 | 24291508 | chr7: 24290083-24291605 | 0.93 | 0.09 | 0.3 | 0.21 | HYPERMETHYLATION |
| SHH | chr7 | 155291537 | 155292091 | chr7: 155288453-155292175 | 0.98 | 0.19 | 0.52 | 0.33 | HYPERMETHYLATION |
| OSR2 | chr8 | 100029764 | 100030536 | chr8: 100029673-100030614 | 1.21 | 0.08 | 0.43 | 0.35 | HYPERMETHYLATION |
| GLIS3 | chr9 | 4288283 | 4289645 | chr9: 4287817-4290182 | 1.24 | 0.06 | 0.24 | 0.18 | HYPERMETHYLATION |
| PRMT8 | chr12 | 3472714 | 3473190 | chr12: 3470227-3473269 | 0.86 | 0.07 | 0.23 | 0.16 | HYPERMETHYLATION |
| TBX3 | chr12 | 113609153 | 113609453 | chr12: 113609112-113609535 | 1.45 | 0.09 | 0.56 | 0.48 | HYPERMETHYLATION |
| chr12 group00801 | chr12 | 118516189 | 118517435 | chr12: 118515877-118517595 | 1.1 | 0.06 | 0.25 | 0.19 | HYPERMETHYLATION |
| PAX9 | chr14 | 36201402 | 36202386 | chr14: 36200932-36202536 | 0.89 | 0.11 | 0.32 | 0.21 | HYPERMETHYLATION |
| SIX1 | chr14 | 60178801 | 60179346 | chr14: 60178707-60179539 | 0.95 | 0.1 | 0.33 | 0.22 | HYPERMETHYLATION |
| ISL2 | chr15 | 74420013 | 74421546 | chr15: 74419317-74422570 | 1.08 | 0.08 | 0.27 | 0.19 | HYPERMETHYLATION |
| DLX4 | chr17 | 45397228 | 45397930 | chr17: 45396281-45398063 | 1.25 | 0.1 | 0.32 | 0.22 | HYPERMETHYLATION |
| CBX4 | chr17 | 75428613 | 75431793 | chr17: 75427586-75433676 | 1 | 0.07 | 0.27 | 0.21 | HYPERMETHYLATION |
| EDG6 | chr19 | 3129836 | 3130874 | chr19: 3129741-3130986 | 1.35 | 0.04 | 0.87 | 0.83 | HYPERMETHYLATION |
| PRRT3 | chr3 | 9963364 | 9964023 | chr3: 9962895-9964619 | −0.85 | 0.9 | 0.09 | −0.81 | HYPOMETHYLATION |
| MGC29506 | chr5 | 138757911 | 138758724 | chr5: 138755609-138758810 | −0.63 | 0.93 | 0.17 | −0.76 | HYPOMETHYLATION |

TABLE 3A-continued

| GENE NAME | CHROM | START | END | CpG ISLAND | MEAN LOG RATIO MICRO-ARRAY | MEAN MATERNAL METHYLATION EPITYPER | MEAN PLACENTA METHYLATION EPITYPER | METHYLATION DIFFERENCE PLACENTA-MATERNAL | RELATIVE METHYLATION PLACENTA TO MATERNAL |
|---|---|---|---|---|---|---|---|---|---|
| TEAD3 | chr6 | 35561812 | 35562252 | chr6: 35561754-35562413 | −1.17 | 0.92 | 0.13 | −0.8 | HYPOMETHYLATION |
| chr12 group00022 | chr12 | 1642456 | 1642708 | chr12: 1642195-1642774 | −1.33 | 0.66 | 0.09 | −0.57 | HYPOMETHYLATION |
| CENTG1 | chr12 | 56406249 | 56407788 | chr12: 56406176-56407818 | −1.07 | 0.95 | 0.19 | −0.77 | HYPOMETHYLATION |
| CENTG1 | chr12 | 56416146 | 56418794 | chr12: 56416095-56416628; chr12: 56418745-56419001 | −0.94 | 0.85 | 0.16 | −0.69 | HYPOMETHYLATION |

Information in Table 5A based on the March 2006 human reference sequence (NCBI Build 36.1), which was produced by the International Human Genome Sequencing Consortium.

TABLE 3B

Non-Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| TFAP2E | Intron | chr1 | 35815000 | 35816200 | YES | YES | NO | NO | Hypermethylation |
| LRRC8D | Intron/Exon | chr1 | 90081350 | 90082250 | YES | YES | NO | NO | Hypermethylation |
| TBX15 | Promoter | chr1 | 119333500 | 119333700 | YES | YES | NO | NO | Hypermethylation |
| C1orf51 | Upstream | chr1 | 148520900 | 148521300 | YES | YES | NO | NO | Hypermethylation |
| chr1: 179553900-179554600 | Intergenic | chr1 | 179553900 | 179554600 | YES | YES | NO | NO | Hypermethylation |
| ZFP36L2 | Exon | chr2 | 43304900 | 43305100 | YES | YES | NO | NO | Hypermethylation |
| SIX2 | Downstream | chr2 | 45081000 | 45086000 | YES | YES | NO | YES | Hypermethylation |
| chr2: 137238500-137240000 | Intergenic | chr2 | 137238500 | 137240000 | YES | YES | NO | NO | Hypermethylation |
| MAP1D | Intron/Exon | chr2 | 172652800 | 172653600 | YES | YES | NO | NO | Hypermethylation |
| WNT6 | Intron | chr2 | 219444250 | 219444290 | YES | YES | NO | NO | Hypermethylation |
| INPP5D | Promoter | chr2 | 233633200 | 233633700 | YES | YES | YES | NO | Hypermethylation |
| chr2: 241211100-241211600 | Intergenic | chr2 | 241211100 | 241211600 | YES | YES | YES | NO | Hypermethylation |
| WNT5A | Intron | chr3 | 55492550 | 55492850 | YES | YES | NO | NO | Hypermethylation |
| chr3: 138971600-138972200 | Intergenic | chr3 | 138971600 | 138972200 | YES | YES | YES | YES | Hypermethylation |
| ZIC4 | Intron | chr3 | 148598200 | 148599000 | YES | YES | NO | NO | Hypermethylation |
| FGF12 | Intron/Exon | chr3 | 193608500 | 193610500 | YES | YES | NO | NO | Hypermethylation |
| GP5 | Exon | chr3 | 195598400 | 195599200 | YES | YES | NO | NO | Hypermethylation |
| MSX1 | Upstream | chr4 | 4910550 | 4911100 | YES | YES | NO | NO | Hypermethylation |
| NKX3-2 | Intron/Exon | chr4 | 13152500 | 13154500 | YES | YES | NO | NO | Hypermethylation |
| chr4: 111752000-111753000 | Intergenic | chr4 | 111752000 | 111753000 | YES | YES | YES | NO | Hypermethylation |
| SFRP2 | Promoter | chr4 | 154928800 | 154930100 | YES | YES | NO | NO | Hypermethylation |
| chr4: 174664300-174664800 | Intergenic | chr4 | 174664300 | 174664800 | YES | YES | NO | NO | Hypermethylation |
| chr4: 174676300-174676800 | Intergenic | chr4 | 174676300 | 174676800 | YES | YES | NO | NO | Hypermethylation |
| SORBS2 | Intron | chr4 | 186796900 | 186797500 | YES | YES | NO | NO | Hypermethylation |
| chr5: 42986900-42988200 | Intergenic | chr5 | 42986900 | 42988200 | YES | YES | NO | NO | Hypermethylation |
| chr5: 72712000-72714100 | Intergenic | chr5 | 72712000 | 72714100 | YES | YES | NO | NO | Hypermethylation |
| chr5: 72767550-72767800 | Intergenic | chr5 | 72767550 | 72767800 | YES | YES | NO | NO | Hypermethylation |
| NR2F1 | Intron/Exon | chr5 | 92955000 | 92955250 | YES | YES | NO | NO | Hypermethylation |
| PCDHGA1 | Intron | chr5 | 140850500 | 140852500 | YES | YES | YES | NO | Hypermethylation |
| chr6: 10489100-10490200 | Intergenic | chr6 | 10489100 | 10490200 | YES | YES | YES | NO | Hypermethylation |
| FOXP4 | Intron | chr6 | 41636200 | 41637000 | YES | YES | NO | YES | Hypermethylation |
| chr7: 19118400-19118700 | Intergenic | chr7 | 19118400 | 19118700 | YES | YES | NO | NO | Hypermethylation |
| chr7: 27258000-27258400 | Intergenic | chr7 | 27258000 | 27258400 | YES | YES | NO | NO | Hypermethylation |
| TBX20 | Upstream | chr7 | 35267500 | 35268300 | YES | YES | NO | NO | Hypermethylation |
| AGBL3 | Promoter | chr7 | 134321300 | 134322300 | YES | YES | NO | NO | Hypermethylation |
| XPO7 | Downstream | chr8 | 21924000 | 21924300 | YES | YES | NO | NO | Hypermethylation |
| chr8: 41543400-41544000 | Intergenic | chr8 | 41543400 | 41544000 | YES | YES | NO | NO | Hypermethylation |
| GDF6 | Exon | chr8 | 97225400 | 97227100 | YES | YES | NO | NO | Hypermethylation |
| OSR2 | Intron/Exon | chr8 | 100029000 | 100031000 | YES | YES | YES | YES | Hypermethylation |
| GLIS3 | Intron/Exon | chr9 | 4288000 | 4290000 | YES | YES | NO | YES | Hypermethylation |
| NOTCH1 | Intron | chr9 | 138547600 | 138548400 | YES | YES | YES | NO | Hypermethylation |
| EGFL7 | Upstream | chr9 | 138672350 | 138672850 | YES | YES | NO | NO | Hypermethylation |
| CELF2 | Intron/Exon | chr10 | 11246700 | 11247900 | YES | YES | NO | NO | Hypermethylation |
| HHEX | Intron | chr10 | 94441000 | 94441800 | YES | YES | NO | NO | Hypermethylation |
| DOCK1/FAM196A | Intron/Exon | chr10 | 128883000 | 128883500 | YES | YES | NO | NO | Hypermethylation |
| PAX6 | Intron | chr11 | 31782400 | 31783500 | YES | YES | NO | NO | Hypermethylation |
| FERMT3 | Intron/Exon | chr11 | 63731200 | 63731700 | YES | YES | YES | NO | Hypermethylation |
| PKNOX2 | Intron | chr11 | 124541200 | 124541800 | YES | YES | NO | NO | Hypermethylation |
| KIRREL3 | Intron | chr11 | 126375150 | 126375300 | YES | YES | NO | NO | Hypermethylation |
| BCAT1 | Intron | chr12 | 24946700 | 24947600 | YES | YES | NO | NO | Hypermethylation |
| HOXC13 | Intron/Exon | chr12 | 52625000 | 52625600 | YES | YES | NO | NO | Hypermethylation |
| TBX5 | Promoter | chr12 | 113330500 | 113332000 | YES | YES | NO | NO | Hypermethylation |
| TBX3 | Upstream | chr12 | 113609000 | 113609500 | YES | YES | NO | YES | Hypermethylation |

TABLE 3B-continued

Non-Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| chr12: 113622100-113623000 | Intergenic | chr12 | 113622100 | 113623000 | YES | YES | YES | NO | Hypermethylation |
| chr12: 113657800-113658300 | Intergenic | chr12 | 113657800 | 113658300 | YES | YES | NO | NO | Hypermethylation |
| THEM233 | Promoter | chr12 | 118515500 | 118517500 | YES | YES | NO | YES | Hypermethylation |
| NCOR2 | Intron/Exon | chr12 | 123516200 | 123516800 | YES | YES | YES | NO | Hypermethylation |
| THEM132C | Intron | chr12 | 127416300 | 127416700 | YES | YES | NO | NO | Hypermethylation |
| PTGDR | Promoter | chr14 | 51804000 | 51805200 | YES | YES | NO | NO | Hypermethylation |
| ISL2 | Intron/Exon | chr15 | 74420000 | 74422000 | YES | YES | NO | YES | Hypermethylation |
| chr15: 87750000-87751000 | Intergenic | chr15 | 87750000 | 87751000 | YES | YES | NO | NO | Hypermethylation |
| chr15: 87753000-87754100 | Intergenic | chr15 | 87753000 | 87754100 | YES | YES | NO | NO | Hypermethylation |
| NR2F2 | Upstream | chr15 | 94666000 | 94667500 | YES | YES | YES | NO | Hypermethylation |
| chr16: 11234300-11234900 | Intergenic | chr16 | 11234300 | 11234900 | YES | YES | NO | NO | Hypermethylation |
| SPN | Exon | chr16 | 29582800 | 29583500 | YES | YES | YES | NO | Hypermethylation |
| chr16: 85469900-85470200 | Intergenic | chr16 | 85469900 | 85470200 | YES | YES | NO | NO | Hypermethylation |
| SLFN11 | Promoter | chr17 | 30725100 | 30725600 | YES | YES | NO | NO | Hypermethylation |
| DLX4 | Upstream | chr17 | 45396800 | 45397800 | YES | YES | NO | YES | Hypermethylation |
| SLC38A10 (MGC15523) | Intron | chr17 | 76873800 | 76874300 | YES | YES | YES | NO | Hypermethylation |
| S1PR4 | Exon | chr19 | 3129900 | 3131100 | YES | YES | YES | YES | Hypermethylation |
| MAP2K2 | Intron | chr19 | 4059700 | 4060300 | YES | YES | YES | NO | Hypermethylation |
| UHRF1 | Intron | chr19 | 4867300 | 4867800 | YES | YES | YES | NO | Hypermethylation |
| DEDD2 | Exon | chr19 | 47395300 | 47395900 | YES | YES | YES | NO | Hypermethylation |
| CDC42EP1 | Exon | chr22 | 36292300 | 36292800 | YES | YES | YES | NO | Hypermethylation |

TABLE 3C

Chromosome 21 differentially methylated regions

| Region Name | Gene Region | Chrom | Start | End | Micro-array Analysis | Epi TYPER 8 Samples | Epi TYPER 73 Samples | Previously Validated Epi TYPER | Relative Methylation Placenta to Maternal |
|---|---|---|---|---|---|---|---|---|---|
| chr21: 9906600-9906800 | Intergenic | chr21 | 9906600 | 9906800 | NO | YES | NO | NO | Hypomethylation |
| chr21: 9907000-9907400 | Intergenic | chr21 | 9907000 | 9907400 | NO | YES | NO | NO | Hypomethylation |
| chr21: 9917800-9918450 | Intergenic | chr21 | 9917800 | 9918450 | NO | YES | NO | NO | Hypomethylation |
| TPTE | Promoter | chr21 | 10010000 | 10015000 | NO | YES | NO | NO | Hypomethylation |
| chr21: 13974500-13976000 | Intergenic | chr21 | 13974500 | 13976000 | NO | YES | NO | NO | Hypomethylation |
| chr21: 13989500-13992000 | Intergenic | chr21 | 13989500 | 13992000 | NO | YES | NO | NO | Hypomethylation |
| chr21: 13998500-14000100 | Intergenic | chr21 | 13998500 | 14000100 | NO | YES | NO | NO | Hypomethylation |
| chr21: 14017000-14018500 | Intergenic | chr21 | 14017000 | 14018500 | NO | YES | NO | NO | Hypomethylation |
| chr21: 14056400-14058100 | Intergenic | chr21 | 14056400 | 14058100 | NO | YES | NO | NO | Hypomethylation |
| chr21: 14070250-14070550 | Intergenic | chr21 | 14070250 | 14070550 | NO | YES | NO | NO | Hypomethylation |
| chr21: 14119800-14120400 | Intergenic | chr21 | 14119800 | 14120400 | NO | YES | NO | NO | Hypomethylation |
| chr21: 14304800-14306100 | Intergenic | chr21 | 14304800 | 14306100 | NO | YES | NO | NO | Hypomethylation |
| chr21: 15649340-15649450 | Intergenic | chr21 | 15649340 | 15649450 | NO | YES | YES | NO | Hypermethylation |
| C21orf34 | Intron | chr21 | 16881500 | 16883000 | NO | YES | NO | NO | Hypomethylation |
| BTG3 | Intron | chr21 | 17905300 | 17905500 | NO | YES | NO | NO | Hypomethylation |
| CHODL | Promoter | chr21 | 18539000 | 18539800 | NO | YES | YES | NO | Hypermethylation |
| NCAM2 | Upstream | chr21 | 21291500 | 21292100 | NO | YES | NO | NO | Hypermethylation |
| chr21: 23574000-23574600 | Intergenic | chr21 | 23574000 | 23574600 | NO | YES | NO | NO | Hypomethylation |
| chr21: 24366920-24367060 | Intergenic | chr21 | 24366920 | 24367060 | NO | YES | NO | NO | Hypomethylation |
| chr21: 25656000-25656900 | Intergenic | chr21 | 25656000 | 25656900 | NO | YES | NO | NO | Hypomethylation |
| MIR155HG | Promoter | chr21 | 25855800 | 25857200 | NO | YES | YES | NO | Hypermethylation |
| CYYR1 | Intron | chr21 | 26830750 | 26830950 | NO | YES | NO | NO | Hypomethylation |
| chr21: 26938800-26939200 | Intergenic | chr21 | 26938800 | 26939200 | NO | YES | NO | NO | Hypomethylation |
| GRIK1 | Intron | chr21 | 30176500 | 30176750 | NO | YES | NO | NO | Hypomethylation |
| chr21: 30741350-30741600 | Intergenic | chr21 | 30741350 | 30741600 | NO | YES | NO | NO | Hypermethylation |
| TIAM1 | Intron | chr21 | 31426800 | 31427300 | NO | YES | YES | NO | Hypermethylation |
| TIAM1 | Intron | chr21 | 31475300 | 31475450 | NO | YES | NO | NO | Hypermethylation |
| TIAM1 | Intron | chr21 | 31621050 | 31621350 | NO | YES | YES | NO | Hypermethylation |
| SOD1 | Intron | chr21 | 31955000 | 31955300 | NO | YES | NO | NO | Hypomethylation |
| HUNK | Intron/Exon | chr21 | 32268700 | 32269100 | NO | YES | YES | NO | Hypermethylation |
| chr21: 33272200-33273300 | Intergenic | chr21 | 33272200 | 33273300 | NO | YES | NO | NO | Hypomethylation |

TABLE 3C-continued

| Chromosome 21 differentially methylated regions | | | | | | | | | |
|---|---|---|---|---|---|---|---|---|---|
| Region Name | Gene Region | Chrom | Start | End | Micro-array Analysis | Epi TYPER 8 Samples | Epi TYPER 73 Samples | Previously Validated Epi TYPER | Relative Methylation Placenta to Maternal |
| OLIG2 | Promoter | chr21 | 33314000 | 33324000 | YES | YES | NO | YES | Hypermethylation |
| OLIG2 | Downstream | chr21 | 33328000 | 33328500 | YES | YES | NO | NO | Hypomethylation |
| RUNX1 | Intron | chr21 | 35185000 | 35186000 | NO | YES | NO | NO | Hypomethylation |
| RUNX1 | Intron | chr21 | 35320300 | 35320400 | NO | YES | NO | NO | Hypermethylation |
| RUNX1 | Intron | chr21 | 35321200 | 35321600 | NO | YES | NO | NO | Hypermethylation |
| RUNX1 | Intron/Exon | chr21 | 35340000 | 35345000 | NO | YES | YES | NO | Hypermethylation |
| chr21: 35499200-35499700 | Intergenic | chr21 | 35499200 | 35499700 | NO | YES | YES | NO | Hypermethylation |
| chr21: 35822800-35823500 | Intergenic | chr21 | 35822800 | 35823500 | NO | YES | YES | NO | Hypermethylation |
| CBR1 | Promoter | chr21 | 36364000 | 36364500 | NO | YES | NO | NO | Hypermethylation |
| DOPEY2 | Downstream | chr21 | 36589000 | 36590500 | NO | YES | NO | NO | Hypomethylation |
| SIM2 | Promoter | chr21 | 36988000 | 37005000 | YES | YES | YES | YES | Hypermethylation |
| HLCS | Intron | chr21 | 37274000 | 37275500 | YES | YES | YES | NO | Hypermethylation |
| DSCR6 | Upstream | chr21 | 37300200 | 37300400 | YES | YES | NO | YES | Hypermethylation |
| DSCR3 | Intron | chr21 | 37551000 | 37553000 | YES | YES | YES | NO | Hypermethylation |
| chr21: 37841100-37841800 | Intergenic | chr21 | 37841100 | 37841800 | NO | YES | YES | NO | Hypermethylation |
| ERG | Intron | chr21 | 38791400 | 38792000 | NO | YES | YES | NO | Hypermethylation |
| chr21: 39278700-39279800 | Intergenic | chr21 | 39278700 | 39279800 | NO | YES | YES | NO | Hypermethylation |
| C21orf129 | Exon | chr21 | 42006000 | 42006250 | NO | YES | YES | NO | Hypermethylation |
| C2CD2 | Intron | chr21 | 42188900 | 42189500 | NO | YES | YES | NO | Hypermethylation |
| UMODL1 | Upstream | chr21 | 42355500 | 42357500 | NO | YES | YES | NO | Hypermethylation |
| UMODL1/C21orf128 | Intron | chr21 | 42399200 | 42399900 | NO | YES | NO | NO | Hypomethylation |
| ABCG1 | Intron | chr21 | 42528400 | 42528600 | YES | YES | NO | NO | Hypomethylation |
| chr21: 42598300-42599600 | Intergenic | chr21 | 42598300 | 42599600 | YES | YES | NO | NO | Hypomethylation |
| chr21: 42910000-42911000 | Intergenic | chr21 | 42910000 | 42911000 | NO | YES | NO | NO | Hypomethylation |
| PDE9A | Upstream | chr21 | 42945500 | 42946000 | NO | YES | NO | NO | Hypomethylation |
| PDE9A | Intron | chr21 | 42961400 | 42962700 | NO | YES | NO | NO | Hypomethylation |
| PDE9A | Intron | chr21 | 42977400 | 42977600 | NO | YES | NO | NO | Hypermethylation |
| PDE9A | Intron/Exon | chr21 | 42978200 | 42979800 | YES | YES | NO | NO | Hypomethylation |
| PDE9A | Intron | chr21 | 43039800 | 43040200 | NO | YES | YES | NO | Hypermethylation |
| chr21: 43130800-43131500 | Intergenic | chr21 | 43130800 | 43131500 | NO | YES | NO | NO | Hypomethylation |
| U2AF1 | Intron | chr21 | 43395500 | 43395800 | NO | YES | NO | NO | Hypermethylation |
| U2AF1 | Intron | chr21 | 43398000 | 43398450 | NO | YES | YES | NO | Hypermethylation |
| chr21: 43446600-43447600 | Intergenic | chr21 | 43446600 | 43447600 | NO | YES | NO | NO | Hypomethylation |
| CRYAA | Intron/Exon | chr21 | 43463000 | 43466100 | NO | YES | NO | NO | Hypomethylation |
| chr21: 43545000-43546000 | Intergenic | chr21 | 43545000 | 43546000 | YES | YES | NO | NO | Hypomethylation |
| chr21: 43606000-43606500 | Intergenic | chr21 | 43606000 | 43606500 | NO | YES | NO | NO | Hypomethylation |
| chr21: 43643000-43644300 | Intergenic | chr21 | 43643000 | 43644300 | YES | YES | YES | YES | Hypermethylation |
| C21orf125 | Upstream | chr21 | 43689100 | 43689300 | NO | YES | NO | NO | Hypermethylation |
| C21orf125 | Downstream | chr21 | 43700700 | 43701700 | NO | YES | NO | NO | Hypermethylation |
| HSF2BP | Intron/Exon | chr21 | 43902500 | 43903800 | YES | YES | NO | NO | Hypomethylation |
| AGPAT3 | Intron | chr21 | 44161100 | 44161400 | NO | YES | YES | NO | Hypermethylation |
| chr21: 44446500-44447500 | Intergenic | chr21 | 44446500 | 44447500 | NO | YES | NO | NO | Hypomethylation |
| TRPM2 | Intron | chr21 | 44614500 | 44615000 | NO | YES | NO | NO | Hypomethylation |
| C21orf29 | Intron | chr21 | 44750400 | 44751000 | NO | YES | NO | NO | Hypomethylation |
| C21orf29 | Intron | chr21 | 44950000 | 44955000 | NO | YES | YES | NO | Hypermethylation |
| ITGB2 | Intron/Exon | chr21 | 45145500 | 45146100 | NO | YES | NO | NO | Hypomethylation |
| POFUT2 | Downstream | chr21 | 45501000 | 45503000 | NO | YES | NO | NO | Hypomethylation |
| chr21: 45571500-45573700 | Intergenic | chr21 | 45571500 | 45573700 | NO | YES | NO | NO | Hypomethylation |
| chr21: 45609000-45610600 | Intergenic | chr21 | 45609000 | 45610600 | NO | YES | NO | NO | Hypomethylation |
| COL18A1 | Intron | chr21 | 45670000 | 45677000 | YES | YES | NO | YES | Hypomethylation |
| COL18A1 | Intron/Exon | chr21 | 45700500 | 45702000 | NO | YES | NO | NO | Hypomethylation |
| COL18A1 | Intron/Exon | chr21 | 45753000 | 45755000 | YES | YES | NO | YES | Hypomethylation |
| chr21: 45885000-45887000 | Intergenic | chr21 | 45885000 | 45887000 | NO | YES | NO | NO | Hypomethylation |
| PCBP3 | Intron | chr21 | 46111000 | 46114000 | NO | YES | NO | NO | Hypomethylation |
| PCBP3 | Intron/Exon | chr21 | 46142000 | 46144500 | NO | YES | NO | NO | Hypomethylation |
| COL6A1 | Intron/Exon | chr21 | 46227000 | 46233000 | NO | YES | NO | NO | Hypomethylation |
| COL6A1 | Intron/Exon | chr21 | 46245000 | 46252000 | NO | YES | NO | NO | Hypomethylation |
| chr21: 46280500-46283000 | Intergenic | chr21 | 46280500 | 46283000 | NO | YES | NO | NO | Hypomethylation |
| COL6A2 | Intron | chr21 | 46343500 | 46344200 | NO | YES | NO | NO | Hypomethylation |
| COL6A2 | Intron/Exon | chr21 | 46368000 | 46378000 | NO | YES | NO | NO | Hypomethylation |
| C21orf56 | Intron/Exon | chr21 | 46426700 | 46427500 | NO | YES | NO | NO | Hypomethylation |
| C21orf57 | Intron | chr21 | 46541568 | 46541861 | NO | YES | NO | NO | Hypermethylation |
| C21orf57 | Exon | chr21 | 46541872 | 46542346 | NO | YES | NO | NO | Hypermethylation |
| C21orf57 | Downstream | chr21 | 46542319 | 46542665 | NO | YES | NO | NO | Hypermethylation |
| C21orf58 | Intron | chr21 | 46546914 | 46547404 | NO | YES | NO | NO | Hypomethylation |
| PRMT2 | Downstream | chr21 | 46911000 | 46913000 | YES | YES | NO | YES | Hypermethylation |
| ITGB2 | Intron | chr21 | 45170700 | 45171100 | NO | YES | YES | NO | Hypermethylation |

TABLE 4

| GENE NAME | CHROM | START | END | SNPs |
|---|---|---|---|---|
| chr13 group00016 | chr13 | 19773745 | 19774050 | rs7996310; rs12870878 |
| chr13 group00005 | chr13 | 19290394 | 19290768 | rs11304938 |
| CENPJ | chr13 | 24404023 | 24404359 | rs7326661 |
| ATP8A2 | chr13 | 25484475 | 25484614 | rs61947088 |
| PDX1 | chr13 | 27400459 | 27401165 | rs58173592; rs55836809; rs61944011 |
| RB1 | chr13 | 47790983 | 47791646 | rs2804094; rs4151432; rs4151433; rs4151434; rs4151435 |
| PCDH17 | chr13 | 57104856 | 57106841 | rs35287822; rs34642962; rs41292834; rs45500496; rs45571031; rs41292836; rs28374395; rs41292838 |
| KLHL1 | chr13 | 69579933 | 69580146 | rs3751429 |
| POU4F1 | chr13 | 78079515 | 78081073 | rs11620410; rs35794447; rs2765065 |
| GPC6 | chr13 | 92677402 | 92678666 | rs35689696; rs11839555; rs55695812; rs35259892 |
| SOX21 | chr13 | 94152286 | 94153047 | rs41277652; rs41277654; rs35276096; rs5805873; rs35109406 |
| ZIC2 | chr13 | 99439660 | 99440858 | rs9585309; rs35501321; rs9585310; rs7991728; rs1368511 |
| IRS2 | chr13 | 109232856 | 109235065 | rs61747993; rs1805097; rs9583424; rs35927012; rs1056077; rs1056078; rs34889228; rs1056080; rs1056081; rs12853546; rs4773092; rs35223808; rs35894564; rs3742210; rs34412495; rs61962699; rs45545638; rs61743905 |
| chr13 group00395 | chr13 | 111808255 | 111808962 | rs930346 |
| MCF2L | chr13 | 112724910 | 112725742 | rs35661110; rs2993304; rs1320519; rs7320418; rs58416100 |
| F7 | chr13 | 112799123 | 112799379 | rs2480951; rs2476320 |
| CIDEA | chr18 | 12244327 | 12244696 | rs60132277 |
| chr18 group00091 | chr18 | 12901467 | 12901643 | rs34568924; rs8094284; rs8094285 |
| C18orf1 | chr18 | 13377536 | 13377654 | rs9957861 |
| KLHL14 | chr18 | 28603978 | 28605183 | rs61737323; rs61737324; rs12960414 |
| CD33L3 | chr18 | 41671477 | 41673011 | rs62095363; rs2919643 |
| ONECUT2 | chr18 | 53254808 | 53259810 | rs35685953; rs61735644; rs8084084; rs35937482; rs35427632; rs7232930; rs3786486; rs34286480; rs3786485; rs28655657; rs4940717; rs4940719; rs3786484; rs34040569; rs35542747; rs33946478; rs35848049; rs7231349; rs7231354; rs34481218; rs12962172; rs3911641 |
| RAX | chr18 | 55086286 | 55086436 | rs58797899; rs45501496 |
| chr18 group00277 | chr18 | 57151972 | 57152311 | rs17062547 |
| TNFRSF11A | chr18 | 58203013 | 58203282 | rs35114461 |
| NETO1 | chr18 | 68685099 | 68687060 | rs4433898; rs34497518; rs35135773; rs6566677; rs57425572; rs36026929; rs34666288; rs10627137; rs35943684; rs9964226; rs4892054; rs9964397; rs4606820; rs12966677; rs8095606 |
| chr18 group00304 | chr18 | 70133945 | 70134397 | rs8086706; rs8086587; rs8090367; rs999332; rs17806420; rs58811193 |
| TSHZ1 | chr18 | 71128742 | 71128974 | rs61732783; rs3744910; rs1802180 |
| chr18 group00342 | chr18 | 74170347 | 74170489 | rs7226678 |
| NFATC1 | chr18 | 75385424 | 75386008 | rs28446281; rs56384153; rs4531815; rs3894049 |
| chr18 group00430 | chr18 | 75653272 | 75653621 | rs34967079; rs35465647 |
| KCNG2 | chr18 | 75760343 | 75760820 | rs3744887; rs3744886 |
| OLIG2 | chr21 | 33317673 | 33321183 | rs2236618; rs11908971; rs9975039; rs6517135; rs2009130; rs1005573; rs1122807; rs10653491; rs10653077; rs35086972; rs28588289; rs7509766; rs62216114; rs35561747; rs7509885; rs11547332 |
| OLIG2 | chr21 | 33327593 | 33328334 | rs7276788; rs7275842; rs7275962; rs7276232; rs16990069; rs13051692; rs56231743; rs35931056 |
| RUNX1 | chr21 | 35180938 | 35185436 | rs2843956; rs55941652; rs56020428; rs56251824; rs13051109; rs13051111; rs3833348; rs7510136; rs743289; rs5843690; rs33915227; rs11402829; rs2843723; rs8128138; rs8131386; rs2843957; rs57537540; rs13048584; rs7281361; rs2843965; rs2843958 |
| SIM2 | chr21 | 36994965 | 36995298 | rs2252821 |
| SIM2 | chr21 | 36999025 | 36999410 | rs58347144; rs737380 |
| DSCAM | chr21 | 41135559 | 41135706 | rs35298822 |
| AIRE | chr21 | 44529935 | 44530388 | rs35110251; rs751032; rs9978641 |
| SUMO3 | chr21 | 45061293 | 45061853 | rs9979741; rs235337; rs7282882 |
| C21orf70 | chr21 | 45202815 | 45202972 | rs61103857; rs9979028; rs881318; rs881317 |
| COL18A1 | chr21 | 45754383 | 45754487 | rs35102708; rs9980939 |
| PRMT2 | chr21 | 46911967 | 46912385 | rs35481242; rs61743122; rs8131044; rs2839379 |
| SIX2 | chr2 | 45081223 | 45082129 | rs62130902 |
| SIX2 | chr2 | 45084851 | 45085711 | rs35417092; rs57340219 |
| SOX14 | chr3 | 138971870 | 138972322 | rs57343003 |
| TLX3 | chr5 | 170674439 | 170676431 | rs11134682; rs35704956; rs2964533; rs35601828 |
| FOXP4 | chr6 | 41623666 | 41624114 | rs12203107; rs1325690 |
| FOXP4 | chr6 | 41636384 | 41636779 | rs56835416 |
| chr7 group00267 | chr7 | 12576755 | 12577246 | rs56752985; rs17149965; rs6948573; rs2240572 |

TABLE 4-continued

| GENE NAME | CHROM | START | END | SNPs |
|---|---|---|---|---|
| NPY | chr7 | 24290224 | 24291508 | rs2390965; rs2390966; rs2390967; rs2390968; rs3025123; rs16146; rs16145; rs16144; rs13235842; rs13235935; rs13235938; rs13235940; rs13235944; rs36083509; rs3025122; rs16143; rs16478; rs16142; rs16141; rs16140; rs16139; rs2229966; rs1042552; rs5571; rs5572 |
| SHH | chr7 | 155291537 | 155292091 | rs9333622; rs1233554; rs9333620; rs1233555 |
| GLIS3 | chr9 | 4288283 | 4289645 | rs56728573; rs12340657; rs12350099; rs35338539; rs10974444; rs7852293 |
| PRMT8 | chr12 | 3472714 | 3473190 | rs12172776 |
| TBX3 | chr12 | 113609153 | 113609453 | rs60114979 |
| chr12 group00801 | chr12 | 118516189 | 118517435 | rs966246; rs17407022; rs970095; rs2711748 |
| PAX9 | chr14 | 36201402 | 36202386 | rs17104893; rs12883298; rs17104895; rs35510737; rs12882923; rs12883049; rs28933970; rs28933972; rs28933971; rs28933373; rs61734510 |
| SIX1 | chr14 | 60178801 | 60179346 | rs761555 |
| ISL2 | chr15 | 74420013 | 74421546 | rs34173230; rs11854453 |
| DLX4 | chr17 | 45397228 | 45397930 | rs62059964; rs57481357; rs56888011; rs17638215; rs59056690; rs34601685; rs17551082 |
| CBX4 | chr17 | 75428613 | 75431793 | rs1285243; rs35035500; rs12949177; rs3764374; rs62075212; rs62075213; rs3764373; rs3764372; rs55973291 |
| EDG6 | chr19 | 3129836 | 3130874 | rs34728133; rs34573539; rs3826936; rs34914134; rs61731111; rs34205484 |
| MGC29506 | chr5 | 138757911 | 138758724 | rs11748963; rs7447765; rs35262202 |
| CENTG1 | chr12 | 56406249 | 56407788 | rs61935742; rs12318065; rs238519; rs238520; rs238521; rs808930; rs2640595; rs2640596; rs2640597; rs2640598; rs34772922 |
| CENTG1 | chr12 | 56416146 | 56418794 | rs11830475; rs34482618; rs2650057; rs2518686; rs12829991 |

TABLE 5

| GENE NAME | RELATIVE METHYLATION PLACENTA TO MATERNAL | PRC2 TARGET |
|---|---|---|
| CRYL1 | HYPOMETHYLATION | TRUE |
| IL17D | HYPOMETHYLATION | TRUE |
| GSH1 | HYPERMETHYLATION | TRUE |
| MAB21L1 | HYPERMETHYLATION | TRUE |
| PCDH17 | HYPERMETHYLATION | TRUE |
| KLHL1 | HYPERMETHYLATION | TRUE |
| POU4F1 | HYPERMETHYLATION | TRUE |
| SOX21 | HYPERMETHYLATION | TRUE |
| ZIC2 | HYPERMETHYLATION | TRUE |
| CIDEA | HYPERMETHYLATION | TRUE |
| KLHL14 | HYPERMETHYLATION | TRUE |
| ONECUT2 | HYPERMETHYLATION | TRUE |
| RAX | HYPERMETHYLATION | TRUE |
| TNFRSF11A | HYPOMETHYLATION | TRUE |
| OLIG2 | HYPERMETHYLATION | TRUE |
| OLIG2 | HYPOMETHYLATION | TRUE |
| SIM2 | HYPERMETHYLATION | TRUE |

TABLE 5-continued

| GENE NAME | RELATIVE METHYLATION PLACENTA TO MATERNAL | PRC2 TARGET |
|---|---|---|
| SIM2 | HYPERMETHYLATION | TRUE |
| SIX2 | HYPERMETHYLATION | TRUE |
| SIX2 | HYPERMETHYLATION | TRUE |
| SOX14 | HYPERMETHYLATION | TRUE |
| TLX3 | HYPERMETHYLATION | TRUE |
| SHH | HYPERMETHYLATION | TRUE |
| OSR2 | HYPERMETHYLATION | TRUE |
| TBX3 | HYPERMETHYLATION | TRUE |
| PAX9 | HYPERMETHYLATION | TRUE |
| SIX1 | HYPERMETHYLATION | TRUE |
| ISL2 | HYPERMETHYLATION | TRUE |
| DLX4 | HYPERMETHYLATION | TRUE |
| CBX4 | HYPERMETHYLATION | TRUE |
| CENTG1 | HYPOMETHYLATION | TRUE |
| CENTG1 | HYPOMETHYLATION | TRUE |

TABLE 6A

| SEQ ID NO | GENE NAME | SEQUENCE |
|---|---|---|
| 1 | chr13 group-00016 | CAGCAGGCGCGCTCCCGGCGAATCTGCCTGAATCGCCGTGAATGCGGTGGGGTGCAGGGCAGGGGCTGGTTTTCTCAGCCGGTCTTGG<br>CTTTTCTCTTTCTCTCCTGCTCCACCAGCAGCCCCTCCGCGGGTCCCATGGGCTCCGCGCTCAGAACAGCCCGGAACCAGGCGCCGCTC<br>GCCGCTCGCTGGGGGCCACCCGCCTCTCCCCGGAACAGCCTCCCGCGGGCCTCTTGGCCTCGCACTGGCGCCCTCACCCACACATCGTCCCTTTATCCGCTCAGACGCTGC<br>AAAGGGCCTTCTGTCTC |
| 2 | CENPJ | GCTTTGGATTTATCCTCATTGGCTAAATCCCTCCTGAAACATGAAACTGAAACAAAGCCCTGAACCCCCTCAGGCTGAAAAGACAAACCCC<br>GCCTGAGGCCGGGTCCCGCTCCCCACCTGGAGGGACCCAATTCTGGGCGCCTTCTGGCGACGGTCCCTGCTAGGGACGCTGCGCTCTC<br>CGAGTGCGAGTTTTCGCCAAACTGATAAAGCACGCAGAACCGCAATCCCCAAACTAACACTGAACCCGGACCCGCGATCCCCAAACTGACAAGGGACCCGGAACA<br>GCGACCCCCAAACCGACACGGGACTCGGGAACCGCTATCTCCAAAGGGCAGC |
| 3 | ATP8A2 | TTTCCACAACAGGGAGCCAGCATTGAGGCGCCCAGATGGCATCTGCTGGAAATCACGGGCCGCTGGTGAAGCACCACGCCTTACCCGACGTGGGGAGGTGAT<br>CCCCCACCTCATCCCACCCCCTTCTGTCTGTCTCCTT |
| 4 | GSH1 | GCTGGACAAGGAGCGCTCACTGTAGCTCTGCTGTGGATTGTGTTGGGGCGAAGAGATGGGTAAGAGGTCAAAGTCGTAGGATTCTGGCG<br>ACCGCCTACCAAGGGATTGGGTCCACAGCACAGAGGTCTGATCGCTTCCTTCTCTGCTCTGCCACCTCCAGACAGCAGCTCTAACCAGCT<br>GCCCAGCAGCAAGAGGATGCGCACGGCTTTCACCAGCACGCAGCTGCTAGAGCTGGAGCGCGAGTTCGCTTCTAATATGTACCTGTCCCGCCTACGTCGCATCGAGATCGCGA |
| 5 | PDX1 | TGCCTGACACTGACCCCAGGCGCAGCCAGGAGGGGCTTTGTGCGGGAGAGGGAGGGGGACCCCAGCTTGCCTGGGGTCCACGGGACT<br>CTCTTCTTCCTAGTTCACTTTCTTGCTAAGGCGAAGGTCCTGAGGCAGGACGAGGGCTGAACTGCGCTGCAATCGTCCCCACCTCCAGCGAAACCCAGTTGAC |
| 6 | PDX1 | TCGGCGGAGAGACCTCGAGGAGAGTATGGGGAAAGGAATGAATGCTGCGGAGCGCCCCTCTGGGCTCCACCCAAGCCTCGGAGGCGG<br>GACGGTGGGCTCCGTCCCGACCCCTTAGGCAGCTGGACCGATACCTCCTGGATCAGACCCCACAGGAAGACTCGCGTGGGGCCCGATA<br>TGTGTACTTCAAACTCTGAGCGGCCACCCTCAGCCAACTGGCCAGTGGATGCGAATCGTGGGCCCTGAGGGGCGAGGGCGCTCGGAAC<br>TGCATGCCTGTGCACGGTGCCGGGCTCTCCAGAGTGAGGGGGCGTAAGGAGATCTCCAAGGAAGCCGAAAAAAGCAGCCAGTTGGGC<br>TTCGGGAAAGACTTTTCTGCAAAGGAAGTGATCTGGTCCCAGAACTCCAGGGTTGACCCCAGTACCTGACTTCTCCGGGAGCTGTCAGCT<br>CTCCTCTGTTCTTCGGGCTTGGCGCGCTCCTTTCATAATGGACAGACACCAGTGGCCTTCAAAAGGTCTGGGGTGGGGGAACGGAGGAA<br>GTGGCCTTGGGTGCAGAGGAAGAGCAGAGCTCCTGCCAAAGCTGAACGCAGTTAGCCCTACCCAAGTGCGCGCTGGCTCGGCATATGC<br>GCTCCAGAGCCGGCAGGACAGCCCGGCCCTGCTCACCCCGAGGAGAAATCCAACAGCGCAGCCTCCTGCACCTCCTTGCCCCAGAGAC |
| 7 | MAB21L1 | AGATCCCGGTGCATTTAAAGGCCGGCGTGATCTGCACCACGTACCTATCTCGGATTCTCAGTTTCACTTCGCTGGTGTCTGCCACCATCTT<br>TACCACATCCCGGTAGCTACATTTGTCTACCGCTTGAGCCACCAGCGTCTGAAACCTGGACCGGATTTTGCGCGCCGAGAGGTAGCCGG<br>AGGCGGTAATGAATTCCACCCAGAGGGACATGCTCCTCTTGCGCCCGTCGCTCAACTTCAGCACCGCGCAGCCGGGCAGTGAGCCATCGTCCACGAAGTTGAACACCC<br>CCATTTGGTTGAGATAAAGCACCACTTCAAATTCGGT |
| 8 | RB1 | ACTATGCCTTGAGGGTCAAAACGTCTGGATTTCCTGATCGATGCTGTCGTCGCTGTCCACGGAGCTACTGTCGCCGTCAGAGCGGGAAG<br>GCACGTTCAGGGAGTAGAAGCGTGGGCTTGCAGAAAGGGACCTGTTGCTGCCTTACATGGGGGCCGGCAGGGTAGTCTTGGAAATGCC<br>CAAGATTGCTTCCGCGCGCGTCAGTTCAGCGGACGTGTCTGCCTGGCACGAGGACCGTTCTACAAACTCGTTCCTGGAAGCCGGGCTCG<br>CTGGAGGCGGAGCTTTGGTTTCCTTCGGGAGCTTGTGGGGAATGGTCAGCGTCTAGGCACCCCGGGCAAGGGTCTGTGGCCTTGGTGG<br>CCACTGGCTTCCTCTAGCTGGGTGTTTTCCTGTGGGTCTCGCGCAAGGCACTTTTTTGTGGCGCTGCTTGTGCTGTGTGCGGGGTCAGGC<br>GTCCTCTCTCCTCCCGGCGCTGGGCCCTCTGGGGCAGGTCCCCGTTGGCCTCCTTGCGTGTTTGCCGCAGCTAGTACACCTGGATGGCC<br>TCCTCAGTGCCGTCGTTGCTGCTGGAGTCTGACGCCTCGGGCGCCTGCGCCGCACTTGTGACTTGCTTTCCCCTTCTCAGGGCGCCAGCGCTCCTCTTGACCC<br>CGCTTTTATTCTGTGGTGCTTCTGAAG |
| 9 | PCDH17 | GCAAGTCGGGTAGCTACCGGGTGCTGGAGAACTCCGCACCGCACCTGCTGGACGTGGACGCAGACAGCGGGCTCCTCTACACCAAGCA<br>GCGCATCGACCGCGAGTCCCTGTGCCGCCACAATGCCAAGTGCCAGCTGTCCCTCGAGGTGTTCGCCAACGACAAGGAGATCTGCATGA<br>TCAAGGTAGAGATCCAGGACATCAACGACAACGCGCCCTCCTTCTCCTCGGACCAGATCGAAATGGACATCTCGGAGAACGCTGCTCCG<br>GGCACCCGCTTCCCCCTCACCAGCGCACATGACCCCGACGCCGGCGAGAATGGGCTCCGCACCTACCTGCTCACGCGCGACGATCACG<br>GCCTCTTTGGACTGGACGTTAAGTCCCGCGGCGACGGCACCAAGTTCCCAGAACTGGTCATCCAGAAGGCTCTGGACCGCGAGCAACAG<br>AATCACCATACGCTCGTGCTGACTGCCCTGGACGGTGGCGAGCCTCCACGTTCCGCCACCGTACAGATCAACGTGAAGGTGATTGACTC |

TABLE 6A-continued

| SEQ ID NO | GENE NAME | SEQUENCE |
|---|---|---|
| | | CAACGACAACAGCCCGGTCTTCGAGGCGCCATCCTACTTGGTGGAACTGCCCGAGAACGCTCCGCTGGGTACAGTGGTCATCGATCTGA<br>ACGCCACCGACGCCGATGAAGGTCCCAATGGTGAAGTGCTCTACTCTTTCAGCAGCTACGTGCCTGACCGCGTGCGGGAGCTCTTCTCC<br>ATCGACCCCAAGACCGGCCTAATCCGTGTGAAGGGCAATCTGGACTATGAGGAAAACGGGATGCTGGAGATTGACGTGCAGGCCCGAGA<br>CCTGGGGCCTAACCCTATCCCAGCCCACTGCAAAGTCACGGTCAAGCTCATCGACCGCAACGACAATGCGCCGTCCATCGGTTTCGTCTC<br>CGTGCGCCAGGGGGCGCTGAGCGAGGCCGCCCCTCCCGGCACCGTCATCGCCCTGGTGCGGGTCACTGACCGGGACTCTGGCAAGAA<br>CGGACAGCTGCAGTGTCGGGTCCTAGGCGGAGGAGGGACGGGCGGCGGCGGGGGCCTGGGCGGGCCCGGGGGTTCCGTCCCCTTCA<br>AGCTTGAGGAGAACTACGACAACTTCTACACGGTGGTGACTGACCGCCCGCTGGACCGCGAGACACAAGACGAGTACAACGTGACCATC<br>GTGGCGCGGGACGGGGGCTCTCCTCCCCTCAACTCCACCAAGTCGTTCGCGATCAAGATTCTAGACGAGAACGACAACCCGCCTCGGTT<br>CACCAAAGGGCTCTACGTGCTTCAGGTGCACGAGAACAACATCCCGGGAGAGTACCTGGGCTCTGTGCTCGCCCAGGATCCCGACCTGG<br>GCCAGAACGGCACCGTATCCTACTCTATCCTGCCCTCGCACATCGGCGACGTGTCTATCTACACCTATGTGTCTGTGAATCCCACGAACG<br>GGGCCATCTACGCCCTGCGCTCCTTTAACTTCGAGCAGACCAAGGCTTTTGAGTTCAAGGTGCTTGCTAAGGACTCGGGGGCGCCCGCG<br>CACTTGGAGAGCAACGCCACGGTGAGGGTGACAGTGCTAGACGTGAATGACAACGCGCCAGTGATCGTGCTCCCCACGCTGCAGAACGA<br>CACCGCGGAGCTGCAGGTGCCGCGCAACGCTGGCCTGGGCTATCTGGTGAGCACTGTGCGCGCCCTAGACAGCGACTTCGGCGAGAGC<br>GGGCGTCTCACCTACGAGATCGTGGACGGCAACGACGACCACCTGTTTGAGATCGACCCGTCCAGCGGCGAGATCCGCACGCTGCACC<br>CTTTCTGGGAGGACGTGACGCCCGTGGTGGAGCTGGTGGTGAAGGTGACCGACCACGGCAAGCCTACCCTGTCCGCAGTGGCCAAGCT<br>CATCATCCGCTCGGTGAGCGGATCCCTTCCCGAGGGGGTACCACGGGTGAATGGCGAGCAGCACCACTGGGACATGTCGCTGCCGCTCATCGTGACTCTGAGCACTATCTC<br>CATCATCCTCCTA |
| 10 | KLHL1 | ATGCGCCCTCTGCACCCCTAGAGCCAGAAGACGCTAGGTGGGCTGCGCGCTCTGCCAGGCGAAGGCTGGAGCGCAGACGGCAAAGCC<br>GCGCGTTTCAGCCGTGGTCGGGTCCGCAGGACCTGGGCGTGGGGACACCACCAGGCAGGAGCAGAGGCAGGACTGGGACGCCAAAAGCTGAGAATCCTCGATGCCC<br>GCGCGAGAGCCCCGTGTTAT |
| 11 | POU4F1 | TTCTGGAAACCGGGCCCCACTTGCAGGCCCGGCCACCTTGGGTTCTGGTGGCCGAAGCCGGAGCTGTGTTTCTCGCAGACTCGGGGAG<br>CTACATTGTGCGTAGGCAATTGTTTAGTTTGAAAGGAGGCACATTTCACCACGCAGCCAGCGCCCTGCATGCAGGAGAAGCCCCCAGGG<br>CCCAGGGTCGGCTGGCTTTAGAGGCCACTTAGGTTGTTTTAAGCACATGTGAAAGGGCAGACAGCAGGGGAGCAGGATATGGGTAAGAT<br>CTTCGGGTCTCAGAACAGGGGCTGCCCTTGGGCTGTCCCGGCGCCCTGGGCTCTGACACTGAAGGGTGGAATGGAGGAAGGAATGGAG<br>AAAGGACGGTGGAACTTTCGCTTCCCCTCTGGGCCGCCTTCCCAGGGTCATGCCTGAGCTGCTTTGATCCCAGTGTCGCGCATCTTGGTC<br>CGCTACCTCCCAGGCGATAGCTACTGGGCTCCTCGCTGGCCTCACTGGGGGCCATCCCGGGCAGTGGCCTGCCCTCCGAGGCCCGCGG<br>GACCCAGCCCAGAGCTGAGGTTGGAGTTCTCCGGGCCACGTTCCGGGTCGCTTAGGCTCGGAGATTTCCCGGAGACCGTCGTCCTCCCT<br>TTCTGCTTGGCACTGCGGAGCTCCCTCGGCCTCTCTCCTCCTCTGGTCCCTAAGGCCCGGAGTGGTTGGCGGTACTGGGGCCCGTCGTC<br>ATCTCTGCTTCTAAGGCATTCAGACTGGGCTCCAGCTGGGACCGGCAGAGGAGGTTCTCAAGGAAACTGGTGGGAAATATAGTTTTCTTT<br>CGTCTGGTCGTTTAATTTAAATGCAACTTCCCTTGGGGACATTTTCCTGGACGTTAACCAGACCACCTTGAGATGTCGTTGATGACCTAGA<br>GACCCAGATGATGCGTCCCAGGAAAGTTCACTGCTGACTATTGTCACTCTTGGCGTTATATCTATAGATATAGACCTATGTACATATCTCCA<br>CCCTGATCTCTCCGTGGACATGAAACCCACCTACCTTGTGAAAGCCCTACGGGTGACACATGACTACTACGTCTCTGTCCCAACAGGGGC<br>TGGGCCTCCCCTGCCTAATAGTTGCCAGGAGTTTCGCAGCCCAAGTGAATAATGTCTTATGGCTGAACGTGGCCAAGGACTCCTGTGATT<br>TAGGTCCCAGGAGGAGCAGAGACGTCCCCGCCCCGCCTGGGCCCTGCCGCATTCAAAGCTGGAAGAAGGCGCTGATCAGAGAAGGGGC<br>TTCCAGGTCCTGGGTTAGAACAACAACAAACAAACGAAACTCCACAACAGACACGCCTGCCCATGACCCCACGCAAGGACATAGGAAGTT<br>CTGTCGCCTTCCTGCTCCGCGGATAGCCGCCTGCCGTCTGCTGCCACCAGAACGCACGGACGCTCGGGGTGGAGGTAGTCAATGGGCA<br>GCAGGGGACCCCCAGCCCCCACAAGCGCGGCTCCGAGGACCTGGAAGCGGGTGCCTGTCGCTCTCCGCAGGCTCCGCTCTGCCTCCAGGAGCAAGATCCCCAAAAGGGT<br>CTGGAAGCTGTGGAGAAAAC |
| 12 | GPC6 | TTTTTTAAACACTTCTTTTCCTTCTCTTCCTCGTTTTGATTGCACCGTTTCCATCTGGGGGCTAGAGGAGCAAGGCAGCAGCCTTCCCAGCC<br>AGCCCTTGTTGGCTTGCCATCGTCCATCTGGCTTATAAAAGTTTGCTGAGCGCAGTCCAGAGGGCTGCGCTGCTCGTCCCCTCGGCTGGC<br>AGAAGGGGGTGACGCTGGGCAGCGGCGAGGAGCGCGCCGCTGCCTCTGGCGGGCTTTCGGCTTGAGGGGCAAGGTGAAGAGCGCACC<br>GGCCGTGGGGTTTACCGAGCTGGATTTGTATGTTGCACCATGCCTTCTTGGATCGGGGCTGTGATTCTTCCCCTCTTGGGGCTGCTGCTC<br>TCCCTCCCCGCCGGGGCGGATGTGAAGGCTCGGAGCTGCGGAGAGGTCCGCCAGGCGTACGGTGCCAAGGGATTCAGCCTGGCGGAC<br>ATCCCCTACCAGGAGATCGCAGGTAAGCGCGGGCGCGCTGCAGGGGCAGGCTGCAGCCCTCGGCTGCCGCACGTCCCACTGGCCGCC<br>CGGCGTCCCCTTCCTTCCCCCTGTTGCTGAGTTGGTGCTCACTTTCTGCCACCGCTATGGGACTCCGCGTCTCCGTGTTGGGCGGCGGA<br>TGCTCCTGCGGCTTCTTCGGCGGGGGAAGGTGTGCGTCTCCGCCGCCTCATTGTGTGCACACGCGGGAGCACCCTGGCTCCCGCCTCC<br>CGCTGCTCTCGCGCCCTTCTACCCCTTAGTTGATGGCTCAGGCCCGGCTGGCCAGGGAGCCCGGGTCACTCCGGGGCGGCTGCAAGGC<br>GCAGACGGAGAGCCGAGCCGGGCGCTCACTCCGCGTTCTGGTTCGGGCAAACTTGGAAGAACTGCGACCGCAGTTTGCCCAGCGCCAC |

TABLE 6A-continued

| SEQ ID NO | GENE NAME | SEQUENCE |
|---|---|---|
| | | AGTCTGAGTGGCGCCTTCTCCACTCCCGCCCTTGCGCCGGCAGGGGCGGTGGAGAGACGCGGAGGGCTCCCCCAGCCCCTCTCTCCCC<br>TATCCGTCCTTCGGGCGACAGAGCGCCCGGCGCTCGGGCCGGGGGCGGGCAAGGCTGGGAGGGACCCTCGCCGGGGACCTGGCCTC<br>TGGACGCCGGCGTTTCAAGGCTGGTTTGGGGACTTCACGGGCTGCCTGTTTCAGATGTGGGGCGGGCTTTCCCGTTAGGGTTCCTCAGT<br>GCTTCCCCAGTTGCTGTTGGCCACTCAGGGCCCGGGGACACCCTGCCACCCGGTCTGGAGCCGGCCTCGTCTGCCAGCGAACAGCCAACTTTAGCGGGTG<br>GCTCAGCTGGGGATT |
| 13 | SOX21 | CACTCAGTGTGTGCATATGAGAGCGGAGAGACAGCGACCTGGAGGCCATGGGTGGGGGCGGGTGGTGAAGCTGCCGAAGCCTACACAT<br>ACACTTAGCTTTGACACTTCTCGTAGGTTCCAAAGACGAAGACACGGTGGCTTCAGGGAGACAAGTCGCAAGGGCGACTTTTCCAAGCGG<br>GAGATGGTGAAGTCTTTGGACGTGTAGTGGGTAGGTGATGATCCCCGCAGCCGCCTGTAGGCCCGCAGACTTCAGAAAACAAGGGCCTT<br>CTGTGAGCGCTGTGTCCTCCCCGGAATCCGCGGCTTAACACATTCTTTCCAGCTGCGGGGCCAGGATCTCCACCCCGCGCATCCGTGGA<br>CACACTTAGGGTCGCCTTTGTTTTGCGCAGTGATTCAAGTTGGGTAACCCTTGCTCAACACTTGGGAAATGGGGAGAATCTCCCCCACCC<br>GCAACCTCCCGCACCCCAGGTTCCCAAAATCTGAATCTGTATCCTAGAGTGGAGGCAGCGTCTAGAAAGCAAAGAAACGGTGTCCAAAGA<br>CCCCGGAGAGTTGAGTGAGCGCAGATCCGTGACGCCTGCGGTACGCTAGGGCATCCAGGCTAGGGTGTGTGTGTGCGGGTCGGGGGG<br>CGCACAGAGACCGCGCTGGTTTAGGTGGACCCGCAGTCCCGCCCGCATCTGGAACGAGCTGCTTCGCAGTTCCGGCTCCCGGCGCCCCAGAGAAGTTCGGGGAG<br>CGGTGAGCCTAGCCGCCGCGCGCTCATGTTTATT |
| 14 | ZIC2 | AGTCACTCCAGGATCAGAGGCCGCGTCGGTTCTGCTTGGGGCATGGGCAGAGGGAGGCTGCTGGGGCCAAGCCCCGGCTGGACGCGA<br>GGGAAGAAACTCGTCCCAGGACCCGCACGCCCATACCTGGCTGTCCCAGAGCTCTTCCCTAGGCCGGCACCTTCGCTCTTCCTCTTCCC<br>CACCCCCTAGCCCTTTTGTCTCTTTTTCAGACGGATGTTTTCAGTCTCAAGTGGTTTTATTTTCCGCACAAAACCCTGAGATCAAGGGCAGA<br>TCACAGACTGTACCGGAGGCTCGGGTTTCCCTGGACTCTGTGCTGTTCTGCGTCCCAGGGTTGGCTAGGAAGGAAGGCCTGGGCCGGC<br>GAGGTGACGGGTCTCCCGCCCAGGTCGGCAGGACGGGGGGAGGTGTGTCCCGGTAGGTCCCTGGTGAGCTCACCCGTGGCATCGGGG<br>ACCCGCGGGAACCCACCGGGCGCCCACTAGAGACTCGGGTCCTACCCTCCCCCACACTACTCCACCGAAATGATCGGAAGGGCGCGCT<br>AGGCCTGCTTCCAAGGGCTCAGTGATAAAGGCCTCAAAATCACACTCCATCAAGACTTGGTTGAAGCTTTGGGTAGGTTTGTTGTTGTTGT<br>TGTTGTTGTTTGTTTGTTTGTTTTAGCAGACACGTCCTGGAAAGAGGTCCTCAGAACCCAAAGGTTCAATAATGATTTGTGGATGGATTGAT<br>TATAGTCTGATATCGCTCTGGTTCCACAGAAACCCGGAGCTCCTTGGCCCACTGTTACCCCAGCAGACCTAAATGGACGGTTTCTGTTTTT<br>CACTGGCAGCTCAGAACTGGACCGGAAGAAGTTCCCCTCCACTTCCCCCCTCCCGACACCAGATCATTGCTGGGTTTTTATTTTCGGGGG<br>AAAAACAACAACAACAACAACAAAAAAAAACACTAGGTCCTTCCAGACTGGATCAGGTGATCGGGCAAAAACCCTCAGGCTAGTCCGGCTG<br>GGTGCCCGAGCATGAAAAGGCCTCCGTGGCCGTTTGAACAGGGTGTTGCAAATGAGAACTTTTGTAAGCCATAACCAGGGCATCCTGAG<br>GGTCTGAGTTCACGGTCAAGGCTGTGGGCTACTAGGTCCAGCGAGTCCAGGCCTCGCCCCGCCCCCGAGCTGCCACAGCCAAGATCTTCGGCAGGGAATTCGAGACCAG<br>GGTCCTCCCACTCCT |
| 15 | chr13<br>group-<br>00385 | TTTCGTGCCGCTGTTTTCAATGCGCTAACGAGGCACGTTATTCTTAGCCGCGTCCGGGAGGGGATCACATTCCTGCGCAGTTGCGCTGCT<br>GGCGGAAGTGACTTGTTTTCTAACGACCCTCGTGACAGCCAGAGAATGTCCGTTTCTCGGAGCGCAGCACAGCCTGTCCCATCGAGAAG<br>CCTCGGGTGAGGGGCCCGGTGGGCGCCCGGAGGCCGCTGGAGGGCTGTGGGAGGGACGGTGGCTCCCCACTCCCGTGGCGAAGGGC<br>AGGCAAACCAGAAGCCTCTTTTGAGAGCCGTTTGGGATTGAGACGAGTAAGCCACAGCGAGTGGTTAGAAGTAGGTTAGGAAGAAGGGGAGGTAAGAAAGCCGAGTAGGGTT |
| 16 | chr13<br>group-<br>00390 | GTTCGGTGGACAAGGGGGCAGCGCCCACAGCAAGCCGGAAAGAGGGAGGCGCGGGGCCGCGCTTGGGGCCTGCCGCTGCACGCCAG<br>CCTGGGCAAAGAGCTGCCACCTTCTGCGGGCGAAGCGGGTCGGGACGCAGGACGGCAGCGGGGCTGGAGGCAGCTACGTGGGTCCAC<br>ACCCCCATGCCCTGCAAGGCTCCTTGGCCCTGCTTCTCCTCTGTCTCGGCGGGAGAGGAGCAGCCTCGGTTTTACAGAATTTC |
| 17 | chr13<br>group-<br>00391 | TGTGCCATTTAGTGAGAGGTGTTTTGGGCAAAGAATCAATTTAACTGTGACTGACCGACGGGCTTGACTGTATTAATTCTGCTACCGAAAA<br>AAAAAAAAAAAAAAAAGCAATGAGCCGCAAGCCTTGGACTCGCAGAGCTGCCGGTGCCCGTCCGAGAGCCCCACCAGCGCGGCTCACGCCTCAGTCTC |
| 18 | chr13<br>group-<br>00395 | AGAGTCCCAGTTCTGCAGGCCGCTCCAGGGCTAGGGGTAGAGATGGTGGCAGGTGGTGCGTCAACTCTCTAGGGAAGAGGAACTTGCAT<br>TACAAAGACTTGTCTTTCTGAGCTGAAGTCAAAACGGGGGCGTCAAGCGCGCTCCGTTTGGCGGCGGTGGAGGGGCCGCGCGCCCGCG<br>CTGTCCCAGCCGGAGCTGCCCTGGCTGGTGATTGGAGGTTTAACGTCCGGAATTCAGGCGCTTCTGCAGCTCAGATTTGCCGGCCAAGG<br>GGCCTCAGTTGCAACTTTTCAAAATGGTGTTTCTGGAAAATAACAAATTCAGACTCAACTGGTGACAGCTTTTGGCTATAGAGAATGAAACT<br>GCTTCCCTTTGGCGGTGGAACTCTTAAACTTCGAAGAGTGAAAGAATACAATGAAATAAAATGCCATAAGATCACTGGATTTTTCAGAAAAA |

TABLE 6A-continued

| SEQ ID NO | GENE NAME | SEQUENCE |
|---|---|---|
| | | GGAAGACCCCAAATTACTCCCAAAATGAGGCTTTGTAAATTCTTGTTAAAAATCTTTAAATCTCGAATTTCCCCCTACAACATCTGATGAGTG CTTTAAGAGCAAACGAGCAAATCCCACCTCGAGAATCAACAAACCCAAGCTCTGGCCAAGGCTCTCCCCGCGTTTTCTTCTCGTGACCTG GGGAATGTCCCGCCCCATCGCTCACCTGGCTCTTGTCATCTCGCTCATCTTGAAGTGACCCGTGGACAATGCTG |
| 19 | chr13 group-00399 | AGCTGCCCTCTGTGGCCATGAGCGGGTGTCCAGCCCCTTCCAAGGCTGCACCGGGGAGACGCTGGTTTTCTGCTCGCTGTGACCGAACA AAGCCCCTAAGAGTCAGTGCGCGGAACAGAAGAGCCGGACCCCGACGGGCCGAGTCCCAACGTGAGGCACCCGGCAGAGAAAACACGT TCACG |
| 20 | PROZ | CCTCGGCAGCACCGGCATGGCTGGAGGCCAGTACGGCCAGGTGTGGCGGGAGGGAGCGCCGTCTGGCTTGGGTCGTCCATCCTGACA GGACGCTGCAAGGGCAGGAGCCCCGCGCCCCGTGTCCTGCGCCCCCGCTCGAGGACAAGCCCCAGCCGCCGGTCTCCGCTGGGTTCCGACAG |
| 21 | CIDEA | CTTTAAGAGGCTGTGCAGGCAGACAGACCTCCAGGCCCGCTAGGGGATCCGCGCCATGGAGGCCGCCCGGGACTATGCAGGAGCCCTC ATCAGGCGAGTGCCCCGCGTCCCCCTGATTGCCGTGCGCTTCCAATCGCCTTGCGTTCGGTGGCCTCATATTCCCCTGTGCGCCTCTAGT ACCGTACCCCGCTCCCTTCAGCCCCCTGCTCCCCGCATTCTCTTGCGCTCCGCGACCCCGCGCACACACCCATCCGCCCCACTGGTGCC CAAGCCGTCCAGCCGCGCCCGCGGGCAGAGCCCAATCCCGTCCCGCGCCTCCTCACCCTCTTGCAGCTGGGCACAGGTACCAGGTGTG GCTCTTGCGAGGTG |
| 22 | chr18 group-00091 | AGACTTGCAGAACTCGGGCCCCCTGGAGGAGACCTAACCGCCACGGTCTTGGGGAGGTTCCGGAGGGCCTCGGTTGTCTGCACTCCCA ACACCAAGAAACCCCTGAGACGCGAAGCTGCCAGCGTGCTGCCCTCAGAGCAGGGCGACGCAAAGCCAGCGGACCCCGGGGTGGCGGG |
| 23 | chr18 group-00094 | TGCTCGGCTGGGGGGCTCGCTCCGCACTTTCGGTGCCAGAAAATGCCCAGAGGAGCGGGGCGGCCCCAGAGCCTCCTTTCGGGGCGC GAGGCCCGGCGCGTGTGTACGGAGTCCAGTCCCCCCAGGGAGTGGGGTGCCCGCACCTTCCCCTCCGCGCTCGGAGCCAC |
| 24 | KLHL14 | TCTTGCACACCTGCTTGTAGTTCTGCACCGAGATCTGGTCGTTGAGGAACTGCACGCAGAGCTTGGTGACCTGGGGGATGTGCAGGATCT TGCTGACCGACAGCACCTCCTCCACCGTGTCCAGGGACAGGGTCACGTTGGCCGTGTAGAGGTACTCGAGCACCAGGCGCAGCCCGAT GGACGAGCAGCCCTGCAGCACCAGGTTGTTGATGGCCCGGGGGCTGGTCAGCAGCTTGTCGTCGGGGGAGGAAGAAGGAGTCCCGGG CTCCTCCTGCGGCGGCGGCTGCTGCTGCTGTGACGGCTGCTGCTGCGGCGGCTGCTGCTGGTCCTTGGGGGCCCCCAGGCCGTCCTG GCCGCCGACCCCTCCCCCGAGAGGGGGGTGGCTGGAGAAGAGCGATCGGAAGTACTGCGAGCAGGAGGCCAGCACGGCCTTGTGGCA ATGGAACTGCTGGCCCTGGGCCGTCAGGGTCACGTCGCAAAACAGCTGCTTCCTCCACAGCAGGTTGAGGCCGTGCAGCAGGTTGTCGC TGTGGCTGGGGTCGAAGGTGGAGGTCCTGTCCCCGGATCTGGACATGGCGAGCTGACTCGGTGCACCTGGCTTTAAACCCTCCTCCAAC CTGGCAGACAGGGGTGGGGGATGGAGGGAGGGGAGCAGGGTGGTGGAGCGGGTGGGGTGTGGTCGGGGTGGGGAAGGGTGTGGA GGGGAGGGGAGGGCGAAGAACAAGAATCAAGGCTCAGCTTGACTCCCTCCTGGCGCGCTCCGGACCCCGACCCTAGGAGGAAAGTCCG AAGACGCTGGATCCGTGAGCGCCACCAGAAGGGCCCTGTCTGGGGTCCCGGCGCCGGTTCTGCGCCCTGCGGCTCCTCTCGCCACCTC CCACACACTTCGTCCCTCACTTTCCTAAAACCAACCACCTCAGCTCGGCTGTTGGCAGCAACAGCAGTGGCAGCAGCGACGGCAAAGTG GCGGCTGAGGCCGAGGCACCTCGTGGGCTCGTGTCCATGCCGGGCCAGATGAAGGGAAAGGCCGGGAAGTGGGGAGCCGGGGGTGC CCTGAAAGCTCAGAGGCGACCGACGGCGAAGGTTCCAGGTCAACTTGTGCCCGAAGCTTTGCTTTTCGCAGTTGGCCCAGTTTGGGGGAGGGGGTAGGAACAGG GGCCCGACCAGCGTGCGGGGTGTGCGAATCTTAGCTCTCCAAAAGCTG |
| 25 | ST8SIA3 | CCTCTGTGTTAGTGCCCTCGGGAATTTGGTTGATGGGGTGTTTG |
| 26 | ONECUT2 | TGATGTCGCACCTGAACGGCCTGCACCACCCGGGCCACACTCAGTCTCACGGGCCGGTGCTGGCACCCAGTCGCGAGCGGCCACCCTC GTCCTCATCGGGCTCGCAGGTGGCCACGTCGGGCCAGCTGGAAGAAATCAACACCAAAGAGGTGGCCCAGCGCATCACAGCGGAGCTG AAGCGCTACAGTATCCCCCAGGCGATCTTTGCGCAGAGGGTGCTGTGCCGGTCTCAGGGGACTCTCTCCGACCTGCTCCGGAATCCAAA ACCGTGGAGTAAACTCAAATCTGGCAGGGAGACCTTCCGCAGGATGTGGAAGTGGCTTCAGGAGCCCGAGTTCCAGCGCATGTCCGCCT TACGCCTGGCAGGTAAGGCCGGGGCTAGCCAGGGGCCAGGCTGCTGGGAAGAGGGCTCCGGGTCCGGTGCTTGTGGCCCAAGTCTGC GCGCCGAGTCACTTCTCTTGATTCTTTCCTTCTCTTTCCTATACACGTCCTCTTTCTTCTCGTTTTTATTTCTTCTTCCATTTTCTCTTTCTCTT CCGCTCTTCCCCTACTTTCCCTTCTCCCTTTTCTTTTTCTTTCTTACTCTCTCCTTGTCCCTGAGCTTTCATTGACCGACCCCCCCCCATTTC ATTCGCCCTCCCCTCAATGTGCCAACCTTTGCCCTATTTCCGATCTTCCCAGGTACTGGGAGGCGGGATGGGGGTGTGCGTTTTCCTCTA GGAGCCCTGTCTTTCCAAGACCCACAGAAACCAGGACCTGCCCTTATTCAAAACCCCATGCACTTCAAGTCTCTTTTAGACAACACATTTC |

TABLE 6A-continued

| SEQ ID NO | GENE NAME | SEQUENCE |
|---|---|---|
| | | AATTTTCCGGGCTGACTAGTCTCCCTGTGCAGAGGCAGTTGAGAGGCTTTGCTCTGCAGAGGGAAAAGAGCTCTCTACTCTCCCACCCAC<br>CATATAGGCAAACTTATTTGGTCATTGGCTGAAGGCACAGCCTTGCCCCCGCGGGGAACCGGCGGCCAGGATACAACAGCGCTCCTGGA<br>GCCCATCTCTGGCCTTGGCGTTGGCGCAGGGACTTTCTGACCGGGCTTGAGGGGCTCGGGCCAGCTCCAATGTCACTACCTACAGCGAG<br>GGCAGGGTGTAAGGTTGAGAAGGTCACATTCACCGCTTTGGGAGGACGTGGGAGAAGAGACTGAGGTGGAAAGCGCTTTGCCTTGCTCA<br>CCGGCCGTCCTTGCCCCGGTCCCAGCGTTTGCTGGGATTTGCCAGGATTTGCCGGGGCTCCGGGAGACCCTGAGCACTCGCAGGAAGA<br>GGTGCTGAGAAATTAAAAATTCAGGTTAGTTAATGCATCCCTGCCGCCGGCTGCAGGCTCCGCCTTTGCATTAAGCGGGCGCTGATTGTG<br>CGCGCCTGGCGACCGCGGGGAGGACTGGCGGCCCGCGGGAGGGGACGGGTAGAGGCGCGGGTTACATTGTTCTGGAGCCGGCTCGG<br>CTCTTTGTGCCTCCTCTAGCGGCCAAGCTGCGAGGTACAGCCCTCTATTGTTCTAGGAGCACAGAAACCTCCTGTGTGGGCGGCGGGTG<br>CGCGAGCTAGAGGGAAAGATGCAGTAGTTACTGCGACTGGCACGCAGTTGCGCGCTTTTGTGCGCACGGACCCCGCGCGGTGTGCGTG<br>GCGACTGCGCTGCCCCTAGGAGCAAGCCACGGGCCCAGAGGGGCAAAATGTCCAGGTCCCCCGCTGGGAAGGACACACTATACCCTAT<br>GGCAAGCCAGGGTGGGCGACTTCCCATGGATCGGGTGGAGGGGGGTATCTTTCAGGATCGGCGGGCGGTCTAGGGGAACAATTCGTGG<br>TGGCGATGATTTGCATAGCGCGGGTCTTGGGATGCGCGCGGTTCCGAGCCAGCCTCGCACAGCTCGCTTCCGGAGCTGCGAGCTCAGG<br>TTTCCACCCCCGATCCCCCGGGCTTTCCTCGCACCGCTGAGCCCAGCTTGTGGGGTGCACTCGACCAACGCCCGACAGGGCTGGGGAA<br>TGTGACAGGCAGCAGGTTCACCCGGGCTTGGGGAGGGGGAGTTTCCGCTTTGACAGCATTTTCCTTTGCCGTCTGCTGGTGGATTCCTAT<br>TCCCAGTCGGTAATCGCCCCGCAGTGTTGATCTAAGAAGGTAAAGAAAACTAGGTTTCCCTGCAAAGAGCCTCCCCCAAATCGGCGGACT<br>CCGGATACTTTGAGTGGATTTAGAAATTTATGTAATCTTTCTCCTTTAGTTTATTTTTCATCCTCTCCTACAGTTTTCTCTGATTTGCTGTTGG<br>TTCGGGGCAAGATAAAGCAGCCAGTAGAGAGCGATAATAATAGCGGCGGGAAATGAACTGGAGACTGGCTGACAGTTCTTAACATTTTGT<br>CATAGATCCCCCCGAATGTCCCAGGCTGTCTCTGGTGGGTTTTAGTACCCGCCGGCTTCTTGGGCACCGGGGACCAGAAGGAACTTGGC<br>AGCTGGTCTTAGGGGTACAGTTAAAGGCAGGATGACAGCTATTCTCCTGCTCATCTCAGAGCGCTGCCGCCCCCTCATGCCGGTCGCGC<br>AAAGAACACAGCTTTTAAAAAACACGTGCCTTCTGCCCATATAGGTCTGAAAGTGATGAGGAAAGTAATGCTTCGCCTATTAGCGAGTTTCA<br>GCTTTTAAAATGATCCCAAGCGTTGCTGAGATGAGAAAGCGTGGCATCCCGGGGGTCCTCAGCCCCACCCGCGCCCATGGTGCAAGTCT<br>GCAGGGACAGGCCCGGGACAGCACTGCCCACGCTGCTAGATTTTCCGCAGAGGATCGCTGAAGCTGCCTTCGTGGGAGACAGAATGCC<br>TCCTCCAGCGAGTGGAAAAGGCCTGCTGAGGACCCCGCTTTGCTCGAGCATTCAAATGTGTGTCTGTTTTATTACCCTGGGTTGAAAAGG<br>GACAAGAGCTTTAGCCTTTTTATCTGGCCATTTTATCAGCAACTACAAGTGTGTTGAGTGGTTATTATTACATAGGAGGCTTTTCAGTTTGG<br>GGTCAGTAGATCAGTCTCTTCAGACACTGATGCAGAAGCTGGGACTGGTAAGTAGGTATTATGTGCTCGGAGCGCTAGGGGACAGGAGC<br>AAATGGAGAAGAAAAGCGGAGGCTTTCTCCGCCCGGAGTATCGATCGGAATCCCCGCCGGTACGCCGCAGAGGGCCCTCGCCGTTGGG<br>CCCCGGGGGTTTAACAAGCCCAGCCGCTCCGCAGGCGGCTCGGCCGGACTCTCAGACCGGTGCCTGGAAGACACCGTCCCTGCCCCCC<br>TCCCGCCAAACCTGCCTCTTCTCTTTCTCTCATAGGTTATAGGTTCCCTTTCTCTCTCATTTTGGCCCCGCCCCCGGGTCCTGCCAAACAG<br>CCAAGCAGGCCGGGGTTTAGGGGGCTCAGAATGAAGAGGTCTGATTTGGCCAGCGCCGGCAAAGCTCACCCTTAGGCGAGGTCACAAC<br>AGAGGCAGGTCCTTCCTGCCCAGCCTGCCGGTGTAGTCACAGCCAAGGGTGGCACTTGAAAGGAAAAGGGAGAAAACTTCGGAGAAATT<br>TAGATTGCCCCAACGTTAGATTTCAGAGAAATTGACTCCAAATGCACGGATTCGTTCGGAAAGGGCGGCTAAGTGGCAGGTGGTTGCAAC<br>CCCGCCCGGTCGGGCCTTCGCAGAGGTTCCCCAAGACCAGCCCTTGCAGGGCGGTTTTCAGCAACCTGACAAGAGGCGGCCAAGACAA<br>ATTTCTGCGGGTTCGAGCACACACTCTCGGGCGTTGGGCCCCAGAGACCTCTAAACCAAGCACAAACAAGAAGGGAGTGAGAGAACCCA<br>GGCTAGAACTTGCACGGGCATCCCACTGAGGAAAAGCGAGGCCTCGGTGGCAGGCATGTTTTCTTCCGACGCCCGAAAATCGAGCCGAG<br>CGCCCGACTACATTTACTGCAGAGGTTTCCGCCTCCAGTGAGCCCGGATCCCCCAGCGGCCTGCCCGGAGCTGGTCTCCAGTCCCCGCC<br>GTAGTCCGACGCACGGCCCTCTCCTGGCAGCAAGCTCCCAGCGGCCAGTCTGAAGCCAATTCTGTTCAGGCGGCCGAGGGCCCTTAGC<br>CAACCCACCATGATGTCGCCTGGGCCACCTGATGCCCGCAGCGGCGGGACACGGCCCGGGCAGTGCGCAGTGGCTCCTGCTAGGGGC<br>ACCGCGTGCGTGCTTGTCTCCCGCTGCGCCGGGGACGTCCTTGGGTGACACGGGCCGCTGGGCACCTCCCAAGCCGAGGAAACGGAC<br>CCCCTTCGCAGAGTCTCGCGCCCACCCCCCAACCTCCCACCTCGTTTCTCGCTGCTAGGGCTCCCGACTCAGCCCACCTCTCCTGGCGG<br>TTTAGTTAGGGATCAGAGCTGGAGAGGCTGAACGCAACCCGTGCCAGTACGGAACAGACGATATGTTTGCCTGCTAGCTGCTTGGATGAA<br>TAATTGAAAAGTTCGCTGCAGTCTGTGCTTCGTCAAGTCCCGGGTGCCGGGAGAACACCTTCCCAACACGCATCAGGGTGGGCGGGAGC<br>GGGCAGAGGAGGCGGGACCCGAGGGAGGAGAGTGAACCCGAGCAGGAGAAGCAGCCCAGGCAGCCAGGCGCCCTCGATGCGAGAGG<br>CTGGGCATTTATTTTTATTCCAGGCTTTCCACTGTGTGGTTATGTCACTTTCTCAAACAAATGTGTATATGGAGGGAGATCGATGCTGATAA<br>TGTTTAGAAGATTAAAAGAGCATTAATGCTGGCAACAATAACGTAAACGTGTGGACCCAGATTTCATTGATCTGGAACTTGATCCGGCGCG<br>TTTCCAGTAAGCCCGACGGCGCGCTCTTCCCAGCAGAGCGCTCACCAGCGCCACGGCCCCGCGGTTTTCCAGCGGTGCCGCTTCGCCA<br>GCTCTGCGCGGGTTCTCCCGTCTGACCGCAGCTCCTCCCCCGCGAGGCCCCAGCCCGCCTTACTTCCCCGAGGTTTTCTCCTCCTCTCG<br>CGGGGCTCTCTGCCCTCTGCACCCCCTCCCCCGACCTCTGCACCACCCGCCCCTGTGCGCACACACCGCTACTTGCGCTTCCGGCGATCCGCCTG |
| 27 | RAX | AACCGGAGATCTGCTTGGTGAACTGAGAGGAGTCCTTAGGAGAGCGGGGACGCCAGGGGCCGGGGGACACTTCGCTCTCGCCCTAGGG<br>AAGGTGGTCTTGACGCTTTCTATTGAAGTCAAACTTGAAAATATCAGCTGCCGCTGGACTAT |

TABLE 6A-continued

| SEQ ID NO | GENE NAME | SEQUENCE |
|---|---|---|
| 28 | chr18 group-00277 | CGTGAGCAGAACGCCCGCCCTGGAGCAGTTAGGACCGAAGGTCTCCGGAGAGTCGCCGGCGGTGCCAGGTAACGCAGAGGGCTCGGG<br>TCGGGCCCCGCTTCTGGGGCTTGGGACTCCGGGCGCGCGGAGCCAGCCCTCTGGGGCGAAATCCCCGGGCGGCGTGCGCGGTCCCTC<br>TCCGCGCTGTGCTCTCCCAGCAACTCCCTGCCACCTCGACGAGCCTACCGGCCGCTCCGAGTTCGACTTCCTCGGACTTAGTGGGAGAAGGGGTTGGAAATGGGCTGC<br>CGGGACTGGGGGAGCTGCTCTCTGGAAGCAGGGAAGCTGGGGCGCACCGGGGCAGGT |
| 29 | NETO1 | TAGAAGAGGAAGACTCCTCTGGCCCCACTAGGTATCATCCGCGCTCTCCCGCTTTCCACCTGCGCCCTCGCTTGGGCCAATCTCTGCCGC<br>ACGTGTCCATCCCTGAACTGCACGCTATCCTCCACCCCCGGGGGGTTCCTGCGCACTGAAAGACCGTTCTCCGGCAGGTTTTGGGATCC<br>GGCGACGGCTGACCGCGCGCCGCCCCCACGCCCGGTTCCACGATGCTGCAATACAGAAAGTTTACGTCGGCCCCGACCCGCGCGGGAC<br>TGCAGGGTCCGCCGGAGCGCGGCGCAGAGGCTTTTCCTGCGCGTTCGGCCCCGGGAAAGGGGCGGGAGGGCTGGCTCCGGGAGCGC<br>ACGGGCGCGGCGGGGAGGGTACTCACTGTGAAGCACGCTGCGCCCATGGATCATGTCTGTGCGTTACACCAGAGGCTCCGGGCTCCAC<br>TAATTCCATTTAGAGACGGGAAGACTTCCAGTGGCGGGGGGAGGACAGGGTCGAGAGGTGTTAAAGACGCAAAGCAAGAAGGAAATAAA<br>GGGGGGCCGAGAGGGAGACCGAGAGGAAGGGGGAGCTCCGAGCCCACGCTGCAGCCAGATCCGGATGAGTCCGTCCTCCGCCCCGG<br>GCGGGCTCTCGCTCTCGCTGGCCCTCAGCGCCGCGCAGCCAGCAGCATCCCCACCGTGACGCTCGCATCACACCCGGGCGCCGGCCG<br>CCACCATCCGCGCCGCCGCCGTCAGGACCCTCCTCCCGGGCATCGTCGCCGCCGCGGGGTCGGGAGGACGCGGCGCGCGGGAGGCG<br>GCGGTCGCAGGGCGAGCCCCGGGACGCCCCGAGCCGGGGCCGGGGCCGGGGAGAGGGCGCAGCGAGGTGGGGGCCAGTCCAGACC<br>GACGGCAGCGACGGAGCGGGCGGCGGCGGCGGCGCCGGCGGCGGCGGGGTGGCTCAGTCCCCAGTCTCAGACGCGCCGCGCAGCA<br>GGTCGGAGCAGCCTCCCCGGGAGGATGTCCAGCGGCAGCGCTCCTCGCTCCAGCCCTTGGGGATCTTCCGCTGAGGCATTGAAGGCAG<br>GAAGAAGGGGTCCGTCATCGGCTCGCCGGGCTGCGCGCCACCTCTGCTATCTTGCGGAAAGAGGAGCGGGTGGGTGGGCGTCTGGGA<br>GGCGGGCTGGAGGGCGGTGCAGGGGAGCGGGGCGGCCGGGGGGGGGGCCGGGGGGCGGGGAAGGGAGGGAGGAGAAAGGAGCCG<br>GAAGAGGGCAGAGTTACCAAATGGGCTCCTTAGTCATGGCTTGGGGCTCCACGACCCTCCTGGAAGCCCGGAGCCTGGGTGGGATAGC<br>GAGGCTGCGCGCGGCCGGCGCCCCGGGGCTGGTGCGCGGCAGAATGGGGCCGCGGCGGCGGCAGCAAGGACATCCCAGCCGCGCG<br>GATCTGGGGGAGGGGCGGGGAGGGGGTGAGGACCCGGCTGGGATCCGCGGCTCGGCCCGCCAGGGCGCAGAGAGAGGATGCAGCCG<br>CAAATCCCGAGCCGGATCCTCGTGCCGGACGGAAGGCGTGGAAGCGGGAGGGGCCTTCGTGTGAAAATCCCTTGTGGGGTTTGGTGTTT<br>CACTTTTTAAAGGTTAGACCTTGCGGGCTCTCTGCCTCCCACCCCTTCTTTTCCATCCGCGTAAAGGAACTGGGCGCCCCCTCTCCCTCCC<br>TCCCTGGGGCGCAGGTTTCGCCGCGGACTCCGCGCTCAGCTTGGGAGACACGGCAGGGGCGCGCCCCAGGGAAAGGCGGCCGTAAAA<br>GTTTCGCGGTTGAGCACTGGGCCTGATGTCCAGTCCCCCCACCAAATTACTCCTGCAAAGACGCGGGCTTCTTGCAATTGAGCCCCCCAC<br>CTCGAGGTATTTAAAACCACCCCAAGGCACACACGGACCCCCGTTCCCCCGCGCCACTTCCTCCTACAGGCTCGCGCGGCGCGTTAAAGTCTGGGAGACACGAGTT<br>GCGGGGAAACAGCACCGGAAG |
| 30 | MBP | AAGAAACAGCTCATTTCGGAGCTGAGGACAAGGCGTGGGAAGAAGACGCGTTTGGTTTCACCCAGGCGGGTGGCGGCAAAGCTGTGGG<br>ATGCGCGCTGCACACTCCTTCCGTCATCCCGTTCCCACCTTCCACACACACCTGCGGGAGGTCGGACATGTCCTGATTGCGTGTTCATCA<br>CGATGGCAAACCGAACATGAGGAGAACGCCACTGACGCTGGGTGCGCCGGCTTTCCCAGCCCTCGTGCATAACGGGGAGGGAGATGCA<br>GAAGTTTTTTCCAACATCGGTGCAAAGGGGAAGCTGAGGTTTTCCTAT |
| 31 | NFATC1 | TCTGTCAGCTGCTGCCATGGGGCAGCGGGAAGGCCCTGGAGGGTGCCTGGGCTGTGTCTGGTCCCGGCCACGCGTCCCTGCAGCGTCT<br>GAGACCTTGTGGAACACACTTGACCCGGCGCTGGGACGGGGTCGGCCCACACGCACCGCCAGCCCGCAGGAGTGAGGTGCAGGCTGC<br>CGCTGGCTCCTTAGGCCTCGACAGCTCTCTTGAGGTCGGCCCTCCTCCCCTCCCGAGAGCTCAGCAGCCGCAGACCCAGGCAGAGAGA<br>GCAAAGGAGGCTGTGGTGGCCCCCGACGGGAACCTGGGTGGCCGGGGGACACACCGAGGAACTTTCCGCCCCCCGACGGGCTCTCCC<br>ACCGAGGCTCAGGTGCTCGTGGGCAGCAAGGGGAAGCCCCATGGCCATGCCGCTTCCCTTTCACCCTCAGCGACGCGCCCTCCTGTGC<br>CCGCGGGGAACAAGACGGCTCTCGGCGGCCATGCAGGCGGCCTGTCCCACGAACACGATGGAGACCTCAGACGCCGTCCCCACCCTGTCACTGTCACCATCAC<br>CCATCCTGTCCCCTCACGCCTCCCCACATCCCATCATTACTAC |
| 32 | chr18 group-00430 | GAAGTAGAATCACAGTAAATGAGGAGTTAGGGAATTTAGGGTAGAGATTAAAGTAATGAACAGAGGAGGAGGCCTGAGACAGCTGCAGAG<br>AGACCCTGTGTTCCCTGTGAGGTGAAGCGTCTGCTGTCAAAGCCGGTTGGCGCTGAGAAGAGGTACCGGGGGCAGCACCCGCCTCCTG<br>GGAGAGGGATGGGCCTGCGGGCACCTGGGGGAACCGCACGGACACAGACGACACTATAAACGCGGGCGAGACATCAGGGACCGGGAAACAGAAGGACGCGCGTTTCGAGCA<br>GCTGCCCAGTGGGCCACAAGCCCCGCCACGCCACAGCCTCTTCCCCTCAGCACGCAGAGA |
| 33 | OLIG2 | TACTCCGGCGACGGGAGGATGTTGAGGGAAGCCTGCCAGGTGAAGAAGGGGCCAGCAGCAGCACAGAGCTTCCGACTTTGCCTTCCAG<br>GCTCTAGACTCGCGCCATGCCAAGACGGGCCCCTCGACTTTCACCCCTGACTCCCAACTCCAGCCACTGGACCGAGCGCGCAAAGAACC<br>TGAGACCGCTTGCTCTCACCGCCGCAAGTCGGTCGCAGGACAGACACCAGTGGGCAGCAACAAAAAAAGAAACCGGGTTCCGGGACAC<br>GTGCCGGCGGCTGGACTAACCTCAGCGGCTGCAACCAAGGAGCGCGCACGTTGCGCCTGCTGGTGTTTATTAGCTACACTGGCAGGCG |

TABLE 6A-continued

| SEQ ID NO | GENE NAME | SEQUENCE |
|---|---|---|
| | | CACAACTCCGCGCCCCGACTGGTGGCCCCACAGCGCGCACCACACATGGCCTCGCTGCTGTTGGCGGGGTAGGCCCGAAGGAGGCATC TACAAATGCCCGAGCCCTTTCTGATCCCCACCCCCCCGCTCCCTGCGTCGTCCGAGTGACAGATTCTACTAATTGAACGGTTATGGGTCA TCCTTGTAACCGTTGGACGACATAACACCACGCTTCAGTTCTTCATGTTTTAAATACATATTTAACGGATGGCTGCAGAGCCAGCTGGGAA ACACGCGGATTGAAAAATAATGCTCCAGAAGGCACGAGACTGGGGCGAAGGCGAGAGCGGGCTGGGCTTCTAGCGGAGACCGCAGAGG GAGACATATCTCAGAACTAGGGGCAATAACGTGGGTTTCTCTTTGTATTTGTTTATTTTGTAACTTTGCTACTTGAAGACCAATTATTTACTA TGCTAATTTGTTTGCTTGTTTTTAAAACCGTACTTGCACAGTAAAAGTTCCCCAACAACGGAAGTAACCCGACGTTCCTCACACTCCCTAGG AGACTGTGTGCGTGTGTGCCCGCGCGTGCGCTCACAGTGTCAAGTGCTAGCATCCGAGATCTGCAGAAACAAATGTCTGAATTCGAAATG TATGGGTGTGAGAAATTCAGCTCGGGGAAGAGATTAGGGACTGGGGGAGACAGGTGGCTGCCTGTACTATAAGGAACCGCCAACGCCAG CATCTGTAGTCCAAGCAGGGCTGCTCTGTAAAGGCTTAGCAATTTTTTCTGTAGGCTTGCTGCACACGGTCTCTGGCTTTTCCCATCTGTA AAATGGGTGAATGCATCCGTACCTCAGCTACCTCCGTGAGGTGCTTCTCCAGTTCGGGCTTAATTCCTCATCGTCAAGAGTTTTCAGGTTT CAGAGCCAGCCTGCAATCGGTAAAACATGTCCCAACGCGGTCGCGAGTGGTTCCATCTCGCTGTCTGGCCCACAGCGTGGAGAAGCCTT GCCCAGGCCTGAAACTTCTCTTTGCAGTTCCAGAAAGCAGGCGACTGGGACGGAAGGCTCTTTGCTAACCTTTTACAGCGGAGCCCTGCT TGGACTACAGATGCCAGCGTTGCCCCTGCCCCAAGGCGTGTGGTGATCACAAAGACGACACTGAAAATACTTACTATCATCCGGCTCCCC TGCTAATAAATGGAGGGGTGTTTAACTACAGGCACGACCCTGCCCTTGTGCTAGCGCGGTTACCGTGCGGAAATAACTCGTCCCTGTACC CACACCATCCTCAACCTAAAGGAGAGTTGTGAATTCTTTCAAAACACTCTTCTGGAGTCCGTCCCCTCCCTCCTTGCCCGCCCTCTACCCC TCAAGTCCCTGCCCCCAGCTGGGGGCGCTACCGGCTGCCGTCGGAGCTGCAGCCACGGCCATCTCCTAGACGCGCGAGTAGAGCACCA AGATAGTGGGGACTTTGTGCCTGGGCATCGTTTACATTTGGGGCGCCAAATGCCCACGTGTTGATGAAACCAGTGAGATGGGAACAGGC GGCGGGAAACCAGACAGAGGAAGAGCTAGGGAGGAGACCCCAGCCCCGGATCCTGGGTCGCCAGGGTTTTCCGCGCGCATCCCAAAAG GTGCGGCTGCGTGGGGCATCAGGTTAGTTTGTTAGACTCTGCAGAGTCTCCAAACCATCCCATCCCCCAACCTGACTCTGTGGTGGCCGT ATTTTTTACAGAAATTTGACCACGTTCCCTTTCTCCCTTGGTCCCAAGCGCGCTCAGCCCTCCCTCCATCCCCCTTGAGCCGCCCTTCTCC TCCCCCTCGCCTCCTCGGGTCCCTCCTCCAGTCCCTCCCCAAGAATCTCCCGGCCACGGGCGCCCATTGGTTGTGCGCAGGGAGGAGG CGTGTGCCCGGCCTGGCGAGTTTCATTGAGCGGAATTAGCCCGGATGACATCAGCTTCCCAGCCCCCCGGCGGGCCCAGCTCATTGGC GAGGCAGCCCCTCCAGGACACGCACATTGTTCCCCGCCCCCGCCCCCGCCACCGCTGCCGCCGTCGCCGCTGCCACCGGGCTATAAAA ACCGGCCGAGCCCCTAAAGGTGCGGATGCTTATTATAGATCGACGCGACACCAGCGCCCGGTGCCAGGTTCTCCCCTGAGGCTTTTCGG AGCGAGCTCCTCAAATCGCATCCAGAGTAAGTGTCCCCGCCCCACAGCAGCCGCAGCCTAGATCCCAGGGACAGACTCTCCTCAACTCG GCTGTGACCCAGAATGCTCCGATACAGGGGGTCTGGATCCCTACTCTGCGGGCCATTTCTCCAGAGCGACTTTGCTCTTCTGTCCTCCCC ACACTCACCGCTGCATCTCCCTCACCAAAAGCGAGAAGTCGGAGCGACAACAGCTCTTTCTGCCCAAGCCCCAGTCAGCTGGTGAGCTC CCCGTGGTCTCCAGATGCAGCACATGGACTCTGGGCCCCGCGCCGGCTCTGGGTGCATGTGCGTGTGCGTGTGTTTGCTGCGTGGTGT CGATGGAGATAAGGTGGATCCGTTTGAGGAACCAAATCATTAGTTCTCTATCTAGATCTCCATTCTCCCCAAAGAAAGGCCCTCACTTCCC ACTCGTTTATTCCAGCCCGGGGGCTCAGTTTTCCCACACCTAACTGAAAGCCCGAAGCCTCTAGAATGCCACCCGCACCCCGAGGGTCAC CAACGCTCCCTGAAATAACCTGTTGCATGAGAGCAGAGGGGAGATAGAGAGAGCTTAATTATAGGTACCCGCGTGCAGCTAAAAGGAGG GCCAGAGATAGTAGCGAGGGGGACGAGGAGCCACGGGCCACCTGTGCCGGGACCCCGCGCTGTGGTACTGCGGTGCAGGCGGGAGCA GCTTTTCTGTCTCTCACTGACTCACTCTCTCTCTCTCTCCCTCTCTCTCTCTCATTCTCTCTCTTTTCTCCTCCTCTCCTGGAAGTTTTCG GGTCCGAGGGAAGGAGGACCCTGCGAAAGCTGCGACGACTATCTTCCCCTGGGGCCATGGACTCGGACGCCAGCCTGGTGTCCAGCCG CCCGTCGTCGCCAGAGCCCGATGACCTTTTTCTGCCGGCCCGGAGTAAGGGCAGCAGCGGCAGCGCCTTCACTGGGGGCACCGTGTCCTCGTCCACCCCG AGTGACTGCCC |
| 34 | SIM2 | TTAATTCGAAAATGGCAGACAGAGCTGAGCGCTGCCGTTCTTTTCAGGATTGAAAATGTGCCAGTGGGCCAGGGGCGCTGGGACCCGCG GTGCGGAAGACTCGGAACAGGAAGAAATAGTGGCGCGCTGGGTGGGCTGCCCCGCCGCCCACGCCGGTTGCCGCTGGTGACAGTGGC TGCCCGGCCAGGCACCTCCGAGCAGCAGGTCTGAGCGTTTTTGGCGTCCCAAGCGTTCCGGGCCGCGTCTTCCAGAGCCTCTGCTCCCA GCGGGGTCGCTGCGGCCTGGCCCGAAGGATTTGACTCTTTGCTGGGAGGCGCGCTGCTCAGGGTTCTG |
| 35 | SIM2 | CCGGTCCCCAGTTTGGAAAAAGGCGCAAGAAGCGGGCTTTTCAGGGACCCCGGGGAGAACACGAGGGCTCCGACGCGGGAGAAGGATT GAAGCGTGCAGAGGCGCCCCAAATTGCGACAATTTACTGGGATCCTTTTGTGGGGAAAGGAGGCTTAGAGGCTCAAGCTATAGGCTGTC CTAGAGCAACTAGGCGAGAACCTGGCCCCAAACTCCCTCCTTACGCCCTGGCACAGGTTCCCGGCGACTGGTGTTCCCAAGGGAGCCCC CTGAGCCTACCGCCCTTGCAGGGGGTCGTGCTGCGGCTTCTGGGTCATAAACGCCGAGGTCGGGGGTGGCGGAGCTGTAGAGGCTGCCCGCGCAGAAAGCTCCAG GATCCCAATATGTG |
| 36 | DSCR6 | GCGCAGGTCCCCCCAGTCCCCGAGGGAGTGCGCCCGACGGAAACGCCCCTAGCCCGCGGGCCTCGCTTTCCTCTCCCGGGTTCCTGGGTCACTTCCCGCTGTCTC |

TABLE 6A-continued

| SEQ ID NO | GENE NAME | SEQUENCE |
|---|---|---|
| 37 | DSCAM | TTCCCTCGCGGCTTTGGAAAGGGGGTGCAAATGCACCCTTCTGCGGGCCCGCTACCCGCTGCAACACCTGTGTTTCCTTTCTGGGCACCT<br>TCTAGGTTTCTAGATATTGCTGTGAATACGGTCCTCCGCTGTACAGTTGAAAACAAA |
| 38 | chr21 group-00165 | TGGGAATTTAGGTCGGGCACTGCCGATATGTCGCCTTCCACAAGGCGGGCCCGGGCCTCTGCTGACCGTGCACCGGTCCTGGGGCTGG<br>GTAATTCTGCAGCAGCAGCGCAGCCCATGCCGGGGAATTTGCGGGCAGAGGAGACAGTGAGGCCCGCGTTCTGTGCGGGAACTCCCGA<br>GCTCACAGAGCCCAAGACCACACGGCTGCATCTGCTTGGCTGACTGGGCCAGGCCCACGCGTAGTAACCCGGACGTCTCTCTCTCACAG<br>TCCCCTTGCGTCTGGCCAGGGAGCTGCCAGGCTGCACCCCGCGGTGGGGATCGGGAGAGGGGCAGTGTCGCCCATCCCCGGAAGGCTGAGCCTGGTGCAG |
| 39 | PRMT2 | CGGTTTTCTCCTGGAGGACTGTGTTCAGACAGATACTGGTTTCCTTATCCGCAGGTGTGCGCGGCGCTCGCAAGTGGTCAGCATAACGCC<br>GGGCGAATTCGGAAAGCCCGTGCGTCCGTGGACGACCCACTTGGAAGGAGTTGGGAGAAGTCCTTGTTCCCACGCGCGGACGCTTCCC<br>TCCGTGTGTCCTTCGAGCCACAAAAAGCCCAGACCCTAACCCGCTCCTTTCTCCCGCCGCGTCCATGCAGAACTCCGCCGTTCCTGGGA<br>GGGGAAGCCCGCGAGGCGTCGGGAGAGGCACGTCCTCCGTGAGCAAAGAGCTCCTCCGAGCGCGCGGCGGGGACGCTGGGCCGACA<br>GGGGACCGCGGGGGCAGGGCGGAGAGGACCCGCCCTCGAGTCGGCCCAGCCCTAACACTCAGGAC |
| 40 | SIX2 | AGGGAATCGGGCTGACCAGTCCTAAGGTCCCACGCTCCCCTGACCTCAGGGCCCAGAGCCTCGCATTACCCCGAGCAGTGCGTTGGTTA<br>CTCTCCCTGGAAAGCCGCCCCCGCCGGGGCAAGTGGGAGTTGCTGCACTGCGGTCTTTGGAGGCCTAGGTCGCCCAGAGTAGGCGGAG<br>CCCTGTATCCCTCCTGGAGCCGGCCTGCGGTGAGGTCGGTACCCAGTACTTAGGGAGGGAGGACGCGCTTGGTGCTCAGGGTAGGCTG<br>GGCCGCTGCTAGCTCTTGATTTAGTCTCATGTCCGCCTTTGTGCCGGCCTCTCCGATTTGTGGGTCCTTCCAAGAAAGAGTCCTCTAGGG<br>CAGCTAGGGTCGTCTCTTGGGTCTGGCGAGGCGGCAGGCCTTCTTCGGACCTATCCCCAGAGGTGTAACGGAGACTTTCTCCACTGCAG<br>GGCGGCCTGGGGCGGGCATCTGCCAGGCGAGGGAGCTGCCCTGCCGCCGAGATTGTGGGGAAACGGCGTGGAAGACACCCCATCGGA<br>GGGCACCCAATCTGCCTCTGCACTCGATTCCATCCTGCAACCCAGGAGAAACCATTTCCGAGTTCCAGCCGCAGAGGCACCCGCGGAGT<br>TGCCAAAAGAGACTCCCGCGAGGTCGCTCGGAACCTTGACCCTGACACCTGGACGCGAGGTCTTTCAGGACCAGTCTCGGCTCGGTAGC<br>CTGGTCCCCGACCACCGCGACCAGGAGTTCCTTCTTCCCTTCCTGCTCACCAGCCGGCCGCCGGCAGCGGCTCCAGGAAGGAGCACCA<br>ACCCGCGCTGGGGGCGGAGGTTCAGGCGGCAGGAATGGAGAGGCTGATCCTCCTCTAGCCCCGGCGCATTCACTTAGGTGCGGGAGCCCTGAGGTTCAGCCTGACTTTC |
| 41 | SIX2 | CACTACGGATCTGCCTGGACTGGTTCAGATGCGTCGTTTAAAGGGGGGGCTGGCACTCCAGAGAGGAGGGGGCGCTGCAGGTTAATT<br>GATAGCCACGGAAGCACCTAGGCGCCCCATGCGCGGAGCCGGAGCCGCCAGCTCAGTCTGACCCCTGTCTTTTCTCTCCTCTTCCCTCT<br>CCCACCCCTCACTCCGGGAAAGCGAGGGCCGAGGTAGGGGCAGATAGATCACCAGACAGGCGGAGAAGGACAGGAGTACAGATGGAG<br>GGACCAGGACACAGAATGCAAAAGACTGGCAGGTGAGAAGAAGGGAGAAACAGAGGGAGAGAGAAAGGGAGAAACAGAGCAGAGGCGG<br>CCGCCGGCCCGGCCGCCCTGAGTCCGATTTCCCTCCTTCCCTGACCCTTCAGTTTCACTGCAAATCCACAGAAGCAGGTTTGCGAGCTCG<br>AATACCTTTGCTCCACTGCCACACGCAGCACCGGGACTGGGCGTCTGGAGCTTAAGTCTGGGGGTCTGAGCCTGGGACCGGCAAATCCG<br>CGCAGCGCATCGCGCCCAGTCTCGGAGACTGCAACCACCGCCAAGGAGTACGCGCGGCAGGAAACTTCTGCGGCCCAATTTCTTCCCCA<br>GCTTTGGCATCTCCGAAGGCACGTACCCGCCCTCGGCACAAGCTCTCTCGTCTTCCACTTCGACCTCGAGGTGGAGAAAGAGGCTGGCA<br>AGGGCTGTGCGCGTCGCTGGTGTGGGGAGGGCAGCAGGCTGCCCCTCCCCGCTTCTGCAGCGAGTTTTCCCAGCCAGGAAAAGGGAGGGAGCTGTTTCAGGAAT<br>TTCAGTGCCTTCACCTAGCGACTGACACAAGTCGTGTGTATAGGAAG |
| 42 | SOX14 | GGAGCCTGAAGTCAGAAAAGATGGGGCCTCGTTACTCACTTTCTAGCCCAGCCCCTGGCCCTGGGTCCCGCAGAGCCGTCATCGCAGGC<br>TCCTGCCCAGCCTCTGGGGTCGGGTGAGCAAGGTGTTCTCTTCGGAAGCGGGAAGGGCTGCGGGTCGGGGACGTCCCTTGGCTGCCAC<br>CCCTGATTCTGCATCCTTTTCGCTCGAATCCCTGCGCTAGGCATCCTCCCCGATCCCCCAAAAGCCCAAGCACTGGGTCTGGGTTGAGGA<br>AGGGAACGGGTGCCCAGGCCGGACAGAGGCTGAAAGGAGGCCTCAAGGTTCCTCTTTGCTACAAAGTGGAGAAGTTGCTCTACTCTGGA<br>GGGCAGTGGCCTTTTCCAAACTTTTCCACTTAGGTCCGTAAGAAAAGCAATTCATACACGATCAGCGCTTTCGGTGCGAGGATGGAAAGAAACTTC |
| 43 | TLX3 | TTTTCCTGTTACAGAGCTGAGCCCACTCATGTGGTGCCAAGTAGCGACTATCTCTCGGCCACCTCCACCCAGAGCAATGTGGGCGCCCCC<br>AGCGGGTGGGAGCGATTGCCGAGCGGCGCAAGGGCGTTTAACGCCTAACCCCCTCCTCCTGGGTTGCCAAGCCGCTAGGTCGCCGTTT<br>CCAACGTGGCTGCGCGGGACTGAAGTCCGACGACTCCTCGTCCTCAGTAGGAGACACACCTCCCACTGCCCCCAGCCACGCGAGCTATG<br>GGCAGAATCGGGGCAACGGTAATATCTGGATGGGGCAGGCTCCCCTGAGGCTGTGCTTAAGAAAAAAGGAATCTGGAGTAGCCTGAGGG<br>GCCCCACGAGGGGGCCTCCTTTGCGATCGTCTCCCAGCCTTAGGCCAAGGCTACGGAGGCAGGCGGCCGAGTGTTGGCGCCCAGCCC<br>GGCCGAGGACTGGATGGAGGACGAGAAGCAGCCTGCCTCTGGGCGACAGCTGCGGACGCAGCCTCGCCGCCTCGCCGCCTCAGCCTC<br>GGTCCCAGCGTCTCTAAAGCCGCGCCCATTTTACAGATGCAGGGCAGGGAGACAAGAGGCATCTCCGGGGGCCGAGTAGAATGATGGC<br>GCGGGTTCTCCCGGCGCCCTGATTTCGAGGCTGCGCCCGGGGCCCTACATGCAGGCGGGGAGGCCTGGGCCGAAGGCGTCTGCAAGG<br>AGGGGCGAGTCTGCCCGGTCCGGGCAGGGAGTGAGGCCACAGTCAGTTCTCCCTAGGAGGCCGCGCAGCGGGTAGGGTATGGACTG |

TABLE 6A-continued

| SEQ ID NO | GENE NAME | SEQUENCE |
|---|---|---|
| | | GGGGACGCAACGGGGACCTGGCCGAATCAGAGCCCTCAGCAGAGAACGCCGAAAACTCTGGGGCCGGCCGCTCGCTTCCCGCTAGTG<br>GGAATGGTTTCCGGTCATCCGTTCCCAGTCCAGCCCCGGGTAGGGAGCTCTGATTTGCAATGCACAGCACTTGCGAGGTTCGAATGCCC<br>CCGCAATTTGCAGATGGAAATACTAAGCCTAGGCCGGGCGTGGTGGCTCAAGCCTATCATCTCAGCCCTTTGGGAGGCCAAGCCGGGAG<br>GATTGTTTGAGCCCAAGAATTCAAAACCAGCCTGAGCAACATAGCGACCCCGTCTCTACAAAATAAAATAAAATAAATTATCCGGGCGTGG<br>TGGCACGCGCCTGTGGTTCCAGCTACTCCGGAGGCTGAGGTGGGAGGATCGCTTGAGTCCGGGAGGTCGAGGCTACAGTGAGCCGTGA<br>TCGCACCACTGCACTCCAGCCTGGGCGACAGAGTGAGACCTTGTCTCAAAAAAGGAAAAAAAGAAAAAGAAAGTAAGCTTCAAAGAAGCT<br>CTGATAATAGTTCTGGGTCGTGCAGCGGTGGCGGCCCCGCGCTCTCGCCCCTAAAGCAAGCGCTCTTTGTACTGGGTGGAGGAGCTTTG<br>AGTAGTGAGGGTGGAGATGCAGCTTCGGGGTGGCGCAGCCACCCTGACACTAGGCCCGGGGTCGCAGTGGGACAGAAGAGTCTGCCG<br>CTCTGACTTGGGCTCTGAGTTCCAAGGGCGCCCGGCACTTCTAGCCTCCCAGGCTTGCGCGCTGGCGCCTTTGCCATCCGTGCCGAAGT<br>GGGGAGACCTAGCCGCGACCACCACGAGCGCAGCGGTGACACCCAGAGGTCCCACCGGGCCCCTGGGCAGGGTAACCTTAGCCTGTC<br>CGCTTCGGCAGCTTTGCGAAGAGTGGCGCGCAGCTAGGGCTGAGGCTCTTGCGGACCTGCGGTCGAAGCAGGCGGCTGAGCCAGTTCG<br>ATCGCCAAGGCCTGGGCTGCCGACAGTGGTGCGCGCTCTGTTCCGCCGCGGCCGGGCCAGGCGCTCTGGAATAGCGATGGGGGGACA<br>CGGCCTCCAACTTTCTGCAGAGACCATCGGGCAGCTCCGGGCCTAAGCAGCGACCTCACCGAAGGTTCCTGGGAACCTTTGCCAAAATCCCAGCCTCTGCCTCGGTCC<br>AGCTAAACCGTGTGTAAACAAGTGCACCAAG |
| 44 | FOXP4 | ATAAAGGACCGGGTAATTTCGCGGAATGCGGATTTTGAGACAGGCCCAGACGGCGGCGGATTCCCTGTGTCCCCCAACTGGGGCGATCT<br>CGTGAACACACCTGCGTCCCACCCCGATCCTAGGTTGGGGGGAAAGGGTATGGGAACCCTGAGCCCAGAGCGCGCCCCGCTCTTTCCTT<br>TGCTCCCCGGCTTCCCTGGCCAGCCCCCTCCCGGCTGGTTTCCTCGCTCACTCGGCGCCTGGCGTTTCGGGCGTCTGGAGATCACCGC<br>GTGTCTGGCACCCCAACGTCTAGTCTCCCCGCAGGTTGACCGCGGCGCCTGGAGCCGGGAATAGGGGTGGGGAGTCCGGAGAACCAAA<br>CCCGAGCCTGAAGTTGCCATTCGGGTGACTCCCGAGAAAGCCCGGGAGCATTTTGGCCAATGCGGGTTTTTACCTGAACTTCAGCATCTTCACC |
| 45 | FOXP4 | AATTGGAAAACCCTGGTATTGTGCCTGTTTGGGGGAAGAAAACGTCAATAAAAATTAATTGATGAGTTGGCAGGGCGGGCGGTGCGGGTT<br>CGCGGCGAGGCGCAGGGTGTCATGGCAAATGTTACGGCTCAGATTAAGCGATTGTTAATTAAAAAGCGACGGTAATTAATACTCGCTACG<br>CCATATGGGCCCGTGAAAAGGCACAAAAGGTTTCTCCGCATGTGGGGTTCCCCTTCTCTTTTCTCCTTCCACAAAAGCACCCCAGCCCGT<br>GGGTCCCCCCTTTGGCCCCAAGGTAGGTGGAACTCGTCACTTCCGGCCAGGGAGGGGATGGGGCGGTCTCCGGCGAGTTCCAAGGGC<br>GTCCCTCGTTGCGCACTCGCCCGCCCAGGTTCTTTGAA |
| 46 | chr7<br>group-<br>00267 | GGGAAGCGATCGTCTCCTCTGTCAACTCGCGCCTGGGCACTTAGCCCCTCCCGTTTCAGGGCGCCGCCTCCCCGGATGGCAAACACTAT<br>AAAGTGGCGGCGAATAAGGTTCCTCCTGCTGCTCTCGGTTTAGTCCAAGATCAGCGATATCACGCGTCCCCCGGAGCATCGCGTGCAGG<br>AGCCATGGCGCGGGAGCTATACCACGAAGAGTTCGCCCGGGCGGGCAAGCAGGCGGGGCTGCAGGTCTGGAGGATTGAGAAGCTGGA<br>GCTGGTGCCCGTGCCCCAGAGCGCTCACGGCGACTTCTACGTCGGGGATGCCTACCTGGTGCTGCACACGGCCAAGACGAGCCGAGGC<br>TTCACCTACCACCTGCACTTCTGGCTCGGTAAGGGACGGCGGGCGGCGGGACCCCGACGCACCAAGGCCGGCGAGGGGAGGGCGTAG<br>GGGTCTGAGATTTGCAGGCGTGGGAGTAAAGGGGACCGCAAACTGAGCTAG |
| 47 | NPY | CTCAGGGGCGGGAAGTGGCGGGTGGGAGTCACCCAAGCGTGACTGCCCGAGGCCCCTCCTGCCGCGGCGAGGAAGCTCCATAAAAGC<br>CCTGTCGCGACCCGCTCTCTGCACCCCATCCGCTGGCTCTCACCCCTCGGAGACGCTCGCCCGACAGCATAGTACTTGCCGCCCAGCCA<br>CGCCCGCGCGCCAGCCACCGTGAGTGCTACGACCCGTCTGTCTAGGGGTGGGAGCGAACGGGGCGCCCGCGAACTTGCTAGAGACGC<br>AGCCTCCCGCTCTGTGGAGCCCTGGGGCCCTGGGATGATCGCGCTCCACTCCCCAGCGGACTATGCCGGCTCCGCGCCCCGACGCGGA<br>CCAGCCCTCTTGGCGGCTAAATTCCACTTGTTCCTCTGCTCCCCTCTGATTGTCCACGGCCCTTCTCCCGGGCCCTTCCCGCTGGGCGGT<br>TCTTCTGAGTTACCTTTTAGCAGATATGGAGGGAGAACCCGGGACCGCTATCCCAAGGCAGCTGGCGGTCTCCCTGCGGGTCGCCGCCT<br>TGAGGCCCAGGAAGCGGTGCGCGGTAGGAAGGTTTCCCCGGCAGCGCCATCGAGTGAGGAATCCCTGGAGCTCTAGAGCCCCGCGCCC<br>TGCCACCTCCCTGGATTCTTGGGCTCCAAATCTCTTTGGAGCAATTCTGGCCCAGGGAGCAATTCTCTTTCCCCTTCCCCACCGCAGTCGT<br>CACCCCGAGGTGATCTCTGCTGTCAGCGTTGATCCCCTGAAGCTAGGCAGACCAGAAGTAACAGAGAAGAAACTTTTCTTCCCAGACAAG<br>AGTTTGGGCAAGAAGGGAGAAAAGTGACCCAGCAGGAAGAACTTCCAATTCGGTTTTGAATGCTAAACTGGCGGGGCCCCCACCTTGCAC<br>TCTCGCCGCGCGCTTCTTGGTCCCTGAGACTTCGAACGAAGTTGCGCGAAGTTTTCAGGTGGAGCAGAGGGGCAGGTCCCGACCGGAC<br>GGCGCCCGGAGCCCGCAAGGTGGTGCTAGCCACTCCTGGGTTCTCTCTGCGGGACTGGGACGAGAGCGGATTGGGGGTCGCGTGTGG<br>TAGCAGGAGGAGGAGCGCGGGGGGCAGAGGAGGGAGGTGCTGCGCGTGGGTGCTCTGAATCCCCAAGCCCGTCCGTTGAGCCTTCTG<br>TGCCTGCAGATGCTAGGTAACAAGCGACTGGGGCTGTCCGGACTGACCCTCGCCCTGTCCCTGCTCGTGTGCCTGGGTGCGCTGGCCG<br>AGGCGTACCCCTCCAAGCCGGACAACCCGGGCGAGGACGCACCAG |

TABLE 6A-continued

| SEQ ID NO | GENE NAME | SEQUENCE |
|---|---|---|
| 48 | SHH | TGGAGAACCTTGGGCTCTGTGGCCTCAAAGGTAGGGGTGATTTCGAGGGGCCGGCACCTCACAGGGCAGGTTCCACCGCGGAAACGCA<br>GTCATCGCCCAGCGACCCTGCTCCTGGCCCTCAGCCTCCCCCAGGTTTCTTTTTCTCTTGAATCAAGCCGAGGTGCGCCAATGGCCTTC<br>CTTGGGTCGGATCCGGGGGGCCAGGGCCAGCTTACCTGCTTTCACCGAGCAGTGGATATGTGCCTTGGACTCGTAGTACACCCAGTCGA<br>AGCCGGCCTCCACCGCCAGGCGGGCCAGCATGCCGTACTTGCTGCGGTCGCGGTCAGACGTGGTGATGTCCACTGCGCGGCCCTCGTA<br>GTGCAGAGACTCCTCTGAGTGGTGGCCATCTTCGTCCCAGCCCTCGGTCACCCGCAGTTTCACTCCTGGCCACTGGTTCATCACCGAGAT<br>GGCCAAAGCGTTCAACTTGTCCTTACACCTCTGCGAAGACAAGGGGACCCCCACCGACGGACACGTTAGCCTGGGCAACCGCCACCCCTCCCGGCCCCTCCAT<br>CAGCCT |
| 49 | OSR2 | TCTCACGACCCATCCGTTAACCCACCGTTCCCAGGAGCTCCGAGGCGCAGCGGCGACAGAGGTTCGCCCCGGCCTGCTAGCATTGGCAT<br>TGCGGTTGACTGAGCTTCGCCTAACAGGCTTGGGGAGGGTGGGCTGGGCTGGGCTGGGCTGGGCTGGGTGCTGCCCGGCTGTCCGCC<br>TTTCGTTTTCCTGGGACCGAGGAGTCTTCCGCTCCGTATCTGCCTAGAGTCTGAATCCGACTTTCTTTCCTTTGGGCACGCGCTCGCCAGT<br>GGAGCACTTCTTGTTCTGGCCCCGGGCTGATCTGCACGCGGACTTGAGCAGGTGCCAAGGTGCCACGCAGTCCCCTCACGGCTTTCGGG<br>GGGTCTTGGAGTCGGGTGGGGAGGGAGACTTAGGTGTGGTAACCTGCGCAGGTGCCAAAGGGCAGAAGGAGCAGCCTTGGATTATAGT<br>CACGGTCTCTCCCTCTCTTCCCTGCCATTTTTAGGGCTTTCTCTACGTGCTGTTGTCTCACTGGGTTTTTGTCGGAGCCCCACGCCCTCCG<br>GCCTCTGATTCCTGGAAGAAAGGGTTGGTCCCCTCAGCACCCCCAGCATCCCGGAAAATGGGGAGCAAGGCTCTGCCAGCGCCCATCCC<br>GCTCCACCCGTCGCTGCAGCTCACCAATTACTCCTTCCTGCAGGCCGTGAACACCTTCCCGGCCACGGTGGACCACCTGCAGGGCCTGTACGGTCTCAGCGCGGTA<br>CAGACCATGCACATGAACCACTGGACGCTGGGGTATCCCAAT |
| 50 | GLIS3 | TGGTTTCCTTTCGCTTCTCGCCTCCCAAACACCTCCAGCAAGTCGGAGGGCGCGAACGCGGAGCCAGAAACCCTTCCCCAAAGTTTCTCC<br>CGCCAGGTACCTAATTGAATCATCCATAGGATGACAAATCAGCCAGGGCCAAGATTTCCAGACACTTGAGTGACTTCCCGGTCCCCGAGG<br>TGACTTGTCAGCTCCAGTGAGTAACTTGGAACTGTCGCTCGGGGCAAGGTGTGTGTCTAGGAGAGAGCCGGCGGCTCACTCACGCTTTC<br>CAGAGAGCGACCCGGGCCGACTTCAAAATACACACAGGGTCATTTATAGGGACTGGAGCCGCGCGCAGGACAACGTCTCCGAGACTGAG<br>ACATTTTCCAAACAGTGCTGACATTTTGTCGGGCCCCATAAAAAATGTAAACGCGAGGTGACGAACCCGGCGGGGAGGGTTCGTGTCTGG<br>CTGTGTCTGCGTCCTGGCGGCGTGGGAGGTTATAGTTCCAGACCTGGCGGCTGCGGATCGCCGGGCCGGTACCCGCGAGGAGTGTAGG<br>TACCCTCAGCCCGACCACCTCCCGCAATCATGGGGACACCGGCTTGGATGAGACACAGGCGTGGAAAACAGCCTTCGTGAAACTCCACA<br>AACACGTGGAACTTGAAAAGACAACTACAGCCCCGCGTGTGCGCGAGAGACCTCACGTCACCCCATCAGTTCCCACTTCGCCAAAGTTTC<br>CCTTCAGTGGGGACTCCAGAGTGGTGCGCCCCATGCCCGTGCGTCCTGTAACGTGCCCTGATTGTGTACCCCTCTGCCCGCTCTACTTG<br>AAATGAAAACACAAAAACTGTTCCGAATTAGCGCAACTTTAAAGCCCCGTTATCTGTCTTCTACACTGGGCGCTCTTAGGCCACTGACAGA<br>AACATGGTTTGAACCCTAATTGTTGCTATCAGTCTCAGTCAGCGCAGGTCTCTCAGTGACCTGTGACGCCGGGAGTTGAGGTGCGCGTAT<br>CCTTAAACCCGCGCGAACGCCACCGGCTCAGCGTAGAAAACTATTTGTAATCCCTAGTTTGCGTCTCTGAGCTTTAACTCCCCCACACTCT<br>CAAGCGCCCGGTTTCTCCTCGTCTCTCGCCTGCGAGCAAAGTTCCTATGGCATCCACTTACCAGGTAACCGGGATTTCCACAACAAAGCC<br>CGGCGTGCGGGTCCCTTCCCCCGGCCGGCCAGCGCGAGTGACAGCGGGCGGCCGGCGCTGGCGAGGAGTAACTTGGGGCTCCAGCC<br>CTTCAGAGCGCTCCGCGGGCTGTGCCTCCTTCGGAAATGAAAACCCCCATCCAAACGGGGGGACGGAGCGCGGAAACCCGGCCCAAGT<br>GCCGTGTGTGCGCGCGCGTCTG |
| 51 | PRMT8 | GAAAGCCATCCTTACCATTCCCCTCACCCTCCGCCCTCTGATCGCCCACCCGCCGAAAGGGTTTCTAAAAATAGCCCAGGGCTTCAAGGC<br>CGCGCTTCTGTGAAGTGTGGAGCGAGCGGGCACGTAGCGGTCTCTGCCAGGTGGCTGGAGCCCTGGAAGCGAGAAGGCGCTTCCTCCC<br>TGCATTTCCACCTCACCCCACCCCCGGCTCATTTTTCTAAGAAAAAGTTTTTGCGGTTCCCTTTGCCTCCTACCCCCGCTGCCGCGCGGG<br>GTCTGGGTGCAGACCCCTGCCAGGTTCCGCAGTGTGCAGCGGCGGCTGCTGCGCTCTCCCAGCCTCGGCGAGGGTTAAAGGCGTCCGG<br>AGCAGGCAGAGCGCCGCGCGCCAGTCTATTTTTACTTGCTTCCCCCGCCGCTCCGCGCTCCCCCTTCTCAGCAGTTGCACATGCCAGCT<br>CTGCTGAAGGCATCAATGAAAACAGCAGTAG |
| 52 | TBX3 | ATCGAAAATGTCGACATCTTGCTAATGGTCTGCAAACTTCCGCCAATTATGACTGACCTCCCAGACTCGGCCCCAGGAGGCTCGTATTAGG<br>CAGGGAGGCCGCCGTAATTCTGGGATCAAAAGCGGGAAGGTGCGAACTCCTCTTTGTCTCTGCGTGCCCGGCGCGCCCCCCTCCCGGT<br>GGGTGATAAACCCACTCTGGCGCCGGCCATGCGCTGGGTGATTAATTTGCGAACAAACAAAAGCGGCCTGGTGGCCACTGCATTCGGGTTAAACATTGGCCAGC<br>GTGTTCCGAAGGCTTGT |
| 53 | chr12<br>group-<br>00801 | ATCAACATCGTGGCTTTGGTCTTTTCCATCATGGTGAGTGAATCACGGCCAGAGGCAGCCTGGGAGGAGAGACCCGGGCGGCTTTGAGC<br>CCCTGCAGGGGAGTCCGCGCGCTCTCTGCGGCTCCCTTCCTCACGGCCCGGCCCGCGCTAGGTGTTCTTTGTCCTCGCACCTCCTCCTC<br>ACCTTTCTCGGGCTCTCAGAGCTCTCCCCGCAATCATCAGCACCTCCTCTGCACTCCTCGTGGTACTCAGAGCCCTGATCAAGCTTCCCC<br>CAGGCTAGCTTTCCTCTTCTTTCCAGCTCCCAGGGTGCGTTTCCTCTCCAACCCGGGGAAGTTCTTCCGTGGACTTTGCTGACTCCTCTGA |

TABLE 6A-continued

| SEQ ID NO | GENE NAME | SEQUENCE |
|---|---|---|
| | | CCTTCCTAGGCACTTGCCCGGGGCTTCTCAACCCTCTTTTCTAGAGCCCCAGTGCGCGCCACCCTAGCGAGCGCAGTAAGCTCATACCCC<br>GAGCATGCAGGCTCTACGTTCCTTTCCCTGCCGCTCCGGGGGCTCCTGCTCTCCAGCGCCCAGGACTGTCTCTATCTCAGCCTGTGCTC<br>CCTTCTCTCTTTGCTGCGCCCAAGGGCACCGCTTCCGCCACTCTCCGGGGGGTCCCCAGGCGATTCCTGATGCCCCCTCCTTGATCCCG<br>TTTCCGCGCTTTGGCACGGCACGCTCTGTCCAGGCAACAGTTTCCTCTCGCTTCTTCCTACACCCAACTTCCTCTCCTTGCCTCCCTCCGG<br>CGCCCCCTTTTTAACGCGCCCGAGGCTGGCTCACACCCACTACCTCTTTAGGCCTTTCTTAGGCTCCCCGTGTGCCCCCCTCACCAGCAA<br>AGTGGGTGCGCCTCTCTTACTCTTTCTACCCAGCGCGTCGTAGTTCCTCCCCGTTTGCTGCGCACTGGCCCTAACCTCTCTTCTCTTGGTG<br>TCCCCCAGAGCTCCCAGGCGCCCCTCCACCGCTCTGTCCTGCGCCCGGGGCTCTCCCGGGAATGAACTAGGGGATTCCACGCAACGTG<br>CGGCTCCGCCCGCCCTCTGCGCTCAGACCTCCCGAGCTGCCCGCCTCTCTAGGAGTGGCCGCTGGGGCCTCTAGTCCGCCCTTCCGGA<br>GCTCAGCTCCCTAGCCCTCTTCAACCCTGGTAGGAACACCCGAGCGAACCCCACCAGGAGGGCGACGAGCGCCTGCTAGGCCCTCGCC<br>TTATTGACTGCAGCAGCTGGCCCGGGGGTGGCGGCGGGGTGAGGTTCGTACCGGCACTGTCCCGGGACAACCCTTGCAGTTGC |
| 54 | PAX9 | ACAAATAAAACACCCTCTAGCTTCCCCTAGACTTTGTTTAACTGGCCGGGTCTCCAGAAGGAACGCTGGGGATGGGATGGGTGGAGAGAG<br>GGAGCGGCTCAAGGACTTTAGTGAGGAGCAGGCGAGAAGGAGCACGTTCAGGCGTCAAGACCGATTTCTCCCCCTGCTTCGGGAGACTT<br>TTGAACGCTCGGAGAGGCCCGGCATCTCACCACTTTACTTGGCCGTAGGGGCCTCCGGCACGGCAGGAATGAGGGAGGGGGTCCGATT<br>GGACAGTGACGGTTTGGGGCCGTTCGGCTATGTTCAGGGACCATATGGTTTGGGGACAGCCCCAGTAGTTAGTAGGGGACGGGTGCGTT<br>CGCCCAGTCCCCGGATGCGTAGGGAGGCCCAGTGGCAGGCAGCTGTCCCAAGCAGCGGGTGCGCGTCCCTGCGCGCTGTGTGTTCATT<br>TTGCAGAGCCAGCCTTCGGGGAGGTGAACCAGCTGGGAGGAGTGTTCGTGAACGGGAGGCCGCTGCCCAACGCCATCCGGCTTCGCAT<br>CGTGGAACTGGCCCAACTGGGCATCCGACCGTGTGACATCAGCCGCCAGCTACGGGTCTCGCACGGCTGCGTCAGCAAGATCCTGGCG<br>CGATACAACGAGACGGGCTCGATCTTGCCAGGAGCCATCGGGGGCAGCAAGCCCCGGGTCACTACCCCCACCGTGGTGAAACACATCC<br>GGACCTACAAGCAGAGAGACCCCGGCATCTTCGCCTGGGAGATCCGGGACCGCCTGCTGGCGGACGGCGTGTGCGACAAGTACAATGT<br>GCCCTCCGTGAGCTCCATCAGCCGCATTCTGCGCAACAAGATCGGCAACTTGGCCCAGCAGGGTCATTACGACTCATACAAGCAGCACC<br>AGCCGACGCCGCAGCCAGCGCTGCCCTACAACCACATCTACTCGTACCCCAGCCCTATCACGGCGGCGGCCGCCAAGGTGCCCACGCCACCCGGGGTGC |
| 55 | SIX1 | AGGAGGCGCAACGCGCTGCCAGGGCGGCTTTATCCTGCCGCCACAGGGCGGGGACCAGCCCGGCAGCCGGGTGTCCAGCGCCGCTCA<br>CGTGCCTCGCCTGGAGCTTAGCTCTCAGACTCCGAAGAGGGCGACTGAGACTTGGGCCTGGGAGTTGGCTTCGGGGTACCCAAGGCGA<br>CGACAGCTGAGTTGTACCACGAAGCTCAGGCCGAGGCCTCCTCCCTTGTCTGGCCTTCGAATCCATACTGGCAGCCTCTCCTCTCAGGCA<br>CTCCGCGGGCCGGGCCACTAGGCCCCCTGCTCCTGGAGCTGCGCTATGATCCGGGTCTTGAGATGCGCGCGATTCTCTCTGAACCGGT<br>GGAGAGGAGGCTCTGCCCCGCGCGGAGCGAGGACAGCGGCGCCCGAGCTTCCCGCGCCTCTCCAGGGCCCAATGGCAAGAACAGCCT<br>CCGAAGTGCGCGGATGACAGGAAAAGATCTTCAGTTCTTCTGCCGCTAGAGAAGTGCGGGATACAAGCCTCTATTGGATCCACAACCTGG<br>AGTCCTGCCTTCGGA |
| 56 | ISL2 | ATCTGCGTGCCCTTTTCTGGGCGAGCCCTGGGAGATCCAGGGAGAACTGGGCGCTCCAGATGGTGTATGTCTGTACCTTCACAGCAAGG<br>CTTCCCTTGGATTTGAGGCTTCCTATTTTGTCTGGGATCGGGGTTTCTCCTTGTCCCAGTGGCAGCCCCGCGTTGCGGGTTCCGGGCGCT<br>GCGCGGAGCCCAAGGCTGCATGGCAGTGTGCAGCGCCCGCCAGTCGGGCTGGTGGGTTGTGCACTCCGTCGGCAGCTGCAGAAAGGT<br>GGGAGTGCAGGTCTTGCCTTTCCTCACCGGGCGGTTGGCTTCCAGCACCGAGGCTGACCTATCGTGGCAAGTTTGCGGCCCCCGCAGAT<br>CCCCAGTGGAGAAAGAGGGCTCTTCCGATGCGATCGAGTGTGCGCCTCCCCGCAAAGCAATGCAGACCCTAAATCACTCAAGGCCTGGA<br>GCTCCAGTCTCAAAGGTGGCAGAAAAGGCCAGACCTAACTCGAGCACCTACTGCCTTCTGCTTGCCCCGCAGAGCCTTCAGGGACTGAC<br>TGGGACGCCCCTGGTGGCGGGCAGTCCCATCCGCCATGAGAACGCCGTGCAGGGCAGCGCAGTGGAGGTGCAGACGTACCAGCCGCC<br>GTGGAAGGCGCTCAGCGAGTTTGCCCTCCAGAGCGACCTGGACCAACCCGCCTTCCAACAGCTGGTGAGGCCCTGCCCTACCCGCCCC<br>GACCTCGGGACTCTGCGGGTTGGGGATTTAGCCACTTAGCCTGGCAGAGAGGGGAGGGGGTGGCCTTGGGCTGAGGGGCTGGGTACA<br>GCCCTAGGCGGTGGGGGAGGGGGAACAGTGGCGGGCTCTGAAACCTCACCTCGGCCCATTACGCGCCCTAAACCAGGTCTCCCTGGAT<br>TAAAGTGCTCACAAGAGAGGTCGCAGGATTAACCAACCCGCTCCCCCGCCCTAATCCCCCCCTCGTGCGCCTGGGGACCTGGCCTCCTT<br>CTCCGCAGGGCTTGCTCTCAGCTGGCGGCCGGTCCCCAAGGGACACTTTCCGACTCGGAGCACGCGGCCCTGGAGCACCAGCTCGCGT<br>GCCTCTTCACCTGCCTCTTCCCGGTGTTTCCGCCGCCCCAGGTCTCCTTCTCCGAGTCCGGCTCCCTAGGCAACTCCTCCGGCAGCGAC<br>GTGACCTCCCTGTCCTCGCAGCTCCCGGACACCCCCAACAGTATGGTGCCGAGTCCCGTGGAGACGTGAGGGGGACCCCTCCCTGCCA<br>GCCCGCGGACCTCGCATGCTCCCTGCATGAGACTCACCCATGCTCAGGCCATTCCAGTTCCGAAAGCTCTCTCGCCTTCGTAATTATTCT<br>ATTGTTATTTATGAGAGAGTACCGAGAGACACGGTCTGGACAGCCCAAGGCGCCAGGATGCAACCTGCTTTCACCAGACTGCAGACCCCT<br>GCTCCGAGGACTCTTAGTTTTTCAAAACCAGAATCTGGGACTTACCAGGGTTAGCTCTGCCCTCTCCTCTCCTCTCTACGTGGCCGCCGCT<br>CTGTCTCTCCACGCCCCACCTGTGT |

TABLE 6A-continued

| SEQ ID NO | GENE NAME | SEQUENCE |
|---|---|---|
| 57 | DLX4 | AGGTCTCTTCAGACTGCCCATTCTCCGGGCCTCGCTGAATGCGGGGGCTCTATCCACAGCGCGCGGGGCCGAGCTCAGGCAGGCTGGG<br>GCGAAGATCTGATTCTTTCCTTCCCGCCGCCAAACCGAATTAATCAGTTTCTTCAACCTGAGTTACTAAGAAAGAAAGGTCCTTCCAAATAA<br>AACTGAAAATCACTGCGAATGACAATACTATACTACAAGTTCGTTTTGGGGCCGGTGGGTGGGATGGAGGAGAAAGGGCACGGATAATCC<br>CGGAGGGCCGCGGAGTGAGGAGGACTATGGTCGCGGTGGAATCTCTGTTCCGCTGGCACATCCGCGCAGGTGCGGCTCTGAGTGCTGG<br>CTCGGGGTTACAGACCTCGGCATCCGGCTGCAGGGGCAGACAGAGACCTCCTCTGCTAGGGCGTGCGGTAGGCATCGTATGGAGCCCA<br>GAGACTGCCGAGAGCACTGCGCACTCACCAAGTGTTAGGGGTGCCCGTGATAGACCGCCAGGGAAGGGGCTGGTTCGGAGGGAATTCC<br>CGCTACCGGGAAGGTCGGAACTCGGGGTGATCAAACAAGGAATGCATCTCACCTCCGTGGGTGCTTGTGCTGCGCAAGGAATTATTACC<br>GGAGCGGTTGCGATGGCCTTTGCCCGGCGACCCAAGAAGAGTAAGCAAACTACCGTCCACCCAGCGGATCAGGTCCAAT |
| 58 | CBX4 | GATGTCCTGTTTCTAGCAGCCTCCAGAGCCAAGCTAGGCGAGAGGCGTAGGAGGCAGAGAGAGCGGGCGCGGGAGGCCAGGGTCCGC<br>CTGGGGGCCTGAGGGGACTTCGTGGGGTCCCGGGAGTGGCCTAGAAACAGGGAGCTGGGAGGGCCGGGAAGAGCTTGAGGCTGAGCG<br>GGGGACGAACGGGCAGCGCAAAGGGGAGATGAACGGAATGGCCGAGGAGCCACGCATTCGCCTTGTGTCCGCGGACCCTTGTTCCCGA<br>CAGGCGACCAAGCCAAGGCCCTCCGGACTGACGCGGCCTGAGCAGCAGCGAGTGTGAAGTTTGGCACCTCCGGCGGCGAGACGGCGC<br>GTTCTGGCGCGCGGCTCCTGCGTCCGGCTGGTGGAGCTGCTGCGCCCTATGCGGCCTGCCGAGGGCGCCGCCGAGGGCCCGCGAGCT<br>CCGTGGGGTCGGGGTGGGGGGACCCGGGAGCGGACAGCGCGGCCCGAGGGGCAGGGGCAGGGGCGCGCCTGGCCTGGGGTGTGTC<br>TGGGCCCCGGCTCCGGGCTCTTGAAGGACCGCGAGCAGGAGGCTTGCGCAATCCCTTGGCTGAGCGTCCACGGAGAAAGAAAAAGAGC<br>AAAAGCAGAGCGAGAGTGGAGCGAGGGATGGGGGCGGGCAAAGAGCCATCCGGGTCTCCACCACCGCCCTGACACGCGACCCGGCTG<br>TCTGTTGGGGACCGCACGGGGGCTCGGGCGAGCAGGGGAGGGAGGAGCCTGCGCGGGGCTCGTGTTCGCCCAGGAATCCCGGAGAA<br>GCTCGAAGACGGTCTGGTGTTGAACGCACACGTGGACTCCATTTCATTACCACCTTGCAGCTCTTGCGCCACGGAGGCTGCTGCTGCCC<br>GGCGGCTGCTACCCACCGAGACCCACGTGGCCCCTCCCCAGGGGTGTAGGGGTGACGGTTGTCTTCTGGTGACAGCAGAGGTGTTGGG<br>TTTGCGACTGATCTCTAACGAGCTTGAGGCGCAAACCTAGGATTCCCTGAGTGTTGGGGTGCGGCGGGGGGGCAAGCAAGGTGGGACG<br>ACGCCTGCCTGGTTTCCCTGACTAGTTGCGGGGGGTGGGGGCCGGCTCTCAGGGGCCACCAGAAGCTGGGTGGGTGTACAGGAAAATA<br>TTTTTCTCCTGCCGTGTTTGGCTTTTTCCTGGCATTTTTGCCCAGGGCGAAGAACTGTCGCGCGGGGCAGCTCCACCGCGGAGGGAGAG<br>GGGTCGCGAGGCTGGCGCGGGAAGCGCTGTAGGTGGCAGTCATCCGTCCACGCCGCACAGGCCGTCTGCGCCGTCGGACCATCGGGA<br>GGTCTGCAGCAACTTTGTCCCGGCCAGTCCCCTTGTCCGGGAAGGGGCTGAGCTTCCCGACACTCTACCCTCCCCCTCTTGAAAATCCCC<br>TGGAAAATCTGTTTGCAATGGGTGTTTCCGCGGCGTCCAGGTCTGGGCTGCCGGGGGAGGCCGAGCGGCTGCTGCAGCCTCCCTGCTG<br>CCAGGGGCGTCGGACTCCGCTTCGCTCACTACGCCCAGGCCCCTCAGGGGCCCACGCTCAGGACTTCGGGGCCACACAGCAGGACCC<br>GGTGCCCCGACGACGAGTTTGCGCAGGACCCGGGCTGGGCCAGCCGCGGAGCTGGGGAGGAAGGGGCGGGGGTCGGTGCAGCGGAT<br>CTTTTCTGTTGCTGCCTGTGCGGCGGCAGGAAGCGTCTTGAGGCTCCCCAAGACTACCTGAGGGGCCGCCCAAGCACTTCAGAAGCCCA<br>AGGAGCCCCCGGCCACCCCCGCTCCTGGCCTTTTTGCCAACGACTTTGAAAGTGAAATGCACAAGCACCAGCAATTGACTTCCCTTCCGT<br>GGTTATTTATTTTGTCTTTGTGGATGGTGGGCAGATGGGGAGAGAGGCCCCTACCTAACCTCGGTGGCTGGTCCCTAGACCACCCCTGCC<br>AGCCGGTGTGGGGAGGAGCTCAGGTCCGCGGGAGAGCGAATGGGCGCCAGGAGGTGGGACAGAATCCTGGGAAGGTACAGCGGACGC<br>CCTGGAAGCTCCCCTGATGCCCCAGAGGGCCCTTCCTGGGAAACCTCCCGGGGGGGTGCCCCATACCATCCCACCCGGCTGTCTTGGC<br>CCCTCCCAGGGAGCCGCAGGAGAAACTAGCCCTACACCTGGGATTCCCAGAGCCTTCTGCTGGGGCTCCTGCCCCCGACTTCGGATAAC<br>CAGCTCCGCACAGGTCCCCGAGAAGGGCCGCTGGCCTGCTTATTTGATACTGCCCCCTCCCAGACAGGGGCTGGTCGAGCCCCTGGTTC<br>TGCTGCCAGACTGAAGCCTTCCAGACGCCACCTCGGTTTGGGCCCCCAGGGCCCTCAGGGGCCCCAGGAGAGGAGAGCTGCTATCTAG<br>CTCAGCCACAGGCTCGCTCCTGGTGGGGGCCAGGCTGAAGGAGTGGACCCTGGAGAGGTCGGGAACCTTTTAACAGCCGTGGGCTGGA<br>GGGTGGCTACTAAGTGTTCGGTCTGGGAAGAGGCATGACCCGCACCATCCCGGGGAAATAAACGACTTCTTAAGGGAATCTTCTCGCTGA<br>GCGGGTGCTCTGGGCCAGGAGATTGCCACCGCCAGCCCACGGAACCCAGATTTGGGCTCTGCCTTGAGCGGGCCGCCTGTGGCTTCCC<br>GGGTCGCTCCCCCGACTCAGAAAGCTCTCAAGTTGGTATCGTTTTCCCGGCCCTCGGAGGTGGATTGCAGATCACCGAGAGGGGATTTA<br>CCAGTAACCACTACAGAATCTACCCGGGCTTTAACAAGCGCTCATTTCTCTCCCTTGTCCTTAGAAAAACTTCGCGCTGGCGTTGATCATAT<br>CGTACTTGTAGCGGCAGCTTAGGGGCAGCGGAACTGGTGGGGTTGTGCGTGCAGGGGGAGGCTGTGAGGGAGCCCTGCACTCCGCCC<br>CTCCACCCTTCTGGAGGAGTGGCTTTGTTTCTAAGGGTGCCCCCCCAACCCCCGGGTCCCCACTTCAATGTTTCTGCTCTTTGTCCCACC<br>GCCCGTGAAAGCTCGGCTTTCATTTGGTCGGCGAAGCCTCCGACGCCCCCGAGTCCCACCCTAGCGGGCCGCGCGGCACTGCAGCCGG<br>GGGTTCCTGCGGACTGGCCCGACAGGGTGCGCGGACGGGGACGCGGGCCCCGAGCACCGCGACGCCAGGGTCCTTTGGCAGGGCCCAAGCACCCCT |
| 59 | EDG6 | TGGCGGCCGGCGGGCACAGCCGGCTCATTGTTCTGCACTACAACCACTCGGGCCGGCTGGCCGGGCGCGGGGGGCCGGAGGATGGC<br>GGCCTGGGGGCCCTGCGGGGGCTGTCGGTGGCCGCCAGCTGCCTGGTGGTGCTGGAGAACTTGCTGGTGCTGGCGGCCATCACCAGC<br>CACATGCGGTCGCGACGCTGGGTCTACTATTGCCTGGTGAACATCACGCTGAGTGACCTGCTCACGGGCGCGGCCTACCTGGCCAACGT<br>GCTGCTGTCGGGGGCCCGCACCTTCCGTCTGGCGCCCGCCCAGTGGTTCCTACGGGAGGGCCTGCTCTTCACCGCCCTGGCCGCCTCC<br>ACCTTCAGCCTGCTCTTCACTGCAGGGGAGCGCTTTGCCACCATGGTGCGGCCGGTGGCCGAGAGCGGGGCCACCAAGACCAGCCGCG |

TABLE 6A-continued

| SEQ ID NO | GENE NAME | SEQUENCE |
|---|---|---|
| | | TCTACGGCTTCATCGGCCTCTGCTGGCTGCTGGCCGCGCTGCTGGGGATGCTGCCTTTGCTGGGCTGGAACTGCCTGTGCGCCTTTGAC CGCTGCTCCAGCCTTCTGCCCCTCTACTCCAAGCGCTACATCCTCTTCTGCCTGGTGATCTTCGCCGGCGTCCTGGCCACCATCATGGGC CTCTATGGGGCCATCTTCCGCCTGGTGCAGGCCAGCGGGCAGAAGGCCCCACGCCCAGCGGCCCGCCGCAAGGCCCGCCGCCTGCTG AAGACGGTGCTGATGATCCTGCTGGCCTTCCTGGTGTGCTGGGGCCCACTCTTCGGGCTGCTGCTGGCCGACGTCTTTGGCTCCAACCT CTGGGCCCAGGAGTACCTGCGGGGCATGGACTGGATCCTGGCCCTGGCCGTCCTCAACTCGGCGGTCAACCCCATCATCTACTCCTTCC GCAGCAGGGAGGTGTGCAGAGCCGTGCTCAGCTTCCTCTGCTGCGGGTGTCTCCGGCTGGGCATGCGAGGGCCCGGGGACTGCCTGG CCCGGGCCGTCGAGGCTCACTCCGGAGCTTCCACCACCGACAGCTCTCTGAGGCCAAGGGACAGCTTTC |
| 60 | chr13 group-00005 | TAGTAAGGCACCGAGGGGTGGCTCCTCTCCCTGCAGCGGCTGTCGCTTACCATCCTGTAGACCGTGACCTCCTCACACAGCGCCAGGAC GAGGATCGCGGTGAGCCAGCAGGTGACTGCGATCCTGGAGCTGGTCGCAGCAGGCCATCCTGCACGCGGTGGAGGCGCCCCCTGCAG GCCGCAGCGCATCCCCAGCTTCTGGACGCACTGTGAGCGGTTATGCAGCAGCACGCTCATATGAGATGCCCCGCAGGGTGCTATGCAGG CCCACGTCCCCACAAAGCCCATGGCAGGCGCCCGGGTGCCGGAGCACGCACTTGGCCCCATGGATCTCTGTGCCCAGGGCTCAGCCAG GCATCTGGCCGCTAAAGGTTT |
| 61 | CRYL1 | TCTCATCTGAGCGCTGTCTTTCACCAGAGCTCTGTAGGACTGAGGCAGTAGCGCTGGCCCGCCTGCGAGAGCCCGACCGTGGACGATGC GTCGCGCCCTTCCCATCGCGGCCTGGGCGGGCCCGCCTGCCCTCGGCTGAGCCCGGTTTCCCTACCCCGGGGCACCTCCCCTCGCCC GCACCCGGCCCCAGTCCCTCCCAGGCTTGCGGGTAGAGCCTGTCTTTGCCCAGAAGGCCGTCTCCAAGCT |
| 62 | IL17D | CAGTCCCCGAGGCCCTCCCCGGTGACTCTAACCAGGGATTTCAGCGCGCGGCGCGGGGCTGCCCCCAGGCGTGACCTCACCCGTGCTC TCTCCCTGCAGAATCTCCTACGACCCGGCGAGGTACCCCAGGTACCTGCCTGAAGCCTACTGCCTGTGCCGGGGCTGCCTGACCGGGCT GTTCGGCGAGGAGGACGTGCGCTTCCGCAGCGCCCCTGTCTACAT |
| 63 | IRS2 | AGAGAGACATTTTCCACGGAGGCCGAGTTGTGGCGCTTGGGGTTGTGGGCGAAGGACGGGGACACGGGGGTGACCGTCGTGGTGGAG GAGAAGGTCTCGGAACTGTGGCGGCGGCGGCCCCCCTGCGGGTCTGCGCGGATGACCTTGGCGCCGCGGTGGGGGTCCGGGGGCTG GCTGGCCTGCAGGAAGGCCTCGACTCCCGACACCTGCTCCATGAGGCTCAGCCTCTTCACGCCCGACGTCGGGCTGGCCACGCGGGCA GCTTCTGGCTTCGGGGGGGCCGCGATAGGTTGCGGCGGGGTGGCGGCCACACCAAAAGCCATCTCGGTGTAGTCACCATTGTCCCCGG TGTCCGAGGACAACGATGAGGCGGCGCCCGGGCCCTGGGCGGTGGCAACGGCCGAGGCGGGGGGCAGGCGGTACAGCTCCCCCGGG GCCGGCGGCGGTGGCGGCGGCTGCAGAGACGACGACGGGGACGCGGACGGACGCGGGGGCAACGGCGGATACGGGGAGGAGGCCT CGGGGGACAGGAGGCCGTCCAAGGAGCCCACGGGGTGGCCGCTCGGGGCGCCCGGCTTAGGAGACTTGGGGGAGCTGAAGTCGAGG TTCATGTAGTCGGAGAGCGGAGACCGCTGCCGGCTGTCGCTGCTGGTGCCCGGGGTGCCTGAGCCCAGCGACGAGGCCGGGCTGCTG GCGGACAAGAGCGAGGAGGACGAGGCCGCCGACGCCAGCAGGGGAGGCGCGGGCGGCGACAGGCGGGCCCCGGGCTCGCCAAAGT CGATGTTGATGTACTCGCCGGGGCTCTTGGGCTCCGGTGGCAGTGGGTACTCGTGCATGCTGGGCAGGCTGGGCAGCCCCTCCAGGGA CAGGCGCGTGGGCCTCACCGCCCGGCCGCGCTGGCCCAAGAAGCCCTCCGGGCGGCCGCCGCTAGGCCGCACGGGCGAAGGCACTA CAGGGTGAGGGGGCTGCGTGGGGCCGGCCCCGAAGGCGCTGGCCGCCTGGCTGGGCCCTGGCGTGGCCTGAGGCTCCAGACGCTCC TCCTCCAGGATGCGCCCCACGGGGGAGCTCATGAGCACGTACTGGTCGCTGTCCCCGCCACAGGTGTAGGGGGCCTTGTAGGAGCGGG GCAAGGAGCTGTAGCAGCAGCCGGGAACGCCCCTGAGCGGCTCCCCGCCGGGGTGCAGGGCTGCGGAGAAGAAGTCGGGCGGGGTG CCCGTGGTGACCGCGTCGCTGGGGGACACGTTGAGGTAGTCCCCGTTGGGCAGCAGCTTGCCATCTGCATGCTCCATGGACAGCTTGG AACCGCACCACATGCGCATGTACCCACTGTCCTCGGGGGAGCTCTCGGCGGGCGAGCTGGCCTTGTAGCCGCCCCCGCTCGCCGGGAA TGTCCTGCCCGCCGCAGAGGTGGGTGCTGGCCCCGCAGGCCCCGCAGAAGGCACGGCGGCGGCGGCGGCGGCGGCGGCCCTGGGCT GCAAGATCTGCTTGGGGGCGGACACGCTGGCGGGGCTCATGGGCATGTAGTCGTCGCTCCTGCAGCTGCCGCTCCCACTGCCCGCGAG GGCCGCGCCGGGCGTCATGGGCATGTAGCCGTCGTCTGCCCCCAGGTTGCTGCTGGAGCTCCTGTGGGAGCCGATCTCGATGTCTCCG TAGTCCTCTGGGTAGGGGTGGTAGGCCACCTTGGGAGAGGACGCGGGGCAGGACGGGCAGAGGCGGCCCGCGCTGCCCGAGAAGGTG GCCCGCATCAGGGTGTATTCATCCAGCGAGGCAGAGGAGGGCTGGGGCACCGGCCGCTGCCGGGCTGGCGTGGTCAGGGAGTAGGTC CTCTTGCGCAGCCCTCGGTCCAGGTCCTGGGCCGCGTCCCCCGAGACCCGGCGGTAGGAGCGGCCACAGTGGCTCAGGGGCCTGTCC ATGGTCATGTACCCGTAGAACTCACCGCCGCCGCCGCCGTCTCGGGCCGGGGGCGTCTCCGCGATGGACTCGGGCGTGTTGCTTCGGT GGCTGCAGAAGGCGCGCAGGTCGCCTGGGCTGGAGCCGTACTCGTCCAGGGACATGAAGCCGGGGTCGCTGGGGGAGCCCGAGGCG GAGGCGCTGCCGCTGGAGGGCCGCTGGCCGGGGCCGTGGTGCAGCGGATGCGGCAGAGGCGGGTGCGGGCCGGGCGGCGGCGGGT AGGAGCCCGAGCCGTGGCCGCTGCTGGACGACAGGGAGC |

TABLE 6A-continued

| SEQ ID NO | GENE NAME | SEQUENCE |
|---|---|---|
| 64 | chr13<br>group-<br>00350 | TAACCTAAAGAATGAAGTCATGCCCCGGCCTGCACCCGGGAAACTGCACACAGCGAAAGATCGCCACTGAGATAAAGAGCTGAAAGCTAT<br>TCCCCAATTCAGCTGTTTCAGCCGTGCGGTCTCACAATGGGCTCACAGACGGCAGCATC |
| 65 | MCF2L | GTTTCCACAATCCACCTCGTAGCTGGGGCGTGCCGCTTGCCTCGGCTTGTCCCGGCAGAACACTCTTACCTTTAATGGCGACTGAAAAGT<br>TGCCACGAGTTCCTGATCATTGTGGTAGGTGCTGCGTGAAGCTGAGACGTGCGTGAGCCACATCCCAGGGGGCTTTGAGCCCCCACCGC<br>GGCGGCGGCTGAGGGGAGGCTTGTCGTACTCGCACAGGAGGACACAGGGCTGCAGTGTTCACTCCAGGGCCTCTTATCATTGGGATCT<br>GAGGAATTTTCCGAGAGGAAGTGCGAATTAACAATGATGAAAGGTTTGTGAGTGAGTGACAGGCACGTTCTATTGAGCACTGCATGGGGC<br>ATTATGTGCCACCAGAGACGGGGGCAGAGGTCAAGAGCCCTCGAGGGCTGGGAGAGTTCGGAGGATAGAAGTCATCAGAGCACAATGAA<br>GCCAGACCCTGCAGCCGCCTTCCCCTTCGGGGGCTTCCTTAGAATGCAGCATTGCGGGGACTGAGCTGTCCCAGGTGAAGGGGGGCCG<br>TCACGGTGTGTGGACGCCCCTCGGCTCAGCCCTCTAAGAGACTCGGCAGCCAGGATGGGCTCAAGGCATGAGCCCTCAAAGGAGGTTA<br>GGAAGGAGCGAGGGAGAAAAGATATGCTTGTGTGACGTCCTGGCCGAAGTGAGAACAATTGTATCAGATAATGAGTCATGTCCCATTGAG<br>GGGTGCCGACAAGGACTCGGGAGGAGGCCACGGAGCCCTGTACTGAGGAGACGCCCACAGGGAGCCTCGGGGGCCCAGCGTCCCGG<br>GATCACTGGATGGTAAAGCCGCCCTGCCTGGCGT |
| 66 | F7 | TCCAGCTGCAGCGAGGGCGGCCAGGCCCCCTTCTCCGACCTGCAGGGGTAGCGCGGCCTCGGCGCCGGAGACCCGCGCGCTGTCTGG<br>GGCTGCGGTGGCGTGGGGAGGGCGCGGCCCCCGGACGCCCCGAGGAAGGGGCACCTCACCGCCCCCACCCAGAGCGCCTGGCCGTG<br>CGGGCTGCAGAGGACCCCTCCGGGGCAGAGGCAGGTTCCACGGAAGACCCCGGCCCGCTGGGGCTTCCCCGGAGACTCCAGAG |
| 67 | chr18<br>group-<br>00039 | ACTTACTGCTTCCAAAAGCGCTGGGCACAGCCTTATATGACTGACCCCGCCCCCGAGTCCCAGGCCGCCCCATGCAACCGCCCAACCGC<br>CCAACCGCCACTCCAAAGGTCACCAACCACTGCTCCAGGCCACGGGCTGCCTCTCCCCACGGCTCTAGGGCCCTTCCCCTCCACCGCAG<br>GCTGAC |
| 68 | C18orf1 | TGCCACACCCAGGTACCGCCCGCCCGCGCGAGAGCCGGGCAGGTGGGCCGCGGATGCTCCCAGAGGCCGGCCCAGCAGAGCGATGG<br>ACTTGGACAGGCTAAGATGGAAGTGACCTGAG |
| 69 | CD33L3 | TCGCCAGCGCAGCGCTGGTCCATGCAGGTGCCACCCGAGGTGAGCGCGGAGGCAGGCGACGCGGCAGTGCTGCCCTGCACCTTCACG<br>CACCCGCACCGCCACTACGACGGGCCGCTGACGGCCATCTGGCGCGCGGGCGAGCCCTATGCGGGCCCGCAGGTGTTCCGCTGCGCT<br>GCGGCGCGGGGCAGCGAGCTCTGCCAGACGGCGCTGAGCCTGCACGGCCGCTTCCGGCTGCTGGGCAACCCGCGCCGCAACGACCTC<br>TCGCTGCGCGTCGAGCGCCTCGCCCTGGCTGACGACCGCCGCTACTTCTGCCGCGTCGAGTTCGCCGGCGACGTCCATGACCGCTACG<br>AGAGCCGCCACGGCGTCCGGCTGCACGTGACAGGCGAGGCGGCGTGGGAGCGGGTCCCCGGCCTCCCTTCCCGCCCTCCCGCCTGCC<br>CCGCCCCAAGGGCTACGTGGGTGCCAGGCGCTGTGCTGAGCCAGGAAGGGCAACGAGACCCAGCCCTCTCCTCTACCCCAGGGATCTC<br>ACACCTGGGGGTAGTTTAGGACCACCTGGGAGCTTGACACAAATGCAGAATCCAGGTCCCAGGAAGGGCTGAGGTGGGCCCGGGAATA<br>GGCATTGCCGTGACTCTCGTAGAGTGACTGTCCCCAGTGGCTCTCAGACGAAGAGGCGAGAAAGACAAGTGAATGGCAATCCTAAATATG<br>CCAAGAGGTGCAATGTGGTGTGTGCTACCAGCCCGGAAAGACACTCGCAGCCCCTCTACCCAGGGGTGCACAGACAGCCCACCAAGTAG<br>TGCCTAGCACTTTGCCAGACCCTGATATACAAAGATGCCTGAACCAGGGTCCCGTCCCTAGAGCAGTGGCTCTCCACTCTAGCCCCCACC<br>CTGCTCTGCGACAATAATGGCCACTTAGCATTTGCTAGGGAGCCGGGACCTAGTCCAAGCACCCACAAGCATGAATTTGCCAAATCTTTTC<br>AGCAACCTCTTAAGGCAACTGCTATCATGATCCTCACTTTACACATGGAGAAGCAGAAGCAGAGATGATAGAATCTTTCGCCCAAGGCCAC<br>ATCTGTATTGGGACGGGGGCAGCCTGGCACCCAAGTGCCCATTCCTCCCTTCTGACCAGCCCCCACCCCTCCGGCTCTGGCGTCCAAAG<br>GGCTAAGGGGAGGGGTGCCCTTGTGACAGTCACCCGCCTTCTCCCCTGCAGCCGCGCCGCGGATCGTCAACATCTCGGTGCTGCCCAG<br>TCCGGCTCACGCCTTCCGCGCGCTCTGCACTGCCGAAGGGGAGCCGCCGCCCGCCCTCGCCTGGTCCGGCCCGGCCCTGGGCAACAG<br>CTTGGCAGCCGTGCGGAGCCCGCGTGAGGGTCACGGCCACCTAGTGACCGCCGAACTGCCCGCACTGACCCATGACGGCCGCTACACG<br>TGTACGGCCGCCAACAGCCTGGGCCGCTCCGAGGCCAGCGTCTACCTGTTCCGCTTCCATGGCGCCAGCGGGGCCTCGACGGTCGCCC<br>TCCTGCTCGGCGCTCTCGGCTTCAAGGCGCT |
| 70 | TNFRSF11A | ATGAACTTCAAGGGCGACATCATCGTGGTCTACGTCAGCCAGACCTCGCAGGAGGGCGCGGCGGCGGCTGCGGAGCCCATGGGCCGCC<br>CGGTGCAGGAGGAGACCCTGGCGCGCCGAGACTCCTTCGCGGGGAACGGCCCGCGCTTCCCGGACCCGTGCGGCGGCCCCGAGGGG<br>CTGCGGGAGCCGGAGAAGGCCTCGAGGCCGGTGCAGGAGCAAGGCGGGGCCAAGGCTTGAGCGCCCCCCATGGCTGGGAGCCCGAA<br>GCTCGGAGC |

TABLE 6A-continued

| SEQ ID NO | GENE NAME | SEQUENCE |
|---|---|---|
| 71 | ZNF236 | TCAGTGTTATGTGGGGAGCGCTAGATCGTGCACACAGTAGGCGTCAGGAAGTGTTTTCCCCAGTAATTTATTCTCCATGGTACTTTGCTAA<br>AGTCATGAAATAACTCAGATTTTGTTTTCCAAGGAAGGAGAAAGGCCCAGAATTTAAGAGCAGGCAGACACACAACCGGGCACCCCCAGA<br>CCCTGGCCCTTCCAGCAGTCAGGAATTGACTTGCCTTCCAAAGCCCCAGCCCGGAGCTTGAGGAACGGACTTTCCTGCGCAGGGGGATC<br>GGGGCGCACTCG |
| 72 | chr18<br>group-<br>00342 | GTGGAAACACAACCTGCCTTCCATTGTCTGCGCCTCCAAAACACACCCCCCGCGCATCCGTGAAGCTGTGTGTTTCTGTGTTACTACAGG<br>GGCCGGCTGTGGAAATCCCACGCTCCAGACCGCGTGCCGGGCAGGCCCAGCC |
| 73 | OLIG2 | TCCACACCTCGGGCAGTCACTAGGAAAAGGGTCGCCAACTGAAAGGCCTGCAGGAACCAGGATGATACCTGCGTCAGTCCCGCGGCTGC<br>TGCGAGTGCGCGCTCTCCTGCCAGGGGGACCTCAGACCCTCCTTTACAGCACACCGAGGGCCCTGCAGACACGCGAGCGGGCCTTCAG<br>TTTGCAAACCCTGAAAGCGGGCGCGGTCCACCAGGACGATCTGGCAGGGCTCTGGGTGAGGAGGCCGCGTCTTTATTTGGGGTCCTCG<br>GGCAGCCACGTTGCAGCTCTGGGGGAAGACTGCTTAAGGAACCCGCTCTGAACTGCGCGCTGGTGTCCTCTCCGGCCCTCGCTTCCCCG<br>ACCCCGCACAGGCTAACGGGAGACGCGCAGGCCCACCCCACCGGCTGGAGACCCCGGCACGGCCCGCATCCGCCAGGATTGAAGCAG<br>CTGGCTTGGACGCGCGCAGTTTTCCTTTGGCGACATTGCAGCGTCGGTGCGGCCACAATCCGTCCACTGGTTGTGGGAACGGTTGGAGG<br>TCCCCCAAGAAGGAGACACGCAGAGCTCTCCAGAACCGCCTACATGCGCATGGGGCCCAAACAGCCTCCCAAGGAGCACCCAGGTCCAT<br>GCACCCGAGCCCAAAATCACAGACCCGCTACGGGCTTTTGCACATCAGCTCCAAACACCTGAGTCCACGTGCACAGGCTCTCGCACAGG<br>GGACTCACGCACCTGAGTTCGCGCTCACAGATC |
| 74 | RUNX1 | CTGCCCTCGCGGATCTCCCCCGGCCTCGCCGGCCTCCGCCTGTCCTCCCACCACCCTCTCCGGGCCAGTACCTTGAAAGCGATGGGCA<br>GGGTCTTGTTGCAGCGCCAGTGCGTAGGCAGCACGGAGCAGAGGAAGTTGGGGCTGTCGGTGCGCACCAGCTCGCCCGGGTGGTCGG<br>CCAGCACCTCCACCATGCTGCGGTCGCCGCTCCTCAGCTTGCCGGCCAGGGCAGCGCCGGCGTCCGGGGCGCCCAGCGGCAACGCCT<br>CGCTCATCTTGCCTGGGCTCAGCGCGGTGGAAGGCGGCGTGAAGCGGCGGCTCGTGCTGGCATCTACGGGGATACGCATCACAACAAG<br>CCGATTGAGTTAGGACCCTGCAAACAGCTCCTACCAGACGGCGACAGGGGCGCGGATCTTCAGCAAGCAGCTCCCGGGAGACCAACATA<br>CACGTTCAGGGGCCTTTATTACTGCGGGGGGTGGGGGGGGGCGGGGGTGGTTAGGGGAGGAGGGAGACTAAGTTACTAACAGTCCAGG<br>AGGGGAAAACGTTCTGGTTCTGCGGATCGGCCTCTGACCCAGGATGGGCTCCTAGCAACCGATTGCTTAGTGCATTAAAAAGTGGAGACT<br>ATCTTCCACGAATCTTGCTTGCAGAGGTTAAGTTCTGTCTTTGGCTGTTAGAAAAGTTCCTGAAGGCAAAATTCTCATACACTTCCTAAAATA<br>TTTATGCGAAGAGTAAAACGATCAGCAAACACATTATTTGGAAGTTCCAGTAGTTAATGCCTGTCAGTTTTTTGCAGGTGAGTTTTGTCTAA<br>AGTCCCAACAGAACACAATTATCTCCCGTAACAAGGCCACTTTTATCATGCAAAACTGGCTTCAGTCCCGAAAAGCAAGAGCTGAGACTTC<br>CAAAGGTAGTGCTACTAATGTATGTGCACGTATATATAAATATATACATATGCTCTACTTCATAAAATATTTACAATACAATCTGTGGAGAATT<br>TAAACACAACAGAAATCCATTAATGTACGCTGCAGATTTTTTTAAGTAGCCTTGAAAATCAGCTTCAGTAGTTGGAGCAGTGCTGAGCTAGA<br>AGTACTTGTCATGTTCTCTGTTCTCTCAATGAATTCTGTCAAAACGCTCAGTGCAGAAAATTCAGCGTTTCAGAGATCTTCAGCTAATCTTAA<br>AACAACAATCATAAGAAGGCCCAGTCGATGACACTCAGGGTTCTACAGCTCTCCCACATCTGTGAACTCGGGTTTGGGGATGTTGGTTAA<br>GTTTGTGGCTGGTCCTCTGGTTTGTTGGGAGTTGAGCAGCCGCAGAGTCACACACATGCAAACACGCACTCTTCGGAAGGCAGCCACTGT<br>CTACATCAGCTGGGTGACTCAGCCCTGACTCGGGCAGCAGCGAGACGATACTCCTCCACCGTCGCCCAGCACCCGCCGGTTAGCTGCTC<br>CGAGGCACGAACACCCACGAGCGCCGCGTAACCGCAGCAGGTGGAGCGGGCCTTGAGGGAGGGCTCCGCGGCGCAGATCGAAACAGA<br>TCGGGCGGCTCGGGTTACACACGCACGCACATCCTGCCACGCACACTGCCACGCACACGCAACTTCACGGCTCGCCTCGGACCACAGA<br>GCACTTTCTCCCCCTGTTGTAAAAGGAAAACAATTGGGGAAAAGTTCGCAGCCAGGAAAGAAGTTGAAAACATCCAGCCAAGAAGCCAGT<br>TAATTCAAAAGGAAGAAAGGGGAAAAACAAAAAAAAACAACAAAAAAAGGAAGGTCCAACGCAGGCCAAGGAGAAGCAGCAGAGGTTGAC<br>TTCCTTCTGGCGTCCCTAGGAGCCCCGGAAAGAAGTGCCTGGCGGCGCAGGGCCGGGCAGCGTGGTGCCCTGGCTGGGTCCGGCCGC<br>GGGGCGCCCGTCCCGCCCGCGCCCGCTGGCTCTATGAATGAGAGTGCCTGGAAATGAACGTGCTTTTACTGTAAGCCCGGCCGGAGGA<br>ATTCCATTCCCTCAGCTCGTTTGCATAGGGGCGGCCGGCGGCCAATCACAGGCCTTTCCGGTATCAGCCAGGGCGCGGCTCGCCGCCG<br>CCGGCTCCTGGAATTGGCCCGCGCGCCCCCGCCGCCGCGCCGCGCGCTACTGTACGCAGCCCGGGCGGGGAGTCGGAGGCCACCCC<br>CGCGCCCCGCATCCAAGCCTGCATGCTGGCCCGGGGCCCCGCCCGCGTGCGGACCCCTTTCCGCAGCCACACGCAGGCTTGTGCGGC<br>TCCGCGAGTGGCCACGGTCCGGAGACCTGGAAAAAGAAAGCAGGCCCCGCCGGCCCGAGGAGGACCCGGCCGGCGCGCCGCACCCG<br>GAGAGGCCCGGCCCCGCGAGCCGCTGCAGGCAGGCGCAGTGGCCGCCACGAGGCTCCCGAACCGGGCTGCAGCCCGCGGACGGCCC<br>CAGATCCTGCGCGGCCGCCCAGGGCCAGGCCTCCGCTTCCAGGGCGGGGGTGCGATTTGGCCGCGGGGCCCGGGGGAGCCACTCCG<br>CGCTCCTGCACCGTCCGGCTGGCAGCTGCGGCGAAGCGGCGCTGATTCCTTGCATGAGGCCGGACGGCGTCCGCGCGTGCCGTTTGCT<br>CTCAGCGTCTTCCCTTGGGTCGGTTTCTGTAATGGGTGTTTTTACCGCTGCGCCCGGGCCGCGGCTCGATCCCTCCGCGCGTCTCACTT<br>GCTGCGTGCGTCAGCGGCCAGCGAAGAGTTTCCTAGTCAGGAAAGACCCCAAGAACGCGCGGCTGGAAGGAAAGTTGAAAGCAGCCAC<br>GCGGCTTGCTCCCGGGCCTTGTAGCGCCGGCACCCGCAGCAGCCGGACAGCCTGCCCGGGCCCCGCGTCTCCCCTCCGGCTCCCCGG |

TABLE 6A-continued

| SEQ ID NO | GENE NAME | SEQUENCE |
|---|---|---|
| | | AAGCGGCCCCCGCTCCTCTCCCCGCCCCCGTGCGCTCGAGCGGCCCCAGGTGCGGAACCCACCCCGGCTTCGCGTGCGGGCGGCCGC<br>TTCCCCCTGCGCCGGTCCCCGCGGTGCTGCGGGCATTTTCGCGGAGCTCGGAGGGCCCCGCCCCCGGTCCGGCGTGCGCTGCCAACT<br>CCGACCCCGCCCGGCGGGGCTCCCTCCCAGCGGAGGCTGCTCCCGTCACCATGAGTCCCTCCACGCCCTCCCTGCCGGGCCCTGCAC<br>CTCCCGGGGCCTCTCATCCACCCCGGGGCTGCAACCCAGTCCCCGGATCCCGGCCCCGTTCCACCGCGGGCTGCTTTGTGGTCCCCGC<br>GGAGCCCCTCAATTAAGCTCCCCGGCGCGGGGGTCCCTCGCCGACCTCACGGGGCCCCTGACGCCCGCTCCTCCCTCCCCCAGGGCTA<br>GGGTGCTGTGGCCGCTGCCGCGCAGGGACTGTCCCCGGGCGTTGCCGCGGGCCCGGACGCAGGAGGGGGCCGGGGTTGACTGGCGT<br>GGAGGCCTTTCCCGGGCGGGCCCGGACTGCGCGGAGCTGTCGGGACGCGCCGCGGGCTCTGGCGGACGCCAGGGGGCAGCAGCCGC<br>CCTCCCTGGACGCCGCGCGCAGTCCCCGGAGCTCCCGGAACGCCCCCGACGGCGCGGGGCTGTGCGGCCCGCCTCGTGGCCTTCGG<br>GTCGCCCGGGAAGAACTAGCGTTCGAGGATAAAAGACAGGAAGCCGCCCCAGAGCCCACTTGAGCTGGAACGGCCAAGGCGCGTTTCC<br>GAGGTTCCAATATAGAGTCGCAGCCGGCCAGGTGGGGACTCTCGGACCAGGCCTCCCCGCTGTGCGGCCCGGTCGGGGTCTCTTCCCG<br>AAGCCCCTGTTCCTGGGGCTTGACTCGGGCCGCTCTTGGCTATCTGTGCTTCAGGAGCCCGGGCTTCCGGGGGGCTAAGGCGGGCGGC<br>CCGCGGCCTCAACCCTCTCCGCCTCCGCTCCCCCTGGGCACTGCCAGCACCCGAGTTCAGTTTTGTTTTAATGGACCTGGGGTCTCGGA<br>AAGAAAACTTACTACATTTTTCTTTTAAAATGATTTTTTTAAGCCTAATTCCAGTTGTAAATCCCCCCCTCCCCCCGCCCAAACGTCCACTTT<br>CTAACTCTGTCCCTGAGAAGAGTGCATCGCGCGCGCCCGCCCGCCCGCAGGGGCCGCAGCGCCTTTGCCTGCGGGTTCGGACGCGGC<br>CCGCTCTAGAGGCAAGTTCTGGGCAAGGGAAACCTTTTCGCCTGGTCTCCAATGCATTTCCCCGAGATCCCACCCAGGGCTCCTGGGGC<br>CACCCCCACGTGCATCCCCCGGAACCCCCGAGATGCGGGAGGGAGCACGAGGGTGTGGCGGCTCCAAAAGTAGGCTTTTGACTCCAGG<br>GGAAATAGCAGACTCGGGTGATTTGCCCCTCGGAAAGGTCCAGGGAGGCTCCTCTGGGTCTCGGGCCGCTTGCCTAAAACCCTAAACCC<br>CGCGACGGGGGCTGCGAGTCGGACTCGGGCTGCGGTCTCCCAGGAGGGAGTCAAGTTCCTTTATCGAGTAAGGAAAGTTGGTCCCAGC<br>CTTGCATGCACCGAGTTTAGCCGTCAGAGGCAGCGTCGTGGGAGCTGCTCAGCTAGGAGTTTCAACCGATAAA |
| 75 | AIRE | TTCGGAAGTGAGAGTTCTCTGAGTCCCGCACAGAGCGAGTCTCTGTCCCCAGCCCCCAAGGCAGCTGCCCTGGTGGGTGAGTCAGGCCA<br>GGCCCGGAGACTTCCCGAGAGCGAGGGAGGGACAGCAGCGCCTCCATCACAGGGAAGTGTCCCTGCGGGAGGCCCTGGCCCTGATTG<br>GGCGCCGGGGCGGAGCGGCCTTTGCTCTTTGCGTGGTCGCGGGGGTATAACAGCGGCGCGCGTGGCTCGCAGACCGGGGAGACGGG<br>CGGGCGCACAGCCGGCGCGGAGGCCCCACAGCCCCGCCGGGACCCGAGGCCAAGCGAGGGGCTGCCAGTGTCCCGGGACCCACCGC<br>GTCCGCCCCAGCCCCGGGTCCCCGCGCCCACCCCATGGCGACGGACGCGGCGCTACGCCGGCTTCTGAGGCTGCACCGCACGGAGAT<br>CGCGGTGGCCGTGGACAG |
| 76 | SUMO3 | ACGCACACTGGGGGTGTGATGGAAAGGGGGACGCGATGGATAGGGGTGGGCGCACACTGGGGGACGCGACGGGGAGGGGTGAGCAC<br>ACACTGGGGGTGTGATGGAGAGGGCGACGCAATAGGGAGGGGTGGGCGCACACCAGGGACGCGATGATGGGGACGGGTGGGCGCAC<br>ACCAGGTGGCATGATGGGGAGGAGTGGGTACACACCATGGGGGGCGTGATGGGGAGGCGTGGGCGTACACCGGGGGGCGCGATGGG<br>GAGGGGTGGGCGCACACCGGGGGACGCGATGGAGGCGGTGGGTGCACACGGGGCGCGATGGGTGGGAGTAGGTGCACACTGAGGGC<br>ACGATTGGGGAGACACGAAGGAGAGGGGTGGGCGCACACTGGGGGACGCGATGGCCGGGACACGATGCGGAGAAGTGGGTGAATACC<br>GGGGTCGCGATGGGCGCCCTGGAAGGACGGCAGTGCTGCTCACAGGGGCCAGGCCCCTCAGAGCGCGCCCCTTGGGGGTAACCCCAG<br>ACGCTTGTTCCCGAGCCGACTCCGTGCACTCGACACAGGATC |
| 77 | C21orf70 | CCACAGGGTGGGGTGCGCCCACCTGCCCTGTCCATGTGGCCTTGGGCCTGCGGGGGAGAGGGAATCAGGACCCACAGGGCGAGCCCC<br>CTCCGTAGCCCGCGGCACCGACTGGATCTCAGTGAACACCCGTCAGCCCATCCAGAGGCTAGAAGGGGGA |
| 78 | C21orf123 | TTGAGGTCTCTGTGCATGCTTGTGCGTACCCTGGACTTTGCCGTGAGGGGTGGCCAGTGCTCTGGGTGCCTTTGCCAGACAACTGGTCT<br>GCCGGGCCGAGCATTCATGCTGGTC |
| 79 | COL18A1 | TGACGCGCCCCTCTCCCCGCAGCTCCACCTGGTTGCGCTCAACAGCCCCCTGTCAGGCGGCATGCGGGGCATCCGCGGGGCCGACTTCCAGTGCTTCCAGCAGG |
| 80 | PRRT3 | AACACACTGTCTCGCACTAGGTGCTCGCGGAAGAGCGCGGCGTCGATGCTGCGGCTCAGGTTGATGGGCGATGGCGGCCGCAGATCCA<br>GCTCGCTCAGCGATGGCGCCGGTCCCACACCGTTGCGGGACAGTCCCGGGCCACCCTGGGGTCCGCGACCCAACGACGCAGCCGAGC<br>CCCAGGCGCCTGAACTGGGCGTGGCCAGCTGCCCACTCTCCGCCGGGTTGCGGATGAGGCTCTTGCTGATGTCCAAGCTGCCTGCACC<br>AACGTTGCTGGGCCCTGCATAGCAGTTATTGGGTCGCTCCGGCACCTCGCTCTTTCCTGACGGCGCCGGGCACGCCAGACGCATCAGCT<br>TAGCCCAGCAAGCGTGCTCCGTGGGCGGCCTGGGTCTCGCGGCAGCCACCGCGGCCAACGCCAGGGCGAGCGCCCATGTCAGCTCCA<br>GGAGGCGCAGCCAGAAGTGGACACCCCACCAGGCCCACGAGAAGCGGCCCACGCGGCCTGGGCCCGGGTACAGCCAGAGCGCAGCC<br>GCCAGCTGCAAGCCGCTAGCCAGCAGCCCCAGCGCGCCCGCCACAGCCAACAGCCGAGGGCCCGGGCTGGCATCCCAGCCCCGTGGG<br>CCGTCCAGCAGGCGGCGACGGCACAGGCAGAGCGTGCCCAGAGCCAC |

TABLE 6A-continued

| SEQ ID NO | GENE NAME | SEQUENCE |
|---|---|---|
| 81 | MGC29506 | GTCTGCACGAAGCCCGCGGCGGCCTGCAGGGGGCCCAGCGACTCGTCCAGGGAACCGGTGCGCAGGAGCAGCCGGGGGCGCGGCGC<br>GCCGGCCGCCCTTGGGGGACTCTGGGGCCGGGGGCGCAGCTCGATCTGACGCTTGGGCACTGTCCGGGGCCTGGCGGGCGCGGCGC<br>CCTCCTCCAGAGCCACCTCCACACACTCGAACTGCGCTGGGGCGGCAGGACTTGGCCCACGGGGCCGCAGCTCTAGGTAGGTGGCCCA<br>GCGGGAGCCACCATCGGGGACCTGGGACTGGCGTGGGACCGCGGCGGGAGACGCTGGCCCCGGCGGCAAGGGGCTGATGAAGGCCG<br>GCTCCGTGAACTGTTGTTGCGCCTCGCGATCGTCTGCGCCGGAGCAGCCGAACAGGGGTCCGACGCCGAAGATGACTTCCATCTCCCCC<br>GACGGCAGCGTGCGCAGCTGGGGCTGGGGTGGCCGTGGGCCGGAACCTGGGCCTCGCGGGAAACCCGAGCCGGGCCCGTGCCGCTG<br>GCGGCTATTCTGGGCGCTGACGGACAGGCGAGGCTGCGCGCCCGCCCCCCGCCCAGGAGCCACCCAGGGCCAATTCGCTGGGCCTTT<br>CGCGTCCGGCCCAACGTCCGGGGGCTCCGGAGAACCTGGAGCCGTGTAGTAGGAGCCTGACGAACCGGAGGAGTCCTGGCGCCGCGC<br>GGGGGCCGTGGGCAGCTGCCTCGGGATCCCAGGCAGGGCTGGCGGGGCGAGCGCGGTCAGCATGGTGGGGCCGGACGCCGTGCACT<br>ATCTCCCTCGCATTCGCCTCCGCTGGTGGCGC |
| 82 | TEAD3 | CTGGAGAGAACTATACGGGCTGTGGGAGTCACCGGGCGACTATCACCGGGCCTCCTTTCCACATCCTCCTCCGGGAAGGGACCCCGTTC<br>CGGGCCTCGACCGGCGCAGACTGGGCTGACCCACTTTCTTGGGCCCACTGAGTCACCTCGAAACCTCCAGGCCGGTAGCGGGGAGGAG<br>AGGAGGAGCAGGCGGGGGTGCCAAGGTGTGGGCTGCGCCCTGGTTAGGGGGCGAGCCCGGCTTGTTTATGAGGAGGAGCGCGGAGGA<br>GGATCCAGACACACAGGCTTGCGCGCCCAGACTCGCCCGGCCAGCGGCTGGCGGCCTCCGACGTCACCAAACCGGTTGGGTGAGAGG<br>GCAGAGAGCAGGGGGAAGGGCCGCAGTCCCGCCCGCGCCCCCCGGCACGCACCGTACATCTTGCCCTCGTCTGACAGGATGATCTTCCG |
| 83 | chr12 group-00022 | GAGTGCGGAGTGAAGGGGTGCACTGGGCACTCAGCGCGGCCCTTGGGAGGCAGGGCCGCCCCAGCCTGCCCTCCTGTCTGGGAAGGC<br>CGTCCAGAAGCAGGAGCCCCGGGGAAAACAACTGGCTGGACGGGGCGGCCTTCAGTGTCTCTCCCAGCCTGAGAGTCGCTTCCCACCA<br>CCTGGGCACGAACCTGCTCTGCGATCTCCGGCAAGTTCCTGCGCCTCCTGTCGGTAAAATGCAGATCGTGGCGTCTT |
| 84 | CENTG1 | TCTTCTTTCCGCCCCTAGGGGGCACAAGCGGGCATGTCCAAGCGCCTAGGAGCCCGTACCGCTGGGGACCTCCCCTTCCGCGAACCCC<br>GAGCGGGTAGACCCAGAGCAATCCGAGTGTGGAAACAATGGAGAGGGGGCGTGTTGAGCTGGGGTCTCCATGCCTCGTTGGGGAGAGG<br>GAGGTGAGTTTGTGTCTTCTGGAAGGCGTGGGGGCTGTGCCCTCGTGGGGGTAGGAAGTGCTCCCGTGGGGCGGGGTGCGGATCGGA<br>GAGGTGAGTGGGTGCGTCTGTCCAGCGGTCCGCCCGGTGTGGTCGTGCCCGGCCCGCGTGGGGATGGGGGTGTCTCTCCCGCTGGGC<br>AACTATACCAGCGCAACCGGGGCGTCGGCGCGGCCCACGCTAGCGGCGCTGCTCCGGCGGCGGGGGCTGGGCGTGGCGGTGATGCT<br>GGGCGTGGTGGCCGCGCTGGGCGTGGTGGCCGCGCTGCCGCCCTCACCCGGGCAGCCGTGCTGGAGAAGGATGTCGGCGCACAGCT<br>GGCTTCCAGCCTGGCGGGCGTAGAACAGCGCCGTGCGGCCCTGGGCGTCACGGGCCGCCACGTCCGCGCCGTACTAGAGGGCGGAAA<br>CGGCCGCGTGACCGCGCGTCCCCAGGGCGCCCACACCCGGCGCCGCCTCCCCCACATGGCCAAGCCTACTTCCGGGGTCCCTCTGGG<br>AATTTCGGGCTTTCCCGCGCCAGGCGTTTTCCGAGATGAAGCCTCAAAGACCCCCTTTCCTCCCCCCAGCTCACGTACCCACAGCAGCAG<br>TTGCGTGATGACGACGTGGGCGAGCTCGGCCGCCAGGTGGAGTGGGGAGCGCAGCTGTGGGTCCTCTACGCTGGTGTCGAGCGGCCC<br>GTGTCGCGCATGGGCCAAAAGCAGGAGAACGGTAGCCACGTCCTGGGCCTGCACGGCGGCCCACAGCTGGCGGCCCAGCGGCTCCTC<br>CGAGGTGCTCAGCGGCGCCAGGAACAGTAGCTGCTCGTACTTGGCGCGAATCCACGACTCGCGCTCCTCCCTGCAAGACCAGGGATCAA<br>CGGAAAAGGCTCTAGGGACCCCCAGCCAGGACTTCTGCCCCTACCCACGGGACCGTCTCAGGTTCGCACACCCTCAGCAACCCTCCCCC<br>CGCTCTGTTCCCTCACGCTTACCGCGAAGAGTCCCGCGAGGGCTTGGCACGGCCTCGCGTGTCGCTTTCCCACACGCGGTTGGCCGTGT<br>CGTTGCCAATAGCCGTCAGCACCAGGGTCAGCTCCCGTGGCCAGTCGTCCAAGTCCAGCGAGCGAACGCGGGACAGGTGTGTGCCCAG<br>GTTGCGGTGGATGCCAGAACACTCGATGCAGATGAGGGCGCCCAGGTTCAAGCTGGCCCACGTGGGGTCTGCGGAAGGAGCGTAGAGG<br>TCGGCTCCCAGCCGGGCAGCACAGGCACCCCGGCATTCACTACACTCCCTAGCCCCTCCGCTGCCTCCTGGCACTCACTGGGGGCCCC<br>GCAGTCCACGCAGATTGAATTCCCCTTGGCGTTCCGGATCGCCTGGAT |
| 85 | CENTG1 | AGCCAGGTCCAGCCCCCGCGCCTGACACCGGCCGGACGTTCCCGGGGCGCCGCAGCTGCGGCGGGAACTCTGGGATCCGGAGCCATC<br>TGCTCCCACCCGCTCCGGAGCCAAACCCCGGGGGCCGCCTCCGCTCCCGGACCCGCCTCCTCTCCCGGGAGTGTGAGCCGAACCAAGA<br>GTCTCCTGCCTATCTCCTCCAGTAGGAAAATAGTAATAATAATAGACACCCTGCCCCCGTAAAAAACACTACCTTCCCCGTACCGCCTCCC<br>AAGTCTCCCGGGGTACGGATTGCCTTTGCAGCAGTTCCGCCCCACCTGACTCACTCCAGGGTCAGCCCCGGGTGGGTTTCAATGCGGCT<br>CTGGGGAGGGGGTGGGCAGTGGGGGAAGTGAGGCTTCCTATCCGCCCCCTCTCACTTCACATTTAAATATTCTGCACGTTCCAGCCCCC<br>GCGGACTCGCGTACCGCCCAATCCGCCTTCACCGCACGAAAAACATCACTAGCCTGCTCTCAGCCCAGGGGACGACTAGTCCCTGGCGA<br>GAAGCTGCCTGCAAGGTCACTGTCATGCCACCTGCCCCAAGTGCTCAGGGGAAACTGAGGCTTCCTCATCCCCTTCACCTTCAACGTCGC<br>TCTAAACACGGCAAAGCCCCGTTTCCATGCTCCCAGAGTTCAGCTGAGGCTGGAAGTGGGGTCCTGGGCTTCTCTGGGAGCAATTTTCTA<br>GTCACTCTGATCAAGGACGTTACTTTCCCAGAAAGCTCTGAGGCTGAGTCCCTCTGAAATCAAGTCCTTTCTCCTGTCGCACAATGTAGCT<br>ACTCGCCCCGCTTCAGGACTCCTATTCTTTGCCCCAATCCTTGACAGAGGGGTGAGCTTGGTTCATCCGCCCACCCCAGAGAAAAGCTTC |

TABLE 6A-continued

| SEQ ID NO | GENE NAME | SEQUENCE |
|---|---|---|
| | | CCTAGTTTCCTGGACCTCGCTCCTCCACCCCAAGCTGAGCATTCCAGGTACCCTTCCCTCCCTGTTCTCAAGCCCTGACTCAACTCACTAG<br>GGGAAGCGCGGAGCTCGGCGCCCAGCAGCTCCCTGGACCCGCTGCCAGAAGACAGGCTGGGGGGTCCGGGAAGGGGCCCGGAGCCA<br>GGAGGCCCTCCTGTGCTCTTGGTGAAGATGCCGCTGATAAACTTGAGCATCTTGCGGTCACGAGTGGATGCTCGGCCCCCCTCCCGGCC<br>CCGTTTCAGCCCCGGAGCTGGAGGCTCCAGAGTGATTGGAGGTGCAGGCCCGGGGGGCTGCGCGGAAGCAGCGGTGACAGCAGTGGC<br>TGGACTCGGAGTTGGTGGGAGGGTTAGCGGAGGAGGAGAGCCGGCAGGCGGTCCCGGATGCAAGTCACTGTTGTCCAAGGTCTTACTC<br>TTGCCTTTCCGAGGGGACAACTTCCCTCGGGCTCCAGCCCCAGCCCCGACCCCACCAGAGGTCGAAGCTGTAGAGCCCCCTCCCCCGG<br>CGGCGGCGGCGGTGGCGGCGGCAGAGACCGAAGCTCCAGTCCCGGCGCTGCTCTTTGACCCCTTGACCCTGGGCTTGCCCTCGCTTTC<br>GGGCCATGACAGGCGGCTACCCGCGCCCTTGCCCCCGCCGGCTTTGGCTCCACTCGTGGTCACGGTCTTGCAAGGCTTGGGAGCCGGC<br>GGAGGAGGCGCCACCTTGAGCCTCCGGCTGCCGGTGCCAGGGTGCGGAGAGGATGAGCCAGGGATGCCGCCGCCCGCCCGGCCTTCG<br>GGCTCCGGGCCGCCCCAGCTCGGGCTGCTGAGCAGGGGGCGCCGGGAGGAGGTGGGGGCGCCCCCAGGCTTGGGGTCGGGGCTCAG<br>TCCCCCGGAGAGCGGGGGTCCCGGAGGGACGGCCCAGAGGGAGAGGCGGCGGCCGGGAGCGGGGGAGACTGGGCGGGCCGGACTG<br>GCCGGAGCCGGGGACAGGGCTGGGGGCTCCGCGCCCCCGGTGCCCGCGCTGCTCGTGCTGATCCACAGCGCATCCTGCCGGTGGAAG<br>AGACGTTCGTGCCGCTTCTTGCCCGGCTCCTCCGCGCCTCGGGGGCTGCCAGGATCCCCAGTCTCGGAGCCTCTGGCACCGGCGGCGC<br>CGGCCGCGGCCGCAGACGGAGAAGGCGGCGGCGGAGGCACCGACTCGAGCTTAACCAGGGTCAGCGAGATGAGGTAGGTCGTTGTCC<br>GGCGCTGAAGCGCGCCCGCGCCCCGGCTCATGGGGCCCGGAGACCCCCGAGCTGGGGAGGGGAGGGGACTCCCCCGGACTGCCTCA<br>GGGGGGCCCGGCCATGGGGCCGCCCTGCTCGCTGCCCCCAGCCCCCGGACCCCGCTGAGCCCCCGGCCCGGCTCCGCTGTCGCCGC<br>CGCCTCCGCCGCCTCCGCTTGCGCCCCCCTCCCATCACATGGGGCGCCCCCTCCCCATGCTCCCCGCCCTGCGCCCCCACCCTCTTGG<br>AGCCCCGGGACCTTGGTGCTGCTCCAGGGAGGCGCGCCGGACCGTCCACCCCGGCCTGGGTGGGGGCGCTGAGATGGGTGGGGGAG<br>GGCGGGGAGGACAGTAGTGGGGGCAAATGGGGGAGAGAGAGGAAAAGGGAGCAGAAAAGGGGACCGGAGGCTAGGGGAAACGAACCT<br>GTGCGGGGGAGGCAGGGGCGGGGAATTGGGACTCAAGGGACAGGGGCCGCGGATGCGGTCGGAAAGAGGGTCTAGAGGAGGGTGGG<br>AAGCTAGTGG |
| 86 | chr18 group-00304 | AGGAGCGCAAGGCTTGCAGGGCATGCTGGGAGAGCGCAGGGAACGCTGGGAGAGCGCGGGAAATACTGGGATTGGCTCCCGAGGGCT<br>GTGAGGAGGGCACGAGGGGACACTCCGATGAAGGCAGGGCACGCGGGGCGAGCCGGGAGCGTCTCCTGAGGGCAGCGAGGAGGGAG<br>CTGAGGCACGCGGGCTCTCAATCGACGCCCCACAGAGACCAAGAGGCCTGGCCTTGGGGGGCAGCTGCTTGAAGGAGGCAGAGCGGA<br>AGCGAGGGAGACTGCTGGAGGCCCTGCCGCCCACCCGCCCTTTCCTCCCCCTGAGGAGACGCCTGACGCATCTGCAGTGCAGGAGGCC<br>GTGGGCGTTAGAAGTGTTGCTTTTCCAGTTTGTAAGACCATTTTCCTGATTCTCTTCCCCACGGTTGCGGAGGAGCAGGTCAGGGCCGCCATGAGGGCAGGATC |
| 87 | TSHZ1 | TCGACCGCTACTATTATGAAAACAGCGACCAGCCCATTGACTTAACCAAGTCCAAGAACAAGCCGCTGGTGTCCAGCGTGGCTGATTCGG<br>TGGCATCACCTCTGCGGGAGAGCGCACTCATGGACATCTCCGACATGGTGAAAAACCTCACAGGCCGCCTGACGCCCAAGTCCTCCACG<br>CCCTCCACAGTTTCAGAGAAGTCCGATGCTGATGGCAGCAGCTTTGAGGAGGC |
| 88 | CTDP1 | TGTGCCGTCGCACACAGACGCCCTCAACGTCGGAGAGCTGTGAGCGGGGCCGTGCTCTTGGGATGGGAGCCCCCGGGAGAGCTGCCC<br>GCCAACACCACTCCGACGTGATCCATGCTGGACATAAAGTGCTCTTCCCTCCGCTAGTCATCGGCCGAGCGGGCCCCTCGCTCCTGGGT<br>GTAAGTTCTTTCTGTGCGTCCTTCTCCCATCTCCGTGCAGTTCAG |
| 89 | KCNG2 | CCATGCGCCGCTGCGCGCGCGAGTTCGGGCTGCTGCTGCTGTTCCTCTGCGTGGCCATGGCGCTCTTCGCGCCACTGGTGCACCTGGC<br>CGAGCGCGAGCTGGGCGCGCGCCGCGACTTCTCCAGCGTGCCCGCCAGCTATTGGTGGGCCGTCATCTCCATGACCACCGTGGGCTAC<br>GGCGACATGGTCCCGCGCAGCCTGCCCGGGCAGGTGGTGGCGCTCAGCAGCATCCTCAGCGGCATCCTGCTCATGGCCTTCCCGGTCA<br>CCTCCATCTTCCACACCTTTTCGCGCTCCTACTCCGAGCTCAAGGAGCAGCAGCAGCGCGCGGCCAGCCCCGAGCCGGCCCTGCAGGA<br>GGACAGCACGCACTCGGCCACAGCCACCGAGGACAGCTCGCAGGGCCCCGACAGCGCGGGCCTGGCCGACGACTCCGCGGATGCGCT<br>GTGGGTGCGGGCAGGGCGCTGACGCCTGCGCCGCCCAC |

TABLE 6B

| SEQ ID NO | GENE NAME | SEQUENCE |
|---|---|---|
| 90 | TFAP2E | GTCCTAACATCCCAGGTGGCGGCGCGCTGGCTCCCTGGAGCGGGGCGGGACGCGGCCGCGCGGACTCACGTGCACAACCGCGCGGGA<br>CGGGGCCACGCGGACTCACGTGCACAACCGCGGGACCCCAGCGCCAGCGGGACCCCAGCGCCAGCGGGACCCCAGCGCCAGCGGGAC<br>CCCAGCGCCAGCGGGACCCCAGCGCCAGCGGGACCCCAGCGCCAGCGGGACCCCAGCGCCAGCGGGTCTGTGGCCCAGTGGAGCGAG<br>TGGAGCGCTGGCGACCTGAGCGGAGACTGCGCCCTGGACGCCCCAGCCTAGACGTCAAGTTACAGCCCGCGCAGCAGCAGCAAAGGGG<br>AAGGGGCAGGAGCCGGGCACAGTTGGATCCGGAGGTCGTGACCCAGGGGAAAGCGTGGGCGGTCGACCCAGGGCAGCTGCGGCGGCG<br>AGGCAGGTGGGCTCCTTGCTCCCTGGAGCCGCCCCTCCCCACACCTGCCCTCGGCGCCCCCAGCAGTTTTCACCTTGGCCCTCCGCGGT<br>CACTGCGGGATTCGGCGTTGCCGCCAGCCCAGTGGGGAGTGAATTAGCGCCCTCCTTCGTCCTCGGCCCTTCCGACGGCACGAGGAACT<br>CCTGTCCTGCCCCACAGACCTTCGGCCTCCGCCGAGTGCGGTACTGGAGCCTGCCCCGCCAGGGCCCTGGAATCAGAGAAAGTCGCTCT<br>TTGGCCACCTGAAGCGTCGGATCCCTACAGTGCCTCCCAGCCTGGGCGGGAGCGGCGGCTGCGTCGCTGAAGGTTGGGGTCCTTGGTGC<br>GAAAGGGAGGCAGCTGCAGCCTCAGCCCCACCCCAGAAGCGGCCTTCGCATCGCTGCGGTGGGCGTTCTCGGGCTTCGACTTCGCCAGC<br>GCCGCGGGGCAGAGGCACCTGGAGCTCGCAGGGCCCAGACCTGGGTTGGAAAAGCTTCGCTGACTGCAGGCAAGCGTCCGGGAGGGGC<br>GGCCAGGCGAAGCCCCGGCGCTTTACCACACACTTCCGGGTCCCATGCCAGTTGCATCCGCGGTATTGGGCAGGAAATGGCAGGGCTGA<br>GGCCGACCCTAGGAGTATAAGGGAGCCCTCCATTTCCTGCCCACATTTGTCACCTCCAGTTTTGCAACCTATCCCAGACACACAGAAAGCAAGCAGGACTG<br>GTGGGGAGACGGAGCTTAACAGGAATATTTTCCAGCAGTGA |
| 91 | LRRC8D | CACCTTCCCCGAGGTAATTATTTTCTGGGGGGTAGGGGTGGGGGTTGGGAGGGTGAAGAAAGGAAGAAAAAGAAGGCCGATCACACTGG<br>GCACCGGCGGAGGAAGCGTGGAGTCCATTGATCTAGGTACTTGTGGGGAGGGGAGAACCCGAGCAGCAGCTGCAAACGGAAGGGCTGTG<br>AGCGAGCGGGCGGGCGGGTGGCTGGCAGCGAGGCCACCAGCAGGGGGGGCCCGGGCCGAGGCCGCGCCACCTCGGCACCACGCGGG<br>CAGCCGGTGCGGCGGGGTCGCCACGGCCAGGGGAGCGCTGGGTGCCCACCATGGCAGTTATGCAAGCGGTGACCCCCTGGTCTTGCCT<br>CCCCGCCGCCCTGCACTCCTTCCTCCCCGCTGCCGACACTTGGATCTCTCTAGCTCTTTCTCTCCCCTGTGTTTTCAAACAGGAAGTGCAC<br>GGCTGTCTATAACGTGCTGCCGGGTCTCAGGATGGAGGAGTGAAGTCTCCTGTCGCCGTGGTTCCAGCCTCCGGAGCTCGCCCAAGCCG<br>CGTCCCCAGAGAGCGCCCTGAGAGAACAGGGTGGCCGCTTGGTCCAGGTGCGCGGGGTCGGGTCTGGGTCCAGGGAGCGGGTCGGGAA<br>GTCTGCGGCACGGAGCACTGCTAGTGTCGGATCTGCATCTCCAGCTCTGTGCTGCAGCTTCACTTGCCCGCCCCCCACCACTGGCTTCTC<br>ACCCGGGGTCTCTGCCAAACTCTGGCTGCTGCCGCCCTGGGTTCGGGCCGGCGGAAGGCCCTGGGCGTGCGCTGCGGAGCCGCCTGCG<br>AGGACTCCACTAGGGCGCTTTCCAGGCTGGACTGCCCCGGGCTGCGCTGGAGCTGCCAGTGCTCGGGGAGTCTTCCTGGAGTCCCCAGCTGCCCTCTCCACC |
| 92 | TBX15 | CTCTTCCCAAGTTACGCCACCGGTCGAGGACGGCAGGAGACCCCCGAGTGCAGAGAAAGCTCAAACCGGCAGCGAAGTCGGTCCTAGCC<br>AAGCTGAAAAAACGTCTCGGATTTCGCGGACAGCGGCCTAGACACAGCCCGATCTTCCAGTCCTAGTGCCCTGGTCGAGACGGTTCTATCCTTTTGCAAAGAAGCCGGAAA |
| 93 | C1orf51 | TCTCGGTTGCAATCCCCACCCTCCTCACCCAGCAGGGCAGGAGGCACCCAACTTGGAGGAGAAAGGGGTGGGGGAGGTGAAACAGAGAC<br>CGGAGAGTCACGAGGGCTGGGCCGCCGAGAGCAGGAGAATATACCGTGTCACACACCTCCATTCTCTCACACACGTTGCAGACACAAATC<br>ACTGACGGTTTCCACGTGCTGCGCTCGTGAGCGGAGGTGTTCAAAGAGGGGGCAGATGAGTTACTTCCCGAGACGGAACCGGGGGTCCC<br>ACGTCCGCCGCCTTCAGTAGCACAACCAATCTCTGAACACTCAAACCGCGCATCTCTGGCGCATCACCATCCTATTTAAGGCCACGGGCTCCGCCCTTTTC<br>CTCCCCTCCCTTCTTTTCCACTCTTTTTCCA |
| 94 | chr1: 179553900-179554600 | CTGCCAGAGATGTGTCTGTCTTGCGCCCCGCATGCACTGCCTGCGGGGCTGCGCTGCACTCCCCGGCGGCGCCACGGGTCTGGCCCCC<br>GCGCTTCTACGTGTTGGGGGGATGCATGGACCTTGGAGATCCGTAGTTGGCCCTAACCTTCTCGGAATCTCCTCTGCACGCGCTGCCTGTT<br>CCTCCTCTGCACGCTCTGTCCGTTCCTTTGCAACTTCTGTGGGAATTGTCCTGGCGTGGGAAACGCCCCCGCGCTCTTTGGCACTTAGGGT<br>GTGAGTGTTGCGCCCCTTGCCGCAGCGCTCAGGGCAGCATCCCGCTCGAGGATGCAGGGTTCTCACCAAGCAGTGAGGGGGACTCACGC<br>GCCGCCGGGGAGCGGAGCCAGGCTCCGAGAAGGGAGCAGGCTCGAGCCGCTGGGTTTTCGCAAGCCTTGGGGCCTCTGGCCGCCCTTC<br>CATGCCTCCGGGCGCGGGCGGCTCAGCAGGTCCCCGGCTTCGGGAAGTTTTGTGCGCGGATCGCTGGTGGGGAGGGCGCGCGGGCCA<br>GTGGCTGAGCTTGCAGCGAAGTTTCCGTGAAGGAAACTGCATGTGCCTTTGGAGGCGACTCGGGACTGCTGTAGGGTGGACTGGGTGTCTATGGAGTTGC<br>GGGTCAGAGCGAGTAGGGTGGGTCCTTTCCTGGGACAGGACTGGGAATTGGGGCTCGAAGTAGGGG |
| 95 | ZFP36L2 | AGGGGTGTCCTCCAACATCTCTGAACCGCCTTCCCTTCCTCCTCACTGGCGCCCTCTTGCCTCAGTCGTCGGAGATGGAGAGGCGGCTGA<br>AGATTGGCAGGCGGCGGCCAGGGTCGAGGCTGGGAGACTCAGAGCCGCTGAGGCTGCCGGAGCTCAGGGAGCCGCTTAGGTAGCTGTCGCGGTCCGAC<br>AGCGAGTCCGGG |

TABLE 6B-continued

| SEQ ID NO | GENE NAME | SEQUENCE |
|---|---|---|
| 96 | SIX2 | TCTGACTCTCGGGCTGGAGCAGCCGAGACAGCGCTCCCCAGCGGGACTACAGAATCCCGGGTGTCGGCCTGGGGGCCCTGGATTGGCA<br>GTGGTGGAGTCTTCTGAGCCTAACAGCTACTAGGAATGACAGAGTTGCAGATGGCTTTGTCGCCCGCGGGGCGGCTCAAGCGTCCTGGGT<br>CCCAGGCCTCTGTCCTACGGCCAGGCCGCCGGCTCAACGGGCCGAAGGGAATCGGGCTGACCAGTCCTAAGGTCCCACGCTCCCCTGAC<br>CTCAGGGCCCAGAGCCTCGCATTACCCCGAGCAGTGCGTTGGTTACTCTCCCTGGAAAGCCGCCCCCGCCGGGGCAAGTGGGAGTTGCT<br>GCACTGCGGTCTTTGGAGGCCTAGGTCGCCCAGAGTAGGCGGAGCCCTGTATCCCTCCTGGAGCCGGCCTGCGGTGAGGTCGGTACCCA<br>GTACTTAGGGAGGGAGGACGCGCTTGGTGCTCAGGGTAGGCTGGGCCGCTGCTAGCTCTTGATTTAGTCTCATGTCCGCCTTTGTGCCGG<br>CCTCTCCGATTTGTGGGTCCTTCCAAGAAAGAGTCCTCTAGGGCAGCTAGGGTCGTCTCTTGGGTCTGGCGAGGCGGCAGGCCTTCTTCG<br>GACCTATCCCCAGAGGTGTAACGGAGACTTTCTCCACTGCAGGGCGGCCTGGGGCGGGCATCTGCCAGGCGAGGGAGCTGCCCTGCCGC<br>CGAGATTGTGGGGAAACGGCGTGGAAGACACCCCATCGGAGGGCACCCAATCTGCCTCTGCACTCGATTCCATCCTGCAACCCAGGAGAA<br>ACCATTTCCGAGTTCCAGCCGCAGAGGCACCCGCGGAGTTGCCAAAAGAGACTCCCGCGAGGTCGCTCGGAACCTTGACCCTGACACCTG<br>GACGCGAGGTCTTTCAGGACCAGTCTCGGCTCGGTAGCCTGGTCCCCGACCACCGCGACCAGGAGTTCCTTCTTCCCTTCCTGCTCACCA<br>GCCGGCCGCCGGCAGCGGCTCCAGGAAGGAGCACCAACCCGCGCTGGGGGCGGAGGTTCAGGCGGCAGGAATGGAGAGGCTGATCCT<br>CCTCTAGCCCCGGCGCATTCACTTAGGTGCGGGAGCCCTGAGGTTCAGCCTGACTTTCCCGACTCCGCCGGGCGCTTGGTGGGCTCCTG<br>GGCTTCTGGGCTCACCCTTACACCTGTGTACTAAAGGGCTGCTACCCTCCCGAGGTGTACGTCCGCCGCCTCGGCGCTCATCGGGGTGTT<br>TTTTCACCCTCTCGCGGTGCACGCTTTTTCTCTCACGTCAGCTCACATCTTTCAGTACACAGCCACTGGGTCTCCCTGCCCCTCCAGCCTTT<br>CCTAGGCAGCTTTGAGGGCCCAGACGACTGAAGTCTTACTGCTAGGATGGGAACACGATGAAAAAGGAAGGGGCCCAGTCAAAAGTCCTC<br>TCCTCTTCGGTTTTTCTTCAACTGTCCTTCACAAAAACATTTATTTCTGTCCCAGCGCCCTGGCGGATTTCGGCAGATGGGCCCTAGGGGGT<br>TGTGGAGGCCAAATTCCCAGGATGCTGGTCCTGCCTTTTTCATTGGCCAAAACTGTATTTCCTACAACGACTAAAGATAACCAAGAACTGAG<br>TAGACCCTGTTCTCTCACCAGATCTCCCTGGCTCTGTTTAACTTTTCCTGGTGCAATGCGATGGCACCACCAGCTCCCCAGGCAGGCACCA<br>CTCCCTCAAGATACCATTTGGGGTAGGGATTTGAGTCCTGGAGAGGGTCAGCGGGGCGCCGGGGTGGGGGTGGGAAGGAGACTGACAG<br>GGACACACCGCGAGCTCCGCATACTCTCCTCTGCCCCCTGTAGCCCGGGGCTTTAATGACCCCAAGCAGATTTCCTGTCTCTGGTCTAGCC<br>AGCTGCCCCTAGGGCTGGATTTTATTTCTTCATGGGGTTTCACCCTAAAGGGCCCCCTGGTCATGGGACCTGGTTGGGAACAAATGAAAGA<br>TGTCTTGTAGCAAATGCTTTCAGGGGAGCAGAAAAGAAGATTGGGCACTTCCAGTCACTTGGTCACTTTAGGTGGCTGGAACAAAACTGGT<br>GACTTTCACGACTGCTACAGGGTGAGGGGGTGAAGGGTGGCAGAGAGGTGACAAGCCACTGGGAATCCTATTCAGTGGGGATGCCGACA<br>GGGAGTGGCTGTAATCAACTGAGCAACATCTGTGTGAATGTTATTCACAGGTCAGGACAGCAGCTTGGTCTTCCCAGGTGAGGAACTGAGG<br>ACTGGCCTGCATAGATTTGTGCAGTAGGTGAGTAGCTTCCAAATTTATTTTCAGAACTTCCATGTAGTACCTGCCTCTCCATTTAAATATTTTT<br>TAAAATTTTATTTATTTAAATATTTTCTTGGTTAGCTTTCCAAGAGGGAGGAAAAGAGGGGAGTTGCAACAAGTAGTGCCCCTATGCTGGGAT<br>TCATTTTCCAGAGTAAAGCCTGGGACTGGCACCCTGACCCCTACCGGCAGGTGAAAACTCCAGGCAAACTGCTGAGATCCCACCTGGGCT<br>GGCTGAGATAGTGCCTGGGGTGCATCCCTCAGCAGCTGCCACCTGGGCCCTGGGGCCATCTCTTTCTCTGGCATCAAGCAGCCAGGTGTC<br>AAGGCCTTCCCAGCAATCCATGCTGCATGGCTGGGTCTTGTTCTAGCAGGTCGATGGGCAGGGACTGGTAGCTTAGCCAGGGCACCAGTG<br>CGTGGCTGTGGGTTTGTGTGCTTCTGTGGAGAAGCATGATGTGTATGTGTGTGTGTGGGCACAGGCATGAGGAAGGGTTCATTTGTGCAG<br>GTATCTCCCATGTATATCAGTGTGGGAGAGTGCCTGAGGATGTGTTTGTGTGTCTGAAAATGGGCGGAGGGTCTGTTGTGCTAATGTGTGC<br>AGGGGTGAACATGTGTGTGACAGTCTGTGTGTTTCCCTGAGTGGTGGCTGCGTGAGAGGGTGAGGGGATTTGGTGTTGTCTACCATGCCC<br>GGCACATAGCAGGCTCTTAATAATCTTGAATTTAATTAATGTTAAATGTGTATGTTCCCATCCTTGTGGAAGTTGGTATAGAGCCTGTTTTCCT<br>GTGATTGTGAGACTGGAAAATGGGGGACGGGCAGGGGCGAGACAGGATACAGAGGCTACTGTTTTCTTCCTCCCTAGAAGTAAGTACATA<br>GAAGAGTGGGCTCTGGCACCTCACGGGACATCACCAAGTCCTGTGTGGCTGGCTAGGCTGTCCCAAGGTGGCTTCAGGCATCACTTGAAT<br>CTTTTGAGACCTTCAGGCAGTAGCCTGCCATTCACCCTGTCAGTCAGCAGAAGTTGGGCCCACACAGGCCATAGAAACACAGAGCAGTTCC<br>CGGGAGGACCTGAGCTGTCCCTGAGAGCAGAGCTTCCAGGAGAGGCCGCAGGAACTGCCTTGACCGGAATTCCTCTTGGGGTGCAAAGG<br>TGGAGGGACACATGGTGCGACCCCAGGCAGAGGACTGCAGCCACTCCGTGCAGTCCCAGCCTCTGGGGTAGCCCCTTGACCTCCAGGCC<br>TGCACAGATCCAAGGCCGAGGTCCAGGCTCCAGCGCCAAATTAGCTGGCCTAGCAGCCTGCAGCCGCTCTAATCTCAACTAGGAAGGAAT<br>CCTTGCGCTTAGAAAGTCCAAGCGAAAGGGTATTCTGATTTTATCCCGGTTTTACCAGAAAATGCTGAAAGGAAAAGCCCCGAGAGGACAC<br>AGTGCTCTAGGAACTCGGGGCGCCACGAGCGCCTCATCCCCTCCCTTCCGCCCGGCCGCGGTGCCCTGGTCGCTGAGGGACGCGGTCA<br>GTACCTACCGCCACTGCGACCCGAGAAGGGAAAGCCTCAACTTCTTCCTCTCGGAGTCCTGCCCACTACGGATCTGCCTGGACTGGTTCA<br>GATGCGTCGTTTAAAGGGGGGGGCTGGCACTCCAGAGAGGAGGGGGCGCTGCAGGTTAATTGATAGCCACGGAAGCACCTAGGCGCCCC<br>ATGCGCGGAGCCGGAGCCGCCAGCTCAGTCTGACCCCTGTCTTTTCTCTCCTCTTCCCTCTCCCACCCCTCACTCCGGGAAAGCGAGGGC<br>CGAGGTAGGGGCAGATAGATCACCAGACAGGCGGAGAAGGACAGGAGTACAGATGGAGGGACCAGGACACAGAATGCAAAAGACTGGCA<br>GGTGAGAAGAAGGGAGAAACAGAGGGAGAGAGAAAGGGAGAAACAGAGCAGAGGCGGCCGCCGGCCCGGCCGCCCTGAGTCCGATTTC<br>CCTCCTTCCCTGACCCTTCAGTTTCACTGCAAATCCACAGAAGCAGGTTTGCGAGCTCGAATACCTTTGCTCCACTGCCACACGCAGCACC |

TABLE 6B-continued

| SEQ ID NO | GENE NAME | SEQUENCE |
|---|---|---|
| | | GGGACTGGGCGTCTGGAGCTTAAGTCTGGGGGTCTGAGCCTGGGACCGGCAAATCCGCGCAGCGCATCGCGCCCAGTCTCGGAGACTGC |
| | | AACCACCGCCAAGGAGTACGCGCGGCAGGAAACTTCTGCGGCCCAATTTCTTCCCCAGCTTTGGCATCTCCGAAGGCACGTACCCGCCCT |
| | | CGGCACAAGCTCTCTCGTCTTCCACTTCGACCTCGAGGTGGAGAAAGAGGCTGGCAAGGGCTGTGCGCGTCGCTGGTGTGGGGAGGGCA |
| | | GCAGGCTGCCCCTCCCCGCTTCTGCAGCGAGTTTTCCCAGCCAGGAAAAGGGAGGGAGCTGTTTCAGGAATTTCAGTGCCTTCACCTAGC |
| | | GACTGACACAAGTCGTGTGTATAGGAAGGCGTCTGGCTGTTTCGGGACTCACCAGAGAGCATCGCCAACCAGAACGGCCCACCCGGGGT |
| | | GTCGAGTCTTGGTAGGGAAATCAGACACAGCTGCACTCCCGGCCCGCGGGCCTTGTGGCATATAACCATTTATATATTTATGATTTCTAATT |
| | | TTATTATAAAATAAAAGCAGAAATATTTCCCGAAGAACATTCACATGAGGGCATTACGGGGAGACGGCAAGTCGGCGGCTCGGGGGGCGCGCTCAGCCGG |
| | | GAGCGCTGTAGTCACAGTCCCGGGAGGAAGAGCGCG |
| 97 | chr2: 137238500-137240000 | TGGAACAAGTGTCAGAGAGTAAGCAAACGACTTTCTGAGCTGTGACTCTGCTCCTCGACTGCCCACGTGCTCTCCGCTGTCTGCACTCCTG |
| | | CCTCACCTGGGCTGACTCGGACTCTCCACCTCCTTTGCTGCTTCCGGCATGAGCTACCCAGGAGCCTAAGGCGCTCCTTCCCGCAACTCC |
| | | GGTCCCCGCGCCCCGGGACTGCAAATCCTTTAAACAGAGGCCCCAGAGCTAGGGGTTTTCCCAGGCTCTGGTGGGCGTGGGCTGACAGT |
| | | CGCTGGGAGCCCCGCAACAGGGGGGATGTCCAGGCAGGTATGCACCCAGCTCCCGGCGTTTCCCGGAGTCACCACAATGTTTCCCTTTCT |
| | | CTCTCCCCCACGTATGCTGCTAGGGGTACTCCCCAGATAGGATTTTCTTTGTCTTTTCTCCTAGTAACACCGAAGCCCTCTCGTGCCCGGG |
| | | GACTGCAGAGGAACGCCAGACCATCCGGACCTTGCGGGATGGCTCGGTGTGTGTGTTTTACTGTGTGTCGGAGTGTCGCGCATGTGTGCG |
| | | TGTTGGGGCGCGTTATCAACAGGGGCCTAGGGCACCCCCACTCTTTCTTGCTCTCTTCCCCCATCACTTCATGGACCTCCGAGGCGCAAAG |
| | | CGCTCGACCCTCTCCTGGGCTCAGTGGCTTGGGTACTCCGGGCTGAGCTCAGCTGGGGAGTCCCCTTACCCAGCCCGCACCGGCACCCC |
| | | GAAGCTTCAAAGTTGCGGCAAACAGTTGCGGGGAGCAGAGGAACTGAGGTCCAGGCCAGCGCGCCCGCGGTCGCTCGCCTTGGGGAGC |
| | | AGGCTGAGCCGAGGGTCGTGCGGGTGCGCGGCAGAGGCGGTAGGAGGCGGAGGAGAGGGGGGAGAAAGAGGGGGCGGTGGGGAACA |
| | | GCTGCCGGGGTAGGCGAGGCGCAAGGTGGCTCCCCGCGGCCCCGCGCCCCGCGGCTCTCGGACGCACCAGGCAGCCAATGGCTGCGC |
| | | AGAGGTGTACAGCAGATGGCGTCTGACTGCGCCGTTCCTTCCTCCTCCTCCTCCTCCTCCTTCTCTTCCTCCTCCTCCTTCTCTTCCTCCTC |
| | | CTCCTCCTTCAGTGCTGAGGAGCCAGAGTCGCCGCCGGGTTGCCAGACGCTGGAATGGGTGGTCTTCCGACACACACCACCATCTTTCTT |
| | | GCGCTCGGGAAGCTCGGGGCTCAGCGGCTCCCAGAGGTTACGGCGGCGGCTCTGGCGAGACGGGTGAGTGCAAGCACGCGGAGCCCC |
| | | GAGTCGGGGATGCCGGGCCCCCTGGCCGGCCGACTGGGGCGCGGGGTGGCAGCGCCGGGGAAGGGGGCGCGCTGCCGGCGCAGACT |
| | | TTGCTCTTTCCTCGCCGGACAGCCATCGTCGCCCCTTCTCCCAGCCAGACGCGGGAACTTGGAAGCGGATCTTCTCGGACGCCTCTGGCTTGGGGCTGCG |
| | | GGAAGCGTGGGCTGCCCGGGGCGCAGTGTGCGGAGACCCTCTAGGCGGGCGGGGACGCCCCAC |
| 98 | MAP1D | GTTATTATCCACGGGGTCCTAATTAAAGCTTGATTAAAATGCCCTTCTTTCTCTAAAAAATTACGAACTAGGCAACTTCATACATTTTGAATGG |
| | | CGCAGTGTTTCCTCTTCCAACTGTTTAGTTTGTAGTATACTATGTAAGCAACATCAATTATCAACCCTTGCAAGATGACAACATGAGCCTGTG |
| | | GGGGAAGCACTTGAGGGGAGGGAGGAGAAACTTCTCTTTTTTAATAATCAGCCGGAAACAATGTTTAACAAGAATCTGATGAGGTCACTGC |
| | | AGTAAATATTTTTCCTCTTACAGAGCCAATCATCACGGAGGGATCCCCTGAATTTAAAGTCCTGGAGGATGCATGGACTGTGGTCTCCCTAG |
| | | ACAATCAAAGGTGTTTGCTTTCTGCTCTGTTGCTTTTAAATTGTATGGGAAAGGAAGATTGGTCCGACGGCGCGCTTGTGGCCCGGCCGGA |
| | | GCTTGCGTGCGCGTTCTGACGGCTGGGTGCTGTGTTACAGGTCGGCGCAGTTCGAGCACACGGTTCTGATCACGTCGAGGGGCGCGCAG |
| | | ATCCTGACCAAACTACCCCATGAGGCCTGAGGAGCCGCCCGAAGGTCGCGGTGACCTGGTGCCTTTTTAAATAAATTGCTGAAATTTGGCT |
| | | GGAGAACTTTTAGAAGAAACAGGGAAATGACCGGTGGTGCGGTAACCTGCGTGGCTCCTGATAGCGTTTGGAAGAACGCGGGGGAGACTG |
| | | AAGAGCAACTGGGAACTCGGATCTGAAGCCCTGCTGGGGTCGCGCGGCTTTGGAAAAACAAATCCTGGC |
| 99 | WNT6 | TCCCTGCTGTGGGACCCGAGGAGAGGAGAACTGGTTCGCT |
| 100 | INPP5D | TCTCTCTCTCTCTCTTGCTTGGTTTCTGTAATGAGGAAGTTCTCCGCAGCTCAGTTTCCTTTCCCTCACTGAGCGCCTGAAACAGGAAGTCA |
| | | GTCAGTTAAGCTGGTGGCAGCAGCCGAGGCCACCAAGAGGCAACGGGCGGCAGGTTGCAGTGGAGGGGCCTCCGCTCCCCTCGGTGGT |
| | | GTGTGGGTCCTGGGGGTGCCTGCCGGCCCGGCCGAGGAGGCCCACGCCCACCATGGTCCCCTGCTGGAACCATGGCAACATCACCCGC |
| | | TCCAAGGCGGAGGAGCTGCTTTCCAGGACAGGCAAGGACGGGAGCTTCCTCGTGCGTGCCAGCGAGTCCATCTCCCGGGCATACGCGCT |
| | | CTGCGTGCTGTGAGTACAACCTGCTCCCTCCCCGGGCACAGATATGACAGAGGGGCTTAGAGGGGGCCCAGCTTTGAGATGGGTTGTTCTTATGTCACAG |
| | | GACAGAGTGATCTGACATGCACACTTCCCCGCCACCCTGTCAT |
| 101 | chr2: 241211100-241211600 | TGTCCTCGAAGAAGGGCCTGAGCAGCAGCAGAGGACCCCAGGCGACCGTGCCTGAGCCGGGCGCCGACGACGACTGAGCACCTGATAT |
| | | GTCCCCGGCACTCGCAGCCCCGCGGCCGGAGTCGCTGTGGGTGAGCGGTCGTCGAGCTTCACAGAGGCCGGGCTCTGTGCCAGGGCCC |
| | | CGACAGGGCAGGAAGCAGATAGAGTCCCACAAGCACAAGCCCAGTGCGCAGAAAGGGTTACTTAAAAAATAAGTTCTGTGATAAAATCAAA |

TABLE 6B-continued

| SEQ ID NO | GENE NAME | SEQUENCE |
|---|---|---|
| | | CAGGGTGAAGGGCTGGAAACAGGTCATGAGGGCGCAAACAGGTCGTGAGGGCGCAAACAGGTCGTGAGGGCGCAAACAGGTCGTGAGG<br>GCGCAAACAGGTCGTGAGGGCGCAAACAGGTCGTGAGGGCGCAAACAGATCGTGAGGGCGCAAACAGGTCGTGAGGGCGCAAACAGGTCGTGAGGGTG<br>CAAACAGGTCGTGAGGGCGCAAACAGGTCGTGAGGGTGCAAACAGGT |
| 102 | WNT5A | AAATGAGACCTCTGGGGAGACTGTCAACCCCAGGGGTAAAACAAAAATTCTGATCAGAAACTGAGTTTCCCAAAGAAGGGGCTAAATGTTTT<br>CCAACACTTTCGGGGCTCAGGGAAGATGACTCTGTAAGGACACTGAGAATCTTCCTCGCGTGCCACGGGGAGGAGGACTGGGGGCGTTTG<br>AGGGGCTCAGCGCACCAGAGGAGTGAGGTGGAGGAGGGCGTTCCCGCGTCCTCCTCTTCAATCCAGAGCAGCTCAACGACGTGGCTCCCTTTCTATGTATCCCTCAAAGC<br>CTTCGCGT |
| 103 | chr3: 138971600-138972200 | TAGGCTCTAGTGGACCTAGCAGTGGGAGAGCTACTTGGGCTGGTTTCTTTCCTGACGCTGCAGGGATGGGCATCGGCCTGGAACCAGAAG<br>CGCAGGAGCTGGGCCACGGCAGAGTAATTAAGAAAATAATGAAATTGATGGCGGATGGGGGCGCTAGAAATCCTGGGGCGTCTACTTAAA<br>ACCAGAGATTCGCGGTCGGCCCCACGGAATCCCGGCTCTGTGTGCGCCCAGGTTCCGGGGCTTGGGCGTTGCCGGTTCTCACACTAGGA<br>AGGAGCCTGAAGTCAGAAAAGATGGGGCCTCGTTACTCACTTTCTAGCCCAGCCCCTGGCCCTGGGTCCCGCAGAGCCGTCATCGCAGGC<br>TCCTGCCCAGCCTCTGGGGTCGGGTGAGCAAGGTGTTCTCTTCGGAAGCGGGAAGGGCTGCGGGTCGGGGACGTCCCTTGGCTGCCACC<br>CCTGATTCTGCATCCTTTTCGCTCGAATCCCTGCGCTAGGCATCCTCCCCGATCCCCCAAAAGCCCAAGCACTGGGTCTGGGTTGAGGAAGGGAACGGGTG<br>CCCAGGCCGGACAGAGGCTGAAAGGAGGCCTCAAGGTTCCTCTTTGCTACA |
| 104 | ZIC4 | GAGGTTGCTGACTCAGGAGCCAGGAGCTGAGAAACTCCTAGGCTAGCAGCCGTTGAGCCTAATTTTATTTTCTGGCTTTCTCCGAAATGTCT<br>CGTTTCCCTCATCTTTCTGGTCCTTTTCGTCTCTCTTATTTTCCCCAAAACGTCTACCTCACTTCGTCTTCCTTTCTCCTCCCCTCCCCCTCTC<br>TTTCCTCTATACTCTCTTCCCATTTAGCCTTGCAGGCCCCTCCTCCCCGGTGTTGGAGAGCTCAAAGACGCGCGAAACTCAAGGATCTGGC<br>CCTGACCAGGGACGGGATTAGGCGGGAAGTGGTGACGGCCTGAAAAGGCTGGGCTCGAACCCGTGCCTTCCTGAAAGGACTCTCCCCGC<br>CACAAGTCACACCCACCCGCAGGCCTGCTGGCCAAAGAAACAAAGGAGTCGGGCGTGGATCCAGGAGAAACAGGTTTTCGCTCTCGGATC<br>TCCCTGGGCAAATCAGGGATCCTGAGCGCTATACCCCGCAGTCGTACGGAGCCTCTGGGAAAGGGGATTTAAGGGTGACTTCCACTTTCA<br>GCTTCGGCTACTTGTTGCCTGCGGTCCAAGCCTTCTCTGCTTCCTCCTACCTCGTCTTAGGCCTCTGTAGAAAGTGCACGCCGCGTTTCCC<br>CTTCCAGGCTCTGAGAGGGCCTGCAGGCCCGTGGCCGCCTCCGACAAGATGCCTTCCAGTGCTAGGGGGGCCACTTTGGCGGGATGGGG<br>GTCGGTTGGTTAAAAAAAACTTAAGTTCTGGCTCAGTCGAGTGTGGCAAAAGCCGAGGGTCGGGGGTTGGGGGG |
| 105 | FGF12 | TACTGACCTGGTCTCCGCCTCACCGGCCTCTTGCGGCCGCTGCAGAAGCGCACTTTGCTGAACACCCCGAGGACGTGCCTCTCGCACAGG<br>GAGCGCCCGTCTTTGCTGGGGCTGGAGCGGCGCTTGGAGGCCGACACTCGGTCGCTGTTGGACTCCCTCGCCTGCCGCTTCTGCCGGAT<br>CAAGGAGCTGGCTATCGCCGCAGCCATAGCTGCTCAGCGAGGGCCTCAGGCCCCAGCCTCTACTGCGCCCTCCGGCTTGCGCTCCGCCG<br>GGGCGAGGGCAGGACCTGGGCGGCCAGGGAAAGGGCAGTCGCGGGGAGGCAGTGCTAAAATTTGAGGAGGCTGCAGTATCGAAAACCC<br>GGCGCTCACAAGGTTAGTCAAAGTCTGGGCAGTGGCGACAAAATGTGTGAAAATCCAGATGTAAACTTCCCCAACCTCTGGCGGCCGGGG<br>GGCGGGGCGGGGCGGTCCCAGGCCCTCTTGCGAAGTAGACGTTTGCACCCCAAACTTGCACCCCAAGGCGATCGGCGTCCAAGGGGCA<br>GTGGGGAGTTTAGTCACACTGCGTTCGGGGTACCAAGTGGAAGGGGAAGAACGATGCCCAAAATAACAAGACGTGCCTCTGTTGGAGAGG<br>CGCAAGCGTTGTAAGGTGTCCAAAGTATACCTACACATACATACATAGAAAACCCGTTTACAAAGCAGAGTCTGGACCCAGGCGGGTAGCG<br>CGCCCCCGGTAGAAAATACTAAAAAGTGAATAAAACGTTCCTTTAGAAAACAAGCCACCAACCGCACGAGAGAAGGAGAGGAAGGCAGCAA<br>TTTAACTCCCTGCGGCCCGCGGTTCTGAAGATTAGGAGGTCCGTCCCAGCAGGGTGAGGTCTACAGAATGCATCGCGCCGGCTGCGGCTT<br>TCCAGGGGCCGGCCACCCGAGTTCTGGAATTCCGAGAGGCGCGAAGTGGGAGCGGTTACCCGGAGTCTGGGTAGGGGCGCGGGGCGG<br>GGGCAGCTGTTTCCAGCTGCGGTGAGAGCAACTCCCGGCCAGCAGCACTGCAAAGAGAGCGGGAGGCGAGGGAGGGGGGAGGGCGCG<br>AGGGAGGGAGGGAGATCCTCGAGGGCCAAGCACCCCTCGGGGAGAAACCAGCGAGAGGCGATCTGCGGGGTCCCAAGAGTGGGCGCTC<br>TTTCTCTTTCCGCTTGCTTTCCGGCACGAGACGGGCACAGTTGGTGATTATTTAGGGAATCCTAAATCTGGAATGACTCAGTAGTTTAAATAA<br>GCCCCCTCAAAAGGCAGCGATGCCGAAGGTGTCCTCTCCAGCTCGGCGCCCACACGCCTTTAACTGGAGCTCCCCGCCATGGTCCACCC<br>GGGGCCGCCGCACCGAGCTGGTCTCCGCACAGGCTCAGAGGGAGCGAGGGAAGGGAGGGAAGGAAGGGGCGCCCTGGCGGGCTCGGG<br>ATCAGGTCATCGCCGCGCTGCTGCCCGTGCCCCCTAGGCTCGCGCGCCCCGGCAGTCAGCAGCTCACAGGCAGCAGATCAGATGGGGAT<br>TACCCGCCGGACGCAAGGCCGATCACTCAGTCCCGCGCCGCCCATCCCGGCCGAGGAAGGAAGTGACCCGCGCGCTGCGAATACCCGC<br>GCGTCCGCTCGGGTGGGGCGGGGGCTGGCTGCAGGCGATGTTGGCTCGCGGCGGCTGAGGCTCCTGGCCGGAGCTGCCCACCATGGT<br>CTGGCGCCAGGGGCGCAGGCGGGGCCCCTAGGCCTCCTGGGGCTACCTCGCGAGGCAGCCGAGGGCGCAACCCGGGCGCTTGGGGCC |

TABLE 6B-continued

| SEQ ID NO | GENE NAME | SEQUENCE |
|---|---|---|
| | | GGAGGCGGAATCAGGGGCCGGGGCCAGGAGGCAGGTGCAGGCGGCTGCCAACTCGCCCAACTTGCTGCGCGGGTGGCCGCTCAGAGC<br>CGCGGGCTTGCGGGGCGCCCCCCGCCGCCGCGCCGCCGCCTCCCCAGGCCCGGGAGGGGGCGCTCAGGGTGGAGTCCCATTCATGGG<br>CTGAGGCTCTGGGCGCGCGGAGCCGCCGCCGCCCCTCCGGCTGGCTCA |
| 106 | GP5 | GGGGGACACAGAGAGGAGGGGTTGCGGGCCTGTGAGAATGAAGAGCACAGAGCGGAGAGGGGGAGGAGGAGGGAAAGGAAGGCGTGG<br>CAGTGAGAGAGAAGAGGAAGAAGAGAGGAGGAGTGGGGAGGGGAGGGAGAGCAAGACAGCAGCGGGTCTGGATTCCCCTCCGAGCCAC<br>ATCTGGTCAGGTTCTAAGTAATTAGAAGATTTTCCCATTGGTTTACCCAAGGGCTCTCTCTCTGATTAATTTTCGAAAGAGTTGGCCAATTTTA<br>ATCATAGCAAACACGATGATCACGGTGATCATGGCCTGAACAGCTAAAAGCAGAAAATAAAACCCCCAGAACGGACTATGATCTTGACCTTT<br>GCCCGTGGTCACCGGCTGGGCCCACACCCAGGGTTCTGAGCTGTTGGGAGCCAAGGCTGGGTGGACAGGGGCTTCCGAGGAGCTGTCC<br>GCAGCGGGGCGGGGAGGCGGGCCCCGGGGGCCCGGGCACTCCGCGTCACCCCCCGGCAGGGCCCAGAGCGGCAGGCCGGCGTGCGC<br>CCCAGGGCCTGCGCACCGTGGGGGCTCTTCCCCGCCCACGAGGCCTAGGTGCTGCCGCAGCCACCCCAGGAAGGGCCCCAGGCCACAG<br>TCGCAGCGCCAGGAGTTGTGCCCCAACAGGACCTCCGTCAGCCGGGGCAGAGCCCCAAACACGTCGCCAGGCAGGGTCTCCAGCTGGTT<br>GTGGTCGAGCTGGACGCTCTCCAGGCTGCTGAGATTGCGGAAGAGGGCACGGGGCAGGGCGCGCAGCCTGTTGCGGCGCAGGGACACC |
| 107 | MSX1 | GCCCCGGTGCACCGCGCGTCCAGCCGGCCCAACTCGAGCTAGAAGCCCCAACCACTGCCCAGTGCCTGAGTTGCAGTCTTGGGTCCTTTA<br>GAAACCTGGAGATGTGCGTAAAATTCAGATGCCGGTATTCCCGAACTTCCCCAGGCCTCAGCATATCTCGGCGGCCTGTGGACAGATGGG<br>AGGCTACCAATCGCTCCGGCGTCCGCAGCCCGACCCCTGCCGCCAGACCCCGGACGTCTTCCGGATAATAAAGTTCCCGCTCTAATTCAT<br>TTTCCCTAATCTGGACGCCCCTAATCTACAGCTTTTATTGCGCCCAGTTAAAAGTCGAGGGAATTCGCTGTCCCTCCGCGCTCGGATAATTA<br>CCCCTAAATGGCCACGGCAGCCCCTTGTGTTTCCTGGAGATTAGAACCCCGCAGTCATCAATGGCAGGGCCGAGTGAGCCGCCAATCACC<br>TCCGCTCACTCCCTGAGAGCCGCTGGCCTGGGCCGCAGGAGGAGAGGCCATAAAGCGACAGGCGCAGAAAATGGCCAAGCCCCGACCCCGCTTCAGGC |
| 108 | NKX3-2 | AGGGTGCCTCTGTTCAAATTAGAAAAAGGCGCCCCCTCAGGGCAGACTCAGCCCAGCTGCCAGGGGACAAGTCCTGGCTAACGGGAGCT<br>GGAGCTGGGTTTCACCTCCAGGTGCCTCCTTGGCGGGGCGCCCCGTGCAGGCTACAGCCTACAGCTGTCAGCGCCGGTCCGGAGCCGG<br>AGCGCGGGAATCACTCGCTGCCTCAGCCCAAGCGGGTTCACTGGGTGCCTGCGGCAGCTGCGCAGGTGGAGAGCGCCCAGCCTGGGAG<br>GCAGTAGTACGGGTAATAGTAGGAGGGCTGCAGTGGCAGAAGCGAGGGTGGCCGCAGCACTTCGCCGGGCAGGTATTGTCTCTGGTCGT<br>CGCGCACCAGCACCTTTACGGCCACCTTCTTGGCGGCGGGCGCCGAGGCCAGCAGGTCGGCTGCCATCTGCCGGCGCTTTGTCTTGTAG<br>CGACGGTTCTGGAACCAGATTTTCACCTGCGTCTCGGTGAGCTTCAGCGACGCGGCCAGGTCTGCGCGCTCGGGCCCGGACAGGTAGCG<br>CTGGTGGTTAAAGCGGCGCTCCAGCTCGAAGACCTGCGCGTGGGAGAAAGCGGCCCGCGAGCGCTTCTTGCGTGGCTTGGGCGCCGCC<br>GGCTCCTCCTCCTCCTCCGCGACGCCTGCCGGCCCGCTGCCGCCCCCGCCGCCGGCCCCGCTGCACAGCGCGGACACGTGTGCACCTC<br>TGGGGCCAACACCGTCGTCCTCGGTCCTTGGGCTGCGGTCGCCTGCGGACCCCGGTGGGAACAGAAACAAGAGACTGTCAGCGCCACAG<br>ACGAGGTGAGGCCGGGCCTCAACTGCAGGGGTCACGGGAGTGGGGCGGAAATACACTTTGATCCCACTCAAGCGGAGCGGAGGTCTGG<br>GAGGCCCTGGGCCCGGGAGACCAGTCTTAGACTCTTGCCCCACTGGGTATCCCATCTAGGCCTCTTCTGGGGAGGGCGGCAGACTCAGC<br>CGCTGTGTCAACGCTGTGTTGTCGAGACCAGCTCCCCACCCTCTCTGGGCCCCAGGCTCCCCTCAGTAACTTGGGGCACTCGACCCGAGC<br>ATCCGCGAAAGCCCTCCCGGCTCTCAGCGTTGAGCATTGGGATTCTAGACTGCATTTCCGTCTCTCTGCTTGGGTTCACGCGCCTCTCCAC<br>ACTTAGTTCACACGCACACACGCGCGCGTCCTCGCAGCACACACTTGTCTGGTGCAGGTAAGGGAAGGTGGAGGCGGATCCTGGGGCCA<br>AAGGTATTTAGAATCTTTCACCCTCAGCCGCCTGGGATTGCTGTGAGAGACATGGAAACAGGCTGAGCCGAGGCCTTAGATGAGAGGATG<br>GACTGGAGAGTAAAGAGGGAGGGTTGCCCCTGCATCGAGTTTTTGGACCCTGATCCCACACCAGCTTCTCGGTCTCGTACCCGCCCTTCC<br>GAAGAACTCCAGCAGAAAGGTCCAGCGGTCCCCTGTGCTTGAGGCCTACAGAAGCTTGTACCCAACTAGGGCAGGCACCCGGGTCTTCCA<br>GACCACAGGACAGGACAGGCCACGGCTGAGGAGGCCTCTCTCCTGCCTCCAGGATGAACTAAAGACCCAATCCGGGATCTTCGGCCTAG<br>GGCTGCTCTCCCAGACCTGGGGTCTGAGAAAGCCAAACCAGCCCTTTCCCCAAAGCTCTAGTTCTGCAGATTCTCAGCTCTGGCCCACTCG<br>GAGGTGTTCTTCACCACCTATCCACCTACTGTGGGGCCCGGCCCTGGGACCTTGAACTGGCAGGTCTCTGGTCCAGAGCTAGGTCACTGG<br>CTACCTGAGGTCTCTGAACCCCTCACTTTTCCGCTTCCCTGATTTTGGGGATTTGGGGACAGACACGGCAGAAAGCACTGGCGACGAACTC<br>AAAAACTCCCGAACGCAAGGGGCAGCGGTTCTCCCAACCCAGTCTAATGCACATTGGCCCAGGATGTCTCAGGCCTCACCCCAGGACGTA<br>GGGCTCTGAGGAGCTACTCCGGTCTCTCGCGGGCT |
| 109 | chr4: 111752000-111753000 | GAGAAGGGATGTGGCGGGGGGCTCCTCCGGCCCTGGACTCCCTGGGTGGACTAGAAAAGGGCAAAGAAGTGGTCACATCTGTGGGCCAG<br>ACTGGTGCGCGATCTTTGGAGGCGCAGCAGCAAGGCCGCGCCAGGGCTGAGCCCAGACCGCCCACGAGGAGGCCCGCCAGGCCCGGA<br>GCAGCGGCGCGTGCGGGGGCGTGCCGAGCGCAGGCTCTAGGGCCCCTGCTTCGCCCCAGCTGGACCCCGCGGGCGGTCGGTGCAGCT<br>CGAGCGTGTGGGCTGCGATGCCCTGCCTGAGACTTCGGGCTAGGGATGCGGGCGGGAAGTGGGGGTGCGGCGGCAGCTGCAGATTAGA |

TABLE 6B-continued

| SEQ ID NO | GENE NAME | SEQUENCE |
|---|---|---|
| | | TTCCTTTTTTTTTTGGCCGGAGGGACGTGCAAACTTCTAGTGCCCGGGCCAAGAGGGCGACCCCGGAGGTGCGTAGGTGGCCCTCCGGGT<br>TCCCGCTTCTCCTAGTGCCTCTGAAAATACCGTCAGGGTAAAGGGAGACAGGCAGTAAGTCTTACCACCACCGCCCTTTCCCCATGTCATT<br>GGCCAAAAACTGAACATTAAGATAAAGCAGCTGTTTCAGTCAATGGAAAGCGGTAGGGCGAGGTTGTACCCAAAACCCGGTTTAGACGGCC<br>AATGAAGTCCTAGGAAAAGCCGCCCCGGGGGCACGTTCAGGTGGAGCGGCTGCACCTCGGGTCGTTCTAAGGGATGGGCTGCGTGGTAC<br>CCACGGAATTCATGGGTCCAAAAGGTCCTGGTCACCTGTCCAAACATCCATCCCCTGGCGCATGGCGGTTGACAAGATGGCCCGGCCACC<br>CAGAGGAAGGAGGATCCGGGACGGGGAACTTCGCGCCGGGAAGCTGTAGCCCAGAGCTGCAGCTCAGCATTCGCAAGAGATTCATCTTTT<br>TTTTCTCTCGTGTTCGGAGAAACAGATAAACAAGACACCGCCTCATCAGATAAGAACGTCTCCTTCGATGTCACGGATTTCAAGAGGTAGCTGGAGAAACTGACGTCA |
| 110 | SFRP2 | CAGGTCAGGCAGAACTTCTGCCCTTCCCGCTACTGGCACCCCAAGCAGGGATGCACTGGGATGCGTGGCAGGGGCGGGATCTCCTGGGA<br>GCGTCTCAGCCCAGCAGGGAGTGGGGAAGCAAGAGGGAAGGCTTACCTTCCTCGGTGGCTGGCAGGAGGTGGTCGCTGCTAGCGAGGG<br>GGATGCAAAGGTCGTTGTCCTGGGGGAAACGGTCGCACTCAAGCATGTCGGGCCAGGGGAAGCCGAAGGCGGACATGACCGGGGCGCA<br>GCGGTCCTTCACCTGCACGCAGAGCGAGTGGCATGGCTGGATGGTCTCGTCTAGGTCATCGAGGCAGACGGGGGCGAAGAGCGAGCACA<br>GGAACTTCTTGGTGTCCGGGTGGCACTGCTTCATGACCAGCGGGATCCAAGCGCCGGCCTGCTCCAGCACCTCCTTCATGGTCTCGTGGC<br>CCAGCAGGTTGGGCAGCCGCATGTTCTGGTATTCGATGCCGTGGCACAGCTGCAGGTTGGCAGGGATGGGCTTGCAATTGCTGCGCTTGT<br>AGGAGAAGTCGGGCTGGCCAAAGAGGAAGAGCCCGCGCGCCGAGCCCAGGCAGCAGTGCGAGGCGAGGAAGAGCAGCAGCAGCGAGC<br>CAGGGCCCTGCAGCATCGTGGGCGCGCGACCCCGAGGGGGCAGAGGGAGCGGAGCCGGGGAAGGGCGAGGCGGCCGGAGTTCGAGC<br>TTGTCCCGGGCCCGCTCTCTTCGCTGGGTGCGACTCGGGGCCCCGAAAAGCTGGCAGCCGGCGGCTGGGGCGCGGAGAAGCGGGACAC<br>CGGGAGGACAGCGCGGGCGAGGCGCTGCAAGCCCGCGCGCAGCTCCGGGGGGCTCCGACCCGGGGGAGCAGAATGAGCCGTTGCTGG<br>GGCACAGCCAGAGTTTTCTTGGCCTTTTTTATGCAAATCTGGAGGGTGGGGGGAGCAAGGGAGGAGCCAATGAAGGGTAATCCGAGGAGG<br>GCTGGTCACTACTTTCTGGGTCTGGTTTTGCGTTGAGAATGCCCCTCACGCGCTTGCTGGAAGGGAATTCTGGCTGCGCCCCCTCCCCTAG<br>ATGCCGCCGCTCGCCCGCCCTAGGATTTCTTTAAACAACAAACAGAGAAGCCTGGCCGCTGCGCCCCCACAGTGAGCGAGCAGGGCGCG<br>GGCTGCGGGAGTGGGGGGCACGCAGGGCACCCCGCGAGCGGCCTCGCGACCAGGTACTGGCGGGAACGCGCCTAGCCCCGCGTGCCG<br>CCGGGGCCCGGGCTTGTTTTGCCCCAGTCCGAAGTTTCTGCTGGGTTGCCAGGCATGAGTG |
| 111 | chr4: 174664300-174664800 | TGCGATCATTAAAATCAGTTCCTTCCCTCCTGTCCTGAGGGTAGGGGCGGGCAGATTTTATTACTTCTCTTTTCCTGATAGCAGAACTGAGG<br>CGGGGTTGTGGAGGAGCGACGGAGGACCACCTCTAACTTCCCTTCACTTCCTGGATTTGAAGCCTCAGGGCCACCGGCCTCAGTCCTGTT<br>ACGGTGGCGGACTCGCGAGGTTTTCCAGCAGCTCATTCCGGGACGGCGGTGTCTAGTCCAGTCCAGGGTAACTGGGCTCTCTGAGAGTCC<br>GACCTCCATCGGTCTGGGAGCGAGTGGTTCGAGTTCAGATGCTGGGAACCGTCGCTTCTCCCCGGCCGGGCTCGCTGTTTTCTCCTCCGC<br>TCGCCGTCATCAAGCCCGGCTATGAGCAGGGCTTTAAATCCTCCCTCCCTCACCCGCAGGTTTACCGAGCAGCCCCGGAGCTCTCAGACA<br>TGCTGCGCTGCGGCGGCCAGAGGAGGGGTGGGGGCATTGCCCTCTGCA |
| 112 | chr4: 174676300-174676800 | GGGCTTGGGCCGCAGGCTTCCCTGGACTTCCGCAGTCCCCCTTCTCCCCATTCCAGAACCTGCCGAGCCCCTGCTGCATCTGGGACCCGC<br>CTTCACCGTTTCCCAATCCCAGCGGTTAGCCCCTGCGCCCCCTTTTTGGTCTCCACTTTGCCGTTCGAAAATGCCTAGGTTGGTGGATCGA<br>CCCTCCGCGGAGCAAAGACGGATGGCTGGCAGGAGCAGGTTCAGGAGCTGGGCCAAGGTATTCTCTGCTTCCGCCTTTGTGTCCGCCCC<br>CCCGCCCCCTGCTCCCCGCTTCCCGCCAGCATCTCTCCTTTTCTGCTCAGGAGTGTTTGGCCCGGCGGTCCACCCCGGCTTCCCGAGATA<br>CGCTAGAGTTGCCCCCACGTCCTGTCCGCCGCGCCCCTACCCACCGGGTTGCCTTCGGGGCCCTTCGGTGCTGTGTAGTCGGCGTGGCG<br>CTGTGAGCTAGGCGAACAGGAACCCCCAGGCCCGCCACGTCTACGCTATTA |
| 113 | SORBS2 | TTCTGGGGCCTGGATGGGTGCGAGCGGGACCCGGGGGAGTGGGAGTCGCCAGGCTCTGAGCAAGCAAGGGCTGCACCTGCACCTCTGC<br>CGGGCATGAAGAAAGGTAAGGAAGGAAGGAGCTCACCCGGGTGGGAGACAGAGCCGGGGCGCGCGAGCTTGGTGTGGGGGCGCCACTC<br>CGGGGCGGAGGGGAGGGGCTACCAGTGACTTCTCCGAGTCGGGAGCTAGAAAGAGGCTTCCGGCCAGGTTCCCTTGGAACAGGTGTCG<br>GAGTTGTTGGGAGAGGGGGCTGCAAGAAAGAGGGGTGCAGAAACTGGTTCATTAGATGGAGGCTCTGGGCGGAACCGCGAGGACACCCT<br>GGCAGCGCGCTGTGCCTGCGTTAGGCCGGGAGGGGAGAGGCCTCCGGACGGCGAAGTGTCCCTAGGGACCCAGACGCCTCGGGAGCG<br>ATCCGGGCCGCTGCGAAGCCCTGCCCACCAGGAGTGGATCCCCAGGATTCACCTCCCGGCTGCCTGCTCTGAGCTGAGAAGGGGATCTG<br>GTTCTTCACAATACCGTGGATGGCGGGGAAGGGGAGGGAGCCTGGGGTAAAATCCCATCTTGGTTTCCTCG |
| 114 | chr5: 42986900-42988200 | TGTCACAGAAACCCCAGCAGCGCAGCCACCGGACTGGGTTCTGGAGGCCGAGCCGCAGTCCGTGCGGCGGCGCTGGGAAGAGAAGGCG<br>CCCCGGCAGCTCCCCTGCCACCGGCCCCGAGGAGCGGCTGGCTCCCCCAGCCCAGCGCCGCCGCCGCCCGGTAACTCCAGGCGCAACT<br>GGGCGCAACTGGGGCAGCTGCGACACCGAATCCCTCACATCTGCAACCTGGGTGCTGCGGCCACTGAGAAAATGGAGGCGCAGACCAAC |

TABLE 6B-continued

| SEQ ID NO | GENE NAME | SEQUENCE |
|---|---|---|
| | | GAGCGGTGCCGCGACCGAGAGACCTCGGCTGGCGAAATGGTGGTGCCGGGAGCCTGCGAGTGACGCCAGCCGGCGGGGTTGTCAAGGA<br>CAACATTCGTTTTGACGCAGCCAATGGCGCCGTCACCAAGAAACCATCGACTCTGAGAAAAAAGAGAGGTTCGGCCACCGAGAAACTCCGT<br>ACGACAAGTGCTGTGGCAGAAAAACCGCCTACTCCGCGCCACAGGCAAAACAGCCAATGGAAACCCCAGGTGCTGCGACCGTGACACCG<br>GCACTAGAGGGTCTCGGATGGAGAAAGCGGCGCACGGAGACCAGGAAACTATGTGTAGCACAACTAGCAGAAAACCGTCTGGTCGGCCAT<br>CCGGGAGAAAGCGCGGATCAGAAACAAGCGACTTCGATGCAGGGAACCGCGCAGCCACTGAAGAAAGTGACCCACGTGGCAGTGGTGCC<br>AGCGAAACACTGCAGTTTGGACGGCAGCTGTGGGGATGCCACAGAGAAACATGCACTGCCACTGAAGTACATCCAGCTCCGCGGAGCTAG<br>TGTTCATATGATCAAGAAACCGCCAGTTGGGCTCTGCTAGAAACTTTTAGTCCTCCCTTAACGGCTATCCTACCCACAACAGACAATGCCTTT<br>ACCCAGCACCTAGCGGTGCTGAGACCCGCCTGGGCCAGCACAGAGCGCAGAGCAGTACGGGTACGGAGAAACGCCGGACTCAGTGAAAC<br>CAGCCTTGCCTCCAGCGGATTCCCCGGCTTCGCCGGACGCCACAGGCAGAGTGCCGCGGGGAAACCTCTGGCTCCCTAAACCGATTAGA<br>TTGTGGGAGTGGGGGGGACACTCACAAGTTGTGTGGAAGGGAACCAGCGGCAATGGGACCCGGCGAGCACTTGCCCGCAGCAAATGCCT<br>GCGCTGCTGCAAAAAAAACAACTTTTGGCGCAAAGAATGTTGCGGCCAGAGAGCATCCGCTGTCGCTGACAAAGGAGTAGCAATGGCAAT<br>GAGAAACCGCCGGCGCCACGGCCGACCGCGGCGGCTCACGCCTATGAT |
| 115 | chr5: 72712000-72714100 | CAAACGCTGAGAGACAAAAAGACACCAACACCCACCAGGACTGCGTCCTGCCAGCTCTTCACTCCGCTGACCTGACCTTCCACGCCCCTA<br>GTCCTCGAGCGGACTTGACCTGTGGGGGAGTACCGAACCGTCCCCATGAGGCCCTCCAAGCGGCCAGGTGGCCTCCGCCACTCTCTCCA<br>CCCCCACCTCCTCCACCCCCCAGCCCATCGGTCCATCTTCGATCTGCAAAACACGCCGGGTCAGCGACGCATCGGTCCCAGGCTTGTGAC<br>CACCTCTTTCTCTGTTACTTGGGGAGCCAGGCCCACCGCTCAGGATCACAGTGAGGAGAAAAAAGACACAAACGCCAGGACAGGGCGGCT<br>GGGGAAGGAAACTGCTAGGGACCGCTCATTGTCAGCCTGGCGTGTCCCACGGATCGCAGGACCCGTCGAGGCTTTGCTCTCTGCGACCC<br>GAATACTCCTGGGCCTCTCGACCTCCTCCTCGGACTCAGGCGTCCGCGTCTCCGGTCATCACGGGAGACCAATTGGTTTACAAATAGTGAT<br>GATAAACCTGGGACCGACCTTGGGGCTGTGTAAAAGTCTACTGACAGATGTAATGGAGGGTTGTTAGCAGTCACAAAGCCTGTCGGACCCG<br>TAGCATTAGTTCAAGAGACTATTTTCGTGTCGCACCAAAATTACTGCGCGTGTAAACCAATTTCCCCGACGGAAGAATAAACAGAGATTCGTT<br>TGAAGCGCGAGATGAAAACAGATGGGGTATCGCAAACAGTTCCCCAAAATACAACAGACTTCTGGGCCAATTACACGTGGTTAGCTCTGAA<br>TGGCAGAGGAAATAGTTTTCTTTGCTGCTAAATGTCACAAAAGTCACCTAAAGGCACAGAGGAGGCCGCTCTGTTTTTGCGAAACTTGCTAA<br>AATTAATCTGCGCTGGGCCACTTGCAGAAAGCAGAACCACCTCCCGCCCCCACCTCGCCTCCAGCCGCCGGGGTTCAGGCGTTTGTGAAA<br>GACAGAACCTTTGGGCTAGGGACCCGGGCACTGGTGCTTCGAAGTCCGAATCCGCCGGCCGAGAAAACGACAAGAGAAAGAAAATCCAGC<br>GGGCGCTCTCTCCAGCGCCAGGCCGGTGTAGGAGGGCGCTGGGGCTCGGCCTGCCACCCCTACCCGACATTGGGAAGCAGCCCCTGCG<br>CTCCCGCGGCGCCTCAGCCTCCGGTCCCCGCCCCGAGGTGCGCGTTCCTCCTCCCGCATGCCCGTCTCGGGCCCCCACGGAGCAAGAAG<br>ATAGACGATGACGAGGCGCGCCCATCCATCCGGGCCGACGAGGTCAGGCCCGCGCCACAGGCAAAAATTGCGCAAGCCCGGCCGCAGG<br>GATTTCGCGGGCGCCTGGGTCCCAGGTGCGCGGCCGAAATCCTCAGGGAAAATCCCGAGGGGCCAACGGTCTAGGCCACAGGGCTGCT<br>GGGCCCGGGCCTGGCTCAGAGCGCATTCGGGCGGGGAGGCCGCACGCCGCACCCGGGCCTCTCCTCCGAGCCCGAGGCAGGCACTGA<br>GCTCCGGGCCAGCCAGGTGCCTCCCGGCTGGTGCGAGACCCCGGGCCTGCTGGGAGGCGTGGGCAGGGCAGGGCAGGGCTGAACCCC<br>AGCGACTGAATCTCGAAGGCAGGAGGCCTCGGAGGTCATCGGCCCAGCTCGCCTGAAACTGTCCCTGCTCGTGCCAGGGCGCGGGCAGA<br>GGAGAAAGGACAGGGCGGAGCAAGCCCACTGCAGAACTGCGGTCGGTGGCTGCGAAGGGTCCGGGTCACCGCGCTCCCGGACGCCGGA<br>AGCCGCGCTGGCGGGGCCGCGGGGAGGGAGGCTGGGTACCGGGGCCGTCCGGCCGGAGGAAGCGGCTCCGGCCGCGCTGTCCGCGC<br>TTGGGAGCCGCGTGCAGGGTTCAGCCGTGTTTCAGTTGCCCTCTGACCTGACCCCGGGCGCACAAAGGCCTCCCGGGTGCGCCGCCATG<br>GCCCAGTCTTCCAGTCGCTGCCAAATTAATGAGCCCACGTCAGGTTGGGTTTACAGCTCGGCCGGGAAGCAGCCGAGTGGAAAATGAGCT<br>CGGGGCCGCTCCAGAGGCTCCCGCACAACTGCAGAGGCTGCCCGCG |
| 116 | chr5: 72767550-72767800 | TTTCCAAGACAGAAGGAGGGAACTAGGCGCCTTTTTTCCACTCCGCTGACCCCAACGTCTGGGCTGTGCGTTGTAACGCAGTTGGCGGGG<br>CCTTCAGCTTGGGATGAGGGCGAAGGGGCTCGGGATGGGTGGGAAAGCAAGGACCGGGCAACAGGTGGGGAGGTGGCGGACTTTTGTC<br>TCGGGGAAGGAAATCGGCTGTGCTGAAAGGGCGGAAAGCAGTAGCGCACAGAACTAGTGTCTGCGGGGTCCC |
| 117 | NR2F1 | CCCTCCTGTGGCTGCTTGGGCAGACGCCTGTGGCCTGTCGGATGCGGCCCACATCGAGAGCCTGCAGGAGAAGTCGCAGTGCGCACTGG<br>AGGAGTACGTGAGGAGCCAGTACCCCAACCAGCCCAGCCGTTTTGGCAAACTGCTGCTGCGACTGCCCTCGCTGCGCACCGTGTCCTCCT<br>CCGTCATCGAGCAGCTCTTCTTCGTCCGTTTGGTAGGTAAAACCCCCATCGAAACTCTCATCCGCGATATG |
| 118 | PCDHGA1 | TCCTCCTTTGTGTATGTCAACCCAGAGGATGGACGGATCTTTGCCCAGCGTACCTTTGACTATGAATTGCTGCAGATGCTGCAGATTGTGGT<br>GGGGGTTCGAGACTCCGGCTCTCCCCCATTGCATGCCAACACATCTCTGCATGTGTTTGTCCTAGACGAGAATGATAATGCCCCAGCTGTG<br>CTGCACCCACGGCCAGACTGGGAACACTCAGCCCCCCAGCGTCTCCCTCGCTCTGCTCCTCCTGGCTCCTTGGTCACCAAGGTGACAGCC |

TABLE 6B-continued

| SEQ ID NO | GENE NAME | SEQUENCE |
|---|---|---|
| | | GTGGATGCTGATGCAGGCCACAATGCGTGGCTCTCCTACTCACTGTTGCCACAGTCCACAGCCCCAGGACTGTTCCTCGTGTCTACACACA<br>CTGGTGAGGTGCGCACAGCCCGGGCCTTACTGGAGGATGACTCTGACACCCAGCAGGTGGTGGTCCTGGTGAGGGACAATGGTGACCCT<br>TCACTCTCCTCCACAGCCACAGTGCTGCTGGTTCTGGAGGATGAGGACCCTGAGGAAATGCCCAAATCCAGTGACTTCCTCATACACCCTC<br>CTGAGCGTTCAGACCTTACCCTTTACCTCATTGTGGCTCTAGCGACCGTCAGTCTCTTATCCCTAGTCACCTTCACCTTTCTGTCAGCGAAG<br>TGCCTTCAGGGAAACGCAGACGGGGACGGGGGTGGAGGGCAGTGCTGCAGGCGCCAGGACTCACCCTCCCCGGACTTCTATAAGCAGTC<br>CAGCCCCAACCTGCAGGTGAGCTCGGACGGCACGCTCAAGTACATGGAGGTGACGCTGCGGCCCACAGACTCGCAGAGCCACTGCTACA<br>GGACGTGCTTTTCACCGGCCTCGGACGGCAGTGACTTCACTTTTCTAAGACCCCTCAGCGTTCAGCAGCCCACAGCTCTGGCGCTGGAGC<br>CTGACGCCATCCGGTCCCGCTCTAATACGCTGCGGGAGCGGAGCCAGGTGAGGGGCTCGGCGCCGCCCCGGGCGACCCCTGGGGGCG<br>GCACTGGAGAAGCCGCCCGTCCTCATAAGGGATTGAACTTGCATCCACTCCTCTCCGGCCGGCTTGGTCGCTGGCTGCGCTCCACCCGAT<br>TCTCGGGATCATTGGACCGTTTGCGCGAAACCAGAGTGGCCGATTAAGGGATGGGGCTCCGAGCACCGGGGGTGGTGGCGACTGTGGGC<br>GAGGGGAGGTGGGACCGACCCCCACCCCTACACTCAAAAAAGGCCGGGGCCTCCTTCGAGCTTCCGGTGAATTTCGGGCGATTTCCGCG<br>GGTGTCGGGGGTCCCGGGAGGAGGCAGTCACAGATCCACCCCTGCAGCCAGCCTCCTAGGCGCCGGCTCCGGCACGCTTCGCCGGTCT<br>GTAGATTTCCTCTTCGATTTCTCCCCAGCTCCCAGCATCTGTGACTTCACTGTTACCCTCCCTATCCCCGCATCACCCAACCGCACCTGTCT<br>GCGGGACTTAGGTGTGCGCGCGGGGCTCATGCGTGTCCTCCCTGCTGGCCACCCCCACGGCCCACACAAGTTGCACGGGCTCGCCACGC<br>CCCGCCAACACGTGCGCGGACGCACGCACGCACTCCTCGCACGTGGGCTTACGCGAATACCAGCTTTCACTGCCACTCGCTCGCGGCCA<br>GATTCACAGGCCTGTTCCGGTCCACTCGCAGCTCCCCTCTGCCGCTCCCTCCGCCGGGCTCAGGAGTACTCGTAGCTGATTGTGCGCGCC<br>TGAGGGTCCCAGATCGCGGCCGCCCAGGACCAGGCGAGGACTCCGGAGCCTCCTCTCACCTCTCCCACCTGCGCCCCGGGCTGGGCCG<br>GGTCGCCTGGGGGGCGGCCTGAGCGAGGCGCGGGGCCAGGAGCGCTGGAGCGACTGCCGCTCTAAGTGCCGGGCGGGCAGGACTCTA<br>CGATCCTTGGGCCAGAGGTCCGGATGGTCCCGGGACTCCGTCTCAAGGGTCGGCGACCCCTCAACCCAGAAGCCTCGAGCAGGCGGACA<br>GGCAGAGCTGCCCAGTGGCCGAGGCGCGG |
| 119 | chr6: 10489100-10490200 | ATTTGTCGTTGTGCCATTGCTGCCACTGTTGTTCTTGTCCAGGGAAACACCGGTGGCCAACCCAGATCGGATACAATGGTGCGGCTCTGGA<br>CTGAGCCTCCAACCACATTAGCCATGGGCAGCATTGTTGCTGCCGCTGCTGTTATTTTAATTATGATTGTACGTTAACCACCACCTTCCTTCC<br>TCTGCCTCCCTTCAGCTGCAATGATGTATGTTACTTTTTGGTAACTGGATTTCATTAACATTTATGAACTCTCATAAAGTAGTAGAAAAAGCAA<br>TTTGTGTGGAAGAATTTTCCACCTCATTAAACAGTGTTCTTTTGGGGGTCAAGCTGATATTTTTTTGTTGTTAGATTTTTTTATAGGTCCTTT<br>GTCCTTCCCTAAGCCCTGGGGGATGAAAGGAGAGCCGTCCACCCAGCGAGGGGCTTGTGTGCCCTAGAGGGCGCTGGGCCCCGCGCGC<br>TTTCCTGGCTGTCCCCGCCGGCTTTCCACCCTCCCCAAAGCCCAGGTGCCCACCGTGGGTCGCTGCGGCCTTTCCCCTTCTTGGCCAAAT<br>CCGATTACTTCGCAGCCTGCAGATGGCATCGCCGGCTAAGGGCAGCCTGCGGCAGGTCCCCGAGCCTGAGCACTCCTCCTATCTGGGGC<br>CTGAGAGGACGCTCTGGGCTTTTTCCCAGGCCCAGGGTGCGCGGCCTGCTAGCGCCTTTCGAGGCACAGTCCCAAGATAGGCTCTTGTCC<br>TTCGACGCCCCCTTGGCACAAGCGCACTGGCGCCCTCCGCTCAACCCACCTTGCCTTTGGGGCGGGCTTCAACCCTGGGAAGACAGGCC<br>TGGGGGAAGCGAGAGGAGAGGCCCGAATAGAGGTTCCGGCTCAATCTTTCCCAGACGGAGGCCTGGTGTTTCCAGCTCAGTTGCATCTTC<br>CAGCCGCGGGCTCCTGGCCCAAACAGAATGTGTTTGCTTTCACACCGGGACGGCAAGCGGAGTCCGCCTCAGTGAGCAGCGAGCTGCGC<br>AGTCCGGACGGGTGTCGCCCCCAGAGACTCGCCAGCCGCCCCCAGACACTCGCCAGCCGTCCCCATCTCTAATCCACCGTCCAGGCCCGGGCCCTGGGAAGA |
| 120 | FOXP4 | CCGTGTCTCCCTTAAGAACTGGGGCCTCATCTCCACTCCAGCTGCGCGTGCACGTGTGCTCCCGGCAGGACGCGCGCCCAGGAGCGCGC<br>TGGGGGCTGCCCCGCCCCTCTCTCCCTCCCCCGCGGGTAAACTCCGGGCATCCATCAGTCTGTTAATTGCACTAATTAGAGATCGCAGAG<br>GTGTTAATTGGAAAACCCTGGTATTGTGCCTGTTTGGGGGAAGAAAACGTCAATAAAAATTAATTGATGAGTTGGCAGGGCGGGCGGTGCG<br>GGTTCGCGGCGAGGCGCAGGGTGTCATGGCAAATGTTACGGCTCAGATTAAGCGATTGTTAATTAAAAAGCGACGGTAATTAATACTCGCT<br>ACGCCATATGGGCCCGTGAAAAGGCACAAAAGGTTTCTCCGCATGTGGGGTTCCCCTTCTCTTTTCTCCTTCCACAAAAGCACCCCAGCCC<br>GTGGGTCCCCCCTTTGGCCCCAAGGTAGGTGGAACTCGTCACTTCCGGCCAGGGAGGGGATGGGGCGGTCTCCGGCGAGTTCCAAGGG<br>CGTCCCTCGTTGCGCACTCGCCCGCCCAGGTTCTTTGAAGAGCCAGGAGCCTCCGGGGAAGTGGGAGCCCCCAGCGGCCCGCAGACTGC<br>CTCAGAGCGGAAGAGGCAGCCGCGGCTTTGACCCAGCTTCCTTCCGACGGCATCTGCAGGAGCCTCTAGGCCTGACATAGGCTCCGAGG<br>TGCCCTGGCTCCCCCACGGGGAATGCTGAGGGTTGGGCCACTAGGTCCTGCCTAAGTGCAGGACCTGAGCCTCAGACAAATC |
| 121 | chr7: 19118400-19118700 | GGGATTGCCGGCTTTGAGAAAATATGAAGAAACCGATTTCTCCTTCCACTTTGCCAGTGCACTTTCCTTCCACTTTCACTGGTGCTGGGGGC<br>GGCGCACTCTTTACGACATATAAGCGGAAAATTCTGCAAAAGTGGCCCCCGGGGATCCCCGCCCGACCCCTGTCTGTCGCTAATGTGGGC<br>CTGTCTCCGGAAATTCGAGGTTGGGCCTTTGCCTGAATCTGTTGCTATTGCTCCCCTTGCTACCGCTGACACTTGGCACCGCCGCCTCCTA<br>GCAGCGGCCAGACGCGGGGCTGGGGGC |

TABLE 6B-continued

| SEQ ID NO | GENE NAME | SEQUENCE |
|---|---|---|
| 122 | chr7: 27258000-27258400 | GTTGCGAGCGCGGCACAGGTTGCTGGTAGCTTCTGGACTCTGGAGGCTTGGCCTTCCTTCTAAGCCGATGGCGGGGAAAGAACCTCGTTT<br>CCACAGCTTCCCCGACCCCCGCCGCTTGCCATTTGGGGACGGGAAGCGCGCCCGGGTCGCTTCACGTCCCTCTGGGCCGGAGCCCTTTC<br>CATGGCTGGCTCCTCTGGGGGCCCTTGGGCCTGTGAGCAGCGTCTACTTCCCTCAGAGAAGAATCCTTTCCTTCCCCCATCGAAGTGTCCC<br>TTTCTGTATCCTGAAATAACCCCTCCTGGGTGAGGCCAGTTCCCCTCTGTCGCCCTCCTCCCGCAGGCGTCCGGGAGCCTCGTGAGGACC<br>CCGTGCAGTTGAGTCCAGGCGACAGGTGCCTCCCCAGGTG |
| 123 | TBX20 | CAGTGCGCCCCTTACCGGAGCACCCATGGCCTCCCGCGTTACCCCAAATTTTGTAGGCAGACTGTCAGAGTTCGAAGCCAGCTGTGTCCT<br>CTGCGGGCCGTGTGACCCTAGGCTATCTGGGCTGCTCGGAGCCTTAGTTTCCCTAGTTGTGAAGAGGGAGGGTGTGACCATGGCCCGGA<br>GCTCTCCGAAAGGCTGTGCGGATTGCTCGGTGGCGGGATGTGGAGCGCGTCTTCTATGATGCCAGGTGCTGGCCAAGCGCTCGATGCAG<br>GCTGCTCCAGTTAGGTCGATGCGATGGCGGGAAGCACTTTCCTCTGCAATGGAGAGACGCCGACACCCCGAGCCCGAAGGCTTGCAAGG<br>CGCGCTCTCGCCACTGGGGTCGGGGATCCGTGGGTTCTCTATCCCGCTTACCCACTCCATCCTTAGCAGCTGTCGTCGGTCCCAGACCTC<br>TACCTTGGAGAGACCAAGGCGGCCCAGAGCCCAGGAGACTACTGCGCGGTACGCCAGGATCCAGAAGTGGATTCTGACTTCTAAAGACCC<br>CTCCCAAGCCAACGCTATCAGGGTCCCTGCAAGCGGTTGACTGTGGCGGAGGCAGAACCAAAACCTTTGCTCTGCCCGCGGCGCTCCAGC<br>CTCTCACCCAGGACAGTGCTCTGGGCTCCAGCCGCTGCAGTGGGGTCGGGACACAGACGCCGAGTTAGAAGCCCCGCCGCTGCAGGTCC<br>CTGCTTGGTCGGCGCGGTGACGGTGTCGCTGGCGGCGGCGGGGGCCTTCCTTTGGCTGCCCGGCCATTTAATCAGAGCTATTAT |
| 124 | AGBL3 | TTTAGTATTTAAGGAGAAAAGCCTCATTTTCCAGAATCGAATAAGCGAATTAATCGCACAATTGTGTAGAATGGAACTCAGTCTGTAAAAAAT<br>CAAGACCAACGTACTTTTTAATATTCTAACATCTCCAAGTAGTAGTTACAAGTATTGTACCCATGAAGTCCAGGTAATTAATTTGTTCAATGTC<br>ACACTGTTAAAAGTCAGGTGGGCTCCAAAGCACAGTCCTAACCAGCATGCTCTACTGCCTCCTCTGAGGCAACAGCCGAAGTGCAGACCAC<br>TGGGAATAAATAGCTGCCCGGTCTTCCCCACTCCTAAATTCTCCCGACAGACCCCAAAGCCTCTCTGAGAGCCTCTCTGACCGCCCTGCGG<br>CCCACCCCGAGTTCCCGGCATCCTCTGGGATCCCTCTTCCTGGAGCCAAAACCTACGCAGGCTCCTTTCCTCCGAGCTGGTTGCTAGGTG<br>ATCTCCGAAGGCTGTCCGAAGTCTCGCGAGGGCGGACCCGTTGCCTGATGACGAGAGTTGGGAGTGTGGCTGGGGCTGCGGATCTCCAG<br>CAGTGGCGTTACTTCTAGCGGCTGGATACCGGGTTCTCCGCGAGATCGCGAGATCCCGAGATATTCTCCCCGCACGGAAGCGACGACTGG<br>CCTGGCCAGAGGACTCGCGTGGGAGCGAGGTGCCGGCCCCGACAGGACGGTGAGGTATGCAGAAGTAAGGCGGGGCGCCCCCTGCGG<br>GAAGCGAGCGCGCCCCGGAAAATGAGCGCCTCCCCACACCAAGGTGTCCAGGAGTGAGTGCGGGAAGGAACTCGGCCGCCCGGAGTTG<br>TGGCCTCATCGTGCTTCCCGCCAAAAACGCCTTGGTACTGTCGGGACGCGGCTAAGCGTGGACGCGCCCGCATCTGCCCCTCCTCCGCA<br>GTGGTGGAAGACACCCGCGGAGCGCCGGTGGATAAGGGCCGTTTCCTGAGACCAGAGCTGTATCCGCAGCAGGTCAGCACTTCGTGCGCCCTGTGTGC |
| 125 | XPO7 | AGCGGCGCTGTTCCCGGGCTGGGTGCAGCTGCTAAGGACAAGGCCCCTGCTCCGAAGAACGCGGTGGCTCGGGGATACCCTGAAAGGG<br>ACGGCCATGGCGCACATGGGATGCCCTAGGGTTCGTGGGAGGGCATGCAGGCGCAGCCCCCGCAGGGGTTGGCCTGCCAGAGAAGGCA<br>GGGGAGAGCACTCGGGGCTGCACAAATGGTGTGGCCGGAGGGAAGGTGCAGCCTTGTGTGTGTCTGGATGAGGGCTGGGCATAGGAGC<br>TTGGTATTTGATCCTGAAAGCTCTGCGTTTCCAAAG |
| 126 | chr8: 41543400-41544000 | GAGTCATACTTGTAGTCACATCCTTTTCCTTTCTCCAACCCACTGGTTAATCATGAAAGGCTCTTCTGATTGGCTGCCTCCTGGCAGTAGTGC<br>CTCAGCGCGACGGTTCGGGAGCAAATAAATAATTCCCGCTGGGAAGCTGTTTCTCAGACAGGAGCAGCGACACCCCTGCCACGCCTGCCG<br>CCTGGAGTTGAGTGGGGTAAGCACGCCGGCCTCCAGGAATCGACGGTGCCACGTGGTTCTTCTTGCACTTCTCTTCTTCTCCAGTTTCAGG<br>GGACACCGTGGGGTGTGCGAGCCCGGGGGAGCGCAGGGAAGGGCGGGTTGGGCTGCAGGTGGGAATGTGCGGTCCTTCTGCGCCCTCA<br>ACAGAGCTTCCTTCCTTTTTGCCAAGGTCCCCGTGCCGCCTTCAGCGCGCCTCCTTATGCACCTCTACCTCTGCTGCAGCGTACCTCTTCC<br>GCAGCCCTAGCGGCCTCCCCGAGGGGCGCCGCGGCCTCGGCTGTCCCTCCCCTGCCTGGCACGACCACCTGACCCCCAGCGACCCAAG<br>AAGCAAGTTGTGTTTGCAGACGCAAAGGGGCTGTCGTTGGTATCGGTGCACTGGTTTGA |
| 127 | GDF6 | ACACTTTCTGTGTGGGAGGGCACAAGACATGGGCTATGACATGGCCAGAGACCCCACCTTCTTTACACATGTAAAAACCAACCAAATCAAG<br>ATGCGTCAACGGTGATTCTTCCTCCCACATTGTTTCCCTTTTTAAACTGTTATTTTTTCAATCCATGGAGCAGTTGAGAAACGGGTATGCATC<br>TCTCCTCCCCTCCCCTTCTATCAAAGCCTGTAAGACACATAAGGAAATCCAAAGCCACAGTAATAGAGAGAGAGAGAGAGAGAGAGAGAGA<br>GAGAGAGAGAGAGAGAGAGAAAACAGAACAAAAGAAATCCTCCTTGGCTTGTTTTTCCAGGGTGGCCAGGCAAGGTGTGAAAATCCATATT<br>TCCCTCTGGGCTGGCAGGTAGAAGTTACTGGGAAGGCTGCGCTCCCTTCTCTCCCACCGGCTCTCACATCCAGGCTGTTCCCTCACCCTCA<br>GCCTCCCCCAGCGCCAGCTTCCTCCTCCGCCTCTCTGCAGCCAGGCCTCCCCTGCAAGGCGGACCTTGGCCCACCTTGGTTCCGGGCCA<br>AGGCGGCGGGAAAGGCACCGCTACCTGCAGCCGCACGACTCCACCACCATGTCCTCGTACTGCTTGTAGACCACATTATTGCCCGCGTCG<br>ATGTATAGAATGCTGATGGGAGTCAATTTGGTGGGCACGCAGCAGCTGGGCGGGGTGGAGCCGGGGTCCATGGAGTTCATCAGCGTCTG |

TABLE 6B-continued

| SEQ ID NO | GENE NAME | SEQUENCE |
| --- | --- | --- |
| | | GATGATGGCGTGGTTGGTGGGCTCCAGGTGCGAGCGCAGCGGGAAGTCGCATACACCCTCGCAGTGATAGGCCTCGTACTCCAGGGGCG<br>CGATAATCCAGTCGTCCCAGCCCAGCTCCTTGAAGTTCACGTGCAGGGGCTTCTTGCTGCAGCGTAGCCTGGACTTCTTGCCGTGCCGCTT<br>GCCATGGCGACTGGCGAAGGCCGTGCGCCGCCGCCGGCGGCCGGGCGAGGGCAGCCAAGGCCTGGCATCCGGGGCGCCCGACGGCG<br>GCGGCCACGACCCCTCGGCGCCCGCGCCCGGGCCCGCAGCCTCGGCCGAGCCCAGCTGCTCGCGCATCTCTGCGAACAGGTTCTTGCG<br>CTGGGATCTGGTGAATACCACCAGCAGGGCCCGCTCCTGGGGAGGCCGCACCCTCCGGCCGAAGCCCAGACTCCGCAGGTCCGGGGGC<br>GGCGGTTGCTGGGGTCCCCGCGCGCGCGCCTCGGCCTCCCCGGCGTCCAGCTCGCCCCATGCGGCCCGCAGCTCCAAGCACAGCTGCT<br>TCCAGGGCTGGTGGCGCAGGCCCTGCCACACGTCGAAGACTTCCCAGCCGGCCGGCGGCGCCCCCTGCGGGTCCAGGGTCCGCGCGTC<br>CAGCAGTAGGGGCGAAAGGCAAGGGAAGAGCTGCACGTGGAGCGGCCCGGCTGGTGGCCCCCAGGGCGCTGAGGGCGCCTGGCGAAA<br>GAGCCGCAGCTCCGCGCCCACCAGCTCTTCTTTGTCTGAGAGCATGGACACATCAAACAAATACTTCTGTCTCCGGAGAGGAGTGTGCGA<br>GAGATCGTCTGCGAGATAAAAAATAATTACAGTCAGTTTCACTTAAGGGGGAGATCAGCCCGGTGCTCTTCGGCCGCCCCGGGAGGAAAA<br>GGGCGGGGAGTGGGGGCAGGTCGGCCGGGCAGTCCAGCTTGCCCGGCCCAGGGCCTGACCACCCCGGCTCCCCATCTGGCTGGTGCATGG |
| 128 | OSR2 | GCCCGCTGTGAATGTAGGTGAGGTGATCCCGGGAACCTGGGTCTGAAATCAGACCTGTGTTGCCATTGGGAGCACGGAGAGAGGGGAAG<br>CGCCCTGCTTAGGCCCAGGCCGGGCGTCCTGGTGGTGGGACCGCAGCCGCACTCACCTCCAGGCCAACGGACAAGGTTCCTGCAAGCCA<br>GCAGGGCCACTCTGTGCTTGGCCTACTGCAGCTCCCCTGCAGCTCCTTTCCTCTCCCTCCCCGGAGCGCTCTCCTCTCTCCTCTCCCCTCT<br>CTTCTCTCTCCTCTCTCGTCTCCTGGGGCATCCCGGGTGGAGGGATGTAGGGGTCGCTCCTCGGTGCCAGGCCGGGAAGCAGCTCAGGC<br>CTCCCAAGAGCTTGGCGCTCAGTCTGGGAAAAGGGGTTCCTCTGGCCTCAGGGACGTTCTCCGCCCCCACCCCACCCCCTGGGAGCCTG<br>AACCATCTGGAAGGGATCTTAGTCGGGGGTTGGGAGGAGAGCCCGTGGATAGGAGGAGGGGGCGATTCTAGGCCGAATCCAGCCCCTGA<br>GGTGTCACTTTTCTTTCCTGCGGCCCGTCACCGCTGATAGATGGGGCTGAGGGCAGAGGAAGGAAAAAGAAAACCTCCGAGGTCAGTGCG<br>GGGCGAGGTGAGCCCCTCCCAGGGCCCTCTGGCCCAGGAGGATGAAGCGCGCCGGCTTCGCTCTTGCACGCCGGCTTGCCATCCGGGT<br>AAGCGCGGGAAAGGCGGCCACAGGGCGCGGCGGCAGCGCAGCGCGTGGGATCTCACGACCCATCCGTTAACCCACCGTTCCCAGGAGC<br>TCCGAGGCGCAGCGGCGACAGAGGTTCGCCCCGGCCTGCTAGCATTGGCATTGCGGTTGACTGAGCTTCGCCTAACAGGCTTGGGGAGG<br>GTGGGCTGGGCTGGGCTGGGCTGGGCTGGGTGCTGCCCGGCTGTCCGCCTTTCGTTTTCCTGGGACCGAGGAGTCTTCCGCTCCGTATC<br>TGCCTAGAGTCTGAATCCGACTTTCTTTCCTTTGGGCACGCGCTCGCCAGTGGAGCACTTCTTGTTCTGGCCCCGGGCTGATCTGCACGCG<br>GACTTGAGCAGGTGCCAAGGTGCCACGCAGTCCCCTCACGGCTTTCGGGGGGTCTTGGAGTCGGGTGGGGAGGGAGACTTAGGTGTGGT<br>AACCTGCGCAGGTGCCAAAGGGCAGAAGGAGCAGCCTTGGATTATAGTCACGGTCTCTCCCTCTCTTCCCTGCCATTTTTAGGGCTTTCTC<br>TACGTGCTGTTGTCTCACTGGGTTTTTGTCGGAGCCCCACGCCCTCCGGCCTCTGATTCCTGGAAGAAAGGGTTGGTCCCCTCAGCACCCC<br>CAGCATCCCGGAAAATGGGGAGCAAGGCTCTGCCAGCGCCCATCCCGCTCCACCCGTCGCTGCAGCTCACCAATTACTCCTTCCTGCAGG<br>CCGTGAACACCTTCCCGGCCACGGTGGACCACCTGCAGGGCCTGTACGGTCTCAGCGCGGTACAGACCATGCACATGAACCACTGGACG<br>CTGGGGTATCCCAATGTGCACGAGATCACCCGCTCCACCATCACGGAGATGGCGGCGGCGCAGGGCCTCGTGGACGCGCGCTTCCCCTT<br>CCCGGCCCTGCCTTTTACCACCCACCTATTCCACCCCAAGCAGGGGGCCATTGCCCACGTCCTCCCAGCCCTGCACAAGGACCGGCCCCG<br>TTTTGACTTTGCCAATTTGGCGGTGGCTGCCACGCAAGAGGATCCGCCTAAGATGGGAGACCTGAGCAAGCTGAGCCCAGGACTGGGTAG<br>CCCCATCTCGGGCCTCAGTAAATTGACTCCGGACAGAAAGCCCTCTCGAGGAAGGTTGCCCTCCAAAACGAAAAAAGAGTTTATCTGCAAG<br>TTTTGCGGCAGACACTTTACCAAATCCTACAATTTGCTCATCCATGAGAGGACCCACACGGACGAGAGGCCGTACACGTGTGACATCTGCC<br>ACAAGGCCTTCCGGAGGCAAGATCACCT |
| 129 | GLIS3 | CACTCCCCCGCCGCCTCCGCCCCTAACCCTCGGCCCCGTGCGCGAGCGAGCGAGGGAGCGAACGCAGCGCAACAAAACAAACTAGTGCC<br>GGCTTCCTGTTGTGCAACTCGCTCCTGAGTGAGTCGGGGGCCGAAAGGGTGCTGCGGCTGGGAAGCCCGGGCGCCGGGGACCTGCGCG<br>CGCTGCCCGGCCTGGCCGGAGCCTGTAGCCCGGGGGCGCCACGGCCGGGCTCGCAGTCCCCCCACGCCGGCCCCCCGGTCCCCGCCG<br>AGCCAGTGTCCTCACCCTGTGGTTTCCTTTCGCTTCTCGCCTCCCAAACACCTCCAGCAAGTCGGAGGGCGCGAACGCGGAGCCAGAAAC<br>CCTTCCCCAAAGTTTCTCCCGCCAGGTACCTAATTGAATCATCCATAGGATGACAAATCAGCCAGGGCCAAGATTTCCAGACACTTGAGTGA<br>CTTCCCGGTCCCCGAGGTGACTTGTCAGCTCCAGTGAGTAACTTGGAACTGTCGCTCGGGGCAAGGTGTGTGTCTAGGAGAGAGCCGGCG<br>GCTCACTCACGCTTTCCAGAGAGCGACCCGGGCCGACTTCAAAATACACACAGGGTCATTTATAGGGACTGGAGCCGCGCGCAGGACAAC<br>GTCTCCGAGACTGAGACATTTTCCAAACAGTGCTGACATTTTGTCGGGCCCCATAAAAAATGTAAACGCGAGGTGACGAACCCGGCGGGGA<br>GGGTTCGTGTCTGGCTGTGTCTGCGTCCTGGCGGCGTGGGAGGTTATAGTTCCAGACCTGGCGGCTGCGGATCGCCGGGCCGGTACCCG<br>CGAGGAGTGTAGGTACCCTCAGCCCGACCACCTCCCGCAATCATGGGGACACCGGCTTGGATGAGACACAGGCGTGGAAAACAGCCTTC<br>GTGAAACTCCACAAACACGTGGAACTTGAAAAGACAACTACAGCCCCGCGTGTGCGCGAGAGACCTCACGTCACCCCATCAGTTCCCACTT<br>CGCCAAAGTTTCCCTTCAGTGGGGACTCCAGAGTGGTGCGCCCCATGCCCGTGCGTCCTGTAACGTGCCCTGATTGTGTACCCCTCTGCC<br>CGCTCTACTTGAAATGAAAACACAAAAACTGTTCCGAATTAGCGCAACTTTAAAGCCCCGTTATCTGTCTTCTACACTGGGCGCTCTTAGGC |

TABLE 6B-continued

| SEQ ID NO | GENE NAME | SEQUENCE |
|---|---|---|
| | | CACTGACAGAAACATGGTTTGAACCCTAATTGTTGCTATCAGTCTCAGTCAGCGCAGGTCTCTCAGTGACCTGTGACGCCGGGAGTTGAGG<br>TGCGCGTATCCTTAAACCCGCGCGAACGCCACCGGCTCAGCGTAGAAAACTATTTGTAATCCCTAGTTTGCGTCTCTGAGCTTTAACTCCCC<br>CACACTCTCAAGCGCCCGGTTTCTCCTCGTCTCTCGCCTGCGAGCAAAGTTCCTATGGCATCCACTTACCAGGTAACCGGGATTTCCACAA<br>CAAAGCCCGGCGTGCGGGTCCCTTCCCCCGGCCGGCCAGCGCGAGTGACAGCGGGCGGCCGGCGCTGGCGAGGAGTAACTTGGGGCT<br>CCAGCCCTTCAGAGCGCTCCGCGGGCTGTGCCTCCTTCGGAAATGAAAACCCCCATCCAAACGGGGGGACGGAGCGCGGAAACCCGGCC<br>CAAGTGCCGTGTGTGCGCGCGCGTCTGCGAGGGCAGCGGCGGCAGGGGGAGGAGGAGGCAGAGGCGGGGTGGCTGGACCCTCGGCAT<br>CAGCTCATTCTCCCCTGCTACACACATACACACACAAATAATGTTTCTAAAAAGTTCAGTTGCGACTTTGTGCCTCGCCTGTCCTGTTCATCC<br>TCGTCCTGGGCCGGGGAATGCTTCTGGGGGCCGACCCCGGGATGCTGGCTAATTGCTGCCGGCGGGTTCCGTCGCCGGTGTGACCCTG<br>GACGGCGCGGACGGCGTACAGGGGGTCCCGGGAGGGGCAGTGGCCGCGGCACTCGCCGCCGGTGCCCGTGCGCGCCGCGCTCTGGG<br>CTGCCCGGGCGGCGCAGTGTGGACGCGG |
| 130 | NOTCH1 | CTGAAAAGCCGTCAGGGAAACCACACATGTTCAACCCCTGGCGGCTCCCCCAAACCTCTCATTTCCAGTAACTGTGTGTTTCCGCTCGTCA<br>ACAGCTGAAACCGAGCGGAACTTGGGGGGCCCCACCACGCGGCCCTGCTGTGCGGCACGGGGCTCATCTGTCCCCCGGCTGCGGGGAG<br>TCAGCTCTCACCGCCCACCTCCTTCCCAGATAGTCTCTGTGCCCACTCGACGGCCCGGCAAGCCCAGCCCCTGCCTGCCACGGCCACAGC<br>AGCCTCAGAGAGCTGCCCTCTCTGGCCAGGGTCAGGGCCTGAGCTGCTGCCTCCCGCAGGGTCGAGGGCAGGACACTTGTCTGAGGCTT<br>GGGTGGGGCAATGGCACCTCCTCAGGGCCTCAGCCCCCGGGCAGGCTCGGTGACCATGGGCCTACAGCAGGGAAAATTCTGGGCCAAAA<br>GCTCCAGCCTCCTACTAGGGCATCTGTCTGCAAATGCACCTTAACCTGACCGCTTGGGCTGTGGGGGAGCCTGTTTCAGGGAAAGTGAGG<br>GACGCGCCAGTTTCCTCCTTTGGACTTGATGAGGCACGAACGCATCTCTAATAAAGCCAGGTCTCCCCGCCGTGGCTCCCTGGGCGGGTG<br>CCTGTGGCTCGGGCCATGAGTCACGCTGGGTAACCCCACTACGGGGAAGAGGGCAGGAAGCTGGGAGCCACCGCCTCTGTGCCCGGTTG<br>TCATCTCGGCACGAGGGCGACCGTCGGCTTCGTCCTGCCCTCATGGCTGAGGGCTTTTGGGATGTGGCGGGAGACGGGGGAGTC |
| 131 | EGFL7 | AAATCATCAGAATGGCTAAAATGAAAAAGACAGACAACAGCAAGTGCTGACAAGGGTGTGGGGCGGCCAAATGCTCCTGCACTGCTGGCA<br>GGGGACCTGAGAACTGCAGGGCATTCCCTGGCTTCCTGCCCCTCCTGGGACTGGGGACCCCCCAGGGACAGCCTAAGGGAACTGCATTT<br>ATCTTCACGTCTGCCAAAAGATAACACGAAGATGTTCAAAGCTAAGCCCCCAGGCTGGTAAGAGCTCCAAGGCACCAGCAGTGTGTGCAGA<br>ACTGGGGGGAGTCTGTTCTCCCAGGGATGCTCCCATCACCTGCTGCCAGCAGTGGGGCATGCCGGTCCCCTGGGGTGTGGCCAAGGGGC<br>TGTGTCTCCTGCCCGGGCTGCCGGCCCCTCTCAGGTTCACTTTCCCATCTCTAAGCCCACGTCTCGCTGCAGTTCAAGTTTGCCAGGCCAC<br>CAACGGGTGACACGCCCGGCGCAGTGGGGGACTCCGCACTTTCTGCGCAC |
| 132 | CELF2 | ACCCTTTGTGCCTGGGTCCCATAAACAATGTGCTTTTTAAAGGGGAGCCCCCTCCCAGCTCCGGCCTTTTTCTCCAGCGTGGGCAGCCAAT<br>CAGCTGCGCAGAGCTGCATAGCTGGACCGCTTTCCATTCTGAGTAGCAACAACGTACTAATTTGATGCACACATGGATGCCTCGCGCACTC<br>TGCAAATTCATCACCCGCATCTTGCATTAGTCATCTGACGGACTGCCAAGTGTTTCATTTTCTTTCCATGTGACTTTATTATTACCACCTCTCT<br>CCTCTCTTCCAAAAACCTCCCAAAAAGGGCGGTGGGGCGGGGGGCGGGGCAGGGAGAGGGAGAGAAATCCAGCAGACATCTAGCTCTGC<br>CTTTCTTTCCCAGCCACAGCCAGGGTAGGGCTGATAAGGCGCTGATGCGTTGATGGCAGCCTTGCAGAGCTAGACCTGCACTTAACTTGCA<br>GCTGCCTCCCGAGCCTCCAAGATGTCCACGCCCTGGGTGACAGGCGGCAGGGCGCTGCCCCGTGCTCCCCCGGCTCTGCTCGACAGCA<br>GCACGCAGTGAGAGCCTCGCCGCCGCCGAGGAGCAACTCATGGTGCCTCCGCTTTGTTTTAGTTCATCAAATTTCTACGACTCATTAGGCA<br>CTTTGCCACTGCTCTTCTTCCTCCTCCTTCCGCCTCCCCGCTCCCCCACCCCCACTATTTTTTCTTCCTGTCCCTCATCGTGCCGCCCCTAAC<br>TCTGGCTCCCGGTTCCGTTTTTGACAGTAACGGCACAGCCAACAAGATGAACGGAGCTTTGGATCACTCAGACCAACCAGACCCAGATGCC<br>ATTAAGATGTTTGTCGGACAGATCCCCCGGTCATGGTCGGAAAAGGAGCTGAAAGAACTTTTTGAGCCTTACGGAGCCGTCTACCAGATCA<br>ACGTCCTCCGGGACCGGAGTCAGAACCCTCCGCAGAGTAAAGGTACAGAGCGCGGGGCGGGGGTCGCCAGGCGTCCAGGTGGGCGTCG<br>CGGGGCACTGGGGCTGTCCGAGCCCCCAGCCTGCAGGAGGAAGGGCGGGTAGGCAGGAGGGCTGGAAGCAGCCGGTGCTGGCGGCCC<br>CTGTGCTCCAGGGGCTGCTCCCGACTCCTCCCCGCACCCCCGCCCGCCTGCCCGCCGGGACAGGTTGGAGGCGGGAGAGAGGGACCGA<br>GGCAGGGCGGGAGCGCAGAGGCTCGGTC |
| 133 | HHEX | TAACAAATAAGCCGCCCGTGGTCCGCGCTGTGGGTGACCCTTGGCGCCTTCGAGGTCTGGAGCCCTAGGGTAAATAAGGAAACGGGGCG<br>CCTCTAGAGTTTTAAATGAACTCTGTTATTGGAAGCTTCAGTAGGGACCCTGAAAACAATTAACGTCTTAATTAGCATTTTAATGTCTCCATTA<br>TTACGGCGCGGGCTCTAGCTCAGCCCTTTACCTTACCTTCTCACCGTTAACAGGGGAGGGGGATTGTATTTTTAGTTCATCTTTTTATGTTTT<br>TGAGTTGTTATCCTGTCTGTCTGATTCCAGCCTCGAGGGTTTGATGATGCGGCCCGAGCCTGGCTGTGGTCGCCTGTCGGGGCTGGAGCG<br>GGACCCTCAGCCGGGCCGGGCCTGGGGGCTAACGTTTTCACAGTGCGCCCTGAGTTTCCTTGGGTTACTGCTGGGACCGCGCAGGAGGA<br>AGCAAAGAGTTTTTCGAGCTAGACCAACAGGAAACACATTGACGGAAATGTTGCCATAGCCCATGGGGTGGCTTTAACTGGCCGCCCCCGC |

TABLE 6B-continued

| SEQ ID NO | GENE NAME | SEQUENCE |
|---|---|---|
| | | GGGCTGGGTGTGAAATCAGAGGAGGCCGCGGCTCCCCCGGCCAGGATTGGAGGCTCCTCGCGCAACCTAATGCGGGTGTCCGGGCCCG<br>AGCGCTTCCCGCGCAGCCAGGCCTTGTCGGTGCAGCAGCCCCGCTCCTCCCCAACACGCACACACCCGGTGTTCGCAAGTGCGGCTCAC<br>CAAGGGAGATCCAAGGGGGCAAAAAGTTATGTATAAATCCGAGAGCCACTGGGGAAAGAGGGTCGTGGTATTGTAAG |
| 134 | DOCK1/ FAM196A | CTACCCTGTGCTATCCTGAGCTGTAGTCTTCTGAAATGATCGTTTGGCTTCCCAGCCAAGGCAGGGCTCCCCCAAAGTTCATTCCCACTCTT<br>GCAGTTTCACCTCGGGATGCTTCCGCAGAATTTCAGCGCCTAAGCAGACAAGGTCAAAGTAAACCGCTTCACCGCTGCTTCTGGCGCAGG<br>GGCCCAGAGCGCGTGCAGCTCCCCAGCACAGACCAACAGCAGGAGAGGGGTCCGGGCGGGAGCCCTGGGCTGTAGATAAGCAAAACGC<br>ACCCATTTTCTCTCCTATTTACTCCAGAGGCACCTCTCCTCCCCCACTCCTGGCATCTCTTTATCACTGGCTCCCTCTCCCTGTGGCATATTT<br>TTGGGTAGTAGAATGCTGAGGTCACAGGGAGCGGCTCTTTATCCAAGCAGTGGGGACATCAGCCTGGAGCCCTGAGCATGAACCAGCAAG<br>ATGCAGACTCTCGCTCTTGACTTTGGGCTCCAGGAGCTGCCCCGACC |
| 135 | PAX6 | CAGTGCTCCGCTCCGGGAAATTGCATCGTCACGACAAACGGGACCGTGATAAAACGACCCTTTCCGTCCTTATTTGTAGATCACTCAGACG<br>AGATTGAACTGCACTTGTTTCCCCTTCGAGGGGAGCCGCGTTTTCAGGGTAGCCGAAGGCTTGGGGCTGAGGGGGGGCCCTCACCAAGG<br>CGCGGGTGGGGGCCGGAGCCTCAACTCGATGAGAAGTGACAGGCGTTTGGGGGATCTGGGCTCCGGCCGGGACCAGCGCAAGCAGGGA<br>CTTTGCGGGGACACCGCTTCTCCAACAGAGCAAGGCCTGGCCCACGTTTCCGGTTTCTCCTAACTTCCTTTTATTGCCTTCCTTTGCTTCGC<br>AAGTTCCATCTACCCCTCCAGCTACAGAGCCCCACCTCTAGGCACAGGAAGCTTCCCGGAAAAAGAAAGGCTGTCCCAGAAAGAGACCGA<br>GAGAGACTTTCCAAACTTCGGGCATAGCCACGGCAATTCCCAGTCTGCTAATGCCAAGGCGGGCGCGTAAGGCCGCCTAAATCTAGACCT<br>CCCTCCTCACTCATTTCAAAAAATAACAACGTGCCAGCCACCTCCGCAGATACCGCCGGCTGGTGCTTGCCCAGGAGACGCCAGGGCCAG<br>AGCGCCACTCCCAGCATCGAAATGGCAGAGAGAAAGCGCAGCTCCAAATTCCCCTTCAGAGGTTAAGCCTCAATCATTGTGTCCCTTCCCT<br>AGGGACTGCTGGCGCTCTCGCCCACTGGCGATGATTATGCGCCTAGAACTCGACCGCGAAGCAACTAATAGGAAAACATATGGTGTCAATT<br>TGGATGCTCCGCGCCTCGCGCACACCCGGGAACGAGCGGCACAAAGCCCTGCCGGCCGGCCCGCGACCCCGCGCCCCTCGGGGCCTG<br>CCAGCCGGGCCGCAGCGACAAACGCTCAGGGCTGCGCGCCCTGGCTGGGGCCCGCCCGAGAGACAGCCTGCGGCTGGGGAGTCTGAG<br>CTCCAAGGGGAGAGCCCAGCCGCCGAAGGCGAGCCTACCGGCCAAGCCCTGGGGTCCGGCAGGTTCTGCACAACTACTCCCGCAAAGCT<br>CGCCACCTTTGTGCCCTTTCCTCAG |
| 136 | FERMT3 | GGGCCCTCGCGGCTCAAGCGCCAGCGCTGGAGAGAGAGTCTGAGGGTACCACGGGCGTGCTGGCCTGGGTGCTCACTCCCGCCCTCCT<br>TCATGAGCGGCTTTCCTCTGGGTGTGTCCAGGGCATCACAGAGCTCTTCTGCCCAAACCCGGAGGCCTACCAGGGCCTGCCCACCTTGCC<br>TCCTTCCACACTCTCTGTAGCAGCAGCCGCAGCCATGGCGGGGATGAAGACAGCCTCCGGGGACTACATCGACTCGTCATGGGAGCTGCG<br>GGTGTTTGTGGGAGAGGAGGACCCAGAGGCCGAGTCGGTCACCCTGCGGGTCACTGGGGAGTCGCACATCGGCGGGGTGCTCCTGAAG<br>ATTGTGGAGCAGATCAGTGAGTGTCCGCTGCCCGCTTGCTGAACTCGGCACCATGGGCGGCCGCCACGGGTGTCTCTGGGCACTTCCGG<br>GCCATCCCTGCTGCTCAGCTCCCGATAATGGTGTCACGGTGACTCAGGCATTAGC |
| 137 | PKNOX2 | TGTTTACGGAATCGGGATCGAGGGGCCGATAAGTAGTTTACACGCCGGCCAGAGCAGAGGGCTGGAGGTCGGAGTTGGGGGCTGGAGGA<br>ACGGGTGGCGTTTTTAGGATTCAGTAACAGGATCACAGCTTTTTCTTGTGGTGGAAGCTATTGGAATTTGGGGAGGGTAGCACGAGGGGTC<br>CTGCAGCTCCGCGTGTGAAAAAGCGTTTAGGTAGGCGATGAAAGTAGTTGATCTGAGCCATGGCAGGCGAGCCCCGAATTTTTGCTGCTTC<br>CCCCTGAAAGTGTTTCTTTAGGAGGAGAGGACTTGGGCCACACAGGACCCGGTCCTAAGAGAGCGATTCCGGGAAGCGGACAGATCGAAG<br>AGACCTTCTGGGCGAAGCGGCAGGGCAGCCTCGCGGGGCTGGGAGTGGATCTGAGGTCCCGACCCAGGCGGCTCGGAGTGCTCCAGGA<br>GCCACCTGGGTCTGCGGGCGCAGCGCGGCGGGGCGGGAGCGGTGGCCCGCAGGGGCCGCGGCCTGCGATGAAGGCCGGGGGGCAGC<br>GCTAGCAGCGAGGTGCCACAGTGGGCCGAGGAGTCTGGGCTGTGGCCCAGGGTAGGACCGGCTCA |
| 138 | KIRREL3 | ACCTAAACCAAGCTCTCCCTCCCTGCCGTCTCCTTCCCTGGCCTGGGTCTGAAGGAGAGGAGGTGCCCAGAAGTTCAGAGCGGCATAACC<br>ACAGAGATACTACCTAATTAACATACCAGAAGCATAAAGAACTCATTTGCATTGGAGAGT |
| 139 | BCAT1 | ATAACTACGGGGGTGGGGGTGGGGAAGGAAGAGATCCAAGGAGGCAGAAGGCTGCGGTCAAAATATTTTGGGGTGGCAGAGTCACGTAG<br>GATGTGGCTGTGGGTTCTGGCAGCCCAGAGATTCAGCTCCCGCCTCCTCCCTCAGAGCGAGTCCATAGCTACCCTCACGTCCCCCGTGGC<br>GGTCCTCGCCACGCTCCGGAGCGGGTTACCCATGAGGGTGCTAGACCTGGGCAGCGGGAACCTCGAAGAGGTGGAGATTGCAGGCTGG<br>GACTCCAGATTTCGGGCAGGGATGCGGGGAAGGGAAGACGCCTCGCTGGAGGCGGAATGGAGGGCAAGGCGAAGGAGGATGGTGCAGG<br>AAACGGCGACAAGGCGCCCGGCCAGGCCCGCGAGCTACCGAGACCCGGGTTCCAATCCTCCCCCCTTCCGCAAACGCCCGGGTTCGAG<br>GTACCTGGCGGGCAAGGGCCGCAGCGGAGCGAAGCGGGCTGGCCATGGGGAGGCTGCGGGGACGCGGGGCTGCAGAGAGCGGCAGT |

TABLE 6B-continued

| SEQ ID NO | GENE NAME | SEQUENCE |
|---|---|---|
| | | GGCACGGAGCGCGCGGCTGGAAGCGAAAGCAGGCGGTGTGGCCAAGCCCCGGCGCACGGCCCATAGGGCGCTGGGTACCACGACCTG<br>GGGCCGCGCGCCAGGGCCAGGCGCAGGGTACGACGCAACCCCTCCAGCATCCCTTGGGGAGGAGCCTCCAACCGTCTCGTCCCAGTCT<br>GTCTGCAGTCGCTAAAACCGAAGCGGTTGTCCCTGTCACCGGGGTCGCTTGCGGAGGCCCGAGAATGCGCGCCACGAACGAGCGCCTTT<br>CCAAGCGCAGATATTTCGCGAGCATCCTTGTTTATTAAACAACCTCTAGGTGAATGGCCGGGAAGCGCCCCTCGGTCAAGGCTAAGGAAACCTCGGAGAAACTACAT |
| 140 | HOXC13 | CAGTCCAGCCGCTTGCCTCACTTCTTCCCGCTTGCCTTATCTCCCCGCAGACGTGGTTCCCCTGCAGCCCGAGGTGAGCAGCTACCGGCG<br>CGGGCGCAAGAAACGCGTGCCCTACACTAAGGTGCAGCTGAAGGAGCTAGAGAAGGAATACGCGGCTAGCAAGTTCATCACCAAAGAGAA<br>GCGCCGGCGCATCTCCGCCACCACGAACCTCTCTGAGCGCCAGGTAACCATCTGGTTCCAGAACCGGCGGGTCAAAGAGAAGAAGGTGG<br>TCAGCAAATCGAAAGCGCCTCATCTCCACTCCACCTGACCACCCACCCGCTGCTTGCCCCATCTATTTATGTCTCCGCTTTGTACCATAACC<br>GAACCCACGGAAAGACGCTGCGCGGGTGCAGAAGAGTATTTAATGTTAAGGAAAGAGAAGAACCGCGCCGCCCGGAGGCAGAGAGGCTC<br>CATGGCCGTGCTGCTGGGCCATCCCCAACTCCCTATCCCATCCCCAGCCTCCACCCCCATCCAGATGGGACTCACGTGGCTTCAACAGCT<br>TTGGAAATGGGTCCCGAGTGGGCCGTGCGAGGAAGGCTGTCGACCTCTACTCCTCCTTGC |
| 141 | TBX5 | CAAGATCGACTTTCTTAGGAAGGGGGAGAGGAGGGAACTCTTCACGAAGGGAGGTGGGAGTCCACCTCAGACCTCTATTGGAAGGAAATC<br>GAGTTGTTCCGGGGGACTGAGGTCTCTTGCATAAGGCATGGGATCCTTATTATTATTATTATTATTTTTAAATCCCCCGCGGAGGAGCTCTG<br>GGCAAATGAATACCGAGGCGCCGCTCTAGCTGGTTAGGCTTGGGATGCGATAACTCAGTGCCCTCTTGCAGACTTGCATAGAAATAATTAC<br>TGGGTTGTCGTGGAGGGGACACGAGACAGAGGGAGTTCTCCGTAATGTGCCTTGCGGAGAGAAAGGTCCAAGAATGCAATTCGTCCCAGA<br>GTGGCCCGGCAGGGGCGGGGTGCGAGTGGGTGGTGGAGTAGGGGTGGGAGTGGAGAGAGGTGGTTTCTGTAGAGAATAATTATTGTACC<br>AGGGCCCGCCGAGGCACGAGGCACTCTATTTTGTTTTGTAATCACGACGACTATTATTTTTAGTCTGATCAATGGGCACAATTTCTAAGCAG<br>CGCAGTGGTGGATGCTCGCAAACTTTTGCGCACCGCTGGAAACCCACTAGGTTGAGTTGCAAAACGTACCGCGTAGACGCCCCTGGTGGC<br>GCCGAGAGAAGAGCTAGGCCTGCCCAGCACAGAGCCGGAGAGCGTCGGGCCTTCCGGAAGGGTAAGTTCTCCGCCAAGGGGTCCCGAG<br>GGAGCTGGACGTCTGAATCTGGACTTGCCCCCAGCTTCGGGGTTCGATTCTGGGTTTTGCGCGTCCCCAACCCCCAGGGCTTTCCGAAGC<br>ATGGCCTGGCTCCAGGCCCGGTCCTGTAAGGACTGGAACGGCAGCAAAATGTGCAGGGAGGCAGTCGGCCGGCAGAGCTGCGGCGGGA<br>GCCAAGGTCAGGCCCGCGGGGAGAGCGGGCAGCTTCCAGCGCCGGCCACAAGCTCCCAGGCCAGCTGGGCCGCAGACCCCTTTGCTTC<br>CAGAGAGCACAACCCGCGTCCTTTCTCTCAGCCAGGCTGCAGTGGCTGCCCCGAGCTTCGCTTTCGTTTCCCAAGCTGTTAATAACGATAT<br>GTCCCCAAATCCGAGGCTCGTGTTTGCTCCCAGATGCCAAGAACGCAACCCGAAATCCTTCTCCCAAACCCTAGGTCGACGAGATGAGTTC<br>CTACTTGACCTCTGAGCCGAGGTGGGCCGGAAACCGAGGCCTAGGCCCCGCCGGGGCTGCAAGGAAAAGGGGAAACTCCGAGCGTAGC<br>GTCTTTTCCTTGTGGTTCCTTTCTCCGGCATCCCGGACTGCGGGCCCTGCAGCCACCTGGACCGGCATTCAAAGGATTCTGCAAGTCCAGC<br>TTCACAGACTGGCTTTCCCAGACGCTCCGAAGCCCGCACCACGAACAGAATAAAGGAGAGACGAGAGATCGCAACTAGATTTGAGAATCCT<br>CGTTCTTTTCCCCAATCGTTCGGGCAGTAAACTCCGGAGCCGGCTACAGCGCGCATCCTC |
| 142 | TBX3 | ACTGTCCTCCTCCCTCAATTGCCTATTTTTTGCCCATAGCTCTAACTTAACCCTGTGATCACCCCAGATCGCTACTTCTGACCCCCATCTCCT<br>CTCCCACACCAACCTCCAGCGCGCGAAGCAGAGAACGAGAGGAAAGTTTGCGGGGTTCGAATCGAAAATGTCGACATCTTGCTAATGGTCT<br>GCAAACTTCCGCCAATTATGACTGACCTCCCAGACTCGGCCCCAGGAGGCTCGTATTAGGCAGGGAGGCCGCCGTAATTCTGGGATCAAA<br>AGCGGGAAGGTGCGAACTCCTCTTTGTCTCTGCGTGCCCGGCGCGCCCCCCTCCCGGTGGGTGATAAACCCACTCTGGCGCCGGCCATG<br>CGCTGGGTGATTAATTTGCGAACAAACAAAAGCGGCCTGGTGGCCACTGCATTCGGGTTAAACATTGGCCAGCGTGTTCCGAAGGCTTGTG<br>CTGGGCCTGGCCTCCAGGAGAACCCACGAGGCCAGCGCTCCCCGGA |
| 143 | chr12: 113622100-113623000 | CTCAGGGAATCACATGTCCGCCTGGCCTGGCCTGGTACCAAATGTTTATAGACAGGACGAGGGTCGCTGGAATCGCCTCGCTCCTTTCAG<br>CTTGGCGCTAAGGCGCGAATCTCGATCCTCCTAGTATTTCTCTGGCGTCTGTCTCTATCTCAGTCTCTGCTTTTGTCTCTTTCTCCCTCCCTC<br>CGCCCCAGTCTTTCCGTCTCTTTTTCCTCGAATGCACGTGGAATTCGGAATTGAAAATTGAGGTCAGAATCTCCCTTTTTCTTCCAGTTATCC<br>GCGCCGCTGCCCCACGCCTAGCGGCTTGGATCTGCATAGACATCTATCTACCCGCAACAAGATCCGAGCTGCAGAAGCAAACCTAATCTGT<br>CTCCGCACCATCCCCTGCTCTGTAGACCCACTGCCCCATCCCACGCCACATCCTTGAGGTTCAAGTAGCGACTCCAGCGGATGATTCGGA<br>GAATGCCCTGCTTTCCAAAGGCCCCAACCCGTGTTTTTATTTTCTTTTTCCTTTGCCCGCTTGACCAACTTTGGTTTCTTTCAGGGCCCGGAG<br>GTGCCTGCGCCGCGCTTGGCTTTGCTTTCCGCCGCCCCAGGAGACCCGGGACTGTGGTTTCCGCTCGCCACATCCCAGCCTGGTGCGCA<br>CACAAGAGCCTGGCGAGCTTCCCTCGCGCGCTTACAGTCAACTACTTTGGGCCTCGGTTTCCCTGCTCCTTGTAGATCAGAGAAGGGACG<br>GGCGAAATGCCTGCGAGGGAGGGTTGGCGAATGGGTTGGTTGGTGGCAAGACTGCAGTTCTTGTACATGGACGGGGTTGGGGGGTCAA<br>CACTGGAAGAACTCCTGCCTGACGCCAAGAGCCACCCGCTTTCCAGCTCGTCCCACTCCGCGGATGTTTACCCACCTTCATG |

TABLE 6B-continued

| SEQ ID NO | GENE NAME | SEQUENCE |
|---|---|---|
| 144 | chr12: 113657800-113658300 | TTTGGGGCACCCAACCCTTCCCAAGCCTCGGTTTTCCCGATCTTGTGGGATCCTTGCGGCGCGAATGGGGTTGGAAGCACCTTGGAAGCT<br>ACAGAGTACCGGGTCGGGACAATTTCCGGCACTGCCCCAGTTCAGTGGTTTATAGAAAATTTCTTTCTCTCTCTCAGGTCCACTAAGACCGA<br>GAGAGAGAGAGAAGTCGACTCTGGCACACCCGGGCGAGGGGCTGCCGGGATTCGGGAGCTGGCGCGGTTGATTTTTTCCGAGAATCCTC<br>CACTTGGGGTGACGTCGGGCAGCGCGCGCGGGCCGTGAGGTTAATGCCCAGGCTTTTCTCTAAAGCGTCCGGGAATGATCCGGCGAATA<br>AAACGGGTGTCTGCAAAGTTAATGAATTGTACAAGGAGGCTGAGGGTGGGGACTTCGACCCGGGGAGCCAGAGGCGGTTCTGGTGGACG<br>CTTCCCCGTGCGCCTAGGGGTGCGCTGGGCTTTCCCAGCCGAGGTCTGCAG |
| 145 | THEM233 | CCAGACAGTTAAGGTAAAACGTTGAAGTCAAGAGGAAGTAGTGAGTCTGTTGCCAACTGGATAGGGTTGGTCCTGTCCCATCTAAATGTATT<br>AGAATTAAGTGGCTTTTAAAAATGAGCTGGTCATCTTCAGCCCACGGGCTGGCCAATTTGGAACTTAATGGGCCTTTGCGTCCTCCTTCCCT<br>GAGCCTCCTTTTATTCCAGACTTCTCAGTGTGAGTCTGTGCGTCCCTCCGACGATCTCAGGGAGTGGGGTGCCTTCATCTGCCTGTTCCCT<br>GTTCCTCAGGCTGACGCTCCCGCTGTCCTCCCCGCCTCCCCTCACTCCTTTTCTCCCTCCCTTCCTCCTTGTGGGGAGGCTCTTGGCCAGG<br>GTCCCTGAGCCCGGGCGGGTGCTGGCAGAGGACGCAGAAGGGGTGAGGTCACGTCTCCCTTGAGCCCCGAGCCGCTGGCTTTTCAGAG<br>CCTCGCCACAAGCCGGCGGCCAGAGCCCCAGACCACACAGACCGTGCGCTCCTCCGCCCTCCCGGCGCCGCCGGCCTCGCCCATGTCT<br>CAGTACGCCCCTAGCCCGGACTTCAAGAGGGCTTTGGACAGCAGTCCCGAGGCCAACACTGAAGATGACAAGACCGAGGAGGACGTGCC<br>CATGCCCAAGAACTACCTGTGGCTCACCATCGTCTCGTGTTTTTGCCCTGCGTACCCCATCAACATCGTGGCTTTGGTCTTTTCCATCATGG<br>TGAGTGAATCACGGCCAGAGGCAGCCTGGGAGGAGAGACCCGGGCGGCTTTGAGCCCCTGCAGGGGAGTCCGCGCGCTCTCTGCGGCT<br>CCCTTCCTCACGGCCCGGCCCGCGCTAGGTGTTCTTTGTCCTCGCACCTCCTCCTCACCTTTCTCGGGCTCTCAGAGCTCTCCCCGCAATC<br>ATCAGCACCTCCTCTGCACTCCTCGTGGTACTCAGAGCCCTGATCAAGCTTCCCCCAGGCTAGCTTTCCTCTTCTTTCCAGCTCCCAGGGT<br>GCGTTTCCTCTCCAACCCGGGGAAGTTCTTCCGTGGACTTTGCTGACTCCTCTGACCTTCCTAGGCACTTGCCCGGGGCTTCTCAACCCTC<br>TTTTCTAGAGCCCCAGTGCGCGCCACCCTAGCGAGCGCAGTAAGCTCATACCCCGAGCATGCAGGCTCTACGTTCCTTTCCCTGCCGCTC<br>CGGGGGCTCCTGCTCTCCAGCGCCCAGGACTGTCTCTATCTCAGCCTGTGCTCCCTTCTCTCTTTGCTGCGCCCAAGGGCACCGCTTCCG<br>CCACTCTCCGGGGGGTCCCCAGGCGATTCCTGATGCCCCCTCCTTGATCCCGTTTCCGCGCTTTGGCACGGCACGCTCTGTCCAGGCAAC<br>AGTTTCCTCTCGCTTCTTCCTACACCCAACTTCCTCTCCTTGCCTCCCTCCGGCGCCCCCTTTTTAACGCGCCCGAGGCTGGCTCACACCC<br>ACTACCTCTTTAGGCCTTTCTTAGGCTCCCCGTGTGCCCCCCTCACCAGCAAAGTGGGTGCGCCTCTCTTACTCTTTCTACCCAGCGCGTC<br>GTAGTTCCTCCCCGTTTGCTGCGCACTGGCCCTAACCTCTCTTCTCTTGGTGTCCCCCAGAGCTCCCAGGCGCCCCTCCACCGCTCTGTCC<br>TGCGCCCGGGGCTCTCCCGGGAATGAACTAGGGGATTCCACGCAACGTGCGGCTCCGCCCGCCCTCTGCGCTCAGACCTCCCGAGCTGC<br>CCGCCTCTCTAGGAGTGGCCGCTGGGGCCTCTAGTCCGCCCTTCCGGAGCTCAGCTCCCTAGCCCTCTTCAACCCTGGTAGGAACACCCG<br>AGCGAACCCCACCAGGAGGGCGACGAGCGCCTGCTAGGCCCTCGCCTTATTGACTGCAGCAGCTGGCCCGGGGGTGGCGGCGGGGTGA<br>GGTTCGTACCGGCACTGTCCCGGGACAACCCTTGCAGTTGCGCTCCCTCCCCCACCGGCTCACCTCGCCTGCAGCTGGGCCACGGAACT<br>CCCCGGCCACAGACGCA |
| 146 | NCOR2 | CTCTCTGGGCCTTAGGAAAATGGAAATGACACCTGTACCTGCCCTTCCAGGACTGACAGGAGGGGCTGCTCCATGAAACCTCACTGCTGC<br>GGTCATAATGTCATTATCTTTTGCCTTAAAGGGATTTCTTCTGCACCAGCACCTAAAGTGGCAGCCCCTTACCCTTGGCCATCAGCTGGACC<br>CTGGTGCTCTCCTGGAGCCCAAAACCTCTGTTTTGTGTTGCATCCTGCTGACCAGCCACAGTCCACACCCATCTGAGTGTCTGAGCAGAAC<br>AGCCCAGAGGCCACACCAGGATGGCTTTCCACCGGTCACCTTCCCCCACCCACTCATAAACCCTGCGTCTCTGGGGGAGAGGGTGGCGA<br>GGTCCCCTCCCCACATAGATGGAAACACTGAGGCCTGATTCATGGTGCCCCCTGTGAAGCGCCTCATGGCCAGCACCGGGGGGCAGCAG<br>GCCAGGGCGGGGACACATACCCGGTTCTCGTCGTAGATGATCTGCACCAGGCTGCGGTGCTTCGACTCGATGGGCGGCGGTGACACGGG<br>CTTCTCAGGCTCGGGCGGCTTGGCAGCCTCCTCCTCCAGCTGTTGCTGTGGGGAGAGGCA |
| 147 | THEM132C | CTTGAAAACTCCCAGCCCCCTTTGTCCAGATGGGGATGGAGGTGGCCAGGCTGCCCCGTTGATTGTGTGCCGAGGAGCCCTCCCCGGGA<br>AGGCTGTGATTTATACGCGCAGGCTTGTCACGGGGTGAAAGGAAGGGCCACTTTTTCATTTTGATCCAATGTTAGGTTTGAAAGCCACCCAC<br>TGCTGTAAACTCAGCTGGATCCGCGGGCCGTGATTAAACACATTGCCCGCTTTGTTGCCGAGATGGTGTTTCGGAAGGCGCTGTGAATGCA<br>CTTCCCTTTGCGGGGCTCACACAGACAAGATGTGTGTTGCAAGGATGAGGCGCCTGCTCGGCCTCCAGCCCAGGGCCGGGAAGGGAGAA<br>GGTGCTGTGCGTCGCTGCCTGTGTCGCCCGCGGCTCTCC |
| 148 | PTGDR | CGCGTCAGGGCCGAGCTCTTCACTGGCCTGCTCCGCGCTCTTCAATGCCAGCGCCAGGCGCTCACCCTGCAGAGCGTCCCGCCTCTCAA<br>AGAGGGGTGTGACCCGCGAGTTTAGATAGGAGGTTCCTGCCGTGGGAACACCCCGCCGCCCTCGGAGCTTTTTCTGTGGCGCAGCTTCT<br>CCGCCCGAGCCGCGCGCGGAGCTGCCGGGGGCTCCTTAGCACCCGGGCGCCGGGGCCCTCGCCCTTCCGCAGCCTTCACTCCAGCCCT<br>CTGCTCCCGCACGCCATGAAGTCGCCGTTCTACCGCTGCCAGAACACCACCTCTGTGGAAAAAGGCAACTCGGCGGTGATGGGCGGGGT |

TABLE 6B-continued

| SEQ ID NO | GENE NAME | SEQUENCE |
|---|---|---|
| | | GCTCTTCAGCACCGGCCTCCTGGGCAACCTGCTGGCCCTGGGGCTGCTGGCGCGCTCGGGGCTGGGGTGGTGCTCGCGGCGTCCACTG<br>CGCCCGCTGCCCTCGGTCTTCTACATGCTGGTGTGTGGCCTGACGGTCACCGACTTGCTGGGCAAGTGCCTCCTAAGCCCGGTGGTGCTG<br>GCTGCCTACGCTCAGAACCGGAGTCTGCGGGTGCTTGCGCCCGCATTGGACAACTCGTTGTGCCAAGCCTTCGCCTTCTTCATGTCCTTCT<br>TTGGGCTCTCCTCGACACTGCAACTCCTGGCCATGGCACTGGAGTGCTGGCTCTCCCTAGGGCACCCTTTCTTCTACCGACGGCACATCAC<br>CCTGCGCCTGGGCGCACTGGTGGCCCCGGTGGTGAGCGCCTTCTCCCTGGCTTTCTGCGCGCTACCTTTCATGGGCTTCGGGAAGTTCGT<br>GCAGTACTGCCCCGGCACCTGGTGCTTTATCCAGATGGTCCACGAGGAGGGCTCGCTGTCGGTGCTGGGGTACTCTGTGCTCTACTCCAG<br>CCTCATGGCGCTGCTGGTCCTCGCCACCGTGCTGTGCAACCTCGGCGCCATGCGCAACCTCTATGCGATGCACCGGCGGCTGCAGCGGC<br>ACCCGCGCTCCTGCACCAGGGACTGTGCCGAGCCGCGCGCGGACGGGAGGGAAGCGTCCCCTCAGCCCCTGGAGGAGCTGGATCACCT<br>CCTGCTGCTGGCGCTGATGACCGTGCTCTTCACTATGTGTTCTCTGCCCGTAATTGTGAGTCCCCGGGCCCCGAGGCAGCAGGGCACTGA<br>GACTGTCCGGCCGCGGATGCGGGGCGGGAAGGGTGGA |
| 149 | ISL2 | CTTCCGCCGCGGTATCTGCGTGCCCTTTTCTGGGCGAGCCCTGGGAGATCCAGGGAGAACTGGGCGCTCCAGATGGTGTATGTCTGTACC<br>TTCACAGCAAGGCTTCCCTTGGATTTGAGGCTTCCTATTTTGTCTGGGATCGGGGTTTCTCCTTGTCCCAGTGGCAGCCCCGCGTTGCGGG<br>TTCCGGGCGCTGCGCGGAGCCCAAGGCTGCATGGCAGTGTGCAGCGCCCGCCAGTCGGGCTGGTGGGTTGTGCACTCCGTCGGCAGCT<br>GCAGAAAGGTGGGAGTGCAGGTCTTGCCTTTCCTCACCGGGCGGTTGGCTTCCAGCACCGAGGCTGACCTATCGTGGCAAGTTTGCGGCC<br>CCCGCAGATCCCCAGTGGAGAAAGAGGGCTCTTCCGATGCGATCGAGTGTGCGCCTCCCCGCAAAGCAATGCAGACCCTAAATCACTCAA<br>GGCCTGGAGCTCCAGTCTCAAAGGTGGCAGAAAAGGCCAGACCTAACTCGAGCACCTACTGCCTTCTGCTTGCCCCGCAGAGCCTTCAGG<br>GACTGACTGGGACGCCCCTGGTGGCGGGCAGTCCCATCCGCCATGAGAACGCCGTGCAGGGCAGCGCAGTGGAGGTGCAGACGTACCA<br>GCCGCCGTGGAAGGCGCTCAGCGAGTTTGCCCTCCAGAGCGACCTGGACCAACCCGCCTTCCAACAGCTGGTGAGGCCCTGCCCTACCC<br>GCCCCGACCTCGGGACTCTGCGGGTTGGGGATTTAGCCACTTAGCCTGGCAGAGAGGGGAGGGGGTGGCCTTGGGCTGAGGGGCTGGG<br>TACAGCCCTAGGCGGTGGGGGAGGGGGAACAGTGGCGGGCTCTGAAACCTCACCTCGGCCCATTACGCGCCCTAAACCAGGTCTCCCTG<br>GATTAAAGTGCTCACAAGAGAGGTCGCAGGATTAACCAACCCGCTCCCCCGCCCTAATCCCCCCCTCGTGCGCCTGGGGACCTGGCCTCC<br>TTCTCCGCAGGGCTTGCTCTCAGCTGGCGGCCGGTCCCCAAGGGACACTTTCCGACTCGGAGCACGCGGCCCTGGAGCACCAGCTCGCG<br>TGCCTCTTCACCTGCCTCTTCCCGGTGTTTCCGCCGCCCCAGGTCTCCTTCTCCGAGTCCGGCTCCCTAGGCAACTCCTCCGGCAGCGAC<br>GTGACCTCCCTGTCCTCGCAGCTCCCGGACACCCCCAACAGTATGGTGCCGAGTCCCGTGGAGACGTGAGGGGGACCCCTCCCTGCCAG<br>CCCGCGGACCTCGCATGCTCCCTGCATGAGACTCACCCATGCTCAGGCCATTCCAGTTCCGAAAGCTCTCTCGCCTTCGTAATTATTCTATT<br>GTTATTTATGAGAGAGTACCGAGAGACACGGTCTGGACAGCCCAAGGCGCCAGGATGCAACCTGCTTTCACCAGACTGCAGACCCCTGCT<br>CCGAGGACTCTTAGTTTTTCAAAACCAGAATCTGGGACTTACCAGGGTTAGCTCTGCCCTCTCCTCTCCTCTCTACGTGGCCGCCGCTCTGT<br>CTCTCCACGCCCCACCTGTGTCCCCATCTCGGCCGGCCCGGAGCTCGCCCACGCGGACCCCCGCCCTGCCCCAGCTCAGCGCTCCCTGG<br>CGGCTTCGCCCGGGCTCCTAGCGGGGAAAAGGAAGGGGATAACTCAGAGGAACAGACACTCAAACTCCCAAAGCGCATGATTGCTGGGAA<br>ACAGTAGAAACCAGACTTGCCTTGAAAGTGTTTAAGTTATTCGACGGAGGACAGAGTATGTGAGCCTTTGCCGAACAAACAAACGTAAGTTA<br>TTGTTATTTATTGTGAGAACAGCCAGTTCATAGTGGGACTTGTATTTTGATCTTAATAAAAAATAATAACCCGGGGCGACGCCACTCCTCTGT<br>GCTGTTGGCGCGGCGGGAGGGCCGGCGGAGGCCAGTTCAGGGGTCAGGCTGGCGTCGGCTGCCGGGGCTCCGCGTGCTGCGGGCGG<br>GGCGGGCCCGGTGGGGATTGGGCGC |
| 150 | chr15: 87750000-87751000 | AGTTTGGGGAGCCTTTTCTCCATTTGAGAAAAAACAAACTTACAGCGAGGGGTGAGGGGTTAGGGTTTGGGATTGGGGAAAATGTGGGTGG<br>GGAGCCCCCCAAGGAAGTGAGGAGGGGGCTGCAAGGATTACACCTGGGCATACGTTTCCCTAGAAATCACATTCATTGTATTTTTATAATT<br>TATTCTAAATCTTTCATGCGAAGAAAGTCAGTAGTGAGTGTTAGTACTGGTGGCCCTCCTGATCACACTTGCATCTCTTGAGTGTGCCTTAAA<br>GGTCTTGGGAATGGAAAATATAAAAACTGCTTCGTGATGCGTCATCTTTATCCCCCACTCCCCCACCCATTCCAATATATTTTCTACTTCCAG<br>CCTAAATTCGGGGCCCCCTACCGAGGCCGGCCATGATCTTGAGGGCGGCATAGGGGAGGCCGCGCTCTGTCCACCCCAGCCTGGTGATG<br>CCGTTCGCTTCTTGTGCCCGGTATTGTGGGCTACATGCCTTTCCGGCGTACGGAGCTGAGCGTCCAGGCCAGTGCCCCTCAACCTCTCAG<br>TAATGTTTACCCGAGGCCGTCGTGCAATGAGACTATTCGCATGGCATTGTCAACGCGGCGGCGCGCGCGTCTCGGCCCTCCGCGGCTTGC<br>CAGACTGTCCTGCAAACCACCTCACCCGTCTCTTTGGCGCAGGAGACTCAGGCTGTAACCGGAGAAAACACTTCACCCTGGAACCCTAACT<br>CAGGTCCTGGCAAAAGATGCGAGAGGAAGACTTGCTCTCTTAATAAATCTCGGCCGCCCGCACATCTGGCCCCTAGACCTGCTCGGTAGA<br>GGACTGGCTGGTGGATGCGCGGTCCAGGCCGTGGGCACTCGACCCACCTCTATTTTCCTTCCCGAGGCGCCCCTGGATTACCACTTTCGG<br>TTTGCGCTTACATCCGGGATGTCGAATTTCCCAGGGAATCATAATTATTTTATCTATAATTTATTCTAACCCCAAGGTTCCAAGAAAATCT |
| 151 | chr15: 87753000-87754100 | ACATTCCTTCTAAAATGTGGGCTTTCTGTGTACATGGGCGCGCATTCCCAGGACTCGGTTCCCTGGGTGGAATTCACCCAGGAATACAATC<br>GATTTTCTGAACCTGCGTAAGGCCACAGGCAGCTCTGAAAATGAAAGCGTTTGCTAAGTGGGGGAGATCTCACCGATCGAACGTTTAAAAA |

TABLE 6B-continued

| SEQ ID NO | GENE NAME | SEQUENCE |
|---|---|---|
| | | TGGCTTTGTCTTCATTCAGCTCTCCCGATTTATTCTGTGTTTTACAAATAGAAGCTCAGAGCTTCTGTCGCCCAGTCCTTGCATGACTCATGG<br>CGGTGGCCACACGGGTTTCAGGGATAACGGGATGTTTAGAAAATCGCTGCATATCGGAGTTTCCTAGCACGTTCCATTTATACTGAACGCA<br>GGCGGCCGCTGAAAATCCAGCCTCGACTCTTGCTAATGACTGGGTAGGACCCTCGGGGTCCTGCGACGGTGCTGGAGGGTGTTCCCGGC<br>TCCGATGTGGGGAGGCCTGCGCGGGGACTAGGTTCTCGAGAGGCGAGCGGGCGCGCCAGAGAACCCGAGACTGCTGCGGGGCCGGAT<br>GCGGGATCCCTGGGCTGCGGTTCTACGCAGAAACGCCAATGGCCATGCCTCCCCAGCTCCTCCCAGCCCCAGTCACTAGGCCGGCGCCT<br>GGCCCGGAGATCCTCCCAGAGCCCTGGCGGTGCCATCATGCCGGAGAAGACAAGCTCGGCCCCGCTGGAATTCGCTCCAAACACAGATG<br>CTCATTTTTGGAATATTCTAGAAAAATAACAAGATCTTGTTTGTCGTTATGATTCACGGGAGGTAACTGATGGGAGGGCCATTTACATGAGGG<br>CAGACACTGTGGGGCGAAGGTGACTTCTGGACGTAGGCTTTAAAGTAGGAACGGCTCCAAATTCCCAATATCTCCGGCCTTACCGGTTGCA<br>AATCGGACCCCTGCGGGAAAACCAGACACTTCTGTTTCGTGGCTTTCGGGCTGCCTCCAGCCCACGCAGGCTCGTTTAGTCCCCGTGGAG<br>TCAGCCCCGAGCCTTCCTAGTCCTGGAACAAGGGCTCCAGGTCGCGGCCGCGGGAAGCCGCCAAGAGGGCGGGGAGTAGGGATTCCCT<br>CCAGCTCCGCAGGGCATC |
| 152 | NR2F2 | TCCTCCTCGGCCTCAGATGTCGTCCCACCTGCCCACGAGCAGGGAACCTGGAACCCACTCTCCCGGCAGTCCCCAGCGGGTTCCGCCAC<br>CCGGCGGCCGCCCCTGACACCGAGTGGGTGGAGGAAGAGGCAGCTGGCGGGGATGGCCATTGAGACCTCTTGAAAAATATTAAAAGA<br>CAGGATGGGTAGAGATTTCTCCGGGAGAAAGTTCGAGGGTGCATCGGGTCGCGGCTGGGAGGAGTACCCGAAATGCCAGCAGGAGAAAT<br>GCAACCTGTTTAGGCCACACCTTCAATCCCCGAGGCTGTCTGGAGAGACTGCGTGCGGGGGACTTGCCGGCGTTCCCACACCGCGCCTG<br>CAATCCACTCCCGCGGCTGCCTGGCCTCTGCCACTCGCGGCTTGAAGCCAGTGGCTCTCAAGCCCTCGGCCCCGCGGCGGCCCGCGCAG<br>CCTTCACCCGGCGCCGGCACCACGAAGCCTGGCCGCAGTGGACTCCCCGCAGCTCGCTGCGCCCTGGCGTCTCCCGTCGAGGAGGGAG<br>GGACGGAGGCCTGAGCCGGGAGCTCCCTGGCGGTGGTCGGGCCGCCCCCCTTGAGGCCTGCTCCCCCCTCTCGGCCTCGCCAAATCCC<br>TGAAAGCCCAGTCCCCCTTCGTCACCCCGGGGGCTTCTAATCACTCGGTATCGATTTCCCTAACTCTTTTCATCCTGTTGAAGACACATCTT<br>AAAACACTCCAGCCCGGAGTGTGCTCTGGGCTTTATCCACACTAATAAAATGATTTACCCTTCTCTCCGCGCTCTCCTCACAGAGGAAAATC<br>GTTCGAGCCCCGGCTATTTGTGTGTGATCAGTAAATATTTAGTGCGCTGACATCCTTAGCTGGGCTTCGGATCGATTCGGGGCCCACCGGG<br>AGGTGCGCACGGTCCGGGCGGGGCCGCGCCGAGCTCGCCGAGGGGGCTCCTCCCGCCCTCGCCGCCGGCCGCTGATTTACGGCCCCT<br>GCAACCAGCTAAGGGGGGCGAAAGCGCGCCTGGAAAATTGGCTTTTCAACCTTTTACTTTTGACATTCAGCCACTTCCCCAGGCTCTAATTC<br>TCGCCCGCACTCCTCCCTCCCGCCCTACTAAGGGTTGCCCTGTGCGCCCTGCGAGCCCTTCCAGCAGCAACGCGCGGCGCTCGCGCCCC<br>CTCGGCCCGGGGACCACCTATCACAGCCCTGAGCCGCGACGCGGGGAGGCCCCGGCCCCTGCTATGGGGGTCGCCTCCTTCGAGGAGA<br>GATGCTCTCCGCCCGCCCACACCTCTGAGGGAGGAGAGGGGGTGGAGAAGCCCAGAGCTGCATCTGCTGGATGACGAGCCGCTCTCCCT<br>GCTACCCTTTCTCCGACCCGTCGGCCTTTCTCCTACTCTGGAGACTGATCCTCGACGTCCATCGGGCCGGATGGCGTCGGGTGGAAGCGT<br>TACTTTCCTCGCAGAAAAACTCCTCCTCTTTCCTAAGATCAGAAAAAGCGCTTAGCTTGGAATTGTTAG |
| 153 | chr16: 11234300-11234900 | CCTAGGCATTCTCAGCCCGTTTTGCTGGAGGGGGCATTTGAGGCCTGGCCAGCTTAGCCAGCCTACAAGGAGTGTTACTGGGGTGAAAAC<br>AGCCAGCGGGGACCAGTCTGCTTGTGGCCCGCCAGGTGCCTGGGATGGGGAAGCAGCAAATGCCCACCTTCCTGCCCAACCCCCTCCTC<br>CCTCTTCATGGGGGGAACTGGGGGTGGCAGCGGCTGCCGGGTGCGAGCGGGCTCAGGCCTGTGGCCCTGCCTGACGTTGGTCCCCATC<br>AAGCCATGTGACGAGACCAGGCCACAAGAAAGAGGTTTCAACAAGCGTTATCGTTTCCTGGAACTCCAACTCGGCGACTTCCCCGAAGACC<br>GGCTGTGCCTGGCGGGCGGGCTGCGCACAGCGGGGACAAGGCTGCCCCCTTCCTCCTCCGCTGCCTCCGCGGCCGCGTCTATCTCAGT<br>CTGACTACCTGGAAGCAGCACTCCACCCTCCAGCCCAGCGGCCCTCGGCTCAGCTGCCAGGTCACCGGCAACCCCGGGAGCGGTGGGG<br>CAGGGGCTGCTCCGCCAGCCTCTGTGATGTTCAGGCCGGGCTGCACCAGCCCGGGACCCCTAGGTG |
| 154 | SPN | GCACTGGTTCCCCTTTACCTGAGCCAACAACCTACCAGGAAGTTTCCATCAAGATGTCATCAGTGCCCCAGGAAACCCCTCATGCAACCAG<br>TCATCCTGCTGTTCCCATAACAGCAAACTCTCTAGGATCCCACACCGTGACAGGTGGAACCATAACAACGAACTCTCCAGAAACCTCCAGTA<br>GGACCAGTGGAGCCCCTGTTACCACGGCAGCTAGCTCTCTGGAGACCTCCAGAGGCACCTCTGGACCCCCTCTTACCATGGCAACTGTCT<br>CTCTGGAGACTTCCAAAGGCACCTCTGGACCCCCTGTTACCATGGCAACTGACTCTCTGGAGACCTCCACTGGGACCACTGGACCCCCTGT<br>TACCATGACAACTGGCTCTCTGGAGCCCTCCAGCGGGGCCAGTGGACCCCAGGTCTCTAGCGTAAAACTATCTACAATGATGTCTCCAACG<br>ACCTCCACCAACGCAAGCACTGTGCCCTTCCGGAACCCAGATGAGAACTCACGAGGCATGCTGCCAGTGGCTGTGCTTGTGGCCCTGCTG<br>GCGGTCATAGTCCTCGTGGCTCTGCTCCTGCTGTGGCGCCGGCGGCAGAAGCGGCGGACTGGGGCCCTCGTGCTGAGCAGAGGCGGCA<br>AGCGTAACGGGGTGGTGGACGCCTGGGCTGGGCCAGCCCAGGTCCCTGAGGAGGGGGCCGTGACAGT |
| 155 | chr16: 85469900-85470200 | TGTCCGACAGGCACACAGAGCGCCGCCAGGCACGGCCCTCATTCTTCACCCCGAGCTCCCGCAAGGTCGGCGAGGAGGCTGGAGCAGC<br>GGGTAGGAAGCGGGCCGAGGCTCCCCCGACGCTGGGCCGCAACTGTCATCGCAGATCCCTGAAAAACGAGCTCTGTAATCGTTGCCGTC |

TABLE 6B-continued

| SEQ ID NO | GENE NAME | SEQUENCE |
|---|---|---|
| | | AGCGGGTGTACAATTGCAGCCTTATGTTTCCTGCCGCTGTTTACCTTCCTGAGCGGCGCCCAGAGATGCACACACGCTGCCCTGAAGCGG GACGTGACCTCTGGGCACCTGTGAGGTCCTGGG |
| 156 | SLFN11 | GTCGGCTCCTGCGCTCCCAACGGGGTGGCCGTTTCCTTCCTCGCACCCTCTTCTCTCCCGGTGCCTGCGGTCCCACCTTCCAGATACCCC TCGGAGAGTCCAGCTGAGCTCTCGCCAGAGCTTTCCCCTTCCAACCCGCTCGACTTGCCCAGATCCCAAGCTGGGCTTCTCTCTCCATCGC CCCAGAAAGTGGGTCTTGGAGACCGAGGCAAGAATTTGGGCCTCCGCTTCTGTTCCAGACCCCGGACCCCTTGCCAAAATGCGGCAGATG TGCAGATTGGGCCGCGCTTGGTTCCTGGCTGGGTTTATGGAGCCTGCGGCTGAGGCAGGCTCCGCAGACCCCGAGCCAGAGTGGGATTT AACGGCGGCCGGTGCGCTGTGCTTGGTCAACCCCGGTAACCGTCACGCTGCTAGTGATATGAAAAAAACCTGCCAGCGTTCTGCTTTTCTG CCCCGCTGCAGTCTTTAGCACCCGCCAGGATTCTGTCCGAGTGTTTGGA |
| 157 | DLX4 | TTTAGTGTGTGCATAAAACATCCCAGCTAATCTCAAATAGACTTTTCCTGAGCAGAGGCTGAAATTTGCAAGTAATGCAAAGAAGACTCCGG GAGAGCGTCGCCGATGGTGGAGCGGGAGACGGGCGTGGGGAGCCCCACTGCAGTGCTGGGATCGAAGTGGTGCTGACCCCAAGACCTC TCCCCTCCTCCTCCCCCGGGAGCTTCTCCAGGGTTATTTGGGAAATGAGGGGGAACTCCAATCCCTGAGAAAGCGCTCAGGGGCTTGCTG AGGTGAGCGCAAATGGAAGCACAAGGCCGGGCTGGCCGTGGGCTCAGTAACCAGTCGGCTGCCCGGCTTGCGCCAGCACTAAATGCTCG ATCAGAAAGAGAAAAAGAGGCGCAATAATTCCAAATTTCAGGAAAAGTCAAATCGGAGAGGGGGGACGCAGGTCTCTTCAGACTGCCCATT CTCCGGGCCTCGCTGAATGCGGGGGCTCTATCCACAGCGCGCGGGGCCGAGCTCAGGCAGGCTGGGGCGAAGATCTGATTCTTTCCTTC CCGCCGCCAAACCGAATTAATCAGTTTCTTCAACCTGAGTTACTAAGAAAGAAAGGTCCTTCCAAATAAAACTGAAAATCACTGCGAATGACA ATACTATACTACAAGTTCGTTTTGGGGCCGGTGGGTGGGATGGAGGAGAAAGGGCACGGATAATCCCGGAGGGCCGCGGAGTGAGGAGG ACTATGGTCGCGGTGGAATCTCTGTTCCGCTGGCACATCCGCGCAGGTGCGGCTCTGAGTGCTGGCTCGGGGTTACAGACCTCGGCATCC GGCTGCAGGGGCAGACAGAGACCTCCTCTGCTAGGGCGTGCGGTAGGCATCGTATGGAGCCCAGAGACTGCCGAGAGCACTGCGCACTC ACCAAGTGTTAGGGGTGCCCGTGATAGACCGCCAGGGAAGGGGCTGGTTCGGAGGGAATTCCCGCTACCGGGAAGGTCGGAACTCGGGGTGATCAAACAA |
| 158 | SLC38A10 | CATGGTGCTTCAGGAAGGGAGGGGACGAGAGCCCTGGGCTTGTGGTGTCCACGTGGACAGCTAATGAGGAGCCTTGCCGATGAGGAGCA TGCGTTCCCGACGGGGCGGCCGAATGCGGAAGGAGCCGCCATTCTCTCCGCCCTGACCGCGGGATTCTCTGCAGCAGATGAGAAACGGC GCTGACTCAGCAGGGTCCCTCCCAGGCCCCGAGCGGTCATCTGGTGACCCCCGCGCTTCCCCCACGGCCCAGCCGGAGAAGGGCAAAG GGAAGTCCCGGCTCCAAGGCGCACCCAGAGATGCGGTGCATGTGGCAGGATGGCCCAGCCCCGTCGGCAGCCCCAGCTTCCTGCCCCT GGTTTCCTTCCTCCCACGGGCTACAGGCCTCTGATGAGCTTTGGAAAGCAGGAAACACACAGGCTAGTAACTATGAATGGGTCCAAAAAAC ACTCCTTATTACTTTAAACTACTTAGGAAGAAGCACAGCGTTGCCAAACGCCAGA |
| 159 | S1PR4 | GCGCGGGGGGCCGGAGGATGGCGGCCTGGGGGCCCTGCGGGGGCTGTCGGTGGCCGCCAGCTGCCTGGTGGTGCTGGAGAACTTGCT GGTGCTGGCGGCCATCACCAGCCACATGCGGTCGCGACGCTGGGTCTACTATTGCCTGGTGAACATCACGCTGAGTGACCTGCTCACGG GCGCGGCCTACCTGGCCAACGTGCTGCTGTCGGGGGCCCGCACCTTCCGTCTGGCGCCCGCCCAGTGGTTCCTACGGGAGGGCCTGCT CTTCACCGCCCTGGCCGCCTCCACCTTCAGCCTGCTCTTCACTGCAGGGGAGCGCTTTGCCACCATGGTGCGGCCGGTGGCCGAGAGCG GGGCCACCAAGACCAGCCGCGTCTACGGCTTCATCGGCCTCTGCTGGCTGCTGGCCGCGCTGCTGGGGATGCTGCCTTTGCTGGGCTGG AACTGCCTGTGCGCCTTTGACCGCTGCTCCAGCCTTCTGCCCCTCTACTCCAAGCGCTACATCCTCTTCTGCCTGGTGATCTTCGCCGGCG TCCTGGCCACCATCATGGGCCTCTATGGGGCCATCTTCCGCCTGGTGCAGGCCAGCGGGCAGAAGGCCCCACGCCCAGCGGCCCGCCG CAAGGCCCGCCGCCTGCTGAAGACGGTGCTGATGATCCTGCTGGCCTTCCTGGTGTGCTGGGGCCCACTCTTCGGGCTGCTGCTGGCCG ACGTCTTTGGCTCCAACCTCTGGGCCCAGGAGTACCTGCGGGGCATGGACTGGATCCTGGCCCTGGCCGTCCTCAACTCGGCGGTCAAC CCCATCATCTACTCCTTCCGCAGCAGGGAGGTGTGCAGAGCCGTGCTCAGCTTCCTCTGCTGCGGGTGTCTCCGGCTGGGCATGCGAGG GCCCGGGGACTGCCTGGCCCGGGCCGTCGAGGCTCACTCCGGAGCTTCCACCACCGACAGCTCTCTGAGGCCAAGGGACAGCTTTCGCG GCTCCCGCTCGCTCAGCTTTCGGATGCGGGAGCCCCTGTCCAGCATCTCCAGCGTGCGGAGCATCTGAAGTTGCAGTCTTGCGTGTGGAT GGTGCAGCCACCGGGTGCGTGCCAGGCAGGCCCTCCTGGGGTACAGGAAGCTGTGTGCACGCAGCCTCGCCTGTATGGGGAGCAGGGA ACGGGACAGGCCCCCATGGTCTTCCCGGTGGCCTCTCGGGGCTTC |
| 160 | MAP2K2 | GGGCGGGTTGCCACACTGTCCCCTTTCTGCATGGGAGGAAGGGGGCTCGAGAACTGAGTCAGCCACACAAAACGAGGATGGACAGAACT CCTGAGTAGCGAGGGTGCCTGCCGGGCGCGAGGAGGAGGGGGAAGACGAGGAAGACGAGGAGGAGGAATAGGGAGCACCACATGACA GAGGGGCTGCCTCAGACCACAAAGCGCTTCCTCATCCTTTCCTCGCCCTTTGATGCCGCCGGCAACGTGACTCTGCGAGCAGCGGGGCAG ACGCCAGGTCTCCCTCGCAGGCGGGAAAGGGGCTCCAAGGCGGGTGCTGCCTTGCTCGGGTCACATGGCTACGTGGGGGCCTTGCTCAA ATTCACTTCCTGCCTTCATTACAAAACTGTCAAAGGGGATCGCACGTTTGCAGGGTGTCACCCAAGCATTCTGGTTTTGCAAACGACGCTGT |

TABLE 6B-continued

| SEQ ID NO | GENE NAME | SEQUENCE |
|---|---|---|
| | | GCGGCAGGCGGTCTGATACCTGATGAGCTCGGTGTGGCGGGGTCGGCAGCATTTCCTCCGGGGTTTTGAGCTCTGGCCACTTCTCCTTTT<br>GTTCCACCCAATCTCACCCACTTCTGGGCTTCGAGGCCAGAGTGTCTTAACAAGGGGGCACGT |
| 161 | UHRF1 | GAGCGAGACTTTGTCTCAAAAAAAAAAAAAAACCAAATAAATTGAAAGCTGAGAAATTCAGAGCACAAGAAGACAAGCGCGCCCCCTCTTTTA<br>GCTGTCAACATGGCGGAGCCGTCCCTGGTGACGCAGCCTCCAAAGGCCTCCCTGTGCCCTCCTGAGACCGCAAGAGGGAAAGTGGCAGC<br>GACAGTGATCGTGGTGTCTTTGTGGCGGTTGTGTTGACCTCACTGACCCCCGAAGTGCCGCTCTAGGGTCTGTCCTCAGCGGTGACCCGG<br>CCGGGTCGAAGGGCAGAGTTCCGCTGTCACTAGCCCTCCACCCGTCCTGTGTGCTGGGATGCCCTCGCGGCGCCGTCCACGCCACCGCC<br>GCCCCCTCTTGTGGGTTCTGTCTCCTCCGTGTCTAGGATCCTCCTGCATCCGTTTTTCCTTCCTCCCTTCTCTCCCTCCGTCTGTCTTGCCC<br>GCACCTGAGGTTGTCGCAGAGGCGCTGAGACGGGCCAGCAGGAGCTGT |
| 162 | DEDD2 | TGCTGTCCCGGTCCTGTCGCAGTCCTCAAAGATGCTAGAGTGACAGTCCTCTAGGGGTAGAGATGGTCGTCCTCCCAGGAGAAGGTGGCC<br>CGGAGACTTGGAGGTGGGATCAATCCTGCCAGTCCTGGATCAGGAGGCCTCTGTCGGGCGCCGCCCCCCTTCCTCCTCCATCAGCAACAG<br>GCGGCGCCGGCCAGCCTCATAGTCAGCCTCATCCACACTGACCAGCAGGCGAACAGCCTCCCGGCCCACAGCCTCTCGCAGGGCCTCAG<br>TCAGGAACACGCCCCGCAGGGCCTGCAGCAGGGCGCCACTCAGGTAGTCGCCCCAGAAGGCGTCCAGATAGGAGAGCTCTGAGAACTTG<br>ATGTCACAAACCACAGAGCCCAGGTCCCTTGAGCGCAGCACTGCGGTGGCCTGCCCAAACACGTCCAGCTGCCGCGCCAGCGCCTGGGG<br>CCGCCGGGATGCCACGCCCTGCTCCAAGGCTGGCCCATGCTCGCAGTACTCTGCTCGAACCCGGAGCCGGATGTCTGCAGGGGAAGGAG<br>GGATTTGTCAGGGAGGGGGCCAACACTAGACACACTTATGGGGAACGCCACCCTTCCTCCCTCC |
| 163 | CDC42EP1 | TGATGCCCGGCCCCCAGGGGGGCAGAGGCGCCGCCACCATGAGCCTGGGCAAGCTCTCGCCTGTGGGCTGGGTGTCCAGTTCACAGGG<br>AAAGAGGCGGCTGACTGCAGACATGATCAGCCACCCACTCGGGGACTTCCGCCACACCATGCATGTGGGCCGTGGCGGGGATGTCTTCG<br>GGGACACGTCCTTCCTCAGCAACCACGGTGGCAGCTCCGGGAGCACCCATCGCTCACCCCGCAGCTTCCTGGCCAAGAAGCTGCAGCTG<br>GTGCGGAGGGTGGGGGCGCCCCCCCGGAGGATGGCATCTCCCCCTGCACCCTCCCCGGCTCCACCGGCCATCTCCCCCATCATCAAGAA<br>CGCCATCTCCCTGCCCCAGCTCAACCAGGCCGCCTACGACAGCCTCGTGGTTGGCAAGCTCAGCTTCGACAGCAGCCCCACCAGCTCCAC<br>GGACGGCCACTCCAGCTACGGTGAGGGCCTGGGCCATCTTGGCCCACTTTTCAGA |

TABLE 6C

| SEQ ID NO | GENE NAME | SEQUENCE |
|---|---|---|
| 164 | chr21: 9906600-9906800 | GGCCGGGCAAAAAGCCGCCGCAACAAAAAGCTGCGCTGACGGGCGGAAAAAGCCGCGGCGGCGGAGCCAAAAAGCCGGGGCGGCAAAA<br>AGCCACGGTGGCGGGCGCAAACAGCCGCAAAAAGCCGCGGTGGTGGGGGCAAAATCAGTGGGAGCAGGGGCAAAAAAACACAAAAAGCCGCGGCGGCGGGGGCAAAAAGCCA |
| 165 | chr21: 9907000-9907400 | TGGCTTTGCTGGAGTGTGATGTGATAGGAAATGTGCAGCCAAAGACAAAAGAAGATGTAAGTAGGCTTGACTCATTGCAGCTAAGAACCCA<br>GATGTTACCTTGAGGGTATTAACTAATAAGCAGTTTAAATCAGAATGGCACATTCTGATTTGTTTTTTGTATGTTCACATTTGGCAGGCATAGA<br>TACTGTTTGAAAAGAGAAAAGTCAGTACATAGAGGTAACAAGCTTAAATATGTGCCAAGTCTAGAAACAAGAGACTAGGGGGATAAGGACCT<br>TTCGAAATTAAATGCAAGATTTGAAAACTGATTGGCTGGGGGATGAGGCAAAGGCAGGTCTTTAAGGTCAATCCCTGTTTTGCTTTAAGTTGTTAGCGGGTGGT<br>TTTATCATATATTGTAGAA |
| 166 | chr21: 9917800-9918450 | TTCCTGGGAATGTCAGCTAACCTGAGCCTAGGGGCCTGAGCCCAAGGGCAGACTGAGGCTCCCCCAGCACAGGGAGGTGCTGCCTGTGA<br>CAAGGGGTAGTGCTGGCACAGTGCAGGCTACTCCCTAGAAAGATCAGCTTGAATATGCAGGAAGAGCAGGACCCTCGGGCTGAGGCAGA<br>GGTGGAATGGGAAGTGCATGGTGGTAATTTAGTTCTCCAGAGGCCAGAAGTAGGAGGAGCGGTTGGAATGCTGATGGCCCAAAGGGAAAC<br>CCTGGACTACCCTGGCCTCCCACAGGACTCTCATAGTAATTGCGGCTCCCTGCAGTGGTGAGGCCAGAAGGAGTGTTGCCCAATGCTGTC<br>ATCATCCAGTCCACCCCCCACCCACCATCAACAGATGAGTATGGTCATGAGTGTGGTCACCTCATCAGTCATTTGCTCAGTTGTGAAAAAGA<br>AATTGTTCAGAGAAGAGCAAAGTGTTTTTCCATGAGCCAAAGGTCAGCCAAGTTATGCTAATGAGGAGGACTGGAGACAGCGTGTCACAGA<br>CACCGAGAAGGAGCACTGGGCAAGGGCACTTCTCCCAGGGCAGAGCCCACAAGAAGCGTCCTGGCACCAGACACTCAGGGAACTGAAGGCTGGCAGGGGCC<br>CGCCCAGT |
| 167 | TPTE | TCCCCCCAGCTGGGTATAAGCAAACTTTCCTGTCTATGGGCCGCAGAGACCACCATCTAGTTCCCCCGCCAAAACTTTACATGATTTTAATT<br>CTCCTGATGAAGATGAGAGGATAACAGCCAACAGAGAGGGCAGAGGATGGGATGGGACTCCCTTGCTCAGAGACCTCACCTCTAGGTCTT<br>TACCTCCTATTGAGAATAAGTCAGTTCTGTAGTAAGAACTCTGTGTCCACGGCAACCCCAAACAGAATCCTAGCGCTCTTGTGATTCTTGTA<br>GAATGGGGAATAGAACGAGCTTGGCCCAAGACTGCACAGACTTAAAAACATACTATTCTTTGAAAATGGCAATCATTAAAAAGTCAGGAAAC<br>AACAGGTGCTGGAGAGGATGTGGAGAAATAGGAACACTTTTACACTGTTGGTGGGACTGTAAACTAGTTCAACCATGGTGGAAGTCAGTGT<br>GGCGATTCCTCAGGGATCTAGAACTAGAAATACCATTTGACCCAGCCATCCCATTACTGGGTATATACCCAAAGGACTATAAATCATGCTGC<br>TATACAGACACATGCACACGTATGTTTACTGCAGCACTATTCACAATAGCAAAGACTTGGAACCAACCCAAATGTCCAACAATGATAGACTG<br>GATTAAGAAAATGTGGCACATATACACCATGGAATACTATGCAGCCATAAAAAATGATGAGTTCATGTCCTTTGTAGGGACATGGATGAAATT<br>GGAAATCATTCTCAGTAAACTATCGCAAGAACAAAAAACCAAACACTGCATATTCTCACTCATAGGTGGGAACTGAACAATGAGAACACGTG<br>GACCCAGGAAGGGGAACATCACACTCTGGGGACTGTTGTGGGGTGGGGGGAGGGGGGAGGGATAGCATTGGGAGATATACCAAATGCTA<br>GATGAGGAGTTTGTGGGTGCAGCGCACCAGCATGTCACACGTTTACATATGTAACTAACCTGCACATTGTGCACATGTACCCTAAAACTTAA<br>AGTATAATAAAAAAAATACTGTTCTGCCATACATACAGATACTCATTAAAGATGAGGGAGAAGGGCATGGGGTGGGGGAGAATGTACCAAAA<br>CCAAAGACCACAGGATAATAACCTCAGAGCAGAGACTATCTCTCTAGTTATTTTTTCTTTTGTATGTAATGGAGAGGATTATTATTTACTCTGA<br>TGAAGAAGTTTACATCAAGTGTTCAGCTTCCTTTGTGGGTTACAGAGAATAACCAGAGGGCTCAGTTATGCTCTCTGAATAACTATGTTTGCT<br>TAGTGTTTTCTAAACAATATTAAATTTCACTAAAATAGACAAGGTTGATAGGACTTGGGGGCATAACTCATTGACTCAAGCTATCATTTTATAG<br>GATTGTGAGAAAACAAATAGATGAACATTTAAAATACACTCATATTCTCGCTAGAAAAGAGGATTTTGAATATTCTTACATCAAAGACATGGTA<br>AATGTTTAAGGCAATGAATATGCTAATTACCATGATTTGATCATTATGCAATGTAAAATGTACTGAAACATCACATTGTACCTCATAAATATGTA<br>CAATTTATTATGTGCGAATTAAAATTTTGAGTATAAGAAAAAATAAACTTCAATTGTAAGAAAACAACCCAACTTTTAAAAAACGGCAAAATA<br>CGTGAACAGATACTTCACTAATAGAGATTTGCAACTGGCAAATAAGCAAATGAAAAACTGGTCATCATCACTATCTATTAGAGAAATGCAGAT<br>TAAAACTACAATAAGAAACAATGCTGCCCGTCCAGACGCATTGTTTTGACCGTTTCCAACTTGTCCCAGCCCTTCCCGGGGCATCGCTGGG<br>GACCCTACGCCGACGTCCCCCCTCCGCCCGCGCCCCAAGGGCCGACTGGGCAAATTGGGAGACCCGCCCCGCGGGGCGACCCAACTTT<br>TCGGAACAGCACCCCACCGCCCACCCCCGCAGACCCCCGGACCCCCGCTCCCGGCGGAGACTCAGGGAACCCCGCACCCCAAGCCCTT<br>CTAAATCGTGCAGCGTGAGTGTGACGGCCAAGAGCGGATGCAGCCCGGGATCGCCCGCACCTTCCCGTGGGCGGAAGCGCAGGAGCCA<br>GCTGGGGAGGGGGCGCCCTAGAGGAGCGGCTAGAAAGCAGACACGGGGAACTCAGGTCATCCTGGGGGGGGACAAGACAACGAGAGCC<br>GGGCGCCTCGGGGGCGGCGCGGGAGCCTCCGCAGGACCGGGCGGGCGCCCCGGCTGGCGCGGGCGGGGGGCGCGCCCCCTTTACCT<br>GCGGCTCCGGCTCCTAGGCCATTTCCTCACGCGGCGGCGGCCGGGACTGAGCTAACACCACTCAGGCCGGCCGGGTTTGAATGAGGAGG<br>AGCGGGCGCGGAGAGGAGGGGACGGGGAGGGCGGAGGGAGGGAGGGAGGCGTCGCGGAGTTTTTCTCGGCCTTTTGTGCGGACACCT<br>CCCGGATTCCGCGCCCGCACCCGGCCCCCCAAAAGACACGGGGAGCCGCGGGCGAGGGGTTCAGCCATCCGCCGAGGCGCCTAGTGCC<br>TTCGCGCCTCCAAGACCCCCCCCCAACAAAAAGGAGCGTCCCCCACCCCTACCCCCGCCCGGAGGACTTAGGGCCTGGGCTCACCTCGG |

TABLE 6C-continued

| SEQ ID NO | GENE NAME | SEQUENCE |
|---|---|---|
| | | GCGCGGAGCTAAGTGTAGGCGCCGGGGGTCCCTAGAGCCGCCGGGGCGCAGCGAGTCCGGCGCTGGGTAACTGTTGGGTCAGAAACTG<br>TTCAGGTAGCAGCTGTTGTGCCCTCCCTTGGCCCCGCCGCTCGGAGACGCCCCGCCCCCTGCCTTGAACGGCCGCCCGGCCCCGCCCCA<br>GCGCCCACGTGACTAGCATAGGCGCGCCCCCGTTCCGCCCGCCGCCGCAGACTCCGCCTCCGGGACGCGAGCGAGCGGCGAGCGCGC<br>GCACTACCAGTTCTTGCTCGGCGACTCCCGCGCACGCGCGCGCCGTGCCACCCTCCCCGCACCCCTCCTCCCGCCATCCGGCTTAACGT<br>GGCGGGCGCGCGCCGCGGCAGTAGCCGTGACAGGTACCCGGCGGGGCGGGGGGGGAGGGGGTTGGCCCGCGAGGGTGTGCGCAGGC<br>ACAGACCCGGGTCCTGTCCCCGCCGCCCCCTCCTCTGCAAGGTGTGCCTGGGCGAGGGGAGGGGCCCGCGGCCCGAACCCCTGGGTCA<br>CCCCCGAATTACAAACAAAAACCTTAACGCCATTGCTCGCGGGTTAGAAGGCAGCTGTGCGTGCTCAGGAAAAGAAGCCACGCACAAGAG<br>ACCGCACGCGGCGTGGATACAGTGACACGAAACACCCAAAATCTCTTTTGAAAGGGAAACCAGGCACAGTGGCTCATGCCTATAATCCCAG<br>CACTTTCGGGGGCCAAGGCGCTCACCTAAACCCGAGAGTTCAAGACCAGCCTGGGCAATACAGCGAAACCCTGTCTCTACGAAAAATATAA<br>AAATTAGCTGGGCATAGGGCTGGGCACGGTGGCTCACGCCTGTAATCCCAGCATTTTGGAGGCCGAGGCGGGCGGATCACGAGGTCAGG<br>AGTTCCAGACCATCCTGGCTAACACAGTGAAACCTTCTCTCTACTAAAAATACAAAAAAAATTAGCCGGGCGTGGTGGCAGGTGCCTGTAGT<br>CCTAGCTACTTGGGAGGTTGAGGCAGGAGAATGGCATGAATCAGGGAGCGGAGGCTGCAGTGAGCTGAGATTGCGCCACTGCACTCCAG<br>CCTGGGGGACAGAGTGAGACTCCGTCTCAAAAAAAAAAAATAATAATTAGCTGGGCATGGTGGCTGGCACACATGGTCCCAGCTACTCAGGA<br>GGCTGAGGTGGAAGGATCTCTTGATCCCGGGGAGGTCAAGGCTGCAGTGAGCCAAGATGGCATCACCGCACTCCAGCCTGGGCCACAGA<br>CCCTGTCTCAAAAAAAAAAGAGAAAGTGGGGAAGAAAATGTAATACAAATTAATATACCAACAGCAATTAGTGAGTACTTTTTCCATGGAGCT<br>GGGAGAGGGAATAAATGTTTGTAAAATTAAAATGTTCTACGCTAGAAATCAACTTTCCTTCTATGCTTTCTTTACTTCACCCCTTATAGCTACT<br>TAGTAAATCTCACAAATCCTATCCTTCTGATCTCTCTGAAATGTATGTACCCTTTCCCTTCTATTCTCACCACCCATGTTTCTTTGTTTCCTTCT<br>AGCCTGTGTAATAATCTCATAATCGCACCTCCTGTACCTGCCTTCTTTCTAGTCCAGAATACGTTTTCCTAAATTCCACCAATAACCATCCTG<br>CTACTGCTTTGTGTGAAATTCTCCAAAAAAAATTTTACTTTTCCAAAATAAGTCAGGCTCCCTCTCTTAGGATACAAAACCACACCATGGTCCC<br>AGCCAATCTTTCAGCCTGATTCACTCAGTATATATTTATTGACCTCTCCTTTCTCCCAAGCACTTGGCTAGATAATAATTAAAGAGTGCGGCA<br>CAAAACAAATTGGATTCCTCCCCTCATGGAGCTTGTATTTTCACAGGAAGCACAGACATTAAATAAATTAAAACACAAAAAAATAGACAAGCA<br>TATAATTACAGTATGTATCCTAGAGAAATATCACTCATGCAGAAAGCATACACAAGGATGCAGCACTGTTTCCAATAGCGAAAAGCTAGAAAC<br>AACCTACATGTTCACCAAAAGAAAATGGCCACATAAACTATACCATATCCAAATTATCCAAATTTTAGAATATAGACAACAGGTTGGGCGCGG<br>TGGCTCACACCTGTAATCCCAGCACTTTGGGAAGCCGAGGCGGGTGGATCACAAGGTCAGGAGTTCAAGACCAGCCTGGCCAACATGGTG<br>AAACCCCGTCTCCTCTAAAAAAACAAAAAAATCAGCTGGGCACTGTGGCAGGAGCCTGTAATCCCAGCTACTGAGGAGACTGAGGCAGGAG<br>AATCGCTTGAACCCTGGAGGCAGAGGTTGCAGTGAGCCAAGATCGCGCCACTGCACTCTAGCCTGGGTGACAGAGCAAGACTCCATCTCAG |
| 168 | chr21: 13974500-13976000 | TGTAGGAGTCCTCCGGTGCTGGAGTCCAGAGCACAGTGAGGCTGGGTCCTCCCGTGCCATAGTGTAGGGCATGGCGGGACAGGGATCCT<br>GCCCTGCGATAGTCCAGTGCTTGAGTCCGCAGTAAGGCAATGGTCCTCCAATGCTGGAGTTCACGGCGTTGTGGGGTCGGGGTCCTTTGG<br>TGACTTAGTCCAGGGCGTACCAGGGCGGGGGTCCACAGTTGCCATAGTGAGGATCTTGGAGGAAGGTGGTTCCTGCCTTGCTGTAGTCCG<br>GGGAGCAGGGGGCAGGGGTCCTCTCTTGTCAGAGTCTCTGGCGCGGGGTGGGGGTGGAGGTGGGGGTTTTCCTATGCGATAGCCCACG<br>GGTCGGTGAAGCCGGGTCCTCCCGTGCCTTTGTCCAGGGCGCAGGGGGGCGAGGGTCTTCGGTGGTGGAGTCCGCGGAGCGGCAGGAC<br>GGGGGTCCTCCAGTGCCATATTCCAGGGCGCGGCGGAGTGGGGGACCTGTCCTGCAGTGGTCCAGGGCATGTGGGAGTGGTGGTCCTG<br>CTGTGCCTCAGTCCAGTGCGCGGTGGGACGGCGGTCCTGCTGTGCTGTAGTGCAGGACGCGGTGGCGCAGGGGTAGTCCAGAGAGCGC<br>CGTGGCAGGGGGTCCTCCAGTGCTGGAATCCAGTGCAAGGCGGGTCAGGGGTCTTACCGTGCCGAAGTCGGTGGCAAGGGTCCTCCCGT<br>GCCATAGTCTAGGGGGCGACGGGGCAGGGTTCTCTAGTGCAGGTGTCCAGGGTGTGGCAGGGCAGGAGTCCTCTTGTGCAGGAGTCCAG<br>GACGTAGCCGAGGAGTCCTCCAATGTCAGAGTCCAGGGCTCTGCGGGGCCGGGTTCCCCCATGCCAGAGTGTAGGGCGCGTTCAGGTGA<br>GGGTCTTGGCGTGCAGTAATCCAGGGTGCGGTGGGGCAGGGGTAGTCCAGACCTCCATGGCGGGCGTCCCTCTGTGCAGGAGCCCAGT<br>GCCTGGCGGATCGGGGGTCCTTCTGTGCTGTAGTCCAGGGCACCGCAAGGTGTGGGTCCTCTGGTGCCCTAGTCCAGGGGGCGGCGAGT<br>CAGAGGTTCTCCCGTGTCTCAGTCTAGGGCCTGGTAGGACTGGGGTCCTGGAGTCCACGTGGTAGCCCAAGTTGCCGCAGGACCAGGTA<br>CTCTGGAACCACAGTCCAGGGCGCTGAGGGGCAGGAGTAGTTCAGGGCGAGCCGGGGCCCAGGTCCTCGGGAGCCAGAGTCCAGGGTG<br>TGGAGGGGTGGGGGTTCTGCAGTGGCACAGTCCAGGACACCGCGGGGCGGGACAGGGCGGGGATCCTCCCGTGCCTTAGTCCAGGGCT<br>GAGCCGCGGGAGAGGTCCTTCAGTAGCACAGTCTAGCGCACGGCGTTGCAGGTGTCCTCCAGTGCCTGAGGCCACGGCAGGTCGCGGGT<br>CCCACTGTGCTCTAGTTCAGGGCGGAGTGGGTCTGAGGTCTTCTCCTGCCTCAGTCTAGGGCGCTGGAGAGCGGGGATCCT |
| 169 | chr21: 13989500-13992000 | GGGTTGGTCCTAGAAAGCGTGAGGATCGCCGAGTGCACTGCCCTCCCAGCCTAGGGTCCACTCTTCCTTGGCCCGAGCCCAGAGCTCGG<br>GGTTTCAGGCGCTGGGCCCTGTGCAGCTGCCCAGAATAGGCTGAGCGGCAGGTTCCCGCCCTGGCAAGGGATCCAGCAGTGGAATCCTC<br>ACTGCTGTTGGCTGCGGGCAAGGTCAGCGGGGTTTCCATCGCTGCTGGTGGGAGCCACCTGGCGGTGGTAGCTGCAAGTGAGCGCGTGG<br>CAGAGACTGGCAGGGCTGGTCCCAGACACCCTGAGGGTCTCTGGGTGCATCGCCCTACCACCCTAGGGTCTGCTCTTCCTTAGCCTGCTC |

TABLE 6C-continued

| SEQ ID NO | GENE NAME | SEQUENCE |
|---|---|---|
| | | CCAGGACGCGGTGTACGAGGGCTAGACTCTGAGCAGCCTCCAGGATGGGGCTGAGCAGCGGATTCCTGCCCTGCTGCAGCTACAGTCTG<br>AATTAGGCGCCACCGCAGTATCTGGCCCTGGGGTACGTGCTACTGGGTGGCATGGACAGAGATGGGGGCTGCCACAGCTGCTATGGGGC<br>TGAGCAGCCGATTCTCGCCCTGCTGCAGCGGGCGACCGCTGCAATCCCCAGCGCTATGGGACCGACCACCTGACTTAGATGCCTTGGAG<br>GCATCCGGTCCTGGGGTCTTGCTGCTGGTGTCTGCGGGCAGGGTCACGGCTGCCACTACTACTGCTGTGCGCCATGGGCAGGTGCCAGC<br>TGCAGCTGAGTCCGAGGCAGATGCTGTCAGGGCTGGTCTGAGGTTGCCTAAGGGTGGCTGAGTGCACCACGCTTCCACCCCAGGGTCCG<br>TTATTCCTAGGCCGGCTCCCAGATTGCAGGGTTGTGGGCGTTGGACACTGTGCAGCCATGAGGATCTGGTTGGGTGCAGATTCCCGCCCT<br>CCTGCAGCTGAGAAGCCAATCTCATAACAGGCGCTGCAGTGACCTCTGGCTCTGCGGTCCGCGCTGCTGCTGGAGCTGGCAGAGAACAGA<br>GCTGCCACCGCTGCTGCTTCCAGGAGTGTGCAGCTGGCAGCTGCAGCTGAGCCCGTGGCGGAGGCTGGAAGGCCTTATTCCAGAAGCCT<br>TGAGGGTCCCCGAATGCACCGCCCTCCCACCCTAAGGTCCAGTCTTCCTTGCCCGCGCCCAGAGAGTTGGATTGCAGGCGCTGAGCACAG<br>TGCAGGTGCTGGGATGGGGCTAAGCTGAAAGTTTCCGCCCTCTGGCTGCTGCGGGGCCGACAGCCTGAGTTATGCGCCGCGGCGGCTTT<br>TGGTCATGGGATCCGCACTGCCGGTGGCTTGCACAGGGTCGGGGGCTGCCACAGCTGCTATAGTTCACCGTGTGCACGTGGCAGCCGCC<br>CCTGAGCCCACCGCTGAGGCTGCAGGGCTGGTCCGGTCCCAGACGGCCTGAGGGCCATTTGCCCGCGCCCAGATCCGGGTGGCTGCGC<br>TGGGCACTGTGCAGCCTCCCGGAATCCGCTGAAGGGCACGTTCCCGCTCTCCTACAGCTGTGGGCCGACTGCCTGATTTTGGCCACTAGG<br>TGGAGTCTGGCTCTAGGGTTTCGAGGCCGCTGGTGTTGGTGGGCGGAGTCCGGGTTTGCCACCGCTGCGCTCCATGAGCAGGTAGCAGC<br>TGCAGCGGAGCTTTAGACCGAGGCTGGCAGGGCTGGCCCCAGACGGCCTGAGGGTCAGGGAGTGCAGGGTCCTCCCACCCTAGGTCCG<br>CTCTTCCTTTCCCCTTACCCAGAGCGGGTTGTGCGGGCTCTGGGCTCTGTGCCGGCGCTGGGCTCTGTGCAGCCGCCGAGATGGGGCTG<br>AGCAGCGGATTTCCTCCCTGCTGCAGCTGGAGGACGATTACCTGCACTAGCCGCTGAGGCGGCATCTGGCCCTGGGTTACTGCAGCTGGT<br>GACGCGGGCAGGGTCAGGGTTGGTTGCAGGTGGCAGCTGCTGCTAAACCCATTGCGAGCCTCAGGGTCACCAAGTTCACCGTCCTTTCAT<br>CATAGTATCTGATCTTTGGCCCGCGCCCAGAGTGCGGACTGGCCTGCGCTGGGGACTGCATAGCTTCTGGGGGCCGGTCAGCGCCAGTTT<br>CACGTCCTCCTGCAGCTGCGTGGCCTAAGGTCTTAGGCGCCGCGGCGCTATCTGGCCCTGCTGTCGACGCTGCTGGTGGTGGGGACAGG<br>GTCAAGGGTTGCCACTGCTGCTCCCGTGCGCCATCGGCAGGTGGCAGTTGCAGATGAGCCCACAATTGAGGCTGTTGGGGCTGCTCCCA<br>GGTTGTTAGAGGGTCGCCGAGTTCACCGACATGCCACCCTAGGTTACGCTCTTGGCCCGCACCCAGAGCGCCGGGTTACGGGTCCTGGG<br>CCCTGTGCAGCCACGGGGATGGTGCTGAGTGCAGGTTCCCGTCTTCCTGAGATGCGGGGCGACCACTGGAATTAGCCTCTGTGGTGGTAT<br>CTGACCCTAGGGTCCGAGCTGCTGGTGGCGTGGGCGGGGTCGAAGTCGCCTCTGTTGCTGCGGCGTGCCATTTGCACCGTCCTCTGGTAC |
| 170 | chr21: 13998500-14000100 | AAATACTCTACTGAAAAAACAGAAATAGTAAATGAATACAGTAAAGTTTTAGAATACAAAATCAGCATAGAAAAATCAGTCGCATTTCTATACC<br>CAACAGCATACCATCTGAAAAAGGAATCAAGAAACCAATCCCATTTAAAATAGCTATAAAAAAATGCCTGGGAATAAACTAAGCCAAATAAAT<br>ATGTCTAAAATGAAAACTATAAAACATTGATAAAAATCAATTGAAAAAGATACAAATAAAGGGAAAGTTATCCCATTTTTATGAATTAGAAGTAT<br>TAATACTGTTAAAATGACCATCATACTCAAATCAGTCTATAGGTCCAATACAATCTCTAACAAATTTCCAATGTAATTCTTCAGAGATGTTAAAA<br>AAGGTTTTAAAAATCGTTCTGCGGATGTTAAAAGGATTTTTAAAACGCTTTTTTCGTTCTGCAGGCGAAGGCTGTGGCCGTGCTCCCGCCGG<br>CCAGTTCCCAGCAGCAGCGCATTGCCCCTGCTCCACGCCTTCGCTCCAGGCCCGCAGGGGCGCAGCCCCGCGGGAATCAGCACTGAGCC<br>GGTCCCGCCGCCGCCCCAGTGTCCGGGCTGCGACTGCGGGGAGCCGATCGCCCAGCGATTGGAGGAGGGCGACGAGGCCTTCCGCCA<br>GAGCGAGTACCAGAAAGCAGCCGGGCTCTTCCGCTCCACGCTGGCCCGGCTGGCGCAGCCCGACCGCGGTCAGTGCCTGAGGCTGGGG<br>AACGCGCTGGCCCGCGCCGACCGCCTCCCGGTGGCCCTGGGCGCGTTCTGTGTCGCCCTGCGGCTCGAGGCGCTGCGGCCGGAGGAG<br>CTGGGAGAGCTGGCAGAGCTGGCGGGCGGCCTGGTGTGCCCCGGCCTGCGCGAACGGCCACTGTTCACGGGGAAGCCGGGCGGCGAG<br>CTTGAGGCGCCAGGCTAGGGAGGGCCGGCCCTGGAGCCCGGCGCGCCCCGCGACCTGCTCGGCTGCCCGCGGCTGCTGCACAAGCCG<br>GTGACACTGCCCTGCGGGCTCACGGTCTGCAAGCGCTGCGTGGAGCCGGGGCCGAGCGGCCACAGGCGCTGCGCGTGAACGTGGTGCT<br>GAGCCGCAAGCTGGAGAGGTGCTTCCCGGCCAAGTGCCCGCTGCTCAGGCTGGAGGGTCAGGCGCGGAGCCTGCAGCGCCAGCAGCAG<br>CCCGAGGCCGCGCTGCTCAGGTGCGACCAGGCCCTGTAGCTGTGACTTGGCTGTGGGGCTGGCCCGCCTCCCTGACCCCTGTCAGGCG<br>GAGCAGCTGGAGCTGACCCACGGGCCTGGGCTTTCGAGCGCTTTGTCCAGGCGCTAATGATGGGAAGGTGAAAGGTGGGGGTGGCCACA<br>CCCTGCAGTCAGGGTGGCAGGTGTCAGAGGCCACATGCAACCCACTGGTTTTGTCTTTTCCAGGATGCTGATAAGTTTCCCGCGGCCCCC<br>GGAGCAGCTCTGTAAGGCCCTGTAATTGCCTTTCGTTCCCTTCTGCTCTATTGAGGAGTGGGAAGATGACAAAGTGTTTTTGCTCAACCCGA<br>AGGAAAATGCACATGGGAGGACACACCGGGTTACTATTTGAGTAGCCCAGACAGGAGAGCAGCGGTCTGCT |
| 171 | chr21: 14017000-14018500 | TGGGTGGATTGCTTGAGCCCAGGAGTTCGAGACCAGCCTGGACAAAATGGCAGAAACTCCATGTCTACAAAAAATACAAAAATTAGCCGGG<br>CATGATGTTCTGCGCCTGTAGTCCCAGCTACTCAGGAGGCTGAGGTGGGAGGATCGCTTGAGCCCAGGAGGCGGAGTTTGCAGTGAGCT<br>GAGATGTCACTGCATTCCAGCCTGGGAGACAGAGCCAGACTCTGTCTCAAAAGAAAAAAAGAAAAAAAAAAAAGAAAAGAAAAAACGAAATT<br>GTATTCTGAATACATCTTCTAAAACACTACATTTACTTGCACTATATTAAACTGGTTTTATCCTGACCACAATTGCAGGTGAAAGATACCACTG<br>TTGTTCTATTTTTCTGGTAAGTAGAGTGAGCCATGTCTTCCCCAGGGAAAGACGCCTCCTAAAAATTTGTAGGACCACCTTTGGTTTTCTTCC |

TABLE 6C-continued

| SEQ ID NO | GENE NAME | SEQUENCE |
|---|---|---|
| | | AGATATTTTTTTTGTCATCGCTTTTCCTGCGCCCAATTCCCATCTGTCTAGCCCTTCTGCCTCCGCTGGTCTTTTTCGCGAGCCTCTCCCCAG<br>CCGCAGGTATTCGTCTGGGCTGCAGCCCCTCCCATCTCCTGGGGCGTGACCACCTGTCCAGGCCCCGCCCCCGTCCAACCCGCGGAGAC<br>CCGCCCCCTTCCCCGGACACCGGGTTCAGCGCCCGAGCGTGCGAGCGCGTCCCCGCTCGTCGCCCGGCTCGGCGTCGGGAGCGCGCTC<br>TGTGTGGTCGCTGCTGCAGTGTTGTTGTGGCTGTGAGAAGGCGGCGGCGGCGGCGGAGCAGCAGCCGGACCAGACTCCCTAGTAGCTCA<br>GGCGCTGCCCTGCGCCGGCCCTGGCAGGGAGCCTGGTGAGATGGTGGAGGAGGAGGCTGTGCCGTGGCTGGCCTTGCTGTGTCCTGCT<br>GCCTGGTTAGAACCCCATCCCCGTCCCCCGTCTCCTCCGGGGGGTGAGGAGGAGCTGGAAGAGGGGCCGGCCTCTGTCCGGCCCGGCC<br>AGGCGGCAGTCACCCTCTGAGGAGGCAGCGCCCGGGGAGGGGCCTCCCAGGCGGCCGCCGCCGCCAGGGGGAGGCGCTGGGAGTGG<br>GAGTGGGAGCGGGACCTCAGCTGCCAAGCTCGGCCCGGACCCTAGGTGCGGGGGAGGCGGGGTCCCGGGCTCGGGCTGCCTGCCCGG<br>ACCTGGCGGGGATGGGCCCGTGCGGCTCCGGGTGTGGGACGTACCCTCAGAGCGCCCGGGGTTATTCCCACTGACTCCAGGGAGGTGA<br>GTGTGCGCCCTTCGCTCCCTGCCGTGTCTGTGAGGGTCCATCGTTGCCGGAGACTGGAGGTCGGGGGCCATGGGAGCCCCGGGGCGAA<br>CGGTGCGGACATGGGCCTTGTGGAAAGGAGGAGTGACCGCCTGAGCGTGCAGCAGGACATCTTCCTGACCTGGTAATAATTAGGTGAGAA<br>GGATGGTTGGGGGCGGTCGGCGTAACTCAGGGAACACTGGTCAGGCTGCTCCCCAAACGATTACGGT |
| 172 | chr21: 14056400-14058100 | GTCTCTAGGACACCCTAAGATGGCGGCGAGGGAGACGGTGAAGGTTGGCTCCCGCCTGTCTGGGCTCTGATCCTCTGTCTCCCCCTCCCC<br>CTGCGGCCGGCTCATGGCCTGGCGGAGGCCCGAACCAAAGACCTCCGCACCGCCGTGTACAACGCCGCCCGTGACGGCAAGGGGGCAG<br>CTGCTCCAGAAGCTGCTCAGCAGCCGGAGCCGGGAGGAACTGGACGAGCTGACTGGCTAGGTGGCCGGCGGGGGGACGCCGCTGCTCA<br>TCGCCGCCTGCTACGGCCACCTGGACGTGGTGGAGTACCTGGTGGACCCGTGCGGCGCGAGCGTGGAGGCCGGTGGCTCGGTGCACTT<br>CGATGGCGAGACCATGGAGGGTGCGCCGCCGCTGTGGGCGCGGACCACCTGGACGTGGTGCGGAGCCTGCTGCGCCGCGGGGCCTCG<br>GTGAACTGCACCACGCGCACCAACTCCACGCCCCTCCGCGCCGCCTGCTTCGAGGGCCTCCTGGAGGTGGTGCGCTACCTGGTCGGCGA<br>GCACCAGGCCAACCTGGAGGTGGCCAACCGGCACGGCCACATGTGCCTCATGATCTCGTGCTACAAGGGCCACCGTGAGATCGCCCGCT<br>ACCTGCTGGAGCAGGGCGCCCAGGTGAACTGGCGCAGCGCCAAGGGCAACACGGCCCTGCACAACTGTGCCGAGACCAGCAGCCTGGA<br>GATCCTGCAGCTGCTGCTGGGGTGCAAGGCCAGCATGGAACGTGATAGCTACGGCATGACCCCGTTGCTCCCGGCCAGCGTGACGGGCC<br>ACACCAACATCGTGGAGTACCTCATCCAGGAGCAGCCCGGCCAGGAGCAGCTCATAGGGGTAGAGGCTCAGCTTAGGCTGCCCCAAGAA<br>GGCTCCTCCACCAGCCAGGGGTGTGCGCAGCCTCAGGGGGCTCCGTGCTGCATCTTCTCCCCTGAGGTACTGAACGGGGAATCTTACCAA<br>AGCTGCTGTCCCACCAGCCGGGAAGCTGCCATGGAAGCCTTGGAATTGCTGGGATCTACCTATGTGGATAAGAAACGAGATCTGCTTGGG<br>GCCCTTAAACACTGGAGGCGGGCCATGGAGCTGCGTCACCAGGGGGGTGAGTACCTGCCCAAACTGGAGCCCCCACAGCTGGTCCTGGC<br>CTATGACTATTCCAGGGAGGTCAACACCACCGAGGAGCTGGAGGCGCTGATCACCGACGCCGATGAGATGCGTATGCAGGCCTTGTTGAT<br>CCGGGAGCGCATCCTCAGTCCCTCGCACCCCGACACTTCCTATTGTATCCGTTACAGGGGCGCAGTGTACGCCGACTCGGGGAATATCGA<br>GTGCTACATCCGCTTGTGGAAGTACGCCCTGGACATGCAACAGAGCAACCTGGAGCCTCTGAGCCCCATGAGCGCCAGCAGCTTCCTCTC<br>CTTCGCCGAACTCTTCTCCTACGTGCTGCAGGACCCGGCTGCCAAAGGCAGCCTGGGCACCCAGATCGGCTTTGCAGACCTCATGGGGGT<br>CCTCACCAAAGGGGTCCGGGAAGTGGAATGGGCCCTGCAGCTGCTCAGGGAGCCTAGAGACTCGGCCCAGTTCAACAAGGCGCTGGCCA<br>TCATCCTCCACCTGCTCTACCTGCTGGAGAAAGTGGAGTGCACCCCCAGCCAGGAGCACCTGAAGCACCAGACCATCTATCGCCTGCTCAAGTGCGC |
| 173 | chr21: 140702500-14070550 | TAAAAATAAATTGTAATAAATATGCCGGCGGATGGTAGAGATGCCGACCCTACCGAGGAGCAGATGGCAGAAACAGAGAGAAACGACGAG<br>GAGCAGTTCGAATGCCAGGAACGGCTCAAGTGCCAGGTGCAGGTGGGGGCCCCCGAGGAGGAGGAGGAGGACGCGGGCCTGGTGGCC<br>AAGGCCGAGGCCGTGGCTGCAGGCTGGATGCTCGATTTCCTCCGCTTCTCTCTTTGCCGAGCTTTCCGCGACGGCCGCTCGGAGGACTTC<br>TGCAGGATCCGCAACAGGGCAGAGGCTATTATT |
| 174 | chr21: 14119800-14120400 | CGCCACCACGTGCGGGTAGCGCCGCATCGCCCCAGCCGTGTTCCTTGGTCTCCGTCTCCGCCGCGCCCGCCTGGTGAACTGGAGCACAG<br>GGACCATAGTTCTGGAAATTTATCCTTTTTCTCTCCATGGATTCAGCAGCAGTGTCTAAAAGAAAAAAATTCATCAATCATTTATGTATATTTTA<br>ATATAAAGGTAAAACACTGCGAACCAGTGGAACCGGATAGAAAGTAATTCAGTTTTACAGAACACAACTGTTTTTCAGGCTCTTTTATTAAAT<br>ATAAAAGAGCCATATATATTTCTGTGGAATTCCCCTTTTACTTAAGAATTCATTATCAGCGAATTAGTTTAAGGAGGCTGTTTTGTTAGAGGCT<br>GTGGTTGCATTCAAAAATTGGAATAGGAACAATGACTTGTAAAAATTCAACATTTTATTTTATTTTTGAGATGGAGTCTCGCTCTGTCGCCCAG<br>GCTGTAGTGCAGTGGCGCGATCTCGGCTCACTGCAACCTCAGCCTCCCGGGTTTAAGGAATTCTCTGCTTCAGCCTCCTGAATAGCTGGGA<br>TTACAGGCGCATGCCACCAAGCCCAGCTAATTTTTTTTGTATTT |
| 175 | chr21: 14304800-14306100 | CCCTGAACAGTCAGAGTTTACTGCCCACTTTTGCTGGAGGAGAAGCTCCTGAACAACTAGAGAGACTGTGGTTCCCAAAGAGCAGCCTGTA<br>GGCCTGAGGACTGCTCTATGACCGGCGTCAGTCCCTGCCTCCCTCCCTCCGTCCCTCCTTCCCTCCTTCCTTCCCAGGCCTTCTCTGACTA<br>CCAGATCCAGCAGATGACGGCCAACTTTGTGGATCAGTTTGGCTTCAATGATGAGGAGTTTGCAGACCATGACAACAACATCAAGTGAGTC |

TABLE 6C-continued

| SEQ ID NO | GENE NAME | SEQUENCE |
| --- | --- | --- |
| | | CACTTGGATGCCCCCTGCACGAGGCACGACTCCCCCTCCTCGCTGCTGAAGTCCCATGGGGGCAGCTCCCTTAGTCCTTGCCGGGAGATA<br>ACAGGTGTTTCCAGTTGCATGAGGGTGCTGAGGCCCCCAGTGAGAACCAGGGGAGGAGCACTGAGGCCTCAGATGAGCACCGGGGGAGG<br>AGCCCTGAGGCCCCAGATGAGCACCAGGGGAGGAGCACTGAGGCCCCAGATGAGCACCGGGGGAGGAGCGTTGAAGCCCCAGATGAGC<br>ACCAGAGGAGGAGAGCTGAGGCCCCAGATGAGCCCCGGGGGAGGAGCTCTGAGGCCCCAGACGAGCACCGGGGGAGGAGCGCCGAGG<br>CCCCAGATGAGCACCGGGGGAGGAGCGCCGAGGCCCCAGATGAGCAGTGGGGGAGGAGCCCCGAGGCCCCCAGATGAGCAGTGGGCG<br>GGGCAGGGAGCGCCGAGGCCATCCCCCTTGCTCTTGCAGCGCCCCATTTGACAGGATCGCGGAGATCAACTTCAACATCGACACTGACGA<br>GGACAGTGTGAGCGAGCGGGGCTGTGCGGGGTCATGCAGGCACCCTGTTCCCAGGCAGCTCAGGCCGCGCCCATGGCTCGGTCTGTGG<br>TGGGCCTGTGCGGTGGGGCTGGGAGAGGCCCCTCTGTGGAGCTAGGAACAGTCGCTTTTCTTGACCCTCCCCATCATGCCCTCCAGCCCA<br>TGGCGCCCACATCCTGAACTAAGCCCCTCTGGGAGCCCTGTGGGGAGAGCGCCTCCTGTCTCCCCCAGACCCTCTGGAAACTGACCTTGG<br>CGTTTTACTCTGCAGCCCAGCGCGGCTCTGAGGCCTGCTGCAGCGACCGCATCCAGCACTTTGATGAGAACGAGGACATCTCGGAGGACA<br>GCGACACTTGCTGTGCTGCCCAGGTGAAGGCCAGAGCCAGGTGCGGGGCCTGCCCATCCCCCCAAAGCCTCTGCCGAGGAGGTGCAGC<br>CCCCAGAACACCCGTCAGATGCCCAGACGCCCTGCTGTTTGTTATGCCGG |
| 176 | chr21: 15649340-15649450 | TTTGGGCCACGAGGCAAGTTCAAAGCGGGAGACTTTTGTTTTATAAAATGATGGTGAGCAGCTCCGGTTTTATGTCAAACATCAGGGTTTCG<br>TGCAGGATATAAACATTT |
| 177 | C21orf34 | ATTGCCGTACTTTGCTTCCCTTTGTATGTATTTCTTGTATGCTGCCGAGTCACTGATGGCTAGCTCTGTCTGGCAAGTAATTCAAAAATGCTG<br>TTTATGTAGAAAGGAAAGGTAGGGACTTTACCACACTCTGTCATTAAAGGGAGCAATTGAAGAACAAAGGAACTGAGTAAATACCTATATATT<br>GCCTTTTGTGTTGCGAAACACTGTAGCACAAACACATTTGTGTTCAGCCAAATGTTTTACTTCCTTTTGTAATAACGCATATAGTAGGTTGTCT<br>CCACATATGTACAAGAATCCATATTTTATTTAAACGTATATAGTCAATTGTTCATATTTATAGGCTGCAAACATTTCTCAATCTCAAAGACTTTT<br>ACATATCCACTCCCACACAGCTATTTGTTATTATTTTAAAAGTTCTTAAATTAAAAAAAAAAATAAAATATACTAATATCTCTGTTGGTTGATTTT<br>ATTAAGCAACTTAGGATTTCAACACAGTTTAAATCATATTGATGACTCAGATCCTGGCAGGTCTTACAATTCCTGTGAAATGAGAGCACAGCT<br>AATAAAAATATTAAGCAATTACTTTTATTAAAATCATAGGGTTTTTTTCATTATCACATAGAAATGATTGATCTATACAGATTGGTCTCACTCAT<br>GTGTCTTTTGGGCTGCTTGGGAGCTTCATGTAGAAGTGGAAAGTCCCCTTTGCTCTTCCTTCGACCAAGGTGGGGAAAATGAAGGCATAGA<br>ATACAATCTAGGGCTATTAAAGAATTGCTGGCATTACTTCTCTCTATCACGTGTGAGCCTGGCTGCCTGCTTCCTGAGGTAGGGGATCCAGG<br>ATGAGACTGTGCCGGAGCCTGTTTCCACAACTGCATTTGGAGATCCGTCTTATTGATTAGCGGGGGAAAGGGGTGGGGATCAGGAGTGTG<br>AGGTGAGGGGAGGACCAACTGACGACTGGCTCAATGAAGCACAAGACATTTTCTTCCGGAAAGATGTCAAACAACTGAGAAACAGCCAGAG<br>AGGAAGTAGAAAGGTGGAAAAATGAGGAGACCCTGGAAGAAATGAAGGCATTTCCTATGAGACAGCCTTGGGGCTTTTTTCTTTTCTTTCTT<br>TTTTTTTGCTTCCATCATCTGACCTGCAAAGGCTAGAGTGACAGCGTCATGCAAATGCTGCAGTCCAGCAGGTCTGGGAGAGGGTGGATGC<br>TAGACTGTGAGTTAATGTTAATGATGAGCGCAGTGAAAATACCAGCCGCTGCCACCCCCTGCTCACAGAAGCGCTCTGAGTCAGCATCAGA<br>TGCTTTGCCTCGCCTCTCGCTGTGTATCTGTATGCCTGTGTGCGCGCGCGTGCTCGCTCGGGCATCCGTGTCTAGCCGAGGGGAGGGGGT<br>GGCGTGTGAGTGCGTGGAGGGTAAAAGCCAGTCAGTCAGTGAGAAGCAAAGGTACGTTGGAGAGCAACTAAAATCTGACTGATTTCCATCT<br>TTGGAGCATCAGATGTATTCCC |
| 178 | BTG3 | GCAGCCTCCTCCTGAAAAATGTAAGCCATTTCCACTTTGTAAAGCTACGTTTATATTCCACCACGATACGATGGAAAAGAAAACCCAAGGCA<br>ATTTAATATACGGGTTGGGAAGAAAGTTTTGCTGATGGAACTACATTAGCCTCCACTCCAGCAAAGCAAACAAGGAACCACACTAAAGAAATGTACTGAATCTTTTAA |
| 179 | CHODL | TGCCTGAGCGCAGAGCGGCTGCTGCTGCTGTGATCCAGGACCAGGGCGCACCGGCTCAGCCTCTCACTTGTCAGAGGCCGGGGAAGAGA<br>AGCAAAGCGCAACGGTGTGGTCCAAGCCGGGGCTTCTGCTTCGCCTCTAGGACATACACGGGACCCCCTAACTTCAGTCCCCCAAACGCG<br>CACCCTCGAAGTCTTGAACTCCAGCCCCGCACATCCACGCGCGGCACAGGCGCGGCAGGCGGCAGGTCCCGGCCGAAGGCGATGCGCG<br>CAGGGGGTCGGGCAGCTGGGCTCGGGCGGCGGGAGTAGGGCCCGGCAGGGAGGCAGGGAGGCTGCAGAGTCAGAGTCGCGGGCTGC<br>GCCCTGGGCAGAGGCCGCCCTCGCTCCACGCAACACCTGCTGCTGCCACCGCGCCGCGATGAGCCGCGTGGTCTCGCTGCTGCTGGGC<br>GCCGCGCTGCTCTGCGGCCACGGAGCCTTCTGCCGCCGCGTGGTCAGCGGTGAGTCAGGGGCCGTCTCCCCGAAGAACGAGCGGGGAG<br>AGGGGACCACGGGGCGCGGCGGGCAGCCTGTTCTCGGGCGGAGGCTCTCCGGGGCGTTGGAAACCTGCATGGTGTAAGGACCCGGGAG<br>GAGGCGGGGAGAAATTGATTGTGCTGTTCTCCTCCCTCTCTTCTCTAACACACACGCAGAAAAGTTTAAATTTTTGTGAAGCGCTTGCTTAC<br>GTAGCTGCGGAGCGAGCCTCTGCTTCATTACGAGCGGCATAGCCTTTTTCAGGAGTGATTTCCACTTTCTTTGTGAGAGAGTTGACCACAC |
| 180 | NCAM2 | TTCAATTTACACTCGCACACGCGGGTACGTGGGTGTTCGGGGTAGGGCACTGATCTGGGGAAGGTCTCCCCCCCGCGACCCAACTCATCT<br>TTGCACATTTGCAGTCCTCCCTCGGTGCACTCCTGGCGGGGATCTGGCCAGTGCAGCGCACTGGGACCGAGGGCAGAGCCCGCGGAGTG |

TABLE 6C-continued

| SEQ ID NO | GENE NAME | SEQUENCE |
|---|---|---|
| | | AGGCCAGGAGAGACTTCAGGCCTCTAAGGACACAGCTGAGGCTAAGGCTGAGTTGAACGCAGCCCCTCCCGCGGCTCGTCCCCTCTCCA<br>GTGTCTCTCCCGTAAGGTGCCGCTCCCAACAGCAATGGGTCGAGATGTAGAGGAAACACTCTGTACGTTATTTTTCCGCCCACCCTTTAGC<br>GCCTGAGGAGACAGACAGTGTAGACTTTAGGGTACAATTGCTTCCCCTCTGTCGCGGCGGGGTGGGGAGCGTGGGAAGGGGACAGCCGC<br>GCAAGGGGCCAGCCTGCTCCAGGTTTGAGCGAGAGAGGGAGAAGGAGGTCCACGGAGAGACAAGAATCTCCCTCCTCCCACGCCCAAAA<br>GGAATAAGCTGCGGGGCACACCGCCCGCCTCCAGATCCCCCATTCACGTTGAGCCGGGGCGCG |
| 181 | chr21: 23574000-23574600 | TCATTATCCGATTGATTTTCCTGGTATCACATCACTTAAGTTTAAGTAGCTCTTATGTTACTTAGTAATGACTGCAAAACACGAGTTGTGATGC<br>GGGCAATTTGGATACAACAAAAAGAAGCCATTAAGTTTGTTCGTTAGTTAACAGGTGAAAGCTCTCAAGTTATTAAGGATAAAAATGCTAGTA<br>TATATATATATGGTTTGGAACTATACTGCGGATTTTGGATCATATCCGCCATGGATAAGGGAGGAATACTATAATCAGGTTTGTTTTAAATTCC<br>ATGTCTAATGACTTCGTTATCTAGATCACCTGTAGAGCTGTTTTTATTGTAGGAGTTTTCCTTGGTTTTAATCTTTTGATTTGTTTTTCATGTTA<br>ATACTGAAATTTTTAAAAATTGCATATTGTACTTCCTATATGAAAATTTTACTATGTATTTTTATTTTTATTTTCCTTTTCCTTTAGGAAGAATTAG<br>TTTGTTCCCTGACAGAGTTAGAGTAAGGGCAAATTACTTGTCTCTATAAACAACTCAGATGTTTTGAGCCGGTGTTGTAGGGGTTATCTTTTT<br>CTGGTTTTGCATTTTATTATAGGACATAGTGCTT |
| 182 | chr21: 24366920-24367060 | AGAAAGAAGAAATCCGGTAAAAGGATGTGTTATTGAGTTTGCAGTTGGTGTTTGATCTTGCACAGATTTTCTCAGGGGCCTTAAGACCGGTG<br>CCTTGGAACTGCCATCTGGGCATAGACAGAAGGGAGCATTTATACGCC |
| 183 | chr21: 25656000-25656900 | CGAAGATGGCGGAGGTGCAGGTCCTGGTGCTCGATGGTCGAGGCCATCTCCTGGTCCGCCTGGCGGCCATCGTGGCTAAACAGGTACTG<br>CTGGGCCGGAAAGTGGTGGTCGTACGCTGCGAAGGCATCAACATTTCTGGCAATTTCTACAGAAACAAGTTGAAGTACCTGGGTTTCCTCC<br>GCAAGCGGATGAACACCCACCTTTCCCGAGGTCCCTACCACTTCCGGGCCCCCCAGCCGCATCTTCTGGCGGACCGTGCGAGGTATGCC<br>GCCCCACAAGACCAAGCGAGGCCAGGCTTCTCTGGACCGCCTCAAGGTGTTTGACCGCATCCCACCGCCCTACGACAAGAAAAAGCGGAT<br>GGTGTTCCTGCTCCCTCAAGGTTGTGCGTCTGAAGCCTACAAGAAAGTTTGCCTATCTGGGGCGCCTGGCTCACGAGGTTGGCTGGAAGT<br>ACCAGGCAGTGACAGCCACCCTGGAGGAGAAGAGGAAAGAGAAAGCCAAGATCCACTACCGGAAGAAGAAACAGCTCATGAGGCTACGG<br>AAACAGGCCGAGAAGAACATGGAGAAGAAAATTGACAAATACACAGAGGTCCTCAAGACCCACAGACTCCTGGTCTGAGCCCAATAAAGAC<br>TGTTAATTCCTCATGCGTGGCCTGCCCTTCCTCCATCGTCGCCCTGGAATGTACGGGACCCAGGGGCAGCAGCAGTCCAGGCGCCACAGG<br>CAGCCTCGGACACAGGAAGCTGGGAGCAAGGAAAGGGTCTTAGTCACTGCCTCCCGAAGTTGCTTGAAAGCACTCGGAGAACTGTGCAGG<br>TGTCATTTATCTATGACCAATAGGAAGAGCAACCAGTTACTATTAGTGAAAGGGAGCCAGAAGACTGATTGGAGGGCCCTATCTTGTGAGC |
| 184 | MIR155HG | GCCTGAAGACCATTTCTTCCTCTCTTAGGGACCTGCTGGTCTCCAGCTGATTCGGTCCAGGAGGAAAAACCTCCCACTTGCTCCTCTCGGG<br>CTCCCTGCAAGGAGAGAGTAGAGACACTCCTGCCACCCAGTTGCAAGAAGTCGCCACTTCCCCCTCCAGCCGACTGAAAGTTCGGGCGAC<br>GTCTGGGCCGTCATTTGAAGGCGTTTCCTTTTCTTTAAGAACAAAGGTTGGAGCCCAAGCCTTGCGGCGCGGTGCAGGAAAGTACACGGC<br>GTGTGTTGAGAGAAAAAAAATACACACACGCAATGACCCACGAGAAAGGGAAAGGGGAAAACACCAACTACCCGGGCGCTGGGCTTTTTC<br>GACTTTTCCTTTAAAAAGAAAAAAGTTTTTCAAGCTGTAGGTTCCAAGAACAGGCAGGAGGGGGGAGAAGGGGGGGGGGGTTGCAGAAAA<br>GGCGCCTGGTCGGTTATGAGTCACAAGTGAGTTATAAAAGGGTCGCACGTTCGCAGGCGCGGGCTTCCTGTGCGCGGCCGAGCCCGGGC<br>CCAGCGCCGCCTGCAGCCTCGGGAAGGGAGCGGATAGCGGAGCCCCGAGCCGCCCGCAGAGCAAGCGCGGGGAACCAAGGAGACGCT<br>CCTGGCACTGCAGGTACGCCGACTTCAGTCTCGCGCTCCCGCCCGCCTTTCCTCTCTTGAACGTGGCAGGGACGCCGGGGGACTTCGGT<br>GCGAGGGTCACCGCCGGGTTAACTGGCGAGGCAAGGCGGGGGCAGCGCGCACGTGGCCGTGGAGCCCGGCCTGGTCCCGCGCGCGCC<br>TGCGGGTGCCCCCTGGGGACTCAGTGGTGTCGCCTCGCCCGGGACCAGAGATTGCGCTGGATGGATTCCCGCGGGCAGAGGCAGGGGG<br>AAGGAGGGGTGTTCGAAACCTAATACTTGAGCTTCTTTGCAAAGTTTCCTTGGATGGTTGGGGACGTACCTGTATAATGGCCCTGGACCAG<br>CTTCCCTGTTGGAGTGGCCAGAGAAGTGTGTAAAACACACTAGAGGGGCAGGGTGGAAAAAGAGACTGCCTTCAAAACTTGTATCTTTTCG<br>ATTTCATTTTGAAAAATAACTACAAATCTATTTTAATTTTACAAAGTTAGACTCATAGCATTTTAGATATCAATGTCTTCATTTAACAGAAGTGAA<br>GATGGAGCAAACGCTCAATCAGCGTCTGTATTTATTCGCTCCTGTTGTGCCAGGGTGCGTTTTTGCCGAGCGGTTGCCTTTCTTTACTCACA<br>AAACCCCCTTGATGTCTGTCCTCCACGTTTTACGAGGGAGAGCCGGATCTTTTGAAGTTTGTATCATCTAAAGCAGGTATATTGGGATGACT<br>ATGGATAGAATTTAACCTGAAAACACTGAAGTTGACAGCTGACAAAG |
| 185 | CYYR1 | CATAACAAGAGTCATTCTAATGTGATTATAAAGGACCCGAAGCTTTGCTTTTAAAATTCAATACTTAGGTAGAAAGAAAATGATAACTTTTTCC<br>CTTTGATTTTTATTCACTATTTTTATAACACTAGCAGCCCTGAGACACCGGATTGGAAATATCTATGCCTCTTGATGTTACCTGGGCACCACTGCATCACAGTCCT |

TABLE 6C-continued

| SEQ ID NO | GENE NAME | SEQUENCE |
|---|---|---|
| 186 | chr21: 26938800-26939200 | AATAGTAATTGCCAACAGTCAAGATATGTACTACCACCAAATTCCGTGTTATTTGTGATCAAAAGATATACACAGATACTTGAAAACTGATTTC<br>TACGTTGCATATGGGAAAAATACCTCATTTTTCTCAGCTGTCCATTATTTTTGAGATATTATGTGCAGTGATAGTAAGAACAAGCAGATTTGGA<br>ACACATCAGCAATAATTTTTTCAATCAGAGTCCTGCCAAAATGAAAGAATTTGACAGTATCCGGCACCCTGTACTCATGCTTGGCTTCTGTAG<br>AAACTGTGGCTTGCAAAAGGGCAGCTGGGTACTGTGTTTTGGTACCTCATTCTTTAAACGTATAATGGGAATCTGGTTGGTTCAGGAAAACC<br>CTTGCCTACTTATTATTACTCTGTTTT |
| 187 | GRIK1 | GGCCCATACTTAATGTATTTTTAAACGTTTTAACATTTACTAATATAGAACCTTCTATTGCCTATTTCCTTCTGGTTTATTCCCTTTCCTTCTGT<br>CATTGAAGAAATGGTTCTAGTGGTAGAAATACTCCACGATTGAGAAGAATGTGGGAAGAAAGGAGGGCTGGTGGGTAAGAATTGCTCATGA<br>TGTCTCCCTCTGAATTCTGTGCTCTCACAATGACACTCCAATGTGTGGTTTGACGCCTGGAAGA |
| 188 | chr21: 30741350-30741600 | TGCTTCAACCGGAAATGTGGTTGAATTACCCTTACAGTGAACCTGATCAGTGGTAACAGGAGATGCTAGAACAGGAAAAGACAAGTTTCCCC<br>TTTCCTCCCTATCCCATCAATTACTTTGAGGTGTATTTTTTCTTTGCAACCCCTCCAGAGAAGTCGGCAATGTTTAACGAGCATGCCTGCCAA<br>GTGGCTTGCCTTATACCTCATTATGAAGTGATACTCAGGGCCACTAACACATCGCACAGCATTGC |
| 189 | TIAM1 | TATGATTCCCTCGATTTCCCTCAATCTTAACCATTGTGGATCACAGCAGGAGGGCCAGAAAGTGAGCTTCAGCCTGGCACCGGGACCTCAG<br>CCTCTCCCTTAAACTTTCCCTAATCCTCGGAGCTAGTGTTACTCAAGTGACTCCACAGTGTTGCCCGATCCCTTCAGACATGGCCTTGATGA<br>TCTCCAAAACTCATGCTACCTTTGCCAGCCTAAAGCATCCACTCTGTGCCCCAAAACGTGAATGTCAAATACCCTTCAAGGCAGAAGGCTAT<br>TTCTATTTTTGTTTGTTTCTGTTTAAGGCAACAATCACCAACATTTGGTACACATGAGCCATCCTGTGAAACATCAAGGCGCTTCGTTGGCAG<br>CAAGTCAACTTCGGTTTCAGAAGAAAGCTGCACTATTTCCTGAGGTTAGAGGTTTAAACCAAAACAAGACAACCACATTTTAACCCCAAATCT<br>GCCGACTGAGGGTAACCATGATCCTTCCTTCACAGCACC |
| 190 | TIAM1 | TACTAAATCAACCCAAACCCGAGAACCCGGTCATGGAGAAATAAATGATAGTAATCTATGCTGTTCATCTGTTCCATCACTCACTCACTCTCT<br>TGCTGAACAAGAAAGGGCCACCCATGTAGCAAACCACATGTAAAGAGCCGGGAAGAC |
| 191 | TIAM1 | TATTATTTTGTTCAAAGTAGACGGGTATACTAACATCTGTGGGCAAGTTTACCACACGCCACTTAAAACAGGCTAACAGGGTCATATGCCAAA<br>ACGTTCAGGTTTGCATTTTTGAAAAGCTCAGAGATCTGACAGATGTGTTCCGGCCGCGATTTAACATGCGGCTCCAGTGAGAAGGAAGCAG<br>ATATGACAAATGGTTCACTTATTTCAGAACTAAAACCCCAGAGGAGCAGCCTGAGCCAAAAAGGGAAGTGATCAATGGAAAAGACGGTCGA<br>ATCTGCTCACAGGCAAGGCAAGGGG |
| 192 | SOD1 | AAGACCTGGAGTTTCCATTACACCGAATTGGCACTTAATAACTGTTGTCGGAGCATTTCTTAAGCCACATTTTCGTAAAGTGGCTTTAAAATT<br>GCTCTGCCAGTAGGCAGGTTGCTAAGATGGTCAGAGACAAACTTCTGAACGACTCTTGTAAAATATACAGAAATATTTTCAGAACTTTTATCA<br>GTAAAATTACAAAACGTGTTGCAAGGAAGGTGCTTGTGATAACACTGTCCCCAGAACCTTAGTGAAGTTACCAACTGGTGGAAAATTTTCTCT<br>TGCACTCGGCTTAAAAATCAT |
| 193 | HUNK | GCAGGGGTGACTGGTCCTCTCTCTCTGCACCTCGCAGGATTTCTCTGGAAGATCTGAGCCCGAGCGTCGTGCTGCACATGACCGAGAAGC<br>TGGGTTACAAGAACAGCGACGTGATCAACACTGTGCTCTCCAACCGCGCCTGCCACATCCTGGCCATCTACTTCCTCTTAAACAAGAAACT<br>GGAGCGCTATTTGTCAGGGGTAAGTGCGACCCTAGAGGCGATCGTCTCTGCTGTCTGTGGAAAAAAGAGCTCCTACACCCAAAGTGCTTCT<br>CAGTTGCTGACACTTGATCCAAGCTGCTAATTTAATCTAATGTGAGGCTGAGTTTTCTGAATGTGGGATAAAGTCGTAGCTAAACCTGCTTCT<br>CAGGGAGTGCCTTTTATCTGCAATGTTTTTCAAAT |
| 194 | chr21: 33272200-33273300 | AAGTAACGGGATCAAATTAATTATTATTTTGGTGGCCGCCTCTCTTCTCCACCCCAAGCCAGGCAAGACTCACCCTCGGCCCTGCCCGCCC<br>CAGCATTTCAAATGGAATACCTAGGTGGCCCAGGGGGACCCCTGACCCCTATATCCTGTTTCTTTCTGCCTGCTTTGCTACTTTTCTCCTTG<br>ATAAAAGGAGAGAGTGAGAGATAATTAACAAAAAACATGGCCCCAGGACAATGAAACAACTGGCCTTGGCCGGCCAGAAATGTATCCTGGT<br>TTTCTAGGTGAACTTTCTCCCATCAATCTTTCCTTTAACCTCTCTGTTAGTGGAAGCAATAGGAACACCCCTCCCCTCCCCTGAGCAAATGCT<br>TTCTTTTGACTGGAAACAAAACAGGGGCTCGGCGAAGGCTGAGGTGAAATCTGGGTGGCATGGGCGCCGCACAATGGGGCCGCTGTTCCC<br>CGGCCCGGGCTTGTGTTTTACAACAGGGGAGGGGCGGGCGTGAATGGTCTGATGATTGGAACAATCCCCCCGATTCAGGCCTACAAACGC<br>ATCTTCTGTTCCACACCGAGGGGACAGAAAGGAGAAAAGTGACAAAGAACGCGGGGCGGGGGGAATTAAAACAAAATGCGCTCGACTAAA<br>AAATCTCTCATATCCTGCATATTCCAGAAAGCGGCTCTATGGAGAGAGCCTTCAGGAGGCCTCAGCCATATCTGAATGGCTTTCTCTGGCCT<br>CTGATTTATTGATGAAGCTGAAGCGACTTGCTGGAGAAAGGCCTGGAGCCTTCTTTGTCTCCGAGATGAAGTACAATAGGCCACAGGGCGG |

TABLE 6C-continued

| SEQ ID NO | GENE NAME | SEQUENCE |
|---|---|---|
| | | AGATCTCTTGTGATGCTCTCGGGTCCTGCCTTTCTCTTGCCCTCTCCTCCCTGCAAATACCAGCAGCGGTGACAAACGATTGGTGGTGTGC<br>CTGGGAGAGCCGGTGACAAGACTGGGCCACTTGAGGTCTCCTTAAGAGGGTATTATGGCCAGGGCGACGTTTGTGCTGTGAAGATGGCAC<br>ACTCCATTTTGTCAATGGCTCTCATCGGCCCAGATAATCGCCCCCTGCCTGCCTGTCAGGGGCGCAGCCGGCCGATTCATGGCGCCCTCGGAGAAAGTA |
| 195 | OLIG2 | GTCTTTCCCGCCCCCTTGTCTAAACTCAAAACCGAGTCCGGGCGCGCCTTGCAGGGCGCCCGAGCTCTGCAGCGGCGTTGCGGGCTGAA<br>CCCATCCGGCACAAACTGCGGGCCACTGGCCCCTCACACCTGGGAGTTTGCGGCGCTGGCCTGCAGCCCGGGGCCCACGTGGCGGAAG<br>CTTTCCCGGGCGCGCGCTGCGCAGCCCCGCGGGGCCGGGGAGACACCGCTCGGGAGTCCTCCGCTCGGCTGCAGAATCTTTATCAGCT<br>GCACTTTACCGCAGCCCTGGCTAGGACGCTAGGCGGTGGAGCGCCCTATCCAGGTGCGCCGCCGCACCATGGATCACCGCGCCCGGTCC<br>CGCAGTCCCGCCATGGCCTGGGGAGGCCCGAAGCCCGGGGACAGTGGCCGGCCCATCTCCGGCTCCGCGGACCCCCGGCTCAGGCGG<br>GAGGGCAGGCGGGTCCCTGCAGGCCCCCAGGGAGCCCGGGAGCCTCTCTCTGGCGTCATTCAGTCCCGGGGCAACCTGAAGCGCGGTA<br>GATATTGGAGAGGGGGCGTCTGTTGGGGGGACCTGGCGTCATTACTGATGGCTAGCAGGGAGGAGGGAACGGGTTGTCACCTCGGCCTC<br>ATAAGGCCGTGAGTGAGTAGTCCAGGGCCTCTTCAGGCATTTTTGAAACTGGATTAACTAGGGGGGAAATTGTAGCACTGAAGCCACCGTG<br>ACTGTCTTTTGCGCTGTGTGGAAACTCCGGTAAAACTCTTTGGGCAACAGTCTTATCACCAGCTCTTCAACGTGTGCAGCCCTTCTGGTCCT<br>GTCCCTGTTCTGGGCCCCAGGAATGCAAAGCAGGTCCAGGCACTGTGAAGACCCTGGCGGTGGAGGAAGAGGCTTCCCGGCTGTGGAGG<br>AAGCCAGACCCTTACAACACAAGACGAGAACCAGACCTGCGTGGGGGAGCTCTGGATGCTACAGGGGCTCAAGGAGGGGTGGAGGGGCC<br>TTCCCAGGCCAACCCCTGAACGGCTTGGACAAGATGCTCAGATGGACGGGAGGAACGGCGTGTGGGATGGGGGAGCTGGAGGCGGGTG<br>GGTGGGGGGGGGAGGATGGGGAAAGCGCTGGCCCACCCAGTGTGGGAGGGGTAGAGGAAAAGCCCGCAGGGGCCAGGTTGGGACCCC<br>GTAGGCCGGGTTAGAGGGCTTGGACTTGATCCTGACAGGCGACAGGGAGACATATTGCTACTTATTATGTGCACAGTGGCCAGATCTCTAA<br>AGAAAACACCATCCCCCACCCCCACCCCCCATATAGTAAACCAGGTGGTCCGCCCAGTGCTCCCAGGGAGGTGATGGGAAATCCCACTCC<br>ATACCCTGCGGTGAGGGGTTCCATGCCCTCCACGTGTGCAACTACTCCGGGCCCAGGGAAACACTGGGCCCCATCCGGTAACCCCCGGC<br>CCAGTCGGGTTTCCCAGTTCACATTATAACCAAACGGTCTTGCCAGCTAGACAGACAGACACCCCTGACCTGTTTACCCTGATCCTCTGCTC<br>TCAGGATTAATCACAACTTGTCGAAGGGGGTGGCTTCCAGTGGGGTGGACCGCTCTGTCAATGCCAGCGTGTGTCTAGCATCTCCTGGGG<br>TGGGGGTGTGGGGAAGGGAGGTGTAGGATGAAGCCCTAGAAGCCTCAGGCAATTGTGATCCGGTGGGCTGGATACTGAAGCCCACCCCT<br>GCCTTGACCTCAATTTTCAGTATCTTCATCTGTAAAATGGGAACAACCTGCCTTCCTCCTAGCCCTAAAGGGGCTGCTGTCAAGATTGGCTG<br>AGATAGCTGTTTGCAAGCTGAGCTCAATGAAAGTTCATTGTGTCCCCCTCAGTCCTATCCCAATATCGTCTCACTGCAAAGGTGGGGGGCA<br>GCTTAACTTCAAGGGCACTTCAAGGATAGCCAGGTGGCTGTCAGCCCAGCTTTCCAGGATGGGAGCAGGATCTTGACAGAAGGGTTGACT<br>GGGAGGGGCAGTTGCTGGTTTGGGCTTCGTTAGGTTGCATTTTTGTTTGTTGTCCTTTCATTTCCCTGGGGCAGCACCCCTTCCTGCAAGCT<br>CCAGGCCTTCCTCTGGAATGCTCCTAGAGCCCAACCTCTGCTGGTGCCTGAGCTTAAGCCAGGCCAGCTAAGGGGATCCTGGATTCACAC<br>GGCCTCACAGTCACTCAGATTGTTAGCAGAAGACAAAAATTACAAGGGGAGGGCGTCATGTGATTCTTACACACCCTCCAAATCCAGCAGA<br>CACCTTGGAAGCCACAGGTAGCTTCAAGAAACCCATTTTACGGATGAGAACCTGAGATGGAGAAAGGACAACTGGAGATCTCTGAGTCTCT<br>GAGCCCACACTCCCTACCTCCCTGCACCTCCAGGCACTCTGCTGGCAGGATCTTGGGCAAATGCCCACAGCTCTCTGAGAGTCAGTTTTCC<br>TGTCTGTAAAATGGGAGTCATACCTTCCTCCTATGGCCGGTGAGAGACTAAATTAAACTATGTCTGTCAAGACACCTGAAACTCCTGGCACA<br>ATTTAGGTTGCCTTCAAGTGGTCACAGTTGTCATTAGGTGGAAGTCAACACCCCAATCATTGTAAAGGTGCCCATATACCCCAAGATCCAGA<br>TTACAGCTCTCACAGTTTATTATATACAGCGAAAAAACACATAACACACCTTTGCCCACATTTACATGTATTTTACGGACCATGTTTCACATCA<br>GTCCGCATGCACATCTGCACGTGTGTGCATTCGGCAGTATTTACCAAGCACCTGCCAAGTGCCAGGGCCTGTCCTCCGCACCCGGCGTGA<br>ACTGTCCTGGACCAGTCCCGGGAGCCGCGGTTCTGACCAGCCGTGCTGACCCTGGACGACTCCATGAGCTGTTTTGTGAGAAAGACACGC<br>CATTTGTTTGCAGAGTTCTGACTTCTGAGGGGTCATGTAGCACATGTTTGGTAGCCAAACGCTGTCATTCACGACCAGGAGCGATGGCTGC<br>AATGCCTTTTTCTTTGCTTTGCTTTCCGGTGCCGGGAGCCTTGCCTCCCGCCGCCACCCCTGGTCAGCTCTGCGCAAGAACGTCGTTCTGT<br>TTGGCAGCCAGGCCGAGACGCAGCCTGAATGTGAGCAGGAACTCGGAGAAGGGAAGGGAGAGAATCAGAAAGAAGGCCCGGGAGGGAC<br>CCGGGAAGCAGTGGGAGGTCTGCGCCCTGGAGCCCCGCGAGAGCCCGCCGGTTTGGCACGGGCTCCTCCCGGGCCGCCCGGCGGTCC<br>AACAAAGGCCGGCCCCGACACGCACCCGGTCTTTTGTGGGAGAGAAACACAAAGAAGAGGGAAAAACACGGAGGAGGCCAACAGCACCA<br>GGACGCGGGGGCCAACCAGGAACTCCCGGAGCCGGGGCCCATTAGCCTCTGCAAATGAGCACTCCATTCCCCAGGAAGGGGCCCCAGCT<br>GCGCGCGCTGGTGGGAACCGCAGTGCCTGGGACCCGCCCAGGTCGCCCACCCCGGGCGCCGGGCGCAGGACCCGGACAAGTCCTGGG<br>GACGCCTCCAGGACGCACCAGGGCAAGCTTGGGCACCGGGATCTAATTTCTAGTTATTCCTGGGACGGGGTGGGGAGGCATAGGAGACA<br>CACCGAGAGGTACTCAGCATCCGATTGGCACCAGGGCCAAGGGAGCCCAGGGGCGACACAGACCTCCCCGACCTCCCAAGCTACTCCGG<br>CGACGGGAGGATGTTGAGGGAAGCCTGCCAGGTGAAGAAGGGGCCAGCAGCAGCACAGAGCTTCCGACTTTGCCTTCCAGGCTCTAGAC<br>TCGCGCCATGCCAAGACGGGCCCCTCGACTTTCACCCCTGACTCCCAACTCCAGCCACTGGACCGAGCGCGCAAAGAACCTGAGACCGCT<br>TGCTCTCACCGCCGCAAGTCGGTCGCAGGACAGACACCAGTGGGCAGCAACAAAAAAAGAAACCGGGTTCCGGGACACGTGCCGGCGGC<br>TGGACTAACCTCAGCGGCTGCAACCAAGGAGCGCGCACGTTGCGCCTGCTGGTGTTTATTAGCTACACTGGCAGGCGCACAACTCCGCGC |

TABLE 6C-continued

| SEQ ID NO | GENE NAME | SEQUENCE |
|---|---|---|
| | | CCCGACTGGTGGCCCCACAGCGCGCACCACACATGGCCTCGCTGCTGTTGGCGGGGTAGGCCCGAAGGAGGCATCTACAAATGCCCGAG<br>CCCTTTCTGATCCCCACCCCCCCGCTCCCTGCGTCGTCCGAGTGACAGATTCTACTAATTGAACGGTTATGGGTCATCCTTGTAACCGTTG<br>GACGACATAACACCACGCTTCAGTTCTTCATGTTTTAAATACATATTTAACGGATGGCTGCAGAGCCAGCTGGGAAACACGCGGATTGAAAA<br>ATAATGCTCCAGAAGGCACGAGACTGGGGCGAAGGCGAGAGCGGGCTGGGCTTCTAGCGGAGACCGCAGAGGGAGACATATCTCAGAAC<br>TAGGGGCAATAACGTGGGTTTCTCTTTGTATTTGTTTATTTTGTAACTTTGCTACTTGAAGACCAATTATTTACTATGCTAATTTGTTTGCTTGT<br>TTTTAAAACCGTACTTGCACAGTAAAAGTTCCCCAACAACGGAAGTAACCCGACGTTCCTCACACTCCCTAGGAGACTGTGTGCGTGTGTGC<br>CCGCGCGTGCGCTCACAGTGTCAAGTGCTAGCATCCGAGATCTGCAGAAACAAATGTCTGAATTCGAAATGTATGGGTGTGAGAAATTCAG<br>CTCGGGGAAGAGATTAGGGACTGGGGGAGACAGGTGGCTGCCTGTACTATAAGGAACCGCCAACGCCAGCATCTGTAGTCCAAGCAGGG<br>CTGCTCTGTAAAGGCTTAGCAATTTTTTCTGTAGGCTTGCTGCACACGGTCTCTGGCTTTTCCCATCTGTAAAATGGGTGAATGCATCCGTA<br>CCTCAGCTACCTCCGTGAGGTGCTTCTCCAGTTCGGGCTTAATTCCTCATCGTCAAGAGTTTTCAGGTTTCAGAGCCAGCCTGCAATCGGTA<br>AAACATGTCCCAACGCGGTCGCGAGTGGTTCCATCTCGCTGTCTGGCCCACAGCGTGGAGAAGCCTTGCCCAGGCCTGAAACTTCTCTTT<br>GCAGTTCCAGAAAGCAGGCGACTGGGACGGAAGGCTCTTTGCTAACCTTTTACAGCGGAGCCCTGCTTGGACTACAGATGCCAGCGTTGC<br>CCCTGCCCCAAGGCGTGTGGTGATCACAAAGACGACACTGAAAATACTTACTATCATCCGGCTCCCCTGCTAATAAATGGAGGGGTGTTTA<br>ACTACAGGCACGACCCTGCCCTTGTGCTAGCGCGGTTACCGTGCGGAAATAACTCGTCCCTGTACCCACACCATCCTCAACCTAAAGGAGA<br>GTTGTGAATTCTTTCAAAACACTCTTCTGGAGTCCGTCCCCTCCCTCCTTGCCCGCCCTCTACCCCTCAAGTCCCTGCCCCCAGCTGGGGG<br>CGCTACCGGCTGCCGTCGGAGCTGCAGCCACGGCCATCTCCTAGACGCGCGAGTAGAGCACCAAGATAGTGGGGACTTTGTGCCTGGGC<br>ATCGTTTACATTTGGGGCGCCAAATGCCCACGTGTTGATGAAACCAGTGAGATGGGAACAGGCGGCGGGAAACCAGACAGAGGAAGAGCT<br>AGGGAGGAGACCCCAGCCCCGGATCCTGGGTCGCCAGGGTTTTCCGCGCGCATCCCAAAAGGTGCGGCTGCGTGGGGCATCAGGTTAGT<br>TTGTTAGACTCTGCAGAGTCTCCAAACCATCCCATCCCCCAACCTGACTCTGTGGTGGCCGTATTTTTTACAGAAATTTGACCACGTTCCCTT<br>TCTCCCTTGGTCCCAAGCGCGCTCAGCCCTCCCTCCATCCCCCTTGAGCCGCCCTTCTCCTCCCCCTCGCCTCCTCGGGTCCCTCCTCCA<br>GTCCCTCCCCAAGAATCTCCCGGCCACGGGCGCCCATTGGTTGTGCGCAGGGAGGAGGCGTGTGCCCGGCCTGGCGAGTTTCATTGAGC<br>GGAATTAGCCCGGATGACATCAGCTTCCCAGCCCCCCGGCGGGCCCAGCTCATTGGCGAGGCAGCCCCTCCAGGACACGCACATTGTTC<br>CCCGCCCCCGCCCCCGCCACCGCTGCCGCCGTCGCCGCTGCCACCGGGCTATAAAAACCGGCCGAGCCCCTAAAGGTGCGGATGCTTAT<br>TATAGATCGACGCGACACCAGCGCCCGGTGCCAGGTTCTCCCCTGAGGCTTTTCGGAGCGAGCTCCTCAAATCGCATCCAGAGTAAGTGT<br>CCCCGCCCCACAGCAGCCGCAGCCTAGATCCCAGGGACAGACTCTCCTCAACTCGGCTGTGACCCAGAATGCTCCGATACAGGGGGTCT<br>GGATCCCTACTCTGCGGGCCATTTCTCCAGAGCGACTTTGCTCTTCTGTCCTCCCCACACTCACCGCTGCATCTCCCTCACCAAAAGCGAG<br>AAGTCGGAGCGACAACAGCTCTTTCTGCCCAAGCCCCAGTCAGCTGGTGAGCTCCCCGTGGTCTCCAGATGCAGCACATGGACTCTGGGC<br>CCCGCGCCGGCTCTGGGTGCATGTGCGTGTGCGTGTGTTTGCTGCGTGGTGTCGATGGAGATAAGGTGGATCCGTTTGAGGAACCAAATC<br>ATTAGTTCTCTATCTAGATCTCCATTCTCCCCAAAGAAAGGCCCTCACTTCCCACTCGTTTATTCCAGCCCGGGGGCTCAGTTTTCCCACAC<br>CTAACTGAAAGCCCGAAGCCTCTAGAATGCCACCCGCACCCCGAGGGTCACCAACGCTCCCTGAAATAACCTGTTGCATGAGAGCAGAGG<br>GGAGATAGAGAGAGCTTAATTATAGGTACCCGCGTGCAGCTAAAAGGAGGGCCAGAGATAGTAGCGAGGGGGACGAGGAGCCACGGGCC<br>ACCTGTGCCGGGACCCCGCGCTGTGGTACTGCGGTGCAGGCGGGAGCAGCTTTTCTGTCTCTCACTGACTCACTCTCTCTCTCTCTCCCTC<br>TCTCTCTCTCTCATTCTCTCTCTTTTCTCCTCCTCTCCTGGAAGTTTTCGGGTCCGAGGGAAGGAGGACCCTGCGAAAGCTGCGACGACTAT<br>CTTCCCCTGGGGCCATGGACTCGGACGCCAGCCTGGTGTCCAGCCGCCCGTCGTCGCCAGAGCCCGATGACCTTTTTCTGCCGGCCCGG<br>AGTAAGGGCAGCAGCGGCAGCGCCTTCACTGGGGGCACCGTGTCCTCGTCCACCCCGAGTGACTGCCCGCCGGAGCTGAGCGCCGAGC<br>TGCGCGGCGCTATGGGCTCTGCGGGCGCGCATCCTGGGGACAAGCTAGGAGGCAGTGGCTTCAAGTCATCCTCGTCCAGCACCTCGTCG<br>TCTACGTCGTCGGCGGCTGCGTCGTCCACCAAGAAGGACAAGAAGCAAATGACAGAGCCGGAGCTGCAGCAGCTGCGTCTCAAGATCAAC<br>AGCCGCGAGCGCAAGCGCATGCACGACCTCAACATCGCCATGGATGGCCTCCGCGAGGTCATGCCGTACGCACACGGCCCTTCGGTGCG<br>CAAGCTTTCCAAGATCGCCACGCTGCTGCTGGCGCGCAACTACATCCTCATGCTCACCAACTCGCTGGAGGAGATGAAGCGACTGGTGAG<br>CGAGATCTACGGGGGCCACCACGCTGGCTTCCACCCGTCGGCCTGCGGCGGCCTGGCGCACTCCGCGCCCCTGCCCGCCGCCACCGCG<br>CACCCGGCAGCAGCAGCGCACGCCGCACATCACCCCGCGGTGCACCACCCCATCCTGCCGCCCGCCGCCGCAGCGGCTGCTGCCGCCG<br>CTGCAGCCGCGGCTGTGTCCAGCGCCTCTCTGCCCGGATCCGGGCTGCCGTCGGTCGGCTCCATCCGTCCACCGCACGGCCTACTCAAG<br>TCTCCGTCTGCTGCCGCGGCCGCCCCGCTGGGGGGCGGGGGCGGCGGCAGTGGGGCGAGCGGGGGCTTCCAGCACTGGGGCGGCATG<br>CCCTGCCCCTGCAGCATGTGCCAGGTGCCGCCGCCGCACCACCACGTGTCGGCTATGGGCGCCGGCAGCCTGCCGCGCCTCACCTCCG<br>ACGCCAAGTGAGCCGACTGGCGCCGGCGCGTTCTGGCGACAGGGGAGCCAGGGGCCGCGGGGAAGCGAGGACTGGCCTGCGCTGGGC<br>TCGGGAGCTCTGTCGCGAGGAGGGGCGCAGGACCATGGACTGGGGGTGGGGCATGGTGGGGATTCCAGCATCTGCGAACCCAAGCAAT<br>GGGGGCGCCCACAGAGCAGTGGGGAGTGAGGGGATGTTCTCTCCGGGACCTGATCGAGCGCTGTCTGGCTTTAACCTGAGCTGGTCCAG<br>TAGACATCGTTTTATGAAAAGGTACCGCTGTGTGCATTCCTCACTAGAACTCATCCGACCCCCGACCCCCACCTCCGGGAAAAGATTCTAAA<br>AACTTCTTTCCCTGAGAGCGTGGCCTGACTTGCAGACTCGGCTTGGGCAGCACTTCGGGGGGGGAGGGGGTGTTATGGGAGGGGGACAC |

TABLE 6C-continued

| SEQ ID NO | GENE NAME | SEQUENCE |
|---|---|---|
| | | ATTGGGGCCTTGCTCCTCTTCCTCCTTTCTTGGCGGGTGGGAGACTCCGGGTAGCCGCACTGCAGAAGCAACAGCCCGACCGCGCCCTCC<br>AGGGTCGTCCCTGGCCCAAGGCCAGGGGCCACAAGTTAGTTGGAAGCCGGCGTTCGGTATCAGAAGCGCTGATGGTCATATCCAATCTCA<br>ATATCTGGGTCAATCCACACCCTCTTAGAACTGTGGCCGTTCCTCCCTGTCTCTCGTTGATTTGGGAGAATATGGTTTTCTAATAAATCTGTG<br>GATGTTCCTTCTTCAACAGTATGAGCAAGTTTATAGACATTCAGAGTAGAACCACTTGTGGATTGGAATAACCCAAAACTGCCGATTTCAGG<br>GGCGGGTGCATTGTAGTTATTATTTTAAAATAGAAACTACCCCACCGACTCATCTTTCCTTCTCTAAGCACAAAGTGATTTGGTTATTTTGGTA<br>CCTGAGAACGTAACAGAATTAAAAGGCAGTTGCTGTGGAAACAGTTTGGGTTATTTGGGGGTTCTGTTGGCTTTTTAAAATTTTCTTTTTTGG<br>ATGTGTAAATTTATCAATGATGAGGTAAGTGCGCAATGCTAAGCTGTTTGCTCACGTGACTGCCAGCCCCATCGGAGTCTAAGCCGGCTTTC<br>CTCTATTTTGGTTTATTTTTGCCACGTTTAACACAAATGGTAAACTCCTCCACGTGCTTCCTGCGTTCCGTGCAAGCCGCCTCGGCGCTGCC<br>TGCGTTGCAAACTGGGCTTTGTAGCGTCTGCCGTGTAACACCCTTCCTCTGATCGCACCGCCCCTCGCAGAGAGTGTATCATCTGTTTTATT<br>TTTGTAAAAACAAAGTGCTAAATAATATTTATTACTTGTTTGGTTGCAAAAACGGAATAAATGACTGAGTGTTGAGATTTTAAATAAAATTTAAA<br>GTAAAGTCGGGGGATTTCCATCCGTGTGCCACCCCGAAAAGGGGTTCAGGACGCGATACCTTGGGACCGGATTTGGGGATCGTTCCCCCA<br>GTTTGGCACTAGAGACACACATGCATTATCTTTCAAACATGTTCCGGGCAAATCCTCCGGGTCTTTTTCACAACTTGCTTGTCCTTATTTTTAT<br>TTTCTGACGCCTAACCCGGAACTGCCTTTCTCTTCAGTTGAGTATTGAGCTCCTTTATAAGCAGACATTTCCTTCCCGGAGCATCGGACTTTG<br>GGACTTGCAGGGTGAGGGCTGCGCCTTTGGCTGGGGGTCTGGGCTCTCAGGAGTCCTCTACTGCTCGATTTTTAGATTTTTATTTCCTTTCT<br>GCTCAGAGGCGGTCTCCCGTCACCACCTTCCCCCTGCGGGTTTCCTTGGCTTCAGCTGCGGACCTGGATTCTGCGGAGCCGTAGCGTTCC<br>CAGCAAAGCGCTTGGGGAGTGCTTGGTGCAGAATCTACTAACCCTTCCATTCCTTTTCAGCCATCTCCACTACCCTCCCCCAGCGGCCACC<br>CCCGCCTTGAGCTGCAAAGGATCAGGTGCTCCGCACCTCTGGAGGAGCACTGGCAGCGCTTTGGCCTCTGTGCTCTTTCCT |
| 196 | OLIG2 | CCGGCACGGCCCGCATCCGCCAGGATTGAAGCAGCTGGCTTGGACGCGCGCAGTTTTCCTTTGGCGACATTGCAGCGTCGGTGCGGCCA<br>CAATCCGTCCACTGGTTGTGGGAACGGTTGGAGGTCCCCCAAGAAGGAGACACGCAGAGCTCTCCAGAACCGCCTACATGCGCATGGGG<br>CCCAAACAGCCTCCCAAGGAGCACCCAGGTCCATGCACCCGAGCCCAAAATCACAGACCCGCTACGGGCTTTTGCACATCAGCTCCAAAC<br>ACCTGAGTCCACGTGCACAGGCTCTCGCACAGGGGACTCACGCACCTGAGTTCGCGCTCACAGATCCACGCACACCGGTGCTTGCACACG<br>CAAGGGCCTAGAACTGCAAAGCAGCGGCCTCTCTGGACCGCCTCCCTCCGGCCCTCCTGAGCCCTACTGAGCCCTGCTGAGTCCTGGAG<br>GCCCTGTGACCCGGTGTCCTTGGACCGCAAGCATCCTGGTTTACCATCCCTAC |
| 197 | RUNX1 | GGACGCGGCCCGCTCTAGAGGCAAGTTCTGGGCAAGGGAAACCTTTTCGCCTGGTCTCCAATGCATTTCCCCGAGATCCCACCCAGGGCT<br>CCTGGGGCCACCCCCACGTGCATCCCCCGGAACCCCCGAGATGCGGGAGGGAGCACGAGGGTGTGGCGGCTCCAAAAGTAGGCTTTTGA<br>CTCCAGGGGAAATAGCAGACTCGGGTGATTTGCCCCTCGGAAAGGTCCAGGGAGGCTCCTCTGGGTCTCGGGCCGCTTGCCTAAAACCCT<br>AAACCCCGCGACGGGGGCTGCGAGTCGGACTCGGGCTGCGGTCTCCCAGGAGGGAGTCAAGTTCCTTTATCGAGTAAGGAAAGTTGGTC<br>CCAGCCTTGCATGCACCGAGTTTAGCCGTCAGAGGCAGCGTCGTGGGAGCTGCTCAGCTAGGAGTTTCAACCGATAAACCCCGAGTTTGA<br>AGCCCGACAAAAAGCTGATAGCAATCACAGCTTTTGCTCCTTGACTCGATGGGATCGCGGGACATTTGGGTTTCCCCGGAGCGGCGCAGG<br>CTGTTAACTGCGCAGCGCGGTGCCCTCTTGAAAAGAAGAAACAGACCAACCTCTGCCCTTCCTTACTGAGGATCTAAAATGAATGGAAAGA<br>GGCAGGGGCTCCGGGGAAAGGGAACCCCTTAGTCGGCCGGGCATTTTACGGAGCCTGCACTTTCAAGGACAGCCACAGCGTGTACGAAG<br>TGAGGAATTCCTTTCCACCAAGAGCGCTCATTTTAGCGACAATACAGAATTCCCCTTCCTTTGCCTAAGGGAGAAAGGAAAGGAAACATTAC<br>CAGGTTCATTCCCAGTGTTTCCCTGGAGTAATGCTAGAATTTACTTTTGTCATAATGCAAAATTAAAAAAAAAAAAAAATACAACGAAGCGATAC<br>GTTGGGCGGATGCTACGTGACAGATTTTTCCAAATTTTGTTGCGGGGAGAGGGAGGGAGGAGAATTGAAAACGGCTCACAACAGGAATGAAATGTA |
| 198 | RUNX1 | TTTTTAATGCTCAGAGAAGTTCGTATTACTGATTCGGGAACACTGAGTTTTTCAGCTCCTGTAAAACTATTTTCAGGTTTATTTTCAAGTACATTCTTTA |
| 199 | RUNX1 | CACCCTAGAGGCAAGGACGGGGTCTGTGTCAAGAGGCTTCCCAGAGAAGTGAAAACTCTGCAGGTGCAGCCGCTGGGAGAGCATCAAGA<br>AGGGCAGGGTGGAGGGGCAGGGGGCGAAGGGAGGGGGTGAAGCCCGCACCCTACCCCCACATGAAACTGATTCCACTACCCCATCTCTG<br>CAAGCGTCCAGAGGCAGAGAGGCCAACATTTCGGGGACAGCTTGGAGGCGGGAGATTTAGGCAGGGCTCCTTAAACTTTTATGTGCATGA<br>AAATCAGGCCAATCACGGGGCTCTTGAGCAAATGGGGACGATGATTCAGCAGGTCTGGGCTGAGGCCTCAGATTCTGCACTTCTAACAAGT<br>TCCCAGGTGGTAGTGATGCTGCCAGTCCAAAGACCACACTG |
| 200 | RUNX1 | TGCTTCAGTGGGGTAAACTTGAACCGCTGAGAAGACAAGCAGGGAGTCGGTCTCGCTGAGATTTTTACCTGTGGTTCTAGGAACGCAGAGG<br>CATGTGAGTGTTCAGGCTTTGCATAGACCACTAAGCCACTTCTAAGAACAAGGCTACCTGAGCCATTTTGCAAAAATATGTACGTGCCGAGG<br>CTTTTCCTCCCCACACCTACCTCAACTCTTTCTGCCGACACACTGCACTTTTCAAGGGAACCCAAGTTTGGGTTCGGCAAGAATTGTACGTT<br>GCACACCGTGTGTGATAATTCCAGGGAATTTCAATCGCATCTTGTCTTCCTTCCTAAGCAAATTCGGTGGGAACCTGGTGTGGTGTGATAGA |

TABLE 6C-continued

| SEQ ID NO | GENE NAME | SEQUENCE |
|---|---|---|
| | | AAAAGCCCCGAGTTCTCTGTGGTAGACCACATCAATTTCATGTGCCAGTCTCTCAGACTCCGGCTTGCCTCTCTCAAGGAAGGGAACAATG |
| | | GTTTGCTTGGCTTCACTCCTCTCTTTCCCCCCAATTTCCACATGGGTATCTGGCTAAAAATGAGTTACAGGTTTCCTTCTGTGAGAATTGCAT |
| | | GGACTGATAAAGTACCATCCCAGGAAGAAAACAAAGATGCTGTCTTCCCTTTCGGCTCACAGTTGCCGTTGGGGAGGGAACACACGCTGTA |
| | | AATTATAGGCAGCCAGAAGTGACCGCATTGACCACTGCGAGTGGCCCAGCTATGGCAACAGGCTGAGAACTCTGGGGGAGAGCCATTTGT |
| | | TGGCAGGGATGGTGATTCTTCTAGCATCAAGCTCTAAGATGATGACCAAACGGTATCAAAAGAAATGATATTTTGCTACCTCTCCGGCTTGG |
| | | GTGAATGATGTGGACAGTTAACCTGGACAATTTAAACCTTTATGTTGATGGATCACTTGGATGAAATTAACCAGGAAATTGCCAAGATTTCAC |
| | | TTGGCCCTCTGACATCAAATCTCAATATTATATATTACCAAATTAGAGATTCTAAAGAACCCTGAGTTCCTTTCACTGAAAGGAAGGAGTGGAAA |
| | | AACCTTTCCAGATGATCCCTTTTGAGTCTTGGTGCGAGCTCAGGCCCTCCCTACACTGCCTCCGTGAAAGCTAACCGACCCTTGTTCCTAAC |
| | | CTAGCGCAGGTCAGCTGAGTGTCCATCGGGCACAGGAGCCCTGGGCTTGTCCGGGAGATAGCCAGACTCCTGCTATTTCCTGATGTCTGC |
| | | ATAGCTCAGCGTGTCCCTCACCATCTTTGCCGTTGGCCAGTAAGGAGAGCCCCAGGGGCCAGCACTGCACACTGAAACCCAACCTATTGCT |
| | | CAATGGAATGCTTAAAAATTTCCTGAATCTGCCTTCCTGAGTTGATAAAATAGGAAACAATACACGTTCTGAGGGGGTACTGAAAGCAGAGT |
| | | AAAGCCAGGAAGATCTTTTTTTTCTGTTATTCTATACAAATATTGCTTCCTCTGCTTGTTAGCAGCCCAGAGGAAATGCAGCCAGGGAGCCGT |
| | | TTGCAGCTTTTCACCAGTGGCCGGTGTCTCTGTGTTACCAACCAAACGACGCTGCAAGACTAGTGACTAACGCACGTCTGCATGATTCAACT |
| | | TCACTAAAATTCCCTCTGCTGCCAGTAAAGAAGCACTTGAAAACTCTTTAATTTGAAACTTGAGCTTGGTTAATGACTTGTTTTCTTCTCTTTC |
| | | TCTTTAACTTCTCTCTTGCCATCTCCAACACACACACACACACACACACACACACACACACACACACACACACACACTCTCTCTCTCTCTCTC |
| | | TCTCTCTCTCTCTCTCTCATCAAGTTTTTTAATTTCAGGGACCCGGAAACATACAGCCCCGTGCATTCACAATAGCATTTGCTGTGATAAAGT |
| | | GGCCGGCAAGCCCTCTGCATTCCCCTGCTCACTTAGCTGTATGAATAAATAATGAGTCACAGATACAATTTGGGTGCTCAAGAGAGTTTGTA |
| | | GCCAGAAAATTAATTATTCTCCCATCCCAGCCCACTCCATCTCAGCTTTGCCAAACCATCAAGATACACTTTGCAGGCACTGGTCAGAGTGC |
| | | GTGCCCCGACGCACACGGCAATGCCTTTGAGACATTTTATGTTATTATTTTTGTTTGTTTAAGCACAGCCCTCTTTTACCACGAAAGATACAC |
| | | AAGACGCACATGCACACACATACTCACACACTCACAGCTCAACCACAGCTTTGTCCATTTCAAGAGGCTGGTTTCAAAAATGGAGACAGGTT |
| | | TTCCACCCTGGCTGTTCCTATTCATAAGCCTGTAATCTAACGACTTAAGCTGCGAGAATGCTTAACTCGGGAAACTTCTCTATTGCCCTTTTC |
| | | CAGAGAGACCTCGGTATGCCACAATTTGCTTCCTTTCTCTCTTGAAAGATGCTGGTTGTCTCTTTGCATTGAGGCTACAAGGAAAAACACAG |
| | | CACAGCCCCATGCTGATGATTTTAACCTAACCAAGTCTGTCAGTCTCCTGTACTCTCTGCCTTATAGAGACAGCTGCCTTGCCACTTTGGCC |
| | | CTGAAGTCCCCAGGCTGGTGCAAGGCTATCTGAGAGCCTCCGCCTCCTGCCCCACACTGGCACCAGCCCTCCTGGCTGGCTCTGTGCATG |
| | | TGCCTGCTAAGCCCCAGGGCAGGCTGCATTCTGGGCCACACAGCATGCCGAGTTAAGGATAACTCAGACACAGGCATTCCGGGCAAGGGA |
| | | CAGCAAAATAAAACCCAGGGAGCTTCGTGCAAGCTTCATAATCTCTAAGCCTTTAAACAAGACCAGCACAACTTACTCGCACTTGACAAAGT |
| | | TCTCACGCACCGACTGAACACTCCAACAGCATAACTAAGTATTTATTAAAACATTTCTGAAGAGCTTCCATCTGATTAGTAAGTAATCCAATA |
| | | GACTTGTAATCATATGCCTCAGTTTGAATTCCTCTCACAAACAAGACAGGGAACTGGCAGGCACCGAGGCATCTCTGCACCGAGGTGAAAC |
| | | AAGCTGCCATTTCATTACAGGCAAAGCTGAGCAAAAGTAGATATTACAAGACCAGCATGTACTCACCTCTCATGAAGCACTGTGGGTACGAA |
| | | GGAAATGACTCAAATATGCTGTCTGAAGCCATCGCTTCCTCCTGAAAATGCACCCTCTTCTGAAGGCGGGGGACTCAATGATTTCTTTTACC |
| | | TTCGGAGCGAAAACCAAGACAGGTCACTGTTTCAGCCTCACCCCTCTAGCCCTACATCTCTCTTTCTTCTCCCCTCTGCTGGATACCTCTGG |
| | | GACTCCCCAAGCCCTATTAAAAAATGCACCTTTGTAAAAACAAATATTCAAATTGTTAAAGATTAAAAAAAAAAAAAAAGCCAGCGCCGCCTT |
| | | GGCTGTGGGTTGGTGATGCTCACCACGCTGCGAAACCCTGTGGTTTGCATTCAGTGTGATTCGTCCTGCCTGCTGACCACTATGCTGGGTT |
| | | CAGACTTCTGACACTGCCAGGCTACCCAACTTGTGGTTCTGTGGTTGTTTATGAGGCCCAAAGAAGTTTTCACACAACCCAAATTACAAATTT |
| | | AACTGTTCCCCTTTCCACAGCCCATCTCAATTGGTTCTTGCCAATCATGTGACTTAAGTGATGTCAATTTTTTTTTTCTTTTCTGAGCAATGC |
| | | CCTTCCTTCCCTCCACCTGCCCTCCCCCAGGCTGTGCAAGAAAATAGCCGAGTAGACTTTGCAAGAGGGGGGGATGTAGAAAAAAGTGACT |
| | | CAGTCACTTATTATATCTCAATGGTCTTTGCTGATTTAGTACAACTCGGCTCCTGTTGTTATTTGTGGTTTTTGGAACTACTGATTATTTTGATA |
| | | AAGATTTCATTGCTGCTTATTCAATAGTAATTCAACGCTGGCATCAAGCCGCTGCTCCGACAGGATGTGGATCCCATCATTTAAAATGCTAG |
| | | GCATCAGCTCCGGGAGAGTTAAGTCCTTGGTAACGTCTATCATGGCATAAGTGAAACTATAAAAGGGAAAAATAAATAAAAAGAAATGTTTTG |
| | | GTGAGAGTCTGACCCCTACAACGGGCTGGCAACTCACAGGTATTTTAAAGCCTGGGAAAGGGAAAGAATTTTACTTTTGAAATAAAAGGACT |
| | | GTTTTAATGAAACCAAAATTATGTGGTTTTATTCCCCCTAAATGGACAACTTTAGTATGTATCTCTTTCAGTAAAGAGATAAAATCATAGTACA |
| | | GTCTTAACACACACACACACACACACACACACACACACACACACACACAAATTAGGAAGCTAAAGGAAAACAAAGCAGAGAGAATTTCTGTATT |
| | | TGGGACAAAGCAGTGGTTACTCTGCAGATGTTTATTTGTATTGTCACTTGGGAAAGCTCCCTGTATTGCCTTTCTCTAGTTCAATTCAAATCA |
| | | ATAGGCTAATTTACACCTGTAGGTAAAACTACACTTTGAGCACATGAGGATGCCACAATAGAAGGGGAACCAGGAGGAGACACTTCTCCTG |
| | | GGGCTGACTAATGAATATTATATAGCGCGTCCTCTACCTTAGAAAGACATGCCTGTTTGAAGATGCTAAAAACAGGATAATTTTGTAAGTGGG |
| | | CAAACCACTGTGGTCACACGTATTTCATTTTCCGGCCCCACTGGCTTTACCTGCTGACAACTAAAACGTCATTTTGTTTTGTAGTTCCAAGAT |
| | | GAAGAAAGGCTTATTTTCCTGATTTACTACCTTATTCATTTGGCTCTGCTCTGCCTACATCCGCCATAGCACTCTGCGCACGTGAAATTTCGA |
| | | CACATAGGGTCAAGAGAACCTGTGTGATGATGGGTTGTAAATGCCAGTCCTGGATTCTAAGCTGCAGTAGCCAGCACAGGCACTTCAGAAA |
| | | GGCTGAACTCCCACAACACTCCCTCGGTTTTCCCTCATCCACTTAATTTCACACACACAAAGACCCACAACGATAGTAGCTTCCATGGCACA |

TABLE 6C-continued

| SEQ ID NO | GENE NAME | SEQUENCE |
|---|---|---|
| | | AGTCTTTCAAAAGGAACAGACACAATTTTTACTTACTCCTGTTTTGACTAAAGCAGGAATTGAAACTCAACAGACCGCTTTCTCTTACACTTGT<br>GAGAAGTTAGCTGGCCACATGT |
| 201 | chr21: 35499200-35499700 | AGGGAAAAGAGATAACGAAAGAAAGAAAGAAAAAAAAAAGGGCCGGCAATTTCATGTACATTTGTTTTGGCATTCGCTGAATTCTAGAGATG<br>AAAACAATCTCCTGCTTTTAATTCAGTCCACGTGCAACAAAGTTGTACGTTGGGAGATCTGGCTTTTAATAAGAACGATTAACAAGCGTTTTT<br>GATCACAGGAAGTTGAGAAGAGTCGCTGCTTCTAAGAATACAATAAACATTGACTAGCAGTTAGACGGTCCATCTTTCTCTATCAGCCGTTTA<br>GCAGCCTCTACTTTGATTTGGGGCAAATGCGAGATGGGACCAGGAGAGAGCTCCCCACACCCCCACCACCACGTGGGCAGTGGTTCTGTT<br>CCAGAGCGCCTTCCTTCCTGTCCAGGGAGGCAGGCTGCTGAGGCCGTTTCTGGGCAAGAGGCCATTGTCGGGATATTTGCTTTAGATAGC<br>TTGCAGCTGGGCTGAGTGGGTGTTTCATTCAGACTCAACACA |
| 202 | chr21: 35822800-35823500 | AGCCTGGCGCACCCGCCCTAATTTGAGTCAGGGACCCTAGGCGCCTGCAGCTCCGGTTCGGGTTGAGTGCCTCCTGTCAGGATGTGAAGC<br>TGCTGTCCCCCCGGGGGCCTCCAGCACTGCTGAGGACTCAGCAGTCAGCCTCTCCTCCCACTTGGGCTCATTTACAGAGAGCATCTCCA<br>GGAATCAGTCATGGGGAAAGGGGAAACGCGGAGTGACAACACAACACGTAGAAAGTTCTCTGCCGCCTTGGTCAGGCTTGTCAGCCTCAC<br>AGCCCATCCTGCTCCTGCGGGAGGAAAAGTGAGCAGAACTCAGCCCGGAGATGAGCCGCAGGCCGGCAGCCCCTGCCTCTGCCCTGCTT<br>GTTGTGACTGCAATGCAAGGCTCTCTGTAGGTGCGGGGGATTCGGGTTAAATGGGTCTCCAGTGGTCCAGCGCTCCCAGCAAAGGCCGAC<br>CACAAGAATTAGCGGGCTAGTTATTTACCATAACCATATACAAAACCACAAGCATCAGCGTTCCCTCAAATACATCCGAGACGCTGTATATCT<br>CTTTATTAAAGCCTGTCAGGGTTTGTTATTGCACAGCTTGGCCTTGAACCCCAACTAAACCAGGCTGCTTGAGCAAAGAACCAAGCAATGCA<br>AGCATTCAGGCAGGACCATTATAACCCTGAGGCCAAAGGCAGAAGCAGGGAGAGGAGACGTCTTCC |
| 203 | CBR1 | AGACCAGCCTCGGTCTTCGGCCTGCGGGTTCTGCAAAGTCAGGCTAGCTGGCTCTCCGCCTGCTCCGCACCCCGGCGAGGTTCCGGTGG<br>GGAGGGGTAGGGATGGTTCAGCCCCGCCCCGCTAGGGCGGGGCCTGCGCCTGCGCGCTCAGCGGCCGGGCGTGTAACCCACGGGTGC<br>GCGCCCACGACCGCCAGACTCGAGCAGTCTCTGGAACACGCTGCGGGGCTCCCGGGCCTGAGCCAGGTCTGTTCTCCACGCAGGTGTTC<br>CGCGCGCCCCGTTCAGCCATGTCGTCCGGCATCCATGTAGCGCTGGTGACTGGAGGCAACAAGGGCATCGGCTTGGCCATCGTGCGCGA<br>CCTGTGCCGGCTGTTCTCGGGGGACGTGGTGCTCACGGCGCGGGACGTGACGCGGGGCCAGGCGGCCGTACAGCAGCTGCAGGCGGA<br>GGGCCTGAGCCCGCGCTTCCACCAGCTGGACATCGACGATCTGCAGAGCATCCGCGCCC |
| 204 | DOPEY2 | AAACGTTTAAAATATATTTCTAAACAGAATGGGCCAATTCAGTCACAGTAACTGTTGATCTCCATAGCAGAGCAACCCACAAAGACAGAACTG<br>ATTTTTTTCCCATAATCAGGGGTGAAAAATATACAACTTGTTTCTGAACCAAAACCACAATTTCTGCAGTTTAAAATGTTTCACTGCTAATATG<br>GCCCTGGTAGAAATTATGTAGTTTCTTTTCTTCTTTAAAAAAAAAAAAAATTAAAAAAATTTCCTAAGACACTAAATGCTCCATCTGGAATGTAG<br>ATTCTGATCACAAAGCAGCTCAGTTAACCTAAAAAATAAAAAATTCCCATCACCTGTCTCAGTAGGGCCTGAGAGTAGTGTGGGGAACCCCA<br>GCTTTGGTATGGAGAGTCATGGCCCCTTGAACCAGATAGAGACCTTGAATAGCCATAGCTGGTGCTTCTCTCAGGATAAACTCTGATGTAG<br>GAAGTATCACCCTCATGAGAGTGGAATTTGGTCATCCAGTTGACGCAGGGCATATTCCATGTCTTCTTTTCTGAGACACCCAACCATCCCCA<br>CTCCATCCTTCTGCACATCCGTGTAACAGGCATCCCCAGCTTCTCGCGTGTGATCCTTCAGGTCCTGCCAGCTGCCTGATGGAAGAAGTCC<br>ATTTCTTCCATAAATAGCATCCTCTGCATCTCGAGGGTCCTCGAAGCGCACGGAGGCGAAGGGCACAAGGCCGTACCGGCTCTTGAGCTC<br>GATCTCGCGGATGCGGCTGTACTTGTAGAACAGGTCCTGCGGCTCCTTCTCGCGCACGTGGGTCGGAAGGTTTCCCCACGTAGATGCACC<br>CGTCGCCCTCCCAGCCGCGCTCGTGTCCGCCCAGCCGGACAACCGCACCGCCCGACGCTGCTGGCCAGCCGCAGCCCGCATCCGCCCG<br>TATCGCCGCCGCTGCCGCCTCAGCACGGCTGCCCCCGCAGCGTCTGTTTTGTTTTATTCTAACAGGGTCTCTCTCTGTCGCCCAGGCTGGA<br>GTGCAGTGGCGTGATCTTGGCTCCCTGCAACCTCTGCCTCCCGGGTTCAAGCGATTCACCTGCCTCAGCCTCCCAAGTAGTGGGCATTATA<br>GGTGCCAGCTAACCATGGCCGGCTAATTTTTTTTTTTTTTTTTTTTTTTTTTTTGAGACAGAGTCTTGCTCTGTCACCCAGGCTGGAGTGCAGT<br>GGCGCGATCTCGGCTCCCTGCAACCTCCGCCTCCTGGGTTCAAGCGATTCTCCTGCCTCAGCCTCCTGAGTAGCTGGGATTACAGCTATGT<br>ACAGCGATGTCTGCAAAGATAGGGATTTAACAGCACTCATATCTTCATGTTCATAAAAAAGTCCTACACGCGTGATGTACGTCTAGATCTTTC<br>CTTTTGTCACAGGATATAGCACGGTAGTTACGGATATAGTCTCCGCAGTGCCTGGGTTTGACTCAGCTTCCCCACGTACTGTCCTGCGCATA<br>TTTTGTGTCTCAGTTTCCTCATCTTTAAGGTAG |
| 205 | SIM2 | CACGCGCCCCGGCCTGGCTGGAGGGGCCAACCCAGCGGGGCCCGCCTGCCCGCCGGCCTTTCTGTAACTTTCTCTCTTTAAACTTCCAAT<br>GAATGAACGTGCCTCTTCTTACGGATTTGTTTAGATTAGGGAATAGATTCCTCGCTGATAGCGTTGCTTTGCAAATAAGACCTCCTATATTAT<br>TCAAACCAAACGAGTTTGTGTCTTTAAAGGACTATAGCAGCCCCATTCTATGTTAAGGGTTGGCTATTACAATTATTATATGCTTAGGGAAAA<br>AATGTAAGCCCCGTAGTTTGTGCTTTTCTTGATGTACAGAAAGGTTTATCTTAGGTGGATAGGTTTTGTTTTGTTTCTTAAATGGGATTTTTTT<br>GGTTCGTGTCTTTGAAGGGCTGTTTCGCGACGTCATTAATGAACTAATCGGTTTTCAGATTTCAAGACGGTGTGTAATTGATGTAACCACTGA |

TABLE 6C-continued

| SEQ ID NO | GENE NAME | SEQUENCE |
|---|---|---|
| | | GGAATTTCAGTGCACACCAGACTAAGACTCTTCCAGCGCAGGGGATTCCAGATGCTTCTTGGGCCCTCTGGAAGCCATGGGGATGTTTCCA<br>GACCGAAAGGAGGGCTTTGCTGGGGAGCAGATGTGCTGCCTCTCCCCGACCCAGGATTTTGAGGCCATGTTTCCGTTAATCTGGACCGAG<br>AGCCCTCTGGGAGAGGGAGGCAGGTCGTAGGGGGCGGGGGTGAGGGGGAGCGAGATGAGGTCGTCGCTGGACGCTGGGCTCCCTTGT<br>CGTTGTCCTTTTCCCCAGAATCCATGGTCAGGCCTAGGGAGCCACCCCTGGGTGCTCGAGATGAGTCCCCACCCTCACTGAAGGTCGGTC<br>ACTGGATGTTTGTGTGCATCGTAAGGGGCCCACCGAAGTCCCGAAGCCTTCTCAGGGACCAGCGAGAAAGAGGAGCAGGCTTGGGAGAC<br>AGGGAAGGAAAATGCAGGGGAAAGGGCTCACCCCTCGACCCCAGGTAAAATTAGAAGGAACGTGTGGCAACCCAGGTGCAGCTTTGGTCG<br>CTCGCTCAAGGACTTTGCTAGTCACTACCATTAATTAATTAATCACTATCATTAACTACCAAGGACACCGTTTTTATTCCCCTAAAAGCGTCAC<br>CTTGAGGGGAATGGAGAATTGGGCAGCAGCTATGCAAATCCTGGGACAGGAGACACTGCCTGAGGACCCTCTCTCACTCCCAATCCCAGA<br>ACCCGAAGTTATCCCCGACAACCAAGTCCAAGCACATGAACCAAGACGATCAGCTTCAGGCAGCTCCTTACCCCCACAAGCGGCCCAGGA<br>GGTGGGCATTATCCCCCACCCCTGGGATTTCTCCATCCCTCCCTCTTCTCTCCTGCGGGAGAGAGAGCTGTGGTCACCCAGTTGGGCGCG<br>ATGGCTCTGGACTAATGGGGTCTCTAGACCCAGGGCACAAAGGCCAATCTGCCAGGGGTTACTGCATGTAATGAGATAATCAGACATGTTG<br>ACCAACCTAAAAGAAAAGACTCTCCCAGGGAGTAACTCCCAGTGAAATAATTTATTAAAAAAAGCAAAAAAGAGACATAAATTTCTCTCTACT<br>ACTTGAGGAAACAGCAAACAGAACGAATTAGGGTCTTGGCCTCTGCAGGAATAAATTATTTCCGACTTGGTCTGGATACCTGTAATTATTTGT<br>AAGCTGTGGGTAGTAATACTGTAATTGTCCCCCGGTCCTTTCTGGAAGTAGCAATGACCCCAAGGACAATTGGTGACGTCTCCACAGGGTT<br>TACACATGGAAAGGAGTGAAAAATCGAGGAATTCTTTCAGATAGCCCAGACCAAAAATCCTCTCAGCCATGAAAAGGTCATATATGTGATGC<br>TGGGCCAAGCGGACTTTTCTGGAGTAACCATATCATAACTGATTGCGGATGTAGACAAGAGCGTATAAACCAAATAGGCTTGAATCAACGCA<br>GTCCTGGATTTTCTGTTGCCTCTGCTTGCTGGGGCAGTGGAAGTTCTTAAACTCCACTTCAGAGGTTGGAAATTCTTCCCCCTCCCCCACCT<br>CCTTAGTGACAAGGTCTCTGATCTCCTGCTGCCACTGCAATAGCCTCTCCCATCCCGCGGGGAACGGCCGGAGTTCTTCCCTTGATCTCTC<br>CCGAGTCGGCTTCCGCTGGGGATGGATCGCAGGTAGGCGCCGGCGCGGCCTGGGGAAGAACAGTTGCGGAGCATCTGAAGCGGAAAAT<br>CCAAGCAGATGTGAGGCGATCCGGGCCCGCCTCGTTCCTCTTGGGGCCTGAATTTCTTCCAGATAAGTTTCCTAATGGAACATTTCTAAGA<br>GGTGGGGTACGAGGCGGCTTGCTCGCACGCGCAGTGGGACAGACTGCGGGTGGGGACGTACTGAGAGGTCCGGACCTCAATGCGTCCG<br>ACCCGTCTCCACACCGCCCTTTTCCAGCCCCCAGTCTCCTTTCATTCCCTACTCTTCAGGCTCCTTTGGGGCCAGTGGGTGAACCGCCATT<br>TAGAACGGTGCCTCGGACTCGGGGGTCGTGCGCTCCATCTCTGCCTCCCCCCTGGGGCCCGCGAGGCTGGTCCGGGCTTTCTGAGCTGG<br>GCGTTCGGCTTTAGGCCCAATACCTGGACCAGGAATTTCTTCTCCCCGCGCCAGAAGGGAAAGACATAGGAGGTGTCCCAATCTGCGGTC<br>ACCGCCGATGCTCCTGACCACTCTAGTGAGCACCTGCCCGGTACTTTTCCATTCCAACAGAGCTTCCAGCTTCATACTAACTATCCCACATA<br>CGGCCTGTGGGTATTAGCTCTAAGTGTCCTTTTCCGAGGGCCCGAGGCTCCCCCTCCAGCAGGGAGAGCTCCGGGACGGCCCCCACCAA<br>GGGTTGGGTTTCTTCCTTCACAATTCCACAGAGGCATCCCTGTCCTTCCTACCTGGGAAACCTCGAGGTGCGGTGCCCGTGTACTTCTGGT<br>ACTTTGCGTGGTGCCATCAGGGACCCCAGAGCCACAGCTGCGTGTGTGTGTGGATGTGTGTGTGTGTGTGCGCGCGCGCGCGTGTACGG<br>CGAAAGGATGTGCTTGGGGGAGCCGAGTACACAACGTCTGCTTGGGCAGCTGCTGGGCAGGCGTTGGGCCTGGAGGTATCTCACACCCA<br>CGTATCTTCCAGTCTTCAAACACGGCATTGCTCTGCCTCCCGTAGCGCGCTTCGAACCTGCCTCGCGGACACGTGAACAGAGGCTGTCCCT<br>GGGAAGATAAGTGCGCTTTCCCGTAAAATCCGGGAAATTTGCCTTGAGGAAAGTTTCCGTTCTTGTTACTTGTCGGGTTTCTCCCACTTCCA<br>CTTAGCCATGTTTCTGCGATCTGGGTAATCCCTTTCAAGCCCAGGAGGAATTCTCCCGGGTCCATAATTGAGGGTCGGAAGCCGTGGGGGT<br>GAGAAACGCATTAAATCCTCCCGAAGCCCAGGAGGTGCCAGAGCGGGCTCAGGGGGCCGCCTGCGGAAGCTGCGGCAGGGGCTGGGTC<br>CGTAGCCTCTAACCCCTTGGAGCTCCTTCTCCCAGAGGCCCGGAGCCGGCAGCTGTCAGCGCAGCCAGGAGCGGGATCCTGGGCGCGGA<br>GGTGGGTCCGACTCGCCAGGCTTGGGCATTGGAGACCCGCGCCGCTAGCCCATGGCCCTCTGCTCAAGCCGCTGCAACAGGAAAGCGCT<br>CCTGGATCCGAAACCCCAAAGGAAAGCGCTGTTACTCTGTGCGTCCGGCTCGCGTGGCGTCGCGGTTTCGGAGCACCAAGCCTGCGAGC<br>CCTGGCCACGATGTGGACTCCGCAAGGGGCTAGGGACAGGCAGGGGGAGAGCCCGGGTTTGCGCACACCTTCCAGCCCCTGGAGGGAG<br>CCTGCTCGGCTTCGAACGCCTTCGAACTTTTGACCTTCAAAGGAGTCCCTGGAAAAGGTCAGGAGCGCCTGCTGCAGGCACGGTTGCCGA<br>AGGCCAGGCCTTCCTGGCGCAGGGGAGGGCCAGGGGAGGGAAGCGGATACTCAGTCGCTGTCCGACGGCGAGTTTTCGGAGCAGCAGG<br>CTCATGATCCCGGGCCAGTGGCGAGAGCAGTGACACCGAGAACCCAAATCTCCGCGCCCCCATCCGCGGCCCGGTGTCCTCCCGGCCCC<br>TGCTGACCTCCAGGTCACGCACCCCACTGCTCCACGGCTCTGCAGCCTGTGGCACACGGCCGAGAGTCCCCACATGATCTCGACGCCAAG<br>GTAAGGAATTGCCCTGCGTCCTCTGAGCCTGTCTCTGGCCTGGGGGGCCGGGAAAGCTGCACTCCTGGAAGAGGTGGGGTTATGTGACC<br>GCCGCTGCAGGGGTGCGCGGAGGACTCCTGGGCCGCACACCCATTTCCAGGCTGCGGGAGCCGGACAGGGGAGGGCAGAGGGGGGAC<br>AAAAGGACTCTTTAGGTCCAAAATGACCCTGAAGGAGAGTCCAGAATGCCCAGTGGCCGCGTCTGCAACGGAGTCTTCTTTCTCCAATTGC<br>CTTCTGCCCCATCACCATGGGCCCCACCTGCGCCACCTGCGCCCACCCTGTGACCCTGGCTCAGCGACCTTGGCCCTTAATCGCCCAACG<br>CCGATTCCTCAAAATTCCGGCTGCGCTGAATCGGGCTGCTTTTGCCGCCGCCCCGGCAGTTGGGCCCTGTTTCCGCCGGCGCCCTGGGA<br>GAGGCCTCACCACTCGGCTGGGCTCCCTGGCCCCTCCCTTCCCCTGGCCTGAGCGCCCCTGCGGCCTCCCGCTCCTCCTGAGAAGGCGA<br>CAATCTCTTTGCACCTTAGTGTTTCGAGGACAGAAAGGGCAGAAGGGTCACTTCGGAGCCACTCGCGCCGTTTTCACGTGTGTGTGTAATG<br>GGGGGAGGGGGGCTCCCGGCTTTCCCCTTTTCAGCTCTTGGACCTGCAACACCGGGAGGGCGAGGACGCGGGACCAGCGCACCCTCGG |

TABLE 6C-continued

| SEQ ID NO | GENE NAME | SEQUENCE |
|---|---|---|
| | | AAGGCTCGATCCTCCCCGGCAGGGCGCCTGGCCAACGAGTCGCGCCGCCTCCTCTCGGCCGCGCCTGCTGGTGACCTTCCCGAGAGCCA CAGGGGCGGCCTCGGCACCCCTCCTTCCCTCGCCCTCCCTGCCGCCCATCCTAGCTCCGGGGTCCGGCGACCGGCGCTCAGGAGCGGG TCCCCGCGGCGCGCCGTGTGCACTCACCGCGACTTCCCCGAACCCGGGAGCGCGCGGGTCTCTCCCGGGAGAGTCCCTGGAGGCAGCG ACGCGGAGGCGCGCCTGTGACTCCAGGGCCGCGGCGGGGTCGGAGGCAAGATTCGCCGCCCCCGCCCCCGCCGCGGTCCCTCCCCCC TCCCGCTCCCCCCTCCGGGACCCAGGCGGCCAGTGCTCCGCCCGAAGGCGGGTCTGCCATAAACAAACGCGGCTCGGCCGCACGTGGA CAGCGGAGGTGCTGCGCCTAGCCACACATCGCGGGCTCCGGCGCTGCGTCTCCAGGCACAGGGAGCCGCCAGGAAGGGCAGGAGAGCG CGCCCGGGCCAGGGCCCGGCCCCAGCCGCCTGCGACTCGCTCCCCTCCGCTGGGCTCCCGCTCCATGGCTCCGCGGCCACCGCCGCCC CTGTCGCCCTCCGGTCCGGAGGGGCCTTGCCGCAGCCGGTTCGAGCACTCGACGAAGGAGTAAGCAGCGCCTCCGCCTCCGCGCCGGC CGCCCCCACCCCCCAGGAAGGCCGAGGCAGGAGAGGCAGGAGGGAGGAAACAGGAGCGAGCAGGAACGGGGCTCCGGTTGCTGCAGG ACGGTCCAGCCCGGAGGAGGCTGCGCTCCGGGCAGCGGCGGGCGGCGCCGCCGGGTTGCTCGGAGCTCAGGCCCGGCGGCTGCGGG GAGGCGTCTCGGAACCCCGGGAGGCCCCCGCACCTGCCCGCGGCCCACTCCGCGGACTCACCTGGCTCCCGGCTCCCCCTTCCCCAT CCCCGCCGCCGCAGCCCGAGCGGGGCTCCGCGGGCCTGGAGCACGGCCGGGTCTAATATGCCCGGAGCCGAGGCGCGATGAAGGAGA AGTCCAAGAATGCGGCCAAGACCAGGAGGGAGAAGGAAAATGGCGAGTTTTACGAGCTTGCCAAGCTGCTCCCGCTGCCGTCGGCCATCA CTTCGCAGCTGGACAAAGCGTCCATCATCCGCCTCACCACGAGCTACCTGAAGATGCGCGCCGTCTTCCCCGAAGGTGAGGCCTCAGGTG GGCGGCCGGGGACGCTGGGGAGCCCGGCGGCCCCGGCCCAGGCGGGAAGCGCAAGCCAGCCCGCCCAGAGGGGTTGCCGCGGCCTG GCGTCCAGAGCTGGGGCGTCTGAGGGAGGTTGCGTGAGGGTCTTCGGCTTCGGCGCTGGCTTGGGGCGAGGGGCCAGGGCCTTGGCGG CCCAGGCGACCAAACCCTCTCCTGGTCCAGGGCTGGGTGAGGGCGAATTACGAATTGTTCCAGGGGCAGGCAGTCCCCCAGCCCGCACG GCCAGCGAGTTCTTTCTGGTTTTGTTCTTTCTCCCTTTCCTCCTTCCTTCCTTCGCCAGTGCATTCTGGTTTGGTTTGGATTTTTTTCTCTCTT TCTTTCCTTTCTTTCTTTCTTTCTCTTTCTTTTTCTTTCTTTCTTCCTCTTTCTTTCATTCTCCCCTTCCTTCCTTCCTTGGCCCCCTCTCTCCCT CCCTCCTTCCTTCCTTCCTTTGCCAATGCATTGGTTTGTTTTCTTTCCTTTTCTGCTTTCCTTCCTTTCTTTGGAAGTTCACTCTGGTTTTGCTT TCTTTCTTTCCCCATCCCTTCCTTTCTTTATCCCTCCTTCCCTTCCTCCTTTTCTTTCTACGATTCCCTTTATTTTTCCTTCATTCCTCCCTCTTT TTGTCTCTTCTGGAGGAGGTGAAGGAGGGTCAGCTTCAGGCGCTGCGAGTCAGCGGGGATCACGGTGAGGCCCAAGCACTGCAGGCTGA GGCCACAGAGCGAACACTTGTGCTGAGCCGGGCCCTCTCGTGAGGCTGGGGTGCGGGAAGTCCGGGCAGGAGAGACCCGCCCCCGCCG TTGCTGAGCTGAGACCCGGCTGAAAGAGAGGGGTCCGATTAATTCGAAAATGGCAGACAGAGCTGAGCGCTGCCGTTCTTTTCAGGATTGA AAATGTGCCAGTGGGCCAGGGGCGCTGGGACCCGCGGTGCGGAAGACTCGGAACAGGAAGAAATAGTGGCGCGCTGGGTGGGCTGCCC CGCCGCCCACGCCGGTTGCCGCTGGTGACAGTGGCTGCCCGGCCAGGCACCTCCGAGCAGCAGGTCTGAGCGTTTTTGGCGTCCCAAGC GTTCCGGGCCGCGTCTTCCAGAGCCTCTGCTCCCAGCGGGGTCGCTGCGGCCTGGCCCGAAGGATTTGACTCTTTGCTGGGAGGCGCGC TGCTCAGGGTTCTGGTGGGTCCTCTGGGCCCAGGAGCTGGGAGGGCTGCGCCGGCCTCTGGAGCCCCGGGAGCCAGTGCCGAGGTAGG GAGACAACTTCCGCCGCAGGGCGCCGGACGGTCGGGGCAGAGCAGGCGACAGGTGTCCCTAGGCCGCAGGGCGCTTCCATAGCGCCAT CCCCACCAGGCACTCTACTCGAAATCGGAAAGCTCGACCTTTTGCGTTCGCCTCTGCCAAGCCTGTTATTTGTGCTGGCCGCTGGGTCTGG AGCTGCGCTTCTCGGCCCCTCCCCGGTGGAGCGCAGAGGGCTGGTCTGCAAGCGCGGCCTCCAGCCCCGCGGCTCCCCGGCCCAGGAG CCAGGCGCGGGCTGACCCGGGAGCACCCGGCAGCGGAGGGGGCTGGAAGCGGACCCTAGGCCTCTCCTGTGCCACCCGGCCCTACCG CGCGGCCGCGGGGCGCTCTCCTCTCGGGCGCAGCGGTCCTTCAGCCCAGGGCAGGTTCCTCCCTTTCCTACTCGGAACGTGGCAAAGAT ACCCCAGTCCCAGCCCCTCCAGCTGAGAGCTGTTGCCCAAGGTCGTCGCTACTTGTCCGCTCAATGGTGACCCCTTGGCAGAGAACTAGG GATGATTCCACTCCGGTTGATGTTTTAGGGGAAATTAAAAGAACATTCGGTTTTCTGAGTCTCCTTCCGGGGAGGCGTGGTGGTAACTGGTT TGCTGGGAAGAGCCGTTCCTTAACCGCATGCAACAAAGCAGGTGTGGAATCCGGACGAGAGGGCACTCACTGCCTTCTGCCCCCTTTGGA AATAGAAAAAGCCTTCGAAGCAGCAATCCAAAGATCAAATGATTTGCGGTCAATGATTTCAATTAAACCAGAAATTAGTAAGGGAGGGCCGA GAAGACACGGCTGCTCAGAAGCTGTTCGCTGTTTGAGGGATTTCCCGGAGAGCCTGTTAAAAGATGCGAAGTGGTGGGTGTACCGCTCAG CCACCTTTAAACCGGCTCTGTGCGTTCTGGCTCTGGAAAGCAAGTCTCCAGGCATTTGGGCTCAGAATTGCTGGGCCCCGAGTTTGGGCG GGGGTGGTCCTTCTGGGGGTCAGGCCTTGAGCAGCTTGCACTGGTGGCAGGTTTGGGAGCAGTTGAGGGGCTTCCTGTGTGTCTTTTGGA GGGGGTGACCCTGGAAGTTGGCACTCTGGAAGGGAGCTGTTTGGCCCTAGAGTTTTGGAAAGGGCCCTGAACCTGTTCGGTCCCCCTCGG AAAGGGAAGGGAGCAGTGGCTTAGTCCCTCCCTCCTCCATTCGTGCAATGCCTGGGGTAGGGGTAGACCTGGAGCCGGTGGACTCATATC CTTGGAATTCGTCAGGACAGCTGCTCCGGGGCCTTGGCCCTCAGTCAGTCTGGGGCTGAGGAGTAGGGAAGCTGGGAACTTGGGGCAGA GGAAGAAGATGCGTTTAGAAAGACCTCCATTATGCAAACTGGAGTCCATTTATGCAAACTGGTCACCCTTCCAGTAGCTCCAAAGAGTGGCA GTGGAGTGGCATCTTGATTGATTTAACCTCTTCTCAGGGGACCTGGGTCTGCGAGGGAGGATATGGCTGCGGGGTTGGAATAGGATCTGT CTGAGCTGCCAGGGTCAGGGTGGTGGCCCTAGGGAGGTTTTAGGGCCAGGGTGGTCCCGGGCTGTGGCAGGGGCTCTCAGATCGCCTC GGGCTCTCAGCTGCAAGGTGAAAAATACCATGAGGAATTGATCTGCCAAGGGCGGTCTTGTCTCAAAGCAAGTGGATTGCTGGGTAAAGA ATCTAGAGACCAGCTTAGGACTCTGGGAGGAAGAAAAAAAAAAAAAGAATAGCATAGTCCTAAGGAACTGCAAGGATCACCAGATTAACCCT TCATACCTGGGGAAATTAAGGCCAGACATGACACAGGCCTTTCCCAAGGCTCTGTAGCAAGGGCAATAGCAGGCCAGTTGCTGCCACTGC |

TABLE 6C-continued

| SEQ ID NO | GENE NAME | SEQUENCE |
|---|---|---|
| | | GGTCCTGTGGGGCATGTTCTCACTCCACTGCACCCAGGAGGCTGCCAGCCTCTGTTCCTTTTAACATAGATCTCCTCAGTTGTTAAGACAGA<br>AAGAGGAACTCAGAGGGGTCCCTGTGTGCAAGGCAGAGGGAGACCACCAGAACCAGGGTAAGCACCCCACTTGGTAGCCAGTTCAAGGA<br>CTTGGGGATGTTTTCAACATTTACAGCGAGGTTTGAGGCCCCATTGTCATGCAGCGCTACTCGGCCTTGGTCTCCTTATCTGTAAAATGGGC<br>CCATTAGCAATGCACAGGGTTGCTGTGATGAAGGGTGAGGTCCCACAAGCAAAAGCTGTGCAGTGAGGGGGGAATCCTAAGCATTGTTCC<br>TATGCCATTCACCCCTTCCTGTGAGCTCCCCATATTCCCTGGCTCAAAGGAGTCTTGAATGGCAGGGATGGAGGACTCACTGCCTGGACTT<br>TGAAGACCCCTGCTTTCTGGGTGACCACCTTTTCTTCCCTTTGACAGTGAACTAATACATTGGAGGTAGATAGTGCTGGGAAGAGGACAGG<br>AGACCACGGCTGACTTTGGACATGGGCTCGAAATTGATAACTTGATGAGTCTTGGAGGGTGGTTAAGATAAGCTCGGGGCTGGGGCAGCG<br>CTGAGGTCTGATGGTCAGCCAGCCCTCCCCAAAGTGTGGCCCTCCGTTCTGGAGATAGGGGCTTTGGAAACTGCAAAAGCGTCCTGGCAG<br>GCCAGCTCTGGTTGCTCCCTGGCCATAGCTGCTCTGACTACAGGCAGCAGGACGCAGGTCGGCCTCTGCCCATCGGAGGTCAGAGGCAG<br>GGCCTCCAGCACCAGACTCAGCAGTGCCACTGCAAACCTGGCACAACAGGCTGGTCCCAGGACTCAGCTCAGCAGTGAAGTTGGAAACCA<br>AGGTTGAGTCTCCCCATCTCCCTTTCCCCAACCCGAAAGACCCAAGATGGGTGTGGGTGAAAGAGGGAGAAAGAATTGCTACTCCAGAAAC<br>TGTCATTTGCCCACACGAAACGAGGTGGGGTTCAAGGTCTGAACTCTTCCAGTGCCTGGGTGCCTTTGGGTTTAAATTCAGCTGCAGGTGC<br>CCCCATCACCACTTCCACCTGAGCACACCACGAGAAGCCAGGTTATCTTAGAAACTGTTTCCCGGAATCAAAGCGACTTGATTTGGAGAGTT<br>GGGTGAGGAGAAACTCACCCCTATACCCCTCAGGGCGTCAGAGATGTGAGGCAATTCTCTACCTCCGCTGGAAAAAATGCAGATTTATTAA<br>AGGTCGACTGTTTAGCAGAACAACGTAGATTTTTTACAACGCTTTCCCCGTCTCTGCTTTGAAGCCTGCCAGGCTGCAGCTGGGGATCCAG<br>GAGGGAAAGCCCGCAGGCGCAGAGGGGACAATCCGGGAAGTGGTAAAGGGGACACCCGGGCACAGGGCCTGTGCTTTCGTTGCAGGCG<br>AGGAAGTGGAGCGCGCGCTGCAGATTCAGCGCGGGGCTAGAGGAGGGGACCTGGATCCCTGAACCCCGGGGCGGAAAGGGAGCCTCCG<br>GGCGGCTGTGGGTGCCGCGCTCCTCGGAGCCAGCAGCTGCTGGGGCGGCGTCCGAACTCCCCAGGTCTGCGCACGGCAATGGGGGCAC<br>CGGGCCTTCTGTCTGTCCTCAGAATACGTAGGATACCCGCGGGCGACAAGCCGGGCCAGGCTAGGAGCCTCCTTCCCTGCCCCTCCCCAT<br>CGGCCGCGGGAGGCTTTCTTGGGGCGTCCCCACGACCACCCCCTTCTCACCCGGTCCCCAGTTTGGAAAAAGGCGCAAGAAGCGGGCTT<br>TTCAGGGACCCCGGGGAGAACACGAGGGCTCCGACGCGGGAGAAGGATTGAAGCGTGCAGAGGCGCCCCAAATTGCGACAATTTACTGG<br>GATCCTTTTGTGGGGAAAGGAGGCTTAGAGGCTCAAGCTATAGGCTGTCCTAGAGCAACTAGGCGAGAACCTGGCCCCAAACTCCCTCCTT<br>ACGCCCTGGCACAGGTTCCCGGCGACTGGTGTTCCCAAGGGAGCCCCCTGAGCCTACCGCCCTTGCAGGGGGTCGTGCTGCGGCTTCTG<br>GGTCATAAACGCCGAGGTCGGGGGTGGCGGAGCTGTAGAGGCTGCCCGCGCAGAAAGCTCCAGGATCCCAATATGTGCTTGCGTGGAGC<br>AGGGAGCGGAAGAGGCAGCCGGTCCTCACCCTCCTCTCCCGCCACGCACATATCCTTCTTGACTTCGAAGTGGTTTGCAATCCGAAAGTG<br>AGACCTTGAGTCCTCAGATGGCCGGCAACGCGCCGAGGTCACGCTCCCCAGAAACACCCCTCTCCCCTCCCCTACCCCAGCTCCCCCTGG<br>GGCGGGTGGTAATTGGGGGAGGAGAGGCCGCAGGCAGGGAAGGGGTGGGAAAGCCAGAGAGGGAGGCACAAAGTGATGGCAGCCCGG<br>CAAACACTGGGGCTTCGGGCTGGGCCGCGCTCGTTTAATCCCACAAAAATCCCATTTTGGAGGTGAGAAATAGAGGTTAGAGGTCGGGCC<br>CTTCTGGAGATCAGACCGAGGAGACGGGCCCAGCTGGCGTCTTAAAGCAAGGAGGGGGAGTCGGGAGGAGGTGAGACCCCTGCACCCA<br>GGTGGGGCTCCCAAACCGTTCTGGATTTACCACACTCCCAGGTCCGATTTTCCATGGAGGGCTGGGGTTAGGGACTGGCACCTTCTTGTTG<br>TTAACCGCATTTGATATTCACAAGAACCCTGTGAGGAGACTTTGTCACCGTTTTTAGATGCCTGAGGTTGCCGGAGGGGCAGTGAGAGAAT<br>CGTCTAACCTGGTGTTCCTACCACAGTCCAGGCCCTGTGTCCTGGGCTGGACCCACAGCCCCTGCCACCACCCAGAGGAAGGCGCGAAG<br>CTGGCTGCCTCCTTTACGGGTCTCCCTTAGGTGCCCTCATGAAGGGGGACGGCCACCTCACAGTGCAGGAACTATCTCCCCGTTTGCTCC<br>CAAATAGTCTTCTTGGTGTGGTGCTGTCTATGGTCTGTGACCTGCATCTGGAGTTACCCCCAGGACCAGCTTCGGAAGAGGAGGGATCGCT<br>TGGAGGCCGTGCAGTGTGAGGAACGGCAGGCAGGGTGTGGGACCAACATGCACACACTCGCAGGTGCTGGGGCCAGGGAGGAATGAGG<br>CGCTGGCTCCCTTTCCCTCCATTTCTCCCTGGGGGTCCCAGCAACCTGGCCATCCCTGACTTCCAACAGCACAGCGTCCCCACAGGTCCT<br>GCAGTGCTCTGCAGGGGTGCAGGGAGCTCCCCTCCCCCCAGCCGCAACCTCACCTTCCTCACCCCCACCCCTCCGGCAGGAAACCACAG<br>GCTGGGTTGGGGACCCCTGGTGCTCCAAGAGAGCAGTGAGTGCTGGGAGCCGCTAACCCCGAGGCGCCTAGCACAGACTCTTCTCACCC<br>CTTATTTCTGAAATAAAGCCCTTCCTTAGGTCCAGATGAGGACCACGTGCTCAGTGCCTCACTTTCGTGGGAGTGTATATCACTTTACAGTAT<br>CAAGACAATTTTCTTTCGTTACAAATCTTTATTTAGTCTCTGCGTTTAGACCAAAGTAGATTTTTATGGGCTGAGTGAAAAAACCTCGCCCGCA<br>TTGGTTTCTGATGGAACAGCTGGCAGCGCCACGGCCCCGGGTGGGGTGGCCTAGAGGCAGGGGTGCTTGGGAGGAACATCTAGCACCCG<br>ACCACCTCCACCAGGTGGGAAAGGGACGTTTGCACCAAATCTCCGCCGGCAAAGCAGAGGCTTTGGGGAATTACAGAAAAACTATAATGAT<br>CTAAAAGAGAACAAGTTATCTTGAACTGTGCGGGTATTTGAATCATACAGAAAATTGTCCTGTGTGCCCAATGCACTTTTGCATGTAGAGCCA<br>GGGCCTTCGAGGAAGCTTTCAGGAGATCCCGGGCAGCGGAGTCTGGTCTGGAGTTTCATTTCCGTAGGTGCAGATTTCTCCCCAAGTCTTC<br>CCGCCATGGGCTTTGCAAGAAGCCAGGGCCCAGAGGCCACGCTCACCGTTAACACTGCACAGGGCAAAGGTGGCTCCAGGACAACTGCC<br>CAACCCCAGGAACGACCCAGCAGCAGAGAAAAGGACAGCTGCCAGGGTGCCTTTGTCGCTTTTTGGAAATCAGAATTCCTGGGTCCTTAGT<br>TAAGTCTTACTTCACCAAATCCCAGGACCTTCACATTTTGGTTCTTGCCATTGCTAACAGTTGTAAATGCTGCCGCCACGAGGCCTGGGAGG<br>AAGGACCCGCTGGTGAGAGCACAGGGAGTGCTGCTGTGATCACGGTGGTGATGCGGGGTGAGCGCGATTTCCCGGGATTAAAAAGCCAC<br>CGCTGCCCCCGTGGTGGAGGCTGGGGGCCCCCGAATAATGAGCTGTGATTGTATTCCCGGGATCGTGTATGTGGAAATTAGCCACCTCCT |

TABLE 6C-continued

| SEQ ID NO | GENE NAME | SEQUENCE |
|---|---|---|
| | | CAGCCAGGATAAGCCCCTAATTCCTTGAGCCCAGGAGGAGAAATTAAAGGTCATCCCTTTTTAAATTGAGGAATAGTGGTTTTTTTTAACTTT<br>TTTTTTTTTAGGTTTTAGTTGCCGAATAGGGAAGGGTTTGCGAAGCCGCTGCCCTGGGCCGAGGTGCATTTTACGCTTCCAGAGGTCGAG<br>GCCTCCAGAGACCGCGATGCCCAGGGCGTTCCCGGGGAGGCTGAGAGACCCAGGGTGCTCTGGGTGACTGCACGGCGACTCCTCGGGA<br>ACCCACTCGTGGCTGCCCGCTTGGAAGGGCTTTGCGGCCCCGGGAACGATCTCCAGGATCTCCACGGCTGGTCAGGTTCCCCGTCCCTC<br>GTATCCCGCGCTGCCCGGGGGCTCCTGCCTTTGGTTCAGTGCTCGCGGCACCACCGCACTCAGGACGGCAGTGGGGGGCTGGGGCTGG<br>GGCTGGGCCTGGCCCAGCGTGGGTTGGGGCGGGGGACGCGCCAGCAGCGCCCGCAGCTCGCTCCGCAGGGGTCGCAGCCAGGGGTCG<br>GGAGCTAGGCTCGTGGGCCGGGAGACGCCGGGCGCGTTGTCCTCCGGGGAGGTTGGGGTGCAGGCGGTGCACCGACCCTCGCCATCTG<br>GCGCTGCAGCCACCAGCCACGGCGCTTAGTGGAGGGTCTGCGGCCAGGCTCCCGGCGGAAAGATTCCGGGGAGGGCTCGGGGGTTGTC<br>CCAGCCCGCGCTAAGCGCCGCAGCCTCGCCCGGCTTTCCTGCTTCCTCGGACTGTGCAGGGGAAGCCTGGGGTCTCGCGGGGCGCAGC<br>AGTCAGGTCGAGGGTGCAGCAGGAGGGGAGTCCTGACGGGCAGGTCCCTCTTTCCCCTGGTGCGCAACACTGGTTGGTAGCTTTTGCGG<br>AGGTGGTGAAGAAGGGCAGGAGGCCTGTTGAGCGGAGGAGTCCGGGGATCCCTAATTATGTGACAGGAGACCCTTTCCAGTTCGGCCTGT<br>GGCCCATCCCTCTCTCACCGCCGGCAGATTGGAGTCTGCTCTCGGGGAGCCCCCAGGTAAACCCCTCACAGGGAGAAGGTTTCGGATTGG<br>AAGGAGGACCGCGCTCGTGGGGCGCCTGTGAGAGCTGGGAAGCCCAAGGGGTAGCGTGTAGGGGGTTTTTTATGCGGGAGGAGCTGCC<br>TCCTGGGCGGCGGGGACTTTCTGTCTCAGCCTGTCTGCCTTTGGGAAAACAAGGAGTTGCCGGAGAAGCAGGGAAAGAAAGGAGGGAGG<br>GAAGGAGGGTCCTTGGGGGAATATTTGCGGGTCAAATCGATATCCCCGTTTGGCCACGAGAATGGCGATTTCAAAGCAGATTAGATTACTT<br>TGTGGCATTTCAAATAAAACGGCAATTTCAGGGCCATGAGCACGTGGGCGACCCGCGGGAGCTGTGGGCCTGGCAGGCTCGCACAGGCG<br>CCCGGGCTGCCGGCCGCTGCGGGGATTTCTCCCCCAGCCTTTTCTTTTTAACAGAGGGCAAAGGGGCGACGGCGAGAGCACAGATGGCG<br>GCTGCGGAGCCGGGGAGGCGGCGGGGAGACGCGCGGGACTCGTGGGGAGGGCTGGCAGGGTGCAGGGGTTCCGCGTGACCTGCCCG<br>GCTCCCAGGCATCGGGCTGGGCGCTGCAGTTTACCGATTTGCTTTCGTCCCTCGTCCAGGTTTAGGAGACGCGTGGGGACAGCCGAGCC<br>GCGCCGGGCCCCTGGACGGCGTCGCCAAGGAGCTGGGATCGCACTTGCTGCAGGTAGAGCGGCCTCGCCGGGGGAGGAGCGCAGCCG<br>CCGCAGGCTCCCTTCCCACCCCGCCACCCCAGCCTCCAGGCGTCCCTTCCCCAGGAGCGCCAGGCAGATCCAGAGGCTGCCGGGGGCT<br>GGGGATGGGGTGGTCCCCACTGCGGAGGGATGGACGCTTAGCATGTCGGATGCGGCCTGCGGCCAACCCTACCCTAACCCTACGTCTGC<br>CCCCACACCCCGCCGAAGGCCCCAGGACTCCCCAGGCCACCTGAGACCTACGCCAGGGGCGCCTCCCGAGCGTGGTCAAGTGCTTTCCA<br>ATCTCACTTCCCTCAGCAGGTTCCACCCAGCGCTTGCTCTGTGCCAGGCGCCAGGGCTGGAGCAGCAGAAATGATTGGGCTGCTCTGAGC<br>TCTGAAGCATTCGGCCGCTGTGTGTGTGCAAGGGGCGCAAGGACGGAGAGACAGCATCAATAATACAATATTAACAGGAGCACTTGTCCAG<br>AGCTTACTGCAAGCCACATTCAGTTCCGGACCTTATTGACTTCCCCCTCCCATCTAGAGTGGATTCTGGTTTTTCAATTTGTTTTGTTTTGTTT<br>TTTGTTTGTTTGTTTGTTTTTGAGACGGAGTCTCACTCTGTGGCCCAGGCTAGAGTGCAATGGCGCGATCTCGGCTCACTCCAACCTCCGCC<br>TCCCGGGTTCAAGCGATTCTCCCGCTTCAGCCTCCCGAGTAGCCAGGATTGCAGGCACCCGCCATCATGCCTGGCTAATTTTTGTAGAGAC<br>AGGGTTTCACCCAGGCTGGTCTCGATCTCCTGACCTCCGATGATCCGCCCACCTCAGCCTTCCAAAGTGTTGGGATTACAGGCGTGAGCCA<br>ACGCGTCCTGCCTTGATTCTGTTTTTAACTCCATTTTTTAGAGGAGGAAATTGAGGCACAGAGAGGTTAAATAACATGTCTAAGGTCACACAG<br>CAAGGGGTGGAGCGGAGTTAGCCCACTGGCCTAGCTCTAGAGCCCACCCGGATAACCAGAACTTGGTGAGGCCTCCGGGCTCTTGCTTG<br>GTTTGGAGCCAGGTGCTTAGCGCCCCGAGCCCGGGGCCATTCACCCTGCAGGAGCTGCACGCGCCCCTGACCTCGGCTTTTCCCTGGCA<br>GCAGAGGGGCTTTGCGGGTCGGCCGGGTAGCCCTGAGCACAGCTCGCCACTTCCAGGTGGGCTGTTGGCGCTGGCTGGGGACACATCC<br>CGATCTTTCAAATGCCCTTTACAGAGCCTCATCAACGACCCGATTCATTCCCCCCTCCTGTCATTTGTCTCTGCCATCGAAAAATGCCTACC<br>GAGAGCTGCTCTGCATTTCCGCCCTCTATTTTGTGTTTTACTTTAAAATAATAATAAAAAAAAATGTTGGCTGCAGGACGCCATGACTTAGGTC<br>AGCGAGTCAGCCGCTAGCTCTGCATTTCCAAAAAGCAGATCTTTTCACAACTCTCTTGCCCCAAGTGCCCTGGTGTGGTTTATTTTTTAAAAT<br>GCATGCCTGCGGAAGAGAAGACCCGGGGAATATTCGAAACCCCGAGCTTTTACAACATAAAGCGCATGGTGTGGCCGCGGCGAGTAATGGCGCT |
| 206 | HLCS | CAAATCACTTGAACTCAAGTTCAAGACCAGCCTGGGCAACATGGTGAAACCACATCTCTACAAAAGTAAAGAAAATTAGCCAGGCATGGTGC<br>TGTGTGCCTGTAGTTCCAGCTACTCCTGGGGAGGTCGAGGCTGCAGTGAGCCGCAATCACGCCACTTGTACTCCAGCCTGGGCGACAGAG<br>CAAGTCCCCATCTCAAAAAAAAAAAAAAAAAAAAAAAAAAAAGGCTGGGTGTGGTGGTCCCAGATACTCAGAGGCTGAAAAGGGAGGATTG<br>CTTGAGCCCAGGAGTTCAAGGCTGCAGTGAGCTGCGATCACATCAATGCACTCCATCCAGCCTGAGCAATGGAGTGAGACCCTGACTATAT<br>TTAAAAAAAAAAAAAATAGGAAGAAACAACTCAACCACAGGGCTAGTATGTTACTCGGTTATAAAATGATAAAGCCCTAAACAGAGAATTAGC<br>CCGTTTCCAGAAGAGGCCAAGAACAGATGATACAGCTGAACTGAACTCCTGCCTGTACAGCTCGTTTTCTACAAGATTCCAGACCTGGAAG<br>ATGATGGCATCCAGCCCCCATTGAAGCACCTCGAACAAGAAAAACGCCGAGTCCGAAGAGCCAGGCCTTGAACACACGATTCCTGTCTATA<br>AATAACTCCCCCTGGGGAATAAAAAGCAGGATCCAAGGCAGGAAACCCGAGCCGTGGAATCTGGTAAGTTCTTAGGAAACCCACTCACGG<br>GCCTGAGTCCCCCGTGGAAGCGGCGACTTCGGCACCTGGACACCCGAGTCCCCAGAGCCCCGGGCGGCCGCGCGTCCCTACCTGCAGG<br>CCTGATACCGGCCGCGGAGCGCTCCTGGCCCCGCTCCCGCCAGGCTCCGGGACCGCTGAAACGCACCCAGGGGGGTGAAGGCGTAGTC<br>GCCAAGGACAGCGCAGATGGCAGCGGAGGCATGGGAGCCGGAACCTACCGTGGCAAAGGGCCAGGTCGGGACGCCCCTCGGCGCAGC |

TABLE 6C-continued

| SEQ ID NO | GENE NAME | SEQUENCE |
|---|---|---|
| | | CCCAAATCCTGCCCGCGCCCCAGCCCCGCTCAGGCCGCGCCCCTGCCACCTCTGGCCACACGGGCTGAGACGTCTGGCTCCTGCACAGC<br>GCACTTCCCGCTGCCCTTCTCCACTGGCTGCTCAGGCCCTGCCTCGCCAGCACGGCATCCGCGGGGGATCCCTACCTGTCCTTTAGGGCT<br>TGCCTCATAGGTCAAACGTCACCTCCCAGGGAGGTATGGCCTGCCCCCTGGCCAGGTGGGCCCCTTCCACGCTCGCCTGCAACACCACCC<br>ACCCACCTTGATAACTGCTTGTAAAGGTTGTACTGCTTTCCCCCTTGAGACTGCAAACCTTCAAGGGCAGGAAATGGGTCTGTTTTCCTGGC<br>AAAATAATGAAGTTGGCTTAAGGTTTTGCTGAATAAAATGAGTGACAGACAAAAGTAGCCAAATTTGGCACTCCTGATGGGTTATTTGATGAA<br>GGAGGTGCAATGTATGGGCTTAACTAGTTATTCTGGATTTCTTTCCCCATGTTA |
| 207 | DSCR6 | CAAGGCCGGTGCACGCGGACCCGAGGATTCGGTAGATGTCCCCGAAGACCCGCTGCCGCTCTAAGGCGGTGGAAGCGAGATTCTCCGGA<br>AACCCAGGGAATCCGATGCTCGCACAGGACCAAAGCCCGAGGCCGCGGGGACCACAGAGGGACGGAGAAGCCGGGACTCCTCACATCC<br>CACATCCGGCAGGGGAAGCCCAG |
| 208 | DSCR3 | CTGATAATAAAGTTTTACCATTTTATAATTTAAAAATGTAAATATGGAGTTGGGCATGGTGGTTGGGAGGCTGAGACCAGAAGATCGCTTGAG<br>CCCAGGGGTTTGAGACCAGCCTGGGCAACATGCAGAAACCCTGTCTCTACAAATAAAAAATTAGCCAAGCGTGGTAGCACGCACCTGTAAT<br>CCCAGCTACTCGGGAGGCTGAGGCAGGAGAATCGCTTGAGCCTGGGAGGTGGAGGCTGCAGTGAGCTGAGACTGTACCACTGCACTCCA<br>GCCTGGGTGACAGAGTGAGGCTCTGTCTCAAAAAAACAAAACACAAAAAAACAAACAAAAAAAAGCAAATATATGTAAAAATAGGAAGTGCG<br>GTTTCCCAAAATGAGGTCTGTAAACAACTGATCTAGAAAATGTTCTGGAAAAAGTAAAAAAGGATCAGGATCTGAGGTCAACTGACCTCTCC<br>CTGCGCTCTGGACAGGCAAACAGGCAAGGTTCCCTCTGAGGCCGTAGCGGCTTCTCGTGGGCGAGTCCCTGTTCGCAGGTGACGTGTGG<br>ACCACGCTCTTCCGAAGCGTCTGGCCTGTGTGCTCTCGGGGAGGGGACGCAGGTCAGCCCACCTAGCCGATGGCTAACAAGTCAGTTTGT<br>TTTCTGAACGGAAGCTTAAACCTAGAAAAGTAACTGGGTTGGGGTGGGGGTGTAGCCACATGCAGTAAAAGCACTGCCTGTCTGTATAACA<br>ACGACCTGATGAAAAAAGGAACGCGTGAAATGGGGAGTGTTAGGGCGTCACAAACTCCAGTGTGGTTGAAATGAAAGCAGAAAGCAAATG<br>GCAAGCTGGCTTCCCCTTCCAGCTTTTCACAACCCTGCCTTGCTCATGGTCAGCCCCAAGCACGGGCGGAAGAAAGGACTGGAGGGGAGG<br>GAAAGGGGTGGGGAGCGAGGGTACCAGAGGCGTGGGAGGACGGGGACAAAGGGGCAGCAAGGGACCGGCGGAAAGGAAAGTCGGCGT<br>TAGCTGGATTGGAAACAGTCCAGACAGAACGATGGGCTCTGCTGCCTCCGGGTGGGGCACCAAGCGGGGAGCGGGGCCACGAGGCAGG<br>GGACAGTGAAGCACCATGCAGCGCCCACCAGCCGGCAGCGCCCACCAGCCTGCGCTGCGCTGCACATGGTACCCGCGGCCCCAGCTGG<br>CCAGTGTGTGGCGGAGATGAGACCCTCGTGAAGAGACTAAGCGGCCACAGCAGGGGGAAGGGTTGCTCACATAACCCCATACTGCTCACA<br>CTACGAGGTTAACTGCCGTGAGATCTGCCTGCAGCCAGCAGAAACCCGTTCTAGGAAAACGTTGCCCAGTGACTTCAGTGAGTGCCACTGA<br>CCCGGGCGCCTCCGCCCCGGCGTCCGGCAGCAGCACCGATTGCGCAGGAGGCACCTTGCAAACAACCTTTCCTGATCCGCGCTGCAGTT<br>CCCAGGCCGGTTGCAGCCGTTTCACAGAGACTGCGCACACAAAGCGTCTCCGTGCCCTGCCATTCACCTTTCGACACAGCCGCAACCCCT<br>CTTTTCAGTGTTAAAACCTGGCGCCAAAAGGAACATGCGATGTGACGTGTTACCTCTGCGCATGCGCCGGGCATTCCCAGCGCCCCGAAC<br>CTGATGAACGCGCGGTGGGGACCCCAGGCTTCCGTGCTTTCGTTTTCCTGGAAGCTACGTGTCCTCAGTCTACATATTGTTACCTGGAAAA<br>TAAAGTTTTCTCCTTTTTTCTTCCTTTGTTAACAGGCAGAAGGTGTAGGCTGCAGGTTTCGGGCCTAAGAGAGGGCATGGCTGGCGACACG<br>GAGTAGACTCCTAGATGACATAACGGAGGCGAGTCTGCACCGGGGACTCGGCATTAGGAGGAGGCAGAGGAAAAGCCCACCACCGTGGC<br>CGAGGGAGATCTAGCAAGCAGCTTGCAGGGGGTGAAGTGTGTGCAAAGCAGGCTGAGACCTGTCCAGTATCGAAACACGCCGCGGTGGT<br>CAAGCAGGCTTTACCATGCT |
| 209 | chr21: 37841100-37841800 | TGAGGCTCAAAACAGGTGTCTGTGAGCTTCACAGGCGGTAAGGCCGTGTCTACATGGCCGGGACATGCATCCCGGGGCTGCCCCTGCCG<br>TGCTGCCCGAGTGCACGGGGGATGAGGACCTGACAAGGCCATTGATCTTGCGGGAGCTTCCTGAACTACTCCAGCGTGAAAATCTTCCAG<br>AAGGATTCTCCACAGGGCAATGAGGCAAGAAATTTACAGCTTAGCCTGATTAATGGGCCAGGCAGTTAAGAGTTCTTTGCCAAGCTATGAG<br>CATAATTTATAGTCATCACGGCAGGAGGAAAGGCCACATAACTCACATCCTTAAAGGGCCCTTAGAACAAGAGACACGCCGGATCATTGAAA<br>ACGTCTCCACTCCTGGCGCCAAAAGAGATCGGCACGTTTCTGGGTATTCTGGTCAAAGAACAGGGAGTCTGGATTAATATACACGGCAGAA<br>AAAAGCGAAGAAAAGACACACAGGTCATATATTTCTGACTGATATTCCGTTTGTTGTTTTCGGAGGGACTTGGTATTTATTTAACCACATTCT<br>CACTTGACACGCCCCCTCCCCACACCTTGTAAATGCCTTCCTCTTTAGCCGAGTCATTTTTCATCACATAGAATTGAAATGTTGCCAGGAAG<br>GCGGTTTATGAGATTGTAGAAATGGCACTAGAGAAAGCAGTGTGAAAAGAGGCCTAGAACGT |
| 210 | ERG | TCTCTACATGCTATCTACTAAAAACTTAGGCAAGGAAATGCATCAGACCAAACACCCCACAGCACAGAGAACCGACCGGCCATTGCTTTCCA<br>ATCTCCGCAAACCTAACCATTGCTGGAAGAAATCTTACTCACAGTGCACAGACAGTAGGTATTTTATTGAAGATAAACATATAGTGGAACAAA<br>CCAAATTACCCCCATTTGAGTTACGTGAGCACTCAGTTCTCAGCGTGGATGTCCCACAAATCAAGTCAACATTTGCGTCCCATTACCAGCAG<br>CCACTTGCCGAGTATCTCTTCGCTTCCACTGGGACTGCCTGGCATCCCTGATGCTAAGGAGCCACTGAAGAGCCTCCAAATGTCTGACATT<br>CACAAACGCATCTTTTGCTTTGACCCGACCCTTCAACCTCTCCGAGTCTGCTGCCTTTTCTCAGACACACATCCAGGCACCGTTAGGGATAG |

TABLE 6C-continued

| SEQ ID NO | GENE NAME | SEQUENCE |
|---|---|---|
| | | TTAGAGAATCTGAAAATTCAGAAGCGCTCCGAAAAGCCTTTCCAAAAGTAATCCACAGCACTCAACAGTGAATTTAGAAACCCCAATTTTTTT<br>CTGAGTTTGAAGTTTTTAAGCCTTGCGGATGGTTGGAGTAGGAAAAA |
| 211 | chr21: 39278700-39279800 | TCAGACAAGCTCTGTGCAGTCGGAATTTTTTAAAGATGCACTGTCACTTGAGGAAGACAGGTGATCTTCCTGCGGCACAAATAGAAGCAAAG<br>AGATTTCTCTTCTTCTCTGTAGAGCAACACAATTGATAAATGGCCGATAATCTCCACCAAATTGGCAGCAGTAGGCTGCCCGAAGGCAGCAG<br>GCATATTCGTCTTTGTGAATTGTTTTACTATGATGCTGTCACATTTCCAGGAATAAGACGGTTAAAATGATATATTGTTGTGGTTTGGCATTTG<br>CAGCTTTGCTCTGACTTCCCTGGTAACTGCCAACATCTGCAAATTATTATGTGCTTAAAAAAAAAATCAACCGCCACCGCAGGCTGCCCCCA<br>CGGTCCCTGGCTGGGCCAGGCCTCCTGCCAGGCCACAGGGCAGAGTTCTTGGACCAGGAGGCAGCAGGGTCAAAACCCAGGTTGCCTAG<br>GAAGCCCCCAAAGACAGTTATGGATAGAGCTGGGAGCCCGAAACACATGCGGCAGTCTCTCAGTTTCCAGGTACCGGTTCTCACATCATCC<br>ATGCATGTGTTTGAGGAAAAACAAAAAAAAATTGATGGTTGCCAAAAACAAAAATGCTTCCATATCAAAGTTTATCAGTGTCAATGTCAAGAG<br>ACTTCTGGTTCGTAGACTCATTTTGGCTTGAGGCCACCAGAAGTGAACTCTGGTTTCTAAATGCAGAAGCAGAGGCACTGGCCGATCATGG<br>AAGATGCAGGGAACTGTTCAAGAGGCCCAAGCCTGGTGCTCAGAAACTTGGCAGGATCAAGCATCTCGCCCAGGAATTCATCCCCTGCTTG<br>TCTAAGCCGGCTGGCTCTCGTGACTGACTCGGAACAACAGAGCAGATGTTTGCGTGGGAGGCAAGCCTCACCCAACATCTGTCCTGCGGC<br>GGGAAGGCCTGGGTGTTCACAGATAGAGCTGGAGTTCCCCGGTGGGTGGCACAGACAATTAGCTGGGGCTGCCTCACATGTAATCTAATT<br>ACAGGGGAAACAGGCTCAAACACCGGGTGATAAGCAGCGCAACTGTTTCGGGTGACTCTGTAATTTTTCCTCCATTAATTTTCTCCATAACGCAC |
| 212 | C21orf129 | GTTGCCTGGGATATGCTTATATCAAAAACTTACGTGTCACTTACCTAGCATTTGCATTTCACTGGGCCTCCTAAATTCTGTGTGGTAACCGAC<br>TGCCACCGGACATGCTGTTTACTTCTCTATCCTCACGCAGCCAGTTGCCACATTCAACATAACACTGCAAATATTGCCGGTGGATCCTGACT<br>TCCTCGTGGACCCTACTGTGTCGGGAAAAACAAACAAACGAACCCTGGAAGGAAACACCATGAGT |
| 213 | C2CD2 | TCATAAATATTTCCAAATGTATTCCTATTTGTCTCTACAGAGTCTAACAGACATAAATAGCGAATTGAAGGTTCTGTCTTAAAACCCAGCAGAA<br>AGAAAAACAATGACCAGAAAAAAAAAACAATTGTCTTTGGCTTCCCAAGAACAGCATCGGATTTCAACTGGAACCACAGATGGTCCGTTGAT<br>AGAAGCGACTACTTTTTAGCTCTGGAGGACGACAAAAGGAACCAGCTTCTTCCTGTGGGTGTCACAGCGAGGTCGCCTGGCCACATCAGGT<br>ACCAGAGCGAGCGCCCTCACCTGATAGGCCCTGTACAACCTCAGCCACAGCACTGTCAGGAGGAACACGCGGAACTAGCAACCTAGGAG<br>GGTAAAGGCGGAGTTGGGAGGGAACACGAGGCAGGCAGGTCGGCTGGCTGCTGAGCTACAGGCTGCACTCCTAGGACGTCTACGTGTAA<br>TTGAGAAAAATAAGACAAAAATAACTTACTGTGCAGGCAATTAATTCTGGTTGGCATAGCGATCCTCTTAAGTTAAAGGGAATGAGCATGAGA<br>TGAAGAGAAGTAAGAGGCAGAAAGAATTATGCAAGAGCAACATCAGAGTGGA |
| 214 | UMODL1 | ACGCCGAGCCGCCTCTGCAGGGGAAACCGAAGCAGATGTGGTGAGATAATACATCCAACCCTGAGTGCTACTCTAACCTGCCAGAGGCGG<br>AGGGTTCTCAGTGAGATGAAAGCATTACAGATGCGTTAGATCTAAGGGAGGGGCCTGCAGATGCGCAGCTGGCAGAGAAACCAGGGAGG<br>GGCTGAACTGTCAGTCGCGACCACCAGGGATCTGAATCAGTTCACCGACAGCCTTGGGGACATTCACCTTGGGCTCCACAACCTGTCAGA<br>AATGCCCCCAAGCCCAAAGGCGTCGAGAGAATGGCCAGGTTGTTTCAGATTGACACATATCCTAATGTACAAGTCAGCCCACACACCCCCAC<br>GTGCACTGAGCGTCTCTTGTTGTTCACCCCAAATAAACTCTGCCGGAACTGGGGCGGGACTCGCAGGGGCGGAGAAGGGGGGAGACGGG<br>CAGAGGGCAGAAGTGGATGGTGAGAAGAGCCAATGGAGGGGCCCCGTGAGAGTGAGCAAGGCTGCACCCCTAACCGACGTCCTGGGGC<br>TACTGTACAAACAAAGAACCACAGGCTGGGAGGCTGAACAACAGACCTGCACTCTCTCGCAGCTCGGAGGCTGCAGGTCTGAAATCGAGG<br>GGCTGACAGCGCTGGTTTCCTCTGGAGGCTGCGAGGGAGAAACCGTCCCCTGCCTCTCCCAGGCTCTGGGGTGAGCCCTTCCTGGCATC<br>CCGGGCTCATTGTAGATGGATCACTCCAATCTCCATGGCTTCTCAGGGCTTCCCTCCATGCACCTCAAATCTCTCTCTCCTTCCTTTTGTAA<br>GGATGCCAGTCATTGGATTTAGGTTCACCTTAAATCCAGGATGATCTCATCTAAATTACATCTGCAAAAAGACCCTTTTTCCAAGTAAGTTGA<br>CATTCACAGGTACCTGGGGTTAGGATTGGACATATCTTTTGCAGGGGTGCAGGGGGCTGCCACTGAGCCCGCTGCACAGGGTGACCTGGG<br>CCAAGGGCCCTTCACTTTCACTTCCTCATTGGCAAGCTGCCCTGTGTTTGGACTGGGTCGAGGCTGTCAACCTTGCTGCCCCTCGGAGTCC<br>CCCCTGGTGTCCCCCAAACAGATTCTAAGCTGCTTTCCTGGGGCTGGAGGCCAGGCATTGGGATTTTTTAAAGAGCTTCCCAGCAGGTGAG<br>CAGCCTTTCATGGGTATCAGGAGACCTTCCTGGCAAATGTGGTGAAGGTCCTTCCTCCTGAGCGATGCCTTAGACCCAGGAGCCCAGGGA<br>GGCTGCTCACCTGATCGTTAGGACAGGAGCAGTGGAAACCTCTGGCCTCAGACCCCCTGGAGGAATCCCTCCCTCTAAGACTCTGGGACT<br>GGTGCACGCAAGGAGCTATCGTGAACATTGCTCCCAACTGGCCGCTTGCTTGTCCCCCGGCTCCCCTTGGCCCCAGTGGCGGCTTTGCCT<br>GAATTAGAGGGCGTGAGAGCCACCTGTGTCTCAGCACTGCAATTAAAGCAGGAAGCCCTTTCGGAAGCAGCCGTGTGCACCAGCCTCCCA<br>TGGGTGGAGCAGAGCAAACCACCCACTTCTGCCCTCTGCCCTTCTTCCCTTTTCTCGACACCCTGCGGCCCCCCAGTTTCAGCAGAGTTTA<br>TTTGGGGTGAAAAACAAGAGATGCTCAGCGCCTGTGGGATGTGTGGGCTGACTCGTACATTAGGATGTGTGTCAATCTGAAATAACCTGGC |

TABLE 6C-continued

| SEQ ID NO | GENE NAME | SEQUENCE |
|---|---|---|
| | | CGTTATATGGATGCCTTGGGGCTTGGGGGGTTTCTGGCAGTCTGTCGAGCCCGAGGTGAATGTCCCCAAGGCTGCTGGTGAATCAGATCC<br>CTGGCGTTCTCCGTTGGCAGTTCAGCCCAACAGTTTCTCTGCCGGCCGTGCCTCTGCAGGTCCCTCCTCTGATCTGATTGGATTAATATTTG<br>AATCAATAGACTGAGTCAAGCAGAATGTGGGTGGGCCTCATGCAATCAGCTGAAGCCCTGAAAAGAGCAAAAGGGCTGCCCCTTCCCCCGAGGAGGAGAGAAC |
| 215 | UMODL1/ C21orf128 | CACATTTCAGAGCTGAGGTGCTGGTGCGGGCAGGTCTCCTGAGCTGGGGGGTCAGCTGTGTGGCCAGTGATGGTGACGCCTCAGGCCGT<br>GCATGGCCGGGGAGGCGGCCCTGCCTCTGCACTCTTTTGACTCCATGACTACTGGTGTCTTCGGACGCCAGAGTCGGGGGAGCAACCAT<br>GGGGCACCGCCCCTGCCTGGGGAGGCAGCACGAGGCCTGAGCCCAGCTTACAGGGGGACATCCACCCCCGCTGAGAGCCCCACCTTCA<br>CGGCGAGGATCTGTAGAAGAAGACATTTGATATTACTCGGCAAAAAAAACAAGAAACGAAAACACAAAAAGAGCTCCTCTGAAGAAGAAAAG<br>GTATTTGCGCTGTGGTCCACCTAGAAATAATGTTGTTGGCACAACTAGAGCATTCCTCAGTCATTCAGGAGCACTCCCTGCCGGTGCGTCC<br>ACATGTCCCAACCCCGATAGATGAGGCGCTGTTCGCCCGTGGAGGGGTCAGGTTGTCGTGACCTTATCTTTACCCTTAGGCCGTCCATCCC<br>GGGGCCTGGGGTTTCCTGCGCCAGTCACGGTGGGCTGTGTAGGTGGCCATGTGTTCGGTCTTTCCCCAGGAGGTACGTACCATGTGCTG<br>GGAGGCCTGGAGGCTGAGCCGCCCCCCGCGCCTATGAGTTGCACCCTCACAGCGGCGGCCAAACCTCCTGC |
| 216 | ABCG1 | CAGGCTTGAGCGGTGACTGGGAGACCCCGGGAATGGAAATGGCGCTCAAATGCTGGTGTGGTGTCCGCAGGGGAACGGCCCGCGGGTG<br>TGTGGAGTCTGCGCCCCTGTGGCTTCAGCTGCGTCGGGGGACTGCGGGAATCTTCCAGACTCCAGTTTAAATCAGAGAGGTGTGTCCACG<br>AAAAGAGTCAAACTAAAACATT |
| 217 | chr21: 42598300-42599600 | AACGAGACAGTGCAAAAAGCCGCTGCCTGGTGACCTGGCATGCAGACTCGGCCCTCCCACTTGCACGGTGATCCACTGAAGACAACAGCT<br>GCCTCTGTACTCACGCTCCCCCACACTCCCCTCCTTCCTGCCCTGGTTTCTCCATCCCTAGATGCCATCCCATGCCCCAAACCATCCGCCA<br>AGCACAATAACCTCGCCCCCACCCACCCCATGAGGTCACTCGAGTTGACAACCAGATAACAGTTTTTGTTTTGTTTTGTTTTGTTTTGTTTTG<br>TTTGTTTTTGAGACGGGGTCTCGCTCTGTTGCCCAGGCTGGAGTGCAATGACGTTATCTCGGCTCACCACAACCTCCGCCTCCCGGGTTCA<br>AGAGATTCTTCTGCCTCAGCTGCCTGAGTAGCTGGGACTACAGGCGCGTGCCACCATTCTCAGCTAACTTTTGTATTTTTAGTAGAGACAGG<br>GTTTCATTATATTGGCCAGGCTGGTCTCGAACTCCTGACCTCTTGATCCGCCCACCTCAGCCTCTCAAAGTGCAGGGATTACAGGCGTGAG<br>CCACCGCGCCCAATAGCAATTTGATGACCCATCCCCTCCACTGCTGGGAAAAGGCTGGGCACCGCCCACACTCCATGCAGCTCTCTTTCCC<br>TGGCTCGGAATCGCTGCAGGCGCCACAGACCAGACGCGCACTGTTCCCCACTCCTGCTTATCGGCCGCGCGGCATCCCCTTGTCGCAGC<br>ACTCCAGCATCCATGCAGCCGCGCGGCACCCCGTCTTCGGAGCACTCCAGAATCCATGCAGAGCGCAGCACCCCACATCCAGAGCGCTC<br>CAGAATCCATGAAGCACGCGGCACCCCCTCGTCAGAGTGCTCCAGAATCCATGAAGTGCGCAGCACCCCTTAATCGGAGCGCTCTAGAAC<br>CCGTGCAGCGAGCAGCACCCCACACCCGGAGCGCTCCAGAATCCATGAAGCCAGCAGCACCCCACACCCGGAGTGCTCCAGAATCCACG<br>CAGCACGTGGCATCTCCTCGTCATAGCGTTCTAGAATCCATGCAGCGAGCAGTACCCCACACCGGGAGCGCTCCAGAATCCACGCAGCGT<br>CTGGCACATCTTTATCAGAGCGCTCCAGAGTCCATGCAGCCACAGTCCTCCAACGGACCCTGAGATTGTTTCTGCAAAAGGCCATGCCTTC<br>ATAAATCTGAAAATTTGGAAAACATCCTTCTACTTATATCCTTACAACCCACCATTCAAGCTGTAGAAGCCTTTCTGGAACCCCAAGCAGAAG<br>GATATCCAAAATGTAAAAACGGTGGGGCCT |
| 218 | chr21: 42910000-42911000 | ATAGTGCGACTGTTCCGAAGTCTTTATCACAGTTACTGGTGATGCTTTTTTCCAGATGTCCTCGACGTGCACCCATGAAGGGCTCCACCTGA<br>GAGTGCCAGGGTCCTCCGTGGGATGGGGCTGGAGGGGGTGCTCTTGCCGTCCTGGGCTCCCAAGCAGCCATAGGAACAATAGGGTGATG<br>GGGTCCCAGAGATAGAGGCCAGTGACAGCAGCGCTTTGAACCCCTCACACGGGCACGGGCCCTCTGGCAGGGATGGGCGTCCCGGTCAC<br>ACGGAGATGGGGGCTGCTGCTGCCTGCAGGTAGAGGAAGGGACGTGTTTGGCAGTCCTGTGACCCCTGGGCACCTCGCCTCCCCCACGG<br>CCGGCTCTGCTTGTAAACAGACAAGTGCACAAGCGCAGCCCGGTGAAGGCACAGCGGTCCCAGGAGGCATCTGGGCTGCACCCCAGCGA<br>GCCGCCCATACACGTGGAGATGCCGGCCAAGGCCCTGCAGCACACGGCAGAGGAAGGCGCGATGGGAGCCATGCTGGGCCCGGAAGGT<br>GCCGCCGCCCGGAGCTGTAGCCATCACTCCAGCTCTTCTTTTAAGTGTTCCCAGAAATTGTGACCCACCAAAATCTGAGAGCACCCGACAG<br>TAAGCCAGAGGACCTTGATGTGAGATCCCAGCACGGTGTGGGGGCGGACTGTGGTGGGTGCTGTCTCGGCCCCCACCCCTTCCACAGGT<br>CGGTGTGCACATCCCACGGCGCCTGCTAAGCTGCAGTCTTCTCCAAAGGGGTCACTCTCCGTGGGAAGGGAGCCACCCGCCCCCGGGTG<br>ATGTCCCCAGTCAGTGACTGACGACAGTCCCCAGCCGAGGTGAGGGACCAGCTCCTGCATCCCTCACTCCGGGGCTTGCCTGTGGGCCA<br>GGGTGGGGGCGAGCCTCAGCAGAGACCGCGTCCCCCTTGCCTGTCCTGCCCTGCCTCCCCTGCCTCCCCCGCGCCTCTGCTGAGCACGC<br>CCAGAGGGAGCTGCTTG |
| 219 | PDE9A | CACTTGAAAAGCACAACTCATGGTGCCAAAGCTCTGACACGGACTCCACTGGAGCTGTGGGCAGGGGGTGCCAAGGTACCGAGTTCCAAG<br>CCGTTGTTATTTGAGAGCGTGCCCCCCGCCATGAGAGCAGGTGGGGGACATAAAGTGACACAGGATGGACTGGCCAAAGGCTGAGGAC<br>GATCACTTACCTCACAGGATGATGCCACCCCCACGGACAGGCAAGGAGCTCTCACCTTCCCCAGGACCCCAGCTGCCACCAGAGCTCCAG |

TABLE 6C-continued

| SEQ ID NO | GENE NAME | SEQUENCE |
|---|---|---|
| | | ATGGCCCTGGGGGTGTCTGTAAAGCCTGTGACCGTCCACCAGGTGGAGACCAGGCTGGCCAGGGGAGGGAGAGGAAGTGACCACTGGC<br>CCTGGCACTGGCTGGCCGGCTCCAGCAGGCCCGAAGGGGAGGGAGGAGCCTGGGTGCACCAGACTCTCTCAATAAGCAGCACCCAGACA<br>CTTAACAGATGGAAAGCGGTGGCTTGGAACTCACTTCCAACGAAACAATAGCAC |
| 220 | PDE9A | AGCACCTCCTACCCCACCCTCCCCATTCCTGCCATCCCCAGGGTCCAGGGAGCCCAGATTCCAGGGAAGGGTTGCATTAGCTCCCACTCG<br>GAGTCCTGATGCAGCAGAGACAGACAGAGGCCCTGGGAGAAGTGAGCATGAATTATTAAGACAAGACAAGGGTGAGGCCCCAGAGAGGG<br>GGTGGCGGAAGGGTCATGTTCATGCAGCGAGAGTTGCTTCGAGCTTGAACCGCGTATCCAGGAGTCAAGCAGATTGCAACTGGCGAGAGG<br>CCTTCAGAAATGCCCCGTGAGAGTCCTGTGTGCAGAGCTCCATCTCAGCACACTTCCTGTTCTTTTGGTTCGTCGATTTTTGCATTTTCAGTC<br>CCCTGTGATCCATTATTTATAACAGTGGAGATTGGCCTCAGACACTAGCAGTGAGGAAAACAAAAGCGAAGCTACGCAGAAAAATGACAAGA<br>GTGATGAGCACAGCAGTCATGACAAATGAGCCCTGTGCGGAGGCCCGGGATCCGCGCAGATGCCGGCGCGGGGAAATGGGCCCTGAA<br>ATCCCACCGTCAGGCCAGGCAGCTCTGAGCGTGACCTGGAGGGCTGTTCAGACGGTCTGGGTAGCCGTGTCCTGCGCATGAACATCCTCC<br>GTCGGGAGAGGAATTCCCCACGGATTATCAGAGCTGCTCCCTCCACCCCCCGCCACGTCCCACGCGGGCCACATCAACTCCCTCTGCAGC<br>CTCTGGCCAGCGGCTGAGCCCTCCGTGTCTCCCCTGTTAATGCCTCCTTCACCATCCCCTCCTGAAGTTTCCCCCATTGCATACACGCGC<br>TGAGGCCCACCCGGTATCAAGGACTCCCATTGCTTGCGAAAAAGATTCCACCCCTCTTAGAACAGAGACCAGGGCCGCTGTAGCAAATGG<br>CCATAAATGCCACAGCTTAAAACAACAGAAACGGATTATCTCGCAGCTCTGGAGGATGGAGTCCAAAATCTGAATCGCTGGGCTGAAATCC<br>AGGTGTGGGCAGGGCCGCGCTCCCTCTAGAGGCTCCCCCGGAGATTCCCTTCCTTGCCTCTTCCAGCTGCTGGTGGCTGCCAGCAGTTTG<br>GGAATTGCGGCCGCATCACACCACCTTTCTGTTTGTTGTTGACATCCCCGCCTCCCCTGCCTGCGGGGTCTTAGATGTCTCTCTCCTTCCC<br>ACTGAGTTTCACTCCACATTTGAATTGGATTAACTCATGCCATGTTAGGCAAACGTGCCCCTCAAATCCTTCCACTTAACAGACATTTATTGA<br>AGGTTCCTGTGTGCGGGGCCCAAGAGAAGGGA |
| 221 | PDE9A | GAATGTTCAAAGAAAGAGCCCTCCTTGCCTTCCTCTTCTTCCACCCCTGCCCTCTGCAGACTGGGGTTCTGTAGACCCCCAAAGTAAGTCC<br>GCCACACCGGAAGGAAGTGAGTTACACAGGGGCCCACATGGGAACCGCTTTTTGTCCTGTCTTGGTGGGAAAATGGCCACGACCCCAGCC<br>CAGGCTCTGCCACGCCACA |
| 222 | PDE9A | CCATCTTCCTAGGCCTGCGTTTCCCCCACACCGGGGACTTGTGCTGGAAAGAAAAGCTGCGTTGGCAGCCAGGAGCCGGGGAAACTGTCC<br>AGGGAGGCATCCTCTGCGATGAAGGCGGGGCCTCGGCGTGGCCCGTTCCGCGCTCTGTCCAGCCCTGGAGAAGCCCCACCCTCACCGA<br>GCTCGAAATACCCCCTCCCTGAGAGCCGAGACTCATGGCCGGGACCCCTTGGACAGAAGATGCGGATGCTAACCCGGCGCTTCCACCACA<br>GCCCCGGCGGCACTGGGGAGCGAGCGCGGCCATCCCGCGCGTAGGTGGTGTTTCTCTGCAGGCGCCAGTTTCACCGCGGGCGCCCAGG<br>ATCCTCAACGGTTCTGTTGTGATGTGATTCCCCTCTTCGACTTCGTCATTCAGCCTCAGTCCCTCAGTCCCCAAATACCGAAAGGCAGTCTT<br>TTTTTTTTTTTTTTGAGACGGAGTTTCACTCTTGTTGCCCAGGCTGGAGTGCAATGGTGCGATCTCGGTTCACTGCAACCTCCGTCTCCCTG<br>GCTCAAGCGATTCTCCCGGCTCAGCCTCCCGAGTAGCTGGGATTACAGGCACCTGCCACCACGCCCGGCTAATTTTTTGTATTTTTAGTAG<br>AGACGGGGTTTCACCATGTTGGCCAGGATGGTCTGGAACTCCTGATCTCAGGTGATCCACCCGCCTCTGCCTCCCAAAGTGCTGGGATTAC<br>AGGCGTGAGCCACCGCGCCCGGCCTTTTTTTCTTTTTTCTTTTGAAGTTAATGAACTTGAATTTTATTTTATTTACAGAATAGCCCCCATGAGA<br>TACTTGAAGACCCGGTGCCAAGCGACAGTGTTGACCCCAGGTGGTCAGTCCTGCCTGGCCCCTTCCGAGGGATGCGCCTTCACCATAACC<br>ATGTCACGGACAGGCGTGTGGGCAAGGGGGCATCGCTGTATTTTTCACAACTCTTTCCACTGAACACGACAATGACATTTTTCACCACCCGT<br>ATGCATCAACCAAATGAAAAGATGAGCCTGTGACATTCCCGTGCGTAGAGTTACAGCTTTTCTTTTCAAAACGAACCTTCAGTTTGGAGCCG<br>AAGCGGAAGCACGTGGCGTCTGACGTCTCCAGGGAGACCCGCCGCCCTCGCTGCCGCCTCACCGCGCTTCTGTTTTGCAGGTAATCTTCA<br>GCAAGTACTGCAACTCCAGCGACATCATGGACCTGTTCTGCATCGCCACCGGCCTGCCTCGGTGAGTGCGCGCTGCGGGCTCTGCCCGG<br>TGACGCCACGCGGCCTCCTCGCCTTTTCGGGATGGCTGGGAGGGGCGGGAAGAGGCGCTGAAGGGCCCGAGGCACCGGCCTTCTACAA<br>GGGGCTCTTCGAAATCAATCAATGCGCAGAATCCCGAGGGAGGCTCAGCCGCCCTCCGGGCCTCTCTGCCTCCACAGGTGATGGCTGTGT<br>CCACAAGGAGGAAACCGTCGGGCTGAATTAAACAGAACCGCCCTCCTAAGAGTGTGGGTTTTTCTGCCGGGCGTGGTGTCTCACACCTGT<br>AATCCCAACACTTTGAGAGGCCGAGGTGGGCAGATCACCTGAGGTCAGGAGTTCGAGACCAGC |
| 223 | PDE9A | AGGCAGCAGGGTTAGGACTTCAACATACAACTTTTGGGGGGAGATGTACTTCAGCCCATAACACACCACGTGGGAGGATAACACCGATTTC<br>AGAGCTTGCAGAGGAAGCCGCCAGGAACTCCAGTGAGACATCAGCCCCCAGGTGCCTGTCAGGCACGCCGGGCTGTGGGGGGCACCTG<br>GGCCCATCTGAGTAACGGAGGCGCATCCGCACTTCCCCCAGGAGTACATTTTTAGAACCCACAGCGCCATAAACCAAAGACAAGGAGACTT<br>CCTGGTGCCCCGTCAGCTTCTGGAGGCGACGTTCTCGGCTGACAGCTCTGGCAGCCTCCCCTGTAGGTGAGAGACAGGTAAATGGGACTC<br>TTGCTTCCAAAACGGAACAGGGTAAAAATTCTCAAGCGTT |

TABLE 6C-continued

| SEQ ID NO | GENE NAME | SEQUENCE |
|---|---|---|
| 224 | chr21: 43130800-43131500 | TGCTGCACCCCCGCTGCCCTCCCTCCCGCTGGCCGGCAGCACCTTCTCCACCCGGGCCCCTCTGCTCACAGCGCTCCCCGCCCCCGTCT<br>CCCCGAGGGGCGGGGAGCCAGGACATGGCCCTGAAAGCCTAGCCCTGGCCTTGACCTCCCCAGAGCGCCCTCCCCACCCTCCGCCCTCT<br>GCCAACCCTGGCCCCTGCCCTGGCCCCGTCCTTGTCCTCTGCTGCTGGCCTTGGGGTCGCGCCCCGCAGACTGGGCTGTGCGTGGGGGT<br>CCTGGCGGCCTGTGCCGTCCCACGCCTACGGGGATGGGCGAGGTCCTTCTTGGGGCTTCTCTTACCCACTCTCCAGTCACCTGAGGGCG<br>CTGCTTCCCTGCGGCCACCCCAGGTTTCTGTGCAGCCGAAGCCTCTGCCTCTGCGGCCGGGTGATCCCAAGACCCCGGGGTCCAGGGAG<br>GCACGGGATCTGCTCCCCCGGTCCCAAATGCACCGGCTGCGCCTTAGGAGGGACGGCCTCCACCCATGGCGCTGGCGCCCAGGGGCCG<br>CTCCTCGGACTACAGCACTTGCTCGTCGCCCTGCGCCCTGTTTAGTTCTCATCACCAGCAGCCTGGACTAGGGCCCTGGTCCTTCTGGCCT<br>CCTTCCACAGCCCGCTGCACATCTCACCCACTTCCCCGAGGTGCTGTCATTGTTTAGCTGGGCCCCTCAGCCTCCG |
| 225 | U2AF1 | TTAAAGGGGAGTGGTTGTATGAAGAGTTCCTCAGTCAAAGGTGTGCAGCTGGGAAGCCCACCCCACCTAAGAGGGAGGTCTGACAAACTG<br>TCCACACTGAACCACTCAGACCTGCATCAGGGCCCCGTTTCTTCCATAAGCCGCCAAGTACAGCCCTGAGTCAACTGAACTCAGGCCTGGG<br>AGGCTTCCCAAAGCTGACTTGACTCAGCTTTGAACTGAAATGACCGTACCATGACAACCCTGATGAAAAGCTAAACTGAGCCCAATTATTCA<br>ACAGTAAAATTCAGTTGGTCTCACTCA |
| 226 | U2AF1 | TGCTACCAGCTGCTTGGGCTTGGGCAAGTCACCCTAGCTCTCAGATGTCATCTGTAAATGATGACAATGCCAATGTGGCACTGTTCTGAGA<br>GTCAGACAGAACGTATGTGTGCTTCACATATGGTGCTCATGAAGTGCTATCATTATCTAAGGAAAACAGAAAACGAAGTTCAGAGTCTCTCT<br>AAACGCATGACACCAGACCAACAGGGAGTTTCAAAAAATAGGTCTGAAGTAAATCAATTCTCCTGGTCTCAATACACTGAAAACAAACTATTA<br>GGGGACTGACCGAACCCACCTTAGGAACCACCTTACGTCACCTTCTGTCTCTACTGCAAAACCCTCCCTTAATACTGTTCAAATACGCTGAC<br>AATCCAGATCCATATCCAATGGAACCAGCAATCATGCCTGTGTGCCAGCAATGTCAGGGAGGGAAGCCGATCTCTGATGAAT |
| 227 | chr21: 43446600-43447600 | CAGGTGCCGGCCACCACACCCGGCTAATTTTTGTGTTTTTAGTGGAGACAGGGTTTCGCCATGTTGGCCGGGCTGGTCTCAAACTCCTGAC<br>CTCATGTGATCCACCCGCCTCGGCCTTCCAAAGTGCTGGGATTACAAGTGTAAGCCACTGCGCCCGGCCAAGAGTGAAGTTCTGATAGCTG<br>GGGTAAGAAAGGCCGTGGGAACAGCCGGTTTCAGACACGCTGGGTCTAAGACGCTGCGTCTGGCGCTGCTCGGCATCCAATGGGAGCCG<br>TGGAGAAGCCAGGCGAGTGCGTAGGGCGGAGCCAGCGCACAGGAAATAGGACGTGATGAGGTCAACCGGCTGGTCCAAGTGTGGACGG<br>AAGTAGAGGATGCAAGCACCGAGCCCCGGGGCCCCCAGCATTGGCGGGGAGGAGCTCGCGGTGCGGGAGAAGCAGGGGACCGCGCAT<br>CCTGGAGACCAGGTGGAGCCAGTGCGCCCGGAAGGGGCGTGGCCCGCTGACAGCCGCCCAGGAGGCCGGGGGAGGCCTGGAGCCGAG<br>GGCCGCGCGTGGCAATGTGGAGAGACATTTTGGTGGAGTCATGGGGCCACAGCCTGATTGGTGAGAACAGGAAGGGAAATTGCAGATGG<br>GCCTGGGCCCCCTGGCTCCCGCATACTCCAGGACCAGGGCTGAGTCATCGTTCACCGTGTGTGACCAGGGCCCCGTGTGGCCGGCTGTC<br>ACTCGGTATCCAGTTACCCTGGGCAGACCACTGGCGGCACCCCCCAGCCAGAGGCCGCAGCAACACACACGCCTGCAGGCGACCAGGCC<br>GGACTGCATGCCCCGTGGGGGAACTGAGGGCGTTTCAGTAACAGAGTGTTAGGGGACACGGGTTGGGTGGCTTGGAAAGGGCCTAAGGT<br>GGGGTTTGTTTTAGATTGGGGTGGTGAGGGCGCAGGGGCCCGGTAGGATTCTCTAACAGGGCAGCAGCCACTCATTTAGCAACAGGAGAG<br>GCGTCCAGCGTTTCGTGGGCT |
| 228 | CRYAA | ACCCAACCACAGGCCTCCTCTCTGAGCCACGGGTGAGCGGTGCAGGTTCTGCTGTTCTGGAGGGCCTGAGTCCCACCCAGCACCTCATAA<br>ACAGGGTCCTCCCCAGGGCTGCTGCAGTAGGCATCAACGCCAGGGTGCAAAATGCCTCAGGGAGCCAAGGCTGAGCCAGGGGAGTGAGA<br>AGGAGCATGTGGAAGTGCGTTTTGGAGAGGCAGCTGCGCAGGCTGTCAGCAGGCTCCGGCCGCTTCTATAGACAGCATGACACCAAGGG<br>CAGTGACCTCATTCCACAGGCTGAGTCCAGCCAGCCAGCCAAGCATCACCAGCCAGACGATTGACCCTAACGGACCAACCAACCCGTAAC<br>GACCCCTCCTACCATAACCAGTAGCCAGCCAGCCCATAACCAGCCAACTTATCTATAACCAGCCACCTGACCATAGCCAAACAACCAGCCG<br>GCCCACCAGTAGCATTCAGCCCCTCAGCTGGCCCTGAGGGTTTGGAGACAGGTCGAGGGTCATGCCTGTCTGTCCAGGAGACAGTCACAG<br>GCCCCCGAAAGCTCTGCCCCACTTGGTGTGTGGGAGAAGAGGCCGGCAGGTGACCGAAGCATCTCTGTTCTGATAACCGGGACCCGCCC<br>TGTCTCTGCCAACCCCAGCAGGGACGGCACCCTCTGGGCAGCTCCACATGGCACGTTTGGATTTCAGGTTCGATCCGACCGGGACAAGTT<br>CGTCATCTTCCTCGATGTGAAGCACTTCTCCCCGGAGGACCTCACCGTGAAGGTGCAGGACGACTTTGTGGAGATCCACGGAAAGCACAA<br>CGAGCGCCAGGTGAGCCCAGGCACTGAGAGGTGGGAGAGGGGGGCGAGTTGGGCGCGAGGACAAGGGGGTCACGGCGGGCACGACCG<br>GGCCTGCACACCTGCACCATGCCTTCAACCCTGGGAGAGGGACGCTCTCCAGGGGACCCCGAATCAGGCCTGGCTTTTCCCCAAGGGAG<br>GGGCCGTGCCCACCTGAGCACAGCCAGCCCCTCCCGGTGACAGAGGTCACCATTCCCGAGCTAATGTGGCTCAGGGATCCAGGTTAGGG<br>TCCCTTCCCGGGCTGCACCCAGCCGTCGCCAGCTCCATCCCTGTCACCTGGATGCCAGGGTGGTCTTAGAAAGAACCCCAGGAAGTGGGA<br>GTGCCCCGGGTGGCCGCCTCCTAGCCAGTGTACATCTTCACATGAACCCTACCTGAGGAAGCCAGTCCCCGACGGCATAGCTGCATCCGC<br>TTGGAATGCTTTACAGGCATTGACACCTTCGCCTCACAGCAGCACTTTGGAACCAGTGTCCTCATTATTCCAGGGCACGGCTGGGGAACAA<br>GGGGGTCCTCAGCCTGCTGGGTCCCACAGCTAGTACCGGGCAGGTGGACGGGAGCTTCTCCCCACAGTCACCCTGATGCCCCGCTCTTG |

TABLE 6C-continued

| SEQ ID NO | GENE NAME | SEQUENCE |
|---|---|---|
| | | CTCGGCTGGAGGCCTCGGATCTCCGTGGTGTTGAGGGAGCCGGGGCACTGGAGCCCTGGTGACCTGCATCTCCTGGCGGAGCCGGGAA GAGCTCATGGACTGTCACAGATGGACAGTGCCCCGCGGGGGCTGGAGAGCAGAGTGGGGCTGGAAGGTGGAACTCTTAGCCAAAGTCTT GGTTTCTTTTGGCCAGGGTCCTCTTTCAATGGCTGGAGAAGGTGGTGCTGGGGGGTGAACGCTGACCTCCTCATGTGCTGCCCCTCCCTC GCCTGGGCCCGGTAAAGCCCCCACGTAGCCCAGCCAGCCTGGAACATGCTTCCTGAGCTCCCAGCTCTTGGTCTTTGCACCCAGTGGAG GAGGAGGTCAGCCCAGGGAGCTGAGTCTGCGGTTTAGGGCGTCCAGGGGACGTGGAAGCATGTGGGTCGTCTGGCCACATTAGGTAGGG CTGCAGAGACCTGGGCTAGAGCAGTCCTGCGGGGTCTGGAAGGGGAAGACTGGCTGAGGTGCGGGGCCTGGTCTGGAATGATCCTGCGA TTTTGGAGTGAAGCCATGGAGCGGGAAGAGACAACCCCCCGCGGGGAATAGCCCGGCAAGTGGCCACGAGGCCAGGCTGAGGTCCAGA GAAGCAGGGGCATGAATCCATAAATCCCAGGGGGCCTGGCCATGGGATGTGCTGGCTGCACCCGGCCCCTGTGAGAGCCCCCGCAGGCT GGCCCCCTTCTGCAGTCAGTGGGGCTGGGGCAGCTTCTCTGGCATGGGGCGAGGCAGCCGCCTGCACAGTGGCCCCCCTGACTGTGCG CCCCCACCCTCTCCAGGACGACCACGGCTACATTTCCCGTGAGTTCCACCGCCGCTACCGCCTGCCGTCCAACGTGGACCAGTCGGCCCT CTCTTGCTCCCTGTCTGCCGATGGCATGCTGACCTTCTGTGGCCCCAAGATCCAGACTGGCCTGGATGCCACCCACGCCGAGCGAGCCAT CCCCGTGTCGCGGGAGGAGAAGCCCACCTCGGCTCCCTCGTCCTAAGCAGGCATTGCCTCGGCTGGCTCCCCTGCAGCCCTGGCCCATC ATGGGGGGAGCACCCTGAGGGCGGGGTGTCTGTCTTCCTTTGCTTCCCTTTTTTCCTTTCCACCTTCTCACATGGAATGAGGGTTTGAGAG AGCAGCCAGGAGAGCTTAGGGTCTCAGGGTGTCCCAGACCCCGACACCGGCCAGTGGCGGAAGTGACCGCACCTCACACTCCTTTAGATA GCAGCCTGGCTCCCCTGGGGTGCAGGCGCCTCAACTCTGCTGAGGGTCCAGAAGGAGGGGGTGACCTCCGGCCAGGTGCCTCCTGACA CACCTGCAGCCTCCCTCCGCGGCGGGCCCTGCCCACACCTCCTGGGGCGCGTGAGGCCCGTGGGGCCGGGGCTTCTGTGCACCTGGGC TCTCGCGGCCTCTTCTCTCAGACCGTCTTCCTCCAACCCCTCTATGTAGTGCCGCTCTTGGGGACATGGGTCGCCCATGAGAGCGCAGCC CGCGGCAATCAATAAACAGCAGGTGATACAAGCAACCCGCCGTCTGCTGGTGCTGTCTCCATCAGGGGCGCGAGGGGCAGGAGGGCGGC GCCGGGAGGGAGGACAGCGGGGTCTCCTGCTCGCGTTGGACCCGGTGGCCTCGGAACGATGG |
| 229 | chr21: 43545000-43546000 | TTTTTGTGTTTTTAGTAGAGATGGGATTTCACCATGTTGGCCAGGCTGGTCTCAAACTCCTGGCCTCATGCAATCCTCCTGCCTCAGTAGTA GTAGTTGGGATTACAGGTGTGAGCTGCCATGCCCAGCTGCAGGTGCGGAAGCTGGGGGCCTCAGAGACTGTGGACTCCTGGCCGGTGAG GAGCGGCATGGGCCGGGAGAGCTGACTCTTCAGCGGGACTGAGGTGGCTGGAGCGTGACCCTTTCCTGAGGGCAAACAGGGAGGGCCT TGGAGCCCGGCGCTCAGGACAGGCCCCTGCTGGCCCGGCAGCCTGAGCTTCCACACTTTTCCAGGGCGTCTCGAGTTCGCCCACAGAGC TGTTGTTTCAGGATAAAAAATGCCCTTGTATTCCACGTTCCAGTTCAGAGGCCCGTCTGTTCCCAAGAGCGGAGGCGTCAGCCGCATGAGT CCCACCGGAAGCCGGGTTGCCGGGTCCCCGTCCCTGCCCTGCAGACGACGCATTCCGGAGCCCCCTTGGGAAGCTGCCTGGCTCTCCCA GGCCTGGCTGCCTTCGCACGAGGGCTCCGAGGCATGCTCATCCTACGTGACTGCCCGAGTGTGCACACGCCTGGCCGTGTGTGGGCGTG TGCCTGGGGCCCGAGCTCAGGAGCAAGGCCTGCGTGGACCTGTTGTCTGAAACAAGCCAGTAGACAGCTGCGTCAATGCAGGCAAGCTG AACAGGGCTGCTTTTTCAGCCTGACAACCCCAGGGGCTGAACAGGAGCTGGGGGAGGAGCAAGGGGCCGTTCCCCTGCCCCACAGCACA GCACACGACCCCGCCTTGGAACCTGGGGCCCGGGGTGAATCGAGGGTCCTGGAGCAAGAGGGGCTGCTCCACAGGAGAGCCTGTCCCG CCACCCCTCAGCCACCAGATTCGGGGCTGCTGGACTTGTTCTCAAACCTGCACAGTGAGTGACAGCTGCTGAGACGGAGGTCTCAGGCAG TGCAGGTGAATCAGCAT |
| 230 | chr21: 43606000-43606500 | TCCTTATTTTTTAGTTCTCAAGCCCTGTAGGGTGTTTTCGGTCGCAGTTGTTTGGGCTGTGGTCCTGACCCTCCTGAGTTCCAGTGGCTCTG TTCAGGAGAGCTGCCTGGGGCCGGGACTTCTGAAACACACACTGAGCCACAGGCCGGCCCGGCGGCTTGGGTTCACCGCCGCCTCTTTG TGTGTGATGTCCTGGGATAGGCCCGTGCACGTTCAGATGACACTGTACATATAAATAACTTGTAGCCGAGAACAGGATGGGGCGGGGAGG AGGGGAGGGCAGAACGTACCACAGCAGCAGAAGTCACTGTGGATGCCTTCGTAAGTTGCATGGAAGGTTTTTAAACCTAGCCCTGCCGAG CAGCCCTCTCCTGGTCCGGGAGAACGATGGGGAGAGAGCTGGCGTTCAGCTTTCATCACTGGAGCCGTTCCTTCTTCCGGCCCCCCGAGG GCCTGTCCATGATCACACTTTGTCTTGTTTCGGGGGTGGCCCCTGTGAC |
| 231 | chr21: 43643000-43644300 | CAAGCCTGTGGTAGGGACCAGGTCAGAGTAAACAGGAAGACAGCTTTCGGCCAGGCGGTGCACCTCGGTGCCGGTGAGTGTGAGCGTGT GTGCGTGTGCACGTGTGCAGATGTGTGTGGACGCTCCCTTCTCCGCAGCAGCTCCTGACCCCCTGCAGGTGACCCTCAGCCAGCCCCAG GGCTGCCCCCACTCTCCCCTGTGGACACCTACCTCATTTGGGGTGAAGTGGGGGGACTGGGGTGTGAGGGGTGCTTTGGGGGGCACACT TCGACCCCTCTCTCTGCAGGCCAAGTCCTGAGGCTCAGTTTCCTCCTCTGTGCCCCGGCGACGTGGTGCAGGCCTCGCGAGTGACGTGAG GGTTCATGACCCAGGTGTGGGCAGCCAGCCCTTCACGGGAGGCCACCCACCTGGCCACAGTGCCTGGGAATTTAGGTCGGGCACTGCCG ATATGTCGCCTTCCACAAGGCGGGCCCGGGCCTCTGCTGACCGTGCACCGGTCCTGGGGCTGGGTAATTCTGCAGCAGCAGCGCAGCCC ATGCCGGGGAATTTGCGGGCAGAGGAGACAGTGAGGCCCGCGTTCTGTGCGGGAACTCCCGAGCTCACAGAGCCCAAGACCACACGGCT GCATCTGCTTGGCTGACTGGGCCAGGCCCACGCGTAGTAACCCGGACGTCTCTCTCTCACAGTCCCCTTGCGTCTGGCCAGGGAGCTGCC AGGCTGCACCCCGCGGTGGGGATCGGAGAGGGGCAGTGTCGCCCATCCCCGGAAGGCTGAGCCTGGTGCAGCCAGGGAGTGAGGGG |

TABLE 6C-continued

| SEQ ID NO | GENE NAME | SEQUENCE |
|---|---|---|
| | | GCGGGAAGCCGGGGTGCTGCCCTGAGGGTGCCCCGACACGCTCTCCTGGGGCCCTGAGCGGCTGCCACGTGCGTCCAGGGTTCTGGCC<br>ACAGGGTGGGCAGGGGCCCTGTGCTCCTCACTGGAGGCCCCTGAGGCTCTGGAACTGAGACCATCCACCCGCCGGCCCCCTCTCGCCG<br>GCTCCGGCACCCCTGCCTACTGTGACTTCCTGCCCCGGACTCGCTCTGCCAGCTTGGGGCAAACCACTTCCCTCTGGGGTTTTCACTTCCC<br>TCTTTCCCAAGTGGGGAAAGACCACCTGTCCCCGACCCAGAAAGGGCCCCTGCCCGAGGGCAGCAGCAGTGCCAGGCTGGCATGTGAGG<br>CTTGGGGCAGGCCCGGCCCCCAGAGGCACAGGGCGATGCTCTGTGGGACGCTGTGTCGTTTCTAAGTACAAGGTCAGGAGAGGAGCCCC<br>CTGACCCCGGAGGGGAGGAGAGGCAGGGCAGGAAACCGCCACCATCTCAGCCCA |
| 232 | C21orf125 | GCCCACTGTGGGTGTGCCCGTGTGTGTGGCTGTGAGGCGTGAGTGCAGGCGTGAAGTGTCTGGGAGTGGGAGCGGGCATGAGTGTGTG<br>CCACGGGCCTGCTGTTGGGTCCTTGGAGGCCACGGTTGCCCCTGAAGGGACTGCAAGCTCTTTTTTGATTTGTAGTTATTTGAGAAGTCTA<br>TACAGGAAGAAAATTAAACCG |
| 233 | C21orf125 | AGCGCCCAGCGCAGGGCCGGGACCCAGAGTGGACTCTACCGTGGGGCTGCCTCAAAGAAATCTCAGCAAACACAGGAAGCCAGCCCACC<br>CGTGCAGCCATGGGGCCAGGAAGCCCGCCCTTTACCAAGTCATTTGGGCATTTTTTCTCTGTGCTAACAGCCCAGATGGAGCCATAGCCTC<br>AACCTCTGTGTTCTGATAACACCAAGCTGGGACGCCGGAGCCATGCAGGGGACAGTGCCCGGCCTGAGGCTGCAGCCTGGGTCTGGATG<br>CCTTTCTAATTCAGGGCCTCCTCATGGCCTGGTTCCATAAATGGTCAAATGCAGCCTGACAGCGCAGCCTCCTATCAGCGCTGGGCTCCGT<br>ACCGCCACACAGCCCACATACCCCGTTCCCCAGGAGACGCCCGCAGGTGGGCAGCGTCACTCCCACCCGCCGAGCACACGCTGTCCCCG<br>TCTCGTGTCCCGAGGAGCCGGAAGCAGCTGCTTCCTCCCAGCCTGAAAGCTGCACCTCGGGCTGCACTCGGCTCCCCGAACCCGCCCTC<br>CGCTGCCCTGCAATTCGCCAAGGGAGCTACCCTTCCCATATAAAAATTTCACCTCCATTTCCTTGTAGAGAAGAAACATTTCTGACAGCAAG<br>GAAGATTCTAATTTGAAAAGCAAGTGATTCATCTCCCGGTGCCAAACAGCAGACGCAGGCGTTACCAGTCTGGGTGGGGCGCCCGAGCTG<br>GGGACCTGGGGTCCTCTGGGAGGGGCAAGAAGGCAGCGATGCTGGCCCCCGCCTCCATCTGCCCATCCCATCTGCTTCCACACACCGCC<br>CTGCCGTAGCTGCTTGCAGCCCTTCTCTGTCAGTTTCTCCATCTTTTGGTTTGGTGATAAATGAGAGTTCCCATCGGGTGTGCCACCCTCTG<br>TGTGACGGGGAGCAGAGAAGACCCTGCGTCCAAGTCCTCCTGGGGGAAGAGCGAAGATGCTGGGACCAGCCCCAGCTGTCAGGGGGTCTCCAATCCCAG |
| 234 | HSF2BP | GGAACGGAGAGCCGCCAGGCCCAAACCTCCCAGAATTTGCGCAGTATTCTCGGCCTAGAGAGCGAGGAGTGGCCTTGGCGAGGTCCCTC<br>TTTGGCTCTTCTGGCTTAGCCGGGGTTTTAAACTTGTTATCTGCAAAGCAGAAGGAAAGTCAGCCCCTGATGTAAGTGTCAAGTAAAATAAA<br>TCGGATGGGTCCTTTCCTGTTTGGCGAGGAATGCTACACTAAGGGGGACTGCGTTCAAATGGGCAGTCTTTGCTGGAAACCTCGCCTCCGC<br>GCGCCTTCCCTCGCTCGGATTCAGGCGCTTTTACGTTAAGGGTTGAATTTTTGTGTCAACAGGCACCTCGGGAGGTCGCCTAGACAACTGA<br>GCGGAGCAACTGAGATAACCCCCGCTACGTGTGGAGTGACCTAGTCCATTAACTTGCCCCAGCACGCCCGCTGAGTCCGCAAAATATAGG<br>ATGGCCTCGGGTTTTAGATGAACCCAAAGCTAAGATTTCTTCCCTCTCTGGAATTAGCAAGCAGCCCGCCCTGCCCAACTCCCCTGGAAGC<br>GCGCGTGCTCGCCAGGCCTCGGGACGCCTGCGCGGGCGCCCTTGCACTGGCACCAGGGCTCCGGGGTAGGGGCGCACCGATCTGCCCA<br>AGCCTCTGCAGGCACTGGAGGAAGGCGAGCCCTCCACCCGCTCAACAGGCCCCAGTGCCGGCCTTTCCTTCCAGTCTCAACTCCACCCG<br>GGGGCCCGGGGGCTCCACAGTTAAAAACTCCACGCCACGGAGATCGCAGGTAAGCTGCTGGCTCAACGAGGTGTGCTAAATGGGATTAAA<br>GATCCTGGACCGTGGCCAGGCGCGGCGGCTCAAGCCTGTAATCCCAGCGATCAGGGAGGCCGCCGCGGGAGGATTGCTTGAGCCCAGG<br>AGTTTGAGACCAGCTTGGGCAACATAGCGAGACACCGTCTCTACAAAAAAATAACAAATAGTGGGGCGTGATGGCGCGCGCCTGTAGTCTC<br>AGCTACTTGGGCGGTCGAGATGGGAGGATCGATCGAGTCTGGGAGGTCGAGGCTGCAGTGAGCCAGGATCACCGCCAAGATCGCGCCAC<br>TGCATTCCAGCCTGGGCGACAGAGGGAGACCCTGTCTCAAAAACAAACAAAAAATCCTAGACCGTTTACAAACAGCCTTCCGTCTCTTCCTG<br>GTCAAGTCCTAACCCTGGCTAACCTCGCCGTCTACAGCCTGAATTTTGGCAACCGAAAGGCAGCGCCGGCGCCACGTGCACACGGGCTGG<br>GCCGCTCCGCCAGCTGCCAGGGCCACTGCCGCGCTCACT |
| 235 | AGPAT3 | CGCACACACAGCACAGACGCCTGCATCTTCCCATGCGTGGTTTCTGCTCTTGCCTCTCTGGGTTTTTGTTTCACTTCGGTCGAGTTTTTGGT<br>GGTGTTGAGCGGATAGCCGGGGAAGTTGGAGTCTTGTTTGTGGCCGCCTCGTGCTCGTGTCTGTATCTAAGATCCTCAGGCTGCTCCTTTT<br>TGGGTAAGGTCTGTTGCTTCTCTAGGAACAGTGACGGTGGCAGAGCCCGTGGCCCCTCTCTCCTGTCCCAGAGCCAAGCTGTTTCCTCTCC<br>CCACTCCCGGGCACCCTGCGGGCAAG |
| 236 | chr21: 44446500-44447500 | CACAGCCCAGCTTCAAGCCTGGCCGACCAGGGGTTTGGCATGAAGACCCCGGCAGGGCTGGGGCTGTGCTGGAATCCACCCGGAAGTTT<br>CCTGCCCCTTGGGCTGCCCACCAGGTCCCCTTTCTGCTCTGATCAAGCTGGACAAAACGTCGTGGGGCCACAGCACAGGGGGCCAACGC<br>AAGCTGGGATCGTCAGACGTTAGGAAATCCCAAGGAAGAAGAGAAAGGGGACACATTCGGGAGACGTCGGCACACGCTCGAAGCAGCGG<br>ACAGGCACCTCTCTGTGGACAAGGCAGACTGGGCGGCCGAGATTCCGCATAGATGCCTGCTTCCTCCACGACCTCCACGTGTGGCTGGCC<br>CAGTCCGGGTCCCCCTCACCTCCTCTGTCTGTCTTGGTGGCCTCACGCCGTGGGCTGTGATGCCGGCTACGCTGCTTGGGTGGCCAAGG |

TABLE 6C-continued

| SEQ ID NO | GENE NAME | SEQUENCE |
|---|---|---|
| | | GTCTGAGCTGCAAGACGCCCAGCCTGGGTCTCTCCCGAGCTCTCCCACGTCCTGTCTGCTCCTCCTCCGAGCTCCCGGTTGACTCTCACG<br>ACTGCACCAGCCTCTCCCCCAGGAAGGCGTGGAAACAACCTCCTTCTCCCAGGCCCGCTCTGCCTCCTGCGTTTCAAGGCAAATCCGTTC<br>CTCCAGGAGATGATGCAACCACATCCTGTTGGAGCCCAGAGAAGTGCGGATGCAGCCCGGGGCTCTTTCTTTCCTAGAACCCTGCCTGGG<br>AGTGGCTTCCCTGAACTAAGGACAGAGACTTTGTCTTCGTTGCCTCTCGGCCTGTGGGCACTGAGCATACAGTAGGTGCTCAGTAAATGCT<br>TGCAGGCCGATGCCCAGAGCCATTAGCCCTCATCATGGTGAGCTCGGCAGCCGGTGTTGGGGCTGGGCTGGGCCTAGGTGTGCGTGGGG<br>GCGGTGCTGGTCTGCTTTGCTGGGAGCCATGGACACCGGAGGAACAGGGCCCCATCAGTGCGGTCAGAGTGCAAACTCGGAGCGTCCTT<br>CTCTGGAAAACGAAT |
| 237 | TRPM2 | GGGAGGGGGCGTGGCCAGCAGGCAGCTGGGTGGGGCTGAGCCAGGGCGATCCGACCCCGAACCGGAGCTTTTAGCACTTTGAGTCCCT<br>GTACTCAGAGGTCTCCTGCAGCCGGGAATCCCACTGTGCTGTGGTCCCTGGCAGCCAGCACCCACCCCCAGCTTCTCCGTCAAGGTTGAG<br>GACGGAGCACTCCTGCCTCTGATTAACTGGACGCAGGAGAAGCAGTTGCTTTAATCCGGAGCCTTGAGTTGGGACAGATAATGAGTCATTC<br>AACCAGATTTTCCAAGGACACACTAACTTTGGTATGATGCGTGTGTGCCCCTGAATCCACGTGGTCAGGAAAGCCCAGGGAACACTGGCCT<br>GTGACTCACTGAGCAGGTTCCCTTGTTACCCCGAGGGGTGATTTACTCCTCTGACAGTGACACGGACACTGTGCGTCCATTCCCCGGGCG<br>GGCAGAGGACACTCCCAGATGCCCACGAGGGGCCCAGCAAGCACTGGCCA |
| 238 | C21orf29 | CTGCAGGACCTGCTCGTTCACAGATGTTCTCCTAGAAGCAGAAGCTGTTTCTTGTTGCAAACAAATTTGCTGTGTCCTGTCTTAGGAGTCTC<br>ACCTGAATTTACCAAGGATGCATCTGTGCTTGGGGATGGCTCGGTTTGAGGGGTCTGAGGAGCGGCTCCCCTGGATCCTTTCCTCCCCAG<br>GAGCCCACCTGCCGAGCTGTCAGCGTCAGCCCCACATCTCAAGATGAGGAAATGGAGGTCGAAGCCATGCACACGCAGGCGTCCTGCTG<br>ACATGCAGGCCAGGCGGGTGCCTCTGTATTCAGCAGCCTCAGGGCTGTGGCCAGTTCAGGCAGCAGAGGGGCCTCATCCCGGTGCTTCC<br>CTGCAGGCAGTTGTGGGGCCGGCCTGCAGCAGGGGCTCAGACAGGGCCTTGGGAGAGGGAGGGATCACAGAGGTGTCCAGTGACAGGC<br>AGGGCGGGCAGAGCCCATGGGGCCTTGGGCTCCTCACTCCTTCGGTCAGTCAGGGTGACATCTGGAGCCACCTCCATTAATGGTGGGTTA<br>TGATTTGGTTCCCATGCAGCCCGTGCCAGCTCGCTGGGAGGAGGACGAGGACGCCTGTGATC |
| 239 | C21orf29 | AAGAGGAAATTCCCACCTAATAAATTTTGGTCAGACCGGTTGATCTCAAAACCCTGTCTCCTGATAAGATGTTATCAATGACAATGGTGCCC<br>GAAACTTCATTAGCAATTTTAATTTCGCCTTGGAGCTGTGGTCCTGTGATCTCGCCCTGCCTCCACTGGCCTTGTGATATTCTATTACCCTGT<br>TAAGTACTTGCTGTCTGTCACCCACACCTATTCGCACACTCCTTCCCCTTTTGAAACTCCCTAATAAAAACTTGCTGGTTTTTGCGGCTTGTG<br>GGGCATCACAGATCCTACCAACGTGTGATGTCTCCCCCGGACGCCCAGCTTTAAAATTTCTCTCTTTTGTACTCTGTCCCTTTATTTCTCAAG<br>CCAGTCGATGCTTAGGAAAATAGAAAAGAACCTACGTGATTATCGGGGCAGGTCCCCCGATAACCCCCAGCTGCAGATCGAGGCCTAGTG<br>CGAGCACAGGTCCCCCCAGACCCTTCCCAGTGCCCACCAACCGGCGGCCTAGGCCAGGTAGAACTGGCAGCGCCTCCCCTGCTGCAACA<br>CCAGGCTCTGGTAGAAACTTCAGAAAACATGCACCGGCAAAACCAAGGAAGGGTGGCTGCGTCCCGGGTTCTTCCGCGCAGCTGTGTGTA<br>CACGCATGCACACACCCACACGCACACACCCACGTGCACACCCCCATGCACACGCACCCACTTGCACGCCCATGCACGCACACACGCGC<br>GTGCACCCATGCGCACGCACCCATGCACACACACGCGCGCACACACCCACGTGCGCACCCACATGTACACACCCACGTGCACACACCCAC<br>GCGTACACACCCACGCGCACACACCGCTGTCCCCAGCCGTGCAGAACGATCCTCCCTGAGTCCCCGGCTCCGACCCACACGCAGCACTC<br>GCTAAACGCTTCCCACGCAGTCGTTTTGCTGGGTTGCGCTTCACCCACTTCTCAGAGGGGGCGGCCGAGGCAGAGGTGTCGGGGATCGA<br>GCAGCTCCGGGCCTCAGGGGTCGCCCCGCCACCGTTTTCCTTTCCCAGATGCTGGGACGGGGGCAGGGAGGGGCTCCCCAGGCTGAAC<br>CCGACTAGGTCACCCTAGAAGCGAGGCGAGCTTCTCTTCTGTTTTTCTTCGGCGCCCCTGAGCCCCTGACAGTGCCCAAGCTGCCCATGG<br>GATTGGATTCGCCAGAGCCTCCTACGCAGACCCCACCCAGGGCCAAAGCCAACCCCAAGCCCCACCACCTTGGTGGTGTGGGATGAAAAG<br>TGAGCCATCGAGAGATGGGGTCCCCCCACCCCCAACCCCTCCAAGGACAAAGGCGGGCTGGGAAGCACCCGCTTTCACGTCCGCCCCTG<br>CCCGGCTTTCCTAGCGGAATTGGCGCCGGCATCAGTTGGGGGTTGTGGGATCAGTGAGGAATCCCGTGGGGTCGCCTCCATTTATCAGTT<br>GTGTGGGGTTGGGCGAGCACCCCTAGCCCCAGCCCAGGCGATCAGGGCGCGAAGCCCACTGGACGCGGATTTGGGATTAGGACGGGGG<br>TGACAGCCAGGAGGACCGCACCTGCCCTCCCCACTCCTGCCGCTCCACCCCTGCCCCCACCGCAACACCAAGGTCTCCACCAGGAAGAT<br>GGGGGTGGGGAAAGGACGCGGGGTGGGGGGGGGTGCGGGGAGAGAGGACACAGGGTCGGAAGGGTGAGGGGTAGTGGCAGAGGCGG<br>AGGCCGAGGCCACGCAGCTGCGGGGCGCAGGGAGGGGCAGAGGAGGGGCGTTCAGATGGGAACCTAGTCCAGACCCGTCGGGGCCCT<br>CGTGTGCGGCTCGTTATCCTGGAACCAGAGAGGCTGGAGACCCTTGGCTTGTCTGGAGCGGAACCGTAGTGTCCAATAGAGTGTGTGGGG<br>CTCAGCCCTAAAGCTAAACATTCTTTATTTCCTGATGACCATGGGGGCGGAGCGGGGGAAAAGCCCTGGCCTTATAGTTTAGAATTTTATAA<br>AAGGAAAGGCGTGGCCACTGACAATTTGCGCTTCAGGAGTCCCAGAGTGACCGCCTGGCTCGGAGCAGGGAATGAGGGGGTCCTTAACT<br>CTGAGATTTGTTTTCTGAGAGACAAAGGTGATGGGTGAGGCGGCTAAGCCTCTGATTCTCTATAGGTGGCGGTCATTCATTTCAGAACATGA<br>ATGGATTCAGTAAATAAACATGATAGAAAAATGCCACAAGCCCTAGGCCCATTGGAGTGGACTGGACAGTCTGTTCCCAGTGTGTCCCTCA<br>GCCTCGGTCCCCCACCCTTCCCGGAGCCCTGGGGGTCACACACATCCCTCCTGGCTGCCTAGCCTGTGCCCCCCGATTCCCCCCCTCCC |

TABLE 6C-continued

| SEQ ID NO | GENE NAME | SEQUENCE |
| --- | --- | --- |
| | | CGCCCCGCGCGTGCACACACACACACACACACACACACACACACACACACCACACAGCACGAGGCGACAGAGATATGAGAGAGAGCG<br>AGCGAGAGAGGACGGGAGAGAGAGGGAGTGCAAGTGTGCGCTGGGGGTAACCCGTGCATGCATGCATTGGGGGTAACAGGCTGGAGCT<br>CAGATCCCTCCCCCAGCCCCCAGCAGGGGGGACTGCAGGCTCCTGGTCTGAGTGGGGAGCTGGGCCCCCTGGACAGAGGACTGGGCTG<br>CGGGGTCAGGAATGGGCACACTTCCTAACTGCAGGACACTCTAAGGGCTTTGGTCATGCACACGCAGCCAAGAGAAGGTGTCGCTGGCAC<br>ACAGCCTTCCAGGAGCGGACTTGGAGACCTCGCCAAGGACCAGGACTCCCCAGCACTCACACTCCCTTAGGCGCTGAAGTCCAGAGGACA<br>GAGGTTGAGGGCAGAGCTCCTGGGAGCACCAGTGGAAGTAGGAGGGCTGGGCTGGAAAACCTCCCCCAACCTCCTATTGCAAAGAGGCT<br>CCAGCCAGCAGCCTCCACACCCCAGTGATCTTTTAAGATGCAAATCTGCGCCATCATTTATTTCCTCAGTGCCTTCTCCAGCTCCTGGGATG<br>CACACTGCCCGTCCCCAGGCCCAGAGACCTGACCACCCTCATTCCTCCCTCAGCCCACCCTGGGGTCTCTCCACCAGCTGACAGCCTTCC<br>TGCAGTCCCCTCCCCGAATGCTGCTCCCTGAGGCCCTCCTGGACACCTGCAGGGCAGGCACAGCCCGCGGGACCTCACAGCACTTGCTC<br>CGGGCAGAGCTGCAGTTTGGCCAAGTTGCCAGCTCCGTGTGGGCAGGGGCCCTGGCCTGTGGCTGCCACATCCCGGGTGGGGGCACGG<br>CCTTTCCTGGCGTGGATGCTGAGCAAACGTAGGGGGAAGGGGAGTGAATGAGGAGAGCCAGGTAGCTCAGGGGCTGAGGCCTCACTGAG<br>CAGGGTCCCGCGTGACCGGTCCCCACCGCTGACGGTTCCTGGGGTAACACTCAGGACAGGGAGAGGCAATGGAAAGAGACGTGGCCGC<br>CCTCGCATCCTGCAGCTCCCGCACTCCCAGCCTCCCAGCCTCCCACCCAGCCCCCCAGAGCCCACCAGTGACCCCGCCCACTGGGTCCT<br>CAGATGGCTCCCACGGGATCTCCTGCCTTGATCTCCTGTCCACATGGAGGTGAAGTGGGTTGCTCTGAATGAGGGGTGCCGAGCCTAGGG<br>CGCAGCCCACTCTCCTGGGTCCGCAGCATCACGCAGCCCGGACCACAGGCTCCTTACAAGAATCGGAAGGGTCCCTGCAATCGCCCTTCG<br>CACTGAGGCTTCCTACTGTGTGGTGTAAAAACACAGGCTTGTCCTCCCTTGCTGCCCACGGGGCTGGAGCCGCCTGAAAATCCCAGCCCA<br>CAACTTCCCCAAAGCCTGGCAGTCACTTGAATAGCCAAATGAGTCCTAGAAAGCGAGAGACGAGAGGGGAATGAGCGCCGAAAATCAAAG<br>CAGGTTCCCCTCCTGACAACTCCAGAGAAGGCGCATGGGCCCCGTGGCAGACCCGAACCCCCAGCCTCGCGACCGCCTGTGACCTGCGG<br>GTCAACCACCCGCCGCGGCTCCACGCCGTGGGCACAGACTCAGGGAGCAGGATGAGAAAGCTGAGACGGCGCAGCCACGGCCCGGTGC<br>CTTCACGCGCACAGCGACACAGCCCCAGCCAGCGGGGCCCACGCTAAGGCGGAATCCCACAGAAGCCTACAGAGCGAGCGCGCGCCTG<br>TGCTTCCCAAAACGGAATGGAACCAAGGTGACTTCTACAGAACGATCTGAAGCCCTGGCTGGCCCTTATGCTAGTCTCTTGGGAGCGTTCC<br>AAATGCAGCTCAATATTACTTACTTGACTTTTATCTTTCCTCCCTGGTTCGTGGTATTTATAACTGGGTCATCTTTTAACTATTTGCAACGTAG<br>CTTCAGGGGAGAGGGGGAGGGCTTTATAAATAACCTGTATTATTATTATGCAGGTTGATTCTGTTCCCTGAGCTAAAGGGAACATGAAAATA<br>CATGTCTGTGACTCATGCCCCCCCACCCCCACTCCAGGGTGTGCTGAGGAGTCTCTCAGCTGCCCCGGGGTCCTCGAGCAGGGGAGGGA<br>GAAAGGCTGGCGCTGCGCCCTCCATCGCGTGAAGCCAGGGGATTTTGCTCTGCGACAAGCTGACTTGGCTCTCGTATTGTTTGCAGAATCA<br>CCCAGTTCCAAGGCAGTCCCTGCGGGCAGGTGCAGCTGTGCGGGAGCTTCAGTCCTGTCCCCAACACCCAGGCAGTAATGGTTCCAGCAC<br>GGAAGGTCTACCTACCTCCCACTGCACAGCCCGAGGGCTGTCCTGGAGGCACAGCCATCCGTCCCTGGGTGGGCAGGCACGTTTATGAC<br>CCCCACCCCCACCCCCACCCCCCACGCGAGTCAGCACGTTCCATACTCGGGTGATCGTGCTCATCCCCTGGTCATGTCATCGGGATCTGA<br>GTGCCATCCGAGCAGAGAGCTGTGGCCCGGTGCCGGGGGTGGACTTCATCTATTCCAGGGAACCAAGGATGCATGATTTGCAAACAAAAC<br>CAGAAGCGCAAGCCATCTCCTCGCCTCCCCTGATAGCCGTGCTGCGGAGCCTGAGTGCTGGAG |
| 240 | ITGB2 | CAGGAACCACGGGACCTGCTGCCTAGCGGCCCTGTTCCACCCTTGGCCGCTCGCAAAATGTTTAGGCTTCATAAGGTTTGCCCAGGGTCA<br>CAAATTTAACTCACAGCAAACAATGAAATCAGCGCATGATTTTCGAGCCCTCGTGGTCACCCTCCCTTCCTCCTGCCCTTTCCTGCATGGGC<br>AGCAGCAGGGTGAGGAGCTGCTCTCCCCAGGCCCAGGCTGGAGTCCCTCAGACGACCTGCCGGCCAGGGTACCCCCCTGCCCCCACACA<br>GCGCCTGACAGAGCCCCCCACACTGGGGGAACGTGGGGACCCAAGCAGGGGCAGCGGCCTCACCGGGCAGGCGGCGACCTGCATCATG<br>GCGTCCAGCCCACCCTCGGGTGCATCCAGGTTTCCGGAAATCAGCTGCTTCCCGACCTCGGTCTGAAACTGGTTGGAGTTGTTGGTCAGC<br>TTCAGCACGTGCCTGAAGGCAAACGGGGGCTGGCACTCTTTCTCCTTGTTGGGGCATGGGTTTCGCAGCTTATCAGGGTGCGTGTTCACG<br>AACGGCAGCACGGTCTTGTCCACGAAGGACCCGAAGCCTGCAGGGCACATGGAGGGGCTGG |
| 241 | ITGB2 | TGCGTTTAGTGTAAAAATATCAGGTGTGGCTGCACGGAGTGAAAAATCACAGGCTCCACGGAGCCGGGAGGCCTGCTGCCCTGCCCTCTT<br>GCTTTGATGAGGAAATGGCGACCGCAGAAGGAAATGTAGCAGCACCGGCAACCGGCATCCGTGGGGCCACGCCGGGCTGCTTCCCAGGG<br>CCCTCCAGCCAAGCAGCCACAGGAAAGAGTAGATGTTGATCCCAAGCTAGGACTGAGGAGTCCGTCCCTAAGAGCCGAGGGAGTCAGGTG<br>GGCGAAACTGGCCGCATGTCTGGGTACAACTGCTCAGGGTTTCTCATCTGCTGAATCACCAAGCTAGGTTCTGAAGCCAGGCGTGAGTGA<br>GCAGGACTGGAGCAGGATTCTGGGAACAATCTTTTCCCTCC |
| 242 | POFUT2 | GCTGGGGAACTGAAGGAAGGGCTGTGGAGCCTGAAGCCTGGGCCTGGCCTGTGCTGCGGCCGCACCGCTGGGTGATGCAGGAGCCACT<br>CCACCTCCCTGGCACCCCAGCCTCATCCGGCAACCTGGGAGCGTGGGCCTCCTGCCCCTCCAGGGAGGCCCTGGCCGTGTCCTCATGGG<br>GCCCCTCCAGGTCCTTGTGGCTCCAGGTCGGGACAGTGGCTGTGAGATCTGACCCTCCCGTTCCCCCTCCACCAAGTAGGAGAAACCCCG<br>GAGCATGAGCCCTCGTCCTTCACCGTCCCGGGGACAGGGGGACCCCCAGATGCTGCACGGCTGACAGGCCAACGTGGCAGAAGCTCCAG |

TABLE 6C-continued

| SEQ ID NO | GENE NAME | SEQUENCE |
|---|---|---|
| | | CTTCACAGGAAGCCAGTGACCATGAGAGTCTGTAGCTGTAACGAAGCCACAGAGCTGTGGCTTTCTTTCCCCTTCAGCTCTAGGAAAGGTT<br>ATCTGCCCTGCACAGATCTCCGGAGGCCTGGCTGGGCTCTGAGAGCATCAGACTGATTATCGTAAGAAAATAATCTCTGCAGACACATTCC<br>TTGCTAGAAGCAGGGGACAAAGCCCAGCTTCAAAGACAATTCCACACACGCCCTCCCTGCCCTGCACAGCTGCCTGCCGGGTGGGAGCAG<br>AGCCCTTGCAGCCGGGCTCAGGGGCCTGGGCAGGGACAGCGTGTGGCAGGGGCACAGCTGAGACAGGAGCCTCAAAGCGACACCAACC<br>CGACGTGAAGCTACAGTTGAGGAGACACAGCTGCCCCCATTCCCGGGCCTCATCTCCACAGTGAGACGCTGGACTCTCTCCCTGACCCAC<br>CGTCTCTTAGAACCTCCCCTCCATCCGGAGCAGTTCGGCAGCCCCAGGGCAGCCAGGGGAACCCTGCCGAGTGCCTCTGGGCCGCCACA<br>GACCGCAGAGCCCGCGGGAGCCTTGCTCACACAGCCTCAGGTCCACTGTGGTCTTGGGGGAAAGCCCTGTCCTGGGACAGGGGAGCCG<br>GGGGTCCTGGCCCTGGACCACCATCTGGGGACCACGTTGTCACGCCTGCAAAGCTCCCTGCCCCACCCCCATGTGCCGGCTGGTGTTGA<br>CACCTTTGTAGAGTGGGAACCTGCCTCCGACCCCAGCCTGCAGCCACAGGGCAGGTTATAGACCAGGTGAGAGGGCGCCGCGCCCAGAA<br>CCAAGGAGCACAAGTCCGCAGTGCCCATGAGATCCTCATGCTGGCCGGCGCAGGAGCCATCCTCGGCCTCTGCAGGTCCTCGTGGGAAA<br>CCGCGGGGGCACGTGGGGCGGCTGCAGGGTCCGCAAAGCCGGCTGTTTGCGAAGGGCGCAGCTCCACCTGGAACAGCCGAGGCCGCC<br>CACGCGCTTCCCGCGGGATCAGAGCAGCCTCCACGGCTGTTGTCTCAGGCACCACGGGATGCCTTTCTTCGTTTCAATAGCTGTGGGAAA<br>GCCTCAATCGGTCCTGAAAGAACCCAGATGTGCAGCAATGACAAGGCCTTCTCTGAGACTCTAGAACCTTCTGCCATCTCAGACAGGAGGG<br>AGCCGTGAGGCAGGCGGGAGATTTGCAGTCAGCAAAGGACGGGCAGGTGGGGCAGCTGCACACCCAGGGCCCTCTCCACGGTCTTCCC<br>GGGCCCACCCCTCCCGCGGTCCTGGGTCATCCACCTGCTGGCCTCACTCTGCCCACGCGGCCAGGTCCCACCGGCCCCTGAGCTCAACA<br>GACCAAAGCTGGCCCGACCCCACCCCCAAGAAGAATGAAACAATTTTTTTTACCTCTTGCAGAAAAGTAAAAGATCATTTATTCATTCTGTT<br>TCTAGATAGCAAAACTAAGTGTCAAAAGCACCTTCTGCACACAGTCTGCACACACTGGCCGGTGGTCCTGTTCCCGCAAGGTTGAGCTGTG<br>TTCCAGAGACATGGGTCCTCCGGGTGATGAGGAGCCGCTGGAGGGCCCTGAGCTGCACGTGCTAATGATTAACGCCCCGTCCGTGCTGG<br>CCGGTTTCTCAAATGCCTCCTGACGATTGCGC |
| 243 | chr21: 45571500-45573700 | GGCCTGAGGAGTCAAACGGTGCAAACCCTGCCCCACTCTGTTTGGGAAGCACCTGCTGTGTGGCAGGCGCTGCGCTTGGTGCTGGGGAT<br>AGACCATGGGGAAGAAACACACAGAACCTGCCCTGCTCTCAAGGAACAGGCCCTGGGGGCGGCCAGGGGCAGAGACCCAAGGCAGACAC<br>CCACACAGTGGCGTAATGACAGTGCTTATGGTGGGGACCTGGCTGCACAGCAGGTCAGCAAGGGGATGTTCAGGTGACACTGGGGGCAC<br>GGAGACCCAGGGGAGAGTGGATTGACAGAGGGGACGCTGGGCAAATGTCCCGAGGCTGAGGTGGAGTTGCGGGAAGGAGGAGGCTGCC<br>GGGCAGAGGCGCAGAGAGCTTTGCAGGTGTTGGCAGAGACCAGCAGGCCCTGCGAGGCCTGGGGTGTGTCCTCAGCTGGGAGGGCCAT<br>AGAAGGATCTGGGCTTGCAGATGCTGGTGCAGACTGGAGGCCTGGGGTGTGAGAGTCCAGGCGGGGCTCCTGCCAACACCCAGGGGAGT<br>GGGCCTGGGCCAGGTGGACCGGGAGCTGGCACGGTGGTCAGGTGCTTGGAGGCTGCGTGCCACGCTGGGGACCTGGAGGTGTGTGAG<br>GAGGTGTCTGTTGCTCCTGGGGCTGCCGCCTGCAGGGCTGGGTGTGCAGCAGTGCGGGGCAATGAAGTGGGCGGGTTCTGGGATGGTG<br>GACGTTCCCTTTGTTGGGAACGTGTTGGTGCCAAGCTGCCATTTGAGTTTGGCTCTGAGGGGTCTGGGCAGGGGACACACAGGGAATCAC<br>ACAGGATGGAGTGAGTTCCCAGGGACCCAGGGTGGCTTGGCCTGAGAACAGCTCCCACTCCCAGATGTGTGGGAAGCCCTCGGCACCAA<br>GCCTCAGCCTCTCCATCTGTGAAATGGAGACAACGTCACTGGACTTGCAGGCTGTCCATGAGGGTGATGCGATCAGAAAGGGTGGAGTTC<br>CTGAACGCCCCGGGGTCGGGGTCTCACAGCAGGAGCTTAGCTGGTGTCGGCATCTCCTGGACCCGTCCTCAGCTCCGAGCGCCCAGTCC<br>TGCCACCTGTGTCCAAGTCTGCACTGTGCCCACGAGGCCCTCAAGGCCGCAGACAGCCCCACACTTCTCGGACGCCGCCCCAGCACGGT<br>CCTTGTGTGAGGTGGACACTCCTTCTGGACGCCGCCCCAGCACGGTCCTTGTGTGAGGTGGACACTCCTTCTGGACGCCGCCCCAGTACG<br>GTCCTTGTGTGAGGTGGACACTCCTTCTAGGGAAGGAGTAGTAACTCTTGGGTGGTCGGGTAGTTGCCATGGAAAGGGGCAGTAATGCCC<br>AGGTATTGCCGTGGCAACCGTAAACTGACATGGCGCACTGGAGGGCGTGCCTCATGGAAAGCTACCTGTGCCCCTGCCCTGTGTTAGCTA<br>GGCCTCAATGTGGTCCAGTATCTGAGCACCGCCTCCTGCCTCAGATGTTCCCGTCTGTCACCCCATTACCAGGGCGGCACTTCGGGTCCTT<br>TCCAGCCATCATTGTCCTGGCATTGCCACAGTGGACACTGCCACACAGGCTTGTGTGCTTGCGCGTACCCAGGTCCTCACCTCTCTGGGAT<br>AAACCAGGCACGTGGCGGCCGCCCCATTTTCCACCCGCCAGCGGTGGAGGAGTTGCCCAGCCTTGCAGGAAAACAGCTCTCATGCCAGC<br>AGCGGAGCATCCTATTCAAGTTTTCTCAGGGCTGCCAGCACAAATGCTGCATGCCGGGCGGCTTCCTCAGCAGACCGTTGTTTCTCTGCGT<br>CCTGGAGGCTGGACGTCCCAGGTCCCCGTGTGGCAGGCCCGGTTCCTCCCGCAGCCTCTCCTTGGCTTGTGGGCGGCGTCTCCTCCCTG<br>GGTCCTCGCAGGGCCACCCCTCCGTGTGTCTGTGTCCTCCCTCCCCTTATAAGGACCCCAGGCAGACTGGATCAGGGCCTGCCCTAAGGA<br>CTGAATTTTACCTTAATCACCTCTTTAAAAGCTGTCTCCAAATACAGTCACCTTCTGGGGTCCTGGCTGTTAGGGCTTTGATGCATGGATTTG<br>GGGGACACCGCTCAGCCCCTAACAGCCCCCATCCTCTGCCTGCCTTTACCATGGGGCTGAGCCCAGCCCTGCAGGAGTCCCCTGGTTTGA<br>TGTCTGCTGTGGCCACGGCGACCCTCAGGCTGCTCCAGCCGCACTTGTGCTT |
| 244 | chr21: 45609000-45610600 | GGGGAGTCTCCAGGGGCTGGGGCTGGAGCCGCATCAGAGAGGAAAGGGGTGTTTGAAAAAGGGGCAGGGCCTGGGACCCAGGAAACTG<br>TTCTTCCAGAGACACCCGTGAAGCTGAGCTTTGCCTCTCAGGGAAGCTGTGACCCCACGGGTGCTGCCCAGAGAGATCGGGCCAGGTGGA<br>GCCAAGATGGACTGGAATTCCCCGACGGGGACAAGGGGCCGGACGAGGCTGACTTGCCCTGTCTGATGAATGGTCAGGTTTGCTTTTTCT |

TABLE 6C-continued

| SEQ ID NO GENE NAME | SEQUENCE |
|---|---|
| | CCTGAAAACACGAGGCAGTGATCCCGGCCAGCTAATTCCAGCAGACTGGAGACGGGATGGTGGAGAATGAGGCTGTGGGCGGGAAGAGC |
| | AGATGGGACTCGCCAGCATCCTCACGGCAGGGCCGCGCTATTGCCCTCCCTCCCCTCCTACTCTCTGGGGTCCCAGGAGCCCCAGATACG |
| | CAATGCTGCCAGGCGATTTCTGGCGCCCCGCAGACCCCTGCCCCTGGAGTTGGGCCAGGTCCCGGCTGGAGCAAAGGGGGCTCCTTCAA |
| | GCCCGCTCCTCCCTGTCAAACCCGAGGAGCCTGACAGGCGCAGCGTCACCAGCGTCACCGGGCCATAGTGAGCGGCCAAGCCAGCGTCA |
| | CCGGGCCATAGTGAGCGGCCAAGCCAGCGTCACCGGGCCATAGTGAGCCGCCAAGCCAGCGTCACCGGGCCATAGTGAGCCGCCAAGC |
| | CAGTGTCACCGGGCCATAGTGAGCGGCCAAGCCTTGGTCTGCCAGAGCCGGCCGCACCAGAAGGATTTCTGGGTCCCCAGTCCTGGAGG |
| | AGCACACGGTTTACACCAGGCCTTGGGAGGGGAAGAGGCAAGGCGTGGGCCCAGCCCTCACTCCCCAGGAGAAACCCTGTTTGAGCGGC |
| | AGAGGAGACTGGAGAGACCCCAGGGCGGGGATCCCTGAGAGGAGAGAAACCCGGAATTCATCCACGGAGGCGTTCACCCAGAGGAGACC |
| | CGGAGCTTCTCCAGGAGAGGCTGGATTGCTCCAACAGGGGCCCTGAGGAGCTGATGGCAAGAGCGGAAGGCAGCTCTGACTCGTGCGTC |
| | TGACTCCAGGTGTGGCCGTTGGGGCTACAGTGGGACCAGCCTGTTGTCACTGAACCCACAAAGTGCCTCCGAGCGCGGGTGGAGAGAGG |
| | GGGACCTCCCACCGTCTGCTGGCCTTGAATCTTGAATCTAATTCCCGTCTGTGCTTTGATGGGAGAGGCACTGGGAGCGGGCGGCTTTTTC |
| | AGTTCCTTTTATCTTGAATGGCCTTTGGGGGATTTTCACAGATTCTGAGTTCAAAGCCCAGGGAGGTGTGGGAACGTGACATTCCTCACCGC |
| | ATTCCTCACCGCATTCCTCTGTAAACCAGGCGGTGTTGGCACCCATGAGCCTGTGTCTTCTATGACATCAGGAGTTTTATCCCTCACGTCAG |
| | AAATCAGGGTTCCAGGCGCCTTGGTTTTTCTTGGCGCCAGCGGCTTGGCTATAGAAGAAAAACTGAAGGGGCCAGGTGCGGTGGCTCACA |
| | CCTGTAATCCCAGCACTTTGGAAGGCCAAGGCGGGTGGATCACGAGGTCAGGGGTTCGAGACCAGCCAACATGGCAA |
| 245 COL18A1 | GCTCCTCAGGGGGAGGTTCGGGGCCTTTGGTCTCTGGACTTGGGCAGCAGAAAGGAAACATCCCTGGGGGCCTGTGGTGACCCCCATCC |
| | TCCCCAGGGTGGTCTGGCAGGGGACACTGTTTTCCAAAGCAAAGCCAGAGCGCCAAGGGCTCTCGGGATTCACGAGATCCACATTTATCC |
| | CAAGTTAGAACAGCACATCTGTGCGTGCAAACTTCATTCTGACTTCGGCCGGCTGTCCTTCTTGCCCAAAGCACCGTGAGGCCTCATCCCT |
| | GCATCCCTGTTGCTTCTTTCATGTGGGATGAGAACCCAGGAAGGGGCTGAGTGTGACTCCTCTGGTTTTTAGAGAGCACTGCCCCCGCCCC |
| | GCCCCCTCCTGCTTCCCCACCTTTTCACAGTTGCCTGGCTGGGGCGTAAGTGAATTGACAGCATTTAGTTTGAGTGACTTTCGAGTTACTTT |
| | TTTTCTTTTTTTGAGACAGAGTCTCGCTCTGTCGCCCAGGGTGGACTGCAGTGGTGTAATCTTGGCTCACTGCAACCTCTACCTCCCGGGTT |
| | CAAGCGATTCTCACATCTCAGCCTCTGGAGTAGCTGGAATTACAGGCGCCCGCCACCACACCTGGCTAATTTTTGTGTTTTTAGTAGAGATG |
| | GGGTTTCACCATGTTGGCCAGGCTGGTCTCGAACTCCTGACCTCAGGTGATCCGCCTGCCTTGGCCTCCCAAAGTGCTGGGATTACAGGT |
| | GTGAGCCACCGAGCCTGGCCTGGAGTTATTTGGGAGAGGGCAGCCCCTGGTTCAGCGTGGCGAGGCTGCGCTTGCTCTCCCGGGCGGG |
| | CGTCCACACCCTCCTCGCCGAGATGGAGAAGCCCAAACCCCTGCAGCGCTCCCCCATCACGTCCGGCCCTGGAAGCCCCCGGAAACCCT |
| | GCCACGCCCTGAGTGGGAGAGCGCAGGTCCCTTTCCGGCCCTGGAAGCCCCCAGAAACCCTTGGGTGCCAGGCCTGGCCGGGACAGCA |
| | GCGACACTGCATGCTCAGCCCTTGCGTGAGACCACGGGAGTGTCCGCCCTCTGCACGTGCTGCTGATTGCCCACTTCGTCCAGCAGGTTT |
| | GGGAGCTTGTGGCTGCATCCTCCTGCAGACACTTGCCCATTCTGGGGCCTCCTCTCTGTCTTTTCTCCTCTGTTGAGGGGTCTGGGAGGGA |
| | GGCCTTGGAGGGTACCCATGCTGCTGGGACTGATGCTCCCCGCGGTGGAAGGAGCTGCCTCTTGAACAGCAGGGGGCTGAGCAGAGGG |
| | GAGGGGATGCGGGGGTGCCGTGCACACAGGTGCTCTCAGGACGCAGGGGCTTCTCAGCCCTGCTGTCCCAGGGCTGCACTCCAGCAGG |
| | GCAGACTCCTGAGGTGCAGACACCCCAGCTTCACGCTCACACTTCTGGAAGGCGATGTCTGTGCGTTTGCTTTCTGCTGCAGTTTAAAAAG |
| | CCGGGCTCTCTCCGGAGCGTGTGTAGGGCCTGGTCACTGGAATATCTGGACTCAGTGTTAATGGCAGCCACGCTGGGGGCTGGGCCCAG |
| | CTTTCTGTTCTCCGTGTGGGTGCCATATCCACCTCCATCGCAGCCCTTTCTCTCTCGACCTTTTAAATCACAGTGTCACCTCCCCCTGCTGT |
| | CCTGCCAGTGGCCCCTGGAGGCTTCTCCCCACCCCTTTCTTCTGGGGCAATTCTTAAGGCTGGCATTGAATCAGGAGGCCAGATGTGGCC |
| | CCTAGTAACTCACCAGCAGTCCCTGAGGCTTCTGGCTCCCCTGGCCCACCAGCCTCCCATGTCTGCCTCAGGCCTCTTGACCCGCCTGGC |
| | ACTGACCAGACTGTGTGCCCGGGTGCCGTGCCCATGGGCTCCGCCTCCCCCAGGCAGGCCCCCTCTTGCTCCGCGGCCACCCCTGCTCT |
| | TGACCTCACACCTCTGCGGTGTGTCTGGACACACCAGCACCACGGCGGGCGGGGAGCGGAATTCTCCAGGTGGGGTGGGCAGGCCGGC |
| | GGGTGTTGAGGTCTCTGTGCATGCTTGTGCGTACCCTGGACTTTGCCGTGAGGGGTGGCCAGTGCTCTGGGTGCCTTTGCCAGACAACTG |
| | GTCTGCCGGGCCGAGCATTCATGCTGGTCGCCATCACGTGACTCCCATGCGCCCTGGCCCTGGGGTTGGGTCTGCAGGACTGAGAACCA |
| | GCGGAAGGGGGGCGAGGCCTCGGGAATGCGCCGGCAACTGGCGATGAGCTCAGGCCTGACTAATGAGCCCAGGTGACTCATACACCCG |
| | GGGCCTGGATGAGTCTGACTGGGTCAGGACTTCCCTGCTTGTTCTGTCCTGGGAGATGTTGTCCCTGGCCCTGCAGAGCCGGGAGGACAC |
| | GAGGCCTCCTGGGTCACAGCCAACGCAGCCTACTCCTGCCCACTGCTCGCGCCGGCCAAGGCCCGTCGGCACCACCTCCTCCATGAAGC |
| | CTTCCTGACTGCCCCCATCCCTCTGTGGGCAGCTCGAGTGTGCATCTTGAGTGCTGTGCAGGTTGGGGTCCGGCGCTCCTGCAGGCAGGC |
| | GGCGTCTGGGCCTGGGGGCTCTCAGAGTTTGAGGAGCGTGTGGTGAGGGTGGCCTCGGGCCTCAAAGACGCAGCGCTGTGGGAACCGG |
| | GAGACTGGCTGAGCCCGCTCTGAGGAAGGTGGGGCCAGGGGCACCCTCAGCTGACCCGGCGTGCAGGGGTGACCAGCCAGGCGTGGCC |
| | AAGGATGGGGTCTCTGGGATCAGGAGACTTCAGTAGCAGCCAGGACCGAGGCCACCAGTTTCCACCCTGGCATTTTCCATCTTTTGAAGGA |
| | CTGGAAACGATTGGATTCTTTAACTTTTTTAAGTTGAGGTGAAATTCACAACGCATAAAATTAACCATCTTAAAGCGAACAATTCGGTGACATT |
| | TAGTACAGCCAGAAGGCTGTGCAGCCATCACCACTGCCCAACTCTAGAACATTCACACGCCGGAGAGAGGGAGCCCTGGGCCATCACGCA |

TABLE 6C-continued

| SEQ ID NO | GENE NAME | SEQUENCE |
|---|---|---|
| | | GCCACCGCCCGGCCCCAAGAACCTGCGAGTCCACTTTCCACCTCTGGATCGGCGGTTCTGGACGTTCATGCAGGTGGTTCCCGCAGTGCG |
| | | AGGCCTTTTGTTTCGGGCTCCTCTCACAAGCCTCACGTTTCCAGGTACGTCGTGGTGTTGTGCAGACCCACAATTCATCCCTTTTCATGGGT |
| | | GTGTAATAGTCCACCATAGATTCTCTACGTTTTAAAGCATGTTTTATGTGCCTGAAATGTCTCTGCACTCGAGACTATAGCTTGCTTTCTTTCT |
| | | TTTCTTTTTTTTTTTTTAATTTGAGACGGAGTCTTGCTCTGTTTTCAGGCTGGAGTGCAGTGGTGCGATCTCGGCTCACTATAACCTCTGCCT |
| | | CCCAGGTTCAACTGATTCTTTTGCCTCAGCCTCCCGAGTAGCTGGGACTATAGGCGCGCCACCCCACCCGGCCAATTTTTTTGTATTTTTAG |
| | | TAGAGATGGGGTTTCATCATGTTGGCCAGGATGGTCTCGATCTTCCGACCTTGTGATCTGCCCGCCTCGGCCTCCCAAATTGTTGGGATTA |
| | | CAGGCGTGAGCCACCGCGCCCAGCCGAGACTACAGCTTTCTTTAACTGCATCCCTGGAGGGATCTGAGAGTCTCTTTCCCTGTCTCCTTTC |
| | | CTTTGGAAAACATTTCAGCCAGGGCTCCCCAAGATGAAAGGCCAGAGTCCCAGGCATGGGCGTTGCAGGTGCACAGTTGCCACGGGGAGC |
| | | TGTGGGTGATGGTCGCTGTCAGCGATGGCTGCTGCAGGTCCCTGTGAGGAAGGGGCAGTGCCACAGCAGGAGGAGAGGGAGTCAGCGG |
| | | ACGTTGATTGGCAGTGCCCGCCCATTCCATCATTCAGTCACCCACTGTGCACCCAGCACCCAGGCTCGGCTGCATAGAACATGGCCCAGG |
| | | AAGGCTCCACTTCCTGTCTCCTCTTCTCCCCTCTCCAGTCTCATGATGGGGCTGGAGGCATCTTCTAGTTTTGAGTTCTGAGCTAATGAACA |
| | | TGCTCATGAGCAGGCGGCAGGATCCCAGGACGGTGGAGCTGGGAGCCTGACTGCGGGTGACGGACAGGCTCTGGCAGCCCCTGTCAGC |
| | | ATCCTCTCCAGGGCATGTGAAAGCCAGTGTGTCCTCAGCTGCCAGTGCCCCCTCCCCACCTCCTCTGGGCCCATGTGCACGGGACCTGGG |
| | | CTCCCCCAACCAAGCCTGCCCGCCTTGGTTCAGCAGAACGGCTCCTGTCTCTACAGCGGTGCCAGGCCAGGAGTGCTGTGTCTGTGAAGC |
| | | GGGGTCATGGTTTTGGGGCCCCTCATCTCCCTCGCGCCCTCTCATTGGGGACCCCCCGTCTCCCTAGCGCCCTCTCGTCCTCTCCTGCATG |
| | | TGCTGTGTCTGTGAAGCGGGGTCATGGTTTTGGGGCCCCCCGTCTCCCTAGCGTTCTCTCGCCCTCTCCAGCATGTGAAGTGGGGTCATG |
| | | GTTTGGGGGCCCCCATCTCCCTAGCGCCCTCTCGTTGGGGACCCCCCGTCTCCCTAGCGCCCTCTCGCCCTCGCCTGCATGTGCTGTGTC |
| | | CATGAAGTGGGGTCATGGTTTGGGGGCCCCCTATCTTTCTAGCACCCTCTCGCCCTCTCCTGTATGTGAAGTGGGGTCATGGTTTGGGGG |
| | | CCGCCATCTTTCTAGCGCCCTCTCGCCTTCTCCTGAGCGTGTGGAACTCTGTGGTGGTCAGAGCTAAGGTTCTGAATAGGTCGAAGCACCT |
| | | CCCCGGTGCCTCTCACCCTGAATGCTCTGGGAGGACACAGCCTTTTCATAGGCTACGACTGACATGGCAGGAGGGGCCTGCCTGCCACCC |
| | | GGGTCCTCTGCTGCCTGCTGCTTGCTGGGGAGGGGGCTCGAGACTGGGATCCTGGGCTTCTGCTCCAGCTGTGCCCAAGGGAGCTGCTG |
| | | AGGAGGGACCGGGTGGGGCATCCACTCTGGGCAGGTTCAGGGTCATTCTTGGTGACCCCGGGTCCGGTTACAAAGGCTGATGGAGCGCG |
| | | TGGGTGGCTGCCTAAGTCTCTGGAAGCCCAAGAATGTGGAGATGGCGCGTCTCGGCCCGGGGTCTCGTGGCTGGTCTGGGAGAACTTGC |
| | | CTTTATTTCTAGGCAGGAGGCTGCACTGCAAGGGAGCGTCAGTGGCCCGGCTGGCTTTCCCCGGCCCTCAGCCCGCACTCGTCCACCAAA |
| | | GCAAGCTCCTTTGTGGGGCTGCCCTGGGAAGCCGGGATCACGAGGCTCTGCCGGCCGTGGTCACCCCATGAGGCAGGGTCAGCTCGGG |
| | | AGCAAGGCGGATCAGATGGAACAGAACACGTAGACCACCTCGCCCGCCCTTAGTCAGCTGGGCCATTGAAAATCAAGTCCGTAGAAAGAC |
| | | CTAGAAATAAGTCCCGGGGTGCCCTTGCCTGTTGACGGGCGGGCCGAGCAGGACTGTTCTCAGGCAGGCACTGGTCTCTTGGCTTCCAGG |
| | | TGGTTTGTTTGCTGGTTTGAGGCTGGGGGTGACGCTCCTGTGCGGGAGGAGGTCGCATTCCATTCATAGCGGCTTATCTGGGCTGTCAGG |
| | | CAGGCCTGGGAGGGAGCCTGCCTCTGTGCTCTCCAAGGGTGGGCGACGGACAGACAGGGTGTCCCACCCCTTCTGGGCCAAGGACAGA |
| | | GGGTCAGTGTTTGCAGAGACCTGGGGAGGCCCAGGTGACCTCCACCGAGCACCTGCTGTGTGCAGGGCCAGTGCTGGCTGCAGAGACAG |
| | | CGGAGCGTGTGTGGACCCGGCGGCCCAGGGGAGGGGGGCAGGCAGGACCCGGCGGCCCAGGGGAGGGGGGCAGGCAGGACCCGGCG |
| | | GCCCAGGGGAGGTGGGCAGGCAGGACCCGGCGGCCCAGGGGAGGGGGGCAGGCAGGACCCGGCGGCCCAGGGGAGGGGGGCAGGCA |
| | | GGACCCGGCGGCCCAGGGGAGGGGGGCAGGCAGGACTCGGCGGCCCAGGGGAGGGGGGCAGGCAGGACCAGGCGGCCCTGGGGGTC |
| | | AGGGGTGGAGGCCAGGCCTAGACGGCCCACAGGAGGGTGGACTCATTCTGACCGATTCCTGGAAGCCCCCGGAAAGTGGTGATGTTCTG |
| | | GAGGGCCCAGCAGACCCCAAGGCCCCCAAGACAATCCCAGCTGGCTCTCTGCGGCTCTCGGTGTCTGCCATTTGAGACAATTTGGGCACA |
| | | GGCAGGGCAGGCCGTCGCGGACGGTCTAAGCCGCGCGCATTGGTGGGGGCAGCAGAGCCCCTGCTCTCAGCTCCTCGGGGTACAGCGG |
| | | GGGTACCAGGCGGGTGAGTGGGTGGGTGGTCACTGCTCCTGCCAAGGGCAGCCCTGGTTTGGTTTGCACTTGCTGCCCTGGTGACGGCT |
| | | GCTCTCATTCCTGCCCCATTGCTAACAAGGGTGTCATAAGCTACTTTCCCGGCCCACATCCTATTAAGCCCATGGAGACCCTCCCACAGCT |
| | | GAGCCTGCTGTGGGCTGCAGGCCCTGGGCGGTGCCCACCTCGGTCCCCACTGGCCTCCTTCCAGCACTTTAGAGCAGACACAGGTTGGA |
| | | GATAAGGAAAGTTCCAGAGCACAGACTGGAACAAGCCCCAGGCCTCTCCCTGCCCCAGCAGGGCCTCCCTGGATTTGGGGGACAGGTGC |
| | | CCTCATGGGGGGTCCTGAAGGTCAGAGCTGGGGCTGGGGCTGGGCTGGCGGAGGTGGCCTTGGCGGAGGCCACATTCCAGGGTCTCAG |
| | | TGAGAGTCTGTGGCAGGCAGCCTTGCAGATGCCGCTGAGGGACCCCCCACTTCATGTTGTGGGTGATGTGGTCCATTGATTGCCTCCAGG |
| | | TTTAAATCAGGTGGATATTTACCTAGCGGCCTCCTCTCCCTCTGCACAGGGCCTGGAGTGGGATGGACTGGGGTGCTCAGCTGGAGGCTC |
| | | TGCAGACACAGCCCCCTGGGCTATGCAGGCCCTGCTGGGAGCCACATTGCCATTTTTCATCACCCACTTTTTGGGTGAGAACCCCCTCGAG |
| | | TCCTAACATCTGCCGCATCTCAGAGCCTGTGGCTCCAGTCAGAGCATCTGGACCATACTGCTGGGGTCAGAGCGCGGCAGGACAATGGC |
| 246 | COL18A1 | TGCCACCACCATCTTCAGGTAGAGCTTCTCTCTCCTCCTTGCTGGGCGGGGCCCCTCCCTGGGGAAGCCTGCAGGACCCAGACAGCCAAG |
| | | GACTCTCGCCCGCCGCAGCCGCTCCCAGCCAGCAGCTCCAACGCCCTGACGTCCGCCTGCGCACGCCACTTCTGCACCCCCTGGTGATG |
| | | GGCTCCCTGGGCAAGCACGCGGCCCCCTCCGCCTTCTCCTCTGGGCTCCCGGGCGCACTGTCTCAGGTCGCAGTCACCACTTTAACCAG |

TABLE 6C-continued

| SEQ ID NO | GENE NAME | SEQUENCE |
|---|---|---|
| | | GGACAGCGGTGCTTGGGTCTCCCACGTGGCTAACTCTGTGGGGCCGGGTCTTGCTAATAACTCTGCCCTGCTCGGGGCTGACCCCGAGG<br>CCCCCGCCGGTCGCTGCCTGCCCCTGCCACCCTCCCTGCCAGTCTGCGGCCACCTGGGCATCTCACGCTTCTGGCTGCCCAACCACCTC<br>CACCACGAGAGCGGCGAGCAGGTGCGGGCCGGGGCACGGGCGTGGGGGGGCCTGCTGCAGACGCACTGCCACCCCTTCCTCGCCTGG<br>TTCTTCTGCCTGCTGCTGGTCCCCCCATGCGGCAGCGTCCCGCCGCCCGCCCCGCCACCCTGCTGCCAGTTCTGCGAGGCCCTGCAGGA<br>TGCGTGTTGGAGCCGCCTGGGCGGGGGCCGGCTGCCCGTCGCCTGTGCCTCGCTCCCGACCCAGGAGGATGGGTACTGTGTGCTCATTG<br>GGCCGGCTGCAGGTAACTGGCCGGCCCCGATCTCCCCACCCTTTCCTTTTTGCCTTGCCAGGTAAGTGTGGGCGGGGCTGACGTGAGCCT<br>GGTACAGGTTCCCCCCACATCGAATCTCTACGTTCAGGGGCCCGTGGCCCTCGGGAGGTGGGAGAGCTGGGAGTGAGGCCTCCTGTGTG<br>GGGAGGAGGCCGGCGTCTGGACAGGAAGAGGGCTGGATGAACCGCAGCCGATGTGTCCAGGTGCCACCTGGGCCTGGAGCTCCCTGAG<br>CATTTTAGCGCATTTAGTCCTCAGCACGGTCCCGAGATACCCTGCCATGCCCCGAGTCACAGAGGGGAAACTGAGGCGTGGGGCAGTGGC<br>GTGACTCACCCCAGGGAGCCGAGATTCCCGCTCAGGTGTGGCTGCATCGACCTTGCTCCGGTCACTAAGCTGCACGGTTCGATGCGCTTC<br>CTGGGAGCCCCAGCGTGCTCGGGCCAAGGGTGCTGCCGCGTGGGCAGTGCAGAGACCCTACCAGCGTGGGGACCAGGGAGGTCTGCAG<br>GGCCCGTCCTGAGAGGGAGCCTTTCATGTCCCCCTCCCCATCCTGAAGCACACAGCCTCCCTGCCACAGTGGGGGCCGCTTCTGGGCCC<br>AGGGGACGTTGCCCCATCACCGTGTGGCCTGGCCTTGTTGCTGGCTGGACAGTTGGGGGCAGGAAGAGGAGGGAAAGGGGGACTCTTTA<br>ACCTCCTGGGGGCAGGGGCAGCCCAGAAAGGACCCCAGCAGATCCCTCCTCTGTGTCCGGGAGTAGACGGGGCCCC |
| 247 | COL18A1 | GGGCTCCACAGCGGCCTGTCTCCTCACAGGGTTCAGCCCAGTCTGCTCTCACTCATTTGCTGATTCATTCTTTCATTCAGCCAGTCAATAGT<br>CATGGCCCCTCCTGTGTGCCGGGTGGCCATGGATATTGCCCTGGGTAACACACAGCCTGGCCCTGTGGAGCAGACAGTGGGGACAGCCA<br>TGTGGACAGGGTGCAGGTGGATGGCAATGGCAGCTGGGTCAGGAGGGGCTGAGGGCCGTGGGGAAAGGTGCAGAATCAATAGGGGCAT<br>CCGGACTGGGGTGCAGGCCTGGGGGCTGGGATTTCTAGGGTGGAGGTCACCTCTGAGGGAGACAGAGCAAGGCCCTGGGAGATTAGAA<br>GGTCGAAGGTCGCCGTGTTGAGGTCAGGGGCCCTGAATTGGAGCCGCGGCAAAGGAGAGGGCAGGTCAGGGCACGTGGTGAGTGATTG<br>CTGCGGCTTCTGAGCACGGCTGGGTCTGTGGGGCCTGAGCAGAGGTGACCCGCGATCCGGCGCCACGGCAGGCAGGACTCCCCACCCT<br>TGCTGCTGCCTACACCCCCAGGGCAGCCCCAGAGTCGGGGGCGCAGCTCCCTGCTTGCCAGTTCAGAGCCCAGCCCCTCTCACCCAGCC<br>CAGAGGAGGACACAGATGGAGGAGGGGCACCCGGAGGGTCCCCCCGCCGACAGGCCCCACGTCTCCCACCTGCAGGACAATGAAGTGG<br>CCGCCTTGCAGCCCCCCGTGGTGCAGCTGCACGACAGCAACCCCTACCCGCGGCGGGAGCACCCCCACCCCACCGCGCGGCCCTGGCG<br>GGCAGATGACATCCTGGCCAGCCCCCCTCGCCTGCCCGAGCCCCAGCCCTACCCCGGAGCCCCGCACCACAGCTCCTACGTGCACCTGC<br>GGCCGGCGCGACCCACAAGCCCACCCGCCCACAGCCACCGCGACTTCCAGCCGGTGGTGAGTGCCCCCCCAAAGTGGGCTTGGCTCCAT<br>CTAGCCCCTCGGCTCTCGGCAGCAGAAGAGGGCCCAGCCCCTGCAGAGCTGCTGGGGGTCCCAGGCTTCGGCCATGGGTGGGGGTCTG<br>GCGGCTCAGGGCCACTCAGGGCGGCTTGGCTGGCCCTGGGACTTGCCCTCTGGTGGCCAAGCAGTGGTCATGAAAGTCCAGCCGCTGTC<br>ACATCCTTGAGGAACCGGCGTACCTCCGCCTACAGCGGCAGCTGGGGGCACCCACGTGGCCCGGGGCTGCTCTGACCTGGCAGCGTATG<br>GGGGCTGCTGCCTGGGCCCCTCAGTGTGTCACTTGCGCGCCTCCCGCTCAGCGCCCCTCGGCCGTGCCTGTCCACACAGGTGCGGGGC<br>CGGGGTGGTGCGCCCGGGGCCTGGGTGCAGGGGGCAGCGTGGGACACAGCCCGTGACGCGCCCCTCTCCCCGCAGCTCCACCTGGTT<br>GCGCTCAACAGCCCCCTGTCAGGCGGCATGCGGGGCATCCGCGGGGCCGACTTCCAGTGCTTCCAGCAGGCGCGGGCCGTGGGGCTGG<br>CGGGCACCTTCCGCGCCTTCCTGTCCTCGCGCCTGCAGGACCTGTACAGCATCGTGCGCCGTGCCGACCGCGCAGCCGTGCCCATCGTC<br>AACCTCAAGGTGGGTCAGTCCAGTCCTGAGGGCGCGGGCTCCTCGGCCCCCACTTGACCTCTGGGGTGAACTCCCAGCGGGGAGCTCCC<br>CTCTAGGGCCTCTGGAGGCCACCATGTTACAGACACTGGCGCCTAGGCTGGCGACTTCAGGGCAGGCTCCGGGTGGGTCACACCCCTCC<br>AGGCTCAGGCCAGGCCTCTGCATCCCTGGGCACTGCCACGTCCCCCAGGGCATCCCATGAGGCCCCCCCGTGGCCCCCTGACCCCCCGC<br>TCCCCCGGCAGTGCCCCTCAGAGGGTCCCATGCTGCTGGACCAAGTGTCCACACAGGTGATAGGGCTCACATACAAGCCTGGAATCAGGA<br>ACCGTCCTTTGGGCCTCTAGTGCCATGCGGGCTGGTGGCCCCTCTGCCA |
| 248 | chr21: 45885000-45887000 | GCCTGGAGTGTAGTCCTGCTGAAGGCCAGAGACCACACACTCCACCCAGACTCCGGATCTCCCTCCCCAGCAGGGGGATGGAGGCCCTG<br>CCGCTGGGAGTGCTGGTGTTATGTGGAAGGGCTGGGCTTCTCCAGGGCTCCTGGGAGGCCTAAACATCTTGCAAGGTTTTGACGTTAATTA<br>CTATTATGATTGCTTTCTGTGTGTTACTGTTTTCCCCACACTTTAGCCAGCTAATGTGGAGCTACAGAAGGCCCTCGCCCCTACCCCTCCAG<br>ATGTCCCAGCCCATGACAAGCAGGAAGGCCGGGTGCTGGGAGACTTCCTGGGGCTGGATCTGACATCATTCCAAGCAGATGATAACCTGC<br>CTTCCCGATTTCCAAACCCACAGCAAGACACCCTGGAGTTATTTATAAATGCGAGCCCCTGGGTGCACTTCTGACGGGACCAGCACCCTGA<br>CGGCCATGAGAGGGTGGAGACAGCGCACCCCGAGCTCAGGGAGGCAGGAAACTCTGGACCTGGAGGCCGGGCACCATGAGGGACACGC<br>TGCAGGCCCAGCTGCTGCCGCCTGGGGCGGGGCTGCCCTGCAGGCTCCGGGAAAACCCAGAACCAGGCCGGATCAGCGTGTGTCAAGA<br>GGCGGGGCGTGAGAGATGAGCTGCTTTTTTTCTTCACAGGGTTGGCAGGAACTGCAAATAATAGAAAGTCTTTAGGGTCTAACACGCTGCC<br>CTGAAAACACTATCATTACTTTCCTAATGACTAACTGTGTCTTTCAGCCGGCGGGGCAGGCAGCTGAGGCCGCAGGCTCCCGCAGAGGAC<br>CGGGGGAGGCTGGCAGCCTGTAATCTGGGGGCGCTGACAGTGCTCTGCCCAGACCCTCGCGCCAGCTCCAGCTCCAGCACAGCAGCCCT |

TABLE 6C-continued

| SEQ ID NO | GENE NAME | SEQUENCE |
|---|---|---|
| | | GGGTCCCTCTGGCCCCCTGCCCGCAGAGTCCAGGTGTGGCAGAGGCCGCCCAGTATCCCTTCTCCTCCTCCTTTTCTAAAAACAGAGTCT |
| | | CACGATGTTTCCCATGCGGGTCTCCAACGCCTGGGCTCAAGCGATCCTTCTGCCTCGGCCTCCCAAAGCGTTGGGATTAAGGGGCGAGCC |
| | | ACCGCGCCCGGCCCACCTTCCCTTCTGGTTCATTTCCAGTAAGGTCCTGTCCACAGCGTCCTTCCCAGCATTCCCACCAGGCTGCAGGCCT |
| | | TGGCCTCCCTCCCCTCCATTCTCATTCTCCCCGAAACCGCCAAGCGCGTCCAAAGCACGGGTTCGCCAAGCGCCCCCCCCGCCCCACTCC |
| | | ACATTCCCTTCCCCGCCGACTCAGCCTCCGTAGCTCGCGGACGGCCCCTCCTCACGCCAGCCCAGGCTTTTTTTTTTTTTTTTTCTTCTATTT |
| | | TAAGGTTGTCTTTTAATGACACAAGCGACATTTGGAGACAAAAGGACACATCTCTTCCTGACCCACCTCCAACCCCAGCTGACGGCCGCCC |
| | | TGAGCCTGGCGTAGACGGCCCGGAACGTTCCCTGCGTGGGTTCCGTCCATCCCGAACCCCTGTCCCCGCGCCGGCTCCGGGGGTGCTCG |
| | | GGGGGCCGCGTGGGGTCTGTGACGTCGCCTCGAGGCTGCATCCCGGTGACCCGGCAGCCCCTGGCGCTCGCGGGAGGCGGGCGGGCG |
| | | CGGACCCCAGGCTTTAGGGCGCGATTCCTGCAGCTGGCTGCCGGCCCGAGGTTCTGGGGTGTCTGAGGTCTCGGGCGGGGCGAGGACG |
| | | TTTCTCCGGCTCAGCCCCCCCACCTCCTGCCCTGCCGCCCCCCACACCCAGCTCCCCACGGACGCCAAGAGGCGCCTCCCACCCCGGCG |
| | | AGGACCCGCGGGGAAACGGGGCCCAGGCGCGGCGACTGCGGAGGACGCGCCTCGGCCCCAGCGCCCTGGTCCTCGGGGCGTCCGGCT |
| | | GCCCTTGCCCGAGGCCGGGGCGGGCGCTCAGCGCCGCGGAAGAAACGCCCGGGCGGGGACGCACAGCGAGGCGGGCTCCGCGGGAA |
| | | GTACCGGGAAAACGGCGCGGAGCGGAACAG |
| 249 | PCBP3 | TGGAGCAATCCCAGAGAGGCTGAGGTGTTCAGGCTGGCCCCAGATGCACACGAGCGTGAAGCCTGTTCAGAAGCCAGCTCCTCACACCCT |
| | | CTCCCCTGCCAGAGGCTCCAGCACCCCCTCCCCTCTCCTCTCCCCTCCCTTCCCTGTGGTCCTCCTGCCCACCCCACCCCCGTCTGCATG |
| | | TGCACCGTCACGGAGATGCGTGTACTAGGGCGGAGGTCGGGGACAGTCGTCAGAAGGACACAGGAAAGAAGGGAACAGGAATCCCATAA |
| | | CAGAACATTATCCGGCAGGAGTAATTAACACAGGCAGGACTGGAGGCTTTGTTTTGTTTTGCTTAAAAAACAGTGGTATTTAAATTAATGGGC |
| | | ATGGGAAGACTATTCAGTGAAAGACATCGGTCATTGAGGTATCTATTCAAAAACACGGTTTAGTACTCTGCCACACACCGAACGCAACGCCA |
| | | CAGCAGCCATAGAAGCGTGTGTGGCTGTTTAACGTGGTCTTTTTGGGGAGGGCATCCTAGGCAGAGCAGGCGTGGAAGGGAAGGCGGCG |
| | | GACGGAACAAAACGCGGGCACGCAACGGCTGCTGCGCCGGATCTGAGGCAGGGCCAGCCTGTGGGAGCAGCAACATCGCTCGCAGGAC |
| | | AGCGATGGAGCCCCCACGAATCCGCGTGAAAGCAGCAACCACCTAGAAATGAACGTACAGCTGCTTAGAAACAGAATACGGATGACCCGA |
| | | AAGACTTCCCGATGGTAGTCACCAGCATACAGGACCTGACACGGGCGTGCGGGCAGGGTGTGCCGCTACGGGGTCCCTGGCGCACCTGC |
| | | TACCCCTGCTACCCGCATTCACCGCACGCGGAGGGTGCGGGCCGTGAAGGTTATACATGCAAATATCCTTCCACCAGCCAGTTCTCCTTCC |
| | | AGGAATCTGCCACCCGACCCTTGTGTTGTGCACAGACATGGTCCAGGTGTTTGCGACGTGATTGTTTATCAGAGAGAGAGAAGGGAAATCT |
| | | CCAGGCTCGCTGTAGCTGCAGGAGCTCTGGGGGCTGCGCCCATCGTGGAGACGGATAGCTGTCTCTCATGAACACAGGACAGCAAGTCC |
| | | GGCTGCGGCCACAGAAGACTCGCCCTCCTGGACGCAGCGTCTTCCTTCCTCAGCCCCACACTGGAGGTGGCCAGTGCCATCCACAGCAG |
| | | AAGGGGCCAGCCGGGACCAGGCTCACGCCGTGGAATTCTGCTCTGTGGTAAGAGGAAGAGCGATAGCTGGAACCCAGCGCCGTCGCACA |
| | | CACAGCGGGGAAGAGTCTCAGAAATGTTACTTTGAGTCAAAAAGCTGGACAAAAAAAGGCGCAAGCCAGATGGTGCTGAAGAGGCCACAG |
| | | GAGGCTGGCAGCCAGGGGGTCTGGCACCTCACTCGGAGGCGCAGTGGGCCCGTCCGGAATTAGTGGCCATACGGCAAGTGCCGAGTGGT |
| | | ACATCAAACCGTCACTTCAGACTCCTGCGCTTCACTGCCTGTCGGTTATGCCTGGGTTTTGAAATCAAGTCACAGAACACCTGGAATGTGGT |
| | | GTTTACGCAGAACAAAGCGGGTGCCTCGGAGGAGAGAGCCTAGGGACAGGGGCACCTCCCGGTGTGGGTGCCCAGGGTTGCAGGGTGG |
| | | CTTCCTCTGTCTGCGCGGTTTTCAGAGCCCCAGGGTCCTGCCTGCCCGGCTGCCTGGAGGCGGCCCACATCCTGCTCTGCGCCGCCGAA |
| | | TCTCAGCCTGAACAGCTTCGCTGGTGTTTGTGTTGACTTATTTGTTCTTTTTTTTTTTTTTTTTTTTTAAATAAAGGATTCCGATGCTGTTACAG |
| | | TCAATAAAAGCCACAGGTCTGGGTGACCTACAAATGTGTGTGTCTGACTTTCTGCAGTTTAAATCGCCACTGAGCCTTAAGGCGTCTGGCCC |
| | | GCGCATTGAGGAATCCACGTGGGTCTCGGGGTCCCCATGCCTGCCCAGCTCCCTGCTTCAGCCTGGGCGGGTCTGGCGGGCATTTCTGC |
| | | GAGCCTGTCCCTGGGCCCGCCTCCTGGCCAGACTTCCAGAAACATTGTCCACATCCCCGTTGCACGTCCCCCCGTCACCGGAAACTGCAG |
| | | CCCACAGCACTGGGAAGAACCCGGGAGGCAGGCGTTAGGACGGGGTGGCCGAGACAGGGAAGGGAGCCATGGCGGACGTCCTCACCCA |
| | | AGCCAGGGCTTCCTGCCCCTGTGGTACTGACAGGAGCCCCGCAGGACGTGGGGTTGGCTTTGGGCAGCTCGGTGGACACTTCTCTTTCAG |
| | | ATCCTGCCACAGCAAAGCTCACGAGACTCACTTCTTCCCATTGGAATTCACTAAGAACAAATTCAACAATTCAGACGCCCCAGCTGGAGGTT |
| | | TATTTTATGGATTTTACCTGTGCGGTATTTAGGGTTGTGTTTATGAATAAAGGTGTGCGTTCTGGCAAGTAGAAATACAGAGCTTGTCTTTCA |
| | | CCCAAGTATCTGTAACTTTCTCCAATGCAGACACTAAAATGCAATAAAAACAAACCAAACCCATTAAACATGAATTAGATGAGGCAGGCTGAT |
| | | GGGAGGTTGTGGGATTAACAGGCCGTCAGCGGATTGAAGCTGCGCACATCGCTGGGATGCTGCTGCGGGAGGATTCGGTCTAATCCGGG |
| | | AGCATCTGGCTGGGCAGTGGGCAGCGTCTGCAGTCGTGGCTGCTTGAAGGTATGAAGGTTGTGGCCTTTGCTTCCCCCCATCAGGCTGCC |
| | | CCACCCTGGACCCCACCCAGACCCCTCGGGCACCCTGGGGTCATCTTCAGCTCCCCCTTCTCTTCCTTCCTTCTCTTCCGCCTGGGCCCCT |
| | | ACTGTGACCCGAGGTCAGCAGAGGACCCTGGCAGGTGGCTGCTCCCTGGGACTCGACTGTGCAGGTGAGGCTTGGGGTGACCGCTGCTC |
| | | CTGCTCCTGCTCCTCTCGCCGTCCCCACCCTCCTCCATCATGCTGTCAACATGCATGTGGGCTGCAGCCCTCAGCCTGCAGGACGCTGTC |
| | | AGTGCAGCTCCTCAGTGGCCAGG |

TABLE 6C-continued

| SEQ ID NO | GENE NAME | SEQUENCE |
|---|---|---|
| 250 | PCBP3 | ATCTTGTCTTCCTTGTCCCAGTCCTGGAACCAGCCACTGCCCCAGCAGCTCCTGTGTGTGGTGGCATGTTCTGGAAGCCAGGATGCATGGT<br>GCTCCTGGGCTGCTGTGGGTCCTGGGCTGCTGTGGGTCCCGAGCTGCTGTGGGTCCTGGGCTGCACCCCTGCAGAACACTTCCTTCCAT<br>GTTCAGCTCCCTATATGGAACCCCAGTTCCAGCCCCACAGCACAGGGTCCCCCAGTTCTTCCTGCCTCAGGTGTGCACCACGAGGAATCCA<br>ACTGCCAGTATCTGTGCGTGGCCTCCCGCCGGGAGGAGGCTGCCGGAGGCTCTGAGCTCTAGCCCCACAGCACTGGCACATCCTAGATTT<br>CCGGGAAGACACGGCCTCCTCCCCAGGGGAAGGTGGTGGTGCCCACACCCAGAGCATTCATTCCTGCAGTGGAGACAGAGGGACCTGCC<br>TCTCCAACTGTGGGTGTCAGGAGCCAAGGCGCATGGTAAATGGGGCTCTCTGTGAGGCCAGGTGCACGGCCCCATCTCCAGCAGCAGCG<br>GCCATGCCACCCAGCTGCACTCTGTGGGGGAGGTGCCATGATTGACGGGGGCCCCTCCCTGTGTCCAGTGTCCTCCTCCCTCCACGGGCT<br>CCCTCTGCACACCGTCCTCACAGTCTCCCTCTGCACACCGTCCTCACAGCCTCCCTCTGCACACCATCCTCATGGTCTCCCTCTGCACACC<br>GTCCTCACAGCCTCCCTCTGCACACCGTCCTCACAGCCTCCCTCTGCACACCGTCCTCACAGCCTCCCTCTGCACACCATCCTCATGGTCT<br>CCCTCTCCTTCCACAGACCCCTCTGCTCGCCATCCTGACGGCCTCCCTCTCCCTCCACGGACCCCTCTACACACTGTCCTCCCAGCCTCCC<br>TCTACACGCCATCCTCACAGCCTCCCTCTCCCTCCACGGGCCCCTCTACACACCGTCCTCACGGCCTCCCTCTCCCTCCACGGGCCCCTCT<br>GCACACCGTCCTCACAGCCTCCCTCTCCCTCCACGGGCCCCTCTGCACGCCGTCCTCACGGCCTCCCTCTGCCTCCACGGGCCCCTCTGC<br>ACGCCGTCCTCACGGCCTCCCTCTGCCTCCACGGGCCCCTCTGCATGCCGTCCTCACGGCCTCCCTCTCTCTCCACGGGCCCCTCTGCAC<br>GCCGTCCTCACGGCCTCCCTCTCTCTCCACGGGCCCCTCTGCACGCCGTCCTCACAGCCTTCCTCTTTTTCCACAGACCCCTCTGCACGCC<br>GTCCTCACGGCCTCCCTCTCCCTCCACGGGCCCCTCTGCATGCCGTCCTCACAGCCTCACCGACGTCACCATTGCTGGCCCCGCTTCAGG<br>TGACAGGCCACAGTAGCACCTGTCAGCTCTGTCCCGCTGCTGGACAGGGAGATACTGGGCCACTCAGCCCAGCGGGGAACGTGTGTCCC<br>GAAACTGCCTTGGGCTCGCCATCAGAACTGTGGCAGCATCTTCCAGCGTTCCTTTTAACAGGCTGCCGTTGGAATAGGAGTCACGGAGCAA<br>TTGCAGTGCTAAGTTTTCTTTAAGTCACACAATTGAAGGAGGCTTTATTTTTCACACATTTCTTCCAGAGTTTCCTGGTAGCCTGAGTGCATG<br>GGTGATGCCCCCTGAGTTATTTATCAGGGGCAGCCAGCTGCCCTCCCCCGGGGCACTTACAGTCAGCCCATCTCTGTCCTGGTCAGGTGG<br>GCGCCAAGGAAGACCCGGCTCAGGGCCTCTGTATGGGCAGCCTGGCTTGTACACACACCCCTCCCCACCAGCAGATTCTGAATTCTCCCT<br>TCTTCATGCACACCGGGAAGGTCCCTTCTGCACTCATACCGGGAAGGTAGGCAGGTTTCGGTAGTGTCTGCCTCCAGTGTTTTCCTCCTCC<br>TGCTCTATGACATCATCTTTCTGTGATTTTTTTTTTTCTTGCAGGAAGTTGGAAGCATCATCGGGAAGGTAATTATTGATTGAATCTCTGCCTCT<br>CCTGGGGTCTCTGTAAGGGGATGGTGAGGATGGCAGCCTCCCTGGGTACTAGGTGGCACCCAGTAGGTGCGCCTTTCCCAGTTGGTGGG<br>TGGTCTGTGTTCCATGAAGACAGGACCCCAGAGGTGTCGCCTTTATGCTGTATGACATTGAAGCTGGTCCCTGGCTCTGCGTGGCCTGAGG<br>GGAAGGGGTTCACTCCAGCTGGTCACCTCGCTGCCCCCTGCCCGTGGCCTTGGTGGCCAGTCCTTCTTTCCCGGTTGAAGACCCCACGAA<br>GAATGATTTCTCACGCCTTCTTCAGCCGGCTGTGTAGTCTGGGTGGTCTCCAGGAGTGCCAGTGGAGGCAGCAGCCCCCAGACAATTCCTT<br>TCCAAATCAGGGCTGGCCCGGGGGAAGTAAGGCCCAGTTTGGAAGCCTGCTGCCCCGGGAGGCCGAGCAGTGAGGGCCACCTCCCTGTC<br>TTCATCACATTTTCACCGCTTCCGGGGGTCCTTCCCCTCAGTCCCACCATGGGGGCGCC |
| 251 | COL6A1 | GCTGGACACCTCTGAGAGCGTGGCCCTGAGGCTGAAGCCCTACGGGGCCCTCGTGGACAAAGTCAAGTCCTTCACCAAGCGCTTCATCGA<br>CAACCTGAGGGACAGGTAGGAGGGACGCCCCGTGACCTTCCTCCTGTGCTTCTGGGCCTCTTGGAGGGAGGGGTGGGGGCCCAGGGGA<br>ACACGGGTGCGACGGCCTCAACCTCCTAAGGTTGGGCGAGCGTTGCCCTGACCGGGGCCCCTCCCGGCGCCCTCCAGAGTGAGGCCGG<br>GGCCCTTTCCGGCGCCCTCCAGAGTGAGCTGGTCTGAGCCTCTCCCAGCGCCTTCCAGAGTGAGCTGGTTTGAGACCCTGCTCGCGGGG<br>GTGGCACCTGTTCAGCAGGGCCGAGGTGACAGTGAGGCTGAGATGTAGGGAAGAGAGGCTCCCGCAGGCTGACCGAGAGGGCTCAGCG<br>CACTGGCCCAGACACGCAGTCCTGCCTGGTGCGCGGGAGCCCCTCACTAACCACCTGGACCCTGGTTTGTTCCGTGGGCAGTGAGAGCC<br>TCTACCTGGGTCCTGGATCCCACGTTCTGAAGGTCCCCGACTCGGGAGCCAGGAGGGGTGTCGCTCTGCAGCCCCAGGGCCCCCAGGCT<br>TGGTTCTGGGCTTGGGACACGGCACCCTCTGCTCCACGTTCCTCCATCTGTGCGTGTGGCTGAGGACAGACCGGGGGGAGAGGGGAGTC<br>GGTCCTGTGGGTGCACAGGGCCGCTGAGGGGGGGGCATGTAGAACGGGGCTCCCCCACTGAGACGGGTCCTGGCAGTGGGGACACAGC<br>TTAGCCGGCGTAGGAACCCCCGTCCTCCTTGACCCTGCTGACTGGCCGCTGGGCCGGAGCCTCCCGCCACCAGAAGGGGCACAGTCAGA<br>GGCTGCCGGTAACAGCAGGGTGGACCTTCCAGCCCACACCGTGCCCAGCAGGAGCCATTGGTACCAGGAACCCTGAGCTTAGTGGACAT<br>GGCCAGGCCCGTGCGGCAGTGTTTGGGGGGGGGTCTGGCTGTGGATGGCACCGGGGAGGGGCGGCCGCGTGGCCCAGCGTCCCCCGA<br>GTCGCCCTTGTTGCCTTTACTCAGTCTCCCCATGACTCAGTTTCCCACCTGTGAAATGGGGCGGAGTCATCCCCATGTCGCTGCCACTGGA<br>TTCCTGCAGGCGCCGTGGTCACTCTGCTGAATGGATGGGAGGGTGGGTGGGGCAGAGGTGGGCCCACCCCAGGCTGGGGCAGAGCAGA<br>CCCCTGAGAGCCTCAGGCTCAGGTGCTCAGAGGGCAGCGAGGGGGCTGCTCAGATCCCCGGGGTGCCTCCTTCCCCCACTGTCATGCTG<br>CCCCACTGCAGGCCCAAGGACCCCACCCCAGCAGGGCCACACACTCAGGGCTCCTGGTCTGAGGGCCTGAGGGATCGGGGCGCAGGTC<br>GCTTGCTGGCCACACCCGCCTGCACAGCCTTCCAGGAGGGCCGGCCTCAGGGCCACAGGGCAAGTCCAGCTGTGTGTCAGCCACGGCCA<br>GGGTGGGGCAGCCTGTCCATCTGGGTGACGTCGCGCCCTGGGACGGGTAGCGATGGCGCCAGGGGCCGCCCGCCTCACGCCCGCCGT<br>GCCTGTTCCTGGCAGGTACTACCGCTGTGACCGAAACCTGGTGTGGAACGCAGGCGCGCTGCACTACAGTGACGAGGTGGAGATCATCCA<br>AGGCCTCACGCGCATGCCTGGCGGCCGCGACGCACTCAAAAGCAGCGTGGACGCGGTCAAGTACTTTGGGAAGGGCACCTACACCGACT |

TABLE 6C-continued

| SEQ ID NO | GENE NAME | SEQUENCE |
|---|---|---|
| | | GCGCTATCAAGAAGGGGCTGGAGCAGCTCCTCGTGGGGTGAGTGGCCCCCAGCCTCCTGCCCACGCCAGTTCTCACGCGTGGTACCCAG |
| | | CCTGGGCTGGGGTTGGCCTGGGGTCCCTGTGCGGCTTCAGCTGCAGCCTCCCTGTTCTCTTGGAGGCTGCACGGCCTCCCTGACCCACTT |
| | | TGTGGGCAGGAAAGAGACGGAGACAGACAGAGACAGAGAGAAACAGAAACAGGGAGAAACAGACACAGAGAGAGACAGAGACAGAGAGA |
| | | GATAGAGACAGAGACAGAGAGAGACAGAGACAAAGAGTGACAGAGGGACCAAGACAGGCAGACAGAGACAAACAGAGACAGAGACAGAG |
| | | ACACAGAGAGAGACACAGAGAGACAGAGACGGGAACAGAGACAGGCAGACAGAGACAGAGAGAGACAGAGACAGAAACAGAGACAGAGG |
| | | GACAGAGACAGGCAGAGAGAGACAGAGAGACAGAGACAGAGACAGACAAACAGAGACAGAGAGACAGAAACAGGGACAGAGACAGAAAG |
| | | AGAGAGAGACAGAGGGAAACAGAGAGAGACAGAGACAGATAGAAAAAGACAGAGGCAGAGAGAAGCAGAGACAGAGAAACAAAGACAGT |
| | | CAGAGACAGACAGAGACAGAGACAGAAACAGAGACAGAGAGACAGAGACAGAGGGGCAGAGACAGGCAGACAGAGAGACAGAGACAGAG |
| | | ACAGCGAAACAGAGACAGAAACATACAGAGACAGAGAGACAGAGAGAAGCAGAGACAGACAGAGGCAGAGAGACAGAGAGAAGCAGAGA |
| | | CAGGGACAGAGACAGAGACAGAAATAGAGAGATAGAGACAGAGGGACAGAGACAGAGAGATAGAGACAGAGAGGGAGACAGAGAGATAG |
| | | AAGCAGAGAGAGAGAGACAAAGACAGAGGCAGAGAGACAGAGAGAGAAGCACAGACAGAGACAGACAGAGAGACAGGGACAGACAGAGA |
| | | CAGAGAGACCGGAAACAGAGGCAGAGAGACTGAGAGACTGAGAGAGACGGGGTGGTTTTCCCCACAGCATCAACACCAAGCAGGGCTAG |
| | | GATCACTGAAACAGACTCATCAGACCCGAAGCATGCGCTTTCTCGGGGTTTTTCTGGACTGAGGGGTTTCCTCTCATCCCAGTGTCCAGCT |
| | | GTGGGGACGCAGGGGCCGCAAGCCCCGGAGTGTCCAGAGGGGAACGTGGCCTCCCCACACCCAGCCCTTCACGAGGCCTCAGGATCCC |
| | | AGTGGGGGTACCCGAGGCTGCCCTGTCCAGCCAGGCGGTGCGGGGGGTTTGGGGAGAGCCTCTCCCCGAGGTCGGTCTCAGAGGGCCA |
| | | CATGGCCGGTGTGGGCCGGACATTCCCTTTCCAATGGTTGTGCCCACTTCCCTCCAGAGTTGGTGCCAAGCTGGGACCTGGGGGACTTGG |
| | | AGTCTCAGGAAGTCGTCCGCTGTCTGCAGGGGGTGCATGGGGGATGTGGCCACACACGTCAGAGTGCGGCCCCCTGTGGAAGCCACAGA |
| | | CAGACACGACTCCCCTAAATGAGCTCGCCCTTCTGGCCGAGATGCTCAGCGTCCCCAGCAGGCTGCCCGACTGCCCTGCGATACTGCCCT |
| | | CCTTCCTGCTGCTCCCACTTTCCCTTTCGGGGGGTTGGATTTGGGGCATTCAGGGATCGCCCTGTTGTTTGCTCATCACACCCATTTCCTGC |
| | | AAGAGCCACGGTGACCGAGCAGCCTTGAGTTGAGGCAGCTTGTGGGTAGACGCGGCGGGCATCTCGGAGGGGCACGCTCCCTGCCACC |
| | | CTCAGCCTCCACTCACTGGTCAGGGGCTTTGCGCCCCAGGGCACCCCAGGAACCGAGCCTCCTTTGGGGTCATGGGTGCCTCTCCTGGG |
| | | AGGGCGTGGATTTTCCAAAGCAGTTTAGAGAAATGAGACCCACAGGCGTTATTTCCCATGGTGAGGTTCTTTTCAGTAACCCCCACCGTATA |
| | | GCCAGGATCAGCAAAGAGAGGCGGCTCCTCCCGGTGAGACAGGGACCAGCACCTCCCGGACAGGCTTGGGTCTCCCTCCAGTTCCCCCA |
| | | CCTAGTCTCGAGGTCTCACGCTGCCCTCTCCTGTCCAGGGGCTCCCACCTGAAGGAGAATAAGTACCTGATTGTGGTGACCGACGGGCAC |
| | | CCCCTGGAGGGCTACAAGGAACCCTGTGGGGGGCTGGAGGATGCTGTGAACGAGGCCAAGCACCTGGGCGTCAAAGTCTTCTCGGTGGC |
| | | CATCACACCCGACCACCTGGTAGGCACCGGCCCCCCCCGGCAGATGCCCCCAACCACAGGGAGTGGCGGCTGCAAGGCCCCCGGCAGC |
| | | TGGGACCGTCTTTTGGTCCTCGGGAGGGTGTGGGTTCTCCAGCCGGCCACCCTTGCCCCTGAGAGGCCAGCCCCTCCTGCTGAGGAGCC |
| | | TGGAGCGCCCCAGCCCAGCCTCCCCTCTGGCCCTGTGGGAAGCGGCCCCGGCCGTCAGGGGTCCCAGCCCTGCTCAGCCCACCCTGAA |
| | | CACTGCCCCCAGGAGCCGCGTCTGAGCATCATCGCCACGGACCACACGTACCGGCGCAACTTCACGGCGGCTGACTGGGGCCAGAGCCG |
| | | CGACGCAGAGGAGGCCATCAGCCAGACCATCGACACCATCGTGGACATGATCGTGAGGCCCCTGCCCAGGAGACGGGGAGGCCCGCGG |
| | | CGGCCGCAGGTGGAAAGTAATTCTGCGTTTCCATTTCTCTTTCCAGAAAAATAACGTGGAGCAAGTGGTAAGAGCCCTCCCCACCACCCCC |
| | | AGCCGTGAGTCTGCACACGTCCACCCACACGTCCACCTGTGTGTTCAGGACGCATGTCCCTATGCATATCCGCCCATGTGCCCGGGACAC |
| | | ATGTCCCCTGCGTGTCTGCCCGTGTGCCCGGGATGTGTGTCCCCCTGCGTGTCCACCTGTGTGTCTGCCCATGTGCCTGGGACATGTGTC |
| | | CGCCTGTGCGTCCATCCGTGTGTCCGTCTGCCCATGTGCCTGGGTCGCATGTCACCCTGTGTCCCAGCCGTATGTCCGTGGCTTTCCCAC |
| | | TGACTCGTCTCCATGCTTTCCCCCCACAGTGCTGCTCCTTCGAATGCCAGGTGAGTGTGCCCCCCGACCCCTGACCCCGCGCCCTGCACC |
| | | CTGGGAACCTGAGTCTGGGGTCCTGGCTGACCGTCCCCTCTGCCTTGCAGCCTGCAAGAGGACCTCCGGGGCTCCGGGGCGACCCCGG |
| | | CTTTGAGGTGAGTGGTGACTCCTGCTCCTCCCATGTGTTGTGGGGCCTGGGAGTGGGGGTGGCAGGACCAAAGCCTCCTGGGCACCCAA |
| | | GTCCACCATGAGGATCCAGAGGGGACGGCGGGGGTCCAGATGGAGGGGACGGCGGGGGTCCAGATGGAGGGGACGGCGGGAGTCCAG |
| | | ATGGAGGGGATGGCGGGGTCCAGATGGAGGGGACGGCGGGGTCCAGATGGAGGGGACGGCGGGGTCCAGATGGAGGGGATGGCGGG |
| | | GTCCAGATGGAGGGGACGGCGGGGTCCAGATGGAGGGGACGGCGGGGTCCAGATGGAGGGGACGTCGGGGCTCCAGATGGAGGGGAC |
| | | GGCGGGAGTCCAGATGGAGGGGACGGCGGGGTCCAGATGGAGGGGACGGCGGGGTCCAGATGGAGGGGACGGCGGGGTCCAGATGGA |
| | | GGGGACGTCGGGGCTCCAGATGGAGGGGACGGCGGGAGTCCAGATGGAGGGGACGGCGTGGTCCAGATGGAGGGGACGGCGGGGTCC |
| | | AGATGGAGGGGACGTCGGGGCTCCAGATGGAGGGGACGGCGGGGGTCCAGATGGAGGGGACGGCGGGGTCCAGATGGAGGGGACGGC |
| | | GGGGTCCAGATGGAGGGGACGGCGGGGTCCAGATGGAGGGGACGGCGGGGTCCAGATGGAGGGGACGGCGGGGTCCAGATGGAGGG |
| | | GACGGCGGGAGTCCAGATGGAGGGGACGGCGTGGTCCAGATGGAGGGGACGGCGGGGTCCAGATGGAGGGGACGTCGGGGCTCCAGA |
| | | TGGAGGGGACGGCGGGGTCCAGATGGAGGGGATGTCGGGGTCCAGATGGAAGGGACGGCGGGGTCCAGCAGGCAGGCTCCGGCCGTG |
| | | CAGGGTGTGGACTGTCCCGGGGGCGCTGGGGGCTTCTGAGGGTGTCTCTGTCCGCCCTGCCCTCAGCCGCACTCTGTTCAGAAGGACCT |
| | | TTCTGGAGGTAGGAGGGTGAGAATGTGGGTCCCCTGCTTCTGTGTGGCTCAC |

TABLE 6C-continued

| SEQ ID NO | GENE NAME | SEQUENCE |
|---|---|---|
| 252 | COL6A1 | GGCCGGGGAGGCGGGGAGGCTGCCCCAAGAGTAAAAGCCTTTCTGACGTGCGCAGGACGCGGCCCTGACTGGTCTAACTGACTCTTTCT<br>CTTCTCCTCAGCTTGCTGTGGTGAGACCCAGGCTCTAGCTCCTGAGAGAATGGATCCCGGGGGTCGGGGAGCGAGGCCTGGGTCCCACA<br>CATGTCACAGGACAGCACATGGCACTCTGGTCCCCGCCCGCAGCTCCCTGCACCTGCCCGCCCCCTCTGGGGCCTGCTCCAAGCCAGCA<br>GGGTTCCCGGGTGTTGGGCTGGGCCCCGCCCTCTTTCACCCATAACTGAAATAACCAGGAGCAGGCTTGGGGGGGTCCCTGCTCCATCAT<br>TCTGGCCCACAGGCCCCACCCTAGCCTGGCTGAGCAACGCCAGCCCTGACCAGCCGCCGGACAGAGCAGCCTTTACGGGGCCATGGGAG<br>GGGGTGGGCTTTTCTGGGGCTGAGACGGGGGGACCCCAACGTGTCAGGTGAGGATGTGGCAGCCAAGGAGGGGCCAGGGCGGTGGAG<br>GGGAGGGGCCAGGGCACTGGAGGGGAGGGGCGTGCTCTGCTGACACCGCCCCCGCCTGCAGAATGCAAGTGCGGCCCCATCGACCTCC<br>TGTTCGTGCTGGACAGCTCAGAGAGCATTGGCCTGCAGAACTTCGAGATTGCCAAGGACTTCGTCGTCAAGGTCATCGACCGGCTGAGCC<br>GGGACGAGCTGGTCAAGGTGAGGCCTCGCCCCGCCCGGCTTTCTCAAGCCCAGGTGCACCCCGACCCTGCCGGCCGCCCCTGCCCGCG<br>CCAGACCTCAGCCTCCCGAGGCCACCGCTGCATCCCTGTGACTTCCCTACTCATGACAAGGATGCCAGGCACGCGCCAGCCCGTCCAGG<br>CCTCCAGCTCCACCTGGCGAGGCTGGCCCATTGTACACAGGCGCCCCAGATGAGGGAGGGTCTCCCCCTCTCCTTGAAGGGCGGTAGTC<br>TGGGGTCCTGAGTGCTGGGTGTGGGCTTGTCCCTCGTGGACAGAACCCAGGAGGGCTTCATCCACCAAGGAAGATTGCTTTGCAGGGTAC<br>CCAGGTCCCGGGGGCTGTGCCACCCTCTGGGCACCCGGAGCCAATCGCAGGGTACCCAGGTCCCGGGGGCTGTGCCACCCTCTGTGCA<br>CCCAGAGCCAATCGCAGGGGACCCAGGTCCTGAGGTCCTGGGGGCCATGCCACCCTCTGGGCACCCGCAGCCAATAGAGTCACCCTTGG<br>GAAGCTTATGCGGACCTGGGGCAGCACTCGCGTCCTGACCCCGGTGCCGGTCCCACAGTTCGAGCCAGGGCAGTCGTACGCGGGTGTGG<br>TGCAGTACAGCCACAGCCAGATGCAGGAGCACGTGAGCCTGCGCAGCCCCAGCATCCGGAACGTGCAGGAGCTCAAGGAGTGAGTGCCC<br>CACGCGGCCAGGACCCTCCCACCCCTCGCCCCGACCGCTGTTCCCACGGCAGGTCGGCCCTGACCCCTGATCCCAGGTGGGCTCGGCC<br>CCGCGGCAGGCCTGGCCCCAACCGGCCCTTCCTGCCCTTTGCTATGCAGAGCCATCAAGAGCCTGCAGTGGATGGCGGGCGGCACCTTC<br>ACGGGGGAGGCCCTGCAGTACACGCGGGACCAGCTGCTGCCGCCCAGCCCGAACAACCGCATCGCCCTGGTCATCACTGACGGGCGCT<br>CAGACACTCAGAGGGACACCACACCGCTCAACGTGCTCTGCAGCCCCGGCATCCAGGTGGGGTGGCCACCCCCAGGCTGCACCTGCCCC<br>GCCTAGGGCGCCCCGCCAGCCAGGGTGGCCTTGTCCCCAGAAAGACGAGGGCAGAGCAGGCTGCGCCACACCGATACTGTCTGTCCCCA<br>CAGGTGGTCTCCGTGGGCATCAAAGACGTGTTTGACTTCATCCCAGGCTCAGACCAGCTCAATGTCATTTCTTGCCAAGGCCTGGCACCAT<br>CCCAGGGCCGGCCCGGCCTCTCGCTGGTCAAGGAGAACTATGCAGAGCTGCTGGAGGATGCCTTCCTGAAGAATGTCACCGCCCAGATCT<br>GCATAGGTGCGCATGGGGCCACCCGGGCAGTCCCAGATCTGCGTAGGTGCGCGCGGGGCCGCCCGGGCAGTCCCAGATCTGCGTAGGT<br>GCACGCGGGGCCGCCCGGGCAGTCCCAGATCTGCGTAGGTGCACGCGGGGCCGCCCAGGGCCGTCCCAGATCTGTGTAGGTGCGCGCA<br>GGCGCCCAGGGCTGTCCCAGAGGCCTCCTCCCAGCTCACTGTTACCTCCAGGGGCACGGCCACCCTGTAGGTGCGCACGGGGCCGCCT<br>GGGGCTGTCCCACAGGCATCCTCCTCCCGGCTCGCTGTGACTTCCGGGGGCACGGCCACCCCTGTGCTCGGCCGGGAGGTCCTGTGACA<br>TCTCCTTGCGGGGTTATAGGTGGAGCAGTGGGCTCACACTGCACGGCTTTTCTCTTTTACAGACAAGAAGTGTCCAGATTACACCTGCCCC<br>AGTGAGTACCTCGGCGGCCGGGACACGTGGGGAGGAGGGCACCGTGGTTGGGGCGAGGGCTCTGAGAGGACGGGGCTCTGGGAGGAG<br>GGCCTGGCGGTCACGAGAGTAGGTGCATGGCTCACTCCGGTGGCTGAGCACCACCGTGCCGTGCCCTCTCTGGGGAGCTTAGACGCTCT<br>CTGGCCGGCCCACTGCGGCTGCATCACCAGGGCCTCATGCTAACGGCTGCCCACCCCGCCCCGCAGTCACGTTCTCCTCCCCGGCTGAC<br>ATCACCATCCTGCTGGACGGCTCCGCCAGCGTGGGCAGCCACAACTTTGACACCACCAAGCGCTTCGCCAAGCGCCTGGCCGAGCGCTT<br>CCTCACAGCGGGCAGGACGGACCCCGCCCACGACGTGCGGGTGGCGGTGGTGCAGTACAGCGGCACGGGCCAGCAGCGCCCAGAGCG<br>GGCGTCGCTGCAGTTCCTGCAGAACTACACGGCCCTGGCCAGTGCCGTCGATGCCATGGACTTTATCAACGACGCCACCGACGTCAACGA<br>TGCCCTGGGCTATGTGACCCGCTTCTACCGCGAGGCCTCGTCCGGCGCTGCCAAGAAGAGGCTGCTGCTCTTCTCAGATGGCAACTCGCA<br>GGGCGCCACGCCCGCTGCCATCGAGAAGGCCGTGCAGGAAGCCCAGCGGGCAGGCATCGAGATCTTCGTGGTGGTCGTGGGCCGCCAG<br>GTGAATGAGCCCCACATCCGCGTCCTGGTCACCGGCAAGACGGCCGAGTACGACGTGGCCTACGGCGAGAGCCACCTGTTCCGTGTCCC<br>CAGCTACCAGGCCCTGCTCCGCGGTGTCTTCCACCAGACAGTCTCCAGGAAGGTGGCGCTGGGCTAGCCCACCCTGCACGCCGGCACCA<br>AACCCTGTCCTCCCACCCCTCCCCACTCATCACTAAACAGAGTAAAATGTGATGCGAATTTTCCCGACCAACCTGATTCGCTAGATTTTTTTT<br>AAGGAAAAGCTTGGAAAGCCAGGACACAACGCTGCTGCCTGCTTTGTGCAGGGTCCTCCGGGGCTCAGCCCTGAGTTGGCATCACCTGCG<br>CAGGGCCCTCTGGGGCTCAGCCCTGAGCTAGTGTCACCTGCACAGGGCCCTCTGAGGCTCAGCCCTGAGCTGGCGTCACCTGTGCAGGG<br>CCCTCTGGGGCTCAGCCCTGAGCTGGCCTCACCTGGGTTCCCCACCCCGGGCTCTCCTGCCCTGCCCTCCTGCCCGCCCTCCCTCCTGC<br>CTGCGCAGCTCCTTCCCTAGGCACCTCTGTGCTGCATCCCACCAGCCTGAGCAAGACGCCCTCTCGGGGCCTGTGCCGCACTAGCCTCCC<br>TCTCCTCTGTCCCCATAGCTGGTTTTTCCCACCAATCCTCACCTAACAGTTACTTTACAATTAAACTCAAAGCAAGCTCTTCTCCTCAGCTTG<br>GGGCAGCCATTGGCCTCTGTCTCGTTTTGGGAAACCAAGGTCAGGAGGCCGTTGCAGACATAAATCTCGGCGACTCGGCCCCGTCTCCTG<br>AGGGTCCTGCTGGTGACCGGCCTGGACCTTGGCCCTACAGCCCTGGAGGCCGCTGCTGACCAGCACTGACCCCGACCTCAGAGAGTACT<br>CGCAGGGGCGCTGGCTGCACTCAAGACCCTCGAGATTAACGGTGCTAACCCCGTCTGCTCCTCCCTCCCGCAGAGACTGGGGCCTGGAC<br>TGGACATGAGAGCCCCTTGGTGCCACAGAGGGCTGTGTCTTACTAGAAACAACGCAAACCTCTCCTTCCTCAGAATAGTGATGTGTTCGAC<br>GTTTTATCAAAGGCCCCCTTTCTATGTTCATGTTAGTTTTGCTCCTTCTGTGTTTTTTTCTGAACCATATCCATGTTGCTGACTTTTCCAAATAA |

TABLE 6C-continued

| SEQ ID NO | GENE NAME | SEQUENCE |
|---|---|---|
| | | AGGTTTTCACTCCTCTCCCTGTGGTTATCTTCCCCACAAAGTAAAATCCTGCCGTGTGCCCCAAAGGAGCAGTCACAGGAGGTTGGGGGGC GTGTGCGTGCGTGCTCACTCCCAACCCCCATCACCACCAGTCCCAGGCCAGAACCAGGGCTGCCCTTGGCTACAGCTGTCCATCCATGCC CCTTATCTGCGTCTGCGTCGGTGACATGGAGACCATGCTGCACCTGTGGACAGAGAGGAGCTGAGAAGGCAACACCCTGGGCTTTGGGGT CGGGAGCAGATCAGGCCTCAGTGGGCTGGGGCCGGCCACATCCACCGAGGTCAACCACAGAGGCCGGCCACAGGTTCTAGGCTTGGTAC TGAAATACCCCTGGGAGCTCGGAAGGGGAGTTGAGATACTGCAGGGCCCATAGGAAGAAGTCTTGGGAGGCTCCACCTTTGGGGCAGAG GAAGAAGTCTTGGGAGGCTCCACCTTTGGGGCAGAGCAAGAAGAGGGCGGAGGGCAGAGGCAGCGAGGGCTCATCCTCAAAAGAAAGAA GTTAGTGGCCCCTGAATCCCAGAATCCGGGGTGCACGGCTGTTCTGGGGGCCGCTAGGGGACTAAGAGGATCGGCCGAGGGCTGGGCT GGAGGAGGGCAGCAGGGATGGGCGGCGAGGGTGAGGGTGGGGCTTCCTGAAGGCCTTCACCTGCGGGGACCCCGGCGAGCCCCTCAG GTGCCACAGGCAGGGACACGCCTCGCTCGATGCGTCACACCATGTGGCCACCAGAGCTGCGGGAAAATGCTGGGGACCCTGCATTTCCG TTTCAGGTGGCGAACAAGCGCCCCTCACAGAACTGCAGGTAGAGACGGGCCCGGGGCAGACGCAGTGAGGCGGTGGGCGGGGCCCGGG GCAGATGCAGTGAGGCGGTGGGCGGGGCCCGGGGCAGAGGCAGCGAGCGGTGGGCGGGGCCCGGGGCAGACGCAGTGAGGCGGTGG GCGGGGCCCGGGGCAGAGGCAGCGGGTGGTGGCCGGGGCCCGGGGCAGACGCAGTGAGGCGGTGGGCGGGGCCCGGGGTAGTCGCA GTAGGTGGTGGGCGGGGCCCGGGGCAGACGCAGTGAGGTGGTGGGCGGGGCCCGGGGCAGACGCAGTGAGGCGGTGGGAGGGGCCC GGGGCAGACGCAGTGAGGCGGTGGGCGGGGCCCGGGTCAGAGGCAACGGGTGGTGGGCGGGGCCCGGGGCAGACGCAGTGAGGCGG TGGGCGGGGCCCGGGGCAGATGCAGTGAGGCGGTGGGCGGGGCCCGGGGCAGATGCAGTGAGGCGGTGGGAGGGGCCCGGGGCAGA CGCAGTGAGGCGGTGGGCGGGGCCCGGGGCAGACGCAGTGAGGCGGTGGGCGGGGCCCGGGGCAGACGCAGTGAGGCAGTTGCCAG CCTCTCTCAGCTGCCTCATGGGATTCGCACTGCAGCTGCGGCCCTGGCGCGACAAGGGCTGGACTTGGCCAGCGGGACGGTCCCTCACG GCGCTGAGGCCCACACTCTGCGTGGAGCCTCCCCGTGCCCAGGCTACCCTGCAAGGTCCTCGGAGAGGCTTCCTCCAGCCCCAGCCCCC ACACAGCTCCGGCCCAGGCCCGCTCTTCCCCATCCCAGTTGCTTTGCGCTGTATACGGCCAGGTGACCCCGAGCCGGCCCTGAGCCCTC GTCCCGGCTTCCTCCCCTGTAAGCTGGGTGAAGGACTCCATGGCACCCACCTGAGAGGGTTGTGGCGAGGCCCAGGCCCCTCGTGCCCA CACGGCCGGCGGCCCATGCCTGGCAGGGGCTGGGAGGAGGCTGGGGCGACCAGAGGGGAGCGGCCTGTCCTGGAGGAGGCCCAGGGA CCCTGGTGAGAGGGTCTCTCCCAAGTGCTCTCTATGGGACCCCCTTCCTCTGCGCCCGTCCTTCACGGACCTCTCCGGGTCACCCCTGGG CTGCACACTGGGTTCAGGGGGGCCTTGAGGTGGGGCCCCTGTTCCCAAGTCCCGGCGGGGTTTCTCCTGAACCTCAACCCATCCTCACCT GCGGGCATTCCCATCCCCCAACGCCTGGGTCACCAGGATTCCAGGCAGGAGGGGCGGTGGGGGTTACCAAGGCCCGGGTTGCCATGCA GAACCCCCAGCCACCACGCAGACCCCCACGGGGCCCAGGGAAGCTCCTGGTCTCACACTGCACCTCACACTTCCTGTGGGGGCAGACTC CAAGGTCCCGGCCTCTCATCTTGTAGAAACTGAGGCACAGGAGGGACACACACTCCCACGGCCGGTCACCGTGGCCCCCACACCTCCCAC TGGACTGACACCTGGCCAGGCTCCGGACACCCGTGGCACAGCCTCAGCCCCTGCGGCCCCTGCTCCGTGGCCCCCAGGCCCCAGCTCC CATGTGCACGTCCTGCCTCAGGCCTGGAGGCCCCTCGGCCCCAAATAATCAGACAATTCAACAGCAAAACTACTTTTTTCAGGCTGGCAGG ACTCTGGGCAACCCCCTGCAACAGCCCCCTGCCCTATCACAGCCACCCTTGCCTCCCAGGCACGGAGACCCCACCATCAGGTCCCAGCCT TGGTTCATCCCCAAGCACCCTGTGTGTTGGGATGGCGATGCTGGCTGAGCCCCTGCATCC |
| 253 | chr21: 46280500-46283000 | AGGGCGTTTGGGAACACCCCTCCCGGAGGGGTGAGGCGGCCCAGCCTGCGGCTGCCAGAGGACACAGGTTCTGCTGCGGAACCTGCAG ACATGGCCATAACAGGCCACAGTGCTCGGGCCCACACAGCCTGGACCCACATGGCCCTGTGTCACCTCCTCAGGGGCAGGCTTCAGGGC CTCGACCCTAGAGGCTGCCCCTCGGTTCTGCTCCATGGACGGCGCAGGCAGGCCCAGGCCTGTGACGAGTTCACGGAAGCTCCAGGATG ACCCCCGCTCTGCGCCCTCCTCCAGCATTCCAGACCACAAACCACTCTGGGCTAAAACGAGGCATCGCCAGAGCATCCCACTTCCTCGGA AAGCTGCGGTCTGGGGACGCGTCTTGGCCCTGAAGAGGCTCCAGATGGCTCCCATCAGGCCTCTCCGCCTACGTGCGGCCGACATGGAG TGACAGAGCGTCGGGGACACAGAATTCAGAGCTGGGCCTGGGGCTGCTTTGAGATACTGATGGCTGCCAGGGGGCACAGAGACCCGTCC TGCAGACAGGGCTGTGAGGGCCACAGGGGGCCTCGGGGAGAGGCAGTGGGAGGGAGGACAGTGGGGGCCTCCAGCTGGGTGAGCAGC TGGAGCGAGGGGGGCCCGGGGCTTGTGATGGTGCTGCCGACCCTAGAGGTGCCGGCCCCACGATGGAGAGCACGTAGTGCCCCCCGGG AGTCAGGAGGCCGGGCCTGACCTCGGGGGCTGCAGCCAGGGGAGGCCGGCACCCCAGATAACCCCCAAAGAACTGCAGGCCCTGAGGC GAGGCCAGAGTGGGGGCGGGGGCAGGTCCCAGCCGAGGAGGTGCTCCGTGCTGCCTCAGCAGAACCCATGATGGGCTGGCCCAAGGCT CTGAAGGTGGAAAGGCCTCACACATTCTGCCCCGGCTGACGCCTTCCTTGGGCCAGTGCTCGGGGGTGTGTAACAAACGCCAAGACGCAT TGTAAAGAAGGAAGCCTGCGTTTCCATCACCGGCTTAATATCAAACAAAAGTGCAATTTTGAAAATGTAGTCCAAGGTTTTCTGTGGTGCGG AAATGGCCAGGCCAGACCTCCGTGGGTGGTCCTTCGTGTCCACGTCAGCGCCCTACATCCACACTGTGGGCACCATGACCTCACATGCGG AGCGGAGCAGGGCCGGCGCCCGGAGAGCCAGGCTGGTCACGAACGAGGCCTAGAGGGCGTCAGGCCCCAAAGCACTCACAGGCTTCTC CTCTGTCCTCGGGGCCTTCAGACACCTGCATGCGCCGATTCAGCCACCCGCGCGCGCCGATTCCCCTGGCCATGGGGTTTCCAAAGTGTG TGCTCAGAGGACAGTTTCCTCCAGGATGACCTGTCAGTGGCTCTCTGTGCCGGGGACGTCGCGTGCTGGGTCCCGGTCTGAATGCTTCCT AACGATTTACCCAGTTCCTTTTCTCCACTCAGGAGGCGTTTGCTGAGAGGCACAGGCTGAGCCCCCGTGCTGATGCCACGACCGAGGGAA CGGGTCTCCCTGTCGGCGTGAACTGACCCGGCCAGGCGTCCACTGCCACTCGGACTGTCTCCCAGGCACGTGGCGCCCACACGGGCAGA |

TABLE 6C-continued

| SEQ ID NO | GENE NAME | SEQUENCE |
|---|---|---|
| | | ACACGCCCTCCACACACGCGGCTTCGGGCAGAACACGAGGCGCCCTCCACACACGCGGCTTCGGGGCTTGTCATGAAAAAAGCTGAATG<br>CTGGGGGTGCAGCTTTCACCAACAGAATCCCGTTTGGAAGGGACGCGGTGAGACATGATCCACCCTAAGTTGTGATCCTGGGTGAGCCGC<br>CGTCCACACCCTGCTGAGGGTCCCTTCACCCACTTTATTCTCCAGAAAACCCTGCCCATCAGGGCTGAGTCCCACGCCTTCCCTCTCCGTC<br>CAGGCCTGGCTTTGACCTCTGGGGTCGTGTGGGGCACAGGGGACACCCTATCCAGGCAGAGGCCCTACGGCTATCTGGAGGAAGTGGTG<br>GGAGCTGGGCTTCTGCCTGGAGGATGCACCCAGAGGGGTCACAGTCCACACAGAGACACACGGGTGCCTTCCAGATGGCTGAGCCAGTC<br>CAGCCCAGAAGGGCCTGGGGGTTGGGGGCTGCACCTGGCCTGTCCCCACCAGCAGGGCTCAGGGCTTCCCAAGGTGTGTGGGGGACGG<br>GGCAGCACCTCTCAACCAGGTCACCTGAAACCCGAACTGAAAGGCATCCTAAGTTAAGACATTAACTCCCATTGTCAAGGTGCCATCGTCA<br>ATTCTGTCTCCAAATCCTTCTTTGTTATTTCATGTATTCACAGAGTGACGCTCCGTGTTTCGTTCAGCCTGCAGGCCTGCAGAAGCTGCATCT<br>CGGGATGGCCAAGAGCCCGGCCAGGCCCCACGGCTGCACCCAGGACGGGATTCATGCCCCATGCCTGGCTTCTCACGACCACAGAGTGC<br>CTTTCCCGGGACTGGATGGAGGCAGAGTGAGAGAAGAGCCTGGAGCAAGTGTTTTGGACCACAGTGATCAAACACGGAGCCCGTGGG |
| 254 | COL6A2 | AAGAAAGGCCAGACCGGGCACGGTGGCTCACGCCTGTAATCCCAACACTTGGGGAGGCCGAGGCGGGCAGATCACCTGAGGTCAGGAGT<br>TCGAGACCAGCCTGGCCAACAGGGTGAAACCCCGTCTCTACTAAAAATACAAAAAAAAATTAGCCGGGCGTGGTGGCAGGCACCTGTAATC<br>CCAGCTAATCGGGAGGCTGAGGCAGGAGAAAATCACTTGAACCTGGGAGGCGGAGGCTGCAGTGAGCTGAGATCGCGCCACTGCACTCC<br>AGCCTGGGTGAGGGAGCGAGACTGTCTCGGAAAGAAAGGCCCGGTGAGATGCTTTCTCTTAAAC<br>ACGGCCCTGCACGTTGAGTTGCTGCCTCCTGTGGCCTATTTCACGTTTATGCAAAGTCGGGCGCCTGATGCGGGGCTCACCCGCCACAAG<br>CAGGGGTCCTGGTGCTGCTCATGGAAGGGGCCCTACCCAGCCCGCGGGGCACTGGCTGGGACGGGGCTGCCCAGGTCCGCCCAGGATC<br>CAAACACCCAGCCCCGCCCAGCGGCCCTTCCTGGCCTGCAGTGGAGGCTGTAATGGGCAGGGGTGGTGGGAATCCCAGCTCACAGGGC<br>GCCTGCTCTTAGAAGGGCGGCATCTGGGTCCAGAGGTCAGAAACGTCAGATGCCCATCCCAGAAGTGGCGGGGA |
| 255 | COL6A2 | GGGTGAATGAGTAGATGTATGGGTGAGTAGGTGGGTAGGTGGGTAGATGGATGGGTGGGTGGGCGAGTGTGTGGTTAGATGATGGATGG<br>CTGAATGGATGAGTGGGGGGATGGATGGGTGAGTGGGTGTATGTATGGATGGGTTAGTGGGTGGGTGGATGAATGGATGGGTGCATAAA<br>GGATGGATGGATGAATGAGTTAGTGGGTTGGCAGATGGATGGATGGGTGAGTCAGTGGATAGATGGATGGGTGGGTGGATAGAGGATGG<br>ATGGTTGGGTAGGTGATGGGTGGATGAGTGGATAGATGGGTATGTGAGTGAGTGGGGGGATGGGTAGGTGGGTGGATGGATGGTTAGGT<br>GAATGAGTGGATGGACAGACGGACAGTGGGTGGATGGATGAGTGAACGGATGGACCGATGGATGAATGGGTGGGTGGGTAGAGGATGGA<br>CGGACAGGTGAGTGGGTGGGTGGATGGATAGATGGGTAAGTGAGTGGATAGATAGATGGGTGGGTGGACAGAGGATGGGTGGATGAATG<br>GATGGGTTAGTGGGTGGCTGGGTGGATGGATGATGGATGGGTGACTGGGTGGATGGATGGATGGGTTAGTGGGTGGCTGGGTGGATAGA<br>TGGATGGGTGATTGGGCGAATGGGCGAATGGGTGGATGGGTGGGCGTGGAGTTGGTGGGTACATGATAATGGGGTGGAATACCCATGGA<br>TTGGAATGAGCTGTTTTGGCTGCTATTTCTGGGACACCCAGCTCTGCCAGGCCCCTACCCCTCTGGTGGGCCAGGCTCTGACGGTGGCCA<br>CTCATGGCCTTTCTAGCTCTGGTGCCAGCATAGGGAAGGAGGAGGCACAGCCTTGTCTTACTCCTTGCACCTGTTAGCCCCCCCCCCCGC<br>CAAGGGAGGACCCGTGGTTGGGGACAGCACAGGGGGCCCTGCTGTGTGCAGGGACTGTCCCTGGGGCCACTGAAGCCCACCTGTTCTTG<br>TTCCTTCTCAGGCGGATCCTGGTCCCCCTGGTGAGCCAGGCCCTCGGGGGCCAAGAGGAGTCCCAGGACCCGAGGTAGGTTGGTGGCCA<br>GTCCCCATGCCCTCCCCCCAACCTGCCAGGCCAACACACACCCAAGCCTCGTGGTTCTGCCCACGGTGGACCCACGTATCAGTGGGCAGT<br>GGCCTGGGAGAGACTCAGCCACCCAGCCTTGGCCCCAGAGTCTCAGCCTCATCCTTCCTTCCCCAGGGTGAGCCCGGCCCCCCTGGAGA<br>CCCCGGTCTCACGGTAGGTGTCACATGGGGCAGAACCAGTGTCCTTCTCCTGCCAAAACTAGACACCAAGAGCAGCAGGGGTGGGGGAA<br>GGTCAGCTGGCACGGTCAGAGAGCAAGATCAGTGGAGGAGGTCAGAGGGCAAGGTCAGAGAGCAAGCTTGGTTGGGGAAGGTCACAGG<br>GCAAGGTTGGTGGGGGGAGGAGGGTGGCAGCGAGGTTGGTAGGGACAGGACCCGCCAGCCTCCCCGCATGGCTGCCTCCACACGTGGG<br>CTGGAATGTCCCGGGACCCCCAGGCCAGGACCTTGCTGTGGAAACTCTTCTGGGGCCCCGGGGGGACTACCCTGCCTGCCGTGTGCATT<br>GCAGGAGTGTGACGTCATGACCTACGTGAGGGAGACCTGCGGGTGCTGCGGTGAGGCACTGCCCACGGCAGGGTCGGGGCCCATGCAC<br>CGGGTGGAGGGCGGGAGTGCAGCAGGGCTGGGTCATCGCTGGGTCCTGCATGTGCACGTGACCCTAGGGTCTGAGGTCTCCCCGGTAC<br>CCCCCGATGACCCTGCCACCCCCCCAGACTGTGAGAAGCGCTGTGGCGCCCTGGACGTGGTCTTCGTCATCGACAGCTCCGAGAGCATT<br>GGGTACACCAACTTCACACTGGAGAAGAACTTCGTCATCAACGTGGTCAACAGGCTGGGTGCCATCGCTAAGGACCCCAAGTCCGAGACA<br>GGTCAGCGGGGCAGGGGCGGGTGCAGCATTGCGGGGGGCCGGGCGGGGCGTGGGAGGCGATGAGATGGGAGAAGTCCAGACGCGTCC<br>CTCCAACGAGGGCCTCTGCATGGCTGGGGATGCCCCAGACCCCGAGGCCTCTGGCAACGACCTCACGCGTGCGGCTTGCAGGGACGCGT<br>GTGGGCGTGGTGCAGTACAGCCACGAGGGCACCTTTGAGGCCATCCAGCTGGACGACGAACGTATCGACTCCCTGTCGAGCTTCAAGGA<br>GGCTGTCAAGAACCTCGAGTGGATTGCGGGCGGCACCTGGACACCCTCAGCCCTCAAGTTTGCCTACGACCGCCTCATCAAGGAGAGCCG<br>GCGCCAGAAGACACGTGTGTTTGCGGTGGTCATCACGGACGGGCGCCACGACCCTCGGGACGATGACCTCAACTTGCGGGCGCTGTGCG<br>ACCGCGACGTCACAGTGACGGCCATCGGCATCGGGGACATGTTCCACGAGAAGCACGAGAGTGAAAACCTCTACTCCATCGCCTGCGACA<br>AGCCACAGCAGGTGCGCAACATGACGCTGTTCTCCGACCTGGTCGCTGAGAAGTTCATCGATGACATGGAGGACGTCCTCTGCCCGGGTG |

TABLE 6C-continued

| SEQ ID NO | GENE NAME | SEQUENCE |
|---|---|---|
| | | AGCGTGTGGGCGCGGGGCAGTCGGCCGAGGAGCAGCAGGCCCCAGCCGCTGTCTAGCGTGAGCCCCAGGGACACCCCTCACCTGAGGG<br>ATGAATGTGCAGCCCAGGATCTTGGGCTGTGGGTGGGAAGGGGTCGGGCCCTCTCGGGGCTGCAGGGCAGAGGCCAGCTGCACCCTGA<br>GCCTGTCTAGGCAGATCAGTGAACGGCCGCTGAGGGTTCGCTAGGGACTGACCCTGGCCTGGCCCGGCCTCTCTCCTCTCTTCCAGACCC<br>TCAGATCGTGTGCCCAGACCTTCCCTGCCAAACAGGTAATGCAGGGCACCCTGAGCCACCACCCCAGACTAGCAAAGCAGCCCTGGTGTC<br>CTTCCTCCTCGAGGGCCGGGCTGGGGGAGGGGCCGTGCAGGGACCCGGGGGGCGGCGGAGCCACTGCGGAGGCTGCTCCTTAGGGAG<br>ATGGCCCCAGGATGGCAGCACAGGGGAGGAGGGGCTTGGGGAAGGCAGGCTCCCAGGAACGCAGGAACAGCATCACGAGGCCATGAGG<br>TGGGTGCTGCTAGCCTGGCGCTGTGCTCGGCATGTGGCCACTGGTCTTGAAGGCCCACCATGGGCCTTGCAGTCTCCCTCAGCTGCCGC<br>CCAGCTCCCATGGGCTGGCCGTGCATGTGCCACTCGGAGGAAGCCCTGGATTCAGTGAGTGAAACCATCCCGGGGTGGAAGCACTGACA<br>CCCCCCAGCACCAGCAGGTCTTGCTCCAACCCTGGCCTGCCTCGGAGCTGCAGCTGCGGCTCTCACATCTCTGGGAGTGGGGGAGCCCA<br>TGTCCCGGATGTGGCCCACGTGGGTGTGAAGCTGGAGCTGGGGGTGCCGTCCAGGCTCTGCTGGACGTGGTGCTGCCCCCATGGTGCAC<br>TGCTGCACCGTACCTGGGCCCACAGGAGGTCCCCGGGGGCGTTAGGAGCTGAGTCCCCCTCAGTGAGCCGTCCCCTCCAGGAGTGTGAG<br>GGTAGGGATGCCATGGAGACAGGGTGGGAGGGTCCGACCTGGAGGACCACAGGGAGGAAACCTCAGGGTCTGCGGTACGAAGTCAGCG<br>CTTCCTCAGCACGCGGGTCGCGGTGTGCGTTCGGGCGTTCCATGGGGAGCTCCCGGTGGGTGAGCTGGGCCACTGAGCACATTCACAGG<br>CCCTGAGGCTGCCCCAGGGGAGGAGCCGTGGACTCAGAGCCGAGGTTCCCCATACGTGCTGCGACAGAGAACCTAGGGCTTGCACCTGG<br>GTCTGGCTGCCCTTCAGCAGGCGGGCAGCCTCTGGCCCCACAACAGTGGGCTGTGCTTCTGCCGCCAAGGTGCAGGCGTCCTCCCCCAG<br>GGTCCACATCAGCAGCAGGGGCACCTGGACCCTGAGGGCAGGAACCAGACCTTGGCTCCTCCACCCACCCCCTCGTTCCTGATGGGGCA<br>GGGAAGTCTCGGGACCCCATGATGGGCGACATGGCGATGGTCACTGTGGGTGCTTTGCTATCAGGTGGGGGGCCTTCCTCTCCACTCTGG<br>GTCCAGTGTGAGTGGCCGCTATGGCTTCCCCTCCACTCCAGGTTCTATCGTGAGTGGGTGGGTGCTGCGTCTGTGGATGTCACGTGACCT<br>TTCCTCTTTAGCCTATCATTGTAGTTGGGAGTTAGTTAGCCCGTTGAGCGTCATTGAATTTCCAGTGTTGAGCCAGCCCTGCGTGCCCGGGA<br>TAAACCCACCTGGCCGTGGTGTGTGGCCCTGTTTATGCACGTGGGCCCTGATTCGCTGATGCCTGCCTGAGGGTTTGCGCTTATCGGCGA<br>CATCAGCCTGCACTTTTCTTTTCTCGTGATCTCTCTGGTTCTGGCCTCAGGGTGACGTGGGCCTCGTAGGGTCCTGTGGTGGCTCCTCCCC<br>AGACGGTGACATGGAGTGAGCCCATTCTCCCTCCTGGGAGTGGGTCACTCAGGCCACCAGAGCACCACAGGGAAAGCAGCCAGGGAGGA<br>CACGGAGGCCCTTGAAGCTCTGGCCTCTTCTGAGGCCTCCAGGACCTGACAGTGAGTGGGAGCAGCCCTGGCAGAACCCCTCCCCTCCT<br>CTCGGCCGCCCTGACACCTCATCCCCGACACTCAGAGCTCATCCTCCTTCCCAGCTGTTTCCAATTTCAAAGTGAACTCGACCTTGTGGCT<br>CCAGGAGATGCAGCAGGGACAGTGTTAAATCGGCTTTCACCAGCCCACACGGCCAGGCATCCTCCTCGGCCCTCCTGGGCACTGGGTGG<br>ACACCACTGGCTGTGGCCTGGCCCTGGCCTTCTCCAGACAGCCCTGTCCACCCCAAAGCCCAGCCACCCTGGGCCTGCAGCAGGCCTGT<br>GGAGTTCTCAGTTGCGTGGGGACCAGAGGGTGCTGGAGAAACAAACCAGACGCAGCTGAAGGCAGTCAGGGCAGGGCGCAATCAGCGAT<br>AAGAGCTGCATAGGGGCCACAGCGTAACCTGAGCTCCAGTCGGTGGAAAGAAAAGGCAGAGACGTTGCAGAGGCCAGGTCTGCTCAGGG<br>GAAGACAGTTCTGGGTGTAGAGGACTCACATCCCAGAGAGGCTGAGGAAGGGTTTACCACCGCAAGCTTTCTCAGGCGGGCTCTTGAGGG<br>GTGGCTGGGGTCTTCCTGGCGACGGGCCTGCGGCACTGGAAGCCCTACTGGAGTTTGGCCTGTCTCCGGCACAGGTTTGGACGGAGCTG<br>TTTTGTGCTGAAAGGTTTTCTCGGGGTCCGTGGTGTCCCCCAAAGGTGCCACCGTGCGGGTCTCCTAGCTCCCTGCCAGCTTCCTGTCCCT<br>GTGCTCACTGCCCCCACGCCTCCTGCCAAGGCCGAGCCACACACCCGCTCCACCTGCATTTCCTCTACCGACTCGCCAGCCCAAATGCCG<br>CTCTTCACTCTGGCCTCGCTGAGCGGCTGCCCGAGGAGGAGCTCTAGGCCGACGCCCACCGCAGGCCTTACAGTCTTCTCTGGACGCTCC<br>CTTGCAGATGCACCGTGGCCTGGCGGCGAGCCCCCGGTCACCTTCCTCCGCACGGAAGAGGGGCCGGACGCCACCTTCCCCAGGACCAT<br>TCCCCTGATCCAACAGTTGCTAAACGCCACGGAGCTCACGCAGGACCCGGCCGCCTACTCCCAGCTGGTGGCCGTGCTGGTCTACACCGC<br>CGAGCGGGCCAAGTTCGCCACCGGGGTAGAGCGGCAGGACTGGATGGAGCTGTTCATTGACACCTTTAAGCTGGTGCACAGGGACATCG<br>TGGGGGACCCCGAGACCGCGCTGGCCCTCTGCTAAAGCCCGGGCACCCGCCCAGCCGGGCTGGGCCCTCCCTGCCACACTAGCTTCCC<br>AGGGCTGCCCCCGACAGGCTGGCTCTCAGTGGAGGCCAGAGATCTGGAATCGGGGTCAGCGGGGCTACAGTCCTTCCAGGGGCTCTGG<br>GGCAGCTCCCAGCCTCTTCCCATGCTGGTGGCCACCGTGTCCCTTGCTGCGGCTGCATCTTCCAGTCTCTCCTCCGTCTTCCTGTGGCCG<br>CTCTCTTTATAAGAACCCTGGTCATTGAATTTAAGGCCCACCCCAAGTCCAGAATGACCTCGCAAGACCCTTAACTCACTCCCGTCTGCAGA<br>GTCCTTCTTTGCTGCATCAGGTCACCCTCACAGGCTCCAGGGTTTGGGTGTGGAAGTCTTTGGAGGCCCTTACTTAGCGGCCCAGCTGGG<br>CTGCCGTGCGTCTGGGATGGGGCTGAGGGAGGGTGCTGCCCAGGTGCTGGAGGATGTTCCAGCACCAGGTTCCAGCGGAGCCTCGGAA<br>ACAGGCCCCAGAGGCTGGTGAGCCTCGCTGGGTGTGGGCACTAATCCCGTGCATGGTGACTCGTGGGCGCTCACGGCCCACCTGGTGGC<br>AGGTGAAGGCTTCCGGTTGGGCAGCAGATAGTCCTGGGGGAAGCTGGCAGTCCTGGCACCATGACGTATCTGGGCTGGTGTCATGCACA<br>GTAGGGCGAATGGCCACAGCTGCCTGCCAGCAGCCCTGATCCCGGGGTGTCTGCACCCTTCCAGCCCAACCTCTGGGTCTCCAAAAGCAC<br>AGTCGGGGGAGCATCCACCAGGCACAACCTCTGCGGTCCTCAGAGGACTGAGCAGAGAATCCCAGGGTCCACAATGTTGGGGAGCGGCA<br>GGGATCACCATCCAAAGGGAGCGGCCCCCACGGCGAGCTGACCCCGACGTTCTGACTGCAGGAGCCCTCATCCAGGCTGGGCTCCTGCC<br>GGGCACGGCTGTGACCATTTCTCAGGGCCAGGTTCTCGTCCCCACACCCACTGCACAGGGCAGGCCAGGCTGGTCTTCCCACTGTGGGG<br>ATGAAGGATCCTCCACAGGAGGAGGAGAGCAGAGTCCACAGACATCCCAACAGCCTCAGCCTCCCTGTGCCTGGCCGGCCCCCACAGCTT |

TABLE 6C-continued

| SEQ ID NO | GENE NAME | SEQUENCE |
|---|---|---|
| | | CCCCGTCTCCTCCAGGCCCCACAGACACTGATGAATGGACAGAGACCCCCAAAACCAGCTGCCCCTTGCATGTCTGTCTCCATATGTTTGG |
| | | TGACAGCAGTGAAAATGTTATTAGTTTTGAGGGGGTTTGGGAAGCCCAGCGGTACCTGAGGAGTTTCTGGACATTTAAGCCGGTTCCTAGG |
| | | TGTGGCCTTAACAGGGAGGCTGCCCTTCCTTTCACTGAATGAGCTGCGTCACTCATAAGCTCACTGAGGGAACCCCATCTGCCAGCTCGTG |
| | | CGTGCTCAGACGGCGTCCATGTCTCAAGCGTTCTGTGAAGGCTGCGGTGCAGCGTGAGGTCACCCTGCTGTGTTCAGAGCTTTGCTCACT |
| | | GCCTGCGGGGCTGGACCGTTGCACCTCCAGGGCCCCCAGAAACCGAGTTTCGGGTCAGGGTCCTCTGTGTGCATTCCTGGGGGTCCATG |
| | | TACCAGCTGTGACGACGTCCAGGGGTTGGGCTGAGAAGCAGACACCCTTGGGGAAACTGGCTCTGTCCCTCCCCTCCCCCATCCCAGGAG |
| | | CTGAGGTCTTGGTGAGGCCACAGGGCCAGGTCCACGCAAGGACTGTCCGTGTCCTGTCCTGTGGTCTCTGGCCCCACGTGACACCCACAC |
| | | GTGTGGTAGGCAGCCTGGCCTGGGTTGTGGCTATGGCCAGGCCCCCAAGCTGTCCCCGATGCCCAGGGCTGGTGACCACCCAGGCAGGT |
| | | GGGGGCCCCACTTGGTAACAGAGTCATAGGGCAGAACCCACCTGGGCTGCCACAGAAGGTCTGGCTGCCCCTGTGCCCACTGCTCCCCA |
| | | CCATGGCCAATCAGAAGAGTCAGGGGCTCCTGGTCTTTCCGGGAGGGACGTGGCCCAGCCAGCTCTAGGTGTTCTGAGCAGCTCTGGGA |
| | | CCCAGCGATTGAGGGGTCAGGCTGGGGGTGTCAGAGCCAGGGTCCTCCTTAAGTACCTCCCACACTACACAGACAGTGGCCCTTTTGTGG |
| | | GCAGCAAATTCTTGAGCCATGAAAGGATGCTTTGGGCCCCTTCCCTCCCAGGAGGGCAGCCTGTGCAGGGATGGTGCTCAGCAGGTGGAC |
| | | AGGGCCTGGGGCCTGTGTCAGGGTCTCAGGCCTGGGAGCACCAGCAGAGGAGATGGCGGCTCCCAGCAGTGCCGCCTGAAAGTGTCTTG |
| | | GGCTAAGGACCCACACCCAGGGCTGCCCTGCAGAAACGCCCCCGCAGAGCCCAGTGGTCTGTGAGGTTGCAGGCAGGGTGCGAATGGAA |
| | | GGGCACAGGTGCGGGGCTGGCACCTGCCCGGTCCTGCCCACCTCCCCTCCGCCCAGCCCGCACCTGCGTCTCCCCACAGAGCTGTCCGT |
| | | GGCACAGTGCACGCAGCGGCCCGTGGACATCGTCTTCCTGCTGGACGGCTCCGAGCGGCTGGGTGAGCAGAACTTCCACAAGGCCCGGC |
| | | GCTTCGTGGAGCAGGTGGCGCGGCGGCTGACGCTGGCCCGGAGGGACGACGACCCTCTCAACGCACGCGTGGCGCTGCTGCAGTTTGG |
| | | TGGCCCCGGCGAGCAGCAGGTGGCCTTCCCGCTGAGCCACAACCTCACGGCCATCCACGAGGCGCTGGAGACCACACAATACCTGAACT |
| | | CCTTCTCGCACGTGGGCGCAGGCGTGGTGCACGCCATCAATGCCATCGTGCGCAGCCCGCGTGGCGGGGCCCGGAGGCACGCAGAGCT |
| | | GTCCTTCGTGTTCCTCACGGACGGCGTCACGGGCAACGACAGTCTGCACGAGTCGGCGCACTCCATGCGCAAGCAGAACGTGGTACCCA |
| | | CCGTGCTGGCCTTGGGCAGCGACGTGGACATGGACGTGCTCACCACGCTCAGCCTGGGTGACCGCGCCGCCGTGTTCCACGAGAAGGAC |
| | | TATGACAGCCTGGCGCAACCCGGCTTCTTCGACCGCTTCATCCGCTGGATCTGCTAGCGCCGCCGCCCGGGCCCCGCAGTCGAGGGTCG |
| | | TGAGCCCACCCCGTCCATGGTGCTAAGCGGGCCCGGGTCCCACACGGCCAGCACCGCTGCTCACTCGGACGACGCCCTGGGCCTGCAC |
| | | CTCTCCAGCTCCTCCCACGGGGTCCCCGTAGCCCCGGCCCCGCCCAGCCCCAGGTCTCCCCAGGCCCTCCGCAGGCTGCCCGGCCTC |
| | | CCTCCCCCTGCAGCCATCCCAAGGCTCCTGACCTACCTGGCCCCTGAGCTCTGGAGCAAGCCCTGACCCAATAAAGGCTTTGAACCCATT |
| | | GCGTGCCTGCTTGCGAGCTTCTGTGCGCAGGAGAGACCTCAAAGGTGTCTTGTGGCCAGGAGGGAAACACTGCAGCTGTCGCTCGCCCA |
| | | CCAGGGTCAATGGCTCCCCCGGGCCCAGCCCTGACCTCCTAGGACATCAACTGCAGGTGCTGGCTGACCCCGCCTGTGCAGACCCCACA |
| | | GCCTTGATCAGCAAACTCTCCCTCCAGCCCCAGCCAGGCCCAAAGTGCTCTAAGAAGTGTCACCATGGCTGAGGGTCTTCTGTGGGTGGA |
| | | CGCATGATTAACACTAGACGGGGAGACAGCAGGTGCTGAGCCTGTTGTGTTCTGTGTGGAGATCTCAGTGAGTTTTTGCTGTTCAGACCCC |
| | | AGGGTCCTTCAGGCTCAGCTCAGGAGCCCCACAGTGAACCAGAGGCTCCACAGGCAGGTGCTGACCTGACAGGAGTGGGCTTGGTGGCC |
| | | ATCACAGGGCACCACAGACACAGCTTGAACAACTACCAGTATCGGCCACAGGCCTGGAGGCATCAGCCGGGCCATGCTTCCTCTGGAGGG |
| | | CTAGAGGAGGACTAGAGAAGGGCCTGCCCCGGCCTCTCCCCAGCATCCCAGGGTTCCTGATCTCCTGGATAAGGATACAAGTCACCACAC |
| | | TGGACTGGGGCTCAGCCTGCTCTAGAATACCTCACCTAAGTCACAGTGGACCAGGCTCAGCCTGCTCTAAGGTGAGCTTACCCGAGACACT |
| | | GGACCAGAGATCAGCCTATCCTGGGATAAGCTCACCCGAGTCACACTGGACCAGGGCTCAGCCTATTCCGGGATGAGCTCACCCGAGTC |
| 256 | C21orf56 | GACACTTCCATGACTGCAGCTGACCAGTCCACCTGCCAGCGGTTGACCACTCCCACTTCGCCAGCGACCGAAGGGGAGGGGAGGGGCCT |
| | | CACCTGAGGGCAACAGCAGAACCCACCACCTGGTCTTGCTTTACTCAGACCTGAGGGTGTGAAAGGTGCCCGTGACCTCCCGCATCAGGG |
| | | AGCTGGCCGCCACCCTCGACTCCCGGGGAGCAGGCGTCCCGCGACCCCCTCATCTACCAGGCCATCTGAGCTGGGCGGCGCCTCACCTC |
| | | CGCTCCCGGGGGAGCCGGCCTCAGGGTAGGCATGCGCCCTGGGTGGGAGCAGGTCGTGGCCGCCGCCCTCCTGGCAGCTCTGGCTGAG |
| | | CAGCCGCCGCAGCATCTGATTCTCCTTCAGGAGGCGCACCTGCTTCTTCAGGTCCGCGTTCTCGCTCAGGAGCCGGCTCATCAGCTCGCC |
| | | GCCTTCAGCCATGGCGGGTGCGTCCCTCCTTGTCCCTCACGGCTCCTGCAGCCCCATGGAGGTGGGAGCCCAGAGCCCGCAGGCACCAC |
| | | AGAAACAGCCCAGGCACGGAGTTCCGTAGCCACCACCGCCTTCCACGCCTTGTGATGTCACTGCCCTAGTGATGAGGTGCCCAGCACCCT |
| | | GCCTGCCCCCGCGATGGCTCATGGCCCCGTTGAGGCAGTGAAGCTGGAGGCCCGTGGCGTGCACAGGCAGCCACTCCCACATTATGACC |
| | | AGGGCCCGAGAATGCCAAGGACATTAGGCAGCTACGGGATGTAGCGACTGTACTCCAAGAGGGGCGTCCAAGCCACTCCCCATTGA |
| 257 | C21orf57 | AGGTGGAGGTTGCAGTGAGCCCTCCTCCCCTCCTCCCCCTTCCCTTCCCACCTCCCATGCCCCCCTTTCTTCCTCCCACTCCCCTCCCGAG |
| | | GCCCCGCTTATTCTCCCGGCCTGTGGCGGTTCGTGCACTCGCTGAGCTCAGGTTCTGGTGAAGGTGCCCGGAGCCGGGTCCCGCCTTCG |
| | | GCCTGAGCTAGAGCCGCGCGGGCGGCCGGCTTCCCCCAAACCCTGTGGGAGGGGCATCCCGAGGAGGCGACCCCAGAGAGTGGGGCG |
| | | CGGACACCTTCCCTGGGGAGGGCCAG |

TABLE 6C-continued

| SEQ ID NO | GENE NAME | SEQUENCE |
|---|---|---|
| 258 | C21orf57 | CCTTCCAGATGTTCCAGAAGGAGAAGGCGGTGCTGGACGAGCTGGGCCGACGCACGGGGACCCGGCTGCAGCCCCTGACCCGGGGCCT<br>CTTCGGAGGGAGCTGAGGGCCGCGTTCCTTCTGAAAGCGGGACGCGGGAGGGGTGGAGGCTGCGGGGAGCCGGGGTCGCACACGAATA<br>AATAACGAATGAACGTACGAGGGGAACCTCCTCTTATTTCCTTCACGTTGCATCGGGTATTTTTCGTTATTGTAAATAAAACGGTTCCGAGCC<br>GTGGCATCGAGAGGGCGTCTGGAGTTCAGGGAACGCGTGGCCCCCGCCCGGGAGCACCGCGCAGCGCTCGCCTCTCGCCCTTCAAGGG<br>GGTCCCTGCCCGGAGCCTGCGCCCCCGGAGAGGAAGGGGCTCGAGGGGCTTGGGTGCCGCAGCGCGTCCTTCCGTAGAAAAGGCTTGC<br>GTCAGTATTTCCTGCTTTTACCTCCTGAG |
| 259 | C21orf57 | CAGTATTTCCTGCTTTTACCTCCTGAGTATTGGAATATTCGAGTAAACCCTGGAGTTTCAGCGCCAGCGCACGCCTCTTCATCAGGGCAGCG<br>CGTCGCGAGCGCGCTGGTTCCCCGGGGCCTCCCGGCCACGGACACCGCTCTAGCCAGGGCCACGGCGAGGCCGCCGAGCAGCACCTCA<br>GAGACCTGCGTGAGTTCTAAAGCCTGGGGCTACTACAATTCTGCTCATCTGTTTGTCCTGTGAAATGATTCAGGGACATGAAAATGCCTTCC<br>CACTGACTTGCGTCCTGTCTTAGCCTGGACTTGTCCCCTTGGGAACACGGGCCAGGCCCCTCTGTTCCTGAAGT |
| 260 | C21orf58 | ATGTCTGCAGGGAAGAAGCAGGGGGACCCTGAATAAAGTTTCCGTTTTTCCTATTTGTTAAAGTGATAGAGCATTATAGGACCAGAGAACAG<br>GTGTGTCTGTACACTGTGCAGGTCCCCGGGGCAGGCTCTGAGTCCGTCTGCACACGGTGCGGGTCCCCGGGGCGCGCCCTGAGCCCGT<br>CTGCACACGGTGCGGGTCCCCGGGGCGCGCCCTGAGCCCGTCTGCACACGGTGCGGGTCCCCGGGGCGCGCCCTGAGCCCGTCTGCA<br>CACGGTGCGGGTCCCCGGGGCGCGCCCTGAGCCCGTCTGCACACGGTGCGGGTCCCCGGGGCGCGCCCTGAGCCCGTCTGCACACGG<br>TGCGGGTCCCCGGGGCGCGCCCTGAGCCCGTCTGTACACGGTGCGGGTCCCCGGGGCGCGCCCTGAGTCTCTACTAAAAATACAAAAAT<br>TAGCCAGGCGTGGTGGTTCAAGCCTGTAATCCCAGCTCCTTGGGAGG |
| 261 | PRMT2 | CATACATGGTTATTAGAAAAGGCATCTCATCCAAATGTGGTGGCTCGTGCTTGTAATCCCAGTGCTTCAGGAGGCCAAGGGAGGAGGATTA<br>CTTGAGCCTAAGAGTTTGAGACCAGCCTGGGCAACACAACAAGACCTTGCCTCTACAAAAAACTTAAAAACTAGCTGGGTATGATGGTGCAC<br>ACCTGTAGTCCCAGCTACTTGGGAGGCGGAGGCGGGCAGATCGCCTGAGGTCAGGAGTTCGAGACCAGCCTGGCCAACATGATGAAACC<br>CCGTCTCTACTAAAAATACAAAAATTAGCCGAGTGTGGTGGTGCATGCCTGTAATCCCAGCTACTCAGGAGGCTGAGGCAGGAGAATCACT<br>TGAACCCGGGAGGCGGAGGTTGCCATGAGCCGAGATCACGTCACTGCACTCCAGCCTGGGTGACAGAGCACAAAAGACAGGCATGACTTT<br>GTACTTAACTGCTCAGCTTTGTAATCACTGGGGGCCCAGATGCTCACTTGGATTCTAACTTTGTTGGCATCTGGGCCTAAAAGCCGTGATGC<br>AGGTGAGCAATGATGCAGAGGGCTCTGTGCGCCTGGCGGGCTCTGTTTGCCTGCTGGGCTCTGTGCGCCTGCTGGGCTCTGTGCGCCCG<br>GGAAGGTGCGGCCACCCTCACGCGGAAGGCGGCCAGCGGATCCCGGTGCGCGCAGCTCCCAGCGCTGGGGTTCCAGCGCCCCGCCTCT<br>TCCTATAGCAACCAGCGGGACCTGCCGTCCCCCGGGGCACCCCGAGGGGTCTGCGCCCGCTTCTTTCCGAAACGGGAAGGCGCTGGGG<br>GCTCGGCAGCCAGAGGGACGGGTTCAGGGAGCGTCCGGTGAGCCTAAGACGCGCCTTTGCCGGGGTTGCCGGGTGTCTGCCTCTCACTT<br>AGGTATTAGGAACCGTGGCACAAATCTGTAGGTTTTCCTCTGGGGGTGGGCGGAGGCTCCAAACCGGACGGTTTTCTCCTGGAGGACTGT<br>GTTCAGACAGATACTGGTTTCCTTATCCGCAGGTGTGCGCGGCGCTCGCAAGTGGTCAGCATAACGCCGGGCGAATTCGGAAAGCCCGTG<br>CGTCCGTGGACGACCCACTTGGAAGGAGTTGGGAGAAGTCCTTGTTCCCACGCGCGGACGCTTCCCTCCGTGTGTCCTTCGAGCCACAAA<br>AAGCCCAGACCCTAACCCGCTCCTTTCTCCCGCCGCGTCCATGCAGAACTCCGCCGTTCCTGGGAGGGGAAGCCCGCGAGGCGTCGGGA<br>GAGGCACGTCCTCCGTGAGCAAAGAGCTCCTCCGAGCGCGCGGCGGGGACGCTGGGCCGACAGGGGACCGCGGGGGCAGGGCGGAGA<br>GGACCCGCCCTCGAGTCGGCCCAGCCCTAACACTCAGGACCGCCTCCAGCCGGAGGTCTGCGCCCTTCTGAGGACCCTGCCTGGGGGA<br>GCTTATTGCGGTTCTTTTGCAAATACCCGCTGCGCTTGGACGGAGGAAGCGCCCACGCGTCGACCCCGGAAACGAAGGCCTCCCTGATGG<br>GAACGCATGCGTCCAGGAGCCTTTATTTACTCTTAATTCTGCCCGATGCTTGTACGTGTGTGAAATGCTTCAGATGCTTTTGGGAGCGAGGT<br>GTTACATAAATCATGGAAATGCCTCCTGGTCTCACCACACCCAGGGTGACAGCTGAGATGCGGCTTCTCCAGGGTGGAGCCTCCTCGTTTT<br>CCAGAGCTGCTTGTTGAAGTCTTCCCAGGGCCCCTGACTTGCACTGGAAACTGCTCACCTTGGCATCGGGATGTGGAGCAAGAAATGCTTT<br>TGTTTTCATTCATCCTAGTGTTCATAAAATGGAAAACAAATAAGGACATACAAAAACATTAATAAAATAAATTAATGGAACTAGATTTTTCAGAA<br>AGCACAACAAACACAAAATCCAAGTATTGCCATGTCAGCAACACATTCCTACTTTAAGTTTTATGAAGTTAATTGGAGTAGTGGAGAACAAAA<br>GTGGATGTGGGGCAG |

Example 14: Fetal DNA Quantification Using Massively Parallel Shotgun Sequencing In this example, fetal-specific DNA methylation markers were utilized to quantify the fraction of circulating cell-free fetal DNA in maternal plasma, using a massively parallel shotgun sequencing (MPSS) platform. For this Example, four types of DNA markers were assayed: 1) fetal-specific methylation markers which allowed selective enrichment and subsequent quantification of fetal DNA (e.g., SOX14, TBX), 2) Y-chromosome markers which confirmed fetal DNA quantification (for samples with a male fetus; e.g., SRY1, SRY2, UTY), 3) total markers avoid of restriction sites which were used to quantify total cell-free DNA, including fetal and maternal DNA (e.g., ALB, APOE, RNAseP, and 4) digestion control markers which monitored the completeness of restriction digestion and hence the accuracy of methylation marker-based fetal quantification (e.g., LDHA, POPS).

Methylation-Specific Restriction Digestion

Fetal methylation DNA markers were enriched by selective digestion of unmethylated maternal DNA, using methylation-sensitive restriction enzymes. Digestion was performed according to the parameters specified in Table 7 below.

TABLE 7

| Methylation-specific restriction digestion | | |
|---|---|---|
| Reagent | Concentration in reaction | Reagent Volume (μL) for n = 1 |
| H2O | N/A | 16.7 |
| 10x PCR Buffer (20 mM MgCl2, Roche) | 1 | 3.5 |
| 25 mM MgCl2 (Roche) | 2 | 2.8 |
| ExoI [U/μl] (NEB) | 0.2857 | 0.5 |
| HhaI [U/μl] (NEB) | 0.2857 | 0.5 |
| HpaII [U/μl] (NEB) | 1.4285 | 1 |
| DNA [μl] | | 10 |
| Final Vol: | | 35 |
| Reaction conditions: | | |
| Digestion | 41° C. 60' | |
| Inactivation | 98° C. 10' | |

Competitive PCR

The digested samples were amplified by PCR together with known copy numbers of competitor oligonucleotides. The competitors were synthetic oligonucleotides having the same nucleotide sequences as the target DNA, except for one base difference at the synthetic target site, which differentiated the target DNA from the competitor. Competitive PCR using target-specific primers allowed for independent quantification of each marker. Competitive PCR was performed according to the parameters specified in Table 8 below.

TABLE 8

| PCR amplification | | |
|---|---|---|
| Reagent | Concentration in reaction | Reagent Volume (μL) for n = 1 |
| Water, HPLC grade | N/A | 6.64 |
| 10x PCR Buffer (20 mM MgCL2, Roche) | 1x (2 mM MgCl2) | 1.5 |
| 25 mM MgCl2 (Roche) | 2 mM | 1.2 |
| dNTPs (25 mM, Roche) | 500 μM | 1 |
| PCR primer (1 uM each) | 0.1 μM | 5 |
| FASTSTART PCR Enzyme (5 U/μl, Roche) | 0.1 U/μl | 1 |
| Competitor MIX (8000/800 c/ul)(1:0.1 c/ul) | | 0.38 |
| DNA (from restriction digestion) | | 35 |
| Total | | 50 |
| PCR Cycling conditions: | | |
| 95° C., 5 min | | |
| 95° C., 45 sec | 35 cycles | |
| 60° C., 30 sec | | |
| 72° C., 45 sec | | |
| 72° C., 3 min | | |
| 4° C. hold | | |

Adaptor Oligonucleotide Ligation

Illumina adaptor oligonucleotides (TRUSEQ adaptors) were ligated to the amplicons generated in the competitive PCR described above. The adaptor-ligated amplicons were subsequently sequenced using the Illumina HISEQ 2000 platform (Illumina, San Diego Calif.). Two different ligation-based approaches were used to flank the amplicons with the adaptors. The ligation procedure was optimized to maximize the amount of double ligation products (i.e., adaptor oligonucleotides ligated to both ends of the amplicon), and minimize single ligation and/or empty ligation (i.e., two adaptor oligonucleotides ligate to each other without amplicon insertion).

Direct Ligation of Adaptors

To render the PCR amplicons compatible for MPSS, the amplicons (which had 3' adenine (A) overhangs generated by Taq polymerase during the PCR reaction) were ligated to adaptor oligonucleotides having 3' thymine (T) overhangs (see FIG. 158). Prior to the ligation reaction, AMPURE XP beads at 2-fold volume of PCR reaction volume were used to remove single-stranded primers and amplicons generated by asymmetric PCR. Cleaned amplicons were quantified by Agilent Bioanalyzer and mixed with Illumina TRUSEQ library adaptors at an 8:1 ratio. 2 μL of T4 DNA ligase (Enzymatics) and 17.5 μL of 2× ligase buffer (Enzymatics) were added, and the ligation reaction was carried out at room temperature for 15 minutes.

Unidirectional Adaptor Ligation

In some cases, a modified protocol to improve ligation efficiency and to ensure unidirectional ligation was used. Single base overhang ligation can be less efficient compared to ligation of longer cohesive ends. Additionally, using single base overhang ligation, PCR amplicons can ligate with Illumina TRUSEQ adaptors in either orientation such that, when the ligated product were sequenced, only about half of the sequence reads covered the target sites for copy number calculation. Modifications of the ligation procedure were thus developed to overcome such limitations. First, tag sequences that were 5 nucleotides long were designed to replace the original tag sequence (10 nucleotides long) in the PCR primers (for the competitive PCR above; provided in Table 9 below). The tags were of different sequences for reverse or forward PCR primers and each had a deoxyuridine at the junction between tag sequence and target-specific sequence. The modified primers were used at equal molar ratio in the competitive PCR reaction above.

After PCR amplification, the tags were cleaved from the amplicons by uracil N-glycosylase (UNG; UDG) and EndoVIII digestion, creating a 5 base overhang that selectively ligated the PCR amplicon to universal or indexed adaptors (provided in Table 9 below) with high efficiency (see FIG. 159). Specifically, 1 μL UDG (5 U/μL, NEB) and 5 μL EndoVIII (10 U/μL, NEB) were added to each reaction and incubated at 37° C. for 30 minutes. The reaction was stopped by heating at 95° C. for 10 minutes to inactivate UDG, after which it was gradually cooled to 25° C. The amplicons were cleaned by AMPURE XP beads prior to the ligation reaction.

TABLE 9

Primer and adaptor sequences

| Target | Forward_Primer (SEQ ID NOS 338-350, respectively, in order of appearance) | Reverse_Primer (SEQ ID NOS 351-363, respectively, in order of appearance) |
|---|---|---|
| ALB | TAGCUGCGTAGCAACCTGTTACATATT | GATCUATACTGAGCAAAGGCAATCAAC |
| APOE | TAGCUCAGTTTCTCCTTCCCCAGAC | GATCUGAATGTGACCAGCAACGCAG |
| RNAseP | TAGCUGGTCAGCTCTTCCCTTCATC | GATCUCCTCCCACATGTAATGTGTTG |
| CDC42EP1 | TAGCUAGCTGGTGCGGAGGGTGGG | GATCUATGGGGGAGATGGCCGGTGGA |
| LDHA | TAGCUGGCCTTTGCAACAAGGATCAC | GATCUCGCAATACTAGAAACCAGGGC |
| MGC15523 | TAGCUTCTGGTGACCCCCGCGCTTC | GATCUCATCTCTGGGTGCGCCTTG |
| POP5 | TAGCUCCCTCCACATCCCGCCATC | GATCUCAGCCGCCTGCTCCATCG |
| SOX14 | TAGCUACGGAATCCCGGCTCTGTG | GATCUCCTTCCTAGTGTGAGAACCG |
| SPN | TAGCUGGCCCTGCTGGCGGTCATA | GATCUTGCTCAGCACGAGGGCCCCA |
| SRY1 | TAGCUAGCAACGGGACCGCTACAG | GATCUTCTAGGTAGGTCTTTGTAGCC |
| SRY2 | TAGCUTAAGTTTCGAACTCTGGCACC | GATCUGAAGCATATGATTGCATTGTCAA |
| TBX3 | TAGCUCTCCTCTTTGTCTCTGCGTG | GATCUTTAATCACCCAGCGCATGGC |
| UTY | TAGCUTGATGCCCGATGCCGCCCTT | GATCUGTCTGTGCTGGGTGTTTTTGC |

Adaptors (SEQ ID NOS 364-366, respectively, in order of appearance)

| | |
|---|---|
| Universal_adaptor | AATGATACGGCGACCACCGAGATCTACACTCTTTCCCTACACGACGCTCTTCCGATCT |
| Index_linker | GCTCTTCCGATCTATAGCT |
| Index_adaptor | 5'phos/ GATCGGAAGAGCACACGTCTGAACTCCAGTCACAGTCAACAATCTCGTATGCCGTCTTCTGCTTG |

Pre-annealed index adaptor and index-linker was prepared by mixing at equal molar ratio, heating to 95° C. for 5 minutes, and gradually cooled to 25° C. Universal adaptor and pre-annealed index adaptor at equal molar ratio were mixed with the UDG/EndoVIII-digested PCR amplicons (having 5 nucleotide overhangs). The ratio of adaptor to amplicon varied from 8:1 to 2:1. 2 μL of T4 DNA ligase (Enzymatics) and 17.5 μL of 2× ligase buffer (Enzymatics) were added, and the ligation reaction was carried out at room temperature for 15 minutes.

For both ligation approaches, the ligated product (5 μL) was amplified using Illumina TRUSEQ PCR mixture and primers as specified in Table 10 below. Amplified libraries were purified using AMPURE XP beads to remove free primers/adaptors and DNA fragments of smaller size.

TABLE 10

PCR amplification of ligation products

| Reagent | Reagent Volume (μL) for n = 1 |
|---|---|
| Water, HPLC grade | 11 |
| TRUSEQ PCR master mix | 20 |
| TRUSEQ PCR primers | 4 |
| Ligation product | 5 |
| Total | 40 |

TABLE 10-continued

PCR amplification of ligation products

| PCR Cycling conditions | |
|---|---|
| 98° C., 5 min | |
| 98° C., 10 sec | 10 cycles |
| 65° C., 30 sec | |
| 72° C., 30 sec | |
| 72° C., 3 min | |
| 4° C. hold | |

Amplified libraries were retained on an Illumina flow cell and bridge amplified to generate clusters for subsequent sequencing on Illumina's HISEQ 2000. Use of indexed adaptors allowed for sequencing of multiple samples in a single lane on the flow cell.

Nucleotide Sequence Read Analysis and Fetal DNA Quantification

Nucleotide sequence reads were analyzed and used to calculate copy number of individual markers and fetal percentage. 50 base pair (bp) nucleotide sequence reads were uniquely aligned to expected chromosome positions, allowing up to 5 mismatches outside the target sites/synthetic target sites. Reads having quality score greater than 13 at the target site with expected target DNA or competitor alleles were used to calculate the copy number of each marker. Specifically, the following formula was used:

$$\text{Copy}(DNA) = \text{Copy}(comp) \times \frac{\text{Reed Counts (expected } DNA \text{ allele)}}{\text{Read Counts (expected } comp \text{ allele)}}$$

Fetal DNA, Y-chromosome DNA and total DNA copy numbers were represented by the mean value of methylation markers, Y-markers and total DNA markers, respectively. Fetal percentage was calculated according to the following formulas:

$$\text{Fetal Fraction (methyl)} = \frac{\text{mean copy number (methylation markers)}}{\text{mean copy number (total markers)}}$$

and $$\text{Fetal Fraction } (Y) = 2 \times \frac{\text{mean copy number } (Y \text{ markers})}{\text{mean copy number (total markers)}}$$

Digestion efficiency was calculated by $$\text{digestion efficiency} = 1 - \frac{\text{mean copy member (digestion markers)}}{\text{mean copy number (total markers)}}$$

Results

The fetal DNA quantification method using MPSS described in this Example was applied to ccfDNA extracted from 48 plasma samples from pregnant women. The results were compared to those obtained from another method that used mass spectrometry (e.g., MASSARRAY) as a detection method instead of MPSS. The results from both methods were highly correlated (see FIGS. 160 and 161). With exception of digestion markers (LDHA and POPS, which were detected at higher levels by the MPSS method), the $R^2$ values were in the range of 0.965-0.998. The fetal fractions derived from methylation markers also were highly correlated between MPSS and mass spectrometry methods (see FIG. 162).

Example 15: SNP Allele Frequency Based Method for Fetal Fraction Quantification In this example, single nucleotide polymorphism (SNP) markers were utilized to detect and quantify circulating cell-free (CCF) fetal DNA in maternal plasma (i.e. fetal fraction). In some cases, fetal fraction was determined by measuring single nucleotide polymorphism alleles using a single tube multiplex PCR for amplicon sequencing via massively parallel shotgun sequencing (MPSS). Advantages of this methodology include, for example: 1) the ability to detect CCF fraction of DNA from both male and female fetuses without prior knowledge of maternal or paternal SNP genotypes; 2) a simplified workflow that generates MPSS ready products without the need for traditional library generation and 3) an ability to perform MPSS fetal fraction quantification on samples multiplexed with genomic libraries on the same flow cell lane.

Materials and Methods

CCF DNA was extracted from 4 mL plasma from 46 pregnant women using QIAAMP Circulating Nucleic Acid kit in an elution volume of 55 μl. DNA also was extracted from maternal buffy coat samples for confirmation of maternal genotypes. Gestational age at collection ranged from 10-17 weeks. Maternal age ranged from 18-42 years. Ethnic background of samples included African American, Asian, Caucasian and Hispanic ethnicities. 150 of CCF DNA underwent PCR for each SNP panel using a single tube multiplex of forward and reverse PCR primers that included adapter sequences to allow secondary amplification with universal PCR primers designed to incorporate index tags. Amplicon libraries with index tags were clustered on the cBOT and sequenced on the HiSeq 2000 for 36 cycles or 27 cycles to generate amplicon sequence reads and 7 cycles to determine the index tag sequence. Reads were aligned to the human genome (hg19) and matched read counts for expected SNP alleles were used to calculate the allele ratio of each SNP within each CCF DNA. 15 μl of CCF DNA also was used for quantification of fetal fraction by fetal specific methylation patterns for comparison with SNP based quantification.

Detection of Paternally Inherited Alleles

CCF fetal DNA in maternal plasma contains both maternally and paternally inherited DNA (e.g., SNP alleles). Detection of paternal SNP alleles not present in the maternal genome can allow confirmation of the presence of fetal DNA. Additionally, quantification of paternal:maternal SNP allele ratios can provide for a determination of fetal DNA fraction in maternal plasma. The likelihood of detecting a paternally inherited allele at a single locus is dependent upon allele frequency and individual inheritance patterns. FIG. 163, for example, provides a summary of expected genotypes and the associated population frequency of each genotype based a SNP having a minor allele population frequency of 0.4. A SNP with a high minor allele frequency may increase the chance that paternal and maternal alleles will differ at a given SNP locus. Provided enough SNPs are interrogated, a high probability can be established that the fetus will contain some paternal alleles that differ from the maternal alleles. Thus, use of multiple SNP alleles increases the likelihood of informative fetal and maternal genotype combinations. Often, no prior knowledge of the paternal genotypes is required because paternal alleles can be inferred by the presence of non-maternal alleles in the maternal/fetal cell free DNA mixture. FIGS. 164 and 165 show how fetal fraction can be calculated using SNP allele frequency.

SNP Panels

High minor allele frequency SNPs that contain only 2 known alleles were identified. Two panels of SNPs were generated: a 67 SNP panel (SNP panel 1) and an 86 SNP panel (SNP panel 2). Individual SNP identifiers for each panel are provided in Table 11A and Table 12A below. Tables 11B and 12B include chromosome identity for each SNP.

TABLE 11A

| SNP Panel 1 | | | | |
|---|---|---|---|---|
| rs10413687 | rs2001778 | rs4453265 | rs539344 | rs7176924 |
| rs10949838 | rs2323659 | rs447247 | rs551372 | rs7525374 |

TABLE 11A-continued

| SNP Panel 1 | | | | |
|---|---|---|---|---|
| rs1115649 | rs2427099 | rs4745577 | rs567681 | rs870429 |
| rs11207002 | rs243992 | rs484312 | rs585487 | rs949312 |
| rs11632601 | rs251344 | rs499946 | rs600933 | rs9563831 |
| rs11971741 | rs254264 | rs500090 | rs619208 | rs970022 |
| rs12660563 | rs2827530 | rs500399 | rs622994 | rs985462 |
| rs13155942 | rs290387 | rs505349 | rs639298 | |
| rs1444647 | rs321949 | rs505662 | rs642449 | |
| rs1572801 | rs348971 | rs516084 | rs6700732 | |
| rs17773922 | rs390316 | rs517316 | rs677866 | |
| rs1797700 | rs3944117 | rs517914 | rs683922 | |
| rs1921681 | rs425002 | rs522810 | rs686851 | |
| rs1958312 | rs432586 | rs531423 | rs6941942 | |
| rs196008 | rs444016 | rs537330 | rs7045684 | |

TABLE 11B

| SNP Panel 1 | | | | | |
|---|---|---|---|---|---|
| SNP_ID | Chromosome | SNP_ID | Chromosome | SNP_ID | Chromosome |
| rs10413687 | chr19 | rs290387 | chr20 | rs537330 | chr8 |
| rs10949838 | chr7 | rs321949 | chr19 | rs539344 | chr19 |
| rs1115649 | chr21 | rs348971 | chr2 | rs551372 | chr11 |
| rs11207002 | chr1 | rs390316 | chr14 | rs567681 | chr11 |
| rs11632601 | chr15 | rs3944117 | chr7 | rs585487 | chr19 |
| rs11971741 | chr7 | rs425002 | chr4 | rs600933 | chr1 |
| rs12660563 | chr6 | rs432586 | chr12 | rs619208 | chr11 |
| rs13155942 | chr5 | rs444016 | chr5 | rs622994 | chr13 |
| rs1444647 | chr12 | rs4453265 | chr11 | rs639298 | chr1 |
| rs1572801 | chr6 | rs447247 | chr6 | rs642449 | chr1 |
| rs17773922 | chr19 | rs4745577 | chr9 | rs6700732 | chr1 |
| rs1797700 | chr12 | rs484312 | chr13 | rs677866 | chr13 |
| rs1921681 | chr4 | rs499946 | chr7 | rs683922 | chr15 |
| rs1958312 | chr14 | rs500090 | chr11 | rs686851 | chr6 |
| rs196008 | chr16 | rs500399 | chr10 | rs6941942 | chr6 |
| rs2001778 | chr11 | rs505349 | chr11 | rs7045684 | chr9 |
| rs2323659 | chr17 | rs505662 | chr6 | rs7176924 | chr15 |
| rs2427099 | chr20 | rs516084 | chr1 | rs7525374 | chr1 |
| rs243992 | chr4 | rs517316 | chr1 | rs870429 | chr3 |
| rs251344 | chr5 | rs517914 | chr4 | rs949312 | chr18 |
| rs254264 | chr19 | rs522810 | chr13 | rs9563831 | chr13 |
| rs2827530 | chr21 | rs531423 | chr1 | rs970022 | chr4 |
| | | | | rs985462 | chr10 |

TABLE 12A

| SNP Panel 2 | | | | |
|---|---|---|---|---|
| rs1005241 | rs1432515 | rs2906237 | rs654065 | rs849084 |
| rs1006101 | rs1452396 | rs2929724 | rs6576533 | rs873870 |
| rs10745725 | rs1518040 | rs3742257 | rs6661105 | rs9386151 |
| rs10776856 | rs16853186 | rs3764584 | rs669161 | rs9504197 |
| rs10790342 | rs1712497 | rs3814332 | rs6703320 | rs9690525 |
| rs11076499 | rs1792205 | rs4131376 | rs675828 | rs9909561 |
| rs11103233 | rs1863452 | rs4363444 | rs6814242 | |
| rs11133637 | rs1991899 | rs4461567 | rs6989344 | |
| rs11974817 | rs2022958 | rs4467511 | rs7120590 | |
| rs12102203 | rs2099875 | rs4559013 | rs7131676 | |
| rs12261 | rs2108825 | rs4714802 | rs7214164 | |
| rs12460763 | rs2132237 | rs4775899 | rs747583 | |
| rs12543040 | rs2195979 | rs4817609 | rs768255 | |
| rs12695642 | rs2248173 | rs488446 | rs768708 | |
| rs13137088 | rs2250246 | rs4950877 | rs7828904 | |
| rs13139573 | rs2268697 | rs530913 | rs7899772 | |
| rs1327501 | rs2270893 | rs6020434 | rs7900911 | |
| rs13438255 | rs244887 | rs6442703 | rs7925270 | |
| rs1360258 | rs2736966 | rs6487229 | rs7975781 | |
| rs1421062 | rs2851428 | rs6537064 | rs8111589 | |

TABLE 12B

| SNP Panel 2 | |
|---|---|
| SNP_ID | Chromosome |
| rs1518040 | chr1 |
| rs16853186 | chr1 |
| rs2268697 | chr1 |
| rs3814332 | chr1 |
| rs4363444 | chr1 |
| rs4950877 | chr1 |
| rs6661105 | chr1 |
| rs6703320 | chr1 |
| rs1432515 | chr2 |
| rs12695642 | chr3 |
| rs2132237 | chr3 |
| rs6442703 | chr3 |
| rs13137088 | chr4 |
| rs13139573 | chr4 |
| rs1452396 | chr4 |
| rs1712497 | chr4 |
| rs4461567 | chr4 |
| rs4467511 | chr4 |
| rs6537064 | chr4 |
| rs6814242 | chr4 |
| rs747583 | chr4 |
| rs1006101 | chr5 |
| rs11133637 | chr5 |
| rs2929724 | chr5 |
| rs4559013 | chr5 |
| rs4714802 | chr6 |
| rs669161 | chr6 |
| rs9386151 | chr6 |
| rs9504197 | chr6 |
| rs11974817 | chr7 |
| rs13438255 | chr7 |
| rs2736966 | chr7 |
| rs2906237 | chr7 |
| rs4131376 | chr7 |
| rs849084 | chr7 |
| rs9690525 | chr7 |
| rs12543040 | chr8 |
| rs1863452 | chr8 |
| rs2022958 | chr8 |
| rs6989344 | chr8 |
| rs7828904 | chr8 |
| rs10776856 | chr9 |
| rs11103233 | chr9 |
| rs1327501 | chr9 |
| rs1360258 | chr9 |
| rs1421062 | chr10 |
| rs2248173 | chr10 |
| rs768255 | chr10 |
| rs7899772 | chr10 |
| rs7900911 | chr10 |
| rs10790342 | chr11 |
| rs1792205 | chr11 |
| rs1991899 | chr11 |
| rs2099875 | chr11 |
| rs2851428 | chr11 |
| rs488446 | chr11 |
| rs7120590 | chr11 |
| rs7131676 | chr11 |
| rs768708 | chr11 |
| rs7925270 | chr11 |
| rs10745725 | chr12 |
| rs2250246 | chr12 |
| rs2270893 | chr12 |
| rs6487229 | chr12 |
| rs7975781 | chr12 |
| rs12261 | chr13 |
| rs3742257 | chr13 |
| rs675828 | chr13 |
| rs12102203 | chr15 |
| rs4775899 | chr15 |
| rs6576533 | chr15 |
| rs11076499 | chr16 |
| rs244887 | chr16 |
| rs654065 | chr16 |
| rs7214164 | chr17 |
| rs9909561 | chr17 |

TABLE 12B-continued

| SNP Panel 2 | |
|---|---|
| SNP_ID | Chromosome |
| rs12460763 | chr19 |
| rs2108825 | chr19 |
| rs2195979 | chr19 |
| rs3764584 | chr19 |
| rs8111589 | chr19 |
| rs873870 | chr19 |
| rs530913 | chr20 |
| rs6020434 | chr20 |
| rs4817609 | chr21 |
| rs1005241 | chr22 |

Generation of Illumina Sequencer Ready Amplicons

For SNP panel 1, PCR primers were designed to amplify the 67 targeted SNPs plus a flanking region of 35 base pairs (bp) surrounding the SNP site. The 67 targeted regions were amplified in a single multiplex reaction. For SNP panel 2, PCR primers were designed to amplify the 86 targeted SNPs plus a flanking region of 26 base pairs (bp) surrounding the SNP site. The 86 targeted regions were amplified in a single multiplex reaction.

PCR primers were modified such that Illumina sequencing adapters could be added via universal tag sequences incorporated onto the 5' end of the SNP-specific PCR primers. Illumina tags were added using two separate PCR reactions (see FIG. 166 and Table 13 below): 1) a loci-specific PCR which incorporated a section of the Illumina sequencing adapters followed by 2) a universal PCR whose primers annealed to the tags in the loci-specific PCR to complete the addition of the adapters whilst allowing the addition of a sample specific index sequence via the reverse primer in the universal PCR. A $3^{rd}$ single cycle PCR was performed to remove heteroduplex secondary structure that can arise in the amplicons during the universal PCR stage due to cross-annealing of shared adapter sequences between different amplicons in the same multiplex. Loci-specific PCR and universal PCR were performed under standard conditions using primers synthesized from Integrated DNA Technologies (IDT; Coralville, Iowa) with no special modifications.

TABLE 13

Sequencing adaptors, loci specific PCR primer tags and universal PCR primer tags

| Name | Sequence (SEQ ID NOS 364 and 367-373, respectively, in order of appearance) |
|---|---|
| TRUSEQ P5 Adapter | 5'-AATGATACGGCGACCACCGAGATCTACACTCTTTCCCTACACGACGCTCTTCCGATCT-3' |
| TRUSEQ Read 1 sequencing primer | 5'-ACACTCTTTCCCTACACGACGCTCTTCCGATCT-3' |
| TRUSEQ P7 adapter, Index 13 | 5'-GATCGGAAGAGCACACGTCTGAACTCCAGTCACAGTCAAATCTCGTATGCCGTCTTCTGCTTG-3' |
| TRUSEQ index read primer | 5'-GATCGGAAGAGCACACGTCTGAACTCCAGTCAC-3' |
| Loci PCR forward tag | 5'-TCTTTCCCTACACGACGCTCTTCCGATCT-3' |
| Loci PCR reverse tag | 5'-GTGACTGGAGTTCAGACGTGTGCTCTTCCGATCT-3' |
| UNIV PCR forward primer | 5'-AATGATACGGCGACCACCGAGATCTACACTCTTTCCCTACACGACGCTC-3' |
| UNIV PCR reverse index 13 primer | 5'-CAAGCAGAAGACGGCATACGAGATTTGACTGTGACTGGAGTTCAGACGTG-3' |

Amplicon Sequencing by Illumina NGS

Universal PCR products were quantified using standard DNA fragment analysis methods such as Caliper LabChip GX or Agilent Bioanalyzer. The sequencer-ready amplicons from up to 12 samples were pooled and sequenced on an Illumina HISEQ apparatus. For SNP panel 1, 36 cycles were used to sequence the target SNP plus the 35 bp flanking region. For SNP panel 2, 27 cycles were used to sequence the target SNP plus the 26 bp flanking region. Samples were de-multiplexed using a 6 bp index identifier incorporated at the universal PCR stage.

Assignment of Informative Alleles and Fetal Fraction Determination

Reads were aligned to the human genome (hg19) with up to 3 mismatches in each read to allow for sequencing error and variant alleles at target SNP position. The frequency of each SNP allele was determined by counting the number of reads having the allele of interest and dividing it by the total number of reads for each SNP locus (i.e., (# reads allele 1)/(# reads allele 1+# reads allele 2)). Based on the frequency value generated from this data, the sequenced genotypes were assigned as Type 0 non-informative genotypes, Type 1 informative genotypes or Type 2 informative genotypes. A Type 0 non-informative genotype is a fetal genotype that cannot be distinguished from the maternal genotype because the fetus has the same genotype as the mother (e.g., mother is "Aa" and fetus is "Aa"). A Type I informative genotype is the situation where the mother is homozygous (AA) and the fetus is heterozygous (Aa). This genotype is informative because allele “a” is from the father. The frequency of a Type 1 informative allele can be indicative of the percentage fetal DNA in the mixture. A Type 2 informative genotype is the situation where the mother is heterozygous (Aa) and the fetus is homozygous (AA). The genotype is informative because the frequency of the maternal allele “a” will deviate from the expected Mendelian frequency of 0.5 when there is fetal DNA contributing additional “A” alleles. This deviation in value from 0.5 can be used to compute the fetal fraction.

Allele frequencies for each of the SNPs was calculated for each sample based on the number of reads containing each allele, as described above. Variation of expected allele frequency could be due to the presence of fetal DNA with a different paternal allele or could be due to mis-incorporated sequences by the Illumina Sequencer (e.g., background noise). In some cases, the amount of background noise associated with each particular SNP amplicon was determined to establish a dynamic cutoff value for each SNP. Maternal DNA (i.e. buffy coat) samples were sequenced and the deviations from the expected Mendelian ratios of 1 for homozygotes and 0.5 for heterozygotes were observed. From these values a median-adjusted deviation (MAD score) was identified for each SNP assay. In some cases, a genotype was identified as being a Type I informative genotype when the paternal allele frequency measured was greater than 3×MAD score. In some cases, multiple Type 1 informative genotypes were identified and an average allele frequency was determined. Fetal fraction was calculated by multiplying the average Type 1 informative allele frequency by 2. For example, an average informative allele frequency of 4.15% indicated a fetal fraction of 8.3%. Fetal Fraction also can be calculated from Type 2 informative genotypes by determining maternal allele “a” frequencies deviating from 0.5 by greater than 3×MAD, for example. Fetal fraction can be identified by multiplying this deviation by 2.

In some cases, informative genotypes were assigned without prior knowledge of maternal or paternal genotypes. Allele frequencies for each SNP (of SNP panel 1) were plotted as shown in FIG. 167 and FIG. 168 for two of the 46 samples tested. Homozygous allele frequencies in maternal buffy coat were close to 0 or 1. Type 1 informative SNPs were identified by allele frequencies that deviated from the expected allele frequency of 0 or 1 due to the presence of a paternal allele from the fetus. The size of the deviation was dependent on the size of the fetal fraction of CCF DNA. A maximum background allele frequency of 0.007 was observed for maternal buffy coat DNA. For this approach, fixed cutoff frequency value of 0.01 was used to distinguish non-informative homozygotes from informative genotypes in plasma samples (see FIGS. 169 and 170, showing the assignment of certain Type 1 informative genotypes). A fixed cutoff value of 0.25 was used to distinguish non-informative heterozygotes from other genotypes. Fetal fractions were calculated for 46 plasma samples by taking the mean of the informative genotype allele frequencies and multiplying this value by 2. Informative genotypes assigned per sample ranged from 1 to 26. Fetal fractions ranged from 2.5% to 14% (see FIG. 171).

To assess performance of the above method, fetal fractions also were determined for the 46 plasma samples using a differential methylation-based fetal quantifier assay. SNP-based fetal fraction estimates showed a linear association with the methylation-based estimates ($r^2$=0.72). FIG. 172 shows linear regression of fetal fraction estimate methods as a diagonal line.

Amplicon Sequence Coverage

Various amounts of SNP amplicon libraries were combined (i.e. diluted) with TRUSEQ libraries to demonstrate that allele frequency determinations can be made at varying levels of amplicon sequence coverage. SNP amplicon libraries from 6 plasma samples and 6 buffy coat samples were combined with 11 TRUSEQ libraries and co-sequenced on a HISEQ 2000 apparatus in the same flowcell lane. Percent (%) of SNP amplicon library combined with TRUSEQ libraries ranged from 50% to 0.8%. After alignment coverage per SNP for each amplicon library ranged from 71619× per SNP (50% amplicon library) to 1413× per SNP (0.8% amplicon library). Fetal fraction estimates were not significantly different even at lowest coverage level (see FIG. 173). These findings indicate that less than 1% of the flowcell clusters on a HISEQ 2000 apparatus can be used to co-sequence amplicon libraries and that high levels of sample multiplexing (e.g., greater than 96) can be achieved.

Example 16: Using Fetal Faction Derived from Sequence Reads to Determine Aneuploidy MPSS samples were classified as euploid or T13/T18/T21 based on fitted ploidy values derived from fetal fraction estimates based on ChrY representation derived from whole-genome sequencing results.

Examples 9 and 10 have demonstrated the accuracy and precision of sequencing-based fetal fractions determinations in male fetuses. In this example, those measurements were used to resolve difficult trisomy cases with low fetal fraction values. As a proof of principle, the method was applied to male pregnancy subsets of the LDTv2CE data set. The same approach can be applied to female pregnancies as well using the methods in Examples 11-15 or similar high-accuracy fetal fraction measurements. FIGS. 175-177 show fitted ploidy values obtained by combining PERUN profiles of chromosomes 13, 18, and 21 with fetal fractions derived from PERUN chromosome Y representations. Similar results were obtained with chromosome X-based fetal fractions.

FIGS. 175-177 illustrate that fitted ploidy extracted from sequencing-based fetal fraction measurements perfectly and accurately distinguished T13, T18, and T21 samples from euploids. Ideally, trisomy and euploid samples should have ploidy values of 1.5 and 1, respectively. The LDTv2CE male trisomy cases have fitted ploidy values that always exceed 1.4, while euploids were always below 1.3 and in a great majority of the cases below 1.2.

This method is insensitive to fetal fraction in that it correctly classified T21, T18, and T13 cases even at extremely low fetal fractions. These samples tend to have borderline Z-scores. Fitted fetal fraction does not have any borderline cases irrespective of the fetal fraction.

Example 17: Examples of Embodiments

Listed hereafter are non-limiting examples of certain embodiments of the technology.

A1. A method for determining a fraction of fetal nucleic acid in circulating cell-free nucleic acid from blood of a pregnant female, comprising:

(a) obtaining counts of nucleic acid sequence reads mapped to genomic sections of a reference genome, which sequence reads are reads of circulating cell-free nucleic acid from the blood of a pregnant female bearing a male fetus;

(b) from the counts in (a), generating an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; (c) determining the fraction of the fetal nucleic acid in the blood of the pregnant female according to the experimental Y chromosome representation generated in (b) and a fitted relationship, wherein:

the fitted relationship is between (i) an experimental Y chromosome representation determined from a set of pregnant females bearing a male fetus and (ii) an X chromosome representation determined from a set of pregnant females; and the fitted relationship is fitted to a median chromosome X representation and a median chromosome Y representation for a set of pregnant females bearing a female fetus.

A2. The method of embodiment A1, wherein the X chromosome representation in (c)(ii) is an experimental X chromosome representation.

A3. The method of embodiment A1 or A2, wherein the X chromosome representation is a ratio of (i) counts of sequence reads mapped to the genomic sections of the reference genome in the X chromosome, and (ii) counts of sequence reads mapped to genomic sections of the reference genome in the genome or segment thereof.

A4. The method of any one of embodiments A1 to A3, wherein the X chromosome representation in (c)(ii) is determined from a set of pregnant females bearing a male fetus.

A5. The method of any one of embodiments A1 to A4, wherein the X chromosome representation in (c)(ii) is determined for pregnant females bearing a male fetus.

A6. The method of any one of embodiments A1 to A5, wherein the fitted relationship is linear.

A7. The method of embodiment A6, wherein the fraction of the fetal nucleic acid is determined according to the slope and intercept of the fitted relationship, the experimental Y chromosome representation generated in (b) and a median X chromosome representation for a set of pregnant females bearing a female fetus.

A8. The method of embodiment A7, wherein the fraction of the fetal nucleic acid is determined according to equation (62):

$$f = 2\frac{I + S\langle x\rangle - y}{S\langle x\rangle} \tag{62}$$

wherein I is the intercept, S is the slope, (x) is the median X chromosome representation for a set of pregnant females bearing a female fetus and y is the experimental Y chromosome representation generated in (b).

A9. The method of any one of embodiments A1 to A8, wherein the median chromosome X representation is a median experimental X chromosome representation.

A10. The method of any one of embodiments A1 to A9, where the median chromosome Y representation is a median experimental Y chromosome representation.

A11. The method of any one of embodiments A1 to A10, wherein the fitted relationship in (c) is determined prior to (a).

A12. The method of any one of embodiments A1 to A11, wherein the fitted relationship in (c) is determined prior to (b).

A13. The method of any one of embodiments A1 to A12, wherein the counts in (a) are obtained from a pregnant female bearing a male fetus having a chromosome aneuploidy.

A14. The method of embodiment A13, wherein the chromosome aneuploidy is a trisomy 21, trisomy 18 and/or trisomy 13.

A15. The method of embodiment A13, wherein the chromosome aneuploidy is a sex chromosome aneuploidy.

A16. The method of any one of embodiments A1 to A15, wherein the set of pregnant females in (c)(i) is a set of about 500 females or more.

A17. The method of any one of embodiments A1 to A16, wherein the set of pregnant females in (c)(ii) is a set of about 500 females or more.

A18. The method of any one of embodiments A1 to A17, wherein the set of pregnant females in (c)(i) and (c)(ii) are the same set.

A19. The method of any one of embodiments A1 to A18, wherein the median chromosome X representation and a median chromosome Y representation is determined for a set of about 500 pregnant females or more.

A20. The method of any one of embodiments A1 to A19, wherein the fraction of fetal nucleic acid in the blood of the pregnant female is provided by a fetal fraction module.

A21. The method of any one of embodiments A1 to A20, comprising normalizing the counts in (a), thereby providing normalized counts mapped to the genomic sections of the reference genome; and which counts in (b) are normalized counts.

A22. The method of embodiment A21, wherein the counts in (b) are normalized by GC content, bin-wise normalization, GC LOESS, PERUN, GCRM, or combinations thereof.

A23. The method of embodiment A19 or A22, wherein the normalized counts are provided by a normalization module.

A24. The method of any one of embodiments A1 to A23, wherein the experimental Y chromosome representation in (b) is provided by an experimental representation module.

A25. The method of any one of embodiments A1 to A24, wherein the fetal fraction in (c) is provided by a fetal fraction module.

A26. The method of any one of embodiments A1 to A25, wherein the fitted relationship is provided by a relationship module.

A27. The method of any one of embodiments A24 to A26, wherein the normalized counts are transferred to the experimental representation module from the normalization module.

A28. The method of any one of embodiments A25 to A27, wherein the experimental Y chromosome representation is transferred to the fetal fraction module from the experimental representation module.

A29. The method of any one of embodiments A1 to A28, which comprises obtaining nucleic acid sequence reads.

A30. The method of embodiment A29, wherein the nucleic acid sequence reads are generated by a sequencing module.

A31. The method of any one of embodiments A1 to A30, wherein the nucleic acid sequence reads are generated by massively parallel sequencing (MPS).

A32. The method of any one of embodiments A1 to A31, which comprises mapping the nucleic acid sequence reads to genomic sections in a segment of the reference genome or to an entire reference genome.

A33. The method of embodiment A32, wherein the nucleic acid sequence reads are mapped to the genomic sections of the reference genome by a mapping module.

A34. The method of any one of embodiments A1 to A33, wherein the nucleic acid sequence reads mapped to the genomic sections of the reference genome are counted by a counting module.

A35. The method of embodiment A33 or A34, wherein the sequence reads are transferred to the mapping module from the sequencing module.

A36. The method of embodiment A34 or A35, wherein the nucleic acid sequence reads mapped to the genomic sections of the reference genome are transferred to the counting module from the mapping module.

A37. The method of any one of embodiments A34 to A36, wherein the counts of the nucleic acid sequence reads mapped to the genomic sections of the reference genome are transferred to the normalization module from the counting module.

A38. The method of any one of embodiments A34 to A37, wherein an apparatus comprises one or more of the sequencing module, a sequence receiving module, the mapping module, the counting module, the normalization module, the experimental representation module, the relationship module, the fetal fraction module, a comparison module, a range setting module, a categorization module, an adjustment module, a plotting module, an outcome module, a data display organization module or a logic processing module, which apparatus comprises, or is in communication with, a processor that is capable of implementing instructions from one or more of the modules.

A39. The method of embodiment A38, wherein a first apparatus comprises one or more of the normalization module, the experimental representation module, the relationship module and the fetal fraction module.

A40. The method of embodiment A38 or A39, wherein a second apparatus comprises the mapping module and the counting module.

A41. The method of any one of embodiments A38 to A40, wherein a third apparatus comprises the sequencing module.

A42. The method of any one of embodiments A21 to A41, wherein the counts that are normalized are raw counts.

A43. The method of any one of embodiments A21 to A42, wherein the counts that are normalized are filtered.

A44. The method of any one of embodiments A21 to A42, wherein the counts that are normalized are not filtered.

A45. The method of any one of embodiments A1 to A44, wherein the genomic sections of the reference genome are chromosomes or genomic sections thereof.

A46. The method of any one of embodiments A1 to A45, wherein the genomic sections of the reference genome are one or more bins.

A47. The method of embodiment A46, wherein each bin is of about an equal number of contiguous nucleotides.

A48. The method of embodiment A46 or A47, wherein each bin is about 50 kb.

A49. The method of any one of embodiments A1 to A48, wherein the fetal fraction is provided with an accuracy of equal to or greater than 90% and/or a precision equal to or greater than 90%.

A50. The method of any one of embodiments A1 to A49, wherein the sequence reads of circulating cell-free nucleic acid from the blood of a pregnant female bearing a male fetus are from a test sample obtained from the pregnant female bearing a male fetus.

A51. The method of any one of embodiments A1 to A50, which comprises determining the presence or absence of nucleic acid sequence reads mapped to the Y chromosome in the reference genome.

A52. The method of embodiment A51, wherein determining the presence or absence of nucleic acid sequence reads mapped to the Y chromosome is performed before performing (b).

A53. The method of embodiment A51 or A52, wherein determining the presence or absence of nucleic acid sequence reads mapped to the Y chromosome of the fetus is determined from the counts of nucleic acid sequence reads mapped to genomic sections of the reference genome obtained in (a).

A54. The method of any one of embodiments A51 to A53, which comprises determining the presence or absence of nucleic acid sequence reads mapped to the Y chromosome before performing (b), and if nucleic acid sequence reads mapped to the Y chromosome are present, then performing (b) and (c).

A55. The method of any one of embodiments A51 to A53, which comprises determining the presence or absence of nucleic acid sequence reads mapped to the Y chromosome before performing (a), and if nucleic acid sequence reads mapped to the Y chromosome are present, then performing (a), (b) and (c).

A56. The method of any one of embodiments A1 to A55, which comprises determining the gender of the fetus.

A57. The method of embodiment A56, wherein the gender of the fetus is determined before performing (b).

A58. The method of embodiment A56 or A57, wherein the gender of the fetus is determined from the counts of nucleic acid sequence reads mapped to genomic sections of the reference genome obtained in (a).

A59. The method of embodiment A56, wherein the gender of the fetus is determined before performing (a).

A60. The method of any one of embodiments A56 to A59, which comprises determining whether the gender of the fetus is male or female before performing (b), and if the gender of the fetus is determined as being male, then performing (b) and (c).

A61. The method of any one of embodiments A56 to A59, which comprises determining whether the gender of the fetus is male or female before performing (a), and if the gender of the fetus is determined as being male, then performing (a), (b) and (c).

A62. The method of any one of embodiments A1 to A61, which comprises determining the presence or absence of a Y chromosome in the fetus.

A63. The method of any one of embodiments A1 to A62, wherein the genomic sections of the Y chromosome in (b)(ii) are a subset of genomic sections of the Y chromosome.

A64. The method of embodiment A63, wherein the subset of genome sections of the Y chromosome comprises one or more polynucleotides located within the first 28 Mb from the 5' end of the Y chromosome.

A65. The method of any one of embodiments A1 to A63, wherein counts of sequence reads that map to both chromosome Y and chromosome X are excluded before performing (b).

A66. The method of any one of embodiments A1 to A65, wherein the counts of sequence reads mapped to the genomic sections of the reference genome in the Y chromosome are substantially unique to the Y chromosome.

A67. The method of embodiment A66, wherein greater than 80% or more of the genomic sections in the Y chromosome are substantially unique to the Y chromosome.

A68. The method of any one of embodiments A1 to A67, wherein the counts of sequence reads mapped to the genomic sections of the reference genome in the Y chromosome do not map to genomic sections of the reference genome in the X chromosome.

A69. The method of any one of embodiments A1 to A68, wherein the counts of sequence reads mapped to genomic sections of the reference genome in the genome or segment thereof in (b)(ii) are counts of sequence reads mapped to autosomes.

A70. The method of embodiment A69, wherein the counts of sequence reads mapped to genomic sections of the reference genome in the genome or segment thereof in (b)(ii) do not include sequence reads mapped to sex chromosomes.

A71. The method of any one of embodiments A1 to A68, wherein the counts of sequence reads mapped to the reference genome in the genome or a segment thereof in (b)(ii) are counts of sequence reads mapped to all chromosomes from which reads are obtained.

B1. A system comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to:

(b) from the counts, generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) determine the fraction of the fetal nucleic acid in the blood of the pregnant female according to the experimental Y chromosome representation generated in (b) and a fitted relationship, wherein:

the fitted relationship is between (i) an experimental Y chromosome representation determined from a set of pregnant females bearing a male fetus and (ii) an X chromosome representation determined from a set of pregnant females; and the fitted relationship is fitted to a median chromosome X representation and a median chromosome Y representation for a set of pregnant females bearing a female fetus.

C1. An apparatus comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to:

(a) from the counts, generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) determine the fraction of the fetal nucleic acid in the blood of the pregnant female according to the experimental Y chromosome representation generated in (b) and a fitted relationship, wherein:

the fitted relationship is between (i) an experimental Y chromosome representation determined from a set of pregnant females bearing a male fetus and (ii) an X chromosome representation determined from a set of pregnant females; and the fitted relationship is fitted to a median chromosome X representation and a median chromosome Y representation for a set of pregnant females bearing a female fetus.

D1. A computer program product tangibly embodied on a computer-readable medium, comprising instructions that when executed by one or more processors are configured to:

(a) obtain counts of nucleic acid sequence reads mapped to genomic sections of a reference genome, which sequence reads are reads of circulating cell-free nucleic acid from the blood of a pregnant female bearing a male fetus;

(b) from the counts in (a), generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof;

(c) determine the fraction of the fetal nucleic acid in the blood of the pregnant female according to the experimental Y chromosome representation generated in (b) and a fitted relationship, wherein:

the fitted relationship is between (i) an experimental Y chromosome representation determined from a set of pregnant females bearing a male fetus and (ii) an X chromosome representation determined from a set of pregnant females; and the fitted relationship is fitted to a median chromosome X representation and a median chromosome Y representation for a set of pregnant females bearing a female fetus.

E1. A method for determining the fraction of fetal nucleic acid in circulating cell-free nucleic acid from the blood of a pregnant female, comprising:

(a) obtaining counts of nucleic acid sequence reads mapped to genomic sections of a reference genome, which sequence reads are reads of circulating cell-free nucleic acid from the blood of a pregnant female bearing a male fetus;

(b) generating an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof; and (c) from the experimental X chromosome representation, determining the fraction of fetal nucleic acid in the blood of the pregnant female according to the experimental X chromosome representation and an expected X chromosome representation, which expected X chromosome representation is a ratio of (i) the number of the genomic sections of the reference genome in the X chromosome, and (ii) the number of the genomic sections of the reference genome in the genome or segment thereof.

E2. The method of embodiment E1, wherein the fraction of fetal nucleic acid in the blood of the pregnant female is determined in (c) according to a ratio of the experimental X chromosome representation and the expected X chromosome representation.

E2.1. The method of embodiment E1 or E2, wherein the fraction of fetal nucleic acid in the blood of the pregnant female is determined according to equation AC.

E3. A method for determining the fraction of fetal nucleic acid in circulating cell-free nucleic acid from the blood of a pregnant female, comprising:

(a) obtaining counts of nucleic acid sequence reads mapped to genomic sections of a reference genome, which sequence reads are reads of circulating cell-free nucleic acid from the blood of a pregnant female bearing a male fetus;

(b) generating an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof; and (c) from the experimental X chromosome representation, determining the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X chromosome representation.

E3.1. The method of embodiment E3, wherein the fraction of fetal nucleic acid in the blood of the pregnant female bearing a fetus having a chromosome aneuploidy is determined according to equation AB.

E3.2. The method of embodiment E3 or E3.1, wherein the fraction of fetal nucleic acid determined in (c)(i) and the experimental X chromosome representation in (c)(ii) are derived from greater than about 500 subjects.

E3.3. The method of any one of embodiments E1 to E3.2, wherein the fraction of fetal nucleic acid in the blood of the pregnant female is provided by a fetal fraction module.

E4. The method of any one of embodiments E3 to E3.2, wherein the relationship is a linear relationship.

E4.1. The method of any one of embodiments E3 to E4, wherein the chromosome aneuploidy is a trisomy 21, trisomy 18 and/or trisomy 13.

E4.2. The method of any one of embodiments E3 to E4.1, wherein the chromosome aneuploidy is a sex chromosome aneuploidy.

E4.3. The method of any one of embodiments E3 to E4.2, wherein the relationship is:

$$F=k-r(MCRx),$$

wherein F is the fraction, MCRx is the experimental X chromosome representation, k is an intercept from the linear relationship and r is a slope from the linear relationship.

E4.3.1. The method of embodiment E4.3, wherein the fraction of fetal nucleic acid in circulating cell-free nucleic acid from the blood of a pregnant female is determined by the relationship in E4.3 and the experimental X chromosome representation.

E4.4. The method of any one of embodiments E3 to E4.3.1, wherein the fraction of fetal nucleic acid determined for nucleic acid from the blood of a pregnant female bearing a fetus having a chromosome aneuploidy in (c)(i) is determined by a process that comprises use of sequence reads mapped to genomic sections of a reference genome.

E4.5. The method of any one of embodiments E3 to E4.3.1, wherein the fraction of fetal nucleic acid determined for nucleic acid from nucleic acid from the blood of a pregnant female bearing a fetus having a chromosome aneuploidy in (c)(i) is determined by a process that does not utilize sequence reads mapped to genomic sections of a reference genome.

E4.6. The method of embodiment E4.5, wherein the process comprises mass spectrometry.

E4.7. The method of any one of embodiments E3 to E4.6, wherein the pregnant female bearing a fetus having a chromosome aneuploidy in (c)(i) is different from the pregnant female in (a).

E4.7.1 The method of embodiment E4.7, wherein the pregnant female bearing a fetus having a chromosome aneuploidy is bearing a male fetus.

E4.8. The method of any one of embodiments E3 to E4.7.1, wherein the nucleic acid from the blood of the pregnant female in (c)(i) is circulating cell-free nucleic acid.

E5. The method of any one of embodiments E1 to E4.8, comprising normalizing the counts mapped to the genomic sections of the reference genome, thereby providing normalized counts mapped to the genomic sections of the reference genome; and which counts in E1 (b) and E3(b) are normalized counts.

E5.1. The method of any one of embodiments E1 to E5, wherein the counts in E1 (b) and E3(b) are normalized by GC content, bin-wise normalization, GC LOESS, PERU N, GCRM, or combinations thereof.

E6. The method of embodiment E5, wherein the normalized counts are provided by a normalization module.

E7. The method of any one of embodiments E1 to E6, wherein the experimental X chromosome representation in E1(b) and E3(b) is provided by a representation module.

E8. The method of any one of embodiments E1 to E7, wherein expected X chromosome representation in E1(c) and E3(c) is determined by an expected representation module.

E9. The method of any one of embodiments E1 to E8, wherein the fetal fraction in E1(c) and E3(c) is provided by a fetal fraction module.

E10. The method of any one of embodiments E3 to E9, wherein the relationship is provided by a relationship module.

E11. The method of any one of embodiments E7 to E10, wherein the normalized mapped counts are transferred to the experimental representation module from the normalization module.

E12. The method of any one of embodiments E8 to E11, wherein the normalized mapped counts are transferred to the expected representation module from the normalization module.

E13. The method of any one of embodiments E9 to E12, wherein the experimental X chromosome representation is transferred to the fetal fraction module from the experimental representation module.

E14. The method of any one of embodiments E9 to E13, wherein the expected X chromosome representation is transferred to the fetal fraction module from the expected representation module.

E15. The method of any one of embodiments E1 to E14, which comprises obtaining nucleic acid sequence reads.

E16. The method of embodiment E15, wherein the nucleic acid sequence reads are generated by a sequencing module.

E16.1 The method of embodiment E15 or E16, wherein the nucleic acid sequencing reads are generated by massively parallel sequencing (MPS).

E17. The method of embodiment E15 or E16, which comprises mapping the nucleic acid sequence reads to the genomic sections of the reference genome or to an entire reference genome.

E18. The method of embodiment E17, wherein the nucleic acid sequence reads are mapped to the genomic sections of the reference genome by a mapping module.

E19. The method of any one of embodiments E1 to E18, wherein the nucleic acid sequence reads mapped to the genomic sections of the reference genome are counted by a counting module.

E20. The method of any one of embodiments E18 to E19, wherein the sequence reads are transferred to the mapping module from the sequencing module.

E21. The method of any one of embodiments E19 to E20, wherein the nucleic acid sequence reads mapped to the genomic sections of the reference genome are transferred to the counting module from the mapping module.

E22. The method of any one of embodiments E19 to E21, wherein the counts of the nucleic acid sequence reads mapped to the genomic sections of the reference genome are transferred to the normalization module from the counting module.

E23. The method of any one of embodiments E1 to E22, wherein an apparatus comprises one or more of a sequencing module, sequence receiving module, mapping module, counting module, normalization module, comparison module, range setting module, categorization module, adjustment module, plotting module, outcome module, data display organization module or logic processing module, which apparatus comprises, or is in communication with, a processor that is capable of implementing instructions from one or more of the modules.

E24. The method of embodiment E23, wherein a first apparatus comprises one or more of the normalization module, the comparison module, the range setting module, the adjustment module, and the outcome module.

E24.1. The method of any one of embodiments E19 to E24, wherein a second apparatus comprises the mapping module and the counting module.

E25. The method of any one of embodiments E16 to E24.1, wherein a third apparatus comprises the sequencing module.

E26. The method of any one of embodiments E5 to E25, wherein the counts that are normalized are raw counts.

E27. The method of any one of embodiments E5 to E26, wherein the counts that are normalized are filtered.

E27.1 The method of any one of embodiments E5 to E26, wherein the counts that are normalized are not filtered.

E28. The method of any one of embodiments E1 to E27, wherein the genomic sections of the reference genome are chromosomes or genomic sections thereof.

E29. The method of any one of embodiments E1 to E28, wherein the genomic sections of the reference genome are one or more bins.

E30. The method of embodiment E29, wherein each bin is of about an equal number of contiguous nucleotides.

E31. The method of embodiment E29 or E30, wherein each bin is about 50 kb.

E32. The method of any one of embodiments E1 to E31, wherein the fetal fraction is provided with an accuracy of equal to or greater than 90% and/or a precision equal to or greater than 90%.

E33. The method of any one of embodiments E1 to E32, wherein the sequence reads of circulating cell-free nucleic acid from the blood of a pregnant female bearing a male fetus are from a test sample obtained from the pregnant female bearing a male fetus.

E34. The method of any one of embodiments E1 to E33, which comprises determining the presence or absence of nucleic acid sequence reads mapped to the Y chromosome in the reference genome.

E35. The method of embodiment E34, wherein determining the presence or absence of nucleic acid sequence reads mapped to the Y chromosome is performed before performing (b).

E36. The method of embodiment E34 or E35, wherein determining the presence or absence of nucleic acid sequence reads mapped to the Y chromosome of the fetus is determined from the counts of nucleic acid sequence reads mapped to genomic sections of the reference genome obtained in (a).

E37. The method of any one of embodiments E34 to E36, which comprises determining the presence or absence of nucleic acid sequence reads mapped to the Y chromosome before performing (b), and if nucleic acid sequence reads mapped to the Y chromosome are present, then performing (b) and (c).

E38. The method of any one of embodiments E34 to E36, which comprises determining the presence or absence of nucleic acid sequence reads mapped to the Y chromosome before performing (a), and if nucleic acid sequence reads mapped to the Y chromosome are present, then performing (a), (b) and (c).

E39. The method of any one of embodiments E1 to E38, which comprises determining the gender of the fetus.

E40. The method of embodiment E39, wherein the gender of the fetus is determined before performing (b).

E41. The method of embodiment E39 or E40, wherein the gender of the fetus is determined from the counts of nucleic acid sequence reads mapped to genomic sections of the reference genome obtained in (a).

E42. The method of embodiment E39, wherein the gender of the fetus is determined before performing (a).

E43. The method of any one of embodiments E39 to E42, which comprises determining whether the gender of the fetus is male or female before performing (b), and if the gender of the fetus is determined as being male, then performing (b) and (c).

E44. The method of any one of embodiments E39 to E42, which comprises determining whether the gender of the fetus is male or female before performing (a), and if the gender of the fetus is determined as being male, then performing (a), (b) and (c).

E45. The method of any one of embodiments E1 to E44, which comprises determining the presence or absence of a Y chromosome in the fetus.

E46. The method of any one of embodiments E1 to E45, wherein the genomic sections of the Y chromosome in (b)(ii) are a subset of genomic sections of the Y chromosome.

E47. The method of embodiment E46, wherein the subset of genome sections of the Y chromosome comprises one or more polynucleotides located within the first 28 Mb from the 5' end of the Y chromosome.

E48. The method of any one of embodiments E1 to E46, wherein counts of sequence reads that map to both chromosome Y and chromosome X are excluded before performing (b).

E49. The method of any one of embodiments E1 to E48, wherein the counts of sequence reads mapped to the genomic sections of the reference genome in the Y chromosome are substantially unique to the Y chromosome.

E50. The method of embodiment E49, wherein greater than 80% or more of the genomic sections in the Y chromosome are substantially unique to the Y chromosome.

E51. The method of any one of embodiments E1 to E50, wherein the counts of sequence reads mapped to the genomic sections of the reference genome in the Y chromosome do not map to genomic sections of the reference genome in the X chromosome.

E52. The method of any one of embodiments E1 to E51, wherein the counts of sequence reads mapped to genomic sections of the reference genome in the genome or segment thereof in (b)(ii) are counts of sequence reads mapped to autosomes.

E53. The method of embodiment E52, wherein the counts of sequence reads mapped to genomic sections of the reference genome in the genome or segment thereof in (b)(ii) do not include sequence reads mapped to sex chromosomes.

E54. The method of any one of embodiments E1 to E51, wherein the counts of sequence reads mapped to the reference genome in the genome or a segment thereof in (b)(ii) are counts of sequence reads mapped to all chromosomes from which reads are obtained.

F1. A method for determining the fraction of fetal nucleic acid in circulating cell-free nucleic acid from the blood of a pregnant female, comprising:

(a) obtaining counts of nucleic acid sequence reads mapped to genomic sections of a reference genome, which sequence reads are reads of circulating cell-free nucleic acid from the blood of a pregnant female bearing a male fetus;

(b) generating an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (c) from the experimental Y chromosome representation, determining the fraction of fetal nucleic acid in the blood of the pregnant female according to the experimental Y chromosome representation and an expected Y chromosome representation, which expected Y chromosome representation is a ratio of (i) the number of the genomic sections of the reference genome in the Y chromosome, and (ii) the number of the genomic sections of the reference genome in the genome or segment thereof.

F2. The method of embodiment F1, wherein the fraction of fetal nucleic acid in the blood of the pregnant female is determined in (c) according to a ratio of the experimental Y chromosome representation and the expected Y chromosome representation.

F2.1. The method of embodiment F1 or F2, wherein the fraction of fetal nucleic acid in the blood of the pregnant female is determined according to equation AC.

F3. A method for determining the fraction of fetal nucleic acid in circulating cell-free nucleic acid from the blood of a pregnant female, comprising:

(a) obtaining counts of nucleic acid sequence reads mapped to genomic sections of a reference genome, which sequence reads are reads of circulating cell-free nucleic acid from the blood of a pregnant female bearing a male fetus;

(b) generating an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (c) from the experimental Y chromosome representation, determining the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental Y chromosome representation.

F3.1. The method of embodiment F3, wherein the fraction of fetal nucleic acid in the blood of the pregnant female bearing a fetus having a chromosome aneuploidy is determined according to equation AB.

F3.2. The method of embodiment F3 or F3.1 wherein the fraction of fetal nucleic acid determined in (c)(i) and the experimental Y chromosome representation in (c)(ii) are derived from greater than about 500 subjects.

F4. The method of embodiment F3, wherein the relationship is a linear relationship.

F4.1. The method of embodiment F3 or F4, wherein the chromosome aneuploidy is a trisomy 21, trisomy 18 and/or trisomy 13.

F4.2. The method of embodiment F3 or F4.1, wherein the chromosome aneuploidy is a sex chromosome aneuploidy.

F4.3. The method of any one of embodiments F4 to F4.2, wherein the relationship is:

$$F=k-r(MCR_Y),$$

wherein F is the fraction, $MCR_Y$ is the experimental Y chromosome representation, k is an intercept from the linear relationship and r is a slope from the linear relationship.

F4.3.1. The method of embodiment F4.3 wherein the fraction of fetal nucleic acid in circulating cell-free nucleic acid from the blood of a pregnant female is determined by the relationship in F4.3 and the experimental Y chromosome representation.

F4.4. The method of any one of embodiments F3 to F4.3.1, wherein the fraction of fetal nucleic acid determined for nucleic acid from the blood of a pregnant female bearing a fetus having a chromosome aneuploidy in (c)(i) is determined by a process that comprises use of sequence reads mapped to genomic sections of a reference genome.

F4.5. The method of any one of embodiments F3 to F4.3.1, wherein the fraction of fetal nucleic acid determined for nucleic acid from nucleic acid from the blood of a pregnant female bearing a fetus having a chromosome aneuploidy in (c)(i) is determined by a process that does not utilize sequence reads mapped to genomic sections of a reference genome.

F4.6. The method of embodiment F4.5, wherein the process comprises mass spectrometry.

F4.7. The method of any one of embodiments F3 to F4.6, wherein the pregnant female bearing a fetus having a chromosome aneuploidy in (c)(i) is different from the pregnant female in (a).

F4.7.1 The method of F.4.7 wherein the pregnant female bearing a fetus having a chromosome aneuploidy is bearing a male fetus.

F4.8. The method of any one of embodiments F3 to F4.7.1, wherein the nucleic acid from the blood of the pregnant female in (c)(i) is circulating cell-free nucleic acid.

F5. The method of any one of embodiments F1 to F4.8, comprising normalizing the counts mapped to the genomic sections of the reference genome, thereby providing normalized counts of the genomic sections of the reference genome; and which counts in F1(b) and F3(b) are normalized counts.

F5.1. The method of any one of embodiments F1 to F5, wherein the counts in F1(b) and F3(b) are normalized by GC content, bin-wise normalization, GC LOESS, PERU N, GCRM, or combinations thereof.

F6. The method of embodiment F5, wherein the normalized counts are provided by a normalization module.

F7. The method of any one of embodiments F1 to F6, wherein the experimental Y chromosome representation in F1(b) and F3(b) is provided by a representation module.

F8. The method of any one of embodiments F1 to F7, wherein expected Y chromosome representation in F1(c) and F3(c) is determined by an expected representation module.

F9. The method of any one of embodiments F1 to F8, wherein the fetal fraction in F1(c) and F3(c) is provided by a fetal fraction module.

F10. The method of any one of embodiments F3 to F9, wherein the relationship is provided by a relationship module.

F11. The method of any one of embodiments F7 to F10, wherein the normalized mapped counts are transferred to the Y experimental module from the normalization module.

F12. The method of any one of embodiments F8 to F11, wherein the normalized mapped counts are transferred to the Y expected module from the normalization module.

F13. The method of any one of embodiments F9 to F12, wherein the experimental Y chromosome representation is transferred to the fetal fraction module from the Y experimental module.

F14. The method of any one of embodiments F9 to F13, wherein the expected Y chromosome representation is transferred to the fetal fraction module from the Y expected module.

F15. The method of any one of embodiments F1 to F14, which comprises obtaining nucleic acid sequence reads.

F16. The method of embodiment F15, wherein the nucleic acid sequence reads are generated by a sequencing module.

F16.1 The method of embodiment F15 or F16, wherein the nucleic acid sequencing reads are generated by massively parallel sequencing (MPS).

F17. The method of embodiment F15 or F16, which comprises mapping the nucleic acid sequence reads to the genomic sections of the reference genome.

F18. The method of embodiment F17, wherein the nucleic acid sequence reads are mapped to the genomic sections of the reference genome by a mapping module.

F19. The method of any one of embodiments F1 to F18, wherein the nucleic acid sequence reads mapped to the genomic sections of the reference genome are counted by a counting module.

F20. The method of any one of embodiments F18 to F19, wherein the sequence reads are transferred to the mapping module from the sequencing module.

F21. The method of any one of embodiments F19 to F20, wherein the nucleic acid sequence reads mapped to the genomic sections of the reference genome are transferred to the counting module from the mapping module.

F22. The method of any one of embodiments F19 to F21, wherein the counts of the nucleic acid sequence reads mapped to the genomic sections of the reference genome are transferred to the normalization module from the counting module.

F23. The method of any one of embodiments F1 to F22, wherein an apparatus comprises one or more of a sequencing module, sequence receiving module, mapping module, counting module, normalization module, comparison module, range setting module, categorization module, adjustment module, plotting module, outcome module, data display organization module, logic processing module, representation module, relationship module or fetal fraction module, which apparatus comprises, or is in communication with, a processor that is capable of implementing instructions from one or more of the modules.

F24. The method of embodiment F23, wherein a first apparatus comprises one or more of the normalization module, the comparison module, the range setting module, the adjustment module, and the outcome module.

F24.1. The method of any one of embodiments F19 to F24, wherein a second apparatus comprises the mapping module and the counting module.

F25. The method of any one of embodiments F16 to F24.1, wherein a third apparatus comprises the sequencing module.

F26. The method of any one of embodiments F5 to F25, wherein the counts that are normalized are raw counts.

F27. The method of any one of embodiments F5 to F26, wherein the counts that are normalized are filtered.

F27.1 The method of any one of embodiments F5 to F26, wherein the counts that are normalized are not filtered.

F28. The method of any one of embodiments F1 to F27, wherein the genomic sections of the reference genome are chromosomes or genomic sections thereof.

F29. The method of any one of embodiments F1 to F28, wherein the genomic sections of the reference genome are one or more bins.

F30. The method of embodiment F29, wherein each bin is of about an equal number of contiguous nucleotides.

F31. The method of embodiment F29 or F30, wherein each bin is about 50 kb.

F32. The method of any one of embodiments F1 to F31, wherein the fetal fraction is provided with an accuracy of equal to or greater than 90% and/or a precision equal to or greater than 90%.

F33. The method of any one of embodiments F1 to F32, wherein the sequence reads of circulating cell-free nucleic acid from the blood of a pregnant female bearing a male fetus are from a test sample obtained from the pregnant female bearing a male fetus.

F34. The method of any one of embodiments F1 to F33, which comprises determining the presence or absence of nucleic acid sequence reads mapped to the Y chromosome in the reference genome.

F35. The method of embodiment F34, wherein determining the presence or absence of nucleic acid sequence reads mapped to the Y chromosome is performed before performing (b).

F36. The method of embodiment F34 or F35, wherein determining the presence or absence of nucleic acid sequence reads mapped to the Y chromosome of the fetus is determined from the counts of nucleic acid sequence reads mapped to genomic sections of the reference genome obtained in (a).

F37. The method of any one of embodiments F34 to F36, which comprises determining the presence or absence of nucleic acid sequence reads mapped to the Y chromosome before performing (b), and if nucleic acid sequence reads mapped to the Y chromosome are present, then performing (b) and (c).

F38. The method of any one of embodiments F34 to F36, which comprises determining the presence or absence of nucleic acid sequence reads mapped to the Y chromosome before performing (a), and if nucleic acid sequence reads mapped to the Y chromosome are present, then performing (a), (b) and (c).

F39. The method of any one of embodiments F1 to F38, which comprises determining the gender of the fetus.

F40. The method of embodiment F39, wherein the gender of the fetus is determined before performing (b).

F41. The method of embodiment F39 or F40, wherein the gender of the fetus is determined from the counts of nucleic acid sequence reads mapped to genomic sections of the reference genome obtained in (a).

F42. The method of embodiment F39, wherein the gender of the fetus is determined before performing (a).

F43. The method of any one of embodiments F39 to F42, which comprises determining whether the gender of the fetus is male or female before performing (b), and if the gender of the fetus is determined as being male, then performing (b) and (c).

F44. The method of any one of embodiments F39 to F42, which comprises determining whether the gender of the fetus is male or female before performing (a), and if the gender of the fetus is determined as being male, then performing (a), (b) and (c).

F45. The method of any one of embodiments F1 to F44, which comprises determining the presence or absence of a Y chromosome in the fetus.

F46. The method of any one of embodiments F1 to F45, wherein the genomic sections of the Y chromosome in (b)(ii) are a subset of genomic sections of the Y chromosome.

F47. The method of embodiment F46, wherein the subset of genome sections of the Y chromosome comprises one or more polynucleotides located within the first 28 Mb from the 5' end of the Y chromosome.

F48. The method of any one of embodiments F1 to F46, wherein counts of sequence reads that map to both chromosome Y and chromosome X are excluded before performing (b).

F49. The method of any one of embodiments F1 to F48, wherein the counts of sequence reads mapped to the genomic sections of the reference genome in the Y chromosome are substantially unique to the Y chromosome.

F50. The method of embodiment F49, wherein greater than 80% or more of the genomic sections in the Y chromosome are substantially unique to the Y chromosome.

F51. The method of any one of embodiments F1 to F50, wherein the counts of sequence reads mapped to the genomic sections of the reference genome in the Y chromosome do not map to genomic sections of the reference genome in the X chromosome.

F52. The method of any one of embodiments F1 to F51, wherein the counts of sequence reads mapped to genomic sections of the reference genome in the genome or segment thereof in (b)(ii) are counts of sequence reads mapped to autosomes.

F53. The method of embodiment F52, wherein the counts of sequence reads mapped to genomic sections of the reference genome in the genome or segment thereof in (b)(ii) do not include sequence reads mapped to sex chromosomes.

F54. The method of any one of embodiments F1 to F51, wherein the counts of sequence reads mapped to the reference genome in the genome or a segment thereof in (b)(ii) are counts of sequence reads mapped to all chromosomes from which reads are obtained.

G1. A method for determining the fraction of fetal nucleic acid in circulating cell-free nucleic acid from the blood of a pregnant female, comprising:

(a) obtaining counts of nucleic acid sequence reads mapped to genomic sections of a reference genome, which sequence reads are reads of circulating cell-free nucleic acid from the blood of a pregnant female bearing a male fetus;

(b) generating an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof, and generating an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (c) from the experimental X chromosome representation and experimental Y chromosome representation, determining the fraction of fetal nucleic acid in the blood of the pregnant female according to:

the experimental X chromosome representation and an expected X chromosome representation, which expected X chromosome representation is a ratio of (i) the number of the genomic sections of the reference genome in the X chromosome, and (ii) the number of the genomic sections of the reference genome in the genome or segment thereof, and the experimental Y chromosome representation and an expected Y chromosome representation, which expected Y chromosome representation is a ratio of (i) the number of the genomic sections of the reference genome in the Y chromosome, and (ii) the number of the genomic sections of the reference genome in the genome or segment thereof.

G2. The method of embodiment G1, wherein the fraction of fetal nucleic acid in the blood of the pregnant female is determined in (c) according to (i) a ratio of the experimental X chromosome representation and the expected X chromosome representation, and (ii) a ratio of the experimental Y chromosome representation and the expected Y chromosome representation.

G2.1. The method of embodiment G1 or G2, wherein the fraction of fetal nucleic acid in the blood of the pregnant female is determined according to equation AC.

G3. A method for determining the fraction of fetal nucleic acid in circulating cell-free nucleic acid from the blood of a pregnant female, comprising:

(a) obtaining counts of nucleic acid sequence reads mapped to genomic sections of a reference genome, which sequence reads are reads of circulating cell-free nucleic acid from the blood of a pregnant female bearing a male fetus;

(b) generating an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof;

generating an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (c) from the experimental X chromosome representation and experimental Y chromosome representation, determining the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X and the experimental Y chromosome representation.

G3.1. The method of embodiment G3, wherein the fraction of fetal nucleic acid in the blood of the pregnant female bearing a fetus having a chromosome aneuploidy is determined according to equation AB.

G3.2. The method of embodiment G3 or G3.1 wherein the fraction of fetal nucleic acid determined in (c)(i) and the experimental X and the experimental Y chromosome representation in (c)(ii) are derived from greater than about 500 subjects.

G4. The method of embodiment G3, wherein the relationship is a linear relationship.

G4.1. The method of embodiment G3 or G4, wherein the chromosome aneuploidy is a trisomy 21, trisomy 18 and/or trisomy 13.

G4.2. The method of embodiment G3 or G4, wherein the chromosome aneuploidy is a sex chromosome aneuploidy.

G4.3. The method of any one of embodiments G4 to G4.2, wherein the relationship is:

$$F=k-r(MCR_x)+t(MCR_y)$$

wherein F is the fraction, $MCR_Y$ is the experimental Y chromosome representation, $MCR_X$ is the experimental X chromosome representation, k is an intercept from the linear relationship and r is a slope from the linear relationship.

G4.3.1. The method of embodiment G4.3, wherein the fraction of fetal nucleic acid in circulating cell-free nucleic acid from the blood of a pregnant female is determined by the relationship in G4.3, the experimental X chromosome representation and the experimental Y chromosome representation.

G4.4. The method of any one of embodiments G3 to G4.3.1, wherein the fraction of fetal nucleic acid determined for nucleic acid from the blood of a pregnant female bearing a fetus having a chromosome aneuploidy in (c)(i) is determined by a process that comprises use of sequence reads mapped to genomic sections of a reference genome.

G4.5. The method of any one of embodiments G3 to G4.3.1, wherein the fraction of fetal nucleic acid determined for nucleic acid from nucleic acid from the blood of a pregnant female bearing a fetus having a chromosome aneuploidy in (c)(i) is determined by a process that does not utilize sequence reads mapped to genomic sections of a reference genome.

G4.6. The method of embodiment G4.5, wherein the process comprises mass spectrometry.

G4.7. The method of any one of embodiments G3 to G4.6, wherein the pregnant female bearing a fetus having a chromosome aneuploidy in (c)(i) is different from the pregnant female in (a).

G4.7.1 The method of embodiment G4.7, wherein the pregnant female bearing a fetus having a chromosome aneuploidy is bearing a male fetus.

G4.8. The method of any one of embodiments G3 to G4.7.1, wherein the nucleic acid from the blood of the pregnant female in (c)(i) is circulating cell-free nucleic acid.

G5. The method of any one of embodiments G1 to G4.8, comprising normalizing the counts mapped to the genomic sections of the reference genome, thereby providing normalized counts of the genomic sections of the reference genome in a genomic section; and which counts in G1(b) and G3(b) are normalized counts.

G5.1 The method of any one of embodiments G1 to G5, wherein the counts in G1(b) and G3(b) are normalized by GC content, bin-wise normalization, GC LOESS, PERUN, GCRM, or combinations thereof.

G6. The method of embodiment G5 or G5.1, wherein the normalized counts are provided by a normalization module.

G7. The method of any one of embodiments G1 to G6, wherein the experimental X chromosome representation in G1(b) and G3(b) is provided by a representation module and the expected X chromosome representation in G1(c) and G3(c) is determined by an expected representation module.

G8. The method of any one of embodiments G1 to G7, wherein the experimental Y chromosome representation in G1(b) and G3(b) is provided by a representation module and the expected Y chromosome representation in G1(c) and G3(c) is determined by an expected representation module.

G9. The method of any one of embodiments G1 to G8, wherein the fetal fraction in G1(c) and G3(c) is provided by a fetal fraction module.

G10. The method of any one of embodiments G3 to G9, wherein the relationship is provided by a relationship module.

G11. The method of any one of embodiments G7 to G10, wherein the normalized mapped counts are transferred to the experimental representation module and expected representation module from the normalization module.

G12. The method of any one of embodiments G8 to G11, wherein the normalized mapped counts are transferred to the Y experimental module and Y expected module from the normalization module.

G13. The method of any one of embodiments G9 to G12, wherein the experimental X chromosome representation is transferred to the fetal fraction module from the experimental representation module and the expected X chromosome representation is transferred to the fetal fraction module from the expected representation module.

G14. The method of any one of embodiments G9 to G12, wherein the experimental Y chromosome representation is transferred to the fetal fraction module from the Y experimental module and the expected Y chromosome representation is transferred to the fetal fraction module from the Y expected module.

G15. The method of any one of embodiments G1 to G14, which comprises obtaining nucleic acid sequence reads.

G16. The method of embodiment G15, wherein the nucleic acid sequence reads are generated by a sequencing module.

G16.1 The method of embodiment G15 or G16, wherein the nucleic acid sequencing reads are generated by massively parallel sequencing (MPS).

G17. The method of embodiment G15 or G16, which comprises mapping the nucleic acid sequence reads to the genomic sections of the reference genome.

G18. The method of embodiment G17, wherein the nucleic acid sequence reads are mapped to the genomic sections of the reference genome by a mapping module.

G19. The method of any one of embodiments G1 to G18, wherein the nucleic acid sequence reads mapped to the genomic sections of the reference genome are counted by a counting module.

G20. The method of any one of embodiments G18 to G19, wherein the sequence reads are transferred to the mapping module from the sequencing module.

G21. The method of any one of embodiments G19 to G20, wherein the nucleic acid sequence reads mapped to the genomic sections of the reference genome are transferred to the counting module from the mapping module.

G22. The method of any one of embodiments G19 to G21, wherein the counts of the nucleic acid sequence reads mapped to the genomic sections of the reference genome are transferred to the normalization module from the counting module.

G23. The method of any one of embodiments G1 to G22, wherein an apparatus comprises one or more of a sequencing module, sequence receiving module, mapping module, counting module, normalization module, comparison module, range setting module, categorization module, adjustment module, plotting module, outcome module, data display organization module or logic processing module, which apparatus comprises, or is in communication with, a processor that is capable of implementing instructions from one or more of the modules.

G24. The method of embodiment G23, wherein a first apparatus comprises one or more of the normalization module, the comparison module, the range setting module, the adjustment module, and the outcome module.

G24.1. The method of any one of embodiments G19 to G24, wherein a second apparatus comprises the mapping module and the counting module.

G25. The method of any one of embodiments G16 to G24.1, wherein a third apparatus comprises the sequencing module.

G26. The method of any one of embodiments G5 to G25, wherein the counts that are normalized are raw counts.

G27. The method of any one of embodiments G5 to G26, wherein the counts that are normalized are filtered.

G27.1 The method of any one of embodiments G5 to G26, wherein the counts that are normalized are not filtered.

G28. The method of any one of embodiments G1 to G27, wherein the genomic sections of the reference genome are chromosomes or genomic sections thereof.

G29. The method of any one of embodiments G1 to G28, wherein the genomic sections of the reference genome are one or more bins.

G30. The method of embodiment G29, wherein each bin is of about an equal number of contiguous nucleotides.

G31. The method of embodiment G29 or G30, wherein each bin is about 50 kb.

G32. The method of any one of embodiments G1 to G31, wherein the fetal fraction is provided with an accuracy of equal to or greater than 90% and/or a precision equal to or greater than 90%.

G33. The method of any one of embodiments G1 to G32, wherein the sequence reads of circulating cell-free nucleic acid from the blood of a pregnant female bearing a male fetus are from a test sample obtained from the pregnant female bearing a male fetus.

G34. The method of any one of embodiments G1 to G33, which comprises determining the presence or absence of nucleic acid sequence reads mapped to the Y chromosome in the reference genome.

G35. The method of embodiment G34, wherein determining the presence or absence of nucleic acid sequence reads mapped to the Y chromosome is performed before performing (b).

G36. The method of embodiment G34 or G35, wherein determining the presence or absence of nucleic acid sequence reads mapped to the Y chromosome of the fetus is determined from the counts of nucleic acid sequence reads mapped to genomic sections of the reference genome obtained in (a).

G37. The method of any one of embodiments G34 to G36, which comprises determining the presence or absence of nucleic acid sequence reads mapped to the Y chromosome before performing (b), and if nucleic acid sequence reads mapped to the Y chromosome are present, then performing (b) and (c).

G38. The method of any one of embodiments G34 to G36, which comprises determining the presence or absence of nucleic acid sequence reads mapped to the Y chromosome before performing (a), and if nucleic acid sequence reads mapped to the Y chromosome are present, then performing (a), (b) and (c).

G39. The method of any one of embodiments G1 to G38, which comprises determining the gender of the fetus.

G40. The method of embodiment G39, wherein the gender of the fetus is determined before performing (b).

G41. The method of embodiment G39 or G40, wherein the gender of the fetus is determined from the counts of nucleic acid sequence reads mapped to genomic sections of the reference genome obtained in (a).

G42. The method of embodiment G39, wherein the gender of the fetus is determined before performing (a).

G43. The method of any one of embodiments G39 to G42, which comprises determining whether the gender of the fetus is male or female before performing (b), and if the gender of the fetus is determined as being male, then performing (b) and (c).

G44. The method of any one of embodiments G39 to G42, which comprises determining whether the gender of the fetus is male or female before performing (a), and if the gender of the fetus is determined as being male, then performing (a), (b) and (c).

G45. The method of any one of embodiments G1 to G44, which comprises determining the presence or absence of a Y chromosome in the fetus.

G46. The method of any one of embodiments G1 to G45, wherein the genomic sections of the Y chromosome in (b)(ii) are a subset of genomic sections of the Y chromosome.

G47. The method of embodiment G46, wherein the subset of genome sections of the Y chromosome comprises one or more polynucleotides located within the first 28 Mb from the 5' end of the Y chromosome.

G48. The method of any one of embodiments G1 to G46, wherein counts of sequence reads that map to both chromosome Y and chromosome X are excluded before performing (b).

G49. The method of any one of embodiments G1 to G48, wherein the counts of sequence reads mapped to the genomic sections of the reference genome in the Y chromosome are substantially unique to the Y chromosome.

G50. The method of embodiment G49, wherein greater than 80% or more of the genomic sections in the Y chromosome are substantially unique to the Y chromosome.

G51. The method of any one of embodiments G1 to G50, wherein the counts of sequence reads mapped to the genomic sections of the reference genome in the Y chromosome do not map to genomic sections of the reference genome in the X chromosome.

G52. The method of any one of embodiments G1 to G51, wherein the counts of sequence reads mapped to genomic sections of the reference genome in the genome or segment thereof in (b)(ii) are counts of sequence reads mapped to autosomes.

G53. The method of embodiment G52, wherein the counts of sequence reads mapped to genomic sections of the reference genome in the genome or segment thereof in (b)(ii) do not include sequence reads mapped to sex chromosomes.

G54. The method of any one of embodiments G1 to G51, wherein the counts of sequence reads mapped to the reference genome in the genome or a segment thereof in (b)(ii) are counts of sequence reads mapped to all chromosomes from which reads are obtained.

H1. A method for determining the fraction of fetal nucleic acid in circulating cell-free nucleic acid from the blood of a pregnant female, comprising:

(a) obtaining counts of nucleic acid sequence reads mapped to genomic sections of a reference genome, which sequence reads are reads of circulating cell-free nucleic acid from the blood of a pregnant female bearing a fetus bearing a trisomy of an autosome, which autosome is an affected autosome;

(b) generating an experimental affected autosome representation, which experimental affected autosome representation is a ratio of (i) counts of sequence reads mapped to the genomic sections of the reference genome in the affected autosome, and (ii) counts of sequence reads mapped to genomic sections of the reference genome in the genome or segment thereof; and (c) from the experimental affected chromosome representation, determining the fraction of fetal nucleic acid in the blood of the pregnant female according to the experimental affected autosome representation and an expected affected autosome representation, which expected affected autosome representation is a ratio of (i) the number of the genomic sections of the reference genome in the affected autosome, and (ii) the number of the genomic sections of the reference genome in the genome or segment thereof.

H2. The method of embodiment H1, wherein the fraction of fetal nucleic acid in the blood of the pregnant female is determined in (c) according to a ratio of the experimental affected autosome representation and the expected a e representation.

H2.1. The method of embodiment H1 or H2, wherein the fraction of fetal nucleic acid in the blood of the pregnant female is determined according to equation AB.

H3. A method for determining the fraction of fetal nucleic acid in circulating cell-free nucleic acid from the blood of a pregnant female, comprising:

(a) obtaining counts of nucleic acid sequence reads mapped to genomic sections of a reference genome, which sequence reads are reads of circulating cell-free nucleic acid from the blood of a pregnant female bearing a fetus bearing a trisomy of an autosome, which autosome is an affected autosome;

(b) generating an experimental affected autosome representation, which experimental affected autosome representation is a ratio of (i) counts of sequence reads mapped to the genomic sections of the reference genome in the affected autosome, and (ii) counts of sequence reads mapped to genomic sections of the reference genome in the genome or segment thereof; and (c) from the experimental affected chromosome representation, determining the fraction of the fetal nucleic acid in the blood of the pregnant female according to a relationship determined from (i) a fraction of fetal nucleic acid determined for nucleic acid from the blood of a pregnant female bearing a fetus having a chromosome aneuploidy, and (ii) the experimental affected autosome representation.

H3.1. The method of embodiment H3, wherein the fraction of fetal nucleic acid in the blood of the pregnant female bearing a fetus having a chromosome aneuploidy is determined according to equation AB.

H3.2. The method of embodiment H3 or H3.1 wherein the fraction of fetal nucleic acid determined in (c)(i) and the experimental affected autosome representation in (c)(ii) are derived from greater than about 500 subjects.

H4. The method of embodiment H3, wherein the relationship is a linear relationship.

H4.1. The method of embodiment H3 or H4, wherein the chromosome aneuploidy is a trisomy 21, trisomy 18 and/or trisomy 13.

H4.2. The method of embodiment H3 or H4, wherein the chromosome aneuploidy is a sex chromosome aneuploidy.

H4.3. The method of any one of embodiments H4 to H4.2, wherein the relationship is:

$$F=k-r(MCRn),$$

wherein F is the fraction, MCRn is the experimental affected autosome representation, k is an intercept from the linear relationship and r is a slope from the linear relationship.

H4.3.1. The method of embodiment H4.3, wherein the fraction of fetal nucleic acid in circulating cell-free nucleic acid from the blood of a pregnant female is determined by the relationship in H4.3 and the experimental affected autosome representation.

H4.4. The method of any one of embodiments H3 to H4.3, wherein the fraction of fetal nucleic acid determined for nucleic acid from the blood of a pregnant female bearing a fetus having a chromosome aneuploidy in (c)(i) is determined by a process that comprises use of sequence reads mapped to genomic sections of a reference genome.

H4.5. The method of any one of embodiments H3 to H4.3, wherein the fraction of fetal nucleic acid determined for nucleic acid from nucleic acid from the blood of a pregnant female bearing a fetus having a chromosome aneuploidy in (c)(i) is determined by a process that does not utilize sequence reads mapped to genomic sections of a reference genome.

H4.6. The method of embodiment H4.5, wherein the process comprises mass spectrometry.

H4.7. The method of any one of embodiments H3 to H4.6, wherein the pregnant female bearing a fetus having a chromosome aneuploidy in (c)(i) is different from the pregnant female in (a).

H4.8. The method of any one of embodiments H3 to H4.7, wherein the nucleic acid from the blood of the pregnant female in (c)(i) is circulating cell-free nucleic acid.

H5. The method of any one of embodiments H1 to H4, comprising normalizing the counts mapped to the genomic sections of the reference genome, thereby providing normalized counts of the genomic sections of the reference genome in a genomic section; and which counts in H1(b) and H3(b) are normalized counts.

H5.1 The method of any one of embodiments H1 to H5, wherein the counts in H1(b) and H3(b) are normalized by GC content, bin-wise normalization, GC LOESS, PERU N, GCRM, or combinations thereof.

H6. The method of embodiment H5, wherein the normalized counts are provided by a normalization module.

H7. The method of any one of embodiments H1 to H6, wherein the experimental affected autosome representation in H1(b) and H3(b) is provided by a representation module.

H8. The method of any one of embodiments H1 to H7, wherein the expected affected autosome representation in H1(c) and H3(c) is determined by an expected representation module.

H9. The method of any one of embodiments H2 to H8, wherein the fetal fraction is provided by a fetal fraction module.

H10. The method of any one of embodiments H3 to H9, wherein the relationship is provided by a relationship module.

H11. The method of any one of embodiments H7 to H10, wherein the normalized mapped counts are transferred to the autosome experimental module from the normalization module.

H12. The method of any one of embodiments H8 to H11, wherein the normalized mapped counts are transferred to the autosome expected module from the normalization module.

H13. The method of any one of embodiments H9 to H12, wherein the experimental affected autosome representation is transferred to the fetal fraction module from the autosome experimental module.

H14. The method of any one of embodiments H9 to H12, wherein the expected affected autosome representation is transferred to the fetal fraction module from the autosome expected module.

H15. The method of any one of embodiments H1 to H14, which comprises obtaining nucleic acid sequence reads.

H16. The method of embodiment H15, wherein the nucleic acid sequence reads are generated by a sequencing module.

H16.1 The method of embodiment H15 or H16, wherein the nucleic acid sequencing reads are generated by massively parallel sequencing (MPS).

H17. The method of embodiment H15 or H16, which comprises mapping the nucleic acid sequence reads to the genomic sections of the reference genome.

H18. The method of embodiment H17, wherein the nucleic acid sequence reads are mapped to the genomic sections of the reference genome by a mapping module.

H19. The method of any one of embodiments H1 to H18, wherein the nucleic acid sequence reads mapped to the genomic sections of the reference genome are counted by a counting module.

H20. The method of any one of embodiments H18 to H19, wherein the sequence reads are transferred to the mapping module from the sequencing module.

H21. The method of any one of embodiments H19 to H20, wherein the nucleic acid sequence reads mapped to the genomic sections of the reference genome are transferred to the counting module from the mapping module.

H22. The method of any one of embodiments H19 to H21, wherein the counts of the nucleic acid sequence reads mapped to the genomic sections of the reference genome are transferred to the normalization module from the counting module.

H23. The method of any one of embodiments H1 to H22, wherein an apparatus comprises one or more of a sequencing module, sequence receiving module, mapping module, counting module, normalization module, comparison module, range setting module, categorization module, adjustment module, plotting module, outcome module, data display organization module or logic processing module, which apparatus comprises, or is in communication with, a processor that is capable of implementing instructions from one or more of the modules.

H24. The method of embodiment H23, wherein a first apparatus comprises one or more of the normalization module, the comparison module, the range setting module, the adjustment module, and the outcome module.

H24.1. The method of any one of embodiments H20 to H24.1, wherein a second apparatus comprises the mapping module and the counting module.

H25. The method of any one of embodiments H16 to H24.1, wherein a third apparatus comprises the sequencing module.

H26. The method of any one of embodiments H5 to H25, wherein the counts that are normalized are raw counts.

H27. The method of any one of embodiments H5 to H26, wherein the counts that are normalized are filtered.

H27.1 The method of any one of embodiments H5 to H26, wherein the counts that are normalized are not filtered.

H28. The method of any one of embodiments H1 to H27, wherein the genomic sections of the reference genome are chromosomes or genomic sections thereof.

H29. The method of any one of embodiments H1 to H28, wherein the genomic sections of the reference genome are one or more bins.

H30. The method of embodiment H29, wherein each bin is of about an equal number of contiguous nucleotides.

H31. The method of embodiment H29 or H30, wherein each bin is about 50 kb.

H32. The method of any one of embodiments H1 to H31, wherein the fetal fraction is provided with an accuracy of equal to or greater than 90% and/or a precision equal to or greater than 90%.

H33. The method of any one of embodiments H1 to H32, wherein the sequence reads of circulating cell-free nucleic acid from the blood of a pregnant female bearing a male fetus are from a test sample obtained from the pregnant female bearing a male fetus.

H33.1. The method of any one of embodiments H1 to H33, comprising determining the presence or absence of a fetal aneuploidy.

H34. The method of any one of embodiments H1 to H33.1, which comprises determining the presence or absence of nucleic acid sequence reads mapped to the Y chromosome in the reference genome.

H35. The method of embodiment H34, wherein determining the presence or absence of nucleic acid sequence reads mapped to the Y chromosome is performed before performing (b).

H36. The method of embodiment H34 or H35, wherein determining the presence or absence of nucleic acid sequence reads mapped to the Y chromosome of the fetus is determined from the counts of nucleic acid sequence reads mapped to genomic sections of the reference genome obtained in (a).

H37. The method of any one of embodiments H34 to H36, which comprises determining the presence or absence of nucleic acid sequence reads mapped to the Y chromosome before performing (b), and if nucleic acid sequence reads mapped to the Y chromosome are present, then performing (b) and (c).

H38. The method of any one of embodiments H34 to H36, which comprises determining the presence or absence of nucleic acid sequence reads mapped to the Y chromosome before performing (a), and if nucleic acid sequence reads mapped to the Y chromosome are present, then performing (a), (b) and (c).

H39. The method of any one of embodiments H1 to H38, which comprises determining the gender of the fetus.

H40. The method of embodiment H39, wherein the gender of the fetus is determined before performing (b).

H41. The method of embodiment H39 or H40, wherein the gender of the fetus is determined from the counts of nucleic acid sequence reads mapped to genomic sections of the reference genome obtained in (a).

H42. The method of embodiment H39, wherein the gender of the fetus is determined before performing (a).

H43. The method of any one of embodiments H39 to H42, which comprises determining whether the gender of the fetus is male or female before performing (b), and if the gender of the fetus is determined as being male, then performing (b) and (c).

H44. The method of any one of embodiments H39 to H42, which comprises determining whether the gender of the fetus is male or female before performing (a), and if the gender of the fetus is determined as being male, then performing (a), (b) and (c).

H45. The method of any one of embodiments H1 to H44, which comprises determining the presence or absence of a Y chromosome in the fetus.

H46. The method of any one of embodiments H1 to H45, wherein the genomic sections of the Y chromosome in (b)(ii) are a subset of genomic sections of the Y chromosome.

H47. The method of embodiment H46, wherein the subset of genome sections of the Y chromosome comprises one or more polynucleotides located within the first 28 Mb from the 5' end of the Y chromosome.

H48. The method of any one of embodiments H1 to H46, wherein counts of sequence reads that map to both chromosome Y and chromosome X are excluded before performing (b).

H49. The method of any one of embodiments H1 to H48, wherein the counts of sequence reads mapped to the genomic sections of the reference genome in the Y chromosome are substantially unique to the Y chromosome.

H50. The method of embodiment H49, wherein greater than 80% or more of the genomic sections in the Y chromosome are substantially unique to the Y chromosome.

H51. The method of any one of embodiments H1 to H50, wherein the counts of sequence reads mapped to the genomic sections of the reference genome in the Y chromosome do not map to genomic sections of the reference genome in the X chromosome.

H52. The method of any one of embodiments H1 to H51, wherein the counts of sequence reads mapped to genomic sections of the reference genome in the genome or segment thereof in (b)(ii) are counts of sequence reads mapped to autosomes.

H53. The method of embodiment H52, wherein the counts of sequence reads mapped to genomic sections of the reference genome in the genome or segment thereof in (b)(ii) do not include sequence reads mapped to sex chromosomes.

H54. The method of any one of embodiments H1 to H51, wherein the counts of sequence reads mapped to the reference genome in the genome or a segment thereof in (b)(ii) are counts of sequence reads mapped to all chromosomes from which reads are obtained.

I1. A system comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to:

(a) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof; and (b) from the experimental X chromosome representation, determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X chromosome representation.

I2. An apparatus comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to:

(a) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof; and (b) from the experimental X chromosome representation, determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X chromosome representation.

I3. A computer program product tangibly embodied on a computer-readable medium, comprising instructions that when executed by one or more processors are configured to:

(a) access counts of nucleic acid sequence reads mapped to genomic sections of a reference genome, which sequence reads are reads of circulating cell-free nucleic acid from the blood of a pregnant female bearing a male fetus;

(b) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof; and (c) from the experimental X chromosome representation, determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X chromosome representation.

J1. A system comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to:

(a) generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) from the experimental Y chromosome representation, determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental Y chromosome representation.

J2. An apparatus comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to:

(a) generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) from the experimental Y chromosome representation, determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental Y chromosome representation.

J3. A computer program product tangibly embodied on a computer-readable medium, comprising instructions that when executed by one or more processors are configured to:

(a) access counts of nucleic acid sequence reads mapped to genomic sections of a reference genome, which sequence reads are reads of circulating cell-free nucleic acid from the blood of a pregnant female bearing a male fetus;

(b) generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (c) from the experimental Y chromosome representation, determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental Y chromosome representation.

K1. A system comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to:

(a) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof, and generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) from the experimental X and the experimental Y chromosome representation, determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X and the experimental Y chromosome representation.

K2. An apparatus comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a male fetus; and which instructions executable by the one or more processors are configured to:

(a) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof, and generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (b) from the experimental X and the experimental Y chromosome representation, determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X and the experimental Y chromosome representation.

K3. A computer program product tangibly embodied on a computer-readable medium, comprising instructions that when executed by one or more processors are configured to:

(a) access counts of nucleic acid sequence reads mapped to genomic sections of a reference genome, which sequence reads are reads of circulating cell-free nucleic acid from the blood of a pregnant female bearing a male fetus;

(b) generate an experimental X chromosome representation, which experimental X chromosome representation is a ratio of (i) counts of sequence reads mapped to the genomic sections of the reference genome in the X chromosome, and (ii) counts of sequence reads mapped to genomic sections of the reference genome in the genome or segment thereof, and generate an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof; and (c) from the experimental X and the experimental Y chromosome representation, determine the fraction of the fetal nucleic acid in the blood of the pregnant female according to a relationship determined from (i) the fraction of fetal nucleic acid determined for nucleic acid from the blood of a pregnant female bearing a fetus having a chromosome aneuploidy, and (ii) the experimental X and the experimental Y chromosome representation.

L1. A system comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a fetus bearing a trisomy of an autosome, which autosome is an affected autosome; and which instructions executable by the one or more processors are configured to:

(a) generate an experimental affected autosome representation, which experimental affected autosome representation is a ratio of (i) counts of sequence reads mapped to the genomic sections of the reference genome in the affected autosome, and (ii) counts of sequence reads mapped to genomic sections of the reference genome in the genome or segment thereof; and (b) from the experimental affected autosome representation, determine the fraction of the fetal nucleic acid in the blood of the pregnant female according to a relationship determined from (i) a fraction of fetal nucleic acid determined for nucleic acid from the blood of a pregnant female bearing a fetus having a chromosome aneuploidy, and (ii) the experimental affected autosome representation.

L2. An apparatus comprising one or more processors and memory, which memory comprises instructions executable by the one or more processors and which memory comprises counts of nucleic acid sequence reads mapped to genomic sections of a reference genome, which sequence reads are reads of circulating cell-free nucleic acid from the blood of a pregnant female bearing a fetus bearing a trisomy of an autosome, which autosome is an affected autosome; and which instructions executable by the one or more processors are configured to:

(a) generate an experimental affected autosome representation, which experimental affected autosome representation is a ratio of (i) counts of sequence reads mapped to the genomic sections of the reference genome in the affected autosome, and (ii) counts of sequence reads mapped to genomic sections of the reference genome in the genome or segment thereof; and (b) from the experimental affected autosome representation, determine the fraction of the fetal nucleic acid in the blood of the pregnant female according to a relationship determined from (i) a fraction of fetal nucleic acid determined for nucleic acid from the blood of a pregnant female bearing a fetus having a chromosome aneuploidy, and (ii) the experimental affected autosome representation.

L3. A computer program product tangibly embodied on a computer-readable medium, comprising instructions that when executed by one or more processors are configured to:

(a) access counts of nucleic acid sequence reads mapped to genomic sections of a reference genome, which sequence reads are reads of circulating cell-free nucleic acid from the blood of a pregnant female bearing a fetus bearing a trisomy of an autosome, which autosome is an affected autosome;

(b) generate an experimental affected autosome representation, which experimental affected autosome representation is a ratio of (i) counts of sequence reads mapped to the genomic sections of the reference genome in the affected autosome, and (ii) counts of sequence reads mapped to genomic sections of the reference genome in the genome or segment thereof; and (c) from the experimental affected autosome representation, determine the fraction of the fetal nucleic acid in the blood of the pregnant female according to a relationship determined from (i) a fraction of fetal nucleic acid determined for nucleic acid from the blood of a pregnant female bearing a fetus having a chromosome aneuploidy, and (ii) the experimental affected autosome representation.

M1. A method for determining fetal ploidy according to nucleic acid sequence reads for a test sample obtained from a pregnant female, comprising:

(a) obtaining counts of sequence reads mapped to portions of a reference genome, which sequence reads are reads of circulating cell-free nucleic acid from sample nucleic acid;

(b) calculating a genomic section level for each of the portions of the reference genome, thereby providing calculated genomic section levels;

(c) determining a fraction of fetal nucleic acid in the test sample according to calculated genomic section levels for a first subset of portions of the reference genome;

(d) determining fetal ploidy according to (i) the calculated genomic section levels for a second subset of portions of the reference genome and (ii) the fraction of fetal nucleic acid determined in (c).

M2. The method of embodiment M1, wherein the calculating in (b) comprises:

(1) determining a guanine and cytosine (GC) bias for each of the portions of the reference genome for multiple samples from a fitted relation for each sample between (i) the counts of the sequence reads mapped to each of the portions of the reference genome, and (ii) GC content for each of the portions; and (2) calculating a genomic section level for each of the portions of the reference genome from a fitted relation between (i) the GC bias and (ii) the counts of the sequence reads mapped to each of the portions of the reference genome, thereby providing calculated genomic section levels, whereby bias in the counts of the sequence reads mapped to each of the portions of the reference genome is reduced in the calculated genomic section levels.

M3. The method of embodiment M1 or M2, wherein the fraction of fetal nucleic acid determined in (c) is determined by any one of embodiments A1 to A71, E1 to E54, F1 to F54, G1 to G54, or H1 to H54.

M4. The method of any one of embodiments M1 to M3, wherein the first subset of portions of the reference genome are portions of a sex chromosome or a segment thereof.

M5. The method of any one of embodiments M1 to M4, wherein the first subset of portions of the reference genome are portions of a Y chromosome or a segment thereof.

M6. The method of any one of embodiments M1 to M5, wherein the second subset of portions of the reference genome are portions of one or more autosomes or a segment thereof.

M7. The method of embodiments M6, wherein the one or more autosomes are selected from chromosomes 18, 13 and 21.

M8. The method of any one of embodiments M1 to M7, wherein the second subset of portions of the reference genome are portions of an X chromosome or a segment thereof.

M9. The method of any one of embodiments M1 to M8, wherein the second subset of portions of the reference genome are portions of all chromosomes or a segment thereof, from which counts were obtained.

M10. The method of any one of embodiments M1 to M9, wherein the fetal ploidy in (d) is determined according to (i) the calculated genomic section levels for a second subset of portions of the reference genome and (ii) the fraction of fetal nucleic acid determined in (c) and maternal ploidy.

M11. The method of any one of embodiments M1 to M10, wherein the fetal ploidy in (d) is determined according to $y_i$ where $y_i$ represents calculated genomic section levels of portions i of a reference genome.

M12. The method of any one of embodiments M1 to M11, wherein the fraction of fetal nucleic acid determined in (c) is fixed at its determined value and fetal ploidy in (d) is determined from the equation below or a derivation thereof:

$$y_i=(1-F)M_if_i+FXf_i,$$

where F represents the fetal fraction, X represents the fetal ploidy, and $M_i$ represents maternal ploidy assigned to each portion i.

M13. The method of any one of embodiments M1 to M12, wherein the fetal fraction determined in (c) is fixed at its determined value and fetal ploidy in (d) is varied to optimize the sum of squared residuals.

M14. The method of any one of embodiments M1 to M13, wherein the fetal ploidy in (d) is determined according to equation 20 below:

$$X = \frac{\sum_{i=1}^{N} \frac{f_i y_i}{\sigma_i^2} - (1-F)\sum_{i=1}^{N} \frac{M_i f_i^2}{\sigma_i^2}}{F\sum_{i=1}^{N} \frac{f_i^2}{\sigma_i^2}}.$$

M15. The method of any one of embodiments M1 to M14, wherein the fetal ploidy in (d) is determined according to equation 21 below:

$$X = \frac{\Xi_{fy} - (1-F)\Xi_{ff}}{F\Xi_{ff}} = \frac{\Xi_{fy}}{F\Xi_{ff}} - \frac{1-F}{F} = 1 + \frac{1}{F}\left(\frac{\Xi_{fy}}{\Xi_{ff}} - 1\right).$$

M16. The method of any one of embodiments M1 to M15, comprising determining the presence or absence of a fetal chromosome aneuploidy according to the fetal ploidy determined in (d).

M17. An apparatus comprising one or more processors and memory, which memory comprises instructions executable by the one or more processors and which memory comprises counts of nucleic acid sequence reads mapped to portions of a reference genome, which sequence reads are reads of circulating cell-free nucleic acid from a test sample obtained from the blood of a pregnant female bearing a fetus; and which instructions executable by the one or more processors are configured to:

(a) calculate a genomic section level for each of the portions of the reference genome, thereby providing calculated genomic section levels;

(b) determine a fraction of fetal nucleic acid in the test sample according to calculated genomic section levels for a first subset of portions of the reference genome;

(c) determine fetal ploidy according to (i) the calculated genomic section levels for a second subset of portions of the reference genome and (ii) the fraction of fetal nucleic acid determined in (b).

M18. A computer program product tangibly embodied on a computer-readable medium, comprising instructions that when executed by one or more processors are configured to:

(a) access counts of sequence reads mapped to portions of a reference genome, which sequence reads are reads of circulating cell-free nucleic acid from a test sample;

(b) calculate a genomic section level for each of the portions of the reference genome, thereby providing calculated genomic section levels;

(c) determine a fraction of fetal nucleic acid in the test sample according to calculated genomic section levels for a first subset of portions of the reference genome;

(d) determine fetal ploidy according to (i) the calculated genomic section levels for a second subset of portions of the reference genome and (ii) the fraction of fetal nucleic acid determined in (c).

M19. A system comprising one or more processors and memory, which memory comprises instructions executable by the one or more processors and which memory comprises counts of nucleic acid sequence reads mapped to portions of a reference genome, which sequence reads are reads of circulating cell-free nucleic acid from test sample obtained from a pregnant female bearing a fetus; and which instructions executable by the one or more processors are configured to:

(a) calculate a genomic section level for each of the portions of the reference genome, thereby providing calculated genomic section levels;

(b) determine a fraction of fetal nucleic acid in the test sample according to calculated genomic section levels for a first subset of portions of the reference genome;

(c) determine fetal ploidy according to (i) the calculated genomic section levels for a second subset of portions of the reference genome and (ii) the fraction of fetal nucleic acid determined in (b).

N1. A method for determining fetal ploidy according to nucleic acid sequence reads, comprising:

(a) determining a fraction of fetal nucleic acid in a sample, which sample comprises circulating cell-free nucleic acid from the blood of a pregnant female bearing a fetus;

(b) obtaining counts of sequence reads mapped to portions of a reference genome, which sequence reads are from the nucleic acid in the sample;

(c) calculating a genomic section level for each of the portions of the reference genome, thereby providing calculated genomic section levels; and (d) determining fetal ploidy according to (i) the calculated genomic section levels for a subset of portions of the reference genome and (ii) the fraction of fetal nucleic acid determined in (a).

N2. The method of embodiment N1, wherein the fetal fraction is determined from a first part of the test sample and the genomic section levels are determined from a second part of the test sample.

N3. The method of embodiment N1 or N2, wherein calculating the genomic section level for each of the portions of the reference genome comprises normalizing counts of reads mapped to the reference genome according to guanine and cytosine (GC) content for each of the portions.

N4. The method of embodiment N3, comprising:

(1) determining a guanine and cytosine (GC) bias for each of the portions of the reference genome for multiple samples from a fitted relation for each sample between (i) the counts of the sequence reads mapped to each of the portions of the reference genome, and (ii) GC content for each of the portions; and (2) calculating the genomic section level for each of the portions of the reference genome from a fitted relation between (i) the GC bias and (ii) the counts of the sequence reads mapped to each of the portions of the reference genome, thereby providing calculated genomic section levels, whereby bias in the counts of the sequence reads mapped to each of the portions of the reference genome is reduced in the calculated genomic section levels.

N5. The method of any one of embodiments N1 to N3, wherein the subset of portions of the reference genome in (d)(i) is portions of one or more autosomes or segment thereof.

N6. The method of embodiment N5, wherein the subset is portions of one autosome or segment thereof.

N7. The method of embodiment N5 or N6, wherein the autosomes are chosen from chromosome 13, chromosome 18 and chromosome 21.

N8. The method of any one of embodiments N1 to N7, wherein the subset of portions of the reference genome are portions of all autosomes or segment thereof.

N9. The method of any one of embodiments N1 to N7, wherein the subset of portions of the reference genome are portions of all chromosomes or segment thereof.

N10. The method of embodiment N8 or N9, wherein the autosomes or segment thereof, or chromosomes or segment thereof, are those from which counts were obtained.

N11. The method of any one of embodiments N1 to N10, wherein the subset of portions of the reference genome are portions of an X chromosome or a segment thereof.

N12. The method of any one of embodiments N1 to N11, comprising determining a reference count.

N12.1. The method of embodiment N12, wherein the reference count is determined according to calculated genomic section levels for a subset of portions of the reference genome for one or more pregnant female bearing a fetus wherein the subset of portions of the reference genome are known to be euploid.

N12.2. The method of embodiment N12, wherein the reference count is not determined from the sample.

N12.3. The method of embodiment N12, wherein the reference count is determined from the same subset of portions of the reference genome as in (d).

N12.4. The method of any one of embodiments N12 to N12.3, wherein the reference count is normalized by bin-wise normalization, normalization by GC content, linear and nonlinear least squares regression, LOESS, GC LOESS, LOWESS, PERUN, RM, GCRM and combinations thereof.

N12.5. The method of any one of embodiments N12 to N12.4, wherein the subset of portions of the reference genome are known to be euploid for the fetus.

N12.6. The method of any one of embodiments N12 to N12.5, wherein the subset of portions of the reference genome are known to be euploid for the mother and the fetus.

N12.7. The method of any one of embodiments N12 to N12.6, wherein the fetal ploidy in (d) is determined according to the reference count.

N12.8. The method of any one of embodiments N1 to N12.7, comprising determining a maternal ploidy.

N12.9. The method of embodiment N12.8, wherein fetal ploidy in (d) is determined according the maternal ploidy.

N12.10. The method of embodiment N12.8 or N12.9, wherein the maternal ploidy is about 1.

N13. The method of any one of embodiments N1 to N12.10, wherein the fetal ploidy is determined in (d) according to (i) the calculated genomic section levels for a subset of portions of the reference genome, (ii) the fraction of fetal nucleic acid determined in (a) and (iii) a maternal ploidy.

N13.1. The method of any one of embodiments N1 to N13, wherein the fetal ploidy is determined according to (i) the calculated genomic section levels for a subset of portions of the reference genome, (ii) the fraction of fetal nucleic acid determined in (a), (iii) a maternal ploidy, (iv) the reference count and (v) an uncertainty value σ for the reference count.

N13.2. The method of embodiment N13.1, wherein the fraction of fetal nucleic acid determined in (a) is fixed at its determined value and fetal ploidy X is determined according to Equation 8 below, or a derivation thereof:

$$y_i=(1-F)M_i f_i+FXf_i \quad (8)$$

where $y_i$ represents the calculated genomic section level for portion i of a reference genome, F represents the fraction of fetal nucleic acid determined in (a), $f_i$ represents a reference count for i, X represents the fetal ploidy, and $M_i$ represents the maternal ploidy of portion i.

N13.3. The method of N13.2, comprising determining the sum of squared residuals according to equation (8) and for multiple bins i for a subset of portions of the reference genome.

N14. The method of embodiment N13.2 or N13.3, wherein the fetal fraction is fixed at a value determined in (a) and the fetal ploidy is varied to optimize the sum of squared residuals according to equation (8) or a variation thereof.

N15. The method of embodiment N14, comprising determining a linear regression according to the sum of square residuals.

N16. The method of any one of embodiments N1 to N15, wherein the fetal ploidy is determined according to the reference count and an uncertainty value σ for the reference count.

N17. The method of embodiment N16, wherein the fetal ploidy is determined according to Equation 20 below:

$$X=\frac{\sum_{i=1}^{N}\frac{f_i y_i}{\sigma_i^2}-(1-F)\sum_{i=1}^{N}\frac{M_i f_i^2}{\sigma_i^2}}{F\sum_{i=1}^{N}\frac{f_i^2}{\sigma_i^2}}. \quad (20)$$

wherein $y_i$ represents the calculated genomic section level for portion i of a reference genome, F represents the fraction of fetal nucleic acid determined in (a), $f_i$ represents a reference count for i, σ represents the uncertainty value for $f_i$, X represents the fetal ploidy, and $M_i$ represents the maternal ploidy of portion i.

N18. The method of any one of embodiments N1 to N17, wherein the fetal ploidy is determined according to Equation 20, wherein the maternal ploidy is 1.

N19. The method of embodiment N18, wherein the fetal ploidy is determined according to Equation 21 below:

$$X=\frac{\Xi_{fy}-(1-F)\Xi_{ff}}{F\Xi_{ff}}=\frac{\Xi_{fy}}{F\Xi_{ff}}-\frac{1-F}{F}=1+\frac{1}{F}\left(\frac{\Xi_{fy}}{\Xi_{ff}}-1\right) \quad (21)$$

wherein $$\Xi_{ff}=\sum_{i=1}^{N}\frac{f_i^2}{\sigma_i^2},\ \Xi_{fy}=\sum_{i=1}^{N}\frac{y_i f_i}{\sigma_i^2},$$

$y_i$ represents the calculated genomic section level for portion i of a reference genome, F represents the fraction of fetal nucleic acid determined in (a), $f_i$ represents a reference count for i, σ represents the uncertainty value for $f_i$, and X represents the fetal ploidy.

N20. The method of any one of embodiments N1 to N19, comprising determining the presence or absence of a fetal chromosome aneuploidy according to the fetal ploidy determined in (d).

N21. The method of embodiment N20, wherein a fetal ploidy of about 1.4 or greater indicates the presence of a fetal chromosome aneuploidy.

N21.1. The method of embodiment N20, wherein a fetal ploidy of about 1.4 to about 1.8 indicates the presence of a fetal chromosome aneuploidy.

N21.2. The method of embodiment N20, wherein a fetal ploidy of about 1.3 or less indicates the absence of a fetal chromosome aneuploidy.

N21.3. The method of embodiment N20, wherein a fetal ploidy of 1.2 or less indicates the absence of a fetal chromosome aneuploidy.

N21.4. The method of embodiment N20, wherein a fetal ploidy of about 1.3 to about 0.8 indicates the absence of a fetal chromosome aneuploidy.

N21.5. The method of embodiment N20, wherein a fetal ploidy of about 1.2 to about 0.8 indicates the absence of a fetal chromosome aneuploidy.

N21.6. The method of any one of embodiments N20 to N21.4, wherein the fetal chromosome aneuploidy is a trisomy.

N21.7. The method of embodiment N21.6, wherein the trisomy is selected from a trisomy of chromosome 13, 18 and 21.

N22. The method of any one of embodiments N1 to N21.7, wherein determining the fraction of fetal nucleic acid comprises analyzing all or a subset of the sequence reads.

N23. The method of embodiment N22, wherein determining the fraction of fetal nucleic acid comprises analyzing the sequence reads mapped to all or a subset of the portions of the reference genome.

N24. The method of embodiment N22 or N23, wherein determining the fraction of fetal nucleic acid comprises analyzing the calculated genomic sections levels for all or a subset of portions of the reference genome.

N25. The method of embodiment N24, wherein determining the fraction of fetal nucleic acid comprises analyzing the calculated genomic sections levels for a subset of portions of the reference genome, which subset is a first subset and the subset in (d) is a second subset.

N26. The method of embodiment N25, wherein the first subset is different than the second subset.

N27. The method of embodiment N25 or N26, wherein the first subset of portions of the reference genome is portions of a sex chromosome or a segment thereof.

N28. The method of embodiment N25 or N26, wherein the first subset of portions of the reference genome is portions of a Y chromosome or a segment thereof.

N29. The method of embodiment N27 or N28, wherein the fetal fraction is determined according to a method of any one of embodiments A1 to A71, E1 to E54, F1 to F54, G1 to G54, H1 to H54, AA1 to AA39, AB1 to AB35, AC1 to AC35 or AE1 to AE41.

N30. The method of any one of embodiments N1 to N29, wherein the sequence reads are obtained by a massively parallel sequencing (MPS) process.

N31. The method of embodiment N30, which MPS process comprises use of a flowcell.

N32. The method of embodiment N31, wherein the sequence reads used for determining the fetal fraction and determining fetal ploidy are obtained in part using the same flowcell.

N33. The method of any one of embodiments N1 to N32, wherein determining the fraction of fetal nucleic acid comprises analyzing one or more loci in sample nucleic acid, wherein at least one of the one or more loci vary between fetal nucleic acid and maternal nucleic acid.

N34. The method of embodiment N33, wherein an amount of the one or more loci is determined.

N35. The method of embodiment N33 or N34, wherein a nucleotide sequence is determined for the one or more loci.

N36. The method of embodiment N35, wherein the sequence is obtained by a massively parallel sequencing (MPS) process.

N37. The method of embodiment N36, which MPS process comprises use of a flowcell.

N38. The method of any one of embodiments N33 to N37, wherein the one or more loci comprise one or more polymorphic sites.

N39. The method of embodiment N38, comprising:

(1) enriching nucleic acid in a first part of the test sample for a plurality of polymorphic sites;

(2) obtaining nucleotide sequences for some or all of the polymorphic sites by a sequencing process;

(3) analyzing the nucleotide sequences of (2); and (4) determining the fraction of fetal nucleic acid based on the analysis of (3), wherein the polymorphic sites and number thereof result in at least five polymorphic sites being informative for determining the fetal fraction for at least 90% of samples.

N40. The method of embodiment N38 or N39, wherein one or more polymorphic sites comprise one or more single nucleotide polymorphisms (SNPs).

N41. The method of any one of embodiments N33 to N40, wherein the one or more loci comprise one or more methylation regions.

N42. The method of embodiment N41, comprising:

(1) contacting the test sample with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid; and (2) determining the fraction of fetal nucleic acid in the sample based on the differentially modified nucleic acid.

N43. The method of embodiment N42, comprising:

contacting under amplification conditions the differentially modified nucleic acid with:

(i) a first set of amplification primers that specifically amplify a first region in sample nucleic acid comprising one or more loci that are differentially methylated between the fetal nucleic acid and maternal nucleic acid, and (ii) a second set of amplification primers that amplify a second region in the sample nucleic acid allowing for a determination of total nucleic acid in the sample, wherein the first region and the second region are different, thereby generating fetal nucleic acid amplification products and total nucleic acid amplification products.

N44. The method of embodiment N42, comprising:

contacting under amplification conditions the differentially modified nucleic acid with:

(i) a first set of amplification primers that specifically amplify a first region in sample nucleic acid comprising one or more loci that are differentially methylated between the fetal nucleic acid and maternal nucleic acid; and (ii) a predetermined copy number of one or more first competitor oligonucleotides that compete with the first region for hybridization of primers of the first amplification primer set, thereby generating fetal nucleic acid amplification products and competitor amplification products.

N45. The method of embodiment N43 or N44 comprising:

(i) incorporating adaptor oligonucleotides into the amplification products thereby generating adaptor-modified amplification products;

(ii) obtaining nucleotide sequences of the adaptor-modified amplification products by a sequencing process, thereby generating sequence reads; and (iii) quantifying the sequence reads of the adaptor-modified amplification products. N46. The method of embodiment N45, wherein determining the fraction of fetal nucleic acid is based on a quantification of the sequence reads in (iii) of N45.

N47. The method of embodiment N44 comprising:

(i) incorporating adaptor oligonucleotides into the amplification products thereby generating adaptor-modified amplification products;

(ii) obtaining nucleotide sequences of the adaptor-modified amplification products by a sequencing process, thereby generating sequence reads;

(iii) quantifying the sequence reads of the adaptor-modified amplification products; and (iv) determining the copy number of fetal nucleic acid in the sample based on a quantification of the sequence reads of the adaptor-modified amplification products and the amount of competitor oligonucleotide used.

N48. The method of embodiment N47, wherein the fraction of fetal nucleic acid is determined according to the copy number of fetal nucleic acid.

N49. The method of any one of embodiments N42 to N48, wherein the one or more agents are methylation sensitive restriction enzymes.

O1. An apparatus comprising one or more processors and memory, which memory comprises instructions executable by the one or more processors and which memory comprises counts of nucleic acid sequence reads mapped to portions of a reference genome, which sequence reads are reads of circulating cell-free nucleic acid from a test sample obtained from a pregnant female bearing a fetus; and which instructions executable by the one or more processors are configured to:

(a) determine a fraction of fetal nucleic acid in the test sample;

(b) calculate a genomic section level for each of the portions of the reference genome, thereby providing calculated genomic section levels; and (c) determine fetal ploidy according to (i) the calculated genomic section levels for a subset of portions of the reference genome and (ii) the fraction of fetal nucleic acid determined in (a).

O2. A computer program product tangibly embodied on a computer-readable medium, comprising instructions that when executed by one or more processors are configured to:

(a) determine a fraction of fetal nucleic acid in a sample, which sample comprises circulating cell-free nucleic acid from the blood of a pregnant female bearing a fetus;

(b) access counts of sequence reads mapped to portions of a reference genome, which sequence reads are from the nucleic acid in the sample;

(c) calculate a genomic section level for each of the portions of the reference genome, thereby providing calculated genomic section levels; and (d) determine fetal ploidy according to (i) the calculated genomic section levels for a subset of portions of the reference genome and (ii) the fraction of fetal nucleic acid determined in (a).

O3. A system comprising one or more processors and memory, which memory comprises instructions executable by the one or more processors and which memory comprises counts of nucleic acid sequence reads mapped to portions of a reference genome, which sequence reads are reads of circulating cell-free nucleic acid from a test sample obtained from a pregnant female bearing a fetus; and which instructions executable by the one or more processors are configured to:

(a) determine a fraction of fetal nucleic acid in the test sample;

(b) calculate a genomic section level for each of the portions of the reference genome, thereby providing calculated genomic section levels; and (c) determine fetal ploidy according to (i) the calculated genomic section levels for a subset of portions of the reference genome and (ii) the fraction of fetal nucleic acid determined in (a).

AA1. A method for determining the amount of fetal nucleic acid in a sample comprising:

(a) contacting a sample nucleic acid with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid;

(b) contacting under amplification conditions the differentially modified sample nucleic acid with:

(i) a first set of amplification primers that specifically amplify a first region in sample nucleic acid comprising one or more loci that are differentially methylated between the fetal nucleic acid and maternal nucleic acid, and (ii) a second set of amplification primers that amplify a second region in the sample nucleic acid allowing for a determination of total nucleic acid in the sample, wherein the first region and the second region are different, thereby generating fetal nucleic acid amplification products and total nucleic acid amplification products;

(c) incorporating adaptor oligonucleotides into the amplification products in (b); thereby generating adaptor-modified amplification products;

(d) obtaining nucleotide sequences of the adaptor-modified amplification products in (c) by a sequencing process, thereby generating sequence reads;

(e) quantifying the sequence reads; and (f) determining the amount of fetal nucleic acid in the sample based on a quantification of the sequence reads in (e).

AA2. The method of embodiment AA1, wherein the first region comprises one or more loci which each contain a restriction site for a methylation-sensitive restriction enzyme.

AA3. The method of embodiment AA2, wherein the one or more agents that differentially modify methylated nucleic acid and unmethylated nucleic acid comprise one or more methylation sensitive restriction enzymes.

AA4. The method of embodiment AA2 or AA3, wherein the second region comprises one or more loci which do not contain a restriction site for a methylation-sensitive restriction enzyme.

AA5. The method of embodiment AA1, wherein the one or more agents that differentially modify methylated nucleic acid and unmethylated nucleic acid comprise bisulfite.

AA6. The method of any one of embodiments AA1 to AA5, wherein the adaptor oligonucleotides are incorporated into the amplification products by ligation.

AA7. The method of embodiment AA6, wherein the ligation is unidirectional ligation.

AA8. The method of any one of embodiments AA1 to AA5, wherein the adaptor oligonucleotides are incorporated into the amplification products using amplification primers comprising the adaptor oligonucleotide sequences.

AA9. The method of any one of embodiments AA1 to AA8, wherein the adaptor oligonucleotides comprise one or more index sequences.

AA10. The method of embodiment AA9, wherein the one or more index sequences comprise a sample-specific index.

AA11. The method of embodiment AA9, wherein the one or more index sequences comprise an aliquot-specific index.

AA12. The method of any one of embodiments AA1 to AA11, wherein at least one of the one or more loci in the first region comprises a nucleotide sequence selected from among SEQ ID NOs:1-261, or a fragment thereof.

AA13. The method of embodiment AA12, wherein at least one of the one or more loci in the first region comprises a nucleotide sequence selected from among SEQ ID NOs: 1-89, or a fragment thereof.

AA14. The method of embodiment AA12, wherein at least one of the one or more loci in the first region comprises a nucleotide sequence selected from among SEQ ID NOs: 90-261, or a fragment thereof.

AA15. The method of embodiment AA12, wherein at least one of the one or more loci in the first region comprises a nucleotide sequence selected from among SEQ ID NOs: 1-59 and SEQ ID NOs:86-89, or a fragment thereof.

AA16. The method of embodiment AA12, wherein at least one of the one or more loci in the first region comprises a nucleotide sequence selected from among SEQ ID NOs: 1-59, or a fragment thereof.

AA17. The method of embodiment AA12, wherein at least one of the one or more loci in the first region comprises a nucleotide sequence selected from among SEQ ID NO:42, SEQ ID NO:52, SEQ ID NO:154, SEQ ID NO:158 and SEQ ID NO:163.

AA18. The method of any one of embodiments AA1 to AA17, wherein the sequencing process is a sequencing by synthesis method.

AA19. The method of any one of embodiments AA1 to AA18, wherein the sequencing process is a reversible terminator-based sequencing method.

AA20. The method of any one of embodiments AA1 to AA19, wherein the amount of fetal nucleic acid determined is the fraction of fetal nucleic acid in the sample based on the amount of each of the fetal nucleic acid amplification products and total nucleic acid amplification products.

AA21. The method of embodiment AA20, wherein the fraction of fetal nucleic acid is a ratio of fetal nucleic acid amplification product amount to total nucleic acid amplification product amount.

AA22. The method of any one of embodiments AA1 to AA21, further comprising contacting under amplification conditions the nucleic acid sample with a third set of amplification primers that amplify a third region in the sample nucleic acid allowing for a determination of the presence or absence of fetal specific nucleic acid.

AA23. The method of embodiment AA22, wherein the fetal specific nucleic acid is Y chromosome nucleic acid.

AA24. The method of embodiment AA23, wherein the third region comprises one or more loci within chromosome Y.

AA25. The method of any one of embodiments AA3 to AA24, further comprising contacting under amplification conditions the nucleic acid sample with a fourth set of amplification primers that amplify a fourth region in the sample nucleic acid allowing for a determination of the amount of digested or undigested nucleic acid, as an indicator of digestion efficiency.

AA26. The method of embodiment AA25, wherein the fourth region comprises one or more loci present in both fetal nucleic acid and maternal nucleic acid and unmethylated in both fetal nucleic acid and maternal nucleic acid.

AA27. The method of any one of embodiments AA1 to AA26, further comprising contacting under amplification conditions the nucleic acid sample with a predetermined copy number of one or more first competitor oligonucleotides that compete with the first region for hybridization of primers of the first amplification primer set.

AA28. The method of any one of embodiments AA1 to AA27, further comprising contacting under amplification conditions the nucleic acid sample with a predetermined copy number of one or more second competitor oligonucleotides that compete with the second region for hybridization of primers of the second amplification primer set.

AA29. The method of any one of embodiments AA22 to AA28, further comprising contacting under amplification conditions the nucleic acid sample with a predetermined copy number of one or more third competitor oligonucleotides that compete with the third region for hybridization of primers of the third amplification primer set.

AA30. The method of any one of embodiments AA25 to AA29, further comprising contacting under amplification conditions the nucleic acid sample with a predetermined copy number of one or more fourth competitor oligonucleotides that compete with the fourth region for hybridization of primers of the fourth amplification primer set.

AA31. The method of any one of embodiments AA27 to AA30, wherein the amount of fetal nucleic acid determined is the copy number of fetal nucleic acid based on the amount of competitor oligonucleotide used.

AA32. The method of any one of embodiments AA1 to AA26, wherein the amount of fetal nucleic acid determined is the copy number of fetal nucleic acid based on a quantification of sequence reads.

AA33. The method of any one of embodiments AA1 to AA32, wherein the sample nucleic acid is extracellular nucleic acid.

AA34. The method of any one of embodiments AA1 to AA33, wherein the nucleic acid sample is obtained from a pregnant female subject.

AA35. The method of embodiment AA34, wherein the subject is human.

AA36. The method of any one of embodiments AA1 to AA35, wherein the sample nucleic acid is from plasma or serum.

AA37. The method of any one of embodiments AA1 to AA36, wherein two or more independent loci in the first region are assayed.

AA38. The method of any one of embodiments AA1 to AA37, wherein the amount of fetal nucleic acid is substantially equal to the amount of fetal nucleic acid determined using a mass spectrometry method.

AA39. The method of any one of embodiments AA1 to AA38, wherein the amount of fetal nucleic acid is determined with an $R^2$ value of 0.97 or greater when compared to an amount of fetal nucleic acid determined using a mass spectrometry method.

AAB1. A method for determining the amount of fetal nucleic acid in a sample comprising:

(a) contacting a sample nucleic acid with one or more methylation sensitive restriction enzymes, which sample nucleic acid comprises differentially methylated fetal nucleic acid and maternal nucleic acid, the combination of the fetal nucleic acid and the maternal nucleic acid comprising total nucleic acid in the sample, thereby generating differentially digested sample nucleic acid;

(b) contacting under amplification conditions the digested sample nucleic acid with:

(i) a first set of amplification primers that specifically amplify a first region in sample nucleic acid comprising one or more loci that are differentially methylated between the fetal nucleic acid and maternal nucleic acid, and (ii) a second set of amplification primers that amplify a second region in the sample nucleic acid allowing for a determination of total nucleic acid in the sample, wherein the first region and the second region are different, thereby generating fetal nucleic acid amplification products and total nucleic acid amplification products;

(c) incorporating adaptor oligonucleotides into the amplification products in (b); thereby generating adaptor-modified amplification products;

(d) obtaining nucleotide sequences of the adaptor-modified amplification products in (c) by a sequencing process, thereby generating sequence reads;

(e) quantifying the sequence reads; and (f) determining the amount of fetal nucleic acid in the sample based on a quantification of the sequence reads in (e).

AAB2. The method of embodiment AB1, wherein the adaptor oligonucleotides are incorporated into the amplification products by ligation.

AB3. The method of embodiment AB2, wherein the ligation is unidirectional ligation.

AB4. The method of any one of embodiments AB1 to AB3, wherein the adaptor oligonucleotides are incorporated into the amplification products using amplification primers comprising the adaptor oligonucleotide sequences.

AB5. The method of any one of embodiments AB1 to AB4, wherein the adaptor oligonucleotides comprise one or more index sequences.

AB6. The method of embodiment AB5, wherein the one or more index sequences comprise a sample-specific index.

AB7. The method of embodiment AB5, wherein the one or more index sequences comprise an aliquot-specific index.

AB8. The method of any one of embodiments AB1 to AB7, wherein at least one of the one or more loci in the first region comprises a nucleotide sequence selected from among SEQ ID NOs:1-261, or a fragment thereof.

AB9. The method of embodiment AB8, wherein at least one of the one or more loci in the first region comprises a nucleotide sequence selected from among SEQ ID NOs:1-89, or a fragment thereof.

AB10. The method of embodiment AB8, wherein at least one of the one or more loci in the first region comprises a nucleotide sequence selected from among SEQ ID NOs:90-261, or a fragment thereof.

AB11. The method of embodiment AB8, wherein at least one of the one or more loci in the first region comprises a nucleotide sequence selected from among SEQ ID NOs:1-59 and SEQ ID NOs:86-89, or a fragment thereof.

AB12. The method of embodiment AB8, wherein at least one of the one or more loci in the first region comprises a nucleotide sequence selected from among SEQ ID NOs:1-59, or a fragment thereof.

AB13. The method of embodiment AB8, wherein at least one of the one or more loci in the first region comprises a nucleotide sequence selected from among SEQ ID NO:42, SEQ ID NO:52, SEQ ID NO:154, SEQ ID NO:158 and SEQ ID NO:163.

AB14. The method of any one of embodiments AB1 to AB13, wherein the sequencing process is a sequencing by synthesis method.

AB15. The method of any one of embodiments AB1 to AB13, wherein the sequencing process is a reversible terminator-based sequencing method.

AB16. The method of any one of embodiments AB1 to AB15, wherein the amount of fetal nucleic acid determined is the fraction of fetal nucleic acid in the sample based on the amount of each of the fetal nucleic acid amplification products and total nucleic acid amplification products.

AB17. The method of embodiment AB16, wherein the fraction of fetal nucleic acid is a ratio of fetal nucleic acid amplification product amount to total nucleic acid amplification product amount.

AB18. The method of any one of embodiments AB1 to AB17, further comprising contacting under amplification conditions the nucleic acid sample with a third set of amplification primers that amplify a third region in the sample nucleic acid allowing for a determination of the presence or absence of fetal specific nucleic acid.

AB19. The method of embodiment AB18, wherein the fetal specific nucleic acid is Y chromosome nucleic acid.

AB20. The method of embodiment AB19, wherein the third region comprises one or more loci within chromosome Y.

AB21. The method of any one of embodiments AB1 to AB20, further comprising contacting under amplification conditions the nucleic acid sample with a fourth set of amplification primers that amplify a fourth region in the sample nucleic acid allowing for a determination of the amount of digested or undigested nucleic acid, as an indicator of digestion efficiency.

AB22. The method of embodiment AB21, wherein the fourth region comprises one or more loci present in both fetal nucleic acid and maternal nucleic acid and unmethylated in both fetal nucleic acid and maternal nucleic acid.

AB23. The method of any one of embodiments AB1 to AB22, further comprising contacting under amplification conditions the nucleic acid sample with a predetermined copy number of one or more first competitor oligonucleotides that compete with the first region for hybridization of primers of the first amplification primer set.

AB24. The method of any one of embodiments AB1 to AB23, further comprising contacting under amplification conditions the nucleic acid sample with a predetermined copy number of one or more second competitor oligonucleotides that compete with the second region for hybridization of primers of the second amplification primer set.

AB25. The method of any one of embodiments AB18 to AB24, further comprising contacting under amplification conditions the nucleic acid sample with a predetermined copy number of one or more third competitor oligonucleotides that compete with the third region for hybridization of primers of the third amplification primer set.

AB26. The method of any one of embodiments AB21 to AB25, further comprising contacting under amplification conditions the nucleic acid sample with a predetermined copy number of one or more fourth competitor oligonucleotides that compete with the fourth region for hybridization of primers of the fourth amplification primer set.

AB27. The method of any one of embodiments AB23 to AB26, wherein the amount of fetal nucleic acid determined is the copy number of fetal nucleic acid based on the amount of competitor oligonucleotide used.

AB28. The method of any one of embodiments AB1 to AB27, wherein the amount of fetal nucleic acid determined is the copy number of fetal nucleic acid based on a quantification of sequence reads.

AB29. The method of any one of embodiments AB1 to AB28, wherein the sample nucleic acid is extracellular nucleic acid.

AB30. The method of any one of embodiments AB1 to AB29, wherein the nucleic acid sample is obtained from a pregnant female subject.

AB31. The method of embodiment AB30, wherein the subject is human.

AB32. The method of any one of embodiments AB1 to AB31, wherein the sample nucleic acid is from plasma or serum.

AB33. The method of any one of embodiments AB1 to AB32, wherein two or more independent loci in the first region are assayed.

AB34. The method of any one of embodiments AB1 to AB33, wherein the amount of fetal nucleic acid is substantially equal to the amount of fetal nucleic acid determined using a mass spectrometry method.

AB35. The method of any one of embodiments AB1 to AB34, wherein the amount of fetal nucleic acid is determined with an $R^2$ value of 0.97 or greater when compared to an amount of fetal nucleic acid determined using a mass spectrometry method.

AC1. A method for determining the copy number of fetal nucleic acid in a sample comprising:

(a) contacting a sample nucleic acid with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid;

(b) contacting under amplification conditions the differentially modified sample nucleic acid with:

(i) a first set of amplification primers that specifically amplify a first region in sample nucleic acid comprising one or more loci that are differentially methylated between the fetal nucleic acid and maternal nucleic acid, and (ii) a predetermined copy number of one or more first competitor oligonucleotides that compete with the first region for hybridization of primers of the first amplification primer set, thereby generating fetal nucleic acid amplification products and competitor amplification products;

(c) incorporating adaptor oligonucleotides into the amplification products in (b); thereby generating adaptor-modified amplification products;

(d) obtaining nucleotide sequences of the adaptor-modified amplification products in (c) by a sequencing process, thereby generating sequence reads;

(e) quantifying the sequence reads; and (f) determining the copy number of fetal nucleic acid in the sample based on a quantification of the sequence reads in (e) and the amount of competitor oligonucleotide used.

AC2. The method of embodiment AC1, wherein the first region comprises one or more loci which each contain a restriction site for a methylation-sensitive restriction enzyme.

AC3. The method of embodiment AC2, wherein the one or more agents that differentially modify methylated nucleic acid and unmethylated nucleic acid comprise one or more methylation sensitive restriction enzymes.

AC4. The method of embodiment AC1, wherein the one or more agents that differentially modify methylated nucleic acid and unmethylated nucleic acid comprise bisulfite.

AC5. The method of any one of embodiments AC1 to AC4, wherein the adaptor oligonucleotides are incorporated into the amplification products by ligation.

AC6. The method of embodiment AC5, wherein the ligation is unidirectional ligation.

AC7. The method of any one of embodiments AC1 to AC4, wherein the adaptor oligonucleotides are incorporated into the amplification products using amplification primers comprising the adaptor oligonucleotide sequences.

AC8. The method of any one of embodiments AC1 to AC7, wherein the adaptor oligonucleotides comprise one or more index sequences.

AC9. The method of embodiment AC8, wherein the one or more index sequences comprise a sample-specific index.

AC10. The method of embodiment AC8, wherein the one or more index sequences comprise an aliquot-specific index.

AC11. The method of any one of embodiments AC1 to AC10, wherein at least one of the one or more loci in the first region comprises a nucleotide sequence selected from among SEQ ID NOs:1-261, or a fragment thereof.

AC12. The method of embodiment AC11, wherein at least one of the one or more loci in the first region comprises a nucleotide sequence selected from among SEQ ID NOs:1-89, or a fragment thereof.

AC13. The method of embodiment AC11, wherein at least one of the one or more loci in the first region comprises a nucleotide sequence selected from among SEQ ID NOs:90-261, or a fragment thereof.

AC14. The method of embodiment AC11, wherein at least one of the one or more loci in the first region comprises a nucleotide sequence selected from among SEQ ID NOs:1-59 and SEQ ID NOs:86-89, or a fragment thereof.

AC15. The method of embodiment AC11, wherein at least one of the one or more loci in the first region comprises a nucleotide sequence selected from among SEQ ID NOs:1-59, or a fragment thereof.

AC16. The method of embodiment AC11, wherein at least one of the one or more loci in the first region comprises a nucleotide sequence selected from among SEQ ID NO:42, SEQ ID NO:52, SEQ ID NO:154, SEQ ID NO:158 and SEQ ID NO:163.

AC17. The method of any one of embodiments AC1 to AC16, wherein the sequencing process is a sequencing by synthesis method.

AC18. The method of any one of embodiments AC1 to AC16, wherein the sequencing process is a reversible terminator-based sequencing method.

AC19 The method of any one of embodiments AC1 to AC18, further comprising contacting under amplification conditions the nucleic acid sample with a second set of amplification primers that amplify a second region in the sample nucleic acid allowing for a determination of total nucleic acid in the sample, wherein the first region and the second region are different.

AC20. The method of embodiment AC19, wherein the second region comprises one or more loci which do not contain a restriction site for a methylation-sensitive restriction enzyme.

AC21. The method of any one of embodiments AC1 to AC20, further comprising contacting under amplification conditions the nucleic acid sample with a third set of amplification primers that amplify a third region in the sample nucleic acid allowing for a determination of the presence or absence of fetal specific nucleic acid.

AC22. The method of embodiment AC21, wherein the fetal specific nucleic acid is Y chromosome nucleic acid.

AC23. The method of embodiment AC22, wherein the third region comprises one or more loci within chromosome Y.

AC24. The method of any one of embodiments AC3 to AC23, further comprising contacting under amplification conditions the nucleic acid sample with a fourth set of amplification primers that amplify a fourth region in the sample nucleic acid allowing for a determination of the amount of digested or undigested nucleic acid, as an indicator of digestion efficiency.

AC25. The method of embodiment AC24, wherein the fourth region comprises one or more loci present in both fetal nucleic acid and maternal nucleic acid and unmethylated in both fetal nucleic acid and maternal nucleic acid.

AC26. The method of any one of embodiments AC19 to AC25, further comprising contacting under amplification conditions the nucleic acid sample with a predetermined copy number of one or more second competitor oligonucleotides that compete with the second region for hybridization of primers of the second amplification primer set.

AC27. The method of any one of embodiments AC21 to AC26, further comprising contacting under amplification conditions the nucleic acid sample with a predetermined copy number of one or more third competitor oligonucleotides that compete with the third region for hybridization of primers of the third amplification primer set.

AC28. The method of any one of embodiments AC24 to AC27, further comprising contacting under amplification conditions the nucleic acid sample with a predetermined copy number of one or more fourth competitor oligonucleotides that compete with the fourth region for hybridization of primers of the fourth amplification primer set.

AC29. The method of any one of embodiments AC1 to AC28, wherein the sample nucleic acid is extracellular nucleic acid.

AC30. The method of any one of embodiments AC1 to AC29, wherein the nucleic acid sample is obtained from a pregnant female subject.

AC31. The method of embodiment AC30, wherein the subject is human.

AC32. The method of any one of embodiments AC1 to AC31, wherein the sample nucleic acid is from plasma or serum.

AC33. The method of any one of embodiments AC1 to AC32, wherein two or more independent loci in the first region are assayed.

AC34. The method of any one of embodiments AC1 to AC33, wherein the copy number of fetal nucleic acid is substantially equal to the copy number of fetal nucleic acid determined using a mass spectrometry method.

AC35. The method of any one of embodiments AC1 to AC34, wherein the copy number of fetal nucleic acid is determined with an $R^2$ value of 0.97 or greater when compared to a copy number of fetal nucleic acid determined using a mass spectrometry method.

AD1. A method for detecting the presence or absence of a fetal aneuploidy in a sample comprising:

(a) contacting a sample nucleic acid with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid;

(b) contacting under amplification conditions the differentially modified sample nucleic acid with:

(i) a first set of amplification primers that specifically amplify one or more loci in a target chromosome that are differentially methylated between the fetal nucleic acid and maternal nucleic acid, and (ii) a second set of amplification primers that specifically amplify one or more loci in a reference chromosome that are differentially methylated between the fetal nucleic acid and maternal nucleic acid, thereby generating target chromosome amplification products and reference chromosome amplification products;

(c) incorporating adaptor oligonucleotides into the amplification products in (b); thereby generating adaptor-modified amplification products;

(d) obtaining nucleotide sequences of the adaptor-modified amplification products in (c) by a sequencing process, thereby generating sequence reads;

(e) quantifying the sequence reads; and (f) detecting the presence or absence of a fetal aneuploidy in the sample based on a quantification of the sequence reads in (e).

AD2. The method of embodiment AD1, wherein the target chromosome comprises one or more loci which each contain a restriction site for a methylation-sensitive restriction enzyme.

AD3. The method of embodiment AD1 or AD2, wherein the reference chromosome comprises one or more loci which each contain a restriction site for a methylation-sensitive restriction enzyme.

AD4. The method of embodiment AD2 or AD3, wherein the one or more agents that differentially modify methylated nucleic acid and unmethylated nucleic acid comprise one or more methylation sensitive restriction enzymes.

AD5. The method of embodiment AD1, wherein the one or more agents that differentially modify methylated nucleic acid and unmethylated nucleic acid comprise bisulfite.

AD6. The method of any one of embodiments AD1 to AD5, wherein the adaptor oligonucleotides are incorporated into the amplification products by ligation.

AD7. The method of embodiment AD6, wherein the ligation is unidirectional ligation.

AD8. The method of any one of embodiments AD1 to AD5, wherein the adaptor oligonucleotides are incorporated into the amplification products using amplification primers comprising the adaptor oligonucleotide sequences.

AD9. The method of any one of embodiments AD1 to AD8, wherein the adaptor oligonucleotides comprise one or more index sequences.

AD10. The method of embodiment AD9, wherein the one or more index sequences comprise a sample-specific index.

AD11. The method of embodiment AD9, wherein the one or more index sequences comprise an aliquot-specific index.

AD12. The method of any one of embodiments AD1 to AD11, wherein at least one of the one or more loci in the target chromosome comprises a nucleotide sequence selected from among SEQ ID NOs:1-261, or a fragment thereof.

AD13. The method of embodiment AD12, wherein at least one of the one or more loci in the target chromosome comprises a nucleotide sequence selected from among SEQ ID NOs:1-89, or a fragment thereof.

AD14. The method of embodiment AD12, wherein at least one of the one or more loci in the target chromosome comprises a nucleotide sequence selected from among SEQ ID NOs:90-261, or a fragment thereof.

AD15. The method of embodiment AD12, wherein at least one of the one or more loci in target chromosome comprises a nucleotide sequence selected from among SEQ ID NOs:1-59 and SEQ ID NOs:86-89, or a fragment thereof.

AD16. The method of embodiment AD12, wherein at least one of the one or more loci in the target chromosome comprises a nucleotide sequence selected from among SEQ ID NOs:1-59, or a fragment thereof.

AD17. The method of embodiment AD12, wherein at least one of the one or more loci in the target chromosome comprises a nucleotide sequence selected from among SEQ ID NO:42, SEQ ID NO:52, SEQ ID NO:154, SEQ ID NO:158 and SEQ ID NO:163.

AD18. The method of any one of embodiments AD1 to AD17, wherein at least one of the one or more loci in the reference chromosome comprises a nucleotide sequence selected from among SEQ ID NOs:1-261, or a fragment thereof.

AD19. The method of embodiment AD18, wherein at least one of the one or more loci in the reference chromosome comprises a nucleotide sequence selected from among SEQ ID NOs:1-89, or a fragment thereof.

AD20. The method of embodiment AD18, wherein at least one of the one or more loci in the reference chromosome comprises a nucleotide sequence selected from among SEQ ID NOs:90-261, or a fragment thereof.

AD21. The method of embodiment AD18, wherein at least one of the one or more loci in reference chromosome comprises a nucleotide sequence selected from among SEQ ID NOs:1-59 and SEQ ID NOs:86-89, or a fragment thereof.

AD22. The method of embodiment AD18, wherein at least one of the one or more loci in the reference chromosome comprises a nucleotide sequence selected from among SEQ ID NOs:1-59, or a fragment thereof.

AD23. The method of embodiment AD18, wherein at least one of the one or more loci in the reference chromosome comprises a nucleotide sequence selected from among SEQ ID NO:42, SEQ ID NO:52, SEQ ID NO:154, SEQ ID NO:158 and SEQ ID NO:163.

AD24. The method of any one of embodiments AD1 to AD23, wherein the sequencing process is a sequencing by synthesis method.

AD25. The method of any one of embodiments AD1 to AD23, wherein the sequencing process is a reversible terminator-based sequencing method.

AD26. The method of any one of embodiments AD1 to AD25, further comprising contacting under amplification conditions the nucleic acid sample with a predetermined copy number of one or more first competitor oligonucleotides that compete with the target chromosome for hybridization of primers of the first amplification primer set.

AD27. The method of any one of embodiments AD1 to AD26, further comprising contacting under amplification conditions the nucleic acid sample with a predetermined copy number of one or more second competitor oligonucleotides that compete with the reference chromosome for hybridization of primers of the second amplification primer set.

AD28. The method of any one of embodiments AD1 to AD27, wherein the sample nucleic acid is extracellular nucleic acid.

AD29. The method of any one of embodiments AD1 to AD28, wherein the nucleic acid sample is obtained from a pregnant female subject.

AD30. The method of embodiment AD29, wherein the subject is human.

AD31. The method of any one of embodiments AD1 to AD30, wherein the sample nucleic acid is from plasma or serum.

AD32. The method of any one of embodiments AD1 to AD31, wherein two or more independent loci in the target chromosome are assayed.

AD33. The method of any one of embodiments AD1 to AD32, wherein two or more independent loci in the reference chromosome are assayed.

AD34. The method of any one of embodiments AD1 to AD33, wherein the target chromosome is chromosome 13.

AD35. The method of any one of embodiments AD1 to AD33, wherein the target chromosome is chromosome 18.

AD36. The method of any one of embodiments AD1 to AD33, wherein the target chromosome is chromosome 21.

AE1. A method for determining fetal fraction in a sample comprising:

(a) enriching a sample nucleic acid for a plurality of polymorphic nucleic acid targets, which sample nucleic acid comprises fetal nucleic acid and maternal nucleic acid;
(b) obtaining nucleotide sequences for some or all of the nucleic acid targets by a sequencing process;
(c) analyzing the nucleotide sequences of (b); and
(d) determining fetal fraction based on the analysis of (c), wherein the polymorphic nucleic acid targets and number thereof result in at least five polymorphic nucleic acid targets being informative for determining the fetal fraction for at least 90% of samples.

AE2. The method of embodiment AE1, wherein the enriching comprises amplifying the plurality of polymorphic nucleic acid targets.

AE3. The method of embodiment AE1 or AE2, wherein the enriching comprises generating amplification products in an amplification reaction.

AE4. The method of embodiment AE3, wherein the amplification reaction is performed in a single vessel.

AE5. The method of any one of embodiments AE1 to AE4, wherein the maternal genotype and the paternal genotype at each of the polymorphic nucleic acid targets are not known prior to (a).

AE5.1 The method of any one of embodiments AE1 to AE5, wherein polymorphic nucleic acid targets having a minor allele population frequency of about 40% or more are selected.

AE6. The method of any one of embodiments AE1 to AE5.1, comprising determining an allele frequency in the sample for each of the polymorphic nucleic acid targets.

AE7. The method of embodiment AE6, wherein determining which polymorphic nucleic acid targets are informative comprises identifying informative genotypes by comparing each allele frequency to one or more fixed cutoff frequencies.

AE7.1 The method of embodiment AE7, wherein the fixed cutoff for identifying informative genotypes from non-informative homozygotes is about a 1% or greater shift in allele frequency.

AE7.2 The method of embodiment AE7, wherein the fixed cutoff for identifying informative genotypes from non-informative homozygotes is about a 2% or greater shift in allele frequency.

AE7.3 The method of embodiment AE7, wherein the fixed cutoff for identifying informative genotypes from non-informative heterozygotes is about a 25% or greater shift in allele frequency.

AE7.4 The method of embodiment AE7, wherein the fixed cutoff for identifying informative genotypes from non-informative heterozygotes is about a 50% or greater shift in allele frequency.

AE8. The method of embodiment AE6, wherein determining which polymorphic nucleic acid targets are informative comprises identifying informative genotypes by comparing each allele frequency to one or more target-specific cutoff frequencies.

AE9. The method of embodiment AE8, wherein the one or more target-specific cutoff frequencies are determined for each polymorphic nucleic acid target.

AE10. The method of embodiment AE8 or AE9, wherein each target-specific cutoff frequency is determined based on the allele frequency variance for the corresponding polymorphic nucleic acid target.

AE11. The method of any one of embodiments AE6 to AE10, further comprising determining an allele frequency mean.

AE12. The method of embodiment AE11, wherein fetal fraction is determined based, in part, on the allele frequency mean.

AE13. The method of any one of embodiments AE1 to AE12, wherein the fetal genotype at one or more informative polymorphic nucleic acid targets is heterozygous.

AE14. The method of any one of embodiments AE1 to AE13, wherein the fetal genotype at one or more informative polymorphic nucleic acid targets is homozygous.

AE15. The method of any one of embodiments AE1 to AE14, wherein fetal fraction is determined with a coefficient of variance (CV) of 0.20 or less.

AE16. The method of embodiment AE15, wherein fetal fraction is determined with a coefficient of variance (CV) of 0.10 or less.

AE17. The method of embodiment AE16, wherein fetal fraction is determined with a coefficient of variance (CV) of 0.05 or less.

AE18. The method of any one of embodiments AE1 to AE17, wherein the polymorphic nucleic acid targets each comprise at least one single nucleotide polymorphism (SNP).

AE19. The method of embodiment AE18, wherein the SNPs are selected from: rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, rs985462, rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

AE20. The method of embodiment AE19, wherein the SNPs are selected from: rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, and rs985462.

AE21. The method of embodiment AE19, wherein the SNPs are selected from: rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

AE22. The method of any one of embodiments AE1 to AE21, wherein the polymorphic nucleic acid targets and number thereof result in at least five polymorphic nucleic acid targets being informative for determining the fetal fraction for at least 95% of samples.

AE23. The method of embodiment AE22, wherein the polymorphic nucleic acid targets and number thereof result in at least five polymorphic nucleic acid targets being informative for determining the fetal fraction for at least 99% of samples.

AE24. The method of any one of embodiments AE1 to AE21, wherein the polymorphic nucleic acid targets and number thereof result in at least ten polymorphic nucleic acid targets being informative for determining the fetal fraction for at least 90% of samples.

AE25. The method of embodiment AE24, wherein the polymorphic nucleic acid targets and number thereof result in at least ten polymorphic nucleic acid targets being informative for determining the fetal fraction for at least 95% of samples.

AE26. The method of embodiment AE25, wherein the polymorphic nucleic acid targets and number thereof result in at least ten polymorphic nucleic acid targets being informative for determining the fetal fraction for at least 99% of samples.

AE27. The method of any one of embodiments AE1 to AE26, wherein 10 or more polymorphic nucleic acid targets are enriched.

AE27.1. The method of embodiment AE27, wherein about 40 to about 100 polymorphic nucleic acid targets are enriched.

AE28. The method of embodiment AE27, wherein 50 or more polymorphic nucleic acid targets are enriched.

AE29. The method of embodiment AE28, wherein 100 or more polymorphic nucleic acid targets are enriched.

AE30. The method of embodiment AE29, wherein 500 or more polymorphic nucleic acid targets are enriched.

AE31. The method of any one of embodiments AE1 to AE30, wherein the sequencing process comprises a sequencing by synthesis method.

AE31.1 The method of embodiment AE31, wherein the sequencing by synthesis method comprises a plurality of synthesis cycles.

AE31.2 The method of embodiment AE31.1, wherein the sequencing by synthesis method comprises about 36 cycles.

AE31.3 The method of embodiment AE31.1, wherein the sequencing by synthesis method comprises about 27 cycles.

AE32. The method of any one of embodiments AE1 to AE30, wherein the sequencing process comprises a sequencing by ligation method.

AE33. The method of any one of embodiments AE1 to AE30, wherein the sequencing process comprises a single molecule sequencing method.

AE34. The method of any one of embodiments AE1 to AE33, wherein the sequencing process comprises sequencing a plurality of samples in a single compartment.

AE35. The method of embodiment AE34, wherein the fetal fraction is determined for 10 or more samples.

AE36. The method of embodiment AE35, wherein the fetal fraction is determined for 100 or more samples.

AE37. The method of embodiment AE36, wherein the fetal fraction is determined for 1000 or more samples.

AE38. The method of any one of embodiments AE1 to AE37, wherein the sample nucleic acid is cell-free ADNAA.

AE39. The method of any one of embodiments AE1 to AE38, wherein the sample nucleic acid is obtained from a pregnant female subject.

AE40. The method of embodiment AE39, wherein the subject is human.

AE41. The method of any one of embodiments AE1 to AE40, wherein the sample nucleic acid is from plasma or serum.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed can be resorted to by those skilled in the art, and such modifications and variations are considered within the scope of this technology.

Certain embodiments of the technology are set forth in the claim(s) that follow(s).

What is claimed is:

1. A computer-implemented method for sequencing a test sample nucleic acid from a pregnant female, generating a classification of a presence of a chromosome aneuploidy for the test sample, and performing a medical procedure comprising amniocentesis or chorionic villus sampling, the method comprising:

(a) sequencing test sample nucleic acid by a genome-wide massively parallel sequencer that generates sequence reads, wherein the test sample nucleic acid comprises circulating cell-free nucleic acid from blood of a pregnant female bearing a fetus;

(b) mapping, using a microprocessor, the sequence reads to portions of a reference genome;

(c) counting, using a microprocessor, the sequence reads mapped to the portions, wherein counting generates counts of sequence reads mapped to the portions;

(d) calculating, using a microprocessor, genomic section levels for the portions of the reference genome, wherein calculating generates calculated genomic section levels;

(e) determining a fraction of fetal nucleic acid in the test sample nucleic acid;

(f) calculating, using a microprocessor, a fetal ploidy determination based on (i) the calculated genomic section levels of (d) for a subset of portions of the reference genome, (ii) the fraction of fetal nucleic acid determined in (e), and (iii) an estimated maternal ploidy;

(g) generating a classification of a presence of a chromosome aneuploidy in the fetus according to the fetal ploidy determination calculated in (f); and (h) performing a medical procedure comprising amniocentesis or chorionic villus sampling for the pregnant female after step (g) based on the classification of the presence of a chromosome aneuploidy in the fetus.

2. A computer-implemented method for sequencing a test sample nucleic acid from a pregnant female and generating a classification of a presence or absence of a chromosome aneuploidy for the test sample, the method comprising:

(a) sequencing test sample nucleic acid by a genome-wide massively parallel sequencer that generates sequence reads, wherein the test sample nucleic acid comprises circulating cell-free nucleic acid from blood of a pregnant female bearing a fetus;

(b) mapping, using a microprocessor, the sequence reads to portions of a reference genome;

(c) counting, using a microprocessor, the sequence reads mapped to the portions, wherein counting generates counts of sequence reads mapped to the portions;

(d) calculating, using a microprocessor, genomic section levels for the portions of the reference genome, wherein calculating generates calculated genomic section levels;

(e) determining a fraction of fetal nucleic acid in the test sample nucleic acid;

(f) calculating, using a microprocessor, a fetal ploidy determination based on (i) the calculated genomic section levels of (d) for a subset of portions of the reference genome, (ii) the fraction of fetal nucleic acid determined in (e), and (iii) an estimated maternal ploidy; and (g) generating, using a microprocessor, a classification of a presence or absence of a chromosome aneuploidy in the fetus according to the fetal ploidy determination calculated in (f).

3. The method of claim 2, wherein the fetal ploidy determination is calculated in (f) according to Equation 8 below, or a rearranged format thereof:

$$y_i(1-F)M_if_i+FXf_i \quad (8)$$

where $y_i$ represents the calculated genomic section level for portion i of a reference genome, F represents the fraction of fetal nucleic acid determined in (d), $f_i$ represents a reference count for i, X represents the fetal ploidy, and $M_i$ represents the maternal ploidy of portion i.

4. The method of claim 2, wherein the sequencing is at about 1-fold coverage or less.

5. The method of claim 2, wherein the nucleic acid is from blood plasma or blood serum.

6. The method of claim 2, wherein calculating the genomic section level for the portions of the reference genome comprises normalizing counts of reads mapped to the reference genome according to guanine and cytosine (GC) content for each of the portions.

7. The method of claim 2, wherein the classification of the presence or absence of a chromosome aneuploidy is generated for one or more of chromosome 13, chromosome 18 and chromosome 21.

8. The method of claim 2, wherein the subset of portions of the reference genome in (f) is portions of a chromosome or segment thereof.

9. The method of claim 8, wherein the chromosome is chosen from chromosome 13, chromosome 18 and chromosome 21.

10. The method of claim 2, comprising determining a reference count and determining an uncertainty value according to the reference count, wherein:

the reference count is determined according to calculated genomic section levels for a subset of portions of the reference genome for one or more pregnant females bearing a fetus;

the subset of portions of the reference genome for one or more pregnant females are known to be euploid for the fetus and/or the mother;

the reference count is not determined from the sample; and the reference count is determined from the same subset of portions of the reference genome as in (f).

11. The method of claim 10, wherein the fetal ploidy determination is calculated in (f) according to (i) the calculated genomic section levels for a subset of portions of the reference genome determined in (d), (ii) the fraction of fetal nucleic acid determined in (e), (iii) the estimated maternal ploidy, and (iv) the reference count.

12. The method of claim 11, wherein the fetal ploidy determination is calculated in (f) by linear regression.

13. The method of claim 12, wherein the fetal ploidy determination is calculated in (f) according to Equation 20 below:

$$X = \frac{\sum_{i=1}^{N} \frac{f_i y_i}{\sigma_i^2} - (1-F)\sum_{i=1}^{N} \frac{M_i f_i^2}{\sigma_i^2}}{F\sum_{i=1}^{N} \frac{f_i^2}{\sigma_i^2}} \quad (20)$$

wherein yi represents the calculated genomic section level for portion i of a reference genome, F represents the fraction of fetal nucleic acid determined in (e), fi represents a reference count for i, σ represents the uncertainty value for fi, X represents the fetal ploidy determination, and Mi represents the estimated maternal ploidy of portion i.

14. The method of claim 12, wherein a classification of an absence of a fetal chromosome trisomy is determined when the fetal ploidy determination is about 1 and a classification of a presence of a fetal chromosome trisomy is determined when the fetal ploidy determination is not about 1.

15. The method of claim 2, wherein determining the fraction of fetal nucleic acid comprises analyzing one or more loci in sample nucleic acid, wherein at least one of the one or more loci vary between fetal nucleic acid and maternal nucleic acid.

16. The method of claim 2, wherein determining the fraction of fetal nucleic acid in (e) comprises:

(1) generating an experimental Y chromosome representation, which experimental Y chromosome representation is a ratio of (i) counts of sequence reads mapped to the genomic sections of the reference genome in the Y chromosome, and (ii) counts of sequence reads mapped to genomic sections of the reference genome in the genome or segment thereof;

(2) determining the fraction of the fetal nucleic acid in the blood of the pregnant female according to the experimental Y chromosome representation generated in (1) and a fitted relationship, wherein:

the fitted relationship is between (i) an experimental Y chromosome representation determined from a set of pregnant females bearing a male fetus and (ii) an X chromosome representation determined from a set of pregnant females; and the fitted relationship is fitted to a median chromosome X representation and a median chromosome Y representation for a set of pregnant females bearing a female fetus.

17. The method of claim 2, further comprising generating and transmitting a laboratory prenatal test report comprising a classification of a presence of a chromosome aneuploidy in the fetus.

18. The method of claim 2, further comprising monitoring health of the fetus and pregnant female from whom the test sample was obtained based on the classification of a chromosome aneuploidy in the fetus.

19. The method of claim 2, further comprising performing a medical procedure comprising amniocentesis or chorionic villus sampling when the classification is a presence of three copies of a chromosome for the test sample.

* * * * *

SEQUENCE LISTING

```
<160> NUMBER OF SEQ ID NOS: 375

<210> SEQ ID NO 1
<211> LENGTH: 305
<212> TYPE: DNA
<213> ORGANISM: Homo sapiens

<400> SEQUENCE: 1

cagcaggcgc gctcccggcg aatctgcctg aatcgccgtg aatgcggtgg ggtgcagggc      60

aggggctggt tttctcagcc ggtcttggct tttctctttc tctcctgctc caccagcagc     120

ccctccgcgg gtcccatggg ctccgcgctc agaacagccc ggaaccaggc gccgctcgcc     180

gctcgctggg ggccacccgc ctctccccgg aacagcctcc cgcgggcctc ttggcctcgc     240

actggcgccc tcacccacac atcgtccctt tatccgctca gacgctgcaa agggccttct     300

gtctc                                                                 305


<210> SEQ ID NO 2
<211> LENGTH: 336
<212> TYPE: DNA
<213> ORGANISM: Homo sapiens

<400> SEQUENCE: 2

gctttggatt tatcctcatt ggctaaatcc ctcctgaaac atgaaactga aacaaagccc      60
```

```
tgaacccct caggctgaaa agacaaaccc cgcctgaggc cgggtcccgc tccccacctg    120

gagggaccca attctgggcg ccttctggcg acggtccctg ctagggacgc tgcgctctcc    180

gagtgcgagt tttcgccaaa ctgataaagc acgcagaacc gcaatcccca aactaacact    240

gaacccggac ccgcgatccc caaactgaca agggacccgg aacagcgacc cccaaaccga    300

cacgggactc gggaaccgct atctccaaag ggcagc                              336


<210> SEQ ID NO 3
<211> LENGTH: 139
<212> TYPE: DNA
<213> ORGANISM: Homo sapiens

<400> SEQUENCE: 3

tttccacaac agggagccag cattgaggcg cccagatggc atctgctgga aatcacgggc     60

cgctggtgaa gcaccacgcc ttacccgacg tggggaggtg atccccccacc tcatcccacc    120

cccttctgtc tgtctcctt                                                 139


<210> SEQ ID NO 4
<211> LENGTH: 292
<212> TYPE: DNA
<213> ORGANISM: Homo sapiens

<400> SEQUENCE: 4

gctggacaag gagcgctcac tgtagctctg ctgtggattg tgttggggcg aagagatggg     60

taagaggtca aagtcgtagg attctggcga ccgcctacca agggattggg tccacagcac    120

agaggtctga tcgcttcctt ctctgctctg ccacctccag acagcagctc taaccagctg    180

cccagcagca agaggatgcg cacggctttc accagcacgc agctgctaga gctggagcgc    240

gagttcgctt ctaatatgta cctgtcccgc ctacgtcgca tcgagatcgc ga            292


<210> SEQ ID NO 5
<211> LENGTH: 190
<212> TYPE: DNA
<213> ORGANISM: Homo sapiens

<400> SEQUENCE: 5

tgcctgacac tgaccccagg cgcagccagg aggggctttg tgcgggagag ggagggggac     60

cccagcttgc ctggggtcca cgggactctc ttcttcctag ttcactttct tgctaaggcg    120

aaggtcctga ggcaggacga gggctgaact gcgctgcaat cgtccccacc tccagcgaaa    180

cccagttgac                                                           190


<210> SEQ ID NO 6
<211> LENGTH: 706
<212> TYPE: DNA
<213> ORGANISM: Homo sapiens

<400> SEQUENCE: 6

tcggcggaga gacctcgagg agagtatggg gaaaggaatg aatgctgcgg agcgcccctc     60

tgggctccac ccaagcctcg gaggcgggac ggtgggctcc gtcccgaccc cttaggcagc    120

tggaccgata cctcctggat cagaccccac aggaagactc gcgtggggcc cgatatgtgt    180

acttcaaact ctgagcggcc accctcagcc aactggccag tggatgcgaa tcgtgggccc    240

tgaggggcga gggcgctcgg aactgcatgc ctgtgcacgg tgccgggctc tccagagtga    300

gggggccgta aggagatctc caaggaagcc gaaaaaagca gccagttggg cttcgggaaa    360

gacttttctg caaaggaagt gatctggtcc cagaactcca gggttgaccc cagtacctga    420
```

```
cttctccggg agctgtcagc tctcctctgt tcttcgggct tggcgcgctc ctttcataat    480

ggacagacac cagtggcctt caaaaggtct ggggtggggg aacggaggaa gtggccttgg    540

gtgcagagga agagcagagc tcctgccaaa gctgaacgca gttagcccta cccaagtgcg    600

cgctggctcg gcatatgcgc tccagagccg gcaggacagc ccggccctgc tcaccccgag    660

gagaaatcca acagcgcagc ctcctgcacc tccttgcccc agagac                   706


<210> SEQ ID NO 7
<211> LENGTH: 325
<212> TYPE: DNA
<213> ORGANISM: Homo sapiens

<400> SEQUENCE: 7

agatcccggt gcatttaaag gccggcgtga tctgcaccac gtacctatct cggattctca     60

gtttcacttc gctggtgtct gccaccatct ttaccacatc ccggtagcta catttgtcta    120

ccgcttgagc caccagcgtc tgaaacctgg accggatttt gcgcgccgag aggtagccgg    180

aggcggtaat gaattccacc cagagggaca tgctcctctt gcgcccgtcg ctcaacttca    240

gcaccgcgca gccgggcagt gagccatcgt ccacgaagtt gaacaccccc atttggttga    300

gataaagcac cacttcaaat tcggt                                          325


<210> SEQ ID NO 8
<211> LENGTH: 663
<212> TYPE: DNA
<213> ORGANISM: Homo sapiens

<400> SEQUENCE: 8

actatgcctt gagggtcaaa acgtctggat ttcctgatcg atgctgtcgt cgctgtccac     60

ggagctactg tcgccgtcag agcgggaagg cacgttcagg gagtagaagc gtgggcttgc    120

agaaagggac ctgttgctgc cttacatggg ggccggcagg gtagtcttgg aaatgcccaa    180

gattgcttcc gcgcgcgtca gttcagcgga cgtgtctgcc tggcacgagg accgttctac    240

aaactcgttc ctggaagccg ggctcgctgg aggcggagct ttggtttcct tcgggagctt    300

gtggggaatg gtcagcgtct aggcaccccg ggcaagggtc tgtggccttg gtggccactg    360

gcttcctcta gctgggtgtt ttcctgtggg tctcgcgcaa ggcacttttt tgtggcgctg    420

cttgtgctgt gtgcggggtc aggcgtcctc tctcctcccg gcgctgggcc ctctggggca    480

ggtccccgtt ggcctccttg cgtgtttgcc gcagctagta cacctggatg gcctcctcag    540

tgccgtcgtt gctgctggag tctgacgcct cgggcgcctg cgccgcactt gtgacttgct    600

ttccccttct cagggcgcca gcgctcctct tgaccccgct tttattctgt ggtgcttctg    660

aag                                                                  663


<210> SEQ ID NO 9
<211> LENGTH: 1985
<212> TYPE: DNA
<213> ORGANISM: Homo sapiens

<400> SEQUENCE: 9

gcaagtcggg tagctaccgg gtgctggaga actccgcacc gcacctgctg gacgtggacg     60

cagacagcgg gctcctctac accaagcagc gcatcgaccg cgagtccctg tgccgccaca    120

atgccaagtg ccagctgtcc ctcgaggtgt tcgccaacga caaggagatc tgcatgatca    180

aggtagagat ccaggacatc aacgacaacg cgccctcctt ctcctcggac cagatcgaaa    240
```

tggacatctc ggagaacgct gctccgggca cccgcttccc cctcaccagc gcacatgacc 300
ccgacgccgg cgagaatggg ctccgcacct acctgctcac gcgcgacgat cacggcctct 360
ttggactgga cgttaagtcc cgcggcgacg gcaccaagtt cccagaactg gtcatccaga 420
aggctctgga ccgcgagcaa cagaatcacc atacgctcgt gctgactgcc ctggacggtg 480
gcgagcctcc acgttccgcc accgtacaga tcaacgtgaa ggtgattgac tccaacgaca 540
acagcccggt cttcgaggcg ccatcctact tggtggaact gcccgagaac gctccgctgg 600
gtacagtggt catcgatctg aacgccaccg acgccgatga aggtcccaat ggtgaagtgc 660
tctactcttt cagcagctac gtgcctgacc gcgtgcggga gctcttctcc atcgacccca 720
agaccggcct aatccgtgtg aagggcaatc tggactatga ggaaaacggg atgctggaga 780
ttgacgtgca ggcccgagac ctggggccta accctatccc agcccactgc aaagtcacgg 840
tcaagctcat cgaccgcaac gacaatgcgc cgtccatcgg tttcgtctcc gtgcgccagg 900
gggcgctgag cgaggccgcc cctcccggca ccgtcatcgc cctggtgcgg gtcactgacc 960
gggactctgg caagaacgga cagctgcagt gtcgggtcct aggcggagga gggacgggcg 1020
gcggcggggg cctgggcggg cccgggggtt ccgtcccctt caagcttgag gagaactacg 1080
acaacttcta cacggtggtg actgaccgcc cgctggaccg cgagacacaa gacgagtaca 1140
acgtgaccat cgtggcgcgg gacgggggct ctcctcccct caactccacc aagtcgttcg 1200
cgatcaagat tctagacgag aacgacaacc cgcctcggtt caccaaaggg ctctacgtgc 1260
ttcaggtgca cgagaacaac atcccgggag agtacctggg ctctgtgctc gcccaggatc 1320
ccgacctggg ccagaacggc accgtatcct actctatcct gccctcgcac atcggcgacg 1380
tgtctatcta cacctatgtg tctgtgaatc ccacgaacgg ggccatctac gccctgcgct 1440
cctttaactt cgagcagacc aaggcttttg agttcaaggt gcttgctaag gactcggggg 1500
cgcccgcgca cttggagagc aacgccacgg tgagggtgac agtgctagac gtgaatgaca 1560
acgcgccagt gatcgtgctc cccacgctgc agaacgacac cgcggagctg caggtgccgc 1620
gcaacgctgg cctgggctat ctggtgagca ctgtgcgcgc cctagacagc gacttcggcg 1680
agagcgggcg tctcacctac gagatcgtgg acggcaacga cgaccacctg tttgagatcg 1740
acccgtccag cggcgagatc cgcacgctgc accctttctg ggaggacgtg acgcccgtgg 1800
tggagctggt ggtgaaggtg accgaccacg gcaagcctac cctgtccgca gtggccaagc 1860
tcatcatccg ctcggtgagc ggatcccttc ccgagggggt accacgggtg aatggcgagc 1920
agcaccactg ggacatgtcg ctgccgctca tcgtgactct gagcactatc tccatcatcc 1980
tccta 1985

<210> SEQ ID NO 10
<211> LENGTH: 213
<212> TYPE: DNA
<213> ORGANISM: Homo sapiens

<400> SEQUENCE: 10
atgcgccctc tgcacccta gagccagaag acgctaggtg ggctgcgcgc tctgccaggc 60
gaaggctgga gcgcagacgg caaagccgcg cgtttcagcc gtggtcgggt ccgcaggacc 120
tgggcgtggg gacaccacca ggcaggagca gaggcaggac tgggacgcca aaagctgaga 180
atcctcgatg cccgcgcgag agccccgtgt tat 213

<210> SEQ ID NO 11
<211> LENGTH: 1558

<212> TYPE: DNA
<213> ORGANISM: Homo sapiens

<400> SEQUENCE: 11
ttctggaaac cgggccccac ttgcaggccc ggccaccttg ggttctggtg gccgaagccg 60
gagctgtgtt tctcgcagac tcggggagct acattgtgcg taggcaattg tttagtttga 120
aaggaggcac atttcaccac gcagccagcg ccctgcatgc aggagaagcc cccagggccc 180
agggtcggct ggctttagag gccacttagg ttgttttaag cacatgtgaa agggcagaca 240
gcaggggagc aggatatggg taagatcttc gggtctcaga acaggggctg cccttgggct 300
gtcccggcgc cctgggctct gacactgaag ggtggaatgg aggaaggaat ggagaaagga 360
cggtggaact ttcgcttccc ctctgggccg ccttcccagg gtcatgcctg agctgctttg 420
atcccagtgt cgcgcatctt ggtccgctac ctcccaggcg atagctactg ggctcctcgc 480
tggcctcact gggggccatc ccgggcagtg gcctgccctc cgaggcccgc gggacccagc 540
ccagagctga ggttggagtt ctccgggcca cgttccgggt cgcttaggct cggagatttc 600
ccggagaccg tcgtcctccc tttctgcttg gcactgcgga gctccctcgg cctctctcct 660
cctctggtcc ctaaggcccg gagtggttgg cggtactggg gcccgtcgtc atctctgctt 720
ctaaggcatt cagactgggc tccagctggg accggcagag gaggttctca aggaaactgg 780
tgggaaatat agttttcttt cgtctggtcg tttaatttaa atgcaacttc ccttggggac 840
attttcctgg acgttaacca gaccaccttg agatgtcgtt gatgacctag agacccagat 900
gatgcgtccc aggaaagttc actgctgact attgtcactc ttggcgttat atctatagat 960
atagacctat gtacatatct ccaccctgat ctctccgtgg acatgaaacc cacctacctt 1020
gtgaaagccc tacgggtgac acatgactac tacgtctctg tcccaacagg ggctgggcct 1080
cccctgccta atagttgcca ggagtttcgc agcccaagtg aataatgtct tatggctgaa 1140
cgtggccaag gactcctgtg atttaggtcc caggaggagc agagacgtcc ccgccccgcc 1200
tgggccctgc cgcattcaaa gctggaagaa ggcgctgatc agagaagggg cttccaggtc 1260
ctgggttaga acaacaacaa acaaacgaaa ctccacaaca gacacgcctg cccatgaccc 1320
cacgcaagga cataggaagt tctgtcgcct tcctgctccg cggatagccg cctgccgtct 1380
gctgccacca gaacgcacgg acgctcgggg tggaggtagt caatgggcag caggggaccc 1440 ccagcccccca caagcgcggc tccgaggacc tggaagcggg tgcctgtcgc tctccgcagg 1500
ctccgctctg cctccaggag caagatcccc aaaagggtct ggaagctgtg gagaaaac 1558

<210> SEQ ID NO 12
<211> LENGTH: 1264
<212> TYPE: DNA
<213> ORGANISM: Homo sapiens

<400> SEQUENCE: 12
ttttttaaac acttcttttc cttctcttcc tcgttttgat tgcaccgttt ccatctgggg 60
gctagaggag caaggcagca gccttcccag ccagcccttg ttggcttgcc atcgtccatc 120
tggcttataa aagtttgctg agcgcagtcc agagggctgc gctgctcgtc ccctcggctg 180
gcagaagggg gtgacgctgg gcagcggcga ggagcgcgcc gctgcctctg gcgggctttc 240
ggcttgaggg gcaaggtgaa gagcgcaccg gccgtggggt ttaccgagct ggatttgtat 300
gttgcaccat gccttcttgg atcggggctg tgattcttcc cctcttgggg ctgctgctct 360
ccctccccgc cggggcggat gtgaaggctc ggagctgcgg agaggtccgc caggcgtacg 420
gtgccaaggg attcagcctg gcggacatcc cctaccagga gatcgcaggt aagcgcgggc 480
gcgctgcagg ggcaggctgc agccctcggc tgccgcacgt cccactggcc gcccggcgtc 540
cccttccttc cccctgttgc tgagttggtg ctcactttct gccaccgcta tgggactccg 600
cgtctccgtg ttgggcggcg gatgctcctg cggcttcttc ggcgggggaa ggtgtgcgtc 660
tccgccgcct cattgtgtgc acacgcggga gcaccctggc tcccgcctcc cgctgctctc 720
gcgcccttct acccettagt tgatggctca ggcccggctg gccagggagc ccgggtcact 780
ccggggcggc tgcaaggcgc agacggagag ccgagccggg cgctcactcc gcgttctggt 840
tcgggcaaac ttggaagaac tgcgaccgca gtttgcccag cgccacagtc tgagtggcgc 900
cttctccact cccgcccttg cgccggcagg ggcggtggag agacgcggag ggctccccca 960
gcccctctct cccctatccg tccttcgggc gacagagcgc ccggcgctcg ggccgggggc 1020
gggcaaggct gggagggacc ctcgccgggg acctggcctc tggacgccgg cgtttcaagg 1080
ctggtttggg gacttcacgg gctgcctgtt tcagatgtgg ggcgggcttt cccgttaggg 1140
ttcctcagtg cttccccagt tgctgttggc cactcagggc ccggggacac cctgccaccc 1200
ggtctggagc cggcctcgtc tgccagcgaa cagccaactt tagcgggtgg ctcagctggg 1260
gatt 1264

<210> SEQ ID NO 13
<211> LENGTH: 761
<212> TYPE: DNA
<213> ORGANISM: Homo sapiens

<400> SEQUENCE: 13
cactcagtgt gtgcatatga gagcggagag acagcgacct ggaggccatg ggtgggggcg 60
ggtggtgaag ctgccgaagc ctacacatac acttagcttt gacacttctc gtaggttcca 120
aagacgaaga cacggtggct tcagggagac aagtcgcaag ggcgactttt ccaagcggga 180
gatggtgaag tctttggacg tgtagtgggt aggtgatgat ccccgcagcc gcctgtaggc 240
ccgcagactt cagaaaacaa gggccttctg tgagcgctgt gtcctccccg gaatccgcgg 300
cttaacacat tctttccagc tgcggggcca ggatctccac cccgcgcatc cgtggacaca 360
cttagggtcg cctttgtttt gcgcagtgat tcaagttggg taacccttgc tcaacacttg 420
ggaaatgggg agaatctccc ccacccgcaa cctcccgcac cccaggttcc caaaatctga 480
atctgtatcc tagagtggag gcagcgtcta gaaagcaaag aaacggtgtc caaagacccc 540
ggagagttga gtgagcgcag atccgtgacg cctgcggtac gctagggcat ccaggctagg 600
gtgtgtgtgt gcgggtcggg gggcgcacag agaccgcgct ggtttaggtg gacccgcagt 660
cccgcccgca tctggaacga gctgcttcgc agttccggct cccggcgccc cagagaagtt 720
cggggagcgg tgagcctagc cgccgcgcgc tcatgtttat t 761

<210> SEQ ID NO 14
<211> LENGTH: 1198
<212> TYPE: DNA
<213> ORGANISM: Homo sapiens

<400> SEQUENCE: 14
agtcactcca ggatcagagg ccgcgtcggt tctgcttggg gcatgggcag agggaggctg 60
ctggggccaa gccccggctg gacgcgaggg aagaaactcg tcccaggacc cgcacgccca 120
tacctggctg tcccagagct cttccctagg ccggcacctt cgctcttcct cttccccacc 180
ccctagccct tttgtctctt tttcagacgg atgttttcag tctcaagtgg ttttattttc 240

```
cgcacaaaac cctgagatca agggcagatc acagactgta ccggaggctc gggtttccct    300

ggactctgtg ctgttctgcg tcccagggtt ggctaggaag gaaggcctgg gccggcgagg    360

tgacgggtct cccgcccagg tcggcaggac ggggggaggt gtgtcccggt aggtccctgg    420

tgagctcacc cgtggcatcg gggacccgcg ggaacccacc gggcgcccac tagagactcg    480

ggtcctaccc tcccccacac tactccaccg aaatgatcgg aagggcgcgc taggcctgct    540

tccaagggct cagtgataaa ggcctcaaaa tcacactcca tcaagacttg gttgaagctt    600

tgggtaggtt tgttgttgtt gttgttgttg tttgtttgtt tgttttagca gacacgtcct    660

ggaaagaggt cctcagaacc caaaggttca ataatgattt gtggatggat tgattatagt    720

ctgatatcgc tctggttcca cagaaacccg gagctccttg gcccactgtt accccagcag    780

acctaaatgg acggtttctg tttttcactg gcagctcaga actggaccgg aagaagttcc    840

cctccacttc ccccctcccg acaccagatc attgctgggt ttttattttc gggggaaaaa    900

caacaacaac aacaacaaaa aaaacactag gtccttccag actggatcag gtgatcgggc    960

aaaaaccctc aggctagtcc ggctgggtgc ccgagcatga aaaggcctcc gtggccgttt   1020

gaacagggtg ttgcaaatga gaacttttgt aagccataac cagggcatcc tgagggtctg   1080

agttcacggt caaggctgtg ggctactagg tccagcgagt ccaggcctcg ccccgccccc   1140

gagctgccac agccaagatc ttcggcaggg aattcgagac cagggtcctc ccactcct     1198
```

<210> SEQ ID NO 15
<211> LENGTH: 377
<212> TYPE: DNA
<213> ORGANISM: Homo sapiens

<400> SEQUENCE: 15

```
tttcgtgccg ctgttttcaa tgcgctaacg aggcacgtta ttcttagccg cgtccgggag     60

gggatcacat tcctgcgcag ttgcgctgct ggcggaagtg acttgttttc taacgaccct    120

cgtgacagcc agagaatgtc cgtttctcgg agcgcagcac agcctgtccc atcgagaagc    180

ctcgggtgag ggcccggtg ggcgcccgga ggccgctgga gggctgtggg agggacggtg     240

gctccccact cccgtggcga agggcaggca aaccagaagc ctcttttgag agccgtttgg    300

gattgagacg agtaagccac agcgagtggt tagaagtagg ttaggaagaa ggggaggtaa    360

gaaagccgag tagggtt                                                   377
```

<210> SEQ ID NO 16
<211> LENGTH: 256
<212> TYPE: DNA
<213> ORGANISM: Homo sapiens

<400> SEQUENCE: 16

```
gttcggtgga caagggggca gcgcccacag caagccggaa agagggaggc gcggggccgc     60

gcttggggcc tgccgctgca cgccagcctg ggcaaagagc tgccaccttc tgcgggcgaa    120

gcgggtcggg acgcaggacg gcagcggggc tggaggcagc tacgtgggtc cacaccccca    180

tgccctgcaa ggctccttgg ccctgcttct cctctgtctc ggcgggagag gagcagcctc    240

ggttttacag aatttc                                                    256
```

<210> SEQ ID NO 17
<211> LENGTH: 189
<212> TYPE: DNA
<213> ORGANISM: Homo sapiens

<400> SEQUENCE: 17
tgtgccattt agtgagaggt gttttgggca aagaatcaat ttaactgtga ctgaccgacg 60
ggcttgactg tattaattct gctaccgaaa aaaaaaaaaa aaaaaaagca atgagccgca 120
agccttggac tcgcagagct gccggtgccc gtccgagagc cccaccagcg cggctcacgc 180
ctcagtctc 189

<210> SEQ ID NO 18
<211> LENGTH: 707
<212> TYPE: DNA
<213> ORGANISM: Homo sapiens

<400> SEQUENCE: 18
agagtcccag ttctgcaggc cgctccaggg ctaggggtag agatggtggc aggtggtgcg 60
tcaactctct agggaagagg aacttgcatt acaaagactt gtctttctga gctgaagtca 120
aaacgggggc gtcaagcgcg ctccgtttgg cggcggtgga ggggccgcgc gcccgcgctg 180
tcccagccgg agctgccctg gctggtgatt ggaggtttaa cgtccggaat tcaggcgctt 240
ctgcagctca gatttgccgg ccaaggggcc tcagttgcaa cttttcaaaa tggtgtttct 300
ggaaaataac aaattcagac tcaactggtg acagcttttg gctatagaga atgaaactgc 360
ttccctttgg cggtggaact cttaaacttc gaagagtgaa agaatacaat gaaataaaat 420
gccataagat cactggattt ttcagaaaaa ggaagacccc aaattactcc caaaatgagg 480
ctttgtaaat tcttgttaaa aatctttaaa tctcgaattt ccccctacaa catctgatga 540
gtgctttaag agcaaacgag caaatcccac ctcgagaatc aacaaaccca agctctggcc 600
aaggctctcc ccgcgttttc ttctcgtgac ctggggaatg tcccgcccca tcgctcacct 660
ggctcttgtc atctcgctca tcttgaagtg acccgtggac aatgctg 707

<210> SEQ ID NO 19
<211> LENGTH: 182
<212> TYPE: DNA
<213> ORGANISM: Homo sapiens

<400> SEQUENCE: 19
agctgccctc tgtggccatg agcgggtgtc cagccccttc caaggctgca ccggggagac 60
gctggttttc tgctcgctgt gaccgaacaa agcccctaag agtcagtgcg cggaacagaa 120
gagccggacc ccgacgggcc gagtcccaac gtgaggcacc cggcagagaa aacacgttca 180
cg 182

<210> SEQ ID NO 20
<211> LENGTH: 179
<212> TYPE: DNA
<213> ORGANISM: Homo sapiens

<400> SEQUENCE: 20
cctcggcagc accggcatgg ctggaggcca gtacggccag gtgtggcggg agggagcgcc 60
gtctggcttg ggtcgtccat cctgacagga cgctgcaagg gcaggagccc cgcgccccgt 120
gtcctgcgcc cccgctcgag gacaagcccc agccgccggt ctccgctggg ttccgacag 179

<210> SEQ ID NO 21
<211> LENGTH: 369
<212> TYPE: DNA
<213> ORGANISM: Homo sapiens

<400> SEQUENCE: 21
ctttaagagg ctgtgcaggc agacagacct ccaggcccgc taggggatcc gcgccatgga 60
ggccgcccgg gactatgcag gagccctcat caggcgagtg ccccgcgtcc ccctgattgc 120
cgtgcgcttc caatcgcctt gcgttcggtg gcctcatatt cccctgtgcg cctctagtac 180
cgtaccccgc tcccttcagc cccctgctcc ccgcattctc ttgcgctccg cgaccccgcg 240
cacacaccca tccgccccac tggtgcccaa gccgtccagc cgcgcccgcg ggcagagccc 300
aatcccgtcc cgcgcctcct caccctcttg cagctgggca caggtaccag gtgtggctct 360
tgcgaggtg 369

<210> SEQ ID NO 22
<211> LENGTH: 176
<212> TYPE: DNA
<213> ORGANISM: Homo sapiens

<400> SEQUENCE: 22
agacttgcag aactcgggcc ccctggagga gacctaaccg ccacggtctt ggggaggttc 60
cggagggcct cggttgtctg cactcccaac accaagaaac ccctgagacg cgaagctgcc 120
agcgtgctgc cctcagagca gggcgacgca aagccagcgg accccggggt ggcggg 176

<210> SEQ ID NO 23
<211> LENGTH: 167
<212> TYPE: DNA
<213> ORGANISM: Homo sapiens

<400> SEQUENCE: 23
tgctcggctg gggggctcgc tccgcacttt cggtgccaga aaatgcccag aggagcgggg 60
cggccccaga gcctcctttc ggggcgcgag gcccggcgcg tgtgtacgga gtccagtccc 120
cccagggagt ggggtgcccg caccttcccc tccgcgctcg gagccac 167

<210> SEQ ID NO 24
<211> LENGTH: 1205
<212> TYPE: DNA
<213> ORGANISM: Homo sapiens

<400> SEQUENCE: 24
tcttgcacac ctgcttgtag ttctgcaccg agatctggtc gttgaggaac tgcacgcaga 60
gcttggtgac ctgggggatg tgcaggatct tgctgaccga cagcacctcc tccaccgtgt 120
ccagggacag ggtcacgttg gccgtgtaga ggtactcgag caccaggcgc agcccgatgg 180
acgagcagcc ctgcagcacc aggttgttga tggcccgggg gctggtcagc agcttgtcgt 240
cgggggagga agaaggagtc ccgggctcct cctgcggcgg cggctgctgc tgctgtgacg 300
gctgctgctg cggcggctgc tgctggtcct tgggggcccc caggccgtcc tggccgccga 360
cccctccccc gagagggggg tggctggaga agagcgatcg gaagtactgc gagcaggagg 420
ccagcacggc cttgtggcaa tggaactgct ggccctgggc cgtcagggtc acgtcgcaaa 480
acagctgctt cctccacagc aggttgaggc cgtgcagcag gttgtcgctg tggctggggt 540
cgaaggtgga ggtcctgtcc ccggatctgg acatggcgag ctgactcggt gcacctggct 600
ttaaaccctc ctccaacctg gcagacaggg gtgggggatg ggagggaggg gagcagggtg 660
gtggagcggg tggggtgtgg tcggggtggg gaagggtgtg gaggggaggg gagggcgaag 720
aacaagaatc aaggctcagc ttgactccct cctggcgcgc tccggacccc gaccctagga 780
ggaaagtccg aagacgctgg atccgtgagc gccaccagaa gggccctgtc tggggtcccg 840

-continued gcgccggttc tgcgccctgc ggctcctctc gccacctccc acacacttcg tccctcactt 900
tcctaaaacc aaccacctca gctcggctgt tggcagcaac agcagtggca gcagcgacgg 960
caaagtggcg gctgaggccg aggcacctcg tgggctcgtg tccatgccgg gccagatgaa 1020
gggaaaggcc gggaagtggg gagccggggg tgccctgaaa gctcagaggc gaccgacggc 1080
gaaggttcca ggtcaacttg tgcccgaagc tttgcttttc gcagttggcc cagtttgggg 1140
gagggggtag gaacaggggc ccgaccagcg tgcggggtgt gcgaatctta gctctccaaa 1200
agctg 1205

<210> SEQ ID NO 25
<211> LENGTH: 44
<212> TYPE: DNA
<213> ORGANISM: Homo sapiens

<400> SEQUENCE: 25
cctctgtgtt agtgccctcg ggaatttggt tgatggggtg tttg 44

<210> SEQ ID NO 26
<211> LENGTH: 5002
<212> TYPE: DNA
<213> ORGANISM: Homo sapiens

<400> SEQUENCE: 26
tgatgtcgca cctgaacggc ctgcaccacc cgggccacac tcagtctcac gggccggtgc 60
tggcacccag tcgcgagcgg ccaccctcgt cctcatcggg ctcgcaggtg gccacgtcgg 120
gccagctgga agaaatcaac accaaagagg tggcccagcg catcacagcg gagctgaagc 180
gctacagtat cccccaggcg atctttgcgc agagggtgct gtgccggtct caggggactc 240
tctccgacct gctccggaat ccaaaaccgt ggagtaaact caaatctggc agggagacct 300
tccgcaggat gtggaagtgg cttcaggagc ccgagttcca gcgcatgtcc gccttacgcc 360
tggcaggtaa ggccggggct agccaggggc caggctgctg ggaagagggc tccgggtccg 420
gtgcttgtgg cccaagtctg cgcgccgagt cacttctctt gattctttcc ttctctttcc 480
tatacacgtc ctctttcttc tcgtttttat ttcttcttcc attttctctt tctcttccgc 540
tcttccccta ctttcccttc tccctttctt ttttctttct tactctctcc ttgtccctga 600
gctttcattg accgaccccc ccccatttca ttcgccctcc cctcaatgtg ccaacctttg 660
ccctatttcc gatcttccca ggtactggga ggcgggatgg gggtgtgcgt tttcctctag 720
gagccctgtc tttccaagac ccacagaaac caggacctgc ccttattcaa aaccccatgc 780
acttcaagtc tcttttagac aacacatttc aattttccgg gctgactagt ctccctgtgc 840
agaggcagtt gagaggcttt gctctgcaga gggaaaagag ctctctactc tcccacccac 900
catataggca aacttatttg gtcattggct gaaggcacag ccttgccccc gcggggaacc 960
ggcggccagg atacaacagc gctcctggag cccatctctg gccttggcgt tggcgcaggg 1020
actttctgac cgggcttgag gggctcgggc cagctccaat gtcactacct acagcgaggg 1080
cagggtgtaa ggttgagaag gtcacattca ccgctttggg aggacgtggg agaagagact 1140
gaggtggaaa gcgctttgcc ttgctcaccg gccgtccttg ccccggtccc agcgtttgct 1200
gggatttgcc aggatttgcc ggggctccgg gagaccctga gcactcgcag gaagaggtgc 1260
tgagaaatta aaaattcagg ttagttaatg catccctgcc gccggctgca ggctccgcct 1320
ttgcattaag cgggcgctga ttgtgcgcgc ctggcgaccg cggggaggac tggcggcccg 1380
cgggagggga cgggtagagg cgcgggttac attgttctgg agccggctcg gctctttgtg 1440

```
cctcctctag cggccaagct gcgaggtaca gccctctatt gttctaggag cacagaaacc   1500
tcctgtgtgg gcggcgggtg cgcgagctag agggaaagat gcagtagtta ctgcgactgg   1560
cacgcagttg cgcgcttttg tgcgcacgga ccccgcgcgg tgtgcgtggc gactgcgctg   1620
cccctaggag caagccacgg gcccagaggg gcaaaatgtc caggtccccc gctgggaagg   1680
acacactata ccctatggca agccagggtg ggcgacttcc catggatcgg gtggaggggg   1740
gtatctttca ggatcggcgg gcggtctagg ggaacaattc gtggtggcga tgatttgcat   1800
agcgcgggtc ttgggatgcg cgcggttccg agccagcctc gcacagctcg cttccggagc   1860
tgcgagctca ggtttccacc cccgatcccc cgggctttcc tcgcaccgct gagcccagct   1920
tgtggggtgc actcgaccaa cgcccgacag ggctggggaa tgtgacaggc agcaggttca   1980
cccgggcttg ggagggggga gtttccgctt tgacagcatt ttcctttgcc gtctgctggt   2040
ggattcctat tcccagtcgg taatcgcccc gcagtgttga tctaagaagg taaagaaaac   2100
taggtttccc tgcaaagagc ctcccccaaa tcggcggact ccggatactt tgagtggatt   2160
tagaaattta tgtaatcttt ctcctttagt ttatttttca tcctctccta cagttttctc   2220
tgatttgctg ttggttcggg gcaagataaa gcagccagta gagagcgata ataatagcgg   2280
cgggaaatga actggagact ggctgacagt tcttaacatt ttgtcataga tccccccgaa   2340
tgtcccaggc tgtctctggt gggttttagt acccgccggc ttcttgggca ccggggacca   2400
gaaggaactt ggcagctggt cttaggggta cagttaaagg caggatgaca gctattctcc   2460
tgctcatctc agagcgctgc cgccccctca tgccggtcgc gcaaagaaca cagcttttaa   2520
aaaacacgtg ccttctgccc atataggtct gaaagtgatg aggaaagtaa tgcttcgcct   2580
attagcgagt ttcagctttt aaaatgatcc caagcgttgc tgagatgaga aagcgtggca   2640
tcccgggggt cctcagcccc acccgcgccc atggtgcaag tctgcaggga caggcccggg   2700
acagcactgc ccacgctgct agattttccg cagaggatcg ctgaagctgc cttcgtggga   2760
gacagaatgc ctcctccagc gagtggaaaa ggcctgctga ggacccccgct ttgctcgagc   2820
attcaaatgt gtgtctgttt tattaccctg ggttgaaaag ggacaagagc tttagccttt   2880
ttatctggcc attttatcag caactacaag tgtgttgagt ggttattatt acataggagg   2940
cttttcagtt tggggtcagt agatcagtct cttcagacac tgatgcagaa gctgggactg   3000
gtaagtaggt attatgtgct cggagcgcta ggggacagga gcaaatggag aagaaaagcg   3060
gaggctttct ccgcccggag tatcgatcgg aatccccgcc ggtacgccgc agagggccct   3120
cgccgttggg ccccgggggt ttaacaagcc cagccgctcc gcaggcggct cggccggact   3180
ctcagaccgg tgcctggaag acaccgtccc tgccccccctc ccgccaaacc tgcctcttct   3240
ctttctctca taggttatag gttccctttc tctctcattt tggccccgcc cccgggtcct   3300
gccaaacagc caagcaggcc ggggtttagg gggctcagaa tgaagaggtc tgatttggcc   3360
agcgccggca aagctcaccc ttaggcgagg tcacaacaga ggcaggtcct tcctgcccag   3420
cctgccggtg tagtcacagc caagggtggc acttgaaagg aaaagggaga aaacttcgga   3480
gaaatttaga ttgccccaac gttagatttc agagaaattg actccaaatg cacggattcg   3540
ttcggaaagg gcggctaagt ggcaggtggt tgcaaccccg cccggtcggg ccttcgcaga   3600
ggttccccaa gaccagccct tgcagggcgg ttttcagcaa cctgacaaga ggcggccaag   3660
acaaatttct gcgggttcga gcacacactc tcgggcgttg ggccccagag acctctaaac   3720
caagcacaaa caagaaggga gtgagagaac ccaggctaga acttgcacgg gcatcccact   3780
```

gaggaaaagc gaggcctcgg tggcaggcat gttttcttcc gacgcccgaa aatcgagccg 3840
agcgcccgac tacatttact gcagaggttt ccgcctccag tgagcccgga tcccccagcg 3900
gcctgcccgg agctggtctc cagtccccgc cgtagtccga cgcacggccc tctcctggca 3960
gcaagctccc agcggccagt ctgaagccaa ttctgttcag gcggccgagg gcccttagcc 4020
aacccaccat gatgtcgcct gggccacctg atgcccgcag cggcgggaca cggcccgggc 4080
agtgcgcagt ggctcctgct aggggcaccg cgtgcgtgct tgtctcccgc tgcgccgggg 4140
acgtccttgg gtgacacggg ccgctgggca cctcccaagc cgaggaaacg gaccccccttc 4200 gcagagtctc gcgcccaccc cccaacctcc cacctcgttt ctcgctgcta gggctcccga 4260
ctcagcccac ctctcctggc ggtttagtta gggatcagag ctggagaggc tgaacgcaac 4320
ccgtgccagt acggaacaga cgatatgttt gcctgctagc tgcttggatg aataattgaa 4380
aagttcgctg cagtctgtgc ttcgtcaagt cccgggtgcc gggagaacac cttcccaaca 4440
cgcatcaggg tgggcgggag cgggcagagg aggcgggacc cgagggagga gagtgaaccc 4500
gagcaggaga agcagcccag gcagccaggc gccctcgatg cgagaggctg ggcatttatt 4560
tttattccag gctttccact gtgtggttat gtcactttct caaacaaatg tgtatatgga 4620
gggagatcga tgctgataat gtttagaaga ttaaaagagc attaatgctg gcaacaataa 4680
cgtaaacgtg tggacccaga tttcattgat ctggaacttg atccggcgcg tttccagtaa 4740
gcccgacggc gcgctcttcc cagcagagcg ctcaccagcg ccacggcccc gcggttttcc 4800
agcggtgccg cttcgccagc tctgcgcggg ttctcccgtc tgaccgcagc tcctcccccg 4860
cgaggcccca gcccgcctta cttccccgag gttttctcct cctctcgcgg ggctctctgc 4920
cctctgcacc ccctcccccg acctctgcac cacccgcccc tgtgcgcaca caccgctact 4980
tgcgcttccg gcgatccgcc tg 5002

<210> SEQ ID NO 27
<211> LENGTH: 150
<212> TYPE: DNA
<213> ORGANISM: Homo sapiens

<400> SEQUENCE: 27
aaccggagat ctgcttggtg aactgagagg agtccttagg agagcgggga cgccaggggc 60
cgggggacac ttcgctctcg ccctagggaa ggtggtcttg acgctttcta ttgaagtcaa 120
acttgaaaat atcagctgcc gctggactat 150

<210> SEQ ID NO 28
<211> LENGTH: 339
<212> TYPE: DNA
<213> ORGANISM: Homo sapiens

<400> SEQUENCE: 28
cgtgagcaga acgcccgccc tggagcagtt aggaccgaag gtctccggag agtcgccggc 60
ggtgccaggt aacgcagagg gctcgggtcg ggccccgctt ctggggcttg ggactccggg 120
cgcgcggagc cagccctctg gggcgaaatc cccgggcggc gtgcgcggtc cctctccgcg 180
ctgtgctctc ccagcaactc cctgccacct cgacgagcct accggccgct ccgagttcga 240
cttcctcgga cttagtggga gaaggggttg gaaatgggct gccgggactg ggggagctgc 300
tctctggaag cagggaagct ggggcgcacc ggggcaggt 339

<210> SEQ ID NO 29
<211> LENGTH: 1961

<212> TYPE: DNA
<213> ORGANISM: Homo sapiens

<400> SEQUENCE: 29
tagaagagga agactcctct ggccccacta ggtatcatcc gcgctctccc gctttccacc 60
tgcgccctcg cttgggccaa tctctgccgc acgtgtccat ccctgaactg cacgctatcc 120
tccacccccg gggggttcct gcgcactgaa agaccgttct ccggcaggtt ttgggatccg 180
gcgacggctg accgcgcgcc gcccccacgc ccggttccac gatgctgcaa tacagaaagt 240
ttacgtcggc cccgacccgc gcgggactgc agggtccgcc ggagcgcggc gcagaggctt 300
ttcctgcgcg ttcggccccg ggaaaggggc gggagggctg gctccgggag cgcacgggcg 360
cggcggggag ggtactcact gtgaagcacg ctgcgcccat ggatcatgtc tgtgcgttac 420
accagaggct ccgggctcca ctaattccat ttagagacgg gaagacttcc agtggcgggg 480
ggaggacagg gtcgagaggt gttaaagacg caaagcaaga aggaaataaa ggggggccga 540
gagggagacc gagaggaagg gggagctccg agcccacgct gcagccagat ccggatgagt 600
ccgtcctccg ccccgggcgg gctctcgctc tcgctggccc tcagcgccgc gcagccagca 660
gcatccccac cgtgacgctc gcatcacacc cgggcgccgg ccgccaccat ccgcgccgcc 720
gccgtcagga ccctcctccc gggcatcgtc gccgccgcgg ggtcgggagg acgcggcgcg 780
cgggaggcgg cggtcgcagg gcgagccccg ggacgccccg agccggggcc ggggccgggg 840
agagggcgca gcgaggtggg ggccagtcca gaccgacggc agcgacggag cgggcggcgg 900
cggcggcgcc ggcggcggcg gggtggctca gtccccagtc tcagacgcgc cgcgcagcag 960
gtcggagcag cctccccggg aggatgtcca gcggcagcgc tcctcgctcc agcccttggg 1020
gatcttccgc tgaggcattg aaggcaggaa gaaggggtcc gtcatcggct cgccgggctg 1080
cgcgccacct ctgctatctt gcggaaagag gagcgggtgg gtgggcgtct gggaggcggg 1140
ctggagggcg gtgcagggga gcggggcggc cggggggggg gccgggggc ggggaaggga 1200 gggaggagaa aggagccgga agagggcaga gttaccaaat gggctcctta gtcatggctt 1260
ggggctccac gaccctcctg gaagcccgga gcctgggtgg gatagcgagg ctgcgcgcgg 1320
ccggcgcccc ggggctggtg cgcggcagaa tggggccgcg gcggcggcag caaggacatc 1380
ccagccgcgc ggatctgggg gaggggcggg gagggggtga ggacccggct gggatccgcg 1440
gctcggcccg ccagggcgca gagagaggat gcagccgcaa atcccgagcc ggatcctcgt 1500
gccggacgga aggcgtggaa gcgggagggg ccttcgtgtg aaaatccctt gtggggtttg 1560
gtgtttcact ttttaaaggt tagaccttgc gggctctctg cctcccaccc cttcttttcc 1620
atccgcgtaa aggaactggg cgccccctct ccctccctcc ctggggcgca ggtttcgccg 1680
cggactccgc gctcagcttg ggagacacgg caggggcgcg ccccagggaa aggcggccgt 1740
aaaagtttcg cggttgagca ctgggcctga tgtccagtcc ccccaccaaa ttactcctgc 1800
aaagacgcgg gcttcttgca attgagcccc ccacctcgag gtatttaaaa ccaccccaag 1860
gcacacacgg acccccgttc ccccgcgcca cttcctccta caggctcgcg cggcgcgtta 1920
aagtctggga gacacgagtt gcggggaaac agcaccggaa g 1961

<210> SEQ ID NO 30
<211> LENGTH: 314
<212> TYPE: DNA
<213> ORGANISM: Homo sapiens

<400> SEQUENCE: 30
aagaaacagc tcatttcgga gctgaggaca aggcgtggga agaagacgcg tttggtttca 60
cccaggcggg tggcggcaaa gctgtgggat gcgcgctgca cactccttcc gtcatcccgt 120
tcccaccttc cacacacacc tgcgggaggt cggacatgtc ctgattgcgt gttcatcacg 180
atggcaaacc gaacatgagg agaacgccac tgacgctggg tgcgccggct ttcccagccc 240
tcgtgcataa cggggaggga gatgcagaag ttttttccaa catcggtgca aaggggaagc 300
tgaggttttc ctat 314

<210> SEQ ID NO 31
<211> LENGTH: 584
<212> TYPE: DNA
<213> ORGANISM: Homo sapiens

<400> SEQUENCE: 31
tctgtcagct gctgccatgg ggcagcggga aggccctgga gggtgcctgg gctgtgtctg 60
gtcccggcca cgcgtccctg cagcgtctga gaccttgtgg aacacacttg acccggcgct 120
gggacggggt cggcccacac gcaccgccag cccgcaggag tgaggtgcag gctgccgctg 180
gctccttagg cctcgacagc tctcttgagg tcggccctcc tcccctcccg agagctcagc 240
agccgcagac ccaggcagag agagcaaagg aggctgtggt ggccccgac gggaacctgg 300 gtggccgggg gacacaccga ggaactttcc gccccccgac gggctctccc accgaggctc 360
aggtgctcgt gggcagcaag gggaagcccc atggccatgc cgcttccctt tcaccctcag 420
cgacgcgccc tcctgtgccc gcggggaaca agacggctct cggcggccat gcaggcggcc 480
tgtcccacga acacgatgga gacctcagac gccgtcccca ccctgtcact gtcaccatca 540
cccatcctgt cccctcacgc ctccccacat cccatcatta ctac 584

<210> SEQ ID NO 32
<211> LENGTH: 349
<212> TYPE: DNA
<213> ORGANISM: Homo sapiens

<400> SEQUENCE: 32
gaagtagaat cacagtaaat gaggagttag ggaatttagg gtagagatta aagtaatgaa 60
cagaggagga ggcctgagac agctgcagag agaccctgtg ttccctgtga ggtgaagcgt 120
ctgctgtcaa agccggttgg cgctgagaag aggtaccggg ggcagcaccc gcctcctggg 180
agagggatgg gcctgcgggc acctggggga accgcacgga cacagacgac actataaacg 240
cgggcgagac atcagggacc gggaaacaga aggacgcgcg tttcgagcag ctgcccagtg 300
ggccacaagc cccgccacgc cacagcctct tcccctcagc acgcagaga 349

<210> SEQ ID NO 33
<211> LENGTH: 3510
<212> TYPE: DNA
<213> ORGANISM: Homo sapiens

<400> SEQUENCE: 33
tactccggcg acgggaggat gttgagggaa gcctgccagg tgaagaaggg gccagcagca 60
gcacagagct tccgactttg ccttccaggc tctagactcg cgccatgcca agacgggccc 120
ctcgactttc acccctgact cccaactcca gccactggac cgagcgcgca aagaacctga 180
gaccgcttgc tctcaccgcc gcaagtcggt cgcaggacag acaccagtgg gcagcaacaa 240
aaaaagaaac cgggttccgg gacacgtgcc ggcggctgga ctaacctcag cggctgcaac 300
caaggagcgc gcacgttgcg cctgctggtg tttattagct acactggcag gcgcacaact 360

```
ccgcgccccg actggtggcc ccacagcgcg caccacacat ggcctcgctg ctgttggcgg    420
ggtaggcccg aaggaggcat ctacaaatgc ccgagccctt tctgatcccc acccccccgc    480
tccctgcgtc gtccgagtga cagattctac taattgaacg gttatgggtc atccttgtaa    540
ccgttggacg acataacacc acgcttcagt tcttcatgtt ttaaatacat atttaacgga    600
tggctgcaga gccagctggg aaacacgcgg attgaaaaat aatgctccag aaggcacgag    660
actggggcga aggcgagagc gggctgggct tctagcggag accgcagagg gagacatatc    720
tcagaactag gggcaataac gtgggtttct ctttgtattt gtttattttg taactttgct    780
acttgaagac caattattta ctatgctaat ttgtttgctt gtttttaaaa ccgtacttgc    840
acagtaaaag ttccccaaca acggaagtaa cccgacgttc ctcacactcc ctaggagact    900
gtgtgcgtgt gtgcccgcgc gtgcgctcac agtgtcaagt gctagcatcc gagatctgca    960
gaaacaaatg tctgaattcg aaatgtatgg gtgtgagaaa ttcagctcgg ggaagagatt   1020
agggactggg ggagacaggt ggctgcctgt actataagga accgccaacg ccagcatctg   1080
tagtccaagc agggctgctc tgtaaaggct tagcaatttt ttctgtaggc ttgctgcaca   1140
cggtctctgg cttttcccat ctgtaaaatg ggtgaatgca tccgtacctc agctacctcc   1200
gtgaggtgct tctccagttc gggcttaatt cctcatcgtc aagagttttc aggtttcaga   1260
gccagcctgc aatcggtaaa acatgtccca acgcggtcgc gagtggttcc atctcgctgt   1320
ctggcccaca gcgtggagaa gccttgccca ggcctgaaac ttctctttgc agttccagaa   1380
agcaggcgac tgggacggaa ggctctttgc taacctttta cagcggagcc ctgcttggac   1440
tacagatgcc agcgttgccc ctgccccaag gcgtgtggtg atcacaaaga cgacactgaa   1500
aatacttact atcatccggc tcccctgcta ataaatggag gggtgtttaa ctacaggcac   1560
gaccctgccc ttgtgctagc gcggttaccg tgcggaaata actcgtccct gtacccacac   1620
catcctcaac ctaaaggaga gttgtgaatt ctttcaaaac actcttctgg agtccgtccc   1680
ctccctcctt gcccgccctc tacccctcaa gtccctgccc ccagctgggg gcgctaccgg   1740
ctgccgtcgg agctgcagcc acggccatct cctagacgcg cgagtagagc accaagatag   1800
tggggacttt gtgcctgggc atcgtttaca tttggggcgc caaatgccca cgtgttgatg   1860
aaaccagtga gatgggaaca ggcggcggga aaccagacag aggaagagct agggaggaga   1920
ccccagcccc ggatcctggg tcgccagggt tttccgcgcg catcccaaaa ggtgcggctg   1980
cgtggggcat caggttagtt tgttagactc tgcagagtct ccaaaccatc ccatccccca   2040
acctgactct gtggtggccg tattttttac agaaatttga ccacgttccc tttctccctt   2100
ggtcccaagc gcgctcagcc ctccctccat ccccccttgag ccgcccttct cctccccctc   2160
gcctcctcgg gtccctcctc cagtccctcc ccaagaatct cccggccacg ggcgcccatt   2220
ggttgtgcgc agggaggagg cgtgtgcccg gcctggcgag tttcattgag cggaattagc   2280
ccggatgaca tcagcttccc agccccccgg cgggcccagc tcattggcga ggcagcccct   2340
ccaggacacg cacattgttc cccgccccccg cccccgccac cgctgccgcc gtcgccgctg   2400
ccaccgggct ataaaaaccg gccgagcccc taaaggtgcg gatgcttatt atagatcgac   2460
gcgacaccag cgcccggtgc caggttctcc cctgaggctt ttcggagcga gctcctcaaa   2520
tcgcatccag agtaagtgtc cccgccccac agcagccgca gcctagatcc cagggacaga   2580
ctctcctcaa ctcggctgtg acccagaatg ctccgataca gggggtctgg atccctactc   2640
tgcgggccat ttctccagag cgactttgct cttctgtcct ccccacactc accgctgcat   2700
```

-continued

```
ctccctcacc aaaagcgaga agtcggagcg acaacagctc tttctgccca agccccagtc   2760

agctggtgag ctccccgtgg tctccagatg cagcacatgg actctgggcc ccgcgccggc   2820

tctgggtgca tgtgcgtgtg cgtgtgtttg ctgcgtggtg tcgatggaga taaggtggat   2880

ccgtttgagg aaccaaatca ttagttctct atctagatct ccattctccc caaagaaagg   2940

ccctcacttc ccactcgttt attccagccc gggggctcag ttttcccaca cctaactgaa   3000

agcccgaagc ctctagaatg ccacccgcac cccgagggtc accaacgctc cctgaaataa   3060

cctgttgcat gagagcagag gggagataga gagagcttaa ttataggtac ccgcgtgcag   3120

ctaaaaggag ggccagagat agtagcgagg gggacgagga gccacgggcc acctgtgccg   3180

ggaccccgcg ctgtggtact gcggtgcagg cgggagcagc ttttctgtct ctcactgact   3240

cactctctct ctctctccct ctctctctct ctcattctct ctcttttctc ctcctctcct   3300

ggaagttttc gggtccgagg gaaggaggac cctgcgaaag ctgcgacgac tatcttcccc   3360

tggggccatg gactcggacg ccagcctggt gtccagccgc ccgtcgtcgc cagagcccga   3420

tgaccttttt ctgccggccc ggagtaaggg cagcagcggc agcgccttca ctgggggcac   3480

cgtgtcctcg tccaccccga gtgactgccc                                    3510
```

<210> SEQ ID NO 34
<211> LENGTH: 333
<212> TYPE: DNA
<213> ORGANISM: Homo sapiens

<400> SEQUENCE: 34

```
ttaattcgaa aatggcagac agagctgagc gctgccgttc ttttcaggat tgaaaatgtg     60

ccagtgggcc aggggcgctg ggacccgcgg tgcggaagac tcggaacagg aagaaatagt    120

ggcgcgctgg gtgggctgcc ccgccgccca cgccggttgc cgctggtgac agtggctgcc    180

cggccaggca cctccgagca gcaggtctga gcgtttttgg cgtcccaagc gttccgggcc    240

gcgtcttcca gagcctctgc tcccagcggg gtcgctgcgg cctggcccga aggatttgac    300

tctttgctgg gaggcgcgct gctcagggtt ctg                                 333
```

<210> SEQ ID NO 35
<211> LENGTH: 385
<212> TYPE: DNA
<213> ORGANISM: Homo sapiens

<400> SEQUENCE: 35

```
ccggtcccca gtttggaaaa aggcgcaaga agcgggcttt tcagggaccc cggggagaac     60

acgagggctc cgacgcggga gaaggattga agcgtgcaga ggcgccccaa attgcgacaa    120

tttactggga tccttttgtg gggaaaggag gcttagaggc tcaagctata ggctgtccta    180

gagcaactag gcgagaacct ggccccaaac tccctcctta cgccctggca caggttcccg    240

gcgactggtg ttcccaaggg agccccctga gcctaccgcc cttgcagggg gtcgtgctgc    300

ggcttctggg tcataaacgc cgaggtcggg ggtggcggag ctgtagaggc tgcccgcgca    360

gaaagctcca ggatcccaat atgtg                                          385
```

<210> SEQ ID NO 36
<211> LENGTH: 105
<212> TYPE: DNA
<213> ORGANISM: Homo sapiens

<400> SEQUENCE: 36

```
gcgcaggtcc ccccagtccc cgagggagtg cgcccgacgg aaacgcccct agcccgcggg     60
```

cctcgctttc ctctcccggg ttcctgggtc acttcccgct gtctc 105

<210> SEQ ID NO 37
<211> LENGTH: 147
<212> TYPE: DNA
<213> ORGANISM: Homo sapiens

<400> SEQUENCE: 37
ttccctcgcg gctttggaaa gggggtgcaa atgcaccctt ctgcgggccc gctacccgct 60
gcaacacctg tgtttccttt ctgggcacct tctaggtttc tagatattgc tgtgaatacg 120
gtcctccgct gtacagttga aaacaaa 147

<210> SEQ ID NO 38
<211> LENGTH: 365
<212> TYPE: DNA
<213> ORGANISM: Homo sapiens

<400> SEQUENCE: 38
tgggaattta ggtcgggcac tgccgatatg tcgccttcca caaggcgggc ccgggcctct 60
gctgaccgtg caccggtcct ggggctgggt aattctgcag cagcagcgca gcccatgccg 120
gggaatttgc gggcagagga gacagtgagg cccgcgttct gtgcgggaac tcccgagctc 180
acagagccca agaccacacg gctgcatctg cttggctgac tgggccaggc ccacgcgtag 240
taacccggac gtctctctct cacagtcccc ttgcgtctgg ccagggagct gccaggctgc 300
accccgcggt ggggatcggg agaggggcag tgtcgcccat ccccggaagg ctgagcctgg 360
tgcag 365

<210> SEQ ID NO 39
<211> LENGTH: 418
<212> TYPE: DNA
<213> ORGANISM: Homo sapiens

<400> SEQUENCE: 39
cggttttctc ctggaggact gtgttcagac agatactggt ttccttatcc gcaggtgtgc 60
gcggcgctcg caagtggtca gcataacgcc gggcgaattc ggaaagcccg tgcgtccgtg 120
gacgacccac ttggaaggag ttgggagaag tccttgttcc cacgcgcgga cgcttccctc 180
cgtgtgtcct tcgagccaca aaaagcccag accctaaccc gctcctttct cccgccgcgt 240
ccatgcagaa ctccgccgtt cctgggaggg gaagcccgcg aggcgtcggg agaggcacgt 300
cctccgtgag caaagagctc ctccgagcgc gcggcgggga cgctgggccg acaggggacc 360
gcgggggcag ggcggagagg acccgccctc gagtcggccc agccctaaca ctcaggac 418

<210> SEQ ID NO 40
<211> LENGTH: 906
<212> TYPE: DNA
<213> ORGANISM: Homo sapiens

<400> SEQUENCE: 40
agggaatcgg gctgaccagt cctaaggtcc cacgctcccc tgacctcagg gcccagagcc 60
tcgcattacc ccgagcagtg cgttggttac tctccctgga aagccgcccc cgccggggca 120
agtgggagtt gctgcactgc ggtctttgga ggcctaggtc gcccagagta ggcggagccc 180
tgtatccctc ctggagccgg cctgcggtga ggtcggtacc cagtacttag ggagggagga 240
cgcgcttggt gctcagggta ggctgggccg ctgctagctc ttgatttagt ctcatgtccg 300

```
cctttgtgcc ggcctctccg atttgtgggt ccttccaaga aagagtcctc tagggcagct    360

agggtcgtct cttgggtctg gcgaggcggc aggccttctt cggacctatc cccagaggtg    420

taacggagac tttctccact gcagggcggc ctggggcggg catctgccag gcgagggagc    480

tgccctgccg ccgagattgt ggggaaacgg cgtggaagac accccatcgg agggcaccca    540

atctgcctct gcactcgatt ccatcctgca acccaggaga aaccatttcc gagttccagc    600

cgcagaggca cccgcggagt tgccaaaaga gactcccgcg aggtcgctcg gaaccttgac    660

cctgacacct ggacgcgagg tctttcagga ccagtctcgg ctcggtagcc tggtccccga    720

ccaccgcgac caggagttcc ttcttccctt cctgctcacc agccggccgc cggcagcggc    780

tccaggaagg agcaccaacc cgcgctgggg gcggaggttc aggcggcagg aatggagagg    840

ctgatcctcc tctagccccg gcgcattcac ttaggtgcgg gagccctgag gttcagcctg    900

actttc                                                                906
```

<210> SEQ ID NO 41
<211> LENGTH: 860
<212> TYPE: DNA
<213> ORGANISM: Homo sapiens

<400> SEQUENCE: 41

```
cactacggat ctgcctggac tggttcagat gcgtcgttta aagggggggg ctggcactcc     60

agagaggagg gggcgctgca ggttaattga tagccacgga agcacctagg cgccccatgc    120

gcggagccgg agccgccagc tcagtctgac ccctgtcttt tctctcctct tccctctccc    180

acccctcact ccgggaaagc gagggccgag gtaggggcag atagatcacc agacaggcgg    240

agaaggacag gagtacagat ggagggacca ggacacagaa tgcaaaagac tggcaggtga    300

gaagaaggga gaaacagagg gagagagaaa gggagaaaca gagcagaggc ggccgccggc    360

ccggccgccc tgagtccgat ttccctcctt ccctgaccct tcagtttcac tgcaaatcca    420

cagaagcagg tttgcgagct cgaatacctt tgctccactg ccacacgcag caccgggact    480

gggcgtctgg agcttaagtc tgggggtctg agcctgggac cggcaaatcc gcgcagcgca    540

tcgcgcccag tctcggagac tgcaaccacc gccaaggagt acgcgcggca ggaaacttct    600

gcggcccaat ttcttcccca gctttggcat ctccgaaggc acgtacccgc cctcggcaca    660

agctctctcg tcttccactt cgacctcgag gtggagaaag aggctggcaa gggctgtgcg    720

cgtcgctggt gtggggaggg cagcaggctg cccctccccg cttctgcagc gagttttccc    780

agccaggaaa agggagggag ctgtttcagg aatttcagtg ccttcaccta gcgactgaca    840

caagtcgtgt gtataggaag                                                 860
```

<210> SEQ ID NO 42
<211> LENGTH: 452
<212> TYPE: DNA
<213> ORGANISM: Homo sapiens

<400> SEQUENCE: 42

```
ggagcctgaa gtcagaaaag atggggcctc gttactcact ttctagccca gcccctggcc     60

ctgggtcccg cagagccgtc atcgcaggct cctgcccagc ctctggggtc gggtgagcaa    120

ggtgttctct tcggaagcgg gaagggctgc gggtcgggga cgtcccttgg ctgccacccc    180

tgattctgca tccttttcgc tcgaatccct gcgctaggca tcctccccga tcccccaaaa    240

gcccaagcac tgggtctggg ttgaggaagg gaacgggtgc ccaggccgga cagaggctga    300

aaggaggcct caaggttcct ctttgctaca aagtggagaa gttgctctac tctggagggc    360
```

agtggccttt tccaaacttt tccacttagg tccgtaagaa aagcaattca tacacgatca 420
gcgctttcgg tgcgaggatg gaaagaaact tc 452

<210> SEQ ID NO 43
<211> LENGTH: 1992
<212> TYPE: DNA
<213> ORGANISM: Homo sapiens

<400> SEQUENCE: 43
ttttcctgtt acagagctga gcccactcat gtggtgccaa gtagcgacta tctctcggcc 60
acctccaccc agagcaatgt gggcgccccc agcgggtggg agcgattgcc gagcggcgca 120
agggcgttta acgcctaacc ccctcctcct gggttgccaa gccgctaggt cgccgtttcc 180
aacgtggctg cgcgggactg aagtccgacg actcctcgtc ctcagtagga gacacacctc 240
ccactgcccc cagccacgcg agctatgggc agaatcgggg caacggtaat atctggatgg 300
ggcaggctcc cctgaggctg tgcttaagaa aaaaggaatc tggagtagcc tgagggggccc 360 cacgaggggg cctcctttgc gatcgtctcc cagccttagg ccaaggctac ggaggcaggc 420
ggccgagtgt tggcgcccag cccggccgag gactggatgg aggacgagaa gcagcctgcc 480
tctgggcgac agctgcggac gcagcctcgc cgcctcgccg cctcagcctc ggtcccagcg 540
tctctaaagc cgcgcccatt ttacagatgc agggcaggga gacaagaggc atctccgggg 600
gccgagtaga atgatggcgc gggttctccc ggcgccctga tttcgaggct gcgcccgggg 660
ccctacatgc aggcggggag gcctgggccg aaggcgtctg caaggagggg cgagtctgcc 720
cggtccgggc agggagtgag gccacagtca gttctcccta ggaggccgcg cagcgggtag 780
ggtatgggac tgggggacgc aacggggacc tggccgaatc agagccctca gcagagaacg 840
ccgaaaactc tggggccggc cgctcgcttc ccgctagtgg gaatggtttc cggtcatccg 900
ttcccagtcc agccccgggt agggagctct gatttgcaat gcacagcact tgcgaggttc 960
gaatgccccc gcaatttgca gatggaaata ctaagcctag gccgggcgtg gtggctcaag 1020
cctatcatct cagccctttg ggaggccaag ccgggaggat tgtttgagcc caagaattca 1080
aaaccagcct gagcaacata gcgaccccgt ctctacaaaa taaaataaaa taaattatcc 1140
gggcgtggtg gcacgcgcct gtggttccag ctactccgga ggctgaggtg ggaggatcgc 1200
ttgagtccgg gaggtcgagg ctacagtgag ccgtgatcgc accactgcac tccagcctgg 1260
gcgacagagt gagaccttgt ctcaaaaaag gaaaaaaaga aaaagaaagt aagcttcaaa 1320
gaagctctga taatagttct gggtcgtgca gcggtggcgg ccccgcgctc tcgcccctaa 1380
agcaagcgct ctttgtactg ggtggaggag ctttgagtag tgagggtgga gatgcagctt 1440
cggggtggcg cagccaccct gacactaggc ccggggtcgc agtgggacag aagagtctgc 1500
cgctctgact tgggctctga gttccaaggg cgcccggcac ttctagcctc ccaggcttgc 1560
gcgctggcgc ctttgccatc cgtgccgaag tggggagacc tagccgcgac caccacgagc 1620
gcagcggtga cacccagagg tcccaccggg cccctgggca gggtaacctt agcctgtccg 1680
cttcggcagc tttgcgaaga gtggcgcgca gctagggctg aggctcttgc ggacctgcgg 1740
tcgaagcagg cggctgagcc agttcgatcg ccaaggcctg ggctgccgac agtggtgcgc 1800
gctctgttcc gccgcggccg ggccaggcgc tctggaatag cgatgggggg acacggcctc 1860
caactttctg cagagaccat cgggcagctc cgggcctaag cagcgacctc accgaaggtt 1920
cctgggaacc tttgccaaaa tcccagcctc tgcctcggtc cagctaaacc gtgtgtaaac 1980
aagtgcacca ag 1992

<210> SEQ ID NO 44
<211> LENGTH: 448
<212> TYPE: DNA
<213> ORGANISM: Homo sapiens

<400> SEQUENCE: 44
ataaaggacc gggtaatttc gcggaatgcg gattttgaga caggcccaga cggcggcgga 60
ttccctgtgt cccccaactg gggcgatctc gtgaacacac ctgcgtccca ccccgatcct 120
aggttggggg gaaagggtat gggaaccctg agcccagagc gcgccccgct ctttcctttg 180
ctccccggct tccctggcca gccccctccc ggctggtttc ctcgctcact cggcgcctgg 240
cgtttcgggc gtctggagat caccgcgtgt ctggcacccc aacgtctagt ctccccgcag 300
gttgaccgcg gcgcctggag ccgggaatag gggtggggag tccggagaac caaacccgag 360
cctgaagttg ccattcgggt gactcccgag aaagcccggg agcattttgg ccaatgcggg 420
tttttacctg aacttcagca tcttcacc 448

<210> SEQ ID NO 45
<211> LENGTH: 395
<212> TYPE: DNA
<213> ORGANISM: Homo sapiens

<400> SEQUENCE: 45
aattggaaaa ccctggtatt gtgcctgttt gggggaagaa aacgtcaata aaaattaatt 60
gatgagttgg cagggcgggc ggtgcgggtt cgcggcgagg cgcagggtgt catggcaaat 120
gttacggctc agattaagcg attgttaatt aaaaagcgac ggtaattaat actcgctacg 180
ccatatgggc ccgtgaaaag gcacaaaagg tttctccgca tgtggggttc cccttctctt 240
ttctccttcc acaaaagcac cccagcccgt gggtcccccc tttggcccca aggtaggtgg 300
aactcgtcac ttccggccag ggaggggatg gggcggtctc cggcgagttc caagggcgtc 360
cctcgttgcg cactcgcccg cccaggttct ttgaa 395

<210> SEQ ID NO 46
<211> LENGTH: 491
<212> TYPE: DNA
<213> ORGANISM: Homo sapiens

<400> SEQUENCE: 46
gggaagcgat cgtctcctct gtcaactcgc gcctgggcac ttagcccctc ccgtttcagg 60
gcgccgcctc cccggatggc aaacactata aagtggcggc gaataaggtt cctcctgctg 120
ctctcggttt agtccaagat cagcgatatc acgcgtcccc cggagcatcg cgtgcaggag 180
ccatggcgcg ggagctatac cacgaagagt tcgcccgggc gggcaagcag gcggggctgc 240
aggtctggag gattgagaag ctggagctgg tgcccgtgcc ccagagcgct cacggcgact 300
tctacgtcgg ggatgcctac ctggtgctgc acacggccaa gacgagccga ggcttcacct 360
accacctgca cttctggctc ggtaagggac ggcgggcggc gggaccccga cgcaccaagg 420
ccggcgaggg gagggcgtag gggtctgaga tttgcaggcg tgggagtaaa ggggaccgca 480
aactgagcta g 491

<210> SEQ ID NO 47
<211> LENGTH: 1284
<212> TYPE: DNA
<213> ORGANISM: Homo sapiens

<400> SEQUENCE: 47
ctcaggggcg ggaagtggcg ggtgggagtc acccaagcgt gactgcccga ggcccctcct 60
gccgcggcga ggaagctcca taaaagccct gtcgcgaccc gctctctgca ccccatccgc 120
tggctctcac ccctcggaga cgctcgcccg acagcatagt acttgccgcc cagccacgcc 180
cgcgcgccag ccaccgtgag tgctacgacc cgtctgtcta ggggtgggag cgaacggggc 240
gcccgcgaac ttgctagaga cgcagcctcc cgctctgtgg agccctgggg ccctgggatg 300
atcgcgctcc actccccagc ggactatgcc ggctccgcgc cccgacgcgg accagccctc 360
ttggcggcta aattccactt gttcctctgc tcccctctga ttgtccacgg cccttctccc 420
gggcccttcc cgctgggcgg ttcttctgag ttacctttta gcagatatgg agggagaacc 480
cgggaccgct atcccaaggc agctggcggt ctccctgcgg gtcgccgcct tgaggcccag 540
gaagcggtgc gcggtaggaa ggtttccccg gcagcgccat cgagtgagga atccctggag 600
ctctagagcc ccgcgccctg ccacctccct ggattcttgg gctccaaatc tctttggagc 660
aattctggcc cagggagcaa ttctctttcc ccttccccac cgcagtcgtc accccgaggt 720
gatctctgct gtcagcgttg atcccctgaa gctaggcaga ccagaagtaa cagagaagaa 780
acttttcttc ccagacaaga gtttgggcaa gaagggagaa aagtgaccca gcaggaagaa 840
cttccaattc ggttttgaat gctaaactgg cggggccccc accttgcact ctcgccgcgc 900
gcttcttggt ccctgagact tcgaacgaag ttgcgcgaag ttttcaggtg gagcagaggg 960
gcaggtcccg accggacggc gcccggagcc cgcaaggtgg tgctagccac tcctgggttc 1020
tctctgcggg actgggacga gagcggattg gggtcgcgt gtggtagcag gaggaggagc 1080
gcggggggca gaggagggag gtgctgcgcg tgggtgctct gaatccccaa gcccgtccgt 1140
tgagccttct gtgcctgcag atgctaggta acaagcgact ggggctgtcc ggactgaccc 1200
tcgccctgtc cctgctcgtg tgcctgggtg cgctggccga ggcgtacccc tccaagccgg 1260
acaacccggg cgaggacgca ccag 1284

<210> SEQ ID NO 48
<211> LENGTH: 554
<212> TYPE: DNA
<213> ORGANISM: Homo sapiens

<400> SEQUENCE: 48
tggagaacct tgggctctgt ggcctcaaag gtaggggtga tttcgagggg ccggcacctc 60
acagggcagg ttccaccgcg gaaacgcagt catcgcccag cgaccctgct cctggccctc 120
agcctccccc caggtttctt tttctcttga atcaagccga ggtgcgccaa tggccttcct 180
tgggtcggat ccggggggcc agggccagct tacctgcttt caccgagcag tggatatgtg 240
ccttggactc gtagtacacc cagtcgaagc cggcctccac cgccaggcgg gccagcatgc 300
cgtacttgct gcggtcgcgg tcagacgtgg tgatgtccac tgcgcggccc tcgtagtgca 360
gagactcctc tgagtggtgg ccatcttcgt cccagccctc ggtcacccgc agtttcactc 420
ctggccactg gttcatcacc gagatggcca aagcgttcaa cttgtcctta cacctctgcg 480
aagacaaggg gacccccacc gacggacacg ttagcctggg caaccgccac ccctcccggc 540
ccctccatca gcct 554

<210> SEQ ID NO 49
<211> LENGTH: 772
<212> TYPE: DNA

<213> ORGANISM: Homo sapiens

<400> SEQUENCE: 49
tctcacgacc catccgttaa cccaccgttc ccaggagctc cgaggcgcag cggcgacaga 60
ggttcgcccc ggcctgctag cattggcatt gcggttgact gagcttcgcc taacaggctt 120
ggggagggtg ggctgggctg ggctgggctg ggctgggtgc tgcccggctg tccgcctttc 180
gttttcctgg gaccgaggag tcttccgctc cgtatctgcc tagagtctga atccgacttt 240
ctttcctttg ggcacgcgct cgccagtgga gcacttcttg ttctggcccc gggctgatct 300
gcacgcggac ttgagcaggt gccaaggtgc cacgcagtcc cctcacggct ttcggggggt 360
cttggagtcg ggtggggagg gagacttagg tgtggtaacc tgcgcaggtg ccaaagggca 420
gaaggagcag ccttggatta tagtcacggt ctctccctct cttccctgcc atttttaggg 480
ctttctctac gtgctgttgt ctcactgggt ttttgtcgga gccccacgcc ctccggcctc 540
tgattcctgg aagaaagggt tggtcccctc agcaccccca gcatcccgga aaatggggag 600
caaggctctg ccagcgccca tcccgctcca cccgtcgctg cagctcacca attactcctt 660
cctgcaggcc gtgaacacct tcccggccac ggtggaccac ctgcagggcc tgtacggtct 720
cagcgcggta cagaccatgc acatgaacca ctggacgctg gggtatccca at 772

<210> SEQ ID NO 50
<211> LENGTH: 1362
<212> TYPE: DNA
<213> ORGANISM: Homo sapiens

<400> SEQUENCE: 50
tggtttcctt tcgcttctcg cctcccaaac acctccagca agtcggaggg cgcgaacgcg 60
gagccagaaa cccttcccca aagtttctcc cgccaggtac ctaattgaat catccatagg 120
atgacaaatc agccagggcc aagatttcca gacacttgag tgacttcccg gtccccgagg 180
tgacttgtca gctccagtga gtaacttgga actgtcgctc ggggcaaggt gtgtgtctag 240
gagagagccg gcggctcact cacgctttcc agagagcgac ccgggccgac ttcaaaatac 300
acacagggtc atttataggg actggagccg cgcgcaggac aacgtctccg agactgagac 360
attttccaaa cagtgctgac attttgtcgg gccccataaa aaatgtaaac gcgaggtgac 420
gaacccggcg gggagggttc gtgtctggct gtgtctgcgt cctggcggcg tgggaggtta 480
tagttccaga cctggcggct gcggatcgcc gggccggtac ccgcgaggag tgtaggtacc 540
ctcagcccga ccacctcccg caatcatggg gacaccggct tggatgagac acaggcgtgg 600
aaaacagcct tcgtgaaact ccacaaacac gtggaacttg aaaagacaac tacagccccg 660
cgtgtgcgcg agagacctca cgtcacccca tcagttccca cttcgccaaa gtttcccttc 720
agtggggact ccagagtggt gcgccccatg cccgtgcgtc ctgtaacgtg ccctgattgt 780
gtacccctct gcccgctcta cttgaaatga aaacacaaaa actgttccga attagcgcaa 840
ctttaaagcc ccgttatctg tcttctacac tgggcgctct taggccactg acagaaacat 900
ggtttgaacc ctaattgttg ctatcagtct cagtcagcgc aggtctctca gtgacctgtg 960
acgccgggag ttgaggtgcg cgtatcctta aacccgcgcg aacgccaccg gctcagcgta 1020
gaaaactatt tgtaatccct agtttgcgtc tctgagcttt aactccccca cactctcaag 1080
cgcccggttt ctcctcgtct ctcgcctgcg agcaaagttc ctatggcatc cacttaccag 1140
gtaaccggga tttccacaac aaagcccggc gtgcgggtcc cttcccccgg ccggccagcg 1200
cgagtgacag cgggcggccg gcgctggcga ggagtaactt ggggctccag cccttcagag 1260
cgctccgcgg gctgtgcctc cttcggaaat gaaaaccccc atccaaacgg ggggacggag 1320
cgcggaaacc cggcccaagt gccgtgtgtg cgcgcgcgtc tg 1362

<210> SEQ ID NO 51
<211> LENGTH: 476
<212> TYPE: DNA
<213> ORGANISM: Homo sapiens

<400> SEQUENCE: 51
gaaagccatc cttaccattc ccctcaccct ccgccctctg atcgcccacc cgccgaaagg 60
gtttctaaaa atagcccagg gcttcaaggc cgcgcttctg tgaagtgtgg agcgagcggg 120
cacgtagcgg tctctgccag gtggctggag ccctggaagc gagaaggcgc ttcctccctg 180
catttccacc tcaccccacc cccggctcat ttttctaaga aaaagttttt gcggttccct 240
ttgcctccta cccccgctgc cgcgcggggt ctgggtgcag acccctgcca ggttccgcag 300
tgtgcagcgg cggctgctgc gctctcccag cctcggcgag ggttaaaggc gtccggagca 360
ggcagagcgc cgcgcgccag tctattttta cttgcttccc ccgccgctcc gcgctccccc 420
ttctcagcag ttgcacatgc cagctctgct gaaggcatca atgaaaacag cagtag 476

<210> SEQ ID NO 52
<211> LENGTH: 300
<212> TYPE: DNA
<213> ORGANISM: Homo sapiens

<400> SEQUENCE: 52
atcgaaaatg tcgacatctt gctaatggtc tgcaaacttc cgccaattat gactgacctc 60
ccagactcgg ccccaggagg ctcgtattag gcagggaggc cgccgtaatt ctgggatcaa 120
aagcgggaag gtgcgaactc ctctttgtct ctgcgtgccc ggcgcgcccc cctcccggtg 180
ggtgataaac ccactctggc gccggccatg cgctgggtga ttaatttgcg aacaaacaaa 240
agcggcctgg tggccactgc attcgggtta aacattggcc agcgtgttcc gaaggcttgt 300

<210> SEQ ID NO 53
<211> LENGTH: 1246
<212> TYPE: DNA
<213> ORGANISM: Homo sapiens

<400> SEQUENCE: 53
atcaacatcg tggctttggt cttttccatc atggtgagtg aatcacggcc agaggcagcc 60
tgggaggaga gacccgggcg gctttgagcc cctgcagggg agtccgcgcg ctctctgcgg 120
ctcccttcct cacggcccgg cccgcgctag gtgttctttg tcctcgcacc tcctcctcac 180
ctttctcggg ctctcagagc tctccccgca atcatcagca cctcctctgc actcctcgtg 240
gtactcagag ccctgatcaa gcttccccca ggctagcttt cctcttcttt ccagctccca 300
gggtgcgttt cctctccaac ccggggaagt tcttccgtgg actttgctga ctcctctgac 360
cttcctaggc acttgcccgg ggcttctcaa ccctcttttc tagagcccca gtgcgcgcca 420
ccctagcgag cgcagtaagc tcataccccg agcatgcagg ctctacgttc ctttccctgc 480
cgctccgggg gctcctgctc tccagcgccc aggactgtct ctatctcagc ctgtgctccc 540
ttctctcttt gctgcgccca agggcaccgc ttccgccact ctccgggggg tccccaggcg 600
attcctgatg ccccctcctt gatcccgttt ccgcgctttg gcacggcacg ctctgtccag 660
gcaacagttt cctctcgctt cttcctacac ccaacttcct ctccttgcct ccctccggcg 720

-continued

```
ccccctttttt aacgcgcccg aggctggctc acacccacta cctctttagg cctttcttag    780

gctccccgtg tgccccccctc accagcaaag tgggtgcgcc tctcttactc tttctaccca    840

gcgcgtcgta gttcctcccc gtttgctgcg cactggccct aacctctctt ctcttggtgt    900

cccccagagc tcccaggcgc ccctccaccg ctctgtcctg cgcccggggc tctcccggga    960

atgaactagg ggattccacg caacgtgcgg ctccgcccgc cctctgcgct cagacctccc   1020

gagctgcccg cctctctagg agtggccgct ggggcctcta gtccgccctt ccggagctca   1080

gctccctagc cctcttcaac cctggtagga acacccgagc gaaccccacc aggagggcga   1140

cgagcgcctg ctaggccctc gccttattga ctgcagcagc tggcccgggg gtggcggcgg   1200

ggtgaggttc gtaccggcac tgtcccggga caacccttgc agttgc                  1246
```

<210> SEQ ID NO 54
<211> LENGTH: 984
<212> TYPE: DNA
<213> ORGANISM: Homo sapiens

<400> SEQUENCE: 54

```
acaaataaaa caccctctag cttcccctag actttgttta actggccggg tctccagaag     60

gaacgctggg gatgggatgg gtggagagag ggagcggctc aaggacttta gtgaggagca    120

ggcgagaagg agcacgttca ggcgtcaaga ccgatttctc cccctgcttc gggagacttt    180

tgaacgctcg gagaggcccg gcatctcacc actttacttg gccgtagggg cctccggcac    240

ggcaggaatg agggaggggg tccgattgga cagtgacggt ttggggccgt tcggctatgt    300

tcagggacca tatggtttgg ggacagcccc agtagttagt aggggacggg tgcgttcgcc    360

cagtccccgg atgcgtaggg aggcccagtg gcaggcagct gtcccaagca gcgggtgcgc    420

gtccctgcgc gctgtgtgtt cattttgcag agccagcctt cggggaggtg aaccagctgg    480

gaggagtgtt cgtgaacggg aggccgctgc ccaacgccat ccggcttcgc atcgtggaac    540

tggcccaact gggcatccga ccgtgtgaca tcagccgcca gctacgggtc tcgcacggct    600

gcgtcagcaa gatcctggcg cgatacaacg agacgggctc gatcttgcca ggagccatcg    660

ggggcagcaa gccccgggtc actaccccca ccgtggtgaa acacatccgg acctacaagc    720

agagagaccc cggcatcttc gcctgggaga tccgggaccg cctgctggcg gacggcgtgt    780

gcgacaagta caatgtgccc tccgtgagct ccatcagccg cattctgcgc aacaagatcg    840

gcaacttggc ccagcagggt cattacgact catacaagca gcaccagccg acgccgcagc    900

cagcgctgcc ctacaaccac atctactcgt accccagccc tatcacggcg gcggccgcca    960

aggtgcccac gccacccggg gtgc                                           984
```

<210> SEQ ID NO 55
<211> LENGTH: 545
<212> TYPE: DNA
<213> ORGANISM: Homo sapiens

<400> SEQUENCE: 55

```
aggaggcgca acgcgctgcc agggcggctt tatcctgccg ccacagggcg gggaccagcc     60

cggcagccgg gtgtccagcg ccgctcacgt gcctcgcctg gagcttagct ctcagactcc    120

gaagagggcg actgagactt gggcctggga gttggcttcg gggtacccaa ggcgacgaca    180

gctgagttgt accacgaagc tcaggccgag gcctcctccc ttgtctggcc ttcgaatcca    240

tactggcagc ctctcctctc aggcactccg cgggccgggc cactaggccc cctgctcctg    300

gagctgcgct atgatccggg tcttgagatg cgcgcgattc tctctgaacc ggtggagagg    360
```

-continued aggctctgcc ccgcgcggag cgaggacagc ggcgcccgag cttcccgcgc ctctccaggg 420
cccaatggca agaacagcct ccgaagtgcg cggatgacag gaaaagatct tcagttcttc 480
tgccgctaga gaagtgcggg atacaagcct ctattggatc cacaacctgg agtcctgcct 540
tcgga 545

<210> SEQ ID NO 56
<211> LENGTH: 1533
<212> TYPE: DNA
<213> ORGANISM: Homo sapiens

<400> SEQUENCE: 56
atctgcgtgc ccttttctgg gcgagccctg ggagatccag ggagaactgg gcgctccaga 60
tggtgtatgt ctgtaccttc acagcaaggc ttcccttgga tttgaggctt cctattttgt 120
ctgggatcgg ggtttctcct tgtcccagtg gcagccccgc gttgcgggtt ccgggcgctg 180
cgcggagccc aaggctgcat ggcagtgtgc agcgcccgcc agtcgggctg gtgggttgtg 240
cactccgtcg gcagctgcag aaaggtggga gtgcaggtct tgcctttcct caccgggcgg 300
ttggcttcca gcaccgaggc tgacctatcg tggcaagttt gcggcccccg cagatcccca 360
gtggagaaag agggctcttc cgatgcgatc gagtgtgcgc ctccccgcaa agcaatgcag 420
accctaaatc actcaaggcc tggagctcca gtctcaaagg tggcagaaaa ggccagacct 480
aactcgagca cctactgcct tctgcttgcc ccgcagagcc ttcagggact gactgggacg 540
cccctggtgg cgggcagtcc catccgccat gagaacgccg tgcagggcag cgcagtggag 600
gtgcagacgt accagccgcc gtggaaggcg ctcagcgagt ttgccctcca gagcgacctg 660
gaccaacccg ccttccaaca gctggtgagg ccctgcccta cccgccccga cctcgggact 720
ctgcgggttg ggatttagcc cacttagcct ggcagagagg ggagggggtg gccttgggct 780
gaggggctgg gtacagccct aggcggtggg ggagggggaa cagtggcggg ctctgaaacc 840
tcacctcggc ccattacgcg ccctaaacca ggtctccctg gattaaagtg ctcacaagag 900
aggtcgcagg attaaccaac ccgctccccc gccctaatcc ccccctcgtg cgcctgggga 960
cctggcctcc ttctccgcag ggcttgctct cagctggcgg ccggtcccca agggacactt 1020
tccgactcgg agcacgcggc cctggagcac cagctcgcgt gcctcttcac ctgcctcttc 1080
ccggtgtttc cgccgcccca ggtctccttc tccgagtccg gctccctagg caactcctcc 1140
ggcagcgacg tgacctccct gtcctcgcag ctcccggaca cccccaacag tatggtgccg 1200
agtcccgtgg agacgtgagg gggacccctc cctgccagcc cgcggacctc gcatgctccc 1260
tgcatgagac tcacccatgc tcaggccatt ccagttccga aagctctctc gccttcgtaa 1320
ttattctatt gttatttatg agagagtacc gagagacacg gtctggacag cccaaggcgc 1380
caggatgcaa cctgctttca ccagactgca gacccctgct ccgaggactc ttagtttttc 1440
aaaaccagaa tctgggactt accagggtta gctctgccct ctcctctcct ctctacgtgg 1500
ccgccgctct gtctctccac gccccacctg tgt 1533

<210> SEQ ID NO 57
<211> LENGTH: 702
<212> TYPE: DNA
<213> ORGANISM: Homo sapiens

<400> SEQUENCE: 57
aggtctcttc agactgccca ttctccgggc ctcgctgaat gcgggggctc tatccacagc 60

-continued

```
gcgcggggcc gagctcaggc aggctggggc gaagatctga ttctttcctt cccgccgcca    120

aaccgaatta atcagtttct tcaacctgag ttactaagaa agaaaggtcc ttccaaataa    180

aactgaaaat cactgcgaat gacaatacta tactacaagt tcgttttggg gccggtgggt    240

gggatggagg agaaagggca cggataatcc cggagggccg cggagtgagg aggactatgg    300

tcgcggtgga atctctgttc cgctggcaca tccgcgcagg tgcggctctg agtgctggct    360

cggggttaca gacctcggca tccggctgca ggggcagaca gagacctcct ctgctagggc    420

gtgcggtagg catcgtatgg agcccagaga ctgccgagag cactgcgcac tcaccaagtg    480

ttaggggtgc ccgtgataga ccgccaggga aggggctggt tcggagggaa ttcccgctac    540

cgggaaggtc ggaactcggg gtgatcaaac aaggaatgca tctcacctcc gtgggtgctt    600

gtgctgcgca aggaattatt accggagcgg ttgcgatggc ctttgcccgg cgacccaaga    660

agagtaagca aactaccgtc cacccagcgg atcaggtcca at                       702


<210> SEQ ID NO 58
<211> LENGTH: 3180
<212> TYPE: DNA
<213> ORGANISM: Homo sapiens

<400> SEQUENCE: 58

gatgtcctgt ttctagcagc ctccagagcc aagctaggcg agaggcgtag gaggcagaga     60

gagcgggcgc gggaggccag ggtccgcctg ggggcctgag gggacttcgt ggggtcccgg    120

gagtggccta gaaacaggga gctgggaggg ccgggaagag cttgaggctg agcgggggac    180

gaacgggcag cgcaaagggg agatgaacgg aatggccgag gagccacgca ttcgccttgt    240

gtccgcggac ccttgttccc gacaggcgac caagccaagg ccctccggac tgacgcggcc    300

tgagcagcag cgagtgtgaa gtttggcacc tccggcggcg agacggcgcg ttctggcgcg    360

cggctcctgc gtccggctgg tggagctgct gcgccctatg cggcctgccg agggcgccgc    420

cgagggcccg cgagctccgt ggggtcgggg tggggggacc cgggagcgga cagcgcggcc    480

cgaggggcag gggcaggggc gcgcctggcc tggggtgtgt ctgggccccg gctccgggct    540

cttgaaggac cgcgagcagg aggcttgcgc aatcccttgg ctgagcgtcc acggagaaag    600

aaaaagagca aaagcagagc gagagtggag cgagggatgg gggcgggcaa agagccatcc    660

gggtctccac caccgccctg acacgcgacc cggctgtctg ttggggaccg cacgggggct    720

cgggcgagca ggggagggag gagcctgcgc ggggctcgtg ttcgcccagg aatcccggag    780

aagctcgaag acggtctggt gttgaacgca cacgtggact ccatttcatt accaccttgc    840

agctcttgcg ccacggaggc tgctgctgcc cggcggctgc tacccaccga gacccacgtg    900

gcccctcccc aggggtgtag gggtgacggt tgtcttctgg tgacagcaga ggtgttgggt    960

ttgcgactga tctctaacga gcttgaggcg caaacctagg attccctgag tgttggggtg   1020

cggcgggggg gcaagcaagg tgggacgacg cctgcctggt ttccctgact agttgcgggg   1080

ggtgggggcc ggctctcagg ggccaccaga agctgggtgg gtgtacagga aaatattttt   1140

ctcctgccgt gtttggcttt ttcctggcat ttttgcccag ggcgaagaac tgtcgcgcgg   1200

ggcagctcca ccgcggaggg agaggggtcg cgaggctggc gcgggaagcg ctgtaggtgg   1260

cagtcatccg tccacgccgc acaggccgtc tgcgccgtcg gaccatcggg aggtctgcag   1320

caactttgtc ccggccagtc cccttgtccg ggaaggggct gagcttcccg acactctacc   1380

ctccccctct tgaaaatccc ctggaaaatc tgtttgcaat gggtgtttcc gcggcgtcca   1440

ggtctgggct gccgggggag gccgagcggc tgctgcagcc tccctgctgc caggggcgtc   1500
```

ggactccgct tcgctcacta cgcccaggcc cctcaggggc ccacgctcag gacttcgggg 1560
ccacacagca ggacccggtg ccccgacgac gagtttgcgc aggacccggg ctgggccagc 1620
cgcggagctg gggaggaagg ggcgggggtc ggtgcagcgg atcttttctg ttgctgcctg 1680
tgcggcggca ggaagcgtct tgaggctccc caagactacc tgaggggccg cccaagcact 1740
tcagaagccc aaggagcccc cggccacccc cgctcctggc ctttttgcca acgactttga 1800
aagtgaaatg cacaagcacc agcaattgac ttcccttccg tggttattta ttttgtcttt 1860
gtggatggtg ggcagatggg gagagaggcc cctacctaac ctcggtggct ggtccctaga 1920
ccacccctgc cagccggtgt ggggaggagc tcaggtccgc gggagagcga atgggcgcca 1980
ggaggtggga cagaatcctg ggaaggtaca gcggacgccc tggaagctcc cctgatgccc 2040
cagagggccc ttcctgggaa acctcccggg ggggtgcccc ataccatccc acccggctgt 2100
cttggcccct cccagggagc cgcaggagaa actagcccta cacctgggat tcccagagcc 2160
ttctgctggg gctcctgccc ccgacttcgg ataaccagct ccgcacaggt ccccgagaag 2220
ggccgctggc ctgcttattt gatactgccc cctcccagac aggggctggt cgagcccctg 2280
gttctgctgc cagactgaag ccttccagac gccacctcgg tttgggcccc cagggccctc 2340
aggggcccca ggagaggaga gctgctatct agctcagcca caggctcgct cctggtgggg 2400
gccaggctga aggagtggac cctggagagg tcgggaacct tttaacagcc gtgggctgga 2460
gggtggctac taagtgttcg gtctgggaag aggcatgacc cgcaccatcc cggggaaata 2520
aacgacttct taagggaatc ttctcgctga gcgggtgctc tgggccagga gattgccacc 2580
gccagcccac ggaacccaga tttgggctct gccttgagcg ggccgcctgt ggcttcccgg 2640
gtcgctcccc cgactcagaa agctctcaag ttggtatcgt tttcccggcc ctcggaggtg 2700
gattgcagat caccgagagg ggatttacca gtaaccacta cagaatctac ccgggcttta 2760
acaagcgctc atttctctcc cttgtcctta gaaaaacttc gcgctggcgt tgatcatatc 2820
gtacttgtag cggcagctta ggggcagcgg aactggtggg gttgtgcgtg caggggggagg 2880 ctgtgaggga gccctgcact ccgcccctcc acccttctgg aggagtggct ttgtttctaa 2940
gggtgccccc ccaacccccg ggtccccact tcaatgtttc tgctctttgt cccaccgccc 3000
gtgaaagctc ggctttcatt tggtcggcga agcctccgac gcccccgagt cccaccctag 3060
cgggccgcgc ggcactgcag ccgggggttc ctgcggactg gcccgacagg gtgcgcggac 3120
ggggacgcgg gccccgagca ccgcgacgcc agggtccttt ggcagggccc aagcacccct 3180

<210> SEQ ID NO 59
<211> LENGTH: 1038
<212> TYPE: DNA
<213> ORGANISM: Homo sapiens

<400> SEQUENCE: 59
tggcggccgg cgggcacagc cggctcattg ttctgcacta caaccactcg ggccggctgg 60
ccgggcgcgg ggggccggag gatggcggcc tgggggccct gcgggggctg tcggtggccg 120
ccagctgcct ggtggtgctg gagaacttgc tggtgctggc ggccatcacc agccacatgc 180
ggtcgcgacg ctgggtctac tattgcctgg tgaacatcac gctgagtgac ctgctcacgg 240
gcgcggccta cctggccaac gtgctgctgt cgggggcccg caccttccgt ctggcgcccg 300
cccagtggtt cctacgggag ggcctgctct tcaccgccct ggccgcctcc accttcagcc 360
tgctcttcac tgcaggggag cgctttgcca ccatggtgcg gccggtggcc gagagcgggg 420

```
ccaccaagac cagccgcgtc tacggcttca tcggcctctg ctggctgctg gccgcgctgc    480

tggggatgct gcctttgctg ggctggaact gcctgtgcgc ctttgaccgc tgctccagcc    540

ttctgcccct ctactccaag cgctacatcc tcttctgcct ggtgatcttc gccggcgtcc    600

tggccaccat catgggcctc tatggggcca tcttccgcct ggtgcaggcc agcgggcaga    660

aggccccacg cccagcggcc cgccgcaagg cccgccgcct gctgaagacg gtgctgatga    720

tcctgctggc cttcctggtg tgctggggcc cactcttcgg gctgctgctg gccgacgtct    780

ttggctccaa cctctgggcc caggagtacc tgcggggcat ggactggatc ctggccctgg    840

ccgtcctcaa ctcggcggtc aaccccatca tctactcctt ccgcagcagg gaggtgtgca    900

gagccgtgct cagcttcctc tgctgcgggt gtctccggct gggcatgcga gggcccgggg    960

actgcctggc ccgggccgtc gaggctcact ccggagcttc caccaccgac agctctctga   1020

ggccaaggga cagctttc                                                 1038
```

<210> SEQ ID NO 60
<211> LENGTH: 374
<212> TYPE: DNA
<213> ORGANISM: Homo sapiens

<400> SEQUENCE: 60

```
tagtaaggca ccgaggggtg gctcctctcc ctgcagcggc tgtcgcttac catcctgtag     60

accgtgacct cctcacacag cgccaggacg aggatcgcgg tgagccagca ggtgactgcg    120

atcctggagc tggtcgcagc aggccatcct gcacgcggtg gaggcgcccc ctgcaggccg    180

cagcgcatcc ccagcttctg gacgcactgt gagcggttat gcagcagcac gctcatatga    240

gatgccccgc agggtgctat gcaggcccac gtccccacaa agcccatggc aggcgcccgg    300

gtgccggagc acgcacttgg ccccatggat ctctgtgccc agggctcagc caggcatctg    360

gccgctaaag gttt                                                      374
```

<210> SEQ ID NO 61
<211> LENGTH: 246
<212> TYPE: DNA
<213> ORGANISM: Homo sapiens

<400> SEQUENCE: 61

```
tctcatctga gcgctgtctt tcaccagagc tctgtaggac tgaggcagta gcgctggccc     60

gcctgcgaga gcccgaccgt ggacgatgcg tcgcgccctt cccatcgcgg cctgggcggg    120

cccgcctgcc ctcggctgag cccggtttcc ctaccccggg gcacctcccc tcgcccgcac    180

ccggccccag tccctcccag gcttgcgggt agagcctgtc tttgcccaga aggccgtctc    240

caagct                                                               246
```

<210> SEQ ID NO 62
<211> LENGTH: 222
<212> TYPE: DNA
<213> ORGANISM: Homo sapiens

<400> SEQUENCE: 62

```
cagtccccga ggccctcccc ggtgactcta accagggatt tcagcgcgcg gcgcggggct     60

gcccccaggc gtgacctcac ccgtgctctc tccctgcaga atctcctacg acccggcgag    120

gtaccccagg tacctgcctg aagcctactg cctgtgccgg ggctgcctga ccgggctgtt    180

cggcgaggag gacgtgcgct tccgcagcgc ccctgtctac at                       222
```

<210> SEQ ID NO 63
<211> LENGTH: 2209
<212> TYPE: DNA
<213> ORGANISM: Homo sapiens

<400> SEQUENCE: 63

```
agagagacat tttccacgga ggccgagttg tggcgcttgg ggttgtgggc gaaggacggg     60
gacacggggg tgaccgtcgt ggtggaggag aaggtctcgg aactgtggcg gcggcggccc    120
ccctgcgggt ctgcgcggat gaccttggcg ccgcggtggg ggtccggggg ctggctggcc    180
tgcaggaagg cctcgactcc cgacacctgc tccatgaggc tcagcctctt cacgcccgac    240
gtcgggctgg ccacgcgggc agcttctggc ttcggggggg ccgcgatagg ttgcggcggg    300
gtggcggcca caccaaaagc catctcggtg tagtcaccat tgtccccggt gtccgaggac    360
aacgatgagg cggcgcccgg gccctgggcg gtggcaacgg ccgaggcggg gggcaggcgg    420
tacagctccc ccggggccgg cggcggtggc ggcggctgca gagacgacga cggggacgcg    480
gacggacgcg gggcaacgg cggatacggg gaggaggcct cgggggacag gaggccgtcc    540
aaggagccca cggggtggcc gctcggggcg cccggcttag gagacttggg ggagctgaag    600
tcgaggttca tgtagtcgga gagcggagac cgctgccggc tgtcgctgct ggtgcccggg    660
gtgcctgagc ccagcgacga ggccgggctg ctggcggaca agagcgagga ggacgaggcc    720
gccgacgcca gcaggggagg cgcgggcggc gacaggcggg ccccgggctc gccaaagtcg    780
atgttgatgt actcgccggg gctcttgggc tccggtggca gtgggtactc gtgcatgctg    840
ggcaggctgg gcagcccctc cagggacagg cgcgtgggcc tcaccgcccg gccgcgctgg    900
cccaagaagc cctccgggcg gccgccgcta ggccgcacgg gcgaaggcac tacagggtga    960
gggggctgcg tggggccggc cccgaaggcg ctggccgcct ggctgggccc tggcgtggcc   1020
tgaggctcca gacgctcctc ctccaggatg cgccccacgg gggagctcat gagcacgtac   1080
tggtcgctgt ccccgccaca ggtgtagggg gccttgtagg agcggggcaa ggagctgtag   1140
cagcagccgg gaacgcccct gagcggctcc ccgccggggt gcagggctgc ggagaagaag   1200
tcgggcgggg tgcccgtggt gaccgcgtcg ctgggggaca cgttgaggta gtccccgttg   1260
ggcagcagct tgccatctgc atgctccatg gacagcttgg aaccgcacca catgcgcatg   1320
tacccactgt cctcgggggga gctctcggcg ggcgagctgg ccttgtagcc gcccccgctc   1380
gccgggaatg tcctgcccgc cgcagaggtg ggtgctggcc ccgcaggccc cgcagaaggc   1440
acggcggcgg cggcggcggc ggcggccctg ggctgcaaga tctgcttggg ggcggacacg   1500
ctggcggggc tcatgggcat gtagtcgtcg ctcctgcagc tgccgctccc actgcccgcg   1560
agggccgcgc cgggcgtcat gggcatgtag ccgtcgtctg cccccaggtt gctgctggag   1620
ctcctgtggg agccgatctc gatgtctccg tagtcctctg ggtaggggtg gtaggccacc   1680
ttgggagagg acgcggggca ggacgggcag aggcggcccg cgctgcccga gaaggtggcc   1740
cgcatcaggg tgtattcatc cagcgaggca gaggagggct ggggcaccgg ccgctgccgg   1800
gctggcgtgg tcagggagta ggtcctcttg cgcagccctc ggtccaggtc ctgggccgcg   1860
tcccccgaga cccggcggta ggagcggcca cagtggctca ggggcctgtc catggtcatg   1920
tacccgtaga actcaccgcc gccgccgccg tctcgggccg ggggcgtctc cgcgatggac   1980
tcgggcgtgt tgcttcggtg gctgcagaag gcgcgcaggt cgcctgggct ggagccgtac   2040
tcgtccaggg acatgaagcc ggggtcgctg ggggagcccg aggcggaggc gctgccgctg   2100
gagggccgct ggccggggcc gtggtgcagc ggatgcggca gaggcgggtg cgggccgggc   2160
```

-continued ggcggcgggt aggagcccga gccgtggccg ctgctggacg acagggagc 2209

<210> SEQ ID NO 64
<211> LENGTH: 149
<212> TYPE: DNA
<213> ORGANISM: Homo sapiens

<400> SEQUENCE: 64
taacctaaag aatgaagtca tgccccggcc tgcacccggg aaactgcaca cagcgaaaga 60
tcgccactga gataaagagc tgaaagctat tccccaattc agctgtttca gccgtgcggt 120
ctcacaatgg gctcacagac ggcagcatc 149

<210> SEQ ID NO 65
<211> LENGTH: 832
<212> TYPE: DNA
<213> ORGANISM: Homo sapiens

<400> SEQUENCE: 65
gtttccacaa tccacctcgt agctggggcg tgccgcttgc ctcggcttgt cccggcagaa 60
cactcttacc tttaatggcg actgaaaagt tgccacgagt tcctgatcat tgtggtaggt 120
gctgcgtgaa gctgagacgt gcgtgagcca catcccaggg ggctttgagc ccccaccgcg 180
gcggcggctg aggggaggct tgtcgtactc gcacaggagg acacagggct gcagtgttca 240
ctccagggcc tcttatcatt gggatctgag gaattttccg agaggaagtg cgaattaaca 300
atgatgaaag gtttgtgagt gagtgacagg cacgttctat tgagcactgc atggggcatt 360
atgtgccacc agagacgggg gcagaggtca agagccctcg agggctggga gagttcggag 420
gatagaagtc atcagagcac aatgaagcca gaccctgcag ccgccttccc cttcgggggc 480
ttccttagaa tgcagcattg cggggactga gctgtcccag gtgaaggggg gccgtcacgg 540
tgtgtggacg cccctcggct cagccctcta agagactcgg cagccaggat gggctcaagg 600
catgagccct caaaggaggt taggaaggag cgagggagaa aagatatgct tgtgtgacgt 660
cctggccgaa gtgagaacaa ttgtatcaga taatgagtca tgtcccattg aggggtgccg 720
acaaggactc gggaggaggc cacggagccc tgtactgagg agacgcccac agggagcctc 780
gggggcccag cgtcccggga tcactggatg gtaaagccgc cctgcctggc gt 832

<210> SEQ ID NO 66
<211> LENGTH: 256
<212> TYPE: DNA
<213> ORGANISM: Homo sapiens

<400> SEQUENCE: 66
tccagctgca gcgagggcgg ccaggccccc ttctccgacc tgcaggggta gcgcggcctc 60
ggcgccggag acccgcgcgc tgtctggggc tgcggtggcg tggggagggc gcggcccccg 120
gacgccccga ggaaggggca cctcaccgcc cccacccaga gcgcctggcc gtgcgggctg 180
cagaggaccc ctccggggca gaggcaggtt ccacggaaga ccccggcccg ctggggcttc 240
cccggagact ccagag 256

<210> SEQ ID NO 67
<211> LENGTH: 184
<212> TYPE: DNA
<213> ORGANISM: Homo sapiens

<400> SEQUENCE: 67
acttactgct tccaaaagcg ctgggcacag ccttatatga ctgaccccgc ccccgagtcc 60

```
caggccgccc catgcaaccg cccaaccgcc caaccgccac tccaaaggtc accaaccact    120

gctccaggcc acgggctgcc tctccccacg gctctagggc ccttcccctc caccgcaggc    180

tgac                                                                 184


<210> SEQ ID NO 68
<211> LENGTH: 118
<212> TYPE: DNA
<213> ORGANISM: Homo sapiens

<400> SEQUENCE: 68

tgccacaccc aggtaccgcc cgcccgcgcg agagccgggc aggtgggccg cggatgctcc     60

cagaggccgg cccagcagag cgatggactt ggacaggcta agatggaagt gacctgag      118


<210> SEQ ID NO 69
<211> LENGTH: 1534
<212> TYPE: DNA
<213> ORGANISM: Homo sapiens

<400> SEQUENCE: 69

tcgccagcgc agcgctggtc catgcaggtg ccacccgagg tgagcgcgga ggcaggcgac     60

gcggcagtgc tgccctgcac cttcacgcac ccgcaccgcc actacgacgg gccgctgacg    120

gccatctggc gcgcgggcga gccctatgcg ggcccgcagg tgttccgctg cgctgcggcg    180

cggggcagcg agctctgcca gacggcgctg agcctgcacg gccgcttccg gctgctgggc    240

aacccgcgcc gcaacgacct ctcgctgcgc gtcgagcgcc tcgccctggc tgacgaccgc    300

cgctacttct gccgcgtcga gttcgccggc gacgtccatg accgctacga gagccgccac    360

ggcgtccggc tgcacgtgac aggcgaggcg gcgtgggagc gggtccccgg cctcccttcc    420

cgccctcccg cctgccccgc cccaagggct acgtgggtgc caggcgctgt gctgagccag    480

gaagggcaac gagacccagc cctctcctct accccaggga tctcacacct gggggtagtt    540

taggaccacc tgggagcttg acacaaatgc agaatccagg tcccaggaag ggctgaggtg    600

ggcccgggaa taggcattgc cgtgactctc gtagagtgac tgtccccagt ggctctcaga    660

cgaagaggcg agaaagacaa gtgaatggca atcctaaata tgccaagagg tgcaatgtgg    720

tgtgtgctac cagcccggaa agacactcgc agcccctcta cccaggggtg cacagacagc    780

ccaccaagta gtgcctagca ctttgccaga ccctgatata caaagatgcc tgaaccaggg    840

tcccgtccct agagcagtgg ctctccactc tagcccccac cctgctctgc gacaataatg    900

gccacttagc atttgctagg gagccgggac ctagtccaag cacccacaag catgaatttg    960

ccaaatcttt tcagcaacct cttaaggcaa ctgctatcat gatcctcact ttacacatgg   1020

agaagcagaa gcagagatga tagaatcttt cgcccaaggc cacatctgta ttgggacggg   1080

ggcagcctgg cacccaagtg cccattcctc ccttctgacc agcccccacc cctccggctc   1140

tggcgtccaa agggctaagg ggaggggtgc ccttgtgaca gtcacccgcc ttctcccctg   1200

cagccgcgcc gcggatcgtc aacatctcgg tgctgcccag tccggctcac gccttccgcg   1260

cgctctgcac tgccgaaggg gagccgccgc ccgccctcgc ctggtccggc ccggccctgg   1320

gcaacagctt ggcagccgtg cggagcccgc gtgagggtca cggccaccta gtgaccgccg   1380

aactgcccgc actgacccat gacggccgct acacgtgtac ggccgccaac agcctgggcc   1440

gctccgaggc cagcgtctac ctgttccgct tccatggcgc cagcggggcc tcgacggtcg   1500

ccctcctgct cggcgctctc ggcttcaagg cgct                               1534
```

<210> SEQ ID NO 70
<211> LENGTH: 269
<212> TYPE: DNA
<213> ORGANISM: Homo sapiens

<400> SEQUENCE: 70
atgaacttca agggcgacat catcgtggtc tacgtcagcc agacctcgca ggagggcgcg 60
gcggcggctg cggagcccat gggccgcccg gtgcaggagg agaccctggc gcgccgagac 120
tccttcgcgg ggaacggccc gcgcttcccg gacccgtgcg gcggccccga ggggctgcgg 180
gagccggaga aggcctcgag gccggtgcag gagcaaggcg gggccaaggc ttgagcgccc 240
cccatggctg ggagcccgaa gctcggagc 269

<210> SEQ ID NO 71
<211> LENGTH: 282
<212> TYPE: DNA
<213> ORGANISM: Homo sapiens

<400> SEQUENCE: 71
tcagtgttat gtggggagcg ctagatcgtg cacacagtag gcgtcaggaa gtgttttccc 60
cagtaattta ttctccatgg tactttgcta aagtcatgaa ataactcaga ttttgttttc 120
caaggaagga gaaaggccca gaatttaaga gcaggcagac acacaaccgg gcacccccag 180
accctggccc ttccagcagt caggaattga cttgccttcc aaagccccag cccggagctt 240
gaggaacgga ctttcctgcg cagggggatc ggggcgcact cg 282

<210> SEQ ID NO 72
<211> LENGTH: 142
<212> TYPE: DNA
<213> ORGANISM: Homo sapiens

<400> SEQUENCE: 72
gtggaaacac aacctgcctt ccattgtctg cgcctccaaa acacaccccc cgcgcatccg 60
tgaagctgtg tgtttctgtg ttactacagg ggccggctgt ggaaatccca cgctccagac 120
cgcgtgccgg gcaggcccag cc 142

<210> SEQ ID NO 73
<211> LENGTH: 741
<212> TYPE: DNA
<213> ORGANISM: Homo sapiens

<400> SEQUENCE: 73
tccacacctc gggcagtcac taggaaaagg gtcgccaact gaaaggcctg caggaaccag 60
gatgatacct gcgtcagtcc cgcggctgct gcgagtgcgc gctctcctgc caggggggacc 120 tcagaccctc ctttacagca caccgagggc cctgcagaca cgcgagcggg ccttcagttt 180
gcaaaccctg aaagcgggcg cggtccacca ggacgatctg gcagggctct gggtgaggag 240
gccgcgtctt tatttggggt cctcgggcag ccacgttgca gctctggggg aagactgctt 300
aaggaacccg ctctgaactg cgcgctggtg tcctctccgg ccctcgcttc cccgaccccg 360
cacaggctaa cgggagacgc gcaggcccac cccaccggct ggagaccccg gcacggcccg 420
catccgccag gattgaagca gctggcttgg acgcgcgcag ttttcctttg gcgacattgc 480
agcgtcggtg cggccacaat ccgtccactg gttgtgggaa cggttggagg tcccccaaga 540
aggagacacg cagagctctc cagaaccgcc tacatgcgca tggggcccaa acagcctccc 600
aaggagcacc caggtccatg cacccgagcc caaaatcaca gacccgctac gggcttttgc 660
acatcagctc caaacacctg agtccacgtg cacaggctct cgcacagggg actcacgcac 720
ctgagttcgc gctcacagat c 741

<210> SEQ ID NO 74
<211> LENGTH: 4498
<212> TYPE: DNA
<213> ORGANISM: Homo sapiens

<400> SEQUENCE: 74
ctgccctcgc ggatctcccc cggcctcgcc ggcctccgcc tgtcctccca ccaccctctc 60
cgggccagta ccttgaaagc gatgggcagg gtcttgttgc agcgccagtg cgtaggcagc 120
acggagcaga ggaagttggg gctgtcggtg cgcaccagct cgcccgggtg gtcggccagc 180
acctccacca tgctgcggtc gccgctcctc agcttgccgg ccagggcagc gccggcgtcc 240
ggggcgccca gcggcaacgc ctcgctcatc ttgcctgggc tcagcgcggt ggaaggcggc 300
gtgaagcggc ggctcgtgct ggcatctacg gggatacgca tcacaacaag ccgattgagt 360
taggaccctg caaacagctc ctaccagacg gcgacagggg cgcggatctt cagcaagcag 420
ctcccgggag accaacatac acgttcaggg gcctttatta ctgcgggggg tggggggggg 480
cgggggtggt taggggagga gggagactaa gttactaaca gtccaggagg ggaaaacgtt 540
ctggttctgc ggatcggcct ctgacccagg atgggctcct agcaaccgat tgcttagtgc 600
attaaaaagt ggagactatc ttccacgaat cttgcttgca gaggttaagt tctgtctttg 660
gctgttagaa aagttcctga aggcaaaatt ctcatacact tcctaaaata tttatgcgaa 720
gagtaaaacg atcagcaaac acattatttg gaagttccag tagttaatgc ctgtcagttt 780
tttgcaggtg agttttgtct aaagtcccaa cagaacacaa ttatctcccg taacaaggcc 840
acttttatca tgcaaaactg gcttcagtcc cgaaaagcaa gagctgagac ttccaaaggt 900
agtgctacta atgtatgtgc acgtatatat aaatatatac atatgctcta cttcataaaa 960
tatttacaat acaatctgtg gagaatttaa acacaacaga aatccattaa tgtacgctgc 1020
agattttttt aagtagcctt gaaaatcagc ttcagtagtt ggagcagtgc tgagctagaa 1080
gtacttgtca tgttctctgt tctctcaatg aattctgtca aaacgctcag tgcagaaaat 1140
tcagcgtttc agagatcttc agctaatctt aaaacaacaa tcataagaag gcccagtcga 1200
tgacactcag ggttctacag ctctcccaca tctgtgaact cgggtttggg gatgttggtt 1260
aagtttgtgg ctggtcctct ggtttgttgg gagttgagca gccgcagagt cacacacatg 1320
caaacacgca ctcttcggaa ggcagccact gtctacatca gctgggtgac tcagccctga 1380
ctcgggcagc agcgagacga tactcctcca ccgtcgccca gcacccgccg gttagctgct 1440
ccgaggcacg aacacccacg agcgccgcgt aaccgcagca ggtggagcgg gccttgaggg 1500
agggctccgc ggcgcagatc gaaacagatc gggcggctcg ggttacacac gcacgcacat 1560
cctgccacgc acactgccac gcacacgcaa cttcacggct cgcctcggac cacagagcac 1620
tttctccccc tgttgtaaaa ggaaaacaat tggggaaaag ttcgcagcca ggaaagaagt 1680
tgaaaacatc cagccaagaa gccagttaat tcaaaaggaa gaaaggggaa aaacaaaaaa 1740
aaacaacaaa aaaaggaagg tccaacgcag gccaaggaga agcagcagag gttgacttcc 1800
ttctggcgtc cctaggagcc ccggaaagaa gtgcctggcg gcgcagggcc gggcagcgtg 1860
gtgccctggc tgggtccggc cgcggggcgc ccgtcccgcc cgcgcccgct ggctctatga 1920
atgagagtgc ctggaaatga acgtgctttt actgtaagcc cggccggagg aattccattc 1980

-continued

```
cctcagctcg tttgcatagg ggcggccggc ggccaatcac aggcctttcc ggtatcagcc   2040
agggcgcggc tcgccgccgc cggctcctgg aattggcccg cgcgccccg ccgccgcgcc   2100
gcgcgctact gtacgcagcc cgggcgggga gtcggaggcc acccccgcgc cccgcatcca   2160
agcctgcatg ctggcccggg gccccgcccg cgtgcggacc cctttccgca gccacacgca   2220
ggcttgtgcg gctccgcgag tggccacggt ccggagacct ggaaaaagaa agcaggcccc   2280
gccggcccga ggaggacccg gccggcgcgc cgcacccgga gaggcccggc cccgcgagcc   2340
gctgcaggca ggcgcagtgg ccgccacgag gctcccgaac cgggctgcag cccgcggacg   2400
gccccagatc ctgcgcggcc gcccagggcc aggcctccgc ttccagggcg ggggtgcgat   2460
ttggccgcgg ggcccggggg agccactccg cgctcctgca ccgtccggct ggcagctgcg   2520
gcgaagcggc gctgattcct tgcatgaggc cggacggcgt ccgcgcgtgc cgtttgctct   2580
cagcgtcttc ccttgggtcg gtttctgtaa tgggtgtttt ttaccgctgc gcccgggccg   2640
cggctcgatc cctccgcgcg tctcacttgc tgcgtgcgtc agcggccagc gaagagtttc   2700
ctagtcagga aagaccccaa gaacgcgcgg ctggaaggaa agttgaaagc agccacgcgg   2760
cttgctcccg ggccttgtag cgccggcacc cgcagcagcc ggacagcctg cccgggcccc   2820
gcgtctcccc tccggctccc cggaagcggc ccccgctcct ctccccgccc ccgtgcgctc   2880
gagcggcccc aggtgcggaa cccaccccgg cttcgcgtgc gggcggccgc ttccccctgc   2940
gccggtcccc gcggtgctgc gggcattttc gcggagctcg gagggccccg cccccggtcc   3000
ggcgtgcgct gccaactccg accccgcccg gcggggctcc ctcccagcgg aggctgctcc   3060
cgtcaccatg agtccctcca cgccctccct gccgggccct gcacctcccg gggcctctca   3120
tccaccccgg ggctgcaacc cagtccccgg atcccggccc cgttccaccg cgggctgctt   3180
tgtggtcccc gcggagcccc tcaattaagc tccccggcgc gggggtccct cgccgacctc   3240
acggggcccc tgacgcccgc tcctccctcc cccagggcta gggtgctgtg gccgctgccg   3300
cgcagggact gtccccgggc gttgccgcgg gcccggacgc aggagggggc cggggttgac   3360
tggcgtggag gcctttcccg ggcgggcccg gactgcgcgg agctgtcggg acgcgccgcg   3420
ggctctggcg gacgccaggg ggcagcagcc gccctccctg gacgccgcgc gcagtccccg   3480
gagctcccgg aacgcccccg acggcgcggg gctgtgcggc ccgcctcgtg gccttcgggt   3540
cgcccgggaa gaactagcgt tcgaggataa aagacaggaa gccgccccag agcccacttg   3600
agctggaacg gccaaggcgc gtttccgagg ttccaatata gagtcgcagc cggccaggtg   3660
gggactctcg gaccaggcct ccccgctgtg cggcccggtc ggggtctctt cccgaagccc   3720
ctgttcctgg ggcttgactc gggccgctct tggctatctg tgcttcagga gcccgggctt   3780
ccggggggct aaggcgggcg gcccgcggcc tcaaccctct ccgcctccgc tcccccctggg   3840
cactgccagc acccgagttc agttttgttt taatggacct ggggtctcgg aaagaaaact   3900
tactacattt ttcttttaaa atgatttttt taagcctaat tccagttgta aatccccccc   3960
tccccccgcc caaacgtcca ctttctaact ctgtccctga gaagagtgca tcgcgcgcgc   4020
ccgcccgccc gcaggggccg cagcgccttt gcctgcgggt tcggacgcgg cccgctctag   4080
aggcaagttc tgggcaaggg aaaccttttc gcctggtctc caatgcattt ccccgagatc   4140
ccacccaggg ctcctggggc cacccccacg tgcatccccc ggaacccccg agatgcggga   4200
gggagcacga gggtgtggcg gctccaaaag taggcttttg actccagggg aaatagcaga   4260
ctcgggtgat ttgcccctcg gaaaggtcca gggaggctcc tctgggtctc gggccgcttg   4320
cctaaaaccc taaaccccgc gacgggggct gcgagtcgga ctcgggctgc ggtctcccag   4380
```

gagggagtca agttccttta tcgagtaagg aaagttggtc ccagccttgc atgcaccgag 4440
tttagccgtc agaggcagcg tcgtgggagc tgctcagcta ggagtttcaa ccgataaa 4498

<210> SEQ ID NO 75
<211> LENGTH: 453
<212> TYPE: DNA
<213> ORGANISM: Homo sapiens

<400> SEQUENCE: 75
ttcggaagtg agagttctct gagtcccgca cagagcgagt ctctgtcccc agccccccaag 60 gcagctgccc tggtgggtga gtcaggccag gcccggagac ttcccgagag cgagggaggg 120
acagcagcgc ctccatcaca gggaagtgtc cctgcgggag gccctggccc tgattgggcg 180
ccggggcgga gcggcctttg ctctttgcgt ggtcgcgggg gtataacagc ggcgcgcgtg 240
gctcgcagac cggggagacg ggcgggcgca cagccggcgc ggaggcccca cagccccgcc 300
gggacccgag gccaagcgag ggctgccag tgtcccggga cccaccgcgt ccgccccagc 360
cccgggtccc cgcgcccacc ccatggcgac ggacgcggcg ctacgccggc ttctgaggct 420
gcaccgcacg gagatcgcgg tggccgtgga cag 453

<210> SEQ ID NO 76
<211> LENGTH: 560
<212> TYPE: DNA
<213> ORGANISM: Homo sapiens

<400> SEQUENCE: 76
acgcacactg gggtgtgat ggaaaggggg acgcgatgga taggggtggg cgcacactgg 60
gggacgcgac ggggaggggt gagcacacac tgggggtgtg atggagaggg cgacgcaata 120
gggaggggtg ggcgcacacc agggacgcga tgatggggac gggtgggcgc acaccaggtg 180
gcatgatggg gaggagtggg tacacaccat ggggggcgtg atggggaggc gtgggcgtac 240
accggggggc gcgatgggga ggggtgggcg cacaccgggg gacgcgatgg aggcggtggg 300
tgcacacggg gcgcgatggg tgggagtagg tgcacactga gggcacgatt ggggagacac 360
gaaggagagg ggtgggcgca cactggggga cgcgatggcc gggacacgat gcggagaagt 420
gggtgaatac cggggtcgcg atgggcgccc tggaaggacg gcagtgctgc tcacaggggc 480
caggcccctc agagcgcgcc ccttgggggt aaccccagac gcttgttccc gagccgactc 540
cgtgcactcg acacaggatc 560

<210> SEQ ID NO 77
<211> LENGTH: 157
<212> TYPE: DNA
<213> ORGANISM: Homo sapiens

<400> SEQUENCE: 77
ccacagggtg gggtgcgccc acctgccctg tccatgtggc cttgggcctg cgggggagag 60
ggaatcagga cccacagggc gagccccctc cgtagcccgc ggcaccgact ggatctcagt 120
gaacacccgt cagcccatcc agaggctaga aggggga 157

<210> SEQ ID NO 78
<211> LENGTH: 114
<212> TYPE: DNA
<213> ORGANISM: Homo sapiens

<400> SEQUENCE: 78

-continued

```
ttgaggtctc tgtgcatgct tgtgcgtacc ctggactttg ccgtgagggg tggccagtgc      60

tctgggtgcc tttgccagac aactggtctg ccgggccgag cattcatgct ggtc           114


<210> SEQ ID NO 79
<211> LENGTH: 104
<212> TYPE: DNA
<213> ORGANISM: Homo sapiens

<400> SEQUENCE: 79

tgacgcgccc ctctccccgc agctccacct ggttgcgctc aacagccccc tgtcaggcgg      60

catgcggggc atccgcgggg ccgacttcca gtgcttccag cagg                      104


<210> SEQ ID NO 80
<211> LENGTH: 659
<212> TYPE: DNA
<213> ORGANISM: Homo sapiens

<400> SEQUENCE: 80

aacacactgt ctcgcactag gtgctcgcgg aagagcgcgg cgtcgatgct gcggctcagg      60

ttgatgggcg atggcggccg cagatccagc tcgctcagcg atggcgccgg tcccacaccg     120

ttgcgggaca gtcccgggcc accctggggt ccgcgaccca acgacgcagc cgagccccag     180

gcgcctgaac tgggcgtggc cagctgccca ctctccgccg ggttgcggat gaggctcttg     240

ctgatgtcca agctgcctgc accaacgttg ctgggccctg catagcagtt attgggtcgc     300

tccggcacct cgctctttcc tgacggcgcc gggcacgcca gacgcatcag cttagcccag     360

caagcgtgct ccgtgggcgg cctgggtctc gcggcagcca ccgcggccaa cgccagggcg     420

agcgcccatg tcagctccag gaggcgcagc cagaagtgga caccccacca ggcccacgag     480

aagcggccca cgcggcctgg gcccgggtac agccagagcg cagccgccag ctgcaagccg     540

ctagccagca gccccagcgc gcccgccaca gccaacagcc gagggcccgg gctggcatcc     600

cagccccgtg ggccgtccag caggcggcga cggcacaggc agagcgtgcc cagagccac      659


<210> SEQ ID NO 81
<211> LENGTH: 813
<212> TYPE: DNA
<213> ORGANISM: Homo sapiens

<400> SEQUENCE: 81

gtctgcacga agcccgcggc ggcctgcagg gggcccagcg actcgtccag ggaaccggtg      60

cgcaggagca gccgggggcg cggcgcgccg gccgcccttg ggggactctg gggccggggg     120

cgcagctcga tctgacgctt gggcactgtc cggggcctgg cgggcgcggc gccctcctcc     180

agagccacct ccacacactc gaactgcgct ggggcggcag gacttggccc acggggccgc     240

agctctaggt aggtggccca gcgggagcca ccatcgggga cctgggactg gcgtgggacc     300

gcggcgggag acgctggccc cggcggcaag gggctgatga aggccggctc cgtgaactgt     360

tgttgcgcct cgcgatcgtc tgcgccggag cagccgaaca ggggtccgac gccgaagatg     420

acttccatct cccccgacgg cagcgtgcgc agctggggct ggggtggccg tgggccggaa     480

cctgggcctc gcgggaaacc cgagccgggc ccgtgccgct ggcggctatt ctgggcgctg     540

acggacaggc gaggctgcgc gcccgccccc cgcccaggag ccacccaggg ccaattcgct     600

gggcctttcg cgtccggccc aacgtccggg ggctccggag aacctggagc cgtgtagtag     660

gagcctgacg aaccggagga gtcctggcgc cgcgcggggg ccgtgggcag ctgcctcggg     720

atcccaggca gggctggcgg ggcgagcgcg gtcagcatgg tggggccgga cgccgtgcac     780
```

tatctccctc gcattcgcct ccgctggtgg cgc 813

<210> SEQ ID NO 82
<211> LENGTH: 440
<212> TYPE: DNA
<213> ORGANISM: Homo sapiens

<400> SEQUENCE: 82
ctggagagaa ctatacgggc tgtgggagtc accgggcgac tatcaccggg cctcctttcc 60
acatcctcct ccgggaaggg accccgttcc gggcctcgac cggcgcagac tgggctgacc 120
cactttcttg ggcccactga gtcacctcga aacctccagg ccggtagcgg ggaggagagg 180
aggagcaggc gggggtgcca aggtgtgggc tgcgccctgg ttagggggcg agcccggctt 240
gtttatgagg aggagcgcgg aggaggatcc agacacacag gcttgcgcgc ccagactcgc 300
ccggccagcg gctggcggcc tccgacgtca ccaaaccggt tgggtgagag ggcagagagc 360
agggggaagg gccgcagtcc cgcccgcgcc ccccggcacg caccgtacat cttgccctcg 420
tctgacagga tgatcttccg 440

<210> SEQ ID NO 83
<211> LENGTH: 252
<212> TYPE: DNA
<213> ORGANISM: Homo sapiens

<400> SEQUENCE: 83
gagtgcggag tgaaggggtg cactgggcac tcagcgcggc ccttgggagg cagggccgcc 60
ccagcctgcc ctcctgtctg ggaaggccgt ccagaagcag gagccccggg gaaaacaact 120
ggctggacgg ggcggccttc agtgtctctc ccagcctgag agtcgcttcc caccacctgg 180
gcacgaacct gctctgcgat ctccggcaag ttcctgcgcc tcctgtcggt aaaatgcaga 240
tcgtggcgtc tt 252

<210> SEQ ID NO 84
<211> LENGTH: 1539
<212> TYPE: DNA
<213> ORGANISM: Homo sapiens

<400> SEQUENCE: 84
tcttctttcc gcccctaggg ggcacaagcg ggcatgtcca agcgcctagg agcccgtacc 60
gctggggacc tccccttccg cgaaccccga gcgggtagac ccagagcaat ccgagtgtgg 120
aaacaatgga gagggggcgt gttgagctgg ggtctccatg cctcgttggg gagagggagg 180
tgagtttgtg tcttctggaa ggcgtggggg ctgtgccctc gtgggggtag gaagtgctcc 240
cgtggggcgg ggtgcggatc ggagaggtga gtgggtgcgt ctgtccagcg gtccgcccgg 300
tgtggtcgtg cccggcccgc gtggggatgg gggtgtctct cccgctgggc aactatacca 360
gcgcaaccgg ggcgtcggcg cggcccacgc tagcggcgct gctccggcgg cgggggctgg 420
gcgtggcggt gatgctgggc gtggtggccg cgctgggcgt ggtggccgcg ctgccgccct 480
cacccgggca gccgtgctgg agaaggatgt cggcgcacag ctggcttcca gcctggcggg 540
cgtagaacag cgccgtgcgg ccctgggcgt cacgggccgc cacgtccgcg ccgtactaga 600
gggcggaaac ggccgcgtga ccgcgcgtcc ccagggcgcc cacacccggc gccgcctccc 660
ccacatggcc aagcctactt ccggggtccc tctgggaatt tcgggctttc ccgcgccagg 720
cgttttccga gatgaagcct caaagacccc ctttcctccc cccagctcac gtacccacag 780

```
cagcagttgc gtgatgacga cgtgggcgag ctcggccgcc aggtggagtg gggagcgcag    840

ctgtgggtcc tctacgctgg tgtcgagcgg cccgtgtcgc gcatgggcca aaagcaggag    900

aacggtagcc acgtcctggg cctgcacggc ggcccacagc tggcggccca gcggctcctc    960

cgaggtgctc agcggcgcca ggaacagtag ctgctcgtac ttggcgcgaa tccacgactc   1020

gcgctcctcc ctgcaagacc agggatcaac ggaaaaggct ctagggaccc ccagccagga   1080

cttctgcccc tacccacggg accgtctcag gttcgcacac cctcagcaac cctccccccg   1140

ctctgttccc tcacgcttac cgcgaagagt cccgcgaggg cttggcacgg cctcgcgtgt   1200

cgctttccca cacgcggttg gccgtgtcgt tgccaatagc cgtcagcacc agggtcagct   1260

cccgtggcca gtcgtccaag tccagcgagc gaacgcggga caggtgtgtg cccaggttgc   1320

ggtggatgcc agaacactcg atgcagatga gggcgcccag gttcaagctg gcccacgtgg   1380

ggtctgcgga aggagcgtag aggtcggctc ccagccgggc agcacaggca ccccggcatt   1440

cactacactc cctagcccct ccgctgcctc ctggcactca ctgggggccc cgcagtccac   1500

gcagattgaa ttccccttgg cgttccggat cgcctggat                           1539
```

<210> SEQ ID NO 85
<211> LENGTH: 2648
<212> TYPE: DNA
<213> ORGANISM: Homo sapiens

<400> SEQUENCE: 85

```
agccaggtcc agcccccgcg cctgacaccg gccggacgtt cccggggcgc cgcagctgcg     60

gcgggaactc tgggatccgg agccatctgc tcccacccgc tccggagcca aaccccgggg    120

gccgcctccg ctcccggacc cgcctcctct cccgggagtg tgagccgaac caagagtctc    180

ctgcctatct cctccagtag gaaaatagta ataataatag acaccctgcc cccgtaaaaa    240

acactacctt ccccgtaccg cctcccaagt ctcccggggt acggattgcc tttgcagcag    300

ttccgcccca cctgactcac tccagggtca gccccgggtg ggtttcaatg cggctctggg    360

gagggggtgg gcagtggggg aagtgaggct tcctatccgc cccctctcac ttcacattta    420

aatattctgc acgttccagc ccccgcggac tcgcgtaccg cccaatccgc cttcaccgca    480

cgaaaaacat cactagcctg ctctcagccc aggggacgac tagtccctgg cgagaagctg    540

cctgcaaggt cactgtcatg ccacctgccc caagtgctca ggggaaactg aggcttcctc    600

atccccttca ccttcaacgt cgctctaaac acggcaaagc cccgtttcca tgctcccaga    660

gttcagctga ggctggaagt ggggtcctgg gcttctctgg gagcaatttt ctagtcactc    720

tgatcaagga cgttactttc ccagaaagct ctgaggctga gtccctctga aatcaagtcc    780

tttctcctgt cgcacaatgt agctactcgc cccgcttcag gactcctatt ctttgcccca    840

atccttgaca gaggggtgag cttggttcat ccgcccaccc cagagaaaag cttccctagt    900

ttcctggacc tcgctcctcc accccaagct gagcattcca ggtacccttc cctccctgtt    960

ctcaagccct gactcaactc actaggggaa gcgcggagct cggcgcccag cagctccctg   1020

gacccgctgc cagaagacag gctgggggt ccgggaaggg gcccggagcc aggaggccct    1080

cctgtgctct tggtgaagat gccgctgata aacttgagca tcttgcggtc acgagtggat   1140

gctcggcccc cctcccggcc ccgtttcagc cccggagctg gaggctccag agtgattgga   1200

ggtgcaggcc cggggggctg cgcggaagca gcggtgacag cagtggctgg actcggagtt   1260

ggtgggaggg ttagcggagg aggagagccg gcaggcggtc ccggatgcaa gtcactgttg   1320

tccaaggtct tactcttgcc tttccgaggg gacaacttcc ctcgggctcc agccccagcc   1380
```

ccgaccccac cagaggtcga agctgtagag ccccctcccc cggcggcggc ggcggtggcg 1440
gcggcagaga ccgaagctcc agtcccggcg ctgctctttg accccttgac cctgggcttg 1500
ccctcgcttt cgggccatga caggcggcta cccgcgccct tgcccccgcc ggctttggct 1560
ccactcgtgg tcacggtctt gcaaggcttg ggagccggcg gaggaggcgc caccttgagc 1620
ctccggctgc cggtgccagg gtgcggagag gatgagccag ggatgccgcc gcccgcccgg 1680
ccttcgggct ccgggccgcc ccagctcggg ctgctgagca gggggcgccg ggaggaggtg 1740
ggggcgcccc caggcttggg gtcggggctc agtcccccgg agagcggggg tcccggaggg 1800
acggcccaga gggagaggcg gcggccggga gcgggggaga ctgggcgggc cggactggcc 1860
ggagccgggg acagggctgg gggctccgcg cccccggtgc ccgcgctgct cgtgctgatc 1920
cacagcgcat cctgccggtg gaagagacgt tcgtgccgct tcttgcccgg ctcctccgcg 1980
cctcgggggc tgccaggatc cccagtctcg gagcctctgg caccggcggc gccggccgcg 2040
gccgcagacg gagaaggcgg cggcggaggc accgactcga gcttaaccag ggtcagcgag 2100
atgaggtagg tcgttgtccg gcgctgaagc gcgcccgcgc cccggctcat ggggcccgga 2160
gacccccgag ctggggaggg gaggggactc ccccggactg cctcaggggg gcccggccat 2220
ggggccgccc tgctcgctgc ccccagcccc cggacccccgc tgagcccccg gcccggctcc 2280
gctgtcgccg ccgcctccgc cgcctccgct tgcgcccccc tcccatcaca tggggcgccc 2340
cctccccatg ctccccgccc tgcgccccca ccctcttgga gccccgggac cttggtgctg 2400
ctccagggag gcgcgccgga ccgtccaccc cggcctgggt gggggcgctg agatgggtgg 2460
gggagggcgg ggaggacagt agtgggggca aatgggggag agagaggaaa agggagcaga 2520
aaaggggacc ggaggctagg ggaaacgaac ctgtgcgggg gaggcagggg cggggaattg 2580
ggactcaagg gacaggggcc gcggatgcgg tcggaaagag ggtctagagg agggtgggaa 2640
gctagtgg 2648

<210> SEQ ID NO 86
<211> LENGTH: 452
<212> TYPE: DNA
<213> ORGANISM: Homo sapiens

<400> SEQUENCE: 86
aggagcgcaa ggcttgcagg gcatgctggg agagcgcagg gaacgctggg agagcgcggg 60
aaatactggg attggctccc gagggctgtg aggagggcac gaggggacac tccgatgaag 120
gcagggcacg cggggcgagc cgggagcgtc tcctgagggc agcgaggagg gagctgaggc 180
acgcgggctc tcaatcgacg ccccacagag accaagaggc ctggccttgg ggggcagctg 240
cttgaaggag gcagagcgga agcgagggag actgctggag gccctgccgc ccacccgccc 300
tttcctcccc ctgaggagac gcctgacgca tctgcagtgc aggaggccgt gggcgttaga 360
agtgttgctt ttccagtttg taagaccatt ttcctgattc tcttccccac ggttgcggag 420
gagcaggtca gggccgccat gagggcagga tc 452

<210> SEQ ID NO 87
<211> LENGTH: 232
<212> TYPE: DNA
<213> ORGANISM: Homo sapiens

<400> SEQUENCE: 87
tcgaccgcta ctattatgaa aacagcgacc agcccattga cttaaccaag tccaagaaca 60
agccgctggt gtccagcgtg gctgattcgg tggcatcacc tctgcgggag agcgcactca 120
tggacatctc cgacatggtg aaaaacctca caggccgcct gacgcccaag tcctccacgc 180
cctccacagt ttcagagaag tccgatgctg atggcagcag ctttgaggag gc 232

<210> SEQ ID NO 88
<211> LENGTH: 221
<212> TYPE: DNA
<213> ORGANISM: Homo sapiens

<400> SEQUENCE: 88
tgtgccgtcg cacacagacg ccctcaacgt cggagagctg tgagcggggc cgtgctcttg 60
ggatgggagc ccccgggaga gctgcccgcc aacaccactc cgacgtgatc catgctggac 120
ataaagtgct cttccctccg ctagtcatcg gccgagcggg cccctcgctc ctgggtgtaa 180
gttctttctg tgcgtccttc tcccatctcc gtgcagttca g 221

<210> SEQ ID NO 89
<211> LENGTH: 477
<212> TYPE: DNA
<213> ORGANISM: Homo sapiens

<400> SEQUENCE: 89
ccatgcgccg ctgcgcgcgc gagttcgggc tgctgctgct gttcctctgc gtggccatgg 60
cgctcttcgc gccactggtg cacctggccg agcgcgagct gggcgcgcgc cgcgacttct 120
ccagcgtgcc cgccagctat tggtgggccg tcatctccat gaccaccgtg ggctacggcg 180
acatggtccc gcgcagcctg cccgggcagg tggtggcgct cagcagcatc ctcagcggca 240
tcctgctcat ggccttcccg gtcacctcca tcttccacac cttttcgcgc tcctactccg 300
agctcaagga gcagcagcag cgcgcggcca gccccgagcc ggccctgcag gaggacagca 360
cgcactcggc cacagccacc gaggacagct cgcagggccc cgacagcgcg ggcctggccg 420
acgactccgc ggatgcgctg tgggtgcggg cagggcgctg acgcctgcgc cgcccac 477

<210> SEQ ID NO 90
<211> LENGTH: 1200
<212> TYPE: DNA
<213> ORGANISM: Homo sapiens

<400> SEQUENCE: 90
gtcctaacat cccaggtggc ggcgcgctgg ctccctggag cggggcggga cgcggccgcg 60
cggactcacg tgcacaaccg cgcgggacgg ggccacgcgg actcacgtgc acaaccgcgg 120
gaccccagcg ccagcgggac cccagcgcca gcgggacccc agcgccagcg ggaccccagc 180
gccagcggga ccccagcgcc agcgggaccc cagcgccagc gggaccccag cgccagcggg 240
tctgtggccc agtggagcga gtggagcgct ggcgacctga gcggagactg cgccctggac 300
gccccagcct agacgtcaag ttacagcccg cgcagcagca gcaaagggga aggggcagga 360
gccgggcaca gttggatccg gaggtcgtga cccaggggaa agcgtgggcg gtcgacccag 420
ggcagctgcg gcggcgaggc aggtgggctc cttgctccct ggagccgccc ctccccacac 480
ctgccctcgg cgcccccagc agttttcacc ttggccctcc gcggtcactg cgggattcgg 540
cgttgccgcc agcccagtgg ggagtgaatt agcgccctcc ttcgtcctcg gcccttccga 600
cggcacgagg aactcctgtc ctgccccaca gaccttcggc ctccgccgag tgcggtactg 660
gagcctgccc cgccagggcc ctggaatcag agaaagtcgc tctttggcca cctgaagcgt 720
cggatcccta cagtgcctcc cagcctgggc gggagcggcg gctgcgtcgc tgaaggttgg 780
ggtccttggt gcgaaaggga ggcagctgca gcctcagccc caccccagaa gcggccttcg 840
catcgctgcg gtgggcgttc tcgggcttcg acttcgccag cgccgcgggg cagaggcacc 900
tggagctcgc agggcccaga cctgggttgg aaaagcttcg ctgactgcag gcaagcgtcc 960
gggaggggcg gccaggcgaa gccccggcgc tttaccacac acttccgggt cccatgccag 1020
ttgcatccgc ggtattgggc aggaaatggc agggctgagg ccgaccctag gagtataagg 1080
gagccctcca tttcctgccc acatttgtca cctccagttt tgcaacctat cccagacaca 1140
cagaaagcaa gcaggactgg tggggagacg gagcttaaca ggaatatttt ccagcagtga 1200

<210> SEQ ID NO 91
<211> LENGTH: 900
<212> TYPE: DNA
<213> ORGANISM: Homo sapiens

<400> SEQUENCE: 91
caccttcccc gaggtaatta ttttctgggg ggtaggggtg ggggttggga gggtgaagaa 60
aggaagaaaa agaaggccga tcacactggg caccggcgga ggaagcgtgg agtccattga 120
tctaggtact tgtggggagg ggagaacccg agcagcagct gcaaacggaa gggctgtgag 180
cgagcgggcg ggcgggtggc tggcagcgag gccaccagca ggggggggccc gggccgaggc 240 cgcgccacct cggcaccacg cgggcagccg gtgcggcggg gtcgccacgg ccaggggagc 300
gctgggtgcc caccatggca gttatgcaag cggtgacccc ctggtcttgc ctccccgccg 360
ccctgcactc cttcctcccc gctgccgaca cttggatctc tctagctctt tctctcccct 420
gtgttttcaa acaggaagtg cacggctgtc tataacgtgc tgccgggtct caggatggag 480
gagtgaagtc tcctgtcgcc gtggttccag cctccggagc tcgcccaagc cgcgtcccca 540
gagagcgccc tgagagaaca gggtggccgc ttggtccagg tgcgcggggt cgggtctggg 600
tccagggagc gggtcgggaa gtctgcggca cggagcactg ctagtgtcgg atctgcatct 660
ccagctctgt gctgcagctt cacttgcccg ccccccacca ctggcttctc acccggggtc 720
tctgccaaac tctggctgct gccgccctgg gttcgggccg gcggaaggcc ctgggcgtgc 780
gctgcggagc cgcctgcgag gactccacta gggcgctttc caggctggac tgccccgggc 840
tgcgctggag ctgccagtgc tcggggagtc ttcctggagt ccccagctgc cctctccacc 900

<210> SEQ ID NO 92
<211> LENGTH: 200
<212> TYPE: DNA
<213> ORGANISM: Homo sapiens

<400> SEQUENCE: 92
ctcttcccaa gttacgccac cggtcgagga cggcaggaga cccccgagtg cagagaaagc 60
tcaaaccggc agcgaagtcg gtcctagcca agctgaaaaa acgtctcgga tttcgcggac 120
agcggcctag acacagcccg atcttccagt cctagtgccc tggtcgagac ggttctatcc 180
ttttgcaaag aagccggaaa 200

<210> SEQ ID NO 93
<211> LENGTH: 400
<212> TYPE: DNA
<213> ORGANISM: Homo sapiens

<400> SEQUENCE: 93
tctcggttgc aatccccacc ctcctcaccc agcagggcag gaggcaccca acttggagga 60

-continued gaaaggggtg ggggaggtga aacagagacc ggagagtcac gagggctggg ccgccgagag 120
caggagaata taccgtgtca cacacctcca ttctctcaca cacgttgcag acacaaatca 180
ctgacggttt ccacgtgctg cgctcgtgag cggaggtgtt caaagagggg gcagatgagt 240
tacttcccga gacggaaccg gggtcccac gtccgccgcc ttcagtagca caaccaatct 300
ctgaacactc aaaccgcgca tctctggcgc atcaccatcc tatttaaggc cacgggctcc 360
gcccttttcc tcccctccct tcttttccac tctttttcca 400

<210> SEQ ID NO 94
<211> LENGTH: 700
<212> TYPE: DNA
<213> ORGANISM: Homo sapiens

<400> SEQUENCE: 94
ctgccagaga tgtgtctgtc ttgcgccccg catgcactgc ctgcggggct gcgctgcact 60
ccccggcggc gccacgggtc tggcccccgc gcttctacgt gttgggggga tgcatggacc 120
ttggagatcc gtagttggcc ctaaccttct cggaatctcc tctgcacgcg ctgcctgttc 180
ctcctctgca cgctctgtcc gttcctttgc aacttctgtg ggaattgtcc tggcgtggga 240
aacgcccccg cgctctttgg cacttagggt gtgagtgttg cgccccttgc cgcagcgctc 300
agggcagcat cccgctcgag gatgcagggt tctcaccaag cagtgagggg gactcacgcg 360
ccgccgggga gcggagccag gctccgagaa gggagcaggc tcgagccgct gggttttcgc 420
aagccttggg gcctctggcc gcccttccat gcctccgggc gcgggcggct cagcaggtcc 480
ccggcttcgg gaagttttgt gcgcggatcg ctggtgggga gggcgcgcgg gccagtggct 540
gagcttgcag cgaagtttcc gtgaaggaaa ctgcatgtgc ctttggaggc gactcgggac 600
tgctgtaggg tggactgggt gtctatggag ttgcgggtca gagcgagtag ggtgggtcct 660
ttcctgggac aggactggga attggggctc gaagtagggg 700

<210> SEQ ID NO 95
<211> LENGTH: 200
<212> TYPE: DNA
<213> ORGANISM: Homo sapiens

<400> SEQUENCE: 95
aggggtgtcc tccaacatct ctgaaccgcc ttcccttcct cctcactggc gccctcttgc 60
ctcagtcgtc ggagatggag aggcggctga agattggcag gcggcggcca gggtcgaggc 120
tgggagactc agagccgctg aggctgccgg agctcaggga gccgcttagg tagctgtcgc 180
ggtccgacag cgagtccggg 200

<210> SEQ ID NO 96
<211> LENGTH: 5000
<212> TYPE: DNA
<213> ORGANISM: Homo sapiens

<400> SEQUENCE: 96
tctgactctc gggctggagc agccgagaca gcgctcccca gcgggactac agaatcccgg 60
gtgtcggcct gggggccctg gattggcagt ggtggagtct tctgagccta acagctacta 120
ggaatgacag agttgcagat ggctttgtcg cccgcggggc ggctcaagcg tcctgggtcc 180
caggcctctg tcctacggcc aggccgccgg ctcaacgggc cgaagggaat cgggctgacc 240
agtcctaagg tcccacgctc ccctgacctc agggcccaga gcctcgcatt accccgagca 300
gtgcgttggt tactctccct ggaaagccgc ccccgccggg gcaagtggga gttgctgcac 360

-continued

```
tgcggtcttt ggaggcctag gtcgcccaga gtaggcggag ccctgtatcc ctcctggagc    420
cggcctgcgg tgaggtcggt acccagtact tagggaggga ggacgcgctt ggtgctcagg    480
gtaggctggg ccgctgctag ctcttgattt agtctcatgt ccgcctttgt gccggcctct    540
ccgatttgtg ggtccttcca agaaagagtc ctctagggca gctagggtcg tctcttgggt    600
ctggcgaggc ggcaggcctt cttcggacct atccccagag gtgtaacgga gactttctcc    660
actgcagggc ggcctggggc gggcatctgc caggcgaggg agctgccctg ccgccgagat    720
tgtggggaaa cggcgtggaa gacaccccat cggagggcac ccaatctgcc tctgcactcg    780
attccatcct gcaacccagg agaaaccatt tccgagttcc agccgcagag gcacccgcgg    840
agttgccaaa agagactccc gcgaggtcgc tcggaacctt gaccctgaca cctggacgcg    900
aggtctttca ggaccagtct cggctcggta gcctggtccc cgaccaccgc gaccaggagt    960
tccttcttcc cttcctgctc accagccggc cgccggcagc ggctccagga aggagcacca   1020
acccgcgctg gggcggaggt ttcaggcggc aggaatggag aggctgatcc tcctctagcc   1080
ccggcgcatt cacttaggtg cgggagccct gaggttcagc ctgactttcc cgactccgcc   1140
gggcgcttgg tgggctcctg ggcttctggg ctcaccctta cacctgtgta ctaaagggct   1200
gctaccctcc cgaggtgtac gtccgccgcc tcggcgctca tcggggtgtt ttttcaccct   1260
ctcgcggtgc acgctttttc tctcacgtca gctcacatct ttcagtacac agccactggg   1320
tctccctgcc cctccagcct ttcctaggca gctttgaggg cccagacgac tgaagtctta   1380
ctgctaggat gggaacacga tgaaaaagga aggggcccag tcaaaagtcc tctcctcttc   1440
ggtttttctt caactgtcct tcacaaaaac atttatttct gtcccagcgc cctggcggat   1500
ttcggcagat gggccctagg gggttgtgga ggccaaattc ccaggatgct ggtcctgcct   1560
ttttcattgg ccaaaactgt atttcctaca acgactaaag ataaccaaga actgagtaga   1620
ccctgttctc tcaccagatc tccctggctc tgtttaactt ttcctggtgc aatgcgatgg   1680
caccaccagc tccccaggca ggcaccactc cctcaagata ccatttgggg tagggatttg   1740
agtcctggag agggtcagcg gggcgccggg gtgggggtgg gaaggagact gacagggaca   1800
caccgcgagc tccgcatact ctcctctgcc ccctgtagcc cggggcttta atgaccccaa   1860
gcagatttcc tgtctctggt ctagccagct gcccctaggg ctggatttta tttcttcatg   1920
gggtttcacc ctaaagggcc ccctggtcat gggacctggt tgggaacaaa tgaaagatgt   1980
cttgtagcaa atgctttcag gggagcagaa aagaagattg ggcacttcca gtcacttggt   2040
cactttaggt ggctggaaca aaactggtga ctttcacgac tgctacaggg tgagggggtg   2100
aagggtggca gagaggtgac aagccactgg gaatcctatt cagtggggat gccgacaggg   2160
agtggctgta atcaactgag caacatctgt gtgaatgtta ttcacaggtc aggacagcag   2220
cttggtcttc ccaggtgagg aactgaggac tggcctgcat agatttgtgc agtaggtgag   2280
tagcttccaa atttattttc agaacttcca tgtagtacct gcctctccat ttaaatattt   2340
tttaaaattt tatttattta aatattttct tggttagctt tccaagaggg aggaaaagag   2400
gggagttgca acaagtagtg cccctatgct gggattcatt ttccagagta aagcctggga   2460
ctggcaccct gacccctacc ggcaggtgaa aactccaggc aaactgctga gatcccacct   2520
gggctggctg agatagtgcc tggggtgcat ccctcagcag ctgccacctg ggccctgggg   2580
ccatctcttt ctctggcatc aagcagccag gtgtcaaggc cttcccagca atccatgctg   2640
catggctggg tcttgttcta gcaggtcgat gggcagggac tggtagctta gccagggcac   2700
```

```
cagtgcgtgg ctgtgggttt gtgtgcttct gtggagaagc atgatgtgta tgtgtgtgtg   2760
tgggcacagg catgaggaag ggttcatttg tgcaggtatc tcccatgtat atcagtgtgg   2820
gagagtgcct gaggatgtgt ttgtgtgtct gaaaatgggc ggagggtctg ttgtgctaat   2880
gtgtgcaggg gtgaacatgt gtgtgacagt ctgtgtgttt ccctgagtgg tggctgcgtg   2940
agagggtgag gggatttggt gttgtctacc atgcccggca catagcaggc tcttaataat   3000
cttgaattta attaatgtta aatgtgtatg ttcccatcct tgtggaagtt ggtatagagc   3060
ctgttttcct gtgattgtga gactggaaaa tgggggacgg gcaggggcga gacaggatac   3120
agaggctact gttttcttcc tccctagaag taagtacata gaagagtggg ctctggcacc   3180
tcacgggaca tcaccaagtc ctgtgtggct ggctaggctg tcccaaggtg gcttcaggca   3240
tcacttgaat cttttgagac cttcaggcag tagcctgcca ttcaccctgt cagtcagcag   3300
aagttgggcc cacacaggcc atagaaacac agagcagttc ccgggaggac ctgagctgtc   3360
cctgagagca gagcttccag gagaggccgc aggaactgcc ttgaccggaa ttcctcttgg   3420
ggtgcaaagg tggagggaca catggtgcga ccccaggcag aggactgcag ccactccgtg   3480
cagtcccagc ctctggggta gccccttgac ctccaggcct gcacagatcc aaggccgagg   3540
tccaggctcc agcgccaaat tagctggcct agcagcctgc agccgctcta atctcaacta   3600
ggaaggaatc cttgcgctta gaaagtccaa gcgaaagggt attctgattt tatcccggtt   3660
ttaccagaaa atgctgaaag gaaaagcccc gagaggacac agtgctctag gaactcgggg   3720
cgccacgagc gcctcatccc ctcccttccg cccggccgcg gtgccctggt cgctgaggga   3780
cgcggtcagt acctaccgcc actgcgaccc gagaagggaa agcctcaact tcttcctctc   3840
ggagtcctgc ccactacgga tctgcctgga ctggttcaga tgcgtcgttt aaaggggggg   3900
gctggcactc cagagaggag gggcgctgc aggttaattg atagccacgg aagcacctag   3960
gcgccccatg cgcggagccg gagccgccag ctcagtctga cccctgtctt ttctctcctc   4020
ttccctctcc cacccctcac tccgggaaag cgagggccga ggtaggggca gatagatcac   4080
cagacaggcg gagaaggaca ggagtacaga tggagggacc aggacacaga atgcaaaaga   4140
ctggcaggtg agaagaaggg agaaacagag ggagagagaa agggagaaac agagcagagg   4200
cggccgccgg cccggccgcc ctgagtccga tttccctcct tccctgaccc ttcagtttca   4260
ctgcaaatcc acagaagcag gtttgcgagc tcgaatacct ttgctccact gccacacgca   4320
gcaccgggac tgggcgtctg gagcttaagt ctgggggtct gagcctggga ccggcaaatc   4380
cgcgcagcgc atcgcgccca gtctcggaga ctgcaaccac cgccaaggag tacgcgcggc   4440
aggaaacttc tgcggcccaa tttcttcccc agctttggca tctccgaagg cacgtacccg   4500
ccctcggcac aagctctctc gtcttccact tcgacctcga ggtggagaaa gaggctggca   4560
agggctgtgc gcgtcgctgg tgtggggagg gcagcaggct gcccctcccc gcttctgcag   4620
cgagttttcc cagccaggaa aagggaggga gctgtttcag gaatttcagt gccttcacct   4680
agcgactgac acaagtcgtg tgtataggaa ggcgtctggc tgtttcggga ctcaccagag   4740
agcatcgcca accagaacgg cccacccggg gtgtcgagtc ttggtaggga aatcagacac   4800
agctgcactc ccggcccgcg ggccttgtgg catataacca tttatatatt tatgatttct   4860
aattttatta taaaataaaa gcagaaatat ttcccgaaga acattcacat gagggcatta   4920
cggggagacg gcaagtcggc ggctcggggg gcgcgctcag ccgggagcgc tgtagtcaca   4980
gtcccgggag gaagagcgcg                                                5000
```

<210> SEQ ID NO 97
<211> LENGTH: 1500
<212> TYPE: DNA
<213> ORGANISM: Homo sapiens

<400> SEQUENCE: 97
tggaacaagt gtcagagagt aagcaaacga ctttctgagc tgtgactctg ctcctcgact 60
gcccacgtgc tctccgctgt ctgcactcct gcctcacctg ggctgactcg gactctccac 120
ctcctttgct gcttccggca tgagctaccc aggagcctaa ggcgctcctt cccgcaactc 180
cggtccccgc gccccgggac tgcaaatcct ttaaacagag gccccagagc taggggtttt 240
cccaggctct ggtgggcgtg ggctgacagt cgctgggagc cccgcaacag gggggatgtc 300
caggcaggta tgcacccagc tcccggcgtt tcccggagtc accacaatgt ttccctttct 360
ctctccccca cgtatgctgc taggggtact ccccagatag gattttcttt gtcttttctc 420
ctagtaacac cgaagccctc tcgtgcccgg ggactgcaga ggaacgccag accatccgga 480
ccttgcggga tggctcggtg tgtgtgtttt actgtgtgtc ggagtgtcgc gcatgtgtgc 540
gtgttggggc gcgttatcaa caggggccta gggcaccccc actctttctt gctctcttcc 600
cccatcactt catggacctc cgaggcgcaa agcgctcgac cctctcctgg gctcagtggc 660
ttgggtactc cgggctgagc tcagctgggg agtcccctta cccagcccgc accggcaccc 720
cgaagcttca aagttgcggc aaacagttgc ggggagcaga ggaactgagg tccaggccag 780
cgcgcccgcg gtcgctcgcc ttggggagca ggctgagccg agggtcgtgc gggtgcgcgg 840
cagaggcggt aggaggcgga ggagaggggg gagaaagagg gggcggtggg gaacagctgc 900
cggggtaggc gaggcgcaag gtggctcccc gcggccccgc gccccgcggc tctcggacgc 960
accaggcagc caatggctgc gcagaggtgt acagcagatg gcgtctgact gcgccgttcc 1020
ttcctcctcc tcctcctcct ccttctcttc ctcctcctcc ttctcttcct cctcctcctc 1080
cttcagtgct gaggagccag agtcgccgcc gggttgccag acgctggaat gggtggtctt 1140
ccgacacaca ccaccatctt tcttgcgctc gggaagctcg gggctcagcg gctcccagag 1200
gttacggcgg cggctctggc gagacgggtg agtgcaagca cgcggagccc cgagtcgggg 1260
atgccgggcc ccctggccgg ccgactgggg cgcggggtgg cagcgccggg gaagggggcg 1320
cgctgccggc gcagactttg ctctttcctc gccggacagc catcgtcgcc ccttctccca 1380
gccagacgcg ggaacttgga agcggatctt ctcggacgcc tctggcttgg ggctgcggga 1440
agcgtgggct gcccggggcg cagtgtgcgg agaccctcta ggcgggcggg gacgccccac 1500

<210> SEQ ID NO 98
<211> LENGTH: 800
<212> TYPE: DNA
<213> ORGANISM: Homo sapiens

<400> SEQUENCE: 98
gttattatcc acggggtcct aattaaagct tgattaaaat gcccttcttt ctctaaaaaa 60
ttacgaacta ggcaacttca tacattttga atggcgcagt gtttcctctt ccaactgttt 120
agtttgtagt atactatgta agcaacatca attatcaacc cttgcaagat gacaacatga 180
gcctgtgggg gaagcacttg aggggaggga ggagaaactt ctcttttta ataatcagcc 240 ggaaacaatg tttaacaaga atctgatgag gtcactgcag taaatatttt tcctcttaca 300
gagccaatca tcacggaggg atcccctgaa tttaaagtcc tggaggatgc atggactgtg 360
gtctccctag acaatcaaag gtgtttgctt tctgctctgt tgcttttaaa ttgtatggga 420

| | |
|---|---|
| aaggaagatt ggtccgacgg cgcgcttgtg gcccggccgg agcttgcgtg cgcgttctga | 480 |
| cggctgggtg ctgtgttaca ggtcggcgca gttcgagcac acggttctga tcacgtcgag | 540 |
| gggcgcgcag atcctgacca aactacccca tgaggcctga ggagccgccc gaaggtcgcg | 600 |
| gtgacctggt gcctttttaa ataaattgct gaaatttggc tggagaactt ttagaagaaa | 660 |
| cagggaaatg accggtggtg cggtaacctg cgtggctcct gatagcgttt ggaagaacgc | 720 |
| gggggagact gaagagcaac tgggaactcg gatctgaagc cctgctgggg tcgcgcggct | 780 |
| ttggaaaaac aaatcctggc | 800 |

<210> SEQ ID NO 99
<211> LENGTH: 40
<212> TYPE: DNA
<213> ORGANISM: Homo sapiens

<400> SEQUENCE: 99

| | |
|---|---|
| tccctgctgt gggacccgag gagaggagaa ctggttcgct | 40 |

<210> SEQ ID NO 100
<211> LENGTH: 500
<212> TYPE: DNA
<213> ORGANISM: Homo sapiens

<400> SEQUENCE: 100

| | |
|---|---|
| tctctctctc tctcttgctt ggtttctgta atgaggaagt tctccgcagc tcagtttcct | 60 |
| ttccctcact gagcgcctga aacaggaagt cagtcagtta agctggtggc agcagccgag | 120 |
| gccaccaaga ggcaacgggc ggcaggttgc agtggagggg cctccgctcc cctcggtggt | 180 |
| gtgtgggtcc tgggggtgcc tgccggcccg gccgaggagg cccacgccca ccatggtccc | 240 |
| ctgctggaac catggcaaca tcacccgctc caaggcggag gagctgcttt ccaggacagg | 300 |
| caaggacggg agcttcctcg tgcgtgccag cgagtccatc tcccgggcat acgcgctctg | 360 |
| cgtgctgtga gtacaacctg ctccctcccc gggcacagat atgacagagg ggcttagagg | 420 |
| gggcccagct ttgagatggg ttgttcttat gtcacaggac agagtgatct gacatgcaca | 480 |
| cttccccgcc accctgtcat | 500 |

<210> SEQ ID NO 101
<211> LENGTH: 500
<212> TYPE: DNA
<213> ORGANISM: Homo sapiens

<400> SEQUENCE: 101

| | |
|---|---|
| tgtcctcgaa gaagggcctg agcagcagca gaggacccca ggcgaccgtg cctgagccgg | 60 |
| gcgccgacga cgactgagca cctgatatgt ccccggcact cgcagcccg cggccggagt | 120 |
| cgctgtgggt gagcggtcgt cgagcttcac agaggccggg ctctgtgcca gggccccgac | 180 |
| agggcaggaa gcagatagag tcccacaagc acaagcccag tgcgcagaaa gggttactta | 240 |
| aaaaataagt tctgtgataa aatcaaacag ggtgaagggc tggaaacagg tcatgagggc | 300 |
| gcaaacaggt cgtgagggcg caaacaggtc gtgagggcgc aaacaggtcg tgagggcgca | 360 |
| aacaggtcgt gagggcgcaa acaggtcgtg agggcgcaaa cagatcgtga gggcgcaaac | 420 |
| aggtcgtgag ggcgcaaaca ggtcgtgagg gtgcaaacag gtcgtgaggg cgcaaacagg | 480 |
| tcgtgagggt gcaaacaggt | 500 |

<210> SEQ ID NO 102
<211> LENGTH: 300

<212> TYPE: DNA
<213> ORGANISM: Homo sapiens

<400> SEQUENCE: 102
aaatgagacc tctggggaga ctgtcaaccc caggggtaaa acaaaaattc tgatcagaaa 60
ctgagtttcc caaagaaggg gctaaatgtt ttccaacact ttcggggctc agggaagatg 120
actctgtaag gacactgaga atcttcctcg cgtgccacgg ggaggaggac tgggggcgtt 180
tgaggggctc agcgcaccag aggagtgagg tggaggaggg cgttcccgcg tcctcctctt 240
caatccagag cagctcaacg acgtggctcc ctttctatgt atccctcaaa gccttcgcgt 300

<210> SEQ ID NO 103
<211> LENGTH: 600
<212> TYPE: DNA
<213> ORGANISM: Homo sapiens

<400> SEQUENCE: 103
taggctctag tggacctagc agtgggagag ctacttgggc tggtttcttt cctgacgctg 60
cagggatggg catcggcctg gaaccagaag cgcaggagct gggccacggc agagtaatta 120
agaaaataat gaaattgatg gcggatgggg gcgctagaaa tcctggggcg tctacttaaa 180
accagagatt cgcggtcggc cccacggaat cccggctctg tgtgcgccca ggttccgggg 240
cttgggcgtt gccggttctc acactaggaa ggagcctgaa gtcagaaaag atggggcctc 300
gttactcact ttctagccca gcccctggcc ctgggtcccg cagagccgtc atcgcaggct 360
cctgcccagc ctctggggtc gggtgagcaa ggtgttctct tcggaagcgg gaagggctgc 420
gggtcgggga cgtcccttgg ctgccacccc tgattctgca tccttttcgc tcgaatccct 480
gcgctaggca tcctccccga tcccccaaaa gcccaagcac tgggtctggg ttgaggaagg 540
gaacgggtgc ccaggccgga cagaggctga aaggaggcct caaggttcct ctttgctaca 600

<210> SEQ ID NO 104
<211> LENGTH: 800
<212> TYPE: DNA
<213> ORGANISM: Homo sapiens

<400> SEQUENCE: 104
gaggttgctg actcaggagc caggagctga gaaactccta ggctagcagc cgttgagcct 60
aattttattt tctggctttc tccgaaatgt ctcgtttccc tcatctttct ggtccttttc 120
gtctctctta ttttccccaa aacgtctacc tcacttcgtc ttcctttctc ctcccctccc 180
cctctctttc ctctatactc tcttcccatt tagccttgca ggcccctcct ccccggtgtt 240
ggagagctca aagacgcgcg aaactcaagg atctggccct gaccagggac gggattaggc 300
gggaagtggt gacggcctga aaaggctggg ctcgaacccg tgccttcctg aaaggactct 360
ccccgccaca agtcacaccc acccgcaggc ctgctggcca aagaaacaaa ggagtcgggc 420
gtggatccag gagaaacagg ttttcgctct cggatctccc tgggcaaatc agggatcctg 480
agcgctatac cccgcagtcg tacggagcct ctgggaaagg ggatttaagg gtgacttcca 540
ctttcagctt cggctacttg ttgcctgcgg tccaagcctt ctctgcttcc tcctacctcg 600
tcttaggcct ctgtagaaag tgcacgccgc gtttcccctt ccaggctctg agagggcctg 660
caggcccgtg gccgcctccg acaagatgcc ttccagtgct agggggccca ctttggcggg 720
atgggggtcg gttggttaaa aaaaacttaa gttctggctc agtcgagtgt ggcaaaagcc 780
gagggtcggg ggttgggggg 800

<210> SEQ ID NO 105
<211> LENGTH: 2000
<212> TYPE: DNA
<213> ORGANISM: Homo sapiens

<400> SEQUENCE: 105
tactgacctg gtctccgcct caccggcctc ttgcggccgc tgcagaagcg cactttgctg 60
aacaccccga ggacgtgcct ctcgcacagg gagcgcccgt ctttgctggg gctggagcgg 120
cgcttggagg ccgacactcg gtcgctgttg gactccctcg cctgccgctt ctgccggatc 180
aaggagctgg ctatcgccgc agccatagct gctcagcgag ggcctcaggc cccagcctct 240
actgcgccct ccggcttgcg ctccgccggg gcgagggcag gacctgggcg gccagggaaa 300
gggcagtcgc ggggaggcag tgctaaaatt tgaggaggct gcagtatcga aaacccggcg 360
ctcacaaggt tagtcaaagt ctgggcagtg gcgacaaaat gtgtgaaaat ccagatgtaa 420
acttccccaa cctctggcgg ccgggggcg gggcggggcg gtcccaggcc ctcttgcgaa 480
gtagacgttt gcaccccaaa cttgcacccc aaggcgatcg gcgtccaagg ggcagtgggg 540
agtttagtca cactgcgttc ggggtaccaa gtggaagggg aagaacgatg cccaaaataa 600
caagacgtgc ctctgttgga gaggcgcaag cgttgtaagg tgtccaaagt atacctacac 660
atacatacat agaaaacccg tttacaaagc agagtctgga cccaggcggg tagcgcgccc 720
ccggtagaaa atactaaaaa gtgaataaaa cgttccttta gaaaacaagc caccaaccgc 780
acgagagaag gagaggaagg cagcaattta actccctgcg gcccgcggtt ctgaagatta 840
ggaggtccgt cccagcaggg tgaggtctac agaatgcatc gcgccggctg cggctttcca 900
ggggccggcc acccgagttc tggaattccg agaggcgcga agtgggagcg gttacccgga 960
gtctgggtag gggcgcgggg cgggggcagc tgtttccagc tgcggtgaga gcaactcccg 1020
gccagcagca ctgcaaagag agcgggaggc gagggagggg ggagggcgcg agggagggag 1080
ggagatcctc gagggccaag cacccctcgg ggagaaacca gcgagaggcg atctgcgggg 1140
tcccaagagt gggcgctctt tctctttccg cttgctttcc ggcacgagac gggcacagtt 1200
ggtgattatt tagggaatcc taaatctgga atgactcagt agtttaaata agccccctca 1260
aaaggcagcg atgccgaagg tgtcctctcc agctcggcgc ccacacgcct ttaactggag 1320
ctccccgcca tggtccaccc ggggccgccg caccgagctg gtctccgcac aggctcagag 1380
ggagcgaggg aagggaggga aggaaggggc gccctggcgg gctcgggatc aggtcatcgc 1440
cgcgctgctg cccgtgcccc ctaggctcgc gcgccccggc agtcagcagc tcacaggcag 1500
cagatcagat ggggattacc cgccggacgc aaggccgatc actcagtccc gcgccgccca 1560
tcccggccga ggaaggaagt gacccgcgcg ctgcgaatac ccgcgcgtcc gctcgggtgg 1620
ggcgggggct ggctgcaggc gatgttggct cgcggcggct gaggctcctg gccggagctg 1680
cccaccatgg tctggcgcca ggggcgcagg cggggcccct aggcctcctg gggctacctc 1740
gcgaggcagc cgagggcgca acccgggcgc ttggggccgg aggcggaatc aggggccggg 1800
gccaggaggc aggtgcaggc ggctgccaac tcgcccaact tgctgcgcgg gtggccgctc 1860
agagccgcgg gcttgcgggg cgccccccgc cgccgcgccg ccgcctcccc aggcccggga 1920
gggggcgctc agggtggagt cccattcatg ggctgaggct ctgggcgcgc ggagccgccg 1980
ccgcccctcc ggctggctca 2000

<210> SEQ ID NO 106
<211> LENGTH: 800

<212> TYPE: DNA
<213> ORGANISM: Homo sapiens

<400> SEQUENCE: 106
gggggacaca gagaggaggg gttgcgggcc tgtgagaatg aagagcacag agcggagagg 60
gggaggagga gggaaaggaa ggcgtggcag tgagagagaa gaggaagaag agaggaggag 120
tggggagggg agggagagca agacagcagc gggtctggat tcccctccga gccacatctg 180
gtcaggttct aagtaattag aagattttcc cattggttta cccaagggct ctctctctga 240
ttaattttcg aaagagttgg ccaattttaa tcatagcaaa cacgatgatc acggtgatca 300
tggcctgaac agctaaaagc agaaaataaa accccccagaa cggactatga tcttgacctt 360
tgcccgtggt caccggctgg gcccacaccc agggttctga gctgttggga gccaaggctg 420
ggtggacagg ggcttccgag gagctgtccg cagcggggcg gggaggcggg ccccgggggc 480
ccgggcactc cgcgtcaccc cccggcaggg cccagagcgg caggccggcg tgcgccccag 540
ggcctgcgca ccgtgggggc tcttccccgc ccacgaggcc taggtgctgc cgcagccacc 600
ccaggaaggg ccccaggcca cagtcgcagc gccaggagtt gtgccccaac aggacctccg 660
tcagccgggg cagagcccca aacacgtcgc caggcagggt ctccagctgg ttgtggtcga 720
gctggacgct ctccaggctg ctgagattgc ggaagagggc acggggcagg gcgcgcagcc 780
tgttgcggcg cagggacacc 800

<210> SEQ ID NO 107
<211> LENGTH: 550
<212> TYPE: DNA
<213> ORGANISM: Homo sapiens

<400> SEQUENCE: 107
gccccggtgc accgcgcgtc cagccggccc aactcgagct agaagcccca accactgccc 60
agtgcctgag ttgcagtctt gggtccttta gaaacctgga gatgtgcgta aaattcagat 120
gccggtattc ccgaacttcc ccaggcctca gcatatctcg gcggcctgtg gacagatggg 180
aggctaccaa tcgctccggc gtccgcagcc cgacccctgc cgccagaccc cggacgtctt 240
ccggataata aagttcccgc tctaattcat tttccctaat ctggacgccc ctaatctaca 300
gcttttattg cgcccagtta aaagtcgagg gaattcgctg tccctccgcg ctcggataat 360 taccccctaaa tggccacggc agccccttgt gtttcctgga gattagaacc ccgcagtcat 420
caatggcagg gccgagtgag ccgccaatca cctccgctca ctccctgaga gccgctggcc 480
tgggccgcag gaggagaggc cataaagcga caggcgcaga aaatggccaa gccccgaccc 540
cgcttcaggc 550

<210> SEQ ID NO 108
<211> LENGTH: 2000
<212> TYPE: DNA
<213> ORGANISM: Homo sapiens

<400> SEQUENCE: 108
agggtgcctc tgttcaaatt agaaaaaggc gccccctcag ggcagactca gcccagctgc 60
caggggacaa gtcctggcta acgggagctg gagctgggtt tcacctccag gtgcctcctt 120
ggcggggcgc cccgtgcagg ctacagccta cagctgtcag cgccggtccg gagccggagc 180
gcgggaatca ctcgctgcct cagcccaagc gggttcactg ggtgcctgcg gcagctgcgc 240
aggtggagag cgcccagcct gggaggcagt agtacgggta atagtaggag ggctgcagtg 300

```
gcagaagcga gggtggccgc agcacttcgc cgggcaggta ttgtctctgg tcgtcgcgca    360

ccagcacctt tacggccacc ttcttggcgg cgggcgccga ggccagcagg tcggctgcca    420

tctgccggcg ctttgtcttg tagcgacggt tctggaacca gattttcacc tgcgtctcgg    480

tgagcttcag cgacgcggcc aggtctgcgc gctcgggccc ggacaggtag cgctggtggt    540

taaagcggcg ctccagctcg aagacctgcg cgtgggagaa agcggcccgc gagcgcttct    600

tgcgtggctt gggcgccgcc ggctcctcct cctcctccgc gacgcctgcc ggcccgctgc    660

cgcccccgcc gccggccccg ctgcacagcg cggacacgtg tgcacctctg gggccaacac    720

cgtcgtcctc ggtccttggg ctgcggtcgc ctgcggaccc cggtgggaac agaaacaaga    780

gactgtcagc gccacagacg aggtgaggcc gggcctcaac tgcaggggtc acgggagtgg    840

ggcggaaata cactttgatc ccactcaagc ggagcggagg tctgggaggc cctgggcccg    900

ggagaccagt cttagactct tgccccactg ggtatcccat ctaggcctct tctggggagg    960

gcggcagact cagccgctgt gtcaacgctg tgttgtcgag accagctccc caccctctct   1020

gggccccagg ctcccctcag taacttgggg cactcgaccc gagcatccgc gaaagccctc   1080

ccggctctca gcgttgagca ttgggattct agactgcatt tccgtctctc tgcttgggtt   1140

cacgcgcctc tccacactta gttcacacgc acacacgcgc gcgtcctcgc agcacacact   1200

tgtctggtgc aggtaaggga aggtggaggc ggatcctggg gccaaaggta tttagaatct   1260

ttcaccctca gccgcctggg attgctgtga gagacatgga aacaggctga gccgaggcct   1320

tagatgagag gatggactgg agagtaaaga gggagggttg cccctgcatc gagtttttgg   1380

accctgatcc cacaccagct tctcggtctc gtacccgccc ttccgaagaa ctccagcaga   1440

aaggtccagc ggtcccctgt gcttgaggcc tacagaagct tgtacccaac tagggcaggc   1500

acccgggtct tccagaccac aggacaggac aggccacggc tgaggaggcc tctctcctgc   1560

ctccaggatg aactaaagac ccaatccggg atcttcggcc tagggctgct ctcccagacc   1620

tggggtctga gaaagccaaa ccagcccttt ccccaaagct ctagttctgc agattctcag   1680

ctctggccca ctcggaggtg ttcttcacca cctatccacc tactgtgggg cccggccctg   1740

ggaccttgaa ctggcaggtc tctggtccag agctaggtca ctggctacct gaggtctctg   1800

aacccctcac ttttccgctt ccctgatttt ggggatttgg ggacagacac ggcagaaagc   1860

actggcgacg aactcaaaaa ctcccgaacg caaggggcag cggttctccc aacccagtct   1920

aatgcacatt ggcccaggat gtctcaggcc tcaccccagg acgtagggct ctgaggagct   1980

actccggtct ctcgcgggct                                                2000
```

<210> SEQ ID NO 109
<211> LENGTH: 1000
<212> TYPE: DNA
<213> ORGANISM: Homo sapiens

<400> SEQUENCE: 109

```
gagaagggat gtggcggggg gctcctccgg ccctggactc cctgggtgga ctagaaaagg     60

gcaaagaagt ggtcacatct gtgggccaga ctggtgcgcg atctttggag gcgcagcagc    120

aaggccgcgc cagggctgag cccagaccgc ccacgaggag gcccgccagg cccggagcag    180

cggcgcgtgc gggggcgtgc cgagcgcagg ctctagggcc cctgcttcgc cccagctgga    240

ccccgcgggc ggtcggtgca gctcgagcgt gtgggctgcg atgccctgcc tgagacttcg    300

ggctagggat gcgggcggga agtgggggtg cggcggcagc tgcagattag attccttttt    360

tttttggccg gagggacgtg caaacttcta gtgcccgggc caagagggcg accccggagg    420
```

tgcgtaggtg gccctccggg ttcccgcttc tcctagtgcc tctgaaaata ccgtcagggt 480
aaagggagac aggcagtaag tcttaccacc accgcccttt ccccatgtca ttggccaaaa 540
actgaacatt aagataaagc agctgtttca gtcaatggaa agcggtaggg cgaggttgta 600
cccaaaaccc ggtttagacg gccaatgaag tcctaggaaa agccgccccg gggcacgtt 660 caggtggagc ggctgcacct cgggtcgttc taagggatgg gctgcgtggt acccacggaa 720
ttcatgggtc caaaaggtcc tggtcacctg tccaaacatc catcccctgg cgcatggcgg 780
ttgacaagat ggcccggcca cccagaggaa ggaggatccg ggacggggaa cttcgcgccg 840
ggaagctgta gcccagagct gcagctcagc attcgcaaga gattcatctt tttttctct 900 cgtgttcgga gaaacagata aacaagacac cgcctcatca gataagaacg tctccttcga 960
tgtcacggat ttcaagaggt agctggagaa actgacgtca 1000

<210> SEQ ID NO 110
<211> LENGTH: 1300
<212> TYPE: DNA
<213> ORGANISM: Homo sapiens

<400> SEQUENCE: 110
caggtcaggc agaacttctg cccttcccgc tactggcacc ccaagcaggg atgcactggg 60
atgcgtggca ggggcgggat ctcctgggag cgtctcagcc cagcagggag tggggaagca 120
agagggaagg cttaccttcc tcggtggctg gcaggaggtg gtcgctgcta gcgagggga 180 tgcaaaggtc gttgtcctgg gggaaacggt cgcactcaag catgtcgggc caggggaagc 240
cgaaggcgga catgaccggg gcgcagcggt ccttcacctg cacgcagagc gagtggcatg 300
gctggatggt ctcgtctagg tcatcgaggc agacgggggc gaagagcgag cacaggaact 360
tcttggtgtc cgggtggcac tgcttcatga ccagcgggat ccaagcgccg gcctgctcca 420
gcacctcctt catggtctcg tggcccagca ggttgggcag ccgcatgttc tggtattcga 480
tgccgtggca cagctgcagg ttggcaggga tgggcttgca attgctgcgc ttgtaggaga 540
agtcgggctg gccaaagagg aagagcccgc gcgccgagcc caggcagcag tgcgaggcga 600
ggaagagcag cagcagcgag ccagggccct gcagcatcgt gggcgcgcga ccccgagggg 660
gcagagggag cggagccggg gaagggcgag gcggccggag ttcgagcttg tcccgggccc 720
gctctcttcg ctgggtgcga ctcggggccc cgaaaagctg gcagccggcg gctggggcgc 780
ggagaagcgg gacaccggga ggacagcgcg ggcgaggcgc tgcaagcccg cgcgcagctc 840
cggggggctc cgacccgggg gagcagaatg agccgttgct ggggcacagc cagagttttc 900
ttggcctttt ttatgcaaat ctggagggtg gggggagcaa gggaggagcc aatgaagggt 960
aatccgagga gggctggtca ctactttctg ggtctggttt tgcgttgaga atgcccctca 1020
cgcgcttgct ggaagggaat tctggctgcg ccccctcccc tagatgccgc cgctcgcccg 1080
ccctaggatt tctttaaaca acaaacagag aagcctggcc gctgcgcccc cacagtgagc 1140
gagcagggcg cgggctgcgg gagtgggggg cacgcagggc accccgcgag cggcctcgcg 1200
accaggtact ggcgggaacg cgcctagccc cgcgtgccgc cggggcccgg gcttgttttg 1260
ccccagtccg aagtttctgc tgggttgcca ggcatgagtg 1300

<210> SEQ ID NO 111
<211> LENGTH: 500
<212> TYPE: DNA
<213> ORGANISM: Homo sapiens

<400> SEQUENCE: 111
tgcgatcatt aaaatcagtt ccttccctcc tgtcctgagg gtaggggcgg gcagatttta 60
ttacttctct tttcctgata gcagaactga ggcggggttg tggaggagcg acggaggacc 120
acctctaact tcccttcact tcctggattt gaagcctcag ggccaccggc ctcagtcctg 180
ttacggtggc ggactcgcga ggttttccag cagctcattc cgggacggcg gtgtctagtc 240
cagtccaggg taactgggct ctctgagagt ccgacctcca tcggtctggg agcgagtggt 300
tcgagttcag atgctgggaa ccgtcgcttc tccccggccg ggctcgctgt tttctcctcc 360
gctcgccgtc atcaagcccg gctatgagca gggctttaaa tcctccctcc ctcacccgca 420
ggtttaccga gcagccccgg agctctcaga catgctgcgc tgcggcggcc agaggagggg 480
tgggggcatt gccctctgca 500

<210> SEQ ID NO 112
<211> LENGTH: 500
<212> TYPE: DNA
<213> ORGANISM: Homo sapiens

<400> SEQUENCE: 112
gggcttgggc cgcaggcttc cctggacttc cgcagtcccc cttctcccca ttccagaacc 60
tgccgagccc ctgctgcatc tgggacccgc cttcaccgtt tcccaatccc agcggttagc 120
ccctgcgccc cctttttggt ctccactttg ccgttcgaaa atgcctaggt tggtggatcg 180
accctccgcg gagcaaagac ggatggctgg caggagcagg ttcaggagct gggccaaggt 240
attctctgct tccgcctttg tgtccgcccc cccgcccccct gctccccgct tcccgccagc 300
atctctcctt ttctgctcag gagtgtttgg cccggcggtc caccccggct tcccgagata 360
cgctagagtt gcccccacgt cctgtccgcc gcgcccctac ccaccgggtt gccttcgggg 420
cccttcggtg ctgtgtagtc ggcgtggcgc tgtgagctag gcgaacagga acccccaggc 480
ccgccacgtc tacgctatta 500

<210> SEQ ID NO 113
<211> LENGTH: 600
<212> TYPE: DNA
<213> ORGANISM: Homo sapiens

<400> SEQUENCE: 113
ttctggggcc tggatgggtg cgagcgggac ccgggggagt gggagtcgcc aggctctgag 60
caagcaaggg ctgcacctgc acctctgccg ggcatgaaga aaggtaagga aggaaggagc 120
tcacccgggt gggagacaga gccggggcgc gcgagcttgg tgtgggggcg ccactccggg 180
gcggagggga ggggctacca gtgacttctc cgagtcggga gctagaaaga ggcttccggc 240
caggttccct tggaacaggt gtcggagttg ttgggagagg gggctgcaag aaagaggggt 300
gcagaaactg gttcattaga tggaggctct gggcggaacc gcgaggacac cctggcagcg 360
cgctgtgcct gcgttaggcc gggaggggag aggcctccgg acggcgaagt gtccctaggg 420
acccagacgc ctcgggagcg atccgggccg ctgcgaagcc ctgcccacca ggagtggatc 480
cccaggattc acctcccggc tgcctgctct gagctgagaa ggggatctgg ttcttcacaa 540
taccgtggat ggcggggaag gggagggagc ctggggtaaa atcccatctt ggtttcctcg 600

<210> SEQ ID NO 114
<211> LENGTH: 1300
<212> TYPE: DNA
<213> ORGANISM: Homo sapiens

<400> SEQUENCE: 114
tgtcacagaa accccagcag cgcagccacc ggactgggtt ctggaggccg agccgcagtc 60
cgtgcggcgg cgctgggaag agaaggcgcc ccggcagctc ccctgccacc ggccccgagg 120
agcggctggc tcccccagcc cagcgccgcc gccgcccggt aactccaggc gcaactgggc 180
gcaactgggg cagctgcgac accgaatccc tcacatctgc aacctgggtg ctgcggccac 240
tgagaaaatg gaggcgcaga ccaacgagcg gtgccgcgac cgagagacct cggctggcga 300
aatggtggtg ccgggagcct gcgagtgacg ccagccggcg gggttgtcaa ggacaacatt 360
cgttttgacg cagccaatgg cgccgtcacc aagaaaccat cgactctgag aaaaaagaga 420
ggttcggcca ccgagaaact ccgtacgaca agtgctgtgg cagaaaaacc gcctactccg 480
cgccacaggc aaaacagcca atggaaaccc caggtgctgc gaccgtgaca ccggcactag 540
agggtctcgg atggagaaag cggcgcacgg agaccaggaa actatgtgta gcacaactag 600
cagaaaaccg tctggtcggc catccgggag aaagcgcgga tcagaaacaa gcgacttcga 660
tgcagggaac cgcgcagcca ctgaagaaag tgacccacgt ggcagtggtg ccagcgaaac 720
actgcagttt ggacggcagc tgtggggatg ccacagagaa acatgcactg ccactgaagt 780
acatccagct ccgcggagct agtgttcata tgatcaagaa accgccagtt gggctctgct 840
agaaactttt agtcctccct taacggctat cctacccaca acagacaatg cctttaccca 900
gcacctagcg gtgctgagac ccgcctgggc cagcacagag cgcagagcag tacgggtacg 960
gagaaacgcc ggactcagtg aaaccagcct tgcctccagc ggattccccg gcttcgccgg 1020
acgccacagg cagagtgccg cggggaaacc tctggctccc taaaccgatt agattgtggg 1080
agtggggggg acactcacaa gttgtgtgga agggaaccag cggcaatggg acccggcgag 1140
cacttgcccg cagcaaatgc ctgcgctgct gcaaaaaaaa caacttttgg cgcaaagaat 1200
gttgcggcca gagagcatcc gctgtcgctg acaaaggagt agcaatggca atgagaaacc 1260
gccggcgcca cggccgaccg cggcggctca cgcctatgat 1300

<210> SEQ ID NO 115
<211> LENGTH: 2100
<212> TYPE: DNA
<213> ORGANISM: Homo sapiens

<400> SEQUENCE: 115
caaacgctga gagacaaaaa gacaccaaca cccaccagga ctgcgtcctg ccagctcttc 60
actccgctga cctgaccttc cacgccccta gtcctcgagc ggacttgacc tgtgggggag 120
taccgaaccg tccccatgag gccctccaag cggccaggtg gcctccgcca ctctctccac 180
ccccacctcc tccacccccc agcccatcgg tccatcttcg atctgcaaaa cacgccgggt 240
cagcgacgca tcggtcccag gcttgtgacc acctctttct ctgttacttg gggagccagg 300
cccaccgctc aggatcacag tgaggagaaa aaagacacaa acgccaggac agggcggctg 360
gggaaggaaa ctgctaggga ccgctcattg tcagcctggc gtgtcccacg gatcgcagga 420
cccgtcgagg ctttgctctc tgcgacccga atactcctgg gcctctcgac ctcctcctcg 480
gactcaggcg tccgcgtctc cggtcatcac gggagaccaa ttggtttaca aatagtgatg 540
ataaacctgg gaccgacctt ggggctgtgt aaaagtctac tgacagatgt aatggagggt 600
tgttagcagt cacaaagcct gtcggacccg tagcattagt tcaagagact attttcgtgt 660
cgcaccaaaa ttactgcgcg tgtaaaccaa tttccccgac ggaagaataa acagagattc 720

-continued

```
gtttgaagcg cgagatgaaa acagatgggg tatcgcaaac agttccccaa aatacaacag    780

acttctgggc caattacacg tggttagctc tgaatggcag aggaaatagt tttctttgct    840

gctaaatgtc acaaaagtca cctaaaggca cagaggaggc cgctctgttt ttgcgaaact    900

tgctaaaatt aatctgcgct gggccacttg cagaaagcag aaccacctcc cgcccccacc    960

tcgcctccag ccgccggggt tcaggcgttt gtgaaagaca gaacctttgg gctagggacc   1020

cgggcactgg tgcttcgaag tccgaatccg ccggccgaga aaacgacaag agaaagaaaa   1080

tccagcgggc gctctctcca gcgccaggcc ggtgtaggag ggcgctgggg ctcggcctgc   1140

cacccctacc cgacattggg aagcagcccc tgcgctcccg cggcgcctca gcctccggtc   1200

cccgccccga ggtgcgcgtt cctcctcccg catgcccgtc tcgggcccca cggagcaaga   1260

agatagacga tgacgaggcg cgcccatcca tccgggccga cgaggtcagg cccgcgccac   1320

aggcaaaaat tgcgcaagcc cggccgcagg gatttcgcgg gcgcctgggt cccaggtgcg   1380

cggccgaaat cctcagggaa aatcccgagg ggccaacggt ctaggccaca gggctgctgg   1440

gcccgggcct ggctcagagc gcattcgggc ggggaggccg cacgccgcac ccgggcctct   1500

cctccgagcc cgaggcaggc actgagctcc gggccagcca ggtgcctccc ggctggtgcg   1560

agaccccggg cctgctggga ggcgtgggca gggcagggca gggctgaacc ccagcgactg   1620

aatctcgaag gcaggaggcc tcggaggtca tcggcccagc tcgcctgaaa ctgtccctgc   1680

tcgtgccagg gcgcgggcag aggagaaagg acagggcgga gcaagcccac tgcagaactg   1740

cggtcggtgg ctgcgaaggg tccgggtcac cgcgctcccg gacgccggaa gccgcgctgg   1800

cggggccgcg gggagggagg ctgggtaccg gggccgtccg gccggaggaa gcggctccgg   1860

ccgcgctgtc cgcgcttggg agccgcgtgc agggttcagc cgtgtttcag ttgccctctg   1920

acctgacccc gggcgcacaa aggcctcccg ggtgcgccgc catggcccag tcttccagtc   1980

gctgccaaat taatgagccc acgtcaggtt gggtttacag ctcggccggg aagcagccga   2040

gtggaaaatg agctcggggc cgctccagag gctcccgcac aactgcagag gctgcccgcg   2100
```

<210> SEQ ID NO 116
<211> LENGTH: 250
<212> TYPE: DNA
<213> ORGANISM: Homo sapiens

<400> SEQUENCE: 116

```
tttccaagac agaaggaggg aactaggcgc ctttttttcca ctccgctgac cccaacgtct     60

gggctgtgcg ttgtaacgca gttggcgggg ccttcagctt gggatgaggg cgaaggggct    120

cgggatgggt gggaaagcaa ggaccgggca acaggtgggg aggtggcgga cttttgtctc    180

ggggaaggaa atcggctgtg ctgaaagggc ggaaagcagt agcgcacaga actagtgtct    240

gcggggtccc                                                          250
```

<210> SEQ ID NO 117
<211> LENGTH: 250
<212> TYPE: DNA
<213> ORGANISM: Homo sapiens

<400> SEQUENCE: 117

```
ccctcctgtg gctgcttggg cagacgcctg tggcctgtcg gatgcggccc acatcgagag     60

cctgcaggag aagtcgcagt gcgcactgga ggagtacgtg aggagccagt accccaacca    120

gcccagccgt tttggcaaac tgctgctgcg actgccctcg ctgcgcaccg tgtcctcctc    180

cgtcatcgag cagctcttct tcgtccgttt ggtaggtaaa acccccatcg aaactctcat    240
```

ccgcgatatg 250

<210> SEQ ID NO 118
<211> LENGTH: 2000
<212> TYPE: DNA
<213> ORGANISM: Homo sapiens

<400> SEQUENCE: 118
tcctcctttg tgtatgtcaa cccagaggat ggacggatct ttgcccagcg tacctttgac 60
tatgaattgc tgcagatgct gcagattgtg gtgggggttc gagactccgg ctctccccca 120
ttgcatgcca acacatctct gcatgtgttt gtcctagacg agaatgataa tgccccagct 180
gtgctgcacc cacggccaga ctgggaacac tcagcccccc agcgtctccc tcgctctgct 240
cctcctggct ccttggtcac caaggtgaca gccgtggatg ctgatgcagg ccacaatgcg 300
tggctctcct actcactgtt gccacagtcc acagccccag gactgttcct cgtgtctaca 360
cacactggtg aggtgcgcac agcccgggcc ttactggagg atgactctga cacccagcag 420
gtggtggtcc tggtgaggga caatggtgac ccttcactct cctccacagc cacagtgctg 480
ctggttctgg aggatgagga ccctgaggaa atgcccaaat ccagtgactt cctcatacac 540
cctcctgagc gttcagacct taccctttac ctcattgtgg ctctagcgac cgtcagtctc 600
ttatccctag tcaccttcac ctttctgtca gcgaagtgcc ttcagggaaa cgcagacggg 660
gacgggggtg gagggcagtg ctgcaggcgc caggactcac cctccccgga cttctataag 720
cagtccagcc ccaacctgca ggtgagctcg gacggcacgc tcaagtacat ggaggtgacg 780
ctgcggccca cagactcgca gagccactgc tacaggacgt gcttttcacc ggcctcggac 840
ggcagtgact tcacttttct aagacccctc agcgttcagc agcccacagc tctggcgctg 900
gagcctgacg ccatccggtc ccgctctaat acgctgcggg agcggagcca ggtgaggggc 960
tcggcgccgc cccgggcgac ccctgggggc ggcactggag aagccgcccg tcctcataag 1020
ggattgaact tgcatccact cctctccggc cggcttggtc gctggctgcg ctccaccccga 1080 ttctcgggat cattggaccg tttgcgcgaa accagagtgg ccgattaagg gatggggctc 1140
cgagcaccgg gggtggtggc gactgtgggc gaggggaggt gggaccgacc cccaccccta 1200
cactcaaaaa aggccggggc ctccttcgag cttccggtga atttcgggcg atttccgcgg 1260
gtgtcggggg tcccgggagg aggcagtcac agatccaccc ctgcagccag cctcctaggc 1320
gccggctccg gcacgcttcg ccggtctgta gatttcctct tcgatttctc cccagctccc 1380
agcatctgtg acttcactgt taccctccct atccccgcat cacccaaccg cacctgtctg 1440
cgggacttag gtgtgcgcgc ggggctcatg cgtgtcctcc ctgctggcca cccccacggc 1500
ccacacaagt tgcacgggct cgccacgccc cgccaacacg tgcgcggacg cacgcacgca 1560
ctcctcgcac gtgggcttac gcgaatacca gctttcactg ccactcgctc gcggccagat 1620
tcacaggcct gttccggtcc actcgcagct cccctctgcc gctccctccg ccgggctcag 1680
gagtactcgt agctgattgt gcgcgcctga gggtcccaga tcgcggccgc ccaggaccag 1740
gcgaggactc cggagcctcc tctcacctct cccacctgcg ccccgggctg ggccgggtcg 1800
cctggggggc ggcctgagcg aggcgcgggg ccaggagcgc tggagcgact gccgctctaa 1860
gtgccgggcg ggcaggactc tacgatcctt gggccagagg tccggatggt cccgggactc 1920
cgtctcaagg gtcggcgacc cctcaaccca gaagcctcga gcaggcggac aggcagagct 1980
gcccagtggc cgaggcgcgg 2000

<210> SEQ ID NO 119
<211> LENGTH: 1100
<212> TYPE: DNA
<213> ORGANISM: Homo sapiens

<400> SEQUENCE: 119
atttgtcgtt gtgccattgc tgccactgtt gttcttgtcc agggaaacac cggtggccaa 60
cccagatcgg atacaatggt gcggctctgg actgagcctc caaccacatt agccatgggc 120
agcattgttg ctgccgctgc tgttatttta attatgattg tacgttaacc accaccttcc 180
ttcctctgcc tcccttcagc tgcaatgatg tatgttactt tttggtaact ggatttcatt 240
aacatttatg aactctcata aagtagtaga aaaagcaatt tgtgtggaag aattttccac 300
ctcattaaac agtgttcttt tgggggtcaa gctgatattt tttttgttgt tagatttttt 360
ttataggtcc tttgtccttc cctaagccct gggggatgaa aggagagccg tccacccagc 420
gaggggcttg tgtgccctag agggcgctgg gccccgcgcg ctttcctggc tgtccccgcc 480
ggctttccac cctccccaaa gcccaggtgc ccaccgtggg tcgctgcggc ctttcccctt 540
cttggccaaa tccgattact tcgcagcctg cagatggcat cgccggctaa gggcagcctg 600
cggcaggtcc ccgagcctga gcactcctcc tatctggggc ctgagaggac gctctgggct 660
ttttcccagg cccagggtgc gcggcctgct agcgcctttc gaggcacagt cccaagatag 720
gctcttgtcc ttcgacgccc ccttggcaca agcgcactgg cgccctccgc tcaaccccacc 780 ttgcctttgg ggcgggcttc aaccctggga agacaggcct gggggaagcg agaggagagg 840
cccgaataga ggttccggct caatctttcc cagacggagg cctggtgttt ccagctcagt 900
tgcatcttcc agccgcgggc tcctggccca aacagaatgt gtttgctttc acaccgggac 960
ggcaagcgga gtccgcctca gtgagcagcg agctgcgcag tccggacggg tgtcgccccc 1020
agagactcgc cagccgcccc cagacactcg ccagccgtcc ccatctctaa tccaccgtcc 1080
aggcccgggc cctgggaaga 1100

<210> SEQ ID NO 120
<211> LENGTH: 800
<212> TYPE: DNA
<213> ORGANISM: Homo sapiens

<400> SEQUENCE: 120
ccgtgtctcc cttaagaact ggggcctcat ctccactcca gctgcgcgtg cacgtgtgct 60
cccggcagga cgcgcgccca ggagcgcgct gggggctgcc ccgcccctct ctccctcccc 120
cgcgggtaaa ctccgggcat ccatcagtct gttaattgca ctaattagag atcgcagagg 180
tgttaattgg aaaaccctgg tattgtgcct gtttggggga agaaaacgtc aataaaaatt 240
aattgatgag ttggcagggc gggcggtgcg ggttcgcggc gaggcgcagg gtgtcatggc 300
aaatgttacg gctcagatta agcgattgtt aattaaaaag cgacggtaat taatactcgc 360
tacgccatat gggcccgtga aaaggcacaa aaggtttctc cgcatgtggg gttccccttc 420
tcttttctcc ttccacaaaa gcaccccagc ccgtgggtcc cccctttggc cccaaggtag 480
gtggaactcg tcacttccgg ccagggaggg gatggggcgg tctccggcga gttccaaggg 540
cgtccctcgt tgcgcactcg cccgcccagg ttctttgaag agccaggagc ctccggggaa 600
gtgggagccc ccagcggccc gcagactgcc tcagagcgga agaggcagcc gcggctttga 660
cccagcttcc ttccgacggc atctgcagga gcctctaggc ctgacatagg ctccgaggtg 720
ccctggctcc cccacgggga atgctgaggg ttgggccact aggtcctgcc taagtgcagg 780
acctgagcct cagacaaatc 800

<210> SEQ ID NO 121
<211> LENGTH: 300
<212> TYPE: DNA
<213> ORGANISM: Homo sapiens

<400> SEQUENCE: 121
gggattgccg gctttgagaa aatatgaaga aaccgatttc tccttccact ttgccagtgc 60
actttccttc cactttcact ggtgctgggg gcggcgcact ctttacgaca tataagcgga 120
aaattctgca aaagtggccc ccggggatcc ccgcccgacc cctgtctgtc gctaatgtgg 180
gcctgtctcc ggaaattcga ggttgggcct ttgcctgaat ctgttgctat tgctcccctt 240
gctaccgctg acacttggca ccgccgcctc ctagcagcgg ccagacgcgg ggctgggggc 300

<210> SEQ ID NO 122
<211> LENGTH: 400
<212> TYPE: DNA
<213> ORGANISM: Homo sapiens

<400> SEQUENCE: 122
gttgcgagcg cggcacaggt tgctggtagc ttctggactc tggaggcttg gccttccttc 60
taagccgatg gcggggaaag aacctcgttt ccacagcttc cccgaccccc gccgcttgcc 120
atttggggac gggaagcgcg cccgggtcgc ttcacgtccc tctgggccgg agccctttcc 180
atggctggct cctctggggg cccttgggcc tgtgagcagc gtctacttcc ctcagagaag 240
aatcctttcc ttcccccatc gaagtgtccc tttctgtatc ctgaaataac ccctcctggg 300
tgaggccagt tcccctctgt cgccctcctc ccgcaggcgt ccgggagcct cgtgaggacc 360
ccgtgcagtt gagtccaggc gacaggtgcc tccccaggtg 400

<210> SEQ ID NO 123
<211> LENGTH: 800
<212> TYPE: DNA
<213> ORGANISM: Homo sapiens

<400> SEQUENCE: 123
cagtgcgccc cttaccggag cacccatggc ctcccgcgtt accccaaatt ttgtaggcag 60
actgtcagag ttcgaagcca gctgtgtcct ctgcgggccg tgtgacccta ggctatctgg 120
gctgctcgga gccttagttt ccctagttgt gaagagggag ggtgtgacca tggcccggag 180
ctctccgaaa ggctgtgcgg attgctcggt ggcgggatgt ggagcgcgtc ttctatgatg 240
ccaggtgctg gccaagcgct cgatgcaggc tgctccagtt aggtcgatgc gatggcggga 300
agcactttcc tctgcaatgg agagacgccg acaccccgag cccgaaggct tgcaaggcgc 360
gctctcgcca ctggggtcgg ggatccgtgg gttctctatc ccgcttaccc actccatcct 420
tagcagctgt cgtcggtccc agacctctac cttggagaga ccaaggcggc ccagagccca 480
ggagactact gcgcggtacg ccaggatcca gaagtggatt ctgacttcta aagacccctc 540
ccaagccaac gctatcaggg tccctgcaag cggttgactg tggcggaggc agaaccaaaa 600
cctttgctct gcccgcggcg ctccagcctc tcacccagga cagtgctctg ggctccagcc 660
gctgcagtgg ggtcgggaca cagacgccga gttagaagcc ccgccgctgc aggtccctgc 720
ttggtcggcg cggtgacggt gtcgctggcg gcggcggggg ccttcctttg gctgcccggc 780
catttaatca gagctattat 800

<210> SEQ ID NO 124
<211> LENGTH: 1000
<212> TYPE: DNA
<213> ORGANISM: Homo sapiens

<400> SEQUENCE: 124
tttagtattt aaggagaaaa gcctcatttt ccagaatcga ataagcgaat taatcgcaca 60
attgtgtaga atggaactca gtctgtaaaa aatcaagacc aacgtacttt ttaatattct 120
aacatctcca agtagtagtt acaagtattg tacccatgaa gtccaggtaa ttaatttgtt 180
caatgtcaca ctgttaaaag tcaggtgggc tccaaagcac agtcctaacc agcatgctct 240
actgcctcct ctgaggcaac agccgaagtg cagaccactg ggaataaata gctgcccggt 300
cttccccact cctaaattct cccgacagac cccaaagcct ctctgagagc ctctctgacc 360
gccctgcggc ccaccccgag ttcccggcat cctctgggat ccctcttcct ggagccaaaa 420
cctacgcagg ctcctttcct ccgagctggt tgctaggtga tctccgaagg ctgtccgaag 480
tctcgcgagg gcggacccgt tgcctgatga cgagagttgg gagtgtggct ggggctgcgg 540
atctccagca gtggcgttac ttctagcggc tggataccgg gttctccgcg agatcgcgag 600
atcccgagat attctccccg cacggaagcg acgactggcc tggccagagg actcgcgtgg 660
gagcgaggtg ccggccccga caggacggtg aggtatgcag aagtaaggcg gggcgccccc 720
tgcgggaagc gagcgcgccc cggaaaatga gcgcctcccc acaccaaggt gtccaggagt 780
gagtgcggga aggaactcgg ccgcccggag ttgtggcctc atcgtgcttc ccgccaaaaa 840
cgccttggta ctgtcgggac gcggctaagc gtggacgcgc ccgcatctgc ccctcctccg 900
cagtggtgga agacacccgc ggagcgccgg tggataaggg ccgtttcctg agaccagagc 960
tgtatccgca gcaggtcagc acttcgtgcg ccctgtgtgc 1000

<210> SEQ ID NO 125
<211> LENGTH: 300
<212> TYPE: DNA
<213> ORGANISM: Homo sapiens

<400> SEQUENCE: 125
agcggcgctg ttcccgggct gggtgcagct gctaaggaca aggcccctgc tccgaagaac 60
gcggtggctc ggggataccc tgaaagggac ggccatggcg cacatgggat gccctagggt 120
tcgtgggagg gcatgcaggc gcagcccccg caggggttgg cctgccagag aaggcagggg 180
agagcactcg gggctgcaca aatggtgtgg ccggagggaa ggtgcagcct tgtgtgtgtc 240
tggatgaggg ctgggcatag gagcttggta tttgatcctg aaagctctgc gtttccaaag 300

<210> SEQ ID NO 126
<211> LENGTH: 600
<212> TYPE: DNA
<213> ORGANISM: Homo sapiens

<400> SEQUENCE: 126
gagtcatact tgtagtcaca tccttttcct ttctccaacc cactggttaa tcatgaaagg 60
ctcttctgat tggctgcctc ctggcagtag tgcctcagcg cgacggttcg ggagcaaata 120
aataattccc gctgggaagc tgtttctcag acaggagcag cgacacccct gccacgcctg 180
ccgcctggag ttgagtgggg taagcacgcc ggcctccagg aatcgacggt gccacgtggt 240
tcttcttgca cttctcttct tctccagttt caggggacac cgtggggtgt gcgagcccgg 300
gggagcgcag ggaagggcgg gttgggctgc aggtgggaat gtgcggtcct tctgcgccct 360
caacagagct tccttccttt ttgccaaggt ccccgtgccg ccttcagcgc gcctccttat 420
gcacctctac ctctgctgca gcgtacctct tccgcagccc tagcggcctc cccgaggggc 480
gccgcggcct cggctgtccc tcccctgcct ggcacgacca cctgaccccc agcgacccaa 540
gaagcaagtt gtgtttgcag acgcaaaggg gctgtcgttg gtatcggtgc actggtttga 600

<210> SEQ ID NO 127
<211> LENGTH: 1700
<212> TYPE: DNA
<213> ORGANISM: Homo sapiens

<400> SEQUENCE: 127
acactttctg tgtgggaggg cacaagacat gggctatgac atggccagag accccacctt 60
ctttacacat gtaaaaacca accaaatcaa gatgcgtcaa cggtgattct tcctcccaca 120
ttgtttccct ttttaaactg ttattttttc aatccatgga gcagttgaga aacgggtatg 180
catctctcct cccctcccct tctatcaaag cctgtaagac acataaggaa atccaaagcc 240
acagtaatag agagagagag agagagagag agagagagag agagagagag agagaaaaca 300
gaacaaaaga aatcctcctt ggcttgtttt tccagggtgg ccaggcaagg tgtgaaaatc 360
catatttccc tctgggctgg caggtagaag ttactgggaa ggctgcgctc ccttctctcc 420
caccggctct cacatccagg ctgttccctc accctcagcc tcccccagcg ccagcttcct 480
cctccgcctc tctgcagcca ggcctcccct gcaaggcgga ccttggccca ccttggttcc 540
gggccaaggc ggcgggaaag gcaccgctac ctgcagccgc acgactccac caccatgtcc 600
tcgtactgct tgtagaccac attattgccc gcgtcgatgt atagaatgct gatgggagtc 660
aatttggtgg gcacgcagca gctgggcggg gtggagccgg ggtccatgga gttcatcagc 720
gtctggatga tggcgtggtt ggtgggctcc aggtgcgagc gcagcgggaa gtcgcataca 780
ccctcgcagt gataggcctc gtactccagg ggcgcgataa tccagtcgtc ccagcccagc 840
tccttgaagt tcacgtgcag gggcttcttg ctgcagcgta gcctggactt cttgccgtgc 900
cgcttgccat ggcgactggc gaaggccgtg cgccgccgcc ggcggccggg cgagggcagc 960
caaggcctgg catccggggc gcccgacggc ggcggccacg acccctcggc gcccgcgccc 1020
gggcccgcag cctcggccga gcccagctgc tcgcgcatct ctgcgaacag gttcttgcgc 1080
tgggatctgg tgaataccac cagcagggcc cgctcctggg gaggccgcac cctccggccg 1140
aagcccagac tccgcaggtc cgggggcggc ggttgctggg gtccccgcgc gcgcgcctcg 1200
gcctccccgg cgtccagctc gccccatgcg gcccgcagct ccaagcacag ctgcttccag 1260
ggctggtggc gcaggccctg ccacacgtcg aagacttccc agccggccgg cggcgccccc 1320
tgcgggtcca gggtccgcgc gtccagcagt aggggcgaaa ggcaagggaa gagctgcacg 1380
tggagcggcc cggctggtgg cccccagggc gctgagggcg cctggcgaaa gagccgcagc 1440
tccgcgccca ccagctcttc tttgtctgag agcatggaca catcaaacaa atacttctgt 1500
ctccggagag gagtgtgcga gagatcgtct gcgagataaa aaataattac agtcagtttc 1560
acttaagggg gagatcagcc cggtgctctt cggccgcccc gggaggaaaa gggcggggag 1620
tgggggcagg tcggccgggc agtccagctt gcccggccca gggcctgacc accccggctc 1680
cccatctggc tggtgcatgg 1700

<210> SEQ ID NO 128
<211> LENGTH: 2000
<212> TYPE: DNA

<213> ORGANISM: Homo sapiens

<400> SEQUENCE: 128
gcccgctgtg aatgtaggtg aggtgatccc gggaacctgg gtctgaaatc agacctgtgt 60
tgccattggg agcacggaga gaggggaagc gccctgctta ggcccaggcc gggcgtcctg 120
gtggtgggac cgcagccgca ctcacctcca ggccaacgga caaggttcct gcaagccagc 180
agggccactc tgtgcttggc ctactgcagc tcccctgcag ctcctttcct ctccctcccc 240
ggagcgctct cctctctcct ctcccctctc ttctctctcc tctctcgtct cctggggcat 300
cccgggtgga gggatgtagg ggtcgctcct cggtgccagg ccgggaagca gctcaggcct 360
cccaagagct tggcgctcag tctgggaaaa ggggttcctc tggcctcagg gacgttctcc 420
gcccccaccc cacccccctgg gagcctgaac catctggaag ggatcttagt cgggggttgg 480
gaggagagcc cgtggatagg aggagggggc gattctaggc cgaatccagc ccctgaggtg 540
tcacttttct ttcctgcggc ccgtcaccgc tgatagatgg ggctgagggc agaggaagga 600
aaaagaaaac ctccgaggtc agtgcggggc gaggtgagcc cctcccaggg ccctctggcc 660
caggaggatg aagcgcgccg gcttcgctct tgcacgccgg cttgccatcc gggtaagcgc 720
gggaaaggcg gccacagggc gcggcggcag cgcagcgcgt gggatctcac gacccatccg 780
ttaacccacc gttcccagga gctccgaggc gcagcggcga cagaggttcg ccccggcctg 840
ctagcattgg cattgcggtt gactgagctt cgcctaacag gcttggggag ggtgggctgg 900
gctgggctgg gctgggctgg gtgctgcccg gctgtccgcc tttcgttttc ctgggaccga 960
ggagtcttcc gctccgtatc tgcctagagt ctgaatccga ctttctttcc tttgggcacg 1020
cgctcgccag tggagcactt cttgttctgg ccccgggctg atctgcacgc ggacttgagc 1080
aggtgccaag gtgccacgca gtcccctcac ggctttcggg gggtcttgga gtcgggtggg 1140
gagggagact taggtgtggt aacctgcgca ggtgccaaag ggcagaagga gcagccttgg 1200
attatagtca cggtctctcc ctctcttccc tgccattttt agggctttct ctacgtgctg 1260
ttgtctcact gggtttttgt cggagcccca cgccctccgg cctctgattc ctggaagaaa 1320
gggttggtcc cctcagcacc cccagcatcc cggaaaatgg ggagcaaggc tctgccagcg 1380
cccatcccgc tccacccgtc gctgcagctc accaattact ccttcctgca ggccgtgaac 1440
accttcccgg ccacggtgga ccacctgcag ggcctgtacg gtctcagcgc ggtacagacc 1500
atgcacatga accactggac gctggggtat cccaatgtgc acgagatcac ccgctccacc 1560
atcacggaga tggcggcggc gcagggcctc gtggacgcgc gcttcccctt cccggccctg 1620
ccttttacca cccacctatt ccaccccaag caggggggcca ttgcccacgt cctcccagcc 1680
ctgcacaagg accggccccg ttttgacttt gccaatttgg cggtggctgc cacgcaagag 1740
gatccgccta agatgggaga cctgagcaag ctgagcccag gactgggtag ccccatctcg 1800
ggcctcagta aattgactcc ggacagaaag ccctctcgag gaaggttgcc ctccaaaacg 1860
aaaaaagagt ttatctgcaa gttttgcggc agacacttta ccaaatccta caatttgctc 1920
atccatgaga ggacccacac ggacgagagg ccgtacacgt gtgacatctg ccacaaggcc 1980
ttccggaggc aagatcacct 2000

<210> SEQ ID NO 129
<211> LENGTH: 2000
<212> TYPE: DNA
<213> ORGANISM: Homo sapiens

<400> SEQUENCE: 129
cactcccccg ccgcctccgc ccctaaccct cggccccgtg cgcgagcgag cgagggagcg 60
aacgcagcgc aacaaaacaa actagtgccg gcttcctgtt gtgcaactcg ctcctgagtg 120
agtcgggggc cgaaagggtg ctgcggctgg gaagcccggg cgccggggac ctgcgcgcgc 180
tgcccggcct ggccggagcc tgtagcccgg gggcgccacg gccgggctcg cagtcccccc 240
acgccggccc cccggtcccc gccgagccag tgtcctcacc ctgtggtttc ctttcgcttc 300
tcgcctccca aacacctcca gcaagtcgga gggcgcgaac gcggagccag aaacccttcc 360
ccaaagtttc tcccgccagg tacctaattg aatcatccat aggatgacaa atcagccagg 420
gccaagattt ccagacactt gagtgacttc ccggtccccg aggtgacttg tcagctccag 480
tgagtaactt ggaactgtcg ctcggggcaa ggtgtgtgtc taggagagag ccggcggctc 540
actcacgctt tccagagagc gacccgggcc gacttcaaaa tacacacagg gtcatttata 600
gggactggag ccgcgcgcag gacaacgtct ccgagactga gacattttcc aaacagtgct 660
gacattttgt cgggccccat aaaaaatgta aacgcgaggt gacgaacccg gcggggaggg 720
ttcgtgtctg gctgtgtctg cgtcctggcg gcgtgggagg ttatagttcc agacctggcg 780
gctgcggatc gccgggccgg tacccgcgag gagtgtaggt accctcagcc cgaccacctc 840
ccgcaatcat ggggacaccg gcttggatga gacacaggcg tggaaaacag ccttcgtgaa 900
actccacaaa cacgtggaac ttgaaaagac aactacagcc ccgcgtgtgc gcgagagacc 960
tcacgtcacc ccatcagttc ccacttcgcc aaagtttccc ttcagtgggg actccagagt 1020
ggtgcgcccc atgcccgtgc gtcctgtaac gtgccctgat tgtgtacccc tctgcccgct 1080
ctacttgaaa tgaaaacaca aaaactgttc cgaattagcg caactttaaa gccccgttat 1140
ctgtcttcta cactgggcgc tcttaggcca ctgacagaaa catggtttga accctaattg 1200
ttgctatcag tctcagtcag cgcaggtctc tcagtgacct gtgacgccgg gagttgaggt 1260
gcgcgtatcc ttaaacccgc gcgaacgcca ccggctcagc gtagaaaact atttgtaatc 1320
cctagtttgc gtctctgagc tttaactccc ccacactctc aagcgcccgg tttctcctcg 1380
tctctcgcct gcgagcaaag ttcctatggc atccacttac caggtaaccg ggatttccac 1440
aacaaagccc ggcgtgcggg tcccttcccc cggccggcca gcgcgagtga cagcgggcgg 1500
ccggcgctgg cgaggagtaa cttggggctc cagcccttca gagcgctccg cgggctgtgc 1560
ctccttcgga aatgaaaacc cccatccaaa cggggggacg gagcgcggaa acccggccca 1620
agtgccgtgt gtgcgcgcgc gtctgcgagg gcagcggcgg cagggggagg aggaggcaga 1680
ggcggggtgg ctggaccctc ggcatcagct cattctcccc tgctacacac atacacacac 1740
aaataatgtt tctaaaaagt tcagttgcga ctttgtgcct cgcctgtcct gttcatcctc 1800
gtcctgggcc ggggaatgct tctgggggcc gaccccggga tgctggctaa ttgctgccgg 1860
cgggttccgt cgccggtgtg accctggacg gcgcggacgg cgtacagggg gtcccgggag 1920
gggcagtggc cgcggcactc gccgccggtg cccgtgcgcg ccgcgctctg ggctgcccgg 1980
gcggcgcagt gtggacgcgg 2000

<210> SEQ ID NO 130
<211> LENGTH: 800
<212> TYPE: DNA
<213> ORGANISM: Homo sapiens

<400> SEQUENCE: 130
ctgaaaagcc gtcagggaaa ccacacatgt tcaacccctg gcggctcccc caaacctctc 60
atttccagta actgtgtgtt tccgctcgtc aacagctgaa accgagcgga acttgggggg 120
ccccaccacg cggccctgct gtgcggcacg gggctcatct gtcccccggc tgcggggagt 180
cagctctcac cgcccacctc cttcccagat agtctctgtg cccactcgac ggcccggcaa 240
gcccagcccc tgcctgccac ggccacagca gcctcagaga gctgccctct ctggccaggg 300
tcagggcctg agctgctgcc tcccgcaggg tcgagggcag gacacttgtc tgaggcttgg 360
gtggggcaat ggcacctcct cagggcctca gcccccgggc aggctcggtg accatgggcc 420
tacagcaggg aaaattctgg gccaaaagct ccagcctcct actagggcat ctgtctgcaa 480
atgcacctta acctgaccgc ttgggctgtg ggggagcctg tttcagggaa agtgagggac 540
gcgccagttt cctcctttgg acttgatgag gcacgaacgc atctctaata aagccaggtc 600
tccccgccgt ggctccctgg gcgggtgcct gtggctcggg ccatgagtca cgctgggtaa 660
ccccactacg gggaagaggg caggaagctg ggagccaccg cctctgtgcc cggttgtcat 720
ctcggcacga gggcgaccgt cggcttcgtc ctgccctcat ggctgagggc ttttgggatg 780
tggcgggaga cgggggagtc 800

<210> SEQ ID NO 131
<211> LENGTH: 500
<212> TYPE: DNA
<213> ORGANISM: Homo sapiens

<400> SEQUENCE: 131
aaatcatcag aatggctaaa atgaaaaaga cagacaacag caagtgctga caagggtgtg 60
gggcggccaa atgctcctgc actgctggca ggggacctga gaactgcagg gcattccctg 120
gcttcctgcc cctcctggga ctggggaccc cccagggaca gcctaaggga actgcattta 180
tcttcacgtc tgccaaaaga taacacgaag atgttcaaag ctaagccccc aggctggtaa 240
gagctccaag gcaccagcag tgtgtgcaga actgggggga gtctgttctc ccagggatgc 300
tcccatcacc tgctgccagc agtggggcat gccggtcccc tggggtgtgg ccaaggggct 360
gtgtctcctg cccgggctgc cggcccctct caggttcact ttcccatctc taagcccacg 420
tctcgctgca gttcaagttt gccaggccac caacgggtga cacgcccggc gcagtggggg 480
actccgcact ttctgcgcac 500

<210> SEQ ID NO 132
<211> LENGTH: 1200
<212> TYPE: DNA
<213> ORGANISM: Homo sapiens

<400> SEQUENCE: 132
accctttgtg cctgggtccc ataaacaatg tgctttttaa aggggagccc cctcccagct 60
ccggcctttt tctccagcgt gggcagccaa tcagctgcgc agagctgcat agctggaccg 120
ctttccattc tgagtagcaa caacgtacta atttgatgca cacatggatg cctcgcgcac 180
tctgcaaatt catcacccgc atcttgcatt agtcatctga cggactgcca agtgtttcat 240
tttctttcca tgtgacttta ttattaccac ctctctcctc tcttccaaaa acctcccaaa 300
aagggcggtg gggcgggggg cggggcaggg agagggagag aaatccagca gacatctagc 360
tctgcctttc tttcccagcc acagccaggg tagggctgat aaggcgctga tgcgttgatg 420
gcagccttgc agagctagac ctgcacttaa cttgcagctg cctcccgagc ctccaagatg 480
tccacgccct gggtgacagg cggcagggcg ctgccccgtg ctcccccggc tctgctcgac 540
agcagcacgc agtgagagcc tcgccgccgc cgaggagcaa ctcatggtgc ctccgctttg 600
ttttagttca tcaaatttct acgactcatt aggcactttg ccactgctct tcttcctcct 660
ccttccgcct ccccgctccc ccaccccccac tattttttct tcctgtccct catcgtgccg 720
ccctaactct ggctcccggt tccgtttttg acagtaacgg cacagccaac aagatgaacg 780
gagctttgga tcactcagac caaccagacc cagatgccat taagatgttt gtcggacaga 840
tcccccggtc atggtcggaa aaggagctga aagaactttt tgagccttac ggagccgtct 900
accagatcaa cgtcctccgg gaccggagtc agaaccctcc gcagagtaaa ggtacagagc 960
gcggggcggg ggtcgccagg cgtccaggtg ggcgtcgcgg ggcactgggg ctgtccgagc 1020
ccccagcctg caggaggaag ggcgggtagg caggagggct ggaagcagcc ggtgctggcg 1080
gcccctgtgc tccaggggct gctcccgact cctccccgca cccccgcccg cctgcccgcc 1140
gggacaggtt ggaggcggga gagagggacc gaggcagggc gggagcgcag aggctcggtc 1200

<210> SEQ ID NO 133
<211> LENGTH: 800
<212> TYPE: DNA
<213> ORGANISM: Homo sapiens

<400> SEQUENCE: 133
taacaaataa gccgcccgtg gtccgcgctg tgggtgaccc ttggcgcctt cgaggtctgg 60
agccctaggg taaataagga aacggggcgc ctctagagtt ttaaatgaac tctgttattg 120
gaagcttcag tagggaccct gaaaacaatt aacgtcttaa ttagcatttt aatgtctcca 180
ttattacggc gcgggctcta gctcagccct ttaccttacc ttctcaccgt taacagggga 240
gggggattgt atttttagtt catcttttta tgtttttgag ttgttatcct gtctgtctga 300
ttccagcctc gagggtttga tgatgcggcc cgagcctggc tgtggtcgcc tgtcggggct 360
ggagcgggac cctcagccgg gccgggcctg ggggctaacg ttttcacagt gcgccctgag 420
tttccttggg ttactgctgg gaccgcgcag gaggaagcaa agagtttttc gagctagacc 480
aacaggaaac acattgacgg aaatgttgcc atagcccatg gggtggcttt aactggccgc 540
ccccgcgggc tgggtgtgaa atcagaggag gccgcggctc ccccggccag gattggaggc 600
tcctcgcgca acctaatgcg ggtgtccggg cccgagcgct tcccgcgcag ccaggccttg 660
tcggtgcagc agccccgctc ctccccaaca cgcacacacc cggtgttcgc aagtgcggct 720
caccaaggga gatccaaggg ggcaaaaagt tatgtataaa tccgagagcc actggggaaa 780
gagggtcgtg gtattgtaag 800

<210> SEQ ID NO 134
<211> LENGTH: 500
<212> TYPE: DNA
<213> ORGANISM: Homo sapiens

<400> SEQUENCE: 134
ctaccctgtg ctatcctgag ctgtagtctt ctgaaatgat cgtttggctt cccagccaag 60
gcagggctcc cccaaagttc attcccactc ttgcagtttc acctcgggat gcttccgcag 120
aatttcagcg cctaagcaga caaggtcaaa gtaaaccgct tcaccgctgc ttctggcgca 180
ggggcccaga gcgcgtgcag ctccccagca cagaccaaca gcaggagagg ggtccgggcg 240
ggagccctgg gctgtagata agcaaaacgc acccattttc tctcctattt actccagagg 300
cacctctcct cccccactcc tggcatctct ttatcactgg ctccctctcc ctgtggcata 360
tttttgggta gtagaatgct gaggtcacag ggagcggctc tttatccaag cagtggggac 420
atcagcctgg agccctgagc atgaaccagc aagatgcaga ctctcgctct tgactttggg 480
ctccaggagc tgccccgacc 500

<210> SEQ ID NO 135
<211> LENGTH: 1100
<212> TYPE: DNA
<213> ORGANISM: Homo sapiens

<400> SEQUENCE: 135
cagtgctccg ctccgggaaa ttgcatcgtc acgacaaacg ggaccgtgat aaaacgaccc 60
tttccgtcct tatttgtaga tcactcagac gagattgaac tgcacttgtt tccccttcga 120
ggggagccgc gttttcaggg tagccgaagg cttggggctg aggggggggcc ctcaccaagg 180 cgcgggtggg ggccggagcc tcaactcgat gagaagtgac aggcgtttgg gggatctggg 240
ctccggccgg gaccagcgca agcagggact ttgcggggac accgcttctc caacagagca 300
aggcctggcc cacgtttccg gtttctccta acttcctttt attgccttcc tttgcttcgc 360
aagttccatc taccccctcca gctacagagc cccacctcta ggcacaggaa gcttcccgga 420
aaaagaaagg ctgtcccaga aagagaccga gagagacttt ccaaacttcg ggcatagcca 480
cggcaattcc cagtctgcta atgccaaggc gggcgcgtaa ggccgcctaa atctagacct 540
ccctcctcac tcatttcaaa aaataacaac gtgccagcca cctccgcaga taccgccggc 600
tggtgcttgc ccaggagacg ccagggccag agcgccactc ccagcatcga aatggcagag 660
agaaagcgca gctccaaatt ccccttcaga ggttaagcct caatcattgt gtcccttccc 720
tagggactgc tggcgctctc gcccactggc gatgattatg cgcctagaac tcgaccgcga 780
agcaactaat aggaaaacat atggtgtcaa tttggatgct ccgcgcctcg cgcacacccg 840
ggaacgagcg gcacaaagcc ctgccggccg gcccgcgacc ccgcgcccct cggggcctgc 900
cagccgggcc gcagcgacaa acgctcaggg ctgcgcgccc tggctggggc ccgcccgaga 960
gacagcctgc ggctggggag tctgagctcc aaggggagag cccagccgcc gaaggcgagc 1020
ctaccggcca agccctgggg tccggcaggt tctgcacaac tactcccgca aagctcgcca 1080
cctttgtgcc ctttcctcag 1100

<210> SEQ ID NO 136
<211> LENGTH: 500
<212> TYPE: DNA
<213> ORGANISM: Homo sapiens

<400> SEQUENCE: 136
gggccctcgc ggctcaagcg ccagcgctgg agagagagtc tgagggtacc acgggcgtgc 60
tggcctgggt gctcactccc gccctccttc atgagcggct ttcctctggg tgtgtccagg 120
gcatcacaga gctcttctgc ccaaacccgg aggcctacca gggcctgccc accttgcctc 180
cttccacact ctctgtagca gcagccgcag ccatggcggg gatgaagaca gcctccgggg 240
actacatcga ctcgtcatgg gagctgcggg tgtttgtggg agaggaggac ccagaggccg 300
agtcggtcac cctgcgggtc actggggagt cgcacatcgg cggggtgctc ctgaagattg 360
tggagcagat cagtgagtgt ccgctgcccg cttgctgaac tcggcaccat gggcggccgc 420
cacgggtgtc tctgggcact tccgggccat ccctgctgct cagctcccga taatggtgtc 480
acggtgactc aggcattagc 500

<210> SEQ ID NO 137
<211> LENGTH: 600

<212> TYPE: DNA
<213> ORGANISM: Homo sapiens

<400> SEQUENCE: 137
tgtttacgga atcgggatcg aggggccgat aagtagttta cacgccggcc agagcagagg 60
gctggaggtc ggagttgggg gctggaggaa cgggtggcgt ttttaggatt cagtaacagg 120
atcacagctt tttcttgtgg tggaagctat tggaatttgg ggagggtagc acgaggggtc 180
ctgcagctcc gcgtgtgaaa aagcgtttag gtaggcgatg aaagtagttg atctgagcca 240
tggcaggcga gccccgaatt tttgctgctt ccccctgaaa gtgtttcttt aggaggagag 300
gacttgggcc acacaggacc cggtcctaag agagcgattc cgggaagcgg acagatcgaa 360
gagaccttct gggcgaagcg gcagggcagc ctcgcggggc tgggagtgga tctgaggtcc 420
cgacccaggc ggctcggagt gctccaggag ccacctgggt ctgcgggcgc agcgcggcgg 480
ggcgggagcg gtggcccgca ggggccgcgg cctgcgatga aggccggggg gcagcgctag 540
cagcgaggtg ccacagtggg ccgaggagtc tgggctgtgg cccagggtag gaccggctca 600

<210> SEQ ID NO 138
<211> LENGTH: 150
<212> TYPE: DNA
<213> ORGANISM: Homo sapiens

<400> SEQUENCE: 138
acctaaacca agctctccct ccctgccgtc tccttccctg gcctgggtct gaaggagagg 60
aggtgcccag aagttcagag cggcataacc acagagatac tacctaatta acataccaga 120
agcataaaga actcatttgc attggagagt 150

<210> SEQ ID NO 139
<211> LENGTH: 900
<212> TYPE: DNA
<213> ORGANISM: Homo sapiens

<400> SEQUENCE: 139
ataactacgg gggtgggggt ggggaaggaa gagatccaag gaggcagaag gctgcggtca 60
aaatattttg ggtggcaga gtcacgtagg atgtggctgt gggttctggc agcccagaga 120
ttcagctccc gcctcctccc tcagagcgag tccatagcta ccctcacgtc ccccgtggcg 180
gtcctcgcca cgctccggag cgggttaccc atgagggtgc tagacctggg cagcgggaac 240
ctcgaagagg tggagattgc aggctgggac tccagatttc gggcagggat gcggggaagg 300
gaagacgcct cgctggaggc ggaatggagg gcaaggcgaa ggaggatggt gcaggaaacg 360
gcgacaaggc gcccggccag gcccgcgagc taccgagacc cgggttccaa tcctcccccc 420
ttccgcaaac gcccgggttc gaggtacctg gcgggcaagg gccgcagcgg agcgaagcgg 480
gctggccatg gggaggctgc ggggacgcgg ggctgcagag agcggcagtg gcacggagcg 540
cgcggctgga agcgaaagca ggcggtgtgg ccaagccccg gcgcacggcc catagggcgc 600
tgggtaccac gacctggggc cgcgcgccag ggccaggcgc agggtacgac gcaacccctc 660
cagcatccct tggggaggag cctccaaccg tctcgtccca gtctgtctgc agtcgctaaa 720
accgaagcgg ttgtccctgt caccggggtc gcttgcggag gcccgagaat gcgcgccacg 780
aacgagcgcc tttccaagcg cagatatttc gcgagcatcc ttgtttatta aacaacctct 840
aggtgaatgg ccgggaagcg cccctcggtc aaggctaagg aaacctcgga gaaactacat 900

<210> SEQ ID NO 140

<211> LENGTH: 600
<212> TYPE: DNA
<213> ORGANISM: Homo sapiens

<400> SEQUENCE: 140
cagtccagcc gcttgcctca cttcttcccg cttgccttat ctccccgcag acgtggttcc 60
cctgcagccc gaggtgagca gctaccggcg cgggcgcaag aaacgcgtgc cctacactaa 120
ggtgcagctg aaggagctag agaaggaata cgcggctagc aagttcatca ccaaagagaa 180
gcgccggcgc atctccgcca ccacgaacct ctctgagcgc caggtaacca tctggttcca 240
gaaccggcgg gtcaaagaga agaaggtggt cagcaaatcg aaagcgcctc atctccactc 300
cacctgacca cccacccgct gcttgcccca tctatttatg tctccgcttt gtaccataac 360
cgaacccacg gaaagacgct gcgcgggtgc agaagagtat ttaatgttaa ggaaagagaa 420
gaaccgcgcc gcccggaggc agagaggctc catggccgtg ctgctgggcc atccccaact 480
ccctatccca tccccagcct ccacccccat ccagatggga ctcacgtggc ttcaacagct 540
ttggaaatgg gtcccgagtg ggccgtgcga ggaaggctgt cgacctctac tcctccttgc 600

<210> SEQ ID NO 141
<211> LENGTH: 1500
<212> TYPE: DNA
<213> ORGANISM: Homo sapiens

<400> SEQUENCE: 141
caagatcgac tttcttagga agggggagag gagggaactc ttcacgaagg gaggtgggag 60
tccacctcag acctctattg gaaggaaatc gagttgttcc gggggactga ggtctcttgc 120
ataaggcatg ggatccttat tattattatt attattttta aatcccccgc ggaggagctc 180
tgggcaaatg aataccgagg cgccgctcta gctggttagg cttgggatgc gataactcag 240
tgccctcttg cagacttgca tagaaataat tactgggttg tcgtggaggg gacacgagac 300
agagggagtt ctccgtaatg tgccttgcgg agagaaaggt ccaagaatgc aattcgtccc 360
agagtggccc ggcaggggcg gggtgcgagt gggtggtgga gtaggggtgg gagtggagag 420
aggtggtttc tgtagagaat aattattgta ccagggcccg ccgaggcacg aggcactcta 480
ttttgttttg taatcacgac gactattatt tttagtctga tcaatgggca caatttctaa 540
gcagcgcagt ggtggatgct cgcaaacttt tgcgcaccgc tggaaaccca ctaggttgag 600
ttgcaaaacg taccgcgtag acgcccctgg tggcgccgag agaagagcta ggcctgccca 660
gcacagagcc ggagagcgtc gggccttccg gaagggtaag ttctccgcca aggggtcccg 720
agggagctgg acgtctgaat ctggacttgc ccccagcttc ggggttcgat tctgggtttt 780
gcgcgtcccc aacccccagg gctttccgaa gcatggcctg gctccaggcc cggtcctgta 840
aggactggaa cggcagcaaa atgtgcaggg aggcagtcgg ccggcagagc tgcggcggga 900
gccaaggtca ggcccgcggg gagagcgggc agcttccagc gccggccaca agctcccagg 960
ccagctgggc cgcagacccc tttgcttcca gagagcacaa cccgcgtcct ttctctcagc 1020
caggctgcag tggctgcccc gagcttcgct ttcgtttccc aagctgttaa taacgatatg 1080
tccccaaatc cgaggctcgt gtttgctccc agatgccaag aacgcaaccc gaaatccttc 1140
tcccaaaccc taggtcgacg agatgagttc ctacttgacc tctgagccga ggtgggccgg 1200
aaaccgaggc ctaggccccg ccggggctgc aaggaaaagg ggaaactccg agcgtagcgt 1260
cttttccttg tggttccttt ctccggcatc ccggactgcg ggccctgcag ccacctggac 1320
cggcattcaa aggattctgc aagtccagct tcacagactg gctttcccag acgctccgaa 1380
gcccgcacca cgaacagaat aaaggagaga cgagagatcg caactagatt tgagaatcct 1440
cgttcttttc cccaatcgtt cgggcagtaa actccggagc cggctacagc gcgcatcctc 1500

<210> SEQ ID NO 142
<211> LENGTH: 500
<212> TYPE: DNA
<213> ORGANISM: Homo sapiens

<400> SEQUENCE: 142
actgtcctcc tccctcaatt gcctattttt tgcccatagc tctaacttaa ccctgtgatc 60
accccagatc gctacttctg acccccatct cctctcccac accaacctcc agcgcgcgaa 120
gcagagaacg agaggaaagt ttgcggggtt cgaatcgaaa atgtcgacat cttgctaatg 180
gtctgcaaac ttccgccaat tatgactgac ctcccagact cggccccagg aggctcgtat 240
taggcaggga ggccgccgta attctgggat caaaagcggg aaggtgcgaa ctcctctttg 300
tctctgcgtg cccggcgcgc ccccctcccg gtgggtgata aacccactct ggcgccggcc 360
atgcgctggg tgattaattt gcgaacaaac aaaagcggcc tggtggccac tgcattcggg 420
ttaaacattg gccagcgtgt tccgaaggct tgtgctgggc ctggcctcca ggagaaccca 480
cgaggccagc gctccccgga 500

<210> SEQ ID NO 143
<211> LENGTH: 900
<212> TYPE: DNA
<213> ORGANISM: Homo sapiens

<400> SEQUENCE: 143
ctcagggaat cacatgtccg cctggcctgg cctggtacca aatgtttata gacaggacga 60
gggtcgctgg aatcgcctcg ctcctttcag cttggcgcta aggcgcgaat ctcgatcctc 120
ctagtatttc tctggcgtct gtctctatct cagtctctgc ttttgtctct ttctccctcc 180
ctccgcccca gtctttccgt ctctttttcc tcgaatgcac gtggaattcg gaattgaaaa 240
ttgaggtcag aatctccctt tttcttccag ttatccgcgc cgctgcccca cgcctagcgg 300
cttggatctg catagacatc tatctacccg caacaagatc cgagctgcag aagcaaacct 360
aatctgtctc cgcaccatcc cctgctctgt agacccactg ccccatccca cgccacatcc 420
ttgaggttca agtagcgact ccagcggatg attcggagaa tgccctgctt tccaaaggcc 480
ccaacccgtg tttttatttt ctttttcctt tgcccgcttg accaactttg gtttctttca 540
gggcccggag gtgcctgcgc cgcgcttggc tttgctttcc gccgccccag gagacccggg 600
actgtggttt ccgctcgcca catcccagcc tggtgcgcac acaagagcct ggcgagcttc 660
cctcgcgcgc ttacagtcaa ctactttggg cctcggtttc cctgctcctt gtagatcaga 720
gaagggacgg gcgaaatgcc tgcgagggag ggttggcgaa tgggttggtt ggtggcaaga 780
ctgcagttct tgtacatgga cgggggttgg ggggtcaaca ctggaagaac tcctgcctga 840
cgccaagagc cacccgcttt ccagctcgtc ccactccgcg gatgtttacc caccttcatg 900

<210> SEQ ID NO 144
<211> LENGTH: 500
<212> TYPE: DNA
<213> ORGANISM: Homo sapiens

<400> SEQUENCE: 144
tttggggcac ccaacccttc ccaagcctcg gttttcccga tcttgtggga tccttgcggc 60

```
gcgaatgggg ttggaagcac cttggaagct acagagtacc gggtcgggac aatttccggc    120
actgccccag ttcagtggtt tatagaaaat ttctttctct ctctcaggtc cactaagacc    180
gagagagaga gagaagtcga ctctggcaca cccgggcgag gggctgccgg gattcgggag    240
ctggcgcggt tgattttttc cgagaatcct ccacttgggg tgacgtcggg cagcgcgcgc    300
gggccgtgag gttaatgccc aggcttttct ctaaagcgtc cgggaatgat ccggcgaata    360
aaacgggtgt ctgcaaagtt aatgaattgt acaaggaggc tgagggtggg gacttcgacc    420
cggggagcca gaggcggttc tggtggacgc ttccccgtgc gcctaggggt gcgctgggct    480
ttcccagccg aggtctgcag                                                500
```

<210> SEQ ID NO 145
<211> LENGTH: 2000
<212> TYPE: DNA
<213> ORGANISM: Homo sapiens

<400> SEQUENCE: 145

```
ccagacagtt aaggtaaaac gttgaagtca agaggaagta gtgagtctgt tgccaactgg     60
atagggttgg tcctgtccca tctaaatgta ttagaattaa gtggctttta aaaatgagct    120
ggtcatcttc agcccacggg ctggccaatt tggaacttaa tgggcctttg cgtcctcctt    180
ccctgagcct ccttttattc cagacttctc agtgtgagtc tgtgcgtccc tccgacgatc    240
tcagggagtg gggtgccttc atctgcctgt tccctgttcc tcaggctgac gctcccgctg    300
tcctccccgc ctcccctcac tccttttctc cctcccttcc tccttgtggg gaggctcttg    360
gccagggtcc ctgagcccgg gcgggtgctg gcagaggacg cagaaggggt gaggtcacgt    420
ctcccttgag ccccgagccg ctggcttttc agagcctcgc cacaagccgg cggccagagc    480
cccagaccac acagaccgtg cgctcctccg ccctcccggc gccgccggcc tcgcccatgt    540
ctcagtacgc ccctagcccg gacttcaaga gggctttgga cagcagtccc gaggccaaca    600
ctgaagatga caagaccgag gaggacgtgc ccatgcccaa gaactacctg tggctcacca    660
tcgtctcgtg tttttgccct gcgtacccca tcaacatcgt ggctttggtc ttttccatca    720
tggtgagtga atcacggcca gaggcagcct gggaggagag acccgggcgg ctttgagccc    780
ctgcagggga gtccgcgcgc tctctgcggc tcccttcctc acggcccggc ccgcgctagg    840
tgttctttgt cctcgcacct cctcctcacc tttctcgggc tctcagagct ctccccgcaa    900
tcatcagcac ctcctctgca ctcctcgtgg tactcagagc cctgatcaag cttcccccag    960
gctagctttc ctcttctttc cagctcccag ggtgcgtttc ctctccaacc cggggaagtt   1020
cttccgtgga ctttgctgac tcctctgacc ttcctaggca cttgcccggg gcttctcaac   1080
cctcttttct agagccccag tgcgcgccac cctagcgagc gcagtaagct catacccga    1140
gcatgcaggc tctacgttcc tttccctgcc gctccggggg ctcctgctct ccagcgccca   1200
ggactgtctc tatctcagcc tgtgctccct tctctctttg ctgcgcccaa gggcaccgct   1260
tccgccactc tccgggggt ccccaggcga ttcctgatgc cccctccttg atcccgtttc    1320
cgcgctttgg cacggcacgc tctgtccagg caacagtttc ctctcgcttc ttcctacacc   1380
caacttcctc tccttgcctc cctccggcgc cccctttta acgcgcccga ggctggctca    1440
cacccactac ctctttaggc ctttcttagg ctccccgtgt gcccccctca ccagcaaagt   1500
gggtgcgcct ctcttactct ttctacccag cgcgtcgtag ttcctccccg tttgctgcgc   1560
actggcccta acctctcttc tcttggtgtc ccccagagct cccaggcgcc cctccaccgc   1620
tctgtcctgc gcccggggct ctcccgggaa tgaactaggg gattccacgc aacgtgcggc   1680
```

tccgcccgcc ctctgcgctc agacctcccg agctgcccgc ctctctagga gtggccgctg 1740
gggcctctag tccgcccttc cggagctcag ctccctagcc ctcttcaacc ctggtaggaa 1800
cacccgagcg aaccccacca ggagggcgac gagcgcctgc taggccctcg ccttattgac 1860
tgcagcagct ggcccggggg tggcggcggg gtgaggttcg taccggcact gtcccgggac 1920
aacccttgca gttgcgctcc ctcccccacc ggctcacctc gcctgcagct gggccacgga 1980
actccccggc cacagacgca 2000

<210> SEQ ID NO 146
<211> LENGTH: 600
<212> TYPE: DNA
<213> ORGANISM: Homo sapiens

<400> SEQUENCE: 146
ctctctgggc cttaggaaaa tggaaatgac acctgtacct gcccttccag gactgacagg 60
aggggctgct ccatgaaacc tcactgctgc ggtcataatg tcattatctt ttgccttaaa 120
gggatttctt ctgcaccagc acctaaagtg gcagcccctt acccttggcc atcagctgga 180
ccctggtgct ctcctggagc ccaaaacctc tgttttgtgt tgcatcctgc tgaccagcca 240
cagtccacac ccatctgagt gtctgagcag aacagcccag aggccacacc aggatggctt 300
tccaccggtc accttccccc acccactcat aaaccctgcg tctctggggg agagggtggc 360
gaggtcccct ccccacatag atggaaacac tgaggcctga ttcatggtgc cccctgtgaa 420
gcgcctcatg gccagcaccg gggggcagca ggccagggcg gggacacata cccggttctc 480
gtcgtagatg atctgcacca ggctgcggtg cttcgactcg atgggcggcg gtgacacggg 540
cttctcaggc tcgggcggct tggcagcctc ctcctccagc tgttgctgtg gggagaggca 600

<210> SEQ ID NO 147
<211> LENGTH: 400
<212> TYPE: DNA
<213> ORGANISM: Homo sapiens

<400> SEQUENCE: 147
cttgaaaact cccagccccc tttgtccaga tggggatgga ggtggccagg ctgccccgtt 60
gattgtgtgc cgaggagccc tccccgggaa ggctgtgatt tatacgcgca ggcttgtcac 120
ggggtgaaag gaagggccac tttttcattt tgatccaatg ttaggtttga aagccaccca 180
ctgctgtaaa ctcagctgga tccgcgggcc gtgattaaac acattgcccg ctttgttgcc 240
gagatggtgt ttcggaaggc gctgtgaatg cacttccctt tgcggggctc acacagacaa 300
gatgtgtgtt gcaaggatga ggcgcctgct cggcctccag cccagggccg ggaagggaga 360
aggtgctgtg cgtcgctgcc tgtgtcgccc gcggctctcc 400

<210> SEQ ID NO 148
<211> LENGTH: 1200
<212> TYPE: DNA
<213> ORGANISM: Homo sapiens

<400> SEQUENCE: 148
cgcgtcaggg ccgagctctt cactggcctg ctccgcgctc ttcaatgcca gcgccaggcg 60
ctcaccctgc agagcgtccc gcctctcaaa gaggggtgtg acccgcgagt ttagatagga 120
ggttcctgcc gtggggaaca ccccgccgcc ctcggagctt tttctgtggc gcagcttctc 180
cgcccgagcc gcgcgcggag ctgccggggg ctccttagca cccgggcgcc ggggccctcg 240
cccttccgca gccttcactc cagccctctg ctcccgcacg ccatgaagtc gccgttctac 300
cgctgccaga acaccacctc tgtggaaaaa ggcaactcgg cggtgatggg cggggtgctc 360
ttcagcaccg gcctcctggg caacctgctg gccctggggc tgctggcgcg ctcggggctg 420
gggtggtgct cgcggcgtcc actgcgcccg ctgccctcgg tcttctacat gctggtgtgt 480
ggcctgacgg tcaccgactt gctgggcaag tgcctcctaa gcccggtggt gctggctgcc 540
tacgctcaga accggagtct gcgggtgctt gcgcccgcat tggacaactc gttgtgccaa 600
gccttcgcct tcttcatgtc cttctttggg ctctcctcga cactgcaact cctggccatg 660
gcactggagt gctggctctc cctagggcac cctttcttct accgacggca catcaccctg 720
cgcctgggcg cactggtggc cccggtggtg agcgccttct ccctggcttt ctgcgcgcta 780
cctttcatgg gcttcgggaa gttcgtgcag tactgccccg gcacctggtg ctttatccag 840
atggtccacg aggagggctc gctgtcggtg ctggggtact ctgtgctcta ctccagcctc 900
atggcgctgc tggtcctcgc caccgtgctg tgcaacctcg gcgccatgcg caacctctat 960
gcgatgcacc ggcggctgca gcggcacccg cgctcctgca ccagggactg tgccgagccg 1020
cgcgcggacg ggagggaagc gtcccctcag cccctggagg agctggatca cctcctgctg 1080
ctggcgctga tgaccgtgct cttcactatg tgttctctgc ccgtaattgt gagtccccgg 1140
gccccgaggc agcagggcac tgagactgtc cggccgcgga tgcggggcgg gaagggtgga 1200

<210> SEQ ID NO 149
<211> LENGTH: 2000
<212> TYPE: DNA
<213> ORGANISM: Homo sapiens

<400> SEQUENCE: 149
cttccgccgc ggtatctgcg tgccctttttc tgggcgagcc ctgggagatc cagggagaac 60
tgggcgctcc agatggtgta tgtctgtacc ttcacagcaa ggcttccctt ggatttgagg 120
cttcctattt tgtctgggat cggggtttct ccttgtccca gtggcagccc cgcgttgcgg 180
gttccgggcg ctgcgcggag cccaaggctg catggcagtg tgcagcgccc gccagtcggg 240
ctggtgggtt gtgcactccg tcggcagctg cagaaaggtg ggagtgcagg tcttgccttt 300
cctcaccggg cggttggctt ccagcaccga ggctgaccta tcgtggcaag tttgcggccc 360
ccgcagatcc ccagtggaga aagagggctc ttccgatgcg atcgagtgtg cgcctccccg 420
caaagcaatg cagaccctaa atcactcaag gcctggagct ccagtctcaa aggtggcaga 480
aaaggccaga cctaactcga gcacctactg ccttctgctt gccccgcaga gccttcaggg 540
actgactggg acgcccctgg tggcgggcag tcccatccgc catgagaacg ccgtgcaggg 600
cagcgcagtg gaggtgcaga cgtaccagcc gccgtggaag gcgctcagcg agtttgccct 660
ccagagcgac ctggaccaac ccgccttcca acagctggtg aggccctgcc ctacccgccc 720
cgacctcggg actctgcggg ttggggattt agccacttag cctggcagag aggggagggg 780
gtggccttgg gctgaggggc tgggtacagc cctaggcggt gggggagggg gaacagtggc 840
gggctctgaa acctcacctc ggcccattac gcgccctaaa ccaggtctcc ctggattaaa 900
gtgctcacaa gagaggtcgc aggattaacc aacccgctcc cccgccctaa tccccccctc 960
gtgcgcctgg ggacctggcc tccttctccg cagggcttgc tctcagctgg cggccggtcc 1020
ccaagggaca ctttccgact cggagcacgc ggccctggag caccagctcg cgtgcctctt 1080
cacctgcctc ttcccggtgt ttccgccgcc ccaggtctcc ttctccgagt ccggctccct 1140
aggcaactcc tccggcagcg acgtgacctc cctgtcctcg cagctcccgg acacccccaa 1200
cagtatggtg ccgagtcccg tggagacgtg agggggaccc ctccctgcca gcccgcggac 1260
ctcgcatgct ccctgcatga gactcaccca tgctcaggcc attccagttc cgaaagctct 1320
ctcgccttcg taattattct attgttattt atgagagagt accgagagac acggtctgga 1380
cagcccaagg cgccaggatg caacctgctt tcaccagact gcagacccct gctccgagga 1440
ctcttagttt ttcaaaacca gaatctggga cttaccaggg ttagctctgc cctctcctct 1500
cctctctacg tggccgccgc tctgtctctc cacgccccac ctgtgtcccc atctcggccg 1560
gcccggagct cgcccacgcg gacccccgcc ctgccccagc tcagcgctcc ctggcggctt 1620
cgcccgggct cctagcgggg aaaaggaagg ggataactca gaggaacaga cactcaaact 1680
cccaaagcgc atgattgctg ggaaacagta gaaaccagac ttgccttgaa agtgtttaag 1740
ttattcgacg gaggacagag tatgtgagcc tttgccgaac aaacaaacgt aagttattgt 1800
tatttattgt gagaacagcc agttcatagt gggacttgta ttttgatctt aataaaaaat 1860
aataacccgg ggcgacgcca ctcctctgtg ctgttggcgc ggcgggaggg ccggcggagg 1920
ccagttcagg ggtcaggctg gcgtcggctg ccggggctcc gcgtgctgcg ggcggggcgg 1980
gcccggtggg gattgggcgc 2000

<210> SEQ ID NO 150
<211> LENGTH: 1000
<212> TYPE: DNA
<213> ORGANISM: Homo sapiens

<400> SEQUENCE: 150
agtttgggga gccttttctc catttgagaa aaaacaaact tacagcgagg ggtgaggggt 60
tagggtttgg gattggggaa aatgtgggtg gggagccccc ccaaggaagt gaggaggggg 120
ctgcaaggat tacacctggg catacgtttc cctagaaatc acattcattg tatttttata 180
atttattcta aatctttcat gcgaagaaag tcagtagtga gtgttagtac tggtggccct 240
cctgatcaca cttgcatctc ttgagtgtgc cttaaaggtc ttgggaatgg aaaatataaa 300
aactgcttcg tgatgcgtca tctttatccc ccactccccc acccattcca atatattttc 360
tacttccagc ctaaattcgg ggccccctac cgaggccggc catgatcttg agggcggcat 420
aggggaggcc gcgctctgtc caccccagcc tggtgatgcc gttcgcttct tgtgcccggt 480
attgtgggct acatgccttt ccggcgtacg gagctgagcg tccaggccag tgcccctcaa 540
cctctcagta atgtttaccc gaggccgtcg tgcaatgaga ctattcgcat ggcattgtca 600
acgcggcggc gcgcgcgtct cggccctccg cggcttgcca gactgtcctg caaaccacct 660
cacccgtctc tttggcgcag gagactcagg ctgtaaccgg agaaaacact tcaccctgga 720
accctaactc aggtcctggc aaaagatgcg agaggaagac ttgctctctt aataaatctc 780
ggccgcccgc acatctggcc cctagacctg ctcggtagag gactggctgg tggatgcgcg 840
gtccaggccg tgggcactcg acccacctct attttccttc ccgaggcgcc cctggattac 900
cactttcggt ttgcgcttac atccgggatg tcgaatttcc cagggaatca taattatttt 960
atctataatt tattctaacc ccaaggttcc aagaaaatct 1000

<210> SEQ ID NO 151
<211> LENGTH: 1100
<212> TYPE: DNA
<213> ORGANISM: Homo sapiens

<400> SEQUENCE: 151

```
acattccttc taaaatgtgg gctttctgtg tacatgggcg cgcattccca ggactcggtt     60

ccctgggtgg aattcaccca ggaatacaat cgattttctg aacctgcgta aggccacagg    120

cagctctgaa aatgaaagcg tttgctaagt gggggagatc tcaccgatcg aacgtttaaa    180

aatggctttg tcttcattca gctctcccga tttattctgt gttttacaaa tagaagctca    240

gagcttctgt cgcccagtcc ttgcatgact catggcggtg gccacacggg tttcagggat    300

aacgggatgt ttagaaaatc gctgcatatc ggagtttcct agcacgttcc atttatactg    360

aacgcaggcg gccgctgaaa atccagcctc gactcttgct aatgactggg taggaccctc    420

ggggtcctgc gacggtgctg gagggtgttc ccggctccga tgtggggagg cctgcgcggg    480

gactaggttc tcgagaggcg agcgggcgcg ccagagaacc cgagactgct gcggggccgg    540

atgcgggatc cctgggctgc ggttctacgc agaaacgcca atggccatgc ctccccagct    600

cctcccagcc ccagtcacta ggccggcgcc tggcccggag atcctcccag agccctggcg    660

gtgccatcat gccggagaag acaagctcgg ccccgctgga attcgctcca aacacagatg    720

ctcatttttg gaatattcta gaaaaataac aagatcttgt ttgtcgttat gattcacggg    780

aggtaactga tgggagggcc atttacatga gggcagacac tgtggggcga aggtgacttc    840

tggacgtagg ctttaaagta ggaacggctc caaattccca atatctccgg ccttaccggt    900

tgcaaatcgg acccctgcgg gaaaaccaga cacttctgtt tcgtggcttt cgggctgcct    960

ccagcccacg caggctcgtt tagtccccgt ggagtcagcc ccgagccttc ctagtcctgg   1020

aacaagggct ccaggtcgcg gccgcgggaa gccgccaaga gggcggggag tagggattcc   1080

ctccagctcc gcagggcatc                                               1100
```

<210> SEQ ID NO 152
<211> LENGTH: 1500
<212> TYPE: DNA
<213> ORGANISM: Homo sapiens

<400> SEQUENCE: 152

```
tcctcctcgg cctcagatgt cgtcccacct gcccacgagc agggaacctg gaacccactc     60

tcccggcagt ccccagcggg ttccgccacc cggcggccgc ccctgacacc gagtgggtgg    120

gaggaagagg cagctggcgg ggatgggcca ttgagacctc ttgaaaaata ttaaaagaca    180

ggatgggtag agatttctcc gggagaaagt tcgagggtgc atcgggtcgc ggctgggagg    240

agtacccgaa atgccagcag gagaaatgca acctgtttag gccacacctt caatccccga    300

ggctgtctgg agagactgcg tgcgggggac ttgccggcgt tcccacaccg cgcctgcaat    360

ccactcccgc ggctgcctgg cctctgccac tcgcggcttg aagccagtgg ctctcaagcc    420

ctcggccccg cggcggcccg cgcagccttc acccggcgcc ggcaccacga agcctggccg    480

cagtggactc cccgcagctc gctgcgccct ggcgtctccc gtcgaggagg gagggacgga    540

ggcctgagcc gggagctccc tggcggtggt cgggccgccc cccttgaggc ctgctccccc    600

ctctcggcct cgccaaatcc ctgaaagccc agtcccccct cgtcaccccg ggggcttcta    660

atcactcggt atcgatttcc ctaactcttt tcatcctgtt gaagacacat cttaaaacac    720

tccagcccgg agtgtgctct gggctttatc cacactaata aaatgattta cccttctctc    780

cgcgctctcc tcacagagga aaatcgttcg agccccggct atttgtgtgt gatcagtaaa    840

tatttagtgc gctgacatcc ttagctgggc ttcggatcga ttcggggccc accgggaggt    900

gcgcacggtc cgggcggggc cgcgccgagc tcgccgaggg ggctcctccc gccctcgccg    960

ccggccgctg atttacggcc cctgcaacca gctaaggggg gcgaaagcgc gcctggaaaa   1020
```

ttggcttttc aacctttac ttttgacatt cagccacttc cccaggctct aattctcgcc 1080
cgcactcctc cctcccgccc tactaagggt tgccctgtgc gccctgcgag cccttccagc 1140
agcaacgcgc ggcgctcgcg ccccctcggc ccggggacca cctatcacag ccctgagccg 1200
cgacgcgggg aggccccggc ccctgctatg gggtcgcct ccttcgagga gagatgctct 1260
ccgcccgccc acacctctga gggaggagag ggggtggaga agcccagagc tgcatctgct 1320
ggatgacgag ccgctctccc tgctaccctt tctccgaccc gtcggccttt ctcctactct 1380
ggagactgat cctcgacgtc catcgggccg gatggcgtcg ggtggaagcg ttactttcct 1440
cgcagaaaaa ctcctcctct ttcctaagat cagaaaaagc gcttagcttg gaattgttag 1500

<210> SEQ ID NO 153
<211> LENGTH: 600
<212> TYPE: DNA
<213> ORGANISM: Homo sapiens

<400> SEQUENCE: 153
cctaggcatt ctcagcccgt tttgctggag ggggcatttg aggcctggcc agcttagcca 60
gcctacaagg agtgttactg gggtgaaaac agccagcggg gaccagtctg cttgtggccc 120
gccaggtgcc tgggatgggg aagcagcaaa tgcccacctt cctgcccaac cccctcctcc 180
ctcttcatgg ggggaactgg gggtggcagc ggctgccggg tgcgagcggg ctcaggcctg 240
tggccctgcc tgacgttggt ccccatcaag ccatgtgacg agaccaggcc acaagaaaga 300
ggtttcaaca agcgttatcg tttcctggaa ctccaactcg gcgacttccc cgaagaccgg 360
ctgtgcctgg cgggcgggct gcgcacagcg gggacaaggc tgccccccttc ctcctccgct 420 gcctccgcgg ccgcgtctat ctcagtctga ctacctggaa gcagcactcc accctccagc 480
ccagcggccc tcggctcagc tgccaggtca ccggcaaccc cgggagcggt ggggcagggg 540
ctgctccgcc agcctctgtg atgttcaggc cgggctgcac cagcccggga cccctaggtg 600

<210> SEQ ID NO 154
<211> LENGTH: 700
<212> TYPE: DNA
<213> ORGANISM: Homo sapiens

<400> SEQUENCE: 154
gcactggttc ccctttacct gagccaacaa cctaccagga agtttccatc aagatgtcat 60
cagtgcccca ggaaacccct catgcaacca gtcatcctgc tgttcccata acagcaaact 120
ctctaggatc ccacaccgtg acaggtggaa ccataacaac gaactctcca gaaacctcca 180
gtaggaccag tggagcccct gttaccacgg cagctagctc tctggagacc tccagaggca 240
cctctggacc ccctcttacc atggcaactg tctctctgga gacttccaaa ggcacctctg 300 gacccccctgt taccatggca actgactctc tggagacctc cactgggacc actggacccc 360
ctgttaccat gacaactggc tctctggagc cctccagcgg ggccagtgga ccccaggtct 420
ctagcgtaaa actatctaca atgatgtctc caacgacctc caccaacgca agcactgtgc 480
ccttccggaa cccagatgag aactcacgag gcatgctgcc agtggctgtg cttgtggccc 540
tgctggcggt catagtcctc gtggctctgc tcctgctgtg gcgccggcgg cagaagcggc 600
ggactggggc cctcgtgctg agcagaggcg gcaagcgtaa cggggtggtg gacgcctggg 660
ctgggccagc ccaggtccct gaggaggggg ccgtgacagt 700

<210> SEQ ID NO 155

<211> LENGTH: 300
<212> TYPE: DNA
<213> ORGANISM: Homo sapiens

<400> SEQUENCE: 155
tgtccgacag gcacacagag cgccgccagg cacggccctc attcttcacc ccgagctccc 60
gcaaggtcgg cgaggaggct ggagcagcgg gtaggaagcg ggccgaggct cccccgacgc 120
tgggccgcaa ctgtcatcgc agatccctga aaaacgagct ctgtaatcgt tgccgtcagc 180
gggtgtacaa ttgcagcctt atgtttcctg ccgctgttta ccttcctgag cggcgcccag 240
agatgcacac acgctgccct gaagcgggac gtgacctctg ggcacctgtg aggtcctggg 300

<210> SEQ ID NO 156
<211> LENGTH: 500
<212> TYPE: DNA
<213> ORGANISM: Homo sapiens

<400> SEQUENCE: 156
gtcggctcct gcgctcccaa cggggtggcc gtttccttcc tcgcaccctc ttctctcccg 60
gtgcctgcgg tcccaccttc cagatacccc tcggagagtc cagctgagct ctcgccagag 120
ctttcccctt ccaacccgct cgacttgccc agatcccaag ctgggcttct ctctccatcg 180
ccccagaaag tgggtcttgg agaccgaggc aagaatttgg gcctccgctt ctgttccaga 240
ccccggaccc cttgccaaaa tgcggcagat gtgcagattg ggccgcgctt ggttcctggc 300
tgggtttatg gagcctgcgg ctgaggcagg ctccgcagac cccgagccag agtgggattt 360
aacggcggcc ggtgcgctgt gcttggtcaa ccccggtaac cgtcacgctg ctagtgatat 420
gaaaaaaacc tgccagcgtt ctgcttttct gccccgctgc agtctttagc acccgccagg 480
attctgtccg agtgtttgga 500

<210> SEQ ID NO 157
<211> LENGTH: 1000
<212> TYPE: DNA
<213> ORGANISM: Homo sapiens

<400> SEQUENCE: 157
tttagtgtgt gcataaaaca tcccagctaa tctcaaatag acttttcctg agcagaggct 60
gaaatttgca agtaatgcaa agaagactcc gggagagcgt cgccgatggt ggagcgggag 120
acgggcgtgg ggagccccac tgcagtgctg ggatcgaagt ggtgctgacc ccaagacctc 180
tcccctcctc ctcccccggg agcttctcca gggttatttg ggaaatgagg gggaactcca 240
atccctgaga aagcgctcag gggcttgctg aggtgagcgc aaatggaagc acaaggccgg 300
gctggccgtg ggctcagtaa ccagtcggct gcccggcttg cgccagcact aaatgctcga 360
tcagaaagag aaaaagaggc gcaataattc caaatttcag gaaaagtcaa atcggagagg 420
ggggacgcag gtctcttcag actgcccatt ctccgggcct cgctgaatgc gggggctcta 480
tccacagcgc gcggggccga gctcaggcag gctggggcga agatctgatt ctttccttcc 540
cgccgccaaa ccgaattaat cagtttcttc aacctgagtt actaagaaag aaaggtcctt 600
ccaaataaaa ctgaaaatca ctgcgaatga caatactata ctacaagttc gttttggggc 660
cggtgggtgg gatggaggag aaagggcacg gataatcccg gagggccgcg gagtgaggag 720
gactatggtc gcggtggaat ctctgttccg ctggcacatc cgcgcaggtg cggctctgag 780
tgctggctcg gggttacaga cctcggcatc cggctgcagg ggcagacaga gacctcctct 840
gctagggcgt gcggtaggca tcgtatggag cccagagact gccgagagca ctgcgcactc 900
accaagtgtt aggggtgccc gtgatagacc gccagggaag gggctggttc ggagggaatt 960
cccgctaccg ggaaggtcgg aactcggggt gatcaaacaa 1000

<210> SEQ ID NO 158
<211> LENGTH: 500
<212> TYPE: DNA
<213> ORGANISM: Homo sapiens

<400> SEQUENCE: 158
catggtgctt caggaaggga ggggacgaga gccctgggct tgtggtgtcc acgtggacag 60
ctaatgagga gccttgccga tgaggagcat gcgttcccga cggggcggcc gaatgcggaa 120
ggagccgcca ttctctccgc cctgaccgcg ggattctctg cagcagatga gaaacggcgc 180
tgactcagca gggtccctcc caggccccga gcggtcatct ggtgaccccc gcgcttcccc 240
cacggcccag ccggagaagg gcaaagggaa gtcccggctc caaggcgcac ccagagatgc 300
ggtgcatgtg gcaggatggc ccagccccgt cggcagcccc agcttcctgc ccctggtttc 360
cttcctccca cgggctacag gcctctgatg agctttggaa agcaggaaac acacaggcta 420
gtaactatga atgggtccaa aaaacactcc ttattacttt aaactactta ggaagaagca 480
cagcgttgcc aaacgccaga 500

<210> SEQ ID NO 159
<211> LENGTH: 1200
<212> TYPE: DNA
<213> ORGANISM: Homo sapiens

<400> SEQUENCE: 159
gcgcgggggg ccggaggatg gcggcctggg ggccctgcgg gggctgtcgg tggccgccag 60
ctgcctggtg gtgctggaga acttgctggt gctggcggcc atcaccagcc acatgcggtc 120
gcgacgctgg gtctactatt gcctggtgaa catcacgctg agtgacctgc tcacgggcgc 180
ggcctacctg gccaacgtgc tgctgtcggg ggcccgcacc ttccgtctgg cgcccgccca 240
gtggttccta cgggagggcc tgctcttcac cgccctggcc gcctccacct tcagcctgct 300
cttcactgca ggggagcgct ttgccaccat ggtgcggccg gtggccgaga gcggggccac 360
caagaccagc cgcgtctacg gcttcatcgg cctctgctgg ctgctggccg cgctgctggg 420
gatgctgcct ttgctgggct ggaactgcct gtgcgccttt gaccgctgct ccagccttct 480
gcccctctac tccaagcgct acatcctctt ctgcctggtg atcttcgccg gcgtcctggc 540
caccatcatg ggcctctatg ggccatcttt ccgcctggtg caggccagcg ggcagaaggc 600
cccacgccca gcggcccgcc gcaaggcccg ccgcctgctg aagacggtgc tgatgatcct 660
gctggccttc ctggtgtgct ggggcccact cttcgggctg ctgctggccg acgtctttgg 720
ctccaacctc tgggcccagg agtacctgcg gggcatggac tggatcctgg ccctggccgt 780
cctcaactcg gcggtcaacc ccatcatcta ctccttccgc agcagggagg tgtgcagagc 840
cgtgctcagc ttcctctgct gcgggtgtct ccggctgggc atgcgagggc ccggggactg 900
cctggcccgg gccgtcgagg ctcactccgg agcttccacc accgacagct ctctgaggcc 960
aagggacagc tttcgcggct cccgctcgct cagctttcgg atgcgggagc ccctgtccag 1020
catctccagc gtgcggagca tctgaagttg cagtcttgcg tgtggatggt gcagccaccg 1080
ggtgcgtgcc aggcaggccc tcctggggta caggaagctg tgtgcacgca gcctcgcctg 1140
tatggggagc agggaacggg acaggccccc atggtcttcc cggtggcctc tcggggcttc 1200

<210> SEQ ID NO 160
<211> LENGTH: 600
<212> TYPE: DNA
<213> ORGANISM: Homo sapiens

<400> SEQUENCE: 160
gggcgggttg ccacactgtc ccctttctgc atgggaggaa gggggctcga gaactgagtc 60
agccacacaa aacgaggatg gacagaactc ctgagtagcg agggtgcctg ccgggcgcga 120
ggaggagggg gaagacgagg aagacgagga ggaggaatag ggagcaccac atgacagagg 180
ggctgcctca gaccacaaag cgcttcctca tcctttcctc gccctttgat gccgccggca 240
acgtgactct gcgagcagcg gggcagacgc caggtctccc tcgcaggcgg gaaaggggct 300
ccaaggcggg tgctgccttg ctcgggtcac atggctacgt gggggccttg ctcaaattca 360
cttcctgcct tcattacaaa actgtcaaag gggatcgcac gtttgcaggg tgtcacccaa 420
gcattctggt tttgcaaacg acgctgtgcg gcaggcggtc tgatacctga tgagctcggt 480
gtggcggggt cggcagcatt tcctccgggg ttttgagctc tggccacttc tccttttgtt 540
ccacccaatc tcacccactt ctgggcttcg aggccagagt gtcttaacaa gggggcacgt 600

<210> SEQ ID NO 161
<211> LENGTH: 500
<212> TYPE: DNA
<213> ORGANISM: Homo sapiens

<400> SEQUENCE: 161
gagcgagact ttgtctcaaa aaaaaaaaaa accaaataaa ttgaaagctg agaaattcag 60
agcacaagaa gacaagcgcg ccccctcttt tagctgtcaa catggcggag ccgtccctgg 120
tgacgcagcc tccaaaggcc tccctgtgcc ctcctgagac cgcaagaggg aaagtggcag 180
cgacagtgat cgtggtgtct ttgtggcggt tgtgttgacc tcactgaccc ccgaagtgcc 240
gctctagggt ctgtcctcag cggtgacccg gccgggtcga agggcagagt tccgctgtca 300
ctagccctcc acccgtcctg tgtgctggga tgccctcgcg gcgccgtcca cgccaccgcc 360
gccccctctt gtgggttctg tctcctccgt gtctaggatc ctcctgcatc cgtttttcct 420
tcctcccttc tctccctccg tctgtcttgc ccgcacctga ggttgtcgca gaggcgctga 480
gacgggccag caggagctgt 500

<210> SEQ ID NO 162
<211> LENGTH: 600
<212> TYPE: DNA
<213> ORGANISM: Homo sapiens

<400> SEQUENCE: 162
tgctgtcccg gtcctgtcgc agtcctcaaa gatgctagag tgacagtcct ctaggggtag 60
agatggtcgt cctcccagga gaaggtggcc cggagacttg gaggtgggat caatcctgcc 120
agtcctggat caggaggcct ctgtcgggcg ccgccccccct tcctcctcca tcagcaacag 180
gcggcgccgg ccagcctcat agtcagcctc atccacactg accagcaggc gaacagcctc 240
ccggcccaca gcctctcgca gggcctcagt caggaacacg ccccgcaggg cctgcagcag 300
ggcgccactc aggtagtcgc cccagaaggc gtccagatag gagagctctg agaacttgat 360
gtcacaaacc acagagccca ggtcccttga gcgcagcact gcggtggcct gcccaaacac 420
gtccagctgc cgcgccagcg cctggggccg ccgggatgcc acgccctgct ccaaggctgg 480
cccatgctcg cagtactctg ctcgaacccg gagccggatg tctgcagggg aaggagggat 540
ttgtcaggga gggggccaac actagacaca cttatgggga acgccaccct tcctccctcc 600

<210> SEQ ID NO 163
<211> LENGTH: 500
<212> TYPE: DNA
<213> ORGANISM: Homo sapiens

<400> SEQUENCE: 163
tgatgcccgg cccccagggg ggcagaggcg ccgccaccat gagcctgggc aagctctcgc 60
ctgtgggctg ggtgtccagt tcacagggaa agaggcggct gactgcagac atgatcagcc 120
acccactcgg ggacttccgc cacaccatgc atgtgggccg tggcggggat gtcttcgggg 180
acacgtcctt cctcagcaac cacggtggca gctccgggag cacccatcgc tcaccccgca 240
gcttcctggc caagaagctg cagctggtgc ggagggtggg ggcgcccccc cggaggatgg 300
catctccccc tgcaccctcc ccggctccac cggccatctc ccccatcatc aagaacgcca 360
tctccctgcc ccagctcaac caggccgcct acgacagcct cgtggttggc aagctcagct 420
tcgacagcag ccccaccagc tccacggacg gccactccag ctacggtgag ggcctgggcc 480
atcttggccc acttttcaga 500

<210> SEQ ID NO 164
<211> LENGTH: 200
<212> TYPE: DNA
<213> ORGANISM: Homo sapiens

<400> SEQUENCE: 164
ggccgggcaa aaagccgccg caacaaaaag ctgcgctgac gggcggaaaa agccgcggcg 60
gcggagccaa aaagccgggg cggcaaaaag ccacggtggc gggcgcaaac agccgcaaaa 120
agccgcggtg gtgggggcaa aatcagtggg agcaggggca aaaaaacaca aaaagccgcg 180
gcggcggggg caaaaagcca 200

<210> SEQ ID NO 165
<211> LENGTH: 400
<212> TYPE: DNA
<213> ORGANISM: Homo sapiens

<400> SEQUENCE: 165
tggctttgct ggagtgtgat gtgataggaa atgtgcagcc aaagacaaaa gaagatgtaa 60
gtaggcttga ctcattgcag ctaagaaccc agatgttacc ttgagggtat taactaataa 120
gcagtttaaa tcagaatggc acattctgat ttgtttttg tatgttcaca tttggcaggc 180
atagatactg tttgaaaaga gaaaagtcag tacatagagg taacaagctt aaatatgtgc 240
caagtctaga aacaagagac tagggggata aggacctttc gaaattaaat gcaagatttg 300
aaaactgatt ggctgggga tgaggcaaag gcaggtcttt aaggtcaatc cctgttttgc 360
tttaagttgt tagcgggtgg ttttatcata tattgtagaa 400

<210> SEQ ID NO 166
<211> LENGTH: 650
<212> TYPE: DNA
<213> ORGANISM: Homo sapiens

<400> SEQUENCE: 166
ttcctgggaa tgtcagctaa cctgagccta ggggcctgag cccaagggca gactgaggct 60
cccccagcac agggaggtgc tgcctgtgac aaggggtagt gctggcacag tgcaggctac 120
tccctagaaa gatcagcttg aatatgcagg aagagcagga ccctcgggct gaggcagagg 180
tggaatggga agtgcatggt ggtaatttag ttctccagag gccagaagta ggaggagcgg 240
ttggaatgct gatggcccaa agggaaaccc tggactaccc tggcctccca caggactctc 300
atagtaattg cggctccctg cagtggtgag gccagaagga gtgttgccca atgctgtcat 360
catccagtcc accccccacc caccatcaac agatgagtat ggtcatgagt gtggtcacct 420
catcagtcat ttgctcagtt gtgaaaaaga aattgttcag agaagagcaa agtgtttttc 480
catgagccaa aggtcagcca agttatgcta atgaggagga ctggagacag cgtgtcacag 540
acaccgagaa ggagcactgg gcaagggcac ttctcccagg gcagagccca caagaagcgt 600
cctggcacca gacactcagg gaactgaagg ctggcagggg cccgcccagt 650

<210> SEQ ID NO 167
<211> LENGTH: 5000
<212> TYPE: DNA
<213> ORGANISM: Homo sapiens

<400> SEQUENCE: 167
tccccccagc tgggtataag caaactttcc tgtctatggg ccgcagagac caccatctag 60
ttcccccgcc aaaactttac atgattttaa ttctcctgat gaagatgaga ggataacagc 120
caacagagag ggcagaggat gggatgggac tcccttgctc agagacctca cctctaggtc 180
tttacctcct attgagaata agtcagttct gtagtaagaa ctctgtgtcc acggcaaccc 240
caaacagaat cctagcgctc ttgtgattct tgtagaatgg ggaatagaac gagcttggcc 300
caagactgca cagacttaaa aacatactat tctttgaaaa tggcaatcat taaaaagtca 360
ggaaacaaca ggtgctggag aggatgtgga gaaataggaa cacttttaca ctgttggtgg 420
gactgtaaac tagttcaacc atggtggaag tcagtgtggc gattcctcag ggatctagaa 480
ctagaaatac catttgaccc agccatccca ttactgggta tatacccaaa ggactataaa 540
tcatgctgct atacagacac atgcacacgt atgtttactg cagcactatt cacaatagca 600
aagacttgga accaacccaa atgtccaaca atgatagact ggattaagaa aatgtggcac 660
atatacacca tggaatacta tgcagccata aaaaatgatg agttcatgtc ctttgtaggg 720
acatggatga aattggaaat cattctcagt aaactatcgc aagaacaaaa aaccaaacac 780
tgcatattct cactcatagg tgggaactga acaatgagaa cacgtggacc caggaagggg 840
aacatcacac tctggggact gttgtggggt ggggggaggg gggagggata gcattgggag 900
atataccaaa tgctagatga ggagtttgtg ggtgcagcgc accagcatgt cacacgttta 960
catatgtaac taacctgcac attgtgcaca tgtaccctaa aacttaaagt ataataaaaa 1020
aaatactgtt ctgccataca tacagatact cattaaagat gagggagaag ggcatggggt 1080
gggggagaat gtaccaaaac caaagaccac aggataataa cctcagagca gagactatct 1140
ctctagttat tttttctttt gtatgtaatg gagaggatta ttatttactc tgatgaagaa 1200
gtttacatca agtgttcagc ttcctttgtg ggttacagag aataaccaga gggctcagtt 1260
atgctctctg aataactatg tttgcttagt gttttctaaa caatattaaa tttcactaaa 1320
atagacaagg ttgataggac ttgggggcat aactcattga ctcaagctat cattttatag 1380
gattgtgaga aaacaaatag atgaacattt aaaatacact catattctcg ctagaaaaga 1440
ggattttgaa tattcttaca tcaaagacat ggtaaatgtt taaggcaatg aatatgctaa 1500
ttaccatgat ttgatcatta tgcaatgtaa aatgtactga aacatcacat tgtacctcat 1560
aaatatgtac aatttattat gtgcgaatta aaattttgag tataagaaaa aataaacttc 1620
aattgtaaga aaacaaccca acttttaaaa aacgggcaaa atacgtgaac agatacttca 1680
ctaatagaga tttgcaactg gcaaataagc aaatgaaaaa ctggtcatca tcactatcta 1740
ttagagaaat gcagattaaa actacaataa gaaacaatgc tgcccgtcca gacgcattgt 1800
tttgaccgtt tccaacttgt cccagccctt cccggggcat cgctggggac cctacgccga 1860
cgtccccct ccgcccgcgc cccaagggcc gactgggcaa attgggagac ccgccccgcg 1920
gggcgaccca acttttcgga acagcacccc accgcccacc cccgcagacc cccggacccc 1980
cgctcccggc ggagactcag ggaaccccgc accccaagcc cttctaaatc gtgcagcgtg 2040
agtgtgacgg ccaagagcgg atgcagcccg ggatcgcccg caccttcccg tgggcggaag 2100
cgcaggagcc agctggggag ggggcgccct agaggagcgg ctagaaagca gacacgggga 2160
actcaggtca tcctgggggg ggacaagaca acgagagccg ggcgcctcgg gggcggcgcg 2220
ggagcctccg caggaccggg cgggcgcccc ggctggcgcg ggcgggggc gcgcccccctt 2280
tacctgcggc tccggctcct aggccatttc ctcacgcggc ggcggccggg actgagctaa 2340
caccactcag gccggccggg tttgaatgag gaggagcggg cgcggagagg aggggacggg 2400
gagggcggag ggagggaggg aggcgtcgcg gagtttttct cggccttttg tgcggacacc 2460
tcccggattc cgcgcccgca cccggccccc caaaagacac ggggagccgc gggcgagggg 2520
ttcagccatc cgccgaggcg cctagtgcct tcgcgcctcc aagaccccccc cccaacaaaa 2580
aggagcgtcc cccaccccta cccccgcccg gaggacttag ggcctgggct cacctcgggc 2640
gcggagctaa gtgtaggcgc cgggggtccc tagagccgcc ggggcgcagc gagtccggcg 2700
ctgggtaact gttgggtcag aaactgttca ggtagcagct gttgtgccct cccttggccc 2760
cgccgctcgg agacgccccg cccctgcct tgaacggccg cccggccccg ccccagcgcc 2820
cacgtgacta gcataggcgc gcccccgttc cgcccgccgc cgcagactcc gcctccggga 2880
cgcgagcgag cggcgagcgc gcgcactacc agttcttgct cggcgactcc cgcgcacgcg 2940
cgcgccgtgc caccctcccc gcacccctcc tcccgccatc cggcttaacg tggcgggcgc 3000
gcgccgcggc agtagccgtg acaggtaccc ggcggggcgg gggggaggg ggttggcccg 3060
cgagggtgtg cgcaggcaca gacccgggtc ctgtccccgc cgcccccctcc tctgcaaggt 3120
gtgcctgggc gaggggaggg gcccgcggcc cgaacccctg ggtcaccccc gaattacaaa 3180
caaaaacctt aacgccattg ctcgcgggtt agaaggcagc tgtgcgtgct caggaaaaga 3240
agccacgcac aagagaccgc acgcggcgtg gatacagtga cacgaaacac ccaaaatctc 3300
ttttgaaagg gaaaccaggc acagtggctc atgcctataa tcccagcact ttcgggggcc 3360
aaggcgctca cctaaacccg agagttcaag accagcctgg gcaatacagc gaaaccctgt 3420
ctctacgaaa aatataaaaa ttagctgggc atagggctgg gcacggtggc tcacgcctgt 3480
aatcccagca ttttggaggc cgaggcgggc ggatcacgag gtcaggagtt ccagaccatc 3540
ctggctaaca cagtgaaacc ttctctctac taaaaataca aaaaaaatta gccgggcgtg 3600
gtggcaggtg cctgtagtcc tagctacttg ggaggttgag gcaggagaat ggcatgaatc 3660
agggagcgga ggctgcagtg agctgagatt gcgccactgc actccagcct gggggacaga 3720
gtgagactcc gtctcaaaaa aaaaaataat aattagctgg gcatggtggc tggcacacat 3780
ggtcccagct actcaggagg ctgaggtgga aggatctctt gatcccgggg aggtcaaggc 3840
tgcagtgagc caagatggca tcaccgcact ccagcctggg ccacagaccc tgtctcaaaa 3900
aaaaaagaga aagtggggaa gaaaatgtaa tacaaattaa tataccaaca gcaattagtg 3960
agtacttttt ccatggagct gggagaggga ataaatgttt gtaaaattaa aatgttctac 4020
gctagaaatc aactttcctt ctatgctttc tttacttcac cccttatagc tacttagtaa 4080
atctcacaaa tcctatcctt ctgatctctc tgaaatgtat gtaccctttc ccttctattc 4140
tcaccaccca tgtttctttg tttccttcta gcctgtgtaa taatctcata atcgcacctc 4200
ctgtacctgc cttctttcta gtccagaata cgttttccta aattccacca ataaccatcc 4260
tgctactgct ttgtgtgaaa ttctccaaaa aaaattttac ttttccaaaa taagtcaggc 4320
tccctctctt aggatacaaa accacaccat ggtcccagcc aatctttcag cctgattcac 4380
tcagtatata tttattgacc tctcctttct cccaagcact tggctagata ataattaaag 4440
agtgcggcac aaaacaaatt ggattcctcc cctcatggag cttgtatttt cacaggaagc 4500
acagacatta aataaattaa aacacaaaaa aatagacaag catataatta cagtatgtat 4560
cctagagaaa tatcactcat gcagaaagca tacacaagga tgcagcactg tttccaatag 4620
cgaaaagcta gaaacaacct acatgttcac caaaagaaaa tggccacata aactatacca 4680
tatccaaatt atccaaattt tagaatatag acaacaggtt gggcgcggtg gctcacacct 4740
gtaatcccag cactttggga agccgaggcg ggtggatcac aaggtcagga gttcaagacc 4800
agcctggcca acatggtgaa accccgtctc ctctaaaaaa acaaaaaaat cagctgggca 4860
ctgtggcagg agcctgtaat cccagctact gaggagactg aggcaggaga atcgcttgaa 4920
ccctggaggc agaggttgca gtgagccaag atcgcgccac tgcactctag cctgggtgac 4980
agagcaagac tccatctcag 5000

<210> SEQ ID NO 168
<211> LENGTH: 1500
<212> TYPE: DNA
<213> ORGANISM: Homo sapiens

<400> SEQUENCE: 168
tgtaggagtc ctccggtgct ggagtccaga gcacagtgag gctgggtcct cccgtgccat 60
agtgtagggc atggcgggac agggatcctg ccctgcgata gtccagtgct tgagtccgca 120
gtaaggcaat ggtcctccaa tgctggagtt cacggcgttg tggggtcggg gtcctttggt 180
gacttagtcc agggcgtacc agggcggggg tccacagttg ccatagtgag gatcttggag 240
gaaggtggtt cctgccttgc tgtagtccgg ggagcagggg gcaggggtcc tctcttgtca 300
gagtctctgg cgcggggtgg gggtggaggt gggggttttc ctatgcgata gcccacgggt 360
cggtgaagcc gggtcctccc gtgcctttgt ccagggcgca ggggggcgag ggtcttcggt 420
ggtggagtcc gcggagcggc aggacggggg tcctccagtg ccatattcca gggcgcggcg 480
gagtggggga cctgtcctgc agtggtccag ggcatgtggg agtggtggtc ctgctgtgcc 540
tcagtccagt gcgcggtggg acggcggtcc tgctgtgctg tagtgcagga cgcggtggcg 600
caggggtagt ccagagagcg ccgtggcagg gggtcctcca gtgctggaat ccagtgcaag 660
gcgggtcagg ggtcttaccg tgccgaagtc ggtggcaagg gtcctcccgt gccatagtct 720
agggggcgac ggggcagggt tctctagtgc aggtgtccag ggtgtggcag ggcaggagtc 780
ctcttgtgca ggagtccagg acgtagccga ggagtcctcc aatgtcagag tccagggctc 840
tgcggggccg ggttcccccca tgccagagtg tagggcgcgt tcaggtgagg gtcttggcgt 900
gcagtaatcc agggtgcggt ggggcagggg tagtccagac ctccatggcg ggcgtccctc 960
tgtgcaggag cccagtgcct ggcggatcgg gggtccttct gtgctgtagt ccagggcacc 1020
gcaaggtgtg ggtcctctgg tgccctagtc cagggggcgg cgagtcagag gttctcccgt 1080
gtctcagtct agggcctggt aggactgggg tcctggagtc cacgtggtag cccaagttgc 1140
cgcaggacca ggtactctgg aaccacagtc cagggcgctg aggggcagga gtagttcagg 1200
gcgagccggg gcccaggtcc tcgggagcca gagtccaggg tgtggagggg tgggggttct 1260
gcagtggcac agtccaggac accgcggggc gggacagggc ggggatcctc ccgtgcctta 1320
gtccagggct gagccgcggg agaggtcctt cagtagcaca gtctagcgca cggcgttgca 1380
ggtgtcctcc agtgcctgag gccacggcag gtcgcgggtc ccactgtgct ctagttcagg 1440
gcggagtggg tctgaggtct tctcctgcct cagtctaggg cgctggagag cggggatcct 1500

<210> SEQ ID NO 169
<211> LENGTH: 2500
<212> TYPE: DNA
<213> ORGANISM: Homo sapiens

<400> SEQUENCE: 169
gggttggtcc tagaaagcgt gaggatcgcc gagtgcactg ccctcccagc ctagggtcca 60
ctcttccttg gcccgagccc agagctcggg gtttcaggcg ctgggccctg tgcagctgcc 120
cagaataggc tgagcggcag gttcccgccc tggcaaggga tccagcagtg gaatcctcac 180
tgctgttggc tgcgggcaag gtcagcgggg tttccatcgc tgctggtggg agccacctgg 240
cggtggtagc tgcaagtgag cgcgtggcag agactggcag ggctggtccc agacaccctg 300
agggtctctg ggtgcatcgc cctaccaccc tagggtctgc tcttccttag cctgctccca 360
ggacgcggtg tacgagggct agactctgag cagcctccag gatggggctg agcagcggat 420
tcctgccctg ctgcagctac agtctgaatt aggcgccacc gcagtatctg gccctggggt 480
acgtgctact gggtggcatg gacagagatg gggggctgcca cagctgctat ggggctgagc 540
agccgattct cgccctgctg cagcgggcga ccgctgcaat ccccagcgct atgggaccga 600
ccacctgact tagatgcctt ggaggcatcc ggtcctgggg tcttgctgct ggtgtctgcg 660
ggcagggtca cggctgccac tactactgct gtgcgccatg ggcaggtgcc agctgcagct 720
gagtccgagg cagatgctgt cagggctggt ctgaggttgc ctaagggtgg ctgagtgcac 780
cacgcttcca ccccagggtc cgttattcct aggccggctc ccagattgca gggttgtggg 840
cgttggacac tgtgcagcca tgaggatctg gttgggtgca gattcccgcc ctcctgcagc 900
tgagaagcca atctcataac aggcgctgca gtgacctctg gctctgcggt ccgcgctgct 960
gctggagctg gcagagaaca gagctgccac cgctgctgct tccaggagtg tgcagctggc 1020
agctgcagct gagcccgtgg cggaggctgg aaggccttat tccagaagcc ttgagggtcc 1080
ccgaatgcac cgccctccca ccctaaggtc cagtcttcct tgcccgcgcc cagagagttg 1140
gattgcaggc gctgagcaca gtgcaggtgc tgggatgggg ctaagctgaa agtttccgcc 1200
ctctggctgc tgcggggccg acagcctgag ttatgcgccg cggcggcttt tggtcatggg 1260
atccgcactg ccggtggctt gcacagggtc gggggctgcc acagctgcta tagttcaccg 1320
tgtgcacgtg gcagccgccc ctgagcccac cgctgaggct gcagggctgg tccggtccca 1380
gacggcctga gggccatttg cccgcgccca gatccgggtg gctgcgctgg gcactgtgca 1440
gcctcccgga atccgctgaa gggcacgttc ccgctctcct acagctgtgg gccgactgcc 1500
tgattttggc cactaggtgg agtctggctc tagggtttcg aggccgctgg tgttggtggg 1560
cggagtccgg gtttgccacc gctgcgctcc atgagcaggt agcagctgca gcggagcttt 1620
agaccgaggc tggcagggct ggccccagac ggcctgaggg tcagggagtg cagggtcctc 1680
ccaccctagg tccgctcttc ctttcccctt acccagagcg ggttgtgcgg gctctgggct 1740
ctgtgccggc gctgggctct gtgcagccgc cgagatgggg ctgagcagcg gatttcctcc 1800
ctgctgcagc tggaggacga ttacctgcac tagccgctga ggcggcatct ggccctgggt 1860
tactgcagct ggtgacgcgg gcagggtcag ggttggttgc aggtggcagc tgctgctaaa 1920
cccattgcga gcctcagggt caccaagttc accgtccttt catcatagta tctgatcttt 1980
ggcccgcgcc cagagtgcgg actggcctgc gctggggact gcatagcttc tgggggccgg 2040
tcagcgccag tttcacgtcc tcctgcagct gcgtggccta aggtcttagg cgccgcggcg 2100
ctatctggcc ctgctgtcga cgctgctggt ggtggggaca gggtcaaggg ttgccactgc 2160
tgctcccgtg cgccatcggc aggtggcagt tgcagatgag cccacaattg aggctgttgg 2220
ggctgctccc aggttgttag agggtcgccg agttcaccga catgccaccc taggttacgc 2280
tcttggcccg cacccagagc gccgggttac gggtcctggg ccctgtgcag ccacggggat 2340
ggtgctgagt gcaggttccc gtcttcctga gatgcggggc gaccactgga attagcctct 2400
gtggtggtat ctgaccctag ggtccgagct gctggtggcg tgggcggggt cgaagtcgcc 2460
tctgttgctg cggcgtgcca tttgcaccgt cctctggtac 2500

<210> SEQ ID NO 170
<211> LENGTH: 1600
<212> TYPE: DNA
<213> ORGANISM: Homo sapiens

<400> SEQUENCE: 170
aaatactcta ctgaaaaaac agaaatagta aatgaataca gtaaagtttt agaatacaaa 60
atcagcatag aaaaatcagt cgcatttcta tacccaacag cataccatct gaaaaaggaa 120
tcaagaaacc aatcccattt aaaatagcta taaaaaaatg cctgggaata aactaagcca 180
aataaatatg tctaaaatga aaactataaa acattgataa aaatcaattg aaaaagatac 240
aaataaaggg aaagttatcc catttttatg aattagaagt attaatactg ttaaaatgac 300
catcatactc aaatcagtct ataggtccaa tacaatctct aacaaatttc caatgtaatt 360
cttcagagat gttaaaaaag gttttaaaaa tcgttctgcg gatgttaaaa ggatttttaa 420
aacgcttttt tcgttctgca ggcgaaggct gtggccgtgc tcccgccggc cagttcccag 480
cagcagcgca ttgcccctgc tccacgcctt cgctccaggc ccgcaggggc gcagccccgc 540
gggaatcagc actgagccgg tcccgccgcc gccccagtgt ccgggctgcg actgcgggga 600
gccgatcgcc cagcgattgg aggagggcga cgaggccttc cgccagagcg agtaccagaa 660
agcagccggg ctcttccgct ccacgctggc ccggctggcg cagcccgacc gcggtcagtg 720
cctgaggctg gggaacgcgc tggcccgcgc cgaccgcctc ccggtggccc tgggcgcgtt 780
ctgtgtcgcc ctgcggctcg aggcgctgcg gccggaggag ctgggagagc tggcagagct 840
ggcgggcggc ctggtgtgcc ccggcctgcg cgaacggcca ctgttcacgg ggaagccggg 900
cggcgagctt gaggcgccag gctagggagg gccggccctg gagcccggcg cgccccgcga 960
cctgctcggc tgcccgcggc tgctgcacaa gccggtgaca ctgccctgcg ggctcacggt 1020
ctgcaagcgc tgcgtggagc cggggccgag cggccacagg cgctgcgcgt gaacgtggtg 1080
ctgagccgca agctggagag gtgcttcccg gccaagtgcc cgctgctcag gctggagggt 1140
caggcgcgga gcctgcagcg ccagcagcag cccgaggccg cgctgctcag gtgcgaccag 1200
gccctgtagc tgtgacttgg ctgtggggct ggcccgcctc cctgacccct gtcaggcgga 1260
gcagctggag ctgacccacg ggcctgggct ttcgagcgct ttgtccaggc gctaatgatg 1320
ggaaggtgaa aggtgggggt ggccacaccc tgcagtcagg gtggcaggtg tcagaggcca 1380
catgcaaccc actggttttg tcttttccag gatgctgata agtttcccgc ggcccccgga 1440
gcagctctgt aaggccctgt aattgccttt cgttcccttc tgctctattg aggagtggga 1500
agatgacaaa gtgtttttgc tcaacccgaa ggaaaatgca catgggagga cacaccgggt 1560
tactatttga gtagcccaga caggagagca gcggtctgct 1600

<210> SEQ ID NO 171
<211> LENGTH: 1500
<212> TYPE: DNA
<213> ORGANISM: Homo sapiens

<400> SEQUENCE: 171
tgggtggatt gcttgagccc aggagttcga gaccagcctg gacaaaatgg cagaaactcc 60
atgtctacaa aaaatacaaa aattagccgg gcatgatgtt ctgcgcctgt agtcccagct 120
actcaggagg ctgaggtggg aggatcgctt gagcccagga ggcggagttt gcagtgagct 180
gagatgtcac tgcattccag cctgggagac agagccagac tctgtctcaa aagaaaaaaa 240
gaaaaaaaaa aaagaaaaga aaaaacgaaa ttgtattctg aatacatctt ctaaaacact 300
acatttactt gcactatatt aaactggttt tatcctgacc acaattgcag gtgaaagata 360
ccactgttgt tctatttttc tggtaagtag agtgagccat gtcttcccca gggaaagacg 420
cctcctaaaa atttgtagga ccacctttgg ttttcttcca gatatttttt ttgtcatcgc 480
ttttcctgcg cccaattccc atctgtctag cccttctgcc tccgctggtc tttttcgcga 540
gcctctcccc agccgcaggt attcgtctgg gctgcagccc ctcccatctc ctggggcgtg 600
accacctgtc caggccccgc ccccgtccaa cccgcggaga cccgcccccct tccccggaca 660 ccgggttcag cgcccgagcg tgcgagcgcg tccccgctcg tcgcccggct cggcgtcggg 720
agcgcgctct gtgtggtcgc tgctgcagtg ttgttgtggc tgtgagaagg cggcggcggc 780
ggcggagcag cagccggacc agactcccta gtagctcagg cgctgccctg cgccggccct 840
ggcagggagc ctggtgagat ggtggaggag gaggctgtgc cgtggctggc cttgctgtgt 900
cctgctgcct ggttagaacc ccatccccgt cccccgtctc ctccgggggg tgaggaggag 960
ctggaagagg ggccggcctc tgtccggccc ggccaggcgg cagtcaccct ctgaggaggc 1020
agcgcccggg gaggggcctc ccaggcggcc gccgccgcca gggggaggcg ctgggagtgg 1080
gagtgggagc gggacctcag ctgccaagct cggcccggac cctaggtgcg ggggaggcgg 1140
ggtcccgggc tcgggctgcc tgcccggacc tggcggggat gggcccgtgc ggctccgggt 1200
gtgggacgta ccctcagagc gcccggggtt attcccactg actccaggga ggtgagtgtg 1260
cgcccttcgc tccctgccgt gtctgtgagg gtccatcgtt gccggagact ggaggtcggg 1320
ggccatggga gccccggggc gaacggtgcg gacatgggcc ttgtggaaag gaggagtgac 1380
cgcctgagcg tgcagcagga catcttcctg acctggtaat aattaggtga gaaggatggt 1440
tgggggcggt cggcgtaact cagggaacac tggtcaggct gctccccaaa cgattacggt 1500

<210> SEQ ID NO 172
<211> LENGTH: 1700
<212> TYPE: DNA
<213> ORGANISM: Homo sapiens

<400> SEQUENCE: 172
gtctctagga caccctaaga tggcggcgag ggagacggtg aaggttggct cccgcctgtc 60
tgggctctga tcctctgtct ccccctcccc ctgcggccgg ctcatggcct ggcggaggcc 120
cgaaccaaag acctccgcac cgccgtgtac aacgccgccc gtgacggcaa gggggcagct 180
gctccagaag ctgctcagca gccggagccg ggaggaactg gacgagctga ctggctaggt 240
ggccggcggg gggacgccgc tgctcatcgc cgcctgctac ggccacctgg acgtggtgga 300
gtacctggtg gacccgtgcg gcgcgagcgt ggaggccggt ggctcggtgc acttcgatgg 360
cgagaccatg gagggtgcgc cgccgctgtg ggcgcggacc acctggacgt ggtgcggagc 420
ctgctgcgcc gcggggcctc ggtgaactgc accacgcgca ccaactccac gcccctccgc 480
gccgcctgct tcgagggcct cctggaggtg gtgcgctacc tggtcggcga gcaccaggcc 540
aacctggagg tggccaaccg gcacggccac atgtgcctca tgatctcgtg ctacaagggc 600
caccgtgaga tcgcccgcta cctgctggag cagggcgccc aggtgaactg gcgcagcgcc 660
aagggcaaca cggccctgca caactgtgcc gagaccagca gcctggagat cctgcagctg 720
ctgctggggt gcaaggccag catggaacgt gatagctacg gcatgacccc gttgctcccg 780
gccagcgtga cgggccacac caacatcgtg gagtacctca tccaggagca gcccggccag 840
gagcagctca taggggtaga ggctcagctt aggctgcccc aagaaggctc ctccaccagc 900
caggggtgtg cgcagcctca gggggctccg tgctgcatct tctcccctga ggtactgaac 960
ggggaatctt accaaagctg ctgtcccacc agccgggaag ctgccatgga agccttggaa 1020
ttgctgggat ctacctatgt ggataagaaa cgagatctgc ttggggccct taaacactgg 1080
aggcgggcca tggagctgcg tcaccagggg ggtgagtacc tgcccaaact ggagcccccca 1140 cagctggtcc tggcctatga ctattccagg gaggtcaaca ccaccgagga gctggaggcg 1200
ctgatcaccg acgccgatga gatgcgtatg caggccttgt tgatccggga gcgcatcctc 1260
agtccctcgc accccgacac ttcctattgt atccgttaca ggggcgcagt gtacgccgac 1320
tcggggaata tcgagtgcta catccgcttg tggaagtacg ccctggacat gcaacagagc 1380
aacctggagc ctctgagccc catgagcgcc agcagcttcc tctccttcgc cgaactcttc 1440
tcctacgtgc tgcaggaccc ggctgccaaa ggcagcctgg gcacccagat cggctttgca 1500
gacctcatgg gggtcctcac caaaggggtc cgggaagtgg aatgggccct gcagctgctc 1560
agggagccta gagactcggc ccagttcaac aaggcgctgg ccatcatcct ccacctgctc 1620
tacctgctgg agaaagtgga gtgcaccccc agccaggagc acctgaagca ccagaccatc 1680
tatcgcctgc tcaagtgcgc 1700

<210> SEQ ID NO 173
<211> LENGTH: 300
<212> TYPE: DNA
<213> ORGANISM: Homo sapiens

<400> SEQUENCE: 173
taaaaataaa ttgtaataaa tatgccggcg gatggtagag atgccgaccc taccgaggag 60
cagatggcag aaacagagag aaacgacgag gagcagttcg aatgccagga acggctcaag 120
tgccaggtgc aggtgggggc ccccgaggag gaggaggagg acgcgggcct ggtggccaag 180
gccgaggccg tggctgcagg ctggatgctc gatttcctcc gcttctctct ttgccgagct 240
ttccgcgacg gccgctcgga ggacttctgc aggatccgca acagggcaga ggctattatt 300

<210> SEQ ID NO 174
<211> LENGTH: 600
<212> TYPE: DNA
<213> ORGANISM: Homo sapiens

<400> SEQUENCE: 174
cgccaccacg tgcgggtagc gccgcatcgc cccagccgtg ttccttggtc tccgtctccg 60
ccgcgcccgc ctggtgaact ggagcacagg gaccatagtt ctggaaattt atccttttttc 120 tctccatgga ttcagcagca gtgtctaaaa gaaaaaaatt catcaatcat ttatgtatat 180
tttaatataa aggtaaaaca ctgcgaacca gtggaaccgg atagaaagta attcagtttt 240
acagaacaca actgtttttc aggctctttt attaaatata aaagagccat atatatttct 300
gtggaattcc ccttttactt aagaattcat tatcagcgaa ttagtttaag gaggctgttt 360
tgttagaggc tgtggttgca ttcaaaaatt ggaataggaa caatgacttg taaaaattca 420
acattttatt ttatttttga gatggagtct cgctctgtcg cccaggctgt agtgcagtgg 480
cgcgatctcg gctcactgca acctcagcct cccgggttta aggaattctc tgcttcagcc 540
tcctgaatag ctgggattac aggcgcatgc caccaagccc agctaatttt ttttgtattt 600

<210> SEQ ID NO 175
<211> LENGTH: 1300
<212> TYPE: DNA
<213> ORGANISM: Homo sapiens

<400> SEQUENCE: 175
ccctgaacag tcagagttta ctgcccactt ttgctggagg agaagctcct gaacaactag 60
agagactgtg gttcccaaag agcagcctgt aggcctgagg actgctctat gaccggcgtc 120
agtccctgcc tccctccctc cgtccctcct tccctccttc cttcccaggc cttctctgac 180
taccagatcc agcagatgac ggccaacttt gtggatcagt ttggcttcaa tgatgaggag 240
tttgcagacc atgacaacaa catcaagtga gtccacttgg atgccccctg cacgaggcac 300
gactccccct cctcgctgct gaagtcccat gggggcagct cccttagtcc ttgccgggag 360
ataacaggtg tttccagttg catgagggtg ctgaggcccc cagtgagaac caggggagga 420
gcactgaggc ctcagatgag caccggggga ggagccctga ggccccagat gagcaccagg 480
ggaggagcac tgaggcccca gatgagcacc gggggaggag cgttgaagcc ccagatgagc 540
accagaggag gagagctgag gccccagatg agccccgggg gaggagctct gaggccccag 600
acgagcaccg gggaggagc gccgaggccc cagatgagca ccgggggagg agcgccgagg 660
ccccagatga gcagtggggg aggagccccg aggcccccag atgagcagtg ggcggggcag 720
ggagcgccga ggccatcccc cttgctcttg cagcgcccca tttgacagga tcgcggagat 780
caacttcaac atcgacactg acgaggacag tgtgagcgag cggggctgtg cggggtcatg 840
caggcaccct gttcccaggc agctcaggcc gcgcccatgg ctcggtctgt ggtgggcctg 900
tgcggtgggg ctgggagagg cccctctgtg gagctaggaa cagtcgcttt tcttgaccct 960
ccccatcatg ccctccagcc catggcgccc acatcctgaa ctaagcccct ctgggagccc 1020
tgtggggaga gcgcctcctg tctcccccag accctctgga aactgacctt ggcgttttac 1080
tctgcagccc agcgcggctc tgaggcctgc tgcagcgacc gcatccagca ctttgatgag 1140
aacgaggaca tctcggagga cagcgacact tgctgtgctg cccaggtgaa ggccagagcc 1200
aggtgcgggg cctgcccatc cccccaaagc ctctgccgag gaggtgcagc ccccagaaca 1260
cccgtcagat gcccagacgc cctgctgttt gttatgccgg 1300

<210> SEQ ID NO 176
<211> LENGTH: 110
<212> TYPE: DNA

<213> ORGANISM: Homo sapiens

<400> SEQUENCE: 176
tttgggccac gaggcaagtt caaagcggga gacttttgtt ttataaaatg atggtgagca 60
gctccggttt tatgtcaaac atcagggttt cgtgcaggat ataaacattt 110

<210> SEQ ID NO 177
<211> LENGTH: 1500
<212> TYPE: DNA
<213> ORGANISM: Homo sapiens

<400> SEQUENCE: 177
attgccgtac tttgcttccc tttgtatgta tttcttgtat gctgccgagt cactgatggc 60
tagctctgtc tggcaagtaa ttcaaaaatg ctgtttatgt agaaaggaaa ggtagggact 120
ttaccacact ctgtcattaa agggagcaat tgaagaacaa aggaactgag taaataccta 180
tatattgcct tttgtgttgc gaaacactgt agcacaaaca catttgtgtt cagccaaatg 240
ttttacttcc ttttgtaata acgcatatag taggttgtct ccacatatgt acaagaatcc 300
atattttatt taaacgtata tagtcaattg ttcatattta taggctgcaa acatttctca 360
atctcaaaga cttttacata tccactccca cacagctatt tgttattatt ttaaaagttc 420
ttaaattaaa aaaaaaaata aaatatacta atatctctgt tggttgattt tattaagcaa 480
cttaggattt caacacagtt taaatcatat tgatgactca gatcctggca ggtcttacaa 540
ttcctgtgaa atgagagcac agctaataaa aatattaagc aattactttt attaaaatca 600
tagggttttt ttcattatca catagaaatg attgatctat acagattggt ctcactcatg 660
tgtcttttgg gctgcttggg agcttcatgt agaagtggaa agtccccttt gctcttcctt 720
cgaccaaggt ggggaaaatg aaggcataga atacaatcta gggctattaa agaattgctg 780
gcattacttc tctctatcac gtgtgagcct ggctgcctgc ttcctgaggt aggggatcca 840
ggatgagact gtgccggagc ctgtttccac aactgcattt ggagatccgt cttattgatt 900
agcgggggaa aggggtgggg atcaggagtg tgaggtgagg ggaggaccaa ctgacgactg 960
gctcaatgaa gcacaagaca ttttcttccg gaaagatgtc aaacaactga gaaacagcca 1020
gagaggaagt agaaaggtgg aaaaatgagg agaccctgga agaaatgaag gcatttccta 1080
tgagacagcc ttggggcttt tttcttttct ttcttttttt ttgcttccat catctgacct 1140
gcaaaggcta gagtgacagc gtcatgcaaa tgctgcagtc cagcaggtct gggagagggt 1200
ggatgctaga ctgtgagtta atgttaatga tgagcgcagt gaaaatacca gccgctgcca 1260
ccccctgctc acagaagcgc tctgagtcag catcagatgc tttgcctcgc ctctcgctgt 1320
gtatctgtat gcctgtgtgc gcgcgcgtgc tcgctcgggc atccgtgtct agccgagggg 1380
agggggtggc gtgtgagtgc gtggagggta aaagccagtc agtcagtgag aagcaaaggt 1440
acgttggaga gcaactaaaa tctgactgat ttccatcttt ggagcatcag atgtattccc 1500

<210> SEQ ID NO 178
<211> LENGTH: 200
<212> TYPE: DNA
<213> ORGANISM: Homo sapiens

<400> SEQUENCE: 178
gcagcctcct cctgaaaaat gtaagccatt tccactttgt aaagctacgt ttatattcca 60
ccacgatacg atggaaaaga aaacccaagg caatttaata tacgggttgg gaagaaagtt 120
ttgctgatgg aactacatta gcctccactc cagcaaagca aacaaggaac cacactaaag 180
aaatgtactg aatcttttaa 200

<210> SEQ ID NO 179
<211> LENGTH: 800
<212> TYPE: DNA
<213> ORGANISM: Homo sapiens

<400> SEQUENCE: 179
tgcctgagcg cagagcggct gctgctgctg tgatccagga ccagggcgca ccggctcagc 60
ctctcacttg tcagaggccg gggaagagaa gcaaagcgca acggtgtggt ccaagccggg 120
gcttctgctt cgcctctagg acatacacgg gaccccctaa cttcagtccc ccaaacgcgc 180
accctcgaag tcttgaactc cagccccgca catccacgcg cggcacaggc gcggcaggcg 240
gcaggtcccg gccgaaggcg atgcgcgcag gggtcgggc agctgggctc gggcggcggg 300
agtagggccc ggcagggagg cagggaggct gcagagtcag agtcgcgggc tgcgccctgg 360
gcagaggccg ccctcgctcc acgcaacacc tgctgctgcc accgcgccgc gatgagccgc 420
gtggtctcgc tgctgctggg cgccgcgctg ctctgcggcc acggagcctt ctgccgccgc 480
gtggtcagcg gtgagtcagg ggccgtctcc ccgaagaacg agcggggaga ggggaccacg 540
gggcgcggcg ggcagcctgt tctcgggcgg aggctctccg gggcgttgga aacctgcatg 600
gtgtaaggac ccgggaggag gcggggagaa attgattgtg ctgttctcct ccctctcttc 660
tctaacacac acgcagaaaa gtttaaattt ttgtgaagcg cttgcttacg tagctgcgga 720
gcgagcctct gcttcattac gagcggcata gccttttca ggagtgattt ccactttctt 780
tgtgagagag ttgaccacac 800

<210> SEQ ID NO 180
<211> LENGTH: 600
<212> TYPE: DNA
<213> ORGANISM: Homo sapiens

<400> SEQUENCE: 180
ttcaatttac actcgcacac gcgggtacgt gggtgttcgg ggtagggcac tgatctgggg 60
aaggtctccc ccccgcgacc caactcatct ttgcacattt gcagtcctcc ctcggtgcac 120
tcctggcggg gatctggcca gtgcagcgca ctgggaccga gggcagagcc cgcggagtga 180
ggccaggaga gacttcaggc ctctaaggac acagctgagg ctaaggctga gttgaacgca 240
gcccctcccg cggctcgtcc cctctccagt gtctctcccg taaggtgccg ctcccaacag 300
caatgggtcg agatgtagag gaaacactct gtacgttatt tttccgccca ccctttagcg 360
cctgaggaga cagacagtgt agactttagg gtacaattgc ttcccctctg tcgcggcggg 420
gtggggagcg tgggaagggg acagccgcgc aaggggccag cctgctccag gtttgagcga 480
gagagggaga aggaggtcca cggagagaca agaatctccc tcctcccacg cccaaaagga 540
ataagctgcg gggcacaccg cccgcctcca gatcccccat tcacgttgag ccggggcgcg 600

<210> SEQ ID NO 181
<211> LENGTH: 600
<212> TYPE: DNA
<213> ORGANISM: Homo sapiens

<400> SEQUENCE: 181
tcattatccg attgattttc ctggtatcac atcacttaag tttaagtagc tcttatgtta 60
cttagtaatg actgcaaaac acgagttgtg atgcgggcaa tttggataca acaaaaagaa 120
gccattaagt ttgttcgtta gttaacaggt gaaagctctc aagttattaa ggataaaaat 180
gctagtatat atatatatgg tttggaacta tactgcggat tttggatcat atccgccatg 240
gataagggag gaatactata atcaggtttg ttttaaattc catgtctaat gacttcgtta 300
tctagatcac ctgtagagct gtttttattg taggagtttt ccttggtttt aatcttttga 360 tttgttttc atgttaatac tgaaattttt aaaaattgca tattgtactt cctatatgaa 420
aattttacta tgtattttta tttttatttt ccttttcctt taggaagaat tagtttgttc 480
cctgacagag ttagagtaag ggcaaattac ttgtctctat aaacaactca gatgttttga 540
gccggtgttg taggggttat ctttttctgg ttttgcattt tattatagga catagtgctt 600

<210> SEQ ID NO 182
<211> LENGTH: 140
<212> TYPE: DNA
<213> ORGANISM: Homo sapiens

<400> SEQUENCE: 182
agaaagaaga aatccggtaa aaggatgtgt tattgagttt gcagttggtg tttgatcttg 60
cacagatttt ctcaggggcc ttaagaccgg tgccttggaa ctgccatctg ggcatagaca 120
gaagggagca tttatacgcc 140

<210> SEQ ID NO 183
<211> LENGTH: 900
<212> TYPE: DNA
<213> ORGANISM: Homo sapiens

<400> SEQUENCE: 183
cgaagatggc ggaggtgcag gtcctggtgc tcgatggtcg aggccatctc ctggtccgcc 60
tggcggccat cgtggctaaa caggtactgc tgggccggaa agtggtggtc gtacgctgcg 120
aaggcatcaa catttctggc aatttctaca gaaacaagtt gaagtacctg ggtttcctcc 180
gcaagcggat gaacacccac ctttcccgag gtccctacca cttccgggcc ccccagccgc 240
atcttctggc ggaccgtgcg aggtatgccg ccccacaaga ccaagcgagg ccaggcttct 300
ctggaccgcc tcaaggtgtt tgaccgcatc ccaccgccct acgacaagaa aaagcggatg 360
gtgttcctgc tccctcaagg ttgtgcgtct gaagcctaca agaaagtttg cctatctggg 420
gcgcctggct cacgaggttg gctggaagta ccaggcagtg acagccaccc tggaggagaa 480
gaggaaagag aaagccaaga tccactaccg gaagaagaaa cagctcatga ggctacggaa 540
acaggccgag aagaacatgg agaagaaaat tgacaaatac acagaggtcc tcaagaccca 600
cagactcctg gtctgagccc aataaagact gttaattcct catgcgtggc ctgcccttcc 660
tccatcgtcg ccctggaatg tacgggaccc aggggcagca gcagtccagg cgccacaggc 720
agcctcggac acaggaagct gggagcaagg aaagggtctt agtcactgcc tcccgaagtt 780
gcttgaaagc actcggagaa ctgtgcaggt gtcatttatc tatgaccaat aggaagagca 840
accagttact attagtgaaa gggagccaga agactgattg gagggcccta tcttgtgagc 900

<210> SEQ ID NO 184
<211> LENGTH: 1400
<212> TYPE: DNA
<213> ORGANISM: Homo sapiens

<400> SEQUENCE: 184
gcctgaagac catttcttcc tctcttaggg acctgctggt ctccagctga ttcggtccag 60
gaggaaaaac ctcccacttg ctcctctcgg gctccctgca aggagagagt agagacactc 120

```
ctgccaccca gttgcaagaa gtcgccactt ccccctccag ccgactgaaa gttcgggcga    180
cgtctgggcc gtcatttgaa ggcgtttcct tttctttaag aacaaaggtt ggagcccaag    240
ccttgcggcg cggtgcagga aagtacacgg cgtgtgttga gagaaaaaaa atacacacac    300
gcaatgaccc acgagaaagg gaaaggggaa aacaccaact acccgggcgc tgggcttttt    360
cgacttttcc tttaaaaaga aaaaagtttt tcaagctgta ggttccaaga acaggcagga    420
gggggagaa gggggggggg gttgcagaaa aggcgcctgg tcggttatga gtcacaagtg    480
agttataaaa gggtcgcacg ttcgcaggcg cgggcttcct gtgcgcggcc gagcccgggc    540
ccagcgccgc ctgcagcctc gggaagggag cggatagcgg agccccgagc cgcccgcaga    600
gcaagcgcgg ggaaccaagg agacgctcct ggcactgcag gtacgccgac ttcagtctcg    660
cgctcccgcc cgcctttcct ctcttgaacg tggcagggac gccgggggac ttcggtgcga    720
gggtcaccgc cgggttaact ggcgaggcaa ggcgggggca gcgcgcacgt ggccgtggag    780
cccggcctgg tcccgcgcgc gcctgcgggt gccccctggg gactcagtgg tgtcgcctcg    840
cccgggacca gagattgcgc tggatggatt cccgcgggca gaggcagggg gaaggagggg    900
tgttcgaaac ctaatacttg agcttctttg caaagtttcc ttggatggtt ggggacgtac    960
ctgtataatg gccctggacc agcttccctg ttggagtggc cagagaagtg tgtaaaacac   1020
actagagggg cagggtggaa aaagagactg ccttcaaaac ttgtatcttt tcgatttcat   1080
tttgaaaaat aactacaaat ctattttaat tttacaaagt tagactcata gcattttaga   1140
tatcaatgtc ttcatttaac agaagtgaag atggagcaaa cgctcaatca gcgtctgtat   1200
ttattcgctc ctgttgtgcc agggtgcgtt tttgccgagc ggttgccttt ctttactcac   1260
aaaacccccct tgatgtctgt cctccacgtt ttacgaggga gagccggatc ttttgaagtt   1320
tgtatcatct aaagcaggta tattgggatg actatggata gaatttaacc tgaaaacact   1380
gaagttgaca gctgacaaag                                               1400
```

<210> SEQ ID NO 185
<211> LENGTH: 200
<212> TYPE: DNA
<213> ORGANISM: Homo sapiens

<400> SEQUENCE: 185

```
cataacaaga gtcattctaa tgtgattata aaggacccga agctttgctt ttaaaattca     60
atacttaggt agaaagaaaa tgataacttt ttccctttga tttttattca ctatttttat    120
aacactagca gccctgagac accggattgg aaatatctat gcctcttgat gttacctggg    180
caccactgca tcacagtcct                                                200
```

<210> SEQ ID NO 186
<211> LENGTH: 400
<212> TYPE: DNA
<213> ORGANISM: Homo sapiens

<400> SEQUENCE: 186

```
aatagtaatt gccaacagtc aagatatgta ctaccaccaa attccgtgtt atttgtgatc     60
aaaagatata cacagatact tgaaaactga tttctacgtt gcatatggga aaaatacctc    120
atttttctca gctgtccatt atttttgaga tattatgtgc agtgatagta agaacaagca    180
gatttggaac acatcagcaa taattttttc aatcagagtc ctgccaaaat gaaagaattt    240
gacagtatcc ggcaccctgt actcatgctt ggcttctgta gaaactgtgg cttgcaaaag    300
```

ggcagctggg tactgtgttt tggtacctca ttctttaaac gtataatggg aatctggttg 360
gttcaggaaa acccttgcct acttattatt actctgtttt 400

<210> SEQ ID NO 187
<211> LENGTH: 250
<212> TYPE: DNA
<213> ORGANISM: Homo sapiens

<400> SEQUENCE: 187
ggcccatact taatgtattt ttaaacgttt taacatttac taatatagaa ccttctattg 60
cctatttcct tctggtttat tccctttcct tctgtcattg aagaaatggt tctagtggta 120
gaaatactcc acgattgaga agaatgtggg aagaaaggag ggctggtggg taagaattgc 180
tcatgatgtc tccctctgaa ttctgtgctc tcacaatgac actccaatgt gtggtttgac 240
gcctggaaga 250

<210> SEQ ID NO 188
<211> LENGTH: 250
<212> TYPE: DNA
<213> ORGANISM: Homo sapiens

<400> SEQUENCE: 188
tgcttcaacc ggaaatgtgg ttgaattacc cttacagtga acctgatcag tggtaacagg 60
agatgctaga acaggaaaag acaagtttcc cctttcctcc ctatcccatc aattactttg 120
aggtgtattt tttctttgca acccctccag agaagtcggc aatgtttaac gagcatgcct 180
gccaagtggc ttgccttata cctcattatg aagtgatact cagggccact aacacatcgc 240
acagcattgc 250

<210> SEQ ID NO 189
<211> LENGTH: 500
<212> TYPE: DNA
<213> ORGANISM: Homo sapiens

<400> SEQUENCE: 189
tatgattccc tcgatttccc tcaatcttaa ccattgtgga tcacagcagg agggccagaa 60
agtgagcttc agcctggcac cgggacctca gcctctccct taaactttcc ctaatcctcg 120
gagctagtgt tactcaagtg actccacagt gttgcccgat cccttcagac atggccttga 180
tgatctccaa aactcatgct acctttgcca gcctaaagca tccactctgt gccccaaaac 240
gtgaatgtca aatacccttc aaggcagaag gctatttcta tttttgtttg tttctgttta 300
aggcaacaat caccaacatt tggtacacat gagccatcct gtgaaacatc aaggcgcttc 360
gttggcagca agtcaacttc ggtttcagaa gaaagctgca ctatttcctg aggttagagg 420
tttaaaccaa aacaagacaa ccacatttta accccaaatc tgccgactga gggtaaccat 480
gatccttcct tcacagcacc 500

<210> SEQ ID NO 190
<211> LENGTH: 150
<212> TYPE: DNA
<213> ORGANISM: Homo sapiens

<400> SEQUENCE: 190
tactaaatca acccaaaccc gagaacccgg tcatggagaa ataaatgata gtaatctatg 60
ctgttcatct gttccatcac tcactcactc tcttgctgaa caagaaaggg ccacccatgt 120
agcaaaccac atgtaaagag ccgggaagac 150

<210> SEQ ID NO 191
<211> LENGTH: 300
<212> TYPE: DNA
<213> ORGANISM: Homo sapiens

<400> SEQUENCE: 191
tattattttg ttcaaagtag acgggtatac taacatctgt gggcaagttt accacacgcc 60
acttaaaaca ggctaacagg gtcatatgcc aaaacgttca ggtttgcatt tttgaaaagc 120
tcagagatct gacagatgtg ttccggccgc gatttaacat gcggctccag tgagaaggaa 180
gcagatatga caaatggttc acttatttca gaactaaaac cccagaggag cagcctgagc 240
caaaaaggga agtgatcaat ggaaaagacg gtcgaatctg ctcacaggca aggcaagggg 300

<210> SEQ ID NO 192
<211> LENGTH: 300
<212> TYPE: DNA
<213> ORGANISM: Homo sapiens

<400> SEQUENCE: 192
aagacctgga gtttccatta caccgaattg gcacttaata actgttgtcg gagcatttct 60
taagccacat tttcgtaaag tggctttaaa attgctctgc cagtaggcag gttgctaaga 120
tggtcagaga caaacttctg aacgactctt gtaaaatata cagaaatatt ttcagaactt 180
ttatcagtaa aattacaaaa cgtgttgcaa ggaaggtgct tgtgataaca ctgtccccag 240
aaccttagtg aagttaccaa ctggtggaaa attttctctt gcactcggct taaaaatcat 300

<210> SEQ ID NO 193
<211> LENGTH: 400
<212> TYPE: DNA
<213> ORGANISM: Homo sapiens

<400> SEQUENCE: 193
gcaggggtga ctggtcctct ctctctgcac ctcgcaggat ttctctggaa gatctgagcc 60
cgagcgtcgt gctgcacatg accgagaagc tgggttacaa gaacagcgac gtgatcaaca 120
ctgtgctctc caaccgcgcc tgccacatcc tggccatcta cttcctctta aacaagaaac 180
tggagcgcta tttgtcaggg gtaagtgcga ccctagaggc gatcgtctct gctgtctgtg 240
gaaaaaagag ctcctacacc caaagtgctt ctcagttgct gacacttgat ccaagctgct 300
aatttaatct aatgtgaggc tgagttttct gaatgtggga taaagtcgta gctaaacctg 360
cttctcaggg agtgcctttt atctgcaatg tttttcaaat 400

<210> SEQ ID NO 194
<211> LENGTH: 1100
<212> TYPE: DNA
<213> ORGANISM: Homo sapiens

<400> SEQUENCE: 194
aagtaacggg atcaaattaa ttattatttt ggtggccgcc tctcttctcc accccaagcc 60
aggcaagact caccctcggc cctgcccgcc ccagcatttc aaatggaata cctaggtggc 120
ccagggggac ccctgacccc tatatcctgt ttctttctgc ctgctttgct acttttctcc 180
ttgataaaag gagagagtga gagataatta acaaaaaaca tggccccagg acaatgaaac 240
aactggcctt ggccggccag aaatgtatcc tggttttcta ggtgaacttt ctcccatcaa 300
tctttccttt aacctctctg ttagtggaag caataggaac acccctcccc tcccctgagc 360

-continued

```
aaatgctttc ttttgactgg aaacaaaaca ggggctcggc gaaggctgag gtgaaatctg    420

ggtggcatgg gcgccgcaca atggggccgc tgttccccgg cccgggcttg tgttttacaa    480

caggggaggg gcgggcgtga atggtctgat gattggaaca atccccccga ttcaggccta    540

caaacgcatc ttctgttcca caccgagggg acagaaagga gaaaagtgac aaagaacgcg    600

gggcgggggg aattaaaaca aaatgcgctc gactaaaaaa tctctcatat cctgcatatt    660

ccagaaagcg gctctatgga gagagccttc aggaggcctc agccatatct gaatggcttt    720

ctctggcctc tgatttattg atgaagctga agcgacttgc tggagaaagg cctggagcct    780

tctttgtctc cgagatgaag tacaataggc cacagggcgg agatctcttg tgatgctctc    840

gggtcctgcc tttctcttgc cctctcctcc ctgcaaatac cagcagcggt gacaaacgat    900

tggtggtgtg cctgggagag ccggtgacaa gactgggcca cttgaggtct ccttaagagg    960

gtattatggc cagggcgacg tttgtgctgt gaagatggca cactccattt tgtcaatggc   1020

tctcatcggc ccagataatc gccccctgcc tgcctgtcag gggcgcagcc ggccgattca   1080

tggcgccctc ggagaaagta                                               1100
```

<210> SEQ ID NO 195
<211> LENGTH: 10000
<212> TYPE: DNA
<213> ORGANISM: Homo sapiens

<400> SEQUENCE: 195

```
gtctttcccg ccccccttgtc taaactcaaa accgagtccg ggcgcgcctt gcagggcgcc     60

cgagctctgc agcggcgttg cgggctgaac ccatccggca caaactgcgg gccactggcc    120

cctcacacct gggagtttgc ggcgctggcc tgcagcccgg ggcccacgtg gcggaagctt    180

tcccgggcgc gcgctgcgca gccccgcggg gccggggaga caccgctcgg gagtcctccg    240

ctcggctgca gaatctttat cagctgcact ttaccgcagc cctggctagg acgctaggcg    300

gtggagcgcc ctatccaggt gcgccgccgc accatggatc accgcgcccg gtcccgcagt    360

cccgccatgg cctggggagg cccgaagccc ggggacagtg gccggcccat ctccggctcc    420

gcggaccccc ggctcaggcg ggagggcagg cgggtccctg caggccccca gggagcccgg    480

gagcctctct ctggcgtcat tcagtcccgg ggcaacctga agcgcggtag atattggaga    540

gggggcgtct gttgggggga cctggcgtca ttactgatgg ctagcaggga ggagggaacg    600

ggttgtcacc tcggcctcat aaggccgtga gtgagtagtc cagggcctct tcaggcattt    660

ttgaaactgg attaactagg ggggaaattg tagcactgaa gccaccgtga ctgtcttttg    720

cgctgtgtgg aaactccggt aaaactcttt gggcaacagt cttatcacca gctcttcaac    780

gtgtgcagcc cttctggtcc tgtccctgtt ctgggcccca ggaatgcaaa gcaggtccag    840

gcactgtgaa gaccctggcg gtggaggaag aggcttcccg gctgtggagg aagccagacc    900

cttacaacac aagacgagaa ccagacctgc gtgggggagc tctggatgct acaggggctc    960

aaggaggggt ggaggggcct tcccaggcca acccctgaac ggcttggaca agatgctcag   1020

atggacggga ggaacggcgt gtgggatggg ggagctggag gcgggtgggt gggggggga   1080

ggatggggaa agcgctggcc cacccagtgt gggaggggta gaggaaaagc ccgcaggggc   1140

caggttggga ccccgtaggc cgggttagag ggcttggact tgatcctgac aggcgacagg   1200

gagacatatt gctacttatt atgtgcacag tggccagatc tctaaagaaa acaccatccc   1260

ccacccccac cccccatata gtaaaccagg tggtccgccc agtgctccca gggaggtgat   1320

gggaaatccc actccatacc ctgcggtgag ggttccatg ccctccacgt gtgcaactac   1380
```

-continued

```
tccgggccca gggaaacact gggccccatc cggtaacccc cggcccagtc gggtttccca   1440
gttcacatta taaccaaacg gtcttgccag ctagacagac agacacccct gacctgttta   1500
ccctgatcct ctgctctcag gattaatcac aacttgtcga agggggtggc ttccagtggg   1560
gtggaccgct ctgtcaatgc cagcgtgtgt ctagcatctc ctggggtggg ggtgtgggga   1620
agggaggtgt aggatgaagc cctagaagcc tcaggcaatt gtgatccggt gggctggata   1680
ctgaagccca cccctgcctt gacctcaatt ttcagtatct tcatctgtaa aatgggaaca   1740
acctgccttc ctcctagccc taaaggggct gctgtcaaga ttggctgaga tagctgtttg   1800
caagctgagc tcaatgaaag ttcattgtgt ccccctcagt cctatcccaa tatcgtctca   1860
ctgcaaaggt ggggggcagc ttaacttcaa gggcacttca aggatagcca ggtggctgtc   1920
agcccagctt tccaggatgg gagcaggatc ttgacagaag ggttgactgg gaggggcagt   1980
tgctggtttg ggcttcgtta ggttgcattt ttgtttgttg tcctttcatt tccctggggc   2040
agcacccctt cctgcaagct ccaggccttc ctctggaatg ctcctagagc ccaacctctg   2100
ctggtgcctg agcttaagcc aggccagcta aggggatcct ggattcacac ggcctcacag   2160
tcactcagat tgttagcaga agacaaaaat tacaagggga gggcgtcatg tgattcttac   2220
acaccctcca aatccagcag acaccttgga agccacaggt agcttcaaga aacccatttt   2280
acggatgaga acctgagatg gagaaaggac aactggagat ctctgagtct ctgagcccac   2340
actccctacc tccctgcacc tccaggcact ctgctggcag gatcttgggc aaatgcccac   2400
agctctctga gagtcagttt tcctgtctgt aaaatgggag tcataccttc ctcctatggc   2460
cggtgagaga ctaaattaaa ctatgtctgt caagacacct gaaactcctg gcacaattta   2520
ggttgccttc aagtggtcac agttgtcatt aggtggaagt caacacccca atcattgtaa   2580
aggtgcccat ataccccaag atccagatta cagctctcac agtttattat atacagcgaa   2640
aaaacacata acacaccttt gcccacattt acatgtattt tacggaccat gtttcacatc   2700
agtccgcatg cacatctgca cgtgtgtgca ttcggcagta tttaccaagc acctgccaag   2760
tgccagggcc tgtcctccgc acccggcgtg aactgtcctg gaccagtccc gggagccgcg   2820
gttctgacca gccgtgctga ccctggacga ctccatgagc tgttttgtga gaaagacacg   2880
ccatttgttt gcagagttct gacttctgag ggtcatgta gcacatgttt ggtagccaaa   2940
cgctgtcatt cacgaccagg agcgatggct gcaatgcctt tttctttgct ttgctttccg   3000
gtgccgggag ccttgcctcc cgccgccacc cctggtcagc tctgcgcaag aacgtcgttc   3060
tgtttggcag ccaggccgag acgcagcctg aatgtgagca ggaactcgga gaagggaagg   3120
gagagaatca gaaagaaggc ccgggaggga cccgggaagc agtgggaggt ctgcgccctg   3180
gagccccgcg agagcccgcc ggtttggcac gggctcctcc cgggccgccc ggcggtccaa   3240
caaaggccgg ccccgacacg cacccggtct tttgtgggag agaaacacaa agaagaggga   3300
aaaacacgga ggaggccaac agcaccagga cgcgggggcc aaccaggaac tcccggagcc   3360
ggggcccatt agcctctgca aatgagcact ccattcccca ggaaggggcc ccagctgcgc   3420
gcgctggtgg gaaccgcagt gcctgggacc cgcccaggtc gcccaccccg ggcgccgggc   3480
gcaggacccg gacaagtcct ggggacgcct ccaggacgca ccagggcaag cttgggcacc   3540
gggatctaat ttctagttat tcctgggacg gggtggggag gcataggaga cacaccgaga   3600
ggtactcagc atccgattgg caccagggcc aagggagccc aggggcgaca cagacctccc   3660
cgacctccca agctactccg gcgacgggag gatgttgagg gaagcctgcc aggtgaagaa   3720
```

-continued

```
ggggccagca gcagcacaga gcttccgact ttgccttcca ggctctagac tcgcgccatg   3780
ccaagacggg cccctcgact ttcacccctg actcccaact ccagccactg gaccgagcgc   3840
gcaaagaacc tgagaccgct tgctctcacc gccgcaagtc ggtcgcagga cagacaccag   3900
tgggcagcaa caaaaaaaga aaccgggttc cgggacacgt gccggcggct ggactaacct   3960
cagcggctgc aaccaaggag cgcgcacgtt gcgcctgctg gtgtttatta gctacactgg   4020
caggcgcaca actccgcgcc ccgactggtg gccccacagc gcgcaccaca catggcctcg   4080
ctgctgttgg cggggtaggc ccgaaggagg catctacaaa tgcccgagcc ctttctgatc   4140
cccacccccc cgctccctgc gtcgtccgag tgacagattc tactaattga acggttatgg   4200
gtcatccttg taaccgttgg acgacataac accacgcttc agttcttcat gttttaaata   4260
catatttaac ggatggctgc agagccagct gggaaacacg cggattgaaa aataatgctc   4320
cagaaggcac gagactgggg cgaaggcgag agcgggctgg gcttctagcg gagaccgcag   4380
agggagacat atctcagaac taggggcaat aacgtgggtt tctctttgta tttgtttatt   4440
ttgtaacttt gctacttgaa gaccaattat ttactatgct aatttgtttg cttgttttta   4500
aaaccgtact tgcacagtaa aagttcccca acaacggaag taacccgacg ttcctcacac   4560
tccctaggag actgtgtgcg tgtgtgcccg cgcgtgcgct cacagtgtca agtgctagca   4620
tccgagatct gcagaaacaa atgtctgaat tcgaaatgta tgggtgtgag aaattcagct   4680
cggggaagag attagggact gggggagaca ggtggctgcc tgtactataa ggaaccgcca   4740
acgccagcat ctgtagtcca agcagggctg ctctgtaaag gcttagcaat tttttctgta   4800
ggcttgctgc acacggtctc tggcttttcc catctgtaaa atgggtgaat gcatccgtac   4860
ctcagctacc tccgtgaggt gcttctccag ttcgggctta attcctcatc gtcaagagtt   4920
ttcaggtttc agagccagcc tgcaatcggt aaaacatgtc ccaacgcggt cgcgagtggt   4980
tccatctcgc tgtctggccc acagcgtgga gaagccttgc ccaggcctga aacttctctt   5040
tgcagttcca gaaagcaggc gactgggacg gaaggctctt tgctaacctt ttacagcgga   5100
gccctgcttg gactacagat gccagcgttg cccctgcccc aaggcgtgtg gtgatcacaa   5160
agacgacact gaaaatactt actatcatcc ggctcccctg ctaataaatg gaggggtgtt   5220
taactacagg cacgaccctg cccttgtgct agcgcggtta ccgtgcggaa ataactcgtc   5280
cctgtaccca caccatcctc aacctaaagg agagttgtga attctttcaa aacactcttc   5340
tggagtccgt cccctccctc cttgcccgcc ctctacccct caagtccctg cccccagctg   5400
ggggcgctac cggctgccgt cggagctgca gccacggcca tctcctagac gcgcgagtag   5460
agcaccaaga tagtggggac tttgtgcctg ggcatcgttt acatttgggg cgccaaatgc   5520
ccacgtgttg atgaaaccag tgagatggga acaggcggcg ggaaaccaga cagaggaaga   5580
gctagggagg agaccccagc cccggatcct gggtcgccag ggttttccgc gcgcatccca   5640
aaaggtgcgg ctgcgtgggg catcaggtta gtttgttaga ctctgcagag tctccaaacc   5700
atcccatccc ccaacctgac tctgtggtgg ccgtattttt tacagaaatt tgaccacgtt   5760
ccctttctcc cttggtccca agcgcgctca gccctccctc catcccccctt gagccgccct   5820
tctcctcccc ctcgcctcct cgggtccctc ctccagtccc tccccaagaa tctcccggcc   5880
acgggcgccc attggttgtg cgcagggagg aggcgtgtgc ccggcctggc gagtttcatt   5940
gagcggaatt agcccggatg acatcagctt cccagccccc cggcgggccc agctcattgg   6000
cgaggcagcc cctccaggac acgcacattg ttccccgccc ccgcccccgc caccgctgcc   6060
gccgtcgccg ctgccaccgg gctataaaaa ccggccgagc ccctaaaggt gcggatgctt   6120
```

```
attatagatc gacgcgacac cagcgcccgg tgccaggttc tcccctgagg cttttcggag   6180
cgagctcctc aaatcgcatc cagagtaagt gtccccgccc cacagcagcc gcagcctaga   6240
tcccagggac agactctcct caactcggct gtgacccaga atgctccgat acaggggtc   6300
tggatcccta ctctgcgggc catttctcca gagcgacttt gctcttctgt cctccccaca   6360
ctcaccgctg catctccctc accaaaagcg agaagtcgga gcgacaacag ctctttctgc   6420
ccaagcccca gtcagctggt gagctccccg tggtctccag atgcagcaca tggactctgg   6480
gccccgcgcc ggctctgggt gcatgtgcgt gtgcgtgtgt ttgctgcgtg gtgtcgatgg   6540
agataaggtg gatccgtttg aggaaccaaa tcattagttc tctatctaga tctccattct   6600
ccccaaagaa aggccctcac ttcccactcg tttattccag cccgggggct cagttttccc   6660
acacctaact gaaagcccga agcctctaga atgccacccg caccccgagg gtcaccaacg   6720
ctccctgaaa taacctgttg catgagagca gaggggagat agagagagct taattatagg   6780
tacccgcgtg cagctaaaag gagggccaga gatagtagcg agggggacga ggagccacgg   6840
gccacctgtg ccgggacccc gcgctgtggt actgcggtgc aggcgggagc agcttttctg   6900
tctctcactg actcactctc tctctctctc cctctctctc tctctcattc tctctctttt   6960
ctcctcctct cctggaagtt ttcgggtccg agggaaggag gaccctgcga aagctgcgac   7020
gactatcttc ccctggggcc atggactcgg acgccagcct ggtgtccagc cgcccgtcgt   7080
cgccagagcc cgatgacctt tttctgccgg cccggagtaa gggcagcagc ggcagcgcct   7140
tcactggggg caccgtgtcc tcgtccaccc cgagtgactg cccgccggag ctgagcgccg   7200
agctgcgcgg cgctatgggc tctgcgggcg cgcatcctgg ggacaagcta ggaggcagtg   7260
gcttcaagtc atcctcgtcc agcacctcgt cgtctacgtc gtcggcggct gcgtcgtcca   7320
ccaagaagga caagaagcaa atgacagagc cggagctgca gcagctgcgt ctcaagatca   7380
acagccgcga gcgcaagcgc atgcacgacc tcaacatcgc catggatggc ctccgcgagg   7440
tcatgccgta cgcacacggc ccttcggtgc gcaagctttc caagatcgcc acgctgctgc   7500
tggcgcgcaa ctacatcctc atgctcacca actcgctgga ggagatgaag cgactggtga   7560
gcgagatcta cgggggccac cacgctggct tccacccgtc ggcctgcggc ggcctggcgc   7620
actccgcgcc cctgcccgcc gccaccgcgc acccggcagc agcagcgcac gccgcacatc   7680
accccgcggt gcaccacccc atcctgccgc ccgccgccgc agcggctgct gccgccgctg   7740
cagccgcggc tgtgtccagc gcctctctgc ccggatccgg gctgccgtcg gtcggctcca   7800
tccgtccacc gcacggccta ctcaagtctc cgtctgctgc cgcggccgcc ccgctggggg   7860
gcgggggcgg cggcagtggg gcgagcgggg gcttccagca ctggggcggc atgccctgcc   7920
cctgcagcat gtgccaggtg ccgccgccgc accaccacgt gtcggctatg ggcgccggca   7980
gcctgccgcg cctcacctcc gacgccaagt gagccgactg gcgccggcgc gttctggcga   8040
caggggagcc aggggccgcg gggaagcgag gactggcctg cgctgggctc gggagctctg   8100
tcgcgaggag gggcgcagga ccatggactg ggggtggggc atggtgggga ttccagcatc   8160
tgcgaaccca agcaatgggg gcgcccacag agcagtgggg agtgagggga tgttctctcc   8220
gggacctgat cgagcgctgt ctggctttaa cctgagctgg tccagtagac atcgttttat   8280
gaaaaggtac cgctgtgtgc attcctcact agaactcatc cgacccccga cccccacctc   8340
cgggaaaaga ttctaaaaac ttctttccct gagagcgtgg cctgacttgc agactcggct   8400
tgggcagcac ttcggggggg gagggggtgt tatgggaggg ggacacattg gggccttgct   8460
```

-continued

```
cctcttcctc ctttcttggc gggtgggaga ctccgggtag ccgcactgca gaagcaacag   8520
cccgaccgcg ccctccaggg tcgtccctgg cccaaggcca ggggccacaa gttagttgga   8580
agccggcgtt cggtatcaga agcgctgatg gtcatatcca atctcaatat ctgggtcaat   8640
ccacaccctc ttagaactgt ggccgttcct ccctgtctct cgttgatttg ggagaatatg   8700
gttttctaat aaatctgtgg atgttccttc ttcaacagta tgagcaagtt tatagacatt   8760
cagagtagaa ccacttgtgg attggaataa cccaaaactg ccgatttcag gggcgggtgc   8820
attgtagtta ttattttaaa atagaaacta ccccaccgac tcatctttcc ttctctaagc   8880
acaaagtgat ttggttattt tggtacctga gaacgtaaca gaattaaaag gcagttgctg   8940
tggaaacagt ttgggttatt tgggggttct gttggctttt taaaattttc tttttggat    9000
gtgtaaattt atcaatgatg aggtaagtgc gcaatgctaa gctgtttgct cacgtgactg   9060
ccagccccat cggagtctaa gccggctttc ctctattttg gtttattttt gccacgttta   9120
acacaaatgg taaactcctc cacgtgcttc ctgcgttccg tgcaagccgc ctcggcgctg   9180
cctgcgttgc aaactgggct ttgtagcgtc tgccgtgtaa caccccttcct ctgatcgcac  9240
cgcccctcgc agagagtgta tcatctgttt tatttttgta aaaacaaagt gctaaataat   9300
atttattact tgtttggttg caaaaacgga ataaatgact gagtgttgag attttaaata   9360
aaatttaaag taaagtcggg ggatttccat ccgtgtgcca ccccgaaaag gggttcagga   9420
cgcgatacct tgggaccgga tttggggatc gttcccccag tttggcacta gagacacaca   9480
tgcattatct ttcaaacatg ttccgggcaa atcctccggg tctttttcac aacttgcttg   9540
tccttatttt tattttctga cgcctaaccc ggaactgcct ttctcttcag ttgagtattg   9600
agctccttta taagcagaca tttccttccc ggagcatcgg actttgggac ttgcagggtg   9660
agggctgcgc ctttggctgg gggtctgggc tctcaggagt cctctactgc tcgattttta   9720
gatttttatt tcctttctgc tcagaggcgg tctcccgtca ccaccttccc cctgcgggtt   9780
tccttggctt cagctgcgga cctggattct gcggagccgt agcgttccca gcaaagcgct   9840
tggggagtgc ttggtgcaga atctactaac ccttccattc cttttcagcc atctccacta   9900
ccctccccca gcggccaccc ccgccttgag ctgcaaagga tcaggtgctc cgcacctctg   9960
gaggagcact ggcagcgctt tggcctctgt gctctttcct                         10000
```

<210> SEQ ID NO 196
<211> LENGTH: 500
<212> TYPE: DNA
<213> ORGANISM: Homo sapiens

<400> SEQUENCE: 196

```
ccggcacggc ccgcatccgc caggattgaa gcagctggct tggacgcgcg cagttttcct     60
ttggcgacat tgcagcgtcg gtgcggccac aatccgtcca ctggttgtgg gaacggttgg    120
aggtccccca agaaggagac acgcagagct ctccagaacc gcctacatgc gcatggggcc    180
caaacagcct cccaaggagc acccaggtcc atgcacccga gcccaaaatc acagacccgc    240
tacgggcttt tgcacatcag ctccaaacac ctgagtccac gtgcacaggc tctcgcacag    300
gggactcacg cacctgagtt cgcgctcaca gatccacgca caccggtgct tgcacacgca    360
agggcctaga actgcaaagc agcggcctct ctggaccgcc tccctccggc cctcctgagc    420
cctactgagc cctgctgagt cctggaggcc ctgtgacccg gtgtccttgg accgcaagca    480
tcctggttta ccatccctac                                                500
```

<210> SEQ ID NO 197
<211> LENGTH: 1000
<212> TYPE: DNA
<213> ORGANISM: Homo sapiens

<400> SEQUENCE: 197
ggacgcggcc cgctctagag gcaagttctg ggcaagggaa accttttcgc ctggtctcca 60
atgcatttcc ccgagatccc acccagggct cctggggcca cccccacgtg catccccccgg 120 aaccccccgag atgcgggagg gagcacgagg gtgtggcggc tccaaaagta ggcttttgac 180
tccaggggaa atagcagact cgggtgattt gcccctcgga aaggtccagg gaggctcctc 240
tgggtctcgg gccgcttgcc taaaacccta aaccccgcga cgggggctgc gagtcggact 300
cgggctgcgg tctcccagga gggagtcaag ttcctttatc gagtaaggaa agttggtccc 360
agccttgcat gcaccgagtt tagccgtcag aggcagcgtc gtgggagctg ctcagctagg 420
agtttcaacc gataaacccc gagtttgaag cccgacaaaa agctgatagc aatcacagct 480
tttgctcctt gactcgatgg gatcgcggga catttgggtt tccccggagc ggcgcaggct 540
gttaactgcg cagcgcggtg ccctcttgaa aagaagaaac agaccaacct ctgcccttcc 600
ttactgagga tctaaaatga atggaaagag gcaggggctc cggggaaagg gaacccctta 660
gtcggccggg cattttacgg agcctgcact ttcaaggaca gccacagcgt gtacgaagtg 720
aggaattcct ttccaccaag agcgctcatt ttagcgacaa tacagaattc cccttccttt 780
gcctaaggga gaaaggaaag gaaacattac caggttcatt cccagtgttt ccctggagta 840
atgctagaat ttacttttgt cataatgcaa aattaaaaaa aaaaaaaata caacgaagcg 900
atacgttggg cggatgctac gtgacagatt tttccaaatt ttgttgcggg gagagggagg 960
gaggagaatt gaaaacggct cacaacagga atgaaatgta 1000

<210> SEQ ID NO 198
<211> LENGTH: 100
<212> TYPE: DNA
<213> ORGANISM: Homo sapiens

<400> SEQUENCE: 198
tttttaatgc tcagagaagt tcgtattact gattcgggaa cactgagttt ttcagctcct 60
gtaaaactat tttcaggttt attttcaagt acattcttta 100

<210> SEQ ID NO 199
<211> LENGTH: 400
<212> TYPE: DNA
<213> ORGANISM: Homo sapiens

<400> SEQUENCE: 199
caccctagag gcaaggacgg ggtctgtgtc aagaggcttc ccagagaagt gaaaactctg 60
caggtgcagc cgctgggaga gcatcaagaa gggcagggtg gaggggcagg gggcgaaggg 120
agggggtgaa gcccgcaccc tacccccaca tgaaactgat tccactaccc catctctgca 180
agcgtccaga ggcagagagg ccaacatttc ggggacagct tggaggcggg agatttaggc 240
agggctcctt aaacttttat gtgcatgaaa atcaggccaa tcacggggct cttgagcaaa 300
tggggacgat gattcagcag gtctgggctg aggcctcaga ttctgcactt ctaacaagtt 360
cccaggtggt agtgatgctg ccagtccaaa gaccacactg 400

<210> SEQ ID NO 200
<211> LENGTH: 5000
<212> TYPE: DNA

<213> ORGANISM: Homo sapiens

<400> SEQUENCE: 200

```
tgcttcagtg gggtaaactt gaaccgctga gaagacaagc agggagtcgg tctcgctgag     60
atttttacct gtggttctag gaacgcagag gcatgtgagt gttcaggctt tgcatagacc    120
actaagccac ttctaagaac aaggctacct gagccatttt gcaaaaatat gtacgtgccg    180
aggcttttcc tccccacacc tacctcaact ctttctgccg acacactgca cttttcaagg    240
gaacccaagt ttgggttcgg caagaattgt acgttgcaca ccgtgtgtga taattccagg    300
gaatttcaat cgcatcttgt cttccttcct aagcaaattc ggtgggaacc tggtgtggtg    360
tgatagaaaa agccccgagt tctctgtggt agaccacatc aatttcatgt gccagtctct    420
cagactccgg cttgcctctc tcaaggaagg gaacaatggt ttgcttggct tcactcctct    480
ctttccccccc aatttccaca tgggtatctg gctaaaaatg agttacaggt ttccttctgt    540
gagaattgca tggactgata aagtaccatc ccaggaagaa aacaaagatg ctgtcttccc    600
tttcggctca cagttgccgt tggggaggga acacacgctg taaattatag gcagccagaa    660
gtgaccgcat tgaccactgc gagtggccca gctatggcaa caggctgaga actctggggg    720
agagccattt gttggcaggg atggtgattc ttctagcatc aagctctaag atgatgacca    780
aacggtatca aaagaaatga tattttgcta cctctccggc ttgggtgaat gatgtggaca    840
gttaacctgg acaatttaaa cctttatgtt gatggatcac ttggatgaaa ttaaccagga    900
aattgccaag atttcacttg gccctctgac atcaaatctc aatattatat taccaaatta    960
gagattctaa agaaccctga gttcctttca ctgaaaggaa ggagtggaaa aacctttcca   1020
gatgatccct tttgagtctt ggtgcgagct caggccctcc ctacactgcc tccgtgaaag   1080
ctaaccgacc cttgttccta acctagcgca ggtcagctga gtgtccatcg ggcacaggag   1140
ccctgggctt gtccgggaga tagccagact cctgctattt cctgatgtct gcatagctca   1200
gcgtgtccct caccatcttt gccgttggcc agtaaggaga gccccagggg ccagcactgc   1260
acactgaaac ccaacctatt gctcaatgga atgcttaaaa atttcctgaa tctgccttcc   1320
tgagttgata aaataggaaa caatacacgt tctgaggggg tactgaaagc agagtaaagc   1380
caggaagatc ttttttttct gttattctat acaaatattg cttcctctgc ttgttagcag   1440
cccagaggaa atgcagccag ggagccgttt gcagcttttc accagtggcc ggtgtctctg   1500
tgttaccaac caaacgacgc tgcaagacta gtgactaacg cacgtctgca tgattcaact   1560
tcactaaaat tccctctgct gccagtaaag aagcacttga aaactcttta atttgaaact   1620
tgagcttggt taatgacttg ttttcttctc tttctcttta acttctctct tgccatctcc   1680
aacacacaca cacacacaca cacacacaca cacacacaca cacacacact ctctctctct   1740
ctctctctct ctctctctct ctctcatcaa gtttttaat ttcagggacc cggaaacata   1800
cagccccgtg cattcacaat agcatttgct gtgataaagt ggccggcaag ccctctgcat   1860
tcccctgctc acttagctgt atgaataaat aatgagtcac agatacaatt tgggtgctca   1920
agagagtttg tagccagaaa attaattatt ctcccatccc agcccactcc atctcagctt   1980
tgccaaacca tcaagataca ctttgcaggc actggtcaga gtgcgtgccc cgacgcacac   2040
ggcaatgcct ttgagacatt ttatgttatt atttttgttt gtttaagcac agccctcttt   2100
taccacgaaa gatacacaag acgcacatgc acacacatac tcacacactc acagctcaac   2160
cacagctttg tccatttcaa gaggctggtt tcaaaaatgg agacaggttt tccaccctgg   2220
ctgttcctat tcataagcct gtaatctaac gacttaagct gcgagaatgc ttaactcggg   2280
```

```
aaacttctct attgcccttt tccagagaga cctcggtatg ccacaatttg cttcctttct   2340
ctcttgaaag atgctggttg tctctttgca ttgaggctac aaggaaaaac acagcacagc   2400
cccatgctga tgattttaac ctaaccaagt ctgtcagtct cctgtactct ctgccttata   2460
gagacagctg ccttgccact ttggccctga agtccccagg ctggtgcaag gctatctgag   2520
agcctccgcc tcctgcccca cactggcacc agccctcctg gctggctctg tgcatgtgcc   2580
tgctaagccc cagggcaggc tgcattctgg gccacacagc atgccgagtt aaggataact   2640
cagacacagg cattccgggc aagggacagc aaaataaaac ccagggagct tcgtgcaagc   2700
ttcataatct ctaagccttt aaacaagacc agcacaactt actcgcactt gacaaagttc   2760
tcacgcaccg actgaacact ccaacagcat aactaagtat ttattaaaac atttctgaag   2820
agcttccatc tgattagtaa gtaatccaat agacttgtaa tcatatgcct cagtttgaat   2880
tcctctcaca aacaagacag ggaactggca ggcaccgagg catctctgca ccgaggtgaa   2940
acaagctgcc atttcattac aggcaaagct gagcaaaagt agatattaca agaccagcat   3000
gtactcacct ctcatgaagc actgtgggta cgaaggaaat gactcaaata tgctgtctga   3060
agccatcgct tcctcctgaa aatgcaccct cttctgaagg cgggggactc aatgatttct   3120
tttaccttcg gagcgaaaac caagacaggt cactgtttca gcctcacccc tctagcccta   3180
catctctctt tcttctcccc tctgctggat acctctggga ctccccaagc cctattaaaa   3240
aatgcacctt tgtaaaaaca aatattcaaa ttgttaaaga ttaaaaaaaa aaaaaaagcc   3300
agcgccgcct tggctgtggg ttggtgatgc tcaccacgct gcgaaaccct gtggtttgca   3360
ttcagtgtga ttcgtcctgc ctgctgacca ctatgctggg ttcagacttc tgacactgcc   3420
aggctaccca acttgtggtt ctgtggttgt ttatgaggcc caaagaagtt ttcacacaac   3480
ccaaattaca aatttaactg ttcccctttc cacagcccat ctcaattggt tcttgccaat   3540
catgtgactt aagtgatgtc aattttttttt tttcttttct gagcaatgcc cttccttccc   3600
tccacctgcc ctcccccagg ctgtgcaaga aaatagccga gtagactttg caagaggggg   3660
ggatgtagaa aaaagtgact cagtcactta ttatatctca atggtctttg ctgatttagt   3720
acaactcggc tcctgttgtt atttgtggtt tttggaacta ctgattattt tgataaagat   3780
ttcattgctg cttattcaat agtaattcaa cgctggcatc aagccgctgc tccgacagga   3840
tgtggatccc atcatttaaa atgctaggca tcagctccgg gagagttaag tccttggtaa   3900
cgtctatcat ggcataagtg aaactataaa agggaaaaat aaataaaaag aaatgttttg   3960
gtgagagtct gacccctaca acgggctggc aactcacagg tattttaaag cctgggaaag   4020
ggaaagaatt ttacttttga aataaaagga ctgttttaat gaaaccaaaa ttatgtggtt   4080
ttattccccc taaatggaca actttagtat gtatctcttt cagtaaagag ataaaatcat   4140
agtacagtct taacacacac acacacacac acacacacac acacacacac acaaattagg   4200
aagctaaagg aaaacaaagc agagagaatt tctgtatttg ggacaaagca gtggttactc   4260
tgcagatgtt tatttgtatt gtcacttggg aaagctccct gtattgcctt tctctagttc   4320
aattcaaatc aataggctaa tttacacctg taggtaaaac tacactttga gcacatgagg   4380
atgccacaat agaaggggaa ccaggaggag acacttctcc tggggctgac taatgaatat   4440
tatatagcgc gtcctctacc ttagaaagac atgcctgttt gaagatgcta aaaacaggat   4500
aattttgtaa gtgggcaaac cactgtggtc acacgtattt cattttccgg ccccactggc   4560
tttacctgct gacaactaaa acgtcatttt gttttgtagt tccaagatga agaaaggctt   4620
```

```
attttcctga tttactacct tattcatttg gctctgctct gcctacatcc gccatagcac   4680

tctgcgcacg tgaaatttcg acacataggg tcaagagaac ctgtgtgatg atgggttgta   4740

aatgccagtc ctggattcta agctgcagta gccagcacag gcacttcaga aaggctgaac   4800

tcccacaaca ctccctcggt tttccctcat ccacttaatt tcacacacac aaagacccac   4860

aacgatagta gcttccatgg cacaagtctt tcaaaaggaa cagacacaat ttttacttac   4920

tcctgttttg actaaagcag gaattgaaac tcaacagacc gctttctctt acacttgtga   4980

gaagttagct ggccacatgt                                               5000


<210> SEQ ID NO 201
<211> LENGTH: 500
<212> TYPE: DNA
<213> ORGANISM: Homo sapiens

<400> SEQUENCE: 201

agggaaaaga gataacgaaa gaaagaaaga aaaaaaaaag ggccggcaat ttcatgtaca     60

tttgttttgg cattcgctga attctagaga tgaaaacaat ctcctgcttt taattcagtc    120

cacgtgcaac aaagttgtac gttgggagat ctggctttta ataagaacga ttaacaagcg    180

tttttgatca caggaagttg agaagagtcg ctgcttctaa gaatacaata aacattgact    240

agcagttaga cggtccatct ttctctatca gccgtttagc agcctctact ttgatttggg    300

gcaaatgcga gatgggacca ggagagagct ccccacaccc ccaccaccac gtgggcagtg    360

gttctgttcc agagcgcctt ccttcctgtc cagggaggca ggctgctgag gccgtttctg    420

ggcaagaggc cattgtcggg atatttgctt tagatagctt gcagctgggc tgagtgggtg    480

tttcattcag actcaacaca                                                500


<210> SEQ ID NO 202
<211> LENGTH: 700
<212> TYPE: DNA
<213> ORGANISM: Homo sapiens

<400> SEQUENCE: 202

agcctggcgc acccgcccta atttgagtca gggaccctag gcgcctgcag ctccggttcg     60

ggttgagtgc ctcctgtcag gatgtgaagc tgctgtcccc cccgggggcc tccagcactg    120

ctgaggactc agcagtcagc ctctcctccc acttgggctc atttacagag agcatctcca    180

ggaatcagtc atggggaaag gggaaacgcg gagtgacaac acaacacgta gaaagttctc    240

tgccgccttg gtcaggcttg tcagcctcac agcccatcct gctcctgcgg gaggaaaagt    300

gagcagaact cagcccggag atgagccgca ggccggcagc ccctgcctct gccctgcttg    360

ttgtgactgc aatgcaaggc tctctgtagg tgcgggggat tcgggttaaa tgggtctcca    420

gtggtccagc gctcccagca aaggccgacc acaagaatta gcgggctagt tatttaccat    480

aaccatatac aaaaccacaa gcatcagcgt tccctcaaat acatccgaga cgctgtatat    540

ctctttatta aagcctgtca gggtttgtta ttgcacagct tggccttgaa ccccaactaa    600

accaggctgc ttgagcaaag aaccaagcaa tgcaagcatt caggcaggac cattataacc    660

ctgaggccaa aggcagaagc agggagagga gacgtcttcc                          700


<210> SEQ ID NO 203
<211> LENGTH: 500
<212> TYPE: DNA
<213> ORGANISM: Homo sapiens

<400> SEQUENCE: 203
```

agaccagcct cggtcttcgg cctgcgggtt ctgcaaagtc aggctagctg gctctccgcc 60
tgctccgcac cccggcgagg ttccggtggg gaggggtagg gatggttcag ccccgccccg 120
ctagggcggg gcctgcgcct gcgcgctcag cggccgggcg tgtaacccac gggtgcgcgc 180
ccacgaccgc cagactcgag cagtctctgg aacacgctgc ggggctcccg ggcctgagcc 240
aggtctgttc tccacgcagg tgttccgcgc gccccgttca gccatgtcgt ccggcatcca 300
tgtagcgctg gtgactggag gcaacaaggg catcggcttg gccatcgtgc gcgacctgtg 360
ccggctgttc tcgggggacg tggtgctcac ggcgcgggac gtgacgcggg gccaggcggc 420
cgtacagcag ctgcaggcgg agggcctgag cccgcgcttc caccagctgg acatcgacga 480
tctgcagagc atccgcgccc 500

<210> SEQ ID NO 204
<211> LENGTH: 1500
<212> TYPE: DNA
<213> ORGANISM: Homo sapiens

<400> SEQUENCE: 204
aaacgtttaa aatatatttc taaacagaat gggccaattc agtcacagta actgttgatc 60
tccatagcag agcaacccac aaagacagaa ctgatttttt tcccataatc aggggtgaaa 120
aatatacaac ttgtttctga accaaaacca caatttctgc agtttaaaat gtttcactgc 180
taatatggcc ctggtagaaa ttatgtagtt tcttttcttc tttaaaaaaa aaaaaaatta 240
aaaaaatttc ctaagacact aaatgctcca tctggaatgt agattctgat cacaaagcag 300
ctcagttaac ctaaaaaata aaaaattccc atcacctgtc tcagtagggc ctgagagtag 360
tgtggggaac cccagctttg gtatggagag tcatggcccc ttgaaccaga tagagacctt 420
gaatagccat agctggtgct tctctcagga taaactctga tgtaggaagt atcaccctca 480
tgagagtgga atttggtcat ccagttgacg cagggcatat tccatgtctt cttttctgag 540
acacccaacc atccccactc catccttctg cacatccgtg taacaggcat ccccagcttc 600
tcgcgtgtga tccttcaggt cctgccagct gcctgatgga agaagtccat ttcttccata 660
aatagcatcc tctgcatctc gagggtcctc gaagcgcacg gaggcgaagg gcacaaggcc 720
gtaccggctc ttgagctcga tctcgcggat gcggctgtac ttgtagaaca ggtcctgcgg 780
ctccttctcg cgcacgtggg tcggaaggtt tccccacgta gatgcacccg tcgccctccc 840
agccgcgctc gtgtccgccc agccggacaa ccgcaccgcc cgacgctgct ggccagccgc 900
agcccgcatc cgcccgtatc gccgccgctg ccgcctcagc acggctgccc ccgcagcgtc 960
tgttttgttt tattctaaca gggtctctct ctgtcgccca ggctggagtg cagtggcgtg 1020
atcttggctc cctgcaacct ctgcctcccg ggttcaagcg attcacctgc ctcagcctcc 1080
caagtagtgg gcattatagg tgccagctaa ccatggccgg ctaatttttt tttttttttt 1140
tttttttttt tgagacagag tcttgctctg tcacccaggc tggagtgcag tggcgcgatc 1200
tcggctccct gcaacctccg cctcctgggt tcaagcgatt ctcctgcctc agcctcctga 1260
gtagctggga ttacagctat gtacagcgat gtctgcaaag atagggattt aacagcactc 1320
atatcttcat gttcataaaa aagtcctaca cgcgtgatgt acgtctagat ctttcctttt 1380
gtcacaggat atagcacggt agttacggat atagtctccg cagtgcctgg gtttgactca 1440
gcttccccac gtactgtcct gcgcatattt tgtgtctcag tttcctcatc tttaaggtag 1500

<210> SEQ ID NO 205

<211> LENGTH: 17000
<212> TYPE: DNA
<213> ORGANISM: Homo sapiens

<400> SEQUENCE: 205
cacgcgcccc ggcctggctg gaggggccaa cccagcgggg cccgcctgcc cgccggcctt 60
tctgtaactt tctctcttta aacttccaat gaatgaacgt gcctcttctt acggatttgt 120
ttagattagg gaatagattc ctcgctgata gcgttgcttt gcaaataaga cctcctatat 180
tattcaaacc aaacgagttt gtgtctttaa aggactatag cagccccatt ctatgttaag 240
ggttggctat tacaattatt atatgcttag ggaaaaaatg taagccccgt agtttgtgct 300
tttcttgatg tacagaaagg tttatcttag gtggataggt tttgttttgt ttcttaaatg 360
ggattttttt ggttcgtgtc tttgaagggc tgtttcgcga cgtcattaat gaactaatcg 420
gttttcagat ttcaagacgg tgtgtaattg atgtaaccac tgaggaattt cagtgcacac 480
cagactaaga ctcttccagc gcaggggatt ccagatgctt cttgggccct ctggaagcca 540
tggggatgtt tccagaccga aaggagggct ttgctgggga gcagatgtgc tgcctctccc 600
cgacccagga ttttgaggcc atgtttccgt taatctggac cgagagccct ctgggagagg 660
gaggcaggtc gtagggggcg ggggtgaggg ggagcgagat gaggtcgtcg ctggacgctg 720
ggctcccttg tcgttgtcct tttccccaga atccatggtc aggcctaggg agccacccct 780
gggtgctcga gatgagtccc caccctcact gaaggtcggt cactggatgt ttgtgtgcat 840
cgtaaggggc ccaccgaagt cccgaagcct tctcagggac cagcgagaaa gaggagcagg 900
cttgggagac agggaaggaa aatgcagggg aaagggctca cccctcgacc ccaggtaaaa 960
ttagaaggaa cgtgtggcaa cccaggtgca gctttggtcg ctcgctcaag gactttgcta 1020
gtcactacca ttaattaatt aatcactatc attaactacc aaggacaccg tttttattcc 1080
cctaaaagcg tcaccttgag gggaatggag aattgggcag cagctatgca aatcctggga 1140
caggagacac tgcctgagga ccctctctca ctcccaatcc cagaacccga agttatcccc 1200
gacaaccaag tccaagcaca tgaaccaaga cgatcagctt caggcagctc cttaccccca 1260
caagcggccc aggaggtggg cattatcccc cacccctggg atttctccat ccctccctct 1320
tctctcctgc gggagagaga gctgtggtca cccagttggg cgcgatggct ctggactaat 1380
ggggtctcta gacccagggc acaaaggcca atctgccagg ggttactgca tgtaatgaga 1440
taatcagaca tgttgaccaa cctaaaagaa aagactctcc cagggagtaa ctcccagtga 1500
aataatttat taaaaaaagc aaaaaagaga cataaatttc tctctactac ttgaggaaac 1560
agcaaacaga acgaattagg gtcttggcct ctgcaggaat aaattatttc cgacttggtc 1620
tggatacctg taattatttg taagctgtgg gtagtaatac tgtaattgtc cccgggtcct 1680
ttctggaagt agcaatgacc ccaaggacaa ttggtgacgt ctccacaggg tttacacatg 1740
gaaaggagtg aaaaatcgag gaattctttc agatagccca gaccaaaaat cctctcagcc 1800
atgaaaaggt catatatgtg atgctgggcc aagcggactt ttctggagta accatatcat 1860
aactgattgc ggatgtagac aagagcgtat aaaccaaata ggcttgaatc aacgcagtcc 1920
tggattttct gttgcctctg cttgctgggg cagtggaagt tcttaaactc cacttcagag 1980
gttggaaatt cttccccctc ccccacctcc ttagtgacaa ggtctctgat ctcctgctgc 2040
cactgcaata gcctctccca tcccgcgggg aacggccgga gttcttccct tgatctctcc 2100
cgagtcggct tccgctgggg atggatcgca ggtaggcgcc ggcgcggcct ggggaagaac 2160
agttgcggag catctgaagc ggaaaatcca agcagatgtg aggcgatccg ggcccgcctc 2220

```
gttcctcttg gggcctgaat ttcttccaga taagtttcct aatggaacat ttctaagagg   2280
tggggtacga ggcggcttgc tcgcacgcgc agtgggacag actgcgggtg gggacgtact   2340
gagaggtccg gacctcaatg cgtccgaccc gtctccacac cgcccttttc cagcccccag   2400
tctcctttca ttccctactc ttcaggctcc tttggggcca gtgggtgaac cgccatttag   2460
aacggtgcct cggactcggg ggtcgtgcgc tccatctctg cctcccccct ggggcccgcg   2520
aggctggtcc gggctttctg agctgggcgt tcggctttag gcccaatacc tggaccagga   2580
atttcttctc cccgcgccag aagggaaaga cataggaggt gtcccaatct gcggtcaccg   2640
ccgatgctcc tgaccactct agtgagcacc tgcccggtac ttttccattc caacagagct   2700
tccagcttca tactaactat cccacatacg gcctgtgggt attagctcta agtgtccttt   2760
tccgagggcc cgaggctccc cctccagcag ggagagctcc gggacggccc ccaccaaggg   2820
ttgggtttct tccttcacaa ttccacagag gcatccctgt ccttcctacc tgggaaacct   2880
cgaggtgcgg tgcccgtgta cttctggtac tttgcgtggt gccatcaggg accccagagc   2940
cacagctgcg tgtgtgtgtg gatgtgtgtg tgtgtgtgcg cgcgcgcgcg tgtacggcga   3000
aaggatgtgc ttgggggagc cgagtacaca acgtctgctt gggcagctgc tgggcaggcg   3060
ttgggcctgg aggtatctca cacccacgta tcttccagtc ttcaaacacg gcattgctct   3120
gcctcccgta gcgcgcttcg aacctgcctc gcggacacgt gaacagaggc tgtccctggg   3180
aagataagtg cgctttcccg taaaatccgg gaaatttgcc ttgaggaaag tttccgttct   3240
tgttacttgt cgggtttctc ccacttccac ttagccatgt ttctgcgatc tgggtaatcc   3300
ctttcaagcc caggaggaat tctcccgggt ccataattga gggtcggaag ccgtgggggt   3360
gagaaacgca ttaaatcctc ccgaagccca ggaggtgcca gagcgggctc agggggccgc   3420
ctgcggaagc tgcggcaggg gctgggtccg tagcctctaa ccccttggag ctccttctcc   3480
cagaggcccg gagccggcag ctgtcagcgc agccaggagc gggatcctgg gcgcggaggt   3540
gggtccgact cgccaggctt gggcattgga gacccgcgcc gctagcccat ggccctctgc   3600
tcaagccgct gcaacaggaa agcgctcctg gatccgaaac cccaaaggaa agcgctgtta   3660
ctctgtgcgt ccggctcgcg tggcgtcgcg gtttcggagc accaagcctg cgagccctgg   3720
ccacgatgtg gactccgcaa ggggctaggg acaggcaggg ggagagcccg ggtttgcgca   3780
caccttccag cccctggagg gagcctgctc ggcttcgaac gccttcgaac ttttgacctt   3840
caaaggagtc cctggaaaag gtcaggagcg cctgctgcag gcacggttgc cgaaggccag   3900
gccttcctgg cgcaggggag ggccagggga gggaagcgga tactcagtcg ctgtccgacg   3960
gcgagttttc ggagcagcag gctcatgatc ccgggccagt ggcgagagca gtgacaccga   4020
gaacccaaat ctccgcgccc ccatccgcgg cccggtgtcc tcccggcccc tgctgacctc   4080
caggtcacgc accccactgc tccacggctc tgcagcctgt ggcacacggc cgagagtccc   4140
cacatgatct cgacgccaag gtaaggaatt gccctgcgtc ctctgagcct gtctctggcc   4200
tggggggccg ggaaagctgc actcctggaa gaggtggggt tatgtgaccg ccgctgcagg   4260
ggtgcgcgga ggactcctgg gccgcacacc catttccagg ctgcgggagc cggacagggg   4320
agggcagagg ggggacaaaa ggactcttta ggtccaaaat gaccctgaag gagagtccag   4380
aatgcccagt ggccgcgtct gcaacggagt cttctttctc caattgcctt ctgccccatc   4440
accatgggcc ccacctgcgc cacctgcgcc caccctgtga ccctggctca gcgaccttgg   4500
cccttaatcg cccaacgccg attcctcaaa attccggctg cgctgaatcg ggctgctttt   4560
```

gccgccgccc cggcagttgg gccctgtttc cgccggcgcc ctgggagagg cctcaccact 4620
cggctgggct ccctggcccc tcccttcccc tggcctgagc gcccctgcgg cctcccgctc 4680
ctcctgagaa ggcgacaatc tctttgcacc ttagtgtttc gaggacagaa agggcagaag 4740
ggtcacttcg gagccactcg cgccgttttc acgtgtgtgt gtaatggggg gagggggct 4800 cccggctttc cccttttcag ctcttggacc tgcaacaccg ggagggcgag gacgcgggac 4860
cagcgcaccc tcggaaggct cgatcctccc cggcagggcg cctggccaac gagtcgcgcc 4920
gcctcctctc ggccgcgcct gctggtgacc ttcccgagag ccacaggggc ggcctcggca 4980
cccctccttc cctcgccctc cctgccgccc atcctagctc cggggtccgg cgaccggcgc 5040
tcaggagcgg gtccccgcgg cgcgccgtgt gcactcaccg cgacttcccc gaacccggga 5100
gcgcgcgggt ctctcccggg agagtccctg gaggcagcga cgcggaggcg cgcctgtgac 5160
tccagggccg cggcggggtc ggaggcaaga ttcgccgccc ccgcccccgc cgcggtccct 5220 ccccctccc gctccccct ccgggaccca ggcggccagt gctccgcccg aaggcgggtc 5280
tgccataaac aaacgcggct cggccgcacg tggacagcgg aggtgctgcg cctagccaca 5340
catcgcgggc tccggcgctg cgtctccagg cacagggagc cgccaggaag ggcaggagag 5400
cgcgcccggg ccagggcccg gccccagccg cctgcgactc gctcccctcc gctgggctcc 5460
cgctccatgg ctccgcggcc accgccgccc ctgtcgccct ccggtccgga ggggccttgc 5520
cgcagccggt tcgagcactc gacgaaggag taagcagcgc ctccgcctcc gcgccggccg 5580
cccccacccc ccaggaaggc cgaggcagga gaggcaggag ggaggaaaca ggagcgagca 5640
ggaacggggc tccggttgct gcaggacggt ccagcccgga ggaggctgcg ctccgggcag 5700
cggcgggcgg cgccgccggg ttgctcggag ctcaggcccg gcggctgcgg ggaggcgtct 5760
cggaaccccg ggaggccccc cgcacctgcc cgcggcccac tccgcggact cacctggctc 5820
ccggctcccc cttccccatc cccgccgccg cagcccgagc ggggctccgc gggcctggag 5880
cacggccggg tctaatatgc ccggagccga ggcgcgatga aggagaagtc caagaatgcg 5940
gccaagacca ggagggagaa ggaaaatggc gagttttacg agcttgccaa gctgctcccg 6000
ctgccgtcgg ccatcacttc gcagctggac aaagcgtcca tcatccgcct caccacgagc 6060
tacctgaaga tgcgcgccgt cttccccgaa ggtgaggcct caggtgggcg gccggggacg 6120
ctggggagcc cggcggcccc ggcccaggcg ggaagcgcaa gccagcccgc ccagaggggt 6180
tgccgcggcc tggcgtccag agctggggcg tctgagggag gttgcgtgag ggtcttcggc 6240
ttcggcgctg gcttggggcg aggggccagg gccttggcgg cccaggcgac caaaccctct 6300
cctggtccag ggctgggtga gggcgaatta cgaattgttc caggggcagg cagtccccca 6360
gcccgcacgg ccagcgagtt ctttctggtt ttgttctttc tccctttcct ccttccttcc 6420
ttcgccagtg cattctggtt tggtttggat ttttttctct ctttctttcc tttctttctt 6480
tctttctctt tctttttctt tctttcttcc tctttctttc attctcccct tccttccttc 6540
cttggccccc tctctccctc cctccttcct tccttccttt gccaatgcat tggtttgttt 6600
tctttccttt tctgctttcc ttcctttctt tggaagttca ctctggtttt gctttctttc 6660
tttccccatc ccttcctttc tttatccctc cttcccttcc tccttttctt tctacgattc 6720
cctttatttt tccttcattc ctccctcttt ttgtctcttc tggaggaggt gaaggagggt 6780
cagcttcagg cgctgcgagt cagcggggat cacggtgagg cccaagcact gcaggctgag 6840
gccacagagc gaacacttgt gctgagccgg gccctctcgt gaggctgggg tgcgggaagt 6900
ccgggcagga gagacccgcc cccgccgttg ctgagctgag acccggctga aagagagggg 6960
tccgattaat tcgaaaatgg cagacagagc tgagcgctgc cgttcttttc aggattgaaa 7020
atgtgccagt gggccagggg cgctgggacc cgcggtgcgg aagactcgga acaggaagaa 7080
atagtggcgc gctgggtggg ctgccccgcc gcccacgccg gttgccgctg gtgacagtgg 7140
ctgcccggcc aggcacctcc gagcagcagg tctgagcgtt tttggcgtcc caagcgttcc 7200
gggccgcgtc ttccagagcc tctgctccca gcggggtcgc tgcggcctgg cccgaaggat 7260
ttgactcttt gctgggaggc gcgctgctca gggttctggt gggtcctctg ggcccaggag 7320
ctgggagggc tgcgccggcc tctggagccc cgggagccag tgccgaggta gggagacaac 7380
ttccgccgca gggcgccgga cggtcggggc agagcaggcg acaggtgtcc ctaggccgca 7440
gggcgcttcc atagcgccat ccccaccagg cactctactc gaaatcggaa agctcgacct 7500
tttgcgttcg cctctgccaa gcctgttatt tgtgctggcc gctgggtctg gagctgcgct 7560
tctcggcccc tccccggtgg agcgcagagg gctggtctgc aagcgcggcc tccagccccg 7620
cggctccccg gcccaggagc caggcgcggg ctgacccggg agcacccggc agcggagggg 7680
gctggaagcg gaccctaggc ctctcctgtg ccacccggcc ctaccgcgcg gccgcggggc 7740
gctctcctct cgggcgcagc ggtccttcag cccagggcag gttcctccct ttcctactcg 7800
gaacgtggca aagataccc agtcccagcc cctccagctg agagctgttg cccaaggtcg 7860
tcgctacttg tccgctcaat ggtgacccct tggcagagaa ctagggatga ttccactccg 7920
gttgatgttt taggggaaat taaaagaaca ttcggttttc tgagtctcct tccggggagg 7980
cgtggtggta actggtttgc tgggaagagc cgttccttaa ccgcatgcaa caaagcaggt 8040
gtggaatccg gacgagaggg cactcactgc cttctgcccc ctttggaaat agaaaaagcc 8100
ttcgaagcag caatccaaag atcaaatgat ttgcggtcaa tgatttcaat taaaccagaa 8160
attagtaagg gagggccgag aagacacggc tgctcagaag ctgttcgctg tttgagggat 8220
ttcccggaga gcctgttaaa agatgcgaag tggtgggtgt accgctcagc cacctttaaa 8280
ccggctctgt gcgttctggc tctggaaagc aagtctccag gcatttgggc tcagaattgc 8340
tgggccccga gtttgggcgg gggtggtcct tctgggggtc aggccttgag cagcttgcac 8400
tggtggcagg tttgggagca gttgaggggc ttcctgtgtg tcttttggag ggggtgaccc 8460
tggaagttgg cactctggaa gggagctgtt tggccctaga gttttggaaa gggccctgaa 8520
cctgttcggt ccccctcgga aagggaaggg agcagtggct tagtccctcc ctcctccatt 8580
cgtgcaatgc ctggggtagg ggtagacctg gagccggtgg actcatatcc ttggaattcg 8640
tcaggacagc tgctccgggg ccttggccct cagtcagtct ggggctgagg agtagggaag 8700
ctgggaactt ggggcagagg aagaagatgc gtttagaaag acctccatta tgcaaactgg 8760
agtccattta tgcaaactgg tcacccttcc agtagctcca aagagtggca gtggagtggc 8820
atcttgattg atttaacctc ttctcagggg acctgggtct gcgagggagg atatggctgc 8880
ggggttggaa taggatctgt ctgagctgcc agggtcaggg tggtggccct agggaggttt 8940
tagggccagg gtggtcccgg gctgtggcag gggctctcag atcgcctcgg gctctcagct 9000
gcaaggtgaa aaataccatg aggaattgat ctgccaaggg cggtcttgtc tcaaagcaag 9060
tggattgctg gggtaaagaa tctagagacc agcttaggac tctgggagga agaaaaaaaa 9120
aaaaagaata gcatagtcct aaggaactgc aaggatcacc agattaaccc ttcatacctg 9180
gggaaattaa ggccagacat gacacaggcc tttcccaagg ctctgtagca agggcaatag 9240
caggccagtt gctgccactg cggtcctgtg gggcatgttc tcactccact gcacccagga 9300
ggctgccagc ctctgttcct tttaacatag atctcctcag ttgttaagac agaaagagga 9360
actcagaggg gtccctgtgt gcaaggcaga gggagaccac cagaaccagg gtaagcaccc 9420
cacttggtag ccagttcaag gacttgggga tgttttcaac atttacagcg aggtttgagg 9480
ccccattgtc atgcagcgct actcggcctt ggtctcctta tctgtaaaat gggcccatta 9540
gcaatgcaca gggttgctgt gatgaagggt gaggtcccac aagcaaaagc tgtgcagtga 9600
ggggggaatc ctaagcattg ttcctatgcc attcacccct tcctgtgagc tccccatatt 9660
ccctggctca aaggagtctt gaatggcagg gatggaggac tcactgcctg gactttgaag 9720
acccctgctt tctgggtgac caccttttct tccctttgac agtgaactaa tacattggag 9780
gtagatagtg ctgggaagag gacaggagac cacggctgac tttggacatg ggctcgaaat 9840
tgataacttg atgagtcttg gagggtggtt aagataagct cggggctggg gcagcgctga 9900
ggtctgatgg tcagccagcc ctccccaaag tgtggccctc cgttctggag ataggggctt 9960
tggaaactgc aaaagcgtcc tggcaggcca gctctggttg ctccctggcc atagctgctc 10020
tgactacagg cagcaggacg caggtcggcc tctgcccatc ggaggtcaga ggcagggcct 10080
ccagcaccag actcagcagt gccactgcaa acctggcaca acaggctggt cccaggactc 10140
agctcagcag tgaagttgga aaccaaggtt gagtctcccc atctcccttt ccccaacccg 10200
aaagacccaa gatgggtgtg ggtgaaagag ggagaaagaa ttgctactcc agaaactgtc 10260
atttgcccac acgaaacgag gtggggttca aggtctgaac tcttccagtg cctgggtgcc 10320
tttgggttta aattcagctg caggtgcccc catcaccact tccacctgag cacaccacga 10380
gaagccaggt tatcttagaa actgtttccc ggaatcaaag cgacttgatt tggagagttg 10440
ggtgaggaga aactcacccc tatacccctc agggcgtcag agatgtgagg caattctcta 10500
cctccgctgg aaaaaatgca gatttattaa aggtcgactg tttagcagaa caacgtagat 10560
tttttacaac gctttccccg tctctgcttt gaagcctgcc aggctgcagc tggggatcca 10620
ggagggaaag cccgcaggcg cagaggggac aatccgggaa gtggtaaagg ggacacccgg 10680
gcacagggcc tgtgctttcg ttgcaggcga ggaagtggag cgcgcgctgc agattcagcg 10740
cggggctaga ggaggggacc tggatccctg aaccccgggg cggaaaggga gcctccgggc 10800
ggctgtgggt gccgcgctcc tcggagccag cagctgctgg ggcggcgtcc gaactcccca 10860
ggtctgcgca cggcaatggg ggcaccgggc cttctgtctg tcctcagaat acgtaggata 10920
cccgcgggcg acaagccggg ccaggctagg agcctccttc cctgcccctc cccatcggcc 10980
gcgggaggct ttcttggggc gtccccacga ccaccccctt ctcacccggt ccccagtttg 11040
gaaaaaggcg caagaagcgg gcttttcagg gaccccgggg agaacacgag ggctccgacg 11100
cgggagaagg attgaagcgt gcagaggcgc cccaaattgc gacaatttac tgggatcctt 11160
ttgtggggaa aggaggctta gaggctcaag ctataggctg tcctagagca actaggcgag 11220
aacctggccc caaactccct ccttacgccc tggcacaggt tcccggcgac tggtgttccc 11280
aagggagccc cctgagccta ccgcccttgc agggggtcgt gctgcggctt ctgggtcata 11340
aacgccgagg tcgggggtgg cggagctgta gaggctgccc gcgcagaaag ctccaggatc 11400
ccaatatgtg cttgcgtgga gcagggagcg gaagaggcag ccggtcctca ccctcctctc 11460
ccgccacgca catatccttc ttgacttcga agtggtttgc aatccgaaag tgagaccttg 11520
agtcctcaga tggccggcaa cgcgccgagg tcacgctccc cagaaacacc cctctcccct 11580
cccctacccc agctccccct ggggcgggtg gtaattgggg gaggagaggc cgcaggcagg 11640
gaaggggtgg gaaagccaga gagggaggca caaagtgatg gcagcccggc aaacactggg 11700
gcttcgggct gggccgcgct cgtttaatcc cacaaaaatc ccattttgga ggtgagaaat 11760
agaggttaga ggtcgggccc ttctggagat cagaccgagg agacgggccc agctggcgtc 11820
ttaaagcaag gagggggagt cgggaggagg tgagacccct gcacccaggt ggggctccca 11880
aaccgttctg gatttaccac actcccaggt ccgattttcc atggagggct ggggttaggg 11940
actggcacct tcttgttgtt aaccgcattt gatattcaca agaaccctgt gaggagactt 12000
tgtcaccgtt tttagatgcc tgaggttgcc ggaggggcag tgagagaatc gtctaacctg 12060
gtgttcctac cacagtccag gccctgtgtc ctgggctgga cccacagccc ctgccaccac 12120
ccagaggaag gcgcgaagct ggctgcctcc tttacgggtc tcccttaggt gccctcatga 12180
agggggacgg ccacctcaca gtgcaggaac tatctccccg tttgctccca aatagtcttc 12240
ttggtgtggt gctgtctatg gtctgtgacc tgcatctgga gttacccccca ggaccagctt 12300 cggaagagga gggatcgctt ggaggccgtg cagtgtgagg aacggcaggc agggtgtggg 12360
accaacatgc acacactcgc aggtgctggg gccagggagg aatgaggcgc tggctccctt 12420
tccctccatt tctccctggg ggtcccagca acctggccat ccctgacttc caacagcaca 12480
gcgtccccac aggtcctgca gtgctctgca ggggtgcagg gagctcccct ccccccagcc 12540
gcaacctcac cttcctcacc cccacccctc cggcaggaaa ccacaggctg ggttggggac 12600
ccctggtgct ccaagagagc agtgagtgct gggagccgct aaccccgagg cgcctagcac 12660
agactcttct cacccccttat ttctgaaata aagcccttcc ttaggtccag atgaggacca 12720
cgtgctcagt gcctcacttt cgtgggagtg tatatcactt tacagtatca agacaatttt 12780
ctttcgttac aaatctttat ttagtctctg cgtttagacc aaagtagatt tttatgggct 12840
gagtgaaaaa acctcgcccg cattggtttc tgatggaaca gctggcagcg ccacggcccc 12900
gggtggggtg gcctagaggc aggggtgctt gggaggaaca tctagcaccc gaccacctcc 12960
accaggtggg aaagggacgt ttgcaccaaa tctccgccgg caaagcagag gctttgggga 13020
attacagaaa aactataatg atctaaaaga gaacaagtta tcttgaactg tgcgggtatt 13080
tgaatcatac agaaaattgt cctgtgtgcc caatgcactt ttgcatgtag agccagggcc 13140
ttcgaggaag ctttcaggag atcccgggca gcggagtctg gtctggagtt tcatttccgt 13200
aggtgcagat ttctccccaa gtcttcccgc catgggcttt gcaagaagcc agggcccaga 13260
ggccacgctc accgttaaca ctgcacaggg caaaggtggc tccaggacaa ctgcccaacc 13320
ccaggaacga cccagcagca gagaaaagga cagctgccag ggtgcctttg tcgctttttg 13380
gaaatcagaa ttcctgggtc cttagttaag tcttacttca ccaaatccca ggaccttcac 13440
attttggttc ttgccattgc taacagttgt aaatgctgcc gccacgaggc ctgggaggaa 13500
ggacccgctg gtgagagcac agggagtgct gctgtgatca cggtggtgat gcggggtgag 13560
cgcgatttcc cgggattaaa aagccaccgc tgccccccgtg gtggaggctg ggggcccccg 13620
aataatgagc tgtgattgta ttcccgggat cgtgtatgtg gaaattagcc acctcctcag 13680
ccaggataag cccctaattc cttgagccca ggaggagaaa ttaaaggtca tccctttttta 13740 aattgaggaa tagtggtttt ttttaacttt ttttttttta ggtttttagt tgccgaatag 13800
ggaagggttt gcgaagccgc tgccctgggc cgaggtgcat tttacgcttc cagaggtcga 13860
ggcctccaga gaccgcgatg cccagggcgt tcccggggag gctgagagac ccagggtgct 13920
ctgggtgact gcacggcgac tcctcgggaa cccactcgtg gctgcccgct tggaagggct 13980
ttgcggcccc gggaacgatc tccaggatct ccacggctgg tcaggttccc cgtccctcgt 14040

-continued

```
atcccgcgct gcccgggggc tcctgccttt ggttcagtgc tcgcggcacc accgcactca  14100
ggacggcagt ggggggctgg ggctggggct gggcctggcc cagcgtgggt tggggcgggg  14160
gacgcgccag cagcgcccgc agctcgctcc gcaggggtcg cagccagggg tcgggagcta  14220
ggctcgtggg ccgggagacg ccgggcgcgt tgtcctccgg ggaggttggg gtgcaggcgg  14280
tgcaccgacc ctcgccatct ggcgctgcag ccaccagcca cggcgcttag tggagggtct  14340
gcggccaggc tcccggcgga aagattccgg ggagggctcg gggttgtcc cagcccgcgc  14400
taagcgccgc agcctcgccc ggctttcctg cttcctcgga ctgtgcaggg gaagcctggg  14460
gtctcgcggg gcgcagcagt caggtcgagg gtgcagcagg aggggagtcc tgacgggcag  14520
gtccctcttt cccctggtgc gcaacactgg ttggtagctt ttgcggaggt ggtgaagaag  14580
ggcaggaggc ctgttgagcg gaggagtccg ggatccccta attatgtgac aggagaccct  14640
ttccagttcg gcctgtggcc catccctctc tcaccgccgg cagattggag tctgctctcg  14700
gggagccccc aggtaaaccc ctcacaggga gaaggtttcg gattggaagg aggaccgcgc  14760
tcgtggggcg cctgtgagag ctgggaagcc caaggggtag cgtgtagggg gttttttatg  14820
cgggaggagc tgcctcctgg gcggcgggga ctttctgtct cagcctgtct gcctttggga  14880
aaacaaggag ttgccggaga agcagggaaa gaaaggaggg agggaaggag ggtccttggg  14940
ggaatatttg cgggtcaaat cgatatcccc gtttggccac gagaatggcg atttcaaagc  15000
agattagatt actttgtggc atttcaaata aaacggcaat ttcagggcca tgagcacgtg  15060
ggcgacccgc gggagctgtg ggcctggcag gctcgcacag gcgcccgggc tgccggccgc  15120
tgcggggatt tctcccccag ccttttcttt ttaacagagg gcaaaggggc gacggcgaga  15180
gcacagatgg cggctgcgga gccggggagg cggcggggag acgcgcggga ctcgtgggga  15240
gggctggcag ggtgcagggg ttccgcgtga cctgcccggc tcccaggcat cgggctgggc  15300
gctgcagttt accgatttgc tttcgtccct cgtccaggtt taggagacgc gtggggacag  15360
ccgagccgcg ccgggcccct ggacggcgtc gccaaggagc tgggatcgca cttgctgcag  15420
gtagagcggc ctcgccgggg gaggagcgca gccgccgcag gctcccttcc caccccgcca  15480
ccccagcctc caggcgtccc ttccccagga gcgccaggca gatccagagg ctgccggggg  15540
ctggggatgg ggtggtcccc actgcggagg gatggacgct tagcatgtcg gatgcggcct  15600
gcggccaacc ctaccctaac cctacgtctg cccccacacc ccgccgaagg ccccaggact  15660
ccccaggcca cctgagacct acgccagggg cgcctcccga gcgtggtcaa gtgctttcca  15720
atctcacttc cctcagcagg ttccacccag cgcttgctct gtgccaggcg ccagggctgg  15780
agcagcagaa atgattgggc tgctctgagc tctgaagcat tcggccgctg tgtgtgtgca  15840
aggggcgcaa ggacggagag acagcatcaa taatacaata ttaacaggag cacttgtcca  15900
gagcttactg caagccacat tcagttccgg accttattga cttccccctc ccatctagag  15960
tggattctgg tttttcaatt tgttttgttt tgttttttgt ttgtttgttt gtttttgaga  16020
cggagtctca ctctgtggcc caggctagag tgcaatggcg cgatctcggc tcactccaac  16080
ctccgcctcc cgggttcaag cgattctccc gcttcagcct ccccgagtagc caggattgca  16140
ggcacccgcc atcatgcctg gctaattttt gtagagacag ggtttcaccc aggctggtct  16200
cgatctcctg acctccgatg atccgcccac ctcagccttc caaagtgttg ggattacagg  16260
cgtgagccaa cgcgtcctgc cttgattctg tttttaactc catttttttag aggaggaaat  16320
tgaggcacag agaggttaaa taacatgtct aaggtcacac agcaaggggt ggagcggagt  16380
tagcccactg gcctagctct agagcccacc cggataacca gaacttggtg aggcctccgg  16440
```

-continued

```
gctcttgctt ggtttggagc caggtgctta gcgccccgag cccggggcca ttcaccctgc  16500

aggagctgca cgcgcccctg acctcggctt ttccctggca gcagaggggc tttgcgggtc  16560

ggccgggtag ccctgagcac agctcgccac ttccaggtgg gctgttggcg ctggctgggg  16620

acacatcccg atctttcaaa tgccctttac agagcctcat caacgacccg attcattccc  16680

ccctcctgtc atttgtctct gccatcgaaa aatgcctacc gagagctgct ctgcatttcc  16740

gccctctatt ttgtgtttta ctttaaaata ataataaaaa aaatgttggc tgcaggacgc  16800

catgacttag gtcagcgagt cagccgctag ctctgcattt ccaaaaagca gatcttttca  16860

caactctctt gccccaagtg ccctggtgtg gtttattttt taaaatgcat gcctgcggaa  16920

gagaagaccc ggggaatatt cgaaaccccg agcttttaca acataaagcg catggtgtgg  16980

ccgcggcgag taatggcgct                                              17000
```

<210> SEQ ID NO 206
<211> LENGTH: 1500
<212> TYPE: DNA
<213> ORGANISM: Homo sapiens

<400> SEQUENCE: 206

```
caaatcactt gaactcaagt tcaagaccag cctgggcaac atggtgaaac cacatctcta     60

caaaagtaaa gaaaattagc caggcatggt gctgtgtgcc tgtagttcca gctactcctg    120

gggaggtcga ggctgcagtg agccgcaatc acgccacttg tactccagcc tgggcgacag    180

agcaagtccc catctcaaaa aaaaaaaaaa aaaaaaaaaa aaaaggctgg gtgtggtggt    240

cccagatact cagaggctga aaagggagga ttgcttgagc ccaggagttc aaggctgcag    300

tgagctgcga tcacatcaat gcactccatc cagcctgagc aatggagtga gaccctgact    360

atatttaaaa aaaaaaaaaa taggaagaaa caactcaacc acagggctag tatgttactc    420

ggttataaaa tgataaagcc ctaaacagag aattagcccg tttccagaag aggccaagaa    480

cagatgatac agctgaactg aactcctgcc tgtacagctc gttttctaca agattccaga    540

cctggaagat gatggcatcc agccccccatt gaagcacctc gaacaagaaa aacgccgagt    600

ccgaagagcc aggccttgaa cacacgattc ctgtctataa ataactcccc ctggggaata    660

aaaagcagga tccaaggcag gaaacccgag ccgtggaatc tggtaagttc ttaggaaacc    720

cactcacggg cctgagtccc ccgtggaagc ggcgacttcg gcacctggac acccgagtcc    780

ccagagcccc gggcggccgc gcgtccctac ctgcaggcct gataccggcc gcggagcgct    840

cctggccccg ctcccgccag gctccgggac cgctgaaacg cacccagggg ggtgaaggcg    900

tagtcgccaa ggacagcgca gatggcagcg gaggcatggg agccggaacc taccgtggca    960

aagggccagg tcgggacgcc cctcggcgca gccccaaatc ctgcccgcgc cccagccccg   1020

ctcaggccgc gcccctgcca cctctggcca cacgggctga gacgtctggc tcctgcacag   1080

cgcacttccc gctgcccttc tccactggct gctcaggccc tgcctcgcca gcacggcatc   1140

cgcgggggat ccctacctgt cctttagggc ttgcctcata ggtcaaacgt cacctcccag   1200

ggaggtatgg cctgcccccct ggccaggtgg gccccttcca cgctcgcctg caacaccacc   1260

cacccacctt gataactgct tgtaaaggtt gtactgcttt ccccccttgag actgcaaacc   1320

ttcaagggca ggaaatgggt ctgttttcct ggcaaaataa tgaagttggc ttaaggtttt   1380

gctgaataaa atgagtgaca gacaaaagta gccaaatttg gcactcctga tgggttattt   1440

gatgaaggag gtgcaatgta tggcttaac tagttattct ggatttcttt ccccatgtta   1500
```

<210> SEQ ID NO 207
<211> LENGTH: 200
<212> TYPE: DNA
<213> ORGANISM: Homo sapiens

<400> SEQUENCE: 207

```
caaggccggt gcacgcggac ccgaggattc ggtagatgtc cccgaagacc cgctgccgct     60

ctaaggcggt ggaagcgaga ttctccggaa acccagggaa tccgatgctc gcacaggacc    120

aaagcccgag gccgcgggga ccacagaggg acggagaagc cgggactcct cacatcccac    180

atccggcagg ggaagcccag                                                200
```

<210> SEQ ID NO 208
<211> LENGTH: 2000
<212> TYPE: DNA
<213> ORGANISM: Homo sapiens

<400> SEQUENCE: 208

```
ctgataataa agttttacca ttttataatt taaaaatgta aatatggagt tgggcatggt     60

ggttgggagg ctgagaccag aagatcgctt gagcccaggg gtttgagacc agcctgggca    120

acatgcagaa accctgtctc tacaaataaa aaattagcca agcgtggtag cacgcacctg    180

taatcccagc tactcgggag gctgaggcag gagaatcgct tgagcctggg aggtggaggc    240

tgcagtgagc tgagactgta ccactgcact ccagcctggg tgacagagtg aggctctgtc    300

tcaaaaaaac aaaacacaaa aaaacaaaca aaaaaaagca aatatatgta aaaataggaa    360

gtgcggtttc ccaaaatgag gtctgtaaac aactgatcta gaaaatgttc tggaaaaagt    420

aaaaaaggat caggatctga ggtcaactga cctctccctg cgctctggac aggcaaacag    480

gcaaggttcc ctctgaggcc gtagcggctt ctcgtgggcg agtccctgtt cgcaggtgac    540

gtgtggacca cgctcttccg aagcgtctgg cctgtgtgct ctcggggagg ggacgcaggt    600

cagcccacct agccgatggc taacaagtca gtttgttttc tgaacggaag cttaaaccta    660

gaaaagtaac tgggttgggg tgggggtgta gccacatgca gtaaaagcac tgcctgtctg    720

tataacaacg acctgatgaa aaaaggaacg cgtgaaatgg ggagtgttag ggcgtcacaa    780

actccagtgt ggttgaaatg aaagcagaaa gcaaatggca agctggcttc cccttccagc    840

ttttcacaac cctgccttgc tcatggtcag ccccaagcac gggcggaaga aaggactgga    900

ggggagggaa aggggtgggg agcgagggta ccagaggcgt gggaggacgg ggacaaaggg    960

gcagcaaggg accggcggaa aggaaagtcg gcgttagctg gattggaaac agtccagaca   1020

gaacgatggg ctctgctgcc tccgggtggg gcaccaagcg gggagcgggg ccacgaggca   1080

ggggacagtg aagcaccatg cagcgcccac cagccggcag cgcccaccag cctgcgctgc   1140

gctgcacatg gtacccgcgg ccccagctgg ccagtgtgtg gcggagatga gaccctcgtg   1200

aagagactaa gcggccacag caggggggaag ggttgctcac ataaccccat actgctcaca   1260

ctacgaggtt aactgccgtg agatctgcct gcagccagca gaaacccgtt ctaggaaaac   1320

gttgcccagt gacttcagtg agtgccactg acccgggcgc ctccgccccg gcgtccggca   1380

gcagcaccga ttgcgcagga ggcaccttgc aaacaacctt tcctgatccg cgctgcagtt   1440

cccaggccgg ttgcagccgt ttcacagaga ctgcgcacac aaagcgtctc cgtgccctgc   1500

cattcacctt tcgacacagc cgcaacccct cttttcagtg ttaaaacctg gcgccaaaag   1560

gaacatgcga tgtgacgtgt tacctctgcg catgcgccgg gcattcccag cgccccgaac   1620

ctgatgaacg cgcggtgggg accccaggct tccgtgcttt cgttttcctg gaagctacgt   1680
```

```
gtcctcagtc tacatattgt tacctggaaa ataaagtttt ctccttttt cttcctttgt   1740

taacaggcag aaggtgtagg ctgcaggttt cgggcctaag agagggcatg gctggcgaca   1800

cggagtagac tcctagatga cataacggag gcgagtctgc accggggact cggcattagg   1860

aggaggcaga ggaaaagccc accaccgtgg ccgagggaga tctagcaagc agcttgcagg   1920

gggtgaagtg tgtgcaaagc aggctgagac ctgtccagta tcgaaacacg ccgcggtggt   1980

caagcaggct ttaccatgct                                               2000


<210> SEQ ID NO 209
<211> LENGTH: 700
<212> TYPE: DNA
<213> ORGANISM: Homo sapiens

<400> SEQUENCE: 209

tgaggctcaa aacaggtgtc tgtgagcttc acaggcggta aggccgtgtc tacatggccg     60

ggacatgcat cccggggctg cccctgccgt gctgcccgag tgcacggggg atgaggacct    120

gacaaggcca ttgatcttgc gggagcttcc tgaactactc cagcgtgaaa atcttccaga    180

aggattctcc acagggcaat gaggcaagaa atttacagct tagcctgatt aatgggccag    240

gcagttaaga gttctttgcc aagctatgag cataatttat agtcatcacg gcaggaggaa    300

aggccacata actcacatcc ttaaagggcc cttagaacaa gagacacgcc ggatcattga    360

aaacgtctcc actcctggcg ccaaaagaga tcggcacgtt tctgggtatt ctggtcaaag    420

aacagggagt ctggattaat atacacggca gaaaaaagcg aagaaaagac acacaggtca    480

tatatttctg actgatattc cgtttgttgt tttcggaggg acttggtatt tatttaacca    540

cattctcact tgacacgccc cctccccaca ccttgtaaat gccttcctct ttagccgagt    600

catttttcat cacatagaat tgaaatgttg ccaggaaggc ggtttatgag attgtagaaa    660

tggcactaga gaaagcagtg tgaaaagagg cctagaacgt                          700


<210> SEQ ID NO 210
<211> LENGTH: 600
<212> TYPE: DNA
<213> ORGANISM: Homo sapiens

<400> SEQUENCE: 210

tctctacatg ctatctacta aaaacttagg caaggaaatg catcagacca aacaccccac     60

agcacagaga accgaccggc cattgctttc caatctccgc aaacctaacc attgctggaa    120

gaaatcttac tcacagtgca cagacagtag gtattttatt gaagataaac atatagtgga    180

acaaaccaaa ttacccccat ttgagttacg tgagcactca gttctcagcg tggatgtccc    240

acaaatcaag tcaacatttg cgtcccatta ccagcagcca cttgccgagt atctcttcgc    300

ttccactggg actgcctggc atccctgatg ctaaggagcc actgaagagc ctccaaatgt    360

ctgacattca caaacgcatc ttttgctttg acccgaccct tcaacctctc cgagtctgct    420

gccttttctc agacacacat ccaggcaccg ttagggatag ttagagaatc tgaaaattca    480

gaagcgctcc gaaaagcctt tccaaaagta atccacagca ctcaacagtg aatttagaaa    540

ccccaatttt tttctgagtt tgaagttttt aagccttgcg gatggttgga gtaggaaaaa    600


<210> SEQ ID NO 211
<211> LENGTH: 1100
<212> TYPE: DNA
<213> ORGANISM: Homo sapiens
```

<400> SEQUENCE: 211

```
tcagacaagc tctgtgcagt cggaattttt taaagatgca ctgtcacttg aggaagacag     60
gtgatcttcc tgcggcacaa atagaagcaa agagatttct cttcttctct gtagagcaac    120
acaattgata aatggccgat aatctccacc aaattggcag cagtaggctg cccgaaggca    180
gcaggcatat tcgtctttgt gaattgtttt actatgatgc tgtcacattt ccaggaataa    240
gacggttaaa atgatatatt gttgtggttt ggcatttgca gctttgctct gacttccctg    300
gtaactgcca acatctgcaa attattatgt gcttaaaaaa aaaatcaacc gccaccgcag    360
gctgccccca cggtccctgg ctgggccagg cctcctgcca ggccacaggg cagagttctt    420
ggaccaggag gcagcagggt caaaacccag gttgcctagg aagcccccaa agacagttat    480
ggatagagct gggagcccga aacacatgcg gcagtctctc agtttccagg taccggttct    540
cacatcatcc atgcatgtgt ttgaggaaaa acaaaaaaaa attgatggtt gccaaaaaca    600
aaaatgcttc catatcaaag tttatcagtg tcaatgtcaa gagacttctg gttcgtagac    660
tcattttggc ttgaggccac cagaagtgaa ctctggtttc taaatgcaga agcagaggca    720
ctggccgatc atggaagatg cagggaactg ttcaagaggc ccaagcctgg tgctcagaaa    780
cttggcagga tcaagcatct cgcccaggaa ttcatcccct gcttgtctaa gccggctggc    840
tctcgtgact gactcggaac aacagagcag atgtttgcgt gggaggcaag cctcacccaa    900
catctgtcct gcggcgggaa ggcctgggtg ttcacagata gagctggagt tccccggtgg    960
gtggcacaga caattagctg ggctgcctc acatgtaatc taattacagg ggaaacaggc   1020
tcaaacaccg ggtgataagc agcgcaactg tttcgggtga ctctgtaatt tttcctccat   1080
taattttctc cataacgcac                                               1100
```

<210> SEQ ID NO 212
<211> LENGTH: 250
<212> TYPE: DNA
<213> ORGANISM: Homo sapiens

<400> SEQUENCE: 212

```
gttgcctggg atatgcttat atcaaaaact tacgtgtcac ttacctagca tttgcatttc     60
actgggcctc ctaaattctg tgtggtaacc gactgccacc ggacatgctg tttacttctc    120
tatcctcacg cagccagttg ccacattcaa cataacactg caaatattgc cggtggatcc    180
tgacttcctc gtggacccta ctgtgtcggg aaaaacaaac aaacgaaccc tggaaggaaa    240
caccatgagt                                                           250
```

<210> SEQ ID NO 213
<211> LENGTH: 600
<212> TYPE: DNA
<213> ORGANISM: Homo sapiens

<400> SEQUENCE: 213

```
tcataaatat ttccaaatgt attcctattt gtctctacag agtctaacag acataaatag     60
cgaattgaag gttctgtctt aaaacccagc agaaagaaaa acaatgacca gaaaaaaaaa    120
acaattgtct ttggcttccc aagaacagca tcggatttca actggaacca cagatggtcc    180
gttgatagaa gcgactactt tttagctctg gaggacgaca aaaggaacca gcttcttcct    240
gtgggtgtca cagcgaggtc gcctggccac atcaggtacc agagcgagcg ccctcacctg    300
ataggccctg tacaacctca gccacagcac tgtcaggagg aacacgcgga actagcaacc    360
taggagggta aaggcggagt tgggagggaa cacgaggcag gcaggtcggc tggctgctga    420
```

```
gctacaggct gcactcctag gacgtctacg tgtaattgag aaaaataaga caaaaataac    480

ttactgtgca ggcaattaat tctggttggc atagcgatcc tcttaagtta aagggaatga    540

gcatgagatg aagagaagta agaggcagaa agaattatgc aagagcaaca tcagagtgga    600


<210> SEQ ID NO 214
<211> LENGTH: 2000
<212> TYPE: DNA
<213> ORGANISM: Homo sapiens

<400> SEQUENCE: 214

acgccgagcc gcctctgcag gggaaaccga agcagatgtg gtgagataat acatccaacc     60

ctgagtgcta ctctaacctg ccagaggcgg agggttctca gtgagatgaa agcattacag    120

atgcgttaga tctaagggag gggcctgcag atgcgcagct ggcagagaaa ccagggaggg    180

gctgaactgt cagtcgcgac caccagggat ctgaatcagt tcaccgacag ccttggggac    240

attcaccttg ggctccacaa cctgtcagaa atgcccccaa gcccaaaggc gtcgagagaa    300

tggccaggtt gtttcagatt gacacatatc ctaatgtaca agtcagccca cacaccccac    360

gtgcactgag cgtctcttgt tgttcacccc aaataaactc tgccggaact ggggcgggac    420

tcgcaggggc ggagaagggg ggagacgggc agagggcaga agtggatggt gagaagagcc    480

aatggagggg ccccgtgaga gtgagcaagg ctgcacccct aaccgacgtc ctggggctac    540

tgtacaaaca aagaaccaca ggctgggagg ctgaacaaca gacctgcact ctctcgcagc    600

tcggaggctg caggtctgaa atcgaggggc tgacagcgct ggtttcctct ggaggctgcg    660

agggagaaac cgtcccctgc ctctcccagg ctctggggtg agcccttcct ggcatcccgg    720

gctcattgta gatggatcac tccaatctcc atggcttctc agggcttccc tccatgcacc    780

tcaaatctct ctctccttcc ttttgtaagg atgccagtca ttggatttag gttcacctta    840

aatccaggat gatctcatct aaattacatc tgcaaaaaga cccttttttcc aagtaagttg    900

acattcacag gtacctgggg ttaggattgg acatatcttt tgcaggggtg caggggggctg    960

ccactgagcc cgctgcacag ggtgacctgg gccaagggcc cttcactttc acttcctcat   1020

tggcaagctg ccctgtgttt ggactgggtc gaggctgtca accttgctgc ccctcggagt   1080

ccccccctggt gtcccccaaa cagattctaa gctgctttcc tggggctgga ggccaggcat   1140

tgggattttt taaagagctt cccagcaggt gagcagcctt tcatgggtat caggagacct   1200

tcctggcaaa tgtggtgaag gtccttcctc ctgagcgatg ccttagaccc aggagcccag   1260

ggaggctgct cacctgatcg ttaggacagg agcagtggaa acctctggcc tcagaccccc   1320

tggaggaatc cctccctcta agactctggg actggtgcac gcaaggagct atcgtgaaca   1380

ttgctcccaa ctggccgctt gcttgtcccc cggctcccct tggccccagt ggcggctttg   1440

cctgaattag agggcgtgag agccacctgt gtctcagcac tgcaattaaa gcaggaagcc   1500

ctttcggaag cagccgtgtg caccagcctc ccatgggtgg agcagagcaa accacccact   1560

tctgccctct gcccttcttc ccttttctcg acaccctgcg gccccccagt ttcagcagag   1620

tttatttggg gtgaaaaaca agagatgctc agcgcctgtg ggatgtgtgg gctgactcgt   1680

acattaggat gtgtgtcaat ctgaaataac ctggccgtta tatggatgcc ttggggcttg   1740

gggggtttct ggcagtctgt cgagcccgag gtgaatgtcc ccaaggctgc tggtgaatca   1800

gatccctggc gttctccgtt ggcagttcag cccaacagtt tctctgccgg ccgtgcctct   1860

gcaggtccct cctctgatct gattggatta atatttgaat caatagactg agtcaagcag   1920
```

aatgtgggtg ggcctcatgc aatcagctga agccctgaaa agagcaaaag ggctgcccct 1980
tcccccgagg aggagagaac 2000

<210> SEQ ID NO 215
<211> LENGTH: 700
<212> TYPE: DNA
<213> ORGANISM: Homo sapiens

<400> SEQUENCE: 215
cacatttcag agctgaggtg ctggtgcggg caggtctcct gagctggggg gtcagctgtg 60
tggccagtga tggtgacgcc tcaggccgtg catggccggg gaggcggccc tgcctctgca 120
ctcttttgac tccatgacta ctggtgtctt cggacgccag agtcggggga gcaaccatgg 180
ggcaccgccc ctgcctgggg aggcagcacg aggcctgagc ccagcttaca gggggacatc 240
cacccccgct gagagcccca ccttcacggc gaggatctgt agaagaagac atttgatatt 300
actcggcaaa aaaaacaaga aacgaaaaca caaaaagagc tcctctgaag aagaaaaggt 360
atttgcgctg tggtccacct agaaataatg ttgttggcac aactagagca ttcctcagtc 420
attcaggagc actccctgcc ggtgcgtcca catgtcccaa ccccgataga tgaggcgctg 480
ttcgcccgtg gaggggtcag gttgtcgtga ccttatcttt acccttaggc cgtccatccc 540
ggggcctggg gtttcctgcg ccagtcacgg tgggctgtgt aggtggccat gtgttcggtc 600
tttccccagg aggtacgtac catgtgctgg gaggcctgga ggctgagccg ccccccgcgc 660
ctatgagttg caccctcaca gcggcggcca aacctcctgc 700

<210> SEQ ID NO 216
<211> LENGTH: 200
<212> TYPE: DNA
<213> ORGANISM: Homo sapiens

<400> SEQUENCE: 216
caggcttgag cggtgactgg gagaccccgg gaatggaaat ggcgctcaaa tgctggtgtg 60
gtgtccgcag gggaacggcc cgcgggtgtg tggagtctgc gcccctgtgg cttcagctgc 120
gtcgggggac tgcgggaatc ttccagactc cagtttaaat cagagaggtg tgtccacgaa 180
aagagtcaaa ctaaaacatt 200

<210> SEQ ID NO 217
<211> LENGTH: 1300
<212> TYPE: DNA
<213> ORGANISM: Homo sapiens

<400> SEQUENCE: 217
aacgagacag tgcaaaaagc cgctgcctgg tgacctggca tgcagactcg gccctcccac 60
ttgcacggtg atccactgaa gacaacagct gcctctgtac tcacgctccc ccacactccc 120
ctccttcctg ccctggtttc tccatcccta gatgccatcc catgccccaa accatccgcc 180
aagcacaata acctcgcccc cacccacccc atgaggtcac tcgagttgac aaccagataa 240
cagtttttgt tttgttttgt tttgttttgt tttgtttgtt tttgagacgg ggtctcgctc 300
tgttgcccag gctggagtgc aatgacgtta tctcggctca ccacaacctc cgcctcccgg 360
gttcaagaga ttcttctgcc tcagctgcct gagtagctgg gactacaggc gcgtgccacc 420
attctcagct aacttttgta tttttagtag agacagggtt tcattatatt ggccaggctg 480
gtctcgaact cctgacctct tgatccgccc acctcagcct ctcaaagtgc agggattaca 540
ggcgtgagcc accgcgccca atagcaattt gatgacccat cccctccact gctgggaaaa 600
ggctgggcac cgcccacact ccatgcagct ctctttccct ggctcggaat cgctgcaggc 660
gccacagacc agacgcgcac tgttccccac tcctgcttat cggccgcgcg gcatcccctt 720
gtcgcagcac tccagcatcc atgcagccgc gcggcacccc gtcttcggag cactccagaa 780
tccatgcaga gcgcagcacc ccacatccag agcgctccag aatccatgaa gcacgcggca 840
ccccctcgtc agagtgctcc agaatccatg aagtgcgcag caccccttaa tcggagcgct 900
ctagaacccg tgcagcgagc agcaccccac acccggagcg ctccagaatc catgaagcca 960
gcagcacccc acacccggag tgctccagaa tccacgcagc acgtggcatc tcctcgtcat 1020
agcgttctag aatccatgca gcgagcagta ccccacaccg ggagcgctcc agaatccacg 1080
cagcgtctgg cacatcttta tcagagcgct ccagagtcca tgcagccaca gtcctccaac 1140
ggaccctgag attgtttctg caaaaggcca tgccttcata aatctgaaaa tttggaaaac 1200
atccttctac ttatatcctt acaacccacc attcaagctg tagaagcctt tctggaaccc 1260
caagcagaag gatatccaaa atgtaaaaac ggtggggcct 1300

<210> SEQ ID NO 218
<211> LENGTH: 1000
<212> TYPE: DNA
<213> ORGANISM: Homo sapiens

<400> SEQUENCE: 218
atagtgcgac tgttccgaag tctttatcac agttactggt gatgcttttt tccagatgtc 60
ctcgacgtgc acccatgaag ggctccacct gagagtgcca gggtcctccg tgggatgggg 120
ctggaggggg tgctcttgcc gtcctgggct cccaagcagc cataggaaca atagggtgat 180
ggggtcccag agatagaggc cagtgacagc agcgctttga acccctcaca cgggcacggg 240
ccctctggca gggatgggcg tcccggtcac acggagatgg gggctgctgc tgcctgcagg 300
tagaggaagg gacgtgtttg gcagtcctgt gacccctggg cacctcgcct cccccacggc 360
cggctctgct tgtaaacaga caagtgcaca agcgcagccc ggtgaaggca cagcggtccc 420
aggaggcatc tgggctgcac cccagcgagc cgcccataca cgtggagatg ccggccaagg 480
ccctgcagca cacggcagag gaaggcgcga tgggagccat gctgggcccg gaaggtgccg 540
ccgcccggag ctgtagccat cactccagct cttcttttaa gtgttcccag aaattgtgac 600
ccaccaaaat ctgagagcac ccgacagtaa gccagaggac cttgatgtga gatcccagca 660
cggtgtgggg gcggactgtg gtgggtgctg tctcggcccc caccccttcc acaggtcggt 720
gtgcacatcc cacggcgcct gctaagctgc agtcttctcc aaaggggtca ctctccgtgg 780
gaagggagcc acccgccccc gggtgatgtc cccagtcagt gactgacgac agtccccagc 840
cgaggtgagg gaccagctcc tgcatccctc actccggggc ttgcctgtgg gccagggtgg 900
gggcgagcct cagcagagac cgcgtccccc ttgcctgtcc tgccctgcct cccctgcctc 960
ccccgcgcct ctgctgagca cgcccagagg gagctgcttg 1000

<210> SEQ ID NO 219
<211> LENGTH: 500
<212> TYPE: DNA
<213> ORGANISM: Homo sapiens

<400> SEQUENCE: 219
cacttgaaaa gcacaactca tggtgccaaa gctctgacac ggactccact ggagctgtgg 60
gcagggggtg ccaaggtacc gagttccaag ccgttgttat ttgagagcgt gccccccgcc 120
atgagagcag gtggggggac ataaagtgac acaggatgga ctggccaaag gctgaggacg 180
atcacttacc tcacaggatg atgccacccc cacggacagg caaggagctc tcaccttccc 240
caggacccca gctgccacca gagctccaga tggccctggg ggtgtctgta aagcctgtga 300
ccgtccacca ggtggagacc aggctggcca ggggagggag aggaagtgac cactggccct 360
ggcactggct ggccggctcc agcaggcccg aaggggaggg aggagcctgg gtgcaccaga 420
ctctctcaat aagcagcacc cagacactta acagatggaa agcggtggct tggaactcac 480
ttccaacgaa acaatagcac 500

<210> SEQ ID NO 220
<211> LENGTH: 1300
<212> TYPE: DNA
<213> ORGANISM: Homo sapiens

<400> SEQUENCE: 220
agcacctcct accccaccct ccccattcct gccatcccca gggtccaggg agcccagatt 60
ccagggaagg gttgcattag ctcccactcg gagtcctgat gcagcagaga cagacagagg 120
ccctgggaga agtgagcatg aattattaag acaagacaag ggtgaggccc cagagagggg 180
gtggcggaag ggtcatgttc atgcagcgag agttgcttcg agcttgaacc gcgtatccag 240
gagtcaagca gattgcaact ggcgagaggc cttcagaaat gccccgtgag agtcctgtgt 300
gcagagctcc atctcagcac acttcctgtt cttttggttc gtcgattttt gcattttcag 360
tcccctgtga tccattattt ataacagtgg agattggcct cagacactag cagtgaggaa 420
aacaaaagcg aagctacgca gaaaaatgac aagagtgatg agcacagcag tcatgacaaa 480
tgagccctgt gcggaggccc gggatccgcg cagatgccgg cgcgggggaa atgggccctg 540
aaatcccacc gtcaggccag gcagctctga gcgtgacctg gagggctgtt cagacggtct 600
gggtagccgt gtcctgcgca tgaacatcct ccgtcgggag aggaattccc cacggattat 660
cagagctgct ccctccaccc cccgccacgt cccacgcggg ccacatcaac tccctctgca 720
gcctctggcc agcggctgag ccctccgtgt ctcccctcgt taatgcctcc ttcaccatcc 780
cctcctgaag tttcccccat tgcatacacg cgctgaggcc cacccggtat caaggactcc 840
cattgcttgc gaaaaagatt ccacccctct tagaacagag accagggccg ctgtagcaaa 900
tggccataaa tgccacagct taaaacaaca gaaacggatt atctcgcagc tctggaggat 960
ggagtccaaa atctgaatcg ctgggctgaa atccaggtgt gggcagggcc gcgctccctc 1020
tagaggctcc cccggagatt cccttccttg cctcttccag ctgctggtgg ctgccagcag 1080
tttgggaatt gcggccgcat cacaccacct ttctgtttgt tgttgacatc cccgcctccc 1140
ctgcctgcgg ggtcttagat gtctctctcc ttcccactga gtttcactcc acatttgaat 1200
tggattaact catgccatgt taggcaaacg tgcccctcaa atccttccac ttaacagaca 1260
tttattgaag gttcctgtgt gcggggccca agagaaggga 1300

<210> SEQ ID NO 221
<211> LENGTH: 200
<212> TYPE: DNA
<213> ORGANISM: Homo sapiens

<400> SEQUENCE: 221
gaatgttcaa agaaagagcc ctccttgcct tcctcttctt ccacccctgc cctctgcaga 60
ctggggttct gtagaccccc aaagtaagtc cgccacaccg gaaggaagtg agttacacag 120
gggcccacat gggaaccgct ttttgtcctg tcttggtggg aaaatggcca cgaccccagc 180
ccaggctctg ccacgccaca 200

<210> SEQ ID NO 222
<211> LENGTH: 1600
<212> TYPE: DNA
<213> ORGANISM: Homo sapiens

<400> SEQUENCE: 222
ccatcttcct aggcctgcgt ttcccccaca ccggggactt gtgctggaaa gaaaagctgc 60
gttggcagcc aggagccggg gaaactgtcc agggaggcat cctctgcgat gaaggcgggg 120
cctcggcgtg gcccgttccg cgctctgtcc agccctggag aagccccacc ctcaccgagc 180
tcgaaatacc ccctccctga gagccgagac tcatggccgg gaccccttgg acagaagatg 240
cggatgctaa cccggcgctt ccaccacagc cccggcggca ctggggagcg agcgcggcca 300
tcccgcgcgt aggtggtgtt tctctgcagg cgccagtttc accgcgggcg cccaggatcc 360
tcaacggttc tgttgtgatg tgattcccct cttcgacttc gtcattcagc ctcagtccct 420
cagtccccaa ataccgaaag gcagtctttt tttttttttt ttgagacgga gtttcactct 480
tgttgcccag gctggagtgc aatggtgcga tctcggttca ctgcaacctc cgtctccctg 540
gctcaagcga ttctcccggc tcagcctccc gagtagctgg gattacaggc acctgccacc 600
acgcccggct aatttttgt atttttagta gagacggggt ttcaccatgt tggccaggat 660
ggtctggaac tcctgatctc aggtgatcca cccgcctctg cctcccaaag tgctgggatt 720
acaggcgtga gccaccgcgc ccggcctttt tttctttttt cttttgaagt taatgaactt 780
gaattttatt ttatttacag aatagccccc atgagatact tgaagacccg gtgccaagcg 840
acagtgttga ccccaggtgg tcagtcctgc ctggcccctt ccgagggatg cgccttcacc 900
ataaccatgt cacggacagg cgtgtgggca agggggcatc gctgtatttt tcacaactct 960
ttccactgaa cacgacaatg acatttttca ccacccgtat gcatcaacca aatgaaaaga 1020
tgagcctgtg acattcccgt gcgtagagtt acagcttttc ttttcaaaac gaaccttcag 1080
tttggagccg aagcggaagc acgtggcgtc tgacgtctcc agggagaccc gccgccctcg 1140
ctgccgcctc accgcgcttc tgttttgcag gtaatcttca gcaagtactg caactccagc 1200
gacatcatgg acctgttctg catcgccacc ggcctgcctc ggtgagtgcg cgctgcgggc 1260
tctgcccggt gacgccacgc ggcctcctcg ccttttcggg atggctggga ggggcgggaa 1320
gaggcgctga agggcccgag gcaccggcct tctacaaggg gctcttcgaa atcaatcaat 1380
gcgcagaatc ccgagggagg ctcagccgcc ctccgggcct ctctgcctcc acaggtgatg 1440
gctgtgtcca caaggaggaa accgtcgggc tgaattaaac agaaccgccc tcctaagagt 1500
gtgggttttt ctgccgggcg tggtgtctca cacctgtaat cccaacactt tgagaggccg 1560
aggtgggcag atcacctgag gtcaggagtt cgagaccagc 1600

<210> SEQ ID NO 223
<211> LENGTH: 400
<212> TYPE: DNA
<213> ORGANISM: Homo sapiens

<400> SEQUENCE: 223
aggcagcagg gttaggactt caacatacaa cttttggggg gagatgtact tcagcccata 60
acacaccacg tgggaggata acaccgattt cagagcttgc agaggaagcc gccaggaact 120
ccagtgagac atcagccccc aggtgcctgt caggcacgcc gggctgtggg gggcacctgg 180

-continued

```
gcccatctga gtaacggagg cgcatccgca cttcccccag gagtacattt ttagaaccca    240

cagcgccata aaccaaagac aaggagactt cctggtgccc cgtcagcttc tggaggcgac    300

gttctcggct gacagctctg gcagcctccc ctgtaggtga gagacaggta aatgggactc    360

ttgcttccaa aacggaacag ggtaaaaatt ctcaagcgtt                          400
```

<210> SEQ ID NO 224
<211> LENGTH: 700
<212> TYPE: DNA
<213> ORGANISM: Homo sapiens

<400> SEQUENCE: 224

```
tgctgcaccc ccgctgccct ccctcccgct ggccggcagc accttctcca cccgggcccc     60

tctgctcaca gcgctccccg cccccgtctc cccgaggggc ggggagccag gacatggccc    120

tgaaagccta gccctggcct tgacctcccc agagcgccct ccccaccctc cgccctctgc    180

caaccctggc ccctgccctg gccccgtcct tgtcctctgc tgctggcctt ggggtcgcgc    240

cccgcagact gggctgtgcg tgggggtcct ggcggcctgt gccgtcccac gcctacgggg    300

atgggcgagg tccttcttgg ggcttctctt acccactctc cagtcacctg agggcgctgc    360

ttccctgcgg ccaccccagg tttctgtgca gccgaagcct ctgcctctgc ggccgggtga    420

tcccaagacc ccggggtcca gggaggcacg ggatctgctc ccccggtccc aaatgcaccg    480

gctgcgcctt aggagggacg gcctccaccc atggcgctgg cgcccagggg ccgctcctcg    540

gactacagca cttgctcgtc gccctgcgcc ctgtttagtt ctcatcacca gcagcctgga    600

ctagggccct ggtccttctg gcctccttcc acagcccgct gcacatctca cccacttccc    660

cgaggtgctg tcattgttta gctgggcccc tcagcctccg                          700
```

<210> SEQ ID NO 225
<211> LENGTH: 300
<212> TYPE: DNA
<213> ORGANISM: Homo sapiens

<400> SEQUENCE: 225

```
ttaaagggga gtggttgtat gaagagttcc tcagtcaaag gtgtgcagct gggaagccca     60

ccccacctaa gagggaggtc tgacaaactg tccacactga accactcaga cctgcatcag    120

ggccccgttt cttccataag ccgccaagta cagccctgag tcaactgaac tcaggcctgg    180

gaggcttccc aaagctgact tgactcagct ttgaactgaa atgaccgtac catgacaacc    240

ctgatgaaaa gctaaactga gcccaattat tcaacagtaa aattcagttg gtctcactca    300
```

<210> SEQ ID NO 226
<211> LENGTH: 450
<212> TYPE: DNA
<213> ORGANISM: Homo sapiens

<400> SEQUENCE: 226

```
tgctaccagc tgcttgggct tgggcaagtc accctagctc tcagatgtca tctgtaaatg     60

atgacaatgc caatgtggca ctgttctgag agtcagacag aacgtatgtg tgcttcacat    120

atggtgctca tgaagtgcta tcattatcta aggaaaacag aaaacgaagt tcagagtctc    180

tctaaacgca tgacaccaga ccaacaggga gtttcaaaaa ataggtctga agtaaatcaa    240

ttctcctggt ctcaatacac tgaaaacaaa ctattagggg actgaccgaa cccaccttag    300

gaaccacctt acgtcacctt ctgtctctac tgcaaaaccc tcccttaata ctgttcaaat    360

acgctgacaa tccagatcca tatccaatgg aaccagcaat catgcctgtg tgccagcaat    420
```

gtcagggagg gaagccgatc tctgatgaat 450

<210> SEQ ID NO 227
<211> LENGTH: 1000
<212> TYPE: DNA
<213> ORGANISM: Homo sapiens

<400> SEQUENCE: 227
caggtgccgg ccaccacacc cggctaattt ttgtgttttt agtggagaca gggtttcgcc 60
atgttggccg ggctggtctc aaactcctga cctcatgtga tccacccgcc tcggccttcc 120
aaagtgctgg gattacaagt gtaagccact gcgcccggcc aagagtgaag ttctgatagc 180
tggggtaaga aaggccgtgg gaacagccgg tttcagacac gctgggtcta agacgctgcg 240
tctggcgctg ctcggcatcc aatgggagcc gtggagaagc caggcgagtg cgtagggcgg 300
agccagcgca caggaaatag gacgtgatga ggtcaaccgg ctggtccaag tgtggacgga 360
agtagaggat gcaagcaccg agccccgggg cccccagcat tggcggggag gagctcgcgg 420
tgcgggagaa gcaggggacc gcgcatcctg gagaccaggt ggagccagtg cgcccggaag 480
gggcgtggcc cgctgacagc cgcccaggag gccgggggag gcctggagcc gagggccgcg 540
cgtggcaatg tggagagaca ttttggtgga gtcatggggc cacagcctga ttggtgagaa 600
caggaaggga aattgcagat gggcctgggc cccctggctc ccgcatactc caggaccagg 660
gctgagtcat cgttcaccgt gtgtgaccag ggccccgtgt ggccggctgt cactcggtat 720
ccagttaccc tgggcagacc actggcggca ccccccagcc agaggccgca gcaacacaca 780
cgcctgcagg cgaccaggcc ggactgcatg ccccgtgggg gaactgaggg cgtttcagta 840
acagagtgtt aggggacacg ggttgggtgg cttggaaagg gcctaaggtg gggtttgttt 900
tagattgggg tggtgagggc gcaggggccc ggtaggattc tctaacaggg cagcagccac 960
tcatttagca acaggagagg cgtccagcgt ttcgtgggct 1000

<210> SEQ ID NO 228
<211> LENGTH: 3100
<212> TYPE: DNA
<213> ORGANISM: Homo sapiens

<400> SEQUENCE: 228
acccaaccac aggcctcctc tctgagccac gggtgagcgg tgcaggttct gctgttctgg 60
agggcctgag tcccacccag cacctcataa acagggtcct ccccagggct gctgcagtag 120
gcatcaacgc cagggtgcaa aatgcctcag ggagccaagg ctgagccagg ggagtgagaa 180
ggagcatgtg gaagtgcgtt ttggagaggc agctgcgcag gctgtcagca ggctccggcc 240
gcttctatag acagcatgac accaagggca gtgacctcat tccacaggct gagtccagcc 300
agccagccaa gcatcaccag ccagacgatt gaccctaacg gaccaaccaa cccgtaacga 360
cccctcctac cataaccagt agccagccag cccataacca gccaacttat ctataaccag 420
ccacctgacc atagccaaac aaccagccgg cccaccagta gcattcagcc cctcagctgg 480
ccctgagggt ttggagacag gtcgagggtc atgcctgtct gtccaggaga cagtcacagg 540
cccccgaaag ctctgcccca cttggtgtgt gggagaagag gccggcaggt gaccgaagca 600
tctctgttct gataaccggg acccgccctg tctctgccaa ccccagcagg gacggcaccc 660
tctgggcagc tccacatggc acgtttggat ttcaggttcg atccgaccgg gacaagttcg 720
tcatcttcct cgatgtgaag cacttctccc cggaggacct caccgtgaag gtgcaggacg 780

```
actttgtgga gatccacgga aagcacaacg agcgccaggt gagcccaggc actgagaggt    840
gggagagggg ggcgagttgg gcgcgaggac aaggggggtca cggcgggcac gaccgggcct    900
gcacacctgc accatgcctt caaccctggg agagggacgc tctccagggg accccgaatc    960
aggcctggct tttccccaag ggagggggccg tgcccacctg agcacagcca gcccctcccg   1020
gtgacagagg tcaccattcc cgagctaatg tggctcaggg atccaggtta gggtcccttc   1080
ccgggctgca cccagccgtc gccagctcca tccctgtcac ctggatgcca gggtggtctt   1140
agaaagaacc ccaggaagtg ggagtgcccc gggtggccgc ctcctagcca gtgtacatct   1200
tcacatgaac cctacctgag gaagccagtc cccgacggca tagctgcatc cgcttggaat   1260
gctttacagg cattgacacc ttcgcctcac agcagcactt tggaaccagt gtcctcatta   1320
ttccagggca cggctgggga acaagggggt cctcagcctg ctgggtccca cagctagtac   1380
cgggcaggtg gacgggagct tctccccaca gtcaccctga tgccccgctc ttgctcggct   1440
ggaggcctcg gatctccgtg gtgttgaggg agccggggca ctggagccct ggtgacctgc   1500
atctcctggc ggagccggga agagctcatg gactgtcaca gatggacagt gccccgcggg   1560
ggctggagag cagagtgggg ctggaaggtg gaactcttag ccaaagtctt ggtttctttt   1620
ggccagggtc ctctttcaat ggctggagaa ggtggtgctg gggggtgaac gctgacctcc   1680
tcatgtgctg cccctccctc gcctgggccc ggtaaagccc ccacgtagcc ccagccagcc   1740
tggaacatgc ttcctgagct cccagctctt ggtctttgca cccagtggag gaggaggtca   1800
gcccagggag ctgagtctgc ggtttagggc gtccagggga cgtggaagca tgtgggtcgt   1860
ctggccacat taggtagggc tgcagagacc tgggctagag cagtcctgcg gggtctggaa   1920
ggggaagact ggctgaggtg cggggcctgg tctggaatga tcctgcgatt ttggagtgaa   1980
gccatggagc gggaagagac aacccccccgc ggggaatagc ccggcaagtg gccacgaggc   2040
caggctgagg tccagagaag caggggcatg aatccataaa tcccaggggg cctggccatg   2100
ggatgtgctg gctgcacccg gcccctgtga gagcccccgc aggctggccc ccttctgcag   2160
tcagtggggc tggggcagct tctctggcat ggggcgaggc agccgcctgc acagtggccc   2220
ccctgactgt gcgcccccac cctctccagg acgaccacgg ctacatttcc cgtgagttcc   2280
accgccgcta ccgcctgccg tccaacgtgg accagtcggc cctctcttgc tccctgtctg   2340
ccgatggcat gctgaccttc tgtggcccca agatccagac tggcctggat gccacccacg   2400
ccgagcgagc catccccgtg tcgcgggagg agaagcccac ctcggctccc tcgtcctaag   2460
caggcattgc ctcggctggc tcccctgcag ccctggccca tcatgggggg agcaccctga   2520
gggcggggtg tctgtcttcc tttgcttccc ttttttcctt tccaccttct cacatggaat   2580
gagggtttga gagagcagcc aggagagctt agggtctcag ggtgtcccag accccgacac   2640
cggccagtgg cggaagtgac cgcacctcac actcctttag atagcagcct ggctcccctg   2700
gggtgcaggc gcctcaactc tgctgagggt ccagaaggag ggggtgacct ccggccaggt   2760
gcctcctgac acacctgcag cctccctccg cggcgggccc tgcccacacc tcctggggcg   2820
cgtgaggccc gtggggccgg ggcttctgtg cacctgggct ctcgcggcct cttctctcag   2880
accgtcttcc tccaacccct ctatgtagtg ccgctcttgg ggacatgggt cgcccatgag   2940
agcgcagccc gcggcaatca ataaacagca ggtgatacaa gcaacccgcc gtctgctggt   3000
gctgtctcca tcaggggcgc gaggggcagg agggcggcgc cgggagggag gacagcgggg   3060
tctcctgctc gcgttggacc cggtggcctc ggaacgatgg                         3100
```

<210> SEQ ID NO 229
<211> LENGTH: 1000
<212> TYPE: DNA
<213> ORGANISM: Homo sapiens

<400> SEQUENCE: 229
tttttgtgtt tttagtagag atgggatttc accatgttgg ccaggctggt ctcaaactcc 60
tggcctcatg caatcctcct gcctcagtag tagtagttgg gattacaggt gtgagctgcc 120
atgcccagct gcaggtgcgg aagctggggg cctcagagac tgtggactcc tggccggtga 180
ggagcggcat gggccgggag agctgactct tcagcgggac tgaggtggct ggagcgtgac 240
cctttcctga gggcaaacag ggagggcctt ggagcccggc gctcaggaca ggcccctgct 300
ggcccggcag cctgagcttc cacacttttc cagggcgtct cgagttcgcc cacagagctg 360
ttgtttcagg ataaaaaatg cccttgtatt ccacgttcca gttcagaggc ccgtctgttc 420
ccaagagcgg aggcgtcagc cgcatgagtc ccaccggaag ccgggttgcc gggtccccgt 480
ccctgccctg cagacgacgc attccggagc cccccttggga agctgcctgg ctctcccagg 540
cctggctgcc ttcgcacgag ggctccgagg catgctcatc ctacgtgact gcccgagtgt 600
gcacacgcct ggccgtgtgt gggcgtgtgc ctggggcccg agctcaggag caaggcctgc 660
gtggacctgt tgtctgaaac aagccagtag acagctgcgt caatgcaggc aagctgaaca 720
gggctgcttt ttcagcctga caaccccagg ggctgaacag gagctggggg aggagcaagg 780
ggccgttccc ctgccccaca gcacagcaca cgaccccgcc ttggaacctg gggcccgggg 840
tgaatcgagg gtcctggagc aagaggggct gctccacagg agagcctgtc ccgccacccc 900
tcagccacca gattcggggc tgctggactt gttctcaaac ctgcacagtg agtgacagct 960
gctgagacgg aggtctcagg cagtgcaggt gaatcagcat 1000

<210> SEQ ID NO 230
<211> LENGTH: 500
<212> TYPE: DNA
<213> ORGANISM: Homo sapiens

<400> SEQUENCE: 230
tccttatttt ttagttctca agccctgtag ggtgttttcg gtcgcagttg tttgggctgt 60
ggtcctgacc ctcctgagtt ccagtggctc tgttcaggag agctgcctgg ggccgggact 120
tctgaaacac acactgagcc acaggccggc ccggcggctt gggttcaccg ccgcctcttt 180
gtgtgtgatg tcctgggata ggcccgtgca cgttcagatg acactgtaca tataaataac 240
ttgtagccga gaacaggatg gggcggggag gaggggaggg cagaacgtac cacagcagca 300
gaagtcactg tggatgcctt cgtaagttgc atggaaggtt tttaaaccta gccctgccga 360
gcagccctct cctggtccgg gagaacgatg gggagagagc tggcgttcag ctttcatcac 420
tggagccgtt ccttcttccg gccccccgag ggcctgtcca tgatcacact ttgtcttgtt 480
tcgggggtgg cccctgtgac 500

<210> SEQ ID NO 231
<211> LENGTH: 1300
<212> TYPE: DNA
<213> ORGANISM: Homo sapiens

<400> SEQUENCE: 231
caagcctgtg gtagggacca ggtcagagta aacaggaaga cagctttcgg ccaggcggtg 60
cacctcggtg ccggtgagtg tgagcgtgtg tgcgtgtgca cgtgtgcaga tgtgtgtgga 120
cgctcccttc tccgcagcag ctcctgaccc cctgcaggtg accctcagcc agccccaggg 180
ctgcccccac tctcccctgt ggacacctac ctcatttggg gtgaagtggg gggactgggg 240
tgtgaggggt gctttggggg gcacacttcg acccctctct ctgcaggcca agtcctgagg 300
ctcagtttcc tcctctgtgc cccggcgacg tggtgcaggc ctcgcgagtg acgtgagggt 360
tcatgaccca ggtgtgggca gccagccctt cacgggaggc cacccacctg gccacagtgc 420
ctgggaattt aggtcgggca ctgccgatat gtcgccttcc acaaggcggg cccgggcctc 480
tgctgaccgt gcaccggtcc tggggctggg taattctgca gcagcagcgc agcccatgcc 540
ggggaatttg cgggcagagg agacagtgag gcccgcgttc tgtgcgggaa ctcccgagct 600
cacagagccc aagaccacac ggctgcatct gcttggctga ctgggccagg cccacgcgta 660
gtaacccgga cgtctctctc tcacagtccc cttgcgtctg gccagggagc tgccaggctg 720
caccccgcgg tggggatcgg gagaggggca gtgtcgccca tccccggaag gctgagcctg 780
gtgcagccag ggagtgaggg ggcgggaagc cggggtgctg ccctgagggt gccccgacac 840
gctctcctgg ggccctgagc ggctgccacg tgcgtccagg gttctggcca cagggtgggc 900
aggggccctg tgctcctcac tggaggcccc tgaggctctg gaactgagac catccacccg 960 ccggcccccct ctcgccggct ccggcacccc tgcctactgt gacttcctgc cccggactcg 1020
ctctgccagc ttggggcaaa ccacttccct ctggggtttt cacttccctc tttcccaagt 1080
ggggaaagac cacctgtccc cgacccagaa agggcccctg cccgagggca gcagcagtgc 1140
caggctggca tgtgaggctt ggggcaggcc cggcccccag aggcacaggg cgatgctctg 1200
tgggacgctg tgtcgtttct aagtacaagg tcaggagagg agccccctga ccccggaggg 1260
gaggagaggc agggcaggaa accgccacca tctcagccca 1300

<210> SEQ ID NO 232
<211> LENGTH: 200
<212> TYPE: DNA
<213> ORGANISM: Homo sapiens

<400> SEQUENCE: 232
gcccactgtg ggtgtgcccg tgtgtgtggc tgtgaggcgt gagtgcaggc gtgaagtgtc 60
tgggagtggg agcgggcatg agtgtgtgcc acgggcctgc tgttgggtcc ttggaggcca 120
cggttgcccc tgaagggact gcaagctctt ttttgatttg tagttatttg agaagtctat 180
acaggaagaa aattaaaccg 200

<210> SEQ ID NO 233
<211> LENGTH: 1000
<212> TYPE: DNA
<213> ORGANISM: Homo sapiens

<400> SEQUENCE: 233
agcgcccagc gcagggccgg gacccagagt ggactctacc gtggggctgc ctcaaagaaa 60
tctcagcaaa cacaggaagc cagcccaccc gtgcagccat ggggccagga agcccgccct 120
ttaccaagtc atttgggcat tttttctctg tgctaacagc ccagatggag ccatagcctc 180
aacctctgtg ttctgataac accaagctgg gacgccggag ccatgcaggg gacagtgccc 240
ggcctgaggc tgcagcctgg gtctggatgc ctttctaatt cagggcctcc tcatggcctg 300
gttccataaa tggtcaaatg cagcctgaca gcgcagcctc ctatcagcgc tgggctccgt 360
accgccacac agcccacata ccccgttccc caggagacgc ccgcaggtgg gcagcgtcac 420
tcccacccgc cgagcacacg ctgtccccgt ctcgtgtccc gaggagccgg aagcagctgc 480
ttcctcccag cctgaaagct gcacctcggg ctgcactcgg ctccccgaac ccgccctccg 540
ctgccctgca attcgccaag ggagctaccc ttcccatata aaaatttcac ctccatttcc 600
ttgtagagaa gaaacatttc tgacagcaag gaagattcta atttgaaaag caagtgattc 660
atctcccggt gccaaacagc agacgcaggc gttaccagtc tgggtggggc gcccgagctg 720
gggacctggg gtcctctggg aggggcaaga aggcagcgat gctggccccc gcctccatct 780
gcccatccca tctgcttcca cacaccgccc tgccgtagct gcttgcagcc cttctctgtc 840
agtttctcca tcttttggtt tggtgataaa tgagagttcc catcgggtgt gccaccctct 900
gtgtgacggg gagcagagaa gaccctgcgt ccaagtcctc ctgggggaag agcgaagatg 960
ctgggaccag ccccagctgt caggggggtct ccaatcccag 1000

<210> SEQ ID NO 234
<211> LENGTH: 1300
<212> TYPE: DNA
<213> ORGANISM: Homo sapiens

<400> SEQUENCE: 234
ggaacggaga gccgccaggc ccaaacctcc cagaatttgc gcagtattct cggcctagag 60
agcgaggagt ggccttggcg aggtccctct ttggctcttc tggcttagcc ggggttttaa 120
acttgttatc tgcaaagcag aaggaaagtc agcccctgat gtaagtgtca agtaaaataa 180
atcggatggg tcctttcctg tttggcgagg aatgctacac taagggggac tgcgttcaaa 240
tgggcagtct ttgctggaaa cctcgcctcc gcgcgccttc cctcgctcgg attcaggcgc 300
ttttacgtta agggttgaat ttttgtgtca acaggcacct cgggaggtcg cctagacaac 360
tgagcggagc aactgagata acccccgcta cgtgtggagt gacctagtcc attaacttgc 420
cccagcacgc ccgctgagtc cgcaaaatat aggatggcct cgggttttag atgaacccaa 480
agctaagatt tcttccctct ctggaattag caagcagccc gccctgccca actcccctgg 540
aagcgcgcgt gctcgccagg cctcgggacg cctgcgcggg cgcccttgca ctggcaccag 600
ggctccgggg taggggcgca ccgatctgcc caagcctctg caggcactgg aggaaggcga 660
gccctccacc cgctcaacag gccccagtgc cggcctttcc ttccagtctc aactccaccc 720
gggggcccgg gggctccaca gttaaaaact ccacgccacg gagatcgcag gtaagctgct 780
ggctcaacga ggtgtgctaa atgggattaa agatcctgga ccgtggccag gcgcggcggc 840
tcaagcctgt aatcccagcg atcagggagg ccgccgcggg aggattgctt gagcccagga 900
gtttgagacc agcttgggca acatagcgag acaccgtctc tacaaaaaaa taacaaatag 960
tggggcgtga tggcgcgcgc ctgtagtctc agctacttgg gcggtcgaga tgggaggatc 1020
gatcgagtct gggaggtcga ggctgcagtg agccaggatc accgccaaga tcgcgccact 1080
gcattccagc ctgggcgaca gagggagacc ctgtctcaaa aacaaacaaa aaatcctaga 1140
ccgtttacaa acagccttcc gtctcttcct ggtcaagtcc taaccctggc taacctcgcc 1200
gtctacagcc tgaattttgg caaccgaaag gcagcgccgg cgccacgtgc acacgggctg 1260
ggccgctccg ccagctgcca gggccactgc cgcgctcact 1300

<210> SEQ ID NO 235
<211> LENGTH: 300
<212> TYPE: DNA
<213> ORGANISM: Homo sapiens

<400> SEQUENCE: 235

```
cgcacacaca gcacagacgc ctgcatcttc ccatgcgtgg tttctgctct tgcctctctg     60

ggtttttgtt tcacttcggt cgagtttttg gtggtgttga gcggatagcc ggggaagttg    120

gagtcttgtt tgtggccgcc tcgtgctcgt gtctgtatct aagatcctca ggctgctcct    180

ttttgggtaa ggtctgttgc ttctctagga acagtgacgg tggcagagcc cgtggcccct    240

ctctcctgtc ccagagccaa gctgtttcct ctccccactc ccgggcaccc tgcgggcaag    300


<210> SEQ ID NO 236
<211> LENGTH: 1000
<212> TYPE: DNA
<213> ORGANISM: Homo sapiens

<400> SEQUENCE: 236

cacagcccag cttcaagcct ggccgaccag gggtttggca tgaagacccc ggcagggctg     60

gggctgtgct ggaatccacc cggaagtttc ctgccccttg ggctgcccac caggtcccct    120

ttctgctctg atcaagctgg acaaaacgtc gtggggccac agcacagggg gccaacgcaa    180

gctgggatcg tcagacgtta ggaaatccca aggaagaaga gaaaggggac acattcggga    240

gacgtcggca cacgctcgaa gcagcggaca ggcacctctc tgtggacaag gcagactggg    300

cggccgagat tccgcataga tgcctgcttc ctccacgacc tccacgtgtg gctggcccag    360

tccgggtccc cctcacctcc tctgtctgtc ttggtggcct cacgccgtgg gctgtgatgc    420

cggctacgct gcttgggtgg ccaagggtct gagctgcaag acgcccagcc tgggtctctc    480

ccgagctctc ccacgtcctg tctgctcctc ctccgagctc ccggttgact ctcacgactg    540

caccagcctc tcccccagga aggcgtggaa acaacctcct tctcccaggc ccgctctgcc    600

tcctgcgttt caaggcaaat ccgttcctcc aggagatgat gcaaccacat cctgttggag    660

cccagagaag tgcggatgca gcccggggct ctttctttcc tagaaccctg cctgggagtg    720

gcttccctga actaaggaca gagactttgt cttcgttgcc tctcggcctg tgggcactga    780

gcatacagta ggtgctcagt aaatgcttgc aggccgatgc ccagagccat tagccctcat    840

catggtgagc tcggcagccg gtgttggggc tgggctgggc ctaggtgtgc gtgggggcgg    900

tgctggtctg ctttgctggg agccatggac accggaggaa cagggcccca tcagtgcggt    960

cagagtgcaa actcggagcg tccttctctg gaaaacgaat                        1000


<210> SEQ ID NO 237
<211> LENGTH: 500
<212> TYPE: DNA
<213> ORGANISM: Homo sapiens

<400> SEQUENCE: 237

gggagggggc gtggccagca ggcagctggg tggggctgag ccagggcgat ccgaccccga     60

accggagctt ttagcacttt gagtccctgt actcagaggt ctcctgcagc cgggaatccc    120

actgtgctgt ggtccctggc agccagcacc cacccccagc ttctccgtca aggttgagga    180

cggagcactc ctgcctctga ttaactggac gcaggagaag cagttgcttt aatccggagc    240

cttgagttgg gacagataat gagtcattca accagatttt ccaaggacac actaactttg    300

gtatgatgcg tgtgtgcccc tgaatccacg tggtcaggaa agcccaggga acactggcct    360

gtgactcact gagcaggttc ccttgttacc ccgaggggtg atttactcct ctgacagtga    420

cacggacact gtgcgtccat tccccgggcg ggcagaggac actcccagat gcccacgagg    480

ggcccagcaa gcactggcca                                                500
```

<210> SEQ ID NO 238
<211> LENGTH: 600
<212> TYPE: DNA
<213> ORGANISM: Homo sapiens

<400> SEQUENCE: 238
ctgcaggacc tgctcgttca cagatgttct cctagaagca gaagctgttt cttgttgcaa 60
acaaatttgc tgtgtcctgt cttaggagtc tcacctgaat ttaccaagga tgcatctgtg 120
cttggggatg gctcggtttg aggggtctga ggagcggctc ccctggatcc tttcctcccc 180
aggagcccac ctgccgagct gtcagcgtca gccccacatc tcaagatgag gaaatggagg 240
tcgaagccat gcacacgcag gcgtcctgct gacatgcagg ccaggcgggt gcctctgtat 300
tcagcagcct cagggctgtg gccagttcag gcagcagagg ggcctcatcc cggtgcttcc 360
ctgcaggcag ttgtggggcc ggcctgcagc aggggctcag acagggcctt gggagaggga 420
gggatcacag aggtgtccag tgacaggcag ggcgggcaga gcccatgggg ccttgggctc 480
ctcactcctt cggtcagtca gggtgacatc tggagccacc tccattaatg gtgggttatg 540
atttggttcc catgcagccc gtgccagctc gctgggagga ggacgaggac gcctgtgatc 600

<210> SEQ ID NO 239
<211> LENGTH: 5000
<212> TYPE: DNA
<213> ORGANISM: Homo sapiens

<400> SEQUENCE: 239
aagaggaaat tcccacctaa taaattttgg tcagaccggt tgatctcaaa accctgtctc 60
ctgataagat gttatcaatg acaatggtgc ccgaaacttc attagcaatt ttaatttcgc 120
cttggagctg tggtcctgtg atctcgccct gcctccactg gccttgtgat attctattac 180
cctgttaagt acttgctgtc tgtcacccac acctattcgc acactccttc cccttttgaa 240
actccctaat aaaaacttgc tggtttttgc ggcttgtggg gcatcacaga tcctaccaac 300
gtgtgatgtc tcccccggac gcccagcttt aaaatttctc tcttttgtac tctgtccctt 360
tatttctcaa gccagtcgat gcttaggaaa atagaaaaga acctacgtga ttatcggggc 420
aggtcccccg ataaccccca gctgcagatc gaggcctagt gcgagcacag gtcccccag 480 acccttccca gtgcccacca accggcggcc taggccaggt agaactggca gcgcctcccc 540
tgctgcaaca ccaggctctg gtagaaactt cagaaaacat gcaccggcaa aaccaaggaa 600
gggtggctgc gtcccgggtt cttccgcgca gctgtgtgta cacgcatgca cacacccaca 660
cgcacacacc cacgtgcaca cccccatgca cacgcaccca cttgcacgcc catgcacgca 720
cacacgcgcg tgcacccatg cgcacgcacc catgcacaca cacgcgcgca cacacccacg 780
tgcgcaccca catgtacaca cccacgtgca cacacccacg cgtacacacc cacgcgcaca 840
caccgctgtc cccagccgtg cagaacgatc ctccctgagt ccccggctcc gacccacacg 900
cagcactcgc taaacgcttc ccacgcagtc gttttgctgg gttgcgcttc acccacttct 960
cagagggggc ggccgaggca gaggtgtcgg ggatcgagca gctccgggcc tcaggggtcg 1020
ccccgccacc gttttccttt cccagatgct gggacggggg cagggagggg ctccccaggc 1080
tgaacccgac taggtcaccc tagaagcgag gcgagcttct cttctgtttt tcttcggcgc 1140
ccctgagccc ctgacagtgc ccaagctgcc catgggattg gattcgccag agcctcctac 1200
gcagacccca cccagggcca aagccaaccc caagccccac caccttggtg gtgtgggatg 1260
aaaagtgagc catcgagaga tggggtcccc ccaccccaa cccctccaag gacaaaggcg 1320

-continued

```
ggctgggaag cacccgcttt cacgtccgcc cctgcccggc tttcctagcg gaattggcgc   1380
cggcatcagt tgggggttgt gggatcagtg aggaatcccg tggggtcgcc tccatttatc   1440
agttgtgtgg ggttgggcga gcacccctag ccccagccca ggcgatcagg gcgcgaagcc   1500
cactggacgc ggatttggga ttaggacggg ggtgacagcc aggaggaccg cacctgccct   1560
ccccactcct gccgctccac ccctgccccc accgcaacac caaggtctcc accaggaaga   1620
tgggggtggg gaaaggacgc ggggtggggg ggggtgcggg gagagaggac acagggtcgg   1680
aagggtgagg ggtagtggca gaggcggagg ccgaggccac gcagctgcgg ggcgcaggga   1740
ggggcagagg aggggcgttc agatgggaac ctagtccaga cccgtcgggg ccctcgtgtg   1800
cggctcgtta tcctggaacc agagaggctg gagacccttg gcttgtctgg agcggaaccg   1860
tagtgtccaa tagagtgtgt ggggctcagc cctaaagcta aacattcttt atttcctgat   1920
gaccatgggg gcggagcggg ggaaaagccc tggccttata gtttagaatt ttataaaagg   1980
aaaggcgtgg ccactgacaa tttgcgcttc aggagtccca gagtgaccgc ctggctcgga   2040
gcagggaatg agggggtcct taactctgag atttgttttc tgagagacaa aggtgatggg   2100
tgaggcggct aagcctctga ttctctatag gtggcggtca ttcatttcag aacatgaatg   2160
gattcagtaa ataaacatga tagaaaaatg ccacaagccc taggcccatt ggagtggact   2220
ggacagtctg ttcccagtgt gtccctcagc ctcggtcccc caccccttccc ggagccctgg   2280
gggtcacaca catccctcct ggctgcctag cctgtgcccc ccgattcccc ccctccccgc   2340
cccgcgcgtg cacacacaca cacacacaca cacacacaca cacacacacc acacagcacg   2400
aggcgacaga gatatgagag agagcgagcg agagaggacg ggagagagag ggagtgcaag   2460
tgtgcgctgg gggtaacccg tgcatgcatg cattgggggt aacaggctgg agctcagatc   2520
cctcccccag cccccagcag gggggactgc aggctcctgg tctgagtggg gagctgggcc   2580
ccctggacag aggactgggc tgcggggtca ggaatgggca cacttcctaa ctgcaggaca   2640
ctctaagggc tttggtcatg cacacgcagc caagagaagg tgtcgctggc acacagcctt   2700
ccaggagcgg acttggagac ctcgccaagg accaggactc cccagcactc acactccctt   2760
aggcgctgaa gtccagagga cagaggttga gggcagagct cctgggagca ccagtggaag   2820
taggagggct gggctggaaa acctccccca acctcctatt gcaaagaggc tccagccagc   2880
agcctccaca ccccagtgat cttttaagat gcaaatctgc gccatcattt atttcctcag   2940
tgccttctcc agctcctggg atgcacactg cccgtcccca ggcccagaga cctgaccacc   3000
ctcattcctc cctcagccca ccctggggtc tctccaccag ctgacagcct tcctgcagtc   3060
ccctccccga atgctgctcc ctgaggccct cctggacacc tgcagggcag gcacagcccg   3120
cgggacctca cagcacttgc tccgggcaga gctgcagttt ggccaagttg ccagctccgt   3180
gtgggcaggg gccctggcct gtggctgcca catcccgggt gggggcacgg cctttcctgg   3240
cgtggatgct gagcaaacgt agggggaagg ggagtgaatg aggagagcca ggtagctcag   3300
gggctgaggc ctcactgagc agggtcccgc gtgaccggtc ccccaccgctg acggttcctg   3360
gggtaacact caggacaggg agaggcaatg gaaagagacg tggccgccct cgcatcctgc   3420
agctcccgca ctcccagcct cccagcctcc cacccagccc cccagagccc accagtgacc   3480
ccgcccactg ggtcctcaga tggctcccac gggatctcct gccttgatct cctgtccaca   3540
tggaggtgaa gtgggttgct ctgaatgagg ggtgccgagc ctagggcgca gcccactctc   3600
ctgggtccgc agcatcacgc agcccggacc acaggctcct tacaagaatc ggaagggtcc   3660
ctgcaatcgc ccttcgcact gaggcttcct actgtgtggt gtaaaaacac aggcttgtcc   3720
```

tcccttgctg cccacggggc tggagccgcc tgaaaatccc agcccacaac ttccccaaag 3780
cctggcagtc acttgaatag ccaaatgagt cctagaaagc gagagacgag aggggaatga 3840
gcgccgaaaa tcaaagcagg ttcccctcct gacaactcca gagaaggcgc atgggccccg 3900
tggcagaccc gaacccccag cctcgcgacc gcctgtgacc tgcgggtcaa ccacccgccg 3960
cggctccacg ccgtgggcac agactcaggg agcaggatga gaaagctgag acggcgcagc 4020
cacggcccgg tgccttcacg cgcacagcga cacagcccca gccagcgggg cccacgctaa 4080
ggcggaatcc cacagaagcc tacagagcga gcgcgcgcct gtgcttccca aaacggaatg 4140
gaaccaaggt gacttctaca gaacgatctg aagccctggc tggcccttat gctagtctct 4200
tgggagcgtt ccaaatgcag ctcaatatta cttacttgac ttttatcttt cctccctggt 4260
tcgtggtatt tataactggg tcatctttta actatttgca acgtagcttc aggggagagg 4320
gggagggctt tataaataac ctgtattatt attatgcagg ttgattctgt tccctgagct 4380
aaagggaaca tgaaaataca tgtctgtgac tcatgccccc ccaccccccac tccagggtgt 4440 gctgaggagt ctctcagctg ccccggggtc ctcgagcagg ggagggagaa aggctggcgc 4500
tgcgccctcc atcgcgtgaa gccaggggat tttgctctgc gacaagctga cttggctctc 4560
gtattgtttg cagaatcacc cagttccaag gcagtccctg cgggcaggtg cagctgtgcg 4620
ggagcttcag tcctgtcccc aacacccagg cagtaatggt tccagcacgg aaggtctacc 4680
tacctcccac tgcacagccc gagggctgtc ctggaggcac agccatccgt ccctgggtgg 4740
gcaggcacgt ttatgacccc cacccccacc cccacccccc acgcgagtca gcacgttcca 4800
tactcgggtg atcgtgctca tcccctggtc atgtcatcgg gatctgagtg ccatccgagc 4860
agagagctgt ggcccggtgc cgggggtgga cttcatctat tccagggaac caaggatgca 4920
tgatttgcaa acaaaaccag aagcgcaagc catctcctcg cctcccctga tagccgtgct 4980
gcggagcctg agtgctggag 5000

<210> SEQ ID NO 240
<211> LENGTH: 600
<212> TYPE: DNA
<213> ORGANISM: Homo sapiens

<400> SEQUENCE: 240
caggaaccac gggacctgct gcctagcggc cctgttccac ccttggccgc tcgcaaaatg 60
tttaggcttc ataaggtttg cccagggtca caaatttaac tcacagcaaa caatgaaatc 120
agcgcatgat tttcgagccc tcgtggtcac cctcccttcc tcctgccctt tcctgcatgg 180
gcagcagcag ggtgaggagc tgctctcccc aggcccaggc tggagtccct cagacgacct 240
gccggccagg gtaccccccct gcccccacac agcgcctgac agagcccccc acactggggg 300
aacgtgggga cccaagcagg ggcagcggcc tcaccgggca ggcggcgacc tgcatcatgg 360
cgtccagccc accctcgggt gcatccaggt ttccggaaat cagctgcttc ccgacctcgg 420
tctgaaactg gttggagttg ttggtcagct tcagcacgtg cctgaaggca aacgggggct 480
ggcactcttt ctccttgttg gggcatgggt ttcgcagctt atcagggtgc gtgttcacga 540
acggcagcac ggtcttgtcc acgaaggacc cgaagcctgc agggcacatg gaggggctgg 600

<210> SEQ ID NO 241
<211> LENGTH: 400
<212> TYPE: DNA
<213> ORGANISM: Homo sapiens

<400> SEQUENCE: 241
tgcgtttagt gtaaaaatat caggtgtggc tgcacggagt gaaaaatcac aggctccacg 60
gagccgggag gcctgctgcc ctgccctctt gctttgatga ggaaatggcg accgcagaag 120
gaaatgtagc agcaccggca accggcatcc gtggggccac gccgggctgc ttcccagggc 180
cctccagcca agcagccaca ggaaagagta gatgttgatc ccaagctagg actgaggagt 240
ccgtccctaa gagccgaggg agtcaggtgg gcgaaactgg ccgcatgtct gggtacaact 300
gctcagggtt tctcatctgc tgaatcacca agctaggttc tgaagccagg cgtgagtgag 360
caggactgga gcaggattct gggaacaatc ttttccctcc 400

<210> SEQ ID NO 242
<211> LENGTH: 2000
<212> TYPE: DNA
<213> ORGANISM: Homo sapiens

<400> SEQUENCE: 242
gctggggaac tgaaggaagg gctgtggagc ctgaagcctg ggcctggcct gtgctgcggc 60
cgcaccgctg ggtgatgcag gagccactcc acctccctgg caccccagcc tcatccggca 120
acctgggagc gtgggcctcc tgcccctcca gggaggccct ggccgtgtcc tcatggggcc 180
cctccaggtc cttgtggctc caggtcggga cagtggctgt gagatctgac cctcccgttc 240
cccctccacc aagtaggaga aaccccggag catgagccct cgtccttcac cgtcccgggg 300
acagggggac ccccagatgc tgcacggctg acaggccaac gtggcagaag ctccagcttc 360
acaggaagcc agtgaccatg agagtctgta gctgtaacga agccacagag ctgtggcttt 420
ctttcccctt cagctctagg aaaggttatc tgccctgcac agatctccgg aggcctggct 480
gggctctgag agcatcagac tgattatcgt aagaaaataa tctctgcaga cacattcctt 540
gctagaagca ggggacaaag cccagcttca aagacaattc cacacacgcc ctccctgccc 600
tgcacagctg cctgccgggt gggagcagag cccttgcagc cgggctcagg ggcctgggca 660
gggacagcgt gtggcagggg cacagctgag acaggagcct caaagcgaca ccaacccgac 720
gtgaagctac agttgaggag acacagctgc ccccattccc gggcctcatc tccacagtga 780
gacgctggac tctctccctg acccaccgtc tcttagaacc tcccctccat ccggagcagt 840
tcggcagccc cagggcagcc aggggaaccc tgccgagtgc ctctgggccg ccacagaccg 900
cagagcccgc gggagccttg ctcacacagc ctcaggtcca ctgtggtctt gggggaaagc 960
cctgtcctgg gacaggggag ccgggggtcc tggccctgga ccaccatctg gggaccacgt 1020
tgtcacgcct gcaaagctcc ctgccccacc cccatgtgcc ggctggtgtt gacacctttg 1080
tagagtggga acctgcctcc gaccccagcc tgcagccaca gggcaggtta tagaccaggt 1140
gagagggcgc cgcgcccaga accaaggagc acaagtccgc agtgcccatg agatcctcat 1200
gctggccggc gcaggagcca tcctcggcct ctgcaggtcc tcgtgggaaa ccgcgggggc 1260
acgtggggcg gctgcagggt ccgcaaagcc ggctgtttgc gaagggcgca gctccacctg 1320
gaacagccga ggccgcccac gcgcttcccg cgggatcaga gcagcctcca cggctgttgt 1380
ctcaggcacc acgggatgcc tttcttcgtt tcaatagctg tgggaaagcc tcaatcggtc 1440
ctgaaagaac ccagatgtgc agcaatgaca aggccttctc tgagactcta gaaccttctg 1500
ccatctcaga caggagggag ccgtgaggca ggcgggagat ttgcagtcag caaaggacgg 1560
gcaggtgggg cagctgcaca cccagggccc tctccacggt cttcccgggc ccacccctcc 1620
cgcggtcctg ggtcatccac ctgctggcct cactctgccc acgcggccag gtcccaccgg 1680

```
cccctgagct caacagacca aagctggccc gaccccaccc ccaagaagaa tgaaacaatt   1740
ttttttacc tcttgcagaa aagtaaaaga tcatttattc attctgtttc tagatagcaa   1800
aactaagtgt caaaagcacc ttctgcacac agtctgcaca cactggccgg tggtcctgtt   1860
cccgcaaggt tgagctgtgt tccagagaca tgggtcctcc gggtgatgag gagccgctgg   1920
agggccctga gctgcacgtg ctaatgatta acgccccgtc cgtgctggcc ggtttctcaa   1980
atgcctcctg acgattgcgc                                             2000
```

<210> SEQ ID NO 243
<211> LENGTH: 2200
<212> TYPE: DNA
<213> ORGANISM: Homo sapiens

<400> SEQUENCE: 243

```
ggcctgagga gtcaaacggt gcaaaccctg ccccactctg tttgggaagc acctgctgtg     60
tggcaggcgc tgcgcttggt gctggggata gaccatgggg aagaaacaca cagaacctgc    120
cctgctctca aggaacaggc cctgggggcg gccaggggca gagacccaag gcagacaccc    180
acacagtggc gtaatgacag tgcttatggt ggggacctgg ctgcacagca ggtcagcaag    240
gggatgttca ggtgacactg gggcacgga gacccagggg agagtggatt gacagagggg    300
acgctgggca aatgtcccga ggctgaggtg gagttgcggg aaggaggagg ctgccgggca    360
gaggcgcaga gagctttgca ggtgttggca gagaccagca ggccctgcga ggcctggggt    420
gtgtcctcag ctgggagggc catagaagga tctgggcttg cagatgctgg tgcagactgg    480
aggcctgggg tgtgagagtc caggcggggc tcctgccaac acccagggga gtgggcctgg    540
gccaggtgga ccgggagctg gcacggtggt caggtgcttg gaggctgcgt gccacgctgg    600
ggacctggag gtgtgtgagg aggtgtctgt tgctcctggg gctgccgcct gcagggctgg    660
gtgtgcagca gtgcggggca atgaagtggg cgggttctgg gatggtggac gttccctttg    720
ttgggaacgt gttggtgcca agctgccatt tgagtttggc tctgaggggt ctgggcaggg    780
gacacacagg gaatcacaca ggatggagtg agttcccagg gacccagggt ggcttggcct    840
gagaacagct cccactccca gatgtgtggg aagccctcgg caccaagcct cagcctctcc    900
atctgtgaaa tggagacaac gtcactggac ttgcaggctg tccatgaggg tgatgcgatc    960
agaaagggtg gagttcctga acgccccggg gtcggggtct cacagcagga gcttagctgg   1020
tgtcggcatc tcctggaccc gtcctcagct ccgagcgccc agtcctgcca cctgtgtcca   1080
agtctgcact gtgcccacga ggccctcaag gccgcagaca gccccacact tctcggacgc   1140
cgccccagca cggtccttgt gtgaggtgga cactccttct ggacgccgcc ccagcacggt   1200
ccttgtgtga ggtggacact ccttctggac gccgccccag tacggtcctt gtgtgaggtg   1260
gacactcctt ctagggaagg agtagtaact cttgggtggt cgggtagttg ccatggaaag   1320
gggcagtaat gcccaggtat tgccgtggca accgtaaact gacatggcgc actggagggc   1380
gtgcctcatg gaaagctacc tgtgcccctg ccctgtgtta gctaggcctc aatgtggtcc   1440
agtatctgag caccgcctcc tgcctcagat gttcccgtct gtcaccccat taccagggcg   1500
gcacttcggg tcctttccag ccatcattgt cctggcattg ccacagtgga cactgccaca   1560
caggcttgtg tgcttgcgcg tacccaggtc ctcacctctc tgggataaac caggcacgtg   1620
gcggccgccc cattttccac ccgccagcgg tggaggagtt gcccagcctt gcaggaaaac   1680
agctctcatg ccagcagcgg agcatcctat tcaagttttc tcagggctgc cagcacaaat   1740
```

-continued

```
gctgcatgcc gggcggcttc ctcagcagac cgttgtttct ctgcgtcctg gaggctggac   1800

gtcccaggtc cccgtgtggc aggcccggtt cctcccgcag cctctccttg gcttgtgggc   1860

ggcgtctcct ccctgggtcc tcgcagggcc acccctccgt gtgtctgtgt cctccctccc   1920

cttataagga ccccaggcag actggatcag ggcctgccct aaggactgaa ttttacctta   1980

atcacctctt taaaagctgt ctccaaatac agtcaccttc tggggtcctg gctgttaggg   2040

ctttgatgca tggatttggg ggacaccgct cagcccctaa cagcccccat cctctgcctg   2100

cctttaccat ggggctgagc ccagccctgc aggagtcccc tggtttgatg tctgctgtgg   2160

ccacggcgac cctcaggctg ctccagccgc acttgtgctt                         2200
```

<210> SEQ ID NO 244
<211> LENGTH: 1600
<212> TYPE: DNA
<213> ORGANISM: Homo sapiens

<400> SEQUENCE: 244

```
ggggagtctc caggggctgg ggctggagcc gcatcagaga ggaaaggggt gtttgaaaaa     60

ggggcagggc ctgggaccca ggaaactgtt cttccagaga cacccgtgaa gctgagcttt    120

gcctctcagg gaagctgtga ccccacgggt gctgcccaga gagatcgggc caggtggagc    180

caagatggac tggaattccc cgacggggac aaggggccgg acgaggctga cttgccctgt    240

ctgatgaatg gtcaggtttg ctttttctcc tgaaaacacg aggcagtgat cccggccagc    300

taattccagc agactggaga cgggatggtg gagaatgagg ctgtgggcgg gaagagcaga    360

tgggactcgc cagcatcctc acggcagggc cgcgctattg ccctccctcc cctcctactc    420

tctggggtcc caggagcccc agatacgcaa tgctgccagg cgatttctgg cgccccgcag    480

acccctgccc ctggagttgg gccaggtccc ggctggagca aagggggctc cttcaagccc    540

gctcctccct gtcaaacccg aggagcctga caggcgcagc gtcaccagcg tcaccgggcc    600

atagtgagcg gccaagccag cgtcaccggg ccatagtgag cggccaagcc agcgtcaccg    660

ggccatagtg agccgccaag ccagcgtcac cgggccatag tgagccgcca agccagtgtc    720

accgggccat agtgagcggc caagccttgg tctgccagag ccggccgcac cagaaggatt    780

tctgggtccc cagtcctgga ggagcacacg gtttacacca ggccttggga ggggaagagg    840

caaggcgtgg gcccagccct cactccccag gagaaaccct gtttgagcgg cagaggagac    900

tggagagacc ccagggcggg gatccctgag aggagagaaa cccggaattc atccacggag    960

gcgttcaccc agaggagacc cggagcttct ccaggagagg ctggattgct ccaacagggg   1020

ccctgaggag ctgatggcaa gagcggaagg cagctctgac tcgtgcgtct gactccaggt   1080

gtggccgttg gggctacagt gggaccagcc tgttgtcact gaacccacaa agtgcctccg   1140

agcgcgggtg gagagagggg gacctcccac cgtctgctgg ccttgaatct tgaatctaat   1200

tcccgtctgt gctttgatgg gagaggcact gggagcgggc ggctttttca gttcctttta   1260

tcttgaatgg cctttggggg attttcacag attctgagtt caaagcccag ggaggtgtgg   1320

gaacgtgaca ttcctcaccg cattcctcac cgcattcctc tgtaaaccag gcggtgttgg   1380

cacccatgag cctgtgtctt ctatgacatc aggagtttta tccctcacgt cagaaatcag   1440

ggttccaggc gccttggttt ttcttggcgc cagcggcttg gctatagaag aaaaactgaa   1500

ggggccaggt gcggtggctc acacctgtaa tcccagcact ttggaaggcc aaggcgggtg   1560

gatcacgagg tcaggggttc gagaccagcc aacatggcaa                         1600
```

<210> SEQ ID NO 245
<211> LENGTH: 7000
<212> TYPE: DNA
<213> ORGANISM: Homo sapiens

<400> SEQUENCE: 245
gctcctcagg gggaggttcg gggcctttgg tctctggact tgggcagcag aaaggaaaca 60
tccctggggg cctgtggtga cccccatcct ccccagggtg gtctggcagg ggacactgtt 120
ttccaaagca aagccagagc gccaagggct ctcgggattc acgagatcca catttatccc 180
aagttagaac agcacatctg tgcgtgcaaa cttcattctg acttcggccg gctgtccttc 240
ttgcccaaag caccgtgagg cctcatccct gcatccctgt tgcttctttc atgtgggatg 300
agaacccagg aaggggctga gtgtgactcc tctggttttt agagagcact gcccccgccc 360
cgccccctcc tgcttcccca ccttttcaca gttgcctggc tggggcgtaa gtgaattgac 420
agcatttagt ttgagtgact ttcgagttac tttttttctt tttttgagac agagtctcgc 480
tctgtcgccc agggtggact gcagtggtgt aatcttggct cactgcaacc tctacctccc 540
gggttcaagc gattctcaca tctcagcctc tggagtagct ggaattacag gcgcccgcca 600
ccacacctgg ctaatttttg tgtttttagt agagatgggg tttcaccatg ttggccaggc 660
tggtctcgaa ctcctgacct caggtgatcc gcctgccttg gcctcccaaa gtgctgggat 720
tacaggtgtg agccaccgag cctggcctgg agttattttg ggagagggca gcccctggtt 780
cagcgtggcg aggctgcgct tgctctcccg ggcgggcgtc cacaccctcc tcgccgagat 840
ggagaagccc aaacccctgc agcgctcccc catcacgtcc ggccctggaa gcccccggaa 900
accctgccac gccctgagtg ggagagcgca ggtccctttc cggccctgga agcccccaga 960
aacccttggg tgccaggcct ggccgggaca gcagcgacac tgcatgctca gcccttgcgt 1020
gagaccacgg gagtgtccgc cctctgcacg tgctgctgat tgcccacttc gtccagcagg 1080
tttgggagct tgtggctgca tcctcctgca gacacttgcc cattctgggg cctcctctct 1140
gtcttttctc ctctgttgag ggtctggga gggaggcctt ggagggtacc catgctgctg 1200
ggactgatgc tccccgcggt ggaaggagct gcctcttgaa cagcaggggg ctgagcagag 1260
gggaggggat gcgggggtgc cgtgcacaca ggtgctctca ggacgcaggg gcttctcagc 1320
cctgctgtcc cagggctgca ctccagcagg gcagactcct gaggtgcaga caccccagct 1380
tcacgctcac acttctggaa ggcgatgtct gtgcgtttgc tttctgctgc agtttaaaaa 1440
gccgggctct ctccggagcg tgtgtagggc ctggtcactg gaatatctgg actcagtgtt 1500
aatggcagcc acgctggggg ctgggcccag ctttctgttc tccgtgtggg tgccatatcc 1560
acctccatcg cagccctttc tctctcgacc ttttaaatca cagtgtcacc tccccctgct 1620
gtcctgccag tggcccctgg aggcttctcc ccaccccttt cttctggggc aattcttaag 1680
gctggcattg aatcaggagg ccagatgtgg cccctagtaa ctcaccagca gtccctgagg 1740
cttctggctc ccctggccca ccagcctccc atgtctgcct caggcctctt gacccgcctg 1800
gcactgacca gactgtgtgc ccgggtgccg tgcccatggg ctccgcctcc cccaggcagg 1860
ccccctcttg ctccgcggcc acccctgctc ttgacctcac acctctgcgg tgtgtctgga 1920
cacaccagca ccacggcggg cggggagcgg aattctccag gtggggtggg caggccggcg 1980
ggtgttgagg tctctgtgca tgcttgtgcg taccctggac tttgccgtga ggggtggcca 2040
gtgctctggg tgcctttgcc agacaactgg tctgccgggc cgagcattca tgctggtcgc 2100
catcacgtga ctcccatgcg ccctggccct ggggttgggt ctgcaggact gagaaccagc 2160

-continued

```
ggaagggggg cgaggcctcg ggaatgcgcc ggcaactggc gatgagctca ggcctgacta   2220
atgagcccag gtgactcata cacccggggc ctggatgagt ctgactgggt caggacttcc   2280
ctgcttgttc tgtcctggga gatgttgtcc ctggccctgc agagccggga ggacacgagg   2340
cctcctgggt cacagccaac gcagcctact cctgcccact gctcgcgccg gccaaggccc   2400
gtcggcacca cctcctccat gaagccttcc tgactgcccc catccctctg tgggcagctc   2460
gagtgtgcat cttgagtgct gtgcaggttg gggtccggcg ctcctgcagg caggcggcgt   2520
ctgggcctgg gggctctcag agtttgagga gcgtgtggtg agggtggcct cgggcctcaa   2580
agacgcagcg ctgtgggaac cgggagactg gctgagcccg ctctgaggaa ggtggggcca   2640
ggggcaccct cagctgaccc ggcgtgcagg ggtgaccagc caggcgtggc caaggatggg   2700
gtctctggga tcaggagact tcagtagcag ccaggaccga ggccaccagt ttccaccctg   2760
gcattttcca tcttttgaag gactggaaac gattggattc tttaactttt ttaagttgag   2820
gtgaaattca caacgcataa aattaaccat cttaaagcga acaattcggt gacatttagt   2880
acagccagaa ggctgtgcag ccatcaccac tgcccaactc tagaacattc acacgccgga   2940
gagagggagc cctgggccat cacgcagcca ccgcccggcc ccaagaacct gcgagtccac   3000
tttccacctc tggatcggcg gttctggacg ttcatgcagg tggttcccgc agtgcgaggc   3060
cttttgtttc gggctcctct cacaagcctc acgtttccag gtacgtcgtg gtgttgtgca   3120
gacccacaat tcatcccttt tcatgggtgt gtaatagtcc accatagatt ctctacgttt   3180
taaagcatgt tttatgtgcc tgaaatgtct ctgcactcga gactatagct tgctttcttt   3240
cttttctttt ttttttttta atttgagacg gagtcttgct ctgttttcag gctggagtgc   3300
agtggtgcga tctcggctca ctataacctc tgcctcccag gttcaactga ttcttttgcc   3360
tcagcctccc gagtagctgg gactataggc gcgccacccc acccggccaa tttttttgta   3420
tttttagtag agatggggtt tcatcatgtt ggccaggatg gtctcgatct tccgaccttg   3480
tgatctgccc gcctcggcct cccaaattgt tgggattaca ggcgtgagcc accgcgccca   3540
gccgagacta cagctttctt taactgcatc cctggaggga tctgagagtc tctttccctg   3600
tctcctttcc tttggaaaac atttcagcca gggctcccca agatgaaagg ccagagtccc   3660
aggcatgggc gttgcaggtg cacagttgcc acggggagct gtgggtgatg gtcgctgtca   3720
gcgatggctg ctgcaggtcc ctgtgaggaa ggggcagtgc cacagcagga ggagagggag   3780
tcagcggacg ttgattggca gtgcccgccc attccatcat tcagtcaccc actgtgcacc   3840
cagcacccag gctcggctgc atagaacatg gcccaggaag gctccacttc ctgtctcctc   3900
ttctcccctc tccagtctca tgatggggct ggaggcatct tctagttttg agttctgagc   3960
taatgaacat gctcatgagc aggcggcagg atcccaggac ggtggagctg ggagcctgac   4020
tgcgggtgac ggacaggctc tggcagcccc tgtcagcatc ctctccaggg catgtgaaag   4080
ccagtgtgtc ctcagctgcc agtgccccct ccccacctcc tctgggccca tgtgcacggg   4140
acctgggctc ccccaaccaa gcctgcccgc cttggttcag cagaacggct cctgtctcta   4200
cagcggtgcc aggccaggag tgctgtgtct gtgaagcggg gtcatggttt tggggccctc   4260
atctccctcg cgccctctca ttggggaccc cccgtctccc tagcgccctc tcgtcctctc   4320
ctgcatgtgc tgtgtctgtg aagcggggtc atggttttgg ggccccccgt ctccctagcg   4380
ttctctcgcc ctctccagca tgtgaagtgg ggtcatggtt tgggggcccc catctcccta   4440
gcgccctctc gttggggacc ccccgtctcc ctagcgccct ctcgccctcg cctgcatgtg   4500
ctgtgtccat gaagtggggt catggtttgg gggcccccta tctttctagc accctctcgc   4560
```

```
cctctcctgt atgtgaagtg gggtcatggt ttgggggccg ccatctttct agcgccctct   4620
cgccttctcc tgagcgtgtg gaactctgtg gtggtcagag ctaaggttct gaataggtcg   4680
aagcacctcc ccggtgcctc tcaccctgaa tgctctggga ggacacagcc ttttcatagg   4740
ctacgactga catggcagga ggggcctgcc tgccacccgg gtcctctgct gcctgctgct   4800
tgctggggag ggggctcgag actgggatcc tgggcttctg ctccagctgt gcccaaggga   4860
gctgctgagg agggaccggg tggggcatcc actctgggca ggttcagggt cattcttggt   4920
gaccccgggt ccggttacaa aggctgatgg agcgcgtggg tggctgccta agtctctgga   4980
agcccaagaa tgtggagatg gcgcgtctcg gcccggggtc tcgtggctgg tctgggagaa   5040
cttgccttta tttctaggca ggaggctgca ctgcaaggga gcgtcagtgg cccggctggc   5100
tttccccggc cctcagcccg cactcgtcca ccaaagcaag ctcctttgtg gggctgccct   5160
gggaagccgg gatcacgagg ctctgccggc cgtggtcacc ccatgaggca gggtcagctc   5220
gggagcaagg cggatcagat ggaacagaac acgtagacca cctcgcccgc ccttagtcag   5280
ctgggccatt gaaaatcaag tccgtagaaa gacctagaaa taagtcccgg ggtgcccttg   5340
cctgttgacg ggcgggccga gcaggactgt tctcaggcag gcactggtct cttggcttcc   5400
aggtggtttg tttgctggtt tgaggctggg ggtgacgctc ctgtgcggga ggaggtcgca   5460
ttccattcat agcggcttat ctgggctgtc aggcaggcct gggagggagc ctgcctctgt   5520
gctctccaag ggtgggcgac ggacagacag ggtgtcccac cccttctggg ccaaggacag   5580
agggtcagtg tttgcagaga cctggggagg cccaggtgac ctccaccgag cacctgctgt   5640
gtgcagggcc agtgctggct gcagagacag cggagcgtgt gtggacccgg cggcccaggg   5700
gagggggca ggcaggaccc ggcggcccag gggaggggg caggcaggac ccggcggccc   5760
aggggaggtg ggcaggcagg acccggcggc ccaggggagg ggggcaggca ggacccggcg   5820
gcccagggga gggggcaggc aggacccggc ggcccagggg agggggcag gcaggactcg   5880
gcggcccagg ggaggggggc aggcaggacc aggcggccct gggggtcagg ggtggaggcc   5940
aggcctagac ggcccacagg agggtggact cattctgacc gattcctgga agcccccgga   6000
aagtggtgat gttctggagg gcccagcaga ccccaaggcc cccaagacaa tcccagctgg   6060
ctctctgcgg ctctcggtgt ctgccatttg agacaatttg ggcacaggca gggcaggccg   6120
tcgcggacgg tctaagccgc gcgcattggt gggggcagca gagcccctgc tctcagctcc   6180
tcggggtaca gcgggggtac caggcgggtg agtgggtggg tggtcactgc tcctgccaag   6240
ggcagccctg gtttggtttg cacttgctgc cctggtgacg gctgctctca ttcctgcccc   6300
attgctaaca agggtgtcat aagctacttt cccggcccac atcctattaa gcccatggag   6360
accctcccac agctgagcct gctgtgggct gcaggccctg ggcggtgccc acctcggtcc   6420
ccactggcct ccttccagca ctttagagca gacacaggtt ggagataagg aaagttccag   6480
agcacagact ggaacaagcc ccaggcctct ccctgcccca gcagggcctc cctggatttg   6540
ggggacaggt gccctcatgg ggggtcctga aggtcagagc tggggctggg gctgggctgg   6600
cggaggtggc cttggcggag gccacattcc agggtctcag tgagagtctg tggcaggcag   6660
ccttgcagat gccgctgagg gaccccccac ttcatgttgt gggtgatgtg gtccattgat   6720
tgcctccagg tttaaatcag gtggatattt acctagcggc ctcctctccc tctgcacagg   6780
gcctggagtg ggatggactg gggtgctcag ctggaggctc tgcagacaca gccccctggg   6840
ctatgcaggc cctgctggga gccacattgc catttttcat cacccacttt ttgggtgaga   6900
```

acccccctcga gtcctaacat ctgccgcatc tcagagcctg tggctccagt cagagcatct 6960
ggaccatact gctggggtca gagcgcggca ggacaatggc 7000

<210> SEQ ID NO 246
<211> LENGTH: 1500
<212> TYPE: DNA
<213> ORGANISM: Homo sapiens

<400> SEQUENCE: 246
tgccaccacc atcttcaggt agagcttctc tctcctcctt gctgggcggg gcccctccct 60
ggggaagcct gcaggaccca gacagccaag gactctcgcc cgccgcagcc gctcccagcc 120
agcagctcca acgccctgac gtccgcctgc gcacgccact tctgcacccc ctggtgatgg 180
gctccctggg caagcacgcg gccccctccg ccttctcctc tgggctcccg ggcgcactgt 240
ctcaggtcgc agtcaccact ttaaccaggg acagcggtgc ttgggtctcc cacgtggcta 300
actctgtggg gccgggtctt gctaataact ctgccctgct cggggctgac cccgaggccc 360
ccgccggtcg ctgcctgccc ctgccaccct ccctgccagt ctgcggccac ctgggcatct 420
cacgcttctg gctgcccaac cacctccacc acgagagcgg cgagcaggtg cgggccgggg 480
cacgggcgtg ggggggcctg ctgcagacgc actgccaccc cttcctcgcc tggttcttct 540
gcctgctgct ggtcccccca tgcggcagcg tcccgccgcc cgccccgcca ccctgctgcc 600
agttctgcga ggccctgcag gatgcgtgtt ggagccgcct gggcgggggc cggctgcccg 660
tcgcctgtgc ctcgctcccg acccaggagg atgggtactg tgtgctcatt gggccggctg 720
caggtaactg gccggccccg atctccccac cctttccttt ttgccttgcc aggtaagtgt 780
gggcggggct gacgtgagcc tggtacaggt tccccccaca tcgaatctct acgttcaggg 840
gcccgtggcc ctcgggaggt gggagagctg ggagtgaggc ctcctgtgtg gggaggaggc 900
cggcgtctgg acaggaagag ggctggatga accgcagccg atgtgtccag gtgccacctg 960
ggcctggagc tccctgagca ttttagcgca tttagtcctc agcacggtcc cgagataccc 1020
tgccatgccc cgagtcacag aggggaaact gaggcgtggg gcagtggcgt gactcacccc 1080
agggagccga gattcccgct caggtgtggc tgcatcgacc ttgctccggt cactaagctg 1140
cacggttcga tgcgcttcct gggagcccca gcgtgctcgg gccaagggtg ctgccgcgtg 1200
ggcagtgcag agaccctacc agcgtgggga ccagggaggt ctgcagggcc cgtcctgaga 1260
gggagccttt catgtccccc tccccatcct gaagcacaca gcctccctgc cacagtgggg 1320
gccgcttctg ggcccagggg acgttgcccc atcaccgtgt ggcctggcct tgttgctggc 1380
tggacagttg ggggcaggaa gaggagggaa agggggactc tttaacctcc tgggggcagg 1440
ggcagcccag aaaggacccc agcagatccc tcctctgtgt ccgggagtag acggggcccc 1500

<210> SEQ ID NO 247
<211> LENGTH: 2000
<212> TYPE: DNA
<213> ORGANISM: Homo sapiens

<400> SEQUENCE: 247
gggctccaca gcggcctgtc tcctcacagg gttcagccca gtctgctctc actcatttgc 60
tgattcattc tttcattcag ccagtcaata gtcatggccc ctcctgtgtg ccgggtggcc 120
atggatattg ccctgggtaa cacacagcct ggccctgtgg agcagacagt ggggacagcc 180
atgtggacag ggtgcaggtg gatggcaatg gcagctgggt caggaggggc tgagggccgt 240
ggggaaaggt gcagaatcaa taggggcatc cggactgggg tgcaggcctg ggggctggga 300

```
tttctagggt ggaggtcacc tctgagggag acagagcaag gccctgggag attagaaggt    360
cgaaggtcgc cgtgttgagg tcaggggccc tgaattggag ccgcggcaaa ggagagggca    420
ggtcagggca cgtggtgagt gattgctgcg gcttctgagc acggctgggt ctgtggggcc    480
tgagcagagg tgacccgcga tccggcgcca cggcaggcag gactccccac ccttgctgct    540
gcctacaccc ccagggcagc cccagagtcg ggggcgcagc tccctgcttg ccagttcaga    600
gcccagcccc tctcacccag cccagaggag gacacagatg gaggaggggc acccggaggg    660
tccccccgcc gacaggcccc acgtctccca cctgcaggac aatgaagtgg ccgccttgca    720
gccccccgtg gtgcagctgc acgacagcaa cccctacccg cggcgggagc acccccaccc    780
caccgcgcgg ccctggcggg cagatgacat cctggccagc ccccctcgcc tgcccgagcc    840
ccagccctac cccggagccc cgcaccacag ctcctacgtg cacctgcggc cggcgcgacc    900
cacaagccca cccgcccaca gccaccgcga cttccagccg gtggtgagtg cccccccaaa    960
gtgggcttgg ctccatctag cccctcggct ctcggcagca gaagagggcc cagcccctgc   1020
agagctgctg gggtcccag gcttcggcca tgggtggggg tctggcggct cagggccact   1080
cagggcggct tggctggccc tggacttgc cctctggtgg ccaagcagtg gtcatgaaag   1140
tccagccgct gtcacatcct tgaggaaccg gcgtacctcc gcctacagcg gcagctgggg   1200
gcacccacgt ggcccggggc tgctctgacc tggcagcgta tgggggctgc tgcctgggcc   1260
cctcagtgtg tcacttgcgc gcctcccgct cagcgcccct cggccgtgcc tgtccacaca   1320
ggtgcggggc cggggtggtg cgcccggggc ctgggtgcag ggggcagcgt gggacacagc   1380
ccgtgacgcg cccctctccc cgcagctcca cctggttgcg ctcaacagcc ccctgtcagg   1440
cggcatgcgg ggcatccgcg gggccgactt ccagtgcttc cagcaggcgc gggccgtggg   1500
gctggcgggc accttccgcg ccttcctgtc ctcgcgcctg caggacctgt acagcatcgt   1560
gcgccgtgcc gaccgcgcag ccgtgcccat cgtcaacctc aaggtgggtc agtccagtcc   1620
tgagggcgcg ggctcctcgg cccccacttg acctctgggg tgaactccca gcggggagct   1680
cccctctagg gcctctggag gccaccatgt tacagacact ggcgcctagg ctggcgactt   1740
cagggcaggc tccgggtggg tcacacccct ccaggctcag gccaggcctc tgcatccctg   1800
ggcactgcca cgtcccccag ggcatcccat gaggcccccc cgtggccccc tgaccccccg   1860
ctcccccggc agtgcccctc agagggtccc atgctgctgg accaagtgtc cacacaggtg   1920
atagggctca catacaagcc tggaatcagg aaccgtcctt tgggcctcta gtgccatgcg   1980
ggctggtggc ccctctgcca                                                2000
```

<210> SEQ ID NO 248
<211> LENGTH: 2000
<212> TYPE: DNA
<213> ORGANISM: Homo sapiens

<400> SEQUENCE: 248

```
gcctggagtg tagtcctgct gaaggccaga gaccacacac tccacccaga ctccggatct     60
ccctccccag caggggatg gaggccctgc cgctgggagt gctggtgtta tgtggaaggg    120
ctgggcttct ccagggctcc tgggaggcct aaacatcttg caaggttttg acgttaatta    180
ctattatgat tgctttctgt gtgttactgt tttccccaca ctttagccag ctaatgtgga    240
gctacagaag gccctcgccc ctacccctcc agatgtccca gcccatgaca agcaggaagg    300
ccgggtgctg ggagacttcc tggggctgga tctgacatca ttccaagcag atgataacct    360
```

-continued

```
gccttcccga tttccaaacc cacagcaaga caccctggag ttatttataa atgcgagccc    420

ctgggtgcac ttctgacggg accagcaccc tgacggccat gagagggtgg agacagcgca    480

ccccgagctc agggaggcag gaaactctgg acctggaggc cgggcaccat gagggacacg    540

ctgcaggccc agctgctgcc gcctggggcg gggctgccct gcaggctccg ggaaaaccca    600

gaaccaggcc ggatcagcgt gtgtcaagag gcggggcgtg agagatgagc tgcttttttt    660

cttcacaggg ttggcaggaa ctgcaaataa tagaaagtct ttagggtcta acacgctgcc    720

ctgaaaacac tatcattact ttcctaatga ctaactgtgt ctttcagccg gcggggcagg    780

cagctgaggc cgcaggctcc cgcagaggac cgggggaggc tggcagcctg taatctgggg    840

gcgctgacag tgctctgccc agaccctcgc gccagctcca gctccagcac agcagccctg    900

ggtccctctg gccccctgcc cgcagagtcc aggtgtggca gaggccgccc agtatccctt    960

ctcctcctcc ttttctaaaa acagagtctc acgatgtttc ccatgcgggt ctccaacgcc   1020

tgggctcaag cgatccttct gcctcggcct cccaaagcgt tgggattaag gggcgagcca   1080

ccgcgcccgg cccaccttcc cttctggttc atttccagta aggtcctgtc cacagcgtcc   1140

ttcccagcat tcccaccagg ctgcaggcct tggcctccct cccctccatt ctcattctcc   1200

ccgaaaccgc caagcgcgtc caaagcacgg gttcgccaag cgcccccccc gccccactcc   1260

acattccctt ccccgccgac tcagcctccg tagctcgcgg acggcccctc ctcacgccag   1320

cccaggcttt tttttttttt ttttcttcta ttttaaggtt gtcttttaat gacacaagcg   1380

acatttggag acaaaaggac acatctcttc ctgacccacc tccaacccca gctgacggcc   1440

gccctgagcc tggcgtagac ggcccggaac gttccctgcg tgggttccgt ccatcccgaa   1500

cccctgtccc cgcgccggct ccgggggtgc tcggggggcc gcgtggggtc tgtgacgtcg   1560

cctcgaggct gcatcccggt gacccggcag cccctggcgc tcgcgggagg cgggcgggcg   1620

cggaccccag gctttagggc gcgattcctg cagctggctg ccggcccgag gttctggggt   1680

gtctgaggtc tcgggcgggg cgaggacgtt tctccggctc agccccccca cctcctgccc   1740

tgccgccccc cacacccagc tccccacgga cgccaagagg cgcctcccac cccggcgagg   1800

acccgcgggg aaacggggcc caggcgcggc gactgcggag gacgcgcctc ggccccagcg   1860

ccctggtcct cggggcgtcc ggctgccctt gcccgaggcc ggggcgggcg ctcagcgccg   1920

cggaagaaac gcccgggcgg ggacgcacag cgaggcgggc tccgcgggaa gtaccgggaa   1980

aacggcgcgg agcggaacag                                               2000


<210> SEQ ID NO 249
<211> LENGTH: 3000
<212> TYPE: DNA
<213> ORGANISM: Homo sapiens

<400> SEQUENCE: 249

tggagcaatc ccagagaggc tgaggtgttc aggctggccc cagatgcaca cgagcgtgaa     60

gcctgttcag aagccagctc ctcacaccct ctcccctgcc agaggctcca gcacccccctc   120

ccctctcctc tcccctccct tccctgtggt cctcctgccc accccacccc cgtctgcatg    180

tgcaccgtca cggagatgcg tgtactaggg cggaggtcgg ggacagtcgt cagaaggaca    240

caggaaagaa gggaacagga atcccataac agaacattat ccggcaggag taattaacac    300

aggcaggact ggaggctttg ttttgttttg cttaaaaaac agtggtattt aaattaatgg    360

gcatgggaag actattcagt gaaagacatc ggtcattgag gtatctattc aaaaacacgg    420

tttagtactc tgccacacac cgaacgcaac gccacagcag ccatagaagc gtgtgtggct    480
```

```
gtttaacgtg gtctttttgg ggagggcatc ctaggcagag caggcgtgga agggaaggcg    540
gcggacggaa caaaacgcgg gcacgcaacg gctgctgcgc cggatctgag gcagggccag    600
cctgtgggag cagcaacatc gctcgcagga cagcgatgga gcccccacga atccgcgtga    660
aagcagcaac cacctagaaa tgaacgtaca gctgcttaga aacagaatac ggatgacccg    720
aaagacttcc cgatggtagt caccagcata caggacctga cacgggcgtg cgggcagggt    780
gtgccgctac ggggtccctg gcgcacctgc taccctgct acccgcattc accgcacgcg     840
gagggtgcgg gccgtgaagg ttatacatgc aaatatcctt ccaccagcca gttctccttc    900
caggaatctg ccacccgacc cttgtgttgt gcacagacat ggtccaggtg tttgcgacgt    960
gattgtttat cagagagaga gaagggaaat ctccaggctc gctgtagctg caggagctct   1020
gggggctgcg cccatcgtgg agacggatag ctgtctctca tgaacacagg acagcaagtc   1080
cggctgcggc cacagaagac tcgccctcct ggacgcagcg tcttccttcc tcagccccac   1140
actggaggtg gccagtgcca tccacagcag aaggggccag ccgggaccag gctcacgccg   1200
tggaattctg ctctgtggta agaggaagag cgatagctgg aacccagcgc cgtcgcacac   1260
acagcgggga agagtctcag aaatgttact ttgagtcaaa aagctggaca aaaaaaggcg   1320
caagccagat ggtgctgaag aggccacagg aggctggcag ccaggggggtc tggcacctca  1380
ctcggaggcg cagtgggccc gtccggaatt agtggccata cggcaagtgc cgagtggaca   1440
tcaaaccgtc acttcagact cctgcgcttc actgcctgtc ggttatgcct gggttttgaa   1500
atcaagtcac agaacacctg gaatgtggtg tttacgcaga acaaagcggg tgcctcggag   1560
gagagagcct agggacaggg gcacctcccg gtgtgggtgc ccagggttgc agggtggctt   1620
cctctgtctg cgcggttttc agagccccag ggtcctgcct gcccggctgc ctggaggcgg   1680
cccacatcct gctctgcgcc gccgaatctc agcctgaaca gcttcgctgg tgtttgtgtt   1740
gacttatttg ttcttttttt tttttttttt ttttaaataa aggattccga tgctgttaca   1800
gtcaataaaa gccacaggtc tgggtgacct acaaatgtgt gtgtctgact ttctgcagtt   1860
taaatcgcca ctgagcctta aggcgtctgg cccgcgcatt gaggaatcca cgtgggtctc   1920
ggggtcccca tgcctgccca gctccctgct tcagcctggg cgggtctggc gggcatttct   1980
gcgagcctgt ccctgggccc gcctcctggc cagacttcca gaaacattgt ccacatcccc   2040
gttgcacgtc cccccgtcac cggaaactgc agcccacagc actgggaaga acccgggagg   2100
caggcgttag gacggggtgg ccgagacagg gaagggagcc atggcggacg tcctcaccca   2160
agccagggct tcctgcccct gtggtactga caggagcccc gcaggacgtg gggttggctt   2220
tgggcagctc ggtggacact tctctttcag atcctgccac agcaaagctc acgagactca   2280
cttcttccca ttggaattca ctaagaacaa attcaacaat tcagacgccc cagctggagg   2340
tttattttat ggattttacc tgtgcggtat ttagggttgt gtttatgaat aaaggtgtgc   2400
gttctggcaa gtagaaatac agagcttgtc tttcacccaa gtatctgtaa ctttctccaa   2460
tgcagacact aaaatgcaat aaaaacaaac caaacccatt aaacatgaat tagatgaggc   2520
aggctgatgg gaggttgtgg gattaacagg ccgtcagcgg attgaagctg cgcacatcgc   2580
tgggatgctg ctgcgggagg attcggtcta atccgggagc atctggctgg gcagtgggca   2640
gcgtctgcag tcgtggctgc ttgaaggtat gaaggttgtg gcctttgctt ccccccatca   2700
ggctgcccca ccctggaccc cacccagacc cctcgggcac cctggggtca tcttcagctc   2760
cccctctct tccttccttc tcttccgcct gggcccctac tgtgacccga ggtcagcaga   2820
```

ggaccctggc aggtggctgc tccctgggac tcgactgtgc aggtgaggct tggggtgacc 2880
gctgctcctg ctcctgctcc tctcgccgtc cccaccctcc tccatcatgc tgtcaacatg 2940
catgtgggct gcagccctca gcctgcagga cgctgtcagt gcagctcctc agtggccagg 3000

<210> SEQ ID NO 250
<211> LENGTH: 2500
<212> TYPE: DNA
<213> ORGANISM: Homo sapiens

<400> SEQUENCE: 250
atcttgtctt ccttgtccca gtcctggaac cagccactgc cccagcagct cctgtgtgtg 60
gtggcatgtt ctggaagcca ggatgcatgg tgctcctggg ctgctgtggg tcctgggctg 120
ctgtgggtcc cgagctgctg tgggtcctgg gctgcacccc tgcagaacac ttccttccat 180
gttcagctcc ctatatggaa ccccagttcc agccccacag cacagggtcc cccagttctt 240
cctgcctcag gtgtgcacca cgaggaatcc aactgccagt atctgtgcgt ggcctcccgc 300
cgggaggagg ctgccggagg ctctgagctc tagccccaca gcactggcac atcctagatt 360
tccgggaaga cacggcctcc tccccagggg aaggtggtgg tgcccacacc cagagcattc 420
attcctgcag tggagacaga gggacctgcc tctccaactg tgggtgtcag gagccaaggc 480
gcatggtaaa tggggctctc tgtgaggcca ggtgcacggc cccatctcca gcagcagcgg 540
ccatgccacc cagctgcact ctgtggggga ggtgccatga ttgacggggg cccctccctg 600
tgtccagtgt cctcctccct ccacgggccc ctctgcacac cgtcctcaca gtctccctct 660
gcacaccgtc ctcacagcct ccctctgcac accatcctca tggtctccct ctgcacaccg 720
tcctcacagc ctccctctgc acaccgtcct cacagcctcc ctctgcacac cgtcctcaca 780
gcctccctct gcacaccatc ctcatggtct ccctctcctt ccacagaccc ctctgctcgc 840
catcctgacg gcctccctct ccctccacgg accccctcac acactgtcct cccagcctcc 900
ctctacacgc catcctcaca gcctccctct ccctccacgg gcccctctac acaccgtcct 960
cacggcctcc ctctccctcc acgggcccct ctgcacaccg tcctcacagc ctccctctcc 1020
ctccacgggc ccctctgcac gccgtcctca cggcctccct ctgcctccac gggcccctct 1080
gcacgccgtc ctcacggcct ccctctgcct ccacgggccc ctctgcatgc cgtcctcacg 1140
gcctccctct ctctccacgg gcccctctgc acgccgtcct cacggcctcc ctctctctcc 1200
acgggcccct ctgcacgccg tcctcacagc cttcctcttt ttccacagac ccctctgcac 1260
gccgtcctca cggcctccct ctccctccac gggcccctct gcatgccgtc ctcacagcct 1320
caccgacgtc accattgctg gccccgcttc aggtgacagg ccacagtagc acctgtcagc 1380
tctgtcccgc tgctggacag ggagatactg ggccactcag cccagcgggg aacgtgtgtc 1440
ccgaaactgc cttgggctcg ccatcagaac tgtggcagca tcttccagcg ttccttttaa 1500
caggctgccg ttggaatagg agtcacggag caattgcagt gctaagtttt ctttaagtca 1560
cacaattgaa ggaggcttta tttttcacac atttcttcca gagtttcctg gtagcctgag 1620
tgcatgggtg atgccccctg agttatttat caggggcagc cagctgccct cccccggggc 1680
acttacagtc agcccatctc tgtcctggtc aggtgggcgc caaggaagac ccggctcagg 1740
gcctctgtat gggcagcctg gcttgtacac acacccctcc ccaccagcag attctgaatt 1800
ctcccttctt catgcacacc gggaaggtcc cttctgcact cataccggga aggtaggcag 1860
gtttcggtag tgtctgcctc cagtgttttc ctcctcctgc tctatgacat catctttctg 1920
tgattttttt tttcttgcag gaagttggaa gcatcatcgg gaaggtaatt attgattgaa 1980
tctctgcctc tcctggggtc tctgtaaggg gatggtgagg atggcagcct ccctgggtac 2040
taggtggcac ccagtaggtg cgcctttccc agttggtggg tggtctgtgt tccatgaaga 2100
caggacccca gaggtgtcgc ctttatgctg tatgacattg aagctggtcc ctggctctgc 2160
gtggcctgag gggaaggggt tcactccagc tggtcacctc gctgcccct gcccgtggcc 2220 ttggtggcca gtccttcttt cccggttgaa gaccccacga agaatgattt ctcacgcctt 2280
cttcagccgg ctgtgtagtc tgggtggtct ccaggagtgc cagtggaggc agcagccccc 2340
agacaattcc tttccaaatc agggctggcc cgggggaagt aaggcccagt ttggaagcct 2400
gctgccccgg gaggccgagc agtgagggcc acctccctgt cttcatcaca ttttcaccgc 2460
ttccgggggt ccttcccctc agtcccacca tgggggcgcc 2500

<210> SEQ ID NO 251
<211> LENGTH: 6000
<212> TYPE: DNA
<213> ORGANISM: Homo sapiens

<400> SEQUENCE: 251
gctggacacc tctgagagcg tggccctgag gctgaagccc tacggggccc tcgtggacaa 60
agtcaagtcc ttcaccaagc gcttcatcga caacctgagg gacaggtagg agggacgccc 120
cgtgaccttc ctcctgtgct tctgggcctc ttggagggag gggtgggggc ccaggggaac 180
acgggtgcga cggcctcaac ctcctaaggt tgggcgagcg ttgccctgac cggggcccct 240
cccggcgccc tccagagtga ggccggggcc ctttccggcg ccctccagag tgagctggtc 300
tgagcctctc ccagcgcctt ccagagtgag ctggtttgag accctgctcg cgggggtggc 360
acctgttcag cagggccgag gtgacagtga ggctgagatg tagggaagag aggctcccgc 420
aggctgaccg agagggctca gcgcactggc ccagacacgc agtcctgcct ggtgcgcggg 480
agcccctcac taaccacctg gaccctggtt tgttccgtgg gcagtgagag cctctacctg 540
ggtcctggat cccacgttct gaaggtcccc gactcgggag ccaggagggg tgtcgctctg 600
cagccccagg gcccccaggc ttggttctgg gcttgggaca cggcaccctc tgctccacgt 660
tcctccatct gtgcgtgtgg ctgaggacag accgggggga gaggggagtc ggtcctgtgg 720
gtgcacaggg ccgctgaggg gggggcatgt agaacggggc tcccccactg agacgggtcc 780
tggcagtggg gacacagctt agccggcgta ggaacccccg tcctccttga ccctgctgac 840
tggccgctgg gccggagcct cccgccacca gaaggggcac agtcagaggc tgccggtaac 900
agcagggtgg accttccagc ccacaccgtg cccagcagga gccattggta ccaggaaccc 960
tgagcttagt ggacatggcc aggcccgtgc ggcagtgttt gggggggggt ctggctgtgg 1020
atggcaccgg ggaggggcgg ccgcgtggcc cagcgtcccc cgagtcgccc ttgttgcctt 1080
tactcagtct ccccatgact cagtttccca cctgtgaaat ggggcggagt catccccatg 1140
tcgctgccac tggattcctg caggcgccgt ggtcactctg ctgaatggat gggagggtgg 1200
gtggggcaga ggtgggccca ccccaggctg gggcagagca gacccctgag agcctcaggc 1260
tcaggtgctc agagggcagc gagggggctg ctcagatccc cggggtgcct ccttccccca 1320
ctgtcatgct gccccactgc aggcccaagg accccacccc agcagggcca cacactcagg 1380
gctcctggtc tgagggcctg agggatcggg gcgcaggtcg cttgctggcc acacccgcct 1440
gcacagcctt ccaggagggc cggcctcagg gccacagggc aagtccagct gtgtgtcagc 1500
cacggccagg gtggggcagc ctgtccatct gggtgacgtc gcgccctggg acgggtagcg 1560

-continued

```
atggcgccag gggccgcccg cctcacgccc gccgtgcctg ttcctggcag gtactaccgc   1620
tgtgaccgaa acctggtgtg gaacgcaggc gcgctgcact acagtgacga ggtggagatc   1680
atccaaggcc tcacgcgcat gcctggcggc cgcgacgcac tcaaaagcag cgtggacgcg   1740
gtcaagtact ttgggaaggg cacctacacc gactgcgcta tcaagaaggg gctggagcag   1800
ctcctcgtgg ggtgagtggc ccccagcctc ctgcccacgc cagttctcac gcgtggtacc   1860
cagcctgggc tggggttggc ctggggtccc tgtgcggctt cagctgcagc ctccctgttc   1920
tcttggaggc tgcacggcct ccctgaccca ctttgtgggc aggaaagaga cggagacaga   1980
cagagacaga gagaaacaga aacagggaga aacagacaca gagagagaca gagacagaga   2040
gagatagaga cagagacaga gagagacaga gacaaagagt gacagaggga ccaagacagg   2100
cagacagaga caaacagaga cagagacaga gacacagaga gagacacaga gagacagaga   2160
cgggaacaga gacaggcaga cagagacaga gagagacaga gacagaaaca gagacagagg   2220
gacagagaca ggcagagaga gacagagaga cagagacaga gacagacaaa cagagacaga   2280
gagacagaaa cagggacaga gacagaaaga gagagagaca gagggaaaca gagagagaca   2340
gagacagata gaaaaagaca gaggcagaga gaagcagaga cagagaaaca aagacagtca   2400
gagacagaca gagacagaga cagaaacaga gacagagaga cagagacaga ggggcagaga   2460
caggcagaca gagagacaga gacagagaca gcgaaacaga gacagaaaca tacagagaca   2520
gagagacaga gagaagcaga gacagacaga ggcagagaga cagagagaag cagagacagg   2580
gacagagaca gagacagaaa tagagagata gagacagagg gacagagaca gagagataga   2640
gacagagagg gagacagaga gatagaagca gagagagaga gacaaagaca gaggcagaga   2700
gacagagaga gaagcacaga cagagacaga cagagagaca gggacagaca gagacagaga   2760
gaccggaaac agaggcagag agactgagag actgagagag acggggtggt tttccccaca   2820
gcatcaacac caagcagggc taggatcact gaaacagact catcagaccc gaagcatgcg   2880
ctttctcggg gtttttctgg actgaggggt ttcctctcat cccagtgtcc agctgtgggg   2940
acgcaggggc cgcaagcccc ggagtgtcca gaggggaacg tggcctcccc acacccagcc   3000
cttcacgagg cctcaggatc ccagtggggg tacccgaggc tgccctgtcc agccaggcgg   3060
tgcggggggt ttggggagag cctctccccg aggtcggtct cagagggcca catggccggt   3120
gtgggccgga cattcccttt ccaatggttg tgcccacttc cctccagagt tggtgccaag   3180
ctgggacctg ggggacttgg agtctcagga agtcgtccgc tgtctgcagg gggtgcatgg   3240
gggatgtggc cacacacgtc agagtgcggc cccctgtgga agccacagac agacacgact   3300
cccctaaatg agctcgccct tctggccgag atgctcagcg tccccagcag gctgcccgac   3360
tgccctgcga tactgccctc cttcctgctg ctcccacttt ccctttcggg gggttggatt   3420
tggggcattc agggatcgcc ctgttgtttg ctcatcacac ccatttcctg caagagccac   3480
ggtgaccgag cagccttgag ttgaggcagc ttgtgggtag acgcggcggg catctcggag   3540
gggcacgctc cctgccaccc tcagcctcca ctcactggtc aggggctttg cgccccaggg   3600
caccccagga accgagcctc ctttggggtc atgggtgcct ctcctgggag ggcgtggatt   3660
ttccaaagca gtttagagaa atgagaccca caggcgttat ttcccatggt gaggttcttt   3720
tcagtaaccc ccaccgtata gccaggatca gcaaagagag gcggctcctc ccggtgagac   3780
agggaccagc acctcccgga caggcttggg tctccctcca gttcccccac ctagtctcga   3840
ggtctcacgc tgccctctcc tgtccagggg ctcccacctg aaggagaata agtacctgat   3900
tgtggtgacc gacgggcacc ccctggaggg ctacaaggaa ccctgtgggg ggctggagga   3960
```

tgctgtgaac gaggccaagc acctgggcgt caaagtcttc tcggtggcca tcacacccga 4020
ccacctggta ggcaccggcc ccccccggca gatgccccca accacaggga gtggcggctg 4080
caaggccccc ggcagctggg accgtctttt ggtcctcggg agggtgtggg ttctccagcc 4140
ggccaccctt gcccctgaga ggccagcccc tcctgctgag gagcctggag cgccccagcc 4200
cagcctcccc tctggccctg tgggaagcgg ccccggccgt caggggtccc agccctgctc 4260
agcccaccct gaacactgcc cccaggagcc gcgtctgagc atcatcgcca cggaccacac 4320
gtaccggcgc aacttcacgg cggctgactg gggccagagc cgcgacgcag aggaggccat 4380
cagccagacc atcgacacca tcgtggacat gatcgtgagg cccctgccca ggagacgggg 4440
aggcccgcgg cggccgcagg tggaaagtaa ttctgcgttt ccatttctct ttccagaaaa 4500
ataacgtgga gcaagtggta agagccctcc ccaccacccc cagccgtgag tctgcacacg 4560
tccacccaca cgtccacctg tgtgttcagg acgcatgtcc ctatgcatat ccgcccatgt 4620
gcccgggaca catgtcccct gcgtgtctgc ccgtgtgccc gggatgtgtg tccccctgcg 4680
tgtccacctg tgtgtctgcc catgtgcctg ggacatgtgt ccgcctgtgc gtccatccgt 4740
gtgtccgtct gcccatgtgc ctgggtcgca tgtcaccctg tgtcccagcc gtatgtccgt 4800
ggctttccca ctgactcgtc tccatgcttt ccccccacag tgctgctcct tcgaatgcca 4860
ggtgagtgtg ccccccgacc cctgaccccg cgccctgcac cctgggaacc tgagtctggg 4920
gtcctggctg accgtcccct ctgccttgca gcctgcaaga ggacctccgg ggctccgggg 4980
cgaccccggc tttgaggtga gtggtgactc ctgctcctcc catgtgttgt ggggcctggg 5040
agtgggggtg gcaggaccaa agcctcctgg gcacccaagt ccaccatgag gatccagagg 5100
ggacggcggg ggtccagatg gaggggacgg cgggggtcca gatggagggg acggcgggag 5160
tccagatgga ggggatggcg gggtccagat ggaggggacg gcggggtcca gatggagggg 5220
acggcggggt ccagatggag gggatggcgg ggtccagatg gaggggacgg cggggtccag 5280
atggagggga cggcggggtc cagatggagg ggacgtcggg gctccagatg gaggggacgg 5340
cgggagtcca gatggagggg acggcggggt ccagatggag gggacggcgg ggtccagatg 5400
gaggggacgg cggggtccag atggagggga cgtcggggct ccagatggag gggacggcgg 5460
gagtccagat ggaggggacg gcgtggtcca gatggagggg acggcggggt ccagatggag 5520
gggacgtcgg ggctccagat ggaggggacg gcgggggtcc agatggaggg gacggcgggg 5580
tccagatgga ggggacggcg gggtccagat ggaggggacg gcggggtcca gatggagggg 5640
acggcggggt ccagatggag gggacggcgg ggtccagatg gaggggacgg cgggagtcca 5700
gatggagggg acggcgtggt ccagatggag gggacggcgg ggtccagatg gaggggacgt 5760
cggggctcca gatggagggg acggcggggt ccagatggag gggatgtcgg ggtccagatg 5820
gaagggacgg cggggtccag caggcaggct ccggccgtgc agggtgtgga ctgtcccggg 5880
ggcgctgggg gcttctgagg gtgtctctgt ccgccctgcc ctcagccgca ctctgttcag 5940
aaggaccttt ctggaggtag gagggtgaga atgtgggtcc cctgcttctg tgtggctcac 6000

<210> SEQ ID NO 252
<211> LENGTH: 7000
<212> TYPE: DNA
<213> ORGANISM: Homo sapiens

<400> SEQUENCE: 252
ggccggggag gcggggaggc tgccccaaga gtaaaagcct ttctgacgtg cgcaggacgc 60
ggccctgact ggtctaactg actctttctc ttctcctcag cttgctgtgg tgagacccag 120
gctctagctc ctgagagaat ggatcccggg ggtcggggag cgaggcctgg gtcccacaca 180
tgtcacagga cagcacatgg cactctggtc cccgcccgca gctccctgca cctgcccgcc 240
ccctctgggg cctgctccaa gccagcaggg ttcccgggtg ttgggctggg ccccgccctc 300
tttcacccat aactgaaata accaggagca ggcttggggg ggtccctgct ccatcattct 360
ggcccacagg ccccacccta gcctggctga gcaacgccag ccctgaccag ccgccggaca 420
gagcagcctt tacggggcca tgggaggggg tgggcttttc tggggctgag acggggggac 480
cccaacgtgt caggtgagga tgtggcagcc aaggaggggc cagggcggtg gaggggaggg 540
gccagggcac tggaggggag gggcgtgctc tgctgacacc gcccccgcct gcagaatgca 600
agtgcggccc catcgacctc ctgttcgtgc tggacagctc agagagcatt ggcctgcaga 660
acttcgagat tgccaaggac ttcgtcgtca aggtcatcga ccggctgagc cgggacgagc 720
tggtcaaggt gaggcctcgc cccgcccggc tttctcaagc ccaggtgcac cccgaccctg 780
ccggccgccc ctgcccgcgc cagacctcag cctcccgagg ccaccgctgc atccctgtga 840
cttccctact catgacaagg atgccaggca cgcgccagcc cgtccaggcc tccagctcca 900
cctggcgagg ctggcccatt gtacacaggc gccccagatg agggagggtc tccccctctc 960
cttgaagggc ggtagtctgg ggtcctgagt gctgggtgtg ggcttgtccc tcgtggacag 1020
aacccaggag ggcttcatcc accaaggaag attgctttgc agggtaccca ggtcccgggg 1080
gctgtgccac cctctgggca cccggagcca atcgcagggt acccaggtcc cgggggctgt 1140
gccaccctct gtgcacccag agccaatcgc aggggaccca ggtcctgagg tcctgggggc 1200
catgccaccc tctgggcacc cgcagccaat agagtcaccc ttgggaagct tatgcggacc 1260
tggggcagca ctcgcgtcct gaccccggtg ccggtcccac agttcgagcc agggcagtcg 1320
tacgcgggtg tggtgcagta cagccacagc cagatgcagg agcacgtgag cctgcgcagc 1380
cccagcatcc ggaacgtgca ggagctcaag gagtgagtgc cccacgcggc caggaccctc 1440
ccacccctcg ccccgaccgc tgttcccacg gcaggtcggc cctgacccct gatcccaggt 1500
gggctcggcc ccgcggcagg cctggcccca accggccctt cctgcccttt gctatgcaga 1560
gccatcaaga gcctgcagtg gatggcgggc ggcaccttca cgggggaggc cctgcagtac 1620
acgcgggacc agctgctgcc gcccagcccg aacaaccgca tcgccctggt catcactgac 1680
gggcgctcag acactcagag ggacaccaca ccgctcaacg tgctctgcag ccccggcatc 1740
caggtggggt ggccaccccc aggctgcacc tgccccgcct agggcgcccc gccagccagg 1800
gtggccttgt ccccagaaag acgagggcag agcaggctgc gccacaccga tactgtctgt 1860
ccccacaggt ggtctccgtg ggcatcaaag acgtgtttga cttcatccca ggctcagacc 1920
agctcaatgt catttcttgc caaggcctgg caccatccca gggccggccc ggcctctcgc 1980
tggtcaagga gaactatgca gagctgctgg aggatgcctt cctgaagaat gtcaccgccc 2040
agatctgcat aggtgcgcat ggggccaccc gggcagtccc agatctgcgt aggtgcgcgc 2100
ggggccgccc gggcagtccc agatctgcgt aggtgcacgc ggggccgccc gggcagtccc 2160
agatctgcgt aggtgcacgc ggggccgccc agggccgtcc cagatctgtg taggtgcgcg 2220
caggcgccca gggctgtccc agaggcctcc tcccagctca ctgttacctc caggggcacg 2280
gccaccctgt aggtgcgcac ggggccgcct ggggctgtcc cacaggcatc ctcctcccgg 2340
ctcgctgtga cttccggggg cacggccacc cctgtgctcg gccgggaggt cctgtgacat 2400
ctccttgcgg ggttataggt ggagcagtgg gctcacactg cacggctttt ctcttttaca 2460

```
gacaagaagt gtccagatta cacctgcccc agtgagtacc tcggcggccg ggacacgtgg   2520
ggaggagggc accgtggttg gggcgagggc tctgagagga cggggctctg ggaggagggc   2580
ctggcggtca cgagagtagg tgcatggctc actccggtgg ctgagcacca ccgtgccgtg   2640
ccctctctgg ggagcttaga cgctctctgg ccggcccact gcggctgcat caccagggcc   2700
tcatgctaac ggctgcccac cccgccccgc agtcacgttc tcctccccgg ctgacatcac   2760
catcctgctg gacggctccg ccagcgtggg cagccacaac tttgacacca ccaagcgctt   2820
cgccaagcgc ctggccgagc gcttcctcac agcgggcagg acggaccccg cccacgacgt   2880
gcgggtggcg gtggtgcagt acagcggcac gggccagcag cgcccagagc gggcgtcgct   2940
gcagttcctg cagaactaca cggccctggc cagtgccgtc gatgccatgg actttatcaa   3000
cgacgccacc gacgtcaacg atgccctggg ctatgtgacc cgcttctacc gcgaggcctc   3060
gtccggcgct gccaagaaga ggctgctgct cttctcagat ggcaactcgc agggcgccac   3120
gcccgctgcc atcgagaagg ccgtgcagga agcccagcgg gcaggcatcg agatcttcgt   3180
ggtggtcgtg ggccgccagg tgaatgagcc ccacatccgc gtcctggtca ccggcaagac   3240
ggccgagtac gacgtggcct acggcgagag ccacctgttc cgtgtcccca gctaccaggc   3300
cctgctccgc ggtgtcttcc accagacagt ctccaggaag gtggcgctgg gctagcccac   3360
cctgcacgcc ggcaccaaac cctgtcctcc cacccctccc cactcatcac taaacagagt   3420
aaaatgtgat gcgaattttc ccgaccaacc tgattcgcta gatttttttt aaggaaaagc   3480
ttggaaagcc aggacacaac gctgctgcct gctttgtgca gggtcctccg gggctcagcc   3540
ctgagttggc atcacctgcg cagggccctc tggggctcag ccctgagcta gtgtcacctg   3600
cacagggccc tctgaggctc agccctgagc tggcgtcacc tgtgcagggc cctctggggc   3660
tcagccctga gctggcctca cctgggttcc ccaccccggg ctctcctgcc ctgccctcct   3720
gcccgccctc cctcctgcct gcgcagctcc ttccctaggc acctctgtgc tgcatcccac   3780
cagcctgagc aagacgccct ctcggggcct gtgccgcact agcctccctc tcctctgtcc   3840
ccatagctgg tttttcccac caatcctcac ctaacagtta ctttacaatt aaactcaaag   3900
caagctcttc tcctcagctt ggggcagcca ttggcctctg tctcgttttg ggaaaccaag   3960
gtcaggaggc cgttgcagac ataaatctcg gcgactcggc cccgtctcct gagggtcctg   4020
ctggtgaccg gcctggacct tggccctaca gccctggagg ccgctgctga ccagcactga   4080
ccccgacctc agagagtact cgcaggggcg ctggctgcac tcaagaccct cgagattaac   4140
ggtgctaacc ccgtctgctc ctccctcccg cagagactgg ggcctggact ggacatgaga   4200
gccccttggt gccacagagg gctgtgtctt actagaaaca acgcaaacct ctccttcctc   4260
agaatagtga tgtgttcgac gttttatcaa aggccccctt tctatgttca tgttagtttt   4320
gctccttctg tgtttttttc tgaaccatat ccatgttgct gacttttcca aataaaggtt   4380
ttcactcctc tccctgtggt tatcttcccc acaaagtaaa atcctgccgt gtgccccaaa   4440
ggagcagtca caggaggttg gggggcgtgt gcgtgcgtgc tcactcccaa cccccatcac   4500
caccagtccc aggccagaac cagggctgcc cttggctaca gctgtccatc catgcccctt   4560
atctgcgtct gcgtcggtga catggagacc atgctgcacc tgtggacaga gaggagctga   4620
gaaggcaaca ccctgggctt tggggtcggg agcagatcag gcctcagtgg gctggggccg   4680
gccacatcca ccgaggtcaa ccacagaggc cggccacagg ttctaggctt ggtactgaaa   4740
taccccctggg agctcggaag gggagttgag atactgcagg gcccatagga agaagtcttg   4800
```

```
ggaggctcca cctttggggc agaggaagaa gtcttgggag gctccacctt tggggcagag   4860

caagaagagg gcggagggca gaggcagcga gggctcatcc tcaaaagaaa gaagttagtg   4920

gcccctgaat cccagaatcc ggggtgcacg gctgttctgg gggccgctag gggactaaga   4980

ggatcggccg agggctgggc tggaggaggg cagcagggat gggcggcgag ggtgagggtg   5040

gggcttcctg aaggccttca cctgcgggga ccccggcgag cccctcaggt gccacaggca   5100

gggacacgcc tcgctcgatg cgtcacacca tgtggccacc agagctgcgg gaaaatgctg   5160

gggaccctgc atttccgttt caggtggcga acaagcgccc ctcacagaac tgcaggtaga   5220

gacgggcccg gggcagacgc agtgaggcgg tgggcggggc ccggggcaga tgcagtgagg   5280

cggtgggcgg ggcccggggc agaggcagcg agcggtgggc ggggcccggg gcagacgcag   5340

tgaggcggtg ggcggggccc ggggcagagg cagcgggtgg tggccggggc ccggggcaga   5400

cgcagtgagg cggtgggcgg ggcccggggt agtcgcagta ggtggtgggc ggggcccggg   5460

gcagacgcag tgaggtggtg ggcggggccc ggggcagacg cagtgaggcg gtgggagggg   5520

cccggggcag acgcagtgag gcggtgggcg gggcccgggt cagaggcaac gggtggtggg   5580

cggggcccgg ggcagacgca gtgaggcggt gggcggggcc cggggcagat gcagtgaggc   5640

ggtgggcggg gcccggggca gatgcagtga ggcggtggga ggggcccggg gcagacgcag   5700

tgaggcggtg ggcggggccc ggggcagacg cagtgaggcg gtgggcgggg cccggggcag   5760

acgcagtgag gcagttgcca gcctctctca gctgcctcat gggattcgca ctgcagctgc   5820

ggccctggcg cgacaagggc tggacttggc cagcgggacg gtccctcacg gcgctgaggc   5880

ccacactctg cgtggagcct ccccgtgccc aggctaccct gcaaggtcct cggagaggct   5940

tcctccagcc ccagccccca cacagctccg gcccaggccc gctcttcccc atcccagttg   6000

ctttgcgctg tatacggcca ggtgaccccg agccggccct gagccctcgt cccggcttcc   6060

tcccctgtaa gctgggtgaa ggactccatg gcacccacct gagagggttg tggcgaggcc   6120

caggcccctc gtgcccacac ggccggcggc ccatgcctgg caggggctgg gaggaggctg   6180

gggcgaccag aggggagcgg cctgtcctgg aggaggccca gggaccctgg tgagagggtc   6240

tctcccaagt gctctctatg ggaccccctt cctctgcgcc cgtccttcac ggacctctcc   6300

gggtcacccc tgggctgcac actgggttca ggggggcctt gaggtggggc ccctgttccc   6360

aagtcccggc ggggtttctc ctgaacctca acccatcctc acctgcgggc attcccatcc   6420

cccaacgcct gggtcaccag gattccaggc aggaggggcg gtgggggtta ccaaggcccg   6480

ggttgccatg cagaaccccc agccaccacg cagaccccca cggggcccag ggaagctcct   6540

ggtctcacac tgcacctcac acttcctgtg ggggcagact ccaaggtccc ggcctctcat   6600

cttgtagaaa ctgaggcaca ggagggacac acactcccac ggccggtcac cgtggccccc   6660

acacctccca ctggactgac acctggccag gctccggaca cccgtggcac agcctcagcc   6720

cctgcggccc ctgctccgtg gcccccaggc cccagctccc atgtgcacgt cctgcctcag   6780

gcctggaggc ccctcggccc caaataatca gacaattcaa cagcaaaact actttttttca   6840

ggctggcagg actctgggca accccctgca acagccccct gccctatcac agccaccctt   6900

gcctcccagg cacggagacc ccaccatcag gtcccagcct tggttcatcc ccaagcaccc   6960

tgtgtgttgg gatggcgatg ctggctgagc ccctgcatcc                         7000
```

<210> SEQ ID NO 253
<211> LENGTH: 2500
<212> TYPE: DNA
<213> ORGANISM: Homo sapiens

<400> SEQUENCE: 253
agggcgtttg ggaacacccc tcccggaggg gtgaggcggc ccagcctgcg gctgccagag 60
gacacaggtt ctgctgcgga acctgcagac atggccataa caggccacag tgctcgggcc 120
cacacagcct ggacccacat ggccctgtgt cacctcctca ggggcaggct tcagggcctc 180
gaccctagag gctgcccctc ggttctgctc catggacggc gcaggcaggc ccaggcctgt 240
gacgagttca cggaagctcc aggatgaccc ccgctctgcg ccctcctcca gcattccaga 300
ccacaaacca ctctgggcta aaacgaggca tcgccagagc atcccacttc ctcggaaagc 360
tgcggtctgg ggacgcgtct tggccctgaa gaggctccag atggctccca tcaggcctct 420
ccgcctacgt gcggccgaca tggagtgaca gagcgtcggg gacacagaat tcagagctgg 480
gcctggggct gctttgagat actgatggct gccagggggc acagagaccc gtcctgcaga 540
cagggctgtg agggccacag ggggcctcgg ggagaggcag tgggagggag gacagtgggg 600
gcctccagct gggtgagcag ctggagcgag gggggcccgg ggcttgtgat ggtgctgccg 660
accctagagg tgccggcccc acgatggaga gcacgtagtg ccccccggga gtcaggaggc 720
cgggcctgac ctcgggggct gcagccaggg gaggccggca ccccagataa cccccaaaga 780
actgcaggcc ctgaggcgag gccagagtgg gggcgggggc aggtcccagc cgaggaggtg 840
ctccgtgctg cctcagcaga acccatgatg ggctggccca aggctctgaa ggtggaaagg 900
cctcacacat tctgccccgg ctgacgcctt ccttgggcca gtgctcgggg gtgtgtaaca 960
aacgccaaga cgcattgtaa agaaggaagc ctgcgtttcc atcaccggct taatatcaaa 1020
caaaagtgca attttgaaaa tgtagtccaa ggtttctgt ggtgcggaaa tggccaggcc 1080
agacctccgt gggtggtcct tcgtgtccac gtcagcgccc tacatccaca ctgtgggcac 1140
catgacctca catgcggagc ggagcagggc cggcgcccgg agagccaggc tggtcacgaa 1200
cgaggcctag agggcgtcag gccccaaagc actcacaggc ttctcctctg tcctcggggc 1260
cttcagacac ctgcatgcgc cgattcagcc acccgcgcgc gccgattccc ctggccatgg 1320
ggtttccaaa gtgtgtgctc agaggacagt ttcctccagg atgacctgtc agtggctctc 1380
tgtgccgggg acgtcgcgtg ctgggtcccg gtctgaatgc ttcctaacga tttacccagt 1440 tcctttctc cactcaggag gcgtttgctg agaggcacag gctgagcccc cgtgctgatg 1500
ccacgaccga gggaacgggt ctccctgtcg gcgtgaactg acccggccag gcgtccactg 1560
ccactcggac tgtctcccag gcacgtggcg cccacacggg cagaacacgc cctccacaca 1620
cgcggcttcg ggcagaacac gaggcgccct ccacacacgc ggcttcgggg cttgtcatga 1680
aaaaagctga atgctggggg tgcagctttc accaacagaa tcccgtttgg aagggacgcg 1740
gtgagacatg atccacccta agttgtgatc ctgggtgagc cgccgtccac accctgctga 1800
gggtcccttc acccacttta ttctccagaa aaccctgccc atcagggctg agtcccacgc 1860
cttccctctc cgtccaggcc tggctttgac ctctggggtc gtgtggggca caggggacac 1920
cctatccagg cagaggccct acggctatct ggaggaagtg gtgggagctg ggcttctgcc 1980
tggaggatgc acccagaggg gtcacagtcc acacagagac acacgggtgc cttccagatg 2040
gctgagccag tccagcccag aagggcctgg gggttggggg ctgcacctgg cctgtcccca 2100
ccagcagggc tcagggcttc ccaaggtgtg tgggggacgg ggcagcacct ctcaaccagg 2160
tcacctgaaa cccgaactga aaggcatcct aagttaagac attaactccc attgtcaagg 2220
tgccatcgtc aattctgtct ccaaatcctt ctttgttatt tcatgtattc acagagtgac 2280

```
gctccgtgtt tcgttcagcc tgcaggcctg cagaagctgc atctcgggat ggccaagagc   2340

ccggccaggc cccacggctg cacccaggac gggattcatg ccccatgcct ggcttctcac   2400

gaccacagag tgcctttccc gggactggat ggaggcagag tgagagaaga gcctggagca   2460

agtgttttgg accacagtga tcaaacacgg agcccgtggg                         2500


<210> SEQ ID NO 254
<211> LENGTH: 700
<212> TYPE: DNA
<213> ORGANISM: Homo sapiens

<400> SEQUENCE: 254

aagaaaggcc agaccgggca cggtggctca cgcctgtaat cccaacactt ggggaggccg     60

aggcgggcag atcacctgag gtcaggagtt cgagaccagc ctggccaaca gggtgaaacc    120

ccgtctctac taaaaataca aaaaaaaatt agccgggcgt ggtggcaggc acctgtaatc    180

ccagctaatc gggaggctga ggcaggagaa aatcacttga acctgggagg cggaggctgc    240

agtgagctga gatcgcgcca ctgcactcca gcctgggtga gggagcgaga ctgtctcaaa    300

aaaaaaaaaa aaaaaaaaaa aaaaggaaag aaaggcccgg tgagatgctt tctcttaaac    360

acggccctgc acgttgagtt gctgcctcct gtggcctatt tcacgtttat gcaaagtcgg    420

gcgcctgatg cggggctcac ccgccacaag caggggtcct ggtgctgctc atggaagggg    480

ccctacccag cccgcggggc actggctggg acggggctgc ccaggtccgc ccaggatcca    540

aacacccagc cccgcccagc ggcccttcct ggcctgcagt ggaggctgta atgggcaggg    600

gtggtgggaa tcccagctca cagggcgcct gctcttagaa gggcggcatc tgggtccaga    660

ggtcagaaac gtcagatgcc catcccagaa gtggcgggga                          700


<210> SEQ ID NO 255
<211> LENGTH: 10000
<212> TYPE: DNA
<213> ORGANISM: Homo sapiens

<400> SEQUENCE: 255

gggtgaatga gtagatgtat gggtgagtag gtgggtaggt gggtagatgg atgggtgggt     60

gggcgagtgt gtggttagat gatggatggc tgaatggatg agtgggggga tggatgggtg    120

agtgggtgta tgtatggatg ggttagtggg tgggtggatg aatggatggg tgcataaagg    180

atggatggat gaatgagtta gtgggttggc agatggatgg atgggtgagt cagtggatag    240

atggatgggt gggtggatag aggatggatg gttgggtagg tgatgggtgg atgagtggat    300

agatgggtat gtgagtgagt ggggggatgg gtaggtgggt ggatggatgg ttaggtgaat    360

gagtggatgg acagacggac agtgggtgga tggatgagtg aacggatgga ccgatggatg    420

aatgggtggg tgggtagagg atggacggac aggtgagtgg gtgggtggat ggatagatgg    480

gtaagtgagt ggatagatag atgggtgggt ggacagagga tgggtggatg aatggatggg    540

ttagtgggtg gctgggtgga tggatgatgg atgggtgact gggtggatgg atggatgggt    600

tagtgggtgg ctgggtggat agatggatgg gtgattgggc gaatgggcga atgggtggat    660

gggtgggcgt ggagttggtg ggtacatgat aatggggtgg aatacccatg gattggaatg    720

agctgttttg gctgctattt ctgggacacc cagctctgcc aggcccctac ccctctggtg    780

ggccaggctc tgacggtggc cactcatggc ctttctagct ctggtgccag catagggaag    840

gaggaggcac agccttgtct tactccttgc acctgttagc cccccccccc gccaagggag    900

gacccgtggt tggggacagc acagggggcc ctgctgtgtg cagggactgt ccctggggcc    960
```

actgaagccc acctgttctt gttccttctc aggcggatcc tggtcccccct ggtgagccag 1020
gccctcgggg gccaagagga gtcccaggac ccgaggtagg ttggtggcca gtccccatgc 1080
cctcccccca acctgccagg ccaacacaca cccaagcctc gtggttctgc ccacggtgga 1140
cccacgtatc agtgggcagt ggcctgggag agactcagcc acccagcctt ggccccagag 1200
tctcagcctc atccttcctt ccccagggtg agcccggccc ccctggagac cccggtctca 1260
cggtaggtgt cacatggggc agaaccagtg tccttctcct gccaaaacta gacaccaaga 1320
gcagcagggg tgggggaagg tcagctggca cggtcagaga gcaagatcag tggaggaggt 1380
cagagggcaa ggtcagagag caagcttggt tggggaaggt cacagggcaa ggttggtggg 1440
gggaggaggg tggcagcgag gttggtaggg acaggacccg ccagcctccc cgcatggctg 1500
cctccacacg tgggctggaa tgtcccggga cccccaggcc aggaccttgc tgtggaaact 1560
cttctggggc cccgggggga ctaccctgcc tgccgtgtgc attgcaggag tgtgacgtca 1620
tgacctacgt gagggagacc tgcgggtgct gcggtgaggc actgcccacg gcagggtcgg 1680
ggcccatgca ccgggtggag ggcgggagtg cagcagggct gggtcatcgc tgggtcctgc 1740
atgtgcacgt gaccctaggg tctgaggtct ccccggtacc ccccgatgac cctgccaccc 1800
ccccagactg tgagaagcgc tgtggcgccc tggacgtggt cttcgtcatc gacagctccg 1860
agagcattgg gtacaccaac ttcacactgg agaagaactt cgtcatcaac gtggtcaaca 1920
ggctgggtgc catcgctaag gaccccaagt ccgagacagg tcagcggggc aggggcgggt 1980
gcagcattgc ggggggccgg gcggggcgtg ggaggcgatg agatgggaga agtccagacg 2040
cgtccctcca acgagggcct ctgcatggct ggggatgccc cagaccccga ggcctctggc 2100
aacgacctca cgcgtgcggc ttgcagggac gcgtgtgggc gtggtgcagt acagccacga 2160
gggcaccttt gaggccatcc agctggacga cgaacgtatc gactccctgt cgagcttcaa 2220
ggaggctgtc aagaacctcg agtggattgc gggcggcacc tggacaccct cagccctcaa 2280
gtttgcctac gaccgcctca tcaaggagag ccggcgccag aagacacgtg tgtttgcggt 2340
ggtcatcacg gacgggcgcc acgaccctcg ggacgatgac ctcaacttgc gggcgctgtg 2400
cgaccgcgac gtcacagtga cggccatcgg catcggggac atgttccacg agaagcacga 2460
gagtgaaaac ctctactcca tcgcctgcga caagccacag caggtgcgca acatgacgct 2520
gttctccgac ctggtcgctg agaagttcat cgatgacatg gaggacgtcc tctgcccggg 2580
tgagcgtgtg ggcgcggggc agtcggccga ggagcagcag gccccagccg ctgtctagcg 2640
tgagccccag ggacacccct cacctgaggg atgaatgtgc agcccaggat cttgggctgt 2700
gggtgggaag gggtcgggcc ctctcggggc tgcagggcag aggccagctg caccctgagc 2760
ctgtctaggc agatcagtga acggccgctg agggttcgct agggactgac cctggcctgg 2820
cccggcctct ctcctctctt ccagaccctc agatcgtgtg cccagacctt ccctgccaaa 2880
caggtaatgc agggcaccct gagccaccac cccagactag caaagcagcc ctggtgtcct 2940
tcctcctcga gggccgggct gggggagggg ccgtgcaggg acccgggggg cggcggagcc 3000
actgcggagg ctgctcctta gggagatggc cccaggatgg cagcacaggg gaggaggggc 3060
ttggggaagg caggctccca ggaacgcagg aacagcatca cgaggccatg aggtgggtgc 3120
tgctagcctg gcgctgtgct cggcatgtgg ccactggtct tgaaggccca ccatgggcct 3180
tgcagtctcc ctcagctgcc gcccagctcc catgggctgg ccgtgcatgt gccactcgga 3240
ggaagccctg gattcagtga gtgaaaccat cccggggtgg aagcactgac accccccagc 3300

-continued accagcaggt cttgctccaa ccctggcctg cctcggagct gcagctgcgg ctctcacatc 3360
tctgggagtg gggagcccca tgtcccggat gtggcccacg tgggtgtgaa gctggagctg 3420
ggggtgccgt ccaggctctg ctggacgtgg tgctgccccc atggtgcact gctgcaccgt 3480
acctgggccc acaggaggtc cccgggggcg ttaggagctg agtccccctc agtgagccgt 3540
cccctccagg agtgtgaggg tagggatgcc atggagacag ggtgggaggg tccgacctgg 3600
aggaccacag ggaggaaacc tcagggtctg cggtacgaag tcagcgcttc ctcagcacgc 3660
gggtcgcggt gtgcgttcgg gcgttccatg gggagctccc ggtgggtgag ctgggccact 3720
gagcacattc acaggccctg aggctgcccc aggggaggag ccgtggactc agagccgagg 3780
ttccccatac gtgctgcgac agagaaccta gggcttgcac ctgggtctgg ctgcccttca 3840
gcaggcgggc agcctctggc cccacaacag tgggctgtgc ttctgccgcc aaggtgcagg 3900
cgtcctcccc cagggtccac atcagcagca ggggcacctg gaccctgagg gcaggaacca 3960
gaccttggct cctccaccca ccccctcgtt cctgatgggg cagggaagtc tcgggacccc 4020
atgatgggcg acatggcgat ggtcactgtg ggtgctttgc tatcaggtgg ggggccttcc 4080
tctccactct gggtccagtg tgagtggccg ctatggcttc ccctccactc caggttctat 4140
cgtgagtggg tgggtgctgc gtctgtggat gtcacgtgac ctttcctctt tagcctatca 4200
ttgtagttgg gagttagtta gcccgttgag cgtcattgaa tttccagtgt tgagccagcc 4260
ctgcgtgccc gggataaacc cacctggccg tggtgtgtgg ccctgtttat gcacgtgggc 4320
cctgattcgc tgatgcctgc ctgagggttt gcgcttatcg gcgacatcag cctgcacttt 4380
tcttttctcg tgatctctct ggttctggcc tcagggtgac gtgggcctcg tagggtcctg 4440
tggtggctcc tccccagacg gtgacatgga gtgagcccat tctccctcct gggagtgggt 4500
cactcaggcc accagagcac cacagggaaa gcagccaggg aggacacgga ggcccttgaa 4560
gctctggcct cttctgaggc ctccaggacc tgacagtgag tgggagcagc cctggcagaa 4620
cccctcccct cctctcggcc gccctgacac ctcatccccg acactcagag ctcatcctcc 4680
ttcccagctg tttccaattt caaagtgaac tcgaccttgt ggctccagga gatgcagcag 4740
ggacagtgtt aaatcggctt tcaccagccc acacggccag gcatcctcct cggccctcct 4800
gggcactggg tggacaccac tggctgtggc ctggccctgg ccttctccag acagccctgt 4860
ccaccccaaa gcccagccac cctgggcctg cagcaggcct gtggagttct cagttgcgtg 4920
gggaccagag ggtgctggag aaacaaacca gacgcagctg aaggcagtca gggcagggcg 4980
caatcagcga taagagctgc ataggggcca cagcgtaacc tgagctccag tcggtggaaa 5040
gaaaaggcag agacgttgca gaggccaggt ctgctcaggg gaagacagtt ctgggtgtag 5100
aggactcaca tcccagagag gctgaggaag ggtttaccac cgcaagcttt ctcaggcggg 5160
ctcttgaggg gtggctgggg tcttcctggc gacgggcctg cggcactgga agccctactg 5220
gagtttggcc tgtctccggc acaggtttgg acggagctgt tttgtgctga aaggttttct 5280
cggggtccgt ggtgtccccc aaaggtgcca ccgtgcgggt ctcctagctc cctgccagct 5340
tcctgtccct gtgctcactg cccccacgcc tcctgccaag gccgagccac acacccgctc 5400
cacctgcatt tcctctaccg actcgccagc ccaaatgccg ctcttcactc tggcctcgct 5460
gagcggctgc ccgaggagga gctctaggcc gacgcccacc gcaggcctta cagtcttctc 5520
tggacgctcc cttgcagatg caccgtggcc tggcggcgag cccccggtca ccttcctccg 5580
cacggaagag gggccggacg ccaccttccc caggaccatt cccctgatcc aacagttgct 5640
aaacgccacg gagctcacgc aggacccggc cgcctactcc cagctggtgg ccgtgctggt 5700

-continued

```
ctacaccgcc gagcgggcca agttcgccac cggggtagag cggcaggact ggatggagct   5760
gttcattgac acctttaagc tggtgcacag ggacatcgtg ggggaccccg agaccgcgct   5820
ggccctctgc taaagcccgg gcacccgccc agccgggctg ggccctccct gccacactag   5880
cttcccaggg ctgcccccga caggctggct ctcagtggag gccagagatc tggaatcggg   5940
gtcagcgggg ctacagtcct tccaggggct ctggggcagc tcccagcctc ttcccatgct   6000
ggtggccacc gtgtcccttg ctgcggctgc atcttccagt ctctcctccg tcttcctgtg   6060
gccgctctct ttataagaac cctggtcatt gaatttaagg cccaccccaa gtccagaatg   6120
acctcgcaag acccttaact cactcccgtc tgcagagtcc ttctttgctg catcaggtca   6180
ccctcacagg ctccagggtt tgggtgtgga agtctttgga ggcccttact tagcggccca   6240
gctgggctgc cgtgcgtctg ggatggggct gagggagggt gctgcccagg tgctggagga   6300
tgttccagca ccaggttcca gcggagcctc ggaaacaggc cccagaggct ggtgagcctc   6360
gctgggtgtg ggcactaatc ccgtgcatgg tgactcgtgg gcgctcacgg cccacctggt   6420
ggcaggtgaa ggcttccggt tgggcagcag atagtcctgg gggaagctgg cagtcctggc   6480
accatgacgt atctgggctg gtgtcatgca cagtagggcg aatggccaca gctgcctgcc   6540
agcagccctg atcccggggt gtctgcaccc ttccagccca acctctgggt ctccaaaagc   6600
acagtcgggg gagcatccac caggcacaac ctctgcggtc ctcagaggac tgagcagaga   6660
atcccagggt ccacaatgtt ggggagcggc agggatcacc atccaaaggg agcggccccc   6720
acggcgagct gaccccgacg ttctgactgc aggagccctc atccaggctg ggctcctgcc   6780
gggcacggct gtgaccattt ctcagggcca ggttctcgtc cccacaccca ctgcacaggg   6840
caggccaggc tggtcttccc actgtgggga tgaaggatcc tccacaggag gaggagagca   6900
gagtccacag acatcccaac agcctcagcc tccctgtgcc tggccggccc ccacagcttc   6960
cccgtctcct ccaggcccca cagacactga tgaatggaca gagaccccca aaaccagctg   7020
ccccttgcat gtctgtctcc atatgtttgg tgacagcagt gaaaatgtta ttagttttga   7080
gggggtttgg gaagcccagc ggtacctgag gagtttctgg acatttaagc cggttcctag   7140
gtgtggcctt aacagggagg ctgcccttcc tttcactgaa tgagctgcgt cactcataag   7200
ctcactgagg gaaccccatc tgccagctcg tgcgtgctca gacggcgtcc atgtctcaag   7260
cgttctgtga aggctgcggt gcagcgtgag gtcaccctgc tgtgttcaga gctttgctca   7320
ctgcctgcgg ggctggaccg ttgcacctcc agggccccca gaaaccgagt ttcgggtcag   7380
ggtcctctgt gtgcattcct gggggtccat gtaccagctg tgacgacgtc caggggttgg   7440
gctgagaagc agacaccctt ggggaaactg gctctgtccc tcccctcccc catcccagga   7500
gctgaggtct tggtgaggcc acagggccag gtccacgcaa ggactgtccg tgtcctgtcc   7560
tgtggtctct ggccccacgt gacacccaca cgtgtggtag gcagcctggc ctgggttgtg   7620
gctatggcca ggcccccaag ctgtccccga tgcccagggc tggtgaccac ccaggcaggt   7680
gggggcccca cttggtaaca gagtcatagg gcagaaccca cctgggctgc cacagaaggt   7740
ctggctgccc ctgtgcccac tgctccccac catggccaat cagaagagtc aggggctcct   7800
ggtctttccg ggagggacgt ggcccagcca gctctaggtg ttctgagcag ctctgggacc   7860
cagcgattga ggggtcaggc tgggggtgtc agagccaggg tcctccttaa gtacctccca   7920
cactacacag acagtggccc ttttgtgggc agcaaattct tgagccatga aaggatgctt   7980
tgggcccctt ccctcccagg agggcagcct gtgcagggat ggtgctcagc aggtggacag   8040
```

-continued ggcctggggc ctgtgtcagg gtctcaggcc tgggagcacc agcagaggag atggcggctc 8100
ccagcagtgc cgcctgaaag tgtcttgggc taaggaccca cacccagggc tgccctgcag 8160
aaacgccccc gcagagccca gtggtctgtg aggttgcagg cagggtgcga atggaagggc 8220
acaggtgcgg ggctggcacc tgcccggtcc tgcccacctc ccctccgccc agcccgcacc 8280
tgcgtctccc cacagagctg tccgtggcac agtgcacgca gcggcccgtg gacatcgtct 8340
tcctgctgga cggctccgag cggctgggtg agcagaactt ccacaaggcc cggcgcttcg 8400
tggagcaggt ggcgcggcgg ctgacgctgg cccggaggga cgacgaccct ctcaacgcac 8460
gcgtggcgct gctgcagttt ggtggccccg gcgagcagca ggtggccttc ccgctgagcc 8520
acaacctcac ggccatccac gaggcgctgg agaccacaca atacctgaac tccttctcgc 8580
acgtgggcgc aggcgtggtg cacgccatca atgccatcgt gcgcagcccg cgtggcgggg 8640
cccggaggca cgcagagctg tccttcgtgt tcctcacgga cggcgtcacg ggcaacgaca 8700
gtctgcacga gtcggcgcac tccatgcgca agcagaacgt ggtacccacc gtgctggcct 8760
tgggcagcga cgtggacatg gacgtgctca ccacgctcag cctgggtgac cgcgccgccg 8820
tgttccacga gaaggactat gacagcctgg cgcaacccgg cttcttcgac cgcttcatcc 8880
gctggatctg ctagcgccgc cgcccgggcc ccgcagtcga gggtcgtgag cccaccccgt 8940
ccatggtgct aagcgggccc gggtcccaca cggccagcac cgctgctcac tcggacgacg 9000
ccctgggcct gcacctctcc agctcctccc acggggtccc cgtagccccg gcccccgccc 9060
agccccaggt ctccccaggc cctccgcagg ctgcccggcc tccctccccc tgcagccatc 9120
ccaaggctcc tgacctacct ggcccctgag ctctggagca agccctgacc caataaaggc 9180
tttgaaccca ttgcgtgcct gcttgcgagc ttctgtgcgc aggagagacc tcaaaggtgt 9240
cttgtggcca ggagggaaac actgcagctg tcgctcgccc accagggtca atggctcccc 9300
cgggcccagc cctgacctcc taggacatca actgcaggtg ctggctgacc ccgcctgtgc 9360
agaccccaca gccttgatca gcaaactctc cctccagccc cagccaggcc caaagtgctc 9420
taagaagtgt caccatggct gagggtcttc tgtgggtgga cgcatgatta acactagacg 9480
gggagacagc aggtgctgag cctgttgtgt tctgtgtgga gatctcagtg agtttttgct 9540
gttcagaccc cagggtcctt caggctcagc tcaggagccc cacagtgaac cagaggctcc 9600
acaggcaggt gctgacctga caggagtggg cttggtggcc atcacagggc accacagaca 9660
cagcttgaac aactaccagt atcggccaca ggcctggagg catcagccgg gccatgcttc 9720
ctctggaggg ctagaggagg actagagaag ggcctgcccc ggcctctccc cagcatccca 9780
gggttcctga tctcctggat aaggatacaa gtcaccacac tggactgggg ctcagcctgc 9840
tctagaatac ctcacctaag tcacagtgga ccaggctcag cctgctctaa ggtgagctta 9900
cccgagacac tggaccagag atcagcctat cctgggataa gctcacccga gtcacactgg 9960
accagggctc agcctattcc gggatgagct cacccgagtc 10000

<210> SEQ ID NO 256
<211> LENGTH: 800
<212> TYPE: DNA
<213> ORGANISM: Homo sapiens

<400> SEQUENCE: 256
gacacttcca tgactgcagc tgaccagtcc acctgccagc ggttgaccac tcccacttcg 60
ccagcgaccg aaggggaggg gaggggcctc acctgagggc aacagcagaa cccaccacct 120
ggtcttgctt tactcagacc tgagggtgtg aaaggtgccc gtgacctccc gcatcaggga 180

```
gctggccgcc accctcgact cccggggagc aggcgtcccg cgaccccctc atctaccagg    240

ccatctgagc tgggcggcgc ctcacctccg ctcccggggg agccggcctc agggtaggca    300

tgcgccctgg gtgggagcag gtcgtggccg ccgccctcct ggcagctctg gctgagcagc    360

cgccgcagca tctgattctc cttcaggagg cgcacctgct tcttcaggtc cgcgttctcg    420

ctcaggagcc ggctcatcag ctcgccgcct tcagccatgg cgggtgcgtc cctccttgtc    480

cctcacggct cctgcagccc catggaggtg ggagcccaga gcccgcaggc accacagaaa    540

cagcccaggc acggagttcc gtagccacca ccgccttcca cgccttgtga tgtcactgcc    600

ctagtgatga ggtgcccagc accctgcctg cccccgcgat ggctcatggc cccgttgagg    660

cagtgaagct ggaggcccgt ggcgtgcaca ggcagccact cccacattat gaccagggcc    720

cgagaatgcc aaggacatta ggcagctacg ggatgtagcg actgtactcc aagaggggcg    780

tccaagccac tccccattga                                                800


<210> SEQ ID NO 257
<211> LENGTH: 293
<212> TYPE: DNA
<213> ORGANISM: Homo sapiens

<400> SEQUENCE: 257

aggtggaggt tgcagtgagc cctcctcccc tcctccccct tcccttccca cctcccatgc     60

ccccctttct tcctcccact cccctcccga ggcccgcctt attctcccgg cctgtggcgg    120

ttcgtgcact cgctgagctc aggttctggt gaaggtgccc ggagccgggt cccgccttcg    180

gcctgagcta gagccgcgcg ggcggccggc ttcccccaaa ccctgtggga ggggcatccc    240

gaggaggcga ccccagagag tggggcgcgg acaccttccc tggggagggc cag           293


<210> SEQ ID NO 258
<211> LENGTH: 474
<212> TYPE: DNA
<213> ORGANISM: Homo sapiens

<400> SEQUENCE: 258

ccttccagat gttccagaag gagaaggcgg tgctggacga gctgggccga cgcacgggga     60

cccggctgca gcccctgacc cggggcctct tcggagggag ctgagggccg cgttccttct    120

gaaagcggga cgcgggaggg gtggaggctg cggggagccg gggtcgcaca cgaataaata    180

acgaatgaac gtacgagggg aacctcctct tatttccttc acgttgcatc gggtattttt    240

cgttattgta aataaaacgg ttccgagccg tggcatcgag agggcgtctg gagttcaggg    300

aacgcgtggc ccccgcccgg gagcaccgcg cagcgctcgc ctctcgccct tcaagggggt    360

ccctgcccgg agcctgcgcc cccggagagg aaggggctcg aggggcttgg gtgccgcagc    420

gcgtccttcc gtagaaaagg cttgcgtcag tatttcctgc ttttacctcc tgag          474


<210> SEQ ID NO 259
<211> LENGTH: 346
<212> TYPE: DNA
<213> ORGANISM: Homo sapiens

<400> SEQUENCE: 259

cagtatttcc tgcttttacc tcctgagtat tggaatattc gagtaaaccc tggagtttca     60

gcgccagcgc acgcctcttc atcagggcag cgcgtcgcga gcgcgctggt tccccggggc    120

ctcccggcca cggacaccgc tctagccagg gccacggcga ggccgccgag cagcacctca    180
```

gagacctgcg tgagttctaa agcctggggc tactacaatt ctgctcatct gtttgtcctg 240
tgaaatgatt cagggacatg aaaatgcctt cccactgact tgcgtcctgt cttagcctgg 300
acttgtcccc ttgggaacac gggccaggcc cctctgttcc tgaagt 346

<210> SEQ ID NO 260
<211> LENGTH: 490
<212> TYPE: DNA
<213> ORGANISM: Homo sapiens

<400> SEQUENCE: 260
atgtctgcag ggaagaagca gggggaccct gaataaagtt tccgtttttc ctatttgtta 60
aagtgataga gcattatagg accagagaac aggtgtgtct gtacactgtg caggtccccg 120
gggcaggctc tgagtccgtc tgcacacggt gcgggtcccc ggggcgcgcc ctgagcccgt 180
ctgcacacgg tgcgggtccc cggggcgcgc cctgagcccg tctgcacacg gtgcgggtcc 240
ccggggcgcg ccctgagccc gtctgcacac ggtgcgggtc cccggggcgc gccctgagcc 300
cgtctgcaca cggtgcgggt ccccggggcg cgccctgagc ccgtctgcac acggtgcggg 360
tccccggggc gcgccctgag cccgtctgta cacggtgcgg gtccccgggg cgcgccctga 420
gtctctacta aaaatacaaa aattagccag gcgtggtggt tcaagcctgt aatcccagct 480
ccttgggagg 490

<210> SEQ ID NO 261
<211> LENGTH: 2000
<212> TYPE: DNA
<213> ORGANISM: Homo sapiens

<400> SEQUENCE: 261
catacatggt tattagaaaa ggcatctcat ccaaatgtgg tggctcgtgc ttgtaatccc 60
agtgcttcag gaggccaagg gaggaggatt acttgagcct aagagtttga gaccagcctg 120
ggcaacacaa caagaccttg cctctacaaa aaacttaaaa actagctggg tatgatggtg 180
cacacctgta gtcccagcta cttgggaggc ggaggcgggc agatcgcctg aggtcaggag 240
ttcgagacca gcctggccaa catgatgaaa ccccgtctct actaaaaata caaaaattag 300
ccgagtgtgg tggtgcatgc ctgtaatccc agctactcag gaggctgagg caggagaatc 360
acttgaaccc gggaggcgga ggttgccatg agccgagatc acgtcactgc actccagcct 420
gggtgacaga gcacaaaaga caggcatgac tttgtactta actgctcagc tttgtaatca 480
ctgggggccc agatgctcac ttggattcta actttgttgg catctgggcc taaaagccgt 540
gatgcaggtg agcaatgatg cagagggctc tgtgcgcctg gcgggctctg tttgcctgct 600
gggctctgtg cgcctgctgg gctctgtgcg cccgggaagg tgcggccacc ctcacgcgga 660
aggcggccag cggatcccgg tgcgcgcagc tcccagcgct ggggttccag cgccccgcct 720
cttcctatag caaccagcgg gacctgccgt cccccggggc accccgaggg gtctgcgccc 780
gcttctttcc gaaacgggaa ggcgctgggg gctcggcagc cagagggacg ggttcaggga 840
gcgtccggtg agcctaagac gcgcctttgc cggggttgcc gggtgtctgc ctctcactta 900
ggtattagga accgtggcac aaatctgtag gttttcctct gggggtgggc ggaggctcca 960
aaccggacgg ttttctcctg gaggactgtg ttcagacaga tactggtttc cttatccgca 1020
ggtgtgcgcg gcgctcgcaa gtggtcagca taacgccggg cgaattcgga aagcccgtgc 1080
gtccgtggac gacccacttg gaaggagttg ggagaagtcc ttgttcccac gcgcggacgc 1140
ttccctccgt gtgtccttcg agccacaaaa agcccagacc ctaacccgct cctttctccc 1200
gccgcgtcca tgcagaactc cgccgttcct gggaggggaa gcccgcgagg cgtcgggaga 1260
ggcacgtcct ccgtgagcaa agagctcctc cgagcgcgcg gcggggacgc tgggccgaca 1320
ggggaccgcg ggggcagggc ggagaggacc cgccctcgag tcggcccagc cctaacactc 1380
aggaccgcct ccagccggag gtctgcgccc ttctgaggac cctgcctggg ggagcttatt 1440
gcggttcttt tgcaaatacc cgctgcgctt ggacggagga agcgcccacg cgtcgacccc 1500
ggaaacgaag gcctccctga tgggaacgca tgcgtccagg agcctttatt tactcttaat 1560
tctgcccgat gcttgtacgt gtgtgaaatg cttcagatgc ttttgggagc gaggtgttac 1620
ataaatcatg gaaatgcctc ctggtctcac cacacccagg gtgacagctg agatgcggct 1680
tctccagggt ggagcctcct cgttttccag agctgcttgt tgaagtcttc ccagggcccc 1740
tgacttgcac tggaaactgc tcaccttggc atcgggatgt ggagcaagaa atgcttttgt 1800
tttcattcat cctagtgttc ataaaatgga aaacaaataa ggacatacaa aaacattaat 1860
aaaataaatt aatggaacta gatttttcag aaagcacaac aaacacaaaa tccaagtatt 1920
gccatgtcag caacacattc ctactttaag ttttatgaag ttaattggag tagtggagaa 1980
caaaagtgga tgtggggcag 2000

<210> SEQ ID NO 262
<211> LENGTH: 88
<212> TYPE: DNA
<213> ORGANISM: Homo sapiens

<400> SEQUENCE: 262
gattgacagt ttctccttcc ccagactggc caatcacagg caggaagatg aaggttctgt 60
gggctgcgtt gctggtcaca ttcctggc 88

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 263
acgttggatg ttgacagttt ctccttcccc 30

<210> SEQ ID NO 264
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 264
acgttggatg gaatgtgacc agcaacgcag 30

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 265
gcaggaagat gaaggtty 18

<210> SEQ ID NO 266
<211> LENGTH: 88
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 266
gattgacagt ttctccttcc ccagactggc caatcacagg caggaagatg aaggttttgt 60
gggctgcgtt gctggtcaca ttcctggc 88

<210> SEQ ID NO 267
<211> LENGTH: 90
<212> TYPE: DNA
<213> ORGANISM: Homo sapiens

<400> SEQUENCE: 267
gagttttgga tagtaaaata agtttcgaac tctggcacct ttcaattttg tcgcactctc 60
cttgtttttg acaatgcaat catatgcttc 90

<210> SEQ ID NO 268
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 268
acgtggatag taaaataagt ttcgaactct g 31

<210> SEQ ID NO 269
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 269
gaagcatatg attgcattgt caaaaac 27

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 270
atttcaattt tgtcgcacty 20

<210> SEQ ID NO 271
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 271
gagttttgga tagtaaaata agtttcgaac tctggcacct ttcaattttg tcgcactttc 60
cttgtttttg acaatgcaat catatgcttc 90

<210> SEQ ID NO 272
<211> LENGTH: 97
<212> TYPE: DNA
<213> ORGANISM: Homo sapiens

<400> SEQUENCE: 272
gaactcctct ttgtctctgc gtgcccggcg cgcccccctc ccggtgggtg ataaacccac 60
tctggcgccg gccatgcgct gggtgattaa tttgcga 97

<210> SEQ ID NO 273
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 273
acgttggatg tctttgtctc tgcgtgccc 29

<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 274
acgttggatg ttaatcaccc agcgcatggc 30

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 275
cccctcccgg tgggtgataa ay 22

<210> SEQ ID NO 276
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 276
gaactcctct ttgtctctgc gtgcccggcg cgcccccctc ccggtgggtg ataaatccac 60
tctggcgccg gccatgcgct gggtgattaa tttgcga 97

<210> SEQ ID NO 277
<211> LENGTH: 86
<212> TYPE: DNA
<213> ORGANISM: Homo sapiens

<400> SEQUENCE: 277
ccattggccg tccgccgtgg cagtgcgggc gggagcgcag ggagagaacc acagctggaa 60
tccgattccc accccaaaac ccagga 86

<210> SEQ ID NO 278
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 278
acgttggatg ccattggccg tccgccgtg 29

<210> SEQ ID NO 279
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 279
acgttggatg tcctgggttt tggggtggga a 31

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 280
ttccagctgt ggttctctc 19

<210> SEQ ID NO 281
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 281
ccattggccg tccgccgtgg cagtgcgggc gggagcgcag agagagaacc acagctggaa 60
tccgattccc accccaaaac ccagga 86

<210> SEQ ID NO 282
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 282
acgttggatg acatggtcgg ccccacggaa t 31

<210> SEQ ID NO 283
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 283
acgttggatg acccattggc cgtccgccgt 30

<210> SEQ ID NO 284
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 284
acgttggatg gaactcctct ttgtctctgc g 31

<210> SEQ ID NO 285
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 285
acgttggatg cgcagcaacg ggaccgctac a 31

<210> SEQ ID NO 286
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 286
acgttgcgta gcaacctgtt acatattaa 29

<210> SEQ ID NO 287
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 287
acgttggatg catagaggcc catgatggtg g 31

<210> SEQ ID NO 288
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 288
acgttggatg gtgtggtcag ctcttccctt cat 33

<210> SEQ ID NO 289
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 289
acgttggatg ctccttccta gtgtgagaac cg 32

<210> SEQ ID NO 290
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
acgttggatg ttttggggtg ggaatcggat t 31

<210> SEQ ID NO 291
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
acgttggatg tggcatggcc ggcgccaga 29

<210> SEQ ID NO 292
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
acgttggcat ctaggtaggt ctttgtagcc aa 32

<210> SEQ ID NO 293
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
acgttggatc tgagcaaagg caatcaacac cc 32

<210> SEQ ID NO 294
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
acgttggatg accttctgcc cctctactcc aa 32

<210> SEQ ID NO 295
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
acgttggccc acatgtaatg tgttgaaaaa gca 33

<210> SEQ ID NO 296
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 296
caggttccgg ggcttggg 18

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 297
cgcagggaga gaaccacag 19

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 298
cccctcccgg tgggtgataa a 21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 299
aaagctgtag gacaatcggg t 21

<210> SEQ ID NO 300
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 300
catttttcta catcctttgt tt 22

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 301
agaagatcac caggcagaag agg 23

<210> SEQ ID NO 302
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 302
acttggagaa caaaggacac cgtta 25

<210> SEQ ID NO 303
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 303
ggtcggcccc acggaatccc ggctctgtgt gcgcccaggt tccggggctt gggtgttgcc 60
ggttctcaca ctaggaagga g 81

<210> SEQ ID NO 304
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 304
ccattggccg tccgccgtgg cagtgcgggc gggagcgcag agagagaacc acagctggaa 60
tccgattccc accccaaaa 79

<210> SEQ ID NO 305
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 305
gaactcctct ttgtctctgc gtgcccggcg cgcccccctc ccggtgggtg ataaatccac 60
tctggcgccg gccatgc 77

<210> SEQ ID NO 306
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 306
gcagcaacgg gaccgctaca gccactggac aaagccgtag gacaatcggg taacattggc 60
tacaaagacc tacctagatg c 81

<210> SEQ ID NO 307
<211> LENGTH: 95
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 307
gcgtagcaac ctgttacata ttaaagtttt attatactac atttttctac atcctttgtt 60
tcagagtgtt gattgccttt gctcagtatc ttcag 95

<210> SEQ ID NO 308
<211> LENGTH: 86
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 308
ccttctgccc ctctactcca agcgctacac cctcttctgc ctggtgatct ttgccggcgt 60
cctggccacc atcatgggcc tctatg 86

<210> SEQ ID NO 309
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 309
gtgtggtcag ctcttccctt catcacatac ttggagaaca aaggacaccg ttatccatgc 60
tttttcaaca cattacatgt ggg 83

<210> SEQ ID NO 310
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 310
acgttggatg ttctgcccct ctactccaag 30

<210> SEQ ID NO 311
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 311
acgttggatg tcagctcttc ccttcatcac 30

<210> SEQ ID NO 312
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 312
acgttggatg cggtcggccc cacggaat 28

<210> SEQ ID NO 313
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 313
acgttggatg cacagctcac cgcagcaacg 30

<210> SEQ ID NO 314
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 314
acgttggatg gactgagccc cagaactcg 29

<210> SEQ ID NO 315
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 315
acgttggatg aagccaagtt tccctccgc 29

<210> SEQ ID NO 316
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 316
acgttagcgt agcaacctgt tacatattaa 30

<210> SEQ ID NO 317
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 317
acgttggatg catagaggcc catgatggtg 30

<210> SEQ ID NO 318
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 318
acgttggatg cctacctccc acatgtaatg t 31

<210> SEQ ID NO 319

<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 319
acgttggatg ctaggtaggt ctttgtagcc aa 32

<210> SEQ ID NO 320
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 320
acgttggatg gtgggtttgt gctttccacg 30

<210> SEQ ID NO 321
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 321
acgttggatg cttttgcttt cccagccagg 30

<210> SEQ ID NO 322
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 322
acgttggatg ctgagcaaag gcaatcaaca 30

<210> SEQ ID NO 323
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 323
ttctgcctgg tgatctt 17

<210> SEQ ID NO 324
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 324
aacaaaggac accgtta 17

<210> SEQ ID NO 325
<211> LENGTH: 17

<212> TYPE: DNA
<213> ORGANISM: Artificial Sequence
<220> FEATURE:
<223> OTHER INFORMATION: Description of Artificial Sequence: Synthetic primer

<400> SEQUENCE: 325
gcaggaagat gaaggtt 17

<210> SEQ ID NO 326
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 326
aaggttccgg ggcttggg 18

<210> SEQ ID NO 327
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 327
atttcaattt tgtcgcact 19

<210> SEQ ID NO 328
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 328
agctgtagga caatcgggt 19

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 329
ccctcccggt gggtgataaa 20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 330
agggccgggg tctgcgcgtg 20

<210> SEQ ID NO 331
<211> LENGTH: 21
<212> TYPE: DNA

<213> ORGANISM: Artificial Sequence
<220> FEATURE:
<223> OTHER INFORMATION: Description of Artificial Sequence: Synthetic primer

<400> SEQUENCE: 331
gaggcactgc ccggacaaac c 21

<210> SEQ ID NO 332
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 332
gtgtggtcag ctcttccctt catcacatac ttggagaaca aaggacaccg ttatccatgc 60
tttttcaaca cattacatgt gggaggtagg 90

<210> SEQ ID NO 333
<211> LENGTH: 98
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 333
aaaaccagag attcgcggtc ggccccacgg aatcccggct ctgtgtgcgc ccaggttccg 60
gggcttgggt gttgccggtt ctcacactag gaaggagc 98

<210> SEQ ID NO 334
<211> LENGTH: 95
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 334
gcagccagct caccgcagca acgggaccgc tacagccact ggacaaagct gtaggacaat 60
cgggtgacat tggctacaaa gacctaccta gatgc 95

<210> SEQ ID NO 335
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 335
gtgggtttgt gctttccacg cgtgcacaca cacgcgcaga ccccggccct tgccccgcct 60
acctccccga gttctggggc tcagtc 86

<210> SEQ ID NO 336
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 336
gcgccagctt ttgctttccc agccagggcg cggtgaggtt tgtccgggca gtgcctcgag 60
caactgggaa ggccaaggcg gagggaaac 89

<210> SEQ ID NO 337
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 337
gcgtagcaac ctgttacata ttaaagtttt attatactac atttttctac atcctttgtt 60
ttagggtgtt gattgccttt gctcagtatc ttcagc 96

<210> SEQ ID NO 338
<211> LENGTH: 27
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer

<400> SEQUENCE: 338
tagcugcgta gcaacctgtt acatatt 27

<210> SEQ ID NO 339
<211> LENGTH: 25
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer

<400> SEQUENCE: 339
tagcucagtt tctccttccc cagac 25

<210> SEQ ID NO 340
<211> LENGTH: 25
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer

<400> SEQUENCE: 340
tagcuggtca gctcttccct tcatc 25

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer

<400> SEQUENCE: 341
tagcuagctg gtgcggaggg tggg 24

<210> SEQ ID NO 342
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 342
tagcuggcct ttgcaacaag gatcac 26

<210> SEQ ID NO 343
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 343
tagcutctgg tgacccccgc gcttc 25

<210> SEQ ID NO 344
<211> LENGTH: 24
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 344
tagcuccctc cacatcccgc catc 24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 345
tagcuacgga atcccggctc tgtg 24

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule:

Synthetic primer

<400> SEQUENCE: 346
tagcuggccc tgctggcggt cata 24

<210> SEQ ID NO 347
<211> LENGTH: 24
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 347
tagcuagcaa cgggaccgct acag 24

<210> SEQ ID NO 348
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 348
tagcutaagt ttcgaactct ggcacc 26

<210> SEQ ID NO 349
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 349
tagcuctcct ctttgtctct gcgtg 25

<210> SEQ ID NO 350
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 350
tagcutgatg cccgatgccg ccctt 25

<210> SEQ ID NO 351
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:

<223> OTHER INFORMATION: Description of Combined DNA/RNA Molecule:
      Synthetic primer

<400> SEQUENCE: 351
gatcuatact gagcaaaggc aatcaac 27

<210> SEQ ID NO 352
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 352
gatcugaatg tgaccagcaa cgcag 25

<210> SEQ ID NO 353
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 353
gatcucctcc cacatgtaat gtgttg 26

<210> SEQ ID NO 354
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 354
gatcuatggg ggagatggcc ggtgga 26

<210> SEQ ID NO 355
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 355
gatcucgcaa tactagaaac cagggc 26

<210> SEQ ID NO 356
<211> LENGTH: 24
<212> TYPE: DNA
<213> ORGANISM: Artificial Sequence
<220> FEATURE:
<223> OTHER INFORMATION: Description of Artificial Sequence: Synthetic
      primer <220> FEATURE:
<223> OTHER INFORMATION: Description of Combined DNA/RNA Molecule:
Synthetic primer

<400> SEQUENCE: 356
gatcucatct ctgggtgcgc cttg 24

<210> SEQ ID NO 357
<211> LENGTH: 23
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer

<400> SEQUENCE: 357
gatcucagcc gcctgctcca tcg 23

<210> SEQ ID NO 358
<211> LENGTH: 25
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer

<400> SEQUENCE: 358
gatcuccttc ctagtgtgag aaccg 25

<210> SEQ ID NO 359
<211> LENGTH: 25
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer

<400> SEQUENCE: 359
gatcutgctc agcacgaggg cccca 25

<210> SEQ ID NO 360
<211> LENGTH: 26
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer

<400> SEQUENCE: 360
gatcutctag gtaggtcttt gtagcc 26

<210> SEQ ID NO 361
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 361
gatcugaagc atatgattgc attgtcaa 28

<210> SEQ ID NO 362
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 362
gatcuttaat cacccagcgc atggc 25

<210> SEQ ID NO 363
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 363
gatcugtctg tgctgggtgt ttttgc 26

<210> SEQ ID NO 364
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 364
aatgatacgg cgaccaccga gatctacact ctttccctac acgacgctct tccgatct 58

<210> SEQ ID NO 365
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 365
gctcttccga tctatagct 19

<210> SEQ ID NO 366
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 366
gatcggaaga gcacacgtct gaactccagt cacagtcaac aatctcgtat gccgtcttct 60
gcttg 65

<210> SEQ ID NO 367
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 367
acactctttc cctacacgac gctcttccga tct 33

<210> SEQ ID NO 368
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 368
gatcggaaga gcacacgtct gaactccagt cacagtcaaa tctcgtatgc cgtcttctgc 60
ttg 63

<210> SEQ ID NO 369
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 369
gatcggaaga gcacacgtct gaactccagt cac 33

<210> SEQ ID NO 370
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 370
tctttcccta cacgacgctc ttccgatct 29

<210> SEQ ID NO 371
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 371
gtgactggag ttcagacgtg tgctcttccg atct 34

<210> SEQ ID NO 372
<211> LENGTH: 49
<212> TYPE: DNA
<213> ORGANISM: Artificial Sequence
<220> FEATURE:
<223> OTHER INFORMATION: Description of Artificial Sequence: Synthetic primer -continued

```
<400> SEQUENCE: 372

aatgatacgg cgaccaccga gatctacact ctttccctac acgacgctc              49


<210> SEQ ID NO 373
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373

caagcagaag acggcatacg agatttgact gtgactggag ttcagacgtg             50


<210> SEQ ID NO 374
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374

cgcaaccact                                                         10


<210> SEQ ID NO 375
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375

cgcgaccact                                                         10
```